United States Patent
Kori et al.

(10) Patent No.: US 6,982,348 B2
(45) Date of Patent: Jan. 3, 2006

(54) AMINOETHANOL DERIVATIVES

(75) Inventors: Masakuni Kori, Kobe (JP); Kazumasa Hamamura, Kawanishi (JP); Hiromitsu Fuse, Tsukuba (JP); Toshihiro Yamamoto, Suita (JP)

(73) Assignee: Takeda Pharmaceutical Company Limited, Osaka (JP)

(*) Notice: Subject to any disclaimer, the term of this patent is extended or adjusted under 35 U.S.C. 154(b) by 68 days.

(21) Appl. No.: 10/470,351

(22) PCT Filed: Jan. 25, 2002

(86) PCT No.: PCT/JP02/00532

§ 371 (c)(1), (2), (4) Date: Jul. 25, 2003

(87) PCT Pub. No.: WO02/059077

PCT Pub. Date: Aug. 1, 2002

(65) Prior Publication Data

US 2004/0127574 A1 Jul. 1, 2004

(30) Foreign Application Priority Data

Jan. 26, 2001 (JP) ........................................ 2001-019280

(51) Int. Cl.
C07C 233/65 (2006.01)
A61K 31/165 (2006.01)

(52) U.S. Cl. .................. 564/158; 560/157; 546/157; 548/492; 549/57; 514/617; 514/478; 514/443; 514/412; 514/311

(58) Field of Classification Search ............. 564/158, 564/180; 560/157; 546/157; 549/57; 514/478, 514/617, 311, 443, 412; 548/492
See application file for complete search history.

(56) References Cited

U.S. PATENT DOCUMENTS

| | | | |
|---|---|---|---|
| 6,080,738 A | 6/2000 | Akahoshi et al. | 514/227.8 |
| 6,426,365 B1 | 7/2002 | Shinkai et al. | 514/513 |
| 6,528,514 B1 | 3/2003 | Kobayashi et al. | 514/269 |

FOREIGN PATENT DOCUMENTS

| | | |
|---|---|---|
| EP | 0231919 | 8/1987 |
| EP | 0992496 A1 | 4/2000 |
| GB | 1217038 | 12/1970 |
| JP | 11-246437 | 9/1999 |
| JP | 11-286478 | 10/1999 |
| JP | 2001-131137 | 5/2001 |
| WO | WO 89/10752 | 11/1989 |
| WO | WO 93/25574 | 12/1993 |

OTHER PUBLICATIONS

Ramaiah et al, J. Phys. Chem., 1992, vol. 96, 1271–1278.*
Piron, et al. "New Methods for Solid Phase Peptide Synthesis of Transition–State Analog Inhibitors of HIV–1 Protease and DPP–IV" Letters in Peptide Science 2: 229–232 (1995).

* cited by examiner

*Primary Examiner*—Shailendra Kumar
(74) *Attorney, Agent, or Firm*—Elaine M. Ramesh; Mark Chao

(57) ABSTRACT

The present invention provides a pharmaceutical agent having cholesteryl ester transfer protein inhibitory action and useful as a blood lipid lowering agent and the like. The present invention relates to a compound represented by the formula

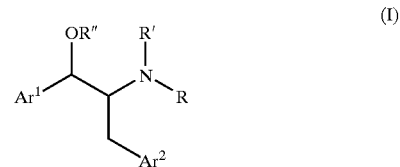

(I)

wherein $Ar^1$ is an aromatic ring group optionally having substituents, $Ar^2$ is an aromatic ring group having substituents, OR" is an optionally protected hydroxyl group, R is an acyl group, R' is a hydrogen atom or a hydrocarbon group optionally having substituents, or a salt thereof, and a pharmaceutical composition containing a compound of the formula (I) or a salt thereof or a prodrug thereof.

55 Claims, No Drawings

AMINOETHANOL DERIVATIVES

TECHNICAL FIELD

The present invention relates to novel aminoethanol derivatives that inhibit cholesteryl ester transfer protein, and the like.

BACKGROUND ART

A number of epidemiological searches have clarified that hypercholesterolemia, particularly, high level of low density lipoprotein (LDL)-cholesterol in serum, is a risk factor of arteriosclerotic diseases (e.g., cardiac infarction, angina pectoris, cerebral infarction and the like). As a pharmaceutical agent to lower serum LDL-cholesterol, pharmaceutical agents that inhibit 3-hydroxy-3-methylglytaryl coenzyme A (HMG-CoA) reductase have been clinically used, and large scale clinical tests have clarified that they show a certain effect on the decrease of incidence of coronary diseases (N. Engl. J. Med., 34, 498–511 (1999)). However, the effect is not fully satisfactory. In addition, it is epidemiologically known that the concentration of high density lipoprotein (HDL)—cholesterol in serum shows an inverse correlation with the incidence of coronary diseases (N. Engl. J. Med., 321, 1311–1316 (1989), Am. Heart J., 110, 1100–1107 (1985)), and a pharmaceutical agent that increases serum HDL-cholesterol has been drawing attention as a pharmaceutical agent for the prophylaxis or treatment of arteriosclerotic diseases.

The cholesteryl ester transfer protein (CETP) catalyzes transfer of cholesteryl ester from HDL to LDL and very low density lipoprotein (VLDL) (J. Lipid Res., 34, 1255–1274 (1993)), and is deeply involved in the inverse transfer system of cholesterol or transfer of cholesterol from peripheral tissues to the liver. As the inverse transfer system of cholesterol, the following three pathways are known.

(1) Free cholesterol accumulated in the peripheral tissues is extracted by HDL, undergoes the action of lecithin-cholesterol acyltransferase (LCAT) and converted to cholesteryl ester on HDL. The cholesteryl ester on HDL is transferred by CETP to LDL or VLDL in exchange of triglyceride, and cholesterol is transferred to the liver via LDL receptor.
(2) HDL becomes apoprotein E-containing HDL and is uptaken into the liver via LDL receptor.
(3) Cholesteryl ester on HDL is directly uptaken into the liver via HDL receptor.

Because CETP is deeply involved in the cholesterol inverse transfer system, the intensity of its activity in blood is considered to be linked to the control of blood HDL-cholesterol concentration. With regard to the correlation between CETP and blood HDL—cholesterol concentration, for example, the following findings are known. When CETP activity is inhibited by CETP monoclonal antibody in rabbit and hamster, serum HDL—cholesterol concentration increases (J. Clin. Invest., 84, 129–137 (1989), Atherosclerosis, 110, 101–109 (1994)). Transgenic mouse and transgenic rat that expressed CETP shows increased LDL-cholesterol concentration (J. Biol. Chem., 266, 10796–10801 (1991), Nat. Med., 5, 1383–1389 (1999)). From epidemiological search, individuals showing decreased or no CETP activity due to genetic mutation also show increased blood HDL—cholesterol concentration (Nature, 342, 448–451 (1989), Atherosclerosis, 58, 175–186 (1985)).

From the above findings, it is considered that intensity of CETP activity has an inverse correlation with arteriosclerosis-suppressive HDL-cholesterol, and inhibition of CETP activity is expected to lower the risk of progression of coronary diseases. In fact, it is known that CETP activity varies depending on the animal species, and arteriosclerosis is induced by cholesterol loading in animals having high CETP activity (rabbit etc.), but arteriosclerosis is not easily induced in animals free of CETP (rat and the like). When CETP activity was inhibited sustainably in rabbit by administration of antisense RNA, blood HDL-cholesterol concentration increased and the progression of arteriosclerotic lesion was suppressed (J. Biol. Chem., 273, 5033–5036 (1998)). Therefore, a pharmaceutical agent that suppresses CETP activity is expected to act suppressively on arteriosclerotic diseases by inhibiting transfer of cholesterol from HDL to LDL or VLDL, increasing arteriosclerosis-suppressive HDL-cholesterol and simultaneously decreasing arteriosclerosis-promotive VLDL-cholesterol or LDL-cholesterol. That is, a pharmaceutical agent that suppresses CETP activity is expected to give a pharmaceutical agent for the prophylaxis or treatment of the diseases such as acute coronary syndrome, acute cardiac infarction, unstable angina pectoris, PTCA or arterial restenosis after stent placement, peripheral arterial occlusion, hyperlipidemia, cerebral infarction, stroke and the like, or an agent for suppressing progression of focal arteriosclerosis.

The pharmaceutical agents having CETP inhibitory action are disclosed in, for example, WO99/41237, lipids, 29, 811–818 (1994), WO98/35937, Atherosclerosis, 128, 59–66 (1997), Bioorg. Med. Chem. Lett., 6, 919–922 (1996), U.S. Pat. No. 5,925,645, U.S. Pat. No. 5,932,587, Europe patent No. 825185, Europe patent No. 818448, Angew. Chem., Int. Ed., 38, 3373–3375 (1999), WO99/14174, WO00/18724, WO00/17164 and the like.

As the aminoethanol derivatives, for example, JP-A-11-286478 discloses tert-butyl benzyl-[2(S)-hydroxy-2-thiazol-2-yl-1(S)-(4-trifluoromethyl-benzyl)-ethyl]-carbamate as a compound to be a starting material for an antivirus agent, WO99/45928 discloses a compound to be a starting material for a compound having an action of improving autoimmune diseases, JP-A-11-246437 discloses a compound to be a starting material for a compound having a gastrointestinal mucosal protective action, WO98/18794 discloses a compound to be a starting material for a compound having a chymase inhibitory action, Lett. Pept. Sci., 2, 229–232 (1995) discloses a compound to be a starting material for a compound having an HIV-1 protease inhibitory action and a DPP-IV inhibitory action, WO93/25574 discloses a compound to be a starting material for a compound having a angiotensin I chymase inhibitory action, WO89/10752 discloses a compound to be a starting material for a compound having a retroviral protease inhibitory action, EP No. 231919 discloses a compound having a renin inhibitory action, and French Patent No. 1578851 discloses a compound having an adrenergic action, but no disclosure is found that these compounds have a prophylactic or therapeutic action on arteriosclerotic diseases or any description suggestive thereof.

As a pharmaceutical agent that increases plasma HDL-cholesterol (HDL-C), fibrate-type pharmaceutical agents and nicotinic acid have been used. They show an indirect HDL-C increasing action and side effects are a concern. As the situation stands, the development of a novel pharmaceutical agent that directly increases HDL-cholesterol and affords a sufficiently satisfactory effect in the prophylaxis or treatment of arteriosclerotic diseases such as ischemic heart and brain diseases, peripheral arterial occlusion and the like is awaited.

DISCLOSURE OF THE INVENTION

The present inventors have found that aminoethanol derivatives having the following specific substituents increase plasma HDL-C by inhibiting cholesterol ester transfer protein (CETP) and have a superior prophylactic or therapeutic effect on arteriosclerotic diseases, which resulted in the completion of the present study.

Accordingly, the present invention relates to:
(1) a compound represented by the formula

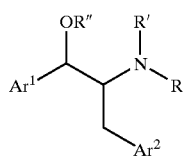

(I)

wherein
Ar$^1$ is an aromatic ring group optionally having substituents,
Ar$^2$ is an aromatic ring group having substituents,
OR" is an optionally protected hydroxyl group,
R is an acyl group, and
R' is a hydrogen atom or a hydrocarbon group optionally having substituents,
or a salt thereof,
except tert-butyl benzyl-[2(S)-hydroxy-2-thiazol-2-yl-1(S)-(4-trifluoromethyl-benzyl)-ethyl]-carbamate;
(2) the compound of the aforementioned (1), wherein Ar$^1$ is a 5- or 6-membered aromatic ring group optionally having substituents;
(3) the compound of the aforementioned (1), wherein Ar$^1$ is a phenyl group optionally having substituents;
(4) the compound of the aforementioned (1), wherein Ar$^2$ is a 5- or 6-membered aromatic ring group having substituents;
(5) the compound of the aforementioned (1), wherein Ar$^2$ is a phenyl group having substituents;
(6) the compound of the aforementioned (1), wherein R is a group represented by the formula R$^{1N}$CO— (R$^{1N}$ is a hydrocarbon group optionally having substituents or a heterocyclic group optionally having substituents);
(7) the compound of the aforementioned (6), wherein R$^{1N}$ is a cyclic hydrocarbon group optionally having substituents or a heterocyclic group optionally having substituents;
(8) the compound of the aforementioned (1), wherein R" is a hydrogen atom or an acyl group;
(9) the compound of the aforementioned (1), wherein R" is a group represented by the formula R$^{1O}$CO— (R$^{1O}$ is a hydrocarbon group optionally having substituents or a heterocyclic group optionally having substituents);
(10) the compound of the aforementioned (8), wherein R$^{1O}$ is an alkyl group optionally having substituents;
(11) the compound of the aforementioned (1), wherein R" is a hydrogen atom;
(12) the compound of the aforementioned (1), wherein R' is a hydrogen atom;
(13) the compound of the aforementioned (1), wherein R is a group represented by the formula R$^{1N}$CO— (R$^{1N}$ is a cyclic hydrocarbon group optionally having substituents or a heterocyclic group optionally having substituents), R" is a hydrogen atom and R' is a hydrogen atom;
(14) the compound of the aforementioned (1), wherein Ar$^1$ is a 5- or 6-membered aromatic ring group optionally having substituents selected from halogen atom, optionally halogenated lower alkyl group, optionally halogenated lower alkoxy group and aryloxy group optionally having substituents, Ar$^2$ is a 5- or 6-membered aromatic ring group having substituents selected from halogen atom, optionally halogenated lower alkyl group and optionally halogenated lower alkoxy group, R is a C$_{1-6}$ alkoxy-carbonyl, a C$_{1-6}$ alkyl-carbonyl, a C$_{6-10}$ aryl-carbonyl, dihydronaphthalenecarbonyl, tetrahydronaphthalenecarbonyl, benzocycloheptenecarbonyl or benzocyclooctenecarbonyl, each of which may have substituent(s) selected from halogen atom, optionally halogenated C$_{1-6}$ alkoxy and optionally halogenated C$_{1-6}$ alkyl, R" is a hydrogen atom, and R' is a hydrogen atom;
(15) the compound of the aforementioned (14), wherein the 5- or 6-membered aromatic ring group is a phenyl group, a pyridyl group, a thienyl group, a furyl group or a thiazolyl group;
(16) the compound of the aforementioned (14), wherein the 5- or 6-membered aromatic ring group is a phenyl group, a pyridyl group or a thienyl group, and R is naphthalenecarbonyl, dihydronaphthalenecarbonyl, tetrahydronaphthalenecarbonyl, benzocycloheptenecarbonyl or benzocyclooctenecarbonyl, each of which may have substituent(s) selected from halogen atom, optionally halogenated C$_{1-6}$ alkoxy and optionally halogenated C$_{1-6}$ alkyl;
(17) the compound of the aforementioned (1), which is N-[(1RS,2SR)-2-(4-fluorophenyl)-2-hydroxy-1-[4-(trifluoromethyl)benzyl]ethyl]-6,7-dihydro-5H-benzo[a]cycloheptene-1-carboxamide, 4-fluoro-N-((1R,2S)-2-(4-fluorophenyl)-2-hydroxy-1-((4-(trifluoromethyl)phenyl)methyl)ethyl)-1-naphthalenecarboxamide, N-[(1R,2S)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide, N-[(1RS,2SR)-2-(4-fluorophenyl)-2-hydroxy-1-[3-(1,1,2,2-tetrafluoroethoxy)benzyl]ethyl]-5,6-dihydronaphthalene-1-carboxamide, N-[(1RS,2SR)-2-(4-fluorophenyl)-2-hydroxy-1-[3-(1,1,2,2-tetrafluoroethoxy)benzyl]ethyl]-6,7,8,9-tetrahydro-5H-benzo[a]cycloheptene-1-carboxamide, 4-fluoro-N-[(1R,2S)-2-(4-fluorophenyl)-2-hydroxy-1-[3-(1,1,2,2-tetrafluoroethoxy)benzyl]ethyl]naphthalene-1-carboxamide, N-[(1RS,2SR)-2-(4-fluorophenyl)-2-hydroxy-1-[3-(1,1,2,2-tetrafluoroethoxy)benzyl]ethyl]-5,6,7,8-tetrahydrobenzo[a]cyclooctene-1-carboxamide, N-[(1RS,2SR)-2-(4-fluorophenyl)-2-hydroxy-1-(4-isopropylbenzyl)ethyl]-6,7-dihydro-5H-benzo[a]cycloheptene-1-carboxamide, N-((1RS,2SR)-2-(3-fluorophenyl)-2-hydroxy-1-((4-(trifluoromethyl)phenyl)methyl)ethyl)-6,7-dihydro-5H-benzo[a]cycloheptene-1-carboxamide, N-((1RS,2SR)-2-hydroxy-2-(4-phenoxyphenyl)-1-((4-(trifluoromethyl)phenyl)methyl)ethyl)-6,7-dihydro-5H-benzo[a]cycloheptene-1-carboxamide, N-[(1RS,2SR)-2-(4-chlorophenyl)-2-hydroxy-1-[3-(1,1,2,2-tetrafluoroethoxy)benzyl]ethyl]-6,7-dihydro-5H-benzo[a]cycloheptene-1-carboxamide, N-((1RS,2SR)-2-hydroxy-2-(4-(phenyloxy)phenyl)-1-((3-((1,1,2,2-tetrafluoroethyl)oxy)phenyl)methyl)ethyl)-6,7-dihydro-5H-benzo[a]cycloheptene-1-carboxamide, N-((1RS,2SR)-2-(4-((4-chloro-3-ethylphenyl)oxy)phenyl)-2-hydroxy-1-((3-((1,1,2,2-tetrafluoroethyl)oxy)phenyl)methyl)ethyl)-6,7-dihydro-5H-benzo[a]cycloheptene-1-carboxamide, N-((1RS,2SR)-2-(2-fluoropyridin-4-yl)-2-hydroxy-1-((3-(1,1,2,2-tetrafluoroethoxy)phenyl)methyl)ethyl)-6,7-dihydro-5H-benzo[a]cycloheptene-1-carboxamide, N-((1RS,2RS)-2-(6-fluoropyridin-2-yl)-2-hydroxy-1-((3-(1,1,2,2-tetrafluoroethoxy)phenyl)methyl)

ethyl)-6,7-dihydro-5H-benzo[a]cycloheptene-1-carboxamide, N-[(1RS,2SR)-1-(4-tert-butylbenzyl)-2-(3-chlorophenyl)-2-hydroxyethyl]-5-chloro-1-naphthamide, 4-fluoro-N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-1-naphthamide or a salt thereof;

(18) a prodrug of a compound represented by the formula

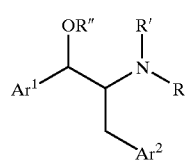

(I)

wherein
Ar¹ is an aromatic ring group optionally having substituents,
Ar² is an aromatic ring group having substituents,
OR" is an optionally protected hydroxyl group,
R is an acyl group, and
R' is a hydrogen atom or a hydrocarbon group optionally having substituents,
or a salt thereof,
except tert-butyl benzyl-[2(S)-hydroxy-2-thiazol-2-yl-1(S)-(4-trifluoromethyl-benzyl)-ethyl]-carbamate;

(19) a pharmaceutical composition comprising a compound represented by the formula

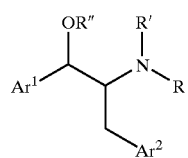

(I)

wherein
Ar¹ is an aromatic ring group optionally having substituents,
Ar² is an aromatic ring group having substituents,
OR" is an optionally protected hydroxyl group,
R is an acyl group, and
R' is a hydrogen atom or a hydrocarbon group optionally having substituents,
or a salt thereof or a prodrug thereof;

(20) the composition of the aforementioned (19), which is a cholesteryl ester transfer protein inhibitor;
(21) the composition of the aforementioned (19), which is a high density lipoprotein—cholesterol elevating agent;
(22) the composition of the aforementioned (19), which is a low density lipoprotein—cholesterol lowering agent;
(23) the composition of the aforementioned (19), which is an very low density lipoprotein—cholesterol lowering agent;
(24) the composition of the aforementioned (19), which is a triglyceride lowering agent;
(25) the composition of the aforementioned (19), which is a prophylactic or therapeutic agent of acute coronary syndrome;
(26) the composition of the aforementioned (19), which is a prophylactic or therapeutic agent of acute cardiac infarction;
(27) the composition of the aforementioned (19), which is a prophylactic or therapeutic agent of unstable angina pectoris;
(28) the composition of the aforementioned (19), which is a prophylactic or therapeutic agent of PTCA or arterial restenosis after stent placement;
(29) the composition of the aforementioned (19), which is a prophylactic or therapeutic agent of peripheral arterial occlusion;
(30) the composition of the aforementioned (19), which is a prophylactic or therapeutic agent of hyperlipidemia;
(31) the composition of the aforementioned (19), which is a prophylactic or therapeutic agent of cerebral infarction;
(32) the composition of the aforementioned (19), which is a prophylactic or therapeutic agent of stroke;
(33) the composition of the aforementioned (19), which is a suppressor of progression of focal arteriosclerosis;
(34) a cholesteryl ester transfer protein inhibitor comprising a compound represented by the formula

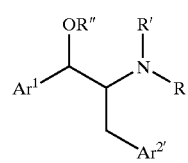

(I')

wherein
Ar¹ is an aromatic ring group optionally having substituents,
Ar² is an aromatic ring group optionally having substituents,
OR" is an optionally protected hydroxyl group,
R is an acyl group, and
R' is a hydrogen atom or a hydrocarbon group optionally having substituents,
or a salt thereof or a prodrug thereof;

(35) the agent of the aforementioned (34), which is a prophylactic or therapeutic agent of hyperlipidemia;
(36) the agent of the aforementioned (34), which is a prophylactic or therapeutic agent of acute coronary syndrome;
(37) the agent of the aforementioned (34), which is a prophylactic or therapeutic agent of acute cardiac infarction;
(38) the agent of the aforementioned (34), which is a prophylactic or therapeutic agent of unstable angina pectoris;
(39) the agent of the aforementioned (34), which is a prophylactic or therapeutic agent of PTCA or arterial restenosis after stent placement;
(40) the agent of the aforementioned (34), which is a prophylactic or therapeutic agent of peripheral arterial occlusion;
(41) the agent of the aforementioned (34), which is a prophylactic or therapeutic agent of cerebral infarction;
(42) the agent of the aforementioned (34), which is a prophylactic or therapeutic agent of stroke;
(43) the agent of the aforementioned (34), which is a suppressor of progression of focal arteriosclerosis;
(44) a method of inhibiting cholesteryl ester transfer protein in a mammal, which comprises administering an effective amount of a compound of the aforementioned (1) or a salt thereof to the mammal;
(45) a method for the prophylaxis or treatment of hyperlipidemia in a mammal, which comprises administering an effective amount of a compound of the aforementioned (1) or a salt thereof to the mammal;
(46) use of a compound of the aforementioned (1) or a salt thereof for the production of a pharmaceutical agent for inhibiting cholesteryl ester transfer protein;
(47) use of a compound of the aforementioned (1) or a salt thereof for the production of a pharmaceutical agent for the prophylaxis or treatment of hyperlipidemia;
(48) a method for the prophylaxis or treatment of acute coronary syndrome in a mammal, which comprises administering an effective amount of a compound of the aforementioned (1) or a salt thereof to the mammal;

(49) a method for the prophylaxis or treatment of acute cardiac infarction in a mammal, which comprises administering an effective amount of a compound of the aforementioned (1) or a salt thereof to the mammal;

(50) a method for the prophylaxis or treatment of unstable angina pectoris in a mammal, which comprises administering an effective amount of a compound of the aforementioned (1) or a salt thereof to the mammal;

(51) a method for the prophylaxis or treatment of PTCA or coronary restenosis after stent placement in a mammal, which comprises administering an effective amount of a compound of the aforementioned (1) or a salt thereof to the mammal;

(52) a method for the prophylaxis or treatment of peripheral arterial occlusion in a mammal, which comprises administering an effective amount of a compound of the aforementioned (1) or a salt thereof to the mammal;

(53) a method for the prophylaxis or treatment of cerebral infarction in a mammal, which comprises administering an effective amount of a compound of the aforementioned (1) or a salt thereof to the mammal:

(54) a method for the prophylaxis or treatment of stroke in a mammal, which comprises administering an effective amount of a compound of the aforementioned (1) or a salt thereof to the mammal;

(55) a method of suppressing progression of focal arteriosclerosis in a mammal, which comprises administering an effective amount of a compound of the aforementioned (1) or a salt thereof to the mammal;

(56) use of a compound of the aforementioned (1) or a salt thereof for the production of a prophylactic or therapeutic agent of acute coronary syndrome;

(57) use of a compound of the aforementioned (1) or a salt thereof for the production of a prophylactic or therapeutic agent of acute cardiac infarction;

(58) use of a compound of the aforementioned (1) or a salt thereof for the production of a prophylactic or therapeutic agent of unstable angina pectoris;

(59) use of a compound of the aforementioned (1) or a salt thereof for the production of a prophylactic or therapeutic agent of peripheral arterial occlusion;

(60) use of a compound of the aforementioned (1) or a salt thereof for the production of a prophylactic or therapeutic agent of hyperlipidemia;

(61) use of a compound of the aforementioned (1) or a salt thereof for the production of a prophylactic or therapeutic agent of cerebral infarction;

(62) use of a compound of the aforementioned (1) or a salt thereof for the production of a prophylactic or therapeutic agent of stroke;

(63) use of a compound of the aforementioned (1) or a salt thereof for the production of a suppressor of progression of focal arteriosclerosis;

(64) a method of inhibiting cholesteryl ester transfer protein in a mammal, which comprises administering an effective amount of a compound represented by the formula (I') of the aforementioned (34) or a salt thereof or a prodrug thereof to the mammal;

(65) use of a compound represented by the formula (I') of the aforementioned (34) or a salt thereof or a prodrug thereof for the production of a pharmaceutical agent for inhibiting cholesteryl ester transfer protein;

(66) a production method of the aforementioned (1) or a salt thereof, which comprises subjecting a compound represented by the formula

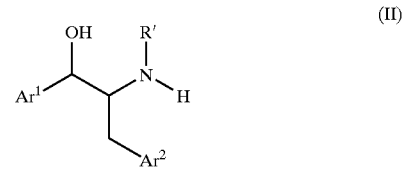

wherein each symbol is as defined in the aforementioned (1), or a salt thereof to an acylation reaction to give a compound represented by the formula

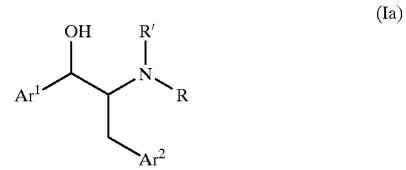

wherein each symbol is as defined in the aforementioned (1), or a salt thereof, and, where desired, subjecting the compound to a hydroxyl group-protecting reaction; and the like.

For the term "acyl group" used in the present specification, acyl groups obtained by removing OH group from carboxylic acids such as $R^1COOH$, $R^1OCOOH$ and the like, sulfonic acids such as $R^1SO_3H$ and the like, sulfinic acids such as $R^1SO_2H$ and the like, phosphoric acids such as $R^1OPO(OR^2)OH$ and the like, carbamic acids such as $R^1N(R^2)COOH$ and the like ($R^1$ is a hydrocarbon group optionally having substituents or a heterocyclic group optionally having substituents, and $R^2$ is a hydrogen atom or a hydrocarbon group optionally having substituents) and the like are used. Specifically, $R^1CO$, $R^1OCO$, $R^1SO_2$, $R^1SO$, $R^1OPO(OR^2)$ $R^1N(R^2)CO$ ($R^1$ is a hydrocarbon group optionally having substituents or a heterocyclic group optionally having substituents and $R^2$ is a hydrogen atom or a hydrocarbon group optionally having substituents) and the like are used.

The "hydrocarbon group" of the term "optionally substituted hydrocarbon group" used in the present specification means, for example, alkyl group, cycloalkyl group, alkenyl group, cycloalkenyl group, alkynyl group, aralkyl group, aryl group and the like.

As the substituent that the "hydrocarbon group" optionally has, those similar to the substituent that the "alkyl group" and "cycloalkyl group" to be mentioned below may have, and the like are used.

As the "alkyl group", for example, "linear or branched $C_{1-15}$ alkyl groups" such as methyl, ethyl, propyl, isopropyl, butyl, isobutyl, sec-butyl, tert-butyl, pentyl, hexyl, heptyl, octyl, nonyl, decyl, undecyl, tridecyl, tetradecyl, pentadecyl and the like, and the like are used.

As the "cycloalkyl group", for example, "$C_{3-10}$ cycloalkyl groups" such as cyclopropyl, cyclobutyl, cyclopentyl, cyclohexyl, cycloheptyl, cyclooctyl, adamantyl and the like, and the like are used.

As the substituent that the "alkyl group" and "cycloalkyl group" may have, for example, (i) nitro group, (ii) hydroxy group, oxo group, (iii) cyano group, (iv) carbamoyl group, (v) mono- or di-$C_{1-4}$ alkyl-carbamoyl group (e.g., N-methylcarbamoyl, N-ethylcarbamoyl, N,N-dimethylcarbamoyl, N,N-diethylcarbamoyl and the like), mono- or di-phenyl-carbamoyl group, mono- or di-benzyl-carbamoyl group, carboxyl-carbamoyl group, $C_{1-4}$ alkoxy-carbonyl-carbamoyl group, (vi) carboxyl group, (vii) $C_{1-4}$ alkoxy-carbonyl group (e.g., methoxycarbonyl, ethoxycarbonyl, propoxycarbonyl, isopropoxycarbonyl and the like), (viii) sulfo group (—$SO_2OH$), (ix) halogen atom (e.g., fluorine, chlorine, bromine, iodine and the like), (x) optionally halogenated $C_{1-4}$ alkoxy group (e.g., methoxy, ethoxy, propoxy, isopropoxy and the like), $C_{1-4}$ alkoxy group optionally substituted by hydroxy group, $C_{1-4}$ alkoxy group optionally substituted by carboxyl group, $C_{1-4}$ alkoxy group optionally substituted by $C_{1-4}$ alkoxy-carbonyl group, $C_{1-4}$ alkoxy-$C_{1-4}$ alkoxy group, (xi) phenoxy group, phenoxy-$C_{1-4}$ alkyl group, phenoxy-$C_{1-4}$ alkoxy group, (xii) optionally halogenated phenyl group, optionally halogenated phenyl-$C_{1-4}$ alkyl group, optionally halogenated phenyl-$C_{2-4}$ alkenyl group, optionally halogenated phenoxy group (e.g., o-, m- or p-chlorophenoxy, o-, m- or p-bromophenoxy and the like), pyridyloxy group, $C_{3-10}$ cycloalkyl group, $C_{3-10}$ cycloalkyl-$C_{1-4}$ alkoxy group, $C_{3-10}$ cycloalkyl-$C_{1-4}$ alkyl group, (xiii) optionally halogenated $C_{1-4}$ alkyl group, optionally halogenated $C_{2-4}$ alkenyl group, optionally halogenated $C_{1-4}$ alkylthio group (e.g., methylthio, ethylthio, n-propylthio, isopropylthio, n-butylthio and the like), $C_{1-4}$ alkyl group optionally substituted by hydroxy group, $C_{1-4}$ alkylthio group optionally substituted by hydroxy group, (xiv) mercapto group, thioxo group, (xv) benzyloxy group or benzylthio group optionally substituted by substituent(s) selected from halogen atom, carboxyl group and $C_{1-4}$ alkoxy-carbonyl group, (xvi) optionally halogenated phenylthio group, pyridylthio group, phenylthio-$C_{1-4}$ alkyl group, pyridylthio-$C_{1-4}$ alkyl group, (xvii) optionally halogenated $C_{1-4}$ alkylsulfinyl group (e.g., methylsulfinyl, ethylsulfinyl and the like), phenylsulfinyl group, phenylsulfinyl-$C_{1-4}$ alkyl group, (xviii) optionally halogenated $C_{1-4}$ alkylsulfonyl group (e.g., methylsulfonyl, ethylsulfonyl and the like), phenylsulfonyl group, phenylsulfonyl-$C_{1-4}$ alkyl group, (xix) amino group, aminosulfonyl group, (xx) $C_{1-3}$ acylamino group (e.g., acetylamino, propionylamino and the like), benzyloxycarbonylamino, (xxi) mono- or di-$C_{1-4}$ alkylamino group (e.g., methylamino, ethylamino, dimethylamino, diethylamino and the like), (xxii) 4- to 6-membered cyclic amino group (e.g., 1-azetidinyl, 1-pyrrolidinyl, piperidino, morpholino, thiomorpholino, 1-piperazinyl and the like), 4- to 6-membered cyclic aminocarbonyl group (e.g., 1-azetidinylcarbonyl, 1-pyrrolidinylcarbonyl, piperidinocarbonyl, morpholinocarbonyl, thiomorpholinocarbonyl, 1-piperazinylcarbonyl and the like), 4- to 6-membered cyclic amino-$C_{1-4}$ alkyl group, (xxiii) $C_{1-6}$ acyl group (e.g., formyl, optionally halogenated $C_{2-6}$ alkanoyl such as acetyl etc., and the like), (xxiv) benzoyl group optionally substituted by halogen atom, (xxv) 5- to 10-membered heterocyclic group (e.g., 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 1,2,3- or 1,2,4-triazolyl, 1H- or 2H-tetrazolyl, 2-, 3- or 4-pyridyl, 2-, 4- or 5-pyrimidinyl, 3- or 4-pyridazinyl, quinolyl, isoquinolylindolyl and the like), (xxvi) 5- to 10-membered heterocyclic-carbonyl group (e.g., 2- or 3-thienylcarbonyl, 2- or 3-furylcarbonyl, 3-, 4- or 5-pyrazolylcarbonyl, 2-, 4- or 5-thiazolylcarbonyl, 3-, 4- or 5-isothiazolylcarbonyl, 2-, 4- or 5-oxazolylcarbonyl, 1,2,3- or 1,2,4-triazolylcarbonyl, 1H- or 2H-tetrazolylcarbonyl, 2-, 3- or 4-pyridylcarbonyl, 2-, 4- or 5-pyrimidinylcarbonyl, 3- or 4-pyridazinylcarbonyl, quinolylcarbonyl, isoquinolylcarbonyl, indolylcarbonyl and the like), (xxvii) optionally halogenated linear or branched $C_{2-5}$ alkyleneoxy group (e.g., ethyleneoxy, propyleneoxy, isobutyleneoxy and the like) and (xxviii) optionally halogenated linear or branched $C_{1-4}$ alkylenedioxy group (e.g., methylenedioxy, ethylenedioxy, propylenedioxy, tetrafluoroethylenedioxy and the like) and the like are used. The "alkyl group" and "cycloalkyl group" may have 1 to 5 of these substituents at substitutable positions.

Preferable "alkyl group" includes, for example, linear or branched $C_{1-6}$ alkyl groups such as methyl, ethyl, propyl, isopropyl, butyl, isobutyl, sec-butyl, tert-butyl, pentyl, hexyl and the like, and as the substituent that the "$C_{1-6}$ alkyl group" may have, for example, 1 to 3 of halogen atom, $C_{1-4}$ alkoxy group, hydroxy group, $C_{1-4}$ alkoxy-carbonyl group, carboxyl group, carbamoyl group, mono- or di-$C_{1-4}$ alkylcarbamoyl group, pyridylthio group and the like are used.

As the "alkenyl group", for example, "$C_{2-18}$ alkenyl group" such as vinyl, allyl, isopropenyl, 3-butenyl, 3-octenyl, 9-octadecenyl and the like, and the like are used.

As the "cycloalkenyl group", for example, "$C_{3-8}$ cycloalkenyl group" such as cyclopropenyl, cyclobutenyl, cyclopentenyl, cyclohexenyl, cycloheptenyl, cyclooctenyl and the like, and the like are used.

As the substituent that the "alkenyl group" and "cycloalkenyl group" may have, those similar to the substituents that the aforementioned "alkyl group" may have are used.

Preferable "alkenyl group" includes, for example, $C_{2-6}$ alkenyl group such as vinyl, allyl, 2-butenyl, 3-butenyl and the like, and the like. As the substituent that the "$C_{2-6}$ alkenyl group" may have, those similar to the substituents that the aforementioned "$C_{1-6}$ alkyl group" may have are used.

As the "alkynyl group", for example, "$C_{2-18}$ alkynyl group" such as ethynyl, propynyl, 1-butynyl, 2-butynyl, 1-pentynyl, 2-pentynyl, 3-pentynyl and the like, and the like are used.

As the substituent that the "alkynyl group" may have, those similar to the substituents that the aforementioned "alkyl group" may have are used.

Preferable "alkynyl group" includes, for example, $C_{2-6}$ alkynyl groups such as ethynyl, propynyl, 1-butynyl, 2-butynyl and the like, and the like. As the substituent that the "$C_{2-6}$ alkynyl group" may have, those similar to the substituents that the aforementioned "$C_{1-6}$ alkyl group" may have are used.

As the "aralkyl group", $C_{7-16}$ aralkyl group and the like are used, and specifically, phenyl-$C_{1-6}$ alkyl groups such as benzyl, phenethyl, 3-phenylpropyl, 4-phenylbutyl and the like, naphthyl-$C_{1-6}$ alkyl groups such as (1-naphthyl)methyl, 2-(1-naphthyl)ethyl, 2-(2-naphthyl)ethyl and the like, and the like are used.

As the substituent that the "aralkyl group" may have, the substituents that the aforementioned "alkyl group" may have, as well as halogen atom (e.g., fluorine, chlorine, bromine, iodine and the like), $C_{1-4}$ alkyl group (e.g., methyl, ethyl, propyl, isopropyl, butyl and the like), $C_{2-6}$ alkenyl group (e.g., vinyl, allyl, 2-butenyl, 3-butenyl and the like), $C_{1-3}$ acyl group (e.g., formyl, acetyl and the like), $C_{1-4}$ alkoxy group (e.g., methoxy, ethoxy, propoxy, isopropoxy and the like), nitro group, cyano group, hydroxy group, $C_{1-4}$ alkoxy-carbonyl group (e.g., methoxycarbonyl, ethoxycarbonyl, propoxycarbonyl, isopropoxycarbonyl and the like), carbamoyl group, mono- or di-$C_{1-4}$ alkylcarbamoyl group (e.g., N-methylcarbamoyl, N-ethylcarbamoyl, N,N-dimethylcarbamoyl, N,N-diethylcarbamoyl and the like), mono- or di-$C_{1-4}$ alkenylcarbamoyl group (e.g., N-vinylcarbamoyl and the like) and the like are mentioned, wherein the "aralkyl group" may have 1 to 4 of these substituents at substitutable positions.

As the "aryl group", for example, aromatic monocyclic, bicyclic or tricyclic $C_{6-14}$ aryl group such as phenyl, 1-naphthyl, 2-naphthyl, phenanthryl, anthryl and the like, biphenyl group, tolyl group and the like are used.

As the substituent that the "aryl group" may have, the substituents that the aforementioned "aralkyl group" may have, as well as oxo group and the like can be used. The "aryl group" may have 1 to 4, preferably 1 or 2, of these substituents at substitutable positions. As the aryl group having an oxo group, for example, benzoquinonyl, naphthoquinonyl, anthraquinonyl and the like can be mentioned.

When the "hydrocarbon group" is cycloalkyl group, aryl group or aralkyl group, for example, it may be substituted by $C_{1-10}$ alkyl group (e.g., methyl, ethyl, propyl, isopropyl, decyl and the like), $C_{2-10}$ alkenyl group (e.g., vinyl, allyl, 2-butenyl, 3-butenyl and the like), phenyl-$C_{2-4}$ alkenyl group (e.g., phenylethenyl and the like), mono- or di-$C_{1-6}$ alkenyl-carbamoyl group (e.g., N-vinylcarbamoyl and the like), $C_{6-14}$aryl group (e.g., phenyl, 1-naphthyl, 2-naphthyl), $C_{7-20}$ aralkyl group (e.g., benzyl, 2-phenylethyl, 3-phenylpropyl, 4-phenylbutyl, 5-phenylpentyl, 6-phenylhexyl, 2-(1-naphthyl)ethyl, 2-(2-naphthyl)ethyl and the like), styryl group, oxo group and the like, wherein the "hydrocarbon group" may have 1 to 4 "substituents" at substitutable positions.

When the "hydrocarbon group" is a cyclic group such as cycloalkyl group, cycloalkenyl group, aralkyl group, aryl group and the like, it may have a substituent such as optionally halogenated $C_{1-4}$ alkylenedioxy group, optionally halogenated $C_{2-5}$ alkyleneoxy group and the like, or these cyclic groups may be condensed with each other to form a bicyclic or tricyclic fused hydrocarbon group, wherein the fused hydrocarbon group may have a group similar to the substituent that the aforementioned "alkyl group" may have.

For the term "heterocyclic group" of the "heterocyclic group optionally having substituents" used in the present specification, a 5- to 8-membered ring or a fused ring thereof (including condensation with benzene ring) having, besides the carbon atom, 1 to 4 hetero atoms selected from oxygen atom, sulfur atom, nitrogen atom and the like, such as a 5-membered ring group having, besides the carbon atom, 1 to 4 hetero atoms selected from oxygen atom, sulfur atom, nitrogen atom and the like, such as 2- or 3-thienyl, 2- or 3-furyl, 2- or 3-pyrrolyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl and the like; a 6-membered ring group having, besides the carbon atom, 1 to 4 hetero atoms selected from oxygen atom, sulfur atom, nitrogen atom and the like, such as 2-, 3- or 4-pyridyl, N-oxide-2-, 3- or 4-pyridyl, 2-, 4- or 5-pyrimidinyl, N-oxide-2-, 4- or 5-pyrimidinyl; thiomorpholinyl, morpholinyl, oxoimidazolyl, dioxotriazinyl, pyrrolidinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl, N-oxide-3- or 4-pyridazinyl and the like; a bicyclic or tricyclic fused ring group having, besides the carbon atom, 1 to 4 hetero atoms selected from oxygen atom, sulfur atom, nitrogen atom and the like, such as benzofuryl, benzothiazolyl, benzooxazolyl, tetrazolo[1,5-b]pyridazinyl, triazolo[4,5-b]pyridazinyl, benzoimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acrydinyl, phenanthridinyl, chromanyl, benzoxazinyl, phenazinyl, phenothiazinyl, phenoxazinyl etc., and the like; and the like are used.

As the "substituent" of the "heterocyclic group optionally having substituents", groups similar to the "substituent" mentioned for the aforementioned "hydrocarbon group optionally having substituents" and the like, particularly, the substituent when the "hydrocarbon group" is cycloalkyl group, aryl group or aralkyl group, and the like are used, wherein 1 to 5, preferably 1 or 2, substituents may be present at substitutable positions on the heterocyclic ring.

The term "lower alkyl group" used in the present specification shows, for example, a linear or branched alkyl group having 1 to 6 carbon atoms, such as methyl, ethyl, propyl, isopropyl, butyl, isobutyl, sec-butyl, tert-butyl, pentyl, hexyl and the like, and the like.

In the aforementioned formulas, $Ar^1$ denotes an aromatic ring group optionally having substituents and $Ar^2$ denotes an aromatic ring group having substituents.

As the "substituent" that the "aromatic ring group" of the "aromatic ring group optionally having substituents" for $Ar^1$ may have and the "substituent" that the "aromatic ring group" of the "aromatic ring group having substituents" for $Ar^2$ has, the groups mentioned as the "substituent" of the aforementioned "hydrocarbon group optionally having substituents" and the like are used, wherein 1 to 5, preferably 1 or 2, substituents may be present at substitutable positions of the aromatic ring group.

As the "substituent" that the "aromatic ring group" of the "aromatic ring group optionally having substituents" for $Ar^1$ may have, halogen atom, optionally halogenated lower alkyl group, optionally halogenated lower alkoxy group, aryloxy group optionally having substituents (e.g., phenoxy group and the like) and the like are preferable. The position of substitution when the "aromatic ring group" of the "aromatic ring group optionally having substituents" for $Ar^1$ is phenyl and the phenyl has one substituent is preferably the meta position or para position.

As the "substituent" that the "aromatic ring group" of the "aromatic ring group having substituents" for $Ar^2$ may have, halogen atom, optionally halogenated lower alkyl group, optionally halogenated lower alkoxy group and the like are preferable. The position of substitution when the "aromatic ring group" of the "aromatic ring group having substituents" for $Ar^2$ is phenyl and the phenyl has one substituent is preferably the meta position or para position.

As the "aromatic ring group" of the "aromatic ring group optionally having substituents" for $Ar^1$ and the "aromatic ring group" of the "aromatic ring group having substituents" for $Ar^2$, aryl group, heteroaryl group and the like are mentioned.

As the "aryl group", for example, aromatic monocyclic, bicyclic or tricyclic $C_{6-14}$ aryl group such as phenyl, 1-naphthyl, 2-naphthyl, phenanthryl, anthryl and the like, biphenyl group, tolyl group and the like are used, with preference given to phenyl.

As the "heteroaryl group", for example, a 5-membered aromatic ring group having, besides the carbon atom, 1 to 4 hetero atoms selected from oxygen atom, sulfur atom, nitrogen atom and the like, such as 2- or 3-thienyl, 2- or 3-furyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl and the like; a 6-membered aromatic ring group having, besides the carbon atom, 1 to 4 hetero atoms selected from oxygen atom, sulfur atom, nitrogen atom and the like, such as 2-, 3- or 4-pyridyl, 2-, 4- or 5-pyrimidinyl, pyridazinyl, pyrazinyl and the like;

a fused ring group formed by these 5- or 6-membered aromatic ring groups liked with each other or these 5- or 6-membered aromatic ring groups linked with a benzene ring (preferably bicyclic fused ring group); and the like are used.

As the "aromatic ring group" of the "aromatic ring group optionally having substituents" for $Ar^1$ and the "aromatic ring group" of the "aromatic ring group having substituents" for $Ar^2$, a 5- or 6-membered aromatic ring group is preferably used for each of them. Particularly, phenyl group, pyridyl group, thienyl group, furyl group, thiazolyl group and the like are preferably used.

In the aforementioned formulas, $Ar^{2'}$ denotes an aromatic ring group optionally having substituents.

As the "aromatic ring group optionally having substituents" for $Ar^{2'}$, those similar to the "aromatic ring group" of the "aromatic ring group having substituents" for $Ar^2$ and "aromatic ring group having substituents" for $Ar^2$ and the like are mentioned.

In the aforementioned formulas, R denotes an acyl group. The "acyl group" may be any of the aforementioned groups, such as acyl group obtained by removing an OH group from carboxylic acid (e.g., $R^{1N}COOH$, $R^{1N}OCOOH$ and the like), sulfonic acid (e.g., $R^{1N}SO_3H$ and the like), sulfinic acid (e.g., $R^{1N}SO_2H$ and the like), phosphoric acid (e.g., $R^{1N}OPO(OR^{2N})OH$ and the like), carbamic acid (e.g., $R^{1N}N(R^{2N})COOH$ and the like wherein $R^{1N}$ denotes a hydrocarbon group optionally having substituents or a heterocyclic group optionally having substituents and $R^{2N}$ denotes a hydrogen atom or a hydrocarbon group optionally having substituents) and the like. Specifically, $R^{1N}CO$, $R^{1N}OCO$, $R^{1N}SO_2$, $R^{1N}SO$, $R^{1N}OPO(OR^{2N})$, $R^{1N}N(R^{2N})CO$ ($R^{1N}$ denotes a hydrocarbon group optionally having substituents or a heterocyclic group optionally having substituents and $R^{2N}$ denotes a hydrogen atom or a hydrocarbon group optionally having substituents), and the like are used. Here, as the "hydrocarbon group optionally having substituents" denoted by $R^{1N}$, the "heterocyclic group optionally having substituents" denoted by $R^{1N}$ and the "hydrocarbon group optionally having substituents" denoted by $R^{2N}$, those similar to "hydrocarbon group optionally having substituents" denoted by the aforementioned $R^1$, the "heterocyclic group optionally having substituents" denoted by the aforementioned $R^1$ and the "hydrocarbon group optionally having substituents" denoted by the aforementioned $R^2$ are used, respectively.

As R, a group represented by the formula $R^{1N}CO$— ($R^{1N}$ is a hydrocarbon group optionally having substituents or a heterocyclic group optionally having substituents) is preferably used. As $R^{1N}$, a cyclic group such as cyclic hydrocarbon group optionally having substituents (e.g., cycloalkyl group optionally having substituents, cycloalkenyl group optionally having substituents, aryl group optionally having substituents and the like), a heterocyclic group optionally having substituents and the like are preferable. Particularly, an aromatic ring group optionally having substituents (a group similar to the "aromatic ring group optionally having substituents" for $Ar^1$ and the like), such as aryl group optionally having substituents, heteroaryl group optionally having substituents and the like are preferably used.

Specifically, as R, $C_{1-6}$ alkoxy-carbonyl, $C_{1-6}$ alkyl-carbonyl, $C_{6-10}$ aryl-carbonyl (e.g., benzoyl, naphthoyl and the like), dihydronaphthalenecarbonyl, tetrahydronaphthalenecarbonyl, benzocycloheptenecarbonyl (preferably benzo[a]cycloheptene-carbonyl and the like), benzocyclooctenecarbonyl, each of which may have 1 to 3 substituents selected from halogen atom, optionally halogenated $C_{1-6}$ alkoxy, optionally halogenated $C_{1-6}$ alkyl and the like, are preferable.

In the aforementioned formulas, OR" denotes an optionally protected hydroxyl group. Here, R" denotes a protecting group of hydrogen atom or hydroxyl group (R" is preferably hydrogen atom or acyl group). As the hydroxyl-protecting group, for example, acyl group, $C_{1-6}$ alkyl optionally having substituents, phenyl optionally having substituents, $C_{7-10}$ aralkyl optionally having substituents, pyranyl optionally having substituents, furanyl-optionally having substituents, silyl optionally having substituents and the like are mentioned.

The acyl group as the "hydroxyl-protecting group" denoted by R" may be any mentioned above, and acyl group obtained by removing OH group from carboxylic acid such as $R^{1O}COOH$, $R^{1O}OCOOH$ and the like, sulfonic acid such as $R^{1O}SO_3H$ and the like, sulfinic acid such as $R^{1O}SO_2H$ and the like, phosphoric acid such as $R^{1O}OPO(OR^{2O})OH$ and the like, carbamic acid such as $R^{1O}N(R^{2O})COOH$ and the like ($R^{1O}$ is a hydrocarbon group optionally having substituents or a heterocyclic group optionally having substituents and $R^{2O}$ is a hydrogen atom or a hydrocarbon group optionally having substituents) and the like are used. Specifically, $R^{1O}CO$, $R^{1O}OCO$, $R^{1O}SO_2$, $R^{1O}SO$, $R^{1O}OPO(OR^{2O})$, $R^{1O}N(R^{2O})CO$ ($R^{1O}$ denotes a hydrocarbon group optionally having substituents or a heterocyclic group optionally having substituents and $R^{2O}$ denotes a hydrogen atom or a hydrocarbon group optionally having substituents) and the like are used. Here, the "hydrocarbon group optionally having substituents" denoted by $R^{1O}$, the "heterocyclic group optionally having substituents" denoted by $R^{1O}$ and the "hydrocarbon group optionally having substituents" denoted by $R^{2O}$, those similar to "hydrocarbon group optionally having substituents" denoted by the aforementioned $R^1$, "heterocyclic group optionally having substituents" denoted by the aforementioned $R^1$ and "hydrocarbon group optionally having substituents" denoted by the aforementioned $R^2$ are used.

As the "acyl group" of the "hydroxyl-protecting group" denoted by R", a group represented by the formula $R^{1O}CO$— ($R^{1O}$ is a hydrocarbon group optionally having substituents or a heterocyclic group optionally having substituents) is preferably used. As the $R^{1O}$, chain hydrocarbon group optionally having substituents (e.g., alkyl group optionally having substituents, alkenyl group optionally having substituents, alkynyl group optionally having substituents and the like) and the like are preferable. Of these, alkyl group optionally having substituents and the like is preferable, and particularly, alkyl group having substituents (e.g., $C_{1-6}$ alkyl group having 1 to 3 substituents selected from halogen atom, $C_{1-4}$ alkoxy group, hydroxy group, $C_{1-4}$ alkoxy-carbonyl group, carboxyl group, carbamoyl group, mono- or di-$C_{1-4}$ alkylcarbamoyl group, amino group, mono- or di-$C_{1-4}$ alkylamino group, pyridylthio group etc., and the like) and the like are preferably used.

As the "$C_{1-6}$ alkyl group" of the "$C_{1-6}$ alkyl group optionally having substituents" as the "hydroxyl-protecting group" denoted by R", for example, methyl, ethyl, propyl, isopropyl, butyl, tert-butyl and the like are mentioned, wherein the "$C_{1-6}$ alkyl group" may have about 1 to 4 substituents such as halogen atom (e.g., fluoro, chloro, bromo, iodo and the like), phenyl, $C_{7-10}$ aralkyl, nitro group and the like.

As the substituent that the "phenyl group" of the "phenyl group optionally having substituents" as the "hydroxyl-protecting group" denoted by R" may have, for example, halogen atom (e.g., fluoro, chloro, bromo, iodo and the like), $C_{1-6}$ alkyl, phenyl, $C_{7-10}$ aralkyl, nitro group and the like are used, wherein the number of substituents is about 1 to 4.

As the "$C_{7-10}$ aralkyl" of the "$C_{7-10}$ aralkyl optionally having substituents" as the "hydroxyl-protecting group" denoted by R", for example, benzyl and the like can be mentioned. As the substituent that the "$C_{7-10}$ aralkyl" may have, for example, halogen atom (e.g., fluoro, chloro, bromo, iodo and the like), $C_{1-6}$ alkyl, phenyl, $C_{7-10}$ aralkyl, nitro group and the like are used, wherein the number of substituents is about 1 to 4.

As the substituent that the "pyranyl group" of the "pyranyl group optionally having substituents" as the "hydroxyl-protecting group" denoted by R" may have, for example, halogen atom (e.g., fluoro, chloro, bromo, iodo and the like), $C_{1-6}$ alkyl, phenyl, $C_{7-10}$ aralkyl, nitro group and the like are used, wherein the number of substituents is about 1 to 4.

As the substituent that the "furanyl group" of the "furanyl group optionally having substituents" as the "hydroxyl-protecting group" denoted by R" may have, for example, halogen atom (e.g., fluoro, chloro, bromo, iodo and the like), $C_{1-6}$ alkyl, phenyl, $C_{7-10}$ aralkyl, nitro group and the like are used, wherein the number of substituents is about 1 to 4.

As the substituent that the "silyl group" of the "silyl group optionally having substituents" as the "hydroxyl-protecting group" denoted by R" may have, for example, $C_{1-6}$ alkyl, phenyl, $C_{7-10}$ aralkyl and the like are used, wherein the number of substituents is about 1 to 4.

As the R", hydrogen atom and the like are preferably used.

In the aforementioned formulas, R' denotes a hydrogen atom or a hydrocarbon group optionally having substituents. As the R', hydrogen atom, lower alkyl group optionally having substituents (preferably $C_{1-6}$ alkyl group optionally having 1 to 3 substituents selected from halogen atom, $C_{1-4}$ alkoxy group, hydroxy group, $C_{1-4}$ alkoxy-carbonyl group, carboxyl group, carbamoyl group, mono- or di-$C_{1-4}$ alkyl-carbamoyl group and pyridylthio group and the like) and the like are preferable, hydrogen atom, $C_{1-6}$ alkyl group and the like are more preferable, and hydrogen atom is particularly preferably used.

As the compound represented by the aforementioned formula (I) or a salt thereof, a compound wherein R is a group represented by the formula $R^{1N}CO-$ ($R^{1N}$ is a cyclic hydrocarbon group optionally having substituents or a heterocyclic group optionally having substituents), R" is a hydrogen atom, and R' is a hydrogen atom, or a salt thereof;

a compound wherein $Ar^1$ is a 5- or 6-membered aromatic ring group optionally having substituents selected from halogen atom, an optionally halogenated lower alkyl group, an optionally halogenated lower alkoxy group and an aryloxy group optionally having substituents (e.g., phenyl group, pyridyl group, thienyl group, furyl group, thiazolyl group and the like; preferably phenyl group and the like), $Ar^2$ is a 5- or 6-membered aromatic ring group having substituents selected from halogen atom, an optionally halogenated lower alkyl group and an optionally halogenated lower alkoxy group (e.g., phenyl group, pyridyl group, thienyl group, furyl group, thiazolyl group and the like; preferably phenyl group and the like), R is $C_{1-6}$ alkoxy-carbonyl, $C_{1-6}$ alkyl-carbonyl, $C_{6-10}$ aryl-carbonyl or benzo[a]cycloheptene-carbonyl, each of which may have a substituent selected from halogen atom, optionally halogenated $C_{1-6}$ alkoxy and optionally halogenated $C_{1-6}$ alkyl, R" is a hydrogen atom, and R' is a hydrogen atom, or a salt thereof; and the like are preferably used.

Since a compound represented by the formula (I) or the formula (I')

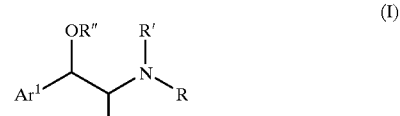

(I)

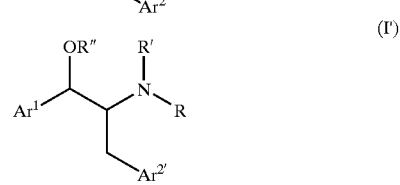

(I')

wherein each symbol is as defined above, has at least two asymmetric carbons, at least 4 optically active forms are present based on these asymmetric carbons. Each of the active forms and optional mixtures thereof are also encompassed in the compound represented by the formula (I).

In addition, as the compound represented by the formula (I) and the formula (I'), compounds represented by the formulas

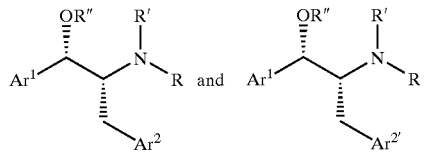

wherein each symbol is as defined above, are preferably used.

As the salt of the compound represented by the formula (I) or the formula (I') of present invention, a salt acceptable as a pharmaceutical product or physiologically acceptable acid addition salt is preferable. As such salt, for example, inorganic acids (e.g., hydrochloric acid, phosphoric acid, hydrobromic acid, sulfuric acid and the like) or organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid and the like) and the like are used. When the compound represented by the formula (I) of the present invention has an acidic group such as carboxylic acid and the like, a compound represented by the formula (I) may form a salt with, for example, an inorganic base (e.g., alkali metal or alkaline earth metal such as sodium, potassium, calcium, magnesium and the like, or ammonia and the like) or an organic base (e.g., tri-$C_{1-3}$ alkylamine such as triethylamine etc., and the like).

While salts similar to those mentioned above are used as the starting compound of a compound represented by the formula (I) of the present invention, they are not particularly limited as long as the reaction is not prohibited.

A prodrug of a compound represented by the formula (I) or a salt thereof [hereinafter sometimes to be referred to as Compound (I)] refers to a compound which is converted to Compound (I) as a result of a reaction with an enzyme, gastric acid etc. under physiological conditions in vivo, thus a compound that undergoes enzymatic oxidation, reduction, hydrolysis etc. to convert into Compound (I) and a compound that undergoes hydrolysis and the like by gastric acid etc. to convert into Compound (I). As a prodrug for Compound (I), a compound obtained by subjecting an amino group in Compound (I) to an acylation, alkylation or phosphorylation (e.g., a compound obtained by subjecting an amino group in Compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, ivaloyloxymethylation, tert-butylation, etc.); a compound obtained by subjecting a hydroxy group in Compound (I) to an acylation, alkylation, phosphorylation and boration (e.g., a compound obtained by subjecting a hydroxy group in Compound (I) to an acetylation, palmitoylation, propanoylation, pivaloylation, succinylation, fumarylation, alanylation, dimethylaminomethylcarbonylation, etc.); a compound obtained by subjecting a carboxyl group in Compound (I) to an esterification or amidation (e.g., a compound obtained by subjecting a carboxyl group in Compound (I) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl) methylesterification, cyclohexyloxycarbonylethylesterification and methylamidation, etc.) and the like can be mentioned. Any of these compounds can be produced from Compound (I) by a method known per se.

A prodrug for Compound (I) may also be one which is converted to Compound (I) under physiological conditions as described in "IYAKUHIN no KAIHATSU (Development of Pharmaceuticals)", Vol. 7, Design of Molecules, p. 163–198, Published by HIROKAWA SHOTEN (1990).

As a prodrug of a compound represented by the formula (I') or a salt thereof [hereinafter sometimes to be referred to as Compound (I')], one similar to the prodrug of Compound (I) can be mentioned.

The Compound (I) and Compound (I') may be a hydrate.

When an optically active form of Compound (I) or Compound (I') is necessary, for example, it can be obtained using an optically active starting material or by resolution of a racemate of the compound by a conventional method.

Preferable examples of Compound (I) of the present invention are shown in the following.
N-[(1RS,2SR)-2-(4-fluorophenyl)-2-hydroxy-1-[4-(trifluoromethyl)benzyl]ethyl]-6,7-dihydro-5H-benzo[a]cycloheptene-1-carboxamide,
4-fluoro-N-((1R,2S)-2-(4-fluorophenyl)-2-hydroxy-1-((4-(trifluoromethyl)phenyl)methyl)ethyl)-1-naphthalenecarboxamide,
N-[(1R,2S)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide,
N-[(1RS,2SR)-2-(4-fluorophenyl)-2-hydroxy-1-[3-(1,1,2-tetrafluoroethoxy)benzyl]ethyl]-5,6-dihydronaphthalene-1-carboxamide,
N-[(1RS,2SR)-2-(4-fluorophenyl)-2-hydroxy-1-[3-(1,1,2,2-tetrafluoroethoxy)benzyl]ethyl]-6,7,8,9-tetrahydro-5H-benzo[a]cycloheptene-1-carboxamide,
4-fluoro-N-[(1R,2S)-2-(4-fluorophenyl)-2-hydroxy-1-[3-(1,1,2,2-tetrafluoroethoxy)benzyl]ethyl]naphthalene-1-carboxamide,
N-[(1RS,2SR)-2-(4-fluorophenyl)-2-hydroxy-1-[3-(1,1,2,2-tetrafluoroethoxy)benzyl]ethyl]-5,6,7,8-tetrahydrobenzo[a]cyclooctene-1-carboxamide,
N-[(1RS,2SR)-2-(4-fluorophenyl)-2-hydroxy-1-(4-isopropylbenzyl)ethyl]-6,7-dihydro-5H-benzo[a]cycloheptene-1-carboxamide,
N-((1RS,2SR)-2-(3-fluorophenyl)-2-hydroxy-1-((4-(trifluoromethyl)phenyl)methyl)ethyl)-6,7-dihydro-5H-benzo[a]cycloheptene-1-carboxamide,
N-((1RS,2SR)-2-hydroxy-2-(4-phenoxyphenyl)-1-((4-(trifluoromethyl)phenyl)methyl)ethyl)-6,7-dihydro-5H-benzo[a]cycloheptene-1-carboxamide,
N-[(1RS,2SR)-2-(4-chlorophenyl)-2-hydroxy-1-[3-(1,1,2,2-tetrafluoroethoxy)benzyl]ethyl]-6,7-dihydro-5H-benzo[a]cycloheptene-1-carboxamide,
N-((1RS,2SR)-2-hydroxy-2-(4-(phenyloxy)phenyl)-1-((3-((1,1,2,2-tetrafluoroethyl)oxy)phenyl)methyl)ethyl)-6,7-dihydro-5H-benzo[a]cycloheptene-1-carboxamide,
N-((1RS,2SR)-2-(4-((4-chloro-3-ethylphenyl)oxy)phenyl)-2-hydroxy-1-((3-((1,1,2,2-tetrafluoroethyl)oxy)phenyl)methyl)ethyl)-6,7-dihydro-5H-benzo[a]cycloheptene-1-carboxamide,
N-((1RS,2SR)-2-(2-fluoropyridin-4-yl)-2-hydroxy-1-((3-(1,1,2,2-tetrafluoroethoxy)phenyl)methyl)ethyl)-6,7-dihydro-5H-benzo[a]cycloheptene-1-carboxamide,
N-((1RS,2RS)-2-(6-fluoropyridin-2-yl)-2-hydroxy-1-((3-(1,1,2,2-tetrafluoroethoxy)phenyl)methyl)ethyl)-6,7-dihydro-5H-benzo[a]cycloheptene-1-carboxamide,
N-[(1RS,2SR)-1-(4-tert-butylbenzyl)-2-(3-chlorophenyl)-2-hydroxyethyl]-5-chloro-1-naphthamide,
4-fluoro-N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-1-naphthamide, salts thereof and the like.

The synthetic method of Compound (I) of the present invention is described in the following. In each synthetic method in the following, a starting compound capable of forming a salt may be used in the form of a salt. While such salt is not particularly limited, for example, the salts such as those mentioned for the aforementioned Compound (I) are used.

In Compound (I) of the present invention, Compound (Ia) wherein R" is a hydrogen atom can be synthesized by, for example, the following method and the like.

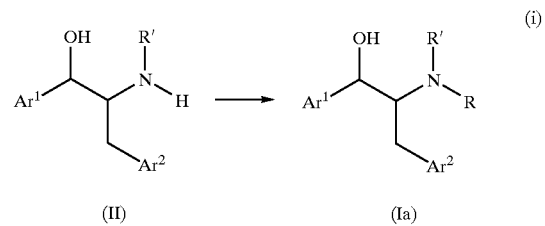

wherein the symbols in the formula are as defined above.

In this method, Compound (II) is acylated to give Compound (I).

The reaction for converting Compound (II) to Compound (I) is known per se, and can be carried out according to or by referring to the conditions described or cited in, for example, 4th ed. *Jikken Kagaku Koza* (Maruzen) vol. 22, Organic Synthesis IV, pp. 138–151, pp. 259–271, vol. 24, Organic Synthesis VI, pp. 391–392, pp. 396–397 and the like.

In Compound (I), Compound (Ia) wherein R" is a hydrogen atom can be converted to Compound (Ib) wherein R" is a hydroxyl-protecting group by subjecting Compound (Ia) to a protecting reaction of hydroxyl group. When R" is an acyl group, for example, a method according to this method can afford the conversion.

The reaction for introducing a protecting group into the hydroxyl group is known per se or a method analogous thereto can be used. The reaction can be carried out according to or by referring to the conditions described or cited in, for example, "PROTECTIVE GROUPS IN ORGANIC SYNTHESIS" Second Edition (JOHN WILEY & SONS, INC.) pp. 10–142 and the like.

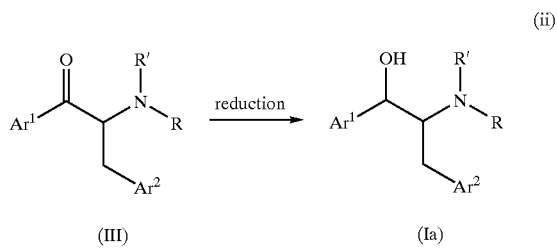

(III) → (Ia)

wherein the symbols in the formula are as defined above.

For reduction reaction of Compound (III), a method comprising use of a reducing agent with Compound (III), catalytic hydrogenation in the presence of a catalyst, electrolytic reduction using lead or platinum as a negative electrode, and the like can be used. As a reducing agent, metal hydrogen complex compounds such as sodium borohydride, sodium cyanoborohydride, lithium aluminum hydride, zinc borohydride and the like, diborane and the like can be mentioned. The reducing agent is used in a monoequivalent amount or large excess (preferably 1–10 equivalents). As the catalyst to be used for hydrogenation, metals such as palladium, platinum, nickel, rhodium and the like, oxides, salts and complexes of thereof, and the like can be mentioned. These catalysts can be also used by being carried on various carriers such as carbon and the like. The hydrogenation can be conducted under normal pressure or under pressurization. The solvent to be used therefor can be appropriately determined depending on the kind of the reducing agent. For example, alcohols (e.g., methanol, ethanol and the like), ethers (e.g., tetrahydrofuran, dioxane, diethyl ether and the like), halogenated hydrocarbon (e.g., methylene chloride, chloroform and the like), aprotic polar solvents (e.g., N,N-dimethylformamide, dimethyl sulfoxide and the like) and the like can be mentioned. In the reduction using a reducing agent, a catalytic amount or large excess (preferably 0.1–2 equivalents) of a metal halide such as zinc chloride, manganese chloride, aluminum chloride, magnesium chloride and the like may be added to control the reaction. The reaction time is 0.5–72 hrs., preferably 1–24 hrs. The reaction temperature is from −100° C. to 100° C. (preferably −80° C. to 50° C.).

Compound (II) can be synthesized according to, for example, the following method.

(i) When R' is a hydrogen atom

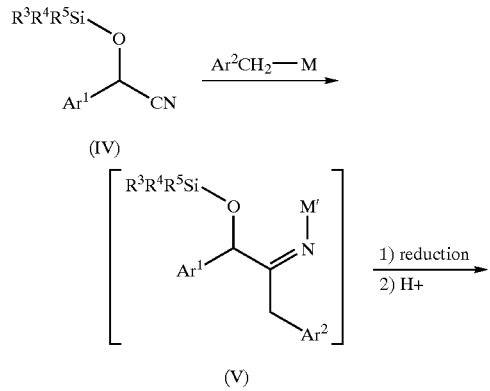

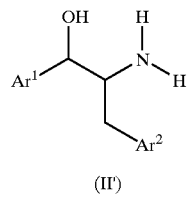

(II')

wherein $R^3$, $R^4$ and $R^5$ are each a $C_{1-6}$ alkyl optionally having substituents, a $C_{7-10}$ aralkyl optionally having substituents or a $C_{7-16}$ aralkyl optionally having substituents, M is a metal atom such as sodium, magnesium and the like (in the case of a divalent metal, the remaining monovalent may be occupied by halogen atom and the like), M' is a hydrogen atom or a metal atom such as sodium, magnesium and the like (in the case of a divalent metal, the remaining monovalent may be occupied by halogen atom and the like), other symbols are as defined above.

In this method, Compound (IV) is reacted with $Ar^2CH_2$-M, the resulting imine or iminium ion (V) is reduced and silyl ether is deprotected with an acid to give Compound (II'). In this reaction, $Ar^2CH_2$-M is used in a monoequivalent amount or large excess (preferably 1–10 equivalents) relative to Compound (IV). For the subsequent reduction reaction, a method comprising use of a reducing agent, catalytic hydrogenation in the presence of a catalyst, electrolytic reduction using lead or platinum as a negative electrode, and the like can be used. As a reducing agent, metal hydrogen complex compounds such as sodium borohydride, sodium cyanoborohydride, lithium aluminum hydride, zinc borohydride and the like, diborane and the like can be mentioned. The reducing agent is used in a monoequivalent amount or large excess (preferably 1–10 equivalents). As the catalyst to be used for hydrogenation, metals such as palladium, platinum, nickel, rhodium and the like, oxides, salts and complexes of thereof, and the like can be mentioned. These catalysts can be also used by being carried on various carriers such as carbon and the like. The hydrogenation can be conducted under normal pressure or under pressurization. As the solvent to be used therefor, for example, ethers (e.g., tetrahydrofuran, dioxane, diethyl ether and the like), hydrocarbon (e.g., toluene, hexane and the like), halogenated hydrocarbon (e.g., methylene chloride, chloroform and the like) and the like can be mentioned. The reaction time is 0.5–72 hrs., preferably 1–24 hrs. The reaction temperature is from −100° C. to 100° C. (preferably −80° C. to 50° C.). After the reduction reaction, an aqueous solution of an acid such as hydrochloric acid, sulfuric acid, acetic acid and the like is added to the reaction mixture to remove silyl ether, whereby Compound (II') can be obtained.

(ii)

(VI) → (II)

wherein D is an amino-protecting group such as tert-butoxycarbonyl, benzyloxycarbonyl, acetyl, trifluoroacetyl, benzyl and the like, and other symbols are as defined above.

In this method, the amino-protecting group of compound (VI) is removed to give Compound (II). The reaction for removing amino-protecting group is known per se, and can be carried out according to such conditions.

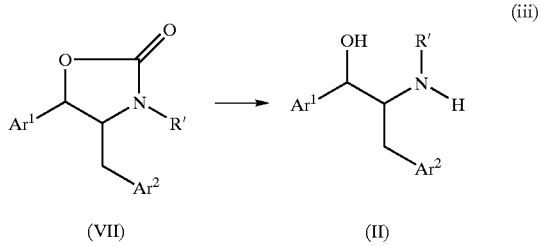

(VII)  (II)

wherein the symbols in the formula are as defined above.

The reaction for converting Compound (VII) to Compound (II) is carried out in the presence of a monoequivalent amount or large excess of an aqueous solution of a metal hydroxide such as sodium hydroxide, potassium hydride and the like, an aqueous solution of an acid such as hydrochloric acid, sulfuric acid and the like, trimethylsilyl iodide and the like. As the solvent to be used therefor, for example, water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), aprotic polar solvents (e.g., N,N-dimethylformamide, dimethyl sulfoxide and the like) and the like can be mentioned. The reaction time is 10 min.–24 hrs. and the reaction temperature is from –20° C. to 200° C. (preferably 0° C. to 100° C.).

Compound (III) can be synthesized by, for example, the following method.

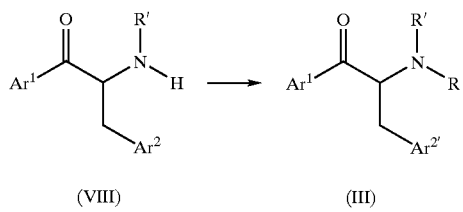

(VIII)  (III)

wherein the symbols in the formula are as defined above.

The reaction for converting Compound (VIII) to Compound (III) is carried out under the same conditions as, for example, the method under (i) in the synthesis of Compound (I).

Compound (IV) can be synthesized by, for example, the following method.

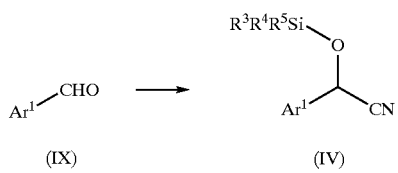

(IX)  (IV)

wherein the symbols in the formula are as defined above.

The reaction for converting Compound (IX) to Compound (IV) is known per se, and can be carried out according to or y referring to the conditions described or cited in, for example, Tetrahedron Lett., 26, 4275–4278 (1985), J. Org. Chem., 51, 413–415 (1986), Tetrahedron Lett., 28, 5513–5516 (1987), Chem. Lett., 537–540 (1991), J. Chem. Soc. Chem. Comm. 1752–1753 (1991), J. Org. Chem., 55, 1479–1483 (1990), J. Fluorine Chem., 35, 287–294 (1987), Tetrahedron Lett., 33, 2159–2162 (1992), Tetrahedron Lett., 34, 4001–4004 (1992) and the like.

Compound (VI) can be synthesized by, for example, the following method.

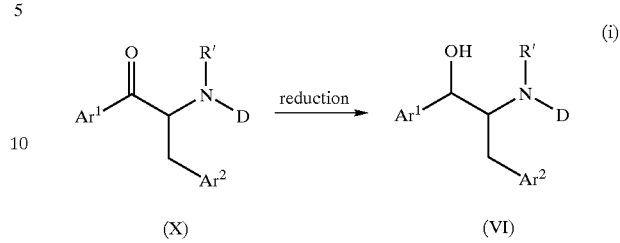

(X)  (VI)

wherein the symbols in the formula are as defined above.

The reaction for converting Compound (X) to Compound (VI) is carried out under the same conditions as, for example, the method under (ii) in the synthesis of Compound (I).

(ii) when R' is a hydrogen atom

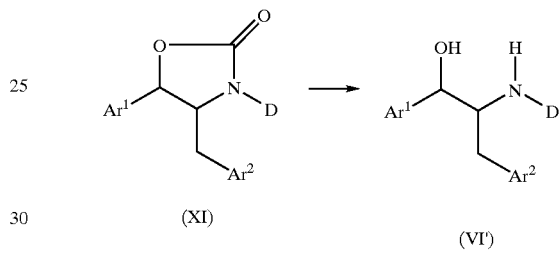

(XI)  (VI')

wherein the symbols in the formula are as defined above.

The reaction for converting Compound (XI) to Compound (VI') is carried out under the same conditions as, for example, the method under (iii) in the synthesis of Compound (II).

Compound (VII) wherein R' is not a hydrogen atom can be synthesized according to, for example, the following method.

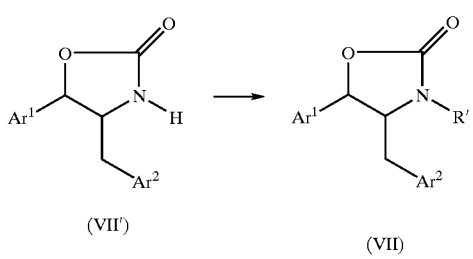

(VII')  (VII)

wherein the symbols in the formula are as defined above.

In this method, Compound (VII') is reacted with an alkylation agent to give Compound (VII). In this reaction, alkylation agent is used in a monoequivalent amount or large excess (preferably 1–10 equivalents) relative to compound (VII'). In this case, for example, 1–10 equivalents of a basic compound such as sodium hydroxide, potassium hydroxide, sodium hydride, potassium carbonate, triethylamine, diisopropylethylamine, pyridine, 4-N,N-dimethylaminopyridine (DMAP), 1,8-diazabicyclo[5.4.0]-7-undecene, 1,4-diazabicyclo[2.2.2]octane (DABCO) and the like may be used. As the alkylation agent to be used, halogenated hydrocarbon, sulfonic acid esters such as alkyl methanesulfonate, alkyl p-toluenesulfonate and the like, and the like can be mentioned. For this reaction, an alkali metal iodide such as sodium iodide and the like can be added in a monoequivalent amount or large-excess (preferably 1–10 equivalents) as a reaction promoter. As the solvent to be used therefor, for example, water, alcohols (e.g., methanol, ethanol and the like), ethers (e.g., tetrahydrofuran, dioxane, diethyl ether and the like), halogenated hydrocarbon (e.g., methylene chloride, chloroform and the like), ketones (e.g., acetone, methyl ethyl ketone and the like), aprotic polar solvents (e.g., N,N-dimethylformamide, dimethyl sulfoxide and the like) and the like can be mentioned. The reaction time is 10 min–24 hrs., preferably 0.5–6 hrs., and the reaction temperature is from –20° C. to 200° C. (preferably 0° C. to 150° C.).

Compound (VII') (compound (VII) wherein R' is a hydrogen atom) can be synthesized according to, for example, the following method.

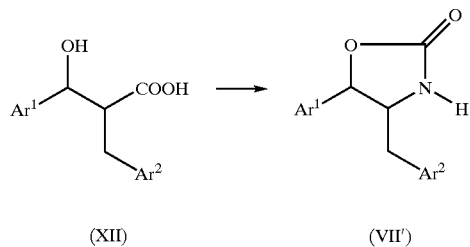

wherein the symbols in the formula are as defined above.

In this method, carboxyl group of Compound (XII) is converted to acyl azide, which is then led to isocyanate using what is called a Curtius rearrangement reaction, and the resulting isocyanate is cyclized with a hydroxyl group in the molecule to give Compound (VII'). During the reaction, acyl azide can be synthesized by, for example, the following three methods.

Method A: Compound (XII) is treated with a monoequivalent amount or large excess of a halogenation agent (e.g., thionyl chloride, oxalyl chloride, phosphorus pentachloride and the like) to convert the compound to acyl halide. In this reaction, a basic compound such as pyridine, 4-N,N-dimethylaminopyridine, triethylamine and the like may be used in 1–10 equivalents. In this reaction, a catalytic amount of N,N-dimethylformamide may be added as a reaction promoter. As the solvent to be used therefor, for example, ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction temperature is from –100° C. to 200° C. (preferably –20° C. to 100° C.). The obtained acyl halide is reacted with a monoequivalent amount or large excess of alkali metal azide salt (e.g., sodium azide and the like) to give acyl azide. In this reaction, a basic compound such as pyridine, 4-N,N-dimethylaminopyridine, triethylamine and the like may be used in 1–10 equivalent amount. As the solvent to be used therefor, for example, ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate, and the like), aprotic polar solvents (e.g., N,N-dimethylformamide, dimethyl sulfoxide and the like) and the like can be mentioned. The reaction temperature is from –100° C. to 200° C. (preferably –20° C. to 100° C.).

Method B: After conversion of Compound (XII) to acyl halide according to Method A, acyl halide is treated with a monoequivalent amount or large excess of hydrazine to give hydrazide. In this reaction, a basic compound such as pyridine, 4-N,N-dimethylaminopyridine, triethylamine and the like may be used in 1–10 equivalent amount. As the solvent to be used therefor, for example, ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction temperature is from –100° C. to 200° C. (preferably –20° C. to 100° C.). The obtained hydrazide is treated with a monoequivalent amount or large excess of nitrous acid (which can be also generated from metal nitrites such as sodium nitrite and the like in the presence of an acid) to give acyl azide. As the solvent to be used therefor, for example, water, alcohols (e.g., methanol, ethanol and the like), ethers (e.g., tetrahydrofuran, dioxane, diethyl ether and the like), halogenated hydrocarbon (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction temperature is from –100° C. to 200° C. (preferably –20° C. to 50° C.).

Method C: Compound (XII) is reacted with a monoequivalent amount or large excess of diphenylphosphoryl azide to give acyl azide. In this case, for example, 1–10 equivalents of a basic compound such as sodium hydroxide, potassium hydroxide, sodium hydride, potassium carbonate, triethylamine, diisopropylethylamine, pyridine, 4-N,N-dimethylaminopyridine (DMAP) 1,8-diazabicyclo[5.4.0]-7-undecene, 1,4-diazabicyclo[2.2.2] octane (DABCO) and the like may be used. As the solvent to be used therefor, for example, water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction time is 10 min–24 hrs., preferably 0.5–6 hrs. and the reaction temperature is from –20° C. to 200° C.

The obtained acyl azide is subjected to a Curtius rearrangement reaction to lead to isocyanate. This reaction is carried out by heating the obtained acyl azide from 30° C. to 200° C. In this case, for example, 1–10 equivalents of a basic compound such as triethylamine, diisopropylethylamine, pyridine, 4-N,N-dimethylaminopyridine (DMAP), 1,8-diazabicyclo[5.4.0]-7-undecene, 1,4-diazabicyclo[2.2.2]octane (DABCO) and the like may be used. The reaction can be also carried out in a solvent such as water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like. The reaction time is 10 min–24 hrs., preferably 0.5–6 hrs. It is also possible to carry out an intramolecular cyclization reaction subsequent to the Curtius reaction under these reaction conditions in the same system to lead to Compound (VII').

The reaction to introduce isocyanate obtained by Curtius reaction to Compound (VII') is conducted by heating the isocyanate from 30° C. to 200° C. In this case, for example, 1–10 equivalents of a basic compound such as triethylamine, diisopropylethylamine, pyridine, 4-N,N-dimethylaminopyridine (DMAP), 1,8-diazabicyclo[5.4.0]-7-undecene, 1,4-diazabicyclo[2.2.2]octane (DABCO) and the like may be used. The reaction can be also carried out in a solvent such as water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like. The reaction time is 10 min–24 hrs., preferably 0.5–6 hrs.

The series of reactions from Compound (XII) to Compound (VII') can be also carried out in the same system without isolation of each intermediate.

Compound (VIII) can be synthesized by, for example, the following method.

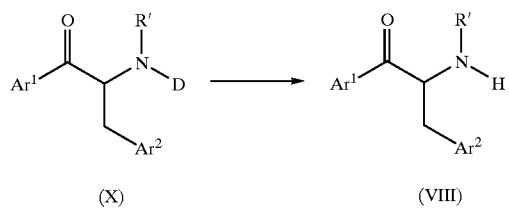

wherein the symbols in the formula are as defined above.

The reaction for converting Compound (X) to Compound (VIII) is carried out under the same conditions as, for example, the method under (ii) in the synthesis of Compound (II).

Compound (X) wherein R' is not a hydrogen atom can be synthesized by, for example, the following method.

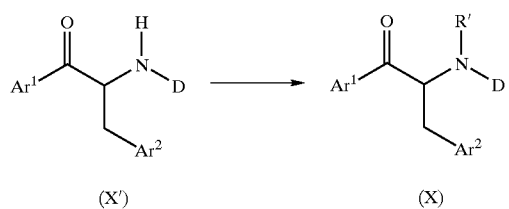

wherein the symbols in the formula are as defined above.

The reaction for converting Compound (X') to Compound (X) is carried out under the same conditions as, for example, the method for the synthesis of Compound (VII).

Compound (X') (compound (X) wherein R' is a hydrogen atom) can be synthesized by, for example, the following method.

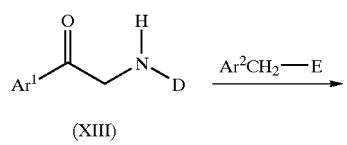

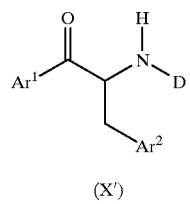

wherein E is a leaving group such as halogen atom (e.g., chloro, bromo, iodo and the like), methanesulfonyloxy, p-toluenesulfonyloxy and the like, and other symbols are as defined above.

In this reaction, Compound (XIII) is reacted with $Ar^2CH_2$-E in the presence of a basic compound to give Compound (X'). In this reaction, a monoequivalent amount or large excess of basic compound and a monoequivalent amount or large excess of $Ar^2CH_2$-E, relative to Compound (XIII), are used. As the basic compound to be used in this case, for example, sodium hydroxide, potassium hydroxide, sodium hydride, potassium carbonate, triethylamine, diisopropylethylamine, pyridine, 4-N,N-dimethylaminopyridine (DMAP), 1,8-diazabicyclo[5.4.0]-7-undecene, 1,4-diazabicyclo[2.2.2]octane (DABCO) and the like can be mentioned. As the solvent to be used therefor, for example, water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction time is 10 min–24 hrs., preferably 0.5–6 hrs. The reaction temperature is from −20° C. to 200° C. (preferably 0° C. to 80° C.).

Compound (XI) can be synthesized by, for example, the following method.

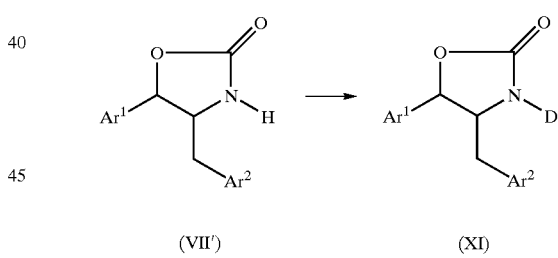

wherein the symbols in the formula are as defined above.

In this reaction, Compound (VII') is reacted with a reagent to introduce an amino-protecting group in the presence of a basic compound to give Compound (XI). In this reaction, a monoequivalent amount or large excess of basic compound and a monoequivalent amount or large excess of a reagent to introduce an amino-protecting group, relative to Compound (VII'), are used. As the basic compound to be used in this case, for example, sodium hydroxide, potassium hydroxide, sodium hydride, potassium carbonate, triethylamine, diisopropylethylamine, pyridine, 4-N,N-dimethylaminopyridine (DMAP), 1,8-diazabicyclo[5.4.0]-7-undecene, 1,4-diazabicyclo[2.2.2]octane (DABCO) and the like can be mentioned. As the reagent to introduce an amino-protecting group to be used here, for example, acetic anhydride, trifluoroacetic anhydride, acetic chloride, benzyl chlorocarbonate, di-tert-butyl dicarbonate and the like can be mentioned. As the solvent to be used therefor, for example, water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction time is 10 min–24 hrs., preferably 0.5–6 hrs. The reaction temperature is from −20° C. to 200° C. (preferably 0° C. to 80° C.).

Compound (XII) can be synthesized by, for example, the following method.

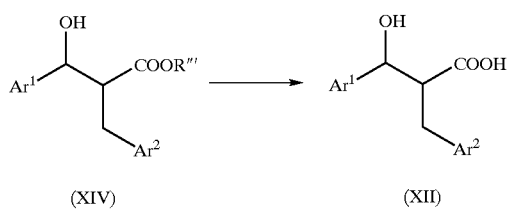

wherein R''' is a $C_{1-6}$ alkyl optionally having substituents, $C_{7-10}$ aralkyl optionally having substituents or $C_{7-16}$ aralkyl optionally having substituents, and other symbols are as defined above.

In this method, an ester group of Compound (XIV) is hydrolyzed to give Compound (XII). The hydrolysis of ester group is all known per se, and can be carried out under such conditions.

Compound (XIII) can be synthesized by, for example, the following method.

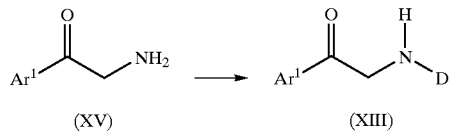

wherein the symbols in the formula are as defined above.

In this method, a protecting group is introduced into amino group of Compound (XV) to give Compound (XIII). The reaction for protecting amino group with a protecting group is known per se, and can be carried out under such conditions.

Compound (XIV) can be synthesized by, for example, the following method.

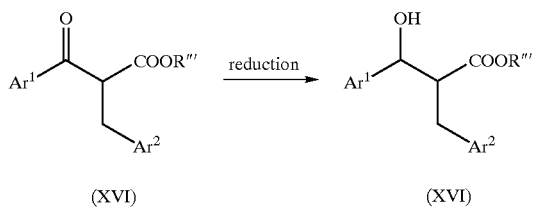

wherein the symbols in the formula are as defined above.

The reaction for converting Compound (XVI) to Compound (XIV) is carried out under the same conditions as, for example, the method under (ii) in the synthesis of Compound (I).

Compound (XV) can be synthesized by, for example, the following method.

wherein the symbols in the formula are as defined above.

For reduction reaction of Compound (XVII), catalytic hydrogenation in the presence of a catalyst and the like can be used. As the catalyst to be used for hydrogenation, metals such as palladium, platinum, nickel, rhodium and the like, oxides, salts and complexes of thereof, and the like can be mentioned. These catalysts can be also used by being carried on various carriers such as carbon and the like. The hydrogenation can be conducted under normal pressure or under pressurization. The solvent to be used therefor can be appropriately determined. For example, alcohols (e.g., methanol, ethanol and the like), ethers (e.g., tetrahydrofuran, dioxane, diethyl ether and the like), halogenated hydrocarbons (e.g., methylene chloride, chloroform and the like), esters (e.g., ethyl acetate and the like), aprotic polar solvents (e.g., N,N-dimethylformamide, dimethyl sulfoxide and the like) and the like can be mentioned. The reaction time is 0.5–72 hrs., preferably 1–24 hrs. The reaction temperature is from −100° C. to 100° C. (preferably −70° C. to 50° C.).

Compound (XVI) can be synthesized by, for example, the following method.

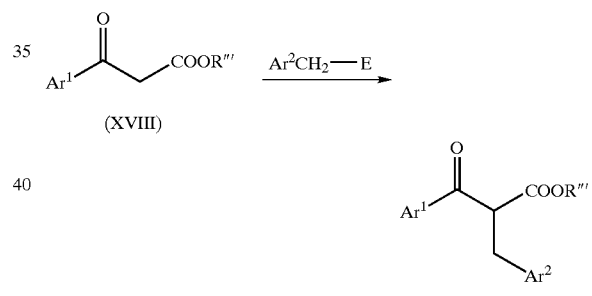

wherein the symbols in the formula are as defined above.

The reaction for converting Compound (XVIII) to Compound (XVI) is carried out under the same conditions as, for example, in the method for the synthesis of Compound (X'). Compound (XVIII), which is a starting compound, can be synthesized from $Ar^1$ COOH according to or by referring to the conditions described or cited in, for example, Heterocycles, 23, 2277–2287 (1985), J. Org. Chem., 53, 869–873 (1988), J. Org. Chem., 53, 873–875 (1986), Chem. Pharm. Bull., 38, 103–109 (1990) and the like; from $Ar^1C$(=O)Cl according to or by referring to the conditions described or cited in, for example, J. Am. Chem. Soc., 109, 7488–7494 (1987), J. Org. Chem., 53, 2968–2971 (1988), Tetrahedron Lett., 32, 7731–7734 (1991) and the like, and from $Ar^1C$(=O)$CH_3$ according to or by referring to the conditions described or cited in, for example, J. Heterocyclic Chem., 22, 1033–1034 (1985), J. Heterocyclic Chem., 25, 1737–1740 (1988), J. Med. Chem., 34, 798–806 (1991), Tetrahedron, 46, 4473–4486 (1990), J. Org. Chem., 64, 1512–1519 (1999) and the like.

Compound (XVII) can be synthesized by, for example, the following method.

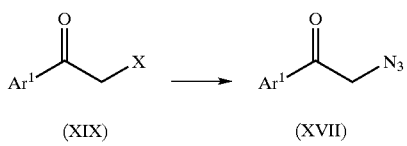

wherein X is a halogen atom, and other symbols are as defined above.

In this reaction, Compound (XIX) is reacted with a monoequivalent amount or large excess of alkali metal azide salt (e.g., sodium azide and the like) to give Compound (XVII). As the solvent to be used therefor, for example, water, alcohols (e.g., methanol, ethanol and the like), ethers (e.g., tetrahydrofuran, dioxane, diethyl ether and the like), halogenated hydrocarbons (e.g., methylene chloride, chloroform and the like), ketones (e.g., acetone, methyl ethyl ketone and the like), esters (e.g., ethyl acetate and the like), aprotic polar solvents (e.g., N,N-dimethylformamide, dimethyl sulfoxide and the like) and the like can be mentioned. The reaction time is 10 min–24 hrs. and the reaction temperature is from –20° C. to 200° C. (preferably 0° C. to 50° C.).

In each reaction for the synthesis of the above-mentioned objective compounds and-starting compounds, when a starting compound to be used has an amino group, a carboxyl group or a hydroxy group as a substituent, such group may be protected by a protecting group generally used for peptide chemical synthesis and the like. After the reaction, the protecting group is removed as necessary to give the objective compound.

As the amino-protecting group, for example, $C_{1-6}$ alkyl-carbonyl (e.g., formyl, methylcarbonyl, ethylcarbonyl and the like), phenylcarbonyl, $C_{1-6}$ alkyl-oxycarbonyl (e.g., methoxycarbonyl, ethoxycarbonyl and the like), $C_{6-10}$ aryl-oxycarbonyl (e.g., phenyloxycarbonyl and the like), $C_{7-10}$ aralkyl-carbonyl (e.g., benzyloxycarbonyl and the like), trityl, phthaloyl, each of which may have substituent(s), and the like are used. As the substituent of these, halogen atom (e.g., fluoro, chloro, bromo, iodo and the like), $C_{1-6}$ alkyl-carbonyl (e.g., methylcarbonyl, ethylcarbonyl, butylcarbonyl and the like), nitro group and the like are used, wherein the number of substituents is about 1 to 3.

As the carboxyl-protecting group, for example, $C_{1-6}$ alkyl (e.g., methyl, ethyl, propyl, isopropyl, butyl, tert-butyl and the like), phenyl, trityl, silyl, each of which may have substituent(s), and the like are used. As the substituent of these, halogen atom (e.g., fluoro, chloro, bromo, iodo and the like), $C_{1-6}$ alkylcarbonyl (e.g., formyl, methylcarbonyl, ethylcarbonyl, butylcarbonyl and the like), nitro group and the like are used, wherein the number of substituents is about 1 to 3.

As the hydroxy-protecting group, for example, $C_{1-6}$ alkyl (e.g., methyl, ethyl, propyl, isopropyl, butyl, tert-butyl and the like), phenyl, $C_{7-10}$ aralkyl (e.g., benzyl and the like), $C_{1-6}$ alkylcarbonyl (e.g., formyl, methylcarbonyl, ethylcarbonyl and the like), $C_{6-10}$ aryl-oxycarbonyl (e.g., phenyloxycarbonyl and the like), $C_{7-10}$ aralkyl-carbonyl (e.g., benzyloxycarbonyl and the like), pyranyl, furanyl, silyl, each of which may have substituent(s), and the like are used. As the substituent of these, halogen atom (e.g., fluoro, chloro, bromo, iodo and the like), $C_{1-6}$ alkyl, phenyl, $C_{7-10}$ aralkyl, nitro group and the like are used, wherein the number of substituents is about 1 to 3.

As a method for removing the protecting group, a method known per se or a method analogous thereto are used. For example, there may be used methods employing treatment with an acid, a base, reduction, ultraviolet rays, hydrazine, phenylhydrazine, sodium N-methyldithiocarbamate, tetrabutylammonium fluoride, palladium acetate and the like are used.

For separation and purification of Compound (I) from a reaction mixture and the starting material thereof, a conventional means for separation and purification (e.g., extraction, concentration, filtration, recrystallization, column chromatography, thin layer chromatography) is performed.

When Compound (I) thus obtained is a free form, it can be converted to a salt by a method known per se or a method analogous thereto (e.g., neutralization etc.). When it is obtained as a salt, it can be converted to a free form or other salt by a method known per se or a method analogous thereto.

Furthermore, when Compound (I) is an optically active form, it can be resolved into a d-form and an l-form by a conventional means for optical resolution.

Compound (I) and Compound (I') of the present invention are low toxic, useful as a pharmaceutical product, and have a cholesteryl ester transfer protein inhibitory action, a superior HDL-cholesterol increasing action, an LDL-cholesterol lowering action, a VLDL cholesterol lowering action and a triglyceride lowering action. Therefore, the agent of the present invention is useful for the prophylaxis or treatment of diseases based on these pharmacological actions. That is, the agent is particularly suitable for the prophylaxis or treatment of the diseases such as hyperlipidemia, particularly high LDL-cholesterolemia, high lipoproteinemia and hypertriglyceridemia, low HDL-cholesterolemia, aterosclerotic vascular lesion resulting therefrom and deuteropathy thereof, acute coronary syndrome such as acute cardiac infarction, unstable angina pectoris and the like, peripheral arterial occlusion, percutaneous transluminal coronary angioplasty (PTCA) or arterial restenosis after stent placement, ischemic heart disease such as cardiac infarction, angina pectoris and the like, arteriosclerosis, intermittent claudication, stroke (cerebral infarction, cerebral embolus, cerebral hemorrhage and the like), lacunar infarction, cerebrovascular dementia, gangrene, glomerulosclerosis, nephropathy, Tangier disease and the like, and for the suppression of progression of focal arteriosclerosis and the like, in mammals (e.g., mouse, rat, hamster, rabbit, cat, dog, bovine, horse, sheep, monkey, human etc.).

When Compound (I) and Compound (I') of the present invention are compared with a pharmaceutical agent that has an LDL-cholesterol lowering action but does not show an HDL-cholesterol increasing action, they are useful for the prophylaxis or treatment of primary hypo-HDL-emia and the like, for which an LDL-cholesterol lowering action alone has no treatment effect. The final object of therapeutic agents of hyperlipidemia is prevention of the onset of deadly diseases such as cardiac infarction and the like, and even a pharmaceutical agent having an LDL lowering action but without an HDL increasing action shows an onset-preventive effect to some degree against cardiac infarction and the like. However, an HDL-cholesterol elevating agent can show stronger prevention of the onset of cardiac infarction and the like. Moreover, it is effective for patients and diseases and conditions (e.g., intractable hyperlipidemia and the like), for which a pharmaceutical agent having an LDL lowering action but without an HDL increasing action fails to show a treatment effect, and even in humans showing a normal level of serum lipid, it suppresses the onset rate of deadly diseases such as cardiac infarction and the like, thereby improving treatment effects.

While Compound (I) and Compound (I') can be used as a bulk powder, it is generally formulated together with suitable amounts of appropriately selected carriers for preparations, such as excipients (e.g., calcium carbonate, kaolin, sodium hydrogen carbonate, lactose, starches, crystalline cellulose, talc, granulated sugar, porous substance etc.), binders (e.g., dextrin, rubbers, alcoholized starch, gelatin, hydroxypropyl cellulose, hydroxypropylmethyl cellulose, pullulan etc.), disintegrants (e.g., carboxymethyl cellulose calcium, croscarmellose sodium, crospovidone, low substituted hydroxypropyl cellulose, partially pregelatinized starch etc.), lubricants (e.g., magnesium stearate, calcium stearate, talc, starch, sodium benzoate etc.), coloring agents (e.g., tar dye, caramel, ferric oxide, titanium oxide, riboflavins etc.), corrigents (e.g., sweeteners, flavoring etc.), stabilizers (e.g., sodium sulfite etc.) and preservatives (e.g., parabens, sorbic acid etc.) and the like according to a conventional method and administered. The prophylactic or therapeutic agent of the present invention containing the aforementioned preparation appropriately contains an effective amount of Compound (I) or Compound (I') for the treatment or prophylaxis of diseases. The content of Compound (I) and Compound (I') in the preparation of the present invention is generally 0.1 to 100 wt % of the entire preparation. The preparation to be used in the present invention may contain a pharmaceutical component other than Compound (I) or Compound (I') as an active ingredient, wherein the component is not particularly limited as long as the object of the present invention can be achieved, and can be used in an appropriately suitable mixing ratio. Examples of the dosage form include tablets (including sugar-coated tablet and film-coated tablet), pill, capsule, granule, fine granules, powder, syrup, emulsion, suspension, injection, inhalant, ointment and the like. These preparations can be prepared according to a conventional method (e.g., method described in Japan Pharmacopoeia etc.).

To be specific, tablets can be produced by adding excipient, binder, disintegrant or other suitable additives to Compound (I) or Compound (I'), admixing homogeneously, granulating by a suitable method to give granules, adding lubricant etc. and compression-forming; or directly compression-forming Compound (I) or Compound (I') as it is or a homogeneous admixture thereof with excipient, binder, disintegrant or other suitable additives; compression-forming granules as they are, which have been prepared in advance or after admixing homogeneously with suitable additives. In addition, coloring agents, corrigents and the like can be added to this agent where necessary. Moreover, a film may be formed on this agent with a suitable coating agent. Injection can be produced by dissolving, suspending or emulsifying a given amount of Compound (I) or Compound (I') in water for injection, physiological saline, Ringer solution and the like in the case of aqueous solvents and generally in vegetable oil and the like in the case of non-aqueous solvents to a given amount or sealing a given amount of Compound (I) or Compound (I') in a vessel for injection.

As the carrier for oral preparation, for example, substances conventionally used in the field of pharmaceutical preparation, such as starch, mannitol, crystalline cellulose, carboxymethyl cellulose sodium and the like, are used. As the carrier for injection, for example, distilled water, physiological saline, glucose solution, transfusion and the like are used. In addition, additives generally used for preparation can be added appropriately.

The preparation of the present invention can be also used as a sustained release preparation. As the sustained release preparation of the present invention, for example. microcapsule (e.g., microsphere microcapsule, microparticle etc.) produced by in-water drying method (o/w method, w/o/w method etc.), phase separation method, spray drying method or a method analogous thereto may-be administered as it is or said microcapsule or a pharmaceutical composition in the form of a sphere, needle, pellet, film or cream as a starting material may be prepared into various dosage forms and administered. As the dosage form, for example, parenteral agents (e.g., intramuscular injection, subcutaneous injection, injection into organ etc. or embedded agent; transmucosal agent to nasal cavity, rectum, uterus etc. and the like), oral agent (e.g., hard capsule, soft capsule, granule, powder, suspension etc.) and the like can be mentioned.

When the sustained release preparation of the present invention is an injection, microcapsules may be prepared with a dispersing agent (e.g., surfactant such as Tween 80, HCO-60 and the like; polysaccharides such as carboxymethyl cellulose, sodium alginate, sodium hyaluronate and the like; protamine sulfate, polyethylene glycol etc.), preservatives (e.g., methylparaben, propylparaben etc.), isotonicity agents (e.g., sodium chloride, mannitol, sorbitol, glucose etc.), local anesthesia (e.g., xylocaine hydrochloride, chlorobutanol etc.) and the like to give an aqueous suspension, or dispersed together with a vegetable oil. (e.g., sesame oil, corn oil etc.) or a mixture of vegetable oil and phospholipid (e.g., lecithin etc.), or middle chain fatty acid triglyceride (e.g., miglyol 812 etc.) to give an oil suspension and used as a sustained release injection.

When the sustained release preparation of the present invention is a microcapsule, its average particle size is about 0.1 to about 300 $\mu$m, preferably about 1 to about 150 $\mu$m, more preferably about 2 to about 100 $\mu$m.

To give a sterile preparation of microcapsule, there can be mentioned, but not particularly limited to, a method comprising sterilizing all the production steps, a method comprising sterilization with gamma rays, a method comprising addition of preservatives and the like.

For the treatment of these diseases, Compound (I) and Compound (I') can be used alone for the prophylaxis and/or treatment or may be used along with other pharmaceutical components such as lipid-lowering drugs, cholesterol-lowering drugs, cardiac muscle protective drugs, therapeutic drugs of coronary diseases, therapeutic drugs of diabetes, therapeutic drugs of hypothyroidism, therapeutic drugs of nephrotic syndrome, therapeutic drugs of osteoporosis and therapeutic drugs of chronic kidney failure. In this case, these compounds are preferably administered as an oral preparation, but where necessary, they may be administered as a rectal preparation in the form of a suppository. As a combinable component in this case, for example, (1) PPAR$_\alpha$ agonists such as fibrates (e.g., clofibrate, bezafibrate, gemfibrogil, fenofibrate etc.) and the like, nicotinic acid, derivatives thereof and analogs thereof (e.g., acipimox, probucol etc.), (2) bile acid binding resin (e.g., colestyramine, colestipol etc.), a compound suppressing absorption of cholesterol (e.g., sitosterol, neomycin etc.), (3) compound inhibiting biosynthesis of cholesterol (e.g., HMG-CoA reductase inhibitors such as lovastatin, simvastatin, pravastatin, cerivastatin, atorvastatin, fluvastatin, itavastatin, rosuvastatin and the like), squalene epoxidase inhibitors (e.g., NB-598 and analog compound thereof etc.), squalene synthase inhibitors (e.g., benzoxazepine derivative etc.) and the like can be mentioned.

Different combinable components are oxide squalene-lanosterol cyclase (e.g., decalin derivative, azadecalin derivative, indan derivative etc.), microsome triglyceride transfer protein inhibitor (implitapide etc.) and the like.

When combined with a therapeutic drug of diabetes [actos, rosiglitazone, kinedak, penfill, humalin, euglucon, glimicron, daonil, novolin, monotard, insulins, glucobay, dimelin, rastinon, bacilcon, deamelin S, iszilins]; therapeutic drugs of hypothyroidism [dry thyroid (thyreoid), levothyroxine sodium (thyrodin S), liothyronine sodium (thyronine, thyronamin); therapeutic drugs of nephrotic syndrome: prednisolone (predonine), prednisolone sodium succinate (predonine), sodium methylprednisolone succinate (solumedrol), betamethasone (rinderon)]; anticoagulative therapy drugs [dipyridamole (persantine), dilazep hydrochloride (comelian), ticlopidine, clobidogrel, Xa inhibitor]; therapeutic drugs of chronic kidney failure [diuretic [e.g., furosemide (lasix), bumetanide (lunetoron), azosemide (diart)], depressor (e.g., ACE inhibitor, (enalapril maleate (renivase)) and Ca antagonists (manidipine), α receptor blocker, AII antagonists (candesartan)) and the like for administration, oral administration is preferable.

Furthermore, Compound (I) and Compound (I') are suitable for the treatment of diseases associated with excessive cell growth. A main example of the diseases associated with excessive cell growth is tumor. It has been reported that tumor growth can be suppressed by lowering serum total cholesterol or LDL-cholesterol or VLDL-cholesterol (Lancet 339: 1154–1156, 1992). Therefore, Compound (I) and Compound (I') can treat tumor because they have an LDL-cholesterol or VLDL-cholesterol lowering action. They can be used for the treatment of tumor by themselves or in combination with known treatment methods. Other applicable diseases include hyperproliferative skin diseases, such as psoriasis, basal cell cancer, squamous cell carcinoma, keratosis and keratosis diseases.

The hyperproliferative vascular diseases, such as angiostenosis and occlusion caused by surgical means such as PTCA (percutaneous transluminal coronary angioplasty) or bypass surgery are based on the growth of smooth muscle cells, and the compound of the present invention is also suitable for the treatment or prophylaxis of these disease in view of its LDL-cholesterol and VLDL-cholesterol lowering action. For this end, the compound is used alone or in combination with known active compound, such as heparin and the like that can be administered intravenously, preferably given by oral administration.

A further possible use of the compound of the present invention is prophylaxis or treatment of gallstone. When cholesterol in the bile has exceeded its maximum solubility, cholesterol precipitates to form gallstone. The lipid-lowering drugs of fibrates increase secretion of neutral steroid into the bile and increases the sensitivity of gallstone formation. In contrast, cholesterol biosynthesis inhibitors such as lovastatin and pravastatin do not promote gallstone forming, but cause lower cholesterol concentration in the bile, which could decrease the gallstone forming index (Gut 31: 348–350, 1990). It has been reported that, when combined with ursodeoxycholic acid, lovastatin is effective for dissolving gallstone (Gastroenterology 102, No. 4, Pt. 2, A319, 1992). In view of the mode of action, therefore, the compound of the present invention is suitable for the prophylaxis or treatment of gallstone. For this end, the compound is used alone or in combination with known therapeutic compound (e.g., ursodeoxycholic acid and the like), or a known treatment method (e.g., shock wave lithotripsy and the like), and can be administered orally.

Compound (I) and Compound (I') of the present invention have a blood HDL-cholesterol increasing action. By the increase in the blood HDL-cholesterol, export of cholesterol from the cell with excess cholesterol is promoted (Current Opinion in Lipidology 4: 392–400). Thus, the Compounds are suitable for the prophylaxis or treatment of atherosclerosis. In consideration of biological characteristics thereof, the Compounds are particularly suitable for the prophylaxis or treatment of atherosclerotic vascular lesion and deuteropathy thereof, such as coronary disease (CHD), cerebral ischemia, intermittent claudication, gangrene and the like.

As another use of the present invention, there is one based on anti-oxidant action of HDL. The lipid peroxide concentration in blood is far higher in HDL than in LDL, and HDL has a role of preventing peroxidation of lipid that occurs in living organisms, such as oxidation of LDL and the like (Current Opinion in Lipidology 4: 392–400, Current Opinion in Lipidology 5: 354–364).

As yet another use of the present invention, there is hypertension and deuteropathy thereof. Hyperlipidemia aggravates arteriosclerosis and induces hypertension. In contrast, HDL is known to prevent biosynthesis and to inhibit release of EDRF (epithelium-derived relaxing factor) by oxidized LDL, and increase prostacyclin, which is a vascular relaxing factor, in macrophages (Current Opinion in Lipidology 5: 354–364). In view of the lipid-lowering action and blood HDL-cholesterol increasing action of the substance of the present invention, it is suitable for the prophylaxis or treatment of hypertension and deuteropathy thereof, such as coronary heart disease (CHD), cerebral ischemia and the like. For this end, the compound of the formula (I) or (I') or a salt thereof is used alone or in combination with a pharmaceutical agent exemplified below and can be administered. The possible combinations in this case are, for example, angiotensin-II antagonists [e.g., losartan potassium (nu-lotan), dandesartan cilexetil (blopress) and the like], ACE inhibitors [e.g., enalapril maleate (renivase), lisinopril (zestril, longes), delapril hydrochloride (adecut), captopril and the like], calcium antagonists [e.g., amlodipine tosilate (amlodin, norvasc), manidipine hydrochloride (calslot) and the like], hypotensive diuretic, α receptor blocker, β receptor blocker and the like can be mentioned.

Some of the possible use of Compound (I) and Compound (I') of the present invention is based on the cell protective action from cytotoxic secretions such as gastric juice, pancreatic juice, bile and the like. Body fluid-tissue interfacial cells mainly expresses apo J, and form a natural barrier against cytotoxic secretions such as gastric juice, pancreatic juice, bile and the like, and HDL is a carrier of apo J (clusterin) (Current Opinion in Lipidology 4: 392–400). In consideration of the blood HDL-cholesterol increasing action of Compound (I) and Compound (I') of the present invention, Compound (I) and Compound (I') of the present invention are suitable for the prophylaxis or treatment of gastric ulcer, pancreatitis, hepatitis and the like.

Some of still other possible use of Compound (I) and Compound (I') of the present invention are based on cell growth activity. HDL alone or together with growth factor promotes cell growth of vascular endothelial cells (EC), corneal endothelium and the like, and HDL promotes growth of human lymphocytes (Current Opinion in Lipidology 3: 222–226). Compound (I) and Compound (I') of the present invention have a blood HDL-cholesterol increasing action. In consideration of these cell growth activities, they are suitable for the prophylaxis or treatment of atherosclerotic vascular lesion and deuteropathy thereof, such as coronary disease, corneal injury and the like. In addition, they are also suitable for the prophylaxis or treatment of diseases based on lowered immunity, such as infectious diseases, malignant tumor and the like.

As an additional use of Compound (I) and Compound (I') of the present invention, HDL specifically acts on human placental transplanted tissue to cause secretion of lactogen, as well as promotes secretion of apoE from macrophages (Current Opinion in Lipidology 3: 222–226). In consideration of the secretion promoting activity, they are also suitable for the prophylaxis or treatment of fetal underdevelopment and the like.

As a more noteworthy application example of Compound (I) and Compound (I'), secondary hyperlipidemia can be mentioned. This includes diabetes, insulin resistance (syndrome X), hypothyroidism, nephrotic syndrome, chronic kidney failure and the like, and these diseases cause onset of hyperlipidemia. In most cases, it is said that hyperlipidemia aggravates these diseases, thereby forming what is called a vicious circle. In view of the lipid lowering action, Compound (I) and Compound (I') are also suitable for the treatment of these diseases and prevention of progression thereof. For this end, Compound (I) and Compound (I') are used alone or in combination with a known active compound, i.e., for combined use with therapeutic drugs of diabetes, for example, (1) diuretic (e.g., forosemide, spironolactone etc.), (2) sympathetic suppressant (e.g., atenolol etc.), (3) angiotensin II antagonists (e.g., losartan, candesartan etc.), (4) angiotensin I-converting enzyme inhibitors (e.g., enalapril maleate, delapril hydrochloride etc.), (5) calcium antagonists (e.g., nifedipine, manidipine hydrochloride etc.) and the like, for combined use with a therapeutic drug of hypothyroidism, dry thyroid, levothyroxine sodium, liothyronine sodium and the like, for combined use with a therapeutic drug of renal disease, prednisolone, sodium methylprednisolone succinate, furosemide, bumetanide, azosemide and the like, preferably by oral administration.

Compound (I) and Compound (I') are also useful for the prophylaxis or treatment of Alzheimer's disease. Increase in blood cholesterol is known to a risk factor of Alzheimer's disease. The CETP inhibitors such as a compound represented by the formula (I) or (I'), a salt thereof, a prodrug thereof and the like can be used for the prophylaxis or treatment of Alzheimer's disease, based on its superior HDL-cholesterol increasing and lipid lowering action thereof. For this end, CETP inhibitors can be administered alone or in combination with pharmaceutical agents exemplified in the following. The possible combination in this case includes, for example, acetylcholine esterase inhibitors (e.g., aricept, exelon and the like), amyloid $\beta$ production. secretion inhibitors (e.g., $\gamma$ or $\beta$ selectase inhibitors such as JT-52, LY-374973 and the like, SIB-1848 and the like), amyloid $\beta$ coagulation inhibitors (e.g., PTI-00703, BETABLOC (AN-1792) and the like) and the like.

A still noteworthy applicable disease for Compound (I) and Compound (I') is osteoporosis associated with increase in blood cholesterol. Because of the superior lipid-lowering action of Compound (I) and Compound (I'), the Compounds can be used for the prophylaxis or treatment of osteoporosis associated with increase in blood cholesterol. For this end, Compound (I) and Compound (I') can be administered alone or in combination with pharmaceutical agents exemplified in the following. The possible combination in this case includes, for example, sex hormone and related pharmaceutical agents [e.g., estrogen preparation, ipriflavone (osten), raloxifene, osateron, tibolone and the like], calcitonins, vitamin D preparations [e.g., alfa calcidol, carcitriol and the like], bone resorption inhibitors such as bisphosphonic acids (e.g., etidronate, clodronate etc.) and the like, osteogenesis promoters such as fluorine compounds, PTH and the like, and the like.

In addition, Compound (I) and Compound (I') are suitable for the treatment of the diseases relating to hyperchylomicronemia such as acute pancreatitis. As the onset mechanism of pancreatitis, it is said that chylomicron produces fine thrombus in pancreatic capillary, or triglyceride is decomposed by pancreatic lipase due to hyperchylomicronemia and the resulting free fatty acid increases to cause strong focal irritation. Since Compound (I) and Compound (I') of the present invention has a triglyceride-lowering action, they can treat pancreatitis, wherein they can be used alone or in combination with known treatment method for the treatment of pancreatitis. For the treatment of this disease, Compound (I) and Compound (I') of the present invention can be administered orally or topically, wherein they can be used alone or in combination with known active compounds. The components that can be combined in this case include, for example, aprotinin (trasylol), gabexate mesylate (FOY), nafamostat mesylate (futhan), citicoline (nicholin), urinastatin (miraclid) and the like for antienzymatic therapy. In addition, for removal of pain, anticholinergic drug, nonnarcotic analgesic, narcotic are also used.

A yet still possible use of Compound (I) and Compound (I') of the present invention is inhibition of thrombus formation. Blood triglyceride level and factor VII involved in blood coagulation are in positive correlation, wherein intake of $\omega$-3 fatty acid lowers triglyceride level as well as inhibits coagulation. Therefore, hypertriglyceridemia promotes formation of thrombus. In addition, since VLDL of hyperlipidemia patients increased secretion of plasminogen activator inhibitor from vascular endothelial cells more strongly than did regular lipidemia patients, triglyceride is also considered to degrade fibrinolytic activity. Therefore, in view of the triglyceride-lowering action, Compound (I) and Compound (I') are suitable for the prophylaxis or treatment of thrombus formation. For this end, they can be used alone or in combination with known therapeutic drugs mentioned below, preferably by oral administration.

prophylactic or therapeutic drug of thrombus formation:
  blood coagulation inhibitors [e.g., heparin sodium, heparin calcium, warfarin calcium (warfarin), Xa inhibitor], thrombolytic agents [e.g., tPA, urokinase], anti-platelet drugs [e.g., aspirin, sulfinpyrazone (anturan), dipyridamole (persantin), ticlopidine (panaldine), cilostazol (pletal), GPIIb/IIIa antagonists (reopro)]
coronary vasodilators: nifedipine, diltiazem, nicoradil, nitrous acid agents;
cardiac muscle protective drug: heart ATP-K opener, endothelin antagonists, urotensin antagonists and the like.

When the compound of the present invention is applied to the above-mentioned diseases, it can be used in combination with biological preparations (e.g.: antibody, vaccine preparations and the like), and it is also possible to apply as a combination therapy by combining with a gene therapy method and the like. As the antibody and vaccine preparation, for example, vaccine preparations to angiotensin II, vaccine preparations to CETP, CETP antibody, $TNF_\alpha$ antibody and antibody to other cytokines, amyloid $\beta$ vaccine preparations, diabetes 1 vaccines (DIAPEP-277 of Peptor Corp. and the like) and the like, as well as antibody or vaccine preparation to cytokine, renin-angiotensin enzymes and the products thereof, antibody or vaccine preparation to enzyme or protein involved in blood lipid metabolism, antibody or vaccine relating to enzyme and protein involved in blood coagulation-fibrinolytic system, antibody or vaccine preparation to protein involved in sugar metabolism and insulin resistance and the like can be mentioned. As the gene therapy method, for example, a therapy method using gene relating to cytokine, renninangiotensin enzymes and products thereof, a therapy method using DNA decoys such as NFκB decoy and the like, a therapy method using antisense, a therapy method using a gene relating to the enzyme and protein involved in blood lipid metabolism (e.g., gene relating to metabolism, excretion and absorption of cholesterol or triglyceride or HDL-cholesterol or blood phospholipid and the like), a therapy method using a gene relating to enzyme and protein (e.g., growth-factors such as HGF, VEGF etc., and the like) involved in angiogenesis therapy targeting peripheral vascular obstruction and the like, a therapy method using a gene relating to protein involved in sugar metabolism and insulin resistance, antisense to cytokines such as TNF and the like and the like can be mentioned. It is also possible to use concurrently with various regeneration methods of organs such as heart regeneration, renal regeneration, pancreatic regeneration, revascularization and the like, and angiogenesis therapy utilizing transplantation of bone marrow cells (bone marrow mononuclear cells, bone marrow stem cells and the like).

The dose of the preparation of the present invention varies depending on the administration route, symptoms, age and body weight of patients and the like. For example, in the case of oral administration to adult patients as a therapeutic agent of arteriosclerosis, it is 0.2–50 mg/day, preferably 1.5–30 mg/day, as Compound (I) or Compound (I'), which is preferably administered once or in several portions. The administration route may be either oral or parenteral.

The dose of the sustained release preparation of the present invention varies depending on the administration route, symptoms, age and body weight of patients and the like, as well as sustained time of release and the like. However, the dose is not particularly limited as long as the effective concentration of Compound (I) or Compound (I'), which is an active ingredient, can be maintained in the body. The administration frequency can be determined appropriately and is once per one day to 3 days or once per 1 week to 3 months and the like.

The experimental results showing the pharmacological effect of Compound (I) and Compound (I') of the present invention are described in the following.

EXPERIMENTAL EXAMPLE 1

Assay of Cholesteryl Ester Transfer Protein Inhibitory Activity

1) Preparation of Very Low Density Lipoprotein (VLDL)—Low Density Lipoprotein (LDL)

Fresh rabbit serum was adjusted with KBr to the density of (1.063 g/ml), and the fractions (VLDL-LDL, density<1.063 g/ml) floated by ultra-centrifugation operation (SW41—Ti, 40,000 rpm, 18 hrs., 4° C., Beckman model L8-55) were collected, subjected to dialysis against 0.15 M NaCl-10 mM Tris-HCl, pH 7.4 (TBS), sterilized by filtration through a filter and preserved at 4° C.

2) Preparation of BODIPY-CE Microemulsion (BOBIPY-CE-ME)

A solution of BODIPY-CE (0.6 mg) in chloroform was added to egg PC (phosphatidylcholine) (5 ng) and triolein (2 mg), and after dissolution, the lipid was air dried under a nitrogen gas reflux and the solvent was removed under high vacuum. To this lipid was added an apo HDL solution (7.5 ml) obtained by defatting human HDL (1.063<d<1.21) with chloroform-methanol (2:1, v/v), dissolving in 6 M urea-containing TBS and dialyzing against TBS, and the mixture was subjected to sonication (BRANSON SONIFIRE CELL DISRUPTOR 200, dial 6, 5 min×4) to give BOBIPY-CE-ME. After centrifugation (CENTRIPREP 10), it was sterilized by filtration through a filter and preserved at 4° C.

3) Standard Measurement System

The test compound (20% DMSO solution, 5 $\mu$l), TS (75 $\mu$l), acceptor lipoprotein (VLDL-LDL, 20 $\mu$l) and partially purified human CETP (25 $\mu$l) were mixed and incubated at 37° C. for 30 min. BODIPY-CE-ME (25 $\mu$l) was added (total 150 $\mu$l) and a transfer reaction was started. After reaction at 37° C. for 30 min., fluorescence intensity was measured at Ex. 490 nm/Em. 530 nm. The CETP inhibitory activity (% inhibition) was calculated by the following formula.

$$\% \text{ inhibition} = \left(1 - \frac{(FU_{test\ 30} - FU_{test\ 0})}{(FU_{test\ 30} - FU_{control\ 0})}\right) \times 100$$

4) 50% Human Plasma-Containing Measurement System

The test compound (20% DMSO solution, 5 $\mu$l), human plasma (75 $\mu$l), acceptor lipoprotein (VLDL-LDL, 20 $\mu$l) and partially purified human CETP (25 $\mu$l) were mixed and incubated at 37° C. for 30 min. BODIPY-CE-ME (25 $\mu$l) was added (total 150 $\mu$l) and a transfer reaction was started. After reaction at 37° C. for 60 min., fluorescence intensity was measured at Ex. 490 nm/Em. 530 nm. The CETP inhibitory activity (% inhibition) was calculated by the following formula.

$$\% \text{ inhibition} = \left(1 - \frac{(FU_{test\ 60} - FU_{test\ 0})}{(FU_{test\ 60} - FU_{control\ 0})}\right) \times 100$$

The IC$_{50}$ value was determined as a concentration showing 50% inhibition by plotting the logarithm of the concentration of test compound and % inhibition.

The results are shown in Table 1.

TABLE 1 cholesteryl ester transfer protein inhibitory activity

| compound (Example No.) | cholesteryl ester transfer protein inhibitory activity IC$_{50}$ ($\mu$M) | |
|---|---|---|
| | Standard measurement system | 50% human plasma-containing measurement system |
| 29 | 0.12 | — |
| 30 | 0.3 | 2.5 |
| 122 | 0.015 | 0.49 |
| 123 | 0.035 | 0.95 |
| 124 | 0.046 | 2.4 |
| 125 | 0.051 | 2.0 |
| 126 | 0.070 | 1.0 |
| 155 | 0.095 | 2.1 |
| 177 | 0.091 | — |
| 210 | 0.088 | 1.4 |
| 216 | 0.040 | 0.70 |
| 217 | 0.0084 | 0.08 |
| 218 | 0.056 | 0.66 |
| 220 | 0.030 | 1.4 |
| 222 | 0.079 | — |
| 271 | 0.17 | 1.4 |
| 274 | 0.052 | 3.1 |
| 226(+)-form | 0.4 | 4.2 |
| 227(+)-form | 0.21 | 1.7 |
| 228(+)-form | 0.030 | 0.99 |
| 229(+)-form | 0.0086 | 0.24 |

As is clear from the above-mentioned results, the present compound has a superior cholesteryl ester transfer protein inhibitory activity.

EXAMPLES

The present invention is explained in detail in the following by referring to Examples and Reference Examples, which are mere examples and do not limit the invention, and may be modified as long as they do not deviate from the scope of the invention.

$^1$H-NMR spectra are determined with tetramethylsilane as the internal standard, using the Varian GEMINI 200 (200 MHz) spectrometer; all δ values are shown in ppm. Unless otherwise specifically indicated, the numeral value shown for mixed solvent is volume mixing ratio of each solvent. Unless otherwise specifically indicated, "%" means % by weight. Unless otherwise specifically indicated, moreover, the elution solvent for silica gel chromatography shows volume ratios. Room temperature (normal temperature) in the present specification means a temperature of from about 20° C. to about 30° C.

Each symbol in Examples and Reference Examples shows the following meaning. s: singlet, d:doublet, t:triplet, q:quartet, br: broad, J: coupling constant, dd: double doublet, m: multiplet, Hz: hertz, CDCl$_3$: deuterated chloroform, DMSO-d$_6$: deuterated dimethyl sulfoxide, CD$_3$OD: deuterated methanol, %: wt %.

Example 1

N-[2-(4-fluorophenyl)-2-hydroxy-1-[[4-(trifluoromethyl)phenyl]methyl]ethyl]-1-naphthalenecarboxamide 1) N-[2-(4-fluorophenyl)-2-oxoethyl]formamide To a solution of α-bromo-4-fluoroacetophenone (30.0 g, 0.138 mol) in N,N-dimethylformamide (200 ml) was added sodium azide (8.99 g, 0.136 mol) under ice-cooling and the mixture was stirred under ice-cooling for 30 min. After diluting the reaction solution with water, the solution was extracted with ethyl acetate. The extract was washed successively with water and saturated brine, dried over magnesium sulfate and concentrated under reduced pressure. The residue was dissolved in methanol (300 ml). 10% Pd/C (containing water by 50%, 3.0 g) and conc. hydrochloric acid (12.7 ml, 0.152 mol) were added and the mixture was stirred under hydrogen stream for 21 hrs. The catalyst was filtered off and the reaction solution was concentrated under reduced pressure. A mixed solution of sodium formate (10.3 g, 0.152 mol), acetic anhydride (140 ml) and formic acid (70 ml) was added to the residue and the mixture was stirred at room temperature for 1 hr. The reaction solution was concentrated under reduced pressure, diluted with water, and extracted with ethyl acetate. The extract was washed with saturated brine, dried over magnesium sulfate and concentrated under reduced pressure. The residue was recrystallized from ethyl acetate-hexane to give the objective substance (20.21 g, 81%) as crystals.

$^1$H-NMR (CDCl$_3$, 200 MHz) δ 4.79 (2H, dd, J=0.6 Hz, 4.4 Hz), 6.73 (1H, br s), 7.14–7.30 (2H, m), 7.97–8.10 (2H, m), 8.35 (1H, s).

2) 2-(4-fluorophenyl)-2-oxo-1-[[4-(trifluoromethyl)phenyl]methyl]ethylformamide

To a solution of a suspension (0.55 g, 0.0138 mol) of 60% sodium hydride in liquid paraffin in N,N-dimethylformamide (16 ml) was added N-[2-(4-fluorophenyl)-2-oxoethyl]formamide (1.66 g, 9.17 mmol) under ice-cooling and the mixture was stirred for 30 min. To the reaction solution was added 4-(trifluoromethyl)benzyl bromide (1.70 ml, 0.011 mol), and the mixture was stirred at room temperature for 2 hrs. The reaction solution was extracted with ethyl acetate. The extract was washed successively with water and saturated brine, dried over magnesium sulfate and concentrated under reduced pressure. The residue was purified by silica gel column chromatography (ethyl acetate/hexane=1/2-1/1) to give the objective substance (1.65 g, 53%) as crystals.

mp 78–81° C.; $^1$H-NMR (CDCl$_3$, 200 MHz) δ 3.13 (1H, dd, J=5.4 Hz, 13.8 Hz), 3.38 (1H, dd, J=6.6 Hz, 14.0 Hz), 5.87–5.96 (1H, m), 6.52 (1H, br d, J=7.8 Hz), 7.07–7.25 (4H, m), 7.48 (2H, d, J=8.0 Hz), 7.93–8.04 (2H, m), 8.25 (1H, s); IR (KBr) 3295, 1680, 1661 cm$^{-1}$; Anal. Calcd for C$_{17}$H$_{13}$F$_4$NO$_2$: C, 60.18; H, 3.86; N, 4.13. Found: C, 59.99; H, 3.87; N, 4.05;

3) 2-(4-fluorophenyl)-2-oxo-1-[[4-(trifluoromethyl)phenyl]methyl]ethylamine hydrochloride To a solution of 2-(4-fluorophenyl)-2-oxo-1-[[4-(trifluoromethyl)phenyl]methyl]ethylformamide (13.87 g, 40.9 mmol) in methanol (100 ml) was added conc. hydrochloric acid (3.8 ml, 45.0 mmol), and the mixture was heated under reflux for 2 hrs. The reaction solution was concentrated under reduced pressure, and the residue was washed with ethyl acetate to give the objective substance.(13.63 g, 96%) as crystals.

$^1$H-NMR (DMSO-d$_6$, 200 MHz) δ 3.17–3.29 (2H, m), 5.48 (1H, t, J=6.6 Hz), 7.27–7.44 (4H, m), 7.59 (2H, d, J=8.0 Hz), 8.04–8.15 (2H, m), 8.38 (2H, br s).

4) N-[2-(4-fluorophenyl)-2-oxo-1-[[4-(trifluoromethyl)phenyl]methyl]ethyl]-1-naphthalenecarboxamide To a solution of 1-naphthoic acid (0.49 g, 2.84 mmol) in N,N-dimethylformamide (10 ml) were added 1-ethyl-3-(3-dimethylaminopropyl)carbodiimide hydrochloride (0.74 g, 3.87 mmol) and 1-hydroxybenzotriazole hydrate (0.59 g, 3.87 mmol) and the mixture was stirred for 5 min. 2-(4-Fluorophenyl)-2-oxo-1-[[4-(trifluoromethyl)phenyl]methyl]ethylamine hydrochloride (0.9 g, 2.58 mmol) and 1,8-diazabicyclo[5.4.0]-7-undecene (0.42 ml, 2.84 mmol) were added and the mixture was stirred for 3 hrs. The reaction solution was extracted with ethyl acetate. The extract was washed successively with water and saturated brine, dried over magnesium sulfate and concentrated under reduced pressure. The residue was purified by silica gel column chromatography (ethyl acetate/hexane=1/4) to give the objective substance (0.92 g, 77%) as crystals.

mp 163–164° C.; $^1$H-NMR (CDCl$_3$, 200 MHz) δ 3.19 (1H, dd, J=6.2 Hz, 13.8 Hz), 3.55 (1H, dd, J=6.2 Hz, 14.0 Hz), 6.16 (1H, dd, J=6.2 Hz, 13.8 Hz), 6.88 (1H, d, J=8.0 Hz), 7.15–7.30 (4H, m), 7.39–7.59 (6H, m), 7.83–7.97 (2H, m), 8.04–8.16 (3H, m); IR (KBr) 3289, 1686, 1640 cm$^{-1}$; Anal.Calcd for C$_{27}$H$_{19}$F$_4$NO$_2$.0.2H$_2$O: C, 69.14; H, 4.17; N, 2.99. Found: C, 69.27; H, 4.07; N, 2.85.

5) N-[2-(4-fluorophenyl)-2-hydroxy-1-[[4-(trifluoromethyl)phenyl]methyl]ethyl]-1-naphthalenecarboxamide To a solution of N-[2-(4-fluorophenyl)-2-oxo-1-[[4-(trifluoromethyl)phenyl]methyl]ethyl]-1-naphthalenecarboxamide (500 mg, 1.08 mmol) in methanol (5 ml) was added sodium borohydride (20 mg, 0.538 mmol) and the mixture was stirred under ice-cooling for 30 min. The reaction solution was extracted with ethyl acetate. The extract was washed successively with 1N aqueous hydrochloric acid solution and saturated brine, dried over magnesium sulfate and concentrated under reduced pressure. The residue was purified by silica gel column chromatography (ethyl acetate/hexane=1/2) to give the objective substance (480 mg, 96%, (1RS,2SR) form/(1RS,2RS) form=1/3) as crystals.

mp 159–181° C.; $^1$H-NMR (CDCl$_3$, 200 MHz) δ 2.86 (1H×1/4, dd, J=11.0 Hz, 14.6 Hz), 3.07 (1H×3/4, dd, J=4.8 Hz, 15.0 Hz), 3.19 (1H, d, J=7.8 Hz), 3.27 (1H×3/4, d, J=4.6 Hz), 3.37 (1H×1/4, d, J=3.6 Hz), 4.61 (1H×3/4, ddd, J=3.4 Hz, 7.6 Hz, 16.8 Hz), 4.73–4.86 (1H×1/4, m), 4.89 (1H×3/4, t, J=7.8 Hz), 5.08 (1H×1/4, t, J=3.6 Hz), 5.98 (1H×1/4, d, J=8.4 Hz), 6.20 (1H×/4, d, J=9.2 Hz), 6.99–7.14 (2H, m), 7.16–7.55 (9H, m), 7.60 (2H, d, J=8.4 Hz), 7.83 (2H, t, J=8.8 Hz); IR (KBr) 3384, 3304, 1645 cm$^{-1}$; Anal. Calcd for C$_{27}$H$_{21}$F$_4$NO$_2$: C, 69.37; H, 4.53; N, 3.00. Found: C, 69.21; H, 4.58; N, 3.03.

Example 2

N-(2-(4-fluorophenyl)-2-hydroxy-1-((4-(trifluoromethyl)phenyl)methyl)ethyl)-4-methyl-1-naphthalenecarboxamide 1) To a solution of 1-(4-fluorophenyl)-1-oxo-3-(4-(trifluoromethyl)phenyl)-2-propylamine hydrochloride (600 mg, 1.73 mmol) and 4-methyl-1-naphthalenecarboxylic acid (354 mg, 1.90 mmol) in N,N-dimethylformamide (10 ml) were added 1-ethyl-3-(3-dimethylaminopropyl) carbodiimide hydrochloride (496 mg, 2.59 mmol), 1-hydroxy-1H-benzotriazole (396 mg, 2.59 mmol) and 1,8-diazabicyclo[5.4.0]-7-undecene (0.28 ml, 1.90 mmol) and the mixture was stirred overnight. To the reaction solution were added 1N aqueous hydrochloric acid solution (10 ml) and water (100 ml), and the mixture was extracted with ethyl acetate (50 ml×2): The extract was washed with 1N aqueous sodium hydroxide solution and saturated brine, dried over anhydrous magnesium sulfate and evaporated under reduced pressure. The residue was purified by silica gel column chromatography (hexane:ethyl acetate=4:1 and recrystallized from ethyl acetate-hexane to give N-(2-(4-fluorophenyl)-2-oxo-1-((4-(trifluoromethyl)phenyl)methyl)ethyl)-4-methyl-1-naphthalenecarboxamide (665 mg, 80%).

mp 149–150° C. IR ν $max^{KBr}cm^{-1}$: 1693, 1634, 1539, 1510. Anal. Calcd for $C_{28}H_{21}F_4NO_2$: C, 70.14; H, 4.41; N, 2.92. Found: C, 70.09; H, 4.42; N, 2.91.

$^1$H-NMR (CDCl$_3$)δ: 2.71 (3H, s), 3.19 (1H, dd, J=14.0, 6.2 Hz), 3.55 (1H, d, J=14.0, 6.2 Hz), 6.16 (1H, q, J=7.0 Hz), 6.83 (1H, d, J=7.4 Hz), 7.14–7.32 (5H, m), 7.36–7.64 (5H, m), 7.98–8.18 (4H, m).

2) To a solution of N-(2-(4-fluorophenyl)-2-oxo-1-((4-(trifluoromethyl)phenyl)methyl)ethyl)-4-methyl-1-naphthalenecarboxamide (400 mg, 0.83 mmol) in methanol (30 ml) was added manganese (II) chloride (210 mg, 1.67 mmol), and the mixture was stirred at room temperature for 30 min. To the reaction solution were added sodium borohydride (63 mg, 1.67 mmol) under ice-cooling, and the mixture was stirred for 1 hr. The reaction solution was poured into 1N hydrochloric acid (30 ml) and extracted with ethyl acetate (50 ml×2). The extract was washed with water and saturated brine, dried over anhydrous magnesium sulfate and evaporated under reduced pressure. The residue was purified by silica gel column chromatography (hexane:ethyl acetate=2:1), and the obtained crude crystal was washed with a mixed solvent of hexane:ethyl acetate=10:1 to give the title compound ((1RS,2SR) form: (1RS,2RS) form=1:2, 329 mg, 82%).

IR ν $max^{KBr}cm^{-1}$: 1634, 1510, 1125. Anal. Calcd for $C_{28}H_{23}F_4NO_2$: C, 69.85; H, 4.81; N, 2.91. Found: C, 69.56; H, 4.75; N, 2.80. $^1$H-NMR (CDCl$_3$)δ: 2.66 (3H, s), 2.70–3.10 (1H, m), 3.44 (2/3H, d, J=4.8 Hz), 3.53 (1/3H, d, J=3.6 Hz), 4.50–4.68 (2/3H, m), 4.70–4.90 (1H, m), 5.04–5.10 (1/3H, m), 5.95 (1/3H, d, J=8.8 Hz), 6.19 (2/3H, d, J=8.8 Hz), 6.96–7.70 (13H, m), 7.96 (1H, d, J=8.4 Hz).

Example 3

N-[2-(4-fluorophenyl)-2-hydroxy-1-[[4-(trifluoromethyl)phenyl]methyl]ethyl]-4-phenylbutylamide 1) N-[2-(4-fluorophenyl)-2-oxo-1-[[4-(trifluoromethyl)phenyl]methyl]ethyl]-4-phenylbutylamide In the same manner as in Example 1 4), the objective substance (1.01 g, 77%) was obtained as crystals.

mp 133–135° C.; $^1$H-NMR (CDCl$_3$, 200 MHz) δ 1.87–2.02 (2H, m), 2.18–2.26 (2H, m), 2.62 (2H, t, J=7.4 Hz), 3.08 (1H, dd, J=5.2 Hz, 14.0 Hz), 3.33 (1H, dd, J=6.6 Hz, 13.8 Hz), 5.78–5.88 (1H, m), 6.26 (1H, d, J=7.6 Hz), 7.05–7.33 (9H, m), 7.45 (2H, d, J=8.2 Hz), 7.92–8.03 (2H, m); IR (KBr) 3281, 1645 cm$^{-1}$; Anal. Calcd for $C_{26}H_{23}F_4NO_2$: C, 68.26; H, 5.07; N, 3.06. Found: C, 68.07; H, 4.79; N, 3.10.

2) N-[2-(4-fluorophenyl)-2-hydroxy-1-[[4-(trifluoromethyl)phenyl]methyl]ethyl]-4-phenylbutylamide In the same manner as in Example 1 5), the objective substance (144 mg, 29%, (1RS,2SR) form/(1RS,2RS) form= 4/1) was obtained as crystals.

mp 145–151° C.; $^1$H-NMR (CDCl$_3$, 200 MHz) δ 1.70–1.90 (2H, m), 2.00–2.14 (2H, m), 2.51 (2H, t, J=7.4 Hz), 2.70–2.94 (2H, m), 3.44 (1H, d, J=3.6 Hz), 4.30–4.56 (1H, m), 4.92–5.00 (1H, m), 5.38 (1H, d, J=7.0 Hz), 7.00–7.60 (13H, m); IR (KBr) 1645 cm$^{-1}$; Anal. Calcd for $C_{26}H_{25}F_4NO_2$: C, 67.96; H, 5.48; N, 3.05. Found: C, 67.85; H, 5.61; N, 3.04.

Example 4

N-(2-(4-fluorophenyl)-2-hydroxy-1-((4-(trifluoromethyl)phenyl)methyl)ethyl)-4-(2-thienyl)butyramide 1) To a solution of 1-(4-fluorophenyl)-1-oxo-3-(4-(trifluoromethyl)phenyl)-2-propylamine hydrochloride (600 mg,1.73 mmol) and 4-(2-thienyl)butyric acid (323 mg, 1.90 mmol) in N,N-dimethylformamide (10 ml) were added 1-ethyl-3-(3-dimethylaminopropyl)carbodiimide hydrochloride (496 mg, 2.59 mmol), 1-hydroxy-1H-benzotriazole (396 mg, 2.59 mmol) and 1,8-diazabicyclo[5.4.0]-7-undecene (0.28 ml, 1.90 mmol) and the mixture was stirred overnight. To the reaction solution were added 1N aqueous hydrochloric acid solution (10 ml) and water (100 ml), and the mixture was extracted with ethyl acetate (50 ml×2). The extract was washed with 1N aqueous sodium hydroxide solution and saturated brine, dried over anhydrous magnesium sulfate and evaporated under reduced pressure. The residue was recrystallized from ethyl acetate-hexane to give N-(2-(4-fluorophenyl)-2-oxo-1-((4-(trifluoromethyl)phenyl)methyl)ethyl)-4-(2-thienyl)butyramide (445 mg, 56%).

mp 123–124° C. IR ν $max^{KBr}cm^{-1}$: 3275, 1651, 1597, 1508, 1325, 1232, 1159, 1124. Anal. Calcd for $C_{24}H_{21}F_4NO_2S$: C, 62.19; H, 4.57; N, 3.02. Found: C, 62.02; H, 4.69; N, 3.28. $^1$H-NMR (CDCl$_3$)δ: 1.94–2.10 (2H, m), 2.26 (2H, t, J=7.4 Hz), 2.84 (2H, t, J=7.4 Hz), 3.08 (1H, dd, J=14.0, 5.2 Hz), 3.33 (1H, d, J=14.0, 5.2 Hz), 5.84 (1H, q, J=-6.4 Hz), 6.28 (1H, d, J=7.4 Hz), 6.74–6.80 (1H, m), 6.86–6.96 (1H, m), 7.04–7.24 (5H, m), 7.46 (2H, d, J=8.0 Hz), 7.92–8.06 (2H, m).

2) To a solution of N-(2-(4-fluorophenyl)-2-oxo-1-((4-(trifluoromethyl)phenyl)methyl)ethyl)-4-(2-thienyl)butyramide (300 mg, 0.65 mmol) in methanol (30 ml) was added manganese (II) chloride (163 mg, 1.30 mmol), and the mixture was stirred at room temperature for 30 min. To the reaction solution was added sodium borohydride (49 mg, 1.30 mmol) under ice-cooling, and the mixture was stirred for 1 hr. The reaction solution was poured into 1N hydrochloric acid (30 ml) and extracted with ethyl acetate (50 ml×2). The extract was washed with water and saturated brine, dried over anhydrous magnesium sulfate and evaporated under reduced pressure. The residue was purified by silica gel column chromatography (hexane:ethyl acetate= 2:1), and the obtained crude crystal was washed with a mixed solvent of hexane:ethyl acetate=10:1 to give the title compound ((1RS,2SR) form: (1RS,2RS) form=1:1, 204 mg, 68%).

IR ν $max^{KBr}cm^{-1}$: 1645, 1510, 1225, 1165, 1125. Anal. Calcd for $C_{24}H_{23}F_4NO_2S$: C, 61.92; H, 4.98; N, 3.01.

Found: C, 61.94; H, 4.98; N, 2.94. $^1$H-NMR (CDCl$_3$)δ: 1.70–1.96 (2H, m), 2.00–2.16 (2H, m), 2.60–3.00 (3H, m), 3.43 (1/2H, d, J=5.2 Hz), 3.51 (1/2H, d, J=3.6 Hz), 4.14–4.32 (1/2H, m), 4.36–4.52 (1/2H, m), 4.68–4.80 (1/2H, m), 4.90–4.98 (1/2H, m), 5.44 (1/2H, d, J=8.4 Hz), 5.66 (1/2H, d, J=8.4 Hz), 6.62–6.72 (1H, m), 6.88–7.60 (10H, m).

Example 5

N-[2-(4-fluorophenyl)-2-hydroxy-1-[[4-(trifluoromethyl)phenyl]methyl]ethyl]cyclopentanecarboxamide 1) 1) N-[2-(4-fluorophenyl)-2-oxo-1-[[4-(trifluoromethyl)phenyl]methyl]ethyl]cyclopentanecarboxamide In the same manner as in Example 1 4), the objective substance, (0.84 g, 71%) was obtained as crystals.

mp 158–159° C.; $^1$H-NMR (CDCl$_3$, 200 MHz) δ 1.64–1.93 (8H, m), 2.47–2.64 (1H, m), 3.08 (1H, dd, J=5.6 Hz, 13.6 Hz), 3.35 (1H, dd, J=6.6 Hz, 13.8 Hz), 5.78–5.88 (1H, m), 6.30 (1H, br d, J=7.2 Hz), 7.09 (2H, d, J=8.0 Hz), 7.12–7.23 (2H, m), 7.47 (2H, d, J=8.0 Hz), 7.94–8.02 (2H, m); IR (KBr) 3274, 1684, 1644 cm$^{-1}$; Anal. Calcd for C$_{22}$H$_{21}$F$_4$NO$_2$: C, 64.86; H, 5.20; N, 3.44. Found: C, 64.77; H, 5.13; N, 3.36.

2) N-[2-(4-fluorophenyl)-2-hydroxy-1-[[4-(trifluoromethyl)phenyl]methyl]ethyl]cyclopentanecarboxamide In the same manner as in Example 1 5), the objective substance (433 mg, 86%, (1RS,2SR) form/(1RS,2RS) form=3/4) was obtained as crystals.

mp 139–155° C.; $^1$H-NMR (CDCl$_3$, 200 MHz) δ 1.40–1.80 (8H, m), 2.36 (1H, br s), 2.71–3.07 (2H, m), 3.73–3.78 (1H, m), 4.12 (1H×4/7, ddd, J=3.6 Hz, 8.0. Hz, 15.4 Hz), 4.33–4.47 (1H×3/7, m), 4.75 (1H×4/7, t, J=7.2 Hz), 4.95 (1H×3/7, t, J=6.6 Hz), 5.40 (1H×3/7, br d, J=8.4 Hz), 5.62 (1H, br d, J=8.0 Hz), 6.94–7.14 (2H, m), 7.17–7.30 (2H, m), 7.32–7.42 (2H, m), 7.47–7.60 (2H, m); IR (KBr) 3312, 1651 cm$^{-1}$; Anal. Calcd for C$_{22}$H$_{23}$F$_4$NO$_2$: C, 64.54; H, 5.66; N, 3.42. Found: C, 64.58; H, 5.89; N, 3.67.

Example 6

4-fluoro-N-[2-(4-fluorophenyl)-2-hydroxy-1-[[4-(trifluoromethyl)phenyl]methyl]ethyl]benzamide 1) 4-fluoro-N-[2-(4-fluorophenyl)-2-oxo-1-[[4-(trifluoromethyl)phenyl]methyl]ethyl]benzamide In the same manner as in Example 1 4), the objective substance (1.16 g, 93%) was obtained as crystals.

mp 171–172° C.; $^1$H-NMR (CDCl$_3$, 200 MHz) δ 3.22 (1H, dd, J=5.0 Hz, 13.8 Hz), 3.49 (1H, dd, J=6.6 Hz, 14.0 Hz), 6.00 (1H, m), 6.97–7.28 (7H, m), 7.46 (2H, d, J=8.0 Hz), 7.74–7.85 (2H, m), 7.97–8.09 (2H, m); IR (KBr) 3316, 1698, 1638 cm$^{-1}$; Anal. Calcd for C$_{23}$H$_{16}$F$_5$NO$_2$: C, 63.74; H, 3.72; N, 3.23. Found: C, 63.57; H, 3.87; N, 3.23.

2) 4-fluoro-N-[2-(4-fluorophenyl)-2-hydroxy-1-[[4-(trifluoromethyl)phenyl]methyl]ethyl]benzamide In the same manner as in Example 1 5), the objective substance (423 mg, 94%, (1RS,2SR) form/(1RS,2RS) form=3/7) was obtained as crystals.

mp 155–179° C.; $^1$H-NMR (CDCl$_3$, 200 MHz) δ 2.90–2.97 (2H×1/3, m), 3.14 (2H×2/3, d, J=7.6 Hz), 3.22 (1H×2/3, d, J=4.2 Hz), 3.48 (1H×1/3, d, J=3.8 Hz), 4.42 (1H×2/3, ddd, J=3.4 Hz, 7.2 Hz, 15.8 Hz), 4.51–4.68 (1H×1/3, m), 4.83 (1H×2/3, t, J=3.9 Hz), 5.08 (1H×1/3, t, J=3.1 Hz), 6.09 (1H×1/3, br d, J=8.4 Hz), 6.34 (1H×2/3, br d, J=8.4 Hz), 6.93–7.13 (4H, m), 7.20–7.32 (2H, m), 7.37–7.62 (6H, m); IR (KBr) 3301, 1636 cm$^{-1}$; Anal. Calcd for C$_{23}$H$_{18}$F$_5$NO$_2$: C, 63.45; H, 4.17; N, 3.22. Found: C, 63.34; H, 4.36; N, 3.24.

Example 7

N-[2-(4-fluorophenyl)-2-hydroxy-1-[[4-(trifluoromethyl)phenyl]methyl]ethyl]-4-methoxybenzamide 1) N-[2-(4-fluorophenyl)-2-oxo-1-[[4-(trifluoromethyl)phenyl]methyl]ethyl]-4-methoxybenzamide In the same manner as in Example 1 4), the objective substance (1.11 g, 87%) was obtained as crystals.

mp 144° C.; $^1$H-NMR (CDCl$_3$, 200 MHz) δ 3.21 (1H, dd, J=4.8 Hz, 14.0 Hz), 3.48 (1H, dd, J=6.6 Hz, 13.6 Hz), 3.86 (3H, s), 6.01 (1H, ddd, J=4.6 Hz, 4.8 Hz, 6.6 Hz), 6.90–7.02 (3H, m), 7.08 (2H, d, J=8.2 Hz), 7.12–7.25 (2H, m), 7.45 (2H, d, J=8.0 Hz), 7.71–7.79 (2H, m), 7.97–8.08 (2H, m); IR (KBr) 3279, 1694, 1651 cm$^{-1}$; Anal. Calcd for C$_{24}$H$_{19}$F$_4$NO$_3$: C, 64.72; H, 4.30; N, 3.14. Found: C, 64.53; H, 4.27; N; 3.25.

2) N-[2-(4-fluorophenyl)-2-hydroxy-1-[[4-(trifluoromethyl)phenyl]methyl]ethyl]-4-methoxybenzamide In the same manner as in Example 1 5), the objective substance (0.48 g, 96%, (1RS,2SR) form/(1RS,2RS) form=3/2) was obtained as crystals.

mp 174–176° C.; $^1$H-NMR (CDCl$_3$, 200 MHz) δ 2.90–2.98 (2H×3/5, m), 3.12 (2H×2/5, d, J=7.4 Hz), 3.76 (1H×2/5, d, J=4.8 Hz), 3.82 (3H, s), 3.99 (1H×3/5, d, J=3.6 Hz), 4.28–4.46 (1H×2/5, m), 4:49–4.66; (1H×3/5, m), 4.81 (1H×2/5, t, J=8.2 Hz), 5.06 (1H×3/5, t, J=3.0 Hz), 6.08 (1H×3/5, d, J=8.2 Hz), 6.32 (1H×2/5, d, J=8.6 Hz), 6.82–7.13 (4H, m), 7.20–7.32 (2H, m), 7.34–7.59 (6H, m); IR (KBr) 3341, 1609 cm$^{-1}$; Anal. Calcd for C$_{24}$H$_{21}$F$_4$NO$_3$: C, 64.43; H, 4.73; N, 3.13. Found: C, 64.49; H, 4.74; N, 3.02.

Example 8

N-[2-(4-fluorophenyl)-2-hydroxy-1-[[4-(trifluoromethyl)phenyl]methyl]ethyl]cyclohexanecarboxamide 1) N-[2-(4-fluorophenyl)-2-oxo-1-[[4-(trifluoromethyl)phenyl]methyl]ethyl]cyclohexanecarboxamide In the same manner as in Example 1 4), the objective substance (0.90 g, 83%) was obtained as crystals.

mp 169–170° C.; $^1$H-NMR (CDCl$_3$, 200 MHz) δ 1.51–1.52 (5H, m), 1.62–1.88 (5H, m), 2.04–2.20 (1H, m), 3.08 (1H, dd, J=4.8 Hz, 14.0 Hz), 3.35 (1H, dd, J=6.2 Hz, 13.8 Hz), 5.76–5.88 (1H, m), 6.30 (1H, d, J=7.6 Hz), 7.07 (2H, d, J=8.2 Hz), 7.17 (2H, t, J=17.2 Hz), 7.47 (2H, d, J=8.0 Hz), 7.93–8.04 (2H, m); IR (KBr) 3274, 1686, 1640 cm$^{-1}$; Anal. Calcd for C$_{23}$H$_{23}$F$_4$NO$_2$: C, 65.55; H, 5.50; N, 3.32. Found: C, 65.52; H, 5.48; N, 3.44.

2) N-[2-(4-fluorophenyl)-2-hydroxy-1-[[4-(trifluoromethyl)phenyl]methyl]ethyl]cyclohexanecarboxamide In the same manner as in Example 1 5), the objective substance (480 mg, 96%, (1RS,2SR) form/(1RS,2RS) form=1/1) was obtained as crystals.

mp 161–178° C.; $^1$H-NMR (CDCl$_3$, 200 MHz) δ 1.08–1.34 (5H, m), 1.48–1.80 (5H, m), 1.92 (1H, br s), 2.77 (0.5H, dd, J=9.8 Hz, 14.6 Hz), 2.90 (0.5H, dd, J=5.4 Hz, 14.6 Hz), 3.06 (1H, d, J=7.8 Hz), 3.76 (0.5H, d, J=2.0 Hz), 3.79 (0.5H, s), 4.11 (0.5H, ddd, 3.8 Hz, 7.8 Hz, 15.8 Hz), 4.33–4.50 (0.5H, m), 4.76 (0.5H, t, J=9.0 Hz), 4.94 (0.5H, t, J=7.0 Hz), 5.38 (0.5H, d, J=8.2 Hz), 5.61 (0.5H, d, J=8.4 Hz), 6.95–7.12 (2H, m), 7.18–7.29 (2H, m), 7.32–7.41 (2H, m), 7.5.4 (2H, t, J=18.0 Hz); IR (KBr) 3384, 3304, 1645 cm$^{-1}$; Anal. Calcd for C$_{23}$H$_{25}$F$_4$NO$_2$: C, 65.24; H, 5.95; N, 3.31. Found: C, 64.99; H, 5.97; N, 3.25.

Example 9

4-chloro-N-[2-(4-fluorophenyl)-2-hydroxy-1-[[4-(trifluoromethyl)phenyl]methyl]ethyl]benzamide

1) 4-chloro-N-[2-(4-fluorophenyl)-2-oxo-1-[[4-(trifluoromethyl)phenyl]methyl]ethyl]benzamide In the same manner as in Example 1 4), the objective substance (1.20 g, 92%) was obtained as crystals.

mp 150–153° C.; $^1$H-NMR (CDCl$_3$, 200 MHz) δ 3.22 (1H, dd, J=4.8 Hz, 14.0 Hz), 3.49 (1H, dd, J=6.2 Hz, 14.0 Hz), 6.00 (1H, ddd, J=4.8 Hz, 6.6 Hz, 6.6 Hz), 7.02 (1H, br s), 7.07 (2H, d, J=7.6 Hz), 7.20 (2H, t, J=8.6 Hz), 7.44 (2H, d, J=8.4 Hz), 7.46 (2H, d, J=8.0 Hz), 7.72 (2H, d, J=8.8 Hz), 7.97–8.08 (2H, m); IR (KBr) 3281, 1686, 1644 cm$^{-1}$; Anal. Calcd for C$_{23}$H$_{16}$ClF$_4$NO$_2$: C, 61.41; H, 3.59; N, 3.11. Found: C, 61.41; H, 3.80; N, 3.09.

2) 4-chloro-N-[2-(4-fluorophenyl)-2-hydroxy-1-[[4-(trifluoromethyl)phenyl]methyl]ethyl]benzamide In the same manner as in Example 1 5), the objective substance (467 mg, 93%, (1RS,2SR) form/(1RS,2RS) form=1/1) was obtained as crystals.

mp 170–180° C.; $^1$H-NMR (CDCl$_3$, 200 MHz) δ 2.92 (0.5H, br s), 2.96 (0.5H, s), 3.04 (0.5H, d, J=4.8 Hz), 3.15 (1H, d, J=7.8 Hz), 3.32 (0.5H, d, J=3.8 Hz), 4.35–4.50 (0.5H, m), 4.53–4.68 (0.5H, m), 4.84 (0.5H, T, J=3.7 Hz), 5.08 (0.5H, t, J=3.8 Hz), 6.08 (0.5H, br d, J=7.4 Hz), 6.34 (0.5H, br d, J=9.2 Hz), 6.94–7.14 (2H, m), 7.21–7.61 (10H, m); IR (KBr) 3310, 1645 cm$^{-1}$; Anal. Calcd for C$_{23}$H$_{18}$ClF$_4$NO$_2$: C, 61.14; H, 4.02; N, 3.10. Found: C, 61.10; H, 4.22; N, 3.15.

Example 10

N-[2-(4-fluorophenyl)-2-hydroxy-1-[[4-(trifluoromethyl)phenyl]methyl]ethyl]-2-phenylbenzamide

1) N-[2-(4-fluorophenyl)-2-oxo-1-[[4-(trifluoromethyl)phenyl]methyl]ethyl]-2-phenylbenzamide In the same manner as in Example 1 4), the objective substance (0.81 g, 57%) was obtained as crystals.

mp 148–149° C.; $^1$H-NMR (CDCl$_3$, 200 MHz) δ 2.93 (1H, dd, J=5.2 Hz, 13.6 Hz), 3.06 (1H, dd, J=6.6 Hz, 14.0 Hz), 5.80 (1H, ddd, J=5.6 Hz, 6.6 Hz, 9.2 Hz), 6.19 (1H, d, J=7.6 Hz), 6.89 (2H, d, J=8.4 Hz), 7.11 (2H, t, J=8.4 Hz), 7.27–7.62 (1H, m), 7.87 (2H, dd, J=5.0 Hz, 8.6 Hz); IR (KBr) 3281, 1684 cm$^{-1}$; Anal. Calcd for C$_{29}$H$_{21}$F$_4$NO$_2$: C, 70.87; H, 4.31; N, 2.85. Found: C, 70.87; H, 4.30; N, 2.83.

2) N-[2-(4-fluorophenyl)-2-hydroxy-1-[[4-(trifluoromethyl)phenyl]methyl]ethyl]-2-phenylbenzamide In the same manner as in Example 1 5), the objective substance (0.48 g, 95%, (1RS,2SR) form/(1RS,2RS) form=2/3) was obtained as crystals.

mp 133–134° C.; $^1$H-NMR (CDCl$_3$, 200 MHz) δ 2.25–2.88 (3H, m), 4.22–4.52 (1H, m), 4.54 (1H×3/5, t, J=4.4 Hz), 4.64 (1H×2/5, t, J=3.8 Hz), 5.39 (1H×2/5, d, J=8.8 Hz), 5.65 (1H×3/5, d, J=8.2 Hz), 6.92–7.15 (4H, m), 7.20–7.56 (13H, m); IR (KBr) 3335, 1645 cm$^{-1}$; Anal. Calcd for C$_{29}$H$_{23}$F$_4$NO$_2$: C, 70.58; H, 4.70; N, 2.84. Found: C, 70.46; H, 4.62; N, 2.93.

Example 11

N-[2-(4-fluorophenyl)-2-hydroxy-1-[[4-(trifluoromethyl)phenyl]methyl]ethyl]-2-thiophenecarboxamide

1) N-[2-(4-fluorophenyl)-2-oxo-1-[[4-(trifluoromethyl)phenyl]methyl]ethyl]-2-thiophenecarboxamide In the same manner as in Example 1 4), the objective substance (0.94 g, 78%) was obtained as crystals.

mp 130–131° C.; $^1$H-NMR (CDCl$_3$, 200 MHz) δ 3.21 (1H, dd, J=4.8 Hz, 13.8 Hz), 3.46 (1H, dd, J=6.4 Hz, 13.6 Hz), 5.93–6.04 (1H, m), 6.91 (1H, d, J=7.0 Hz), 7.05–7.24 (5H, m), 7.45 (2H, d, J=8.2 Hz), 7.50–7.54 (2H, m), 7.96–8.06 (2H, m); IR (KBr) 3308, 1694, 1682 cm$^{-1}$; Anal. Calcd for C$_{21}$H$_{15}$F$_4$NO$_2$S: C, 59.85; H, 3.59; N, 3.32. Found: C, 59.83; H, 3.34; N, 3.24.

2) N-[2-(4-fluorophenyl)-2-hydroxy-1-[[4-(trifluoromethyl)phenyl]methyl]ethyl]-2-thiophenecarboxamide In the same manner as in Example 1 5), the objective substance (0.45 g, 89%, (1RS,2SR) form/(1RS,2RS) form=2/1) was obtained as crystals.

mp 135–164° C.; $^1$H-NMR (CDCl$_3$, 200 MHz) δ 2.92 (2H×2/3, d, J=7.8 Hz), 3.10–3.15 (1H, m), 3.40 (1H×2/3, d, J=3.8 Hz), 4.30–4.64 (1H, m), 4.82 (1H×1/3, t, J=4.0 Hz), 5.08 (1H×2/3, t, J=3.3 Hz), 6.00 (1H×2/3, br d, J=8.4 Hz), 6.25 (1H×1/3, br d, J=8.4 Hz), 6.94–7.14 (3H, m), 7.21–7.61 (8H, m); IR (KBr) 3301, 1636 cm$^{-1}$; Anal. Calcd for C$_{21}$H$_{17}$F$_4$NO$_2$S: C, 59.57; H, 4.05; N, 3.31. Found: C, 59.59; H, 4.15; N, 3.24.

Example 12

N-[2-(4-fluorophenyl)-2-hydroxy-1-[[4-(trifluoromethyl)phenyl]methyl]ethyl]-4-(trifluoromethyl)benzamide

1) N-[2-(4-fluorophenyl)-2-oxo-1-[[4-(trifluoromethyl)phenyl]methyl]ethyl]-4-(trifluoromethyl)benzamide In the same manner as in Example 1 4), the objective substance (1.32 g, 95%) was obtained as crystals.

mp 172–174° C.; $^1$H-NMR (CDCl$_3$, 200 MHz) δ 3.23 (1H, dd, J=4.8 Hz, 13.8 Hz), 3.51 (1H, dd, J=6.2 Hz, 14.0 Hz), 6.01 (1H, ddd, J=5.2 Hz, 6.4 Hz, 7.0 Hz), 7.08 (2H, d, J=8.0 Hz), 7.14 (1H, br s), 7.21 (2H, t, J=8.6 Hz), 7.47 (2H, d, J=8.0 Hz), 7.73 (2H, d, J=8.4 Hz), 7.88 (2H, d, J=8.4 Hz), 7.98–8.10 (2H, m); IR (KBr) 3303, 1688, 1645 cm$^{-1}$; Anal. Calcd for C$_{24}$H$_{16}$F$_7$NO$_2$: C, 59.63; H, 3.34; N, 2.90. Found: C, 59.55; H, 3.58; N, 2.89.

2) N-[2-(4-fluorophenyl)-2-hydroxy-1-[[4-(trifluoromethyl)phenyl]methyl]ethyl]-4-(trifluoromethyl)benzamide In the same manner as in Example 1 5), the objective substance (444 mg, 88%, (1RS,2SR) form/(1RS,2RS) form=1/6) was obtained as crystals.

mp 167–169° C.; $^1$H-NMR (CDCl$_3$, 200 MHz) δ 2.87 (1H, d, J=4.4 Hz), 3.17 (2H, d, J=7.6 Hz), 4.40–4.56 (1H, m), 4.86 (1H×6/7, t, J=3.4 Hz), 5.10 (1H×1/7, s), 6.43 (1H, d, J=8.8 Hz), 6.95–7.14 (2H, m), 7.22–7.32 (2H, m), 7.43 (2H, d, J=8.2 Hz), 7.59 (2H, d, J=8.4 Hz), 7.67 (4H, s); IR (KBr) 3426, 3335, 1645 cm$^{-1}$; Anal. Calcd for C$_{24}$H$_{18}$F$_7$NO$_2$: C, 59.39; H, 3.74; N, 2.89. Found: C, 59.34; H, 3.961; N, 2.89.

Example 13

4-butyl-N-[2-(4-fluorophenyl)-2-hydroxy-1-[[4-(trifluoromethyl)phenyl]methyl]ethyl]benzamide

1) 4-butyl-N-[2-(4-fluorophenyl)-2-oxo-1-[[4-(trifluoromethyl)phenyl]methyl]ethyl]benzamide In the same manner as in Example 1 4), the objective substance (1.16 g, 86%) was obtained as crystals.

mp 120–121° C.; $^1$H-NMR (CDCl$_3$, 200 MHz) δ 0.93 (3H, t, J=7.1 Hz), 1.26–1.46 (2H, m), 1.53–1.70 (2H, m), 2.67 (2H, t, J=7.6 Hz), 3.21 (1H, dd, J=4.6 Hz, 13.8 Hz), 3.49 (1H, dd, J=6.4 Hz, 13.6 Hz), 6.02 (1H, ddd, J=4.8 Hz, 6.4 Hz, 7.4 Hz), 7.00–7.28 (7H, m), 7.45 (2H, d, J=8.2 Hz), 7.69 (2H, d, J=8.2 Hz), 7.97–8.08 (2H, m); IR (KBr) 3281, 1688, 1636 cm$^{-1}$; Anal. Calcd for C$_{27}$H$_{25}$F$_4$NO$_2$: C, 68.78; H, 5.34; N, 2.97. Found: C, 68.95; H, 5.43; N, 2.96.

2) 4-butyl-N-[2-(4-fluorophenyl)-2-hydroxy-1-[[4-(trifluoromethyl)phenyl]methyl]ethyl]benzamide In the same manner as in Example 1 5), the objective substance (946 mg, 95%, (1RS,2SR) form/(1RS,2RS) form= 4/3) was obtained as crystals.

mp 138–158° C.; $^1$H-NMR (CDCl$_3$, 200 MHz) δ 0.92 (3H, t, J=7.1 Hz), 1.24–1.43 (2H, m), 1.50–1.67 (2H, m), 2.63 (2H, t, J=7.7 Hz), 2.90 (1H×4/7,d, J=3.4 Hz), 2.94 (1H×4/7, s), 3.13 (2H×3/7, d, J=4.4 Hz), 3.88 (1H×4/7, d, J=3.8 Hz), 4.37 (1H×3/7, ddd, J=2.8 Hz, 7.0 Hz, 15.4 Hz), 4.52–4.67 (1H×4/7, m), 4.82 (1H×3/7, t, J=4.2 Hz), 5.06 (1H×4/7, t, J=3.5 Hz), 6.14 (1H×4/7, d, J=8.2 Hz), 6.37 (1H×3/7, d, J=8.6 Hz), 6.91–7.32 (6H, m), 7.35–7.59 (6H, m); IR (KBr) 3274, 1615 cm$^{-1}$; Anal. Calcd for C$_{27}$H$_{27}$F$_4$NO$_2$: C, 68.49; H, 5.75; N, 2.96. Found: C, 68.35; H, 5.89; N, 3.04.

Example 14

N-[2-(4-fluorophenyl)-2-hydroxy-1-[[4-(trifluoromethyl)phenyl]methyl]ethyl]-2-naphthalenecarboxamide 1) N-[2-(4-fluorophenyl)-2-oxo-1-[[4-(trifluoromethyl)phenyl]methyl]ethyl]-2-naphthalenecarboxamide In the same manner as in Example 1 4), the objective substance (1.03 g, 77%) was obtained as crystals.

mp 139–141° C.; $^1$H-NMR (CDCl$_3$, 200 MHz) δ 3.26 (1H, dd, J=4.8 Hz, 14.0 Hz), 3.54 (1H, dd, J=6.6 Hz, 13.4 Hz), 6.04–6.14 (1H, m), 7.11 (2H, d, J=8.2 Hz), 7.17–7.28 (3H, m), 7.46 (2H, d, J=8.0 Hz), 7.51–7.64 (2H, m), 7.80–7.97 (4H, m), 8.01–8.11 (2H, m), 8.29 (1H, s); IR (KBr) 3293, 1694, 1645 cm$^{-1}$; Anal. Calcd for C$_{27}$H$_{19}$F$_4$NO$_2$: C, 69.67; H, 4.11; N, 3.01. Found: C, 69.67; H, 4.11; N, 3.01.

2) N-[2-(4-fluorophenyl)-2-hydroxy-1-[[4-(trifluoromethyl)phenyl]methyl]ethyl]-2-naphthalenecarboxamide In the same manner as in Example 1 5), the objective substance (0.50 g, 100%, (1RS,2SR) form/(1RS,2RS) form= 1/1) was obtained as crystals.

mp 148–150° C.; $^1$H-NMR (CDCl$_3$, 200 MHz) δ 3.00 (1H, d, J=7.8 Hz), 3.20 (1H, d, J=7.8 Hz), 3.38–3.53 (0.5H, m), 3.67–3.77 (0.5H, m), 4.39–4.55 (0.5H, m), 4.59–4.75 (0.5H, m), 4.85–4.93 (0.5H, m), 5.14 (0.5H, t, J=3.0 Hz), 6.28 (0.5H, br s), 6.53 (0.5H, br s), 6.94–7.13 (2H, m), 7.26–7.36 (2H, m), 7.41–7.65 (7H, m), 7.82–7.89 (3H, m), 8.04 (1H, d, J=4.4 Hz); IR (KBr) 3351, 1640 cm$^{-1}$; Anal. Calcd for C$_{27}$H$_{21}$F$_4$NO$_2$: C, 69.37; H, 4.53; N, 3.00. Found: C, 68.51; H, 5.02; N, 2.67.

Example 15

N-[2-(4-fluorophenyl)-2-hydroxy-1-[[4-(trifluoromethyl)phenyl]methyl]ethyl]adamantane-1-carboxamide 1) N-[2-(4-fluorophenyl)-2-oxo-1-[[4-(trifluoromethyl)phenyl]methyl]ethyl]adamantane-1-carboxamide In the same manner as in Example 1 4), the objective substance (0.89 g, 78%) was obtained as crystals.

mp 169–170° C.; $^1$H-NMR (CDCl$_3$, 200 MHz) δ 1.71 (6H, d, J=2.6 Hz), 1.81 (6H, d, J=3.0 Hz), 2.04 (3H, br s), 3.08 (1H, dd, J=5.2 Hz, 13.6 Hz), 3.34 (1H, dd, J=6.6 Hz, 14.0 Hz), 5.75–5.85 (1H, m), 6.49 (1H, br d, J=7.6 Hz), 7.07 (1H, d, J=7.8 Hz), 7.11–7.23 (2H, m), 7.47 (2H, d, J=8.0 Hz), 7.93–8.03 (2H, m); IR (KBr) 3347, 1682, 1632 cm$^{-1}$; Anal. Calcd for C$_{27}$H$_{27}$F$_4$NO$_2$: C, 68.49; H, 5.75; N, 2.96. Found: C, 68.41; H, 5.70; N, 2.93.

2) N-[2-(4-fluorophenyl)-2-hydroxy-1-[[4-(trifluoromethyl)phenyl]methyl]ethyl]adamantane-1-carboxamide In the same manner as in Example 1 5), the objective substance (488 mg, 97%, (1RS,2SR) form/(1RS,2RS) form= 3/2) was obtained as an amorphous compound.

$^1$H-NMR (CDCl$_3$, 200 MHz) δ 1.55–1.74 (12H, m), 1.97 (3H, br s), 2.63–3.06 (2H, m), 4.01 (1H, br t, J=3.4 Hz), 4.09 (1H×2/5, ddd, J=4.0 Hz, 7.6 Hz, 15.6 Hz), 4.33–4.47 (1H× 3/5, m), 4.75 (1H×2/5, t, J=8.8 Hz), 4.91 (1H×3/5, t, J=6.6 Hz), 5.48 (1H×3/5, d, J=7.6 Hz), 5.76 (1H×2/5, d, J=8.0 Hz), 6.94–7.13 (2H, m), 7.17–7.28 (2H, m), 7.30–7.40 (2H, m), 7.48–7.59 (2H, m); IR (KBr) 3441, 3353, 1634 cm$^{-1}$; Anal. Calcd for C$_{27}$H$_{29}$F$_4$NO$_2$: C, 68.20; H, 6.15; N, 2.95. Found: C, 67.72; H, 6.31; N, 2.86.

Example 16

N-[2-(4-fluorophenyl)-2-hydroxy-1-[[4-(trifluoromethyl)phenyl]methyl]ethyl]-2,2-dimethylpropionamide 1) N-[2-(4-fluorophenyl)-2-oxo-1-[[4-(trifluoromethyl)phenyl]methyl]ethyl]-2,2-dimethylpropionamide In the same manner as in Example 1 4), the objective substance (0.89 g, 78%) was obtained as crystals.

mp 147–150° C.; $^1$H-NMR (CDCl$_3$, 200 MHz) δ 1.17 (9H, s), 3.08 (1H, dd, J=5.2 Hz, 13.6 Hz), 3.35 (1H, dd, J=6.2 Hz, 14.0 Hz), 5.74–5.84 (1H, m), 6.52 (1H, br d, J=6.6 Hz), 7.08 (2H, d, J=7.6 Hz), 7.12–7.24 (2H, m), 7.47 (2H, d, J=8.0 Hz), 7.94–8.04 (2H, m); IR (KBr) 3391, 1682, 1634 cm$^{-1}$; Anal. Calcd for C$_{21}$H$_{21}$F$_4$NO$_2$: C, 63.79; H, 5.35; N, 3.54. Found: C, 63.72; H, 5.21; N, 3.48.

2) N-[2-(4-fluorophenyl)-2-hydroxy-1-[[4-(trifluoromethyl)phenyl]methyl]ethyl]-2,2-dimethylpropionamide In the same manner as in Example 1 5), the objective substance (498 mg, 99%, (1RS,2SR) form/(1RS,2RS) form= 3/2) was obtained as crystals.

mp 97–99° C.; $^1$H-NMR (CDCl$_3$, 200 MHz) δ 1.00 (9H, s), 2.69–3.08 (2H, m), 3.83 (1H, br s), 4.13 (1H×2/5, ddd, J=3.6 Hz, 8.0 Hz, 15.8 Hz), 4.34–4.47 (1H×3/5, m), 4.76 (1H×2/5, t, J=4.0 Hz), 4.92 (1H×3/5, t, J=3.2 Hz), 5.54 (1H×3/5, t, J=7.0 Hz), 5.83 (1H×2/5, m), 6.95–7.12 (2H, m), 7.17–7.25 (2H, m), 7.31–7.40 (2H, m), 7.47–7.59 (2H, m); IR (KBr) 3333, 1645 cm$^{-1}$; Anal. Calcd for C$_{21}$H$_{23}$F$_4$NO$_2$: C, 63.47; H, 5.83; N, 3.52. Found: C, 63.33; H, 5.74; N, 3.50.

Example 17

N-[2-(4-fluorophenyl)-2-hydroxy-1-[[4-(trifluoromethyl)phenyl]methyl]ethyl]-2,4,6-trimethylbenzamide N-[2-(4-fluorophenyl)-2-oxo-1-[[4-(trifluoromethyl)phenyl]methyl]ethyl]-2,4,6-trimethylbenzamide In the same manner as in Example 1 4), the objective substance (0.48 g, 36%) was obtained as crystals.

mp 141–143° C.; $^1$H-NMR (CDCl$_3$, 200 MHz) δ 2.08 (6H, s), 2.25 (3H, s), 3.14 (1H, dd, J=7.2 Hz, 14.0 Hz), 3.36 (1H, dd, J=6.2 Hz, 14.0 Hz), 6.07–6.18 (1H, m), 6.37 (1H, br d, J=8.4 Hz), 6.80 (2H, s), 7.18 (2H, t, J=8.4 Hz), 7.24–7.31 (2H, m), 7.50 (2H, d, J=8.0 Hz), 8.01–8.11 (2H, m); IR (KBr) 3237, 1694, 1634 cm$^{-1}$; Anal. Calcd for C$_{26}$H$_{23}$F$_4$NO$_2$: C, 68.26; H, 5.07; N, 3.06. Found: C, 68.23; H, 5.25; N, 2.91.

2) N-[2-(4-fluorophenyl)-2-hydroxy-1-[[4-(trifluoromethyl)phenyl]methyl]ethyl]-2,4,6-trimethylbenzamide In the same manner as in Example 1 5), the objective substance (325 mg, 92%, (1RS,2SR) form/(1RS,2RS) form= 1/10) was obtained as an amorphous compound.

¹H-NMR (CDCl₃, 200 MHz) δ 1.86 (6H, s), 2.22 (3H, s), 3.03 (1H, dd, J=7.3 Hz, 13.9 Hz), 3.12 (1H, dd, J=7.6 Hz, 13.4 Hz), 3.15–3.28 (1H, m), 4.58 (1H, ddd, J=3.5 Hz, 7.8 Hz, 15.8 Hz), 4.70 (1H, br s), 6.01 (1H, br d, J=9.2 Hz), 6.73 (2H, s), 6.94–7.13 (2H, m), 7.22–7.31 (2H, m), 7.45 (2H, d, J=8.4 Hz), 7.58 (2H, d, J=8.0 Hz); IR (KBr) 3268, 1620 cm⁻¹; Anal. Calcd for $C_{26}H_{25}F_4NO_2$: C, 67.96; H, 5.48; N, 3.05. Found: C, 67.80; H, 5.74; N, 3.04.

Example 18

2-fluoro-N-[2-(4-fluorophenyl)-2-hydroxy-1-[[4-(trifluoromethyl)phenyl]methyl]ethyl]benzamide 1) 2-fluoro-N-[2-(4-fluorophenyl)-2-oxo-1-[[4-(trifluoromethyl)phenyl]methyl]ethyl]benzamide In the same manner as in Example 1 4), the objective substance (136 mg, 90%) was obtained as crystals.

mp 109–111° C.; ¹H-NMR (CDCl₃, 200 MHz) δ 3.22 (1H, dd, J=5.2 Hz, 13.6 Hz), 3.46 (1H, dd, J=6.2 Hz, 13.4 Hz), 5.98–6.11 (1H, m), 7.09–7.33 (6H, m), 7.43–7.69 (4H, m), 7.97–8.11 (3H, m); IR (KBr) 3439, 1686, 1655 cm⁻¹; Anal. Calcd for $C_{23}H_{16}F_5NO_2$: C, 63.74; H, 3.72; N, 3.23. Found: C, 63.56; H, 3.66; N, 3.40.

2) 2-fluoro-N-[2-(4-fluorophenyl)-2-hydroxy-1-[[4-(trifluoromethyl)phenyl]methyl]ethyl]benzamide In the same manner as in Example 1 5), the objective substance (367 mg, 68%, (1RS,2SR) form/(1RS,2RS) form=1/2) was obtained as crystals.

mp 115–117° C.; ¹H-NMR (CDCl₃, 200 MHz) δ 3.00–3.22 (3H, m), 4.42–4.58 (1H, m), 4.82 (1H, m), 6.92–7.60 (12H, m); IR (KBr) 3447, 3333, 1644 cm⁻¹; Anal. Calcd for $C_{23}H_{18}F_5NO_2$: 63.45; H, 4.17; N, 3.22. Found: C, 63.45; H, 4.22; N, 3.15.

Example 19

4-tert-butyl-N-[2-(4-fluorophenyl)-2-hydroxy-1-[[4-(trifluoromethyl)phenyl]methyl]ethyl]benzamide 1) 4-tert-butyl-N-[2-(4-fluorophenyl)-2-oxo-1-[[4-(trifluoromethyl)phenyl]methyl]ethyl]benzamide In the same manner as in Example 1 4), the objective substance (1.06 g, 78%) was obtained as crystals.

mp 58° C.; ¹H-NMR (CDCl₃, 200 MHz) δ 1.34 (9H, s), 3.21 (1H, dd, J=5.6 Hz, 14.0 Hz), 3.48 (1H, dd, J=6.6 Hz, 14.0 Hz), 6.03 (1H, ddd, J=4.8 Hz, 5.6 Hz, 6.6 Hz), 7.04–7.26 (5H, m), 7.41–7.50 (4H, m), 7.68–7.75 (2H, m), 7.97–8.08 (2H, m); IR (KBr) 3299, 1694 cm⁻¹; Anal. Calcd for $C_{27}H_{25}F_4NO_2 \cdot 0.1H_2O$: C, 68.52; H, 5.37; N, 2.96. Found: C, 68.33; H, 5.22; N, 2.92.

2) 4-tert-butyl-N-[2-(4-fluorophenyl)-2-hydroxy-1-[[4-(trifluoromethyl)phenyl]methyl]ethyl]benzamide In the same manner as in Example 1 5), the objective substance (0.50 g, 97%, (1RS,2SR) form/(1RS,2RS) form=3/2) was obtained as an amorphous compound.

¹H-NMR (CDCl₃, 200 MHz) δ 1.31 (9H, s), 2.90–2.95 (2H×3/5, m), 3.14 (2H×2/5, d, J=7.4 Hz), 3.64 (1H×2/5, d, J=3.4 Hz), 3.83 (1H×3/5, d, J=3.4 Hz), 4.37 (2H×2/5, ddd, J=3.2 Hz, 7.2 Hz, 15.6 Hz), 4.53–4.68 (1H×3/5, m), 4.83 (1H×2/5, t, J=4.0 Hz), 5.06 (1H×3/5, t, J=6.6 Hz), 6.13 (1H×3/5, d, J=8.2 Hz), 6.37 (1H×2/5, d, J=8.4 Hz), 6.92–7.13 (2H, m), 7.21–7.32 (2H, m), 7.36–7.59 (8H, m); IR (KBr) 3301, 1620 cm⁻¹; Anal. Calcd for $C_{27}H_{27}F_4NO_2 \cdot 0.2H_2O$: C, 67.97; H, 5.79; N, 2.94. Found: C, 67.97; H, 5.80; N, 2.89.

Example 20

N-[2-(4-fluorophenyl)-2-hydroxy-1-[[4-(trifluoromethyl)phenyl]methyl]ethyl]-4-phenylbenzamide 1) N-[2-(4-fluorophenyl)-2-oxo-1-[[4-(trifluoromethyl)phenyl]methyl]ethyl]-4-phenylbenzamide In the same manner as in Example 1 4), the objective substance (1.24 g, 88%) was obtained as crystals.

mp 169° C.; ¹H-NMR (CDCl₃, 200 MHz) δ 3.24 (1H, dd, J=4.6 Hz, 14.0 Hz), 3.52 (1H, dd, J=6.4 Hz, 14.0 Hz), 6.04 (1H, ddd, J=4.6 Hz, 5.2 Hz, 6.4 Hz), 7.07–7.25 (5H, m), 7.38–7.52 (5H, m), 7.58–7.72 (4H, m), 7.86 (2H, d, J=8.8 Hz), 7.99–8.10 (2H, m); IR (KBr) 3291, 1688, 1645 cm⁻¹; Anal. Calcd for $C_{29}H_{21}F_4NO_2$: C, 70.87; H, 4.31; N, 2.85. Found: C, 70.89; H, 4.23; N, 2.86.

2) N-[2-(4-fluorophenyl)-2-hydroxy-1-[[4-(trifluoromethyl)phenyl]methyl]ethyl]-4-phenylbenzamide In the same manner as in Example 1 5), the objective substance (0.49 g, 96%, (1RS,2SR) form/(1RS,2RS) form=3/2) was obtained as crystals.

mp 178–185° C.; ¹H-NMR (CDCl₃, 200 MHz) δ 2.93–3.00 (2H×3/5, m), 3.17 (2H×2/5, d, J=7.6 Hz), 3.36 (1H×2/5, d, J=4.4 Hz), 3.63 (1H×3/5, d, J=3.2 Hz), 4.35–4.52 (1H×2/5, m), 4.55–4.71 (1H×3/5, m), 4.87 (1H×2/5, t, J=3.9 Hz), 5.11 (1H×3/5, t, J=3.6 Hz), 6.17 (1H×3/5, d, J=8.6 Hz), 6.42 (1H×2/5, d, J=8.0 Hz), 6.95–7.13 (2H, m), 7.24–7.68 (15H, m); IR (KBr) 3304, 1634 cm⁻¹; Anal. Calcd for $C_{29}H_{23}F_4NO_2$: C, 70.58; H, 4.70; N, 2.84. Found: C, 70.53; H, 4.72; N, 2.72.

Example 21

N-[2-(4-fluorophenyl)-2-hydroxy-1-[[4-(trifluoromethyl)phenyl]methyl]ethyl]-3-pyridinecarboxamide 1) N-[2-(4-fluorophenyl)-2-oxo-1-[[4-(trifluoromethyl)phenyl]methyl]ethyl]-3-pyridinecarboxamide In the same manner as in Example 1 4), the objective substance (0.74 g, 62%) was obtained as crystals.

mp 137–138° C.; ¹H-NMR (CDCl₃, 200 MHz) δ 3.23 (1H, dd, J=5.0 Hz, 13.8 Hz), 3.49 (1H, dd, J=6.6 Hz, 14.0 Hz), 5.98–6.07 (1H, m), 7.06–7.26 (5H, m), 7.37–7.43 (1H, m), 7.47 (2H, d, J=8.4 Hz), 7.98–8.11 (3H, m), 8.76 (1H, dd, J=1.8 Hz, 4.8 Hz), 9.00 (1H, dd, J=0.8 Hz, 2.2 Hz); IR (KBr) 3287, 1694, 1661 cm⁻¹; Anal. Calcd for $C_{22}H_{16}F_4N_2O_2$: C, 63.46; H, 3.87; N, 6.73. Found: C, 63.19; H, 4.03; N, 6.68.

2) N-[2-(4-fluorophenyl)-2-hydroxy-1-[[4-(trifluoromethyl)phenyl]methyl]ethyl]-3-pyridinecarboxamide In the same manner as in Example 1 5), the objective substance (0.43 g, 86%, (1RS,2SR) form/(1RS,2RS) form=5/2) was obtained as crystals.

mp 160–165° C.; ¹H-NMR (CDCl₃, 200 MHz) δ 2.95 (2H×5/7, br s), 3.10 (1H×2/7, br s), 3.16 (2H×2/7, d, J=7.0 Hz), 3.35 (1H×5/7, br s), 4.43–4.75 (1H, m), 4.86 (1H×2/7, br s), 5.10 (1H×5/7, br s), 6.25 (1H×5/7, br d, J=8.6 Hz), 6.48 (1H×2/7, br d, J=8.8 Hz), 6.95–7.16 (2H, m), 7.21–7.62 (7H, m), 7.87–7.95 (1H, m), 8.66–8.80 (2H, m); IR (KBr) 3324, 3142, 1644 cm⁻¹; Anal. Calcd for $C_{22}H_{18}F_4N_2O_2$: C, 63.16; H, 4.34; N, 6.70. Found: C, 62.97; H, 4.24; N, 6.51.

Example 22

N-(2-(4-fluorophenyl)-2-hydroxy-1-((4-(trifluoromethyl)phenyl)methyl)ethyl)-4-oxo-4H-pyran-2-carboxamide and N-(2-(4-fluorophenyl)-2-hydroxy-1-((4-(trifluoromethyl)phenyl)methyl)ethyl)-4-hydroxytetrahydro-2H-pyran-2-carboxamide 1) To a solution of 1-(4-fluorophenyl)-1-oxo-3-(4-(trifluoromethyl)phenyl)-2-propylamine hydrochloride (600 mg, 1.73 mmol) and 4-oxo-4H-pyran-2-carboxylic acid (266 mg, 1.90 mmol) in N,N-dimethylformamide (10 ml) were added 1-ethyl-3-(3-dimethylaminopropyl)carbodiimide hydrochloride (496 mg, 2.59 mmol), 1-hydroxy-1H-benzotriazole (396 mg, 2.59 mmol) and 1,8-diazabicyclo[5.4.0]-7-undecene (0.28 ml, 1.90 mmol) and the mixture was stirred overnight. To the reaction solution were added 1N aqueous hydrochloric acid solution (10 ml) and water (100 ml) and the mixture was extracted with ethyl acetate (50 ml×2). The extract was washed with 1N aqueous sodium hydroxide solution and saturated brine, dried over anhydrous magnesium sulfate and evaporated under reduced pressure. The residue was purified by silica gel column chromatography (ethyl acetate) and recrystallized from ethyl acetate-hexane to give N-(2-(4-fluorophenyl)-2-oxo-1-((4-(trifluoromethyl)phenyl)methyl)ethyl)-4-oxo-4H-pyran-2-carboxamide (570 mg, 76%).

mp 115–116° C. IR ν max$^{KBr}$cm$^{-1}$: 1661, 1620, 1597, 1510, 1412. Anal. Calcd for $C_{22}H_{15}F_4NO_4 \cdot 0.1H_2O$: C, 60.72; H, 3.52; N, 3.22. Found: C, 60.60; H, 3.55; N, 3.24. $^1$H-NMR (CDCl$_3$)δ: 3.23 (1H, dd, J=14.0, 5.2 Hz), 3.43 (1H, dd, J=14.0, 5.2 Hz), 5.93 (1H, q, J=6.4 Hz), 6.44 (1H, dd, J=5.8, 2.6 Hz), 7.07 (2H, d, J=8.0 Hz), 7.10–7.26 (2H, m), 7.48 (2H, d, J=8.0 Hz), 7.59 (1H, d, J=7.4 Hz), 7.77 (1H, d, J=6.0 Hz), 7.92–8.06 (2H, m).

2) To a solution of N-(2-(4-fluorophenyl)-2-oxo-1-((4-(trifluoromethyl)phenyl)methyl)ethyl)-4-oxo-4H-pyran-2-carboxamide (400 mg, 0.92 mmol) in methanol (30 ml) was added manganese (II) chloride (232 mg, 1.85 mmol), and the mixture was stirred at room temperature for 30 min. To the reaction solution was added sodium borohydride (70 mg, 1.85 mmol) under ice-cooling and the mixture was stirred for 1 hr. The reaction solution was poured into 1N hydrochloric acid (30 ml), and extracted with ethyl acetate (50 ml×2). The extract was washed with water and saturated brine, dried over anhydrous magnesium sulfate and evaporated under reduced pressure. The residue was purified by silica gel column chromatography (ethyl acetate). High polar fractions were collected and concentrated, and the obtained crude crystal was washed with hexane to give N-(2-(4-fluorophenyl)-2-hydroxy-1-((4-(trifluoromethyl)phenyl)methyl)ethyl)-4-oxo-4H-pyran-2-carboxamide ((1RS,2SR) form: (1RS,2RS) form=3:2, 139 mg, 35%).

IR ν max$^{KBr}$cm$^{-1}$: 1659, 1607, 1512, 1416. Anal. Calcd for $C_{22}H_{17}F_4NO_4 \cdot 0.1H_2O$: C, 60.44; H, 3.97; N, 3.20. Found: C, 61.24; H, 3.93; N, 3.03. $^1$H-NMR (CDCl$_3$)δ: 2.60–2.82 (1H, m), 2.90–2.96 (1H, m), 3.04–3.20 (1H, m), 4.40–4.70 (1H, m), 4.78–4.84 (2/5H, m), 5.02–5.10 (3/5H, m), 6.36–6.42 (1H, m), 6.70–7.80 (11H, m).

Simultaneously, less polar fractions were collected and concentrated to give N-(2-(4-fluorophenyl)-2-hydroxy-1-((4-(trifluoromethyl)phenyl)methyl)ethyl)-4-hydroxytetrahydro-2H-pyran-2-carboxamide((1RS,2SR) form: (1RS,2RS) form=7:3, 139 mg, 35%) as an amorphous compound.

IR ν max$^{KBr}$cm$^{-1}$: 1645, 1510. Anal. Calcd for $C_{22}H_{23}F_4NO_4$: C, 59.86; H, 5.25; N, 3.17. Found: C, 60.02; H, 5.01; N, 3.04. $^1$H-NMR (CDCl$_3$)δ: 1.70–2.00 (3H, m), 2.70–3.40 (3H, m), 3.70–4.60 (4H, m), 4.68–4.78 (0.3H, m), 4.92–5.04 (0.7H, m), 6.00 (0.3H, d, J=4.8 Hz), 6.05 (0.7H, d, J=4.6 Hz), 4.58–6.70 (0.7H, m), 6.76–6.90 (0.3H, m), 6.95–7.60 (8H, m).

Example 23

4-fluoro-N-[2-(4-fluorophenyl)-2-hydroxy-1-[[4-(trifluoromethyl)phenyl]methyl]ethyl]benzenesulfonamide 1) 4-fluoro-N-[2-(4-fluorophenyl)-2-oxo-1-[[4-(trifluoromethyl)phenyl]methyl]ethyl]benzenesulfonamide To a solution of 2-(4-fluorophenyl)-2-oxo-1-[[4-(trifluoromethyl)phenyl]methyl]ethylamine hydrochloride (1.0 g, 2.88 mmol) in N,N-dimethylformamide, (10 ml) were added 4-fluorobenzenesulfonyl chloride (0.84 g, 4.32 mmol) and 1,8-diazabicyclo[5.4.0]-7-undecene (1.3 ml, 8.64 mmol) and the mixture was stirred for 4 hrs. The reaction solution was extracted with ethyl acetate. The extract was washed successively with water and saturated brine, dried over magnesium sulfate and concentrated under reduced pressure. The residue was recrystallized from ethyl acetate-hexane to give the objective substance (1.02 g, 76%) as crystals.

mp 209–210° C.; $^1$H-NMR (CDCl$_3$, 200 MHz) δ 2.96 (1H, dd, J=6.6 Hz, 14.0 Hz), 3.20 (1H, dd, J=5.6 Hz, 14.6 Hz), 5.05–5.18 (1H, m), 5.62 (1H, br d, J=6.4 Hz), 7.00 (2H, t, J=8.6 Hz), 7.04–7.20 (4H, m), 7.45 (2H, d, J=8.0 Hz), 7.65–7.72 (2H, m), 7.77–7.84 (2H, m); IR (KBr) 3229, 1676, 1595 cm$^{-1}$; Anal. Calcd for $C_{22}H_{16}F_5NO_3S$: C, 56.29; H, 3.44; N, 2.98. Found: C, 56.15; H, 3.46; N, 3.26.

2) 4-fluoro-N-[2-(4-fluorophenyl)-2-hydroxy-1-[[4-(trifluoromethyl)phenyl]methyl]ethyl]benzenesulfonamide To a solution of 4-fluoro-N-[2-(4-fluorophenyl)-2-oxo-1-[[4-(trifluoromethyl)phenyl]methyl]ethyl]benzenesulfonamide (0.5 g, 1.07 mmol) in methanol (5 ml) was added sodium borohydride (45 mg, 1.19 mmol) under ice-cooling and the mixture-was stirred for 1 hr. 1N Hydrochloric acid was added to the reaction solution and the mixture was stirred at room temperature for 10 min. The reaction solution was extracted with ethyl acetate. The extract was washed successively with water and saturated brine, dried over magnesium sulfate and concentrated under reduced pressure. The residue was purified by silica gel column chromatography (ethyl acetate/hexane=1/2) to give the objective substance (0.45 g, 89%, ⅓ mixture of isomers) as crystals.

mp 141–161° C.; $^1$H-NMR (CDCl$_3$, 200 MHz) δ 2.30 (3/4H, d, J=3.4 Hz), 2.52–2.79 (6/4H, m), 3.13 (3/4H, dd, J=7.0 Hz, 14.0 Hz), 3.59 (1H, ddd, J=3.6 Hz, 7.4 Hz, 15.8 Hz), 4.75–4.83 (7/4H, m), 5.08–5.13 (1/4H, m), 6.83–7.00 (4H, m), 7.04–7.22 (4H, m), 7.29–7.49 (4H, m); IR (KBr) 3482, 3293 cm$^{-1}$

Example 24

1,1-dimethylethyl(1RS,2RS)-2-(4-fluorophenyl)-2-hydroxy-1-((4-(trifluoromethyl)phenyl)methyl)ethylcarbamate 1) To a solution of 4'-fluoroacetophenone (57.8 g, 0.307 mol) and ethanol (1 ml) in diethyl carbonate (300 ml) was added sodium hydride (24.5 g, 60% in oil, 0.63 mol) by small portions. Because heat is gradually generated, the mixture was ice-cooled and stirred at room temperature for 2 hrs. To the reaction solution was added 6N hydrochloric acid to quench the reaction. Water (300 ml) was added and the mixture was extracted with ethyl acetate. The extract was washed with water, dried over anhydrous magnesium sulfate and evaporated under reduced pressure. The residue was purified by silica gel column chromatography (hexane:ethyl acetate=50:1–5:1) to give ethyl 3-(4-fluorophenyl)-3-oxopropionate (71.2 g, 89%).

IR ν max$^{KBr}$cm$^{-1}$: 1744, 1696, 1431, 1325, 1202, 1132, 1069, 1017, 853. $^1$H-NMR (CDCl$_3$)δ: 1.28 (3H×0.62, t, J=7.8 Hz), 1.37 (3H×0.38, t, J=7.8 Hz), 4.04 (2H×0.62, s), 4.25 (2H×0.62, q, J=7.8 Hz), 4.31 (2H×0.38, q, J=7.8 Hz), 5.75 (1H×0.38, s), 7.28 (1H×0.62, s), 7.70 (2H×0.38, d, J=8.0 Hz), 7.78 (2H×0.62, d, J=8.0 Hz), 7.90 (2H×0.38, d, J=8.0 Hz), 8.08 (2H×0.62, d, J=8.0 Hz).

2) To a solution of ethyl 3-(4-fluorophenyl)-3-oxopropionate (34.7 g, 115.5 mmol) in acetonitrile (300 ml) were added 4-trifluoromethylbenzyl bromide (27.6 g, 115.5 mmol) and potassium carbonate (31.9 g, 231 mmol), and the mixture was stirred at room temperature for 4 hrs. The reaction solution was diluted with water (1 L) and extracted with ethyl acetate (500 ml×2). The extract was washed with water and saturated brine, dried over anhydrous magnesium sulfate and evaporated under reduced pressure. Hexane was added to the residue and the precipitated crystals were washed with hexane to give ethyl 3-(4-fluorophenyl)-3-oxo-2-((4-(trifluoromethyl)phenyl)methyl)propionate (31 g, 76%).

mp 56–57° C. IR ν max$^{KBr}$cm$^{-1}$: 1738, 1688, 1618, 1599, 1508. Anal. Calcd for C$_{19}$H$_{16}$F$_4$O$_3$: C, 61.96; H, 4.38 Found: C, 61.90; H, 4.43. $^1$H-NMR (CDCl$_3$)δ: 1.16 (3H, t, J=6.8 Hz), 3.38 (2H, d, J=7.6 Hz), 4.14 (2H, q, J=6.8 Hz), 4.58 (1H, t, J=7.6 Hz), 7.04–7.20 (2H, m), 7.35 (2H, d, J=8.0 Hz), 7.52 (2H, d, J=8.0 Hz), 7.92–8.08 (2H, m).

3) To a solution of ethyl 3-(4-fluorophenyl)-3-oxo-2-((4-(trifluoromethyl)phenyl)methyl)propionate (6 g, 16.3 mmol) in methanol (100 ml) was added sodium borohydride (640 mg, 16.9 mmol) under ice-cooling, and the mixture was stirred for 20 min. The reaction solution was poured into 1N hydrochloric acid (50 ml), and extracted with ethyl acetate (100 ml×2). The extract was washed with water and saturated brine, dried over anhydrous magnesium sulfate and evaporated under reduced pressure. The residue was purified by silica gel column chromatography (hexane:ethyl acetate= 4:1) to give ethyl (2RS,3SR)-3-(4-fluorophenyl)-3-hydroxy-2-((4-(trifluoromethyl)phenyl)methyl)propionate (5.1 g, 84%) as a colorless oil.

IR ν max$^{KBr}$cm$^{-1}$: 1728, 1607, 1510. Anal. Calcd for C$_{19}$H$_{18}$F$_4$O$_3$: C, 61.62; H, 4.90. Found: C, 61.52; H, 4.88. $^1$H-NMR (CDCl$_3$)δ: 0.99 (3H, t, J=7.4 Hz), 2.70–3.10 (3H, m), 3.13 (1H, d, J=6.2 Hz), 3.99 (2H, q, J=7.4 Hz), 4.76–4.86 (1H, m), 6.98–7.16 (2H, m), 7.20–7.40 (4H, m), 7.52 (2H, d, J=8.0 Hz).

4) To a solution of ethyl (2RS,3SR)-3-(4-fluorophenyl)-3-hydroxy-2-((4-(trifluoromethyl)phenyl)methyl)propionate (4.85 g, 13.1 mmol) in methanol (20 ml) was added 1N aqueous sodium hydroxide solution (13.1 ml, 13.1 mmol), and the mixture was stirred at room temperature for 6 hrs. The reaction solution was evaporated under reduced pressure, diluted with 1N hydrochloric acid (50 ml), and extracted with ethyl acetate (100 ml×2). The extract was washed with water and saturated brine, dried over anhydrous magnesium sulfate and evaporated under reduced pressure. The residue was recrystallized from ethyl acetate-hexane to give (2RS,3SR)-3-(4-fluorophenyl)-3-hydroxy-2-((4-(trifluoromethyl)phenyl)methyl)propionic acid (3.8 g, 84%).

mp 136–139° C.; $^1$H-NMR (CDCl$_3$, 200M Hz)δ2.75 (1H, dd, J=5.8 Hz, 13.4 Hz), 2.95 (1H, dd, J=9.2 Hz, 13.2 Hz), 3.08 (2H, d, J=8.0 Hz), 4.82 (1H, d, J=7.0 Hz), 7.08 (2H, t, J=8.8 Hz), 7.22 (2H, d, J=8.0 Hz), 7.34 (2H, dd, J=5.3 Hz, 8.8 Hz); IR (KBr) 3351, 3500–2400, 1713 cm$^{-1}$; Anal. Calcd for C$_{17}$H$_{14}$F$_4$O$_3$: C, 59.65; H, 4.12. Found: C, 59.52; H, 4.17.

5) To a solution of (2RS,3SR)-3-(4-fluorophenyl)-3-hydroxy-2-((4-(trifluoromethyl)phenyl)methyl)propionic acid (3.75 g, 11.0 mmol) in tetrahydrofuran (70 ml) were added diphenylphosphoryl azide (2.6 ml, 12.1 mmol) and triethylamine (2.30 ml, 16.4 mmol) and the mixture was heated under reflux for 3 hrs. The reaction solution was diluted with water (300 ml), and extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=2:1–1:1) and recrystallized from ethyl acetate-hexane to give (4RS, 5RS)-5-(4-fluorophenyl)-4-((4-(trifluoromethyl)phenyl)methyl)-1,3-oxazolidin-2-one (3.28 g, 88%).

mp 83–84° C. IR ν max$^{KBr}$cm$^{-1}$: 1755, 1609, 1514, 1420, 1387. Anal. Calcd for C$_{17}$H$_{13}$F$_4$NO$_2$: C, 60.18; H, 3.86; N, 4.13. Found: C, 60.08; H, 3.56; N, 4.10. $^1$H-NMR (CDCl$_3$)δ: 2.90–3.16 (2H, m), 3.95 (1H, dd, J=12.8, 6.2 Hz), 5.19 (1H, d, J=6.2 Hz), 5.73 (1H, brs), 7.00–7.12 (2H, m), 7.12–7.40 (4H, m), 7.60 (2H, d, J=8.0 Hz).

6) To a solution of (4RS,5RS)-5-(4-fluorophenyl)-4-((4-(trifluoromethyl)phenyl)methyl)-1,3-oxazolidin-2-one (3.19 g, 9.41 mmol) in acetonitrile (30 ml) were added di-t-butyl dicarbonate (2.46 g, 11.29 mmol) and 4-dimethylaminopyridine (114 mg, 0.94 mmol) and the mixture was stirred at room temperature for 1 hr. The reaction solution was diluted with water (100 ml), and extracted with ethyl acetate (100 ml×2). The extract was washed with saturated brine, dried over anhydrous magnesium sulfate and evaporated under reduced pressure. Recrystallization from ethyl acetate-hexane gave 1,1-dimethylethyl (4RS, 5RS)-5-(4-fluorophenyl)-2-oxo-4-((4-(trifluoromethyl)phenyl)methyl)-1,3-oxazolidine-3-carboxylate (3.84 g, 93%).

mp 126–127° C. IR ν max$^{KBr}$cm$^{-1}$: 1817, 1724, 1514, 1325. Anal. Calcd for C$_{22}$H$_{21}$F$_4$NO$_4$: C, 60.14; H, 4.82; N, 3.19. Found: C, 60.05; H, 5.12; N, 3.11. $^1$H-NMR (CDCl$_3$)δ: 1.58 (9H, s), 3.01 (1H, dd, J=13.2, 9.8 Hz), 3.51 (1H, dd, J=13.2, 3.6 Hz), 4.26–4.38 (1H, m), 5.13 (1H, d, J=2.6 Hz), 6.80–7.04 (4H, m), 7.38 (2H, d, J=8.0 Hz), 7.65 (2H, d, J=8.0 Hz).

7) To a solution of 1,1-dimethylethyl (4RS,5RS)-5-(4-fluorophenyl)-2-oxo-4-((4-(trifluoromethyl)phenyl)methyl)-1,3-oxazolidine-3-carboxylate (3.7 g, 8.42 mmol) in methanol (20 ml) was gradually added a solution of sodium hydroxide (0.40 g, 10.10 mmol) in methanol (20 ml) under ice-cooling. The reaction solution was stirred for 1 hr, diluted with 1N hydrochloric acid (15 ml) and water (100 ml), and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (2.24 g, 64%).

mp 95–96° C. IR ν max$^{KBr}$cm$^{-1}$: 1688, 1510. Anal. Calcd for C$_{21}$H$_{23}$F$_4$NO$_3$: C, 61.01; H, 5.61; N, 3.39. Found: C, 60.92; H, 5.55; N, 3.28. $^1$H-NMR (CDCl$_3$)δ: 1.31 (9H, s), 2.80–3.10 (3H, m), 3.80–4.02 (1H, m), 4.62–4.80 (2H, m), 6.96–7.10 (2H, m), 7.22–7.40 (4H, m), 7.55 (2H, d, J=8.2 Hz).

Example 25

2-(ethyloxy)-N-((1RS,2RS)-2-(4-fluorophenyl)-2-hydroxy-1-((4-(trifluoromethyl)phenyl)methyl)ethyl)-1-naphthalenecarboxamide 1) To a solution of 1-(4-fluorophenyl)-1-oxo-3-(4-(trifluoromethyl)phenyl)-2-propylamine hydrochloride (600 mg, 1.73 mmol) and 2-ethyloxy-1-naphthalenecarboxylic acid (411 mg, 1.90 mmol) in N,N-dimethylformamide (10 ml) were added 1-ethyl-3-(3-dimethylaminopropyl) carbodiimide hydrochloride (496 mg, 2.59 mmol), 1-hydroxy-1H-benzotriazole (396 mg, 2.59 mmol) and 1,8-diazabicyclo[5.4.0]-7-undecene (0.28 ml, 1.90 mmol) and the mixture was stirred overnight. To the reaction solution were added 1N aqueous hydrochloric acid solution (10 ml) and water (100 ml) and the mixture was extracted with ethyl acetate (50 ml×2). The extract was washed with 1N aqueous sodium hydroxide solution and saturated brine, dried over anhydrous magnesium sulfate and evaporated under reduced pressure. Recrystallization from ethyl acetate-hexane gave 2-(ethyloxy)-N-(2-(4-fluorophenyl)-2-oxo-1-((4-(trifluoromethyl)phenyl)methyl)ethyl)-1-naphthalenecarboxamide (670 mg, 76%).

mp 188–189° C. IR ν max$^{KBr}$cm$^{-1}$: 1688, 1634, 1597, 1508, 1325. Anal. Calcd for $C_{29}H_{23}F_4NO_3$: C, 68.36; H, 4.55; N, 2.75. Found: C, 68.25; H, 4.58; N, 2.76. $^1$H-NMR (CDCl$_3$)δ: 1, 24 (3H, t, J=7.0 Hz), 3.20 (1H, dd, J=14.0, 6.4 Hz), 3.46 (1H, dd, J=14.0, 6.4 Hz), 4.13 (2H, q, J=7.0 Hz), 6.23 (1H, q, J=6.6 Hz), 6.96 (1H, d, J=8.4 Hz), 7.10–7.56 (9H, m), 7.60–7.80 (2H, m), 7.85 (1H, d, J=9.0 Hz), 8.04–8.18 (2H, m).

2) To a solution of 2-(ethyloxy)-N-(2-(4-fluorophenyl)-2-oxo-1-((4-(trifluoromethyl)phenyl)methyl)ethyl)-1-naphthalenecarboxamide (400 mg, 0.79 mmol) in methanol (30 ml) was added manganese (II) chloride (198 mg, 1.57 mmol), and the mixture was stirred at room temperature for 30 min. To the reaction solution was added sodium borohydride (30 mg, 0.79 mmol) under ice-cooling, and the mixture was stirred for 1 hr. The reaction solution was poured into 1N hydrochloric acid (30 ml), and extracted with ethyl acetate (50 ml×2). The extract was washed with water and saturated brine, dried over anhydrous magnesium sulfate and evaporated under reduced pressure. The residue was purified by silica gel column chromatography (hexane:ethyl acetate=2:1–1:1 and recrystallized from ethyl acetate-hexane to give the title compound (227 mg, 57%).

mp 186–187° C. IR ν max$^{KBr}$cm$^{-1}$: 1639, 1512, 1242, 1165. Anal. Calcd for $C_{29}H_{25}F_4NO_3$: C, 68.09; H, 4.93; N, 2.74. Found: C, 68.04; H, 4.79; N, 2.85. $^1$H-NMR (CDCl$_3$)δ: 1.37 (3H, t, 6.8 Hz), 2.84–3.28 (2H, m), 3.34 (1H, d, J=3.8 Hz), 4.08–4.26 (2H, m), 4.60–4.84 (2H, m), 6.15 (1H, d, J=8.6 Hz), 6.96–7.16 (3H, m), 7.20–7.50 (7H, m), 7.58 (2H, d, J=8.4 Hz), 7.76 (2H, dd, J=18.2, 9.2 Hz).

Example 26

N-((1RS,2RS)-2-(4-fluorophenyl)-2-hydroxy-1-((4-(trifluoromethyl)phenyl)methyl)ethyl)-1-naphthalenecarboxamide 1) To a solution of 1,1-dimethylethyl (1RS,2RS)-2-(4-fluorophenyl)-2-hydroxy-1-((4-(trifluoromethyl)phenyl)methyl)ethylcarbamate (2.1 g, 5.08 mmol) in ethanol (25 ml) was added 20% hydrogen chloride ethanol solution (25 ml) and the mixture was heated under reflux for 1 hr. The reaction solution was evaporated under reduced pressure, and the residue was washed with diethyl ether to give (1RS,2RS)-1-(4-fluorophenyl)-1-hydroxy-3-(4-(trifluoromethyl)phenyl)-2-propylamine hydrochloride (1.7 g, 96%).

mp 166–167° C. IR ν max$^{KBr}$cm$^{-1}$: 1605, 1514, 1497. Anal. Calcd for $C_{16}H_{16}ClF_4NO$: C, 54.11; H, 4.71; N, 3.94. Found: C, 54.10; H, 4.62; N, 3.83. $^1$H-NMR (CD$_3$OD)δ: 2.98 (2H, d, J=7.4 Hz), 3.60–3.78 (1H, m), 4.63 (1H, d, J=6.2 Hz), 7.04–7.16 (2H, m), 7.36–7.50 (4H, m), 7.61 (2H, d, J=8.4 Hz).

2) To a solution of (1RS,2RS)-1-(4-fluorophenyl)-1-hydroxy-3-(4-(trifluoromethyl)phenyl)-2-propylamine hydrochloride (150 mg, 0.43 mmol) in ethyl acetate (5 ml) were added 1-naphthoyl chloride (97 mg, 0.64 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1–1:1), and recrystallized from ethyl acetate-hexane to give the title compound (145 mg, 72%).

mp 134–135° C. IR ν max$^{KBr}$cm$^{-1}$: 1634, 1510. Anal. Calcd for $C_{27}H_{21}F_4NO_2$: C, 69.37; H, 4.53; N, 3.00. Found: C, 69.08; H, 4.80; N, 3.01. $^1$H-NMR (CDCl$_3$)δ: 3.18–3.30 (3H, m), 4.54–4.72 (1H, m), 4.92 (1H, brs), 6.20 (1H, d, J=8.8 Hz), 6.96–7.14 (2H, m), 7.16–7.70 (11H, m), 7.78–7.90 (2H, m).

Example 27

N-((1RS,2RS)-2-(4-fluorophenyl)-2-hydroxy-1-((4-(trifluoromethyl)phenyl)methyl)ethyl)-4-(trifluoromethyl)benzamide To a solution of (1RS,2RS)-1-(4-fluorophenyl)-1-hydroxy-3-(4-(trifluoromethyl)phenyl)-2-propylamine hydrochloride (150 mg, 0.43 mmol) in ethyl acetate (5 ml) were added 4-trifluorobenzoyl chloride (96 mg, 0.64 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (129 mg, 62%).

mp 162–163° C. IR ν max$^{KBr}$cm$^{-1}$: 1653, 1508, 1329. Anal. Calcd for $C_{24}H_{18}F_7NO_2$: C, 59.39; H, 3.74; N, 2.89. Found: C, 59.20; H, 4.01; N, 2.91. $^1$H-NMR (CDCl$_3$)δ: 3.18–3.30 (3H, m), 4.54–4.72 (1H, m), 4.92 (1H, brs), 6.20 (1H, d, J=8.8 Hz), 6.96–7.14 (2H, m), 7.16–7.70 (11H, m), 7.78–7.90 (2H, m).

Example 28

1,1-dimethylethyl (1RS,2SR)-2-(4-fluorophenyl)-2-hydroxy-1-((4-(trifluoromethyl)phenyl)methyl)ethylcarbamate 1) To a solution of ethyl 3-(4-fluorophenyl)-3-oxo-2-((4-(trifluoromethyl)phenyl)methyl)propionate (20.8 g, 56.5 mmol) in methanol (500 ml) was added manganese (II) chloride (14.2 g, 113 mmol), and the mixture was stirred at room temperature for 30 min. To the reaction solution was added sodium borohydride (4.28 g, 113 mmol) under ice-cooling, and the mixture was stirred for 20 min. The reaction solution was poured into 1N hydrochloric acid (300 ml) and extracted with ethyl acetate (500 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(4-fluorophenyl)-3-hydroxy-2-((4-(trifluoromethyl)phenyl)methyl)propionate (11.1 g, 53%) as a colorless oil.

IR ν max$^{KBr}$cm$^{-1}$: 1726, 1618, 1607, 1510. Anal. Calcd for $C_{19}H_{18}F_4O_3$: C, 61.62; H, 4.90. Found: C, 61.62; H, 5.06. $^1$H-NMR (CDCl$_3$)δ: 0.91 (3H, t, J=7.0 Hz), 2.88–3.10 (4H, m), 3.88 (2H, q, J=7.0 Hz), 4.98–5.06 (1H, m), 6.96–7.12 (2H, m), 7.20 (2H, d, J=8.0 Hz), 7.30–7.44 (2H, m), 7.49 (2H, d, J=8.0 Hz).

2) To a solution of ethyl (2RS,3RS)-3-(4-fluorophenyl)-3-hydroxy-2-((4-(trifluoromethyl)phenyl)methyl)propionate (11.0 g, 29.7 mmol) in methanol (90 ml) was added 1N aqueous sodium hydroxide solution (59.6 ml, 59.6 mmol), and the mixture was stirred at room temperature for 6 hrs. The reaction solution was evaporated under reduced pressure, diluted with 1N hydrochloric acid (100 ml), and extracted with ethyl acetate (200 ml×2). The extract was washed with water and saturated brine, dried over anhydrous magnesium sulfate and evaporated under reduced pressure. Recrystallization from ethyl acetate-hexane gave (2RS,3RS)-3-(4-fluorophenyl)-3-hydroxy-2-((4-(trifluoromethyl)phenyl)methyl)propionic acid (8.6 g, 85%).

mp 111–112° C. IR ν max$^{KBr}$cm$^{-1}$: 1713, 1607, 1512. Anal. Calcd for $C_{17}H_{14}O_3F_4$: C, 59.65; H, 4.12. Found: C, 59.65; H, 4.07. $^1$H-NMR (CDCl$_3$)δ: 2.08 (1H, s), 2.94–3.20 (3H, m), 5.04–5.10 (1H, m), 6.98–7.12 (2H, m), 7.18 (2H, d, J=8.0 Hz), 7.30–7.42 (2H, m), 7.48 (2H, d, J=8.0 Hz).

3) To a solution of (2RS,3RS)-3-(4-fluorophenyl)-3-hydroxy-2-((4-(trifluoromethyl)phenyl)methyl)propionic acid (4.30 g, 12.6 mmol) in tetrahydrofuran (80 ml) were added diphenylphosphoryl azide (3.0 ml, 13.8 mmol) and triethylamine (2.63 ml, 18.8 mmol) and the mixture was heated under reflux for 4 hrs. The reaction solution was diluted with water (300 ml) and extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=2:1–1:1) and recrystallized from ethyl acetate-hexane to give (4RS,5SR)-5-(4-fluorophenyl)-4-((4-(trifluoromethyl)phenyl)methyl)-1,3-oxazolidin-2-one (3.55 g, 83%).

mp 154–155° C. IR ν max$^{KBr}$cm$^{-1}$: 1755, 1611, 1514, 1235. Anal. Calcd for $C_{17}H_{13}F_4NO_2$: C, 60.18; H, 3.86; N, 4.13. Found: C, 60.20; H, 3.80; N, 4.21. $^1$H-NMR (CDCl$_3$)δ: 2.20–2.44 (2H, m), 4.26 (1H, q, J=8.0 Hz), 5.25 (1H, brs), 5.79 (1H, d, J=8.0 Hz), 7.06–7.20 (4H, m), 7.28–7.40 (2H, m), 7.54 (2H, d, J=8.0 Hz).

4) To a solution of (4RS,5SR)-5-(4-fluorophenyl)-4-((4-(trifluoromethyl)phenyl)methyl)-1,3-oxazolidin-2-one (3.50 g, 10.32 mmol) in acetonitrile (30 ml) were added di-t-butyl dicarbonate (2.70 g, 12.39 mmol) and 4-dimethylaminopyridine (126 mg, 1.03 mmol) and the mixture was stirred at room temperature for 1 hr. The reaction solution was diluted with water (100 ml) and extracted with ethyl acetate (100 ml×2). The extract was washed with saturated brine, dried over anhydrous magnesium sulfate and evaporated under reduced pressure. Recrystallization from ethyl acetate-hexane gave 1,1-dimethylethyl (4RS,5SR)-5-(4-fluorophenyl)-2-oxo-4-((4-(trifluoromethyl)phenyl)methyl)-1,3-oxazolidine-3-carboxylate (4.09 g, 90%).

mp 155–156° C. IR ν max$^{KBr}$cm$^{-1}$: 1821, 1724, 1514, 1360. Anal. Calcd for $C_{22}H_{21}F_4NO_4$: C, 60.14; H, 4.82; N, 3.19. Found: C, 60.16; H, 4.84; N, 3.25. $^1$H-NMR (CDCl$_3$)δ: 1.48 (9H, s), 2.61 (1H, dd, J=14.2, 8.4 Hz), 2.91 (1H, dd, J=14.2, 5.2 Hz), 4.80 (1H, dd, J=8.4, 7.0 Hz), 5.68 (1H, d, J=7.0 Hz), 6.82 (2H, d, J=8.0 Hz), 6.92–7.06 (2H, m), 7.10–7.24 (2H, m), 7.36 (2H, d, J=8.0 Hz).

5) To a solution of 1,1-dimethylethyl (4RS,5SR)-5-(4-fluorophenyl)-2-oxo-4-((4-(trifluoromethyl)phenyl)methyl)-1,3-oxazolidine-3-carboxylate (4.0 g, 9.10 mmol) in methanol (22 ml) was gradually added a solution of sodium hydroxide (0.44 g, 10.92 mmol) in methanol (22 ml) under ice-cooling. The reaction solution was stirred for 3 hrs., diluted with 1N hydrochloric acid (12 ml) and water (100 ml), and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (2.90 g, 77%).

mp 158–159° C. IR ν max$^{KBr}$cm$^{-1}$: 3358, 1682, 1532, 1514. Anal. Calcd for $C_{21}H_{23}F_4NO_3$: C, 61.01; H, 5.61; N, 3.39. Found: C, 60.95; H, 5.59; N, 3.20. $^1$H-NMR (CDCl$_3$)δ: 1.32 (9H, s), 2.60–2.90 (2H, m), 3.11 (1H, brs), 4.00–4.20 (1H, m), 4.58 (1H, d, J=8.4 Hz), 4.92 (1H, s), 7.02–7.14 (2H, m), 7.22 (2H, d, J=8.0 Hz), 7.32–7.44 (2H, m), 7.51 (2H, d, J=8.0 Hz).

Example 29

N-[(1RS,2SR)-2-(4-fluorophenyl)-2-hydroxy-1-[4-(trifluoromethyl)benzyl]ethyl]-6,7-dihydro-5H-benzo[a]cycloheptene-1-carboxamide 1) 6,7-dihydro-5H-benzo[a]cyclohepten-1-ylmethanol To a solution of tert-butyl(6,7-dihydro-5H-benzo[a]cyclohepten-1-ylmethoxy)dimethylsilane (see *Tetrahedron*, 53, 15969–15982 (1990))(1.079 g, 3.740 mmol) in tetrahydrofuran (30 ml) was added a 1.0 M solution (3.74 ml, 3.74 mmol) of tetrabutylammonium fluoride in tetrahydrofuran, and the mixture was stirred at room temperature for 15 min. The reaction solution was concentrated and the obtained crude product was purified by silica gel column chromatography (hexane/ethyl acetate=6/1–1/1) to give the objective substance.

colorless liquid yield 0.573 g, 88% $^1$H-NMR (CDCl$_3$, 200 MHz) δ 1.99–2.25 (4H, m), 2.71 (2H, t, J=6.0 Hz), 4.73 (2H, s), 6.18 (1H, td, J=5.5 Hz, 11.6 Hz), 6.73 (1H, d, J=11.6 Hz), 7.11–7.25 (3H, m); IR (neat) 3330, 2930, 1449, 1067, 1020, 995, 772 cm$^{-1}$ 2) 6,7-dihydro-5H-benzo[a]cycloheptene-1-carboxylic acid To a solution of 6,7-dihydro-5H-benzo[a]cyclohepten-1-ylmethanol (31.41 g, 180.3 mmol) in acetone (500 ml) was slowly added dropwise a solution of chromic anhydride (36.1 g, 361 mmol) and conc. sulfuric acid (30 ml) dissolved in water (120 ml) under-ice-cooling. After the completion of the dropwise addition, the mixture was stirred at room temperature for 1 hr. The reaction solution was again ice-cooled, and after adding isopropanol (60 ml), the mixture was stirred as it was for 0.5 hr. Acetone in the reaction solution was evaporated under reduced pressure. The residue was diluted with ethyl acetate, washed three times with water and dried over anhydrous magnesium sulfate. The solvent was evaporated under reduced pressure and the obtained residue was crystallized from cold diisopropyl ether to give the objective substance.

white crystal yield 19.78 g, 58% mp 146–147° C.; $^1$H-NMR (CDCl$_3$, 200 MHz) δ 2.08–2.16 (4H, m), 2.70 (2H, t, J=6.4 Hz), 6.24 (1H, td, J=6.4 Hz, 11.1 Hz), 7.14 (1H, d, J=11.4 Hz), 7.23 (1H, t, J=7.3 Hz), 7.39 (1H, d, J=7.2 Hz), 7.92 (1H, dd, J=1.5 Hz, 7.7 Hz); IR (KBr) 3065–2530, 1686, 1451, 1414, 1300, 1277, 926, 779 cm$^{-1}$; Anal. Calcd for $C_{12}H_{12}O_2 \cdot 0.1H_2O$: C, 75.85; H, 6.47. Found: C, 75.88; H, 6.35.

3) (1RS,2SR)-2-amino-1-(4-fluorophenyl)-3-[4-(trifluoromethyl)phenyl]propan-1-ol (4RS,5SR)-5-(4-Fluorophenyl)-4-[4-(trifluoromethyl)benzyl]-1,3-oxazolidin-2-one (18.75 g, 55.26 mmol) and sodium hydroxide (8.84 g, 221 mmol) were heated under reflux in ethanol (100 ml)-water (10 ml) for 5 hrs. The reaction solution was diluted with water and extracted twice with ethyl acetate. The collected organic-layer was dried over anhydrous sodium sulfate, and the solvent was evaporated under reduced pressure. The residue was purified by silica gel (APS type) column chromatography (hexane/ethyl acetate=1/1-ethyl acetate) and crystallized from diethyl ether-hexane to give the objective substance.

white crystal yield 16.38 g, 95% mp 87–88° C.; $^1$H-NMR (CDCl$_3$, 200 MHz) δ 1.60 (2H, br s), 2.43 (1H, dd, J=10.2 Hz, 13.6 Hz), 2.87 (1H, dd, J=3.1 Hz, 13.7 Hz), 3.29 (1H, ddd J=3.3 Hz, 5.2 Hz, 10.3 Hz), 4.66 (1H, d, J=5.0 Hz), 7.08 (2H, t, J=8.7 Hz), 7.27 (2H, d, J=8.0 Hz), 7.38 (2H, dd, J=5.4 Hz, 8.4 Hz), 7.55 (2H, d, J=7.6 Hz); IR (neat) 3360–2865, 1508, 1325, 1225, 1163, 1121, 1067, 826 cm$^{-1}$; Anal. Calcd for C$_{16}$H$_{15}$F$_4$NO: C, 61.34; H, 4.83; N, 4.47. Found: C, 61.32; H, 4.62; N, 4.48.

4) N-[(1RS,2SR)-2-(4-fluorophenyl)-2-hydroxy-1-[4-(trifluoromethyl)benzyl]ethyl]-6,7-dihydro-5H-benzo[a]cycloheptene-1-carboxamide While stirring (1RS,2SR)-2-amino-1-(4-fluorophenyl)-3-[4-(trifluoromethyl)phenyl]propan-1-ol (0.157 g, 0.501 mmol), 6,7-dihydro-5H-benzo[a]cycloheptene-1-carboxylic acid (94 mg, 0.50 mmol) and 1-hydroxybenzotriazole hydrate (77 mg, 0.50 mmol) in acetonitrile (10 ml), 1-ethyl-3-(3-dimethylaminopropyl)carbodiimide hydrochloride (96 mg, 0.50 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.134 g, 55% mp 197–198° C.; $^1$H-NMR (CDCl$_3$-DMSO-d$_6$, 200 MHz) δ 1.91–2.04 (2H, m), 2.17–2.27 (2H, m), 2.65 2.70 (2H, m), 2.83–3.00 (2H, m), 4.62–4.76 (1H, m), 4.97 (1H, t, J=4.0 Hz), 5.04 (1H, d, J=3.8 Hz), 5.84 (1H, td, J=5.1 Hz, 12.2 Hz), 6.11 (1H, d, J=12.0 Hz), 6.81 (1H, d, J=8.8 Hz), 6.91 (1H, dd, J=1.9 Hz, 7.3 Hz), 7.01–7.14 (4H, m), 7.31 (2H, d, J=8.2 Hz), 7.47–7.54 (4H, m); IR (KBr) 3279, 2940, 1640, 1534, 1514, 1325, 1229, 1163, 1121, 1069, 831 cm$^{-1}$; Anal. Calcd for C$_{28}$H$_{25}$F$_4$NO$_2$: C, 69.56; H, 5.21; N, 2.90. Found: C, 69.41; H, 5.15; N, 2.91.

Example 30

4-fluoro-N-((1RS,2SR)-2-(4-fluorophenyl)-2-hydroxy-1-((4-(trifluoromethyl)phenyl)methyl)ethyl)-1-naphthalenecarboxamide 1) To a solution of 1,1-dimethylethyl (1RS,2SR)-2-(4-fluorophenyl)-2-hydroxy-1-((4-(trifluoromethyl)phenyl)methyl)ethylcarbamate (2.58 g, 6.24 mmol) in ethanol (35 ml) was. added 20% hydrogen chloride ethanol solution (35 ml) and the mixture was heated under reflux for 30 min. The reaction solution was evaporated under reduced pressure and the residue was washed with diethyl ether. to give (1RS,2SR)-1-(4-fluorophenyl)-1-hydroxy-3-(4-(trifluoromethyl)phenyl)-2-propylamine hydrochloride (2.05 g, 94%).

mp 173–174° C. IR ν max$^{KBr}$cm$^{-1}$: 3314, 3009, 1611, 1512, 1331. Anal. Calcd for C$_{16}$H$_{16}$ClF$_4$NO.0.5H$_2$O: C, 53.57; H, 4.78; N, 3.90. Found: C, 53.81; H, 4.81; N, 3.74.

$^1$H-NMR (DMSO-d$_6$)δ: 2.79 (2H, d, J=6.6 Hz), 3.64–3.80 (1H, m), 5.03 (1H, s), 6.30 (1H, d, J4.0 Hz), 7.10–7.24 (2H, m), 7.33 (2H, d, J=8.0 Hz), 7.38–7.50 (2H, m), 7.59 (2H, d, J=8.0 Hz), 8.07 (2H, brs).

2) To a solution of 4-fluoro-1-naphthalenecarboxylic acid (163 mg), 0.86 mmol) in tetrahydrofuran (5 ml) were added oxalyl chloride (0.15 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (200 mg, 0.57 mmol) and saturated aqueous sodium hydrogen carbonate (5 ml) and the mixture was stirred at room temperature for 2 hrs. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1) and recrystallized from ethyl acetate-hexane to give the title compound (214 mg, 77%).

mp 210–211° C. IR ν max$^{KBr}$cm$^{-1}$: 3275, 1642, 1626, 1601. Anal. Calcd for C$_{27}$H$_{20}$F$_5$NO$_2$: C, 66.80; H, 4.15; N, 2.89. Found: C, 66.79; H, 4.19; N, 2.82. $^1$H-NMR (CDCl$_3$)δ: 2.80–3.16 (2H, m), 3.18 (1H, d, J=3.6 Hz), 4.72–4.94 (1H, m), 5.08–5.16 (1H, m), 5.92 (1H, d, J=8.2 Hz), 7.00–7.70 (13H, m), 8.09 (1H, d, J=8.0 Hz).

Example 31

4-fluoro-N-[(1RS,2SR)-2-(4-fluorophenyl)-2-hydroxy-1-[4-(trifluoromethyl)benzyl]ethyl]-5,6,7,8-tetrahydronaphthalene-1-carboxamide 1) methyl 4-amino-5,6,7,8-tetrahydronaphthalene-1-carboxylate A solution of methyl 4-nitro-5,6,7,8-tetrahydronaphthalene-1-carboxylate (see Chem. Abstr., 43, 202f (1949), Chem. Abstr., 43, 202b (1949)) (1.816 g, 7.720 mmol) in methanol (30 ml) was hydrogenated under normal temperature and normal pressure using 10% palladium/carbon (containing water by 50%) (0.5 g) as a catalyst until the starting material disappeared. The catalyst was filtered off and the filtrate was passed through a short silica gel column chromatography. The solvent was evaporated under reduced pressure to give the objective substance.

yellow crystal yield 1.574 g, 99%

Recrystallization from ethyl acetate-hexane gave pale-yellow crystals.

mp 120–121° C.; $^1$H-NMR (CDCl$_3$, 200 MHz) δ 1.68–1.90 (4H, m), 2.44 (2H, t, J=6.2 Hz), 3.10 (2H, t, J=6.0 Hz), 3.81 (3H, s), 3.92 (2H, br s), 6.50 (1H, d, J=8.4 Hz), 7.69 (1H, d, J=8.4 Hz); IR (KBr) 3486, 3374, 2948, 2930, 2868, 1688, 1626, 1590, 1481, 1449, 1431, 1310, 1267, 1253, 1196, 1142, 775 cm$^{-1}$; Anal. Calcd for C$_{12}$H$_{15}$NO$_2$: C, 70.22; H, 7.37; N, 6.82. Found: C, 70.25; H, 7.33; N, 6.67.

2) methyl 4-fluoro-5,6,7,8-tetrahydronaphthalene-1-carboxylate

While stirring methyl 4-amino-5,6,7,8-tetrahydronaphthalene-1-carboxylate (1.210 g, 5.895 mmol) and conc. hydrochloric acid (2 ml) in water (20 ml), a solution of sodium nitrite (0.49 g, 7.07 mmol) in water (1 ml) was added dropwise under ice-cooling and the mixture was stirred at said temperature for 10 min. To the reaction solution was added a 60% aqueous hexafluorophosphoric acid solution (1.48 ml, 10.0 mmol) with vigorous stirring under ice-cooling and the mixture was stirred as it was for 0.5 hr. The resulting precipitate was filtered, washed with water and methanol-diethyl ether (1:4) and dried to give diazonium salt as a white powder. The obtained diazonium salt was heated in liquid paraffin (8 ml) at 170° C. for. 0.5 hr. The mixture was cooled to room temperature and aqueous sodium hydrogen carbonate solution was added. The mixture was extracted twice with ethyl acetate. The collected organic layer was dried over anhydrous magnesium sulfate, and the solvent was evaporated under reduced pressure. The obtained crude product was purified by silica gel column chromatography (hexane/ethyl acetate=200/1–15/1) to give the objective substance.

white crystal yield 0.487 g, 40% mp 44–45° C.; $^1$H-NMR (CDCl$_3$, 200 MHz) δ 1.72–1.83 (4H, m), 2.74 (2H, br s), 3.08 (2H, br s), 3.86 (3H, s), 6.87 (1H, t, J=8.6 Hz), 7.73 (1H, dd, J=6.0 Hz, 8.6 Hz); IR (KBr) 2944, 1721, 1582, 1472, 1433, 1260, 1254, 1190, 1157, 1130, 1038, 770 cm$^{-1}$; Anal. Calcd for C$_{12}$H$_{13}$FO$_2$: C, 69.22; H, 6.29. Found: C, 69.39; H, 6.43.

3) 4-fluoro-5,6,7,8-tetrahydronaphthalene-1-carboxylic acid

To a solution of methyl 4-fluoro-5,6,7,8-tetrahydronaphthalene-1-carboxylate (0.434 g, 2.084 mmol) in methanol (10 ml)-tetrahydrofuran (10 ml) was added 1N aqueous sodium hydroxide solution (4.17 ml, 4.17 mmol), and the mixture was stirred overnight at room temperature. The reaction solution was concentrated, diluted with water, acidified with 1N hydrochloric acid, and extracted twice with ethyl acetate. The collected organic layer was dried over anhydrous sodium sulfate, and the solvent was evaporated under reduced pressure. The residue was crystallized from diethyl ether-hexane to give the objective substance.

white crystal yield 0.308 g, 76% mp 172–173° C.; $^1$H-NMR (CDCl$_3$, 200 MHz) δ 1.74–1.82 (4H, m), 2.76 (2H, br s), 3.16 (2H, br s), 6.91 (1H, t, J=8.8 Hz), 7.91 (1H, dd, J=6.1 Hz, 8.5 Hz); IR (KBr) 3100–2600, 1686, 1588, 1429, 1304, 1273, 1250, 1188 cm$^{-1}$; Anal. Calcd for C$_{11}$H$_{11}$FO$_2$: C, 68.03; H, 5.71. Found: C, 68.10; H, 6.00.

4) 4-fluoro-N-[(1RS,2SR)-2-(4-fluorophenyl)-2-hydroxy-1-[4-(trifluoromethyl)benzyl]ethyl]-5,6,7,8-tetrahydronaphthalene-1-carboxamide While stirring (1RS,2SR)-2-amino-1-(4-fluorophenyl)-3-[4-(trifluoromethyl)phenyl]propan-1-ol (0.164 g, 0.523 mmol), 4-fluoro-5,6,7,8-tetrahydronaphthalene-1-carboxylic acid (0.10 g, 0.52 mmol) and 1-hydroxybenzotriazole hydrate (80 mg, 0.52 mmol) in acetonitrile (10 ml), 1-ethyl-3-(3-dimethylaminopropyl)carbodiimide hydrochloride (0.10 g, 0.52 mmol) was added, and the mixture was stirred overnight at room temperature. The reaction solution was diluted with ethyl acetate, washed with aqueous sodium hydrogen-carbonate solution, dried over anhydrous magnesium sulfate, and passed through silica gel. The solvent was evaporated under reduced pressure and the obtained residue was crystallized from ethyl acetate-diisopropyl ether-hexane to give the objective substance.

white crystal yield 0.220 g, 86% mp 241–242° C.; $^1$H-NMR (CDCl$_3$-DMSO-d$_6$, 200 MHz) δ 1.53–1.75 (4H, m), 2.11–2.26 (1H, m), 2.30 2.48 (1H, m), 2.61–2.67 (2H, m), 2.78–3.02 (2H, m), 4.59–4.73 (1H, m), 4.95 (1H, t, J=3.9 Hz), 5.10 (1H, d, J=3.6 Hz), 6.69–6.87 (3H, m), 7.06 (2H, t, J=8.6 Hz), 7.30 (2H, d, J=8.2 Hz), 7.47–7.54 (4H, m); IR (KBr) 3272, 2942, 1642, 1514, 1327, 1229, 1165, 1121, 1069, 831 cm$^{-1}$; Anal. Calcd for C$_{27}$H$_{24}$F$_5$NO$_2$: C, 66.25; H, 4.94; N, 2.86. Found: C, 66.30; H, 5.18; N, 2.66.

Example 32

5-fluoro-N-[(1RS,2SR)-2-(4-fluorophenyl)-2-hydroxy-1-[4-(trifluoromethyl)benzyl]ethyl] naphthalene-1-carboxamide 1) ethyl 5-nitro-1-naphthoate A solution of 5-nitro-1-naphthoic acid (see *Chem. Pharm. Bull.*, 32, 3968–80 (1984)) (5.995 g, 27.60 mmol) and conc. sulfuric acid (2 ml) in ethanol (100 ml) was heated under reflux for one day. The reaction solution was concentrated, diluted with ethyl acetate, and washed with aqueous sodium hydrogen carbonate solution and water. The obtained ethyl acetate solution was dried over anhydrous magnesium sulfate, and the solvent was evaporated under reduced pressure to give the objective substance.

yellow solid yield 6.212 g, 92%

Recrystallization from ethanol gave a pale-yellow powder. mp 92–93° C.; $^1$H-NMR (CDCl$_3$, 200 MHz) δ 1.48 (3H, t, J=7.2 Hz), 4.50 (2H, q, J=7.1 Hz), 7.67 (1H, dd, J=7.6 Hz, 8.8 Hz), 7.74 (1H, dd, J=7.2 Hz, 8.8 Hz), 8.20 (1H, dd, J=1.1 Hz, 7.7 Hz), 8.29 (1H, dd, J=1.1 Hz, 7.3 Hz), 8.66 (1H, td, J=1.0 Hz, 8.8 Hz), 9.26 (1H, td, J=1.0 Hz, 8.6 Hz); IR (KBr) 1725, 1520, 1354, 1277, 1155, 793, 764 cm$^{-1}$; Anal. Calcd for C$_{13}$H$_{11}$NO$_4$: C, 63.67; H, 4.52; N, 5.71. Found: C, 63.45; H, 4.47; N, 5.69.

2) ethyl 5-amino-1-naphthoate

A solution of ethyl 5-nitro-1-naphthoate (3.304 g, 13.47 mmol) in ethanol (10 ml)-tetrahydrofuran (20 ml) was hydrogenated under normal temperature and normal pressure using 10% palladium/carbon (containing water by 50%) (0.5 g) as a catalyst until the starting material disappeared. The catalyst was filtered off and the solvent was evaporated under reduced pressure. The obtained crude product was purified by silica gel column chromatography (hexane/ethyl acetate=6/1–3/1) to give the objective substance.

yellow liquid yield 2.797 g, 97% $^1$H-NMR (CDCl$_3$, 200 MHz) δ 1.45 (3H, t, J=7.1 Hz), 4.16 (2H, br s), 4.47 (2H, q, J=7.1 Hz), 6.85 (1H, dd, J=0.8 Hz, 7.4 Hz), 7.41 (1H, dd, J=7.5 Hz, 8.5 Hz), 7.47 (1H, dd, J=7.2 Hz, 8.6 Hz), 8.05 (1H, td, J=1.1 Hz, 8.5 Hz), 8.11 (1H, dd, J=1.2 Hz, 7.2 Hz), 8.28 (1H, td, J=0.9 Hz, 8.6 Hz); IR (neat) 3378, 2980, 1705, 1634, 1582, 1464, 1260, 1213, 1107, 783 cm$^{-1}$ 3) 5-fluoro-1-naphthoic acid While stirring ethyl 5-amino-1-naphthoate (1.380 g, 6.411 mmol) and conc. hydrochloric acid (2 ml) in water (15 ml), a solution of sodium nitrite (0.53 g, 7.69 mmol) in water (1.5 ml) was added dropwise under ice-cooling, and the mixture was stirred at said temperature for 10 min. To the reaction solution was added a 60% aqueous hexafluotophosphoric acid solution (1.61 ml, 10.9 mmol) with vigorous stirring under ice-cooling and the mixture was stirred as it was for 0.5 hr. The resulting precipitate was filtered, washed with water and methanol-diethyl ether (1:4) and dried to give a diazonium salt as a brown powder. The obtained diazonium salt was heated in liquid paraffin (8 ml) at 170° C. for 0.5 hr. The mixture was cooled to room temperature and aqueous sodium hydrogen carbonate solution was added. The mixture was extracted twice with ethyl acetate. The collected organic layer was dried over anhydrous magnesium sulfate, and the solvent was evaporated under reduced pressure. The obtained crude product was purified by silica gel column chromatography (hexane/ethyl acetate=15/1) to give a mixture of ethyl 5-fluoro-1-naphthoate and liquid paraffin as a colorless liquid. To a solution of obtained liquid in ethanol (30 ml)-tetrahydrofuran (30 ml) was added 1N aqueous sodium hydroxide solution (8 ml, 8 mmol), and the mixture was stirred overnight at room temperature. The reaction solution was concentrated, diluted with water, and washed with diethyl ether. The obtained aqueous solution was acidified with 1N hydrochloric acid and the resulting crystals were filtered and washed with water and hexane to give the objective substance.

white crystal yield 0.409 g, 34% mp 214–216° C.; $^1$H-NMR (DMSO-d$_6$, 200 MHz) δ 7.44 (1H, dd, J=7.8 Hz, 10.4 Hz), 7.60–7.75 (2H, m), 8.25 (1H, d, J=7.0 Hz), 8.32 (1H, d, J=8.8 Hz), 8.70 (1H, d, J=8.4 Hz); IR (KBr) 3100–2500, 1678, 1599, 1302, 1246, 1117, 887, 781 cm$^{-1}$; Anal. Calcd for C$_{11}$H$_7$FO$_2$: C, 69.47; H, 3.71. Found: C, 69.24; H, 3.45.

4) 5-fluoro-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.163 g, 0.520 mmol), 5-fluoro-1-naphthoic acid (0.10 g, 0.52 mmol) and 1-hydroxybenzotriazole hydrate (80 mg, 0.52 mmol) in acetonitrile (10 ml), 1-ethyl-3-(3-dimethylaminopropyl) carbodiimide hydrochloride (0.10 g, 0.52 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.216 g, 86% mp 222–224° C.; $^1$H-NMR (CDCl$_3$-DMSO-d$_6$, 200 MHz) 68 2.93 (1H, dd, J=10.8 Hz, 14.0 Hz), 3.19 (1H, dd, J=3.5 Hz, 14.5 Hz), 4.65–4.80 (1H, m), 4.91 (1H, t, J=4.8 Hz), 5.44 (1H, d, J=4.0 Hz), 7.02–7.29 (6H, m), 7.38–7.59 (7H, m), 7.90 (1H, d, J=9.4 Hz), 8.08 (1H, d, J=8.4 Hz); IR (KBr) 3283, 1642, 1537, 1514, 1327, 1248, 1227, 1163, 1121, 1069, 831, 783 cm$^{-1}$; Anal. Calcd for C$_{27}$H$_{20}$F$_5$NO$_2$: C, 66.80; H, 4.15; N, 2.89. Found: C, 66.65; H, 4.21; N, 2.68.

Example 33

N-[(1RS,2SR)-2-(4-fluorophenyl)-2-hydroxy-1-[4-(trifluoromethyl)benzyl]ethyl]-5,6,7,8-tetrahydronaphthalene-1-carboxamide While stirring (1RS,2SR)-2-amino-1-(4-fluorophenyl)-3-[4-(trifluoromethyl)phenyl]propan-1-ol (0.168 g, 0.536 mmol), 1,2,3,4-tetrahydronaphthalene-1-carboxylic acid (see *Tetrahedron*, 53, 15969–15982 (1990))(94 mg, 0.54 mmol) and 1-hydroxybenzotriazole hydrate (82 mg, 0.54 mmol) in acetonitrile (10 ml), 1-ethyl-3-(3-dimethylaminopropyl)carbodiimide hydrochloride (0.10 g, 0.54 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.161 g, 64% mp 219–221° C.; $^1$H-NMR (CDCl$_3$-DMSO-d$_6$, 200 MHz) δ 1.50–1.73 (4H, m), 2.05–2.35 (2H, m), 2.70 (2H, t, J=6.4 Hz), 2.88 (1H, dd, J=10.8 Hz, 14.4 Hz), 3.06 (1H, dd, J=3.8 Hz, 14.0 Hz), 4.55–4.70 (1H, m), 4.87 (1H, t, J=4.4 Hz), 5.33 (1H, d, J=3.6 Hz), 6.74 (1H, dd, J=2.8 Hz, 5.6 Hz), 6.95–7.09 (4H, m), 7.28–7.37 (3H, m), 7.47–7.54 (4H, m); IR (KBr) 3330, 1624, 1534, 1329, 1159, 1123, 1069, 831 cm$^{-1}$; Anal. Calcd for C$_{27}$H$_{25}$F$_4$NO$_2$: C, 68.78; H, 5.34; N, 2.97. Found: C, 68.62; H, 5.38; N, 2.90.

Example 34

4-chloro-N-[(1RS,2SR)-2-(4-fluorophenyl)-2-hydroxy-1-[4-(trifluoromethyl)benzyl]ethyl]naphthalene-1-carboxamide 1) 4-amino-1-naphthoic acid.hydrochloride 4-Amino-1-naphthalenecarbonitrile (9.948 g, 59.14 mmol) and potassium hydroxide (25 g) were heated under reflux in water (150 ml) for one day. The reaction solution was cooled to room temperature and diluted with water (150 ml). The insoluble materials were filtered off. The filtrate was acidified with conc. hydrochloric acid and resulting precipitate was collected by filtration and washed with ethanol and water to give the objective substance.

brown powder yield 4.67 g, 35% $^1$H-NMR (DMSO-d$_6$, 200 MHz) δ 6.75 (1H, d, J=8.4 Hz), 7.40–7.48 (1H, m), 7.52–7.61 (1H, m), 8.06 (1H, d, J=8.6 Hz), 8.16 (1H, d, J=7.6 Hz), 9.10 (1H, d, J=7.8 Hz); IR (KBr) 2838, 1686, 1503, 1260, 1204, 1094, 766 cm$^{-1}$ 2) methyl 4-chloro-1-naphthoate While stirring 4-amino-1-naphthoic acid hydrochloride (2.330 g, 10.42 mmol) in conc. hydrochloric acid (20 ml), a solution of sodium nitrite (0.72 g, 10.4 mmol) in water (2 ml) was dropwise added under ice-cooling, and the mixture was stirred at said temperature for 0.5 hr. To the reaction solution was added a solution of copper(I) chloride (0.57 g, 5.73 mmol) in conc. hydrochloric acid (4 ml) and conc. hydrochloric acid (50 ml) under ice-cooling and the mixture was stirred at 100° C. for 4 hrs. The mixture was cooled to room temperature, and the resulting precipitate was collected by filtration, and washed with water. The obtained precipitate was stirred in a solution (40 ml) of 10% hydrogen chloride in methanol at 70° C. overnight. The solvent of the reaction solution was evaporated under reduced pressure and the obtained crude product was purified by silica gel column chromatography (hexane/ethyl acetate=9/1) to give the objective substance.

yellow liquid yield 0.299 g, 13% $^1$H-NMR (CDCl$_3$, 200 MHz) δ 4.00 (3H, s), 7.58–7.73 (3H, m), 8.09 (1H, d, J=7.8 Hz), 8.32–8.38 (1H, m), 8.92–9.01 (1H, m); IR (neat) 1717, 1508, 1275, 1246, 1194, 1140, 1024, 787, 766 cm$^{-1}$ 3) 4-chloro-1-naphthoic acid To a solution of methyl 4-chloro-1-naphthoate (0.299 g, 1.355 mmol) in methanol (10 ml)-tetrahydrofuran (5 ml) was added 1N aqueous sodium hydroxide solution (2.71 ml, 2.71 mmol), and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from diethyl ether-hexane to give the objective substance.

pale-brown crystal yield 0.234 g, 84% mp 215–217° C.; $^1$H-NMR (DMSO-d$_6$, 200 MHz) δ 7.74–7.85 (3H, m), 8.12 (1H, d, J=7.6 Hz), 8.27 8.35 (1H, m), 8.91–9.00 (1H, m); IR (KBr) 3100–2500, 1690, 1510, 1283, 1252, 785, 762 cm$^{-1}$; Anal. Calcd for C$_{11}$H$_7$ClO$_2$.0.2H$_2$O: C, 62.85; H, 3.55. Found: C, 62.99; H, 3.31.

4) 4-chloro-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.155 g, 0.495 mmol), 4-chloro-1-naphthoic acid (0.10 g, 0.49 mmol) and 1-hydroxybenzotriazole hydrate (76 mg, 0.49 mmol) in acetonitrile (10 ml), 1-ethyl-3-(3-dimethylaminopropyl) carbodiimide hydrochloride (95 mg, 0.49 mmol) was added and the mixture was stirred overnight at room temperature. The reaction solution was diluted with ethyl acetate, washed with aqueous sodium hydrogen carbonate solution, dried over anhydrous magnesium sulfate, and passed through silica gel. The solvent was evaporated under reduced pressure and the obtained residue was crystallized from ethyl acetate-hexane to give the objective substance.

white crystal yield 0.173 g, 70% mp 222–223° C.; $^1$H-NMR (CDCl$_3$-DMSO-d$_6$, 200 MHz) δ 2.92 (1H, dd, J=10.5 Hz, 14.1 Hz), 3.07 (1H, dd, J=3.1 Hz, 14.1 Hz), 4.70–4.85 (1H, m), 5.00 (1H, t, J=3.8 Hz), 5.23 (1H, d, J=3.8 Hz), 7.07 (1H, d, J=8.8 Hz), 7.13 (2H, t, J=8.6 Hz), 7.27–7.62 (11H, m), 8.24 (1H, d, J=8.4 Hz); IR (KBr) 3274, 1638, 1537, 1514, 1327, 1163, 1125, 1069, 833 cm$^{-1}$; Anal. Calcd for C$_{27}$H$_{20}$ClF$_4$NO$_2$: C, 64.61; H, 4.02; N, 2.79. Found: C, 64.26; H, 3.88; N, 2.59.

Example 35

N-[(1RS,2SR)-2-(4-fluorophenyl)-2-hydroxy-1-[4-(trifluoromethyl)benzyl]ethyl]naphthalene-1-carboxamide 1) (1RS,2SR)-2-amino-1-(4-fluorophenyl)-3-[4-(trifluoromethyl)phenyl]propan-1-ol hydrochloride To a solution of tert-butyl N-[(1RS,2SR)-2-(4-fluorophenyl)-2-hydroxyethyl-1-[4-(trifluoromethyl)benzyl]]carbamate (2.58 g, 6.24 mmol) in ethanol (35 ml) was added 20% hydrogen chloride ethanol solution (35 ml) and the mixture was heated under reflux for 30 min. The reaction solution was concentrated under reduced pressure, and the residue was washed with diethyl ether to give the objective substance (2.05 g, 94%) as crystals.

mp 173–174° C.; $^1$H-NMR (DMSO-d$_6$, 200 MHz) δ 2.79. (2H, d, J=6.6 Hz), 3.64–3.80 (1H, m), 5.03 (1H, s), 6.30. (1H, d, J=4.0 Hz), 7.10–7.24 (2H, m), 7.33 (2H, d, J=8.0 Hz), 7.38–7.50 (2H, m), 7.59. (2H, d, J=8.0 Hz), 8.07 (2H, br s); IR (KBr) 3314, 3009 cm$^{-1}$; Anal. Calcd for C$_{16}$H$_{16}$ClF$_4$NO.0.5H$_2$O: C, 53.57; H, 4.78; N, 3.90. Found: C, 53.81; H, 4.81; N, 3.74.

2) N-[(1RS,2SR)-2-(4-fluoropheny)-2-hydroxy-1-[4-(trifluoromethyl) phenvl]ethyl]naphthalene-1-carboxamide To a solution of (1RS,2SR)-2-amino-1-(4-fluorophenyl)-3-[4-(trifluoromethyl)benzyl]propan-1-ol hydrochloride (780 mg, 1.89 mmol) in ethyl acetate (5 ml) were added 1-naphthoyl chloride (0.43 ml, 2.84 mmol) and saturated aqueous sodium hydrogen carbonate (5 ml) and the mixture was stirred for 30 min. The reaction solution was diluted with water and extracted with ethyl acetate. The extract was washed with saturated brine, dried over magnesium sulfate and concentrated under reduced pressure. The residue was purified by silica gel column chromatography (ethyl acetate/hexane=1/2) and recrystallized from ethyl acetate-hexane to give the objective substance (354 mg, 40%) as crystals.

mp 214–216° C.; $^1$H-NMR (CDCl$_3$, 200 MHz) δ 2.89 (1H, dd, J=11.0 Hz, 14.0 Hz), 3.09 (1H, dd, J=4.6 Hz, 13.6 Hz), 3.28 (1H, br s), 4.74–4.91 (1H, m), 5.12 (1H, br s), 5.94 (1H, br d, J=9.4 Hz), 7.05–7.24 (2H, m), 7.30–7.66 (1H, m), 7.84 (2H, t, J=9.3 Hz); IR (KBr) 3366, 3285, 1636 cm$^{-1}$; Anal. Calcd for C$_{27}$H$_{21}$F$_4$NO$_2$: C, 69.37; H, 4.53; N, 3.00. Found: C, 69.17; H, 4.56; N, 2.88.

Example 36

N-((1RS,2SR)-2-(4-fluorophenyl)-2-hydroxy-1-((4-(trifluoromethyl)phenyl)methyl)ethyl)-4-methyl-1-naphthalenecarboxamide To a solution of (1RS,2SR)-2-amino-1-(4-fluorophenyl)-3-(4-(trifluoromethyl)phenyl)-1-propanol (450 mg, 1.44 mmol) in acetonitrile (30 ml) were added 4-methyl-1-naphthalenecarboxylic acid (268 mg, 1.44 mmol) and 1-ethyl-3-(3-dimethylaminopropyl)carbodiimide hydrochloride (413 mg, 2.15 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:acetone=1:1) and recrystallized from ethyl acetate-hexane to give the title compound (487 mg, 70%).

mp 198–199° C. IR ν max$^{KBr}$cm$^{-1}$: 1636, 1620, 1607. Anal. Calcd for C$_{28}$H$_{23}$F$_4$NO$_2$: C, 69.85; H, 4.81; N, 2.91. Found: C, 69.80; H, 4.92; N, 2.79. $^1$H-NMR (CDCl$_3$)δ: 2.58 (3H, s), 2.66–3.06 (1H, m), 3.33 (1H, brs), 4.60–4.80 (1H, m), 4.98–5.06 (1H, m), 5.80 (1H, d, J=8.2 Hz), 6.92–7.54 (12H, m), 7.59 (1H, d, J=8.6 Hz), 7.89 (1H, d, J=8.2 Hz).

Example 37

5-chloro-N-[(1RS,2SR)-2-(4-fluorophenyl)-2-hydroxy-1-[4-(trifluoromethyl)benzyl]ethyl]naphthalene-1-carboxamide 1) ethyl 5-chloro-1-naphthoate While stirring ethyl 5-amino-1-naphthoate (1.358 g, 6.309 mmol) in conc. hydrochloric acid (10 ml), a solution of sodium nitrite (0.52 g, 7.57 mmol) in water (1 ml) was added dropwise under ice-cooling and the mixture was stirred at said temperature for 0.5 hr. To the reaction solution was added a solution of copper(I) chloride (0.34 g, 3.47 mmol) in conc. hydrochloric acid (2 ml) under ice-cooling, and the mixture. was stirred at 100° C. for 0.5 hr. After cooling to room temperature, the reaction solution was diluted with water and extracted twice with ethyl acetate. The collected organic layer was dried over anhydrous sodium sulfate, and the solvent was evaporated under reduced pressure. The obtained crude product was purified by silica gel column chromatography (hexane/ethyl acetate=15/1) to give the objective substance.

colorless liquid yield 0.713 g, 48% $^1$H-NMR (CDCl$_3$, 200 MHz) δ 1.47 (3H, t, J=7.2 Hz), 4.48 (2H, q, J=7.3 Hz), 7.47–7.66 (3H, m), 8.22 (1H, dd, J=1.1 Hz, 7.3 Hz), 8.53 (1H, d, J=8.6 Hz), 8.85 (1H, d, J=8.4 Hz); IR (neat) 1717, 1262, 1196, 1142, 789 cm$^{-1}$ 2) 5-chloro-1-naphthoic acid To a solution of ethyl 5-chloro-1-naphthoate (0.713 g, 3.038 mmol) in methanol (20 ml)-tetrahydrofuran (10 ml) was added 1N aqueous sodium hydroxide solution (4.56 ml, 4.56 mmol), and the mixture was stirred overnight at room temperature. The reaction solution was concentrated, diluted with water and acidified with 1N hydrochloric acid. The resulting precipitate was collected by filtration, washed with water and hexane to give the objective substance.

white crystal yield 0.547 g, 87% mp 248–250° C.; $^1$H-NMR (DMSO-d$_6$, 200 MHz) δ 7.64 (1H, t, J=8.0 Hz), 7.74–7.83 (2H, m), 8.23 (1H, d, J=6.6 Hz), 8.46 (1H, d, J=8.6 Hz), 8.84 (1H, d, J=8.8 Hz); IR (KBr) 3100–2550, 1678, 1302, 783 cm$^{-1}$; Anal. Calcd for C$_{11}$H$_7$ClO$_2$: C, 63.94; H, 3.41. Found: C, 63.96; H, 3.60.

3) 5-chloro-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.163 g, 0.520 mmol), 5-chloro-1-naphthoic acid (0.11 g, 0.52 mmol) and 1-hydroxybenzotriazole hydrate (80 mg, 0.52 mmol) in acetonitrile (10 ml), 1-ethyl-3-(3-dimethylaminopropyl) carbodiimide hydrochloride (0.10 g, 0.52 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.223 g, 85% mp 211–212° C.; $^1$H-NMR (CDCl$_3$-DMSO-d$_6$, 200 MHz) δ 2.92 (1H, dd, J=10.8 Hz, 14.0 Hz), 3.14 (1H, dd, J=2.7 Hz, 13.7 Hz), 4.68–4.83 (1H, m), 4.94 (1H, t, J=4.5 Hz), 5.36 (1H, d, J=3.6 Hz), 7.08 (2H, t, J=8.8 Hz), 7.17–7.58 (11H, m), 7.75 (1H, d, J=10.0 Hz), 8.27 (1H, d, J=8.4 Hz); IR (KBr) 3277, 1636, 1537, 1514, 1327, 1229, 1169, 1121, 1069, 1020, 833, 785 cm$^{-1}$; Anal. Calcd for C$_{27}$H$_{20}$ClF$_4$NO$_2$: C, 64.61; H, 4.02; N, 2.79. Found: C, 64.47; H, 4.00; N, 2.58.

Example 38

N-[(1RS,2SR)-2-(4-fluorophenyl)-2-hydroxy-1-[4-(trifluoromethyl)benzyl]ethyl]-4-nitro-5,6,7,8-tetrahydronaphthalene-1-carboxamide While stirring (1RS,2SR)-2-amino-1-(4-fluorophenyl)-3-[4-(trifluoromethyl)phenyl]propan-1-ol (0.139 g, 0.444 mmol), 4-nitro-5,6,7,8-tetrahydronaphthalene-1-carboxylic acid (see Chem. Pharm. Bull., 32, 3968–80 (1984))(98 mg, 0.44 mmol) and 1-hydroxybenzotriazole hydrate (68 mg, 0.44 mmol) in acetonitrile (10 ml), 1-ethyl-3-(3-dimethylaminopropyl)carbodiimide hydrochloride (85 mg, 0.44 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-duisopropyl ether-hexane to give the objective substance.

white crystal yield 0.146 g, 64% mp 207–209° C.; $^1$H-NMR (CDCl$_3$-DMSO-d$_6$, 200 MHz) δ 1.51–1.75 (4H, m), 2.00–2.15 (1H, m), 2.28 2.43 (1H, m), 2.80–3.07 (4H, m), 4.62–4.76 (1H, m), 4.93 (H, t, J=4.2 Hz), 5.11 (1H, d, J=3.6 Hz), 6.89 (1H, d, J=8.0 Hz), 7.08 (2H, t, J=8.8 Hz), 7.18 (1H, d, J=9.2 Hz), 7.32 (2H, d, J=8.2 Hz), 7.48–7.54 (5H, m); IR (KBr) 3275, 2944, 1644, 1526, 1331, 1159, 1127, 1069, 835 cm$^{-1}$; Anal. Calcd for C$_{27}$H$_{24}$F$_4$N$_2$O$_4$: C, 62.79; H, 4.68; N, 5.42. Found: C, 62.53; H, 4.49; N, 5.30.

Example 39

6-fluoro-N-[(1RS,2SR)-2 (4-fluorophenyl)-2-hydroxy-1-[4-(trifluoromethyl)benzyl]ethyl] naphthalene-1-carboxamide While stirring (1RS,2SR)-2-amino-1-(4-fluorophenyl)-3-[4-(trifluoromethyl)phenyl]propan-1-ol (0.234 g, 0.747 mmol), 6-fluoro-1-naphthoic acid (see EP0931547A1) (0.14 g, 0.75 mmol) and 1-hydroxybenzotriazole hydrate (0.11 g, 0.75 mmol) in acetonitrile (10 ml), 1-ethyl-3-(3-dimethylaminopropyl)carbodiimide hydrochloride (0.14 g, 0.75 mmol) was added, and the mixture was stirred overnight at room temperature. The reaction solution was diluted with ethyl acetate, washed with aqueous sodium hydrogen carbonate solution, dried over anhydrous magnesium sulfate, and passed through silica gel. The solvent was evaporated under reduced pressure and the obtained residue was crystallized from ethyl acetate-hexane to give the objective substance.

white crystal yield 0.302 g, 83% mp 223–224° C.; $^1$H-NMR (CDCl$_3$-DMSO-d$_6$, 200 MHz) δ 2.85–3.08 (2H, m), 4.73–4.87 (1H, m), 5.04 (1H, s), 5.12 (1H, s), 7.05–7.16 (3H, m), 7.21–7.44 (6H, m), 7.50–7.58 (5H, m), 7.79 (1H, d, J=8.2 Hz); IR (KBr) 3268, 1638, 1516, 1325, 1227, 1167, 1121, 1069, 864, 829 cm$^{-1}$; Anal. Calcd for C$_{27}$H$_{20}$F$_5$NO$_2$.0.1H$_2$O: C, 66.56; H, 4.18; N, 2.87. Found: C, 66.38; H, 4.28; N, 3.11.

Example 40

N-[(1RS,2SR)-2-(4-fluorophenyl)-2-hydroxy-1-[4-(trifluoromethyl)benzyl]ethyl]-5-nitronaphthalene-1-carboxamide While stirring (1RS,2SR)-2-amino-1-(4-fluorophenyl)-3-[4-(trifluoromethyl)phenyl]propan-1-ol (0.166 g, 0.530 mmol), 5-nitro-1-naphthoic acid (0.12 g, 0.5.3 mmol) and 1-hydroxybenzotriazole hydrate (81 mg, 0.53 mmol) in, acetonitrile (10 ml), 1-ethyl-3-(3-dimethylaminopropyl) carbodiimide hydrochloride (0.10 g, 0.53 mmol) was added, and the mixture was stirred overnight at room temperature. The reaction solution was diluted with ethyl acetate, washed with aqueous sodium hydrogen carbonate solution, dried over anhydrous magnesium sulfate, and passed through silica gel. The solvent was evaporated under reduced pressure and the obtained residue was crystallized from ethyl acetate-hexane to give the objective substance.

white crystal yield 0.258 g, 95% mp 211–214° C.; $^1$H-NMR (CDCl$_3$-DMSO-d$_6$, 200 MHz) δ 2.85–3.13 (2H, m), 4.74–4.88 (1H, m), 5.00 (1H, t, J=4.3 Hz), 5.19 (1H, d, J=3.6 Hz), 7.10 (2H, t, J=8.6 Hz), 7.34–7.42 (4H; m), 7.50–7.70 (7H, m), 8.15 (1H, dd, J=1.1 Hz, 7.7 Hz), 8.49 (1H, d, J=8.4 Hz); IR (KBr) 3287, 1680, 1526, 1329, 1115 cm$^{-1}$; Anal. Calcd for C$_{27}$H$_{20}$F$_4$N$_2$O$_4$.DMF: C, 61.54; H, 4.65; N, 7.18. Found: C, 61.24; H, 4.62; N, 7.17.

Example 41

N-[(1RS,2SR)-2-(4-fluorophenyl)-2-hydroxy-1-[4-(trifluoromethyl)benzyl]ethyl]-1,2,3,4-tetrahydronaphthalene-1-carboxamide 1) 1,2,3,4-tetrahydronaphthalene-1-carboxylic acid Diethyl 3,4-dihydronaphthalene-1,1 (2H)-dicarboxylate (see J. Org. Chem., 54, 2713–18 (1989)) (5.129 g, 18.56 mmol), sodium chloride (2.17 g, 37.1 mmol) and water (1 ml) were heated in dimethyl sulfoxide (10 ml) at 180° C. for 1.5 days. After cooling to room temperature, water was added, and the mixture was extracted twice with ethyl acetate. The collected organic layer was dried over anhydrous magnesium sulfate. The solvent was evaporated under reduced pressure and the obtained residue was purified by silica gel column chromatography (hexane/ethyl acetate=15/1) to give a crude product of ethyl 1,2,3,4-tetrahydronaphthalene-1-carboxylate as a yellow liquid. To a solution of the obtained liquid in methanol (20 ml)-tetrahydrofuran (10 ml) was added 1N aqueous sodium hydroxide solution (30 ml, 30 mmol), and the mixture was stirred overnight at room temperature. The reaction solution was concentrated, diluted with water, and washed with diethyl ether. The obtained aqueous solution was acidified with 1N hydrochloric acid and extracted twice with diethyl ether. The collected organic layer was dried over anhydrous magnesium sulfate. The solvent was evaporated under reduced pressure and the obtained residue was crystallized from diethyl ether-hexane to give the objective substance.

white crystal yield 0.350 g, 11% mp 80–82° C.; $^1$H-NMR (CDCl$_3$, 200 MHz) δ 1.67–2.27 (4H, m), 2.67–2.93 (2H, m), 3.85 (1H, t, J=5.5 Hz), 7.08–7.26 (4H, m); IR (KBr) 3065–2500, 1692, 1298, 1225, 951, 752 cm$^{-1}$; Anal. Calcd for C$_{11}$H$_{12}$O$_2$: C, 74.98; H, 6.86. Found: C, 74.58; H, 7.05.

2) N-[(1RS,2SR)-2-(4-fluorophenyl)-2-hydroxy-1-[4-(trifluoromethyl)benzyl]ethyl]-1,2,3,4-tetrahydronaphthalene-1-carboxamide While stirring (1RS,2SR)-2-amino-1-(4-fluordphenyl)-3-[4-(trifluoromethyl)phenyl]propan-1-ol (0.295 g, 0.942 mmol), 1,2,3,4-tetrahydronaphthalene-1-carboxylic acid (0.17 g, 0.94 mmol) and 1-hydroxybenzotriazole hydrate (0.14 g, 0.94 mmol) in acetonitrile (10 ml), 1-ethyl-3-(3-dimethylaminopropyl)carbodiimide hydrochloride (0.18 g, 0.94 mmol) was added, and the mixture was stirred overnight at room temperature. The reaction solution was diluted with ethyl acetate, washed with aqueous sodium hydrogen carbonate solution, dried over anhydrous magnesium sulfate, and passed through silica gel. The solvent was evaporated under reduced pressure and the obtained residue was crystallized from ethyl acetate-hexane to give the objective substance.

white crystal yield 0.359 g, 81% mp 205–214° C.; $^1$H-NMR (CDCl$_3$-DMSO-d$_6$, 200 MHz) δ 1.35–1.95 (4H, m), 2.59–2.87 (4H, m), 3.45 (1H, t, J=6.1 Hz), 4.38–4.49 (1H, m), 4.73 (0.5H, t, J=4.4 Hz), 4.82 (0.5H, t, J=4.1 Hz), 5.28 (1H, d, J=4.0 Hz), 6.32 (0.5H, d, J=8.8 Hz), 6.40 (0.5H, d, J=8.4 Hz), 6.56 (1H, d, J=7.4 Hz), 6.91–7.23 (7H, m), 7.34–7.50 (4H, m); IR (KBr) 3279, 1647, 1514, 1329, 1167, 1113, 1069 cm$^{-1}$; Anal. Calcd for C$_{27}$H$_{25}$F$_4$NO$_2$: C, 68.78; H, 5.34; N, 2.97. Found: C, 68.62; H, 5.24; N, 2.90.

Example 42

N-[(1RS,2SR)-2-(4-fluorophenyl)-2-hydroxy-1-[4-(trifluoromethyl)benzyl]ethyl]-6,7,8,9-tetrahydro-5H-benzo[a]cycloheptene-1-carboxamide 1) 6,7,8,9-tetrahydro-5H-benzo[a]cycloheptene-1-carboxylic acid To a solution of 6,7,8,9-tetrahydro-5H-benzo[a]cyclohepten-1-ylmethanol (see *Tetrahedron*, 53, 15969–15982 (1990)) (1.232 g, 6.990 mmol) in acetone (50 ml) was slowly added dropwise a solution of chromic anhydride (2.10 g, 21.0 mmol) and conc. sulfuric acid (2 ml) dissolved in water (9 ml) under ice-cooling. After the completion of the dropwise. addition, the mixture was stirred at room temperature for 2 hrs. The reaction solution was again ice-cooled, isopropanol (5 ml) was added, and the mixture was stirred as it was for 0.5 hr. The reaction solution was diluted with ethyl acetate, washed three times with water and dried over anhydrous magnesium sulfate. The solvent was evaporated under reduced pressure, and the obtained residue was crystallized from ethanol-water to give the objective substance.

white crystal yield 0.916 g, 69% mp 111–112° C.; $^1$H-NMR (CDCl$_3$, 200 MHz) δ 1.60–1.90 (6H, m), 2.88 (2H, t, J=5.5 Hz), 3.17 (2H, t, J=5.1 Hz), 7.14 (1H, t, J=7.5 Hz), 7.28 (1H, d, J=7.8 Hz), 7.69 (1H, dd, J=1.5 Hz, 7.7 Hz); IR (KBr) 3200–2500, 1690, 1437, 1408, 1283, 1273, 916, 758 cm$^{-1}$; Anal. Calcd for C$_{12}$H$_{14}$O$_2$: C, 75.76; H, 7.42. Found: C, 75.71; H, 7.21.

2) N-[(1RS,2SR)-2-(4-fluorophenyl)-2-hydroxy-1-[4-(trifluoromethyl)benzyl]ethyl]-6,7,8,9-tetrahydro-5H-benzo[a]cycloheptene-1-carboxamide While stirring (1RS,2SR)-2-amino-1-(4-fluorophenyl)-3-[4-(trifluoromethyl)phenyl]propan-1-ol (0.163 g, 0.520 mmol), 6,7,8,9-tetrahydro-5H-benzo[a]cycloheptene-1-carboxylic acid (99 mg, 0.52 mmol) and 1-hydroxybenzotriazole hydrate (80 mg, 0.52 mmol) in acetonitrile (10 ml), 1-ethyl-3-(3-dimethylaminopropyl)carbodiimide hydrochloride (0.10 g, 0.52 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance. white crystal yield 0.156 g, 62% mp 210–211° C.; $^1$H-NMR (CDCl$_3$-DMSO-d$_6$, 200 MHz) δ 1.35–1.48 (2H, m), 1.51–1.61 (2H, m), 1.68 1.81 (2H, m), 2.39–2.47 (2H, m), 2.69–2.80 (2H, m), 2.85–3.02 (2H, m), 4.63–4.77 (1H, m), 4.86 (1H, d, J=3.8 Hz), 4.98 (1H, t, J=3.6 Hz), 6.67 (1H, d, J=9.0 Hz), 6.76 (1H, dd, J=1.4 Hz, 7.4 Hz), 6.94 7.11 (4H, m), 7.30 (2H, d, J=8.0 Hz), 7.46–7.53 (4H, m); IR (KBr) 3335, 2922, 1622, 1532, 1508, 2327, 1171, 1127, 831 cm$^{-1}$; Anal. Calcd for C$_{28}$H$_{27}$F$_4$NO$_2$: C, 69.27; H, 5.61; N, 2.88. Found: C, 69.20; H, 5.62; N, 2.86.

Example 43

4-bromo-N-[(1RS,2SR)-2-(4-fluorophenyl)-2-hydroxy-1-[4-(trifluoromethyl)benzyl]ethyl] naphthalene-1-carboxamide 1) (4-bromo-1-naphthyl)methyl acetate A solution of 1-bromo-4-methylnaphthaleneacetate (14.98 g, 67.75 mmol), N-bromosuccinimide (12.1 g, 67.8 mmol) and 2,2'-azobis(isobutyronitrile) (50 mg) in carbon tetrachloride (50 ml) was heated under reflux for 0.5 hr. After cooling the reaction solution to room temperature, white precipitate was filtered off, and the precipitate was washed with diethyl ether. The solvent of the collected filtrate was evaporated under reduced pressure to give a crude product of 1-bromo-4-(bromomethyl)naphthalene as a pale-yellow liquid. The obtained liquid was dissolved in N,N-dimethylformamide (30 ml), sodium acetate (11.1 g, 136 mmol) was added and the mixture was stirred at 60° C. for 6 hrs. After cooling to room temperature, the reaction solution was diluted with water and extracted twice with ethyl acetate. The collected organic layer was dried over anhydrous sodium sulfate, and the solvent was evaporated under reduced pressure. The obtained crude product was purified by silica gel column chromatography (hexane/ethyl acetate=20/1–6/1) to give the objective substance.

yellow liquid yield 14.97 g, 79% $^1$H-NMR (CDCl$_3$, 200 MHz) δ 2.11 (3H, s), 5.53 (2H, s), 7.40 (1H, d, J=7.8 Hz), 7.58–7.69 (2H, m), 7.77 (1H, d, J=7.4 Hz), 7.97–8.05 (1H, m), 8.28–8.36 (1H, m); IR (neat) 1740, 1381, 1366, 1225, 1024, 824, 758 cm$^{-1}$ 2) (4-bromo-1-naphthyl)methanol (4-Bromo-1-naphthyl)methyl acetate (14.97 g, 53.63 mmol) and sodium hydroxide (3.22 g, 80.4 mmol) were stirred in methanol (50 ml)-water (30 ml)-tetrahydrofuran (30 ml) at room temperature for 30 min. The reaction solution was concentrated, diluted with water, and extracted twice with ethyl acetate. The collected organic layer was dried over anhydrous sodium sulfate and the solvent was evaporated under reduced pressure. The obtained crude product was purified by silica gel column chromatography (hexane/ethyl acetate=3/1–2/1) and crystallized from ethyl acetate-hexane to give the objective substance.

white crystal yield 11.77 g, 93% mp 92–93° C.; $^1$H-NMR (CDCl$_3$, 200 MHz) δ 1.80 (1H, t, J=5.9 Hz), 5.13 (2H, d, J=5.8 Hz), 7.38 (1H, d, J=7.6 Hz), 7.56–7.68 (2H, m), 7.76 (1H, d, J=7.6 Hz), 8.07–8.15 (1H, m), 8.27–8.35 (1H, m); IR (KBr) 3214, 1375, 1258, 1073, 997, 822, 748 cm$^{-1}$; Anal. Calcd for C$_{11}$H$_9$BrO: C, 55.72; H, 3.83. Found: C, 55.86; H, 3.70.

3) 4-bromo-1-naphthoic acid

To a solution of (4-bromo-1-naphthyl)methanol (1.329 g, 6.027 mmol) in acetone (50 ml) was added dropwise slowly a solution of chromic anhydride (1.81 g, 18.1 mmol) and conc. sulfuric acid (2 ml) dissolved in water (9 ml) under ice-cooling. After the completion of the dropwise addition, the mixture was stirred at room temperature for 2 hrs. Acetone of the reaction solution was evaporated under reduced pressure. The residue was diluted with ethyl acetate, washed three times with water, and dried over anhydrous magnesium sulfate. The solvent was evaporated under reduced pressure and the obtained residue was crystallized from ethanol-water to give the objective substance.

pale-brown crystal yield 1.272 g, 84% mp 223–224° C.; $^1$H-NMR (CDCl$_3$-DMSO-d$_6$, 200 MHz). δ 7.60–7.69 (2H, m), 7.83 (1H, d, J=7.8 Hz), 8.06 (1H, d, J=8.2 Hz), 8.28–8.36 (1H, m), 8.99–9.08 (1H, m); IR (KBr) 3100–2500, 1694, 1566, 1508, 1279, 1252, 1190, 903, 785, 762 cm$^{-1}$; Anal. Calcd for C$_{11}$H$_7$BrO$_2$: C, 52.62; H, 2.81. Found: C, 52.42; H, 2.87.

4) 4-bromo-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.209 g; 0.667 mmol), 4-bromo-1-naphthoic acid (0.17 g, 0.67 mmol) and 1-hydroxybenzotriazole hydrate (0.10 g, 0.67 mmol) in acetonitrile (10 ml), 1-ethyl-3-(3-dimethylaminopropyl) carbodiimide hydrochloride (0.13 g, 0.67 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.309 g, 85% mp 229–231° C.; $^1$H-NMR (CDCl$_3$-DMSO-d$_6$, 200 MHz) δ 2.84–3.11 (2H, m), 4.71–4.85 (1H, m), 5.00 (1H, t, J=4.0 Hz), 5.24 (1H, d, J=3.8 Hz), 7.04–7.13 (3H, m), 7.33–7.60 (10H, m), 7.69 (1H, d, J=7.4 Hz), 8.20 (1H, d, J=8.8 Hz); IR (KBr) 3262, 1638, 1537, 1514, 1329, 1163, 1125, 1069, 833, 754 cm$^{-1}$; Anal. Calcd for C$_{27}$H$_{20}$BrF$_4$NO$_2$: C, 59.36; H, 3.69; N, 2.56. Found: C, 59.31; H, 3.84; N, 2.72.

Example 44

2-cyclopentyl-N-[(1RS,2SR)-2-(4-fluorophenyl)-2-hydroxy-1-[4-(trifluoromethyl)benzyl]ethyl] acetamide While stirring (1RS,2SR)-2-amino-1-(4-fluorophenyl)-3-[4-(trifluoromethyl)phenyl]propan-1-ol (0.156 g, 0.498 mmol), cyclopentylacetic acid (64 mg, 0.50 mmol) and 1-hydroxybenzotriazole hydrate (76 mg, 0.50 mmol) in acetonitrile (10 ml), 1-ethyl-3-(3-dimethylaminopropyl) carbodiimide hydrochloride (95 mg, 0.50 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from hexane to give the objective substance.

white crystal yield 0.185 g, 88% mp 195–196° C.; $^1$H-NMR (CDCl$_3$-DMSO-d$_6$, 200 MHz) δ 0.75–1.05 (2H, m), 1.25–1.65 (6H, m), 1.92 2.12 (3H, m), 2.77–2.81 (2H, m), 4.39–4.52 (1H, m), 4.65 (1H, d, J=3.4 Hz), 4.93 (1H, t, J=3.3 Hz), 6.10 (1H, br d, J=8.4 Hz), 7.06 (2H, t, J=8.8 Hz), 7.21 (2H, d, J=8.0 Hz), 7.39–7.49 (4H, m); IR (KBr) 3301, 2949, 1645, 1539, 1514, 1327, 1163, 1125, 1069, 829 cm$^{-1}$; Anal. Calcd for C$_{23}$H$_{25}$F$_4$NO$_2$: C, 65.24; H, 5.95; N, 3.31. Found: C, 65.08; H, 5.90; N, 3.41.

Example 45

3-cyclopentyl-N-[(1RS,2SR)-2-(4-fluorophenyl)-2-hydroxy-1-[4-(trifluoromethyl)benzyl]ethyl] propionamide While stirring (1RS,2SR)-2-amino-1-(4-fluorophenyl)-3-[4-(trifluoromethyl)phenyl]propan-1-ol (0.157 g, 0.501 mmol), 3-cyclopentylpropionic acid (71 mg, 0.50 mmol) and 1-hydroxybenzotriazole hydrate (77 mg, 0.50. mmol) in acetonitrile (10 ml), 1-ethyl-3-(3-dimethylaminopropyl) carbodiimide hydrochloride (96 mg, 0.50 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from hexane to give the objective substance.

white crystal yield. 0.180 g, 82% mp 169–170° C.; $^1$H-NMR (CDCl$_3$, 200 MHz) δ 0.98 (2H, br s), 1.35–1.70 (9H, m), 2.07 (2H, dt, J=2.6 Hz, 7.4 Hz), 2.76 (1H, dd, J=10.4 Hz, 14.4 Hz), 2.90 (1H, dd, J=4.4 Hz, 14.6 Hz), 3.61 (1H, d, J=3.6 Hz), 4.36–4.50 (1H, m), 4.97 (1H, t, J=3.5 Hz), 5.39 (1H, br d, J=7.8 Hz), 7.08 (2H, t, J=8.8 Hz), 7.21 (2H, d, J=7.8 Hz), 7.39 (2H, dd, J=5.6 Hz, 8.4 Hz), 7.51 (2H, d, J=8.0 Hz); IR (KBr) 3303, 2951, 1645, 1537, 1514, 1327, 1163, 1123, 1069, 829 cm$^{-1}$; Anal. Calcd for C$_{24}$H$_{27}$F$_4$NO$_2$: C, 65.89; H, 6.22; N, 3.20. Found: C, 65.61; H, 6.16; N, 3.32.

Example 46

N-[(1RS,2SR)-2-(4-fluorophenyl)-2-hydroxy-1-[4-(trifluoromethyl)benzyl]ethyl]-1-benzothiophene-3-carboxamide While stirring (1RS,2SR)-2-amino-1-(4-fluorophenyl)-3-[4-(trifluoromethyl)phenyl]propan-1-ol (0.173 g, 0.552 mmol), 1-benzothiophene-3-carboxylic acid (see Synth. Commun., 15, 711–713 (1984)) (0.10 g, 0.55 mmol) and 1-hydroxybenzotriazole hydrate (85 mg, 0.55 mmol) in acetonitrile (10 ml), 1-ethyl-3-(3-dimethylaminopropyl) carbodiimide hydrochloride (0.11 g, 0.55 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diethyl ether-hexane to give the objective substance.

white crystal yield 0.204 g, 78% mp 188–189° C.; $^1$H-NMR (CDCl$_3$, 200 MHz) δ 2.88–3.08 (2H, m), 3.64 (1H, d, J=3.6 Hz), 4.59–4.72 (1H, m), 5.13 (1H, t, J=3.2 Hz), 6.04 (1H, d, J=8.8 Hz), 7.09 (2H, t, J=8.8 Hz), 7.31–7.60 (9H, m), 7.82–7.92 (2H, m); IR (KBr) 3333, 1622, 1537, 1510, 1331, 1159, 1123, 1069, 833, 766 cm$^{-1}$; Anal. Calcd for C$_{25}$H$_{19}$F$_4$NO$_2$S: C, 63.42; H, 4.04; N, 2.96. Found: C, 63.50; H, 4.10; N, 2.90.

Example 47

N-((1RS,2SR)-2-(4-fluorophenyl)-2-hydroxy-1-((4-(trifluoromethyl)phenyl)methyl)ethyl)-4-phenylbutyramide To a solution of 4-phenylbutyric acid (141 mg, 0.86 mmol) in tetrahydrofuran (5 ml) were added oxalyl chloride (0.15 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (200 mg, 0.57 mmol) and saturated aqueous sodium hydrogen carbonate (5 ml), and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1–1:1) and recrystallized from ethyl acetate-hexane to give the title compound (179 mg, 68%).

mp 150–151° C. IR ν max$^{KBr}$cm$^{-1}$: 1645, 1508. Anal. Calcd for $C_{26}H_{25}F_4NO_2$: C, 67.96; H, 5.48; N, 3.05. Found: C, 67.91; H, 5.35; N, 2.98. $^1$H-NMR (CDCl$_3$)δ: 1.70–1.90 (2H, m), 2.00–2.14 (2H, m), 2.51 (2H, t, J=7.4 Hz), 2.70–2.94 (2H, m), 3.44 (1H, d, J=3.6 Hz), 4.30–4.56 (1H, m), 4.92–5.00 (1H, m), 5.38 (1H, d, J=7.0 Hz), 7.00–7.60 (13H, m).

Example 48

N-((1RS,2SR)-2-(4-fluorophenyl)-2-hydroxy-1-((4-(trifluoromethyl)phenyl)methyl)ethyl)-3-phenylpropanamide To a solution of (1RS,2SR)-2-amino-1-(4-fluorophenyl)-3-(4-(trifluoromethyl)phenyl)-1-propanol (450 mg, 1.44 mmol) in ethyl acetate (20 ml) were added 3-phenylpropionyl chloride (320 ml, 2.15 mmol) and saturated aqueous sodium hydrogen carbonate (20 ml) and the mixture was stirred overnight at room temperature. The reaction solution was diluted with water (100 ml), and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (560 mg, 88%).

mp 144–145° C. IR ν max$^{KBr}$cm$^{-1}$: 1636, 1541. Anal. Calcd for $C_{25}H_{23}F_4NO_2$: C, 67.41; H, 5.20; N, 3.14. Found: C, 67.30; H, 5.21; N, 3.38. $^1$H-NMR (CDCl$_3$)δ: 2.30–2.44 (2H, m), 2.58–2.94 (4H, m), 3.29 (1H, d, J=4.0 Hz), 4.30–4.48 (1H, m), 4.76–7.86 (1H, m), 5.33 (1H, d, J=8.4 Hz), 6.98–7.38 (11H, m), 7.46 (2H, d, J=8.0 Hz).

Example 49

4,4,4-trifluoro-N-[(1RS,2SR)-2-(4-fluorophenyl)-2-hydroxy-1-[4-(trifluoromethyl)benzyl]ethyl]-3-methyl-2-butenamide While stirring (1RS,2SR)-2-amino-1-(4-fluorophenyl)-3-[4-(trifluoromethyl)phenyl]propan-1-ol (0.154 g, 0.492 mmol), 4,4,4-trifluoro-3-methyl-2-butenoic acid (76 mg, 0.49 mmol) and 1-hydroxybenzotriazole hydrate (75 mg, 0.49 mmol) in acetonitrile (10 ml), 1-ethyl-3-(3-dimethylaminopropyl)carbodiimide hydrochloride (94 mg, 0.49 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white crystal yield 0.178 g, 81% mp 182–183° C.; $^1$H-NMR (CDCl$_3$-DMSO-d$_6$, 200 MHz) δ 2.04 (3H, s), 2.80–2.84 (2H, m), 4.41–4.54 (1H, m), 4.84 (1H, d, J=3.2 Hz), 4.94 (1H, t, J=3.3 Hz), 6.24–6.26 (1H, m), 7.06 (2H, t, J=8.6 Hz), 7.20 (2H, d, J=7.8 Hz), 7.33 (1H, d, J=8.6 Hz), 7.42–7.49 (4H, m); IR (KBr) 3297, 1647, 1541, 1514, 1329, 1167, 1119, 1069, 831 cm$^{-1}$; Anal. Calcd for $C_{21}H_{18}F_7NO_2$: C, 56.13; H, 4.04; N, 3.12. Found: C, 56.02; H, 4.04; N, 2.82.

Example 50

2,3-dichloro-N-((1RS,2SR)-2-(4-fluorophenyl)-2-hydroxy-1-((4-(trifluoromethyl)phenyl)methyl)ethyl)benzamide To a solution of (1RS,2RS)-1-(4-fluorophenyl)-1-hydroxy-3-(4-(trifluoromethyl)phenyl)-2-propylamine hydrochloride (150 mg, 0.43 mmol) in ethyl acetate (5 ml) were added 2,3-dichlorobenzoyl chloride (135 mg, 0.64 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1) and recrystallized from ethyl acetate-hexane to give the title compound (161 mg, 77%).

mp 187–188° C. IR ν max$^{KBr}$cm$^{-1}$: 1647, 1537, 1514. Anal. Calcd for $C_{23}H_{17}Cl_2F_4NO_2$: C, 56.81; H, 3.52; N, 2.88. Found: C, 56.82; H, 3.38; N, 2.85. $^1$H-NMR (CDCl$_3$)δ: 2.80–3.10 (3H, m), 4.60–4.80 (1H, m), 5.08 (1H, d, J=3.8 Hz), 6.06 (1H, d, J=8.8 Hz), 6.96–7.38 (6H, m), 7.40–7.62 (5H, m).

Example 51

N-[(1RS,2SR)-2-(4-fluorophenyl)-2-hydroxy-1-[4-(trifluoromethyl)benzyl]ethyl]-6-nitronaphthalene-1-carboxamide While stirring (1RS,2SR)-2-amino-1-(4-fluorophenyl)-3-[4-(trifluoromethyl)phenyl]propan-1-ol (0.178 g, 0.568 mmol), 6-nitro-1-naphthoic acid (see J. Org. Chem., 54, 3596–602 (1989)) (0.12 g, 0.57 mmol) and 1-hydroxybenzotriazole hydrate (87 mg, 0.57 mmol) in acetonitrile (10 ml), 1-ethyl-3-(3-dimethylaminopropyl) carbodiimide hydrochloride (0.11 g, 0.57 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance. white crystal yield 0.256 g, 88% mp 206–207° C.; $^1$H-NMR (CDCl$_3$-DMSO-d$_6$, 200 MHz) δ 2.93 (1H, dd, J=11.0 Hz, 13.8 Hz), 3.20 (1H, dd, J=3.1 Hz, 14.1 Hz), 4.67–4.82 (1H, m), 4.93 (1H, t, J=4.7 Hz), 5.44 (1H, d, J=4.0 Hz), 7.09 (2H, t, J=8.6 Hz), 7.38–7.42 (3H, m), 7.51–7.61 (6H, m), 7.95–8.09 (3H, m), 8.76 (1H, d, J=2.2 Hz); IR (KBr) 3297, 1638, 1535, 1346, 1327, 1113, 1069 cm$^{-1}$; Anal. Calcd for $C_{27}H_{20}F_4N_2O_4$: C, 63.28; H, 3.93; N, 5.47. Found: C, 63.11; H, 3.80; N, 5.34.

Example 52

N-((1RS,2SR)-2-(4-fluorophenyl)-2-hydroxy-1-((4-(trifluoromethyl)phenyl)methyl)ethyl)cyclohexanecarboxamide To a solution of (1RS,2SR)-1-(4-fluorophenyl)-1-hydroxy-3-(4-(trifluoromethyl)phenyl)-2-propylamine hydrochloride (200 mg, 0.57 mmol) in ethyl acetate (5 ml) were added cyclohexanecarbonyl chloride (126 mg, 0.86 mmol) and saturated aqueous sodium hydrogen carbonate (5 ml) and the mixture was stirred at room temperature for 1 hr. The reaction solution was diluted with water (50 ml), and extracted with ethyl acetate (50 ml×2). The extract was washed with saturated brine, dried over anhydrous magnesium sulfate and evaporated under reduced pressure. Recrystallization from ethyl acetate-hexane gave the title compound (166 mg, 69%).

mp 203–204° C. IR ν max$^{KBr}$cm$^{-1}$: 3275, 1645, 1512. Anal. Calcd for $C_{23}H_{25}F_4NO_2$: C, 65.24; H, 5.95; N, 3.31. Found: C, 65.14; H, 5.83; N, 3.50. $^1$H-NMR (CDCl$_3$)δ: 1.00–1.40 (6H, m), 1.50–1.80 (4H, m), 1.80–2.10 (1H, m), 2.72–3.00 (2H, m), 3.73 (1H, d, J=3.6 Hz), 4.32–4.52 (1H, m), 4.94–5.00 (1H, m), 5.36 (1H, d, J=8.0 Hz), 7.02–7.16 (2H, m), 7.21 (2H, d, J=8.4 Hz), 7.30–7.44 (2H, m), 7.51 (2H, d, J=8.4 Hz).

Example 53

N-((1RS,2SR)-2-(4-fluorophenyl)-2-hydroxy-1-((4-(trifluoromethyl)phenyl)methyl)ethyl)-3-oxo-2,3-dihydro-1H-indene-1-carboxamide To a solution of (1RS,2RS)-1-(4-fluorophenyl)-1-hydroxy-3-(4-(trifluoromethyl)phenyl)-2-propylamine (150 mg, 0.42 mmol) in acetonitrile (10 ml) were added 3-oxo-2,3-dihydro-1H-indene-1-carboxylic acid (73 mg, 0.42 mmol), 1-ethyl-3-(3-dimethylaminopropyl)carbodiimide hydrochloride (119 mg, 0.62 mmol) and 1-hydroxy-1H-benzotriazole (63.6 mg, 0.42 mmol) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate= 1:1) and recrystallized from ethyl acetate-hexane to give a highly polar isomer (61 mg, 31%) of the title compound.

mp 242–243° C. IR ν max$^{KBr}$cm$^{-1}$: 1703, 1649, 1539, 1510. Anal. Calcd for $C_{26}H_{21}F_4NO_3 \cdot 0.1H_2O$: C, 65.99; H, 4.52; N, 2.96. Found: C, 65.70; H, 4.41; N, 2.83. $^1$H-NMR (CDCl$_3$)δ: 2.20–2.60 (2H, m), 2.70–3.00 (3H, m), 3.86–3.98 (1H, m), 4.40–4.62 (1H, m), 4.92–5.02 (1H, m), 6.46–6.60 (1H, m), 6.60–7.00 (1H, m), 7.00–7.20 (2H, m), 7.20–7.60 (8H, m), 7.70 (1H, d, J=6.2 Hz).

Simultaneously, a less polar isomer (74 mg, 38%) of the title compound was obtained.

mp 237–238° C. IR ν max$^{KBr}$cm$^{-1}$: 1715, 1651, 1549, 1513. Anal. Calcd for $C_{26}H_{21}F_4NO_3$: C, 66.24; H, 4.49; N, 2.97. Found: C, 66.19; H, 4.36; N, 2.90. $^1$H-NMR (CDCl$_3$)δ: 2.64–2.92 (4H, m), 3.92–4.00 (1H, m), 4.36–4.52 (1H, m), 4.83 (1H, d, J=4.6 Hz), 6.81 (1H, d, J=7.8 Hz), 7.00–7.22 (5H, m), 7.38–7.58 (5H, m), 7.54 (1H, d, J=7.0 Hz)

Example 54

4-cyano-N-[(1RS,2SR)-2-(4-fluorophenyl)-2-hydroxy-1-[4-(trifluoromethyl)benzyl]ethyl] naphthalene-1-carboxamide 1) 4-(methoxycarbonyl)-1-naphthoic acid While stirring naphthalene-1,4-dicarboxylic acid (25.90 g, 119.8 mmol) in tetrahydrofuran (80 ml)-N,N-dimethylformamide (50 ml), 1,8-diazabicyclo[5.4.0]-7-undecene (18.2 g, 120 mmol) was added at room temperature and the mixture was stirred as it was for 0.5 hr. To the reaction solution was added iodomethane (51.0 g, 359 mmol) at room temperature and the mixture was stirred as it was overnight. The reaction solution was diluted with aqueous sodium hydrogen carbonate solution, and washed with ethyl acetate. The obtained aqueous solution was acidified with conc. hydrochloric acid and extracted twice with ethyl acetate. The collected organic layer was dried over anhydrous magnesium sulfate. The solvent was evaporated under reduced pressure and the obtained residue was purified by silica gel column chromatography (hexane/ethyl acetate=1/1) and crystallized from ethyl acetate-hexane, to give the objective substance.

pale-brown crystal yield 6.309 g, 23% mp 148–150° C.; $^1$H-NMR (CDCl$_3$-DMSO-d$_6$, 200 MHz) δ 4.02 (3H, s), 7.59–7.68 (2H, m), 8.09 (1H, d, J=7.4 Hz), 8.14 (1H, d, J=7.4 Hz), 8.75–8.84 (1H, m), 8.88–8.96 (1H, m); IR (KBr) 3100–2635, 1723, 1701, 1291, 1281, 1256, 1206, 1152, 775 cm$^{-1}$; Anal. Calcd for $C_{13}H_{10}O_4$: C, 67.82; H, 4.38. Found: C, 67.82; H, 4.28.

2) methyl 4-(aminocarbonyl)-1-naphthoate

To a solution of 4-(methoxycarbonyl)-1-naphthoic acid (2.553 g, 11.09 mmol) and N,N-dimethylformamide (2 drops) in tetrahydrofuran (40 ml) was dropwise added oxalyl chloride (1.93 ml, 22.2 mmol) at room temperature and the mixture was stirred for 0.5 hr. The solvent of the reaction solution was evaporated under reduced pressure to give a crude product of acid chloride as a liquid. While stirring 15% aqueous ammonia (1.52 g, 22.2 mmol) and sodium hydrogen carbonate (1.86 g, 22.2 mmol) in tetrahydrofuran (40 ml) under ice-cooling, the liquid obtained above was dissolved in tetrahydrofuran (40 ml) and added dropwise, and the mixture was stirred under ice-cooling for 0.5 hr. and at room temperature for 0.5 hr. The reaction solution was poured into aqueous sodium hydrogen carbonate solution and extracted twice with ethyl acetate. The collected organic layer was dried over anhydrous magnesium sulfate, and the solvent was evaporated under reduced pressure. The obtained residue was crystallized from ethyl acetate-diethyl ether-hexane to give the objective substance.

pale-brown crystal yield 2.418 g, 95% mp 182–184° C.; $^1$H-NMR (CDCl$_3$, 200 MHz) δ 4.02 (3H, s), 6.64 (1H, br s), 7.21 (1H, br s), 7.56–7.71 (3H, m), 8.13 (1H, d, J=7.8 Hz), 8.34–8.43 (1H, m), 8.83–8.91 (1H, m); IR (KBr) 3374, 3193, 1719, 1647, 1578, 1279, 1250, 1198, 1127, 783 cm$^{-1}$; Anal. Calcd for $C_{13}H_{11}NO_3$: C, 68.11; H, 4.84; N, 6.11. Found: C, 67.77; H, 5.20; N, 5.79.

3) methyl 4-cyano-1-naphthoate

Methyl 4-(aminocarbonyl)-1-naphthoate (1.756 g, 7.660 mmol) and thionyl chloride (0.68 ml, 15.3 mmol) were stirred in toluene (30 ml) at 80° C. for 30 min. The reaction solution was poured into aqueous sodium hydrogen carbonate solution, and extracted twice with ethyl acetate. The collected organic layer was dried over anhydrous magnesium sulfate, and the solvent was evaporated under reduced pressure. The obtained residue was purified by silica gel column chromatography (hexane/ethyl acetate=6/1) and crystallized from ethyl acetate-hexane to give the objective substance. white crystal yield 1.021 g, 63% mp 109–110° C.; $^1$H-NMR (CDCl$_3$, 200 MHz) δ 4.05 (3H, s), 7.69–7.80 (2H, M), 7.94 (1H, d, J=7.6 Hz), 8.15 (1H, d, J=7.6 Hz), 8.28–8.36 (1H, m), 8.86–8.94 (1H, m); IR (KBr) 2332, 1717, 1298, 1256, 766 cm$^{-1}$; Anal. Calcd for $C_{13}H_9NO_2$: C, 73.92; H, 4.29; N, 6.63. Found: C, 73.93; H, 4.29; N, 6.65.

4) 4-cyano-1-naphthoic acid

To a solution of methyl 4-cyanonaphthoate (0.862 g, 4.081 mmol) in methanol (20 ml)-tetrahydrofuran (20 ml)

was added 1N aqueous sodium hydroxide solution (8.16 ml, 8.16 mmol), and the mixture was stirred overnight at room temperature. The reaction solution was concentrated, diluted with water, acidified with 1N hydrochloric acid, and extracted twice with ethyl acetate. The collected organic layer was dried over anhydrous sodium sulfate, and the solvent was evaporated under reduced pressure. The residue was crystallized from ethyl acetate-hexane to give the objective substance.

white crystal yield 0.730 g, 91% mp 237–238° C.; $^1$H-NMR (DMSO-d$_6$, 200 MHz) δ 7.77–7.91 (2H, m), 8.14–8.27 (3H, m), 8.83–8.92 (1H, m); IR (KBr) 3100–2550, 2226, 1698, 1516, 1285, 1264, 1204, 795, 770 cm$^{-1}$; Anal. Calcd for $C_{12}H_7NO_2$: C, 73.09; H, 3.58; N, 7.10. Found: C, 72.96; H, 3.42; N, 7.07.

5) 4-cyano-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.155 g, 0.495 mmol), 4-cyano-1-naphthoic acid (0.10 g, 0.49 mmol) and 1-hydroxybenzotriazole hydrate (76 mg, 0.49 mmol) in acetonitrile (10 ml), 1-ethyl-3-(3-dimethylaminopropyl) carbodiimide hydrochloride (94 mg, 0.49 mmol) was added, and the mixture was stirred overnight at room temperature. The reaction solution was diluted with ethyl cetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.204 g, 84% mp 199–201° C.; $^1$H-NMR (CDCl$_3$-DMSO-d$_6$, 200 MHz) δ 2.84–2.98 (1H, m), 3.18–3.28 (1H, m), 4.65 4.80 (1H, m), 4.85 (1H, t, J=5.3 Hz), 5.53 (1H, d, J=4.0 Hz), 7.09 (2H, t, J=8.8 Hz), 7.17–7.26 (2H, m), 7.37–7.44 (3H, m), 7.52–7.58 (4H, m), 7.64–7.72 (1H, m), 7.86 (1H, d, J=7.4 Hz), 8.13–8.22 (2H, m); IR (KBr) 3283, 2228, 1642, 1539, 1512, 1327, 1163, 1125, 1111, 1069, 839 cm$^{-1}$; Anal. Calcd for $C_{28}H_{20}F_4N_2O_2 \cdot 0.1H_2O$: C, 68.04; H, 4.12; N, 5.67. Found: C, 67.8.6; H, 4.19; N, 5.55.

Example 55

4-fluoro-N-((1RS,2SR)-2-(4-fluorophenyl)-2-hydroxy-1-((4-(trifluoromethyl)phenyl)methyl)ethyl) benzamide To a solution of (1RS,2SR)-1-(4-fluorophenyl)-1-hydroxy-3-(4-(trifluoromethyl)phenyl)-2-propylamine hydrochloride (200 mg, 0.57 mmol) in ethyl acetate (5 ml) were added 4-fluorobenzoyl chloride (136 mg, 0.86 mmol) and saturated aqueous sodium hydrogen carbonate (5 ml) and the mixture was stirred at room temperature for 1 hr. The reaction solution was diluted with water (50 ml), and extracted with ethyl acetate (50 ml×2). The extract was washed with saturated brine, dried over anhydrous magnesium sulfate and evaporated under reduced pressure. Recrystallization from ethyl acetate-hexane gave the title compound (182 mg, 73%).

mp 202–203° C. IR ν max$^{KBr}$cm$^{-1}$: 3297, 1640, 1607, 1508. Anal. Calcd for $C_{23}H_{18}F_5NO_2$: C, 63.45; H, 4.17; N, 3.22. Found: C, 63.30; H, 4.26; N, 3.28. $^1$H-NMR (CDCl$_3$)δ: 2.80–3.06 (2H, m), 3.43 (1H, d, J=3.8 Hz), 4.50–4.70 (1H, m), 5.04–5.14 (1H, m), 6.07 (1H, d, J=9.0 Hz), 7.00–7.20 (4H, m), 7.20–7.36 (2H, m), 7.40–7.64 (6H, m).

Example 56

N-((1RS,2SR)-2-(4-fluorophenyl)-2-hydroxy-1-((4-(trifluoromethyl)phenyl)methyl)ethyl)-6-(methyloxy)-1-naphthalenecarboxamide To a solution of 6-methoxy-1-naphthalenecarboxylic acid (129 mg, 0.64 mmol) in tetrahydrofuran (5 ml) were added oxalyl chloride (0.11 ml, 1.28 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1) and recrystallized from ethyl acetate-hexane to give the title compound (148 mg, 69%).

mp 193–194° C. IR ν max$^{KBr}$cm$^{-1}$: 1636, 1512. Anal. Calcd for $C_{28}H_{23}F_4NO_3 \cdot 0.1H_2O$: C, 67.36; H, 4.68; N, 2.81. Found: C, 67.24; H, 4.71; N, 2.81. $^1$H-NMR (CDCl$_3$)δ: 2.80–3.16 (2H, m), 3.37 (1H, brs), 3.91 (3H, s), 4.70–4.90 (1H, m), 5.09 (1H, brs), 5.95 (1H, d, J=8.4. Hz), 6.98–7.18 (5H, m), 7.20–7.40 (3H, m), 7.40–7.60 (5H, m), 7.75 (1H, d, J=8.0 Hz).

Example 57

N-((1RS,2SR)-2-(4-fluorophenyl)-2-hydroxy-1-((4-(trifluoromethyl)phenyl)methyl)ethyl)-4-quinolinecarboxamide To a solution of 4-quinolinecarboxylic acid (111 mg, 0.64 mmol) in tetrahydrofuran (5 ml) were added oxalyl chloride (0.11 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (ethyl acetate) and recrystallized from ethyl acetate-hexane to give the title compound (63 mg, 32%).

mp 227–228° C. IR ν max$^{KBr}$cm$^{-1}$: 1644, 1508, 1331. Anal. Calcd for $C_{26}H_{20}F_4N_2O_2 \cdot 0.5H_2O$:, C, 65.41; H, 4.43; N, 5.87. Found: C, 65.31; H, 4.68; N, 5.61. $^1$H-NMR (CDCl$_3$)δ: 2.76–2.98 (1H, m), 3.00–3.16 (1H, m), 4.72–4.92 (1H, m), 5.05 (1H, d, J=4.0 Hz), 6.60–6.80 (1H, m), 7.02–7.20 (3H, m), 7.22–7.60 (8H, m), 7.62–7.78 (1H, m), 8.05 (1H, d, J=8.4 Hz), 8.82 (1H, brs).

Example 58

3-fluoro-N-[(1RS,2SR)-2-(4-fluorophenyl)-2-hydroxy-1-[4-(trifluoromethyl)benzyl]ethyl] haphthalene-1-carboxamide 1) ethyl 3-nitro-1-naphthoate A solution of 3-nitro-1-naphthoic acid (see *J. Org. Chem.*, 54, 3596–602 (1989)) (3.020 g, 13.91 mmol) and conc. sulfuric acid (1 ml) in ethanol (50 ml) was heated under reflux for 1 day. The reaction solution was concentrated, diluted with ethyl acetate, and washed with aqueous sodium hydrogen carbonate solution and water. The obtained ethyl acetate solution was dried over anhydrous magnesium sulfate. The solvent was evaporated under reduced pressure and the obtained residue was crystallized from diethyl ether-hexane to give the objective substance.

yellow crystal yield 3.137 g, 92% mp 78–79° C.; $^1$H-NMR (CDCl$_3$, 200 MHz) δ 1.50 (3H, t, J=7.1 Hz), 4.53 (2H, q, J=7.1 Hz), 7.71 (1H, ddd, J=1.0 Hz, 6.8 Hz, 8.2 Hz), 7.83 (1H, ddd, J=1.3 Hz, 6.7 Hz, 8.8 Hz), 8.10 (1H, d, J=8.8 Hz), 8.92 (1H, d, J=2.6 Hz), 8.96 (1H, d, J=2.6 Hz), 9.03 (1H, d, J=8.8 Hz); IR (KBr) 1717, 1603, 1526, 1453, 1339, 1281, 1240, 1190, 1155, 1140 1024, 795, 766 cm$^{-1}$; Anal. Calcd for C$_{13}$H$_{11}$NO$_4$: C, 63.67; H, 4.52; N, 5.71. Found: C, 63.64; H, 4.44; N, 5.64.

2) ethyl 3-amino-1-naphthoate

A solution of ethyl 3-nitro-1-naphthoate (5.371 g, 21.90 mmol) in ethanol (30 ml) was hydrogenated under normal temperature and normal pressure using 10% palladium/carbon (containing water by 50%) (0.5 g) as a catalyst until the starting material disappeared. The catalyst was filtered off and the solvent was evaporated under reduced pressure. The obtained crude product was purified by silica gel column chromatography (hexane/ethyl acetate=6/1–3/1) to give the objective substance.

orange liquid yield 4.681 g, 99% $^1$H-NMR (CDCl$_3$, 200 MHz) δ 1.45 (3H, t, J=7.1 Hz), 3.89 (2H, br s), 4.46 (2H, q, J=7.1 Hz), 7.15 (1H, d, J=2.2 Hz), 7.30–7.45 (2H, m), 7.60–7.66 (2H, m), 8.70 (1H, dd, J=1.6 Hz, 8.2 Hz); IR (neat) 3465, 3374, 2980, 1705, 1626, 1236, 1202 cm$^{-1}$ 3) 3-fluoro-1-naphthoic acid While stirring ethyl 3-amino-1-naphthoate (2.318 g, 10.77 mol) and conc. hydrochloric acid (4 ml) in water (30 ml), a solution of sodium nitrite (0.89 g, 12.9 mmol) in water (2 ml) was added dropwise under ice-cooling and the mixture was stirred at said temperature for 10 min. To the reaction solution was added a 60% aqueous hexafluorophosphoric acid solution (2.70 ml, 18.3 mmol) with vigorous stirring under ice-cooling and the mixture was stirred as it was for 0.5 hr. The resulting precipitate was filtered, washed with water and methanol-diethyl ether (1:4) and dried to give a diazonium salt as a brown powder. The obtained diazonium salt was heated in liquid paraffin (8 ml) at 170° C. for 0.5 hr. After cooling to room temperature, aqueous sodium hydrogen carbonate solution was added, and the mixture was extracted twice with ethyl acetate. The collected organic layer was dried over anhydrous magnesium sulfate. The solvent was evaporated under reduced pressure and the obtained crude product was purified by silica gel column chromatography (hexane/ethyl acetate=15/1) to give a mixture of ethyl 3-fluoro-1-naphthoate and liquid paraffin as a pale-yellow liquid. To a solution of the obtained liquid in ethanol (30 ml)-tetrahydrofuran (40 ml) was added 1N aqueous sodium hydroxide solution (10 ml, 10 mmol), and the mixture was stirred overnight at room temperature. The reaction solution was concentrated, diluted with water, acidified with dilute hydrochloric acid, and extracted twice with ethyl acetate. The collected organic layer was dried over anhydrous sodium sulfate, and the solvent was evaporated under reduced pressure. The residue was crystallized from ethyl acetate-hexane to give the objective substance.

pale-yellow crystal yield 0.629 g, 31% mp 185–187° C.; $^1$H-NMR (DMSO-d$_6$, 200 MHz) δ 7.58–7.66 (2H, m), 7.94–8.03 (3H, m), 8.82–8.88 (1H, m); IR (KBr) 3150–2550, 1696, 1682, 1296, 1252, 1221, 750 cm$^{-1}$; Anal. Calcd for C$_{11}$H$_7$FO$_2$: C, 69.47; H, 3.71. Found: C, 69.57; H, 3.80.

4) 3-fluoro-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.158 g, 0.504 mmol), 3-fluoro-1-naphthoic acid (0.10 g, 0.50 mmol) and 1-hydroxybenzotriazole hydrate (77 mg, 0.50 mmol) in acetonitrile (10 ml), 1-ethyl-3-(3-dimethylaminopropyl)carbodiimide hydrochloride (0.10 g, 0.50 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.199 g, 81% mp 223–225° C.; $^1$H-NMR (CDCl$_3$-DMSO-d$_6$, 200 MHz) δ 2.92 (1H, dd, J=11.3 Hz, 14.3 Hz), 3.17, (1H, dd, J=3.3 Hz, 13.9 Hz), 4.64–4.80 (1H, m), 4.91 (1H, t, J=4.4 Hz), 5.45 (1H, d, J=4.0 Hz), 6.98 (1H, dd, J=2.4 Hz, 8.8 Hz), 7.08 (2H, t, J=8.8 Hz), 7.21–7.60 (10H, m), 7.74 (1H, d, J=8.6 Hz), 7.99 (1H, d, J=10.0 Hz); IR (KBr) 3277, 1642, 1624, 1537, 1514, 1325, 1231, 1165, 1127, 1069, 831 cm$^{-1}$; Anal. Calcd for C$_{27}$H$_{20}$F$_5$NO$_2$: C, 66.80; H, 4.15; N, 2.89. Found: C, 66.66; H, 4.21; N, 2.70.

Example 59

4,4,4-trifluoro-N-[(1RS,2SR)-2-(4-fluorophenyl)-2-hydroxy-1-[4-(trifluoromethyl)benzyl]ethyl]butylamide While stirring (1RS,2SR)-2-amino-1-(4-fluorophenyl)-3-[4-(trifluoromethyl)phenyl]propan-1-ol (0.170 g, 0.543. mmol), 4,4,4-trifluorobutanoic acid (77 mg, 0.54 mmol) and 1-hydroxybenzotriazole hydrate (83 mg, 0.54 mmol) in acetonitrile (10 ml), 1-ethyl-3-(3-dimethylaminopropyl)carbodiimide hydrochloride (0.10 g, 0.54 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white crystal yield 0.210 g, 88% mp 178–179° C.; $^1$H-NMR (CDCl$_3$-DMSO-d$_6$, 200 MHz) δ 2.15–2.45 (4H, m), 2.74–2.81 (2H, m), 4.33 4.46 (1H, m), 4.88 (1H, d, J=3.2 Hz), 4.92 (1H, t, J=3.3 Hz), 7.05 (2H, t, J=8.8 Hz), 7.07 (1H, d, J=8.8 Hz), 7.20 (2H, d, J=8.0 Hz), 7.38–7.47 (4H, m); IR (KBr) 3299, 1655, 1557, 1514, 1329, 1229, 1107, 1069, 829 cm$^{-1}$; Anal. Calcd for C$_{20}$H$_{18}$F$_7$NO$_2$: C, 54.93; H, 4.15; N, 3.20. Found: C, 54.96; H, 4.22; N, 2.95.

Example 60

N-((1RS,2SR)-2-(4-fluorophenyl)-2-hydroxy-1-((4-(trifluoromethyl)phenyl)methyl)ethyl)-4-(methyloxy)benzamide To a solution of (1RS,2SR)-1-(4-fluorophenyl)-1-hydroxy-3-(4-(trifluoromethyl)phenyl)-2-propylamine hydrochloride (200 mg, 0.57 mmol) in ethyl acetate (5 ml) were added 4-anisoyl chloride (146 mg, 0.86 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (185 mg, 72%).

mp 192–193° C. IR ν max$^{KBr}$cm$^{-1}$: 1624, 1609, 1539, 1507, 1329. Anal. Calcd for $C_{24}H_{21}F_4NO_3$: C, 64.43; H, 4.73; N, 3.13. Found: C, 64.44; H, 4.66; N, 3.09. $^1$H-NMR (CDCl$_3$)δ: 2.86–3.00 (2H, m), 3.84 (3H, s), 3.80–3.88 (1H, m), 4.50–4.66 (1H, m), 5.06–5.14 (1H, m), 6.00 (1H, d, J=8.0 Hz), 6.88 (2H, d, J=8.8 Hz), 7.02–7.14 (2H, m), 7.20–7.30 (2H, m), 7.36–7.60 (6H, m).

Example 61

N-((1RS,2SR)-2-(4-fluorophenyl)-2-hydroxy-1-((4-(trifluoromethyl)phenyl)methyl)ethyl)-9-oxo-9H-fluorene-4-carboxamide To a solution of 9-oxo-9H-fluorene-4-carboxylic acid (144 mg, 0.64 mmol) in tetrahydrofuran (5 ml) were added oxalyl chloride (0.11 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1–1:1) and recrystallized from ethyl acetate-hexane to give the title compound (154 mg, 69%).

mp 231–232° C. IR ν max$^{KBr}$cm$^{-1}$: 1725, 1638, 1607. Anal. Calcd for $C_{30}H_{21}F_4NO_3$: C, 69.36; H, 4.07; N, 2.70. Found: C, 69.13; H, 4.22; N, 2.53. $^1$H-NMR (CD$_3$OD)δ: 2.78–2.96 (1H, m), 3.49 (1H, d, J=13.2 Hz), 4.70–4.80 (2H, m), 6.72 (1H, d, J=7.4 Hz), 6.89 (1H, d, J=7.8 Hz), 7.04–7.32 (5H, m), 7.46–7.66 (8H, m).

Example 62

3,3-dimethyl-N-[(1RS,2SR)-2-(4-fluorophenyl)-2-hydroxy-1-[4-(trifluoromethyl)benzyl]ethyl] butylamide While stirring (1RS,2SR)-2-amino-1-(4-fluorophenyl)-3-[4-(trifluoromethyl)phenyl]propan-1-ol (0.168 g, 0.536 mmol), 3,3-dimethylbutanoic acid (62 mg, 0.54 mmol) and 1-hydroxybenzotriazole hydrate (82 mg, 0.54 mmol) in acetonitrile (10 ml), 1-ethyl-3-(3-dimethylaminopropyl) carbodiimide hydrochloride (0.10 g, 0.54 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from hexane to give the objective substance.

white crystal yield 0.155 g, 70% mp 140–141° C.; $^1$H-NMR (CDCl$_3$, 200 MHz) δ 0.81 (9H, s), 1.87. (1H, d, J=12.8 Hz), 1.99 (1H, d, J=13.0 Hz), 2.71 (1H, dd, J=10.8 Hz, 14.8 Hz), 2.91 (1H, dd, J=4.4 Hz, 15.0 Hz), 3.47 (1H, d, J=3.6 Hz), 4.32–4.56 (1H, m), 4.97 (1H, t, J=3.1 Hz), 5.31 (1H, br d, J=8.4 Hz), 7.07 (2H, t, J=8.6 Hz), 7.22 (2H, d, J=8.4 Hz), 7.40 (2H, dd, J=5.4 Hz, 8.4 Hz), 7.50 (2H, d, J=8.0 Hz); IR (KBr) 3337, 2963, 1626, 1534, 1510, 1333, 1231, 1159, 1127, 1071, 826 cm$^{-1}$; Anal. Calcd for $C_{22}H_{25}F_4NO_2$: C, 64.22; H, 6.12; N, 3.40. Found: C, 64.03; H, 6.20; N, 3.16.

Example 63

N-((1RS,2SR)-2-(4-fluorophenyl)-2-hydroxy-1-((4-(trifluoromethyl)phenyl)methyl)ethyl)-2-naphthalenecarboxamide To a solution of (1RS,2SR)-1-(4-fluorophenyl)-1-hydroxy-3-(4-(trifluoromethyl)phenyl)-2-propylamine hydrochloride (200 mg, 0.57 mmol) in ethyl acetate (5 ml) were added 2-naphthoyl chloride (164 mg, 0.86 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (175 mg, 65%).

mp 174–175° C. IR ν max$^{KBr}$cm$^{-1}$: 1640, 1537, 1514. Anal. Calcd for $C_{27}H_{21}F_4NO_2$: C, 69.37; H, 4.53; N, 3.00. Found: C, 69.23; H, 4.49; N, 2.92. $^1$H-NMR (CDCl$_3$)δ: 2.96–3.04 (2H, m), 3.70 (1H, d, J=3.6 Hz), 4.58–4.76 (1H, m), 5.12–5.20 (1H, m), 6.26 (1H, d, J=8.0 Hz), 7.02–7.16 (2H, m), 7.31 (1H, s), 7.40–7.64 (7H, m), 7.80–7.90 (3H, m), 8.04 (1H, s)

Example 64

4-(difluoromethyl)-N-((1S,2R)-2-(4-fluorophenyl)-2-hydroxy-1-((4-(trifluoromethyl)phenyl)methyl) ethyl)-1-naphthalenecarboxamide 1) To a solution of 4-methyl-1-naphthalenecarboxylic acid (4.14 g, 22.2 mmol) in methanol (50 ml) was added thionyl chloride (3 ml), and the mixture was stirred at 60° C. overnight. The reaction solution was concentrated, water (100 ml) was added and the mixture was extracted with ethyl acetate (100 ml×2). The extract was washed successively with saturated aqueous sodium hydrogen carbonate and saturated brine, dried over anhydrous magnesium sulfate and evaporated under reduced ressure to give methyl 4-methyl-1-naphthalenecarboxylate (4.32 g, 97%) as a colorless oil.

IR ν max$^{KBr}$cm$^{-1}$: 1715, 1591. $^1$H-NMR (CDCl$_3$)δ: 2.75 (3H, s), 3.99 (3H, s), 7.35 (1H, d, J=7.6 Hz), 7.50–7.68 (2H, m), 8.00–8.14 (2H, m), 8.92–9.02 (1H, m).

2) To a solution of methyl 4-methyl-1-naphthalenecarboxylate (4.23 g, 21.1 mmol) in chloroform (70 ml) were added N-bromosuccinimide (4.1 g, 23.2 mmol) and 2,2'-azobis (isobutyronitrile) (175 mg, 1.05 mmol) and the mixture was heated under reflux for 30 min. The reaction solution was concentrated, water (100 ml) was added and the mixture was extracted with ethyl acetate (100 ml×2). The extract was washed with saturated brine, dried over anhydrous magnesium sulfate and evaporated under reduced pressure. The residue-was dissolved in N,N-dimethylformamide (50 ml) and sodium acetate (3.46 g, 42.2 mmol) was added. The mixture was stirred at room temperature for 1 hr. and at 60° C. overnight. The reaction solution was concentrated, water (100 ml) was added and the mixture was extracted with ethyl acetate (100 ml×2). The extract was washed with saturated brine, dried over anhydrous magnesium sulfate and evaporated under reduced pressure. The residue was purified by silica gel column chromatography (hexane:ethyl acetate= 20:1) to give methyl 4-((acetyloxy)methyl)-1-naphthalenecarboxylate (4.1 g, 74%).

IR ν max$^{KBr}$cm$^{-1}$: 1744, 1717, 1595, 1518. Anal. Calcd for $C_{15}H_{14}O_4$: C, 69.76; H, 5.46. Found: C, 69.63; H, 5.54. $^1$H-NMR (CDCl$_3$)δ: 2.14 (3H, s), 4.00 (3H, s), 5.59 (2H, s), 7.52–7.70 (3H, m), 7.98–8.08 (1H, m), 8.12 (1H, d, J=7.2 Hz), 8.90–9.00 (1H, m), 3) To a solution of methyl 4-((acetyloxy)methyl)-1-naphthalenecarboxylate (3.91 g, 15.1 mmol) in methanol (20 ml) was added 1N aqueous sodium hydroxide solution (15.1 ml, 15.1 mmol), and the mixture was stirred at room temperature for 5 min. 1N Hydrochloric acid was added to the reaction solution (20 ml) and the mixture was extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=1:1) to give methyl 4-(hydroxymethyl)-1-naphthalenecarboxylate (2.78 g, 85%).

IR ν max$^{KBr}$cm$^{-1}$: 1715. Anal. Calcd for $C_{13}H_{12}O_3$: C, 72.21; H, 5.59. Found: C, 71.92; H, 5.49. $^1$H-NMR (CDCl$_3$) δ: 3.99 (3H, s), 5.16 (2H, s), 7.50–7.68 (3H, m), 8.00–8.16 (2H, m), 8.88–8.96 (1H, m).

4) To a solution of methyl 4-(hydroxymethyl)-1-naphthalenecarboxylate (2.0 g, 9.25 mmol) in chloroform (40 ml) was added manganese dioxide (4.0 g), and the mixture was stirred at room temperature for 2 hrs. Manganese dioxide was filtered from the reaction solution using celite and the filtrate was evaporated under reduced pressure. The residue was purified by silica gel column chromatography (hexane:ethyl acetate=2:1) and recrystallized from ethyl acetate-hexane to give methyl 4-formyl-1-naphthalenecarboxylate (1.41 g, 85%).

mp 95–96° C. IR ν max$^{KBr}$cm$^{-1}$: 1723, 1696. Anal. Calcd for $C_{13}H_{10}O_3$: C, 72.89; H, 4.71. Found: C, 72.81; H, 4.87. $^1$H-NMR (CDCl$_3$)δ: 4.04 (3H, s), 7.60–7.78 (2H, m), 7.98 (1H, d, J=7.2 Hz), 8.17 (1H, d, J=7.2 Hz), 8.76–8.82 (1H, m), 9.20–9.28 (1H, m), 10.47 (1H, s).

5) To a solution of methyl 4-formyl-1-naphthalenecarboxylate (800 mg, 3.73 mmol) in toluene (15 ml) was added diethylaminosulfur trifluoride (750 ml, 5.1 mmol) and the mixture was stirred overnight at room temperature. To the reaction solution was added saturated aqueous sodium hydrogen carbonate (10 ml) and the mixture was extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=10:1) to give methyl 4-(difluoromethyl)-1-naphthalenecarboxylate (522 mg, 59%).

IR ν max$^{KBr}$cm$^{-1}$: 1723. Anal. Calcd for $C_{13}H_{10}F_2O_2$: C, 66.10; H, 4.27. Found: C, 66.07; H, 4.35. $^1$H-NMR (CDCl$_3$) δ: 4.03 (3H, s), 7.19 (1H, t, J=55.0 Hz), 7.60–7.70 (2H, m), 7.75 (1H, d, J=7.8 Hz), 8.10–8.22 (2H, m), 8.86–8.96 (1H, m).

6) To a solution of methyl 4-(difluoromethyl)-1-naphthalenecarboxylate (450 mg, 1.91 mmol) in methanol (5 ml) was added 2N aqueous sodium hydroxide solution (1.9 ml, 3.8 mmol), and the mixture was stirred overnight at room temperature. 1N Hydrochloric acid was added to the reaction solution (5 ml) and the mixture was extracted with ethyl acetate (20 ml×2). The extract was washed with saturated brine, dried over anhydrous magnesium sulfate and evaporated under reduced pressure. The residue was recrystallized from ethyl acetate-hexane to give 4-(difluoromethyl)-1-naphthalenecarboxylic acid (344 mg, 81%).

mp 179–180° C. IR ν max$^{KBr}$cm$^{-1}$: 1701. Anal. Calcd for $C_{12}H_8F_2O_2$: C, 64.87; H, 3.63. Found: C, 64.76; H, 3.55. $^1$H-NMR (CDCl$_3$)δ: 7.22 (1H, t, J=54.8 Hz), 7.62–7.70 (2H, m), 7.81 (1H, d, J=7.6 Hz), 8.21 (1H, d, J=6.6 Hz), 8.39 (1H, d, J=7.6 Hz), 9.02–9.18 (1H, m).

7) To a solution of (1RS,2SR)-2-amino-1-(4-fluorophenyl)-3-(4-(trifluoromethyl)phenyl)-1-propanol (300 mg, 0.96 mmol) in acetonitrile (30 ml) were added 4-(difluoromethyl)-1-naphthalenecarboxylic acid (213 mg, 0.96 mmol), 1-ethyl-3-(3-dimethylaminopropyl)carbodiimide hydrochloride (275 mg, 1.44 mmol) and 1-hydroxy-1H-benzotriazole (147 mg, 0.96 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane:ethyl acetate=4:1) and recrystallized from ethyl acetate-hexane to give the-title compound (410 mg, 83%).

mp 212–213° C. IR ν max$^{KBr}$cm$^{-1}$: 1640, 1618, 1513. Anal. Calcd for $C_{28}H_{21}F_6NO_2$: C, 64.99; H, 4.09; N, 2.71. Found: C, 64.77; H, 4.36; N, 2.45. $^1$H-NMR (CDCl$_3$)δ: 2.85 (1H, dd, J=14.6, 11.0 Hz), 3.00–3.16 (2H, m), 4.76–4.92 (1H, m), 5.04–5.12 (1H, m), 6.00 (1H, d, J=9.2 Hz), 6.82–7.66 (14H, m), 8.10 (1H, d, J=8.4 Hz).

Example 65

N-((1RS,2SR)-2-(4-fluorophenyl)-2-hydroxy-1-((4-(trifluoromethyl)phenyl)methyl)ethyl)-4-((methyloxy)methyl)-1-naphthalenecarboxamide 1) To a solution of methyl 4-(hydroxymethyl)-1-naphthalenecarboxylate (1.0 g, 4.62 mmol) in N,N-dimethylformamide (10 ml) was added methyl iodide (1 ml), and sodium hydride (222 mg, 5.55 mmol, 60% in oil) was further added at 0° C., and the mixture was stirred at room temperature for 10 min. To the reaction solution was added water (30 ml) and the mixture was extracted with ethyl acetate (50 ml×2). The extract was washed with saturated brine, dried over anhydrous magnesium sulfate and evaporated under reduced pressure. The residue was purified by silica gel column chromatography (hexane:ethyl acetate= 20:1–10:1) to give methyl 4-((methyloxy)methyl)-1-naphthalenecarboxylate (898 mg, 84%).

IR ν max$^{KBr}$cm$^{-1}$: 1717. Anal. Calcd for $C_{14}H_{14}O_3 \cdot 0.1H_2O$: C, 72.46; H, 6.16. Found: C, 72.66; H, 6.09. $^1$H-NMR (CDCl$_3$)δ: 3.48 (3H, s), 4.00 (3H, s), 4.94 (2H, s), 7.50–7.68 (3H, m), 8.04–8.18. (2H, m), 8.90–8.98 (1H, m).

2) To a solution of methyl 4-((methyloxy)methyl)-1-naphthalenecarboxylate (780 mg, 3.38 mmol) in methanol (10 ml) was added 1N aqueous sodium hydroxide solution (6.76 ml, 6.76 mmol), and the mixture was stirred overnight at room temperature. 1N Hydrochloric acid was added to the reaction solution (10 ml) and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give 4-((methyloxy)methyl)-1-naphthalenecarboxylic acid (615 mg, 84%).

mp 133–134° C. IR ν max$^{KBr}$cm$^{-1}$: 1694. Anal. Calcd for C$_{13}$H$_{12}$O$_3$: C, 72.21; H, 5.59. Found: C, 72.10; H, 5.64. $^1$H-NMR (CDCl$_3$)δ: 3.52 (3H, s), 4.99 (2H, s), 7.56–7.70 (3H, m), 8.10–8.18 (1H, m), 8.37 (1H, d, J=7.2 Hz), 9.10–9.16 (1H, m).

3) To a solution of (1RS,2SR)-2-amino-1-(4-fluorophenyl)-3-(4-(trifluoromethyl)phenyl)-1-propanol (300 mg, 0.96 mmol) in acetonitrile (30 ml) were added 4-((methyloxy)methyl)-1-naphthalenecarboxylic acid (207 mg, 0.96 mmol), 1-ethyl-3-(3-dimethylaminopropyl)carbodiimide hydrochloride (275 mg, 1.44 mmol) and 1-hydroxy-1H-benzotriazole (147 mg, 0.96 mmol) and the mixture was stirred overnight at room temperature. The reaction solution was diluted with water (100 ml), and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane:ethyl acetate=4:1–2:1) and recrystallized from ethyl acetate-hexane to give the title compound (340 mg, 69%).

mp 170–171° C. IR ν max$^{KBr}$cm$^{-1}$: 1638, 1618, 1607, 1510. Anal. Calcd for C$_{29}$H$_{25}$F$_4$NO$_3$: C, 68.09; H, 4.93; N, 2.74. Found: C, 67.89; H, 5.05; N, 2.45. $^1$H-NMR (CDCl$_3$)δ: 2.82 (1H, dd, J=14.6, 11.0 Hz), 3.03 (1H, dd, J=14.6, 4.4 Hz), 3.46 (3H, s), 4.68–4.88 (1H, m), 4.85 (2H, s), 4.92–5.00 (1H, m), 6.05 (1H, d, J=8.8 Hz), 7.00–7.16 (3H, m), 7.22–7.62 (10H, m), 8.01 (1H, d, J=8.4 Hz).

Example 66

N-((1RS,2SR)-2-(4-fluorophenyl)-2-hydroxy-1-((4-(trifluoromethyl)phenyl)methyl)ethyl)-1-anthracenecarboxamide To a solution of 1-anthracenecarboxylic acid (143 mg, 0.64 mmol). in tetrahydrofuran (5 ml) were added oxalyl chloride (0.11 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate= 2:1) and recrystallized from ethyl acetate-hexane to give the title compound (147 mg, 66%).

mp 227–228° C. IR ν max$^{KBr}$cm$^{-1}$: 1638, 1615, 1514, 1323. Anal. Calcd for C$_{31}$H$_{23}$F$_4$NO$_2$: C, 71.70; H, 4.50; N, 2.70. Found: C, 71.57; H, 4.41; N, 2.68. $^1$H-NMR (CDCl$_3$)δ: 2.90 (1H, dd, J=13.2, 9.8 Hz), 3.54 (1H, d, J=13.2 Hz), 4.70–4.90 (2H, m), 6.94 (1H, d, J=7.0 Hz), 7.06–7.20 (2H, m), 7.28–7.40 (1H, m), 7.40–7.78 (9H, m), 7.81 (1H, s), 7.92–8.06 (2H, m), 8.41 (1H, s).

Example 67

N-[(1RS,2SR)-2-(4-fluorophenyl)-2-hydroxy-1-[4-(trifluorbmethyl)benzyl]ethyl]-2-methylnaphthalene-1-carboxamide While stirring (1RS,2SR)-2-amino-1-(4-fluorophenyl)-3-[4-(trifluoromethyl)phenyl]propan-1-ol (0.224 g, 0.715 mmol), 2-methyl-1-naphthoic acid (0.13 g, 0.71 mmol) and 1-hydroxybenzotriazole hydrate (0.11 g, 0.71 mmol) in acetonitrile (10 ml), 1-ethyl-3-(3-dimethylaminopropyl) carbodiimide hydrochloride (0.14 g, 0.71 mmol) was added, and the mixture was stirred at 70° C. for 5 hrs. The reaction solution was diluted with ethyl acetate, washed with aqueous sodium hydrogen carbonate solution and dried over anhydrous magnesium sulfate. The solvent was evaporated under reduced pressure and the obtained crude product was purified by silica gel column chromatography (hexane/ethyl acetate=3/1–1/1) and crystallized from diethyl ether-hexane to give the objective substance.

white crystal yield 0.233 g, 68% mp 96–98° C.; $^1$H-NMR (CDCl$_3$, 200 MHz) δ 2.11 (3H, s), 2.69 (1H, dd, J=11.1 Hz, 14.5 Hz), 2.99 3.08 (2H, m), 4.96–5.14 (2H, m), 5.88 (1H, d, J=9.6 Hz), 7.02–7.41 (8H, m), 7.46–7.57 (4H, m), 7.68 7.75 (2H, m); IR (KBr) 3241, 3058, 1632, 1510, 1327, 1225, 1163, 1123, 1069, 814 cm$^{-1}$; Anal. Calcd for C$_{28}$H$_{23}$F$_4$NO$_2$: C, 69.85; H, 4.81; N, 2.91. Found: C, 69.64; H, 4.72; N, 2.82.

Example 68

N-[(1RS,2SR)-2-(4-fluorophenyl)-2-hydroxy-1-[4-(trifluoromethyl)benzyl]ethyl]benzamide While stirring (1RS,2SR)-2-amino-1-(4-fluorophenyl)-3-[4-(trifluoromethyl)phenyl]propan-1-ol (0.166 g, 0.530 mmol), benzoic acid (65 mg, 0.53 mmol) and 1-hydroxybenzotriazole hydrate (81 mg, 0.53 mmol) in acetonitrile (10 ml), 1-ethyl-3-(3-dimethylaminopropyl) carbodiimide hydrochloride (0.10 g, 0.53 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance. white crystal yield 0.178 g, 81% mp 193–194° C.; $^1$H-NMR (CDCl$_3$-DMSO-d$_6$, 200 MHz) δ 2.86 (1H, dd, J=4.2 Hz, 14.6 Hz), 2.99 (1H, dd, J=10.5 Hz, 14.1 Hz), 4.56–4.69 (1H, m), 5.06 (1H, t, J=2.9 Hz), 5.12 (1H, d, J=3.2 Hz), 7.06 (2H, t, J=8.7 Hz), 7.17–7.26 (3H, m), 7.35–7.53 (7H, m), 7.67 (2H, d, J=8.0 Hz); IR (KBr) 3303, 1638, 1534, 1325, 1227, 1167, 1125, 1069, 829, 698 cm$^{-1}$; Anal. Calcd for C$_{23}$H$_{19}$F$_4$NO$_2$: C, 66.18; H, 4.59; N, 3.36. Found: C, 66.05; H, 4.51; N, 3.44.

Example 69

N-((1RS,2SR)-2-(4-fluorophenyl)-2-hydroxy-1-((4-(trifluoromethyl)phenyl)methyl)ethyl)-2-phenylacetamide To a solution of (1RS,2SR)-2-amino-1-(4-fluorophenyl)-3-(4-(trifluoromethyl)phenyl)-1-propanol (450 mg, 1.44 mmol) in ethyl acetate (20 ml) were added phenylacetyl chloride (285 ml, 2.15 mmol) and saturated aqueous sodium hydrogen carbonate (20 ml) and the mixture was stirred overnight at room temperature. The reaction solution was diluted with water (100 ml), and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (578 mg, 93%).

mp 173–174° C. IR ν max$^{KBr}$cm$^{-1}$: 1651, 1539, 1514. Anal. Calcd for C$_{24}$H$_{21}$F$_4$NO$_2$: C, 66.82; H, 4.91; N, 3.25.

Found: C, 66.63; H, 4.78; N, 3.19. $^1$H-NMR (CDCl$_3$)δ: 2.62 (1H, dd, J=14.2, 10.6 Hz), 2.81 (1H, dd, J=14.2, 4.4 Hz), 3.44 (2H, s), 3.50 (1H, d, J=3.6 Hz), 4.28–4.42 (1H, m), 4.84–4.92 (1H, m), 5.25 (1H, d, J=8.2 Hz), 6.90–7.10 (6H, m), 7.24–7.36 (5H, m), 7.45 (2H, d, J=7.6 Hz).

Example 70

N-[(1RS,2SR)-2-(4-fluorophenyl)-2-hydroxy-1-[4-(trifluoromethyl)benzyl]ethyl]-2,2,2-trifluoroacetamide While stirring (1RS,2SR)-2-amino-1-(4-fluorophenyl)-3-[4-(trifluoromethyl)phenyl]propan-1-ol (0.155 g, 0.495 mmol) and sodium hydrogen carbonate (83 mg, 0.99 mmol) in tetrahydrofuran (10 ml), trifluoroacetic anhydride (0.08 ml, 0.59 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.154 g, 76% mp 162–163° C.; $^1$H-NMR (CDCl$_3$-DMSO-d$_6$, 200 MHz) δ 2.81–2.97 (2H, m), 4.31–4.48 (1H, m), 4.85 5.00 (2H, m), 7.01–7.11 (2H, m), 7.17 (2H, d, J=8.0 Hz), 7.39–7.47 (4H, m), 7.79–7.92 (1H, m); IR (KBr) 3301, 1701, 1564, 1514, 1327, 1233, 1182, 1128, 1069, 833 cm$^{-1}$; Anal. Calcd for C$_{18}$H$_{14}$F$_7$NO$_2$: C, 52.82; H, 3.45; N, 3.42. Found: C, 52.98; H, 3.43; N, 3.25.

Example 71

N-[(1RS,2SR)-2-(4-fluorophenyl)-2-hydroxy-1-[4-(trifluoromethyl)benzyl]ethyl]-2,2,3,3-tetrafluoropropionamide While stirring (1RS,2SR)-2-amino-1-(4-fluorophenyl)-3-[4-(trifluoromethyl)phenyl]propan-1-ol (0.153 g, 0.488 mmol), 2,2,3,3-tetrafluoropropionic acid (71 mg, 0.49 mmol) and 1-hydroxybenzotriazole hydrate (75 mg, 0.49 mmol) in acetonitrile (10 ml), 1-ethyl-3-(3-dimethylaminopropyl)carbodiimide hydrochloride (94 mg, 0.49 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained crude product was purified by silica gel column chromatography (hexane/ethyl acetate=1/1) and crystallized from hexane to give the objective substance.

white crystal yield 90 mg, 42% mp 164–166° C.; $^1$H-NMR (CDCl$_3$, 200 MHz) δ 2.66. (1H, br s), 2.79–2.96 (2H, m), 4.41–4.55 (1H, m), 4.97 (1H, d, J=4.0 Hz), 5.94 (1H, tt, J=5.5 Hz, 52.9 Hz), 6.55 (1H, br d, J=9.2 Hz), 7.10 (2H, t, J=8.6 Hz), 7.18 (2H, d, J=8.0 Hz), 7.40 (2H, dd, J=5.8 Hz, 8.6 Hz), 7.50 (2H, d, J=8.0 Hz); IR (KBr) 3304, 1686, 1329, 1231, 1175, 1113, 1069, 829 cm$^{-1}$ Example 72

N-((1RS,2SR)-2-(4-fluorophenyl)-2-hydroxy-1-((4-(trifluoromethyl)phenyl)methyl)ethyl)-1,3-benzodioxole-5-carboxamide To a solution of (1RS,2RS)-1-(4-fluorophenyl)-1-hydroxy-3-(4-(trifluoromethyl)phenyl)-2-propylamine hydrochloride (150 mg, 0.43 mmol) in ethyl acetate (5 ml) were added pivaloyl chloride (119 mg, 0.64 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (160 mg, 81%).

mp 180–181° C. IR ν max$^{KBr}$cm$^{-1}$: 1640, 1605, 1507, 1485. Anal. Calcd for C$_{24}$H$_{19}$F$_4$NO$_4$: C, 62.47; H, 4.15; N, 3.04. Found: C, 62.43; H, 4.06; N, 3.06. $^1$H-NMR (CDCl$_3$)δ: 2.80–3.06 (2H, m), 3.70 (1H, d, J=3.6 Hz), 4.50–4.66 (1H, m), 5.02–5.10 (1H, m), 5.90–6.10 (1H, m), 6.02 (2H, s), 6.77 (1H, d, J=8.8 Hz), 7.00–7.16 (4H, m), 7.20–7.30 (2H, m), 7.36–7.58 (4H, m).

Example 73

4-(4-fluorophenyl)-N-[(1RS,2SR)-2-(4-fluorophenyl)-2-hydroxy-1-[4-(trifluoromethyl)benzyl]ethyl]-5-methyl-2-(1-methylethyl)furan-3-carboxamide 1) 1-fluoro-4-(2-nitro-1-propenyl)benzene A mixture of 4-fluorobenzaldehyde (17.02 g, 137.1 mmol), acetic acid (11.5 g, 192 mmol), methylamine hydrochloride (3.70 g, 54.9 mmol), sodium acetate (4.50 g, 54.9 mmol) and nitroethane (41.2 g, 549 mmol) was stirred at 100° C. for 1.5 hrs. The reaction solution was poured into water, and extracted three times with ethyl acetate. The collected organic layer was dried over anhydrous sodium sulfate and the solvent was evaporated under reduced pressure. The residue was crystallized from diethyl ether-hexane to give the objective substance.

yellow crystal yield 18.40 g, 74% mp 59–61° C.; $^1$H-NMR (CDCl$_3$, 200 MHz) δ 2.45 (3H, s), 7.16 (2H, d, J=8.6 Hz), 7.44 (2H, dd, J=5.4 Hz, 8.8 Hz), 8.06 (1H, s); IR (KBr) 1514, 1318, 1225, 982, 847 cm$^{-1}$; Anal. Calcd for C$_9$H$_8$FNO$_2$: C, 59.67; H, 4.45; N, 7.73. Found: C, 59.51; H, 4.39; N, 7.80.

2) ethyl 4-(4-fluorophenyl)-5-methyl-2-(1-methylethyl)furan-3-carboxylate

To a solution of ethyl isobutyrylacetate (20.06 g, 126.8 mmol) and 1-fluoro-4-(2-nitro-1-propenyl)benzene (23.0 g, 127 mmol) in ethanol (100 ml) was added piperidine (12.5 ml, 127 mmol) at room temperature, and the mixture was stirred overnight at room temperature and at 80° C. for 1 hr. The solvent of the reaction solution was evaporated under-reduced pressure, water (50 ml) and conc. hydrochloric acid (30 ml) were added to the residue, and the mixture was stirred at room temperature for 1 hr. The reaction solution was extracted twice with ethyl acetate and the collected organic layer was dried over anhydrous sodium sulfate. The solvent was evaporated under reduced pressure and the residue was purified by silica gel column chromatography (hexane/ethyl acetate=20/1) to give the objective substance.

pale-yellow solid yield 5.958 g, 16%

Recrystallization from cold methanol gave white crystals.

mp 27–28° C.; $^1$H-NMR (CDCl$_3$, 200 MHz) δ 1.09 (3H, t, J=7.2 Hz), 1.30 (6H, d, J=7.4 Hz), 2.18 (3H, s), 3.65–3.79 (1H, m), 4.11 (2H, q, J=7.2 Hz), 7.04 (2H, t, J=8.8 Hz), 7.21 (2H, dd, J=5.6 Hz, 8.8 Hz); IR (neat) 2974, 1707, 1578, 1510, 1221, 1149, 1059 cm$^{-1}$; Anal. Calcd for C$_{17}$H$_{19}$FO$_3$: C, 70.33; H, 6.60. Found: C, 70.36; H, 6.53.

3) 4-(4-fluorophenyl)-5-methyl-2-(1-methylethyl)furan-3-carboxylic acid

Ethyl 4-(4-fluorophenyl)-5-methyl-2-(1-methylethyl)furan-3-carboxylate (1.500 g, 5.167 mmol) and sodium hydroxide (1.65 g, 41.3 mmol) were stirred in methanol (15 ml)-water (5 ml) at 70° C. for 8 hrs. The reaction solution was diluted with water, acidified with dilute hydrochloric acid, and extracted twice with ethyl acetate. The collected organic layer was dried over anhydrous sodium sulfate, and the solvent was evaporated under reduced pressure. The residue was recrystallized from hexane to give the objective substance.

white crystal yield 0.958 g, 71% mp 176–177° C.; $^1$H-NMR (CDCl$_3$, 200 MHz) δ 1.28 (6H, d, J=7.0 Hz), 2.17 (3H, s), 3.71–3.84 (1H, m), 7.05 (2H, t, J=8.8 Hz), 7.22 (2H, dd, J=5.4 Hz, 8.8 Hz); IR (KBr) 3050–2500, 1680, 1512, 1225, 1074, 845 cm$^{-1}$; Anal. Calcd for C$_{15}$H$_{15}$FO$_3$: C, 68.69; H, 5.76. Found: C, 68.57; H, 5.84.

4) 4-(4-fluorophenyl)-N-[(1RS,2SR)-2-(4-fluorophenyl)-2-hydroxy-1-[4-(trifluoromethyl)benzyl]ethyl]-5-methyl-2-(1-methylethyl)furan-3-carboxamide While stirring (1RS,2SR)-2-amino-1-(4-fluorophenyl)-3-[4-(trifluoromethyl)phenyl]propan-1-ol (0.211 g, 0.673 mmol), 4-(4-fluorophenyl)-5-methyl-2-(1-methylethyl)furan-3-carboxylic acid (0.18 g, 0.67 mmol) and 1-hydroxybenzotriazole hydrate (0.10 g, 0.67 mmol) in acetonitrile (10 ml), 1-ethyl-3-(3-dimethylaminopropyl)carbodiimide hydrochloride (0.13 g, 0.67 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white powder yield 0.288 g, 77% mp 134–136° C.; $^1$H-NMR (CDCl$_3$, 200 MHz) δ 1.19 (3H, d, J=7.0 Hz), 1.25 (3H, d, J=7.0 Hz), 2.09 (3H, s), 2.38 (1H, dd, J=10.5 Hz, 14.9 Hz), 2.71 (1H, dd, J=4.3 Hz, 14.3 Hz), 3.51–3.65 (1H, m), 3.76 (1H, d, J=4.4 Hz), 4.40–4.53 (1H, m), 4.80 (1H, t, J=3.3 Hz), 5.19 (1H, d, J=8.0 Hz), 6.90–7.13 (7H, m), 7.23–7.30 (3H, m), 7.45 (2H, d, J=8.0 Hz); IR (KBr) 3347, 2973, 2634, 1620, 1605, 1512, 1329, 1223, 1163, 1125, 1069, 839 cm$^{-1}$; Anal. Calcd for C$_{31}$H$_{28}$F$_5$NO$_3$: C, 66.78; H, 5.06; N, 2.51. Found: C, 66.43; H, 5.20; N, 2.41.

Example 74

N-((1RS,2SR)-2-(4-fluorophenyl)-2-hydroxy-1-((4-(trifluoromethyl)phenyl)methyl)ethyl)[1,1'-biphenyl]-3-carboxamide To a solution of 3-biphenylcarboxylic acid (127 mg, 0.64 mmol) in tetrahydrofuran (5 ml) were added oxalyl chloride (0.11 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (147 mg, 69%).

mp 165–166° C. IR ν max$^{KBr}$cm$^{-1}$: 1641, 1539, 1510. Anal. Calcd for C$_{29}$H$_{23}$F$_4$NO$_2$: C, 70.58; H, 4.70; N, 2.84. Found: C, 70.32; H, 4.80; N, 2.67. $^1$H-NMR (CDCl$_3$)δ: 2.90–3.02 (1H, m), 2.99 (1H, s), 3.64 (1H, d, J=3.6 Hz), 4.50–4.70 (1H, m), 5.08–5.18 (1H, m), 6.14 (1H, d, J=6.4 Hz), 7.02–7.18 (2H, m), 7.24–7.34 (2H, m), 7.38–7.58 (11H, m), 7.70–7.76 (2H, m).

Example 75

4-(dimethylamino)-N-((1RS,2SR)-2-(4-fluorophenyl)-2-hydroxy-1-((4-(trifluoromethyl)phenyl)methyl)ethyl)-1-naphthalenecarboxamide To a solution of (1RS,2RS)-1-(4-fluorophenyl)-1-hydroxy-3-(4-(trifluoromethyl)phenyl)-2-propylamine (150 mg, 0.42 mmol) in acetonitrile (10 ml) were added 4-dimethylaminonaphthalenecarboxylic acid (89 mg, 0.42 mmol), 1-ethyl-3-(3-dimethylaminopropyl)carbodiimide hydrochloride (119 mg, 0.62 mmol) and 1-hydroxy-1H-benzotriazole (63.6 mg, 0.42 mmol) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=1:1) and recrystallized from ethyl acetate-hexane to give the title compound (149 mg, 70%).

mp 169–170° C. IR ν max$^{KBr}$cm$^{-1}$: 1634, 1578, 1510. Anal. Calcd for C$_{29}$H$_{26}$F$_4$N$_2$O$_2$: C, 68.23; H, 5.13; N, 5.49. Found: C, 68.09; H, 5.11; N, 5.32. $^1$H-NMR (CDCl$_3$)δ: 2.88 (6H, s), 2.76–3.14 (2H, m), 3.71 (1H, d, J=4.0 Hz), 4.66–4.84 (2H, m), 5.04–5.12 (1H, m), 5.90 (1H, d, J=8.4 Hz), 6.86 (1H, d, J=7.6 Hz), 7.02–7.18 (3H, m), 7.30–7.60 (8H, m), 7.75 (1H, d, J=8.4 Hz), 8.17 (1H, d, J=8.4 Hz).

Example 76

3-chloro-N-[(1RS,2SR)-2-(4-fluorophenyl)-2-hydroxy-1-[4-(trifluoromethyl)benzyl]ethyl] naphthalene-1-carboxamide 1) ethyl 3-chloro-1-naphthoate While stirring ethyl 3-amino-1-naphthoate (2.317 g, 10.76 mmol) in conc. hydrochloric acid (30 ml), a solution of sodium nitrite (0.89 g, 12.9 mmol) in water (2 ml) was added dropwise under ice-cooling and the mixture was stirred at said temperature for 0.5 hr. To the reaction solution under ice-cooling was added a solution of copper(I) chloride (0.53 g, 5.38 mmol) in conc. hydrochloric acid (4 ml) under ice-cooling and the mixture was stirred at 100° C. for 0.5 hr. After cooling to room temperature, the reaction-solution was diluted with water, and extracted twice with ethyl acetate. The collected organic layer was dried over anhydrous sodium sulfate. The solvent was evaporated under reduced pressure and the obtained crude product was purified by silica gel column chromatography (hexane/ethyl acetate=15/1) to give the objective substance.

colorless liquid yield 1.058 g, 42% $^1$H-NMR (CDCl$_3$, 200 MHz) δ 1.47 (3H, t, J=7.0 Hz), 4.48 (2H, q, J=7.1 Hz), 7.51–7.65 (2H, m), 7.80 (1H, dd, J=2.2 Hz, 7.2 Hz), 7.99 (1H, d, J=2.2 Hz), 8.12 (1H, d, J=2.2 Hz), 8.87 (1H, dd, J=2.2 Hz, 7.4 Hz); IR (KBr) 1717, 1279, 1240, 1188, 1142 cm$^{-1}$ 2) 3-chloro-1-naphthoic acid To a solution of ethyl 3-chloro-1-naphthoate (1.056 g, 4.500 mmol) in methanol (10 ml)-tetrahydrofuran (10 ml)

was added 1N aqueous sodium hydroxide solution (9.00 ml, 9.00 mmol), and the mixture was stirred overnight at room temperature. The reaction solution was concentrated, diluted with water, acidified with 1N hydrochloric acid, and extracted twice with ethyl acetate. The collected organic layer was dried over anhydrous sodium sulfate and the solvent was evaporated under reduced pressure. The residue was crystallized from ethyl acetate-hexane to give the objective substance.

white crystal yield 0.769 g, 83% mp 217–218° C.; $^1$H-NMR (DMSO-$d_6$, 200 MHz) δ 7.59–7.72 (2H, m), 7.97–8.07 (2H, m), 8.30 (1H, d, J=2.2 Hz), 8.81–8.86 (1H, m); IR (KBr) 3100–2600, 1699, 1285, 1254, 1196, 883, 793, 745 cm$^{-1}$; Anal. Calcd for $C_{11}H_7ClO_2$: C, 63.94; H, 3.41. Found: C, 64.00; H, 3.44.

3) 3-chloro-N-[(1RS,2SR)-2-(4-fluorophenyl)-2-hydroxy-1-[4-(trifluoromethyl)benzyl]ethyl]naphthalene-1-carboxamide While stirring (1RS,2SR)-2-amino-1-(4-fluorophenyl)-3-[4-(trifluoromethyl)phenyl]propan-1-ol (0.153 g, 0.488 mmol), 3-chloro-1-naphthoic acid (0.10 g, 0.49 mmol) and 1-hydroxybenzotriazole hydrate (75 mg, 0.49 mmol) in acetonitrile (10 ml), 1-ethyl-3-(3-dimethylaminopropyl) carbodiimide hydrochloride (94 mg, 0.49 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.210 g, 86% mp 220–221° C.; $^1$H-NMR (CDCl$_3$-DMSO-$d_6$, 200 MHz) δ 2.91 (1H, dd, J=10.7 Hz, 13.5 Hz), 3.19 (1H, dd, J=2.2Hz, 13.2 Hz), 4.62–4.77 (1H, m), 4.89 (1H, t, J=5.0 Hz), 5.50 (1H, d, J=4.4 Hz), 7.04–7.13 (3H, m), 7.22–7.34 (2H, m), 7.38–7.59 (7H, m), 7.73 (1H, d, J=8.0 Hz), 7.82 (1H, d, J=2.0 Hz), 8.10 (1H, d, J=10.0 Hz); IR (KBr) 3285, 1642, 1541, 1514, 1325, 1163, 1119, 1069, 837 cm$^{-1}$; Anal. Calcd for $C_{27}H_{20}ClF_4NO_2$: C, 64.61; H, 4.02; N, 2.79. Found: C, 64.82; H, 4.17; N, 2.74.

Example 77

N-((1RS,2SR)-2-(4-fluorophenyl)-2-hydroxy-1-((4-(trifluoromethyl)phenyl)methyl)ethyl)-2,3-dihydro-1-benzofuran-7-carboxamide To a solution of 2,3-dihydro-1-benzofuran-7-carboxylic acid (106 mg, 0.64 mmol) in tetrahydrofuran (5 ml) were added oxalyl chloride (0.11 ml, 1.72 mmol) and N,N-dimethylformamide (0.01 ml) and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (160 mg, 81%).

mp 121–122° C. IR ν max$^{KBr}$cm$^{-1}$: 1780, 1644, 1537. Anal. Calcd for $C_{25}H_{21}F_4NO_3$: C, 65.36; H, 4.61; N, 3.05. Found: C, 65.41; H, 4.38; N, 2.76. $^1$H-NMR (CDCl$_3$)δ: 2.76–3.00 (2H, m), 3.18–3.30 (2H, m), 4.12 (1H, d, J=3.6 Hz), 4.48–4.76 (4H, m), 5.08 (1H, s) 6.90–7.16 (2H, m), 7.20–7.52 (6H, m), 7.60 (1H, d, J=7.6 Hz), 7.85 (1H, d, J=7.6 Hz).

Example 78

2-bromo-N-((1RS,2SR)-2-(4-fluorophenyl)-2-hydroxy-1-((4-(trifluoromethyl)phenyl)methyl)ethyl)acetamide To a solution of (1RS,2RS)-1-(4-fluorophenyl)-1-hydroxy-3-(4-(trifluoromethyl)phenyl)-2-propylamine (2.0 g, 5.54 mmol) in ethyl acetate (50 ml) were added bromoacetyl bromide (723 ml, 8.30 mmol) and saturated aqueous sodium hydrogen carbonate (50 ml) and the mixture was stirred at room temperature for 3 hrs. The reaction solution was diluted with water (100 ml) and extracted with ethyl acetate (200 ml×2). The extract was washed with saturated brine, dried over anhydrous magnesium sulfate and evaporated under reduced pressure. The residue was purified by silica gel column chromatography (hexane:ethyl acetate= 2:1–1:1). Recrystallization from ethyl acetate-hexane gave the title compound (2.0 g, 83%).

mp 151–152° C. IR ν max$^{KBr}$cm$^{-1}$: 1659, 1647, 1547. Anal. Calcd for $C_{18}H_{16}BrF_4NO_2$: C, 49.79; H, 3.71; N, 3.23. Found: C, 49.80; H, 3.41; N, 3.03. $^1$H-NMR (CDCl$_3$)δ: 2.72–2.96 (3H, m), 3.74 (2H, dd, J=18.4, 13.6 Hz), 4.38–4.52 (1H, m), 4.92–5.00 (1H, m), 6.53 (1H, d, J=8.4 Hz), 7.02–7.18 (2H, m), 7.22 (2H, d, J=8.0 Hz), 7.32 7.50 (2H, m), 7.51 (2H, d, J=8.0 Hz).

Example 79

4-butyl-N-((1RS,2SR)-2-(4-fluorophenyl)-2-hydroxy-1-((4-(trifluoromethyl)phenyl)methyl)ethyl)benzamide To a solution of 4-n-butylbenzoic acid (153 mg, 0.86 mmol) in tetrahydrofuran (5 ml) were added oxalyl chloride (0.15 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (200 mg, 0.57 mmol) and saturated aqueous sodium hydrogen carbonate (5 ml) and the mixture was stirred overnight at room temperature. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1–1:1). Recrystallization from ethyl acetate-hexane gave the title compound (172 mg, 64%).

mp 171–172° C. IR ν max$^{KBr}$cm$^{-1}$: 1638, 1609, 1537, 1512. Anal. Calcd for $C_{27}H_{27}F_4NO_2$: C, 68.49; H, 5.75; N, 2.96. Found: C, 68.46; H, 5.89; N, 2.94. $^1$H-NMR (CDCl$_3$)δ: 0.92 (3H, t, J=7.2 Hz), 1.22–1.44 (2H, m), 1.48–1.70 (2H, m), 2.63 (2H, t, J=8.0 Hz), 2.80–3.06 (2H, m), 3.84 (1H, d, J=3.0 Hz), 4.50–4.70 (1H, m), 5.08 (1H, s), 6.12 (1H, d, J=8.2 Hz), 7.00–7.36 (6H, m), 7.38–7.58 (6H, m).

Example 80

N-((1RS,2SR)-2-(4-fluorophenyl)-2-hydroxy-1-((4-(trifluoromethyl)phenyl)methyl)ethyl)-8-quinolinecarboxamide To a solution of (1RS,2SR)-2-amino-1-(4-fluorophenyl)-3-(4-(trifluoromethyl)phenyl)-1-propanol (4.50 mg, 1.44 mmol) in acetonitrile (30 ml) were added 8-quinolinecarboxylic acid (249 mg, 1.44 mmol), 1-ethyl-3-(3-dimethylaminopropyl)carbodiimide hydrochloride (413 mg, 2.15 mmol) and 1-hydroxy-1H-benzotriazole (220 mg, 1.44 mmol) and the mixture was stirred overnight at room temperature. The reaction solution was diluted with water (100 ml), and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate=1:1). Recrystallization from ethyl acetate-hexane gave the title compound (162 mg, 24%).

mp 83–84° C. IR ν max$^{KBr}$cm$^{-1}$: 1644, 1574, 1549. Anal. Calcd for $C_{26}H_{20}F_4N_2O_2 \cdot 1.0H_2O$: C, 64.19; H, 4.56; N, 5.76. Found: C, 64.07; H, 4.39; N, 5.61. $^1$H-NMR (CDCl$_3$)δ: 2.99 (2H, d, J=7.4 Hz), 4.52 (1H, d, J=3.6 Hz), 4.70–4.90 (1H, m), 5.12–5.20 (1H, m), 6.96–7.08 (2H, m), 7.31 (2H, d, J=8.0 Hz), 7.36–7.54 (5H, m), 7.67 (1H, t, J=7.6 Hz), 7.98 (1H, dd, J=8.0, 1.8 Hz), 8.28 (1H, dd, J=8.0, 1.8 Hz), 8.71 (1H, dd, J=4.0, 1.8 Hz), 8.79 (1H, dd, J=7.4, 1.8 Hz), 11.49 (1H, d, J=7.6 Hz).

Example 81

N-((1RS,2SR)-2-(4-fluorophenyl)-2-hydroxy-1-((4-(trifluoromethyl)phenyl)methyl)ethyl)-4-(trifluoromethyl)benzamide To a solution of (1RS,2SR)-1-(4-fluorophenyl)-1-hydroxy-3-(4-(trifluoromethyl)phenyl)-2-propylamine hydrochloride (200 mg, 0.57 mmol) in ethyl acetate (5 ml) were added 4-(trifluoromethyl)benzoyl chloride (179 mg, 0.86 mmol) and saturated aqueous sodium hydrogen carbonate (5 ml) and the mixture was stirred at room temperature for 1 hr. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1). Recrystallization from ethyl acetate-hexane gave the title compound (171 mg, 62%).

mp 228–229° C. IR ν max$^{KBr}$cm$^{-1}$: 3285, 1641, 1329. Anal. Calcd for $C_{24}H_{18}F_7NO_2$: C, 59.39; H, 3.74; N, 2.89. Found: C, 59.30; H, 3.74; N, 3.04. $^1$H-NMR (CDCl$_3$)δ: 2.90–3.08 (3H, m), 4.56–4.70 (1H, m), 5.04–5.14 (1H, m), 6.06–6.20 (1H, m), 7.00–7.20 (2H, m), 7.20–7.34 (2H, m), 7.36–7.56 (4H, m), 7.60–7.70 (4H, m).

Example 82

N-((1RS,2SR)-2-(4-fluorophenyl)-2-hydroxy-1-((4-(trifluoromethyl)phenyl)methyl)ethyl)-2-(1-naphthalenyl)acetamide To a solution of 1-naphthaleneacetic acid (160 mg, 0.86 mmol) in tetrahydrofuran (5 ml) were added oxalyl chloride (0.15 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (200 mg, 0.57 mmol) and saturated aqueous sodium hydrogen carbonate (5 ml) and the mixture was stirred at room temperature for 2 hrs. The reaction solution was diluted with water (50 ml), and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1–1:1). Recrystallization from ethyl acetate-hexane gave the title compound (175 mg, 64%).

mp 186–187° C. IR ν max$^{KBr}$cm$^{-1}$: 3285, 1657, 1539, 1512, 1120. Anal. Calcd for $C_{28}H_{23}F_4NO_2$: C, 69.85; H, 4.81; N, 2.91. Found: C, 69.62; H, 4.68; N, 2.85. $^1$H-NMR (CDCl$_3$)δ: 2.40 (1H, dd, J=14.2, 10.4 Hz), 2.70 (1H, dd, J=14.2, 4.0 Hz), 3.28 (2H, d, J=3.6 Hz), 3.90 (2H, d, J=2.2 Hz), 4.24–4.40 (1H, m), 4.70–4.84 (1H, m), 5.15 (1H, d, J=7.8 Hz), 6.78 (2H, d, J=8.0 Hz), 6.88–7.00 (2H, m), 7.04–7.20 (3H, m), 7.20–7.34 (2H, m), 7.36–7.60 (3H, m), 7.70–7.94 (3H, m).

Example 83

2-(ethyloxy)-N-((1RS,2SR)-2-(4-fluorophenyl)-2-hydroxy-1-((4-(trifluoromethyl)phenyl)methyl) ethyl)-1-naphthalenecarboxamide To a solution of 2-(ethyloxy)-N-(2-(4-fluorophenyl)-2-oxo-1-((4-(trifluoromethyl)phenyl)methyl)ethyl)-1-aphthalenecarboxamide (400 mg, 0.79 mmol) in methanol (30 ml) was added manganese (II) chloride (198 mg, 1.57 mmol), and the mixture was stirred at room temperature for 30 min. To the reaction solution was added sodium borohydride (30 mg, 0.79 mmol) under ice-cooling and the mixture was stirred for 1 hr. The reaction solution was poured into 1N hydrochloric acid (30 ml), and extracted with ethyl acetate (50 ml×2). The extract was washed with water and saturated brine, dried over anhydrous magnesium sulfate and evaporated under reduced pressure. The residue was purified by silica gel column chromatography (hexane:ethyl acetate=2:1–1:1). Recrystallization from ethyl acetate-hexane gave 2-(ethyloxy)-N-((1RS,2SR)-2-(4-fluorophenyl)-2-hydroxy-1-((4-(trifluoromethyl)phenyl) methyl)ethyl)-1-naphthalenecarboxamide. The mother liquor after recrystallization was evaporated under reduced pressure, and the obtained crude crystal was washed with a mixed solvent of hexane:ethyl acetate=10:1 to give the title compound (37.2 mg, 9%).

mp 157–158° C. IR ν max$^{KBr}$cm$^{-1}$: 1622, 1510, 1300, 1236. Anal. Calcd for $C_{29}H_{25}F_4NO_3$: C, 68.09; H, 4.93; N, 2.74. Found: C, 67.96; H, 4.86; N, 2.82. $^1$H-NMR (CDCl$_3$)δ: 1.38 (3H, t, 7.0 Hz), 2.62–3.10 (2H, m), 3.28 (1H, d, J=4.0 Hz), 4.06–4.30 (2H; m), 4.88–5.04 (1H, m), 5.10–5.22 (1H, m), 6.03 (1H, d, J=9.6 Hz), 7.00–7.20 (3H, m), 7.20–7.60 (9H, m), 7.77 (2H, dd, J=20.0, 8.2 Hz).

Example 84

N-((1RS,2SR)-2-(4-fluorophenyl)-2-hydroxy-1-((4-(trifluoromethyl)phenyl)methyl)ethyl)-9-anthracenecarboxamide To a solution of 9-anthracenecarboxylic acid (143 mg, 0.64 mmol) in tetrahydrofuran (5 ml) were added oxalyl chloride (0.11 ml, 1.72 mmol) and N,N-dimethylformamide (0.01 ml) and the mixture was stirred at room temperature for 30 min. The reaction solution was evaporated under reduced pressure.

To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1) and recrystallized from ethyl acetate-hexane to give the title compound (136 mg, 61%).

mp 251–252° C. IR ν max$^{KBr}$cm$^{-1}$: 1655, 1514, 1335, 1161, 1111. Anal. Calcd for $C_{31}H_{23}F_4NO_2$: C, 71.95; H, 4.48; N, 2.71. Found: C, 71.81; H, 4.55; N, 2.74. $^1$H-NMR (CDCl$_3$)δ: 2.82 (1H, dd, J=14.2, 11.8 Hz), 3.59 (1H, d, J=14.0 Hz), 4.74 (1H, d, J=8.0 Hz), 5.16–5.32 (1H, m), 6.57 (1H, d, J=8.8 Hz), 6.76 (1H, d, J=8.8 Hz), 6.96–7.10 (1H, m), 7.10–7.30 (3H, m), 7.30–7.46 (2H, m), 7.54–7.76 (6H, m), 7.84–8.00 (2H, m), 8.42 (1H, s).

Example 85

N-((1RS,2SR)-2-(4-fluorophenyl)-2-hydroxy-1-((4-(trifluoromethyl)phenyl)methyl)ethyl)-9-oxo-9H-fluorene-1-carboxamide To a solution of 9-oxo-9H-fluorene-1-carboxylic acid (144 mg, 0.64 mmol) in tetrahydrofuran (5 ml) were added oxalyl chloride (0.11 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml) were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was, stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (137 mg, 61%).

mp 185–186° C. IR ν max$^{KBr}$cm$^{-1}$: 1698, 1607, 1574. Anal. Calcd for $C_{30}H_{21}F_4NO_3.0.1H_2O$: C, 69.12; H, 4.10; N, 2.69. Found: C, 68.98; H, 3.91; N, 2.63. $^1$H-NMR (CDCl$_3$)δ: 2.90–3.12 (2H, m), 3.85 (1H, s), 4.64–4.80 (1H, m), 5.20 (1H, s), 7.00–7.16 (2H, m), 7.20–7.70 (12H, m), 8.12 (1H, dd, J=7.2, 2.0 Hz), 10.16 (1H, d, J=7.6 Hz).

Example 86

N-((1RS,2SR)-2-(4-fluorophenyl)-2-hydroxy-1-((4-(trifluoromethyl)phenyl)methyl)ethyl)-3,5-bis(trifluoromethyl)benzamide To a solution of (1RS,2SR)-1-(4-fluorophenyl)-1-hydroxy-3-(4-(trifluoromethyl)phenyl)-2-propylamine hydrochloride (150 mg, 0.43 mmol) in ethyl acetate (5 ml) were-added 3,5-bis(trifluoromethyl)benzoyl chloride (117 ml, 0.64 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from diisopropyl ether-hexane to give the title compound (73 mg, 31%).

mp 150–151° C. IR ν max$^{KBr}$cm$^{-1}$: 1651, 1620, 1543, 1512. Anal. Calcd for $C_{25}H_{17}F_{10}NO_2$: C, 54.26; H, 3.10; N, 2.53. Found: C, 54.12; H, 2.95; N, 2.38. $^1$H-NMR (CDCl$_3$)δ: 2.80–3.04 (3H, m), 4.60–4.78 (1H, m), 5.13 (1H, s), 6.24 (1H, d, J=8.4 Hz), 7.02–7.20 (2H, m), 7.20–7.32 (2H, m), 7.40–7.56 (4H, m), 7.90–8.02 (3H, m).

Example 87

8-bromo-N-((1RS,2SR)-2-(4-fluorophenyl)-2-hydroxy-1-((4-(trifluoromethyl)phenyl)methyl)ethyl)-1-naphthalenecarboxamide To a solution of 8-bromo-1-naphthalenecarboxylic acid (161 mg, 0.64-mmol) in tetrahydrofuran (5 ml) were added oxalyl chloride (0.11 ml, 1.72 mmol) and N,N-dimethylformamide (0.01 ml), and the mixture was stirred at room temperature for 30 min. The reaction solution was evaporated under reduced pressure. To a solution of the residue in ethyl acetate (5 ml). were added (1RS,2SR)-1-(4-fluorophenyl)-1-hydroxy-3-(4-(trifluoromethyl)phenyl)-2-propylamine hydrochloride (150 mg, 0.43 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=2:1-1:1). Recrystallization from ethyl acetate-hexane gave the title compound (67 mg, 29%).

mp 191–192° C. IR ν max$^{KBr}$cm$^{-1}$: 1653, 1634, 1510. Anal. Calcd for $C_{27}H_{20}BrF_4NO_2.0.2H_2O$: C, 58.97; H, 3.74; N, 2.55. Found: C, 58.73; H, 3.44; N, 2.49. $^1$H-NMR (CDCl$_3$)δ: 2.80–3.02 (2H, m), 4.78 (1H, brs), 5.02–5.20 (1H, m), 5.60–5.80 (1H, m), 7.04–7.20 (2H, m), 7.22–7.44 (5H, m), 7.44–7.70 (4H, m), 7.74–7.96 (3H, m).

Example 88

4-(4-fluorobenzoyl)-N-[(1RS,2SR)-2-(4-fluorophenyl)-2-hydroxy-1-[4-(trifluoromethyl)benzyl]ethyl]benzenecarboxamide While stirring (1RS,2SR)-2-amino-1-(4-fluorophenyl)-3-[4-(trifluoromethyl)phenyl]propan-1-ol (0.224 g, 0.715 mmol), 4-(4-fluorobenzoyl)benzoic acid (0.17 g, 0.71 mmol) and 1-hydroxybenzotriazole hydrate (0.11 g, 0.71 mmol) in acetonitrile (10 ml), 1-ethyl-3-(3-dimethylaminopropyl)carbodiimide hydrochloride (0.14 g, 0.71 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained-residue was crystallized from ethyl acetate-hexane to give the objective substance.

white crystal yield 0.321 g, 83% mp 156–157° C.; $^1$H-NMR (CDCl$_3$-DMSO-d$_6$, 200 MHz) δ 2.83–3.06 (2H, m), 4.60–4.71 (1H, m), 4.91 (1H, d, J=3.2 Hz), 5.08 (1H, t, J=3.1 Hz), 7.08 (2H, t, J=8.6 Hz), 7.14–7.31 (5H, m), 7.45 (2H, d, J=7.4 Hz), 7.50 (2H, dd, J=5.6 Hz, 8.8 Hz), 7.77 (4H, s), 7.83 (2H, dd, J=5.4 Hz, 9.0 Hz); IR (KBr) 3536, 3303, 1644, 1601, 1541, 1507, 1329, 1281, 1225, 1161, 1111, 1069, 864, 849 cm$^{-1}$; Anal. Calcd for $C_{30}H_{22}F_5NO_3.0.2H_2O$: C, 66.35; H, 4.16; N, 2.58. Found: C, 66.14; H, 4.06; N, 2.57.

Example 89

4-[(Z)-2-(4-chlorophenyl)ethenyl]-N-[(1RS,2SR)-2-(4-fluorophenyl)-2-hydroxy-1-[4-(trifluoromethyl)benzyl]ethyl]benzenecarboxamide While stirring (1RS,2SR)-2-amino-1-(4-fluorophenyl)-3-[4-(trifluoromethyl)phenyl]propan-1-ol (0.245 g, 0.782 mmol), (Z)-4-[2-(4-chlorophenyl)ethenyl]benzoic acid (0.20 g, 0.78 mmol) and 1-hydroxybenzotriazole hydrate (0.12 g, 0.78 mmol) in acetonitrile (10 ml), 1-ethyl-3-(3-dimethylaminopropyl)carbodiimide hydrochloride (0.15 g, 0.78 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized ethyl acetate-hexane to give the objective substance.

white crystal yield 0.378 g, 87% mp 193–194° C.; $^1$H-NMR (CDCl$_3$-DMSO-d$_6$, 200 MHz) δ 2.77–3.03 (2H, m), 4.56–4.69 (1H, m), 4.82 (1H, d, J=3.4 Hz), 5.05 (1H, t, J=2.8 Hz), 6.61 (2H, s), 6.95 (1H, d, J=9.0 Hz), 7.06 (2H, t, J=8.6 Hz), 7.14–7.30 (8H, m), 7.42–7.56 (6H, m); IR (KBr) 3260, 1642, 1512, 1325, 1165, 1115, 1067, 872, 826 cm$^{-1}$; Anal. Calcd for C$_{31}$H$_{24}$ClF$_4$NO$_2$: C, 67.21; H, 4.37; N, 2.53. Found: C, 67.00; H, 4.42; N, 2.48.

Example 90

4-(4-chlorophenoxy)-N-[(1RS,2SR)-2-(4-fluorophenyl)-2-hydroxy-1-[4-(trifluoromethyl)benzyl]ethyl]benzenecarboxamide While stirring (1RS,2SR)-2-amino-1-(4-fluorophenyl)-3-[4-(trifluoromethyl)phenyl]propan-1-ol (0.235 g, 0.750 mmol), 4-(4-chlorophenoxy)benzoic acid (0.19 g, 0.75 mmol) and 1-hydroxybenzotriazole hydrate (0.11 g, 0.75 mmol) in acetonitrile (10 ml), 1-ethyl-3-(3-dimethylaminopropyl)carbodiimide hydrochloride (0.14 g, 0.75 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white crystal yield 0.353 g, 87% mp 188–189° C.; $^1$H-NMR (CDCl$_3$-DMSO-d$_6$, 200 MHz) δ 2.77–3.03 (2H, m), 4.56–4.69 (1H, m), 4.75 (1H, d, J=3.2 Hz), 5.06 (1H, t, J=3.1 Hz), 6.85 (1H, d, J=8.4 Hz), 6.95 (2H, d, J=8.8 Hz), 6.97 (2H, d, J=9.2 Hz), 7.07 (2H, t, J=8.8 Hz), 7.23 (2H, d, J=8.0 Hz), 7.33 (2H, d, J=9.2 Hz), 7.43–7.51. (4H, m), 7.64 (2H, d, J=9.2 Hz); IR (KBr) 3291, 1636, 1512, 1487, 1329, 1256, 1121, 1069, 837, 828 cm$^{-1}$; Anal. Calcd for C$_{29}$H$_{22}$ClF$_4$NO$_3$: C, 64.04; H, 4;08; N, 2.58. Found: C, 63.86; H, 4.06; N, 2.55.

Example 91

4-(4-fluorophenyl)-N-[(1RS,2SR)-2-(4-fluorophenyl)-2-hydroxy-1-[4-(trifluoromethyl)benzyl]ethyl]-5-[(methoxy)methyl]-2-phenylfuran-3-carboxamide 1) ethyl 4-(4-fluorophenyl)-5-methyl-2-phenylfuran-3-carboxylate To a solution of ethyl benzoylacetate (12.43 g, 64.67 mmol) and 1-fluoro-4-(2-nitro-1-propenyl)benzene (11.7 g, 64.7 mmol) in ethanol (60 ml) was added piperidine (6.40 ml, 64.7 mmol) at room temperature, and the mixture was stirred overnight at room temperature. To the reaction solution were added water (50 ml) and conc. hydrochloric acid (15 ml), and the mixture was stirred at room temperature for 1 hr. The reaction solution was extracted twice with ethyl acetate, and the collected organic layer was dried over anhydrous sodium sulfate. The solvent was evaporated under reduced pressure. The residue was purified by silica gel column chromatography (hexane/ethyl acetate=20/1) to give the objective substance.

pale-yellow solid yield 7.860 g, 38%

Recrystallization from methanol gave a white powder.

mp 78–79° C.; $^1$H-NMR (CDCl$_3$, 200 MHz) δ 1.02 (3H, t, J=7.1 Hz), 2.30 (3H, s), 4.10 (2H, q, J=7.1 Hz), 7.09 (2H, t, J=8.6 Hz), 7.19–7.48 (5H, m), 7.82 (2H, dd, J=1.9 Hz, 7.7 Hz); IR (KBr) 1716, 1510, 1323, 1223, 1105 cm$^{-1}$; Anal. Calcd for C$_{20}$H$_{17}$FO$_3$: C, 74.06; H, 5.28. Found: C, 73.82; H, 5.35.

2) ethyl 5-[(acetoxy)methyl]-4-(4-fluorophenyl)-2-phenylfuran-3-carboxylate

A solution of ethyl 4-(4-fluorophenyl)-5-methyl-2-phenylfuran-3-carboxylate (19.06 g, 58.76 mmol), N-bromosuccinimide (10.5 g, 58.8 mmol) and 2,2'-azobis (isobutyronitrile) (50 mg) in carbon tetrachloride (50 ml) was heated under reflux for 0.5 hr. After cooling the reaction solution to room temperature, white precipitate was removed by filtration, and the precipitate was washed with diethyl ether. The solvent of the collected filtrate was evaporated under reduced pressure to give a crude product of ethyl 5-(bromomethyl)-4-(4-fluorophenyl)-2-phenylfuran-3-carboxylate as a yellow liquid. The obtained liquid was dissolved in N,N-dimethylformamide (40 ml) and sodium acetate (9.64 g, 118 mmol) was added. The mixture was stirred overnight at room temperature. The reaction solution was diluted with water and extracted twice with ethyl acetate. The collected organic layer was dried over anhydrous sodium sulfate and the solvent was evaporated under reduced pressure. The obtained crude product was purified by silica gel column chromatography (hexane/ethyl acetate=6/1) to give the objective substance.

pale-yellow solid yield 17.24 g, 77%

Recrystallization from diisopropyl ether gave a pale-brown powder.

mp 114–116° C.; $^1$H-NMR (CDCl$_3$, 200 MHz) δ 1.02 (3H, t, J=7.1 Hz), 2.10 (3H, s), 4.11 (2H, q, J=7.1 Hz), 5.01 (2H, s), 7.11 (2H, t, J=8.6 Hz), 7.33 (2H, dd, J=5.6 Hz, 8.8 Hz), 7.42–7.51 (3H, m), 7.81–7.87 (2H, m); IR (KBr) 1740, 1717, 1508, 1242, 1223, 1130, 1024, 849, 700 cm$^{-1}$; Anal. Calcd for C$_{22}$H$_{19}$FO$_5$: C, 69.10; H, 5.01. Found: C, 69.08; H, 5.07.

3) ethyl 4-(4-fluorophenyl)-5-[(methoxy)methyl]-2-phenylfuran-3-carboxylate

A mixture of ethyl 5-[(acetoxy)methyl]-4-(4-fluorophenyl)-2-phenylfuran-3-carboxylate (4.020 g, 10.51 mmol) and a solution (50 ml) of 10% hydrogen chloride in methanol was stirred at room temperature for 2.5 days. The solvent of the reaction solution was evaporated under reduced pressure and the obtained crude product was purified by silica gel column chromatography (hexane/ethyl acetate=9/1) to give the objective substance.

yellow liquid yield 2.130 g, 57% $^1$H-NMR (CDCl$_3$, 200 MHz) δ 1.02 (3H, t, J=7.1 Hz), 3.37 (3H, s), 4.12 (2H, q, J=7.2 Hz), 4.33 (2H, s), 7.10 (2H, t, J=8.8 Hz), 7.36 (2H, dd, J=5.4 Hz, 8.8 Hz), 7.40–7.49 (3H, m), 7.81–7.89 (2H, m); IR (neat) 1717, 1508, 1223, 1109, 1096 cm$^{-1}$ 4) 4-(4-fluorophenyl)-5-[(methoxy)methyl]-2-phenylfuran-3-carboxylic acid Ethyl 4-(4-fluorophenyl)-5-[(methoxy)methyl]-2-phenylfuran-3-carboxylate (1.535 g, 4.332 mmol) and 2N aqueous sodium hydroxide solution (4.33 ml, 8.66 mmol) were stirred in methanol (20 ml) at 70° C. for 8 hrs. The reaction solution was diluted with water, acidified with dilute hydrochloric acid, and extracted twice with ethyl acetate. The collected organic layer was dried over anhydrous sodium sulfate, and the solvent was evaporated under reduced pressure. The residue was purified by silica gel column chromatography (hexane/ethyl acetate=3/1-ethyl acetate). Crystallization from hexane gave the objective substance.

pale-brown crystal yield 1.006 g, 71% mp 175–176° C.; $^1$H-NMR (CDCl$_3$, 200 MHz) δ 3.36 (3H, s), 4.31 (2H, s), 7.08 (2H, t, J=8.8 Hz), 7.35 (2H, dd, J=5.6 Hz, 8.8 Hz), 7.41–7.44 (3H, m), 7.78–7.85 (2H, m); IR (KBr) 3055–2555, 1686, 1508, 1225, 1100, 851 cm$^{-1}$; Anal. Calcd for C$_{19}$H$_{15}$FO$_4$: C, 69.93; H, 4.63. Found: C, 69.76; H, 4.71.

5) 4-(4-fluorophenyl)-N-[(1RS,2SR)-2-(4-fluorophenyl)-2-hydroxy-1-[4-(trifluoromethyl)benzyl]ethyl]-5-[(methoxy)methyl]-2-phenylfuran-3-carboxamide While stirring (1RS,2SR)-2-amino-1-(4-fluorophenyl)-3-[4-(trifluoromethyl)phenyl]propan-1-ol (0.228 g, 0.728 mmol), 4-(4-fluorophenyl)-5-[(methoxy)methyl]-2-phenylfuran-3-carboxylic acid (0.24 g, 0.73 mmol) and 1-hydroxybenzotriazole hydrate (0.11 g, 0.73 mmol) in acetonitrile (10 ml), 1-ethyl-3-(3-dimethylaminopropyl)carbodiimide hydrochloride (0.14 g, 0.73 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white crystal yield 0.341 g, 75% mp 204–206° C.; $^1$H-NMR (CDCl$_3$, 200 MHz) δ 2.48 (1H, d, J=4.0 Hz), 2.51–2.70 (2H, m), 3.43 (3H, s), 4.32 (2H, s), 4.51–4.64 (1H, m), 4.75 (1H, t, J=3.7 Hz), 5.61 (1H, d, J=8.4 Hz), 6.90–7.00 (4H, m), 7.09 (2H, t, J=8.6 Hz), 7.19 (2H, dd, J=5.2 Hz, 8.6 Hz), 7.30–7.42 (7H, m), 7.56–7.61 (2H, m); IR (KBr) 3301, 1636, 1512, 1329, 1223, 1163, 1123, 1094, 1069, 839 cm$^{-1}$; Anal. Calcd for C$_{35}$H$_{28}$F$_5$NO$_4$: C, 67.63; H, 4.54; N, 2.25. Found: C, 67.46; H, 4.71; N, 2.25.

Example 92

4-[2-(4-chlorophenyl)ethyl]-N-[(1RS,2SR)-2-(4-fluorophenyl)-2-hydroxy-1-[4-(trifluoromethyl)benzyl]ethyl]benzenecarboxamide While stirring (1RS,2SR)-2-amino-1-(4-fluorophenyl)-3-[4-(trifluoromethyl)phenyl]propan-1-ol (0.219 g, 0.699 mmol), 4-[2-(4-chlorophenyl)ethyl]benzoic acid (0.18 g, 0.70 mmol) and 1-hydroxybenzotriazole hydrate (0.11 g, 0.70 mmol) in acetonitrile (10 ml), 1-ethyl-3-(3-dimethylaminopropyl)carbodiimide hydrochloride (0.13 g, 0.70 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white crystal yield 0.345 g, 89% mp 211–212° C.; $^1$H-NMR (CDCl$_3$-DMSO-d$_6$, 200 MHz) δ 2.56–3.06 (6H, m), 4.53–4.66 (1H, m), 5.03 (1H, t, J=3.1 Hz), 5.32 (1H, d, J=3.6 Hz), 7.01–7.27 (9H, m), 7.36–7.54 (6H, m), 7.60 (2H, d, J=8.2 Hz); IR (KBr) 3287, 1638, 1541, 1512, 1325, 1229, 1163, 1115, 1067, 837 cm$^{-1}$; Anal. Calcd for C$_{31}$H$_{26}$ClF$_4$NO$_2$: C, 66.97; H, 4.71; N, 2.52. Found: C, 66.65; H, 4.62; N, 2.51.

Example 93

4-[cis-3-(4-chlorophenyl)oxiran-2-yl]-N-[(1RS,2SR)-2-(4-fluorophenyl)-2-hydroxy-1-[4-(trifluoromethyl)benzyl]ethyl]benzenecarboxamide While stirring (1RS,2SR)-2-amino-1-(4-fluorophenyl)-3-[4-(trifluoromethyl)phenyl]propan-1-ol (0.264 g, 0.843 mmol), cis-4-[3-(4-chlorophenyl)oxiran-2-yl]benzoic acid (0.23 g, 0.84 mmol) and 1-hydroxybenzotriazole hydrate (0.13 g, 0.84 mmol) in acetonitrile (10 ml), 1-ethyl-3-(3-dimethylaminopropyl)carbodiimide hydrochloride (0.16 g, 0.84 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent, was evaporated under reduced pressure and the obtained residue was crystallized ethyl acetate-hexane to give the objective substance.

white powder yield 0.288 g, 60% mp 162–166° C.; $^1$H-NMR (CDCl$_3$, 200 MHz) δ 2.91 (2H, d, J=7.4 Hz), 3.49 (1H, dd, J=3.5 Hz, 10.5 Hz), 4.36 (2H, S), 4.46–4.63 (1H, m), 5.05 (1H, t, J=3.1 Hz), 6.03–6.08 (1H, m), 7.02–7.23 (10H, m), 7.36–7.43 (4H, m), 7.47 (2H, d, J=8.0 Hz); IR (KBr) 3289, 1642, 1541, 1510, 1325, 1229, 1163, 1111, 1067, 1019, 828 cm$^{-1}$; Anal. Calcd for C$_{31}$H$_{24}$ClF$_4$NO$_3$: C, 65.32; H, 4.24; N, 2.46. Found: C, 65.21; H, 4.01; N, 2.44.

Example 94

N-[(1RS,2SR)-2-(4-fluorophenyl)-2-hydroxy-1-[4-(trifluoromethyl)benzyl]ethyl]-4-(2-phenyl-1,3-dithiolan-2-yl)benzenecarboxamide While stirring (1RS,2SR)-2-amino-1-(4-fluorophenyl)-3-[4-(trifluoromethyl)phenyl]propan-1-ol (0.218 g, 0.696 mmol), 4-(2-phenyl-1,3-dithiolan-2-yl)benzoic acid (0.21 g, 0.70 mmol) and 1-hydroxybenzotriazole hydrate (0.11 g, 0.70 mmol) in acetonitrile (10 ml), 1-ethyl-3-(3-dimethylaminopropyl)carbodiimide hydrochloride (0.13 g, 0.70 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white amorphous powder yield 0.363 g, 87% $^1$H-NMR (CDCl$_3$, 200 MHz) δ 2.82–2.99 (2H, m), 3.32–3.51 (4H, m), 3.56 (1H, d, J=3.6 Hz), 4.54–4.68 (1H, m), 5.06 (1H, t, J=3.1 Hz), 6.12 (1H, d, J=8.4 Hz), 7.08 (2H, t, J=8.6 Hz), 7.22–7.35 (6H, m), 7.38–7.57 (7H, m), 7.64 (2H, d, J=8.4 Hz); IR (KBr) 3241, 1640, 1624, 1541, 1510, 1325, 1223, 1161, 1119, 1067, 829 cm$^{-1}$; Anal. Calcd for C$_{32}$H$_{27}$F$_4$NO$_2$S$_2$: C, 64.31; H, 4.55; N, 2.34. Found: C, 64.20; H, 4.44; N, 2.60.

Example 95

5-(4-fluorophenyl)-N-[(1RS,2SR)-2-(4-fluorophenyl)-2-hydroxy-1-[4-(trifluoromethyl)benzyl]ethyl]-2-methylfuran-3-carboxamide 1) methyl 5-(4-fluorophenyl)-2-methyl-3-furancarboxylate To a solution of 1,8-diazabicyclo[5.4.0]-7-undecene (44.2 g, 290 mmol) in toluene (250 ml) was added methyl acetoacetate (33.7 g, 290 mmol) at room temperature, and 2-chloro-4'-fluoroacetophenone (50.08 g, 290.2 mmol) was added thereto. The mixture was stirred at room temperature for 1 hr. The obtained toluene solution was washed three times with water and p-toluenesulfonic acid monohydrate (5 g) was added. The mixture was heated under reflux for 1 hr in a reaction container equipped with a Dean-Stark trap under dehydrated conditions. The reaction solution was cooled to room temperature, washed with water, dried over anhydrous magnesium sulfate and the solvent was evaporated under reduced pressure. The obtained crude product was purified by silica gel column chromatography (hexane/ethyl acetate= 20/1–9/1). Crystallization from cold methanol gave the objective substance.

yellow crystal yield 31.26 g, 46% mp 96–97° C.; $^1$H-NMR (CDCl$_3$, 200 MHz) δ 2.64 (3H, s), 3.85 (3H, s), 6.81 (1H, s), 7.08 (2H, t, J=8.8 Hz), 7.60 (2H, dd, J=5.4 Hz, 9.0 Hz); IR (KBr) 1705, 1501, 1449, 1233, 1105, 1044, 843, 829, 779 cm$^{-1}$; Anal. Calcd for C$_{13}$H$_{11}$FO$_3$: C, 66.66; H, 4.73. Found: C, 66.63; H, 4.56.

2) 5-(4-fluorophenyl)-2-methyl-3-furancarboxylic acid

Methyl 5-(4-fluorophenyl)-2-methyl-3-furancarboxylate (15.36 g, 65.58 mmol) and sodium hydroxide (5.25 g, 131 mmol) were stirred in methanol (100 ml) and water (50 ml) at room temperature overnight. The reaction solution was concentrated, diluted with water, acidified with conc. hydrochloric acid and washed three times with ethyl acetate. The collected organic layer was dried over anhydrous sodium sulfate, and the solvent was evaporated under reduced pressure. The residue was crystallized from ethyl acetate-hexane to give the objective substance.

pale-yellow crystal yield 13.42 g, 93% mp 217–218° C.; $^1$H-NMR (CDCl$_3$-DMSO-d$_6$, 200 MHz) δ 2.65 (3H, s), 6.83 (1H, s), 7.07 (2H, t, J=8.6 Hz), 7.60 (2H, dd, J=5.0 Hz, 8.8 Hz); IR (KBr) 3100–2500, 1694, 1505, 1474, 1233, 774 cm$^{-1}$; Anal. Calcd for C$_{12}$H$_9$FO$_3$: C, 65.46; H, 4.12. Found: C, 65.50; H, 4.15.

3) 5-(4-fluorophenyl)-N-[(1RS,2SR)-2-(4-fluorophenyl)-2-hydroxy-1-[4-(trifluoromethyl)benzyl]ethyl]-2-methylfuran-3-carboxamide While stirring (1RS,2SR)-2-amino-1-(4-fluorophenyl)-3-[4-(trifluoromethyl)phenyl]propan-1-ol (0.219 g, 0.699 mmol), 5-(4-fluorophenyl)-2-methyl-3-furancarboxylic acid (0.15 g, 0.70 mmol) and 1-hydroxybenzotriazole hydrate (0.11 g, 0.70 mmol) in acetonitrile (10 ml), 1-ethyl-3-(3-dimethylaminopropyl)carbodiimide hydrochloride (0.13 g, 0.70 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white powder yield 0.273 g, 76% mp 179–181° C.; $^1$H-NMR (CDCl$_3$, 200 MHz) δ 2.52 (3H, s), 2.76–2.99 (2H, m), 3.73 (1H, d, J=3.6 Hz), 4.51–4.66 (1H, m), 5.08 (1H, t, J=3.3 Hz), 5.74 (1H, d, J=8.2 Hz), 6.35 (1H, s), 7.03–7.15 (4H, m), 7.24 (2H, d, J=8.0 Hz), 7.43 (2H, dd, J=5.4 Hz, 8.8 Hz), 7.49–7.58 (4H, m); IR (KBr) 3266, 1640, 1510, 1501, 1327, 1233, 1165, 1123, 1069, 837 cm$^{-1}$ Example 96

4-[(Z)-2-(2-chlorophenyl)ethenyl]-N-[(1RS,2SR)-2-(4-fluorophenyl)-2-hydroxy-1-[4-(trifluoromethyl)benzyl]ethyl]benzenecarboxamide While stirring (1RS,2SR)-2-amino-1-(4-fluorophenyl)-3-[4-(trifluoromethyl)phenyl]propan-1-ol (0.208 g, 0.664 mmol), (Z)-4-[2-(2-chlorophenyl)ethenyl]benzoic acid (0.17 g, 0.66 mmol) and 1-hydroxybenzotriazole hydrate (0.10 g, 0.66 mmol) in acetonitrile (10 ml), 1-ethyl-3-(3-dimethylaminopropyl)carbodiimide hydrochloride (0.13 g, 0.66 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white powder yield 0.312 g, 85% mp 153–154° C.; $^1$H-NMR (CDCl$_3$-DMSO-d$_6$, 200 MHz) δ 2.81–2.97 (2H, m), 3.60 (1H, d, J=3.4 Hz), 4.51–4.64 (1H, m), 5.06 (1H, s), 6.09 (1H, d, J=8.4 Hz), 6.68 (1H, d, J=12.2 Hz), 6.78 (1H, d, J=12.4 Hz), 6.99–7.26 (9H, m), 7.36–7.50 (7H, m); IR (KBr) 3291, 1638, 1539, 1514, 1325, 1231, 1165, 1119, 1069 cm$^{-1}$; Anal. Calcd for C$_{31}$H$_{24}$ClF$_4$NO$_2$: C, 67.21; H, 4.37; N, 2.53. Found: C, 66.90; H, 4.01; N, 2.39.

Example 97

N-[(1RS,2SR)-2-(4-fluorophenyl)-2-hydroxy-1-[4-(trifluoromethyl)benzyl]ethyl]-2-[(phenylthio)methyl]naphthalene-1-carboxamide 1) methyl 2-methyl-1-naphthoate To a solution of 2-methyl-1-naphthoate (7.579 g, 40.70 mol) and N,N-dimethylformamide (3 drops) in tetrahydrofuran (40 ml) was dropwise added oxalyl chloride (7.10 ml, 81.4 mmol) at room temperature and the mixture was stirred for 0.5 hr. The solvent of the reaction solution was evaporated under reduced pressure to give a crude product of the acid chloride as a liquid. To a solution of methanol (2.47 ml, 61.1 mmol), 4-N,N-dimethylaminopyridine (0.50 g, 4.07 mmol) and triethylamine (8.51 ml, 61.1 mmol) in acetonitrile (50 ml) was dropwise added a solution of the liquid obtained above dissolved in acetonitrile (20 ml) under ice-cooling, and the mixture was stirred overnight at room temperature. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=6/1) to give the objective substance.

pale-yellow liquid yield 7.866 g, 97% $^1$H-NMR (CDCl$_3$, 200 MHz) δ 2.51 (3H, s), 4.04 (3H, s), 7.32 (1H, d, J=8.4 Hz), 7.41–7.55 (2H, m), 7.77–7.83 (3H, m); IR (neat) 1728, 1435, 1281, 1244, 1219, 1138, 1051, 814 cm$^{-1}$ 2) methyl 2-[(phenylthio)methyl]-1-naphthoate A solution of methyl 2-methyl-1-naphthoate (1.277 g, 6.377 mmol), N-bromosuccinimide (1.14 g, 6.38 mmol) and 2,2'-azobis(isobutyronitrile) (10 mg) in carbon tetrachloride (10 ml) was heated under reflux for 0.5 hr. After cooling the reaction solution to room temperature, the white precipitate was removed by filtration, and the precipitate was washed with diethyl ether. The solvent of the collected filtrate was evaporated under reduced pressure to give a crude product of methyl 2-bromomethyl-1-naphthoate as a pale-yellow liquid. The obtained liquid, thiophenol (0.84 g, 7.65 mmol) and 1,8-diazabicyclo[5.4.0]-7-undecene (1.14 ml, 7.65 mmol) were stirred in acetonitrile (20 ml) overnight at room temperature. The solvent of the reaction solution was evaporated under reduced pressure, and the obtained crude product was purified by silica gel column chromatography (hexane/ethyl acetate=20/1–9/1) to give the objective substance.

yellow liquid yield 1.606 g, 82% $^1$H-NMR (CDCl$_3$, 200 MHz) δ 3.99 (3H, s), 4.32 (2H, s), 7.14–7.35 (5H, m), 7.40–7.56 (3H, m), 7.79–7.88 (3H, m); IR (neat) 1723, 1437, 1287, 1252, 1233, 1209, 1140, 1036, 747 cm$^{-1}$ 3) 2-[(phenylthio)methyl]-1-naphthoate Methyl 2-[(phenylthio)methyl]-1-naphthoate (1.477 g, 4.789 mmol) and sodium hydroxide (2.50 g, 62.5 mmol) were heated under reflux in methanol (30 ml) and tetrahydrofuran (20 ml) for 6 hrs. The reaction solution was concentrated, diluted with water, acidified with conc. hydrochloric acid and extracted twice with ethyl acetate. The collected organic layer was dried over anhydrous sodium sulfate, and the solvent was evaporated under reduced pressure. The residue was purified by silica gel column chromatography (hexane/ethyl acetate=3/1–1/1). Crystallization from diethyl ether-hexane gave the objective substance.

pale-yellow crystal yield 0.880 g, 62% mp 100–101° C.; $^1$H-NMR (CDCl$_3$, 200 MHz) δ 4.47 (2H, s), 7.16–7.58 (8H, m), 7.81–7.87 (2H, m), 8.13–8.18 (1H, m); IR (KBr) 3100–2600, 1680, 1283, 1262, 756, 733 cm$^{-1}$; Anal. Calcd for C$_{18}$H$_{14}$O$_2$S: C, 73.44; H, 4.79. Found: C, 73.17; H, 4.81.

4) N-[(1RS,2SR)-2-(4-fluorophenyl)-2-hydroxy-1-[4-(trifluoromethyl)benzyl]ethyl]-2-[(phenylthio)methyl]naphthalene-1-carboxamide While stirring (1RS,2SR)-2-amino-1-(4-fluorophenyl)-3-[4-(trifluoromethyl)phenyl]propan-1-ol (0.260 g, 0.830 mmol), 2-[(phenylthio)methyl]-1-naphthoate (0.24 g, 0.83 mmol) and 1-hydroxybenzotriazole hydrate (0.13 g, 0.83 mmol) in acetonitrile (10 ml), 1-ethyl-3-(3-dimethylaminopropyl)carbodiimide hydrochloride (0.16 g, 0.83 mmol) was added and the mixture was stirred overnight at 80° C. The reaction solution was diluted with ethyl acetate, washed with aqueous sodium hydrogen carbonate solution, dried over anhydrous magnesium sulfate and the solvent was evaporated under reduced pressure. The obtained crude product was purified by silica gel column chromatography (hexane/ethyl acetate=3/1–1/1). Crystallization from ethyl acetate-hexane gave the objective substance.

white powder yield 0.337 g, 69% mp 102–104° C.; $^1$H-NMR (CDCl$_3$, 200 MHz) δ 2.65–2.91 (2H, m), 3.05 (1H, d, J=4.0 Hz), 3.97–4.17 (1H, m), 4.35 (1H, br s), 4.92–5.04 (1H, m), 5.14 (1H, s), 6.21 (1H, d, J=8.6 Hz), 6.70 (1H, br s), 7.03–7.55 (16H, m), 7.73 (2H, d, J=8.6 Hz); IR (KBr) 3212, 3056, 1628, 1512, 1329, 1227, 1165, 1117, 1069, 762 cm$^{-1}$; Anal. Calcd for C$_{34}$H$_{27}$F$_4$NO$_2$S: C, 69.26; H, 4.62; N, 2.38. Found: C, 69.45; H, 4.93; N, 2.22.

Example 98

N-[(1RS,2SR)-2-(4-fluorophenyl)-2-hydroxy-1-[4-(trifluoromethyl)benzyl]ethyl]-1-methyl-1H-indole-3-carboxamide While stirring (1RS,2SR)-2-amino-1-(4-fluorophenyl)-3-[4-(trifluoromethyl)phenyl]propan-1-ol (0.172 g, 0.549 mmol), 1-methylindole-3-carboxylic acid (0.10 g, 0.55 mmol) and 1-hydroxybenzotriazole hydrate (84 mg, 0.55 mmol) in acetonitrile (10 ml), 1-ethyl-3-(3-dimethylaminopropyl)carbodiimide hydrochloride (0.11 g, 0.55 mmol) was added and the mixture was stirred overnight at room temperature. The reaction solution was diluted with ethyl acetate, washed with aqueous sodium hydrogen carbonate solution, dried over anhydrous magnesium sulfate and the solvent was evaporated under reduced pressure. The obtained residue was purified by silica gel column chromatography (hexane/ethyl acetate=2/1–1/1). Crystallization from diethyl ether-hexane gave the objective substance.

white crystal yield 0.183 g, 71% mp 129–131° C.; $^1$H-NMR (CDCl$_3$, 200 MHz) δ 2.91 (1H, dd, J=9.5 Hz, 13.9 Hz), 3.01 (1H, dd, J=5.2 Hz, 14.8 Hz), 3.76 (3H, s), 4.58–4.71 (1H, m), 4.73 (1H, br s), 5.10 (1H, br s), 5.89 (1H, d, J=7.8 Hz), 7.05 (2H, t, J=8.8 Hz), 7.11–7.19 (1H, m), 7.23–7.30 (4H, m), 7.36–7.51 (6H, m); IR (KBr) 3328, 1624, 1545, 1508, 1325, 1229, 1163, 1128, 1067, 747 cm$^{-1}$; Anal. Calcd for C$_{26}$H$_{22}$F$_4$N$_2$O$_2$: C, 66.38; H, 4.71; N, 5.95. Found: C, 66.27; H, 4.71; N, 5.82.

Example 99

N-((1RS,2SR)-2-(4-fluorophenyl)-2-hydroxy-1-((4-(trifluoromethyl)phenyl)methyl)ethyl)-5-phenylpentanamide To a solution of (1RS,2SR)-2-amino-1-(4-fluorophenyl)-3-(4-(trifluoromethyl)phenyl)-1-propanol (450 mg, 1.44 mmol) in acetonitrile (30 ml) were added 5-phenylpentanoic acid (257 mg, 1.44 mmol), 1-ethyl-3-(3-dimethylaminopropyl)carbodiimide hydrochloride (413 mg, 2.15 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate=1:1). Recrystallization from ethyl acetate-hexane gave the title compound (471 mg, 69%).

mp 152–153° C. IR ν max$^{KBr}$cm$^{-1}$: 1647, 1549, 1512. Anal. Calcd for C$_{27}$H$_{27}$F$_4$NO$_2$: C, 68.49; H, 5.75; N, 2.96. Found: C, 68.39; H, 5.52; N, 2.78. $^1$H-NMR (CDCl$_3$)δ: 1.40–1.56 (4H, m), 2.00–2.16 (2H, m), 2.48–2.64 (2H, m), 2.64–2.94 (2H, m), 3.52 (1H, d, J=3.8 Hz), 4.32–4.50 (1H, m), 4.90–5.00 (1H, m), 5.36 (1H, d, J=8.4 Hz) 7.00–7.56 (13H, m).

Example 100

1,1-dimethylethyl (1S)-2-(((1RS,2SR)-2-(4-fluorophenyl)-2-hydroxy-1-((4-(trifluoromethyl)phenyl)methyl)ethyl)amino)-2-oxo-1-(phenylmethyl)ethylcarbamate To a solution of (1RS,2SR)-2-amino-1-(4-fluorophenyl)-3-(4-(trifluoromethyl)phenyl)-1-propanol (450 mg, 1.44 mmol) in acetonitrile (30 ml) were added N-t-butyloxycarbonyl-L-phenylalanine (382 mg, 1.44 mmol), 1-ethyl-3-(3-dimethylaminopropyl)carbodiimide hydrochloride (413 mg, 2.15 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave the title compound (315 mg, 39%).

mp 230–231° C. IR ν max$^{KBr}$cm$^{-1}$: 1678, 1659, 1524. $^1$H-NMR (CDCl$_3$)δ: 1.36 (9H, s), 2.60–2.90 (4H, m), 3.78–3.90 (4H, m), 4.10–4.40 (2H, m), 4.60–4.68 (1H, m), 5.50 (1H, d, J=8.8 Hz), 6.96–7.50 (13H, m).

Example 101

N-[(1RS,2SR)-2-(4-fluorophenyl)-2-hydroxy-1-[4-(trifluoromethyl)benzyl]ethyl]-4-methoxynaphthalene-1-carboxamide While stirring (1RS,2SR)-2-amino-1-(4-fluorophenyl)-3-[4-(trifluoromethyl)phenyl]propan-1-ol (0.174 g, 0.555 mmol), 4-methoxy-1-naphthoate (0.11 g, 0.56 mmol) and 1-hydroxybenzotriazole hydrate (85 mg, 0.56 mmol) in acetonitrile (10 ml), 1-ethyl-3-(3-dimethylaminopropyl)carbodiimide hydrochloride (0.11 g, 0.56 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was, evaporated under reduced pressure and the obtained residue was crystallized from ethyl acetate-hexane to give the objective substance.

white crystal yield 0.209 g, 76% mp 227–228° C.; $^1$H-NMR (CDCl$_3$-DMSO-d$_6$, 200 MHz) δ 88–3.20 (2H, m), 4.00 (3H, s), 4.60–4.75 (1H, m), 4.93 (1H, t, J=4.2 Hz), 5.49 (1H, d, J=3.6 Hz), 6.72 (1H, d, J=8.0 Hz), 7.03–7.19 (3H, m), 7.29–7.71 (10H, m), 8.19 (1H, d, J=7.8 Hz); IR (KBr) 3281, 1636, 1588, 1530, 1512, 1327, 1265, 1167, 1125, 1069, 839 cm$^{-1}$; Anal. Calcd for C$_{28}$H$_{23}$F$_4$NO$_3$: C, 67.60; H, 4.66; N, 2.82. Found: C, 67.58; H, 4.83; N, 2.73.

Example 102

N-[(1RS,2SR)-2-(4-fluorophenyl)-2-hydroxy-1-[4-(trifluoromethyl)benzyl]ethyl]-3-nitronaphthalene-1-carboxamide While stirring (1RS,2SR)-2-amino-1-(4-fluorophenyl)-3-[4-(trifluoromethyl)phenyl]propan-1-ol (0.174 g, 0.555 mmol) 3-nitro-1-naphthoate (0.12 g, 0.56 mmol) and 1-hydroxybenzotriazole hydrate (85 mg, 0.56 mmol) in acetonitrile (10 ml), 1-ethyl-3-(3-dimethylaminopropyl)carbodiimide hydrochloride (0.11 g, 0.56 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under-reduced ressure and the obtained residue was crystallized from ethyl acetate-hexane to give the objective substance.

pale-yellow crystal yield 0.239 g, 84% mp 231–232° C.; $^1$H-NMR (CDCl$_3$-DMSO-d$_6$, 200 MHz) δ 2.92 (1H, dd, J=11.4 Hz, 14.0 Hz), 3.20 (1H, dd, J=3.6 Hz, 13.0 Hz), 4.65–4.79 (1H, m), 4.94 (1H, t, J=4.5 Hz), 5.53 (1H, d, J=4.4 Hz), 7.10 (2H, t, J=8.6 Hz), 7.36–7.66 (9H, m), 7.95 (1H, d, J=2.6 Hz), 8.03 (1H, d, J=8.0 Hz), 8.18 (1H, d, J=9.2 Hz), 8.78 (1H, d, J=2.2 Hz); IR (KBr) 3283, 1642, 1537, 1327, 1123, 1169, 835 cm$^{-1}$; Anal. Calcd for C$_{27}$H$_{20}$F$_4$N$_2$O$_4$: C, 63.28; H, 3.93; N, 5.47. Found: C, 63.23; H, 3.65; N, 5.73.

Example 103 methyl 4-[[[(1RS,2SR)-2-(4-fluorophenyl)-2-hydroxy-1-[4-(trifluoromethyl) benzyl]ethyl]amino]carbonyl]-1-naphthoate While stirring (1RS,2SR)-2-amino-1-(4-fluorophenyl)-3-[4-(trifluoromethyl)phenyl]propan-1-ol (0.287 g, 0.916 mmol), 4-(methoxycarbonyl)-1-naphthoate (0.21 g, 0.92 mmol) and 1-hydroxybenzotriazole hydrate (0.14 g, 0.92 mmol) in acetonitrile (10 ml), 1-ethyl-3-(3-dimethylaminopropyl)carbodiimide hydrochloride (0.18 g, 0.92 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-hexane to give the objective substance.

white amorphous powder yield 0.449 g, 93% $^1$H-NMR (CDCl$_3$-DMSO-d$_6$, 200 MHz) δ 2.92 (1H, dd, J=11.0 Hz, 14.0 Hz), 3.17 (1H, dd, J=3.2 Hz, 14.0 Hz), 3.99 (3H, s), 4.72–4.85 (1H, m), 4.93 (1H, d, J=5.4 Hz), 5.35 (1H, br s), 7.09 (2H, t, J=8.6 Hz), 7.13 (1H, d, J=7.4 Hz), 7.26–7.42 (4H, m), 7.52–7.60 (5H, m), 7.86 (1H, d, J=9.2 Hz), 8.03 (1H, d, J=7.2 Hz), 8.77 (1H, d, J=8.8 Hz); IR (KBr) 3283, 1721, 1640, 1512, 1327, 1254, 1163, 1123, 1069, 839 cm$^{-1}$; Anal. Calcd for C$_{29}$H$_{23}$F$_4$NO$_4$: C, 66.28; H, 4.41; N, 2.67. Found: C, 66.06; H, 4.49; N, 2.58.

Example 104

N1-[(1RS,2SR)-2-(4-fluorophenyl)-2-hydroxy-1-[4-(trifluoromethyl)benzyl]ethyl]naphthalene-1,4-dicarboxamide 1) 4-(aminocarbonyl)-1-naphthoate To a solution of methyl 4-(aminocarbonyl)-1-naphthoate (0.499 g, 2.177 mmol) in methanol (20 ml) and tetrahydrofuran (20 ml) was added 1N aqueous sodium hydroxide solution (6.53 ml, 6.53 mmol) and the mixture was stirred overnight at room temperature. The reaction solution was concentrated, diluted with water and acidified with dilute hydrochloric acid. The resulting precipitate was collected by filtration and washed with water and hexane to give the objective substance.

white powder yield 0.340 g, 73% mp 294–295° C.; $^1$H-NMR (DMSO-d$_6$, 200 MHz) δ 7.58–7.71 (3H, m), 7.76 (1H, br s), 8.10–8.13 (2H, m), 8.25–8.30 (1H, m), 8.84–8.89 (1H, m); IR (KBr) 3191, 3300–2500, 1694, 1466, 1410, 1368, 1325, 1294, 1264, 770 cm$^{-1}$; Anal. Calcd for C$_{12}$H$_9$NO$_3$: C, 66.97; H, 4.22; N, 6.51. Found: C, 66.85; H, 4.11; N, 6.68.

2) N1-[(1RS,2SR)-2-(4-fluorophenyl)-2-hydroxy-1-[4-(trifluoromethyl)benzyl]ethyl]naphthalene-1,4-dicarboxamide While stirring (1RS,2SR)-2-amino-1-(4-fluorophenyl)-3-[4-(trifluoromethyl)phenyl]propan-1-ol (0.154 g, 0.492 mmol), 4-(aminocarbonyl)-1-naphthoate (0.11 g, 0.49 mmol) and 1-hydroxybenzotriazole hydrate (75 mg, 0.49 mmol) in acetonitrile (10 ml), 1-ethyl-3-(3-dimethylaminopropyl)carbodiimide hydrochloride (94 mg, 0.49 mmol) was added and the mixture was stirred overnight at room temperature. The reaction solution was diluted with water, the resulting precipitate was collected by filtration and washed with water and diethyl ether to give the objective substance.

white powder yield 0.221 g, 88% mp 255–256° C.; $^1$H-NMR (CDCl$_3$-DMSO-d$_6$, 200 MHz) δ 2.86–2.97 (1H, m), 3.15–3.24 (1H, m), 4.67–4.81 (1H, m), 4.89 (1H, t, J=5.0 Hz), 5.46 (1H, d, J=4.0 Hz), 6.89 (1H, br s), 7.08 (2H, t, J=8.8 Hz), 7.11 (1H, d, J=7.0 Hz), 7.29–7.58. (11H, m), 7.94 (1H, d, J=9.2 Hz), 8.32 (1H, d, J=8.4 Hz); IR (KBr) 3283, 1638, 1510, 1329, 1161, 1123, 1069, 837 cm$^{-1}$; Anal. Calcd for C$_{28}$H$_{22}$F$_4$N$_2$O$_3$·0.5H$_2$O: C, 64.74; H, 4.46; N, 5.39. Found: C, 64.60; H, 4.72; N, 5.42.

Example 105

N-((1RS,2SR)-2-(4-fluorophenyl)-2-hydroxy-1-((4-(trifluoromethyl)phenyl)methyl)ethyl)-4-(hydroxymethyl)-1-naphthalenecarboxamide 1) To a solution of methyl 4-(hydroxymethyl)-1-naphthalenecarboxylate (700 mg, 3.24 mmol) in methanol (10 ml) was added 1N aqueous sodium hydroxide solution (3.24 ml, 3.24 mmol) and the mixture was stirred overnight at room temperature. 1N Hydrochloric acid was added to the reaction solution (5 ml) and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give 4-(hydroxymethyl)-1-naphthalenecarboxylic acid (570 mg, 87%).

mp 183–184° C. IR ν max$^{KBr}$cm$^{-1}$: 1694, 1593, 1518. $^1$H-NMR (CDCl$_3$)δ: 5.02 (2H, s), 7.54–7.70 (3H, m), 8.04–8.18 (2H, m), 8.86–8.98 (1H, m).

2) To a solution of (1RS,2SR)-2-amino-1-(4-fluorophenyl)-3-(4-(trifluoromethyl)phenyl)-1-propanol (300 mg, 0.96 mmol) in acetonitrile (30 ml) were added 4-(hydroxymethyl)-1-naphthalenecarboxylic acid (194 mg, 0.96 mmol), 1-ethyl-3-(3-dimethylaminopropyl) carbodiimide hydrochloride (275 mg, 1.44 mmol) and 1-hydroxy-1H-benzotriazole (147 mg, 0.96 mmol) and the mixture was stirred overnight at room temperature. The reaction solution was diluted with water (100 ml), and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane: ethyl acetate=2:1). Recrystallization from ethyl acetate-hexane gave the title compound (365 mg, 77%).

mp 202–203° C. IR ν max$^{KBr}$cm$^{-1}$: 1638, 1618, 1605, 1537. Anal. Calcd for C$_{28}$H$_{23}$F$_4$NO$_3$: C, 67.60; H, 4.66; N, 2.82. Found: C, 67.41; H, 4.64; N, 2.53. $^1$H-NMR (CDCl$_3$)δ: 1.88 (1H, br s), 2.87 (1H, dd, J=14.4, 10.6 Hz), 3.09 (1H, dd, J=14.4, 4.4 Hz), 4.72–4.90 (1H, m), 5.02–5.16 (3H, m), 5.94 (1H, d, J=8.0 Hz), 7.04–7.66 (13H, m), 8.02 (1H, d, J=8.4 Hz).

Example 106

4-[[[(1RS,2SR)-2-(4-fluorophenyl)-2-hydroxy-1-[4-(trifluoromethyl)benzyl]ethyl]amino]carbonyl]-1-naphthoate To a solution of methyl 4-[[[(1RS,2SR)-2-(4-fluorophenyl)-2-hydroxy-1-[4-(trifluoromethyl)benzyl]ethyl]amino]carbonyl]-1-naphthoate (0.216 g, 0.411 mmol) in methanol (5 ml)—tetrahydrofuran (5 ml) was added 1N aqueous sodium hydroxide solution (1.64 ml, 1.64 mmol) and the mixture was stirred at room temperature for 5 hrs. The reaction solution was concentrated, diluted with water and acidified with dilute hydrochloric acid. The resulting precipitate was collected by filtration and washed with water and hexane to give the objective substance.

white powder yield 0.148 g, 70% mp 209–212° C.; $^1$H-NMR (CDCl$_3$-DMSO-d$_6$, 200 MHz) δ 2.92 (1H, dd, J=11.2 Hz, 14.0 Hz), 3.14 (1H, dd, J=3.1 Hz, 13.7 Hz), 4.71–4.86 (1H, m), 4.95 (1H, d, J=3.6 Hz), 5.31 (1H, br s), 7.09 (2H, t, J=8.8 Hz), 7.16 (1H, d, J=7.4 Hz), 7.31–7.41 (4H, m), 7.50–7.59 (5H, m), 7.79 (1H, d, J=9.8 Hz), 8.08 (1H, d, J=7.4 Hz), 8.91 (1H, 6, J=8.8 Hz); IR (KBr) 3281, 1690, 1640, 1532, 1512, 1329, 1233, 1165, 1125, 1069, 837 cm$^{-1}$; Anal. Calcd for C$_{28}$H$_{21}$F$_4$NO$_4$·1.0H$_2$O: C, 63.52; H, 4.38; N, 2.65. Found: C, 63.45; H, 4.53; N, 2.49.

Example 107

N-((1RS,2SR)-2-(4-fluorophenyl)-2-hydroxy-1-((4-(trifluoromethyl)phenyl)methyl)ethyl)-3-phenoxybenzamide To a solution of (1RS,2SR)-2-amino-1-(4-fluorophenyl)-3-(4-(trifluoromethyl)phenyl)-1-propanol (400 mg, 1.28 mmol) in acetonitrile (20 ml) were added 3-phenoxybenzoic acid (274 mg, 1.28 mmol), 1-ethyl-3-(3-dimethylaminopropyl)carbodiimide hydrochloride (368 mg, 1.92 mmol) and 1-hydroxy-1H-benzotriazole (196 mg, 1.28 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (400 mg, 61%).

mp 144–145° C. IR ν max$^{KBr}$cm$^{-1}$: 1644, 1580, 1510, 1491, 1481. Anal. Calcd for C$_{29}$H$_{23}$F$_4$NO$_3$·0.1H$_2$O: C, 68.13; H, 4.57; N, 2.74. Found: C, 67.85; H, 4.51; N, 2.53. $^1$H-NMR (CDCl$_3$)δ: 2.80–3.00 (2H, m), 3.30–3.70 (1H, m), 4.50–4.64 (1H, m), 5.05 (1H, d, J=3.2 Hz), 6.11 (1H, d, J=8.6 Hz), 6.96–7.52 (17H, m).

Example 108

N-((1RS,2SR)-2-(4-fluorophenyl)-2-hydroxy-1-((4-(trifluoromethyl)phenyl)methyl)ethyl)-4-phenoxybenzamide To a solution of (1RS,2SR)-2-amino-1-(4-fluorophenyl)-3-(4-(trifluoromethyl)phenyl)-1-propanol (400 mg, 1.28 mmol) in acetonitrile (20 ml) were added 4-phenoxybenzoic acid (274 mg, 1.28 mmol), 1-ethyl-3-(3-dimethylaminopropyl)carbodiimide hydrochloride (368 mg, 1.92 mmol) and 1-hydroxy-1H-benzotriazole (196 mg, 1.28 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (451 mg, 69%).

mp 186–187° C. IR ν max$^{KBr}$cm$^{-1}$: 1622, 1609, 1590, 1532, 1510, 1501, 1489. $^1$H-NMR (CDCl$_3$)δ: 2.80–3.02 (2H, m), 3.80–4.00 (1H, m), 4.50–4.70 (1H, m), 5.06 (1H, d, J=3.2 Hz), 6.17 (1H, d, J=8.4 Hz), 6.90–7.60 (17H, m).

Example 109

N-[(1RS,2SR)-2-(4-fluorophenyl)-2-hydroxy-1-[4-(trifluoromethyl)benzyl]ethyl]-3,3,3-trifluoropropionamide While stirring (1RS,2SR)-2-amino-1-(4-fluorophenyl)-3-[4-(trifluoromethyl)phenyl]propan-1-ol (0.166 g, 0.530 mmol), 3,3,3-trifluoropropionic acid (68 mg, 0.53 mmol) and 1-hydroxybenzotriazole hydrate (81 mg, 0.53 mmol) in acetonitrile (10 ml), 1-ethyl-3-(3-dimethylaminopropyl) carbodiimide hydrochloride (0.10 g, 0.53 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from hexane to give the objective substance.

white crystal yield 0.185 g, 83% mp 179–180° C; $^1$H-NMR (CDCl$_3$-DMSO-d$_6$, 200 MHz) δ 2.79–2.83 (2H, m), 2.90 (1H, d, J=10.6 Hz), 3.01 (1H, d, J=10.6 Hz), 4.35–4.49 (1H, m), 4.64 (1H, d, J=3.2 Hz), 4.93 (1H, t, J=3.4

Hz), 7.06 (2H, t, J=8.6 Hz), 7.17–7.21 (3H, m), 7.40–7.47 (4H, m); IR (KBr) 3308, 1663, 1514, 1327, 1238, 1175, 1113, 1069, 831 cm$^{-1}$; Anal. Calcd for $C_{19}H_{16}F_7NO_2$: C, 53.91; H, 3.81; N, 3.31. Found: C, 53;84; H, 3.61; N, 3.13.

Example 110

2-cyclopentyl-N-[(1RS,2SR)-2-(4-fluorophenyl)-2-hydroxy-1-[4-(trifluoromethyl)benzyl]ethyl]-2-phenylacetamide While stirring (1RS,2SR)-2-amino-1-(4-fluorophenyl)-3-[4-(trifluoromethyl)phenyl]propan-1-ol (0.156 g, 0.498 mmol), 2-cyclopentyl-2-phenylacetic acid (0.10 g, 0.50 mmol) and 1-hydroxybenzotriazole hydrate (76 mg, 0.50 mmol) in acetonitrile (10 ml), 1-ethyl-3-(3-dimethylaminopropyl)carbodiimide hydrochloride (95 mg, 0.50 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white crystal yield 0.208 g, 84% mp 201–202° C; $^1$H-NMR (CDCl$_3$, 200 MHz) δ 0.73–1.08 (2H, m), 1.30–1.70 (6H, m), 2.38–2.93 (4H, m), 3.43 (0.5H, d, J=3.6 Hz), 3.53 (0.5H, d, J=3.6 Hz), 4.34–4.48 (1H, m), 4.80–4.85 (1H, m), 5.23 (0.5H, br d, J=8.4 Hz), 5.34 (0.5H, br d, J=6.6 Hz), 6.88–7.31 (12H, m), 7.43 (1H, d, J=8.0 Hz); IR (KBr) 3316, 2957, 1645, 1530, 1514, 1327, 1233, 1167, 1123, 1069, 831 cm$^{-1}$; Anal. Calcd for $C_{29}H_{29}F_4NO_2$: C, 69.73; H, 5.8.5; N, 2.80. Found: C, 69.71; H, 5.95; N, 2.63.

Example 111

N-[(1RS,2SR)-2-(4-fluorophenyl)-2-hydroxy-1-[4-(trifluoromethyl)benzyl]ethyl]-3-nitro-5,6,7,8-tetrahydronaphthalene-1-carboxamide While stirring (1RS,2SR)-2-amino-1-(4-fluorophenyl)-3-[4-(trifluoromethyl)phenyl]propan-1-ol (0.150 g, 0.479 mmol), 3-nitro-5,6,7,8-tetrahydronaphthalene-1-carboxylic acid (see *Chem. Pharm. Bull.*, 32, 3968–80 (1984)) (0.11 g, 0.48 mmol) and 1-hydroxybenzotriazole hydrate (73 mg, 0.48 mmol) in acetonitrile (10 ml), 1-ethyl-3-(3-dimethylaminopropyl)carbodiimide hydrochloride (92 mg, 0.48 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white crystal yield 0.180 g, 73% mp 216–217° C; $^1$H-NMR (CDCl$_3$-DMSO-d$_6$, 200 MHz) δ 1.49–1.78 (4H, m), 1.97–2.13 (1H, m), 2.36–2.52 (1H, m), 2.77–2.93 (3H, m), 3.02 (1H, dd, J=4.3 Hz, 14.5 Hz), 4.58–4.73 (1H, m), 4.96 (1H, t, J=4.2 Hz), 5.28 (1H, d, J=3.6 Hz), 7.08 (2H, t, J=8.8 Hz), 7.30–7.56 (6H, m), 7.72 (1H, d, J=2.2 Hz), 7.89 (1H, d, J=2.2 Hz); IR (KBr) 3260, 1642, 1534, 1514, 1346, 1327, 1231, 1165, 1123, 1067, 837 cm$^{-1}$; Anal. Calcd for $C_{27}H_{24}F_4N_2O_4$: C, 62.79; H, 4.68; N, 5.42. Found: C, 62.68; H, 4.45; N, 5.33.

Example 112

2-benzyl-N-[(1RS,2SR)-2-(4-fluorophenyl)-2-hydroxy-1-[4-(trifluoromethyl)benzyl]ethyl]-3,3-dimethylbutyramide While stirring (1RS,2SR)-2-amino-1-(4-fluorophenyl)-3-[4-(trifluoromethyl)phenyl]propan-1-ol (0.264 g, 0.843 mmol), 2-benzyl-3,3-dimethylbutanoic acid (0.17 g, 0.84 mmol), 4-N,N-dimethylaminopyridine (0.10 g, 0.84 mmol) and 1-hydroxybenzotriazole hydrate (0.13 g, 0.84 mmol) in acetonitrile (10 ml), 1-ethyl-3-(3-dimethylaminopropyl)carbodiimide hydrochloride (0.16 g, 0.84 mmol) was added and the mixture was stirred at 60° C. for 3 days. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.206 g, 49% mp 175–176° C.; $^1$H-NMR (CDCl$_3$, 200 MHz) δ 0.76 (3.5H, s), 0.90 (5.5 H, s), 1.80–1.93 (1H, m), 2.15–3.02 (5H, m), 4.25–4.40 (1H, m), 4.48–4.53 (1H, m), 4.92–5.04 (1H, m), 6.76–7.45 (13H, m); IR (KBr) 3551, 2967, 1651, 1507, 1333, 1154, 1127, 1123, 1069, 835 cm$^{-1}$; Anal. Calcd for $C_{29}H_{31}F_4NO_2$: C, 69.45; H, 6.23; N, 2.79. Found: C, 69.09; H, 6.28; N, 2.80.

Example 113

N-[(1RS,2SR)-2-(4-fluorophenyl)-2-hydroxy-1-[4-(trifluoromethyl)benzyl]ethyl]-3,4-dihydro-2H-1,5-benzodioxepine-6-carboxamide 1) methyl 2,3-dihydroxybenzoate 2,3-Dihydroxybenzoic acid (5.029 g, 32.63 mmol) was heated under reflux in a solution (80 ml) of 10% hydrogen chloride in methanol for 3 days. The solvent of the reaction solution was evaporated under reduced pressure, diluted with water and extracted with ethyl acetate. The obtained ethyl acetate solution was dried over anhydrous magnesium sulfate and passed through silica gel. The solvent was evaporated under reduced pressure. The obtained residue was crystallized from cold diisopropyl ether-hexane to give the objective substance.

brown crystal yield 4.439 g, 81% mp 77–78° C.; $^1$H-NMR (CDCl$_3$, 200 MHz) δ 3.96 (3H, s), 5.65 (1H, s), 6.80 (1H, t, J=8.1 Hz), 7.11 (1H, dd, J=1.5 Hz, 7.7 Hz), 7.37 (1H, dd, J=1.1 Hz, 8.1 Hz), 10.89 (1H, s); IR (KBr) 3465, 3100 2850, 1674, 1468, 1437, 1321, 1269, 1194, 1152, 1076, 1009, 837, 758 cm$^{-1}$; Anal. Calcd for $C_8H_8O_4$: C, 57.14; H, 4.80. Found: C, 56.93; H, 4.94.

2) methyl 3,4-dihydro-2H-1,5-benzodioxepine-6-carboxylate

Methyl 2,3-dihydroxybenzoate (1.870 g, 11.12 mmol), 1,3-dibromopropane (2.25 g, 11.1 mmol) and potassium carbonate (6.15 g, 44.5 mmol) were stirred in N,N-dimethylformamide (20 ml) overnight at 60° C. The reaction solution was poured into water and extracted twice with ethyl acetate. The collected organic layer was dried over anhydrous sodium sulfate and the solvent was evaporated under reduced pressure. The residue was purified by silica gel column chromatography (hexane/ethyl acetate=6/1–3/1) to give the objective substance.

colorless liquid yield 1.711 g, 74% $^1$H-NMR (CDCl$_3$, 200 MHz) δ 2.18–2.29 (2H, m), 3.89 (3H, s), 4.25 (2H, t, J=5.7 Hz), 4.30 (2H, t, J=5.7 Hz), 6.95 (1H, t, J=7.9 Hz), 7.12 (1H, dd, J=1.8 Hz, 8.0 Hz), 7.36 (1H, dd, J=1.8 Hz, 7.8 Hz); IR (neat) 2953, 1732, 1478, 1454, 1296, 1262, 1225, 1138, 1080, 1044 cm$^{-1}$ 3) 3,4-dihydro-2H-1,5-benzodioxepine-6-carboxylic acid To a solution of methyl 3,4-dihydro-2H-1,5-benzodioxepine-6-carboxylate (1.615 g, 7.757 mmol) in methanol (20 ml)—tetrahydrofuran (10 ml) was added 1N aqueous sodium hydroxide solution (15.5 ml, 15.5 mmol) and the mixture was stirred overnight at room temperature.

The reaction solution was concentrated, diluted with water, acidified with dilute hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 1.376 g, 91% mp 68–70° C.; $^1$H-NMR (CDCl$_3$, 200 MHz) δ 2.29–2.40 (2H, m), 4.30 (2H, t, J=5.8 Hz), 4.52 (2H, t, J=5.6 Hz), 7.09 (1H, t, J=7.9 Hz), 7.24 (1H, dd, J=2.0 Hz, 8.2 Hz), 7.85 (1H, dd, J=1.8 Hz, 7.6 Hz); IR (KBr) 3171, 1725, 1478, 1348, 1264, 1022, 752 cm$^{-1}$; Anal. Calcd for C$_{10}$H$_{10}$O$_4$: C, 61.85; H, 5.19. Found: C, 61.77; H, 5.49.

4) N-[(1RS,2SR)-2-(4-fluorophenyl)-2-hydroxy-1-[4-(trifluoromethyl)benzyl]ethyl]-3,4-dihydro-2H-1,5-benzodioxepine-6-carboxamide While stirring (1RS,2SR)-2-amino-1-(4-fluorophenyl)-3-[4-(trifluoromethyl)phenyl]propan-1-ol (0.262 g, 0.836 mmol), 3,4-dihydro-2H-1,5-benzodioxepine-6-carboxylic acid (0.16 g, 0.84 mmol) and 1-hydroxybenzotriazole hydrate (0.13 g, 0.84 mmol) in acetonitrile (10 ml), 1-ethyl-3-(3-dimethylaminopropyl)carbodiimide hydrochloride (0.16 g, 0.84 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.361 g, 88% mp 155–156° C.; $^1$H-NMR (CDCl$_3$, 200 MHz) δ 2.05–2.16 (2H, m), 2.93–2.97 (2H, m), 3.69–3.86 (2H, m), 4.09–4.20 (3H, m), 4.55–4.67 (1H, m), 5.10 (1H, t, J=3.3 Hz), 6.98–7.15 (4H, m), 7.26 (2H, d, J=7.8 Hz), 7.38–7.52 (4H, m), 7.76 (1H, dd, J=1.8 Hz, 7.8 Hz), 7.92 (1H, br d, J=7.8 Hz); IR (KBr) 3279, 1636, 1541, 1512, 1325, 1264, 1231, 1169, 1121, 1069, 1044, 837 cm$^{-1}$; Anal. Calcd for C$_{26}$H$_{23}$F$_4$NO$_4$: C, 63.80; H, 4.74; N, 2.86. Found: C, 63.63; H, 4.72; N, 2.80.

Example 114 benzyl N-[(1RS,2SR)-2-(4-fluorophenyl)-2-hydroxy-1-[4-(trifluoromethyl)benzyl]ethyl] carbamate While stirring (1RS,2SR)-2-amino-1-(4-fluorophenyl)-3-[4-(trifluoromethyl)phenyl]propan-1-ol (0.159 g, 0.508 mmol) and sodium hydrogen carbonate (85 mg, 1.02 mmol) in tetrahydrofuran (10 ml), benzyl chlorocarbonate (0.09 ml, 0.61 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.190 g, 84% mp 151–152° C.; $^1$H-NMR (CDCl$_3$, 200 MHz) δ 2.68–2.91 (3H, m), 4.08–4.22 (1H, m), 4.81 (1H, br d, J=8.8 Hz), 4.94 (1H, br s), 5.00 (2H, s), 7.06 (2H, t, J=8.6 Hz), 7.17–7.40 (9H, m), 7.48 (2H, d, J=7.8 Hz); IR (KBr) 3337, 1694, 1539, 1327, 1163, 1121, 1069, 829 cm$^{-1}$; Anal. Calcd for C$_{24}$H$_{21}$F$_4$NO$_3$: C, 64.43; H, 4.73; N, 3.13. Found: C, 64.46; H, 4.77; N, 2.94.

Example 115 ethyl N-[(1RS,2SR)-2-(4-fluorophenyl)-2-hydroxy-1-[4-(trifluoromethyl)benzyl]ethyl]carbamate While stirring (1RS,2SR)-2-amino-1-(4-fluorophenyl)-3-[4-(trifluoromethyl)phenyl]propan-1-ol (0.401 g, 1.280 mmol) and sodium hydrogen carbonate (0.22 g, 2.56 mmol) in tetrahydrofuran (10 ml)—water (2 ml), ethyl chlorocarbonate (0.15 ml, 1.54 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white crystal yield 0.413 g, 84% mp 143–144° C.; $^1$H-NMR (CDCl$_3$, 200 MHz) δ 1.15 (3H, t, J=7.0 Hz), 2.67–2.95 (3H, m), 3.93–4.20 (3H, m), 4.71 (1H, d, J=8.6 Hz), 4.95 (1H, s), 7.08 (2H, t, J=8.6 Hz), 7.21 (2H, d, J=8.0 Hz), 7.39 (2H, dd, J=5.5 Hz, 8.5 Hz), 7.51 (2H, d, J=8.0 Hz); IR (KBr) 3318, 1690, 1547, 1329, 1163, 1117, 1069, 829 cm$^{-1}$; Anal. Calcd for C$_{19}$H$_{19}$F$_4$NO$_3$: C, 59.22; H, 4.97;, N, 3.63. Found: C, 59.28; H, 5.10; N, 3.63.

Example 116 neopentyl N-[(1RS,2SR)-2-(4-fluorophenyl)-2-hydroxy-1-[4-(trifluoromethyl)benzyl]ethyl] carbamate While stirring (1RS,2SR)-2-amino-1-(4-fluorophenyl)-3-[4-(trifluoromethyl)phenyl]propan-1-ol (0.171 g, 0.546 mmol) and sodium hydrogen carbonate (92 mg, 1.09 mmol) in tetrahydrofuran (10 ml), neopentyl chlorocarbonate (0.10 ml, 0.65 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from hexane to give the objective substance.

white crystal yield 0.168 g, 72% mp 112–113° C.; $^1$H-NMR (CDCl$_3$, 200 MHz) δ 0.82 (9H, s), 2.66–2.92 (3H, m), 3.67 (2H, br s), 4.14 (1H, br s), 4.72 (1H, br d, J=8.2 Hz), 4.95 (1H, br s), 7.08 (2H, t, J=8.6 Hz), 7.22 (2H, d, J=8.0 Hz), 7.39 (2H, dd, J=5.2 Hz, 8.4 Hz), 7.50 (2H, d, J=8.0 Hz); IR (KBr) 3326, 2967, 1690, 1545, 1327, 1127, 1069, 833 cm$^{-1}$; Anal. Calcd for C$_{22}$H$_{25}$F$_4$NO$_3$: C, 61.82; H, 5.90; N, 3.28. Found: C, 61.47; H, 5.85; N, 3.04.

Example 117

N-((1RS,2SR)-2-(4-fluorophenyl)-2-hydroxy-1-((4-(trifluoromethyl)phenyl)methyl)ethyl)-1-naphthalenesulfonamide To a solution of (1RS,2SR)-1-(4-fluorophenyl)-1-hydroxy-3-(4-(trifluoromethyl)phenyl)-2-propylamine hydrochloride (150 mg, 0.43 mmol) in ethyl acetate (5 ml) were added 1-naphthalenesulfonyl chloride (107 mg, 0.47 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1). Recrystallization from ethyl acetate-hexane gave the title compound (109 mg, 50%).

mp 176–177° C. IR ν max$^{KBr}$cm$^{-1}$: 1508, 1325, 1223, 1161, 1129. Anal. Calcd for C$_{26}$H$_{21}$F$_4$NO$_3$S: C, 62.02; H, 4.20; N, 2.78. Found: C, 61.73; H, 4.20; N, 2.74. $^1$H-NMR (CDCl₃)δ: 2.40–2.62 (2H, m), 2.95 (1H, br s), 3.56–3.70 (1H, m), 5.15 (2H, s), 6.60 (2H, d, J=8.0 Hz), 6.79 (2H, d, J=8.0 Hz), 6.90–7.04 (2H, m), 7.20–7.40 (3H, m), 7.40–7.56 (2H, m), 7.70–7.84 (1H, m), 7.91 (1H, d, J=8.0 Hz), 8.05 (1H, d, J=8.0 Hz), 8.20–8.30 (1H, m).

Example 118

N-((1RS,2SR)-2-(4-fluorophenyl)-2-hydroxy-1-((4-(trifluoromethyl)phenyl)methyl)ethyl)-N'-(1-naphthalenyl)urea To a solution of (1RS,2SR)-1-(4-fluorophenyl)-1-hydroxy-3-(4-(trifluoromethyl)phenyl)-2-propylamine hydrochloride (150 mg, 0.43 mmol) in acetonitrile (10 ml) were added triethylamine (0.089 ml, 0.64 mmol) and 1-naphthyl isocyanate (0.062 ml, 0.43 mmol) and the mixture was stirred overnight at room temperature. The reaction solution was diluted with water (50 ml) and extracted with ethyl acetate (50 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (135 mg, 65%).

mp 222–223° C. IR ν max$^{KBr}$cm$^{-1}$: 1661, 1638, 1557, 1510. Anal. Calcd for $C_{27}H_{22}F_4N_2O_2$: C, 67.21; H, 4.60; N, 5.81. Found: C, 67.02; H, 4.47; N, 5.78. $^1$H-NMR (CDCl₃)δ: 2.47 (1H, dd, J=14.4, 10.0 Hz), 2.78 (1H, dd, J=14.4, 3.6 Hz), 4.20–4.40 (3H, m), 4.91 (1H, br s), 6.36 (1H, s), 6.92–7.10 (5H, m), 7.22–7.40 (5H, m), 7.40–7.58 (2H, m), 7.74–7.94 (3H, m).

Example 119

N-((1RS,2SR)-2-(4-fluorophenyl)-2-hydroxy-1-((4-(trifluoromethyl)phenyl)methyl)ethyl)-N'-(4-(trifluoromethyl)phenyl)urea To a solution of (1RS,2SR)-1-(4-fluorophenyl)-1-hydroxy-3-(4-(trifluoromethyl)phenyl)-2-propylamine hydrochloride (150 mg, 0.43 mmol) in acetonitrile (10 ml) were added triethylamine (0.089 ml, 0.64 mmol) and 4-trifluoromethylphenyl isocyanate (0.061 ml, 0.43 mmol) and the mixture was stirred overnight at room temperature. The reaction solution was diluted with water (50 ml) and extracted with ethyl acetate (50 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (139 mg, 65%).

mp 160–161° C. IR ν max$^{KBr}$cm$^{-1}$: 1659, 1605, 1557, 1508. Anal. Calcd for $C_{24}H_{19}F_7N_2O_2$: C, 57.60; H, 3.83; N, 5.60. Found: C, 57.61; H, 3.59; N, 5.65. $^1$H-NMR (CDCl₃)δ: 2.60–2.92 (2H, m), 3.50 (1H, br s), 4.22–4.50 (1H, m), 4.80 (1H, d, J=8.0 Hz), 5.01 (1H, s), 6.75 (1H, s), 7.00–7.18 (2H, m), 7.18–7.60 (10H, m).

Example 120

N-((1RS,2SR)-2-(4-fluorophenyl)-2-hydroxy-1-((4-(trifluoromethyl)phenyl)methyl)ethyl)-N-(1-naphthalenylmethyl)acetamide 1) To a solution of (4RS,5SR)-5-(4-fluorophenyl)-4-((4-(trifluoromethyl)phenyl)methyl)-1,3-oxazolidin-2-one (1 g, 2.95 mmol) in N,N-dimethylformamide (10 ml) was added 60% sodium hydride (142 mg, 3.54 mmol) and the mixture was stirred at room temperature for 15 min. To the reaction solution was added 1-naphthylmethyl chloride (480 ml, 3.25 mmol) and the mixture was stirred for 1 hr. The reaction solution was diluted with water (100 ml) and extracted with ethyl acetate (100 ml×2). The extract was washed with water and saturated brine, dried over anhydrous magnesium sulfate and evaporated under reduced pressure. The residue was purified by silica gel column chromatography (hexane:ethyl acetate=4:1). Recrystallization from diisopropyl ether-hexane gave (4RS,5SR)-5-(4-fluorophenyl)-3-(1-naphthalenylmethyl)-4-((4-(trifluoromethyl)phenyl)methyl)-1,3-oxazolidin-2-one (1.23 g, 87%).

mp 136–137° C. IR ν max$^{KBr}$cm$^{-1}$: 1748, 1609. Anal. Calcd for $C_{28}H_{21}F_4NO_2$: C, 70.14; H, 4.41; N, 2.92. Found: C, 70.15; H, 4.23; N, 2.78. $^1$H-NMR (CDCl₃)δ: 2.34 (1H, dd, J=14.4, 8.0 Hz), 2.81 (1H, dd, J=14.4, 5.2 Hz), 3.70–3.84 (1H, m), 4.24 (1H, d, J=15.2 Hz), 5.28 (1H, d, J=7.6 Hz), 5.40 (1H, d, J=15.2 Hz), 6.48 (2H, d, J=8.2 Hz), 6.76–7.10 (5H, m), 7.14–7.56 (5H, m), 7.70–8.00 (3H, m).

2) To a solution of (4RS,5SR)-5-(4-fluorophenyl)-3-(1-naphthalenylmethyl)-4-((4-(trifluoromethyl)phenyl)methyl)-1,3-oxazolidin-2-one (100 mg, 0.21 mmol) in ethanol (2 ml) was added 8N aqueous sodium hydroxide solution (130 ml) and the mixture was heated under reflux for 4 hrs. The reaction solution was diluted with water (50 ml) and extracted with ethyl acetate (50 ml×2). The extract was washed with water and saturated brine, dried over anhydrous magnesium sulfate and evaporated under reduced pressure. The residue was purified by silica gel column chromatography (hexane:ethyl acetate=2:1). Recrystallization from diisopropyl ether-hexane gave (1RS,2SR)-1-(4-fluorophenyl)-2-((1-naphthalenylmethyl)amino)-3-(4-(trifluoromethyl)phenyl)-1-propanol (29.6 mg, 31%).

mp 94–95° C. IR ν max$^{KBr}$cm$^{-1}$: 1605, 1510, 1325. Anal. Calcd for $C_{27}H_{23}F_4NO$: C, 71.51; H, 5.11; N, 3.09. Found: C, 71.40; H, 5.07; N, 2.98. $^1$H-NMR (CDCl₃)δ: 2.45 (2H, d, J=7.4 Hz), 3.02–3.14 (1H, m), 3.71 (1H, br s), 4.03 (1H, d, J=13.2 Hz), 4.33 (1H, d, J=13.2 Hz), 5.06 (1H, d, J=3.6 Hz), 6.92 (2H, d, J=7.6 Hz), 7.00–7.16 (2H, m), 7.20–7.58 (9H, m), 7.70–7.88 (2H, m).

3) To a solution of (1RS,2SR)-1-(4-fluorophenyl)-2-((1-naphthalenylmethyl)amino)-3-(4-(trifluoromethyl)phenyl)-1-propanol (100 mg, 0.22 mmol) in ethyl acetate (5 ml) were added acetyl chloride (225 ml, 3.3 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=1:1) to give the title compound (45 mg, 41%).

IR ν max$^{KBr}$cm$^{-1}$: 1622, 1508, 1456. $^1$H-NMR (CDCl₃)δ: 2.32 (3H, s), 2.73 (1H, d, J=11.0 Hz), 3.32–3.76 (3H, m), 4.76 (1H, s), 4.82 (1H, d, J=15.6 Hz), 6.50–6.64 (2H, m), 6.70–6.84 (2H, m), 7.00–7.18 (3H, m), 7.40–7.60 (6H, m), 7.82–8.00 (2H, m).

Example 121

N-((1RS,2SR)-2-(4-fluorophenyl)-2-hydroxy-1-((4-(trifluoromethyl)phenyl)methyl)ethyl)-N-methyl-1-naphthalenecarboxamide 1) To a solution of (4RS,5SR)-5-(4-fluorophenyl)-4-((4-(trifluoromethyl)phenyl)methyl)-1,3-oxazolidin-2-one (5 g, 14.7 mmol) in N,N-dimethylformamide (30 ml) was added 60% sodium hydride (710 mg, 17.7 mmol) and the mixture was stirred at room temperature for 15 min. To the reaction solution was added methyl iodide (5 ml, 80 mmol) and the mixture was stirred for 1 hr. The reaction solution was diluted with water (300 ml) and extracted with ethyl acetate (200 ml×2). The extract was washed with water and saturated brine, dried over anhydrous magnesium sulfate and evaporated under reduced pressure. The residue was recrystallized from diisopropyl ether-hexane to give (4RS,5SR)-5-(4-fluorophenyl)-3-methyl-4-((4-(trifluoromethyl)phenyl) methyl)-1,3-oxazolidin-2-one (4.76 g, 91%).

mp 77–78° C. IR ν max$^{KBr}$cm$^{-1}$: 1759, 1609, 1514. Anal. Calcd for $C_{18}H_{15}F_4NO_2$: C, 61.19; H, 4.28; N, 3.96. Found: C, 61.25; H, 4.21; N, 3.96. $^1$H-NMR (CDCl$_3$)δ: 2.45 (1H, dd, J=14.2, 7.2 Hz), 2.77 (1H, dd, 14.2, 7.2 Hz), 4.30 (1H, q, J=6.6 Hz), 5.59 (1H, d, J=8.0 Hz), 6.92 (2H, d, J=8.0 Hz), 6.94–7.08 (2H, m), 7.10–7.20 (2H, m), 7.44 (2H, d, J=8.0 Hz).

2) To a solution of (4RS,5SR)-5-(4-fluorophenyl)-3-methyl-4-((4-(trifluoromethyl)phenyl)methyl)-1,3-oxazolidin-2-one (4.56 g, 12.9 mmol) in ethanol (20 ml) was added 8N aqueous sodium hydroxide solution (8.07 ml) and the mixture was heated under reflux for 3 hrs. The reaction solution was diluted with water (200 ml) and extracted with ethyl acetate (200 ml×2). The extract was washed with water and saturated brine, dried over anhydrous magnesium sulfate and evaporated under reduced pressure. The residue was recrystallized from diisopropyl ether-hexane to give (1RS, 2SR)-1-(4-fluorophenyl)-2-(methylamino)-3-(4-(trifluoromethyl)phenyl)-1-propanol (3.34 mg, 79%).

mp 79–80° C. IR ν max$^{KBr}$cm$^{-1}$: 1618, 1605, 1510. Anal. Calcd for $C_{17}H_{17}F_4NO$: C, 62.38; H, 5.23; N, 4.28. Found: C, 62.38; H, 5.11; N, 4.27. $^1$H-NMR (CDCl$_3$)δ: 2.41 (3H, s), 2.44–2.60 (2H, m), 2.84–2.96 (1H, m), 4.94 (1H, d, J=3.2 Hz), 7.00–7.12 (2H, m), 7.18 (2H, d, J=8.0 Hz), 7.32–7.50 (2H, m), 7.52 (2H, d, J=8.0 Hz).

3) To a solution of (1RS,2SR)-1-(4-fluorophenyl)-2-(methylamino)-3-(4-(trifluoromethyl)phenyl)-1-propanol (150 mg, 0.46 mmol) in ethyl acetate (5 ml) were added 1-naphthoyl chloride (76 ml, 0.50 mmol) and saturated aqueous sodium hydrogen carbonate (5 ml) and the mixture was stirred at room temperature for 6 hrs. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1–1:1) and recrystallized from ethyl acetate-hexane to give the title compound (166 mg, 75%).

mp 196–197° C. IR ν max$^{KBr}$cm$^{-1}$: 1605, 1510, 1325. Anal. Calcd for $C_{28}H_{23}F_4NO_2$: C, 69.85; H, 4.81; N, 2.91. Found: C, 69.76; H, 4.89; N, 2.80. $^1$H-NMR (CDCl$_3$)δ: 2.48 (3H, d, J=4.4 Hz), 3.02–3.30 (1H, m), 3.60–3.78 (1H, m), 6.08 (1H, d, J=8.6 Hz), 6.24–6.36 (1H, m), 7.00–7.50 (6H, m), 7.58–7.80 (9H, m).

Example 122

N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide 1) ethyl 3-(4-fluorophenyl)-3-oxo-2-[3-(1,1,2,2-tetrafluoroethoxy)benzyl]propionate A solution of 3-(1,1,2,2-tetrafluoroethoxy)toluene (6.70 g, 32.2 mmol), N-bromosuccinimide (5.73 g, 32.2 mmol) and 2,2'-azobis(isobutyronitrile) (10 mg) in carbon tetrachloride (30 ml) was heated under reflux for 0.5 hr. After cooling the reaction solution to room-temperature, the white precipitate was removed by filtration and the precipitate was washed with diethyl ether. The solvent of the collected filtrate was evaporated under reduced pressure to give a crude product of 3-(1,1,2,2-tetrafluoroethoxy)benzyl bromide as a pale-yellow liquid.

To a solution of ethyl (4-fluorobenzoyl)acetate (6.153 g, 29.27 mmol) in 1,2-dimethoxyethane (50 ml) was added a suspension (1.17 g, 29.3 mmol) of 60% sodium hydride in liquid paraffin under ice-cooling and the mixture was stirred as it as under ice-cooling for 0.5 hr. A solution of 3-(1,1,2, 2-tetrafluoroethoxy)benzyl bromide obtained above in 1,2-dimethoxyethane (10 ml) was added thereto at room temperature, and the mixture was stirred at room temperature for 8 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1). Crystallization from hexane gave the objective substance.

white crystal yield 7.539 g, 62% mp 53–54° C.; $^1$H-NMR (CDCl$_3$, 200 MHz) δ 1.12 (3H, t, J=7.1 Hz), 3.34 (2H, d, J=7.6 Hz), 4.10 (2H, q, J=7.1 Hz), 4.56 (1H, t, J=7.3 Hz), 5.89 (1H, tt, J=2.8 Hz, 53.1 Hz), 7.04–7.16 (5H, m), 7.27 (1H, t, J=7.7 Hz), 7.99 (2H, dd, J=5.5 Hz, 8.7 Hz); IR (KBr) 1728, 1682, 1597, 1325, 1275, 1236, 1205, 1157, 1134, 1100, 847 cm$^{-1}$; Anal. Calcd for $C_{20}H_{17}F_5O_4$: C, 57.70; H, 4.12. Found: C, 57.71; H, 4.15.

2) ethyl (2RS,3RS)-3-(4-fluorophenyl)-3-hydroxy-2-[3-(1, 1,2,2-tetrafluoroethoxy)benzyl]propionate While stirring zinc chloride (4.70 g, 34.5 mmol) in diethyl ether (80 ml), sodium borohydride (2.61 g, 68.9 mmol) was added as it was at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-fluorophenyl)-3-oxo-2-[3-(1,1,2,2-tetrafluoroethoxy) benzyl]propionate (7.176 g, 17.24 mmol) in diethyl ether (30 ml) at room temperature and the mixture was stirred as it was at room temperature for 2 hrs. Dilute hydrochloric acid was added to the solution by small portions to decompose excess zinc borohydride and the mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 7.295 g, 100% $^1$H-NMR (CDCl$_3$, 200 MHz) δ 0.93 (3H, t, J=7.1 Hz), 2.90–3.04 (4H, m), 3.89 (2H, q, J=7.1 Hz), 5.02 (1H, t, J=3.6 Hz), 5.88 (1H, tt, J=2.9 Hz, 53.2 Hz), 6.95–7.10 (5H, m), 7.24 (1H, t, J=7.8 Hz), 7.37 (2H, dd, J=5.5 Hz, 8.7 Hz); IR (neat) 3463, 1725, 1510, 1302, 1279, 1227, 1198, 1159, 1123, 839 cm$^{-1}$ 3) (2RS,3RS)-3-(4-fluorophenyl)-3-hydroxy-2-[3-(1,1,2,2-tetrafluoroethoxy)benzyl]propionic acid To a solution of ethyl (2RS,3RS)-3-(4-fluorophenyl)-3-hydroxy-2-[3-(1,1,2,2-tetrafluoroethoxy)benzyl]propionate (7.252 g, 17.33 mmol) in methanol (30 ml)—tetrahydrofuran (30 ml) was added 1N aqueous sodium hydroxide solution (34.7 ml, 34.7 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 5.795 g, 86% mp 116–117° C.; $^1$H-NMR (CDCl$_3$, 200 MHz) δ 2.92–3.08 (3H, m), 5.06 (1H, s), 5.88 (1H, tt, J=2.9 Hz, 53.2 Hz), 6.94–7.09 (5H, m), 7.23 (1H, t, J=7.9 Hz), 7.36 (2H, dd, J=5.4 Hz, 8.6 Hz); IR (KBr) 3370–2850, 1713, 1229, 1206, 1186, 1115, 841 cm$^{-1}$; Anal. Calcd for C$_{18}$H$_{15}$F$_5$O$_4$: C, 55.39; H, 3.87. Found: C, 55.51; H, 3.68.

4) (4RS,5SR)-5-(4-fluorophenyl)-4-[3-(1,1,2,2-tetrafluoroethoxy)benzyl]-1,3-oxazolidin-2-one To a solution of (2RS,3RS)-3-(4-fluorophenyl)-3-hydroxy-2-[3-(1,1,2,2-tetrafluoroethoxy)benzyl]propionic acid (4.544 g, 11.64 mmol) in tetrahydrofuran (40 ml) were added triethylamine (2.43 ml, 17.5 mmol) and diphenylphosphoryl azide (3.52 g, 12.8 mmol) and the mixture was heated under reflux overnight. The solvent of the reaction solution was evaporated under reduced pressure and the obtained crude product was purified by silica gel column chromatography (hexane/ethyl acetate=3/1–1/1). Crystallization from diethyl ether-hexane gave the objective substance.

white crystal yield 4.241 g, 94% mp 135–136° C.; $^1$H-NMR (CDCl$_3$, 200 MHz) δ 2.20–2.36 (2H, m), 4.26 (1H, dt, J=5.5 Hz, 8.6 Hz), 4.97 (1H, br s), 5.80 (1H, d, J=8.2 Hz), 5.90 (1H, tt, J=2.8 Hz, 53.0 Hz), 6.88 (1H, s), 6.95 (1H, d, J=7.6 Hz), 7.07–7.17 (3H, m), 7.31–7.39 (3H, m); IR (KBr) 3241, 1740, 1514, 1236, 1223, 1196, 1144, 1127, 851 cm$^{-1}$; Anal. Calcd for C$_{18}$H$_{14}$F$_5$NO$_3$: C, 55.82; H, 3.64; N, 3.62. Found: C, 55.96; H, 3.77; N, 3.38.

5) (1RS,2SR)-2-amino-1-(4-fluorophenyl)-3-[3-(1,1,2,2-tetrafluoroethoxy)phenyl]propan-1-ol (4RS,5SR)-5-(4-Fluorophenyl)-4-[3-(1,1,2,2-tetrafluoroethoxy)benzyl]-1,3-oxazolidin-2-one (4.069 g, 10.51 mmol) and sodium hydroxide (1.68 g, 42.0 mmol) was heated under reflux in ethanol (30 ml)—water (2 ml) for 6 hrs. The reaction solution was diluted with water and extracted twice with ethyl acetate. The collected organic layer was dried over anhydrous sodium sulfate and the solvent was evaporated under reduced pressure. The residue was crystallized from diisopropyl ether-hexane to give the objective substance.

white crystal yield 2.961 g, 7.8% mp 87–88° C.; $^1$H-NMR (CDCl$_3$, 200 MHz) δ 2.38 (1H, dd, J=10.4 Hz, 13.8 Hz), 2.81 (1H, dd, J=3.0 Hz, 14.0 Hz), 3.27 (1H, ddd, J=3.4 Hz, 4.9 Hz, 10.4 Hz), 4.65 (1H, d, J=5.2 Hz), 5.89 (1H, tt, J=2.8 Hz, 53.1 Hz), 7.00–7.13 (5H, m), 7.30–7.40 (3H, m); IR (KBr) 3368, 3250–2720, 1508, 1211, 1199, 1127, 1101, 1044 cm$^{-1}$; Anal. Calcd for C$_{17}$H$_{16}$F$_5$NO$_2$: C, 56.51; H, 4.46; N, 3.88. Found: C, 56.43; H, 4.50; N, 3.58.

6) N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide While stirring (1RS,2SR)-2-amino-1-(4-fluorophenyl)-3-[3-(1,1,2,2-tetrafluoroethoxy)phenyl]propan-1-ol (0.173 g, 0.479 mmol), 6,7-dihydro-5H-benzo[a]cycloheptene-1-carboxylic acid (90 mg, 0.48 mmol) and 1-hydroxybenzotriazole hydrate (73 mg, 0.48 mmol) in acetonitrile (10 ml), 1-ethyl-3-(3-dimethylaminopropyl)carbodiimide hydrochloride (92 mg, 0.48 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.216 g, 85% mp 176–177° C.; $^1$H-NMR (CDCl$_3$, 200 MHz) δ 1.93–2.05 (2H, m), 2.15–2.24 (2H, m), 2.67 (2H, t, J=5.8 Hz), 2.78 (1H, dd, J=10.8 Hz, 14.4 Hz), 3.00 (1H, dd, J=4.2 Hz, 14.4 Hz), 3.61 (1H, d, J=3.6 Hz), 4.60–4.73 (1H, m), 5.03 (1H, t, J=3.8 Hz), 5.73 (1H, d, J=8.2 Hz), 5.88 (1H, tt, J=2.5 Hz, 53.1 Hz), 5.92 (1H, td, J=5.4 Hz, 12.2 Hz), 6.20 (1H, d, J=11.8 Hz), 6.94–7.17 (8H, m), 7.30 (1H, t, J=7.8 Hz), 7.43 (2H, dd, J=5.6 Hz, 8.4 Hz); IR (KBr) 3270, 1640, 1510, 1227, 1198, 1127 cm$^{-1}$; Anal. Calcd for C$_{29}$H$_{26}$F$_5$NO$_3$: C, 65.53; H, 4.93; N, 2.64. Found: C, 65.39; H, 4.84; N, 2.63.

Example 123

N-[(1RS,2SR)-2-(4-fluorophenyl)-2-hydroxy-1-[3-(1,1,2,2-tetrafluoroethoxy)benzyl]ethyl]-5,6-dihydronaphthalene-1-carboxamide 1) methyl 5,6-dihydronaphthalene-1-carboxylate Methyl 8-hydroxy-5,6,7,8-tetrahydronaphthalene-1-carboxylate (see *Tetrahedron*, 53, 15969–15982; (1990)) (5.029 g, 32.63 mmol) was heated under reflux in a solution (80 ml) of 10% hydrogen chloride in methanol overnight. The solvent of the reaction solution was evaporated under reduced pressure. The obtained residue was purified by silica gel column chromatography (hexane/ethyl acetate=6/1) to give the objective substance.

colorless liquid yield 0.239 g, 17% $^1$H-NMR (CDCl$_3$, 200 MHz) δ 2.23–2.34 (2H, m), 2.81 (2H, t, J=8.2 Hz), 3.89 (3H, s), 6.22 (1H, td, J=4.8 Hz, 9.7 Hz), 7.14 (1H, t, J=7.5 Hz), 7.25 (1H, d, J=7.4 Hz), 7.33 (1H, td, J=1.6 Hz, 10.2 Hz), 7.69 (1H, dd, J=1.5 Hz, 7.7 Hz); IR (neat) 1721, 1264, 1142, 781 cm$^{-1}$ 2) 5,6-dihydronaphthalene-1-carboxylic acid To a solution of methyl 5,6-dihydronaphthalene-1-carboxylate (0.276 g, 1.466 mmol) in methanol (30 ml) was added 1N aqueous sodium hydroxide solution (8.80 ml, 8.80 mmol) and the mixture was stirred at 70° C. for 8 hrs. The reaction solution was diluted with water, acidified with dilute hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 0.158 g, 62% mp 119–120° C.; $^1$H-NMR (CDCl$_3$, 200 MHz) δ 2.25–2.36 (2H, m), 2.83 (2H, t, J=8.2 Hz), 6.27 (1H, td, J=4.8 Hz, 9.7 Hz), 7.19 (1H, t, J=7.6 Hz), 7.32 (1H, d, J=7.4 Hz), 7.49 (1H, td, J=1.6 Hz, 10.0 Hz), 7.87 (1H, dd, J=1.3 Hz, 7.9 Hz), 11.60 (1H, br s);

3) N-[(1RS,2SR)-2-(4-fluorophenyl)-2-hydroxy-1-[3-(1,1,2,2-tetrafluoroethoxy)benzyl]ethyl]-5,6-dihydronaphthalene-1-carboxamide While stirring (1RS,2SR)-2-amino-1-(4-fluorophenyl)-3-[3-(1,1,2,2-tetrafluoroethoxy)phenyl]propan-1-ol (0.203 g, 0.562 mmol), 5,6-dihydronaphthalene-1-carboxylic acid (98 mg, 0.56 mmol) and 1-hydroxybenzotriazole hydrate (86 mg, 0.56 mmol) in acetonitrile (10 ml), 1-ethyl-3-(3-dimethylaminopropyl)carbodiimide hydrochloride (0.11 g, 0.56 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield. 0.242 g, 83% mp 165–166° C.; $^1$H-NMR (CDCl$_3$, 200 MHz) δ 2.18–2.28 (2H, m), 2.70–2.85 (3H, m), 3.01 (1H, dd, J=4.5 Hz, 14.3 Hz), 3.57 (1H, d, J=3.6 Hz), 4.59–4.73 (1H, m), 5.04, (1H, t, J=3.8 Hz), 5.67 (1H, d, J=8.2 Hz), 5.89 (1H, tt, J=2.8 Hz, 53.1 Hz), 6.00 (1H, td, J=9.3 Hz, 9.4 Hz), 6.34 (1H, d, J=10.0 Hz), 6.85 (1H, d, J=6.6 Hz), 6.99–7.14 (7H, m), 7.31 (1H, t, J=7.6 Hz), 7.43 (2H, dd, J=5.4 Hz, 8.8 Hz); IR (KBr) 3266, 1640, 1514, 1209, 1123 cm$^{-1}$; Anal. Calcd for $C_{28}H_{24}F_5NO_3$: C, 64.99; H, 4.67; N, 2.71. Found: C, 65.05; H, 4.66; N, 2.75.

Example 124

N-[(1RS,2SR)-2-(4-fluorophenyl)-2-hydroxy-1-[3-(1,1,2,2-tetrafluoroethoxy)benzyl]ethyl]-6,7,8,9-tetrahydro-5H-benzo[a]cycloheptene-1-carboxamide While stirring (1RS,2SR)-2-amino-1-(4-fluorophenyl)-3-[3-(1,1,2,2-tetrafluoroethoxy)phenyl]propan-1-ol (0.259 g, 0.717 mmol), 6,7,8,9-tetrahydro-5H-benzo[a]cycloheptene-1-carboxylic acid (0.14 g, 0.72 mmol) and 1-hydroxybenzotriazole hydrate (0.11 g, 0.72 mmol) in acetonitrile (10 ml), 1-ethyl-3-(3-dimethylaminopropyl)carbodiimide hydrochloride (0.14 g, 0.72 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.339 g, 89% mp 194–195° C.; $^1$H-NMR (CDCl$_3$, 200 MHz) δ 1.41–1.63 (4H, m), 1.71–1.80 (2H, m), 2.57–2.63 (2H, m), 2.72 (1H, dd, J=10.9 Hz, 14.5 Hz), 2.73–2.79 (2H, m), 3.03 (1H, dd, J=3.8 Hz, 14.4 Hz), 3.52 (1H, d, J=3.8 Hz), 4.63–4.76 (1H, m), 5.02 (1H, t, J=3.8 Hz), 5.60 (1H, d, J=8.8 Hz), 5.89 (1H, tt, J=2.8 Hz, 53.1 Hz), 6.68 (1H, dd, J=1.5 Hz, 7.4 Hz), 6.93–7.14 (6H, m), 7.26–7.35 (2H, m), 7.43 (2H, dd, J=5.4 Hz, 8.6 Hz); IR (KBr) 3270, 2926, 1638, 1530, 1514, 1227, 1211, 1125 cm$^{-1}$; Anal. Calcd for $C_{29}H_{28}F_5NO_3$: C, 65.28; H, 5.29; N, 2.63. Found: C, 65.23; H, 5.58; N, 2.64.

Example 125

4-fluoro-N-[(1RS,2SR)-2-(4-fluorophenyl)-2-hydroxy-1-[3-(1,1,2,2-tetrafluoroethoxy)benzyl]ethyl]naphthalene-1-carboxamide While stirring (1RS,2SR)-2-amino-1-(4-fluorophenyl)-3-[3-(1,1,2,2-tetrafluoroethoxy)phenyl]propan-1-ol (0.165 g, 0.457 mmol), 4-fluoro-1-naphthoate (87 mg, 0.46 mmol) and 1-hydroxybenzotriazole hydrate (70 mg, 0.46 mmol) in acetonitrile (10 ml), 1-ethyl-3-(3-dimethylaminopropyl)carbodiimide hydrochloride (87 mg, 0.46 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.198 g, 81% mp 186–187° C.; $^1$H-NMR (CDCl$_3$-DMSO-d$_6$, 200 MHz) δ 2.89 (1H, dd, J=10.1 Hz, 14.1 Hz), 3.00 (1H, dd, J=4.8 Hz, 14.4 Hz), 4.69–4.84 (1H, m), 5.00–5.06 (2H, m), 5.93 (1H, tt, J=2.9 Hz, 53.1 Hz), 6.98–7.57 (13H, m), 7.75 (1H, d, J=8.0 Hz), 8.06 (1H, d, J=7.4 Hz); IR (KBr) 3272, 1640, 1624, 1601, 1535, 1512, 1229, 1198, 1127, 835, 760 cm$^{-1}$; Anal. Calcd for $C_{28}H_{21}F_6NO_3$: C, 63.04; H, 3.97; N, 2.63. Found: C, 63.05; H, 4.17; N, 2.49.

Example 126

N-[(1RS,2SR)-2-(4-fluorophenyl)-2-hydroxy-1-[3-(1,1,2,2-tetrafluoroethoxy)benzyl]ethyl]-5,6,7,8-tetrahydrobenzo[a]cyclooctene-1-carboxamide 1) 7,8,9,10-tetrahydrobenzo[a]cycloocten-5(6H)-one To a solution of 6-phenylhexanoic acid (26.16 g, 136.1 mmol) and N,N-dimethylformamide (0.1 ml) in tetrahydrofuran (130 ml) was dropwise added oxalyl chloride (17.8 ml, 204 mmol) at room temperature and the mixture was stirred as it was at room temperature for 0.5 hr. The solvent of the reaction mixture was evaporated under reduced pressure to give an acid chloride as a yellow liquid.

While stirring a suspension of aluminum chloride (36.3 g, 272 mmol) in methylene chloride (250 ml), a solution of the acid chloride obtained above in methylene chloride (1.2 l) was dropwise added over 3 days. To the reaction solution under ice-cooling was added water to quench the reaction. The methylene chloride layer of the mixture was separated and the aqueous layer was extracted with diethyl ether. The collected organic layer was dried over anhydrous magnesium sulfate and the solvent was evaporated under reduced pressure. The obtained residue was purified by silica gel column chromatography (hexane/ethyl acetate=15/1–6/1) to give the objective substance.

pale-yellow liquid yield 16.91 g, 71% $^1$H-NMR (CDCl$_3$, 200 MHz) δ 1.47–1.59 (2H, m), 1.75–1.91 (4H, m), 2.93 (2H, t, J=6.8 Hz), 3.05 (2H, t, J=6.6 Hz), 7.16–7.44 (3H, m), 7.65 (1H, dd, J=1.5 Hz, 7.7 Hz); IR (neat) 2930, 1667, 1445, 1260, 752 cm$^{-1}$ 2) 5,6,7,8,9,10-hexahydrobenzo[a]cycloocten-5-ol To a solution of 7,8,9,10-tetrahydrobenzo[a]cycloocten-5(6H)-one (16.91 g, 97.05 mmol) in methanol (100 ml) was added sodium borohydride (3.67 g, 97.1 mmol) by small portions under ice-cooling and the mixture was stirred at room temperature for 1 hr. The reaction solution was diluted with water and stirred at room temperature for 0.5 hr. The resulting precipitate was collected and washed with water to give the objective substance.

white crystal yield 16.57 g, 97% mp 79–80° C.; $^1$H-NMR (CDCl$_3$, 200 MHz) δ 0.87–1.06 (1H, m), 1.30–1.66 (5H, m), 1.85 (1H, d, J=2.8 Hz), 1.88–2.00 (1H, m), 2.05–2.22 (1H, m), 2.69–2.86 (2H, m), 5.12–5.21 (1H, m), 7.08–7.30 (3H, m), 7.54 (1H, dd, J=1.4 Hz, 7.4 Hz); IR (KBr) 3293, 2917, 1451, 1028, 760 cm$^{-1}$; Anal. Calcd for $C_{12}H_{16}O$·0.1H$_2$O: C, 80.95; H, 9.17. Found: C, 80.93; H, 9.14.

3) 4-(hydroxymethyl)-5,6,7,8,9,10-hexahydrobenzo[a]cycloocten-5-ol

To a solution of 5,6,7,8,9,10-hexahydrobenzo[a]cycloocten-5-ol (16.34 g, 92.70 mmol) and N,N,N',N'-tetramethylethylenediamine (30.8 g, 204 mmol) in hexane (200 ml) was dropwise added a solution (127 ml, 204 mmol) of 1.6 M n-butyllithium in hexane under ice-cooling and the mixture was stirred overnight at 35° C. The reaction mixture was cooled to −78° C. and the crushed dry ice (40 g) was added. The reaction mixture was warmed to room temperature under stirring. The reaction solution was diluted with water, acidified with conc. hydrochloric acid and washed three times with ethyl acetate. The collected organic layer was dried over anhydrous magnesium sulfate and the solvent was evaporated under reduced pressure. The obtained crude product was passed through silica gel column chromatography (hexane/ethyl acetate=6/1) to give a crude product (15.85 g) of 6,7,8,9,10,10a-hexahydro-2H-cycloocta[cd][2]benzofuran-2-one as a yellow liquid.

To a suspension of lithium aluminum hydride (2.97 g, 78.4 mmol) in tetrahydrofuran (150 ml) was dropwise added a solution of the liquid obtained above in tetrahydrofuran (100 ml) under ice-cooling and the mixture was stirred at room temperature for 1 hr. The reaction solution was ice-cooled and water (3 ml), 15% aqueous sodium hydroxide solution (3 ml) and water (8 ml) were successively dropwise added thereto to decompose excess lithium aluminum hydride. The mixture was stirred as it was at room temperature for 2 hrs. The resulting precipitate was removed by filtration and the precipitate was washed with ethyl acetate. The solvent of the collected filtrate was evaporated under reduced pressure. The obtained crude product was purified by silica gel column chromatography (hexane/ethyl acetate= 6/1-ethyl acetate). Crystallization from diisopropyl ether gave the objective substance.

white crystal yield 11.74 g, 61% mp 137–138° C.; $^1$H-NMR (CDCl$_3$, 200 MHz) δ 0.66–0.85 (1H, m), 1.24–1.44 (2H, m), 1.55–1.79 (2H, m), 1.93–2.11 (3H, m), 2.76–2.84 (2H, m), 2.94 (1H, s), 3.46 (1H, br s), 4.46 (1H, dd, J=8.4 Hz, 11.2 Hz), 5.02 (1H, dd, J=2.9 Hz, 11.7 Hz), 5.44 (1H, t, J=8.1 Hz), 7.06–7.23 (3H, m); IR (KBr) 3220, 2922, 1449, 1053, 1009, 754 cm$^{-1}$; Anal. Calcd for C$_{13}$H$_{18}$O$_2$: C, 75.69; H, 8.80. Found: C, 75.72; H, 8.99.

4) 4-[[[tert-butyl(dimethyl)silyl]oxy]methyl]-5,6,7,8,9,10-hexahydrobenzo[a]cycloocten-5-ol To a solution of 4-(hydroxymethyl)-5,6,7,8,9,10-hexahydrobenzo[a]cycloocten-5-ol (11.51 g, 55.80 mmol), 4-N,N-dimethylaminopyridine (0.5 g) and triethylamine (9.33 ml, 67.0 mmol) in tetrahydrofuran (70 ml) was added tert-butyldimethylchlorosilane (9.25 g, 61.4 mmol) at room temperature and the mixture was stirred as it was overnight at room temperature. The reaction solution was poured into water and extracted twice with ethyl acetate. The collected organic layer was dried over anhydrous magnesium sulfate and the solvent was evaporated under reduced pressure. The obtained crude product was purified by silica gel column chromatography (hexane/ethyl acetate=15/1–9/1) to give the objective substance.

colorless liquid yield 17.90 g, 100% $^1$H-NMR (CDCl$_3$, 200 MHz) δ 0.08 (3H, s), 0.14 (3H, s), 0.91 (9H, s), 1.23–1.57 (2H, m), 1.60–1.77 (2H, m), 1.91–2.06 (2H, m), 2.86 (2H, t, J=4.8 Hz), 3.93 (1H, br d, J=4.8 Hz), 4.79 (1H, d, J=12.4 Hz), 5.04 (1H, d, J=12.0 Hz), 5.30–5.40 (1H, m), 7.07 (1H, dd, J=2.0 Hz, 7.2 Hz), 7.16 (1H, t, J=7.3 Hz), 7.23 (1H, dd, J=2.0 Hz, 7.4 Hz); IR (neat) 3412, 2928, 2855, 1472, 1462, 1254, 1073, 835, 779 cm$^{-1}$ 5) tert-butyl(5,6,7,8-tetrahydrobenzo[a] cycloocten-1-ylmethoxy)dimethylsilane To a solution of 4-[[[tert-butyl(dimethyl)silyl]oxy] methyl]-5,6,7,8,9,10-hexahydrobenzo[a]cycloocten-5-ol (17.90 g, 55.84 mmol), triethylamine (15.6 ml, 112 mmol) and 4-N,N-dimethylaminopyridine (0.68 g, 5.58 mmol) in acetonitrile (100 ml) was dropwise-added a solution of methanesulfonyl chloride (9.59 g, 83.8 mmol) in acetonitrile (10 ml) under ice-cooling. Lithium chloride (3.55 g, 83.8 mmol) was added thereto and the mixture was stirred at room temperature for 6 hrs. The reaction solution was poured into water and extracted twice with ethyl acetate. The collected organic layer was dried over anhydrous magnesium sulfate and the solvent was evaporated under reduced pressure. The obtained residue was dissolved in N,N-dimethylformamide (80 ml). 1,8-Diazabicyclo[5.4.0]-7-undecene (16.7 ml, 112 mmol) was added and the mixture was stirred overnight at 80° C. The reaction solution was poured into water and extracted twice with ethyl acetate. The collected organic layer was dried over anhydrous magnesium sulfate and the solvent was evaporated under reduced pressure. The obtained crude product was purified by silica gel column chromatography (hexane/ethyl acetate=15/1) to give the objective substance.

colorless liquid yield 10.94 g, 65% $^1$H-NMR (CDCl$_3$, 200 MHz) δ 0.10 (6H, s), 0.95 (9H, s), 1.37–1.49 (2H, m), 1.67 (2H, br s), 1.99–2.07 (2H, m); 2.74 (2H, t, J=5.9 Hz), 4.67 (2H, s), 5.95 (1H, td, J=6.7 Hz, 11.5 Hz), 6.32 (1H, d, J=11.2 Hz), 7.10 (1H, dd, J=1.3 Hz, 7.5 Hz), 7.22 (1H, t, J=7.8 Hz), 7.35 (1H, d, J=7.6 Hz); IR (neat) 2928, 2855, 1472, 1464, 1254, 1111, 1078, 837, 777 cm$^{-1}$ 6) 5,6,7,8-tetrahydrobenzo[a]cycloocten-1-ylmethanol To a solution of tert-butyl(5,6,7,8-tetrahydrobenzo[a] cycloocten-1-ylmethoxy)dimethylsilane (10.94 g, 36.16 mmol) in tetrahydrofuran (100 ml) was added a solution (43.4 ml, 43.4 mmol) of 1.0 M tetrabutylammonium fluoride in tetrahydrofuran at room temperature and the mixture was stirred at room temperature for 15 min. The reaction solution was poured into water and extracted twice with ethyl acetate. The collected organic layer was dried over anhydrous magnesium sulfate and the solvent was evaporated under reduced pressure. The obtained crude product was purified by silica gel column chromatography (hexane/ethyl acetate= 6/1–3/1) to give the objective substance.

colorless liquid yield 5.499 g, 81% $^1$H-NMR (CDCl$_3$, 200 MHz) δ 1.40–1.52 (2H, m), 1.60–1.74 (3H, m), 2.00–2.11 (2H, m), 2.76 (2H, t, J=5.8 Hz), 4.68 (2H, d, J=5.6 Hz), 6.03 (1H, td, J=6.7 Hz, 11.7 Hz), 6.50 (1H, d, J=11.6 Hz), 7.14–7.28 (3H, m); IR (neat) 3324, 2926, 2853, 1449, 1065, 1007, 766 cm$^{-1}$ 7) 5,6,7,8-tetrahydrobenzo[a]cycloocten-1-carboxylic acid To a solution of 5,6,7,8-tetrahydrobenzo[a]cycloocten-1-ylmethanol (5.419 g, 28.78 mmol) in acetone (100 ml) were dropwise added slowly a solution of chromic anhydride (7.20 g, 72.0 mmol) and conc. sulfuric acid (6 ml) dissolved in water (20 ml) under ice-cooling. After completion of the dropwise addition, the mixture was stirred at room temperature for 0.5 hr. The reaction solution was ice-cooled again, isopropanol (20 ml) was added, and the mixture was stirred as it was for 0.5 hr. Acetone of the reaction solution was evaporated under reduced pressure. The residue was diluted with ethyl acetate, washed three times with water, dried over anhydrous magnesium sulfate and the solvent was evaporated under reduced pressure. The obtained residue was crystallized from ethyl acetate-hexane to give the objective substance.

white crystal yield 2.413 g, 42% mp 164–165° C.; $^1$H-NMR (CDCl$_3$, 200 MHz) δ 1.46 (2H, br s), 1.72 (2H, br s), 2.03 (2H, br s), 2.81 (2H, t, J=5.8 Hz), 5.98 (1H, td, J=7.2 Hz, 11.6 Hz), 6.85 (1H, d, J=11.8 Hz), 7.29 (1H, t, J=7.8 Hz), 7.45 (1H, dd, J=1.4 Hz, 7.8 Hz), 7.94 (1H, dd, J=1.4 Hz, 7.8 Hz); IR (KBr) 3080–2520, 1690, 1451, 1408, 1275, 924, 770 cm$^{-1}$; Anal. Calcd for C$_{13}$H$_{14}$O$_2$: C, 77.20; H, 6.98. Found: C, 77.38; H, 7.06.

8) N-[(1RS,2SR)-2-(4-fluorophenyl)-2-hydroxy-1-[3-(1,1,2,2-tetrafluoroethoxy)benzyl]ethyl]-5,6,7,8-tetrahydrobenzo[a]cyclooctene-1-carboxamide While stirring (1RS,2SR)-2-amino-1-(4-fluorophenyl)-3-[3-(1,1,2,2-tetrafluoroethoxy)phenyl]propan-1-ol (0.274 g, 0.758 mmol), 5,6,7,8-tetrahydrobenzo[a]cyclooctene-1-carboxylic acid (0.15 g, 0.76 mmol) and 1-hydroxybenzotriazole hydrate (0.12 g, 0.76 mmol) in acetonitrile (10 ml), 1-ethyl-3-(3-dimethylaminopropyl) carbodiimide hydrochloride (0.15 g, 0.76 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white powder yield 0.365 g, 86% mp 189–190° C.; $^1$H-NMR (CDCl$_3$, 200 MHz) δ 1.34–1.49 (2H, m), 1.53–1.73 (2H, m), 1.95–2.06 (2H, m), 2.70 (2H, t, J=5.9 Hz), 2.77 (1H, dd, J=10.4 Hz, 14.4 Hz), 2.97 (1H, dd, J=4.2 Hz, 14.4 Hz), 3.91 (1H, br s), 4.58–4.71 (1H, m), 5.04 (1H, t, J=3.7 Hz), 5.80 (1H, td, J=6.8 Hz, 11.8 Hz), 5.88 (1H, tt, J=2.9 Hz, 53.0 Hz), 6.01 (1H, d, J=7.8 Hz), 6.10 (1H, d, J=11.8 Hz), 7.00–7.13 (5H, m), 7.17–7.32 (4H, m), 7.41 (2H, dd, J=5.5 Hz, 8.5 Hz); IR (KBr) 3272, 2928, 1640, 1535, 1514, 1225, 1198, 1128, 777 cm$^{-1}$; Anal. Calcd for C$_{30}$H$_{28}$F$_5$NO$_3$: C, 66.05; H, 5.17; N, 2.57. Found: C, 65.96; H, 5.13; N, 2.55.

Example 127

N-[(1RS,2SR)-2-(4-fluorophenyl)-2-hydroxy-1-[3-(1,1,2,2-tetrafluoroethoxy)benzyl]ethyl]-8-methyl-6,7-dihydro-5H-benzo[a]cycloheptene-1-carboxamide 1) methyl 6-methyl-5-oxo-6,7,8,9-tetrahydro-5H-benzo[a]cycloheptene-6-carboxylate To a solution of 6,7,8,9-tetrahydro-5H-benzo[a]cyclohepten-5-one (24.99 g, 156.0 mmol) and dimethyl carbonate (42.2 g, 468 mmol) in tetrahydrofuran (150 ml) was added a suspension (12.5 g, 312 mmol) of 60% sodium hydride in liquid paraffin at room temperature and the mixture was heated under reflux for 1 hr. The reaction solution was poured into water, acidified with 1N hydrochloric acid and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1) to give methyl 5-oxo-6,7,8,9-tetrahydro-5H-benzo[a]cycloheptene-6-carboxylate as a yellow liquid.

To a solution of the liquid obtained above in tetrahydrofuran (250 ml) was added a suspension (6.86 g, 172 mmol) of 60% sodium hydride in liquid paraffin under ice-cooling and the mixture was stirred as it was under ice-cooling for 0.5 hr. Methyl iodide (33.2 g, 234 mmol) was added to the mixture at 0° C. and the mixture was stirred as it was at room temperature for 1 hr. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=20/1–6/1) to give the objective substance.

pale-yellow liquid yield 35.13 g, 97% $^1$H-NMR (CDCl$_3$, 200 MHz) δ 1.49 (3H, s), 1.69–2.08 (3H, m), 2.25–2.38 (1H, m), 2.70–3.00 (2H, m), 3.62 (3H, s), 7.13 (1H, d, J=7.4 Hz), 7.23–7.46 (3H, m); IR (neat) 2949, 1740, 1686, 1451, 1262, 1236, 1215, 963 cm$^{-1}$ 2) 6-methyl-6,7,8,9-tetrahydro-5H-benzo[a]cyclohepten-5-one A solution of methyl 6-methyl-5-oxo-6,7,8,9-tetrahydro-5H-benzo[a]cycloheptene-6-carboxylate (35.13 g, 151.2 mmol) and conc. hydrochloric acid (50 ml) in acetic acid (100 ml) was stirred overnight at 110° C. The reaction solution was concentrated, diluted with water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=6/1) to give the objective substance.

yellow liquid yield 25.36 g, 96% $^1$H-NMR (CDCl$_3$, 200 MHz) δ 1.22 (3H, d, J=6.6 Hz), 1.51–2.15 (4H, m), 2.85–3.10 (3H, m), 7.19–7.42 (3H, m), 7.67 (1H, dd, J=1.7 Hz, 7.5 Hz); IR (neat) 2932, 1686, 1597, 1448, 1223, 737 cm$^{-1}$ 3) 6-methyl-6,7,8,9-tetrahydro-5H-benzo[a]cyclohepten-5-ol To a solution of 6-methyl-6,7,8,9-tetrahydro-5H-benzo[a]cyclohepten-5-one (24.93 g, 143.1 mmol) in methanol (150 ml) was added sodium borohydride (5.41 g, 143 mmol) by small portions under ice-cooling and the mixture was stirred at room temperature for 1 hr. The solvent of the reaction solution was evaporated under reduced pressure, water was added, and the mixture was extracted twice with ethyl acetate. The collected organic layer was dried over anhydrous magnesium sulfate and the solvent was evaporated under reduced pressure. The obtained residue was purified by silica gel column chromatography (hexane/ethyl acetate=2/1) to give the objective substance.

colorless liquid yield 25.60 g, 100% $^1$H-NMR (CDCl$_3$, 200 MHz) δ 0.85 (1.5H, d, J=7.0 Hz), 0.90 (1.5H, d, J=6.8 Hz), 1.52–2.18 (6H, m), 2.59–2.73 (1H, m), 2.92–3.10 (1H, m), 4.61 (0.5H, dd, J=2.2 Hz, 6.8 Hz), 4.89 (0.5H, s), 7.05–7.23 (3H, m), 7.28–7.35 (1H, m); IR (neat) 3382, 2924, 1454, 1034, 747 cm$^{-1}$ 4) 4-[[[tert-butyl(dimethyl)silyl]oxy]methyl]-6-methyl-6,7,8,9-tetrahydro-5H-benzo[a]cyclohepten-5-ol To a solution of 6-methyl-6,7,8,9-tetrahydro-5H-benzo[a]cyclohepten-5-ol (25.17 g, 142.8 mmol) and N,N,N',N'-tetramethylethylenediamine (47.4 g, 314 mmol) in hexane (250 ml) was dropwise added a solution (196 ml, 314 mmol) of 1.6 M n-butyllithium in hexane under ice-cooling and the mixture was stirred overnight at 35° C. The reaction mixture was cooled to −78° C. and the crushed dry ice (30 g) was added. The mixture was warmed to room temperature understirring. The reaction solution was diluted with water, acidified with conc. hydrochloric acid and washed three times with ethyl acetate. The collected organic layer was dried over anhydrous magnesium sulfate and the solvent was evaporated under reduced pressure. The obtained crude product was passed through silica gel column chromatography (hexane/ethyl acetate=6/1) to give a crude product (9.06 g) of 9-methyl-7,8,9,9a-tetrahydrocyclopenta[cd][2]benzofuran-2(6H)-one as a yellow liquid.

To a suspension of lithium aluminum hydride (1.70 g, 44.8 mmol) in tetrahydrofuran (100 ml) was dropwise added a solution of the liquid obtained above in tetrahydrofuran (80 ml) under ice-cooling and the mixture was stirred at room temperature for 1 hr. The reaction solution was ice-cooled and water (1.5 ml), 15% aqueous sodium hydroxide solution (1.5 ml) and water (4 ml) were successively dropwise added thereto to decompose excess aluminum lithium hydride and the mixture was stirred as it was at room temperature for 2 hrs. The resulting precipitate was removed by filtration and the precipitate was washed with ethyl acetate. The solvent of the collected filtrate was evaporated under reduced pressure. The obtained residue was passed through silica gel column chromatography (hexane/ethyl acetate=6/1–1/2) to give a crude product (8.762 g) of 4-(hydroxymethyl)-6-methyl-6,7,8,9-tetrahydro-5H-benzo[a]cyclohepten-5-ol as a colorless liquid.

To a solution of the liquid obtained above, 4-N,N-dimethylaminopyridine (0.2 g) and triethylamine (7.49 ml, 53.7 mmol) in tetrahydrofuran (100 ml) was added tert-butyldimethylchlorosilane (7.42 g, 49.2 mmol) at room temperature and the mixture was stirred as it was overnight at room temperature. The reaction solution was poured into water and extracted twice with ethyl acetate. The collected organic layer was dried over anhydrous magnesium sulfate and the solvent was evaporated under reduced pressure. The obtained crude product was purified by silica gel column chromatography (hexane/ethyl acetate=15/1–6/1) to give the objective substance.

colorless liquid yield 14.43 g, 32% $^1$H-NMR (CDCl$_3$, 200 MHz) δ 0.08–0.13 (6H, m), 0.91–1.16 (12H, m), 1.39–2.11 (5H, m), 2.54–2.70 (2H, m), 3.18–3.33 (1H, m), 4.57–5.11 (3H, m), 7.04–7.14 (3H, m); IR (neat) 3416, 2955, 2928, 2857, 1472, 1462, 1256, 1070, 837, 775 cm$^{-1}$ 5) tert-butyl(8-methyl-6,7-dihydro-5H-benzo[a]cyclohepten-1-ylmethoxy)dimethylsilane To a solution of 4-[[[tert-butyl(dimethyl)silyl]oxy]methyl]-6-methyl-6,7,8,9-tetrahydro-5H-benzo[a]cyclohepten-5-ol (14.43 g, 45.02 mmol), triethylamine (7.53 ml, 54.0 mmol) and 4-N,N-dimethylaminopyridine (0.55 g, 4.50 mmol) in acetonitrile (50 ml) was dropwise added a solution of methanesulfonyl chloride (5.67 g, 49.5 mmol) in acetonitrile (10 ml) under ice-cooling. Lithium chloride (2.86 g, 67.5 mmol) was added thereto and the mixture was stirred at room temperature for 6 hrs. The reaction solution was poured into water and extracted twice with ethyl acetate. The collected organic layer was dried over anhydrous magnesium sulfate and the solvent was evaporated under reduced pressure. The obtained residue was dissolved in N,N-dimethylformamide (50 ml). 1,8-Diazabicyclo[5.4.0]-7-undecene (13.5 ml, 90.0 mmol) was added and the mixture was stirred overnight at 80° C. The reaction solution was poured into water and extracted twice with ethyl acetate. The collected organic layer was dried over anhydrous magnesium sulfate and the solvent was evaporated under reduced pressure. The obtained crude product was purified by silica gel column chromatography (hexane/ethyl acetate=50/1) to give the objective substance.

colorless liquid yield 5.608 g, 41% $^1$H-NMR (CDCl$_3$, 200 MHz) δ 0.10 (6H, s), 0.94 (9H, s), 1.92–2.17 (4H, m), 2.00 (3H, s), 2.60 (2H, t, J=6.4 Hz), 4.70 (2H, s), 6.32 (1H, s), 7.04–7.15 (2H, m), 7.32 (1H, d, J=7.8 Hz); IR (neat) 2928, 2857, 1254, 1109, 1078, 835, 775 cm$^{-1}$ 6) 8-methyl-6,7-dihydro-5H-benzo[a]cyclohepten-1-ylmethanol To a solution of tert-butyl(8-methyl-6,7-dihydro-5H-benzo[a]cyclohepten-1-ylmethoxy)dimethylsilane (5.594 g, 18.49 mmol) in tetrahydrofuran (50 ml) was added a solution (22.2 ml, 22.2 mmol) of 1.0 M tetrabutylammonium fluoride in tetrahydrofuran at room temperature and the mixture was stirred at room temperature for 15 min. The reaction solution was poured into water and extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1) to give the objective substance.

colorless liquid yield 3.000 g, 86% $^1$H-NMR (CDCl$_3$, 200 MHz) δ 1.59 (1H, t, J=6.0 Hz), 1.99–2.19 (4H, m), 2.01 (3H, d, J=1.6 Hz), 2.62 (2H, t, J=6.4 Hz), 4.69 (2H, d, J=5.8 Hz), 6.47 (1H, d, J=1.6 Hz), 7.11–7.24 (3H, m); IR (neat) 3333, 2928, 1454, 1019, 791 cm$^{-1}$ 7) 8-methyl-6,7-dihydro-5H-benzo[a]cycloheptene-1-carboxylic acid To a solution of 8-methyl-6,7-dihydro-5H-benzo[a]cyclohepten-1-ylmethanol (2.939 g, 15.61 mmol) in acetone (50 ml) was dropwise added slowly a solution of chromic anhydride (3.90 g, 39.0 mmol) and conc. sulfuric acid (3 ml) in water (10 ml) under ice-cooling. After completion of the dropwise addition, the mixture was stirred at room temperature for 0.5 hr. The reaction solution was ice-cooled again, isopropanol (10 ml) was added, and the mixture was stirred as it was for 0.5 hr. Acetone of the reaction solution was evaporated under reduced pressure. The residue was diluted with ethyl acetate, washed three times with water three times, dried over anhydrous magnesium sulfate and the solvent was evaporated under reduced pressure. The obtained residue was crystallized from ethyl acetate-hexane to give the objective substance.

white crystal yield 1.086 g, 34% mp 139–140° C.; $^1$H-NMR (CDCl$_3$, 200 MHz) δ 1.96–2.21 (4H, m), 2.05 (3H, d, J=1.4 Hz), 2.63 (2H, t, J=6.6 Hz), 6.90 (1H, d, J=1.2 Hz), 7.191 (1H, t, J=7.7 Hz), 7.38 (1H, d, J=7.8 Hz), 7.90 (1H, dd, J=1.3 Hz, 7.9 Hz); IR (KBr) 3055–2530, 1682, 1449, 1310, 1298, 1277, 1262 cm$^{-1}$; Anal. Calcd for C$_{13}$H$_{14}$O$_2$: C, 77.20; H, 6.98. Found: C, 77.25; H, 7.00.

8) N-[(1RS,2SR)-2-(4-fluorophenyl)-2-hydroxy-1-[3-(1,1,2,2-tetrafluoroethoxy)benzyl]ethyl]-8-methyl-6,7-dihydro-5H-benzo[a]cycloheptene-1-carboxamide While stirring (1RS,2SR)-2-amino-1-(4-fluorophenyl)-3-[3-(1,1,2,2-tetrafluoroethoxy)phenyl]propan-1-ol (0.272 g, 0.753 mmol), 8-methyl-6,7-dihydro-5H-benzo[a]cycloheptene-1-carboxylic acid (0.15 g, 0.75 mmol) and 1-hydroxybenzotriazole hydrate (0.12 g, 0.75 mmol) in acetonitrile (10 ml), 1-ethyl-3-(3-dimethylaminopropyl)carbodiimide hydrochloride (0.14 g, 0.75 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.365 g, 89% mp 149–150° C.; $^1$H-NMR. (CDCl$_3$, 200 MHz) δ 1.86 (3H, s), 1.96–2.14 (4H, m), 2.58 (2H, t, J=6.1 Hz), 2.78 (1H, dd, J=10.1 Hz, 14.5 Hz), 2.97 (1H, dd, J=4.6 Hz, 14.4 Hz), 3.93 (1H, br s), 4.57–4.70 (1H, m), 5.03 (1H, s), 5.87 (1H, tt, J=3.0 Hz, 52.9 Hz), 5.89 (1H, s), 6.14 (1H, s), 6.99–7.33 (9H, m), 7.42 (2H, dd, J=5.4 Hz, 8.4 Hz); IR (KBr) 3266, 2938, 1638, 1512, 1198, 1128 cm$^{-1}$; Anal. Calcd for C$_{30}$H$_{28}$F$_5$NO$_3$: C, 66.05; H, 5.17; N, 2.57. Found: C, 66.02; H, 5.28; N, 2.57.

Example 128

N-[(1RS,2SR)-2-(4-fluorophenyl)-2-hydroxy-1-[3-(1,1,2,2-tetrafluoroethoxy)benzyl]ethyl]-3,4-dihydro-2H-1,5-benzodioxepine-6-carboxamide While stirring (1RS,2SR)-2-amino-1-(4-fluorophenyl)-3-[3-(1,1,2,2-tetrafluoroethoxy)phenyl]propan-1-ol (0.221 g, 0.612 mmol), 3,4-dihydro-2H-1,5-benzodioxepine-6-carboxylic acid (0.12 g, 0.61 mmol) and 1-hydroxybenzotriazole hydrate (94 mg, 0.61 mmol) in acetonitrile (10 ml), 1-ethyl-3-(3-dimethylaminopropyl)carbodiimide hydrochloride (0.12 g, 0.61 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.261 g, 79% mp 147–148° C.; $^1$H-NMR (CDCl$_3$, 200 MHz) δ 2.04–2.17 (2H, m), 2.82 (1H, dd, J=9.9 Hz, 14.7 Hz), 2.95 (1H, dd, J=5.0 Hz, 15.0 Hz), 3.84 (2H, t, J=5.7 Hz), 4.05–4.22 (2H, m), 4.27 (1H, d, J=4.2 Hz), 4.58–4.70 (1H, m), 5.09 (1H, t, J=3.1 Hz), 5.86 (1H, tt, J=2.8 Hz, 53.0 Hz), 6.97–7.13 (7H, m), 7.26 (1H, t, J=7.9 Hz), 7.42 (2H, dd, J=5.2 Hz, 8.6 Hz), 7.77 (1H, dd, J=2.1 Hz, 7.5 Hz), 7.94 (1H, br d, J=7.0 Hz); IR (KBr) 3283, 1636, 1547, 1512, 1304, 1264, 1229, 1204, 1125, 1044 cm$^{-1}$; Anal. Calcd for C$_{27}$H$_{24}$F$_5$NO$_5$: C, 60.34; H, 4.50; N, 2.61. Found: C, 60.43; H, 4.46; N, 2.82.

Example 129 ethyl N-[(1RS,2SR)-2-(4-fluorophenyl)-2-hydroxy-1-[3-(1,1,2,2-tetrafluoroethoxy)benzyl]ethyl]carbamate While stirring (1RS,2SR)-2-amino-1-(4-fluorophenyl)-3-[3-(1,1,2,2-tetrafluoroethoxy)phenyl]propan-1-ol (1.604 g, 4.439 mmol) and sodium hydrogen carbonate (0.75 g, 8.88 mmol) in tetrahydrofuran (30 ml), ethyl chlorocarbonate (0.47 ml, 4.88 mmol) was added and the mixture was stirred overnight, at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 1.696 g, 88% mp 113–114° C.; $^1$H-NMR (CDCl$_3$, 200 MHz) δ 1.16 (3H, t, J=6.9 Hz), 2.68 (1H, dd, J=9.8 Hz, 14.6 Hz), 2.80 (1H, dd, J=5.2 Hz, 14.6 Hz), 3.01 (1H, br s), 3.95–4.17 (3H, m), 4.71 (1H, d, J=8.8 Hz), 4.93 (1H, s), 5.89 (1H, tt, J=2.9 Hz, 53.1 Hz), 6.95–7.14 (5H, m), 7.27 (1H, t, J=7.9 Hz), 7.38 (2H, dd, J=5.3 Hz, 8.7 Hz); IR (KBr) 3333, 1686, 1541, 1231, 1206, 1132 cm$^{-1}$; Anal. Calcd for C$_{20}$H$_{20}$F$_5$NO$_4$: C, 55.43; H, 4.65; N, 3.23. Found: C, 55.65; H, 4.41; N, 3.15.

Example 130 tert-butyl N-[(1RS,2SR)-2-(4-fluorophenyl)-2-hydroxy-1-[3-(1,1,2,2-tetrafluoroethoxy)benzyl]ethyl]carbamate (1RS,2SR)-2-Amino-1-(4-fluorophenyl)-3-[3-(1,1,2,2-tetrafluoroethoxy)phenyl]propan-1-ol (2.085 g, 5.771 mmol) and di-tert-butyl dicarbonate (1.51 g, 6.92 mmol) were stirred in tetrahydrofuran (50 ml) at room temperature for 1 hr. The solvent of the reaction solution was evaporated under reduced pressure and the obtained residue was crystallized from hexane to give the objective substance.

white crystal yield 2.555 g, 96% mp 145–146° C.; $^1$H-NMR (CDCl$_3$, 200 MHz) δ 1.35 (9H, s), 2.63–2.85 (2H, m), 3.25 (1H, br s), 4.00–4.12 (1H, m), 4.56 (1H, br d, J=8.8 Hz), 4.92 (1H, br s), 5.89 (1H, tt, J=2.8 Hz, 53.1 Hz), 6.97–7.11 (5H, m), 7.27 (1H, t, J=7.8 Hz), 7.38 (2H, dd, J=5.4 Hz, 8.4 Hz); IR (KBr) 3357, 1682, 1532, 1211, 1123 cm$^{-1}$; Anal. Calcd for C$_{22}$H$_{24}$F$_5$NO$_4$: C, 57.27; H, 5.24; N, 3.04. Found: C, 57.29; H, 5.20; N, 2.96.

Example 131

4-fluoro-N-[(1RS,2SR)-2-(4-fluorophenyl)-2-hydroxy-1-[4-(1,1,2,2-tetrafluoroethoxy)benzyl]ethyl]naphthalene-1-carboxamide 1) ethyl 3-(4-fluorophenyl)-3-oxo-2-[4-(1,1,2,2-tetrafluoroethoxy)benzyl]propionate A solution of 4-(1,1,2,2-tetrafluoroethoxy)toluene (6.73 g, 32.3 mmol), N-bromosuccinimide (5.75 g, 32.3 mmol) and 2,2-azobis(isobutyronitrile) (0.2 g) in carbon tetrachloride (30 ml) was heated under reflux for 0.5 hr. After cooling the reaction solution to room temperature, the white precipitate as removed by filtration and the precipitate was washed with diethyl ether. The solvent of the collected filtrate was evaporated under reduced pressure to give a crude product of 4-(1,1,2,2-tetrafluoroethoxy)benzyl bromide as a pale-yellow liquid.

To a solution of ethyl (4-fluorobenzoyl)acetate (6.177 g, 29.39 mmol) in 1,2-dimethoxyethane (50 ml) was added a suspension (1.18 g, 29.4 mmol) of 60% sodium hydride in liquid paraffin under ice-cooling and the mixture was stirred as it was for 0.5 hr. A solution of 4-(1,1,2,2-tetrafluoroethoxy)benzyl bromide obtained above in 1,2-dimethoxyethane (10 ml) was added thereto at room temperature and the mixture was stirred at room temperature for 8 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography-(hexane/ethyl acetate=15/1–9/1) and crystallized from hexane to give the objective substance.

white crystal yield 8.228 g, 67% mp 67–68° C.; $^1$H-NMR (CDCl$_3$, 200 MHz) δ 1.11 (3H, t, J=7.1 Hz), 3.32 (2H, d, J=7.4 Hz), 4.10 (2H, q, J=7 1 Hz), 4.55 (1H, t, J=7.3 Hz), 5.88 (1H, tt, J=2.9 Hz, 53.1 Hz), 7.08–7.26 (6H, m), 7.98 (2H, dd, J=5.3 Hz, 8.9 Hz); IR (KBr) 1725, 1676, 1599, 1512, 1304, 1281, 1242, 1215, 1202, 1186, 1155, 1115, 1098, 843 cm$^{-1}$; Anal. Calcd for C$_{20}$H$_{17}$F$_5$O$_4$: C, 57.70; H, 4.12. Found: C, 57.70; H, 4.22.

2) ethyl (2RS,3RS)-3-(4-fluorophenyl)-3-hydroxy-2-[4-(1,1,2,2-tetrafluoroethoxy)benzyl]propionate While stirring zinc chloride (5.15 g, 37.8 mmol) in diethyl ether (80 ml), sodium borohydride (2.86 g, 75.6 mmol) was added as it was at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-fluorophenyl)-3-oxo-2-[4-(1,1,2,2-tetrafluoroethoxy)benzyl]propionate (7.865 g, 18.89 mmol) in diethyl ether (30 ml) at room temperature and the mixture was stirred as it was for 2 hrs. Dilute hydrochloric acid was added to the reaction solution by small portions to decompose excess zinc borohydride. The mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 7.687 g, 97% $^1$H-NMR (CDCl$_3$, 200 MHz) δ 0.91 (3H, t, J=7.2 Hz), 2.88–3.03 (4H, m), 3.88 (2H, dq, J=1.7 Hz, 7.1 Hz), 5.02 (1H, t, J=3.3 Hz), 5.88 (1H, tt, J=2.9 Hz, 53.1 Hz), 7.05 (2H, t, J=8.8 Hz), 7.08 (4H, s), 7.37 (2H, dd, J=5.6 Hz, 8.8 Hz); IR (neat) 3468, 1725, 1508, 1306, 1277, 1190, 1159, 1123, 837 cm$^{-1}$ 3) (2RS,3RS)-3-(4-fluorophenyl)-3-hydroxy-2-[4-(1,1,2,2-tetrafluoroethoxy)benzyl]propionic acid To a solution of ethyl (2RS,3RS)-3-(4-fluorophenyl)-3-hydroxy-2-[4-(1,1,2,2-tetrafluoroethoxy)benzyl]propionate (7.556 g, 18.06 mmol) in methanol (30 ml)—tetrahydrofuran (30 ml) was added 1N aqueous sodium hydroxide solution (36.1 ml, 36.1 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 6.260 g, 89% mp 128–129° C.; $^1$H-NMR (CDCl$_3$, 200 MHz) δ 2.91–3.07 (3H, m), 5.05 (1H, s), 5.88 (1H, tt, J=2.8 Hz, 53.1 Hz), 7.04 (2H, t, J=8.6 Hz), 7.07 (4H, s), 7.35 (2H, dd, J=5.3 Hz, 8.5 Hz); IR (KBr) 3630, 3200–2480, 1698, 1512, 1283, 1233, 1190, 1128, 1100, 839 cm$^{-1}$; Anal. Calcd for C$_{18}$H$_{15}$F$_5$O$_4$: C, 55.39; H, 3.87. Found: C, 55.42; H, 3.71.

4) (4RS,5SR)-5-(4-fluorophenyl)-4-[4-(1,1,2,2-tetrafluoroethoxy)benzyl]-1,3-oxazolidin-2-one To a solution of (2RS,3RS)-3-(4-fluorophenyl)-3-hydroxy-2-[4-(1,1,2,2-tetrafluoroethoxy)benzyl]propionic acid (5.072 g, 12.99 mmol) in tetrahydrofuran (40 ml) were added triethylamine (2.72 ml, 19.5 mmol) and diphenylphosphoryl azide (3.93 g, 14.3 mmol) and the mixture was heated under reflux overnight. The solvent of the reaction solution was evaporated under reduced pressure. The obtained crude product was purified by silica gel column chromatography (hexane/ethyl acetate=3/1–1/1) and crystallized from diethyl ether-hexane to give the objective substance.

white crystal yield 4.673 g, 93% mp 154–155° C.; $^1$H-NMR (CDCl$_3$, 200 MHz) δ 2.18–2.35 (2H, m), 4.24 (1H, dt, J=5.4 Hz, 8.7 Hz), 5.05 (1H, br s), 5.80 (1H, d, J=8.0 Hz), 5.90 (1H, tt, J=2.8 Hz, 53.1 Hz), 7.05 (2H, t, J=8.4 Hz), 7.14 (2H, d, J=8.8 Hz), 7.15 (2H, d, J=8.6 Hz), 7.36 (2H, dd, J=5.2 Hz, 8.6 Hz); IR (KBr) 3258, 1736, 1510, 1231, 1213, 1192, 1128, 1105 cm$^{-1}$; Anal. Calcd for C$_{18}$H$_{14}$F$_5$NO$_3$: C, 55.82; H, 3.64; N, 3.62. Found: C, 55.89; H, 3.63; N, 3.44.

5) (1RS,2SR)-2-amino-1-(4-fluorophenyl)-3-[4-(1,1,2,2-tetrafluoroethoxy)phenyl]propan-1-ol (4RS,5SR)-5-(4-Fluorophenyl)-4-[4-(1,1,2,2-tetrafluoroethoxy)benzyl]-1,3-oxazolidin-2-one (4.485 g, 11.58 mmol) and sodium hydroxide (1.85 g, 46.3 mmol) were heated under reflux in ethanol (30 ml)—water (2 ml) for 6 hrs. The reaction solution was diluted with water and extracted twice with ethyl acetate. The collected organic layer was dried over anhydrous sodium sulfate and the solvent was evaporated under reduced pressure. The residue was purified by silica gel (APS type) column chromatography (hexane/ethyl acetate=3/1-ethyl acetate) and crystallized from diisopropyl ether-hexane to give the objective substance.

white crystal yield 3.447 g, 82% mp 78–79° C.; $^1$H-NMR (CDCl$_3$, 200 MHz) δ 2.36 (1H, dd, J=10.5 Hz, 13.7 Hz), 2.80 (1H, dd, J=3.0 Hz, 13.8 Hz), 3.26 (1H, ddd, J=3.5 Hz, 4.9 Hz, 10.2 Hz), 4.65 (1H, d, J=4.8 Hz), 5.90 (1H, tt, J=3.0 Hz, 53.1 Hz), 7.08 (2H, t, J=8.6 Hz), 7.14 (4H, s), 7.37 (2H, dd, J=5.6 Hz, 8.4 Hz); IR (KBr) 3360, 2740, 1508, 1275, 1231, 1215, 1192, 1119, 1096, 1040, 856 cm$^{-1}$; Anal. Calcd for C$_{17}$H$_{16}$F$_5$NO$_2$: C, 56.51; H, 4.46; N, 3.88. Found: C, 56.52; H, 4.41; N, 3.66.

6) 4-fluoro-N-[(1RS,2SR)-2-(4-fluorophenyl)-2-hydroxy-1-[4-(1,1,2,2-tetrafluoroethoxy)benzyl]ethyl]naphthalene-1-carboxamide While stirring (1RS,2SR)-2-amino-1-(4-fluorophenyl)-3-[4-(1,1,2,2-tetrafluoroethoxy)phenyl]propan-1-ol (0.163 g, 0.451 mmol), 4-fluoro-1-naphthoate (86 mg, 0.45 mmol) and 1-hydroxybenzotriazole hydrate (69 mg, 0.45 mmol) in acetonitrile (10 ml), 1-ethyl-3-(3-dimethylaminopropyl)carbodiimide hydrochloride (86 mg, 0.45 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.212 g, 88% mp 192–193° C.; $^1$H-NMR (CDCl$_3$-DMSO-d$_6$, 200 MHz) δ 2.87 (1H, dd, J=10.4 Hz, 14.4 Hz), 2.97 (1H, dd, J=4.8 Hz, 13.8 Hz), 4.68–4.82 (1H, m), 5.01–5.08 (2H, m), 5.94 (1H, tt, J=2.9 Hz, 53.1 Hz), 6.99–7.12 (6H, m), 7.19–7.26 (3H, m), 7.41–7.58 (4H, m), 7.73 (1H, d, J=8.2 Hz), 8.07 (1H, d, J=7.8 Hz); IR (KBr) 3285, 1644, 1628, 1601, 1535, 1508, 1314, 1264, 1233, 1200, 1127, 1113, 1094, 837 cm$^{-1}$; Anal. Calcd for C$_{28}$H$_{21}$F$_6$NO$_3$: C, 63.04; H, 3.97; N, 2.63. Found: C, 62.98; H, 3.86; N, 2.60.

Example 132

4-fluoro-N-[(1RS,2SR)-2-(4-fluorophenyl)-2-hydroxy-1-[3-(trifluoromethoxy)benzyl]ethyl]naphthalene-1-carboxamide

1) ethyl 3-(4-fluorophenyl)-3-oxo-2-[3-(trifluoromethoxy)benzyl]propionate

To a solution of ethyl (4-fluorobenzoyl)acetate (4.530 g, 21.55 mmol) in 1,2-dimethoxyethane (50 ml) was added a suspension (0.86 g, 21.6 mmol) of 60% sodium hydride in liquid paraffin under ice-cooling and the mixture was stirred as it was for 0.5 hr. A solution of 3-(trifluoromethoxy)benzyl bromide (5.50 g, 21.6 mmol) in 1,2-dimethoxyethane (10 ml) was added at room temperature and the mixture was stirred at room temperature for 8 hrs. The reaction solution was poured into water and extracted twice with ethyl acetate. The collected organic layer was dried over anhydrous magnesium-sulfate and the solvent was evaporated under reduced pressure. The obtained residue was purified by silica gel column chromatography (hexane/ethyl acetate=15/1–9/1) and crystallized from hexane to give the objective substance.

white crystal yield 6.824 g, 82% mp 56–57° C.; $^1$H-NMR (CDCl$_3$, 200 MHz) δ 1.12 (3H, t, J=7.1 Hz), 3.34 (2H, d, J=7.6 Hz), 4.10 (2H, q, J=7.1 Hz), 4.55 (1H, t, J=7.6 Hz), 7.03–7.16 (5H, m), 7.28 (1H, dt, J=0.7 Hz, 7.7 Hz), 7.98 (2H, dd, J=5.3 Hz, 8.9 Hz); IR (KBr) 1717, 1686, 1599, 1271, 1258, 1236, 1217, 1177, 1152 cm$^{-1}$; Anal. Calcd for C$_{19}$H$_{16}$F$_4$O$_4$: C, 59.38; H, 4.20. Found: C, 59.33; H, 4.38.

2) ethyl (2RS,3RS)-3-(4-fluorophenyl)-3-hydroxy-2-[3-(trifluoromethoxy)benzyl]propionate While stirring zinc chloride (4.65 g, 34.1 mmol) in diethyl ether (50 ml), sodium borohydride (2.58 g, 68.3 mmol) was added as it was and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-fluorophenyl)-3-oxo-2-[3-(trifluoromethoxy)benzyl]propionate (6.559 g, 17.07 mmol) in diethyl ether (30 ml) at room temperature and the mixture was stirred as it was for 2 hrs. Dilute hydrochloric acid was added to the solution by small portions to decompose excess zinc borohydride. The mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 6.574 g, 100%. $^1$H-NMR (CDCl$_3$, 200 MHz) δ 0.93 (3H, t, J=7.1 Hz), 2.89 (1H, d, J=2.8 Hz), 2.91–3.07 (3H, m), 3.88 (2H, q, J=7.2 Hz), 5.02 (1H, t, J=3.6 Hz), 6.95–7.11 (5H, m), 7.25 (1H, t, J=7.9 Hz), 7.37 (2H, dd, J=5.2 Hz, 8.4 Hz); IR (neat) 3445, 1728, 1715, 1512, 1260, 1219, 1161, 839 cm$^{-1}$

3) (2RS,3RS)-3-(4-fluorophenyl)-3-hydroxy-2-[3-(trifluoromethoxy)benzyl]propionic acid To a solution of ethyl (2RS,3RS)-3-(4-fluorophenyl)-3-hydroxy-2-[3-(trifluoromethoxy)benzyl]propionate (6.391 g, 16.54 mmol) in methanol (30 ml)—tetrahydrofuran (20 ml) was added 1N aqueous sodium hydroxide solution (33.1 ml, 33.1 mol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 5.055 g, 85% mp 108–110° C.; $^1$H-NMR (CDCl$_3$, 200 MHz) δ 2.90–3.10 (3H, m), 5.06 (1H, s), 6.95–7.11 (5H, m), 7.25 (1H, t, J=7.9 Hz), 7.36 (2H, dd, J=5.6 Hz, 8.8 Hz); IR (KBr) 3343, 3020–2550, 1694, 1516, 1283, 1258, 1238, 1225, 1165, 837 cm$^{-1}$; Anal. Calcd for C$_{17}$H$_{14}$F$_4$O$_4$: C, 56.99; H, 3.94. Found: C, 56.98; H, 3.85.

4) (4RS,5SR)-5-(4-fluorophenyl)-4-[3-(trifluoromethoxy) benzyl]-1,3-oxazolidin-2-one To a solution of (2RS,3RS)-3-(4-fluorophenyl)-3-hydroxy-2-[3-(trifluoromethoxy)benzyl]propionic acid (4.649 g, 12.98 mmol) in tetrahydrofuran (50 ml) were added triethylamine (2.71 ml, 19.5 mmol) and diphenylphosphoryl azide (3.93 g, 14.3 mmol) and the mixture was heated under reflux overnight. The solvent of the reaction solution was evaporated under reduced pressure. The obtained crude product was purified by silica gel column chromatography (hexane/ethyl acetate=3/1–1/1) and crystallized from diethyl ether-hexane to give the objective substance.

white crystal yield 4.330 g, 94% mp 145–146° C.; $^1$H-NMR (CDCl$_3$, 200 MHz) δ 2.21–2.37 (2H, m), 4.26 (1H, dt, J=6.1 Hz, 8.3 Hz), 5.11 (1H, br s), 5.80 (1H, d, J=8.0 Hz), 6.87 (1H, s), 6.96 (1H, d, J=7.2 Hz), 7.09–7.19 (3H, m), 7.28 7.39 (3H, m); IR (KBr) 3248, 1736, 1516, 1256, 1227, 1163 cm$^{-1}$; Anal. Calcd for C$_{17}$H$_{13}$F$_4$NO$_3$: C, 57.47; H, 3.69; N, 3.94. Found: C, 57.54; H, 3.73; N, 4.01

5) (1RS,2SR)-2-amino-1-(4-fluorophenyl)-3-[3-(trifluoromethoxy)phenyl]propan-1-ol (4RS,5SR)-5-(4-Fluorophenyl)-4-[3-(trifluoromethoxy) benzyl]-1,3-oxazolidin-2-one (4.071 g, 11.46 mmol) and sodium hydroxide (1.83 g, 45.8 mmol) were heated under reflux in ethanol (30 ml)—water (2 ml) for 6 hrs. The reaction solution was diluted with water and extracted twice with ethyl acetate. The collected organic layer was dried over anhydrous sodium sulfate and the solvent was evaporated under reduced pressure. The residue was purified by silica gel (APS type) column chromatography (hexane/ethyl acetate=3/1-ethyl acetate) to give the objective substance.

pale-yellow liquid yield 3.722 g, 99% $^1$H-NMR (CDCl$_3$, 200 MHz) δ 2.38 (1H, dd, J=10.3 Hz, 13.9 Hz) 2.82 (1H, dd, J=3.3 Hz, 13.9 Hz), 3.27 (1H, ddd, 3.4 Hz, 4.8 Hz, 10.3 Hz), 4.65 (1H, d, J=5.0 Hz), 7.01–7.13 (5H, m), 7.27–7.42 (3H, m); IR (neat) 2260–2860, 1508, 1260, 1217, 1159 cm$^{-1}$ 6) 4-fluoro-N-[(1RS,2SR)-2-(4-fluorophenyl)-2-hydroxy-1-[3-(trifluoromethoxy)benzyl]ethyl]naphthalene-1-carboxamide While stirring (1RS,2SR)-2-amino-1-(4-fluorophenyl)-3-[3-(trifluoromethoxy)phenyl]propan-1-ol (0.247 g, 0.750 mmol), 4-fluoro-1-naphthoate (0.14 g, 0.75 mmol) and 1-hydroxybenzotriazole hydrate (0.11 g, 0.75 mmol) in acetonitrile (10 ml), 1-ethyl-3-(3-dimethylaminopropyl) carbodiimide hydrochloride (0.14 g, 0.75 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.262 g, 70% mp 189–190° C.; $^1$H-NMR (CDCl$_3$-DMSO-d$_6$, 200 MHz) δ 2.90 (1H, dd, J=10.7 Hz, 14.3 Hz), 3.04 (1H, dd, J=4.3 Hz, 14.1 Hz), 4.67–4.81 (1H, m), 5.00 (1H, t, J=4.0 Hz), 5.21 (1H, d, J=3.6 Hz), 6.99–7.34 (8H, m), 7.39–7.57 (5H, m), 7.69 (1H, d, J=8.0 Hz), 8.06 (1H, d, J=7.2 Hz); IR (KBr) 3268, 1642, 1624, 1601, 1537, 1512, 1269, 1227, 1173, 835, 760 cm$^{-1}$; Anal. Calcd for C$_{27}$H$_{20}$F$_5$NO$_3$: C, 64.67; H, 4.02; N, 2.79. Found: C, 64.58; H, 4.05; N, 2.59.

Example 133

N-[(1RS,2SR)-2-(4-fluorophenyl)-2-hydroxy-1-[3-(trifluoromethoxy)benzyl]ethyl]-6,7-dihydro-5H-benzo[a]cycloheptene-1-carboxamide While stirring (1RS,2SR)-2-amino-1-(4-fluorophenyl)-3-[3-(trifluoromethoxy)phenyl]propan-1-ol (0.239 g, 0.726 mmol), 6,7-dihydro-5H-benzo[a]cycloheptene-1-carboxylic acid (0.14 g, 0.73 mmol) and 1-hydroxybenzotriazole hydrate (0.11 g, 0.73 mmol) in acetonitrile (10 ml), 1-ethyl-3-(3-dimethylaminopropyl)carbodiimide hydrochloride (0.14 g, 0.73 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.274 g, 76% mp 177–178° C.; $^1$H-NMR (CDCl$_3$-DMSO-d$_6$, 200 MHz) δ 1.91–2.04 (2H, m), 2.18–2.27 (2H, m), 2.68 (2H, t, J=5.9 Hz), 2.78–2.96 (2H, m), 4.60–4.74 (1H, m), 4.93 (1H, d, J=3.6 Hz), 4.98 (1H, t, J=3.7 Hz), 5.88 (1H, td, J=5.3 Hz, 11.9 Hz), 6.18 (1H, d, J=12.2 Hz), 6.73 (1H, d, J=9.2 Hz), 6.92 (1H, dd, J=1.9 Hz, 7.3 Hz), 7.01–7.16 (7H, m), 7.26 (1H, d, J=8.8 Hz), 7.49 (2H, dd, J=5.5 Hz, 8.5 Hz); IR (KBr) 3268, 1640, 1539, 1512, 1269, 1221, 1153 cm$^{-1}$; Anal. Calcd for C$_{28}$H$_{25}$F$_4$NO$_3$: C, 67.33; H, 5.04; N, 2.80. Found: C, 67.22; H, 4.98; N, 2.78.

Example 134

4-fluoro-N-[(1RS,2SR)-2-(4-fluorophenyl)-2-hydroxy-1-[4-(trifluoromethoxy)benzyl]ethyl] naphthalene-1-carboxamide 1) ethyl 3-(4-fluorophenyl)-3-oxo-2-[4-(trifluoromethoxy) benzyl]propionate To a solution of ethyl (4-fluorobenzoyl)acetate (4.140 g, 19.70 mmol) in 1,2-dimethoxyethane (50 ml) was added a suspension (0.79 g, 19.7 mmol) of 60% sodium hydride in liquid paraffin under ice-cooling and the mixture was stirred as it was for 0.5 hr. A solution of 4-(trifluoromethoxy)benzyl bromide (5.02 g, 19.7 mmol) in 1,2-dimethoxyethane (10 ml) was added at room temperature and the mixture was stirred at room temperature for 8 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) and crystallized from hexane to give the objective substance.

white crystal yield 5.869 g, 78% mp 53.5–54.5° C.; $^1$H-NMR (CDCl$_3$, 200 MHz) δ 1.11 (3H, t, J=7.1 Hz); 3.32 (2H, d, J=7.4 Hz), 4.10 (2H, q, J=7.1 Hz), 4.54 (1H, t, J=7.3 Hz), 7.10 (2H, d, J=8.4 Hz), 7.12 (2H, t, J=8.6 Hz), 7.25 (2H, d, J=8.8 Hz), 7.98 (2H, dd, J=5.2 Hz, 9.0 Hz); IR (KBr) 1732, 1682, 1597, 1507, 1325, 1273, 1236, 1152, 1101, 851 cm$^{-1}$; Anal. Calcd for C$_{19}$H$_{16}$F$_4$O$_4$: C, 59.38; H, 4.20. Found: C, 59.38; H, 4.27.

2) ethyl (2RS,3RS)-3-(4-fluorophenyl)-3-hydroxy-2-[4-(trifluoromethoxy)benzyl]propionate While stirring zinc chloride (3.98 g, 29.2 mmol) in diethyl ether (50 ml), sodium borohydride (2.21 g, 58.4 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-fluorophenyl)-3-oxo-2-[4-(trifluoromethoxy)benzyl] propionate (5.610 g, 14.60 mmol) in diethyl ether (30 ml) at room temperature and the mixture was stirred as it was for 2 hrs. Dilute hydrochloric acid was added to the reaction solution by small portions to decompose excess zinc borohydride. The mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate= 6/1–3/1) to give the objective substance.

colorless liquid yield 5.601 g, 99% $^1$H-NMR (CDCl$_3$, 200 MHz) δ 0.91 (3H, t, J=7.2 Hz), 2.89 (1H, d, J=2.6 Hz), 2.93–3.03 (3H, m), 3.88 (2H, dq, J=1.5 Hz, 7.2 Hz), 5.02 (1H, t, J=3.6 Hz), 7.05 (2H, t, J=8.8 Hz), 7.09 (4H, s), 7.37 (2H, dd, J=5.6 Hz, 8.4 Hz); IR (neat) 3445, 1728, 1715, 1510, 1264, 1225, 1161, 839 cm$^{-1}$ 3) (2RS,3RS)-3-(4-fluorophenyl)-3-hydroxy-2-[4-(trifluoromethoxy)benzyl]propionic acid To a solution of ethyl (2RS,3RS)-3-(4-fluorophenyl)-3-hydroxy-2-[4-(trifluoromethoxy)benzyl]propionate (5.440 g, 14.08 mmol) in methanol (30 ml)—tetrahydrofuran (20 ml) was added 1N aqueous sodium hydroxide solution (28.2 ml, 28.2 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 4.071 g, 80% mp 111–112° C.; $^1$H-NMR (CDCl$_3$, 200 MHz) δ 2.90–3.10 (3H, m), 5.05–5.08 (1H, m), 7.05 (2H, t, J=8.4 Hz), 7.08 (4H, s), 7.36 (2H, dd, J=5.6 Hz, 8.8 Hz); IR (KBr) 3343, 3100–2550, 1692, 1514, 1285, 1208, 1163, 839 cm$^{-1}$; Anal. Calcd for C$_{17}$H$_{14}$F$_4$O$_4$: C, 56.99; H, 3.94. Found: C, 56.97; H, 4.05.

4) (4RS,5SR)-5-(4-fluorophenyl)-4-[4-(trifluoromethoxy)benzyl]-1,3-oxazolidin-2-one To a solution of (2RS,3RS)-3-(4-fluorophenyl)-3-hydroxy-2-[4-(trifluoromethoxy)benzyl]propionic acid (3.637 g, 10.15 mmol) in tetrahydrofuran (50 ml) were added triethylamine (2.12 ml, 15.2 mmol) and diphenylphosphoryl azide (3.07 g, 11.2 mmol) and the mixture was heated under reflux overnight. The solvent of the reaction solution was evaporated under reduced pressure. The obtained crude product was purified by silica gel column chromatography. (hexane/ethyl acetate=3/1–1/1) and crystallized from diethyl ether-hexane to give the objective substance.

white crystal yield 3.340 g, 93% mp 163–164° C.; $^1$H-NMR (CDCl$_3$, 200 MHz) δ 2.19–2.35 (2H, m), 4.17–4.29 (1H, m), 4.96 (1H, br s), 5.80 (1H, d, J=8.2 Hz), 7.02–7.17 (6H, m), 7.36 (2H, dd, J=5.2 Hz, 9.0 Hz); IR (KBr) 3243, 1736, 1510, 1275, 1236, 1150 cm$^{-1}$; Anal. Calcd for C$_{17}$H$_{13}$F$_4$NO$_3$: C, 57.47; H, 3.69; N, 3.94. Found: C, 57.48; H, 3.58; N, 4.04.

5) (1RS,2SR)-2-amino-1-(4-fluorophenyl)-3-[4-(trifluoromethoxy)phenyl]propan-1-ol (4RS,5SR)-5-(4-Fluorophenyl)-4-[4-(trifluoromethoxy)benzyl]-1,3-oxazolidin-2-one (3.057 g, 8.604 mmol) and sodium hydroxide (1.38 g, 34.4 mmol) was heated under reflux in ethanol (30 ml)—water (1.5 ml) for 6 hrs. The reaction solution was diluted with water and extracted twice with ethyl acetate. The collected organic layer was dried over anhydrous sodium sulfate and the solvent was evaporated under reduced pressure. The residue was purified by silica gel (APS type) column chromatography (hexane/ethyl acetate=3/1-ethyl acetate) and crystallized from diisopropyl ether-hexane to give the objective substance.

white crystal yield 2.406 g, 85% mp 84–85° C.; $^1$H-NMR (CDCl$_3$, 200 MHz) δ 2.36 (1H, dd, J=10.3 Hz, 13.9 Hz), 2.81 (1H, dd, J=3.3 Hz, 13.5 Hz), 3.26 (1H, ddd, J=3.3 Hz, 4.8 Hz, 10.3 Hz), 4.65 (1H, d, J=4.8 Hz), 7.07 (2H, t, J=8.8 Hz), 7.15 (4H, s), 7.37 (2H, dd, J=5.2 Hz, 8.4 Hz); IR (KBr) 3350–2750, 1598, 1277, 1217, 1194, 1165, 1047 cm$^{-1}$; Anal. Calcd for C$_{16}$H$_{15}$F$_4$NO$_2$: C, 58.36; H, 4.59; N, 4.25. Found: C, 58.43; H, 4.54; N, 4.31.

6) 4-fluoro-N-[(1RS,2SR)-2-(4-fluorophenyl)-2-hydroxy-1-[4-(trifluoromethoxy)benzyl]ethyl]naphthalene-1-carboxamide While stirring (1RS,2SR)-2-amino-1-(4-fluorophenyl)-3-[4-(trifluoromethoxy)phenyl]propan-1-ol (0.212 g, 0.644 mmol), 4-fluoro-1-naphthoate (0.12 g, 0.64 mmol) and 1-hydroxybenzotriazole hydrate (0.10 g, 0.64 mmol) in acetonitrile (10 ml), 1-ethyl-3-(3-dimethylaminopropyl) carbodiimide hydrochloride (0.12 g, 0.64 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white crystal yield 0.276 g, 86% mp 230–231° C.; $^1$H-NMR (CDCl$_3$-DMSO-d$_6$, 200 MHz) δ 2.87 (1H, dd, J=10.8 Hz, 14.6 Hz), 3.00 (1H, dd, J=4.2 Hz, 14.2 Hz), 4.67–4.81 (1H, m), 5.02 (1H, t, J=4.1 Hz), 5.19 (1H, d, J=3.8 Hz), 6.99–7.57 (13H, m), 7.67 (1H, d, J=8.4 Hz), 8.06 (1H, d, J=8.0 Hz); IR (KBr) 3281, 1644, 1537, 1512, 1269, 1227, 1217, 1175, 835 cm$^{-1}$; Anal. Calcd for C$_{27}$H$_{20}$F$_5$NO$_3$: C, 64.67; H, 4.02; N, 2.79. Found: C, 64.57; H, 4.02; N, 2.61.

Example 135

N-[(1RS,2SR)-2-(4-fluorophenyl)-2-hydroxy-1-[4-(trifluoromethoxy)benzyl]ethyl]-6,7-dihydro-5H-benzo[a]cycloheptene-1-carboxamide While stirring (1RS,2SR)-2-amino-1-(4-fluorophenyl)-3-[4-(trifluoromethoxy)phenyl]propan-1-ol (0.238 g, 0.723 mmol), 6,7-dihydro-5H-benzo[a]cycloheptene-1-carboxylic acid (0.14 g, 0.72 mmol) and 1-hydroxybenzotriazole hydrate (0.11 g, 0.72 mmol) in acetonitrile (10 ml), 1-ethyl-3-(3-dimethylaminopropyl)carbodiimide hydrochloride (0.14 g, 0.72 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.279 g, 77% mp 202–203° C.; $^1$H-NMR (CDCl$_3$-DMSO-d$_6$, 200 MHz) δ 1.91–2.04 (2H, m), 2.18–2.27 (2H, m), 2.68 (2H, t, J=5.9 Hz), 2.78–2.92 (2H, m), 4.62–4.72 (1H, m), 4.96–5.02 (2H, m), 5.88 (1H, td, J=5.3 Hz, 11.7 Hz), 6.17 (1H, d, J=12.2 Hz), 6.74 (1H, d, J=10.0 Hz), 6.90 (1H, dd, J=2.0 Hz, 7.6 Hz), 7.01–7.15 (6H, m), 7.22 (2H, d, J=8.8 Hz), 7.50 (2H, dd, J=5.6 Hz, 8.6 Hz); IR (KBr) 3272, 1640, 1539, 1512, 1269, 1229, 1202, 1159 cm$^{-1}$; Anal. Calcd for $C_{28}H_{25}F_4NO_3$: C, 67.33; H, 5.04; N, 2.80. Found: C, 67.16; H, 4.94; N, 2.75.

Example 136

N-((1RS,2SR)-2-(4-fluorophenyl)-2-hydroxy-1-((3-(trifluoromethyl)phenyl)methyl)ethyl)-1-naphthalenecarboxamide 1) A mixture of ethyl 3-(4-fluorophenyl)-3-oxopropionate (10 g, 47.6 mmol), 3-trifluoromethylbenzyl chloride (8.33 g, 42.8 mmol), potassium carbonate (13.2 g, 95.1 mmol) and acetonitrile (200 ml) was stirred at 60° C. for 24 hrs. The reaction solution was concentrated under reduced pressure, water (200 ml) was added, and the mixture was extracted with ethyl acetate (200, 100 ml). The extract was washed with water, dried over anhydrous magnesium sulfate and evaporated under reduced pressure. The residue was purified by silica gel column chromatography (hexane:toluene= 1:1–1:2-toluene) to give ethyl 3-(4-fluorophenyl)-3-oxo-2-(3-trifluoromethylbenzyl)propionate (10.2 g, 65%) as an oil.

IR ν max$^{Neat}$cm$^{-1}$: 1736, 1690, 1599, 1331, 1161, 1127, 1074. $^1$H-NMR (CDCl$_3$)δ: 1.12 (3H, t, J=7.1 Hz), 3.38 (2H, d, J=7.4 Hz), 4.10 (2H, q, J=7.1 Hz), 4.57 (1H, t, J=7.4 Hz), 7.13 (2H, t, J=8.8 Hz), 7.35–7.60 (4H, m), 7.95–8.10 (2H, m).

2) To a solution of anhydrous zinc chloride (7.4 g, 54.3 mmol) in diethyl ether (50 ml) was added sodium borohydride (4.11 g, 0.11 mol) and the mixture was stirred at room temperature for 2 hrs. The insoluble material was removed by filtration. To the filtrate was added a solution of ethyl 3-(4-fluorophenyl)-3-oxo-2-(3-trifluoromethylbenzyl)propionate (10 g, 27.1 mmol) in diethyl ether (20 ml) and the mixture was stirred at room temperature for 1 hr. 1N Hydrochloric acid was added to the reaction solution to terminate the reaction. The reaction solution was extracted with ethyl acetate (100 ml). The extract was washed with water and saturated aqueous sodium hydrogen carbonate solution, dried over anhydrous magnesium sulfate and evaporated under reduced pressure. The residue was purified by silica gel column chromatography (hexane:ethyl acetate= 20:1–5:1) to give ethyl (2RS,3RS)-3-(4-fluorophenyl)-3-hydroxy-2-(3-trifluoromethylbenzyl)propionate (7.9 g, 79%) as a colorless oil.

IR ν max$^{Neat}$cm$^{-1}$: 1717, 1510, 1329, 1161, 1127, 1074, 839. $^1$H-NMR (CDCl$_3$)δ: 0.92 (3H, t, J=7.2 Hz), 2.93 (1H, d, J=2.6 Hz), 2.90–3.12 (3H, m), 3.88 (2H, q, J=7.2 Hz), 5.00–5.10 (1H, m), 7.05 (2H, t, J=8.7 Hz), 7.20–7.55 (6H, m).

3) To a solution of ethyl (2RS,3RS)-3-(4-fluorophenyl)-3-hydroxy-2-(3-trifluoromethylbenzyl)propionate (7.9 g, 21.3 mmol) in methanol (50 ml) was added 1N aqueous sodium hydroxide solution (42.7 ml, 42.7 mmol) and the mixture was stirred at room temperature for 3 hrs. The reaction solution was acidified with 1N hydrochloric acid (100 ml) and extracted with ethyl acetate (200 ml×2). The extract was washed with water, dried over anhydrous magnesium sulfate and evaporated under reduced pressure. The residue was crystallized from a mixture of hexane and diethyl ether to give (2RS,3RS)-3-(4-fluorophenyl)-3-hydroxy-2-(3-trifluoromethylbenzyl)propionic acid (6.20 g, 85%).

mp 116–118° C. IR ν max$^{KBr}$cm$^{-1}$: 3424, 1717, 1678, 1514, 1325, 1238, 1128, 1074, 839. elemental analysis for $C_{17}H_{14}F_4O_3$, Calcd: C, 59.65; H, 4.12. Found: C, 59.55; H, 4.10. $^1$H-NMR (DMSO-d$_6$)δ: 2.80–2.95 (1H, m), 2.99 (1H, d, J=10.4 Hz), 3.15 (1H, d, J=10.4 Hz), 4.74 (1H, d, J=6.2 Hz), 5.65–5.90 (1H, br), 7.12 (2H, t, J=8.8 Hz), 7.32–7.60 (6H, m).

4) To a solution of (2RS,3RS)-3-(4-fluorophenyl)-3-hydroxy-2-(3-trifluoromethylbenzyl)propionic acid (5.85 g, 17.1 mmol) in tetrahydrofuran (100 ml) were added diphenylphosphoryl azide (4.78 ml, 22.2 mmol) and triethylamine (3.33 ml, 23.9 mmol). The reaction solution was-heated under reflux for 4 hrs. After cooling, water (200 ml) was added, and the mixture was extracted with ethyl acetate (200 ml). The extract was washed with 1N hydrochloric acid and saturated aqueous sodium hydrogen carbonate solution, dried over anhydrous magnesium sulfate and evaporated under reduced pressure. The residue was purified by silica gel column chromatography (chloroform:ethyl acetate= 10:1–5:1) to give (4RS,5SR)-5-(4-fluorophenyl)-4-((3-(trifluoromethyl)phenyl)methyl)-1,3-oxazolidin-2-one (5.30 g, 91%) as crystals.

mp 177–178° C. elemental analysis for $C_{17}H_{13}F_4NO_2$, Calcd: C, 60.18; H, 3.86; N, 4.13. Found: C, 60.20; H, 3.83; N, 4.09. $^1$H-NMR (CDCl$_3$)δ: 2.30–2.45 (2H, m), 4.20–4.40 (1H, m), 5.11 (1H, brs), 5.80 (1H, d, J=8.0 Hz), 7.13 (2H, t, J=8.6 Hz), 7.15–7.60 (6H, m).

5) To a solution of (4RS,5SR)-5-(4-fluorophenyl)-4-((3-(trifluoromethyl)phenyl)methyl)-1,3-oxazolidin-2-one (4.0 g, 11.8 mmol) in ethanol (80 ml) was added 8N aqueous sodium hydroxide solution (7.4 ml, 59 mmol) and the mixture was heated under reflux for 4 hrs. The reaction solution was concentrated, diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(3-(trifluoromethyl)phenyl)-1-propanol (2.97 g, 80%).

mp 76–77° C. IR ν max$^{KBr}$cm$^{-1}$: 1605. Anal. Calcd for $C_{16}H_{15}F_4NO$: C, 61.34; H, 4.83; N, 4.47. Found: C, 61.19; H, 4.82; N, 4.36. $^1$H-NMR (CDCl$_3$)δ: 2.42 (1H, dd, J=13.8, 10.2 Hz), 2.89 (1H, dd, J=13.8, 3.2 Hz), 3.20–3.38 (1H, m), 4.66 (1H, d, J=4.6 Hz), 7.00–7.16 (2H, m), 7.22–7.52 (6H, m).

6) To a solution of (1RS,2SR)-2-amino-1-(4-fluorophenyl)-3-(3-(trifluoromethyl)phenyl)-1-propanol (450 mg, 1.44 mmol) in ethyl acetate (15 ml) were added 1-naphthoyl chloride (282 ml, 1.87 mmol) and saturated aqueous sodium hydrogen carbonate (15 ml) and the mixture was stirred at room temperature for 2 hrs. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (582 mg, 87%).

mp 158–159° C. IR ν max$^{KBr}$cm$^{-1}$: 1638, 1622, 1534. Anal. Calcd for $C_{27}H_{21}F_4NO_2$: C, 69.37; H, 4.53; N, 3.00, Found: C, 69.47; H, 4.23; N, 2.97. $^1$H-NMR (CDCl$_3$)δ: 2.79 (1H, dd, J=14.4, 11.0 Hz), 2.97 (1H, dd, J=14.4, 4.0 Hz), 3.93 (1H, s), 4.70–4.90 (1H, m), 5.18 (1H, s), 5.98 (1H, d, J=8.2 Hz), 6.92–7.08 (2H, m), 7.10–7.30 (3H, m), 7.32–7.80 (8H, m), 7.80–7.96 (2H, m).

Example 137

4-fluoro-N-((1RS,2SR)-2-(4-fluorophenyl)-2-hydroxy-1-((3-(trifluoromethyl)phenyl)methyl)ethyl)-1-naphthalenecarboxamide To a solution of (1RS,2SR)-2-amino-1-(4-fluorophenyl)-3-(3-(trifluoromethyl)phenyl)-1-propanol (450 mg, 1.44 mmol) in acetonitrile (30 ml) were added 4-fluoronaphthalenecarboxylic acid (274 mg, 1.44 mmol), 1-ethyl-3-(3-dimethylaminopropyl)carbodiimide hydrochloride (358 mg, 1.87 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave the title compound (490 mg, 70%).

mp 193–194° C. IR ν max$^{KBr}$cm$^{-1}$: 1642, 1626, 1601, 1514, 1329. Anal. Calcd for $C_{27}H_{20}F_5NO_2$: C, 66.80; H, 4.15; N, 2.89. Found: C, 66.70; H, 4.11; N, 2.75. $^1$H-NMR (CDCl$_3$)δ: 2.89 (1H, dd, J=14.2, 10.6 Hz), 3.09 (1H, dd, J=14.2, 4.0 Hz), 3.34 (1H, s), 4.70–4.84 (1H, m), 5.06–5.14 (1H, m), 5.98 (1H, d, J=8.8 Hz), 6.92–7.20 (4H, m), 7.40–7.60 (8H, m), 7.75 (1H, d, J=8.0 Hz), 8.08 (1H, d, J=8.0 Hz).

Example 138

N-((1RS,2SR)-2-(4-fluorophenyl)-2-hydroxy-1-((3-(trifluoromethyl)phenyl)methyl)ethyl) cyclohexanecarboxamide To a solution of (1RS,2SR)-2-amino-1-(4-fluorophenyl)-3-(3-(trifluoromethyl)phenyl)-1-propanol (450 mg, 1.44 mmol) in ethyl acetate (15 ml) were added cyclohexanecarbonyl chloride (288 ml, 2.15 mmol) and-saturated aqueous sodium hydrogen carbonate (15 ml) and the mixture was stirred at room temperature for 3 hrs. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (532 mg, 87%).

mp 190–191° C. IR ν max$^{KBr}$cm$^{-1}$: 1645, 1541, 1516, 1331. Anal. Calcd for $C_{23}H_{25}F_4NO_2$: C, 65.24; H, 5.95; N, 3.31. Found: C, 65.27; H, 5.92; N, 3.21. $^1$H-NMR (CDCl$_3$)δ: 1.00–1.38 (5H, m), 1.50–1.80 (5H, m), 1.84–2.06 (1H, m), 2.78 (1H, dd, J=14.4, 10.2 Hz), 2.93 (1H, dd, J=14.4, 4.4 Hz), 3.83 (1H, d, J=3.2 Hz), 4.30–4.50 (1H, m), 4.97 (1H, brs), 5.42 (1H, d, J=8.4 Hz), 7.02–7.18 (2H, m), 7.24–7.54 (6H, m).

Example 139

N-((1RS,2SR)-2-(4-fluorophenyl)-2-hydroxy-1-((3-(trifluoromethyl)phenyl)methyl)ethyl)-4-phenylbutyramide To a solution of (1RS,2SR)-2-amino-1-(4-fluorophenyl)-3-(3-(trifluoromethyl)phenyl)-1-propanol (450 mg, 1.44 mmol) in acetonitrile (30 ml) were added 4-phenyl-n-butyric acid (236 mg, 1.44 mmol), 1-ethyl-3-(3-dimethylaminopropyl)carbodiimide hydrochloride (358 mg, 1.87 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave the title compound (432 mg, 65%).

mp 110–111° C. IR ν max$^{KBr}$cm$^{-1}$: 1644, 1605, 1510. Anal. Calcd for $C_{26}H_{25}F_4NO_2$: C, 67.96; H, 5.48; N, 3.05. Found: C, 67.99; H, 5.63; N, 2.96. $^1$H-NMR (CDCl$_3$)δ: 1.66–1.90 (2H, m), 1.96–2.16 (2H, m), 2.40–2.56 (2H, m), 2.68–2.96 (2H, m), 3.56 (1H, d, J=3.8 Hz), 4.32–4.50 (1H, m), 4.90–5.00 (1H, m), 5.46 (1H, d, J=8.4 Hz), 7.00–7.50 (13H, m).

Example 140

N-((1RS,2SR)-2-(4-fluorophenyl)-2-hydroxy-1-((2-(trifluoromethyl)phenyl)methyl)ethyl)-1-naphthalenecarboxamide 1) A mixture of ethyl 3-(4-fluorophenyl)-3-oxopropionate (18 g, 85.7 mmol), 2-trifluoromethylbenzyl chloride (15.0 g, 77.1 mmol), potassium carbonate (23.7 g, 0.17 mol) and acetonitrile (200 ml) was stirred at 60° C. for 10 hrs. The reaction solution was concentrated under reduced pressure, water (200 ml) was added and the mixture was extracted with ethyl acetate (200 ml×2). The extract was washed with water, dried over anhydrous magnesium sulfate and evaporated under reduced pressure. The residue was purified by silica gel column chromatography (hexane:toluene=1:1) to give-ethyl 3-(4-fluorophenyl)-3-oxo-2-(2-trifluoromethyl)benzylpropionate (22.3 g, 71%) as an oil.

IR ν max$^{Neat}$cm$^{-1}$: 1738, 1690, 1599, 1316, 1159, 1121, 1040, 851. $^1$H-NMR (CDCl$_3$)δ: 1.11 (3H, t, J=7.2 Hz), 3.53 (2H, d, J=7.4 Hz), 4.10 (2H, q, J=7.2 Hz), 4.63 (1H, t, J=7.2 Hz), 7.10 (2H, t, J=8.6 Hz), 7.20–7.45 (3H, m), 7.64 (1H, d, J=7.2 Hz), 7.90–8.03 (2H, m);

2) To a solution of anhydrous zinc chloride (15.4 g, 0.113 mol) in diethyl ether (200 ml) was added sodium borohydride (9.5 g, 0.226 mol) and the mixture was stirred at room temperature for 2 hrs. The insoluble material was removed by filtration. To the filtrate was added a solution of ethyl 3-(4-fluorophenyl)-3-oxo-2-(2-trifluoromethyl)benzylpropionate (20.8 g, 56.5 mmol) in diethyl ether (50 ml) and the mixture was stirred at room temperature for 1 hr. 1N Hydrochloric acid was added to the reaction solution under ice-cooling to terminate the reaction. To the reaction solution were added water (200 ml) and ethyl acetate (300 ml) and extracted. The extract was washed with water and saturated aqueous sodium hydrogen carbonate solution, dried over anhydrous magnesium sulfate and evaporated under reduced pressure. The residue was purified by silica gel column chromatography (hexane:ethyl acetate= 20:1–10:1) to give ethyl (2RS,3RS)-3-(4-fluorophenyl)-3-hydroxy-2-(2-trifluoromethyl)benzylpropionate (16.9 g, 82%) as a colorless oil.

IR ν max$^{Neat}$cm$^{-1}$: 1715, 1607, 1510, 1316, 1225, 1159, 1121, 1040, 839. $^1$H-NMR (CDCl$_3$)δ: 0.91 (3H, t, J=7.1 Hz), 2.98–3.30 (4H, m), 3.88 (2H, q, J=7.1 Hz), 5.00–5.10 (1H, m), 7.59 (1H, d, J=7.4 Hz).

3) To a solution of ethyl (2RS,3RS)-3-(4-fluorophenyl)-3-hydroxy-2-(2-trifluoromethyl)benzylpropionate (16.7 g, 45 mmol) in methanol (100 ml) was added 2N aqueous sodium hydroxide solution (45 ml, 90.2 mmol) and the mixture was stirred at room temperature for 4 hrs. The reaction solution was acidified with 1N hydrochloric acid (150 ml) and extracted with ethyl acetate (150 ml×2). The extract was washed with water, dried over anhydrous magnesium sulfate and evaporated under reduced pressure. The residue was crystallized from hexane to give (2RS,3RS)-3-(4-fluorophenyl)-3-hydroxy-2-(2-trifluoromethyl)benzylpropionic acid (12.6 g, 82%).

mp 158–159° C. IR ν max$^{KBr}$cm$^{-1}$: 1694, 1514, 1319, 1227, 1115, 1042, 839. elemental analysis for $C_{17}H_{14}F_4O_3$, Calcd: C, 59.65; H, 4.12. Found: C, 59.56; H, 4.07. $^1$H-NMR (DMSO-d$_6$)δ: 2.70–2.95 (1H, m), 2.98–3.17 (1H, m), 4.70–4.82 (1H, m), 5.70–5.85 (1H, m), 7.13 (2H, t, J=9.0 Hz), 7.32–7.50 (4H, m), 7.50–7.70 (2H, m).

4) To a solution of (2RS,3RS)-3-(4-fluorophenyl)-3-hydroxy-2-(2-trifluoromethyl)benzylpropionic acid (12.3 g, 35.9 mmol) in tetrahydrofuran (100 ml) were added diphenylphosphoryl azide (10.0 ml, 46.7 mmol) and triethylamine (7.0 ml, 50.3 mmol) and the mixture was stirred for 30 min. The mixture was further heated under reflux for 4 hrs and allowed to stand at room temperature. Water (200 ml) was added and the mixture was extracted with ethyl acetate (200 ml). The extract was washed with 1N hydrochloric acid and saturated aqueous sodium hydrogen carbonate solution, dried over anhydrous magnesium sulfate and evaporated under reduced pressure. The residue was purified by silica gel column chromatography (chloroform:ethyl acetate= 10:1–5:1) to give (4RS,5SR)-5-(4-fluorophenyl)-4-((2-(trifluoromethyl)phenyl)methyl)-1,3-oxazolidin-2-one (11.8 g, 97%) as crystals.

mp 138–140° C. IR ν max$^{KBr}$cm$^{-1}$: 1761, 1609, 1514, 1316, 1235, 1154, 1115, 1063, 964, 833. elemental analysis for C$_{17}$H$_{13}$F$_4$NO$_2$ Calcd: C, 60.18; H, 3.86; N, 4.13. Found: C, 60.18; H, 4.05; N, 4.06. $^1$H-NMR (CDCl$_3$)δ: 2.20–2.40 (1H, m), 2.50–2.65 (1H, m), 4.18–4.35 (1H, m), 5.09 (1H, brs), 5.84 (1H, d, J=7.6 Hz), 7.10–7.60 (7H, m), 7.66 (1H, d, J=8.4 Hz).

5) To a solution of (4RS,5SR)-5-(4-fluorophenyl)-4-((2-(trifluoromethyl)phenyl)methyl)-1,3-oxazolidin-2-one (10.95 g, 32.3 mmol) in ethanol (200 ml) was added 8N aqueous sodium hydroxide solution (20 ml, 160 mmol) and the mixture was heated under reflux for 4 hrs. The reaction solution was concentrated, diluted with water (200 ml) and extracted with ethyl, acetate (200 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(2-(trifluoromethyl)phenyl)-1-propanol (7.56 g, 75%).

mp 57–58° C. Anal. Calcd for C$_{16}$H$_{15}$F$_4$NO: C, 61.34; H, 4.83; N, 4.47. Found: C, 61.52; H, 4.78; N, 4.39. IR ν max$^{KBr}$cm$^{-1}$: 1607, 1508, 1316. $^1$H-NMR (CDCl$_3$)δ: 2.34–2.52 (1H, m), 2.90–3.10 (1H, m), 3.30–3.42 (1H, m), 4.74 (1H, d, J=4.4 Hz), 7.02–7.16 (2H, m), 7.20–7.52 (5H, m), 7.63 (1H, d, J=7.6 Hz).

6) To a solution of (1RS,2SR)-2-amino-1-(4-fluorophenyl)-3-(2-(trifluoromethyl)phenyl)-1-propanol (450 mg, 1.44 mmol) in ethyl acetate (15 ml) were added 1-naphthoyl chloride (282 ml, 1.87 mmol) and saturated aqueous sodium hydrogen carbonate (15 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (536 mg, 80%).

mp 193–194° C. IR ν max$^{KBr}$cm$^{-1}$: 1636, 1622, 1607, 1539. Anal. Calcd for C$_{27}$H$_{21}$F$_4$NO$_2$: C, 69.37; H, 4.53; N, 3.00. Found: C, 69.13; H, 4.37; N, 3.09. $^1$H-NMR (CDCl$_3$)δ: 2.90–3.20 (2H, m), 3.33 (1H, d, J=3.0 Hz), 4.80–5.00 (1H, m), 5.12–5.20 (1H, m), 6.07 (1H, d, J=8.8 Hz), 7.00–7.20 (3H, m), 7.24–7.58 (8H, m), 7.60–7.78 (2H, m), 7.80–7.92 (2H, m).

Example 141

4-fluoro-N-((1RS,2SR)-2-(4-fluorophenyl)-2-hydroxy-1-((2-(trifluoromethyl)phenyl)methyl) ethyl)-1-naphthalenecarboxamide To a solution of (1RS,2SR)-2-amino-1-(4-fluorophenyl)-3-(2-(trifluoromethyl)phenyl)-1-propanol (450 mg, 1.44 mmol) in acetonitrile (30 ml) were added 4-fluoronaphthalenecarboxylic acid (274 mg, 1.44 mmol), 1-ethyl-3-(3-dimethylaminopropyl)carbodiimide hydrochloride (358 mg, 1.87 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate= 1:1). Recrystallization from ethyl acetate-hexane gave the title compound (548 mg, 79%).

mp 200–201° C. IR ν max$^{KBr}$cm$^{-1}$: 1640, 1626, 1601, 1537. Anal. Calcd for C$_{27}$H$_{20}$F$_5$NO$_2$: C, 66.80; H, 4.15; N, 2.89. Found: C, 66.67; H, 4.12; N, 2.80. $^1$H-NMR (CDCl$_3$)δ: 2.98–3.22 (3H, m), 4.80–4.98 (1H, m), 5.14–5.20 (1H, m), 6.04 (1H, d, J=8.4 Hz), 6.96–7.20 (4H, m), 7.26–7.60 (7H, m), 7.65 (1H, d, J=7.8 Hz), 7.75 (1H, d, J=8.4 Hz), 8.08 (1H, d, J=8.2 Hz).

Example 142

N-((1RS,2SR)-2-(4-fluorophenyl)-2-hydroxy-1-((2-(trifluoromethyl)phenyl)methyl)ethyl) cyclohexanecarboxamide To a solution of (1RS,2SR)-2-amino-1-(4-fluorophenyl)-3-(2-(trifluoromethyl)phenyl)-1-propanol (450 mg, 1.44 mmol) in ethyl acetate (15 ml) were added cyclohexanecarbonyl chloride (288 ml, 2.15 mmol) and saturated aqueous sodium hydrogen carbonate (15 ml) and the mixture was stirred at room temperature for 3 hrs. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (434 mg, 87%).

mp 216–217° C. IR ν max$^{KBr}$cm$^{-1}$: 1645, 1607, 1539. Anal. Calcd for C$_{23}$H$_{25}$F$_4$NO$_2$: C, 65.24; H, 5.95; N, 3.31. Found: C, 64.96; H, 5.92; N, 3.19. $^1$H-NMR (CDCl$_3$)δ: 1.00–1.30 (5H, m), 1.40–1.80 (5H, m), 1.80–2.02 (1H, m), 2.80–3.02 (2H, m), 3.70 (1H, d, J=3.6 Hz), 4.40–4.60 (1H, m), 4.98–5.06 (1H, m), 5.51 (1H, d, J=8.2 Hz), 7.00–7.16 (2H, m), 7.20–7.52 (5H, m), 7.59 (1H, d, J=7.6 Hz).

Example 143

N-((1RS,2SR)-2-(4-fluorophenyl)-2-hydroxy-1-((2-(trifluoromethyl)phenyl)methyl)ethyl)-4-phenylbutyramide To a solution of (1RS,2SR)-2-amino-1-(4-fluorophenyl)-3-(2-(trifluoromethyl)phenyl)-1-propanol (450 mg, 1.44 mmol) in acetonitrile (30 ml) were added 4-phenyl-n-butyric acid (236 mg, 1.44 mmol), 1-ethyl-3-(3-dimethylaminopropyl)carbodiimide hydrochloride (358 mg, 1.87 mmol) and 1-hydroxy-1H-benzotriazole (220 mg, 1.44 mmol) and the mixture was stirred overnight at room temperature. The reaction solution was diluted with water (100 ml) and extracted with ethyl acetate (100 ml×2) The extract was washed with saturated brine, dried over anhydrous magnesium sulfate and evaporated under reduced pressure. The residue was purified by silica gel column chromatography (hexane:acetone=1:1). Recrystallization from ethyl acetate-hexane gave the title compound (501 mg, 76%).

mp 161–162° C. IR ν max$^{KBr}$cm$^{-1}$: 1645, 1537, 1514. Anal. Calcd for C$_{26}$H$_{25}$F$_4$NO$_2$: C, 67.96; H, 5.48; N, 3.05. Found: C, 67.96; H, 5.41; N, 2.94. $^1$H-NMR (CDCl$_3$)δ: 1.64–1.84 (2H, m), 1.86–2.12 (2H, m), 2.38–2.44 (2H, m), 2.91 (2H, d, J=7.2 Hz), 3.29 (1H, d, J=3.6 Hz), 4.40–4.60 (1H, m), 4.98–5.06 (1H, m), 5.51 (1H, d, J=7.6 Hz), 7.00–7.34 (9H, m), 7.36–7.48 (3H, m), 7.57 (1H, d, J=7.6 Hz)

Example 144

N-((1RS,2SR)-2-(4-fluorophenyl)-1-((4-fluorophenyl)methyl)-2-hydroxyethyl)-1-naphthalenecarboxamide 1) A mixture of ethyl 3-(4-fluorophenyl)-3-oxopropionate (20 g, 95.1 mmol), 4-fluorobenzyl bromide (18.0 g, 85.6 mmol), potassium carbonate (26.3 g, 0.19 mol) and acetonitrile (300 ml) was stirred at 60° C. for 2 hrs. The reaction solution was concentrated under reduced pressure, water (200 ml) was added, and the mixture was extracted with ethyl acetate (200, 100 ml). The extract was washed with water, dried over anhydrous magnesium sulfate and evaporated under reduced pressure. The residue was purified by silica gel column chromatography (hexane:toluene=1:1–1:5) to give ethyl 2-(4-fluorobenzyl)-3-(4-fluorophenyl)-3-oxopropionate (19.0 g, 63%) as an oil.

IR ν max$^{Neat}$cm$^{-1}$: 1732, 1688, 1599, 1510, 1159, 851. $^1$H-NMR (CDCl$_3$)δ: 1.12 (3H, t, J=7.1 Hz), 3.29 (2H, d, J=7.4 Hz), 4.01 (2H, q, J=7.1 Hz), 4.53 (1H, t, J=7.4 Hz), 6.88–7.30 (6H, m), 7.90–8.08 (2H, m).

2) To a solution of anhydrous zinc chloride (15.4 g, 0.113 mol) in diethyl ether (200 ml) was added sodium borohydride (9.5 g, 0.226 mol) and the mixture was stirred at room temperature for 2 hrs. The insoluble material was removed by filtration. To the filtrate was added a solution of ethyl 2-(4-fluorobenzyl)-3-(4-fluorophenyl) 3-oxopropionate (18 g, 56.5 mmol) in diethyl ether (50 ml) and the mixture was stirred at room temperature for 1 hr. 1N Hydrochloric acid was added to the reaction solution under ice-cooling to terminate the reaction. Water (200 ml) and ethyl acetate (200 ml) were added to the reaction solution and the mixture was extracted. The extract was washed with water and saturated aqueous sodium hydrogen carbonate solution, dried over anhydrous magnesium sulfate and evaporated under reduced pressure. The residue was purified by silica gel column chromatography (hexane:ethyl acetate=10:1–3:1) to give ethyl (2RS,3RS)-2-(4-fluorobenzyl)-3-(4-fluorophenyl)-3-hydroxypropionate (16.8 g, 93%) as a colorless oil.

IR ν max$^{Neat}$cm$^{-1}$: 1726, 1713, 1605, 1510, 1225, 1159, 1030, 835. $^1$H-NMR (CDCl$_3$)δ: 0.94 (3H, t, J=7.0 Hz), 2.80–3.02 (4H, m), 3.88 (2H, q, J=7.0 Hz), 4.99 (1H, d, J=4.8 Hz), 6.85–7.15 (6H, m), 7.30–7.50 (2H, m).

3) To a solution of ethyl (2RS,3RS)-2-(4-fluorobenzyl)-3-(4-fluorophenyl)-3-hydroxypropionate (16.5 g, 51.5 mmol) in methanol (50 ml) was added 2N aqueous sodium hydroxide solution (51.5 ml, 0.103 mol) and the mixture was stirred at room temperature for 3 hrs. The reaction solution was acidified with 1N hydrochloric acid (130 ml) and extracted with ethyl acetate (200, 100 ml). The extract was washed with water, dried over anhydrous magnesium sulfate and evaporated under reduced pressure. The residue was crystallized from, hexane to give (2RS,3RS)-3-(4-fluorophenyl)-2-(4-fluorobenzyl)-3-hydroxypropionic acid (14.2 g, 94%).

mp 169–170° C. IR ν max$^{KBr}$cm$^{-1}$: 1692, 1607, 1510, 1231, 1015, 839, 826. elemental analysis for C$_{16}$H$_{14}$F$_2$O$_3$, Calcd: C, 66.75; H, 4.83. Found: C, 66.76; H, 4.64. $^1$H-NMR (DMSO-d$_6$)δ: 2.70–2.95 (2H, m), 3.05 (1H, d, J=11.0 Hz), 4.60–4.80 (1H, m), 5.65–5.80 (1H, m), 6.97–7.22 (6H, m), 7.30–7.45 (2H, m), 11.80–12.00 (1H, br, OH).

4) To a solution of (2RS,3RS)-3-(4-fluorophenyl)-2-(4-fluorobenzyl)-3-hydroxypropionic acid (13.8 g, 47.2 mmol) in tetrahydrofuran (150 ml) were added diphenylphosphoryl azide (13.2 ml, 61.4 mmol) and triethylamine (9.2 ml, 66.1 mmol) and the mixture was stirred for 30 min. The mixture was further heated under reflux for 4 hrs. and allowed to stand at room temperature. Water (200 ml) was added and the mixture was extracted with ethyl acetate (200 ml). The extract was washed with 1N hydrochloric acid and saturated aqueous sodium hydrogen carbonate solution, dried over anhydrous magnesium sulfate, passed through a small amount of silica gel and evaporated under reduced pressure. The residue was crystallized from hexane-ethyl acetate to give (4RS,5SR)-5-(4-fluorophenyl)-4-((4-fluorophenyl)methyl)-1,3-oxazolidin-2-one (12.8 g, 94%) as crystals.

mp 197–198° C. IR ν max$^{KBr}$cm$^{-1}$: 1738, 1611, 1510, 1231, 1069, 1013, 980, 853. elemental analysis for C$_{16}$H$_{13}$F$_2$NO$_2$, Calcd: C, 66.43; H, 4.53; N, 4.84. Found: C, 66.39; H, 4.40; N, 4.79. $^1$H-NMR (CDCl$_3$)δ: 2.10–2.35 (2H, m), 4.10–4.30 (1H, m), 4.91 (1H, s), 5.79 (1H, d, J=7.6 Hz), 6.98 (4H, d, J=7.4 Hz), 7.13 (2H, t, J=8.4 Hz), 7.30–7.43 (2H, m).

5) To a solution of (4RS,5SR)-5-(4-fluorophenyl)-4-((4-fluorophenyl)methyl)-1,3-oxazolidin-2-one (11.87 g, 41.0 mmol) in ethanol (200 ml) was added 8N aqueous sodium hydroxide solution (25.6 ml, 205 mmol) and the mixture was heated under reflux for 4 hrs. The reaction solution was concentrated, diluted with water (200 ml) and extracted with ethyl acetate (200 ml×2). The extract was washed with saturated brine, dried over anhydrous magnesium sulfate and evaporated under reduced pressure. The residue was recrystallized from ethyl acetate-hexane to give (1RS,2SR)-2-amino-1,3-bis(4-fluorophenyl)-1-propanol (9.33 g, 86%).

mp 66–67° C. IR ν max$^{KBr}$cm$^{-1}$: 1603, 1510, 1225. Anal. Calcd for C$_{15}$H$_{15}$F$_2$NO: C, 68.43; H, 5.74; N, 5.32. Found: C, 68.30; H, 5.68; N, 5.17. $^1$H-NMR (CDCl$_3$)δ: 2.32 (1H, dd, J=13.4, 10.2 Hz), 2.77 (1H, dd, J=13.4, 3.0 Hz), 3.16–3.30 (1H, m), 4.64 (1H, d, J=5.2 Hz), 6.90–7.18 (6H, m), 7.30–7.42 (2H, m).

6) To a solution of (1RS,2SR)-2-amino-1,3-bis(4-fluorophenyl)-1-propanol (450 mg, 1.71 mmol) in ethyl acetate (15 ml) were added 1-naphthoyl chloride (386 ml, 2.56 mmol) and saturated aqueous sodium hydrogen carbonate (15 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:acetone=1:1). Recrystallization from ethyl acetate-hexane gave the title compound (515 mg, 72%).

mp 199–200° C. IR ν max$^{KBr}$cm$^{-1}$: 1640, 1605, 1539, 1510. Anal. Calcd for C$_{26}$H$_{21}$F$_2$NO$_2$: C, 74.81; H, 5.07; N, 3.36. Found: C, 74.56; H, 5.04; N, 3.27. $^1$H-NMR (CDCl$_3$)δ: 2.75 (1H, dd, J=14.2, 10.6 Hz), 3.01 (1H, dd, J=14.2, 4.0 Hz), 3.63 (1H, d, J=4.0 Hz), 4.68–4.84 (1H, m), 5.04–5.10 (1H, m), 5.89 (1H, d, J=8.4 Hz), 6.92–7.30 (7H, m), 7.32–7.52 (5H, m), 7.69 (1H, d, J=8.2 Hz), 7.78–7.92 (2H, m).

Example 145

4-fluoro-N-((1RS,2SR)-2-(4-fluorophenyl)-1-((4-fluorophenyl)methyl)-2-hydroxyethyl)-7–1-naphthalenecarboxamide To a solution of (1RS,2SR)-2-amino-1,3-bis(4-fluorophenyl)-1-propanol (450 mg, 1.71 mmol) in acetonitrile (30 ml) were added 4-fluoronaphthalenecarboxylic acid (325 mg, 1.71 mmol), 1-ethyl-3-(3-dimethylaminopropyl) carbodiimide hydrochloride (491 mg, 2.56 mmol) and 1-hydroxy-1H-benzotriazole (261 mg, 1.71 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica, gel column chromatography (ethyl acetate). Recrystallization from ethyl acetate-hexane gave the title compound (571 mg, 77%).

mp 233–234° C. IR ν max$^{KBr}$cm$^{-1}$: 1644, 1626, 1601, 1508. Anal. Calcd for $C_{26}H_{20}F_3NO_2$: C, 71.72; H, 4.63; N, 3.22. Found: C, 71.58; H, 4.56; N, 3.12. $^1$H-NMR (CDCl$_3$)δ: 2.77 (1H, dd, J=14.4, 11.0 Hz), 3.03 (1H, dd, J=14.4, 4.4 Hz), 3.42–3.50 (1H, m), 4.64–4.84 (1H, m), 5.04–5.12 (1H, m), 5.84 (1H, d, J=8.4 Hz), 6.92–7.32 (8H, m), 7.40–7.60 (4H, m), 7.74 (1H, d, J=8.0 Hz), 8.09 (1H, d, J=8.4 Hz).

Example 146

N-((1RS,2SR)-2-(4-fluorophenyl)-1-((4-fluorophenyl)methyl)-2-hydroxyethyl) cyclohexanecarboxamide To a solution of (1RS,2RS)-2-amino-1,3-bis(4-fluorophenyl)-1-propanol (450 mg, 1.71 mmol) in ethyl acetate (15 ml) were added cyclohexanecarbonyl chloride (342 ml, 2.56 mmol) and saturated aqueous sodium hydrogen carbonate (15 ml) and the mixture was stirred at room temperature for 3 hrs. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (553 mg, 87%).

mp 203–204° C. IR ν max$^{KBr}$cm$^{-1}$: 1645, 1537, 1512. Anal. Calcd for $C_{22}H_{25}F_2NO_2$: C, 70.76; H, 6.75; N, 3.75. Found: C, 70.79; H, 6.80; N, 3.63. $^1$H-NMR (CDCl$_3$)δ: 1.02–1.38 (5H, m), 1.50–1.80 (5H, m), 1.82–2.04 (1H, m), 2.63 (1H, dd, J=14.4, 10.4 Hz), 2.84 (1H, dd, J=14.4, 4.4 Hz), 4.06 (1H, d, J=4.0 Hz), 4.30–4.46 (1H, m), 4.90–4.96 (1H, m), 5.29 (1H, d, J=8.4 Hz), 6.90–7.14 (6H, m), 7.30–7.42 (2H, m).

Example 147

N-((1RS,2SR)-2-(4-fluorophenyl)-1-((4-fluorophenyl)methyl)-2-hydroxyethyl)-4-phenylbutyramide To a solution of (1RS,2SR)-2-amino-1,3-bis(4-fluorophenyl)-1-propanol (450 mg, 1.71 mmol) in acetonitrile (30 ml) were added 4-phenyl-n-butyric acid (280 mg, 1.71 mmol), 1-ethyl-3-(3-dimethylaminopropyl) carbodiimide hydrochloride (491 mg, 2.56 mmol) and 1-hydroxy-1H-benzotriazole (261 mg, 1.71 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave the title compound (523 mg, 75%).

mp 147–148° C. IR ν max$^{KBr}$cm$^{-1}$: 1645, 1609, 1549. Anal. Calcd for $C_{25}H_{25}F_2NO_2$: C, 73.33; H, 6.15; N, 3.42. Found: C, 73.34; H, 6.09; N, 3.35. $^1$H-NMR (CDCl$_3$)δ: 1.70–1.90 (2H, m), 2.00–2.12 (2H, m), 2.44–2.58 (2H, m), 2.62 (1H, dd, J=14.4, 10.4 Hz), 2.80 (1H, dd, J=14.4, 4.4 Hz), 3.74 (1H, s), 4.32–4.48 (1H, m), 4.90–4.98 (1H, m), 5.32 (1H, d, J=7.6 Hz), 6.84–7.16 (8H, m), 7.20–7.42 (5H, m).

Example 148

N-((1RS,2SR)-2-(4-fluorophenyl)-2-hydroxy-1-((4-(methyloxy)phenyl)methyl)ethyl)-1-naphthalenecarboxamide 1) A mixture of ethyl 3-(4-fluorophenyl)-3-oxopropionate (20 g, 95.1 mmol), 4-methoxybenzyl chloride (11.6 ml, 85.6 mmol), potassium carbonate (26.3 g, 0.19 mol) and acetonitrile (300 ml) was stirred at 60° C. for 6 hrs. The reaction solution was concentrated under reduced pressure, water (300 ml) was added, and the mixture was extracted with ethyl acetate (300 ml×2). The extract was washed with water, dried over anhydrous magnesium sulfate and evaporated under reduced pressure. The residue was purified by silica gel column chromatography (hexane:ethyl acetate=10:1–5:1) to give ethyl 3-(4-fluorophenyl)-3-oxo-2-(4-methoxybenzyl)propionate (26.6 g, 85%) as an oil.

IR ν max$^{Neat}$cm$^{-1}$: 1734, 1686, 1597, 1514, 1250, 1179, 1159, 1034, 849, 824. $^1$H-NMR (CDCl$_3$)δ: 1.13 (3H, t, J=7.2 Hz), 3.26 (2H, d, J=7.6 Hz), 3.76 (3H, s), 4.10 (2H, q, J=7.2 Hz), 4.53 (2H, t, J=7.2 Hz), 6.79 (2H, d, J=8.2 Hz), 6.95–7.20 (3H, m), 7.90–8.10 (2H, m).

2) To a solution of zinc chloride (21.2 g, 0.156 mol) in diethyl ether (200 ml) was added sodium borohydride (13.1 g, 0.31 mol) and the mixture was stirred at room temperature for 2 hrs. The insoluble material was removed by filtration. To the filtrate was added a solution of ethyl 3-(4-fluorophenyl)-3-oxo-2-(4-methoxybenzyl)propionate (25.7 g, 77.8 mmol) in diethyl ether (50 ml) and the mixture was stirred at room temperature for 1 hr. 1N Hydrochloric acid was added to the reaction solution under ice-cooling to terminate the reaction. Water (200 ml) and ethyl acetate (200 ml) were added to the mixture and the mixture was extracted. The extract was washed with water and saturated aqueous sodium hydrogen carbonate solution, dried over anhydrous magnesium sulfate and evaporated under reduced pressure. The residue was purified by silica gel column chromatography (hexane:ethyl acetate=10:1–3:1) to give ethyl (2RS,3RS)-3-(4-fluorophenyl)-3-hydroxy-2-(4-methoxybenzyl)propionate (23.3 g, 90%) as a colorless oil.

IR ν max$^{Neat}$cm$^{-1}$: 1726, 1607, 1512, 1248, 1223, 1179, 1034, 839. $^1$H-NMR (CDCl$_3$)δ: 0.95 (3H, t, J=7.2 Hz), 2.85–3.00 (3H, m), 3.76 (3H, s, OMe), 3.89 (2H, q, J=7.2 Hz), 4.95–5.07 (1H, m), 6.70–6.88 (2H, m), 6.93–7.12 (4H, m), 7.30–7.47 (2H, m).

3) To a solution of ethyl (2RS,3RS)-3-(4-fluorophenyl)-3-hydroxy-2-(4-methoxybenzyl)propionate (22.8 g, 68.6 mmol) in methanol (100 ml) was added 2N aqueous sodium hydride solution (69 ml, 0.137 mol) and the mixture was stirred at room temperature for 4 hrs. The reaction solution was acidified with 6N hydrochloric acid, water (300 ml) was added, and the mixture was extracted with ethyl acetate (200 ml×2). The extract was washed with water, dried over anhydrous magnesium sulfate and evaporated under reduced pressure. The residue was crystallized from a mixture of hexane and diethyl ether to give (2RS,3RS)-3-(4-fluorophenyl)-3-hydroxy-2-(4-methoxybenzyl)propionic acid (14.8 g, 71%).

mp 96–98° C. IR ν max$^{KBr}$cm$^{-1}$: 1690, 1611, 1514, 1254, 1235, 1036, 837. elemental analysis for $C_{17}H_{17}FO_4$, Calcd: C, 67.10; H, 5.63. Found: C, 67.11; H, 5.65. $^1$H-NMR (DMSO-d$_6$)δ: 2.70–2.90 (2H, m), 2.95–3.10 (1H, m), 3.70 (3H, s), 4.60–4.75 (1H, m), 5.60–5.75 (1H, m), 6.79 (2H, d, J=8.8 Hz), 7.00–7.20 (4H, m), 7.30–7.45 (2H, m), 11.80–11.95 (1H, br, OH).

4) To a solution of (2RS,3RS)-3-(4-fluorophenyl)-3-hydroxy-2-(4-methoxybenzyl)propionic acid (13.7 g, 45.0 mmol) in tetrahydrofuran (150 ml) were added diphenylphosphoryl azide (12.6 ml, 58.5 mmol) and triethylamine (8.78 ml, 63.0 mmol) and the mixture was stirred for 30 min. The mixture was further heated under reflux for 4 hrs and allowed to stand at room temperature. Water (2.00 ml) was added and the mixture was extracted with ethyl acetate (200 ml). The extract was washed with 1N hydrochloric acid and saturated aqueous sodium hydrogen carbonate solution, dried over anhydrous magnesium sulfate and evaporated under reduced pressure. The residue was purified by silica gel column chromatography (chloroform:ethyl acetate= 4:1–2:1) to give (4RS,5SR)-5-(4-fluorophenyl)-4-((4-(methyloxy)phenyl)methyl)-1,3-oxazolidin-2-one (13.0 g, 96%) as crystals.

mp 125–126° C. IR ν max$^{KBr}$cm$^{-1}$: 1738, 1613, 1514, 1248, 1107, 1036, 845, 824. elemental analysis for C$_{17}$H$_{16}$FNO$_3$.1/4H$_2$O, Calcd: C, 66.77; H, 5.44; N, 4.58. Found: C, 66.57; H, 5.31; N, 4.49. $^1$H-NMR (CDCl$_3$)δ: 2.10–2.30 (3H, m), 3.78 (3H, s), 4.10–4.30 (1H, m), 4.94 (1H, brs), 5.78 (1H, d, J=7.6 Hz), 6.78–6.90 (2H, m), 6.90–7.00 (2H, m), 7.07–7.20 (2H, m), 7.30–7.45 (2H, m).

5) To a solution of (4RS,5SR)-5-(4-fluorophenyl)-4-((4-(methyloxy)phenyl)methyl)-1,3-oxazolidin-2-one (12.8 g, 42.5 mmol) in ethanol (200 ml) was added 8N aqueous sodium hydroxide solution (26.6 ml, 210 mmol) and the mixture was heated under reflux for 4 hrs. The reaction solution was concentrated, diluted with water (200 ml) and extracted with ethyl acetate (200 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(4-(methyloxy)phenyl)-1-propanol (10.08 g, 86%).

mp 78–79° C. IR ν max$^{KBr}$cm$^{-1}$: 1611, 1603, 1584, 1512. Anal. Calcd for C$_{16}$H$_{18}$FNO$_2$: C, 69.80; H, 6.59; N, 5.09. Found: C, 69.69; H, 6.65; N, 5.00. $^1$H-NMR (CDCl$_3$)δ: 2.27 (1H, dd, J=13.8, 10.4 Hz), 2.72 (1H, dd, J=13.8, 3.2 Hz), 3.16–3.28 (1H, m), 3.78 (3H, s), 4.65 (1H, d, J=4.6 Hz), 6.78–6.86 (2H, m), 7.00–7.12 (4H, m), 7.32–7.72 (2H, m).

6) To a solution of (1RS,2SR)-2-amino-1-(4-fluorophenyl)-3-(4-(methyloxy)phenyl)-1-propanol (450 mg, 1.64 mmol) in ethyl acetate (15 ml) were added 1-naphthoyl chloride (369 ml, 2.45 mmol) and saturated aqueous sodium hydrogen carbonate (15 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (622 mg, 89%).

mp 198–199° C. IR ν max$^{KBr}$cm$^{-1}$: 1640, 1611, 1541, 1510. Anal. Calcd for C$_{27}$H$_{24}$FNO$_3$: C, 75.51; H, 5.63; N, 3.26. Found: C, 75.25; H, 5.88; N, 3.18. $^1$H-NMR (CDCl$_3$)δ: 2.69 (1H, dd, J=14.2, 10.6 Hz), 3.01 (1H, dd, J=14.2, 4.0 Hz), 3.80 (3H, s), 3.93 (1H, d, J=4.0 Hz), 4.70–4.88 (1H, m), 5.02–5.10 (1H, m), 5.82 (1H, d, J=8.2 Hz), 6.86 (2H, d, J=8.6 Hz), 7.00–7.20 (4H, m), 7.20–7.52 (6H, m), 7.73 (1H, d, J=8.0 Hz), 7.80–7.92 (2H, m).

Example 149

4-fluoro-N-((1RS,2SR)-2-(4-fluorophenyl)-2-hydroxy-1-((4-(methyloxy)phenyl)methyl)ethyl)-1-naphthalenecarboxamide To a solution of (1RS,2SR)-2-amino-1-(4-fluorophenyl)-3-(4-(methyloxy)phenyl)-1-propanol (450 mg, 1.64 mmol) in acetonitrile (30 ml) were added 4-fluoronaphthalenecarboxylic acid (311 mg, 1.64 mmol), 1-ethyl-3-(3-dimethylaminopropyl)carbodiimide hydrochloride (470 mg, 2.43 mmol) and 1-hydroxy-1H-benzotriazole (250 mg, 1.64 mmol) and the mixture was stirred overnight at room temperature. The reaction solution was diluted-with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate= 1:1). Recrystallization from ethyl acetate-hexane gave the title compound (558 mg, 76%).

mp 210–211° C. IR ν max$^{KBr}$cm$^{-1}$: 1640, 1624, 1599, 1539, 1512. Anal. Calcd for C$_{27}$H$_{23}$F$_2$NO$_3$: C, 72.47; H, 5.18; N, 3.13. Found: C, 72.39; H, 5.08; N, 3.01. $^1$H-NMR (CDCl$_3$)δ: 2.70 (1H, dd, J=14.4, 10.8 Hz), 3.00 (1H, dd, J=14.4, 4.0 Hz), 3.80 (3H, s), 3.84 (1H, d, J=3.6 Hz), 4.66–4.84 (1H, m), 5.02–5.10 (1H, m), 5.81 (1H, d, J=7.6 Hz), 6.85 (2H, d, J=8.8 Hz), 6.92–7.22 (6H, m), 7.40–7.60 (4H, m), 7.76 (1H, d, J=8.4 Hz), 8.08 (1H, d, J=8.0 Hz).

Example 150

N-((1RS,2SR)-2-(4-fluorophenyl)-2-hydroxy-1-((4-(methyloxy)phenyl)methyl)ethyl) cyclohexanecarboxamide A solution of (1RS,2SR)-2-amino-1-(4-fluorophenyl)-3-(4-(methyloxy)phenyl)-1-propanol (450 mg, 1.64 mmol) in ethyl acetate (15 ml) were added cyclohexanecarbonyl chloride (328 ml, 2.45 mmol) and saturated aqueous sodium hydrogen carbonate (15 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (529 mg, 84%).

mp 193–194° C. IR ν max$^{KBr}$cm$^{-1}$: 1647, 1539, 1512. Anal. Calcd for C$_{23}$H$_{28}$FNO$_3$: C, 71.66; H, 7.32; N, 3.63. Found: C, 71.57; H, 7.40; N, 3.55. $^1$H-NMR (CDCl$_3$)δ: 1.02–1.40 (5H, m), 1.54–1.80 (5H, m), 1.88–2.08 (1H, m), 2.56 (1H, dd, J=14.4, 10.2 Hz), 2.82 (1H, dd, J=14.4, 5.2 Hz), 3.78 (3H, s), 4.30–4.50 (1H, m), 4.45 (1H, d, J=4.4 Hz), 4.88–4.92 (1H, m), 5.24 (1H, d, J=7.0 Hz), 6.81 (2H, d, J=8.8 Hz), 6.98–7.10 (4H, m), 7.28–7.40 (2H, m).

Example 151

N-((1RS,2SR)-2-(4-fluorophenyl)-2-hydroxy-1-((4-(methyloxy)phenyl)methyl)ethyl)-4-phenylbutyramide To a solution of (1RS,2SR)-2-amino-1-(4-fluorophenyl)-3-(4-(methyloxy)phenyl)-1-propanol (450 mg, 1.64 mmol) in acetonitrile (30 ml) were added 4-phenyl-n-butyric acid (268 mg, 1.64 mmol), 1-ethyl-3-(3-dimethylaminopropyl) carbodiimide hydrochloride (470 mg, 2.45 mmol) and 1-hydroxy-1H-benzotriazole (250 mg, 1.64 mmol) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:acetone=1:1). Recrystallization from ethyl acetate-hexane gave the title compound (575 mg, 83%).

mp 130–131° C. Ir ν max$^{KBr}$cm$^{-1}$: 1645, 1607, 1512. Anal. Calcd for C$_{26}$H$_{28}$FNO$_3$: C, 74.09; H, 6.70; N, 3.32. Found: C, 74.05; H, 6.82; N, 3.24. $^1$H-NMR (CDCl$_3$)δ: 1.70–1.90 (2H, m), 2.00–2.12 (2H, m), 2.40–2.62 (3H, m), 2.80 (1H, dd, J=14.2, 4.4 Hz), 3.72 (3H, s), 4.05 (1H, d, J=4.4 Hz), 4.32–4.48 (1H, m), 4.88–4.98 (1H, m), 5.27 (1H, d, J=7.2 Hz), 6.79 (2H, d, J=8.6 Hz), 6.96–7.14 (6H, m), 7.16–7.40 (5H, m).

Example 152 tert-butyl N-[(1RS,2SR)-1-(4-cyanobenzyl)-2-(4-fluorophenyl)-2-hydroxyethyl]carbamate 1) ethyl 2-(4-cyanobenzyl)-3-(4-fluorophenyl)-3-oxopropionate To a solution of ethyl (4-fluorobenzoyl)acetate (15.30 g, 72.79 mmol) in 1,2-dimethoxyethane (100 ml) was added a suspension (2.91 g, 72.8 mmol) of 60% sodium hydride in liquid paraffin under ice-cooling and the mixture was stirred as it was for 0.5 hr. A solution of 4-cyanobenzyl bromide (14.3 g, 72.8 mmol) in 1,2-dimethoxyethane (50 ml) was added at room temperature and the mixture was stirred at room temperature for 4 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/toluene=1/1–1/1.5) and crystallized from diethyl ether-hexane to give the objective substance.

white crystal yield 20.60 g, 87% mp 85–86° C.; $^1$H-NMR (CDCl$_3$, 200 MHz) δ 1.12 (3H, t, J=7.2 Hz), 3.38 (2H, d, J=7.2 Hz), 4.10 (2H, q, J=7.1 Hz), 4.56 (1H, t, J=7.5 Hz), 7.14 (2H, t, J=8.6 Hz), 7.35 (2H, d, J=8.0 Hz), 7.56 (2H, d, J=8.0 Hz), 8.00 (2H, dd, J=5.4 Hz, 9.0 Hz); IR (KBr) 2230, 1730, 1692, 1599, 1508, 1306, 1285, 1236, 1202, 1161, 851 cm$^{-1}$; Anal. Calcd for C$_{19}$H$_{16}$FNO$_3$: C, 70.14; H, 4.96; N, 4.31. Found: C, 70.20; H, 4.84; N, 4.29.

2) ethyl (2RS,3RS)-2-(4-cyanobenzyl)-3-(4-fluorophenyl)-3-hydroxypropionate

While stirring zinc chloride (8.52 g, 62.5 mmol) in diethyl ether (100 ml), sodium borohydride (4.73 g, 125 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 2-(4-cyanobenzyl)-3-(4-fluorophenyl)-3-oxopropionate (10.17 g, 31.26 mmol) in diethyl ether (50 ml) at room temperature and the mixture was stirred as it was for 2 hrs. Dilute hydrochloric acid was added to the reaction solution by small portions to decompose excess zinc borohydride. The mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=3/1–2/1) to give the objective substance.

colorless liquid yield 4.297 g, 42% $^1$H-NMR (CDCl$_3$, 200 MHz) δ 0.93 (3H, t, J=7.1 Hz), 2.82 (1H, d, J=2.8 Hz), 2.89–3.08 (3H, m), 3.88 (2H, q, J=7.2 Hz), 5.03 (1H, dd, J=2.5 Hz, 5.1 Hz), 7.05 (2H, t, J=8.8 Hz), 7.20 (2H, d, J=8.4 Hz), 7.37 (2H, dd, J=5.2 Hz, 8.4 Hz), 7.53 (2H, d, J=8.4 Hz); IR (neat) 3484, 2230, 1725, 1607, 1508, 1223, 1179, 1159, 1032, 839 cm$^{-1}$ 3) (2RS,3RS)-2-(4-cyanobenzyl)-3-(4-fluorophenyl)-3-hydroxypropionic acid To a solution of ethyl (2RS,3RS)-2-(4-cyanobenzyl)-3-(4-fluorophenyl)-3-hydroxypropionate (4.145 g, 12.66 mmol) in methanol (30 ml)—tetrahydrofuran (20 ml) was added 1N aqueous sodium hydroxide solution (25.3 ml, 25.3 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from diethyl ether-hexane to give the objective substance.

white crystal yield 3.559 g, 94% mp 165–168° C.; $^1$H-NMR (CDCl$_3$-DMSO-d$_6$, 200 MHz) δ 2.89–3.15 (3H, m), 5.03 (1H, d, J=5.0 Hz), 7.03 (2H, t, J=8.6 Hz), 7.24 (2H, d, J=8.2 Hz), 7.40 (2H, dd, J=5.5 Hz, 8.5 Hz), 7.51 (2H, d, J=8.4 Hz); IR (KBr) 3476, 3152, 2232, 1719, 1678, 1605, 1508, 1406, 1225, 1175, 1157, 845 cm$^{-1}$; Anal. Calcd for C$_{17}$H$_{14}$FNO$_3$: C, 68.22; H, 4.71; N, 4.68. Found: C, 67.98; H, 4.83; N, 4.47.

4) (4RS,5SR)-4-(4-cyanobenzyl)-5-(4-fluorophenyl)-1,3-oxazolidin-2-one

To a solution of (2RS,3RS)-2-(4-cyanobenzyl)-3-(4-fluorophenyl)-3-hydroxypropionic acid (3.385 g, 11.31 mmol) in tetrahydrofuran (50 ml) were added triethylamine (2.36 ml, 17.0 mmol) and diphenylphosphoryl azide (3.42 g, 12.4 mmol) and the mixture, was heated under reflux overnight. The solvent of the reaction solution was evaporated under reduced pressure. The obtained crude product was purified by silica gel column chromatography (hexane/ethyl acetate=3/1–1/2) and crystallized from diethyl ether-hexane to give the objective substance.

white crystal yield 2.741 g, 82% mp 170–173° C.; $^1$H-NMR (CDCl$_3$, 200 MHz) δ 2.36 (2H, d, J=6.6 Hz), 4.27 (1H, dt, J=7.5 Hz, 7.5 Hz), 5.17 (1H, br s), 5.81 (1H, d, J=7.8 Hz), 7.13 (2H, t, J=8.6 Hz), 7.13 (2H, d, J=8.0 Hz), 7.35 (2H, dd, J=5.2 Hz, 8.4 Hz), 7.59 (2H, d, J=8.0 Hz); IR (KBr) 3324, 2240, 1748, 1514, 1225 cm$^{-1}$; Anal. Calcd for C$_{17}$H$_{13}$FN$_2$O$_2$: C, 68.91; H, 4.42; N, 9.45. Found: C, 68.98; H, 4.43; N, 9.33.

5) tert-butyl (4RS,5SR)-4-(4-cyanobenzyl)-5-(4-fluorophenyl)-2-oxo-1,3-oxazolidine-3-carboxylate A solution of (4RS,5SR)-4-(4-cyanobenzyl)-5-(4-fluorophenyl)-1,3-oxazolidin-2-one (2.622 g, 8.849 mmol), di-tert-butyl dicarbonate (2.32 g, 10.6 mmol) and 4-N,N-dimethylaminopyridine (0.11 g, 0.88 mmol) in acetonitrile (30 ml) was stirred overnight at room temperature. The reaction solution was diluted with ethyl acetate, washed with water, dried over anhydrous magnesium sulfate and passed through silica gel. The solvent was evaporated under reduced pressure. The obtained residue was crystallized from ethyl acetate-hexane to give the objective substance.

white crystal yield 3.243 g, 92% mp 161–163° C.; $^1$H-NMR (CDCl$_3$, 200 MHz) δ 1.51 (9H, s), 2.63 (1H, dd, J=8.6 Hz, 14.2 Hz), 2.93 (1H, dd, J=4.7 Hz, 14.3 Hz), 4.74–4.85 (1H, m), 5.68 (1H, d, J=6.6 Hz), 6.80 (2H, d, J=8.0 Hz), 7.00 (2H, t, J=8.6 Hz), 7.16 (2H, dd, J=5.4 Hz, 8.6 Hz), 7.39 (2H, d, J=8.0 Hz); IR (KBr) 2982, 2228, 1815, 1721, 1514, 1368, 1152, 1069 cm$^{-1}$; Anal. Calcd for C$_{22}$H$_{21}$FN$_2$O$_4$: C, 66.66; H, 5.34; N, 7.07. Found: C, 66.76; H, 5.37; N, 7.09.

6) tert-butyl N-[(1RS,2SR)-1-(4-cyanobenzyl)-2-(4-fluorophenyl)-2-hydroxyethyl]carbamate To a solution of tert-butyl (4RS,5SR)-4-(4-cyanobenzyl)-5-(4-fluorophenyl)-2-oxo-1,3-oxazolidine-3-carboxylate (3.014 g, 7.603 mmol) in methanol (20 ml) and tetrahydrofuran (10 ml) was added a solution of sodium hydroxide (0.33 g, 8.36 mmol) in methanol (20 ml) under ice-cooling and the mixture was stirred at room temperature for 3 hrs.

The reaction solution was diluted with ethyl acetate, washed with dilute hydrochloric acid, dried over anhydrous magnesium sulfate and passed through silica gel. The solvent was evaporated under reduced pressure. The obtained residue was crystallized from ethyl acetate-hexane to give the objective substance.

white crystal yield 2.366 g, 84% mp 203–204° C.; $^1$H-NMR (CDCl$_3$, 200 MHz) δ 1.33 (9H, s), 2.67–2.98 (3H, m), 4.06 (1H, br s), 4.63 (1H, br d, J=8.4 Hz), 4.93 (1H, br s), 7.07 (2H, t, J=8.6 Hz), 7.21 (2H, d, J=8.2 Hz), 7.38 (2H, dd, J=5.4 Hz, 8.6 Hz), 7.54 (2H, d, J=8.4 Hz); IR (KBr) 3466, 3366, 2236, 1684, 1508, 1530, 1221, 1171 cm$^{-1}$; Anal. Calcd for C$_{21}$H$_{23}$FN$_2$O$_3$: C, 68.09; H, 6.26; N, 7.56. Found: C, 68.20; H, 6.18; N, 7.60.

Example 153

N-[(1RS,2SR)-1-(4-cyanobenzyl)-2-(4-fluorophenyl)-2-hydroxyethyl]-4-fluoronaphthalene-1-carboxamide 1) (1RS,2SR)-2-amino-3-(4-cyanophenyl)-1-(4-fluorophenyl)propan-1-ol A solution of tert-butyl N-[(1RS,2SR)-1-(4-cyanobenzyl)-2-(4-fluorophenyl)-2-hydroxyethyl]carbamate (2.199 g, 5.937 mmol) and conc. hydrochloric acid (4 ml) in methanol (30 ml)—tetrahydrofuran (20 ml) was stirred at 60° C. for 30 min. The reaction solution was diluted with water, alkalified with potassium carbonate and extracted twice with ethyl acetate. The collected organic layer was dried over anhydrous sodium sulfate and the solvent was evaporated under reduced pressure. The residue was allowed to precipitate with diethyl ether-hexane to give the objective substance.

white amorphous powder yield 1.557 g, 97% $^1$H-NMR (CDCl$_3$, 200 MHz) δ 2.44 (1H, dd, J=10.3 Hz, 13.5 Hz), 2.88 (1H, dd, J=2.9 Hz, 13.9 Hz), 3.28 (1H, ddd, J=3.2 Hz, 5.1 Hz, 10.2 Hz), 4.64 (1H, d, J=5.2 Hz), 7.08 (2H, t, J=8.8 Hz), 7.27 (2H, d, J=8.6 Hz), 7.37 (2H, dd, J=5.6 Hz, 8.8 Hz), 7.58 (2H, d, J=8.0 Hz); IR (KBr) 3350–2750, 2224, 1605, 1507, 1221, 1044, 828 cm$^{-1}$; Anal. Calcd for C$_{16}$H$_{15}$FN$_2$O. 0.2H$_2$O: C, 70.16; H, 5.67; N, 10.23. Found: C, 70.55; H, 5.84; N, 9.95.

2) N-[(1RS,2SR)-1-(4-cyanobenzyl)-2-(4-fluorophenyl)-2-hydroxyethyl]-4-fluoronaphthalene-1-carboxamide While stirring (1RS,2SR)-2-amino-3-(4-cyanophenyl)-1-(4-fluorophenyl)propan-1-ol (0.168 g, 0.622 mmol), 4-fluoro-1-naphthoate (0.12 g, 0.62 mmol) and 1-hydroxybenzotriazole hydrate (0.10 g, 0.62 mmol) in acetonitrile (10 ml), 1-ethyl-3-(3-dimethylaminopropyl)carbodiimide hydrochloride (0.12 g, 0.62 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white crystal yield 0.217 g, 79% mp 248–249° C.; $^1$H-NMR (CDCl$_3$-DMSO-d$_6$, 200 MHz) δ 2.93 (1H, dd, J=11.0 Hz, 14.4 Hz), 3.14 (1H, dd, J=3.4 Hz, 13.6 Hz), 4.64–4.79 (1H, m), 4.94 (1H, t, J=4.6 Hz), 5.42 (1H, d, J=4.2 Hz), 7.02–7.12 (3H, m), 7.20 (1H, dd, J=5.5 Hz, 7.7 Hz), 7.37–7.58 (9H, m), 7.78 (1H, d, J=9.4 Hz), 8.05 (1H, d, J=7.6 Hz); IR (KBr) 3476, 3291, 2232, 1642, 1626, 1603, 1537, 1508, 1225, 847 cm$^{-1}$; Anal. Calcd for C$_{27}$H$_{20}$F$_2$N$_2$O$_2$: C, 73.29; H, 4.56; N, 6.33. Found: C, 73.08; H, 4.43; N, 6.10.

Example 154

4-fluoro-N-[(1RS,2SR)-2-(4-fluorophenyl)-2-hydroxy-1-(4-isopropylbenzyl)ethyl]naphthalene-1-carboxamide 1) ethyl 3-(4-fluorophenyl)-2-(4-isopropylbenzyl)-3-oxopropionate To a solution of ethyl (4-fluorobenzoyl)acetate (23.21 g, 110.4 mmol) in 1,2-dimethoxyethane (150 ml) was added a suspension (4.42 g, 110 mmol) of 60% sodium hydride in liquid paraffin under ice-cooling and the mixture was stirred as it was for 0.5 hr. A solution of 4-isopropylbenzyl chloride (18.6 g 110 mmol) in 1,2-dimethoxyethane (50 ml) was added at room temperature and the mixture was stirred at 70° C. overnight. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) to give the objective substance.

yellow liquid yield 21.01 g, 56% $^1$H-NMR (CDCl$_3$, 200 MHz) δ 1.12 (3H, t, J=7.1 Hz), 1.20 (6H, d, J=7.0 Hz), 2.78–2.91 (1H, m), 3.28 (2H, d, J=7.2 Hz), 4.10 (2H, q, J=7.1 Hz), 4.55 (1H, t, J=7.3 Hz), 7.06–7.26 (6H, m), 7.98 (2H, dd, J=5.7 Hz, 8.7 Hz); IR (neat) 2961, 1738, 1688, 1599, 1508, 1271, 1235, 1159, 849 cm$^{-1}$ 2) ethyl (2RS,3RS)-3-(4-fluorophenyl)-3-hydroxy-2-(4-isopropylbenzyl)propionate While stirring zinc chloride (8.41 g, 61.7 mmol) in diethyl ether (100 ml), sodium borohydride (4.67 g, 123 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-fluorophenyl)-2-(4-isopropylbenzyl)-3-oxopropionate (10.57 g, 30.87 mmol) in diethyl ether (50 ml) at room temperature and the mixture was stirred as it was for 2 hrs. Dilute hydrochloric acid was added to the reaction solution by small portions to decompose excess zinc borohydride. The mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 8.433 g, 79% $^1$H-NMR (CDCl$_3$, 200 MHz) δ 0.91 (3H, t, J=7.1 Hz), 1.20 (6H, d, J=7.0 Hz), 2.71–3.09 (4H, m), 3.80–4.96 (2H, m), 5.00 (1H, s), 6.94–7.11 (6H, m), 7.37 (2H, dd, J=5.6 Hz, 8.6 Hz); IR (neat) 3445, 2961, 1726, 1713, 1510, 1225, 1157, 1032, 837 cm$^{-1}$ 3) (2RS,3RS)-3-(4-fluorophenyl)-3-hydroxy-2-(4-isopropylbenzyl)propionic acid To a solution of ethyl (2RS,3RS)-3-(4-fluorophenyl)-3-hydroxy-2-(4-isopropylbenzyl)propionate (8.267 g, 24.00 mmol) in methanol (40 ml) and tetrahydrofuran (50 ml) was added 1N aqueous sodium hydroxide solution (48.0 ml, 48.0 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from diethyl ether-hexane to give the objective substance.

white crystal yield 6.275 g, 83% mp 147–148° C.; $^1$H-NMR (CDCl$_3$, 200 MHz) δ 1.21 (6H, d, J=7.0 Hz), 2.78–3.09 (4H, m), 5.04 (1H, d, J=4.4 Hz), 6.98–7.12 (6H, m), 7.36 (2H, dd, J=5.2 Hz, 8.6 Hz); IR (KBr) 3330, 3050–2600, 1690, 1518, 1240, 1221, 1196, 849, 839 cm$^{-1}$; Anal. Calcd for $C_{19}H_{21}FO_3$: C, 72.13; H, 6.69. Found: C, 72.03; H, 6.55.

4) (4RS,5SR)-5-(4-fluorophenyl)-4-(4-isopropylbenzyl)-1,3-oxazolidin-2-one

To a solution of (2RS,3RS)-3-(4-fluorophenyl)-3-hydroxy-2-(4-isopropylbenzyl)propionic acid (6.128 g, 19.37 mmol) in tetrahydrofuran (80 ml) were added triethylamine (4.05 ml, 29.1 mmol) and diphenylphosphoryl azide (5.86 g, 21.3 mmol) and the mixture was heated under reflux overnight. The solvent of the reaction solution was evaporated under reduced pressure. The obtained crude product was purified by silica gel column chromatography (hexane/ethyl acetate=3/1–1/1) and crystallized from toluene-hexane to give the objective substance.

white crystal yield 5.680 g, 94% mp 185–186° C.; $^1$H-NMR (CDCl$_3$, 200 MHz) δ 1.22 (6H, d, J=7.0 Hz), 2.10–2.30 (2H, m), 2.80–2.94 (1H, m), 4.20 (1H, ddd, J=4.2 Hz, 7.8 Hz, 10.4 Hz), 4.90 (1H, br s), 5.79 (1H, d, J=7.6 Hz), 6.95 (2H, d, J=8.0 Hz), 7.09–7.18 (4H, m), 7.37 (2H, dd, J=5.2 Hz, 8.8 Hz); IR (KBr) 3262, 2961, 1738, 1514, 1231, 1009, 855 cm$^{-1}$; Anal. Calcd for $C_{19}H_{20}FNO_2$: C, 72.82; H, 6.43; N, 4.47. Found: C, 72.68; H, 6.30; N, 4.65.

5) (1RS,2SR)-2-amino-1-(4-fluorophenyl)-3-(4-isopropylphenyl)propan-1-ol (4RS,5SR)-5-(4-Fluorophenyl)-4-(4-isopropylbenzyl)-1,3-oxazolidin-2-one (5.503 g, 17.56 mmol) and sodium hydroxide (2.81 g, 70.2 mmol) were heated under reflux in ethanol (40 ml) and water (3 ml) for 7 hrs. The reaction solution was diluted with water and stirred at room temperature for 10 min. The resulting precipitate was collected by filtration and washed with water to give the objective substance.

white crystal yield 4.097 g, 81% mp 74–75° C.; $^1$H-NMR (CDCl$_3$, 200 MHz) δ 1.23 (6H, d, J=6.8 Hz), 2.29 (1H, dd, J=10.4 Hz, 13.8 Hz), 2.75 (1H, dd, J=2.8 Hz, 13.2 Hz), 2.80–2.94 (1H, m), 3.26 (1H, ddd, J=3.5 Hz, 4.8 Hz, 10.5 Hz), 4.66 (1H, d, J=5.2 Hz), 7.03–7.17 (6H, m), 7.37 (2H, dd, J=5.6 Hz, 8.4 Hz); IR (KBr) 3627, 3349, 3281, 3150–2700, 1507, 1219, 1042, 855, 924 cm$^{-1}$; Anal. Calcd for $C_{18}H_{22}FNO.0.2H_2O$: C, 74.30; H, 7.76; N, 4.81. Found: C, 74.38; H, 7.80; N, 4.65.

6) 4-fluoro-N-[(1RS,2SR)-2-(4-fluorophenyl)-2-hydroxy-1-(4-isopropylbenzyl)ethyl]naphthalene-1-carboxamide While stirring (1RS,2SR)-2-amino-1-(4-fluorophenyl)-3-(4-isopropylphenyl)propan-1-ol (0.164 g, 0.571 mmol), 4-fluoro-1-naphthoate (0.11 g, 0.57 mmol) and 1-hydroxybenzotriazole hydrate (87 mg, 0.57 mmol) in acetonitrile (10 ml), 1-ethyl-3-(3-dimethylaminopropyl) carbodiimide hydrochloride (0.11 g, 0.57 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white crystal yield 0.211 g, 80% mp 189–192° C.; $^1$H-NMR (CDCl$_3$-DMSO-d$_6$, 200 MHz) δ 1.23 (6H, d, J=6.8 Hz), 2.77–3.06 (3H, m), 4.62–4.76 (1H, m), 4.95 (1H, t, J=4.2 Hz), 5.33 (1H, d, J=4.0 Hz), 6.99–7.24 (8H, m), 7.37–7.65 (6H, m), 8.04 (1H, d, J=8.6 Hz); IR (KBr) 3299, 2959, 1642, 1626, 1539, 1512, 1227, 835 cm$^{-1}$; Anal. Calcd for $C_{29}H_{27}F_2NO_2$: C, 75.80; H, 5.92; N, 3.05. Found: C, 75.67; H, 5.77; N, 2.87.

Example 155

N-[(1RS,2SR)-2-(4-fluorophenyl)-2-hydroxy-1-(4-isopropylbenzyl)ethyl]-6,7-dihydro-5H-benzo[a]cycloheptene-1-carboxamide While stirring (1RS,2SR)-2-amino-1-(4-fluorophenyl)-3-(4-isopropylphenyl)propan-1-ol (0.219 g, 0.762 mmol), 6,7-dihydro-5H-benzo[a]cycloheptene-1-carboxylic acid (0.14 g, 0.76 mmol) and 1-hydroxybenzotriazole hydrate (0.12 g, 0.76 mmol) in acetonitrile (10 ml), 1-ethyl-3-(3-dimethylaminopropyl)carbodiimide hydrochloride (0.15 g, 0.76 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white powder yield 0.294 g, 84% mp 168–169° C.; $^1$H-NMR (CDCl$_3$, 200 MHz) δ 1.23 (6H, d, J=7.0 Hz), 1.95–2.06 (2H, m), 2.14–2.23 (2H, m), 2.61–2.76 (3H, m), 2.86 (1H, dd, J=6.6 Hz, 14.0 Hz), 2.97 (1H, dd, J=4.4 Hz, 13.6 Hz), 4.14 (1H, d, J=4.4 Hz), 4.61–4.74 (1H, m), 5.02 (1H, t, J=3.1 Hz), 5.63 (1H, d, J=7.8 Hz), 5.93 (1H, td, J=5.7 Hz, 11.3 Hz), 6.24 (1H, d, J=11.8 Hz), 6.89 (1H, d, J=7.4 Hz), 7.00–7.18 (8H, m), 7.42 (2H, dd, J=5.4 Hz, 8.6 Hz); IR (KBr) 3291, 1638, 1534, 1512, 1225, 1038, 826 cm$^{-1}$; Anal. Calcd for $C_{30}H_{32}FNO_2$: C, 78.75; H, 7.05; N, 3.06. Found: C, 78.66; H, 6.98; N, 3.06.

Example 156

N-((1RS,2SR)-2-(4-fluorophenyl)-1-((3-fluoro-4-(trifluoromethyl)phenyl)methyl)-2-hydroxyethyl)-4-fluoro-1-naphthalenecarboxamide 1) To a solution of 3-fluoro-4-(trifluoromethyl)benzoic acid (10.5 g, 50.7 mmol) in tetrahydrofuran (30 ml) was added a 1M tetrahydrofuran solution of borane (63 ml, 63 mmol) and the mixture was stirred at room temperature for 8 hrs. 1N Hydrochloric acid (100 ml) was added to the reaction solution and the mixture was extracted with ethyl acetate (300 ml×2). The extract was washed with saturated brine, dried over anhydrous magnesium sulfate and evaporated under reduced pressure. The residue was purified by silica gel column chromatography (ethyl acetate) to give 3-fluoro-4-(trifluoromethyl)benzyl alcohol (10.3 g, purity 90%, 94%).

$^1$H-NMR (CDCl$_3$)δ: 1.91 (1H, t, J=5.4 Hz), 4.78 (2H, d, J=5.4 Hz), 7.16–7.30 (2H, m), 7.59 (1H, t, J=7.6 Hz).

2) To absolution of 3-fluoro-4-(trifluoromethyl)benzyl alcohol (10 g, 52 mmol) in chloroform (20 ml) was added thionyl chloride (18.5 ml, 257 mmol) and the mixture was heated under ref lux for 4 hrs. The reaction solution was concentrated. The residue was purified by silica gel column chromatography (hexane:ethyl acetate=4:1) to give 3-fluoro-4-(trifluoromethyl)benzyl chloride (9.52 g, 87%).

IR ν max$^{KBr}$cm$^{-1}$: 1634, 1589, 1512, 1435. $^1$H-NMR (CDCl$_3$)δ: 4.58 (2H, s), 7.20–7.32 (2H, m), 7.60 (1H, t, J=7.6 Hz).

3) To a solution of ethyl 3-(4-fluorophenyl)-3-oxopropionate (8.9 g, 42.3 mmol) in 1,2-dimethoxyethane (50 ml) was added sodium hydride (60% in oil, 1.69 g, 42.3 mmol) under ice-cooling and the mixture was stirred at room temperature for 30 min. To the reaction solution was dropwise added a solution of 3-fluoro-4-(trifluoromethyl)benzyl bromide (9.0 g, 42.3 mmol) in 1,2-dimethoxyethane (50 ml) and the reaction solution was stirred at room temperature for 3 hrs. The reaction solution was poured into water (200 ml) and extracted with ethyl acetate (200 ml×2). The extract was washed with water and saturated brine, dried over anhydrous magnesium sulfate and evaporated under reduced pressure. The residue was purified by silica gel column chromatography (toluene:hexane=1:1-toluene) and recrystallized from diisopropyl ether-hexane to give ethyl 3-(4-fluorophenyl)-2-((3-fluoro-4-(trifluoromethyl)phenyl)methyl)-3-oxopropionate (10.8 g, 66%).

mp 56–57° C. IR ν max$^{KBr}$cm$^{-1}$: 1738, 1688, 1630, 1599, 1508. Anal. Calcd for $C_{19}H_{15}O_3F_5$: C, 59.07; H, 3.91. Found: C, 59.10; H, 3.68. $^1$H-NMR (CDCl$_3$)δ: 1.13 (3H, t, J=7.2 Hz), 3.37 (2H, d, J=7.2 Hz), 4.12 (2H, q, J=7.2 Hz), 4.57 (1H, t, J=7.2 Hz), 7.02–7.20 (4H, m), 7.50 (1H, t, J=8.0 Hz), 7.96–8.10 (2H, m).

4) To a solution of zinc chloride (7.06 g, 51.8 mmol) in diethyl ether (100 ml) was added sodium borohydride (3.92 g, 103.5 mmol) and the mixture was stirred at room temperature for 30 min. The insoluble material was filtered off. To the filtrate was added a solution of ethyl 3-(4-fluorophenyl)-2-((3-fluoro-4-(trifluoromethyl)phenyl)methyl)-3-oxopropionate (10 g, 25.9 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was ashed with water and saturated brine, dried over anhydrous magnesium sulfate and evaporated under reduced pressure. The residue was purified by silica gel column chromatography (ethyl acetate) to give ethyl (2RS,3RS)-3-(4-fluorophenyl)-2-((3-fluoro-4-(trifluoromethyl)phenyl)methyl)-3-hydroxypropionate (10.0 g, 99%) as a colorless oil.

IR ν max$^{KBr}$cm$^{-1}$: 1715, 1632, 1607, 1584. Anal. Calcd for $C_{19}H_{17}O_3F_5$: C, 58.77; H, 4.41. Found: C, 58.54; H, 4.51. $^1$H-NMR (CDCl$_3$)δ: 0.95 (3H, t, J=7.2 Hz), 2.86–3.10 (4H, m), 3.91 (2H, q, J=7.2 Hz), 4.98–5.06 (1H, m), 6.90–7.10 (4H, m), 7.30–7.50 (3H, m).

5) To a solution of ethyl (2RS,3RS)-3-(4-fluorophenyl)-2-((3-fluoro-4-(trifluoromethyl)phenyl)methyl)-3-hydroxypropionate (9.9 g, 25.5 mmol) in methanol (40 ml) was added 2N aqueous sodium hydroxide solution (25.5 ml, 51.0 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-(4-fluorophenyl)-2-((3-fluoro-4-(trifluoromethyl)phenyl)methyl)-3-hydroxypropionic acid (8.3 g, 90%).

mp 74–75° C. IR ν max$^{KBr}$cm$^{-1}$: 1713, 1632, 1607, 1586, 1512, 1435. $^1$H-NMR (CDCl$_3$)δ: 2.80–3.16 (3H, m), 5.09 (1H, d, J=4.2 Hz), 6.88–7.12 (4H, m), 7.30–7.52 (3H, m).

6) To a solution of (2RS,3RS)-3-(4-fluorophenyl)-2-((3-fluoro-4-(trifluoromethyl)phenyl)methyl)-3-hydroxypropionic acid (7.0 g, 19.4 mmol) in tetrahydrofuran (180 ml) were added diphenylphosphoryl azide (4.6 ml, 21.4 mmol) and triethylamine (4.1 ml, 29.2 mmol) and the mixture was heated under reflux for 6 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate). The residue was recrystallized from ethyl acetate-hexane to give (4RS,5SR)-5-(4-fluorophenyl)-4-((3-fluoro-4-(trifluoromethyl)phenyl)methyl)-1,3-oxazolidin-2-one (5.26 g, 76%).

mp 122–123° C. IR ν max$^{KBr}$cm$^{-1}$: 1759, 1632, 1611, 1586, 1514, 1435. Anal. Calcd for $C_{17}H_{12}O_2F_5N$: C, 57.15; H, 3.39; N, 3.92. Found: C, 57.18; H, 3.39; N, 3.75. $^1$H-NMR (CDCl$_3$)δ: 2.35 (2H, d, J=7.4 Hz), 4.22–4.36 (1H, m), 5.44 (1H, s), 5.80 (1H, d, J=7.8 Hz), 6.80–6.96 (2H, m), 7.04–7.20 (2H, m), 7.22–7.42 (2H, m), 7.46–8.00 (1H, m).

7) To a solution of (4RS,5SR)-5-(4-fluorophenyl)-4-((3-fluoro-4-(trifluoromethyl)phenyl)methyl)-1,3-oxazolidin-2-one (4.0 g, 11.2 mmol) in ethanol (70 ml) was added 8N aqueous sodium hydroxide solution (7.0 ml, 56 mmol) and the mixture was heated under reflux for 6 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(3-fluoro-4-(trifluoromethyl)phenyl)-1-propanol (3.21 g, 87%).

mp 86–87° C. IR ν max$^{KBr}$cm$^{-1}$: 1630, 1590, 1508, 1433, 1331. Anal. Calcd for $C_{16}H_{14}F_5NO$: C, 58.01; H, 4.26; N, 4.23. Found: C, 58.02; H, 4.29; N, 4.00. $^1$H-NMR (CDCl$_3$)δ: 2.44 (1H, dd, J=13.6, 10.2 Hz), 2.87 (1H, dd, J=13.6, 2.6 Hz), 3.22–3.36 (1H, m), 4.64 (1H, d, J=5.2 Hz), 6.96–7.16 (4H, m), 7.30–7.42 (2H, m), 7.44–7.58 (1H, m).

8) To a solution of (1RS,2SR)-2-amino-1-(4-fluorophenyl)-3-(3-fluoro-4-(trifluoromethyl)phenyl)-1-propanol (400 mg, 1.21 mmol) in acetonitrile (30 ml) were added 4-fluoronaphthalenecarboxylic acid (230 mg, 1.21 mmol), 1-ethyl-3-(3-dimethylaminopropyl)carbodiimide hydrochloride (347 mg, 1.81 mmol) and 1-hydroxy-1H-benzotriazole (185 mg, 1.21 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (525 mg, 86%).

mp 212–213° C. IR ν max$^{KBr}$cm$^{-1}$: 1640, 1626, 1599, 1514, 1435, 1325. Anal. Calcd for $C_{27}H_{19}F_6NO_2 \cdot 0.1H_2O$: C, 64.19; H, 3.83; N, 2.77. Found: C, 63.97; H, 3.83; N, 2.52. $^1$H-NMR (CDCl$_3$)δ: 2.82–3.16 (3H, m), 4.70–4.90 (1H, m), 5.12 (1H, d, J=3.6 Hz), 6.05 (1H, d, J=8.8 Hz), 7.00–7.30 (6H, m), 7.40–7.62 (5H, m), 7.72 (1H, d, J=8.0 Hz), 8.11 (1H, d, J=7.8 Hz).

Example 157

N-((1RS,2SR)-2-(4-fluorophenyl)-1-((3-fluoro-4-(trifluoromethyl)phenyl)methyl)-2-hydroxyethyl)-3-phenylpropanamide To a solution of (1RS,2SR)-2-amino-1-(4-fluorophenyl)-3-(3-fluoro-4-(trifluoromethyl)phenyl)-1-propanol (400 mg, 1.21 mmol) in ethyl acetate (20 ml) were added 3-phenylpropionyl chloride (269 ml, 1.81 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (486 mg, 87%).

mp 126–127° C. IR ν max$^{KBr}$cm$^{-1}$: 1632, 1510, 1435, 1325. Anal. Calcd for $C_{25}H_{22}F_5NO_2$: C, 64.79; H, 4.78; N, 3.02. Found: C, 64.61; H, 4.77; N, 2.80. $^1$H-NMR (CDCl$_3$)δ: 2.32–2.44 (2H, m), 2.58–2.80 (2H, m), 2.88 (2H, t, J=7.4 Hz), 3.00 (1H, d, J=4.2 Hz), 4.26–4.42 (1H, m), 4.76–4.84 (1H, m), 5.38 (1H, d, J=8.4 Hz), 6.78–6.90 (2H, m), 7.00–7.50 (10H, m).

Example 158

4-fluoro-N-((1RS,2SR)-2-(4-fluorophenyl)-2-hydroxy-1-((4-(phenyloxy)phenyl)methyl)ethyl)-1-naphthalenecarboxamide 1) To a solution of 4-(phenyloxy)benzoic acid (10.4 g, 48.7 mmol) in tetrahydrofuran (30 ml) was added 1M tetrahydrofuran solution of borane (63 ml, 63 mmol) at room temperature and the mixture was stirred overnight. 1N Hydrochloric acid was added to the reaction solution for quenching and the mixture was extracted with ethyl acetate (100 ml×2). The extract was washed successively with water and saturated brine, dried over anhydrous magnesium sulfate and evaporated under reduced pressure. The residue was purified by silica gel column chromatography (ethyl acetate) and recrystallized from hexane to give (4-(phenyloxy)phenyl)methanol (8.51 g, 87%).

mp 48–49° C. IR ν max$^{KBr}$cm$^{-1}$: 1590, 1507, 1489, 1240. Anal. Calcd for $C_{13}H_{12}O_2$: C, 77.98; H, 6.04. Found: C, 77.94; H, 5.74. $^1$H-NMR (CDCl$_3$)δ: 1.67 (1H, brs), 4.67 (2H, d, J=4.0 Hz), 6.96–7.18 (5H, m), 7.22–7.40 (4H, m).

2) To a solution of (4-(phenyloxy)phenyl)methanol (8 g, 40.0 mmol) in chloroform (20 ml) was added thionyl chloride (36 ml, 500 mmol) and the mixture was heated under reflux overnight. The reaction solution was concentrated. The residue was purified by silica gel column chromatography (ethyl acetate) to give 1-(chloromethyl)-4-(phenyloxy)benzene (8.1 g, 93%).

IR ν max$^{KBr}$cm$^{-1}$: 1590, 1507, 1489, 1240. $^1$H-NMR (CDCl$_3$)δ: 3.93 (1H, brs), 4.57 (2H, s), 6.80–7.40 (9H, m).

3) To a solution of ethyl 3-(4-fluorophenyl)-3-oxopropionate (6.49 g, 30.9 mmol) in 1,2-dimethoxyethane (50 ml) was added sodium hydride (60% in oil, 1.23 g, 30.9 mmol) under ice-cooling and the mixture was stirred at room temperature for 30 min. To the reaction solution was dropwise added a solution of 1-(chloromethyl)-4-(phenyloxy)benzene (8.1 g, 37.0 mmol) in 1,2-dimethoxyethane (50 ml) and the reaction solution was heated under reflux overnight. The reaction solution was poured into water (200 ml) and extracted with ethyl acetate (200 ml×2). The extract was washed with water and saturated brine, dried over anhydrous magnesium sulfate and evaporated under reduced pressure. The residue was purified by silica gel column chromatography (toluene:hexane=1:1-toluene) to give ethyl 3-(4-fluorophenyl)-3-oxo-2-((4-(phenyloxy)phenyl)methyl)propionate (7.76 g, crude, 64%).

$^1$H-NMR (CDCl$_3$)δ: 1.14 (3H, t, J=7.4 Hz), 3.30 (2H, d, J=7.6 Hz), 4.12 (2H, q, J=7.4 Hz), 4.56 (1H, t, J=7.6 Hz), 6.80–7.40 (11H, m), 7.90–8.08 (2H, m).

4) To a solution of zinc chloride (5.39 g, 39.6 mmol) in diethyl ether (100 ml) was added sodium borohydride (3.00 g, 79.1 mmol) and the mixture was stirred at room temperature for 30 min. The insoluble material was filtered off. To the filtrate was added a solution of ethyl 3-(4-fluorophenyl)-3-oxo-2-((4-(phenyloxy)phenyl)methyl)propionate (7.76 g, 19.8 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1–1:1) to give ethyl (2RS,3RS)-3-(4-fluorophenyl)-3-hydroxy-2-((4-(phenyloxy) phenyl)methyl)propionate (6.66 g, 85%) as a colorless oil.

IR ν max$^{KBr}$cm$^{-1}$: 1726, 1590, 1507, 1489. $^1$H-NMR (CDCl$_3$)δ: 0.97 (3H, t, J=7.0 Hz), 2.90–3.00 (4H, m), 3.91 (2H, q, J=7.0 Hz), 5.00 (1H, brs), 6.82–7.20 (9H, m), 7.24–7.42 (4H, m).

5) To a solution of ethyl (2RS,3RS)-3-(4-fluorophenyl)-3-hydroxy-2-((4-(phenyloxy)phenyl)methyl)propionate (6.6 g, 16.7 mmol) in methanol (30 ml) was added 2N aqueous sodium hydroxide solution (16.7 ml, 33.4 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=1:1) to give (2RS,3RS)-3-(4-fluorophenyl)-3-hydroxy-2-((4-(phenyloxy)phenyl)methyl) propionic acid (5.8 g, 95%).

IR ν max$^{KBr}$cm$^{-1}$: 1713, 1590. Anal. Calcd for $C_{22}H_{19}FO_4$: C, 72.12; H, 5.23. Found: C, 72.20; H, 5.23. $^1$H-NMR (CDCl$_3$)δ: 2.90–3.08 (3H, m), 3.92 (1H, s), 5.05 (1H, d, J=4.4 Hz), 6.80–7.20 (9H, m), 7.30–7.44 (4H, m).

6) To a solution of (2RS,3RS)-3-(4-fluorophenyl)-3-hydroxy-2-((4-(phenyloxy)phenyl)methyl)propionic acid (5.5 g, 15.0 mmol) in tetrahydrofuran (150 ml) were added diphenylphosphoryl azide (3.56 ml, 16.5 mmol)-and triethylamine (3.15 ml, 22.5 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=4:1–1:1) and recrystallized from ethyl acetate-hexane to give (4RS,5SR)-5-(4-fluorophenyl)-4-((4-(phenyloxy)phenyl) methyl)-1,3-oxazolidin-2-one (3.74 g, 69%).

mp 144–145° C. IR ν max$^{KBr}$cm$^{-1}$: 1755, 1590, 1505. $^1$H-NMR (CDCl$_3$)δ: 2.16–2.30 (2H, m), 4.16–4.30 (1H, m), 5.14 (1H, s), 5.79 (1H, d, J=8.0 Hz), 6.80–7.42 (13H, m).

7) To a solution of (4RS,5SR)-5-(4-fluorophenyl)-4-((4-(phenyloxy)phenyl)methyl)-1,3-oxazolidin-2-one (2.5 g, 6.88 mmol) in ethanol (20 ml) was added 8N aqueous sodium hydroxide solution (4.30 ml, 34.4 mmol) and the mixture was heated under reflux for 6 hrs. The reaction solution was concentrated, diluted with water (100 ml) and extracted with ethyl acetate (100 ml×2). The extract was washed with saturated brine, dried over anhydrous magnesium sulfate and evaporated under reduced pressure to give (1RS,2SR)-2-amino-1-(4-fluorophenyl)-3-(4-(phenyloxy) phenyl)-1-propanol (2.2 g, 95%).

Ir ν max$^{KBr}$cm$^{-1}$: 1590, 1507, 1489, 1238. $^1$H-NMR (CDCl$_3$)δ: 2.00–2.40 (2H, m), 3.93 (1H, s), 5.11 (1H, d, J=7.4 Hz), 6.80–7.40 (13H, m).

8) To a solution of (1RS,2SR)-2-amino-1-(4-fluorophenyl)-3-(4-(phenyloxy)phenyl)-1-propanol (353 mg, 1.05 mmol) in acetonitrile (20 ml) were added 4-fluoronaphthalenecarboxylic acid (200 mg, 1.05 mmol), 1-ethyl-3-(3-dimethylaminopropyl)carbodiimide hydrochloride (302 mg, 1.58 mmol) and 1-hydroxy-1H-benzotriazole (161 mg, 1.05 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane:ethyl acetate=4:1–1:1). Recrystallization from ethyl acetate-hexane gave the title compound (166 mg, 31%).

mp 104–105° C. IR ν $max^{KBr}cm^{-1}$: 1644, 1626, 1601, 1590, 1507, 1489. $^1$H-NMR (CDCl$_3$)δ: 2.75 (1H, dd, J=14.4, 11.0 Hz), 3.06 (1H, dd, J=14.4, 4.0 Hz), 3.64–3.70 (1H, m), 4.70–4.88 (1H, m), 5.04–5.12 (1H, m), 5.90 (1H, d, J=8.4 Hz), 6.90–7.60 (17H, m), 7.78–7.86 (1H, m), 8.09 (1H, d, J=7.8 Hz).

Example 159

N-(1RS,2SR)-(2-(4-fluorophenyl)-2-hydroxy-1-((4-(phenyloxy)phenyl)methyl)ethyl)-3-phenylpropanamide To a solution of (1RS,2SR)-2-amino-1-(4-fluorophenyl)-3-(4-(phenyloxy)phenyl)-1-propanol (550 mg, 1.63 mmol) in ethyl acetate (20 ml) were added 3-phenylpropionyl chloride (360 ml, 2.45 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate=4:1–1:1) and recrystallized from ethyl acetate-hexane to give the title compound (152 mg, 20%).

mp 108–110° C. IR ν $max^{KBr}cm^{-1}$: 1644, 1605, 1507, 1489. $^1$H-NMR (CDCl$_3$)δ: 2.24–2.40 (2H, m), 2.40–3.00 (5H, m), 4.30–4.44 (1H, m), 4.76–4.84 (1H, m), 5.69 (1H, d, J=8.0 Hz), 6.80–7.36 (18H, m).

Example 160

4-fluoro-N-((1RS,2SR)-2-(4-fluorophenyl)-2-hydroxy-1-((3-(phenyloxy)phenyl)methyl)ethyl)-1-naphthalenecarboxamide 1) To a solution of (3-(phenyloxy)phenyl)methanol (10 g, 49.4 mmol) in chloroform (20 ml) was added thionyl chloride (36 ml, 500 mmol) and the mixture was heated under reflux overnight. The reaction solution was concentrated. The residue was purified by silica gel column chromatography (ethyl acetate) to give 1-(chloromethyl)-3-(phenyloxy)benzene (10.7 g, 98%).

IR ν $max^{KBr}cm^{-1}$: 1584, 1487, 1445. $^1$H-NMR (CDCl$_3$)δ: 4.53 (2H, s), 6.80–7.40 (9H, m).

2) To a solution of ethyl 3-(4-fluorophenyl)-3-oxopropanoate (7.2 g, 34.3 mmol) in 1,2-dimethoxyethane (50 ml) was added sodium hydride (60% in oil, 1.37 g, 34.3 mmol) under ice-cooling and the mixture was stirred at room temperature for 30 min. To the reaction solution was dropwise added a solution of 1-(chloromethyl)-3-(phenyloxy)benzene (9.0 g, 41.6 mmol) in 1,2-dimethoxyethane (50 ml) and the reaction solution was heated under reflux overnight. The reaction solution was poured into water (200 ml) and extracted with ethyl acetate (200 ml×2). The extract was washed with water and saturated brine, dried over anhydrous magnesium sulfate and evaporated under reduced pressure. The residue was purified by silica gel column chromatography (toluene:hexane=1:1-toluene) to give ethyl 3-(4-fluorophenyl)-3-oxo-2-((3-(phenyloxy)phenyl)methyl)propionate (10.2 g, crude, 76%).

$^1$H-NMR (CDCl$_3$)δ: 1.12 (3H, t, J=7.0 Hz), 3.29 (2H, d, J=7.2 Hz), 4.09 (2H, q, J=7.0 Hz), 4.55 (1H, t, J=7.2 Hz), 6.70–7.40 (11H, m), 7.90–8.04 (2H, m).

3) To a solution of zinc chloride (7.08 g, 51.9 mmol) in diethyl ether (100 ml) was added sodium borohydride (3.93 g, 103.9 mmol) and the mixture was stirred at room temperature for 30 min. The insoluble material was filtered off. To the filtrate was added a solution of ethyl 3-(4-fluorophenyl)-3-oxo-2-((3-(phenyloxy)phenyl)methyl)propionate (10.2 g, 26.0 mmol) in diethyl ether (50 ml) and the mixture was stirred at room temperature for 30 min. 1N Hydrochloric acid was added to the reaction solution under ice-cooling for quenching, water (200 ml) was further added, and the mixture was extracted with ethyl acetate (300 ml×2). The extract was washed with water and saturated brine, dried over anhydrous magnesium sulfate and evaporated under reduced pressure. The residue was purified by silica gel column chromatography (ethyl acetate) to give ethyl (2RS,3RS)-3-(4-fluorophenyl)-3-hydroxy-2-((3-(phenyloxy)phenyl)methyl)propionate (5.26 g, 51%) as a colorless oil.

IR ν $max^{KBr}cm^{-1}$: 1728, 1715, 1582, 1487. $^1$H-NMR (CDCl$_3$)δ: 0.96 (3H, t, J=7.2 Hz), 2.82–3.04 (4H, m), 3.89 (2H, q, J=7.2 Hz), 5.00 (1H, brs), 6.78–7.40 (13H, m).

4) To a solution of ethyl (2RS,3RS)-3-(4-fluorophenyl)-3-hydroxy-2-((3-(phenyloxy)phenyl)methyl)propionate (5.26 g, 13.3 mmol) in methanol (40 ml) was added 2N aqueous sodium hydroxide solution (13.4 ml, 26.8 mmol) and the mixture was stirred overnight at room temperature. The reaction solution was acidified with 1N hydrochloric acid and extracted with ethyl acetate (200 ml×2). The extract was washed with water and saturated-brine, dried over anhydrous magnesium sulfate and evaporated under reduced pressure. The residue was purified by silica gel column chromatography (hexane:ethyl acetate=1:1) to give (2RS,3RS)-3-(4-fluorophenyl)-3-hydroxy-2-((3-(phenyloxy)phenyl)methyl)propionic acid (2.31 g, 47%).

IR ν $max^{KBr}cm^{-1}$: 1713, 1584, 1510, 1487. $^1$H-NMR (CDCl$_3$)δ: 2.84–3.06 (4H, m), 5.04 (1H, d, J=4.4 Hz), 6.76–7.40 (13H, m).

5) To a solution of (2RS,3RS)-3-(4-fluorophenyl)-3-hydroxy-2-((3-(phenyloxy)phenyl)methyl)propionic acid (2.2 g, 6.00 mmol) in tetrahydrofuran (60 ml) were added diphenylphosphoryl azide (1.42 ml, 6.60 mmol) and triethylamine (1.26 ml, 9.00 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=4:1–1:1) to give (4RS,5SR)-5-(4-fluorophenyl)-4-((3-(phenyloxy)phenyl)methyl)-1,3-oxazolidin-2-one (1.69 g, 77%).

Ir ν $max^{KBr}cm^{-1}$: 1759, 1608, 1584. $^1$H-NMR (CDCl$_3$)δ: 2.10–2.32 (2H, m), 4.16–4.30 (1H, m), 5.13 (1H, s), 5.77 (1H, d, J=7.8 Hz), 6.60–7.40 (13H, m).

6) To a solution of (4RS,5SR)-5-(4-fluorophenyl)-4-((3-(phenyloxy)phenyl)methyl)-1,3-oxazolidin-2-one (877 mg, 2.41 mmol) in ethanol (10 ml) was added 8N aqueous sodium hydroxide solution (1.51 ml, 12.1 mmol) and the mixture was heated under reflux for 6 hrs. The reaction solution was concentrated, diluted with water (100 ml) and extracted with ethyl acetate (10.0 ml×2). The extract was washed with saturated brine, dried over anhydrous magnesium sulfate and evaporated under reduced pressure to give (1RS,2SR)-2-amino-1-(4-fluorophenyl)-3-(3-(phenyloxy)phenyl)-1-propanol (831 mg, 100%).

IR ν max$^{KBr}$cm$^{-1}$: 1582, 1507, 1487, 1445. $^1$H-NMR (CDCl$_3$)δ: 2.31 (1H, dd, J=13.6, 10.2 Hz), 2.75 (1H, dd, J=13.6, 3.0 Hz), 3.18–3.36 (1H, m), 4.65 (1H, d, J=4.6 Hz), 6.78–7.40 (13H, m).

7) To a solution of (1RS,2SR)-2-amino-1-(4-fluorophenyl)-3-(3-(phenyloxy)phenyl)-1-propanol (300 mg, 0.89 mmol) in acetonitrile (20 ml) were added 4-fluoronaphthalenecarboxylic acid (169 mg, 0.89 mmol), 1-ethyl-3-(3-dimethylaminopropyl)-carbodiimide hydrochloride (256 mg, 1.33 mmol) and 1-hydroxy-1H-benzotriazole (136 mg, 0.89 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane:ethyl acetate=4:1–1:1). Recrystallization from ethyl acetate-hexane gave the title compound (148 mg, 33%).

mp 120–121° C. IR ν max$^{KBr}$cm$^{-1}$: 1642, 1626, 1601, 1584. Anal. Calcd for C$_{32}$H$_{25}$F$_2$NO$_3$: C, 75.43; H, 4.95; N, 2.75. Found: C, 75.33; H, 5.05; N, 2.54. $^1$H-NMR (CDCl$_3$)δ: 2.73 (1H, dd, J=14.4, 10.6 Hz), 3.02 (1H, dd, J=14.4, 4.0 Hz), 3.60–3.64 (1H, m), 4.66–4.82 (1H, m), 5.04–5.12 (1H, m), 5.87 (1H, d, J=8.4 Hz), 6.80–7.36 (13H, m), 7.38–7.62 (4H, m), 7.81 (1H, d, J=8.0 Hz), 8.09 (1H, d, J=7.8 Hz).

Example 161

N-(1RS,2SR)-(2-(4-fluorophenyl)-2-hydroxy-1-((3-(phenyloxy)phenyl)methyl)ethyl)-3-phenylpropanamide To a solution of (1RS,2SR)-2-amino-1-(4-fluorophenyl)-3-(3-(phenyloxy)phenyl)-1-propanol (550 mg, 1.63 mmol) in ethyl acetate (20 ml) were added 3-phenylpropionyl chloride (360 ml, 2.45 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (hexane:ethyl acetate=4:1–1:1) and recrystallized from ethyl acetate-hexane to give the title compound (422 mg, 55%).

mp 91–93° C. IR ν max$^{KBr}$cm$^{-1}$: 1645, 1584, 1510, 1487, 1447. $^1$H-NMR (CDCl$_3$)δ: 2.22–2.90 (6H, m), 4.22–4.42 (1H, m), 4.81 (1H, s), 5.30 (1H, d, J=8.2 Hz), 6.62–7.40 (18H, m).

Example 162

1,1-dimethylethyl (1RS,2SR)-2-(4-fluorophenyl)-2-hydroxy-1-((5-(trifluoromethyl)-2-furanyl)methyl)ethylcarbamate 1) To a solution of ethyl trifluoroacetate (75 g, 407 mmol) in 1,2-dimethoxyethane (200 ml) was added sodium hydride (60% in oil, 16.3 g, 407 mmol) under ice-cooling and the mixture was stirred at room temperature for 30 min. To the reaction solution was dropwise added a solution of chloroacetone (43.3 g, 469 mmol) in 1,2-dimethoxyethane (50 ml) and potassium iodide (800 mg, 4.8 mmol) was further added. The reaction solution was heated under reflux overnight. The reaction solution was poured into water (500 ml) and extracted with diethyl ether (500 ml×2). The extract was washed with water and saturated brine, dried over anhydrous magnesium sulfate and evaporated under reduced pressure. The residue was distilled under reduced pressure to give ethyl 4-oxo-2-(2,2,2-trifluoroacetyl)valerate (40.5 g, 41%).

IR ν max$^{KBr}$cm$^{-1}$: 1742, 1723. $^1$H-NMR (CDCl$_3$)δ: 1.28 (3H, t, J=7.0 Hz), 2.22 (3H, s), 3.26 (2H, d, J=7.0 Hz), 4.10–4.50 (3H, m). bp 110–125° C./0.1 mmHg 2) To a solution of ethyl 4-oxo-2-(2,2,2-trifluoroacetyl)valerate (40 g, 167 mmol) in toluene (250 ml) was added p-toluenesulfonic acid (3 g, 16 mmol) and the mixture was heated under reflux overnight in a Dean-Stark apparatus under dehydrated conditions. The reaction solution was concentrated. The residue was purified by silica gel column chromatography (hexane:ethyl acetate=10:1) to give ethyl 5-methyl-2-(trifluoromethyl)-3-furancarboxylate (25.8 g, 70%).

IR ν max$^{KBr}$cm$^{-1}$: 1732, 1574. $^1$H-NMR (CDCl$_3$)δ: 1.35 (3H, t, J=7.4 Hz), 2.35 (3H, s), 4.32 (2H, q, J=7.4 Hz), 4.62 (1H, s).

3) To a solution of ethyl 5-methyl-2-(trifluoromethyl)-3-furancarboxylate (25 g, 113 mmol) in ethanol (200 ml) was added 2N aqueous sodium hydroxide solution (61.9 ml, 123.8 mmol) and the mixture was heated under reflux for 45 min. The reaction solution was concentrated, diluted with water (150 ml), and 6N hydrochloric acid was gradually added to adjust to about pH 5. The precipitated crystals were collected by filtration, washed with water to give 5-methyl-2-(trifluoromethyl)-3-furancarboxylic acid (20.5 g, 94%).

IR ν max$^{KBr}$cm$^{-1}$: 1711, 1574. mp 118–119° C. $^1$H-NMR (CDCl$_3$)δ: 2.38 (3H, s), 6.52 (1H, s).

4) To a solution of 5-methyl-2-(trifluoromethyl)-3-furancarboxylic acid (20 g, 103 mmol) in quinoline (36 ml) was added copper (I) sulfate (1 g, 6.3 mmol). While bubbling nitrogen, the mixture was immersed in an oil bath at 230° C. until gas generation ceased. The generated gas was collected and distilled again to give 2-methyl-5-(trifluoromethyl)furan (8.34 g, 54%).

$^1$H-NMR (CDCl$_3$)δ: 2.34 (3H, s), 6.05 (1H, d, J=3.4 Hz), 6.60 (1H, d, J=2.2 Hz). bp 80–85° C./760 mmHg (Lit. 81–82° C., J. Hetrocyclic Chem., 5, 95 (1968))

5) To a solution of 2-methyl-5-(trifluoromethyl)furan (4 g, 26.6 mmol) in chloroform (60 ml) were added N-bromosuccinimide (5.2 g, 29.3 mmol) and 2,2'-azobis (isobutyronitrile) (220 mg, 1.33 mmol). The reaction solution was heated under reflux for 15 min. The reaction solution was cooled, poured into water (200 ml) and was extracted with chloroform. The extract was washed with water and saturated brine, dried over anhydrous magnesium sulfate and evaporated under reduced pressure to give 2-(bromomethyl)-5-(trifluoromethyl)furan (4.79 g, 78%).

Ir ν max$^{KBr}$cm$^{-1}$: 1738, 1688, 1599, 1559. $^1$H-NMR (CDCl$_3$)δ: 4.46 (2H, s), 6.45 (1H, d, J=3.8 Hz), 6.75 (1H, d, J=3.8 Hz).

6) To a solution of ethyl 3-(4-fluorophenyl)-3-oxopropionate (5.0 g, 24 mmol) in 1,2-dimethoxyethane (40 ml) was added sodium hydride (60% in oil, 576 mg, 24 mmol) under ice-cooling and the mixture was stirred at room temperature for 1 hr. To the reaction solution was dropwise added a solution of. 2-(bromomethyl)-5-(trifluoromethyl)furan (6 g, 26 mmol) in 1,2-dimethoxyethane (50 ml) and the reaction solution was stirred overnight at room temperature. The reaction solution was poured into water (200 ml), saturated aqueous sodium hydrogen carbonate was added, and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) to give ethyl 3-(4-fluorophenyl)-3-oxo-2-((5-(trifluoromethyl)-2-furanyl)methyl)propionate (4.5 g, 52%).

IR ν max$^{KBr}$cm$^{-1}$: 1738, 1688, 1599, 1559. $^1$H-NMR (CDCl$_3$)δ: 1.16 (3H, t, J=7.2 Hz), 3.14–3.50 (2H, m), 4.14 (2H, q, J=7.2 Hz), 4.73 (1H, t, J=7.4 Hz), 6.15 (1H, d, J=4.0 Hz), 6.60–6.66 (1H, m), 7.08–7.30 (3H, m), 7.98–8.10 (2H, m).

7) To a solution of zinc chloride (3.35 g, 24.6 mmol) in diethyl ether (70 ml) was added sodium borohydride (1.86 g, 49.1 mmol) and the mixture was stirred at room temperature for 30 min. The insoluble material was filtered off. To the filtrate was added a solution of ethyl 3-(4-fluorophenyl)-3-oxo-2-((5-(trifluoromethyl)-2-furanyl)methyl)propionate (4.40 g, 12.3 mmol) in diethyl ether (30 ml) and the mixture was stirred at room temperature for 2 hrs. 1N Hydrochloric acid was added to the reaction solution under ice-cooling for quenching, water (100 ml) was further added, and the mixture as extracted with ethyl acetate (100 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(4-fluorophenyl)-3-hydroxy-2-((5-(trifluoromethyl)-2-furanyl)methyl)propionate (3.46 g, 78%).

IR ν max$^{KBr}$cm$^{-1}$: 1717, 1607, 1561. $^1$H-NMR (CDCl$_3$)δ: 1.06 (3H, t, J=7.0 Hz), 2.90–3.22 (4H, m), 4.00 (2H, q, J=7.0 Hz), 5.00–5.08 (1H, m), 6.05 (1H, d, J=3.4 Hz), 6.58–6.64 (1H, m), 6.98–7.10 (2H, m), 7.30–7.42 (2H, m).

8) To a solution of ethyl (2RS,3RS)-3-(4-fluorophenyl)-3-hydroxy-2-((5-(trifluoromethyl)-2-furanyl)methyl) propionate (3.3 g, 9.16 mmol) in methanol (9.2 ml) was added 2N aqueous sodium hydroxide solution (9.2 ml,18.4 mmol) and the mixture was stirred overnight at room temperature. The reaction solution was acidified with 1N hydrochloric acid and extracted with ethyl acetate (100 ml×2). The extract was washed with water and saturated brine, dried over anhydrous magnesium sulfate and evaporated under reduced pressure. The residue was recrystallized from diisopropyl ether-hexane to give (2RS,3RS)-3-(4-fluorophenyl)-3-hydroxy-2-((5-(trifluoromethyl)-2-furanyl) methyl)propionic acid (2.43 g, 80%).

IR ν max$^{KBr}$cm$^{-1}$: 1715, 1563, 1513. mp 86–87° C. $^1$H-NMR (CDCl$_3$)δ: 2.92–3.22 (3H, m), 5.13 (1H, d, J=4.0 Hz), 6.06 (1H, d, J=3.2 Hz), 6.60–6.68 (1H, m), 7.00–7.16 (2H, m), 7.30–7.44 (2H, m).

9) To a solution of (2RS,3RS)-3-(4-fluorophenyl)-3-hydroxy-2-((5-(trifluoromethyl)-2-furanyl)methyl) propionic acid (2.33 g, 7.01 mmol) in tetrahydrofuran (60 ml) were added diphenylphosphoryl azide (1.66 ml, 7.71 mmol) and triethylamine (1.47 ml, 10.5 mmol) and the mixture was heated under reflux for 4 hrs. The reaction solution was allowed to stand at room temperature, water (50 ml) was added, and the extract was extracted with ethyl acetate (100 ml×2). The extract was washed successively with water and saturated brine, dried over anhydrous magnesium sulfate and evaporated under reduced pressure. The residue was purified by silica gel column chromatography (ethyl acetate) and recrystallized from ethyl acetate-hexane to give (4RS,5SR)-5-(4-fluorophenyl)-4-((5-(trifluoromethyl)-2-furanyl)methyl)-1,3-oxazolidine-2-one (1.78 mg, 77%).

IR ν max$^{KBr}$cm$^{-1}$: 1759, 1611, 1559, 1514. mp 177–179° C. $^1$H-NMR (CDCl$_3$)δ: 2.30–2.58 (2H, m), 4.32–4.50 (1H, m), 5.67 (1H, brs), 5.80 (1H, d, J=8.0 Hz), 6.00 (1H, d, J=3.6 Hz), 6.65 (1H, d, J=2.2 Hz), 7.02–7.20 (2H, m), 7.24–7.40 (2H, m).

10) To a solution of (4RS,5SR)-5-(4-fluorophenyl)-4-((5-(trifluoromethyl)-2-furanyl)methyl)-1,3-oxazolidine-2-one (1.60 g, 4.86 mmol) in acetonitrile (15 ml) were added di-t-butyl dicarbonate (1.27 g, 5.83 mmol) and dimethylaminopyridine (60 mg, 0.49 mmol) and the mixture was stirred at room temperature for 30 min. The reaction solution was concentrated, diluted with water (30 ml) and extracted with ethyl acetate (30 ml×2). The extract was washed with saturated brine, dried over anhydrous magnesium sulfate and evaporated under reduced pressure. The residue was purified by silica gel column chromatography (hexane:ethyl acetate=1:1) and recrystallized from ethyl acetate-hexane to give 1,1-dimethylethyl (4RS,5SR)-5-(4-fluorophenyl)-2-oxo-4-((5-(trifluoromethyl)-2-furanyl)methyl)-1,3-oxazolidine-3-carboxylate (1.99 g, 95%).

IR ν max$^{KBr}$cm$^{-1}$: 1823, 1728, 1615, 1559. mp 134–135° C. $^1$H-NMR (CDCl$_3$)δ: 1.55 (9H, s), 2.70–2.98 (2H, m), 4.86–4.98 (1H, m), 5.52 (1H, d, J=3.2 Hz), 5.70 (1H, d, J=7.0 Hz), 6.46–6.52 (1H, m), 6.94–7.06 (2H, m), 7.12–7.22 (2H, m).

11) To 1,1-dimethylethyl (4RS,5SR)-5-(4-fluorophenyl)-2-oxo-4-((5-(trifluoromethyl)-2-furanyl)methyl)-1,3-oxazolidine-3-carboxylate (1.91 g, 4.45 mmol) in methanol (10.7 ml) was added a methanol solution (10.7 ml, 5.35 mmol) of 0.5N sodium hydroxide under ice-cooling and the mixture was stirred at room temperature for 10 min. Water (50 ml) was added to the reaction solution and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give the title compound (1.79 g, 100%).

IR ν max$^{KBr}$cm$^{-1}$: 1692, 1561, 1510. mp 111–112° C. $^1$H-NMR (CDCl$_3$)δ: 1.39 (9H, s), 2.78–2.90 (2H, m), 3.12 (1H, brs), 4.02–4.20 (1H, m), 4.76 (1H, d, J=8.4 Hz), 4.92 (1H, brs), 6.12 (1H, d, J=3.0 Hz), 6.62–6.68 (1H, m), 7.00–7.12 (2H, m), 7.28–7.42 (2H, m).

Example 163

4-fluoro-N-((1RS,2SR)-2-(4-fluorophenyl)-2-hydroxy-1-((5-(trifluoromethyl)-2-furanyl)methyl) ethyl)-1-naphthalenecarboxamide 1) To 1,1-dimethylethyl (1RS,2SR)-2-(4-fluorophenyl)-2-hydroxy-1-((5-(trifluoromethyl)-2-furanyl)methyl) ethylcarbamate (1.70 g, 4.21 mmol) was added trifluoroacetic acid (15 ml) at 0° C. and the mixture was stirred for 10 min. The reaction solution was concentrated, diluted with water (20 ml) and extracted with ethyl acetate (20 ml×2). The extract was washed with saturated brine, dried over anhydrous magnesium sulfate and evaporated under reduced pressure. The residue was recrystallized from diisopropyl ether-hexane to give (1RS,2SR)-2-amino-1-(4-fluorophenyl)-3-(5-(trifluoromethyl)-2-furanyl)-1-propanol (1.30 g, 100%).

IR ν max$^{KBr}$cm$^{-1}$: 1605, 1558, 1510. $^1$H-NMR (CDCl$_3$)δ: 2.07 (2H, brs), 2.56 (1H, dd, J=15.0, 9.8 Hz), 2.78 (1H, dd, J=15.0, 3.6 Hz), 3.32–3.46 (1H, m), 4.66 (1H, d, J=4.8 Hz), 6.12 (1H, d, J=3.4 Hz), 6.62–6.70 (1H, m), 7.00–7.12 (2H, m), 7.30–7.42 (2H, m).

2) To a solution of (1RS,2SR)-2-amino-1-(4-fluorophenyl)-3-(5-(trifluoromethyl)-2-furanyl)-1-propanol (300 mg, 0.99 mmol) in acetonitrile (20 ml) were added 4-fluoronaphthalenecarboxylic acid (188 mg, 0.99 mmol), 1-ethyl-3-(3-dimethylaminopropyl)carbodiimide hydrochloride (283 mg, 1.48 mmol) and 1-hydroxy-1H-benzotriazole (151 mg, 0.99 mmol) and the mixture was stirred overnight at room temperature. The reaction solution was diluted with water (100 ml) and extracted with ethyl acetate (100 ml×2). The extract was washed successively with water and saturated brine, dried over anhydrous magnesium sulfate and evaporated under reduced pressure. The residue was purified by silica gel column chromatography (hexane:ethyl acetate=4:1). Recrystallization from ethyl acetate-hexane gave the title compound (191 mg, 41%).

IR $\nu$ max$^{KBr}$cm$^{-1}$: 1643, 1601, 1512. mp 153–154° C. $^1$H-NMR (CDCl$_3$)δ: 3.54 (2H, d, J=7.4 Hz), 3.23 (1H, d, J=3.4 Hz), 4.68–4.86 (1H, m), 5.06–5.12 (1H, m), 6.12–6.28 (2H, m), 6.72 (1H, d, J=2.2 Hz), 7.00–7.16 (3H, m), 7.32–7.62 (5H, m), 8.00–8.20 (2H, m).

Example 164

N-((1RS,2SR)-2-(4-fluorophenyl)-2-hydroxy-1-((5-(trifluoromethyl)-2-furanyl)methyl)ethyl)-3-phenylpropanamide To a solution of (1RS,2SR)-2-amino-1-(4-fluorophenyl)-3-(5-(trifluoromethyl)-2-furanyl)-1-propanol (300 mg, 099 mmol) in ethyl acetate (10 ml) were added 3-phenylpropionyl chloride (220 ml, 1.48 mmol) and saturated aqueous sodium hydrogen carbonate (10 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (321 mg, 75%).

IR $\nu$ max$^{HBr}$cm$^{-1}$: 1645, 1559, 1510. mp 91–92° C. $^1$H-NMR (CDCl$_3$)δ: 2.32–2.60 (2H, m), 2.73 (2H, d, J=7.6 Hz), 2.80–3.00 (2H, m), 3.10 (1H, s), 4.30–4.48 (1H, m), 4.76–4.84 (1H, m), 5.58 (1H, d, J=7.6 Hz), 6.00 (1H, d, J=3.4 Hz), 6.58–6.64 (1H, m), 6.92–7.10 (2H, m), 7.10–7.36 (7H, m).

Example 165

N-[(1RS,2SR)-1-[4-(difluoromethyl)benzyl]-2-(4-fluorophenyl)-2-hydroxyethyl]-4-fluoronaphthalene-1-carboxamide 1) methyl 4-(difluoromethyl)benzoate To a solution of (diethylamino)sulfur trifluoride (12.8 g, 79.4 mmol) in toluene (30 ml) was added a solution of methyl 4-formylbenzoate (10.86 g, 66.15 mmol) in toluene (50 ml) at −78° C. and the mixture was stirred at room temperature for 3 hrs. Aqueous sodium hydrogen carbonate solution was added to the reaction solution. The mixture was stirred and the toluene layer was separated. The aqueous layer was extracted with ethyl acetate. The collected organic layer was dried over anhydrous magnesium sulfate and the solvent was evaporated under reduced pressure. The obtained residue was purified by silica gel column chromatography (hexane/ethyl acetate=20/1–15/1) to give the objective substance.

pale-yellow solid yield 9.671 g, 79% mp 37–38° C.; $^1$H-NMR (CDCl$_3$, 200 MHz) δ 3.95 (3H, s), 6.69 (1H, t, J=56.2 Hz), 7.59 (2H, d, J=8.2 Hz), 8.13 (2H, d, J=8.4 Hz); IR (neat) 1728, 1437, 1283, 1219, 1113, 1074, 1034, 1020 cm$^{-1}$; Anal. Calcd for $C_9H_8F_2O_2$: C, 58.07; H, 4.33. Found: C, 58.31; H, 4.24.

2) 4-(difluoromethyl)benzyl alcohol

To a suspension of lithium aluminum hydride (2.86 g, 75.3 mmol) in tetrahydrofuran (50 ml) was dropwise added a solution of methyl 4-(difluoromethyl)benzoate (9.341 g, 50.18 mmol) in tetrahydrofuran (50 ml) under ice-cooling and the mixture was stirred at room temperature for 1 hr. The reaction solution was ice-cooled and water (3 ml), 15% aqueous sodium hydroxide solution (3 ml) and water (8 ml) were dropwise added successively to decompose excess lithium aluminum hydride. The mixture was stirred as it was at room temperature for 2 hrs. The resulting precipitate was removed by filtration and the precipitate was washed with ethyl acetate. The solvent of the collected filtrate was evaporated under reduced pressure. The obtained residue was purified by silica gel column chromatography (hexane/ethyl acetate=3/1–1/1) to give the objective-substance.

colorless liquid yield 7.948 g, 100% $^1$H-NMR (CDCl$_3$, 200 MHz) δ 1.78 (1H, t, J=6.0 Hz), 4.76 (2H, d, J=5.4 Hz), 6.65 (1H, t, J=56.4 Hz), 7.45 (2H, d, J=8.6 Hz), 7.52 (2H, d, J=8.6 Hz); IR (neat) 3330, 1379, 1221, 1074, 1019 cm$^{-1}$ 3) ethyl 2-[4-(difluoromethyl)benzyl]-3-(4-fluorophenyl)-3-oxopropionate To a solution of 4-(difluoromethyl)benzyl alcohol (2.65 g, 16.7 mmol) and triethylamine (3.50 ml, 25.1 mmol) in ethyl acetate (40 ml) was dropwise added a solution of methanesulfonyl chloride (2.11 g, 18.4 mmol) in ethyl acetate (10 ml) under ice-cooling and the mixture was stirred as it was for 10 min. The resulting precipitate was removed by filtration and the precipitate was washed with diethyl ether. The solvent of the collected filtrate was evaporated under reduced pressure to give a crude product of the methanesulfonic acid ester as a yellow liquid.

To a solution of ethyl (4-fluorobenzoyl)acetate (3.516 g, 16.73 mmol) in 1,2-dimethoxyethane (30 ml) was added a suspension (0.67 g, 16.7 mmol)of 60% sodium hydride in liquid paraffin under ice-cooling and the mixture was stirred as it was for 0.5 hr. A solution of the methanesulfonic acid ester obtained above in 1,2-dimethoxyethane (10 ml) was added thereto at room temperature and the mixture was stirred at room temperature for 8 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) and crystallized from hexane to give the objective substance.

white crystal yield 3.044 g, 52% mp 54–55° C.; $^1$H-NMR (CDCl$_3$, 200 MHz) δ 1.11 (3H, t, J=7.2 Hz), 3.36 (2H, d, J=7.4 Hz), 4.10 (2H, q, J=7.2 Hz), 4.57 (1H, t, J=7.5 Hz), 6.59 (1H, t, J=56.4 Hz), 7.12 (2H, t, J=8.6 Hz), 7.31 (2H, d, J=8.4 Hz), 7.41 (2H, d, J=7.8 Hz), 8.00 (2H, dd, J=5.4 Hz, 8.8 Hz); IR (KBr) 1721, 1684, 1597, 1327, 1281, 1231, 1177, 1155, 1024, 847 cm$^{-1}$; Anal. Calcd for $C_{19}H_{17}F_3O_3$: C, 65.14; H, 4.89. Found: C, 65.21; H, 4.82.

4) ethyl (2RS,3RS)-2-[4-(difluoromethyl)benzyl]-3-(4-fluorophenyl)-3-hydroxypropionate While stirring zinc chloride (2.17 g, 16.0 mmol) in diethyl ether (50 ml), sodium borohydride (1.21 g, 31.9 mmol) as added at room temperature and the mixture was stirred as it was for 2 hrs. The insoluble material of the mixture was removed by filtration (washed with diethyl ether) to give a solution of zinc borohydride in diethyl ether. To the obtained solution was added a solution of ethyl 2-[4-(difluoromethyl)

benzyl]-3-(4-fluorophenyl)-3-oxopropionate (2.794 g, 7.975 mmol) in diethyl ether (30 ml) at room temperature and the mixture was stirred as it was for 2 hrs. To the reaction solution was added dilute hydrochloric acid by small portions to decompose excess zinc borohydride and the mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 2.800 g, 100% $^1$H-NMR (CDCl$_3$, 200 MHz) δ 0.92 (3H, t, J=7.1 Hz), 2.90 (1H, d, J=2.8 Hz), 2.93–3.06 (3H, m), 3.88 (2H, q, J=7.2 Hz), 5.02 (1H, dd, J=2.6 Hz, 4.6 Hz), 6.59 (1H, t, J=56.6 Hz), 7.05 (2H, t, J=8.6 Hz), 7.17 (2H, d, J=8.0 Hz), 7.34–7.41 (4H, m); IR (neat) 3445, 1725, 1715, 1510, 1377, 1223, 1026, 839 cm$^{-1}$ 5) (2RS,3RS)-2-[4-(difluoromethyl)benzyl]-3-(4-fluorophenyl)-3-hydroxypropionic acid To a solution of ethyl (2RS,3RS)-2-[4-(difluoromethyl)benzyl]-3-(4-fluorophenyl)-3-hydroxypropionate (2.739 g, 7.774 mmol) in methanol (20 ml) and tetrahydrofuran (20 ml) was added 1N aqueous sodium hydroxide solution (15.5 ml, 15.5 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 2.232 g, 89% mp 132–133° C.; $^1$H-NMR (CDCl$_3$, 200 MHz) δ 2.95–3.10 (3H, m), 5.06 (1H, s), 6.60 (1H, t, J=56.6 Hz), 7.05 (2H, t, J 8.8 Hz), 7.16 (2H, d, J=8.0 Hz), 7.33–7.40 (4H, m); IR (KBr) 3349, 3020–2550, 1694, 1514, 1238, 1022, 841 cm$^{-1}$; Anal. Calcd for C$_{17}$H$_{15}$F$_3$O$_3$: C, 62.96; H, 4.66. Found: C, 63.04; H, 4.85.

6) (4RS,5SR)-4-[4-(difluoromethyl)benzyl]-5-(4-fluorophenyl)-1,3-oxazolidin-2-one To a solution of (2RS,3RS)-2-[4-(difluoromethyl)benzyl]-3-(4-fluorophenyl)-3-hydroxypropionic acid (2.060 g, 6.352 mmol) in-tetrahydrofuran (40 ml) were added triethylamine (1.33 ml, 9.53 mmol) and diphenylphosphoryl azide (1.92 g, 6.99 mmol) and the mixture was heated under reflux overnight. The solvent of the reaction solution was evaporated under reduced pressure. The obtained crude product was purified by silica gel column chromatography (hexane/ethyl acetate=3/1–1/1) and crystallized from diethyl ether-hexane to give the objective substance.

white crystal yield 1.888 g, 93% mp 161–162° C.; $^1$H-NMR (CDCl$_3$, 200 MHz) δ 2.22–2.38 (2H, m), 4.25 (1H, dt, J=4.8 Hz, 8.7 Hz), 5.02 (1H, br s), 5.80 (1H, d, J=8.0 Hz), 6.61, (1H, t, J=56.4 Hz), 7.09–7.19 (4H, m), 7.34 (2H, dd, J=5.2 Hz, 8.6 Hz), 7.44 (2H, d, J=8.0 Hz); IR (KBr) 3250, 1734, 1516, 1383, 1229, 1076, 1032, 849 cm$^{-1}$; Anal. Calcd for C$_{17}$H$_{14}$F$_3$NO$_2$: C, 63.55; H, 4.39; N, 4.36. Found: C, 63.63; H, 4.42; N, 4.16.

7) (1RS,2SR)-2-amino-3-[4-(difluoromethyl)phenyl]-1-(4-fluorophenyl)propan-1-ol (4RS,5SR)-4-[4-(Difluoromethyl)benzyl]-5-(4-fluorophenyl)-1,3-oxazolidin-2-one (1.705 g, 5.307 mmol) and sodium hydroxide (0.85 g, 21.2 mmol) were heated under reflux in ethanol (20 ml) and water (1 ml) for 6 hrs. The reaction solution was diluted with water and extracted twice with ethyl acetate. The collected organic layer was dried over anhydrous sodium sulfate and the solvent was evaporated under reduced pressure. The residue was crystallized from diisopropyl ether-hexane to give the objective substance.

white crystal yield 1.268 g, 81% mp 89–90° C.; $^1$H-NMR (CDCl$_3$, 200 MHz) δ 2.40 (1H, dd, J=10.3 Hz, 13.1 Hz), 2.84 (1H, d, J=14.0 Hz), 3.24–3.34 (1H, m), 4.67 (1H, d, J=4.8 Hz), 6.621 (1H, t, J=56.6 Hz), 7.08 (2H, t, J=8.8 Hz), 7.24 (2H, d, J=8.0 Hz), 7.38 (2H, dd, J=5.6 Hz, 8.6 Hz), 7.44 (2H, d, J=8.0 Hz); IR (KBr) 3350 2870, 1593, 1508, 1381, 1215, 1047, 1001, 829 cm$^{-1}$; Anal. Calcd for C$_{16}$H$_{16}$F$_3$NO: C, 65.08; H, 5.46; N, 4.74. Found: C, 65.10; H, 5.72; N, 4.47.

8) N-[(1RS,2SR)-1-[4-(difluoromethyl)benzyl]-2-(4-fluorophenyl)-2-hydroxyethyl]-4-fluoronaphthalene-1-carboxamide While stirring (1RS,2SR)-2-amino-3-[4-(difluoromethyl)phenyl]-1-(4-fluorophenyl)propan-1-ol (0.167 g, 0.566 mmol), 4-fluoro-1-naphthoate (0.11 g, 0.57,mmol) and 1-hydroxybenzotriazole hydrate (87 mg, 0.57 mmol) in acetonitrile (10 ml), 1-ethyl-3-(3-dimethylaminopropyl)carbodiimide hydrochloride (0.11 g, 0.57 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white crystal yield 0.222 g, 84% mp 212–213° C.; $^1$H-NMR (CDCl$_3$-DMSO-d$_6$, 200 MHz) δ 2.84–3.05 (2H, m), 4.71–4.85 (1H, m), 4.97–5.16 (2H, m), 6.63 (1H, t, J=56.4 Hz), 6.98–7.63 (14H, m), 8.06 (1H, d, J=8.4 Hz); IR (KBr) 3274, 1642, 1626, 1537, 1512, 1229, 1030, 837 cm$^{-1}$; Anal. Calcd for C$_{27}$H$_{21}$F$_4$NO$_2$: C, 69.37; H, 4.53; N, 3.00. Found: C, 69.11; H, 4.72; N, 2.74.

Example 166

N-[(1RS,2SR)-1-[4-(1,1-difluoroethyl)benzyl]-2-(4-fluorophenyl)-2-hydroxyethyl]-4-fluoronaphthalene-1-carboxamide 1) methyl 4-(1,1-difluoroethyl)benzoate To a solution of (diethylamino)sulfur trifluoride (10.6 g, 66.1 mmol) in toluene (30 ml) was added a solution of methyl 4-acetylbenzoate (10.58 g, 55.04 mmol) in toluene (50 ml) at −78° C. and the mixture was stirred at room temperature for 1 week and at 50° C. for 1 day. To the reaction solution was further added (diethylamino)sulfur trifluoride (5.32 g, 33.0 mmol) and the mixture was stirred at 60° C. for 3 days. Aqueous sodium hydrogen carbonate solution was added to the reaction solution. The mixture was stirred and the toluene layer was separated. The aqueous layer was extracted with ethyl acetate. The collected organic layer was dried over anhydrous magnesium sulfate and the solvent was evaporated under reduced pressure. The obtained residue was purified by silica gel column chromatography (hexane/ethyl acetate=9/1) to give the objective substance.

yellow liquid yield 3.958 g, 34% $^1$H-NMR (CDCl$_3$, 200 MHz) δ 1.41 (3H, t, J=7.1 Hz), 1.93 (3H, t, J=18.1 Hz), 4.40 (2H, q, J=7.2 Hz), 7.57 (2H, d, J=8.0 Hz), 8.10 (2H, d, J=8.0 Hz); IR (neat) 1721, 1277, 1101 cm$^{-1}$ 2) 4-(1,1-difluoroethyl)benzyl alcohol To a suspension of lithium aluminum hydride (1.03 g, 27.3 mol) in tetrahydrofuran (30 ml) was dropwise added a solution of methyl 4-(1,1-difluoroethyl)benzoate (3.894 g, 18.18 mmol) in tetrahydrofuran (50 ml) under ice-cooling and the mixture was stirred at room temperature for 1 hr. The reaction solution was ice-cooled and water (1 ml), 15% aqueous sodium hydroxide solution (1 ml) and water (2.5 ml) were dropwise added successively to decomposed excess lithium aluminum hydride. The mixture was stirred as it was at room temperature for 2 hrs. The resulting precipitate was removed by filtration and the precipitate was washed with ethyl acetate. The solvent of the collected filtrate was evaporated under reduced pressure. The obtained residue was purified by silica gel column chromatography (hexane/ethyl acetate=3/1–1/1) to give the objective substance.

colorless liquid yield 2.700 g, 86% $^1$H-NMR (CDCl$_3$, 200 MHz) δ 1.72 (1H, t, J=5.8 Hz), 1.92 (3H, t, J=18.1 Hz), 4.74 (2H, d, J=6.0 Hz), 7.42 (2H, d, J=8.4 Hz), 7.51 (2H, d, J=8.4 Hz); IR (neat) 3330, 1296, 1175, 918 cm$^{-1}$ 3) ethyl 2-[4-(1,1-difluoroethyl)benzyl]-3-(4-fluorophenyl)-3-oxopropionate To a solution of 4-(1,1-difluoroethyl)benzyl alcohol (2.65 g, 15.4 mmol) and triethylamine (3.22 ml, 23.1 mmol) in ethyl acetate (40 ml) was dropwise added a solution of methanesulfonyl chloride (1.94 g, 16.9 mmol) in ethyl acetate (10 ml) under ice-cooling and the mixture was stirred as it was for 10 min. The resulting precipitate was removed by filtration and the precipitate was washed with ethyl ether. The solvent of the collected filtrate was evaporated under reduced pressure to give a crude product of the methanesulfonic acid ester as a yellow liquid.

To a solution of ethyl (4-fluorobenzoyl)acetate (3.235 g, 15.39 mmol) in 1,2-dimethoxyethane (30 ml) was added a suspension (0.62 g, 15.4 mmol) of 60% sodium hydride in liquid paraffin under ice-cooling and the mixture was stirred as it was for 0.5 hr. A solution of the methanesulfonic acid ester obtained above in 1,2-dimethoxyethane (10 ml) was added thereto at room temperature and the mixture was stirred at room temperature for 8 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) and crystallized from hexane to give the objective substance.

white crystal yield 2.790 g, 50% mp 56–57° C.; $^1$H-NMR (CDCl$_3$, 200 MHz) δ 1.12 (3H, t, J=7.2 Hz), 1.88 (3H, t, J=18.2 Hz), 3.35 (2H, d, J=7.2 Hz), 4.11 (2H, q, J=7.2 Hz), 4.57 (1H, t, J=7.4 Hz), 7.13 (2H, t, J=8.6 Hz), 7.28 (2H, d, J=8.0 Hz), 7.40 (2H, d, J=8.0 Hz), 8.00 (2H, dd, J=5.4 Hz, 8.8 Hz); IR (KBr) 1719, 1678, 1599, 1300, 1231, 1154, 924, 847 cm$^{-1}$; Anal. Calcd for C$_{20}$H$_{19}$F$_3$O$_3$: C, 65.93; H, 5.26. Found: C, 66.03; H, 5.28.

4) ethyl (2RS,3RS)-2-[4-(1,1-difluoroethyl)benzyl]-3-(4-fluorophenyl)-3-hydroxypropionate While stirring zinc chloride (1.91 g, 14.0 mmol) in diethyl ether (50 ml), sodium borohydride (1.06 g, 28.1 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 2-[4-(1,1-difluoroethyl)benzyl]-3-(4-fluorophenyl)-3-oxopropionate (2.556 g, 7.015 mmol) in diethyl ether (30 ml) at room temperature and the mixture was stirred as it was for 2 hrs. To the reaction solution was added dilute hydrochloric acid by small portions to decompose excess zinc borohydride and the mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 2.615 g, 100% $^1$H-NMR (CDCl$_3$, 200 MHz) δ 0.92 (3H, t, J=7.1 Hz), 1.88 (3H, t, J=18.2 Hz), 2.91 (1H, d, J=2.6 Hz), 2.94–3.12 (3H, m), 3.88 (2H, q, J=7.2 Hz), 5.02 (1H, t, J=3.6 Hz), 7.05 (2H, t, J=8.6 Hz), 7.14 (2H, d, J=8.2 Hz), 7.35–7.41 (4H, m); IR (neat) 3461, 1717, 1510, 1298, 1225, 1177, 1159, 837 cm$^{-1}$ 5) (2RS,3RS)-2-[4-(1,1-difluoroethyl)benzyl]-3-(4-fluorophenyl)-3-hydroxypropionic acid To a solution of ethyl (2RS,3RS)-2-[4-(1,1-difluoroethyl) benzyl]-3-(4-fluorophenyl)-3-hydroxypropionate (2.489 g, 6.793 mmol) in methanol (20 ml) and tetrahydrofuran (20 ml) was added 1N aqueous sodium hydroxide solution (13.6 ml, 13.6 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 1.986 g, 86% mp 127–128° C.; $^1$H-NMR (CDCl$_3$, 200 MHz.) δ 1.89 (3H, t, J=18.1 Hz), 2.89–3.10 (3H, m), 5.06 (1H, d, J=3.2 Hz), 7.05 (2H, t, J=8.7 Hz), 7.13 (2H, d, J=8.4 Hz), 7.33–7.39 (4H, m); IR (KBr) 3330, 3010–2550, 1688, 1518, 1300, 1240, 1225, 1198, 839 cm$^{-1}$; Anal. Calcd for C$_{18}$H$_{17}$F$_3$O$_3$: C, 63.90; H, 5.06. Found: C, 64.09; H, 5.03.

6) (4RS,5SR)-4-[4-(1,1-difluoroethyl)benzyl]-5-(4-fluorophenyl)-1,3-oxazolidin-2-one To a-solution of (2RS,3RS)-2-[4-(1,1-difluoroethyl) benzyl]-3-(4-fluorophenyl)-3-hydroxypropionic acid (1.836 g, 5.427 mmol) in tetrahydrofuran (40 ml) were added triethylamine (1.13 ml, 8.14 mmol) and diphenylphosphoryl azide (1.64 g, 5.97 mmol) and the mixture was heated under reflux overnight. The solvent of the reaction solution was evaporated under reduced pressure, the obtained crude product was purified by silica gel column chromatography (hexane/ethyl acetate=3/1–1/1) and crystallized from diethyl ether-hexane to give the objective substance.

white crystal yield 1.704 g, 94% mp 205–206° C.; $^1$H-NMR (CDCl$_3$, 200 MHz) δ 1.90 (3H, t, J=18.2 Hz), 2.19–2.40 (2H, m), 4.23 (1H, dt, J=5.3 Hz, 8.7 Hz), 4.92 (1H, br s), 5.80 (1H, d, J=8.0 Hz), 7.09 (2H, d, J=7.6 Hz), 7.14 (2H, t, J=8.8 Hz), 7.37 (2H, dd, J=5.0 Hz, 8.4 Hz), 7.43 (2H, d, J=8.8 Hz); IR (KBr) 3245, 1732, 1385, 1300, 1231, 1107, 1011, 924 cm$^{-1}$; Anal. Calcd for C$_{18}$H$_{16}$F$_3$NO$_2$: C, 64.47; H, 4.81; N, 4.18. Found: C, 64.47; H, 4.82; N, 4.02.

7) (1RS,2SR)-2-amino-3-[4-(1,1-difluoroethyl)phenyl]-1-(4-fluorophenyl)propan-1-ol (4RS,5SR)-4-[4-(1,1-Difluoroethyl)benzyl]-5-(4-fluorophenyl)-1,3-oxazolidin-2-one (1.557 g, 4.643 mmol) and sodium hydroxide (0.74 g, 18.6 mmol) were heated under reflux in ethanol (20 ml) and water (1 ml) for 6 hrs. The reaction solution was diluted with water and extracted twice with ethyl acetate. The collected organic layer was dried over anhydrous sodium sulfate and the solvent was evaporated under reduced pressure. The residue was purified by silica gel (APS type) column chromatography (hexane/ethyl acetate=3/1-ethyl acetate) to give the objective substance.

yellow liquid yield 0.916 g, 64% $^1$H-NMR (CDCl$_3$, 200 MHz) δ 1.91 (3H, t, J=18.3 Hz), 2.38 (1H, dd, J=10.4 Hz, 13.6 Hz), 2.83 (1H, dd, J=3.0 Hz, 13.8 Hz), 3.29 (1H, ddd, J=3.3 Hz, 4.8 Hz, 10.3 Hz), 4.67 (1H, d, J=5.2 Hz), 7.08 (2H, t, J=8.8 Hz), 7.20 (2H, d, J=7.6 Hz), 7.38 (2H, dd, J=5.6 Hz, 8.4 Hz), 7.44 (2H, d, J=7.6 Hz); IR (neat) 3360–2860, 1605, 1508, 2385, 1298, 1223, 1175, 918, 826 cm$^{-1}$ 8) N-[(1RS,2SR)-1-[4-(1,1-difluoroethyl)benzyl]-2-(4-fluorophenyl)-2-hydroxyethyl]-4-fluoronaphthalene-1-carboxamide While stirring (1RS,2SR)-2-amino-3-[4-(1,1-difluoroethyl)phenyl]-1-(4-fluorophenyl)propan-1-ol (0.173 g, 0.559 mmol), 4-fluoro-1-naphthoate (0.11 g, 0.56 mmol) and 1-hydroxybenzotriazole hydrate (86 mg, 0.56 mmol) in acetonitrile (10 ml), 1-ethyl-3-(3-dimethylaminopropyl)carbodiimide hydrochloride (0.11 g, 0.56 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether to give the objective substance.

white crystal yield 0.245 g, 91% mp 220–221° C.; $^1$H-NMR (CDCl$_3$-DMSO-d$_6$, 200 MHz) δ 1.90 (3H, t, J=18.1 Hz), 2.84–3.06 (2H, m), 4.69–4.84 (1H, m)), 5.03 (1H, t, J=3.5 Hz), 5.16 (1H, d, J=3.8 Hz), 6.99–7.12 (3H, m), 7.18–7.30 (4H, m), 7.39–7.65 (7H, m), 8.06 (1H, d, J=8.4 Hz); IR (KBr) 3281, 1642, 1626, 1539, 1512, 1298, 1231, 1163, 843, 835, 758 cm$^{-1}$; Anal. Calcd for C$_{28}$H$_{23}$F$_4$NO$_2$: C, 69.85; H, 4.81; N, 2.91. Found: C, 69.70; H, 4.98; N, 2.84.

Example 167

N-[(1RS,2SR)-1-[(2,2-difluoro-1,3-benzodioxol-5-yl)methyl]-2-(4-fluorophenyl)-2-hydroxyethyl]-4-fluoronaphthalene-1-carboxamide 1) (2,2-difluoro-1,3-benzodioxol-5-yl)methanol To a suspension of lithium aluminum hydride (1.86 g, 48.9 mmol) in tetrahydrofuran (30 ml) was dropwise added a solution of 2,2-difluoro-1,3-benzodioxole-5-carboxylic acid (4.942 g, 24.45 mmol) in tetrahydrofuran (30 ml) under ice-cooling and the mixture was stirred at room temperature for 1 hr. The reaction solution was ice-cooled and water (2 ml), 15% aqueous sodium hydroxide solution (2 ml) and water (5 ml) was dropwise added successively to decompose excess lithium aluminum hydride. The mixture was stirred as it was at room temperature for 2 hrs. The resulting-precipitate was removed by filtration and the precipitate was washed with ethyl acetate. The solvent of the collected filtrate was evaporated under reduced pressure. The obtained residue was purified by silica gel column chromatography (hexane/ethyl acetate=6/1–1/1) to give the objective substance.

colorless liquid yield 3.658 g, 80% $^1$H-NMR (CDCl$_3$, 200 MHz) δ 1.73 (1H, t, J=6.0 Hz), 4.68 (2H, d, J=5.8 Hz), 7.02 (1H, d, J=8.4 Hz), 7.08 (1H, d, J=8.0 Hz), 7.23 (1H, s); IR (neat) 3318, 1501, 1449, 1238, 1148, 1036 cm$^{-1}$ 2) ethyl 2-[(2,2-difluoro-1,3-benzodioxol-5-yl)methyl]-3-(4-fluorophenyl)-3-oxopropionate To a solution of (2,2-difluoro-1,3-benzodioxol-5-yl)methanol (3.60 g, 19.1 mmol) and triethylamine (4.00 ml, 28.7 mmol) in ethyl acetate (40 ml) was dropwise added a solution of methanesulfonyl chloride (2.41 g, 21.1 mmol) in ethyl acetate (10 ml) under ice-cooling and the mixture was stirred as it was for 10 min. The resulting precipitate was removed by filtration and the precipitate was washed with diethyl ether. The solvent of the collected filtrate was evaporated under reduced pressure to give a crude product of the methanesulfonic acid ester as a yellow liquid.

To a solution of ethyl (4-fluorobenzoyl)acetate (4.024 g, 19.14 mmol) in 1,2-dimethoxyethane (30 ml) was added a suspension (0.77 g, 19.1 mmol) of 60% sodium hydride in liquid paraffin under ice-cooling and the mixture was stirred as it was for 0.5 hr. A solution of the methanesulfonic acid ester obtained above in 1,2-dimethoxyethane (10 ml) was added thereto at room temperature and the mixture was stirred at room temperature for 8 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) and crystallized from hexane to give the objective substance.

white crystal yield 5.047 g, 69% mp 66–67° C.; $^1$H-NMR (CDCl$_3$, 200 MHz) δ 1.13 (3H, t, J=7.2 Hz), 3.31 (2H, d, J=7.4 Hz), 4.11 (2H, q, J=7.2 Hz), 4.51 (1H, t, J=7.3 Hz), 6.93–6.97 (3H, m), 7.14 (2H, t, J=8.6 Hz), 8.00 (2H, dd, J=5.4 Hz, 9.0 Hz); IR (KBr) 1725, 1682, 1597, 1501, 1258, 1233, 1150 cm$^{-1}$; Anal. Calcd for C$_{19}$H$_{15}$F$_3$O$_5$: C, 60.00; H, 3.98. Found: C, 60.03; H, 4.02.

3) ethyl (2RS,3RS)-2-[(2,2-difluoro-1,3-benzodioxol-5-yl)methyl]-3-(4-fluorophenyl)-3-hydroxypropionate While stirring zinc chloride (3.50 g, 25.7 mmol) in diethyl ether (50 ml), sodium borohydride (1.94 g, 51.4 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 2-[(2,2-difluoro-1,3-benzodioxol-5-yl)methyl]-3-(4-fluorophenyl)-3-oxopropionate (4.888 g, 12.85 mmol) in diethyl ether (30 ml) at room, temperature and the mixture was stirred as it was for 2 hrs. To the reaction solution was added dilute hydrochloric acid by small portions to decompose excess zinc borohydride and the mixture was extracted twice with ethyl acetate. The collected organic layer was dried over anhydrous magnesium sulfate and the solvent was evaporated-under reduced pressure. The obtained crude product was purified by silica gel column chromatography (hexane/ethyl acetate=6/1–3/1) to give the objective substance.

colorless liquid yield 4.849 g, 99% $^1$H-NMR (CDCl$_3$, 200 MHz) δ 0.96 (3H, t, J=7.1 Hz), 2.82 (1H, d, J=2.6 Hz), 2.85–3.02 (3H, m), 3.91 (2H, q, J=7.1 Hz), 4.99 (1H, dd, J=2.5 Hz, 5.1 Hz), 6.75–6.81 (2H, m), 6.91 (1H, d, J=8.0 Hz), 7.05 (2H, t, J=8.6 Hz), 7.36 (2H, dd, J=5.3 Hz, 8.7 Hz); IR (neat) 3468, 1725, 1499, 1449, 1240, 1155, 1036, 839 cm$^{-1}$ 4) (2RS,3RS)-2-[(2,2-difluoro-1,3-benzodioxol-5-yl)methyl]-3-(4-fluorophenyl)-3-hydroxypropionic acid To a solution of ethyl (2RS,3RS)-2-[(2,2-difluoro-1,3-benzodioxol-5-yl)methyl]-3-(4-fluorophenyl)-3-hydroxypropionate (4.725 g, 12.36 mmol) in methanol (30 ml) and tetrahydrofuran (30 ml) was added 1N aqueous sodium hydroxide solution (24.7 ml, 24.7 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from hexane to give the objective substance.

white crystal yield 3.743 g, 86% mp 115–117° C.; $^1$H-NMR (CDCl$_3$, 200 MHz) δ 2.97 (3H, s), 5.03–5.06 (1H, m), 6.76 (1H, dd, J=1.6 Hz, 8.2 Hz), 6.80 (1H, s), 6.90 (1H, d, J=8.2 Hz), 7.05 (2H, t, J=8.6 Hz), 7.36 (2H, dd, J=5.4 Hz, 8.6 Hz); IR (KBr) 3333, 3100–2550, 1694, 1518, 1499, 1447, 1273, 1260, 1244, 1163, 1148, 841 cm$^{-1}$; Anal. Calcd for $C_{17}H_{13}F_3O_5$: C, 57.63; H, 3.70. Found: C, 57.64; H, 3.51.

5) (4RS,5SR)-4-[(2,2-difluoro-1,3-benzodioxol-5-yl)methyl]-5-(4-fluorophenyl)-1,3-oxazolidin-2-one To a solution of (2RS,3RS)-2-[(2,2-difluoro-1,3-benzodioxol-5-yl)methyl]-3-(4-fluorophenyl)-3-hydroxypropionic acid (3.387 g, 9.560 mmol) in tetrahydrofuran (50 ml) were added triethylamine (2.00 ml, 14.3 mmol) and diphenylphosphoryl azide (2.89 g, 10.5 mmol) and the mixture was heated under reflux overnight. The solvent of the reaction solution was evaporated under reduced pressure. The obtained crude product was purified by silica gel column chromatography (hexane/ethyl acetate= 3/1–1/1) and crystallized from diethyl ether-hexane to give the objective substance.

white crystal yield 3.144 g, 94% mp 177–178° C.; $^1$H-NMR (CDCl$_3$, 200 MHz) δ 2.16–2.35 (2H, m), 4.13–4.25 (1H, m), 5.10 (1H, br s), 5.79 (1H, d, J=7.6 Hz), 6.72 (1H, d, J=8.4 Hz), 6.74 (1H, s), 6.98 (1H, d, J=8.6 Hz), 7.14 (2H, t, J=8.6 Hz), 7.36 (2H, dd, J=5.0 Hz, 8.8 Hz); IR (KBr) 3241, 3139, 1736, 1501, 1258, 1238, 1152 cm$^{-1}$; Anal. Calcd for $C_{17}H_{12}F_3NO_4$: C, 58.13; H, 3.44; N, 3.99. Found: C, 58.16; H, 3.42; N, 3.85.

6) (1RS,2SR)-2-amino-3-(2,2-difluoro-1,3-benzodioxol-5-yl)-1-(4-fluorophenyl)propan-1-ol (4RS,5SR)-4-[(2,2-Difluoro-1,3-benzodioxol-5-yl)methyl]-5-(4-fluorophenyl)-1,3-oxazolidin-2-one (2.962 g, 8.432 mmol) and sodium hydroxide (1.35 g, 33.7 mmol) were heated under reflux in ethanol (30 ml) and water (1.5 ml) for 6 hrs. The reaction solution was diluted with water and extracted twice with ethyl acetate. The collected organic layer was dried over anhydrous sodium sulfate and the solvent was evaporated under reduced pressure. The residue was purified by silica gel (APS type) column chromatography (hexane/ethyl acetate=3/1-ethyl acetate) and crystallized from diisopropyl ether-hexane to give the objective substance.

white crystal yield 2.225 g, 81% mp. 77–78° C.; $^1$H-NMR (CDCl$_3$, 200 MHz) δ 2.36 (1H, dd, J=10.1 Hz, 13.7 Hz), 2.81 (1H, dd, J=3.1 Hz, 13.7 Hz), 3.22 (1H, ddd, J=3.2 Hz, 5.2 Hz, 10.0 Hz), 4.63 (1H, d, J=5.2 Hz), 6.82–6.87 (2H, m), 6.97 (1H, d, J=8.0 Hz), 7.08 (2H, t, J=8.8 Hz), 7.37 (2H, dd, J=5.4 Hz, 8.6 Hz); IR (KBr) 3340–2865, 1501, 1447, 1262, 1242, 1213, 1157, 1063, 779 cm$^{-1}$; Anal. Calcd for $C_{16}H_{14}F_3NO_3$: C, 59.08; H, 4.34; N, 4.31. Found: C, 59.08; H, 4.39; N, 4.10.

7) N-[(1RS,2SR)-1-[(2,2-difluoro-1,3-benzodioxol-5-yl)methyl]-2-(4-fluorophenyl)-2-hydroxyethyl]-4-fluoronaphthalene-1-carboxamide While stirring (1RS,2SR)-2-amino-3-(2,2-difluoro-1,3-benzodioxol-5-yl)-1-(4-fluorophenyl)propan-1-ol (0.167 g, 0.513 mmol), 4-fluoro-1-naphthoate (0.10 g, 0.51 mmol) and 1-hydroxybenzotriazole hydrate (79 mg, 0.51 mmol) in acetonitrile (10 ml), 1-ethyl-3-(3-dimethylaminopropyl)carbodiimide hydrochloride (0.10 g, 0.51 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.230 g, 90% mp 219–220° C.; $^1$H-NMR (CDCl$_3$-DMSO-d$_6$, 200 MHz) δ 2.85 (1H, dd, J=10.0 Hz, 14.4 Hz), 2.97 (1H, dd, J=4.2 Hz, 13.8 Hz), 4.64–4.78 (1H, m), 5.01 (1H, t, J=3.8 Hz), 5.10 (1H, d, J=3.6 Hz), 6.93–7.13 (6H, m), 7.25–7.58 (6H, m), 7.69 (1H, d, J=8.0 Hz), 8.07 (1H, d, J=8.0 Hz); IR (KBr) 3266, 1644, 1626, 1541, 1514, 1497, 1244, 1146 cm$^{-1}$; Anal. Calcd for $C_{27}H_{19}F_4NO_4$: C, 65.19; H, 3.85; N, 2.82. Found: C, 65.22; H, 3.87; N, 2.57.

Example 168 tert-butyl N-[(1RS,2SR)-2-(4-fluorophenyl)-2-hydroxy-1-[[2-(trifluoromethyl)-1,3-thiazol-5-yl]methyl]ethyl]carbamate 1) ethyl 2-(trifluoromethyl)-1,3-thiazole-5-carboxylate 2,2,2-Trifluoroacetamide (12.27 g, purity 85%, 80.8 mmol), potassium salt of ethyl chloroformylacetate (15.2 g, 80.8 mmol) and acetic acid (4.85 g, 80.8 mmol) were heated under reflux in ethanol (100 ml) overnight. The solvent of the reaction solution was evaporated under reduced pressure. The residue was diluted with aqueous sodium-hydrogen carbonate solution and extracted twice with ethyl acetate. The collected organic layer was dried over anhydrous sodium sulfate and the solvent was evaporated under reduced pressure. The residue was purified by silica gel column chromatography (hexane/ethyl acetate=9/1) to give the objective substance.

yellow liquid yield 12.72 g, 70% $^1$H-NMR (CDCl$_3$, 200 MHz) δ 1.41 (3H, t, J=7.1 Hz), 4.43 (2H, q, J=7.1 Hz), 8.49 (1H, s); IR (neat) 1728, 1522, 1304, 1285, 1246, 1196, 1152, 1094, 1038 cm$^{-1}$ 2) [2-(trifluoromethyl)-1,3-thiazol-5-yl]methanol To a suspension of lithium aluminum hydride (2.17 g, 57.1 mmol) in tetrahydrofuran (80 ml) was dropwise added a solution of ethyl 2-(trifluoromethyl)-1,3-thiazole-5-carboxylate (8.579 g, 38.10 mmol) in tetrahydrofuran (40 ml) under ice-cooling and the mixture was stirred at 0° C. 1 hr. The reaction solution was ice-cooled and water (2 ml), 15% aqueous sodium hydroxide solution (2 ml) and water (5 ml) were dropwise added successively to decompose excess lithium aluminum hydride. The mixture was stirred at room temperature as it was for 2 hrs. The resulting precipitate was removed by filtration and the precipitate was washed with ethyl acetate. The solvent of the collected filtrate was evaporated under reduced pressure. The obtained residue was purified by silica gel column chromatography (hexane/ethyl acetate=6/1–1/1) to give the objective substance.

brown liquid yield 5.499 g, 79% $^1$H-NMR (CDCl$_3$, 200 MHz) δ 2.24 (1H, t, J=5.7 Hz), 4.97 (2H, d, J=5.6 Hz), 7.82 (1H, s); IR (neat) 3308, 1532, 1456, 1333, 1312, 1196, 1144, 1036 cm$^{-1}$ 3) ethyl 3-(4-fluorophenyl)-3-oxo-2-[[2-(trifluoromethyl)-1,3-thiazol-5-yl]methyl]propionate To a solution of [2-(trifluoromethyl)-1,3-thiazol-5-yl]methanol (2.61 g, 14.3 mmol) and triethylamine (2.39 ml, 17.1 mmol) in ethyl acetate (40 ml) was dropwise added a solution of methanesulfonyl chloride (1.80 g, 15.7 mmol) in ethyl acetate (10 ml) under ice-cooling and the mixture was stirred as it was for 10 min. The resulting precipitate was removed by filtration and the precipitate was washed with diethyl ether. The solvent of the collected filtrate was evaporated under reduced pressure to give a crude product of methanesulfonic acid ester as a yellow liquid.

To a solution of ethyl (4-fluorobenzoyl)acetate (2.998 g, 14.26 mmol) in 1,2-dimethoxyethane (30 ml) was added a suspension (0.57 g, 14.3 mmol) of 60% sodium hydride in liquid paraffin under ice-cooling and the mixture was stirred as it was for 0.5 hr. A solution of the methanesulfonic acid ester obtained above in 1,2-dimethoxyethane (10 ml) was added thereto at room temperature and the mixture was stirred overnight at room temperature. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=9/1–6/1) to give the objective substance.

white crystal yield 4.275 g, 80% $^1$H-NMR (CDCl$_3$, 200 MHz) δ 1.15 (3H, t, J=7.1 Hz), 3.61 (2H, d, J=7.0 Hz), 4.15 (2H, q, J=7.1 Hz), 4.57 (1H, t, J=7.1 Hz), 7.17 (2H, t, J=8.6 Hz), 7.70 (1H, s), 8.04 (2H, dd, J=5.3 Hz, 8.9 Hz); IR (neat) 1740, 1732, 1682, 1599, 1508, 1456, 1329, 1300, 1238, 1194, 1157, 1034, 849 cm$^{-1}$ 4) ethyl (1RS,2RS)-3-(4-fluorophenyl)-3-hydroxy-2-[[2-(trifluoromethyl)-1,3-thiazol-5-yl]methyl]propionate While stirring zinc chloride (2.80 g, 20.5 mmol) in diethyl ether (50 ml), sodium borohydride (1.55 g, 41.1 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-fluorophenyl)-3-oxo-2-[[2-(trifluoromethyl)-1,3-thiazol-5-yl]methyl]propionate (3.856 g, 10.27 mmol) in diethyl ether (30 ml) at room temperature and the mixture was stirred as it was for 2 hrs. To the reaction solution was added dilute hydrochloric acid by small portions to decompose excess zinc borohydride and the mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 1.989 g, 51% $^1$H-NMR (CDCl$_3$, 200 MHz) δ 1.27 (3H, t, J=7.1 Hz), 2.64 (1H, d, J=3.0 Hz), 2.98 (1H, ddd, J=4.0 Hz, 6.2 Hz, 10.2 Hz), 3.23 (1H, dd, J=4.2 Hz, 15.2 Hz), 3.39 (1H, dd, J=10.2 Hz, 15.2 Hz), 3.99 (2H, q, J=7.1 Hz), 5.03 (1H, dd, J=2.9 Hz, 6.3 Hz), 7.06 (2H, t, J=8.6 Hz), 7.36 (2H, dd, J=5.3 Hz, 8.7 Hz), 7.59 (1H, s); IR (neat) 3409, 1726, 1510, 1454, 1329, 1300, 1225, 1192, 1150, 1034, 839 cm$^{-1}$ 5) (1RS,2RS)-3-(4-fluorophenyl)-3-hydroxy-2-[[2-(trifluoromethyl)-1,3-thiazol-5-yl]methyl]propionic acid To a solution of ethyl (1RS,2RS)-3-(4-fluorophenyl)-3-hydroxy-2-[[2-(trifluoromethyl)-1,3-thiazol-5-yl]methyl] propionate (1.883 g, 4.990 mmol) in methanol (20 ml) was added 1N aqueous sodium hydroxide solution (9.98 ml, 9.98 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The obtained crude product was purified by silica gel column chromatography (hexane/ethyl acetate=3/1–1/1) to give the objective substance.

pale-yellow liquid yield 1.420 g, 82% $^1$H-NMR (CDCl$_3$, 200 MHz) δ 3.04 (1H, ddd, J=4.0 Hz, 5.8 Hz, 9.7 Hz), 3.18 (1H, dd, J=3.6 Hz, 15.0 Hz), 3.40 (1H, dd, J=10.0 Hz, 15.4 Hz), 5.13 (1H, d, J=5.4 Hz), 7.08 (2H, t, J=8.8 Hz), 7.38 (2H, dd, J=5.4 Hz, 8.6 Hz), 7.59 (1H, s); IR (neat) 3500–2900, 1715, 1510, 1456, 1331, 1300, 1227, 1196, 1152, 1040, 841 cm$^{-1}$ 6) (4RS,5SR)-5-(4-fluorophenyl)-4-[[2-(trifluoromethyl)-1,3-thiazol-5-yl]methyl]-1,3-oxazolidin-2-one To a solution of (1RS,2RS)-3-(4-fluorophenyl)-3-hydroxy-2-[[2-(trifluoromethyl)-1,3-thiazol-5-yl]methyl] propionic acid (1.310 g, 1.310 mmol) in tetrahydrofuran (50 ml) were added triethylamine (0.78 ml, 5.63 mmol) and diphenylphosphoryl azide (1.14 g, 4.13 mmol) and the mixture was heated under reflux overnight. The solvent of the reaction solution was evaporated under reduced pressure. The obtained crude product was purified by silica gel column chromatography (hexane/ethyl acetate=3/1–1/1) to give the objective substance.

$^1$H-NMR (CDCl$_3$, 200 MHz) δ 2.58 (1H, dd, J=5.2 Hz, 15.0 Hz) 2.69 (1H, dd, J=8.8 Hz, 15.0 Hz), 4.23–4.35 (1H, m), 5.67 (1H, br s), 5.83 (1H, d, J=7.6 Hz), 7.13 (2H, t, J=8.6 Hz), 7.32 (2H, dd, J=5.2 Hz, 8.8 Hz), 7.49 (1H, s); IR (neat) 3272, 1780–1730, 1514, 1456, 1331, 1300, 1233, 1194, 1148, 1032 cm$^{-1}$ 7) tert-butyl (4RS,5SR)-5-(4-fluorophenyl)-2-oxo-4-[[2-(trifluoromethyl)-1,3-thiazol-5-yl]methyl]-1,3-oxazolidine-3-carboxylate A solution of (4RS,5SR)-5-(4-fluorophenyl)-4-[[2-(trifluoromethyl)-1,3-thiazol-5-yl]methyl]-1,3-oxazolidin-2-one (1.062 g, 3.067 mmol), di-tert-butyl dicarbonate (0.80 g, 3.68 mmol) and 4-N,N-dimethylaminopyridine (37 mg, 0.31 mmol) in acetonitrile (10 ml) was stirred overnight at room temperature. The reaction solution was diluted with ethyl acetate, washed with water, dried over anhydrous magnesium sulfate and passed through silica gel. The solvent was evaporated under reduced pressure. The obtained residue was crystallized from ethyl acetate-hexane to give the objective substance.

white crystal yield 1.186 g, 87% mp 192–193° C.; $^1$H-NMR (CDCl$_3$, 200 MHz) δ 1.55 (9H, s), 2.99 (1H, dd, J=7.4 Hz, 15.0 Hz), 3.09 (1H, dd, J=5.2 Hz, 15.4 Hz), 4.75 (1H, dt, J=4.9 Hz, 14.9 Hz), 5.73 (1H, d, J=7.0 Hz), 7.04 (1H, s), 7.06 (2H, t, J=8.6 Hz), 7.22 (2H, dd, J=5.2 Hz, 8.4 Hz); IR (KBr) 1792, 1370, 1304, 1192, 1163, 1034 cm$^{-1}$; Anal. Calcd for C$_{19}$H$_{18}$F$_4$N$_2$O$_4$S: C, 51.12; H, 4.06; N, 6.28. Found: C, 50.94; H, 4.10; N, 6.48.

8) tert-butyl N-[(1RS,2SR)-2-(4-fluorophenyl)-2-hydroxy-1-[[2-(trifluoromethyl)-1,3-thiazol-5-yl]methyl]ethyl] carbamate To a solution of tert-butyl (4RS,5SR)-5-(4-fluorophenyl)-2-oxo-4-[[2-(trifluoromethyl)-1,3-thiazol-5-yl]methyl]-1,3-oxazolidine-3-carboxylate (1.079 g, 2.417 mmol) in methanol (10 ml) and tetrahydrofuran (10 ml) was added a solution of sodium hydroxide (0.11 g, 2.66 mmol) in methanol (5 ml) under ice-cooling and the mixture was stirred at room temperature for 3 hrs. The reaction solution was diluted with ethyl acetate, washed with water, dried over anhydrous magnesium sulfate and passed through silica gel. The solvent was evaporated under reduced pressure. The obtained residue was crystallized from diisopropyl ether-hexane to give the objective substance.

white crystal yield 0.842 g, 83% mp 137–138° C.; $^1$H-NMR (CDCl$_3$, 200 MHz) δ 1.38 (9H, s), 2.61 (1H, br s), 3.07 (2H, d, J=7.0 Hz), 3.94–4.05 (1H, m), 4.76 (1H, br d, J=8.4 Hz), 4.91 (1H, br s), 7.08 (2H, t, J=8.6 Hz), 7.38 (2H, dd, J=5.4 Hz, 8.6 Hz), 7.61 (1H, s); IR (KBr) 3337, 1682, 1532, 1138, 1038 cm$^{-1}$; Anal. Calcd for C$_{18}$H$_{20}$F$_4$N$_2$O$_3$S: C, 51.42; H, 4.79; N, 6.66. Found: C, 51.50; H, 4.70; N, 6.90.

Example 169

4-fluoro-N-[(1RS,2SR)-2-(4-fluorophenyl)-2-hydroxy-1-[[2-(trifluoromethyl)-1,3-thiazol-5-yl] methyl]ethyl]naphthalene-1-carboxamide 1) (1RS,2SR)-2-amino-1-(4-fluorophenyl)-3-[2-(trifluoromethyl)-1,3-thiazol-5-yl]propan-1-ol A solution of tert-butyl N-[(1RS,2SR)-2-(4-fluorophenyl)-2-hydroxy-1-[[2-(trifluoromethyl)-1,3-thiazol-5-yl]methyl]ethyl]carbamate (0.711 g, 1.691 mmol)

and conc. hydrochloric acid (0.5 ml) in methanol (5 ml) was heated under reflux for 10 min. The reaction solution was diluted with water, alkalified with potassium carbonate and extracted twice with ethyl acetate. The collected organic layer was dried over anhydrous sodium sulfate and the solvent was evaporated under reduced pressure. The residue was purified by silica gel (APS type) column chromatography (ethyl acetate) to give the objective substance.

colorless liquid yield 0.534 g, 99% $^1$H-NMR (CDCl$_3$, 200 MHz) δ 2.82 (1H, dd, J=9.4 Hz, 14.8 Hz), 3.08–3.26 (2H, m), 4.56 (1H, d, J=5.8 Hz), 7.09 (2H, t, J=8.6 Hz), 7.36 (2H, dd, J=5.6 Hz, 8.8 Hz), 7.68 (1H, s); IR (neat) 3364, 1507, 1456, 1331, 1300, 1225, 1192, 1144, 1032, 837 cm$^{-1}$ 2) 4-fluoro-N-[(1RS,2SR)-2-(4-fluorophenyl)-2-hydroxy-1-[[2-(trifluoromethyl)-1,3-thiazol-5-yl]methyl]ethyl] naphthalene-1-carboxamide While stirring (1RS,2SR)-2-amino-1-(4-fluorophenyl)-3-[2-(trifluoromethyl)-1,3-thiazol-5-yl]propan-1-ol (0.226 g, 0.702 mmol), 4-fluoro-1-naphthoate (0.13 g, 0.71 mmol) and 1-hydroxybenzotriazole hydrate (0.11 g, 0.71 mmol) in acetonitrile (10 ml), 1-ethyl-3-(3-dimethylaminopropyl) carbodiimide hydrochloride (0.14 g, 0.71 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.301 g, 87% mp 197–198° C.; $^1$H-NMR (CDCl$_3$-DMSO-d$_6$, 200 MHz) δ 3.28 (2H, d, J=7.0 Hz), 4.62–4.76 (1H, m), 4.97 (1H, t, J=3.9 Hz), 5.18 (1H, d, J=3.2 Hz), 7.08 (2H, t, J=8.8 Hz), 7.11 (1H, d, J=9.2 Hz), 7.38 (1H, dd, J=5.4 Hz, 7.8 Hz), 7.47–7.65 (5H, m), 7.68 (1H, s), 7.80–7.86 (1H, m), 8.08–8.12 (1H, m); IR (KBr) 3264, 1642, 1626, 1601, 1535, 1512, 1454, 1331, 1300, 1227, 1192, 1140, 1040, 760 cm$^{-1}$; Anal. Calcd for C$_{24}$H$_{17}$F$_5$N$_2$O$_2$S: C, 58.53; H, 3.48; N, 5.69. Found: C, 58.30; H, 3.68; N, 5.76.

Example 170

N-((1RS,2SR)-2-(4-fluorophenyl)-2-hydroxy-1-((3-(2,2,2-trifluoroethoxy)phenyl)methyl)ethyl)-4-fluoro-1-naphthalenecarboxamide 1) To a solution of 3-hydroxytoluene (5.0 g, 46.2 mmol) in N,N-dimethylformamide (50 ml) were added 2,2,2-trifluoro-1-iodoethane (10.7 g, 50.9 mmol) and potassium carbonate (12.8 g, 92.5 mmol) and the mixture was stirred overnight at 80° C. The reaction solution was diluted with water (200 ml) and extracted with diethyl ether (300 ml×2). The extract was washed successively with water and saturated brine, dried-over anhydrous magnesium sulfate and evaporated under reduced pressure. The residue was purified by silica gel column chromatography (hexane:ethyl acetate= 10:1) to give 3-(2,2,2-trifluoroethoxy)toluene (7.60 g, 86%) as a colorless oil.

IR ν max$^{KBr}$cm$^{-1}$: 1752, 1680, 1615, 1588, 1487. $^1$H-NMR (CDCl$_3$)δ: 2.34 (3H, s), 4.33 (2H, q, J=8.0 Hz), 6.70–6.90 (3H, m), 7.20 (1H, t, J=7.6 Hz).

2) To a solution of 3-(2,2,2-trifluoroethoxy)toluene (7.34 g, 38.6 mmol) in carbon tetrachloride (100 ml) were added N-bromosuccinimide (7.56 g, 42.5 mmol) and 2,2'-azobis (isobutyronitrile) (633 mg, 3.86 mmol) and the mixture was heated under reflux overnight. The insoluble material was filtered using celite and the filtrate was concentrated to prepare a bromo form. To a solution of ethyl 3-oxo-3-(4-fluorophenyl)propionate (7.3 g, 34.7 mmol) in 1,2-dimethoxyethane (70 ml) was added sodium hydride (60% in oil, 1.39 g, 34.7 mmol) under ice-cooling and the mixture was stirred at room temperature for 30 min. To the reaction solution was dropwise added a solution of the bromo form synthesized above in 1,2-dimethoxyethane (20 ml) and the reaction solution was stirred at room temperature for 1 hr. The reaction solution was poured into water (200 ml) and extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) and recrystallized from diisopropyl ether-hexane to give ethyl-3-(4-fluorophenyl)-3-oxo-2-((3-(2,2,2-trifluoroethoxy)phenyl)methyl) propionate (4.23 g, 31%).

mp 48–49° C. IR ν max$^{KBr}$cm$^{-1}$: 1738, 1688, 1599, 1508, 1493, 1453. Anal. Calcd for C$_{20}$H$_{18}$F$_4$O$_4$: C, 60.30; H, 4.55. Found: C, 60.11; H, 4.36. $^1$H-NMR (CDCl$_3$)δ: 1.23 (3H, t, J=7.0 Hz), 3.30 (2H, d, J=7.2 Hz), 4.11 (2H, q, J=7.0 Hz), 4.30 (2H, q, J=8.0 Hz), 4.56 (1H, t, J=7.2 Hz), 6.70–6.96 (3H, m), 7.06–7.30 (3H, m), 7.92–8.10 (2H, m).

3) To a solution of zinc chloride (2.81 g, 20.6 mmol) in diethyl ether (100 ml) was added sodium borohydride (1.56 g, 41.2 mmol) and the mixture was stirred at room temperature for 30 min. The insoluble material was filtered off. To the filtrate was added a solution of ethyl 3-(4-fluorophenyl)-3-oxo-2-((3-(2,2,2-trifluoroethoxy)phenyl)methyl) propionate (4.10 g, 10.3 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(4-fluorophenyl)-3-hydroxy-2-((3-(2,2,2-trifluoroethoxy)phenyl)methyl)propionate (3.51 g, 85%) as a colorless oil.

IR ν max$^{KBr}$cm$^{-1}$: 1715, 1605, 1590, 1510. Anal. Calcd for C$_{20}$H$_{20}$F$_4$O$_4$.0.1H$_2$O: C, 59.73; H, 5.06. Found: C, 59.55; H, 5.06. $^1$H-NMR (CDCl$_3$)δ: 0.94 (3H, t, J=7.0 Hz), 2.88–3.00 (3H, m), 3.90 (2H, q, J=7.0 Hz), 4.30 (2H, q, J=8.0 Hz), 5.01 (1H, brs), 6.60–6.82 (3H, m), 7.00–7.30 (3H, m), 7.32–7.44 (2H, m).

4) To a solution of ethyl (2RS,3RS)-3-(4-fluorophenyl)-3-hydroxy-2-((3-(2,2,2-trifluoroethoxy)phenyl)methyl) propionate (3.4 g, 8.49 mmol) in methanol (15 ml) was added 2N aqueous sodium hydroxide solution (8.5 ml, 17.0 mmol) and the mixture was stirred overnight at room temperature. The reaction solution was acidified with 1N hydrochloric acid and extracted with ethyl acetate (100 ml×2). The extract was washed with water and saturated brine, dried over anhydrous magnesium sulfate and evaporated under reduced pressure. The residue was recrystallized from ethyl acetate-hexane to give (2RS,3RS)-3-(4-fluorophenyl)-3-hydroxy-2-((3-(2,2,2-trifluoroethoxy) phenyl)methyl)propionic acid (2.78 g, 88%).

mp 142–143° C. IR ν max$^{KBr}$cm$^{-1}$: 1715, 1607, 1588. Anal. Calcd for C$_{18}$H$_{16}$F$_4$O$_4$: C, 58.07; H, 4.33. Found: C, 58.00; H, 4.27. $^1$H-NMR (CDCl$_3$)δ: 2.82–3.10 (3H, m), 4.29 (2H, q, J=8.0 Hz), 5.06 (1H, d, J=4.4 Hz), 6.69 (1H, s), 6.70–7.02 (2H, m), 7.00–7.24 (3H, m), 7.30–7.44 (2H, m).

5) To a solution of (2RS,3RS)-3-(4-fluorophenyl)-3-hydroxy-2-((3-(2,2,2-trifluoroethoxy)phenyl)methyl) propionic acid (2.68 g, 7.20 mmol) in tetrahydrofuran (60 ml) were added diphenylphosphoryl azide (1.71 ml,7.92 mmol) and triethylamine (1.51 ml, 10.8 mmol) and the mixture was heated under reflux for 3 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was recrystallized from ethyl acetate-hexane to give (4RS,5SR)-5-(4-fluorophenyl)-4-((3-(2,2,2-trifluoroethoxy)phenyl)methyl)-1,3-oxazolidin-2-one (2.31 g, 87%).

mp 148–149° C. IR ν max$^{KBr}$cm$^{-1}$: 1759, 1609, 1590, 1514. Anal. Calcd for $C_{18}H_{15}F_4NO_3$: C, 58.54; H, 4.09; N, 3.79. Found: C, 58.54; H, 4.01; N, 3.88. $^1$H-NMR (CDCl$_3$)δ: 2.12–2.38 (2H, m), 4.16–4.28 (1H, m), 4.32 (1H, q, J=8.0 Hz), 5.17 (1H, brs), 5.79 (1H, d, J=8.0 Hz), 6.62 (1H, d, J=1.8 Hz), 6.72 (1H, d, J=7.6 Hz), 6.77–6.84 (1H, m), 7.04–7.42 (5H, m).

6) To a solution of (4RS,5SR)-5-(4-fluorophenyl)-4-((3-(2,2,2-trifluoroethoxy)phenyl)methyl)-1,3-oxazolidin-2-one (1.2 g, 3.25 mmol) in ethanol (10 ml) was added 8N aqueous sodium hydroxide solution (2.0 ml, 16 mmol) and the mixture was heated under reflux for 2 hrs. The reaction solution was concentrated, diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(3-(2,2,2-trifluoroethoxy)phenyl)-1-propanol (913 mg, 82%).

mp 94–95° C. IR ν max$^{KBr}$cm$^{-1}$: 1605, 1588, 1508, 1489, 1454 Anal. Calcd for $C_{17}H_{17}F_4NO_2$: C, 59.47; H, 4.99; N, 4.08. Found: C, 59.34; H, 4.87; N, 4.19. $^1$H-NMR (CDCl$_3$)δ: 2.33 (1H, dd, J=14.0, 10.6 Hz), 2.78 (1H, dd, J=14.0, 3.0 Hz), 3.20–3.34 (1H, m), 4.33 (2H, q, J=8.0 Hz), 4.66 (1H, d, J=4.6 Hz), 6.70–6.90 (3H, m), 7.00–7.16 (2H, m), 7.20–7.30 (1H, m), 7.30–7.44 (2H, m).

7) To a solution of (1RS,2SR)-2-amino-1-(4-fluorophenyl)-3-(3-(2,2,2-trifluoroethoxy)phenyl)-1-propanol (181 mg, 0.53 mmol) in acetonitrile (20 ml) were added 4-fluoronaphthalenecarboxylic acid (100 mg, 0.53 mmol), 1-ethyl-3-(3-dimethylaminopropyl)carbodiimide hydrochloride (151 mg, 0.79 mmol) and 1-hydroxy-1H-benzotriazole (81 mg, 0.53 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (206 mg, 76%).

mp 192–193° C. IR ν max$^{KBr}$cm$^{-1}$: 1642, 1626, 1601, 1512. Anal. Calcd for $C_{28}H_{22}F_5NO_3 \cdot 0.1H_2O$: C, 65.02; H, 4.32; N, 2.71. Found: C, 64.89; H, 4.43; N, 2.93. $^1$H-NMR (CDCl$_3$)δ: 2.78 (1H, dd, J=14.6, 11.0 Hz), 3.04 (1H, dd, J=14.6, 4.0 Hz), 4.28 (2H, q, J=8.0 Hz), 4.70–4.88 (1H, m), 5.09 (1H, d, J=3.8 Hz), 5.90 (1H, d, J=8.8 Hz), 6.76–7.36 (8H, m), 7.40–7.60 (4H, m), 7.77 (1H, d, J=7.6 Hz), 8.09 (1H, d, J=7.6 Hz).

Example 171

N-((1RS,2SR)-2-(4-fluorophenyl)-2-hydroxy-1-((3-(2,2,2-trifluoroethoxy)phenyl)methyl)ethyl)-6,7-dihydro-5H-benzo[a]cycloheptene-1-carboxamide To a solution of (1RS,2SR)-2-amino-1-(2-fluorophenyl)-3-(3-(2,2,2-trifluoroethoxy)phenyl)-1-propanol (183 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl)carbodiimide hydrochloride (153 mg, 0.80 mmol) and 1-hydroxy-1H-benzotriazole (81 mg, 0.53 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (225 mg, 82%).

mp 172–173° C. IR ν max$^{KBr}$cm$^{-1}$: 1636, 1605, 1588, 1510. $^1$H-NMR (CDCl$_3$)δ: 1.90–2.08 (2H, m), 2.10–2.36 (2H, m), 2.60–2.80 (3H, m), 2.97 (1H, dd, J=14.2, 4.0 Hz), 3.78 (1H, s), 4.30 (2H, q, J=8.2 Hz), 4.60–4.76 (1H, m), 5.01 (1H, d, J=3.2 Hz), 5.75 (1H, d, J=8.4 Hz), 5.82–6.00 (1H, m), 6.17 (1H, d, J=11.8 Hz), 6.77 (1H, s), 6.80–6.92 (1H, m), 6.94–7.30 (7H, m), 7.38–7.50 (2H, m).

Example 172

N-((1RS,2SR)-2-(4-fluorophenyl)-2-hydroxy-1-((3-(2,2,3,3-tetrafluoropropyloxy)phenyl)methyl)ethyl)-4-fluoro-1-naphthalenecarboxamide 1) To a solution of 3-hydroxytoluene (5.0 g, 46.2 mmol) in N,N-dimethylformamide (50 ml) were added 2,2,3,3-tetrafluoro-1-iodopropane (12.3 g, 50.9 mmol) and potassium carbonate (12.8 g, 92.5 mmol) and the mixture was stirred overnight at 80° C. The reaction solution was diluted with water (200 ml) and extracted with diethyl ether (300 ml×2). The extract was washed successively with water and saturated brine, dried over anhydrous magnesium sulfate and evaporated under reduced pressure. The residue was purified by silica gel column chromatography (hexane:ethyl acetate=10:1) to give 3-(2,2,3,3-tetrafluoropropyloxy)toluene (10.0 g, 97%) as a colorless oil.

IR ν max$^{KBr}$cm$^{-1}$: 1607, 1588, 1491, 1458. Anal. Calcd for $C_{10}H_{10}F_4O \cdot 0.2H_2O$: C, 53.20; H, 4.64 Found: C, 53.01; H, 4.40. $^1$H-NMR (CDCl$_3$)δ: 2.34 (3H, s), 4.32 (2H, tt, J=12.0, 1.6 Hz), 6.07 (1H, tt, J=53.2, 5.0 Hz), 6.70–6.90 (3H, m), 7.16–7.24 (1H, m).

2) To a solution of 3-(2,2,3,3-tetrafluoropropyloxy)toluene (7.0 g, 31.5 mmol) in carbon tetrachloride (100 ml) were added N-bromosuccinimide (6.17 g, 34.7 mmol) and 2,2'-azobis(isobutyronitrile) (517 mg, 3.15 mmol) and the mixture was heated under reflux overnight. The insoluble material was filtered using celite and the filtrate was concentrated to prepare a bromo form. To a solution of ethyl 3-(4-fluorophenyl)-3-oxopropionate (5.96 g, 28.4 mmol) in 1,2-dimethoxyethane (60 ml) was added sodium hydride (60% in oil, 1.13 g, 28.4 mmol) under ice-cooling and the mixture was stirred at room temperature for 30 min. To the reaction solution was dropwise added a solution of the bromo form synthesized above in 1,2-dimethoxyethane (20 ml) and the reaction solution was stirred at room temperature for 1 hr. The reaction solution was poured into water (200 ml) and extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) and recrystallized from diisopropyl ether-hexane to give ethyl 3-(4-fluorophenyl)-3-oxo-2-((3-(2,2,3,3-tetrafluoropropyloxy)phenyl)methyl) propionate (5.63 g, 46%).

mp 55–56° C. IR ν max$^{KBr}$cm$^{-1}$: 1738, 1688, 1599, 1508, 1489, 1449. Anal. Calcd for $C_{21}H_{19}F_5O_4$: C, 58.61; H, 4.45.

Found: C, 58.50; H, 4.41. $^1$H-NMR (CDCl$_3$)δ: 1.13 (3H, t, J=7.2 Hz), 3.30 (2H, d, J=7.2 Hz), 4.11 (2H, q, J=7.2 Hz), 4.20–4.38 (2H, m), 4.56 (1H, t, J=7.2 Hz), 6.05 (1H, tt, J=53.0, 5.0 Hz), 6.70–6.88 (2H, m), 6.91 (1H, d, J=7.2 Hz), 7.06–7.30 (3H, m), 7.92–8.08 (2H, m).

3) To a solution of zinc chloride (3.50 g, 25.6 mmol) in diethyl ether (100 ml) was added sodium borohydride (1.93 g, 51.1 mmol) and the mixture was stirred at room temperature for 30 min. The insoluble material was filtered off. To the filtrate was added a solution of ethyl 3-(4-fluorophenyl)-3-oxo-2-((3-(2,2,3,3-tetrafluoropropyloxy)phenyl)methyl) propionate (5.50 g, 12.8 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(4-fluorophenyl)-3-hydroxy-2-((3-(2,2,3,3-tetrafluoropropyloxy)phenyl)methyl)propionate (4.99 g, 90%) as a colorless oil.

IR ν max$^{KBr}$cm$^{-1}$: 1725, 1605, 1588, 1511. Anal. Calcd for C$_{21}$H$_{21}$F$_5$O$_4$: C, 58.33; H, 4.90. Found: C, 58.20; H, 4.92. $^1$H-NMR (CDCl$_3$)δ: 0.94 (3H, t, J=7.0 Hz), 2.89 (1H, d, J=2.8 Hz), 2.92–3.02 (3H, m), 3.90 (2H, q, J=7.0 Hz), 4.29 (2H, t, J=12.0 Hz), 5.02 (1H, s), 6.05 (1H, tt, J=53.0, 5.0 Hz), 6.62–6.82 (3H, m), 7.00–7.24 (3H, m), 7.32–7.44 (2H, m).

4) To a solution of ethyl (2RS,3RS)-3-(4-fluorophenyl)-3-hydroxy-2-((3-(2,2,3,3-tetrafluoropropyloxy)phenyl) methyl)propionate (4.75 g, 11.0 mmol) in methanol (40 ml) was added 2N aqueous sodium hydroxide solution (11 ml, 22.0 mmol) and the mixture was stirred overnight at room temperature. The reaction solution was acidified with 1N hydrochloric acid and extracted with ethyl acetate (100 ml×2). The extract was washed with water and saturated brine, dried over anhydrous magnesium sulfate and evaporated under reduced pressure. The residue was recrystallized from diisopropyl ether-hexane to give (2RS,3RS)-3-(4-fluorophenyl)-3-hydroxy-2-((3-(2,2,3,3-tetrafluoropropyloxy)phenyl)methyl)propionic acid (3.91 g, 88%).

mp 114–115° C. IR ν max$^{KBr}$cm$^{-1}$: 1715, 1607, 1512. Anal. Calcd for C$_{19}$H$_{17}$F$_5$O$_4$: C, 56.44; H, 4.24. Found: C, 56.52; H, 4.35. $^1$H-NMR (CDCl$_3$)δ: 2.84–3.08 (3H, m), 4.19–4.37 (2H, m), 5.06 (1H, d, J=4.4 Hz), 6.04 (1H, tt, J=53.0, 5.0 Hz), 6.60–6.68 (1H, m), 6.68–6.80 (2H, m), 7.00–7.30 (3H, m), 7.30–7.42 (2H, m).

5) To a solution of (2RS,3RS)-3-(4-fluorophenyl)-3-hydroxy-2-((3-(2,2,3,3-tetrafluoropropyloxy)phenyl) methyl)propionic acid (2.0 g, 4.95 mmol) in tetrahydrofuran (40 ml) were added diphenylphosphoryl azide (1.17 ml, 5.44 mmol) and triethylamine (1.04 ml, 7.43 mmol) and the mixture was heated under reflux for 3 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was recrystallized from ethyl acetate-hexane to give (4RS,5SR)-5-(4-fluorophenyl)-4-((3-(2,2,3,3-tetrafluoropropyloxy)phenyl)methyl)-1,3-oxazolidin-2-one (1.68 g, 85%).

mp 113–114° C. IR ν max$^{KBr}$cm$^{-1}$: 1759, 1608, 1588, 1514. Anal. Calcd for C$_{19}$H$_{16}$F$_5$NO$_3$: C, 56.89; H, 4.02; N, 3.49. Found: C, 56.99; H, 4.15; N, 3.53. $^1$H-NMR (CDCl$_3$)δ: 2.10–2.40 (2H, m), 4.18–4.40 (3H, m), 5.22 (1H, brs), 5.79 (1H, d, J=8.4 Hz), 6.05 (1H, tt, J=53.2, 5.0 Hz), 6.59 (1H, s), 6.66–6.82 (2H, m), 7.04–7.40 (5H, m).

6) To a solution of (4RS,5SR)-5-(4-fluorophenyl)-4-((3-(2,2,3,3-tetrafluoropropyloxy)phenyl)methyl)-1,3-oxazolidin-2-one (1.0 g, 2.49 mmol) in ethanol (10 ml) was added 8N aqueous sodium hydroxide solution (1.56 ml, 12.5 mmol) and the mixture was heated under reflux for 3 hrs. The reaction solution was concentrated, diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(3-(2,2,3,3-tetrafluoropropyloxy)phenyl)-1-propanol (825 mg, 88%).

mp 77–78° C. IR ν max$^{KBr}$cm$^{-1}$: 1605, 1586, 1508, 1489. Anal. Calcd for C$_{18}$H$_{18}$F$_5$NO$_2$: C, 57.60; H, 4.83; N, 3.73. Found: C, 57.62; H, 4.70; N, 3.76. $^1$H-NMR (CDCl$_3$)δ: 2.33 (1H, dd, J=14.0, 10.4 Hz), 2.79 (1H, dd, J=14.0, 3.0 Hz), 3.22–3.34 (1H, m), 4.32 (2H, t, J=12.0 Hz), 4.66 (1H, d, J=4.8 Hz), 6.06 (1H, tt, J=53.0, 5.0 Hz), 6.70–6.90 (3H, m), 7.00–7.14 (2H, m), 7.20–7.30 (1H, m), 7.30–7.44 (2H, m).

7) To a solution of (1RS,2SR)-2-amino-1-(4-fluorophenyl)-3-(3-(2,2,3,3-tetrafluoropropyloxy)phenyl)-1-propanol (197 mg, 0.53 mmol) in acetonitrile (20 ml) were added 4-fluoronaphthalenecarboxylic acid (100 mg, 0.53 mmol), 1-ethyl-3-(3-dimethylaminopropyl)carbodiimide hydrochloride (151 mg, 0.79 mmol) and 1-hydroxy-1H-benzotriazole (81 mg, 0.53 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (240 mg, 84%).

mp 160–161° C. IR ν max$^{KBr}$cm$^{-1}$: 1641, 1626, 1601, 1535, 1512. Anal. Calcd for C$_{29}$H$_{23}$F$_6$NO$_3$.0.2H$_2$O: C, 63.21; H, 4.28; N, 2.54. Found: C, 62.99; H, 4.39; N, 2.84. $^1$H-NMR (CDCl$_3$)δ: 2.79 (1H, dd, J=14.4, 10.6 Hz), 3.04 (1H, dd, J=14.4, 4.0 Hz), 4.28 (2H, t, J=12.0 Hz), 4.70–4.84 (1H, m), 5.10 (1H, d, J=4.0 Hz), 5.90 (1H, d, J=8.4 Hz), 6.01 (1H, tt, J=53.0, 5.0 Hz), 6.74–7.30 (8H, m), 7.40–7.60 (4H, m), 7.77 (1H, d, J=8.2 Hz), 8.09 (1H, d, J=7.6 Hz).

Example 173

N-(1RS,2SR)-2-(4-fluorophenyl)-2-hydroxy-1-((3-(2,2,3,3-tetrafluoropropyloxy)phenyl)methyl)ethyl)-6,7-dihydro-5H-benzo[a]cycloheptene-1-carboxamide To a solution of (1RS,2SR)-2-amino-1-(2-fluorophenyl)-3-(3-(2,2,3,3-tetrafluoropropyloxy)phenyl)-1-propanol (200 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl) carbodiimide hydrochloride (153 mg, 0.80 mmol) and 1-hydroxy-1H-benzotriazole (81 mg, 0.53 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (224 mg, 77%).

mp 169–170° C. IR ν max$^{KBr}$cm$^{-1}$: 1640, 1605, 1587, 1510. $^1$H-NMR (CDCl$_3$)δ: 1.90–2.08 (2H, m), 2.10–2.28 (2H, m), 2.60–2.80 (3H, m), 2.97 (1H, dd, J=14.6, 4.0 Hz), 3.77 (1H, brs), 4.30 (2H, t, J=12.0 Hz), 4.58–4.76 (1H, m), 5.02 (1H, d, J=3.6 Hz), 5.70–5.82 (1H, m), 5.84–5.98 (1H, m), 6.04 (1H, tt, J=53.0, 5.0 Hz), 6.17 (1H, d, J=12.0 Hz), 6.75 (1H, s), 6.78–6.90 (2H, m), 6.90–7.30 (6H, m), 7.38–7.50 (2H, m).

Example 174

4-fluoro-N-((1RS,2SR)-2-hydroxy-2-phenyl-1-((4-(trifluoromethyl)phenyl)methyl)ethyl)-1-naphthalenecarboxamide 1) To a solution of ethyl 3-oxo-3-phenylpropionate (28.6 g, 145 mmol) in 1,2-dimethoxyethane (1.50 ml) was added sodium hydride (60% in oil, 5.65 g, 141 mmol) under ice-cooling and the mixture was stirred at room temperature for 1 hr. To the reaction solution was dropwise added a solution of 4-trifluoromethylbenzyl bromide (33.8 g, 141 mmol) in 1,2-dimethoxyethane (50 ml) and the reaction solution was stirred at room temperature for 2 hrs. The reaction solution was poured into water (500 ml) and extracted with ethyl acetate (500 ml×2). The extract was washed with water and saturated brine, dried over anhydrous magnesium sulfate and evaporated under reduced pressure. The residue was purified by silica gel column chromatography (toluene) to give ethyl 3-oxo-3-phenyl-2-((4-(trifluoromethyl)phenyl)methyl)propionate (45.4 g, 75%) as a yellow oil.

IR ν max$^{KBr}$cm$^{-1}$: 1738, 1688. $^1$H-NMR (CDCl$_3$)δ: 1.11 (3H, t, J=7.2 Hz), 3.39 (2H, d, J=7.8 Hz), 4.10 (2H, q, J=7.2 Hz), 4.63 (1H, t, J=8.4 Hz), 7.10–7.64 (7H, m), 7.96 (2H, d, J=8.4 Hz).

2) To a solution of zinc chloride (14.7 g, 108 mmol) in diethyl ether (250 ml) was added sodium borohydride (8.2 g, 216 mmol) and the mixture was stirred at room temperature for 2 hrs. The insoluble material was filtered off. To the filtrate was added a solution of 3-oxo-3-phenyl-2-((4-(trifluoromethyl)phenyl)methyl)propionic acid (22 g, 54 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (toluene) to give ethyl (2RS,3RS)-3-hydroxy-3-phenyl-2-((4-(trifluoromethyl)phenyl)methyl)propionate (15.6 g, 83%) as a colorless oil.

IR ν max$^{KBr}$cm$^{-1}$: 1717. Anal. Calcd for C$_{19}$H$_{19}$F$_3$O$_3$: C, 64.77; H, 5.44. Found: C, 64.65; H, 5.67. $^1$H-NMR (CDCl$_3$) δ: 0.91 (3H, t, J=7.2 Hz), 2.96–3.10 (3H, m), 3.88 (2H, q, J=7.2 Hz), 5.00–5.08 (1H, m), 7.12–7.56 (9H, m).

3) To a solution of ethyl (2RS,3RS)-3-hydroxy-3-phenyl-2-((4-(trifluoromethyl)phenyl)methyl)propionate (10.0 g, 28.4 mmol) in methanol (40 ml) was added 2N aqueous sodium hydroxide solution (28.4 ml, 56.8 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-hydroxy-3-phenyl-2-((4-(trifluoromethyl)phenyl)methyl)propionic acid (7.87 g, 86%).

mp 138–139° C. IR ν max$^{KBr}$cm$^{-1}$: 1694. Anal. Calcd for C$_{17}$H$_{15}$F$_3$O$_3$: C, 62.96; H, 4.66. Found: C, 62.90; H, 4.89.

$^1$H-NMR (CDCl$_3$)δ: 2.90–3.12 (3H, m), 5.11 (1H, d, J=3.0 Hz), 7.17 (2H, d, J=8.0 Hz), 7.30–7.42 (5H, m), 7.46 (2H, d, J=8.0 Hz).

4) To a solution of (2RS,3RS)-3-hydroxy-3-phenyl-2-((4-(trifluoromethyl)phenyl)methyl)propionic acid (7 g, 21.6 mmol) in tetrahydrofuran (200 ml) were added diphenylphosphoryl azide (5.12 ml, 23.7 mmol) and triethylamine (4.5 ml, 32.4 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was recrystallized from ethyl acetate-hexane to give (4RS,5SR)-5-phenyl-4-((4-(trifluoromethyl)phenyl)methyl)-1,3-oxazolidin-2-one (6.5 g, 93%).

mp 158–159° C. IR ν max$^{KBr}$cm$^{-1}$: 1732. Anal. Calcd for C$_{17}$H$_{14}$F$_3$NO$_2$: C, 63.55; H, 4.39; N, 4.36. Found: C, 63.38; H, 4.60; N, 4.21. $^1$H-NMR (CDCl$_3$)δ: 2.22–2.42 (1H, m), 2.37 (1H, s), 4.20–4.34 (1H, m), 5.05 (1H, s), 5.83 (1H, d, J=8.0 Hz), 7.14 (2H, d, J=8.0 Hz), 7.30–7.50 (5H, m), 7.54 (2H, d, J=8.0 Hz).

5) To a solution of (4RS,5SR)-5-phenyl-4-((4-(trifluoromethyl)phenyl)methyl)-1,3-oxazolidin-2-one (6.0 g, 18.7 mmol) in ethanol (100 ml) was added 8N aqueous sodium hydroxide solution (11.7 ml, 93 mmol) and the mixture was heated under reflux for 4 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was recrystallized from diisopropyl ether-hexane to give (1RS,2SR)-2-amino-1-phenyl-3-(4-(trifluoromethyl)phenyl)-1-propanol (4.8 g, 87%).

mp 64–65° C. IR ν max$^{KBr}$cm$^{-1}$: 1584, 1331. Anal. Calcd for C$_{16}$H$_{16}$F$_3$NO: C, 65.08; H, 5.46; N, 4.74. Found: C, 65.05; H, 5.65; N, 4.62. $^1$H-NMR (CDCl$_3$)δ: 2.45 (1H, dd, J=13.8, 10.2 Hz), 2.91 (1H, dd, J=13.8, 2.8 Hz), 3.22–3.36 (1H, m), 4.65 (1H, d, J=5.0 Hz), 7.20–7.42 (7H, m), 7.53 (2H, d, J=8.0 Hz).

6) To a solution of (1RS,2SR)-2-amino-1-phenyl-3-(4-(trifluoromethyl)phenyl)-1-propanol (500 mg, 1.69 mmol) in acetonitrile (30 ml) were added 4-fluoronaphthalenecarboxylic acid (322 mg, 1.69 mmol), 1-ethyl-3-(3-dimethylaminopropyl)carbodiimide hydrochloride (487 mg, 2.54 mmol) and 1-hydroxy-1H-benzotriazole (259 mg, 1.69 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (ethyl acetate). Recrystallization from ethyl acetate-hexane gave the title compound (650 mg, 84%).

mp 217–218° C. IR ν max$^{KBr}$cm$^{-1}$: 1644, 1626, 1601, 1537. Anal. Calcd for C$_{27}$H$_{21}$F$_4$NO$_2$: C, 69.37; H, 4.53; N, 3.00. Found: C, 69.15; H, 4.59; N, 2.80. $^1$H-NMR (CDCl$_3$)δ: 2.89 (1H, dd, J=14.2, 10.6 Hz), 3.02–3.20 (2H, m), 4.78–4.96 (1H, m), 5.13 (1H, d, J=3.8 Hz), 4.97 (1H, d, J=9.2 Hz), 6.94–7.08 (1H, m), 7.10–7.70 (13H, m), 8.08 (1H, d, J=7.6 Hz).

Example 175

N-((1RS,2SR)-2-hydroxy-2-phenyl-1-((4-(trifluoromethyl)phenyl)methyl)ethyl)-3-phenylpropanamide To a solution of (1RS,2SR)-2-amino-1-phenyl-3-(4-(trifluoromethyl)phenyl)-1-propanol (500 mg, 1.69 mmol)

in ethyl acetate (15 ml) were added 3-phenylpropionyl chloride; (377 ml, 2.54 mmol) and saturated aqueous sodium hydrogen carbonate (15 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (628 mg, 87%).

mp 147–148° C. IR ν max$^{KBr}$cm$^{-1}$: 1632, 1547, 1537. Anal. Calcd for $C_{25}H_{24}F_3NO_2$: C, 70.24; H, 5.66; N, 3.28. Found: C, 70.28; H, 5.85; N, 3.13. $^1$H-NMR (CDCl$_3$)δ: 2.38 (2H, t, J=7.4 Hz), 2.60–2.80 (2H, m), 2.86 (2H, t, J=7.4 Hz), 3.08 (1H, d, J=4.0 Hz), 4.38–4.50 (1H, m), 4.80–4.88 (1H, m), 5.34 (1H, d, J=8.8 Hz), 7.04–7.40 (12H, m), 7.46 (2H, d, J=8.0 Hz).

Example 176

4-fluoro-N-((1RS,2SR)-2-(3-fluorophenyl)-2-hydroxy-1-((4-(trifluoromethyl)phenyl)methyl)ethyl)-1-naphthalenecarboxamide 1) To a solution of 3-fluorobenzoic acid (25.5 g, 182 mmol) in tetrahydrofuran (300 ml) was added 1,1'-carbonylbis-1H-imidazole (32.4 g, 200 mmol) and the mixture was stirred at room temperature for 30 min. Monoethyl malonate magnesium salt (27.1 g, 94.7 mmol) was added to the reaction solution and the mixture was heated under reflux for 30 min. Ethyl acetate (50 ml) and water (50 ml) were added to the reaction solution, and conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(3-fluorophenyl)-3-oxopropionate (34.6 g, 91%) as a colorless oil.

IR ν max$^{KBr}$cm$^{-1}$: 1738, 1694, 1651, 1589. Anal. Calcd for $C_{11}H_{11}FO_3$: C, 62.85; H, 5.27. Found: C, 62.76; H, 5.24. $^1$H-NMR (CDCl$_3$)δ: 1.26 (9/4H, t, J=7.0 Hz), 1.34 (3/4H, t, J=7.0 Hz), 3.97 (6/4H, s), 4.18–4.32 (2H, m), 5.66 (1/4H, s), 7.10–7.76 (4H, m).

2) To a solution of ethyl 3-(3-fluorophenyl)-3-oxopropionate (20 g, 95 mmol) in 1,2-dimethoxyethane (100 ml) was added sodium hydride (60% in oil, 3.80 g, 95 mmol) under ice-cooling and the mixture was stirred at room temperature for 30 min. To the reaction solution was dropwise added a solution of 4-trifluoromethylbenzyl bromide (22.7 g, 95 mmol) in 1,2-dimethoxyethane (50 ml) and the reaction solution was stirred at room temperature for 4 hrs. The reaction solution was poured into water (300 ml) and extracted with ethyl acetate (500 ml×2). The extract was washed with water and saturated brine, dried over anhydrous magnesium sulfate and evaporated under reduced pressure. The residue was purified by silica gel column chromatography (toluene:hexane=1:1-toluene) and recrystallized from ethyl acetate-hexane to give ethyl 3-(3-fluorophenyl)-3-oxo-2-((4-(trifluoromethyl)phenyl)methyl)propionate (28.8 g, 82%).

mp 50–51° C. IR ν max$^{KBr}$cm$^{-1}$: 1738, 1694, 1618, 1590. Anal. Calcd for $C_{19}H_{16}F_4O_3$: C, 61.96; H, 4.38. Found: C, 61.96; H, 4.33. $^1$H-NMR (CDCl$_3$)δ: 1.12 (3H, t, J=7.0 Hz), 3.39 (2H, d, J=7.4 Hz), 4.12 (2H, q, J=7.0 Hz), 4.57 (1H, t, J=7.4 Hz), 7.22–7.80 (8H, m).

3) To a solution of zinc chloride (14.8 g, 108.6 mmol) in diethyl ether (150 ml) was added sodium borohydride (8.22 g, 217 mmol) and the mixture was stirred at room temperature for 30 min. The insoluble material was filtered off. To the filtrate was added a solution of ethyl 3-(3-fluorophenyl)-3-oxo-2-((4-(trifluoromethyl)phenyl)methyl)propionate (20 g, 54.3 mmol) in diethyl ether (50 ml), and the mixture was stirred at room temperature for 30 min. 1N Hydrochloric acid was added to the reaction-solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=2:1–1:1) to give ethyl (2RS, 3RS)-3-(3-fluorophenyl)-3-hydroxy-2-((4-(trifluoromethyl)phenyl)methyl)propionate (19.4 g, 96%) as a colorless oil.

IR ν max$^{KBr}$cm$^{-1}$: 1726, 1713, 1617, 1593. Anal. Calcd for $C_{19}H_{18}F_4O_3$: C, 61.62; H, 4.90. Found: C, 61.46; H, 4.83. $^1$H-NMR (CDCl$_3$)δ: 0.94 (3H, t, J=7.0 Hz), 2.90–3.16 (4H, m), 3.91 (2H, q, J=7.0 Hz), 5.00–5.10 (1H, m), 6.92–7.40 (6H, m), 7.48 (2H, d, J=8.0 Hz).

4) To a solution of ethyl (2RS,3RS)-3-(3-fluorophenyl)-3-hydroxy-2-((4-(trifluoromethyl)phenyl)methyl)propionate (19 g, 51.3 mmol) in methanol (100 ml) was added 2N aqueous sodium hydroxide solution (51 ml, 102 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-(3-fluorophenyl)-3-hydroxy-2-((4-(trifluoromethyl)phenyl)methyl)propionic acid (15.6 g, 89%).

mp 128–129° C. IR ν max$^{KBr}$cm$^{-1}$: 1713, 1618, 1593. Anal. Calcd for $C_{17}H_{14}F_4O_3$: C, 59.65; H, 4.12. Found: C, 59.53; H, 3.85. $^1$H-NMR (CDCl$_3$)δ: 2.87–3.17 (3H, m), 5.13 (1H, s), 6.90–7.42 (6H, m), 7.47 (2H, d, J=8.0 Hz).

5) To a solution of (2RS,3RS)-3-(3-fluorophenyl)-3-hydroxy-2-((4-(trifluoromethyl)phenyl)methyl)propionic acid (10.0 g, 29.2 mmol) in tetrahydrofuran (250 ml) were added diphenylphosphoryl azide (6.9 ml, 32.1 mmol) and triethylamine (6.1 ml, 43.8 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was recrystallized from ethyl acetate-hexane to give (4RS,5SR)-5-(3-fluorophenyl)-4-((4-(trifluoromethyl)phenyl)methyl)-1,3-oxazolidin-2-one (8.88 g, 90%).

mp 143–144° C. IR ν max$^{KBr}$cm$^{-1}$: 1761, 1618, 1593. Anal. Calcd for $C_{17}H_{13}F_4NO_2$: C, 60.18; H, 3.86; N, 4.13. Found: C, 60.06; H, 3.85; N, 4.06. $^1$H-NMR (CDCl$_3$)δ: 2.24–2.48 (2H, m), 4.20–4.36 (1H, m), 5.03 (1H, s), 5.81 (1H, d, J=7.6 Hz), 7.02–7.22 (5H, m), 7.36–7.50 (1H, m), 7.56 (2H, d, J=8.0 Hz).

6) To a solution of (4RS,5SR)-5-(3-fluorophenyl)-4-((4-(trifluoromethyl)phenyl)methyl)-1,3-oxazolidin-2-one (7.0 g, 20.6 mmol) in ethanol (100 ml) was added 8N aqueous sodium hydroxide solution (12.9 ml, 103 mmol) and the mixture was heated under reflux for 4 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(3-fluorophenyl)-3-(4-(trifluoromethyl)phenyl)-1-propanol (5.43 g, 84%).

mp 81–82° C. IR ν max$^{KBr}$cm$^{-1}$: 1616, 1590. Anal. Calcd for $C_{16}H_{15}F_4NO$: C, 61.34; H, 4.83; N, 4.47. Found: C, 61.31; H, 4.81; N, 4.37. $^1$H-NMR (CDCl$_3$)δ: 0.80–1.70 (2H, br), 2.43 (1H, dd, J=13.6, 9.8 Hz), 2.83 (1H, dd, J=13.6, 2.8 Hz), 3.26–3.40 (1H, m), 4.69 (1H, d, J=4.8 Hz), 6.94–7.08 (1H, m), 7.16 (2H, d, J=8.0 Hz), 7.20–7.42 (3H, m), 7.55 (2H, d, J=8.0 Hz).

7) To a solution of (1RS,2SR)-2-amino-1-(3-fluorophenyl)-3-(4-(trifluoromethyl)phenyl)-1-propanol (450 mg, 1.44 mmol) in acetonitrile (20 ml) were added 4-fluoronaphthalenecarboxylic acid (274 mg, 1.44 mmol), 1-ethyl-3-(3-dimethylaminopropyl)carbodiimide hydrochloride (412 mg, 2.15 mmol) and 1-hydroxy-1H-benzotriazole (221 mg, 1.44 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (573 mg, 82%).

mp 200–201° C.

IR ν max$^{KBr}$cm$^{-1}$: 1644, 1626. Anal. Calcd for $C_{27}H_{20}F_5NO_2 \cdot 0.1H_2O$: C, 66.56; H, 4.18; N, 2.87. Found: C, 66.39; H, 3.99; N, 2.97. $^1$H-NMR (CDCl$_3$)δ: 2.80–3.12 (2H, m), 3.20–3.50 (1H, br), 4.72–4.90 (1H, m), 5.15 (1H, d, J=3.2 Hz), 6.02 (1H, d, J=8.0 Hz), 6.92–7.62 (12H, m), 7.67 (1H, d, J=8.0 Hz), 8.08 (1H, d, J=8.4 Hz).

Example 177

N-((1RS,2SR)-2-(3-fluorophenyl)-2-hydroxy-1-((4-(trifluoromethyl)phenyl)methyl)ethyl)-6,7-dihydro-5H-benzo[a]cycloheptene-1-carboxamide To a solution of (1RS,2SR)-2-amino-1-(3-fluorophenyl)-3-(4-(trifluoromethyl)phenyl)-1-propanol (167 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl)carbodiimide hydrochloride (153 mg, 0.80 mmol) and 1-hydroxy-1H-benzotriazole (81 mg, 0.53 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (209 mg, 81%).

mp 151–152° C. IR ν max$^{KBr}$cm$^{-1}$: 1638, 1618, 1590, 1518, 1327. Anal. Calcd for $C_{28}H_{25}F_4NO_2 \cdot 0.2H_2O$: C, 69.04; H, 5.25; N, 2.88. Found: C, 68.98; H, 5.16; N, 2.94. $^1$H-NMR (CDCl$_3$)δ: 1.90–2.10 (2H, m), 2.12–2.28 (2H, m), 2.60–2.70 (2H, m), 2.84 (1H, dd, J=14.4, 10.6 Hz), 3.00 (1H, dd, J=15.0, 4.0 Hz), 3.61 (1H, brs), 4.60–4.80 (1H, m), 5.09 (1H, brs), 5.82 (1H, d, J=8.2 Hz), 5.84–5.98 (1H, m), 6.16 (1H, d, J=11.6 Hz), 6.92–7.42 (9H, m), 7.53 (2H, d, J=8.0 Hz).

Example 178

N-((1RS,2SR)-2-(3-fluorophenyl)-2-hydroxy-1-((4-(trifluoromethyl)phenyl)methyl)ethyl)-3-phenylpropanamide To a solution of (1RS,2SR)-2-amino-1-(3-fluorophenyl)-3-(4-(trifluoromethyl)phenyl)-1-propanol (450 mg, 1.44 mmol) in ethyl acetate (20 ml) were added 3-phenylpropionyl chloride (320 ml, 2.15 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (528 mg, 83%).

mp 151–152° C. IR ν max$^{KBr}$cm$^{-1}$: 1651, 1620, 1590. Anal. Calcd for $C_{25}H_{23}F_4NO_2$: C, 67.41; H, 5.20; N, 3.14. Found: C, 67.38; H, 5.05; N, 3.10. $^1$H-NMR (CDCl$_3$)δ: 2.36–2.44 (2H, m), 2.60–2.76 (2H, m), 2.80–2.94 (2H, m), 3.20–3.28 (1H, m), 4.30–4.48 (1H, m), 4.80–4.90 (1H, m), 5.35 (1H, d, J=7.8 Hz), 6.92–7.40 (11H, m), 7.46 (2H, d, J=8.0 Hz).

Example 179

4-fluoro-N-((1RS,2SR)-2-(2-fluorophenyl)-2-hydroxy-1-((4-(trifluoromethyl)phenyl)methyl)ethyl)-1-naphthalenecarboxamide 1) To a solution of 2-fluorobenzoic acid (25.3 g, 181 mmol) in tetrahydrofuran (300 ml) was added 1,1'-carbonylbis-1H-imidazole (32.2 g, 198 mmol) and the mixture was stirred at room temperature for 30 min. To the reaction solution was added monoethyl malonate magnesium salt (27.1 g, 94.7 mmol) and the mixture was heated under reflux for 30 min. Ethyl acetate (50 ml) and water (50 ml) were added to the reaction solution, and conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(2-fluorophenyl)-3-oxopropionate (31.9 g, 84%) as a colorless oil.

IR ν max$^{KBr}$cm$^{-1}$: 1748, 1694, 1651, 1611. Anal. Calcd for $C_{11}H_{11}FO_3$: C, 62.85; H, 5.27. Found: C, 62.74; H, 5.24. $^1$H-NMR (CDCl$_3$)δ: 1.26 (3H; t, J=7.2 Hz), 3.99 (8/5H, d, J=3.6 Hz), 4.18–4.30 (2H, m), 5.85 (1/5H, s); 7.06–7.32 (4H, m), 7.32–7.52 (2/5H, m), 7.52–7.64 (8/5H, m), 7.82–8.02 (2H, m).

2) To a solution of ethyl 3-(2-fluorophenyl)-3-oxopropionate (20 g, 95 mmol) in 1,2-dimethoxyethane (100 ml) was added sodium hydride (60% in oil, 3.80 g, 95 mmol) under ice-cooling and the mixture was stirred at room temperature for 30 min. To the reaction solution was dropwise added a solution of 4-trifluoromethylbenzyl bromide (22.7 g, 95 mmol) in 1,2-dimethoxyethane (50 ml) and the reaction solution was stirred at room temperature for 4 hrs. The reaction solution was poured into water (300 ml) and extracted with ethyl acetate (500 ml×2). The extract was washed with water and saturated brine, dried over anhydrous magnesium sulfate and evaporated under reduced pressure. The residue was purified by silica gel column chromatography (toluene:hexane=1:1-toluene) to give ethyl 3-(2-fluorophenyl)-3-oxo-2-((4-(trifluoromethyl)phenyl)methyl) propionate (25.7 g, 73%) as a colorless oil.

IR ν max$^{KBr}$cm$^{-1}$: 1744, 1690. Anal. Calcd for $C_{19}H_{16}F_4O_3$: C, 61.96; H, 4.38. Found: C, 62.04; H, 4.31. $^1$H-NMR (CDCl$_3$)δ: 1.12 (3H, t, J=7.0 Hz), 3.24–3.50 (2H, m), 4.12 (2H, q, J=7.0 Hz), 4.58 (1H, t, J=7.2 Hz), 7.04–7.60 (7H, m), 7.78–7.90 (1H, m).

3) To a solution of zinc chloride (14.8 g, 108.6 mmol) in diethyl ether (150 ml) was added sodium borohydride (8.22 g, 217 mmol) and the mixture was stirred at room temperature for 30 min. The insoluble material was filtered off. To the filtrate was added a solution of ethyl 3-(2-fluorophenyl)-3-oxo-2-((4-(trifluoromethyl)phenyl)methyl)propionate (20 g, 54.3 mmol) in diethyl ether (50 ml) and the mixture was stirred at room temperature for 30 min. 1N Hydrochloric acid was added to the reaction solution under ice-cooling for quenching, water (200 ml was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=9:1–4:1) to give ethyl (2RS, 3RS)-3-(2-fluorophenyl)-3-hydroxy-2-((4-(trifluoromethyl) phenyl)methyl)propionate (16.2 g, 81%) as a colorless oil.

IR ν max$^{KBr}$cm$^{-1}$: 1717, 1618, 1586. Anal. Calcd for $C_{19}H_{18}F_4O_3$: C, 61.62; H, 4.90. Found: C, 61.51; H, 4.74. $^1$H-NMR (CDCl$_3$)δ: 0.96 (3H, t, J=7.4 Hz), 2.84–3.20 (3H, m), 3.22 (1H, d, J=3.8 Hz), 3.94 (2H, q, J=7.4 Hz), 5.30–5.40 (1H, m), 6.98–7.38 (5H, m), 7.40–7.62 (3H, m).

4) To a solution of ethyl (2RS,3RS)-3-(2-fluorophenyl)-3-hydroxy-2-((4-(trifluoromethyl)phenyl)methyl)propionate (15.7 g, 42.5 mmol) in methanol (100 ml) was added 2N aqueous sodium, hydroxide solution (43 ml, 86 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-(2-fluorophenyl)-3-hydroxy-2-((4-(trifluoromethyl)phenyl)methyl)propionic acid (11.7 g, 80%).

mp 122–123° C. IR ν max$^{KBr}$cm$^{-1}$: 1713, 1491. Anal. Calcd for $C_{17}H_{14}F_4O_3$: C, 59.65; H, 4.12. Found: C, 59.60; H, 4.03. $^1$H-NMR (CDCl$_3$)δ: 2.82–3.12 (2H, m), 3.12–3.30 (1H, m), 5.44 (1H, d, J=4.0 Hz), 6.96–7.40 (5H, m), 7.40–7.60 (3H, m).

5) To a solution of (2RS,3RS)-3-(2-fluorophenyl)-3-hydroxy-2-((4-(trifluoromethyl)phenyl)methyl)propionic acid (10.0 g, 29.2 mmol) in tetrahydrofuran (250 ml) were added diphenylphosphoryl azide (6.9 ml, 32.1 mmol) and triethylamine (6.1 ml, 43.8 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was recrystallized from ethyl acetate-hexane to give (4RS,5SR)-5-(2-fluorophenyl)-4-((4-(trifluoromethyl)phenyl)methyl)-1,3-oxazolidin-2-one (8.73 g, 88%).

mp 146–147° C. IR ν max$^{KBr}$cm$^{-1}$: 1767. Anal. Calcd for $Cl_7H_{13}F_4NO_2$: C, 60.18; H, 3.86; N, 4.13. Found: C, 59.99; H, 3.92; N, 3.90. $^1$H-NMR (CDCl$_3$)δ: 2.20–2.60 (2H, m), 4.26–4.46 (1H, m), 5.06 (1H, s), 6.05 (1H, d, J=7.8 Hz), 7.00–7.70 (8H, m).

6) To a solution of (4RS,5SR)-5-(2-fluorophenyl)-4-((4-(trifluoromethyl)phenyl)methyl)-1,3-oxazolidin-2-one (7.0 g, 20.6 mmol) in ethanol (100 ml) was added 8N aqueous sodium hydroxide solution (12.9 ml, 103 mmol) and the mixture was heated under reflux for 6 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was purified by silica gel column chromatography (ethyl acetate) to give (1RS,2SR)-2-amino-1-(2-fluorophenyl)-3-(4-(trifluoromethyl)phenyl)-1-propanol (6.2 g, 96%) as a colorless oil.

IR ν max$^{KBr}$cm$^{-1}$: 1618, 1584, 1487. Anal. Calcd for $C_{16}H_{15}F_4NO.0.1H_2O$: C, 60.99; H, 4.86; N, 4.45. Found: C, 60.90; H, 4.81; N, 4.20. $^1$H-NMR (CDCl$_3$)δ: 1.0–1.8 (2H, br), 2.41. (1H, dd, J=13.6, 11.0 Hz), 2.86 (1H, dd, J=14.0, 2.2 Hz), 3.36–3.48 (1H, m), 5.06 (1H, d, J=4.4 Hz), 7.00–7.38 (5H, m), 7.48–7.62 (3H, m).

7) To a solution of (1RS,2SR)-2-amino-1-(2-fluorophenyl)-3-(4-(trifluoromethyl)phenyl)-1-propanol (450 mg, 1.44 mmol) in acetonitrile (20 ml) were added 4-fluoronaphthalenecarboxylic acid (274 mg, 1.44 mmol), 1-ethyl-3-(3-dimethylaminopropyl)carbodiimide hydrochloride (412 mg, 2.15 mmol) and 1-hydroxy-1H-benzotriazole (221 mg, 1.44 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane:ethyl acetate=4:1). Recrystallization from ethyl acetate-hexane gave the title compound (465 mg, 67%).

mp 190–191° C. IR ν max$^{KBr}$cm$^{-1}$: 1645, 1628, 1601, 1537. Anal. Calcd for $C_{27}H_{20}F_5NO_2$: C, 66.80; H, 4.15; N, 2.89. Found: C, 66.58; H, 4.12; N, 2.79. $^1$H-NMR (CDCl$_3$)δ: 2.94 (1H, dd, J=14.2, 11.0 Hz), 3.23 (1H, dd, J=14.2, 4.0 Hz), 3.72 (1H, d, J=4.2 Hz), 4.74–4.94 (1H, m), 5.36–5.46 (1H, m), 5.96 (1H, d, J=8.4 Hz), 6.96–7.74 (13H, m), 8.08 (1H, d, J=8.4 Hz).

Example 180

N-((1RS,2SR)-2-(2-fluorophenyl)-2-hydroxy-1-((4-(trifluoromethyl)phenyl)methyl)ethyl)-3-phenylpropanamide To a solution of (1RS,2SR)-2-amino-1-(2-fluorophenyl)-3-(4-(trifluoromethyl)phenyl)-1-propanol (450 mg, 1.44 mmol) in ethyl acetate (20 ml) were added 3-phenylpropionyl chloride (320 ml, 2.15 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (497 mg, 78%).

mp 124–125° C. IR ν max$^{KBr}$cm$^{-1}$: 1651, 1620, 1520. Anal. Calcd for $C_{25}H_{23}F_4NO_2$: C, 67.41; H, 5.20; N, 3.14. Found: C, 67.30; H, 5.19; N, 2.89. $^1$H-NMR (CDCl$_3$)δ: 2.30–2.42 (2H, m), 2.66–2.98 (4H, m), 3.92–4.04 (1H, m), 4.28–4.46 (1H, m), 5.12–5.22 (1H, m), 5.39 (1H, d, J=8.8 Hz), 6.98–7.40 (10H, m), 7.40–7.56 (3H, m).

Example 181

N-((1RS,2SR)-2-(2,4-difluorophenyl)-2-hydroxy-1-((4-(trifluoromethyl)phenyl)methyl)ethyl)-4-fluoro-1-naphthalenecarboxamide 1) To a solution of 2,4-difluorobenzoic acid (10 g, 63.3 mmol) in tetrahydrofuran (150 ml) was added 1,1'- carbonylbis-1H-imidazole (11.3 g, 69.6 mmol) and the mixture was stirred at room temperature for 30 min. Monoethyl malonate magnesium salt (10 g, 34.8 mmol) was added to the reaction solution and the mixture was stirred at room temperature for 2 hrs. To the reaction solution were added ethyl acetate (50 ml) and water (50 ml), and conc. hydrochloric acid was added until the aqueous layer showed acidic pH. The reaction solution was extracted with ethyl acetate (200 ml×2). The extract-was washed with saturated brine, dried-over anhydrous magnesium sulfate and evaporated under reduced pressure. The residue was purified by silica gel column chromatography (hexane:ethyl acetate=4:1) to give ethyl 3-(2,4-difluorophenyl)-3-oxopropionate (9.85 g, 74%) as a brown oil.

IR ν max$^{KBr}$cm$^{-1}$: 1746, 1690, 1615, 1507. Anal. Calcd for $C_{11}H_{10}O_3F_2 \cdot 0.1H_2O$: C, 57.45; H, 4.47. Found: C, 57.56; H, 4.48. $^1$H-NMR (CDCl$_3$)δ: 1.26 (3H×5/6, t, J=7.4 Hz), 1.34 (3H×1/6, t, J=7.4 Hz), 3.96 (2H×5/6, d, J=4.0 Hz), 4.18–4.32 (2H, m), 5.80 (1H×1/6, s), 6.80–7.06 (2H, m), 7.80–8.06 (1H, m).

2) To a solution of ethyl 3-(2,4-difluorophenyl)-3-oxopropionate (9 g, 39.4 mmol) in 1,2-dimethoxyethane (50 ml) was added sodium hydride (60% in oil, 1.58 g, 39.4 mmol) under ice-cooling and the mixture was stirred at room temperature for 30 min. To the reaction solution was dropwise added a solution of 4-trifluoromethylbenzyl bromide (9.43 g, 39.4 mmol) in 1,2-dimethoxyethane (50 ml) and the reaction solution was stirred at room temperature for 3 hrs. The reaction solution was poured into water (200 ml) and extracted with ethyl acetate (200 ml×2). The extract was washed with water and saturated brine, dried over anhydrous magnesium sulfate and evaporated under reduced-pressure. The residue was purified by silica gel column chromatography (toluene:hexane=1:1-toluene) and recrystallized from diisopropyl ether-hexane to give ethyl 3-(2,4-difluorophenyl)-3-oxo-2-((4-(trifluoromethyl)phenyl)methyl)propionate (11.6 g, 77%).

mp 34–35° C. IR ν max$^{KBr}$cm$^{-1}$: 1742, 1690, 1613, 1593, 1499, 1429. Anal. Calcd for $C_{19}H_{15}O_3F_5$: C, 59.07; H, 3.91. Found: C, 58.86; H, 3.67. $^1$H-NMR (CDCl$_3$)δ: 1.13 (3H, t, J=7.4 Hz), 3.22–3.50 (2H, m), 4.13 (2H, q, J=7.4 Hz), 4.53 (1H, t, J=7.2 Hz), 6.80–7.02 (2H, m), 7.38 (2H, d, J=8.0 Hz), 7.52 (2H, d, J=8.0 Hz), 7.82–8.00 (1H, m).

3) To a solution of zinc chloride (7.06 g, 51.8 mmol) in *diethyl ether (100 ml) was added sodium borohydride (3.92 g, 103.5 mmol) and the mixture was stirred at room temperature for 30 min. The insoluble material was filtered off. To the filtrate was added a solution of ethyl 3-(2,4-difluorophenyl)-3-oxo-2-((4-(trifluoromethyl)phenyl)methyl)propionate (10 g, 25.9 mmol) in diethyl ether (50 ml) and the mixture was stirred at room temperature for 30 min. 1N Hydrochloric acid as added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(2,4-difluorophenyl)-3-hydroxy-2-((4-(trifluoromethyl)phenyl)methyl)propionate (8.23 g, 82%) as a colorless oil.

IR ν max$^{KBr}$cm$^{-1}$: 1713, 1618, 1505, 1420. Anal. Calcd for $C_{19}H_{17}O_3F_5 \cdot 0.2H_2O$: C, 58.23; H, 4.47. Found: C, 58.04; H, 4.60. $^1$H-NMR (CDCl$_3$)δ: 0.97 (3H, t, J=7.0 Hz), 2.80–3.18 (3H, m), 3.25 (1H, d, J=3.6 Hz), 3.95 (2H, q, J=7.0 Hz), 5.28–5.38 (1H, m), 6.72–7.00 (2H, m), 7.18 (2H, d, J=8.0 Hz), 7.48 (2H, d, J=8.0 Hz), 7.40–7.60 (1H, m).

4) To a solution of ethyl (2RS,3RS)-3-(2,4-difluorophenyl)-3-hydroxy-2-((4-(trifluoromethyl)phenyl)methyl)propionate (8.1 g, 20.8 mmol) in methanol (40 ml) was added 2N aqueous sodium hydroxide solution (20.8 ml, 41.6 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-(2,4-difluorophenyl)-3-hydroxy-2-((4-(trifluoromethyl)phenyl)methyl)propionic acid (6.0 g, 80%).

mp 120–121° C. IR ν max$^{KBr}$cm$^{-1}$: 1713, 1620, 1505, 1418. Anal. Calcd for $C_{17}H_{13}O_3F_5$: C, 56.57; H, 3.64. Found: C, 56.68; H, 3.59. $^1$H-NMR (CDCl$_3$)δ: 2.84–3.24 (3H, m), 5.38 (1H, d, J=4.0 Hz), 6.70–6.98 (2H, m), 7.16 (2H, d, J=8.0 Hz), 7.46 (2H, d, J=8.0 Hz), 7.50–7.58 (1H, m).

5) To a solution of (2RS,3RS)-3-(2,4-difluorophenyl)-3-hydroxy-2-((4-(trifluoromethyl)phenyl)methyl)propionic acid (5.0 g, 13.9 mmol) in tetrahydrofuran (150 ml) were added diphenylphosphoryl azide (3.3 ml, 15.3 mmol) and triethylamine (2.9 ml, 20.8 mmol) and the mixture was heated under reflux for 6 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate). The residue was recrystallized from ethyl acetate-hexane to give (4RS,5SR)-5-(2,4-difluorophenyl)-4-((4-(trifluoromethyl)phenyl)methyl)-1,3-oxazolidin-2-one (3.86 g, 78%).

mp 147–148° C. IR ν max$^{KBr}$cm$^{-1}$: 1767, 1622, 1607, 1507. Anal. Calcd for $C_{17}H_{12}O_2F_5N$: C, 57.15; H, 3.39; N, 3.92. Found: C, 57.12; H, 3.12; N, 3.63. $^1$H-NMR (CDCl$_3$)δ: 2.24–2.56 (2H, m), 4.28–4.44 (1H, m), 5.12 (1H, s), 5.99 (1H, d, J=7.6 Hz), 6.78–6.92 (1H, m), 6.92–7.08 (1H, m), 7.17 (2H, d, J=7.6 Hz), 7.50–7.64 (3H, m).

6) To a solution of (4RS,5SR)-5-(2,4-difluorophenyl)-4-((4-(trifluoromethyl)phenyl)methyl)-1,3-oxazolidin-2-one (3.5 g, 9.8 mmol) in ethanol (60 ml) was added 8N aqueous sodium hydroxide solution (6.1 ml, 49 mmol) and the mixture was heated under reflux for 6 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(2,4-difluorophenyl)-3-(4-(trifluoromethyl)phenyl)-1-propanol (2.27 g, 70%).

mp 99–100° C. IR ν max$^{KBr}$cm$^{-1}$: 1618, 1501, 1427, 1420. Anal. Calcd for $C_{16}H_{14}OF_5N$: C, 58.01; H, 4.26; N, 4.23. Found: C, 58.09; H, 4.14; N, 4.07. $^1$H-NMR (CDCl$_3$)δ: 2.39 (1H, dd, J=14.0, 10.6 Hz), 2.83 (1H, dd, J=14.0, 3.0 Hz), 3.36–3.48 (1H, m), 5.01 (1H, d, J=4.4 Hz), 6.78–7.00 (2H, m), 7.24 (2H, d, J=8.0 Hz), 7.54 (2H, d, J=8.0 Hz), 7.50–7.62 (1H, m).

7) To a solution of (1RS,2SR)-2-amino-1-(2,4-difluorophenyl)-3-(4-(trifluoromethyl)phenyl)-1-propanol (400 mg, 1.21 mmol) in acetonitrile (30 ml) were added 4-fluoronaphthalenecarboxylic acid (230 mg, 1.21 mmol), 1-ethyl-3-(3-dimethylaminopropyl)carbodiimide hydrochloride (347 mg, 1.81 mmol) and 1-hydroxy-1H- benzotriazole (185 mg, 1.21 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (538 mg, 89%).

mp 194–195° C. IR ν max$^{KBr}$cm$^{-1}$: 1645, 1622, 1601, 1537, 1507. Anal. Calcd for $C_{27}H_{19}O_2F_6N$: C, 64.42; H, 3.80; N, 2.78. Found: C, 64.14; H, 3.59; N, 2.63. $^1$H-NMR (CDCl$_3$)δ: 2.92 (1H, dd, J=14.6, 11.2 Hz), 3.19 (1H, dd, J=14.6, 3.8 Hz), 3.88 (1H, brs), 4.70–4.88 (1H, m), 5.33 (1H, d, J=4.0 Hz), 5.96 (1H, d, J=8.8 Hz), 6.78–7.18 (4H, m), 7.22–7.70 (8H, m), 8.08 (1H, d, J=8.4 Hz).

Example 182

N-((1RS,2SR)-2-(2,4-difluorophenyl)-2-hydroxy-1-((4-(trifluoromethyl)phenyl)methyl)ethyl)-3-phenylpropanamide To a solution of (1RS,2SR)-2-amino-1-(2,4-difluorophenyl)-3-(4-(trifluoromethyl)phenyl)-1-propanol (400 mg, 1.21 mmol) in ethyl acetate (20 ml) were added 3-phenylpropionyl chloride (269 ml, 1.81 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (498 mg, 89%).

mp 126–127° C. IR ν max$^{KBr}$cm$^{-1}$: 1645, 1620, 1503, 1427. Anal. Calcd for $C_{25}H_{22}O_2F_5N$: C, 64.79; H, 4.78; N, 3.02. Found: C, 64.82; H, 4.57; N, 2.86. $^1$H-NMR (CDCl$_3$)δ: 2.30–2.46 (2H, m), 2.64–2.92 (4H, m), 4.11 (1H, d, J=4.0 Hz), 4.22–4.38 (1H, m), 5.04–5.14 (1H, m), 5.39 (1H, d, J=8.0 Hz), 6.70–6.92 (2H, m), 7.02–7.52 (10H, m).

Example 183

N-((1RS,2SR)-2-(3,4-difluorophenyl)-2-hydroxy-1-((4-(trifluoromethyl)phenyl)methyl)ethyl)-4-fluoro-1-naphthalenecarboxamide 1) To a solution of 3,4-difluorobenzoic acid (10 g, 63.3 mmol) in tetrahydrofuran (300 ml) was added 1,1'-carbonylbis-1H-imidazole (11.3 g, 69.6 mmol) and the mixture was stirred at room temperature for 30 min. To the reaction solution was added monoethyl malonate magnesium salt (10 g, 34.8 mmol) and the mixture was stirred at room temperature for 2 hrs. To the reaction solution were added ethyl acetate (50 ml) and water (50 ml), and conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(3,4-difluorophenyl)-3-oxopropionate (10.3 g, 77%) as a brown oil.

IR ν max$^{KBr}$cm$^{-1}$: 1742, 1694, 1613, 1520, 1433. Anal. Calcd for $C_{11}H_{10}O_3F_2$: C, 57.90; H, 4.42. Found: C, 57.78; H, 4.56. $^1$H-NMR (CDCl$_3$)δ: 1.26 (3H×4/5, t, J=7.4 Hz), 1.33 (3H×1/5, t, J=7.4 Hz), 3.94 (2H×4/5, s), 4.10–4.32 (2H, m), 5.60 (1H×1/5, s), 7.12–7.34 (1H, m), 7.48–7.86 (2H, m).

2) To a solution of ethyl 3-(3,4-difluorophenyl)-3-oxopropionate (9 g, 39.4 mmol) in 1,2-dimethoxyethane (50 ml) was added sodium hydride (60% in oil, 1.58 g, 39.4 mmol) under ice-cooling and the mixture was stirred at room temperature for 30 min. To the reaction solution was dropwise added a solution of 4-trifluoromethylbenzyl bromide (9.43 g, 39.4 mmol) in 1,2-dimethoxyethane (50 ml) and the reaction solution was stirred at room temperature for 3 hrs. The reaction solution was poured into water (200 ml) and extracted with ethyl acetate (200ml×2). The extract was washed with water and saturated brine, dried over anhydrous magnesium sulfate and evaporated under reduced pressure. The residue was purified by silica gel column chromatography (toluene:hexane=1:1) and recrystallized from diisopropyl ether-hexane to give ethyl 3-(3,4-difluorophenyl)-3-oxo-2-((4-(trifluoromethyl)phenyl)methyl)propionate (10.9 g, 71%).

mp 48–49° C. IR ν max$^{KBr}$cm$^{-1}$: 1738, 1694, 1615, 1518, 1429. Anal. Calcd for $C_{19}H_{15}O_3F_5$: C, 59.07; H, 3.91. Found: C, 59.06; H, 3.87. $^1$H-NMR (CDCl$_3$)δ: 1.30 (3H, t, J=7.2 Hz), 3.38 (2H, d, J=7.2 Hz), 4.11 (2H, q, J=7.2 Hz), 4.53 (1H, t, J=7.2 Hz), 7.16–7.30 (1H, m), 7.34 (2H, d, J=8.0 Hz), 7.53 (2H, d, J=8.0 Hz), 7.70–7.90 (2H, m).

3) To a solution of zinc chloride (7.06 g, 51.8 mmol) in diethyl ether. (100 ml) was added sodium borohydride (3.92 g, 103.5 mmol) and the mixture was stirred at room temperature for 30 min. The insoluble material was filtered off. To the filtrate was added a solution of ethyl 3-(3,4-difluorophenyl)-3-oxo-2-((4-(trifluoromethyl)phenyl)methyl)propionate (10 g, 25.9 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(3,4-difluorophenyl)-3-hydroxy-2-((4-(trifluoromethyl)phenyl)methyl)propionate (9.84 g, 98%) as a colorless oil.

IR ν max$^{KBr}$cm$^{-1}$: 1715, 1620, 1520, 1435. Anal. Calcd for $C_{19}H_{17}O_3F_5.0.2H_2O$: C, 58.23; H, 4.47. Found: C, 58.07; H, 4.41. $^1$H-NMR (CDCl$_3$)δ: 0.95 (3H, t, J=7.2 Hz), 2.86–3.12 (4H, m), 3.91 (2H, q, J=7.2 Hz), 5.00–5.05 (1H, m), 7.04–7.34 (5H, m), 7.49 (2H, d, J=8.0 Hz).

4) To a solution of ethyl (2RS,3RS)-3-(3,4-difluorophenyl)-3-hydroxy-2-((4-(trifluoromethyl)phenyl)methyl)propionate (9.7 g, 25.0 mmol) in methanol (40 ml) was added 2N aqueous sodium hydroxide solution (25 ml, 50.0 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-(3,4-difluorophenyl)-3-hydroxy-2-((4-(trifluoromethyl)phenyl)methyl)propionic acid (6.7 g, 74%).

mp 76–77° C. IR ν max$^{KBr}$cm$^{-1}$: 1713, 1620, 1520, 1435. $^1$H-NMR (CDCl$_3$)δ: 2.90–3.18 (3H, m), 5.07 (1H, s), 7.04–7.34 (5H, m), 7.49 (2H, d, J=8.0 Hz).

5) To a solution of (2RS,3RS)-3-(3,4-difluorophenyl)-3-hydroxy-2-((4-(trifluoromethyl)phenyl)methyl)propionic acid (5.0 g, 13.9 mmol) in tetrahydrofuran (150 ml) were added diphenylphosphoryl azide (3.3 ml, 15.3 mmol) and triethylamine (2.9 ml, 20.8 mmol) and the mixture was heated under reflux for 6 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate). The residue was recrystallized from ethyl acetate-hexane to give (4RS,5SR)-5-(3,4-difluorophenyl)-4-((4-(trifluoromethyl)phenyl)methyl)-1,3-oxazolidin-2-one (3.81 g, 77%).

mp 157–158° C. IR ν max$^{KBr}$cm$^{-1}$: 1761, 1617, 1524. Anal. Calcd for $C_{17}H_{12}O_2F_5N$: C, 57.15; H, 3.39; N, 3.92. Found: C, 57.12; H, 3.26; N, 3.76. $^1$H-NMR (CDCl$_3$)δ: 2.24–2.44 (2H, m), 4.20–4.38 (1H, m), 5.31 (1H, s), 5.76 (1H, d, J=7.6 Hz), 7.04–7.30 (5H, m), 7.55 (2H, d, J=8.0 Hz).

6) To a solution of (4RS,5SR)-5-(3,4-difluorophenyl)-4-((4-(trifluoromethyl)phenyl)methyl)-1,3-oxazolidin-2-one (3.5 g, 9.8 mmol) in ethanol (60 ml) was added 8N aqueous sodium hydroxide solution (6.1 ml, 49 mmol) and the mixture was heated under reflux for 6 hrs. The reaction solution was concentrated, diluted with water (300 ml), and extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(3,4-difluorophenyl)-3-(4-(trifluoromethyl)phenyl)-1-propanol (2.43 g, 75%).

mp 99–100° C. IR ν max$^{KBr}$cm$^{-1}$: 1618, 1576, 1518, 1429. Anal. Calcd for $C_{16}H_{14}OF_5N$: C, 58.01; H, 4.26; N, 4.23. Found: C, 58.01; H, 3.97; N, 4.05. $^1$H-NMR (CDCl$_3$)δ: 2.41 (1H, dd, J=14.0, 10.4 Hz), 2.79 (1H, dd, J=14.0, 3.0 Hz), 3.22–3.36 (1H, m), 4.66 (1H, d, J=4.8 Hz), 7.04–7.32 (5H, m), 7.55 (2H, d, J=8.2 Hz).

7) To a solution of (1RS,2SR)-2-amino-1-(3,4-difluorophenyl)-3-(4-(trifluoromethyl)phenyl)-1-propanol (400 mg, 1.21 mmol) in acetonitrile (30 ml) were added 4-fluoronaphthalenecarboxylic acid (230 mg, 1.21 mmol), 1-ethyl-3-(3-dimethylaminopropyl)carbodiimide hydrochloride (347 mg, 1.81-mmol) and 1-hydroxy-1H-benzotriazole (185 mg, 1.21 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (522 mg, 86%).

mp 197–198° C. IR ν max$^{KBr}$cm$^{-1}$: 1642, 1626, 1601, 1522, 1424. Anal. Calcd for $C_{27}H_{19}O_2F_6N$: C, 64.42; H, 3.80; N, 2.78. Found: C, 64.20; H, 3.68; N, 2.69. $^1$H-NMR (CDCl$_3$)δ: 2.80–3.10 (2H, m), 4.64–4.84 (1H, m), 5.06–5.18 (1H, m), 6.01 (1H, d, J=8.8 Hz), 6.94–7.72 (12H, m), 8.09 (1H, d, J=8.8 Hz).

Example 184

N-((1RS,2SR)-2-(3,4-difluorophenyl)-2-hydroxy-1-((4-(trifluoromethyl)phenyl)methyl)ethyl)-3-phenylpropanamide To a solution of (1RS,2SR)-2-amino-1-(3,4-difluorophenyl)-3-(4-(trifluoromethyl)phenyl)-1-propanol (400 mg, 1.21 mmol) in ethyl acetate (20 ml) were added 3-phenylpropionyl chloride (269 ml, 1.81 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (471 mg, 84%).

mp 114–115° C. IR ν max$^{KBr}$cm$^{-1}$: 1647, 1620, 1518, 1433. Anal. Calcd for $C_{25}H_{22}O_2F_5N$: C, 64.79; H, 4.78; N, 3.02. Found: C, 64.88; H, 4.59; N, 2.90. $^1$H-NMR (CDCl$_3$)δ: 2.26–2.50 (2H, m), 2.58–2.80 (2H, m), 2.82–2.96 (2H, m), 3.36 (1H, brs), 4.22–4.40 (1H, m), 4.81 (1H, d, J=2.6 Hz), 5.34 (1H, d, J=7.2 Hz), 6.98–7.38 (10H, m), 7.47 (2H, d, J=8.0 Hz).

Example 185

N-((1RS,2SR)-2-hydroxy-2-(1-naphthalenyl)-1-((4-(trifluoromethyl)phenyl)methyl)ethyl)-1-naphthalenecarboxamide 1) To a solution of 1'-acetonaphthone (28.29 g, 0.1662 mmol) and ethanol (0.5 ml) in diethyl carbonate (200 ml) was added sodium hydride (13.3 g, 60% in oil, 0.332 mol) by small portions and the mixture was stirred at 80° C. for 1.5 hrs. The reaction solution was poured into water, acidified with dilute hydrochloric acid and extracted twice with ethyl acetate. The extract was washed with water, dried over anhydrous magnesium sulfate and evaporated under reduced pressure. The residue was purified by silica gel column chromatography (hexane:ethyl acetate=20:1–6:1) to give ethyl (1-naphthoyl)acetate (38.14 g, 95%) as a yellow liquid.

$^1$H-NMR (CDCl$_3$, 200M Hz) δ 1.21 (2.4H, t, J=7.2 Hz), 1.36 (0.6H, t, J=7.1 Hz), 4.11 (1.6H, s), 4.20 (1.6H, q, J=7.2 Hz), 4.31 (0.4H, q, J=7.1 Hz), 5.50 (0.2H, s), 7.44–7.67 (4H, m), 7.86–7.95 (2H, m), 8.03 (1H, d, J=8.0 Hz), 8.75 (1H, d, J=8.4 Hz); IR (neat) 1740, 1682, 1315, 1211, 802, 775 cm$^{-1}$ 2) To a solution of ethyl (1-naphthoyl)acetate (10.2 g, 39.9 mmol) in acetonitrile (100 ml) was added 4-(trifluoromethyl)benzyl bromide (9.54 g, 39.9 mmol) and the mixture was stirred overnight at room temperature. The reaction solution was concentrated, diluted with water (500 ml) and extracted with ethyl acetate (300 ml×2). The extract was washed with saturated brine, dried over anhydrous magnesium sulfate and evaporated under reduced pressure. The residue was purified by silica gel column chromatography (hexane:toluene=1:1). To a solution of the crude product of the obtained monoalkyl form (7.46 g, 18.63 mmol) in ether (100 ml) was added a solution of $Zn(NH_4)_2$ in ether (100 ml), which was prepared from zinc chloride (5.07 g, 37.3 mmol) and sodium borohydride (2.82 g, 74.5 mmol), and the mixture was stirred at room temperature for 30 min. The reaction solution was ! poured into 1N aqueous hydrochloric acid solution (100 ml) and extracted with ethyl acetate (300 ml×2). The extract was washed with saturated brine, dried over anhydrous magnesium sulfate and evaporated under reduced pressure. The residue was purified by silica gel column chromatography (toluene). To a solution of the crude product of the obtained reduced compound (3.74 g, 9.29 mmol) in methanol (40 ml) was added 1N aqueous sodium hydroxide solution (20 ml, 20 mmol) and the mixture was stirred at room temperature for 4 hrs. The reaction solution was poured into 1N aqueous hydrochloric acid solution (40 ml) and extracted with ethyl acetate (100 ml×2). The extract was washed with saturated brine, dried over anhydrous magnesium sulfate and evaporated under reduced pressure. The residue was recrystallized from diisopropyl ether-hexane to give (2RS,3RS)-3-hydroxy-3-(1- naphthalenyl)-2-((4-(trifluoromethyl)phenyl)methyl) propionic acid (2.48 g, 16%).

mp 151–152° C. IR ν max$^{KBr}$cm$^{-1}$: 1713. Anal. Calcd for $C_{21}H_{17}F_3O_3.0.1H_2O$: C, 67.05; H, 4.61. Found: C, 67.02; H, 4.45. $^1$H-NMR (CDCl$_3$)δ: 2.87 (1H, d, J=14.0 Hz), 3.10–3.40 (2H, m), 6.04 (1H, d, J=2.8 Hz), 6.98 (2H, d, J=8.0 Hz), 7.34 (2H, d, J=8.0 Hz), 7.42–7.62 (3H, m), 7.72–7.98 (3H, m), 8.03 (1H, d, J=9.2 Hz).

3) To a solution of (2RS,3RS)-3-hydroxy-3-(1-naphthalenyl)-2-((4-(trifluoromethyl)phenyl)methyl) propionic acid (2.64 g, 7.05 mmol) in tetrahydrofuran (50 ml) were added diphenylphosphoryl azide (1.67 ml, 7.76 mmol) and triethylamine (1.5 ml, 10.6 mmol) and the mixture was heated under reflux for 1 hr. The reaction solution was diluted with water (300 ml) and extracted with ethyl acetate (200 ml×2). The extract was washed with saturated brine, dried over anhydrous magnesium sulfate and evaporated under reduced, pressure. The residue was recrystallized from ethyl acetate-hexane to give (4RS,5SR)-5-(1-naphthalenyl)-4-((4-(trifluoromethyl)phenyl)methyl)-1,3-oxazolidin-2-one (2.19 g, 84%).

mp 202–203° C. IR ν max$^{KBr}$cm$^{-1}$: 1761. Anal. Calcd for $C_{21}H_{16}F_3NO_2$: C, 67.92; H, 4.34; N, 3.77. Found: C, 67.90; H, 4.15; N, 3.63. $^1$H-NMR (CDCl$_3$)δ: 2.15 (1H, dd, J=13.6, 4.4 Hz), 2.37 (1H, dd, J=13.6, 10.2 Hz), 4.46–4.64 (1H, m), 5.38 (1H, brs), 6.53 (1H, d, J=7.6 Hz), 6.97 (2H, d, J=8.0 Hz), 7.39 (2H, d, J=8.0 Hz), 7.46–7.80 (4H, m), 7.80–8.00 (3H, m).

4) To a solution of (4RS,5SR)-5-(1-naphthalenyl)-4-((4-(trifluoromethyl)phenyl)methyl)-1,3-oxazolidin-2-one (2.10 g, 5.66 mmol) in ethanol (30 ml) was added 8N aqueous sodium hydroxide solution (3.53 ml, 28.3 mmol) and the mixture was heated under reflux for 1 hr. The reaction solution was concentrated, diluted with water (100 ml) and extracted with ethyl acetate (100 ml×2). The extract was washed with saturated brine, dried over anhydrous magnesium sulfate and evaporated under-reduced pressure. To a solution of the residue in ethyl acetate (100 ml) was added a solution of HCl in ethyl acetate and the solvent was concentrated. The obtained crude crystals were washed with ether to give (1RS,2SR)-1-hydroxy-1-(1-naphthalenyl)-3-(4-(trifluoromethyl)phenyl)-2-propylamine hydrochloride (1.56 g, 72%).

mp 229–230° C. IR ν max$^{KBr}$cm$^{-1}$: 1761. Anal. Calcd for $C_{20}H_{19}ClF_3NO.0.1H_2O$: C, 62.62; H, 5.04; N, 3.65. Found: C, 62.44; H, 5.07; N, 3.88. $^1$H-NMR (CD$_3$OD)δ: 2.80–3.04 (2H, m), 3.96–4.10 (1H, m), 5.93 (1H, d, J=2.6 Hz), 7.02 (2H, d, J=8.0 Hz), 7.37 (2H, d, J=8.0 Hz), 7.46–7.62 (3H, m), 7.78–7.96 (3H, m), 8.07 (1H, d, J=8.0 Hz).

5) A solution of (1RS,2SR)-1-hydroxy-1-(1-naphthalenyl)-3-(4-(trifluoromethyl)phenyl)-2-propylamine hydrochloride (150 mg, 0.39 mmol) in ethyl acetate (5 ml) were added 1-naphthoyl chloride (89 ml, 0.59 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (172 mg, 88%).

mp 217–218° C. IR ν max$^{KBr}$cm$^{-1}$: 1615, 1591, 1537, 1526. Anal. Calcd for $C_{31}H_{24}F_3NO_2$: C, 74.54; H, 4.84; N; 2.80. Found: C, 74.33; H, 4.96; N, 2.76. $^1$H-NMR (CDCl$_3$)δ: 2.80–3.14 (3H, m), 4.94–5.12 (1H, m), 6.04 (1H, brs), 6.32 (1H, d, J=8.8 Hz), 7.17 (2H, d, J=8.2 Hz), 7.20–8.00 (15H, m), 8.45 (1H, d, J=8.4 Hz).

Example 186

4-fluoro-N-((1RS,2SR)-2-hydroxy-2-(1-naphthalenyl)-1-((4-(trifluoromethyl)phenyl)methyl)ethyl)-1-naphthalenecarboxamide To a solution of 4-fluoronaphthalene-1-carboxylic acid (112 mg, 0.59 mmol) in tetrahydrofuran (5 ml) were added oxalyl chloride (0.10 ml, 1.18 mmol) and N,N-dimethylformamide (0.01 ml) and the mixture was stirred at room temperature for 30 min. The reaction solution was evaporated under reduced pressure. To a solution of the residue in ethyl acetate (5 ml) were added (1RS,2SR)-1-hydroxy-1-(1-naphthalenyl)-3-(4-(trifluoromethyl)phenyl)-2-propylamine hydrochloride (150 mg, 0.39 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1). Recrystallization from ethyl acetate-hexane gave the title compound (147 mg, 72%).

mp 195–196° C. IR ν max$^{KBr}$cm$^{-1}$: 1644, 1620, 1514. Anal. Calcd for $C_{31}H_{23}F_4NO_2$: C, 71.95; H, 4.48; N, 2.71. Found: C, 71.67; H, 4.63; N, 2.56; $^1$H-NMR (CDCl$_3$)δ: 2.78 (1H, d, J=3.0 Hz), 2.80–3.16 (2H, m), 4.96–5.14 (1H, m), 6.05 (1H, s), 6.27 (1H, d, J=8.8 Hz), 6.98–7.10 (1H, m), 7.14–7.30 (3H, m), 7.40–8.00 (11H, m), 8.09 (1H, d, J=8.4 Hz), 8.44 (1H, d, J=8.4 Hz).

Example 187

N-((1RS,2SR)-2-hydroxy-2-(1-naphthalenyl)-1-((4-(trifluoromethyl)phenyl)methyl)ethyl)-2-naphthalenecarboxamide To a solution of (1RS,2SR)-1-hydroxy-1-(1-naphthalenyl)-3-(4-(trifluoromethyl)phenyl)-2-propylamine hydrochloride (150 mg, 0.39 mmol) in ethyl acetate (5 ml) were added 2-naphthoyl chloride (112 mg, 0.59 mmol) and saturated aqueous sodium hydrogen carbonate (5 ml) and the mixture was stirred overnight at room temperature. The reaction solution diluted with water (50 ml) and extracted with ethyl acetate (50 ml×2). The extract was washed with saturated brine, dried over anhydrous magnesium sulfate and evaporated under-reduced pressure. The residue was recrystallized from ethyl acetate-hexane to give the title compound (160 mg, 82%).

mp 251–252° C. IR ν max$^{KBr}$cm$^{-1}$: 1644, 1620. Anal. Calcd for $C_{31}H_{24}F_3NO_2$: C, 74.54; H, 4.84; N, 2.80. Found: C, 74.25; H, 4.56; N, 2.75. $^1$H-NMR (CDCl$_3$)δ: 2.82–3.30 (3H, m), 4.80–5.00 (1H, m), 6.08 (1H, s), 6.59 (1H, d, J=7.4 Hz), 7.15 (2H, d, J=8.2 Hz), 7.40 (2H, d, J=8.2 Hz), 7.50–7.80 (6H, m), 7.80–7.98 (6H, m), 8.12 (1H, s), 8.45 (1H, d, J=8.4 Hz).

Example 188

4-fluoro-N-((1RS,2SR)-2-hydroxy-2-(1-naphthalenyl)-1-((4-(trifluoromethyl)phenyl)methyl)ethyl)benzamide To a solution of (1RS,2SR)-1-hydroxy-1-(1-naphthalenyl)-3-(4-(trifluoromethyl)phenyl)-2-propylamine hydrochloride (150 mg, 0.39 mmol) in ethyl acetate (5 ml) were added 4-fluorobenzoyl chloride (70 ml, 0.59 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (152 mg, 83%).

mp 194–195° C. IR ν max$^{KBr}$cm$^{-1}$: 1638, 1605, 1539, 1501. Anal. Calcd for $C_{27}H_{21}F_4NO_2$: C, 69.37; H, 4.53; N, 3.00. Found: C, 69.32; H, 4.54; N, 2.94. $^1$H-NMR (CDCl$_3$)δ: 2.80–3.18 (3H, m), 4.76–4.92 (1H, m), 5.98 (1H, brs), 6.40 (1H, d, J=8.4 Hz), 7.00–7.14 (4H, m), 7.38 (2H, d, J=8.4 Hz), 7.46–7.70 (5H, m), 7.80–7.96 (3H, m), 8.38 (1H, d, J=8.4 Hz).

Example 189

N-((1RS,2SR)-2-hydroxy-2-(1-naphthalenyl)-1-((4-(trifluoromethyl)phenyl)methyl)ethyl)-4-(trifluoromethyl)benzamide To a solution of (1RS,2SR)-1-hydroxy-1-(1-naphthalenyl)-3-(4-(trifluoromethyl)phenyl)-2-propylamine hydrochloride (150 mg, 0.39 mmol) in ethyl acetate (5 ml) were added 4-trifluoromethylbenzoyl chloride (87.5 ml, 0.59 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (178 mg, 88%).

mp 232–233° C. IR ν max$^{KBr}$cm$^{-1}$: 1644, 1534. Anal. Calcd for $C_{28}H_{21}F_6NO_2$: C, 64.99; H, 4.09; N, 2.71. Found: C, 64.77; H, 3.93; N, 2.55. $^1$H-NMR (CDCl$_3$)δ: 2.68–2.74 (1H, m), 2.80–3.20 (2H, m), 4.82–5.00 (1H, m), 6.00 (1H, s), 6.39 (1H, d, J=8.4 Hz), 7.12 (2H, d, J=8.4 Hz), 7.40 (2H, d, J=8.4 Hz), 7.50–7.78 (7H, m), 7.82–7.98 (3H, m), 8.39 (1H, d, J=8.0 Hz).

Example 190

N-((1RS,2SR)-2-hydroxy-2-(1-naphthalenyl)-1-((4-(trifluoromethyl)phenyl)methyl)ethyl)cyclohexanecarboxamide To a solution of (1RS,2SR)-1-hydroxy-1-(1-naphthalenyl)-3-(4-(trifluoromethyl)phenyl)-2-propylamine hydrochloride (150 mg, 0.39 mmol) in ethyl acetate (5 ml) were added cyclohexanecarbonyl chloride (87.8 ml, 0.59 mmol) and saturated-aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give the title compound (141 mg, 79%).

mp156–157° C. IR ν max$^{KBr}$cm$^{-1}$: 1645, 1508. Anal. Calcd for $C_{27}H_{28}F_3NO_2$: C, 71.19; H, 6.20; N, 3.07. Found: C, 71.14; H, 6.43; N, 3.06. $^1$H-NMR (CDCl$_3$)δ: 1.00–1.44 (5H, m), 1.50–1.80 (5H, m), 1.86–2.10 (1H, m), 2.70–3.10 (2H, m), 3.15 (1H, d, J=3.0 Hz), 4.52–4.70 (1H, m), 5.74 (1H, d, J=8.0 Hz), 5.84 (1H, s), 7.05 (2H, d, J=8.2 Hz), 7.39 (2H, d, J=8.2 Hz), 7.44–7.70 (3H, m), 7.78–7.98 (3H, m), 8.29 (1H, d, J=8.4 Hz).

Example 191

N-((1RS,2SR)-2-hydroxy-2-(1-naphthalenyl)-1-((4-(trifluoromethyl)phenyl)methyl)ethyl)-4-(2-thienyl)butyramide To a solution of 4-(2-thienyl)butyric acid (86 ml, 0.59 mmol) in tetrahydrofuran (5 ml) were added oxalyl chloride (0.10 ml, 1.18 mmol) and N,N-dimethylformamide (0.01 ml) and the mixture was stirred at room temperature for 30 min. The reaction solution was evaporated under reduced pressure. To a solution of the residue in ethyl acetate (5 ml) was added (1RS,2SR)-1-hydroxy-1-(1-naphthalenyl)-3-(4-(trifluoromethyl)phenyl)-2-propylamine hydrochloride (150 mg, 0.39 mmol) and saturated aqueous sodium hydrogen carbonate (5 ml) and the mixture was stirred overnight at room temperature. The reaction solution was diluted with water (50 ml) and extracted with ethyl acetate (50 ml×2). The extract was washed with saturated brine, dried over anhydrous magnesium sulfate and evaporated under reduced pressure. The residue was recrystallized from ethyl acetate-hexane to give the title compound (110. mg, 56%).

mp 139–140° C. IR ν max$^{KBr}$cm$^{-1}$: 1651, 1644, 1514. Anal. Calcd for $C_{28}H_{26}F_3NO_2S.0.1H_2O$: C, 67.34; H, 5.29; N, 2.80. Found: C, 67.18; H, 5.44; N, 2.69. $^1$H-NMR (CDCl$_3$)δ: 1.80–2.00 (2H, m), 2.02–2.30 (2H, m), 2.60–3.04 (5H, m), 4.58–4.76 (1H, m), 5.75 (1H, d, J=8.4 Hz), 5.85 (1H, S), 6.64–6.70 (1H, m), 6.86–6.96 (1H, m), 7.00–7.18 (3H, m), 7.36–7.70 (5H, m), 7.76–7.96 (3H, m), 8.30 (1H, d, J=8.4 Hz)

Example 192

4-fluoro-N-((1RS,2SR)-2-hydroxy-2-(4-methoxyphenyl)-1-((4-(trifluoromethyl)phenyl)methyl)ethyl)-1-naphthalenecarboxamide 1) To a solution of 4-methoxybenzoic acid (26.2 g, 172 mmol) in tetrahydrofuran (150 ml) was added 1,1'-carbonylbis-1H-imidazole (30.7 g, 189 mmol) and the mixture was stirred at room temperature for 5 hrs. To the reaction solution was added monoethyl-malonate magnesium salt (27.1 g, 94.7 mmol) was added and the mixture was stirred at 60° C. for 2 hrs. Ethyl acetate (50 ml) and water (50 ml) were added to the reaction solution, and conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(4-methoxyphenyl)-3-oxopropionate (37.6 g, 94% w/w,. 92%) as a colorless oil.

IR ν max$^{KBr}$cm$^{-1}$: 1738, 1682, 1601, 1576. Anal. Calcd for $C_{12}H_{14}O_4$: C, 64.85; H, 6.35. Found: C, 64.93; H, 6.26. $^1$H-NMR (CDCl$_3$)δ: 1.26 (3H, t, J=7.0 Hz), 3.85 (3/10H, s), 3.88 (27/10H, s), 3.94 (18/10H, s), 4.21 (2H, q, J=7.0 Hz), 5.58 (1/10H, s), 6.90–7.00 (2H, m), 7.70–7.78 (2/10H, m), 7.88–7.98 (18/10H, m).

2) To a solution of ethyl 3-(4-methoxyphenyl)-3-oxopropionate (20 g, 84.6 mmol) in acetonitrile (200 ml) were added 4-trifluoromethylbenzyl bromide (20.2 g, 84.6 mmol) and potassium carbonate (23.4 g, 169 mmol) and the mixture was stirred at 60° C. for 2 hrs. The reaction solution was evaporated under reduced pressure, diluted with water (500 ml) and extracted with ethyl acetate (500 ml×2). The extract was washed with water and saturated brine, dried over anhydrous magnesium sulfate and evaporated under reduced pressure. The residue was purified by silica gel column chromatography (toluene:hexane=1:1-toluene) to give ethyl 3-(4-methoxyphenyl)-3-oxo-2-((4-(trifluoromethyl)phenyl)methyl)propionate (19.2 g, 56%) as a colorless oil.

IR ν max$^{KBr}$cm$^{-1}$: 1732, 1682, 1601, 1576. Anal. Calcd for $C_{20}H_{19}F_3O_4$: C, 63.15; H, 5.03. Found: C, 63.14; H, 4.83. $^1$H-NMR (CDCl$_3$)δ: 1.12 (3H, t, J=7.4 Hz), 3.37 (2H, d, J=7.2 Hz), 3.85 (3H, s), 4.10 (2H, q, J=7.4 Hz), 4.58 (1H, t, J=7.2 Hz), 6.92 (2H, d, J=8.8 Hz), 7.35 (2H, d, J=8.0 Hz), 7.51 (2H, d, J=8.0 Hz), 7.95 (2H, d, J=8.8 Hz).

3) To a solution of zinc chloride (12.3 g, 90.4 mmol) in diethyl ether (150 ml) was added sodium borohydride (6.85 g, 181 mmol) and the mixture was stirred at room temperature for 30 min. The insoluble material was filtered off. To the filtrate was added a solution of ethyl 3-(4-methoxyphenyl)-3-oxo-2-((4-(trifluoromethyl)phenyl)methyl)propionate (17.2 g, 45.2 mmol) in diethyl ether (50 ml) and the mixture was stirred at room temperature for 30 min. 1N Hydrochloric acid was added to the reaction solution under ice-cooling for quenching, water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate= 4:1–2:1) to give ethyl (2RS,3RS)-3-hydroxy-3-(4-methoxyphenyl)-2-((4-(trifluoromethyl)phenyl)methyl) propionate (15.1 g, 87%) as a colorless oil.

IR ν max$^{KBr}$cm$^{-1}$: 1728, 1615, 1586, 1514. Anal. Calcd for $C_{20}H_{21}F_3O_4$: C, 62.82; H, 5.54. Found: C, 62.71; H, 5.42. $^1$H-NMR (CDCl$_3$)δ: 0.91 (3H, t, J=7.0 Hz), 2.72 (1H, d, J=2.6 Hz), 2.90–3.10 (3H, m), 3.81 (3H, s), 3.87 (2H, q, J=7.0 Hz), 4.96–5.04 (1H, m), 6.89 (2H, d, J=8.8 Hz), 7.22 (2H, d, J=8.0 Hz), 7.31 (2H, d, J=8.8 Hz), 7.48 (2H, d, J=8.0 Hz)

4) To a solution of ethyl (2RS,3RS)-3-hydroxy-3-(4-methoxyphenyl)-2-((4-(trifluoromethyl)phenyl)methyl) propionate (14.7 g, 38.4 mmol) in methanol (60 ml) was added 2N aqueous sodium hydroxide solution (38.5 ml, 77 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-hydroxy-3-(4-methoxyphenyl)-2-((4-(trifluoromethyl)phenyl)methyl) propionic acid (11.7 g, 86%).

mp 113–114° C. IR ν max$^{KBr}$cm$^{-1}$: 1715, 1614, 1514. Anal. Calcd for $C_{18}H_{17}F_3O_4$: C, 61.02; H, 4.84. Found: C, 61.03; H, 4.85. $^1$H-NMR (CDCl$_3$)δ: 3.03 (3H, s), 3.80 (3H, s), 4.98–5.06 (1H, m), 6.89 (2H, d, J=8.8 Hz), 7.19 (2H, d, J=8.0 Hz), 7.29 (2H, d, J=8.8 Hz), 7.47 (2H, d, J=8.0 Hz).

5) To a solution of (2RS,3RS)-3-hydroxy-3-(4-methoxyphenyl)-2-((4-(trifluoromethyl)phenyl)methyl) propionic acid (10.0 g, 28.2 mmol) in tetrahydrofuran (250 ml) were added diphenylphosphoryl azide (6.7 ml, 31.1 mmol) and triethylamine (5.9 ml, 42.3 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was recrystallized from ethyl acetate-hexane to give (4RS,5SR)-5-(4-methoxyphenyl)-4-((4-(trifluoromethyl)phenyl)methyl)-1,3-oxazolidin-2-one (9.89 g, 99%).

mp 164–165° C. IR ν max$^{KBr}$cm$^{-1}$: 1755, 1615, 1516. Anal. Calcd for $C_{18}H_{16}F_3NO_3$: C, 61.54; H, 4.59; N, 3.99. Found: C, 61.25; H, 4.50; N, 3.82. $^1$H-NMR (CDCl$_3$)δ: 2.37 (2H, d, J=7.4 Hz), 3.83 (3H, s), 4.23 (1H, q, J=7.8 Hz), 5.32 (1H, brs), 5.75 (1H, d, J=7.8 Hz), 6.88–7.00 (2H, m), 7.11 (2H, d, J=8.0 Hz), 7.20–7.32 (2H, m), 7.52 (2H, d, J=8.0 Hz).

6) To a solution of (4RS,5SR)-5-(4-methoxyphenyl)-4-((4-(trifluoromethyl)phenyl)methyl)-1,3-oxazolidin-2-one (7.0 g, 19.9 mmol) in ethanol (100 ml) was added 8N aqueous sodium hydroxide solution (12.45 ml, 99.6 mmol) and the mixture was heated under reflux for 4 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-methoxyphenyl)-3-(4-(trifluoromethyl)phenyl)-1-propanol (5.87 g, 91%).

mp 116–117° C. IR ν max$^{KBr}$cm$^{-1}$: 1614, 1584, 1514. Anal. Calcd for $C_{17}H_{18}F_3NO_2$: C, 62.76; H, 5.58; N, 4.31. Found: C, 62.74; H, 5.58; N, 4.23. $^1$H-NMR (CDCl$_3$)δ: 1.40–1.80 (2H, br), 2.45 (1H, dd, J=13.6, 10.0 Hz), 2.95 (1H, dd, J=13.6, 3.2 Hz), 3.18–3.34 (1H, m), 3.82 (3H, s), 4.58 (1H, d, J=5.0 Hz), 6.92 (2H, d, J=8.8 Hz), 7.22–7.38 (4H, m), 7.54 (2H, d, J=8.4 Hz).

7) To a solution of (1RS,2SR)-2-amino-1-(4-methoxyphenyl)-3-(4-(trifluoromethyl)phenyl)-1-propanol (450 mg, 1.38 mmol) in acetonitrile (20 ml) was added 4-fluoronaphthalenecarboxylic acid (263 mg, 1.38 mmol), 1-ethyl-3-(3-dimethylaminopropyl)carbodiimide hydrochloride (397 mg, 2.08 mmol) and 1-hydroxy-1H-benzotriazole (212 mg, 1.38 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was recrystallized from ethyl acetate-hexane to give the title compound (558 mg, 81%).

mp 184–185° C. IR ν max$^{KBr}$cm$^{-1}$: 1643, 1626, 1601. Anal. Calcd for $C_{28}H_{23}F_4NO_3$: C, 67.60; H, 4.66; N, 2.82. Found: C, 67.37; H, 4.49; N, 2.87. $^1$H-NMR (CDCl$_3$)δ: 2.83 (1H, dd, J=14.4, 10.6 Hz), 3.07 (1H, dd, J=14.4, 4.0 Hz), 3.81 (3H, s), 4.70–4.90 (1H, m), 4.99 (1H, d, J=3.6 Hz), 6.05 (1H, d, J=8.8 Hz), 6.88–7.00 (3H, m), 7.04–7.16 (1H, m), 7.24–7.44 (5H, m), 7.44–7.60 (4H, m), 8.05 (1H, d, J=8.0 Hz).

Example 193

N-((1RS,2SR)-2-hydroxy-2-(4-methoxyphenyl)-1-((4-(trifluoromethyl)phenyl)methyl)ethyl)-3-phenylpropanamide To a solution of (1RS,2SR)-2-amino-1-(4-methoxyphenyl)-3-(4-(trifluoromethyl)phenyl)-1-propanol (450 mg, 1.38 mmol) in ethyl acetate (20 ml) were added 3-phenylpropionyl chloride (308 ml, 2.07 mmol) and saturated aqueous sodium hydrogen carbonate (20 ml) and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title-compound (574 mg, 91%).

mp 116–117° C. IR ν max$^{KBr}$cm$^{-1}$: 1645, 1615. Anal. Calcd for $C_{26}H_{26}F_3NO_3$: C, 68.26; H, 5.73; N, 3.06. Found: C, 68.10; H, 5.99; N, 2.99. $^1$H-NMR (CDCl$_3$)δ: 2.37 (2H, t, J=7.2 Hz), 2.60–2.90 (4H, m), 3.04–3.20 (1H, m), 3.81 (3H, s), 4.32–4.50 (1H, m), 4.72–4.84 (1H, m), 5.35 (1H, d, J=8.4 Hz), 6.88 (2H, d, J=8.8 Hz), 7.08–7.40 (9H, m), 7.46 (2H, d, J=8.0 Hz).

Example 194

N-[(1RS,2SR)-2-(4-chlorophenyl)-2-hydroxy-1-[4-(trifluoromethyl)benzyl]ethyl]-4-fluoronaphthalene-1-carboxamide 1) ethyl (4-chlorobenzoyl)acetate To a solution of 4-chlorobenzoic acid (15.77 g, 100.7 mmol) in tetrahydrofuran (100 ml) was added 1,1'-carbonyldiimidazole (18.0 g, 111 mmol) at room temperature and the mixture was stirred as it was for 6 hrs. To the mixture was added monoethyl malonate monomagnesium salt (15.9 g, 55.4 mmol) at room temperature and the mixture was stirred at 60° C. for 3 hrs. The reaction solution was diluted with ethyl acetate and water and acidified with conc. hydrochloric acid. The ethyl acetate layer was separated and the aqueous layer was extracted with ethyl acetate. The collected organic layer was dried over anhydrous sodium sulfate and the solvent was evaporated under reduced pressure. The obtained crude product was purified by silica gel column chromatography (hexane/ethyl acetate=6/1) to give the objective substance.

red liquid yield 19.64 g, 86% $^1$H-NMR (CDCl$_3$, 200 MHz) δ 1.26 (2.4H, t, J=7.4 Hz), 1.34 (0.6H, t, J=7.0 Hz), 3.97 (1.6H, s), 4.22 (1.6H, q, J=7.1 Hz), 4.27 (0.4H, q, J=7.1 Hz), 5.64 (0.2H, s), 7.40 (0.4H, d, J=8.8 Hz), 7.46 (1.6H, d, J=8.6 Hz), 7.72 (0.4H, d, J=8.6 Hz), 7.90 (1.6H, d, J=8.0 Hz); IR (neat) 1742, 1690, 1622, 1590, 1325, 1265, 1200, 1092, 1013 cm$^{-1}$ 2) ethyl 3-(4-chlorophenyl)-3-oxo-2-[4-(trifluoromethyl)benzyl]propionate To a solution of ethyl (4-chlorobenzoyl)acetate (14.28 g, 63.00 mmol) in 1,2-dimethoxyethane (100 ml) was added a suspension (2.52 g, 63.0 mmol) of 60% sodium hydride in liquid paraffin under ice-cooling and the mixture was stirred as it was for 0.5 hr. A solution of 4-(trifluoromethyl)benzyl bromide (15.1 g, 63.0 mmol) in 1,2-dimethoxyethane (20 ml) was added at room temperature and the mixture was stirred at room temperature for 6 hrs. The reaction solution was poured into water and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) and crystallized from hexane to give the objective substance.

white crystal yield 18.87 g, 78% mp 69–70° C.; $^1$H-NMR (CDCl$_3$, 200 MHz) δ 1.12 (3H, t, J=7.1 Hz), 3.38 (2H, d, J=7.4 Hz), 4.10 (2H, q, J=7.3 Hz), 4.56 (1H, t, J=7.5 Hz), 7.34 (2H, d, J=8.0 Hz), 7.43 (2H, d, J=8.8 Hz), 7.52 (2H, d, J=8.0 Hz), 7.90 (2H, d, J=8.4 Hz); IR (KBr) 1717, 1690, 1590, 1329, 1283, 1229, 1179, 1157, 1111, 1092, 1071, 845, 828 cm$^{-1}$; Anal. Calcd for C$_{19}$H$_{16}$ClF$_3$O$_3$: C, 59.31; H, 4.19. Found: C, 59.29; H, 4.05.

3) ethyl (2RS,3RS)-3-(4-chlorophenyl)-3-hydroxy-2-[4-(trifluoromethyl)benzyl]propionate While stirring zinc chloride (7.18 g, 52.7 mmol) in diethyl ether (100 ml), sodium borohydride (3.98 g, 105 mmol) was added at room temperature and the mixture was stirred as it was for 2 hrs. The insoluble material of the mixture was removed by filtration and washed with diethyl ether to give a solution of zinc borohydride in diethyl ether. To the obtained solution was added a solution of ethyl 3-(4-chlorophenyl)-3-oxo-2-[4-(trifluoromethyl)benzyl]propionate (10.13 g, 26.33 mmol) in diethyl ether (50 ml) at room temperature and the mixture was stirred as it was for 2 hrs. Dilute hydrochloric acid was added to the reaction solution by small portions to decompose excess zinc borohydride and extracted twice with ethyl acetate. The collected organic layer was dried over anhydrous magnesium sulfate and the solvent was evaporated under reduced pressure. The obtained crude product was purified by silica gel column chromatography (hexane/ethyl acetate=9/1–3/1) to give the objective substance.

colorless liquid yield 9.971 g, 98% $^1$H-NMR (CDCl$_3$, 200 MHz) δ 0.93 (3H, t, J=7.1 Hz), 2.90–3.14 (4H, m), 3.90 (2H, q, J=7.1 Hz), 5.04 (1H, dd, J=3.0 Hz, 4.8 Hz), 7.19 (2H, d, J=8.2 Hz), 7.34 (4H, s), 7.48 (2H, d, J=8.2 Hz); IR (neat) 3466, 1715, 1325, 1163, 1125, 1109, 1069, 1019, 829 cm$^{-1}$ 4) (2RS,3RS)-3-(4-chlorophenyl)-3-hydroxy-2-[4-(trifluoromethyl)benzyl]propionic acid To a solution of ethyl (2RS,3RS)-3-(4-chlorophenyl)-3-hydroxy-2-[4-(trifluoromethyl)benzyl]propionate (9.756 g, 25.22 mmol) in methanol (40 ml) and tetrahydrofuran (40 ml) was added 1N aqueous sodium hydroxide solution (50.4 ml, 50.4 mmol) and the mixture was stirred overnight at room temperature. The reaction solution was concentrated, diluted with water, acidified with 1N hydrochloric acid and extracted twice with ethyl acetate. The collected organic layer was dried over anhydrous sodium sulfate and the solvent was evaporated under reduced pressure. The residue was crystallized from diethyl ether-hexane to give the objective substance.

white crystal yield. 7.152 g, 79% mp 100–101° C.; $^1$H-NMR (CDCl$_3$200 MHz) δ 2.94–3.13 (3H, m), 5.09 (1H, t, J=2.2 Hz), 7.18 (2H, d, J=7.6 Hz), 7.34 (4H, s), 7.48 (2H, d, J=8.0 Hz); IR (KBr) 3400–2550, 1696, 1323, 1167, 1130, 1119, 1107, 828 cm$^{-1}$; Anal. Calcd for C$_{17}$H$_{14}$ClF$_3$O$_3$: C, 56.92; H, 3.93. Found: C, 56.98; H, 3.73.

5) (4RS,5SR)-5-(4-chlorophenyl)-4-[4-(trifluoromethyl)benzyl]-1,3-oxazolidin-2-one To a solution of (2RS,3RS)-3-(4-chlorophenyl)-3-hydroxy-2-[4-(trifluoromethyl)benzyl]propionic acid (6.931 g, 19.32 mmol) in tetrahydrofuran (80 ml) were added triethylamine (4.04 ml, 29.0 mmol) and diphenylphosphoryl azide (5.85 g, 21.3 mmol) and the mixture was heated under reflux overnight. The solvent of the reaction solution was evaporated under reduced pressure, the obtained crude product was purified by silica gel column chromatography (hexane/ethyl acetate=3/1–1/1) and crystallized from ethyl acetate-hexane to give the objective substance.

white crystal yield 6.120 g, 89% mp 159–160° C.; $^1$H-NMR (CDCl$_3$, 200 MHz) δ 2.24–2.40 (2H, m), 4.20–4.32 (1H, m), 5.02 (1H, br s), 5.80 (1H, d, J=8.2 Hz), 7.15 (2H, d, J=8.0 Hz), 7.32 (2H, d, J=8.4 Hz), 7.42 (2H, d, J=8.4 Hz), 7.55 (2H, d, J=8.0 Hz); IR (KBr) 3248, 1736, 1327, 1167, 1138, 1109, 1096, 1067 cm$^{-1}$; Anal. Calcd for C$_{17}$H$_{13}$ClF$_3$NO$_2$: C, 57.40; H, 3.68; N, 3.94. Found: C, 57.41; H, 3.58; N, 3.85.

6) (1RS,2SR)-2-amino-1-(4-chlorophenyl)-3-[4-(trifluoromethyl)phenyl]propan-1-ol (4RS,5SR)-5-(4-Chlorophenyl)-4-[4-(trifluoromethyl)benzyl]-1,3-oxazolidin-2-one (5.902 g, 16.59 mmol) and sodium hydroxide (2.65 g, 66.4 mmol) were heated under reflux in ethanol (40 ml) and water (2.5 ml) for 7 hrs. The reaction solution was diluted with water and stirred as it was for 10 min. The resulting precipitate was collected by filtration and washed with water to give the objective substance.

white crystal yield 4.902 g, 90% mp 103–105° C.; $^1$H-NMR (CDCl$_3$, 200 MHz) δ 2.41 (1H, dd, J=10.3 Hz, 13.5 Hz.), 2.83 (1H, dd, J=3.1 Hz, 13.7 Hz), 3.29 (1H, ddd, J=3.3 Hz, 4.9 Hz, 10.5 Hz), 4.66 (1H, d, J=4.8 Hz), 7.25 (2H, d, J=8.0 Hz), 7.31–7.40 (4H, m), 7.54 (2H, d, J=8.0 Hz); IR (KBr) 3150–2760, 1329, 1165, 1130, 1115, 1069, 1042, 851 cm$^{-1}$; Anal. Calcd for C$_{16}$H$_{15}$ClF$_3$NO: C, 58.28; H, 4.59; N, 4.25. Found: C, 58.03; H, 4.72; N, 4.16.

7) N-[(1RS,2SR)-2-(4-chlorophenyl)-2-hydroxy-1-[4-(trifluoromethyl)benzyl]ethyl]-4-fluoronaphthalene-1-carboxamide While stirring (1RS,2SR)-2-amino-1-(4-chlorophenyl)-3-[4-(trifluoromethyl)phenyl]propan-1-ol (0.173 g, 0.525 mmol), 4-fluoro-1-naphthoate (0.10 g, 0.52 mmol) and 1-hydroxybenzotriazole hydrate (80 mg, 0.52 mmol) in acetonitrile (10 ml), 1-ethyl-3-(3-dimethylaminopropyl)carbodiimide hydrochloride (0.10 g, 0.52 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-hexane to give the objective substance.

white crystal yield 0.216 g, 82% mp 203–204° C.; $^1$H-NMR (CDCl$_3$-DMSO-d$_6$, 200 MHz) δ 2.93 (1H, dd, J=10.6 Hz, 14.4 Hz), 3.11 (1H, dd, J=3.1 Hz, 13.3 Hz), 4.66–4.81 (1H, m), 4.95 (1H, t, J=4.6 Hz), 5.43 (1H, d, J=4.0 Hz), 7.05 (1H, dd, J=7.7 Hz, 9.9 Hz), 7.20 (1H, dd, J=5.5 Hz, 8.1 Hz), 7.33–7.57 (11H, m), 7.71 (1H, d, J=9.6 Hz), 8.05 (1H, d, J=8.4 Hz); IR (KBr) 3343, 1638, 1620, 1601, 1534, 1327, 1159, 1125, 1069, 833 cm$^{-1}$; Anal. Calcd for C$_{27}$H$_{20}$ClF$_4$NO$_2$: C, 64.61; H, 4.02; N, 2.79. Found: C, 64.42; H, 3.98; N, 2.61.

Example 195

4-fluoro-N-((1RS,2SR)-2-(3-furanyl)-2-hydroxy-1-((4-(trifluoromethyl)phenyl)methyl)ethyl)-1-naphthalenecarboxamide 1) To a solution of 3-furancarboxylic acid (25.5 g, 227 mmol) in tetrahydrofuran (200 ml) was added 1,1'-carbonylbis-1H-imidazole (40.5 g, 250 mmol) and the mixture was stirred at 60° C. for 2 hrs. To the reaction solution was added monoethyl malonate magnesium salt (35.8 g, 125 mmol) and the mixture was heated under reflux for 30 min. Ethyl acetate (50 ml) and water (50 ml) were added the reaction solution, and conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(3-furanyl)-3-oxopropionate (42 g, 100%) as a colorless oil.

IR ν max$^{KBr}$cm$^{-1}$: 1738, 1682. Anal. Calcd for C$_9$H$_{10}$O$_4$·0.1H$_2$O: C, 58.76; H, 5.59. Found: C, 58.90; H, 5.56. $^1$H-NMR (CDCl$_3$)δ: 1.27 (3H, t, J=7.0 Hz), 3.78 (18/10H, s), 4.21 (2H, q, J=7.0 Hz), 5.37 (1/10H, s), 6.57 (1/10H, s), 6.79 (9/10H, s), 7.40–7.50 (1H, m), 7.90 (1/10H, s), 8.11 (9/10H, s).

2) To a solution of ethyl 3-(3-furanyl)-3-oxopropionate (20 g, 110 mmol) in 1,2-dimethoxyethane (100 ml) was added sodium hydride (60% in oil, 4.4 g, 110 mmol) under ice-cooling and the mixture was stirred at room temperature for 30 min. To the reaction solution was dropwise added a solution of 4-trifluoromethylbenzyl bromide (26.2 g, 110 mmol) in 1,2-dimethoxyethane (50 ml) and the reaction solution was stirred at room temperature for 3 hrs. The reaction solution was poured into water (300 ml) and extracted with ethyl acetate (500 ml×2). The extract was washed with water and saturated brine, dried over anhydrous magnesium sulfate and evaporated under reduced pressure. The residue was recrystallized from diisopropyl ether-hexane to give ethyl 3-(3-furanyl)-3-oxo-2-((4-(trifluoromethyl)phenyl)methyl)propionate (28.8 g, 77%).

mp 55–56° C. IR ν max$^{KBr}$cm$^{-1}$: 1738, 1682. Anal. Calcd for C$_{17}$H$_{15}$F$_3$O$_4$: C, 60.00; H, 4.44. Found: C, 59.89; H, 4.38. $^1$H-NMR (CDCl$_3$)δ: 1.16 (3H, t, J=7.0 Hz), 3.35 (2H, d, J=7.6 Hz), 4.06–4.24 (3H, m), 6.76–6.80 (1H, m), 7.34 (2H, d, J=8.0 Hz), 7.40–7.48 (1H, m), 7.53 (2H, d, J=8.0 Hz), 8.09 (1H, s).

3) To a solution of zinc chloride (16.0 g, 117 mmol) in diethyl ether (250 ml) was added sodium borohydride (8.9 g, 235 mmol) and the mixture was stirred at room temperature for 2 hrs. The insoluble material was filtered off. To the filtrate was added a solution of ethyl 3-(3-furanyl)-3-oxo-2-((4-(trifluoromethyl)phenyl)methyl)propionate (20 g, 58.8 mmol) in diethyl ether (50 ml) and the mixture was stirred at room temperature for 30 min. 1N Hydrochloric acid was added to the reaction solution under ice-cooling for quenching, water (200 ml), and the mixture was extracted with ethyl acetate (300 ml×2). The extract was washed with water and saturated brine, dried over anhydrous magnesium sulfate and evaporated under reduced pressure to give ethyl (2RS,3RS)-3-(3-furanyl)-3-hydroxy-2-((4-(trifluoromethyl)phenyl)methyl)propionate (19.7 g, 98%) as a colorless oil.

IR ν max$^{KBr}$cm$^{-1}$: 1728. Anal. Calcd for C$_{17}$H$_{17}$F$_3$O$_4$: C, 59.65; H, 5.01. Found: C, 59.35; H, 5.19. $^1$H-NMR (CDCl$_3$) δ: 1.00 (3H, t, J=7.2 Hz), 2.80 (1H, d, J=3.8 Hz), 2.86–3.14 (3H, m), 3.96 (2H, q, J=7.2 Hz), 5.01 (1H, t, J=4.0 Hz), 6.40 (1H, s), 7.25 (2H, d, J=8.0 Hz), 7.38–7.60 (4H, m).

4) To a solution of ethyl (2RS,3RS)-3-(3-furanyl)-3-hydroxy-2-((4-(trifluoromethyl)phenyl)methyl)propionate (19.0 g, 55.5 mmol) in methanol (100 ml) was added 2N aqueous sodium hydroxide solution (55.5 ml, 111 mmol) and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from diisopropyl ether-hexane to give (2RS,3RS)-3-(3-furanyl)-3-hydroxy-2-((4-(trifluoromethyl)phenyl)methyl)propionic acid (15.1 g, 86%).

mp 104–105° C. IR ν max$^{KBr}$cm$^{-1}$: 1713. Anal. Calcd for C$_{15}$H$_{13}$F$_3$O$_4$: C, 57.33; H, 4.17. Found: C, 57.42; H, 4.15. $^1$H-NMR (CDCl$_3$)δ: 2.90–3.20 (3H, m), 5.02 (1H, d, J=4.0 Hz), 6.39 (1H, s), 7.26 (2H, d, J=8.2 Hz), 7.40–7.50 (2H, m), 7.52 (2H, d, J=8.2 Hz).

5) To a solution of (2RS,3RS)-3-(3-furanyl)-3-hydroxy-2-((4-(trifluoromethyl)phenyl)methyl)propionic acid (10.0 g, 31.8 mmol) in tetrahydrofuran (250 ml) were added diphenylphosphoryl azide (7.5 ml, 35.0 mmol) and triethylamine (6.7 ml, 47.7 mmol) and the mixture was heated under reflux for 4 hrs. The reaction solution was allowed to stand at room temperature, water (200 ml) was added, and the mixture was extracted with ethyl acetate (200 ml×2). The extract was washed successively with 1N hydrochloric acid, saturated aqueous-sodium hydrogen carbonate and saturated brine, dried, over anhydrous magnesium sulfate and evaporated under reduced pressure. The residue was recrystallized from diisopropyl ether-hexane to give (4RS,5SR)-5-(3-furanyl)-4-((4-(trifluoromethyl)phenyl)methyl)-1,3-oxazolidin-2-one (8.25 g, 83%)

mp 111–112° C. IR ν max$^{KBr}$cm$^{-1}$: 1759. Anal. Calcd for C$_{15}$H$_{12}$F$_3$NO$_3$: C, 57.88; H, 3.89; N, 4.50. Found: C, 57.94; H, 3.97; N, 4.38. $^1$H-NMR (CDCl$_3$)δ: 2.48–2.72 (2H, m), 3.97 (1H, m), 4.12–4.28 (1H, m), 5.09 (1H, brs), 5.75 (1H, d, J=7.8 Hz), 6.47 (1H, s), 7.22 (2H, d, J=8.0 Hz), 7.48–7.62 (4H, m).

6) To a solution of (4RS,5SR)-5-(3-furanyl)-4-((4-(trifluoromethyl)phenyl)methyl)-1,3-oxazolidin-2-one (7.0 g, 22.5 mmol) in ethanol (100 ml) was added 8N aqueous sodium hydroxide solution (14.0 ml, 112.5 mmol) and the mixture was heated under reflux for 3 hrs. The reaction solution was concentrated, diluted with water (300 ml) and extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(3-furanyl)-3-(4-(trifluoromethyl)phenyl)-1-propanol (5.54 g, 86%).

mp 91–92° C. IR ν max$^{KBr}$cm$^{-1}$: 1572, 1500, 1331. Anal. Calcd for $C_{14}H_{14}F_3NO_2$: C, 58.95; H, 4.95; N, 4.91. Found: C, 58.91; H, 5.08; N, 4.78. $^1$H-NMR (CDCl$_3$)δ: 2.49 (1H, dd, J=13.6, 9.8 Hz), 2.96 (1H, dd, J=14.0, 3.6 Hz), 3.20–3.32 (1H, m), 4.62 (1H, d, J=5.2 Hz), 6.44 (1H, s), 7.30 (2H, d, J=8.0 Hz), 7.40–7.50 (2H, m), 7.56 (2H, d, J=8.0 Hz).

7) To a solution of (1RS,2SR)-2-amino-1-(3-furanyl)-3-(4-(trifluoromethyl)phenyl)-1-propanol (500 mg, 1.75 mmol) in acetonitrile (30 ml) were added 4-fluoronaphthalenecarboxylic acid (333 mg, 1.75 mmol), 1-ethyl-3-(3-dimethylaminopropyl)carbodiimide hydrochloride (504 mg, 2.63 mmol) and 1-hydroxy-1H-benzotriazole (268 mg, 1.75 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (hexane:ethyl acetate=4:1). Recrystallization from ethyl acetate-hexane gave the title compound (573 mg, 71%).

mp 206–207° C. IR ν max$^{KBr}$cm$^{-1}$: 1644, 1626, 1601, 1537, 1329. Anal. Calcd for $C_{25}H_{19}F_4NO_3$: C, 65.64; H, 4.19; N., 3.06. Found: C, 65.49; H, 4.37; N, 2.91. $^1$H-NMR (CDCl$_3$)δ: 2.89 (1H, dd, J=14.2, 10.2 Hz), 3.15 (1H, dd, J=14.2, 4.2 Hz), 3.24 (1H, brs), 4.70–4.88 (1H, m), 5.03 (1H, d, J=3.2 Hz), 6.02 (1H, d, J=8.6 Hz), 6.51 (1H, s), 6.92–7.08 (1H, m), 7.12–7.24 (1H, m), 7.30–7.62 (8H, m), 7.70 (1H, d, J=8.4 Hz), 8.08 (1H, d, J=8.2 Hz).

Example 196

N-((1RS,2SR)-2-(3-furanyl)-2-hydroxy-1-((4-(trifluoromethyl)phenyl)methyl)ethyl)-3-phenylpropanamide To a solution of (1RS,2SR)-2-amino-1-(3-furanyl)-3-(4-(trifluoromethyl)phenyl)-1-propanol (500 mg, 1.75 mmol) in ethyl acetate (20 ml) were added 3-phenylpropionyl chloride (390 ml, 2.63 mmol) and saturated aqueous sodium hydrogen carbonate (20 ml) and the mixture was stirred overnight-at room temperature. The reaction solution was diluted with water (100 ml) and extracted with ethyl acetate (100 ml×2). The extract was washed with saturated-brine, dried over anhydrous magnesium sulfate and evaporated under reduced pressure. The residue was recrystallized from ethyl acetate-hexane to give the title compound (650 mg, 89%).

mp 134–135° C. IR ν max$^{KBr}$cm$^{-1}$: 1645, 1520. Anal. Calcd for $C_{23}H_{22}F_3NO_3$: C, 66.18; H, 5.31; N, 3.36. Found: C, 66.18; H, 5.40; N, 3.22. $^1$H-NMR (CDCl$_3$)δ: 2.39 (2H, t, J=7.0 Hz), 2.64–2.92 (4H, m), 3.08–3.36 (1H, m), 4.26–4.44 (1H, m), 4.75 (1H, s), 5.30–5.50 (1H, m), 6.31 (1H, s), 7.06–7.34 (7H, m), 7.38 (2H, d, J=6.8 Hz), 7.49 (2H, d, J=8.2 Hz).

Example 197

N-[(1RS,2RS)-2-(5-chloro-2-thienyl)-2-hydroxy-1-[4-(trifluoromethyl)benzyl]ethyl]-4-fluoronaphthalene-1-carboxamide 1) ethyl 3-(5-chloro-2-thienyl)-3-oxopropionate To a solution of 5-chlorothiophene-2-carboxylic acid (10.12 g, 62.24 mmol) in tetrahydrofuran (80 ml) was added 1,1'-carbonyldiimidazole (11.1 g, 68.5 mmol) at room temperature and the mixture was stirred as it was for 6 hrs. Monoethyl malonate monomagnesium salt (9.81 g, 34.2 mmol) was added to this mixture at room temperature and the mixture was stirred at 60° C. for 3 hrs. The reaction solution was diluted with ethyl acetate and water, and acidified with conc. hydrochloric acid. The ethyl acetate layer was separated, and the aqueous layer was extracted with ethyl acetate. The collected organic layer was dried over anhydrous sodium sulfate and the solvent was evaporated under reduced pressure. The obtained crude product was purified by silica gel column chromatography (hexane/ethyl acetate=6/1) to give the objective substance.

dark red liquid yield 13.89 g, 96% $^1$H-NMR (CDCl$_3$, 200 MHz) δ 1.27 (3H, t, J=7.2 Hz), 3.85 (2H, s), 4.21 (2H, q, J=7.1 Hz), 6.99 (1H, d, J=4.0 Hz), 7.53 (1H, d, J=4.0 Hz); IR (neat) 1738, 1667, 1418, 1329, 1215, 1017 cm$^{-1}$ 2) ethyl 3-(5-chloro-2-thienyl)-3-oxo-2-[4-(trifluoromethyl)benzyl]propionate To a solution of ethyl 3-(5-chloro-2-thienyl)-3-oxopropionate (13.57 g, 58.32 mmol) in 1,2-dimethoxyethane (100 ml) was added a suspension (2.33 g, 58.3 mmol) of 60% sodium hydride in liquid paraffin under ice-cooling, and the mixture was stirred as it was for 0.5 hr. A solution of 4-(trifluoromethyl)benzyl bromide (13.9 g, 58.3 mmol) in 1,2-dimethoxyethane (20 ml) was added at room temperature, and the mixture was stirred at room temperature was for 6 hrs. The reaction solution was poured into water, and extracted twice with ethyl acetate. The collected organic layer was dried over anhydrous magnesium sulfate and the solvent was evaporated under reduced pressure. The obtained residue was purified by silica gel column chromatography (hexane/ethyl acetate=15/1–9/1) and crystallized from hexane to give the objective substance.

white crystal yield 18.30 g, 80% mp 87–88° C.; $^1$H-NMR (CDCl$_3$, 200 MHz) δ 1.16 (3H, t, J=7.2 Hz), 3.36 (2H, d, J=7.8 Hz), 4.14 (2H, q, J=7.2 Hz), 4.35 (1H, t, J=7.5 Hz), 6.94 (1H, d, J=4.0 Hz), 7.33 (2H, d, J=8.0 z), 7.53 (2H, d, J=8.4 Hz), 7.55 (1H, d, J=4.0 Hz); IR (KBr) 1721, 1659, 1418, 1329, 1285, 1236, 1155, 1119, 1071 cm$^{-1}$; Anal. Calcd for $C_{17}H_{14}ClF_3O_3S$: C, 52.25; H, 3.61. Found: C, 52.22; H, 3.42.

3) ethyl (2RS,3RS)-3-(5-chloro-2-thienyl)-3-hydroxy-2-[4-(trifluoromethyl)benzyl]propionate While stirring zinc chloride (6.47 g, 47.5 mmol) in diethyl ether (100 ml), sodium borohydride (3.59 g, 94.9 mmol) was added at room temperature, and the mixture was-stirred as it was for 2 hrs. The insoluble material of the mixture was removed by filtration (washed with diethyl ether) to give a solution of zinc borohydride in diethyl ether. To the obtained solution was added a solution of ethyl 3-(5-chloro-2-thienyl)-3-oxo-2-[4-(trifluoromethyl)benzyl]propionate (9.272 g, 23.73 mmol) in diethyl ether (50 ml) at room temperature, and the mixture was stirred as it was for 2 hrs. Dilute hydrochloric acid was added to the reaction solution by small portions to decompose excess zinc borohydride. The mixture was extracted twice with ethyl acetate. The collected organic layer was dried over anhydrous magnesium sulfate and the solvent was evaporated under reduced pressure. The obtained crude product was purified by silica gel column chromatography (hexane/ethyl acetate=9/1–3/1) to give the objective substance.

colorless liquid yield 9.093 g, 98% $^1$H-NMR (CDCl$_3$, 200 MHz) δ 0.99 (3H, t, J=7.1 Hz), 2.96–3.16 (4H, m), 3.96 (2H, q, J=7.1 Hz), 5.15 (1H, t, J=4.2 Hz), 6.76 (1H, d, J=3.8 Hz), 6.79 (1H, d, J=3.6 Hz), 7.26 (2H, d, J=8.2 Hz), 7.52 (2H, d, J=8.0 Hz); IR (neat) 3459, 1715, 1325, 1163, 1125, 1109, 1069, 1020 cm$^{-1}$ 4) (2RS,3RS)-3-(5-chloro-2-thienyl)-3-hydroxy-2-[4-(trifluoromethyl)benzyl]propionic acid To a solution of ethyl (2RS,3RS)-3-(5-chloro-2-thienyl)-3-hydroxy-2-[4-(trifluoromethyl)benzyl]propionate (8.878 g, 22.60 mmol) in methanol (30 ml)-tetrahydrofuran (30 ml) was added 1N aqueous sodium hydroxide solution (45.2 ml, 45.2 mmol) and the mixture was stirred overnight at room temperature. The reaction solution was concentrated, diluted with water, acidified with 1N hydrochloric acid, and extracted twice with ethyl acetate. The collected-organic layer was dried over anhydrous sodium sulfate and the solvent was evaporated under reduced pressure. The residue was crystallized from diethyl ether-hexane to give the objective substance.

white crystal yield 7.092 g, 86% mp 150–151° C.; $^1$H-NMR (CDCl$_3$, 200 MHz) δ 3.06–3.15 (3H, m), 5.17 (1H, d, J=4.8 Hz), 6.79 (2H, s), 7.27 (2H, d, J=8.0 Hz), 7.53 (2H, d, J=8.4 Hz); IR (KBr) 3382, 3050–2650, 1698, 1333, 1159, 1130, 1111, 1071, 802 cm$^{-1}$; Anal. Calcd for C$_{15}$H$_{12}$ClF$_3$O$_3$S: C, 49.39; H, 3.32. Found: C, 49.40; H, 3.29.

5) (4RS,5RS)-5-(5-chloro-2-thienyl)-4-[4-(trifluoromethyl)benzyl]-1,3-oxazolidin-2-one To a solution of (2RS,3RS)-3-(5-chloro-2-thienyl)-3-hydroxy-2-[4-(trifluoromethyl)benzyl]propionic acid (6.918 g, 18.97 mmol) in tetrahydrofuran (80 ml) were added triethylamine (3.97 ml, 28.4 mmol) and diphenylphosphoryl azide (5.74 g, 20.9 mmol), and the mixture was heated under reflux overnight. The solvent of the reaction solution was evaporated under reduced pressure. The obtained crude product was purified by silica gel column chromatography (hexane/ethyl acetate=3/1–1/1) and crystallized from diethyl ether-hexane to give the objective substance.

white crystal yield 5.985 g, 87% mp 127–128° C.; $^1$H-NMR (CDCl$_3$, 200 MHz) δ 2.54–2.75 (2H, m), 4.25 (1H, ddd, 4.7 Hz, 8.0 Hz, 10.1 Hz), 5.10 (1H, br s), 5.72 (1H, d, J=7.6 Hz), 6.89 (2H, s), 7.22 (2H, d, J=8.0 Hz), 7.58 (2H, d, J=8.6 Hz); IR (KBr) 3248, 1736, 1327, 1159, 1127, 1069 cm$^{-1}$; Anal. Calcd for C$_{15}$H$_{11}$ClF$_3$NO$_2$S: C, 49.80; H, 3.06; N, 3.87. Found: C, 49.77; H, 2.95; N, 3.65.

6) (1RS,2RS)-2-amino-1-(5-chloro-2-thienyl)-3-[4-(trifluoromethyl)phenyl]propan-1-ol (4RS,5RS)-5-(5-Chloro-2-thienyl)-4-[4-(trifluoromethyl)-benzyl]-1,3-oxazolidin-2-one (2.951 g, 8.157 mmol) and sodium hydroxide (1.31 g, 32.6 mmol) were heated under reflux in ethanol (30 ml)-water (1.5 ml) for 7 hrs. The reaction solution was diluted with brine, and extracted twice with ethyl acetate. The collected organic layer was dried over anhydrous sodium sulfate and the solvent was evaporated under reduced pressure. The residue was purified by silica gel (APS type) column chromatography (hexane/ethyl acetate=3/1-ethyl acetate) and crystallized from ethyl acetate-hexane to give the objective substance.

white crystal yield 1.318 g, 48% mp 86–87° C.; $^1$H-NMR (CDCl$_3$, 200 MHz) δ 2.49 (1H, dd, J=9.7 Hz, 13.7 Hz), 2.92 (1H, dd, J=3.9 Hz, 13.7 Hz), 3.28–3.38 (1H, m), 4.77 (1H, d, J=4.8 Hz), 6.79 (1H, d, J=3.8 Hz), 6.83 (1H, d, J=3.6 Hz), 7.30 (2H, d, J=8.6 Hz), 7.57 (2H, d, J=8.0 Hz); IR (KBr) 3100–2700, 1327, 1163, 1117, 1069, 1038, 802 cm$^{-1}$; Anal. Calcd for C$_{14}$H$_{13}$ClF$_3$NOS: C, 50.08; H, 3.90; N, 4.17. Found: C, 49.99; H, 3.92; N, 4.11.

7) N-[(1RS,2RS)-2-(5-chloro-2-thienyl)-2-hydroxy-1-[4-(trifluoromethyl)benzyl]ethyl]-4-fluoronaphthalene-1-carboxamide While stirring (1RS,2RS)-2-amino-1-(5-chloro-2-thienyl)-3-[4-(trifluoromethyl)phenyl]propan-1-ol (0.168 g, 0.500 mmol), 4-fluoro-1-naphthoic acid (0.10 g, 0.50 mmol) and 1-hydroxybenzotriazole hydrate (77 mg, 0.50 mmol) in acetonitrile (10 ml), 1-ethyl-3-(3-dimethylaminopropyl) carbodiimide hydrochloride (0.10 g, 0.50 mmol) was added, and the mixture was stirred overnight at room temperature. The reaction was diluted with ethyl acetate, washed with aqueous sodium hydrogen carbonate solution, dried over anhydrous magnesium sulfate and passed through silica gel. Thee solvent was evaporated under reduced pressure. The obtained residue was crystallized from ethyl acetate-hexane to give the objective substance.

white crystal yield 0.186 g, 73% mp 201–203° C.; $^1$H-NMR (CDCl$_3$-DMSO-d$_6$, 200 MHz) δ 2.95 (1H, dd, J=10.6 Hz, 14.0 Hz), 3.21 (1H, dd, J=2.8 Hz, 14.6 Hz), 4.66–4.80 (1H, m), 5.10 (1H, t, J=4.7 Hz), 5.86 (1H, d, J=4.4 Hz), 6.85 (1H, d, J=3.6 Hz), 6.91 (1H, d, J=4.0 Hz), 7.07 (1H, dd, J=7.9 Hz, 10.1 Hz), 7.28 (1H, dd, J=5.4 Hz, 8.0 Hz), 7.39–7.64 (7H, m), 7.79 (1H, d, J=9.6 Hz), 8.06 (1H, d, J=7.8 Hz); IR (KBr) 3275, 1644, 1626, 1537, 1325, 1167, 1121, 1069, 760 cm$^{-1}$; Anal. Calcd for C$_{25}$H$_{18}$ClF$_4$NO$_2$S: C, 59.12; H, 3.57; N, 2.76. Found: C, 59.05; H; 3.47; N, 2.49.

Example 198

N-[(1RS,2RS)-2-(5-chloro-2-thienyl)-2-hydroxy-1-[4-(trifluoromethyl)benzyl]ethyl]-6,7-dihydro-5H-benzo[a]cycloheptene-1-carboxamide While stirring (1RS,2RS)-2-amino-1-(5-chloro-2-thienyl)-3-[4-(trifluoromethyl)phenyl]propan-1-ol (0.235 g, 0.700 mmol), 6,7-dihydro-5H-benzo[a]cycloheptene-1-carboxylic acid (0.13 g, 0.70 mmol) and 1-hydroxybenzotriazole hydrate (0.11 g, 0.70 mmol) in acetonitrile (10 ml), 1-ethyl-3-(3-dimethylaminopropyl) carbodiimide hydrochloride (0.13 g, 0.70 mmol) was added, and the mixture was stirred overnight at room temperature. The reaction was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white-crystal yield 0.298 g, 84% mp 184–185° C.; $^1$H-NMR (CDCl$_3$, 200 MHz) δ 1.94–2.06 (2H, m), 2.15–2.24 (2H, m), 2.67 (2H, t, J=5.8 Hz), 2.86 (1H, dd, J=10.5 Hz, 14.5 Hz), 3.09 (1H, dd, J=4.5 Hz, 14.1 Hz), 4.25 (1H, d, J=4.0 Hz), 4.63–4.76 (1H, m), 0.15 (1H, t, J=3.8 Hz), 5.83 (1H, d, J=8.8 Hz), 5.91 (1H, td, J=5.3 Hz, 11.8 Hz), 6.19 (1H, d, J=11.8 Hz), 6.84 (2H, s), 7.00–7.21 (3H, m), 7.33 (2H, d, J=8.0 Hz), 7.57 (2H, d, J=8.0 Hz); IR (KBr) 3283, 1638, 1526, 1327, 1161, 1125, 1069 cm$^{-1}$; Anal. Calcd for C$_{26}$H$_{23}$ClF$_3$NO$_2$S: C, 61.72; H, 4.58; N, 2.77. Found: C, 61.57; H, 4.35; N, 2.71.

Example 199

1,1-dimethylethyl (1RS,2SR)-2-hydroxy-2-(4-pyridyl)-1-((4-(trifluoromethyl)phenyl)methyl)ethylcarbamate 1) To a solution of 4-pyridinecarboxylic acid (50.0 g, 406 mmol) in tetrahydrofuran (250 ml) was added 1,1'- carbonylbis-1H-imidazole (72.5 g, 447 mmol), and the mixture was stirred at room temperature for 30 min. To the reaction solution was added monoethyl malonate magnesium salt (82.9 g, 487 mmol), and the mixture was heated under reflux for 30 min. To the reaction solution were added ethyl acetate (200 ml) and water (200 ml), and citric acid was added until the pH of the aqueous layer became 7. The reaction solution was extracted with ethyl acetate (400 ml×2). The extract was washed with saturated brine, dried over anhydrous magnesium sulfate and evaporated under reduced pressure. The residue was washed with diisopropyl ether-hexane and recrystallized from diisopropyl ether-hexane to give ethyl 3-oxo-3-(4-pyridyl)propionate (13.3 g, 17%).

mp 60–61° C. IR ν max$^{KBr}$cm$^{-1}$: 1744, 1699, 1651, 1634, 1595, 1553. Anal. Calcd for $C_{10}H_{11}NO_3$: C, 62.17; H, 5.74; N, 7.25. Found: C, 62.17; H, 5.86; N, 7.22. $^1$H-NMR (CDCl$_3$)δ: 1.26 (3/7H, t, J=7.2 Hz), 1.35 (18/7H, t, J=7.2 Hz), 4.00 (2/7H, s), 4.18–4.40 (2H, m), 5.77 (6/7H, s), 7.61. (12/7H, d, J=4.8 Hz), 7.74 (2/7H, d, J=4.8 Hz), 8.71 (12/7H, d, J=4.8 Hz), 8.83 (2/7H, d, J=4.8 Hz), 12.44 (6/7H, s).

2) To a solution of ethyl 3-oxo-3-(4-pyridyl)propionate (13.9 g, 72.0 mmol) in 1,2-dimethoxyethane (100 ml) was added sodium hydride (60% in oil, 2.88 g, 72.0 mmol) under ice-cooling, and the mixture was stirred at room temperature for 30 min. To the reaction solution was dropwise added a solution of 4-trifluoromethylbenzyl bromide (17.2 g, 72.0 mmol) in 1,2-dimethoxyethane (50 ml), and the mixture was stirred at room temperature for 4 hrs. The reaction solution was poured into water (300 ml), and extracted with ethyl acetate (500 ml×2). The extract was washed with water and saturated brine, dried over anhydrous magnesium sulfate and evaporated under reduced pressure. The residue was purified by silica gel column chromatography (hexane:ethyl acetate=4:1) and recrystallized from ethyl acetate-hexane to give ethyl 3-oxo-3-(4-pyridyl)-2-((4-(trifluoromethyl)phenyl)methyl)propionate (10.9 g, 43%).

mp 64–65° C. IR ν max$^{KBr}$cm$^{-1}$: 1738, 1699. Anal. Calcd for $C_{18}H_{16}F_3NO_3$: C, 61.54; H, 4.59; N, 3.99. Found: C, 61.61; H, 4.44; N, 3.93. $^1$H-NMR (CDCl$_3$)δ: 1.11 (3H, t, J=7.0 Hz), 3.39 (2H, d, J=7.4 Hz), 4.11 (2H, q, J=7.0 Hz), 4.56 (1H, t, J=7.4 Hz), 7.35 (2H, d, J=8.0 Hz), 7.54 (2H, d, J=8.0 Hz), 7.66–7.78 (2H, m), 8.76–8.88 (2H, m).

3) To a solution of zinc chloride (8.14 g, 59.8 mmol) in diethyl ether (200 ml) was added sodium borohydride (4.53 g, 120 mmol), and the mixture was stirred at room temperature for 30 min. The insoluble material was filtered off, and to the filtrate was added ethyl 3-oxo-3-(4-pyridyl)-2-((4-(trifluoromethyl)phenyl)methyl)propionate (10.5 g, 29.9 mmol) in diethyl ether (50 ml). The mixture was stirred at room temperature for 30 min. and 1N hydrochloric acid was added to the reaction solution under ice-cooling to quench the reaction. Saturated aqueous sodium hydrogen carbonate was added until the pH became 8, and the mixture was extracted with ethyl acetate (300 ml×2). The extract was washed with water and saturated brine, dried over anhydrous magnesium sulfate and evaporated under reduced pressure. The residue was purified by silica gel column chromatography (ethyl acetate) and recrystallized from diisopropyl ether-hexane to give ethyl (2RS,3RS)-3-hydroxy-3-(4-pyridyl)-2-((4-(trifluoromethyl)phenyl)methyl)propionate (9.52 g, 90%).

mp 78–80° C. IR ν max$^{KBr}$cm$^{-1}$: 1726, 1630, 1618. $^1$H-NMR (CDCl$_3$)δ: 0.98 (3H, t, J=7.4 Hz), 2.72–2.82 (1H, m), 2.90–3.20 (2H, m), 3.58 (1H, d, J=2.6 Hz), 3.97 (2H, q, J=7.4 Hz), 5.21 (1H, s), 7.16 (2H, d, J=8.0 Hz), 7.40–7.70 (4H, m), 8.59 (2H, d, J=6.2 Hz).

4) To a solution of ethyl (2RS,3RS)-3-hydroxy-3-(4-pyridyl)-2-((4-(trifluoromethyl)phenyl)methyl)propionate (9.36 g, 26.5 mmol) in methanol (40 ml) was added 2N aqueous sodium hydroxide solution (26 ml, 52 mmol), and the mixture was stirred overnight at room temperature. The reaction solution was acidified with 1N hydrochloric acid, saturated aqueous sodium hydrogen carbonate was added to adjust the pH to 6, and the mixture was extracted with ethyl acetate (200 ml×2). The extract was washed with water and saturated brine, dried over anhydrous magnesium sulfate and evaporated under reduced pressure to give (2RS,3RS)-3-hydroxy-3-(4-pyridyl)-2-((4-(trifluoromethyl)phenyl)methyl)propionic acid (7.8 g, 90%).

IR ν max$^{KBr}$cm$^{-1}$: 1725. $^1$H-NMR (CD$_3$OD)δ: 3.10–3.24 (3H, m), 5.26 (1H, d, J=4.8 Hz), 7.34 (2H, d, J=8.0 Hz), 7.49 (2H, d, J=8.0 Hz), 8.07 (2H, d, J=6.6 Hz), 8.73 (2H, d, J=6.6 Hz).

5) To a solution of (2RS,3RS)-3-hydroxy-3-(4-pyridyl)-2-((4-(trifluoromethyl)phenyl)methyl) propionic acid (7.8 g, 24.0 mmol) in tetrahydrofuran (100 ml) were added diphenylphosphoryl azide (4.6 ml, 21.3 mmol) and triethylamine (6.76 ml, 48.4 mmol), and the mixture was heated under reflux overnight. The reaction solution was allowed to cool, water (200 ml) was added and the mixture was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=1:1) and recrystallized from diisopropyl ether-hexane to give (4RS,5SR)-5-(4-pyridyl)-4-((4-(trifluoromethyl)phenyl)methyl)-1,3-oxazolidin-2-one (2.50 g, 58%).

mp 212–213° C. IR ν max$^{KBr}$cm$^{-1}$: 1755, 1609. Anal. Calcd for $C_{16}H_{13}F_3N_2O_2$: C, 59.63; H, 4.07; N, 8.69. Found: C, 59.71; H, 3.99; N, 8.56. $^1$H-NMR (CDCl$_3$)δ: 2.20–2.48 (2H, m), 4.26–4.38 (1H, m), 5.33 (1H, brs), 5.80 (1H, d, J=8.2 Hz), 7.16 (2H, d, J=8.0 Hz), 7.33 (2H, d, J=6.0 Hz), 7.56 (2H, d, J=8.0 Hz), 7.68 (2H, d, J=6.0 Hz).

6) To a solution of (4RS,5SR)-5-(4-pyridyl)-4-((4-(trifluoromethyl)phenyl)methyl)-1,3-oxazolidin-2-one (500 mg, 1.55 mmol) in acetonitrile (5 ml) were added di-t-butyl dicarbonate (406 mg, 1.86 mmol) and dimethylaminopyridine (19.6 mg, 0.16 mmol), and the mixture was stirred at room temperature for 1 hr. To the reaction solution was added water (20 ml) and the mixture was extracted with ethyl acetate (20 ml×2). The extract was washed with saturated brine, dried over anhydrous magnesium sulfate and evaporated under reduced pressure. The residue was recrystallized from ethyl acetate-hexane to give 1,1-dimethylethyl (4RS,5SR)-2-oxo-5-(4-pyridyl)-4-((4-(trifluoromethyl)phenyl)methyl)-1,3-oxazolidine-3-carboxylate (571 mg, 87%).

mp 166–168° C. IR ν max$^{KBr}$cm$^{-1}$: 1821, 1726. Anal. Calcd for $C_{21}H_{21}F_3N_2O_4$: C, 59.71; H, 5.01; N, 6.63. Found: C, 59.65; H, 5.05; N, 6.34. $^1$H-NMR (CDCl$_3$)δ: 1.48 (9H, s), 2.61 (1H, dd, J=14.2, 8.0 Hz), 2.91 (1H, dd, J=14.2, 5.4 Hz), 4.80–4.98 (1H, m), 5.67 (1H, d, J=7.0 Hz), 6.84 (2H, d, J=8.0 Hz), 7.13 (2H, d, J=6.0 Hz), 7.37 (2H, d, J=8.0 Hz), 8.54 (2H, d, J=6.0 Hz).

7) To a solution of 1,1-dimethylethyl (4RS,5SR)-2-oxo-5-(4-pyridyl)-4-((4-(trifluoromethyl)phenyl)methyl)-1,3-oxazolidine-3-carboxylate (500 mg, 1.18 mmol) in methanol (2.8 ml) was added 0.5N sodium hydroxide (2.8 ml, 1.40 mmol), and the mixture was stirred at room temperature for 1 hr. To the reaction solution was added water (20 ml), and the mixture was extracted with ethyl acetate (20 ml×2). The extract was washed with saturated brine, dried over anhydrous magnesium sulfate and evaporated under reduced pressure. The residue was recrystallized from ethyl acetate-hexane to give the title compound (391 mg, 83%).

mp 198–200° C. IR ν max$^{KBr}$cm$^{-1}$: 1682, 1605, 1528. $^1$H-NMR (CDCl$_3$)δ: 1.35 (9H, s), 2.72–2.82 (2H, m), 3.61 (1H, brs), 4.11 (1H, brs), 4.65 (1H, d, J=8.6 Hz), 4.99 (1H, s), 7.20 (2H, d, J=8.0 Hz), 7.36 (2H, d, J=6.0 Hz), 7.51 (2H, d, J=8.0 Hz), 8.61 (2H, d, J=6.0 Hz)

Example 200

4-fluoro-N-((1S,2R)-2-hydroxy-2-(4-pyridyl)-1-((4-(trifluoromethyl)phenyl)methyl)ethyl)-1-naphthalenecarboxamide 1) To 1,1-dimethylethyl (1RS,2SR)-2-hydroxy-2-(4-pyridyl)-1-((4-(trifluoromethyl)phenyl)methyl) ethylcarbamate (300 mg, 0.76 mmol) was added trifluoroacetic acid (3 ml), and the mixture was stirred at room temperature for 10 min. To the reaction solution was added 1N aqueous sodium hydroxide solution (10 ml) and the mixture was extracted with ethyl acetate (20 ml×2). The extract was washed with saturated brine, dried over anhydrous magnesium sulfate and evaporated under reduced pressure. The residue was recrystallized from ethyl acetate-diisopropyl ether to give (1RS,2SR)-2-amino-1-(4-pyridyl)-3-(4-(trifluoromethyl)phenyl)-1-propanol (135 mg, 60%).

mp 97–98° C. IR ν max$^{KBr}$cm$^{-1}$: 1603, 1418. $^1$H-NMR (CDCl$_3$)δ: 2.43 (1H, dd, J=13.6, 10.6 Hz), 2.71 (1H, dd, J=13.6, 2.8 Hz), 3.30–3.42 (1H, m), 4.74 (1H, d, J=4.4 Hz), 7.23 (2H, d, J=8.2 Hz), 7.35 (2H, d, J=6.0 Hz), 7.55 (2H, d, J=8.2 Hz), 8.62 (2H, d, J=6.0 Hz).

2) To a solution of (1RS,2SR)-2-amino-1-(4-pyridyl)-3-(4-(trifluoromethyl)phenyl)-1-propanol (70 mg, 0.24 mmol) in acetonitrile (5 ml) were added 4-fluoronaphthalenecarboxylic acid (45 mg, 0.24 mmol), 1-ethyl-3-(3-dimethylaminopropyl)carbodiimide hydrochloride (68 mg, 0.35 mmol) and 1-hydroxy-1H-benzotriazole (36 mg, 0.24 mmol) and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. The residue was purified by silica gel column chromatography (ethyl acetate) and recrystallized from ethyl acetate-diisopropyl ether to give the title compound (55 mg, 50%).

mp 239–243° C. IR ν max$^{KBr}$cm$^{-1}$: 1638, 1620, 1603. $^1$H-NMR (CDCl$_3$+CD$_3$OD)δ: 2.80–3.00 (2H, m), 4.70–4.92 (1H, m), 5.05 (1H, brs), 7.00–7.60 (13H, m), 8.07 (1H, d, J=8.4 Hz), 8.50–8.62 (2H, m), Example 201

1,1-dimethylethyl (1RS,2SR)-2-(6-chloro-3-pyridyl)-2-hydroxy-1-((4-(trifluoromethyl)phenyl) methyl)ethylcarbamate 1) To a solution of 6-chloro-3-pyridinecarboxylic acid (10 g, 63.5 mmol) in tetrahydrofuran (150 ml) was added 1,1'-carbonylbis-1H-imidazole (11.3 g, 69.8 mmol), and the mixture was heated under reflux for 30 min. The reaction solution was cooled and monoethyl malonate magnesium salt (10 g, 34.9 mmol) was added. The mixture was stirred at room temperature for 30 min. To the reaction solution was added water (200 ml) and the mixture was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(6-chloro-3-pyridyl)-3-oxopropionate (9.28 g, 64%) as a brown oil.

IR ν max$^{KBr}$cm$^{-1}$: 1740, 1694, 1628, 1584. $^1$H-NMR (CDCl$_3$)δ: 1.16 (3H×3/5, t, J=7.4 Hz), 1.24 (3H×2/5, t, J=7.0 Hz), 3.88 (2H×3/5, s), 4.04–4.24 (2H, m), 5.58 (1H×2/5; s), 7.29 (1H×2/5, d, J=8.0 Hz), 7.37 (1H×3/5, d, J=8.0 Hz), 7.90 (1H×2/5, dd, J=8.0, 2.6 Hz), 8.11 (1H×3/5, dd, J=8.0, 2.6 Hz), 8.66 (1H×2/5, d, J=2.6 Hz), 8.81 (1H×3/5, d, J=2.6 Hz).

2) To a solution of ethyl 3-(6-chloro-3-pyridyl)-3-oxopropionate (9.0 g, 39.5 mmol) in 1,2-dimethoxyethane (50 ml) was added sodium hydride (60% in oil, 1.58 g, 39.5 mmol) under ice-cooling, and the mixture was stirred at room temperature for 2 hrs. To the reaction solution was dropwise added a solution of 4-trifluoromethylbenzyl bromide (9.45 g, 39.5 mmol) in 1,2-dimethoxyethane (50 ml), and the mixture was stirred overnight at room temperature. The reaction solution was poured into water (200 ml), saturated aqueous sodium hydrogen carbonate was added, and the mixture was extracted with ethyl acetate (200 ml×2). The extract was washed with water and saturated brine, dried over anhydrous magnesium sulfate and evaporated under reduced pressure. The residue was purified by silica gel column chromatography (toluene:ethyl acetate=1:1) to give ethyl 3-(6-chloro-3-pyridyl)-3-oxo-2-((4-(trifluoromethyl)phenyl)methyl)propionate (14.2 g, 93%) as a colorless oil.

IR ν max$^{KBr}$cm$^{-1}$: 1740, 1694, 1582. $^1$H-NMR (CDCl$_3$)δ: 1.13 (3H, t, J=7.0 Hz), 3.40 (2H, d, J=7.4 Hz), 4.12 (2H, q, J=7.0 Hz), 4.54 (1H, t, J=7.4 Hz), 7.35 (2H, d, J=8.4 Hz), 7.44 (1H, d, J=7.0 Hz), 7.53 (2H, d, J=8.4 Hz), 8.16–8.24 (1H, m), 8.95 (1H, d, J=2.6 Hz).

3) To a solution of zinc chloride (9.89 g, 72.6 mmol) in diethyl ether (150 ml) was added sodium borohydride (5.49 g, 145 mmol), and the mixture was stirred at room temperature for 30 min. The insoluble material was filtered off, and a solution of ethyl 3-(6-chloro-3-pyridyl)-3-oxo-2-((4-(trifluoromethyl)phenyl)methyl)propionate (14 g, 36.3 mmol) in diethyl ether (50 ml) was added to the filtrate. The mixture was stirred at room temperature for 30 min. 1N Hydrochloric acid was added to the reaction solution under ice-cooling to quench the reaction and water (200 ml) was added. The mixture was extracted with ethyl acetate (300 ml×2). The extract was washed with water and saturated brine, dried over anhydrous magnesium sulfate and evaporated under reduced pressure. The residue was purified by medium pressure silica gel column chromatography (hexane:ethyl acetate=4:1) to give ethyl(2RS,3RS)-3-(6-chloro-3-pyridyl)-3-hydroxy-2-((4-(trifluoromethyl)phenyl) methyl)propionate (9.32 g, 66%) as a colorless oil.

IR ν max$^{KBr}$cm$^{-1}$: 1728, 1618, 1588, 1568. $^1$H-NMR (CDCl$_3$)δ: 0.95 (3H, t, J=7.0 Hz), 2.92–3.18 (3H, m), 3.35 (1H, d, J=2.4 Hz), 3.92 (2H, q, J=7.0 Hz), 5.04–5.12 (1H, m), 7.20 (2H, d, J=8.2 Hz), 7.32 (1H, d, J=8.4 Hz), 7.50 (2H, d, J=8.2 Hz), 7.73 (1H, dd, J=8.8, 2.8 Hz), 8.38 (1H, d, J=8.4 Hz).

4) To a solution of ethyl(2RS,3RS)-3-(6-chloro-3-pyridyl)-3-hydroxy-2-((4-(trifluoromethyl)phenyl)methyl) propionate (9.0 g, 23.2 mmol) in methanol (23 ml) was added 2N aqueous sodium hydroxide solution (23.2 ml, 46.4 mmol), and the mixture was stirred overnight at room temperature. The reaction solution was acidified with 1N hydrochloric acid, and saturated aqueous sodium hydrogen carbonate was added to adjust the pH to 8. The mixture was extracted with ethyl acetate (200 ml×2). The extract was washed with water and saturated brine, dried over anhydrous magnesium sulfate and evaporated under reduced pressure. The residue was recrystallized from diisopropyl ether-hexane to give (2RS,3RS)-3-(6-chloro-3-pyridyl)-3-hydroxy-2-((4-(trifluoromethyl)phenyl)methyl)propionic acid (7.4 g, 89%).

mp 145–146° C. IR ν max$^{KBr}$cm$^{-1}$: 1715, 1591, 1464. Anal. Calcd for C$_{16}$H$_{13}$NO$_3$ClF$_3$: C, 53.42; H, 3.64; N, 3.89. Found: C, 53.48; H, 3.93; N, 3.66. $^1$H-NMR (CDCl$_3$)δ: 2.90–3.20 (3H, m), 5.11 (1H, d, J=4.4 Hz), 7.24 (2H, d, J=8.4 Hz), 7.33 (1H, d, J=8.2 Hz), 7.49 (2H, d, J=8.4 Hz), 7.78 (1H, dd, J=8.2, 2.2 Hz), 8.35 (1H, d, J=2.2 Hz).

5) To a solution of (2RS,3RS)-3-(6-chloro-3-pyridyl)-3-hydroxy-2-((4-(trifluoromethyl)phenyl)methyl)propionic acid (5.0 g, 13.9 mmol) in tetrahydrofuran (150 ml) were added diphenylphosphoryl azide (3.3 ml, 15.3 mmol) and triethylamine (2.9 ml, 20.9 mmol), and the mixture was heated under reflux for 1 hr. The reaction solution was allowed to cool and water (200 ml) was added. The mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate) and recrystallized from ethyl acetate-hexane to give (4RS,5SR)-5-(6-chloro-3-pyridyl)-4-((4-(trifluoromethyl)phenyl)methyl)-1,3-oxazolidin-2-one (4.29 g, 87%).

mp 176–177° C. IR ν max$^{KBr}$cm$^{-1}$: 1767, 1590, 1568. Anal. Calcd for C$_{16}$H$_{12}$N$_2$O$_2$ClF$_3$: C, 53.87; H, 3.39; N, 7.85. Found: C, 53.86; H, 3.57; N, 7.66. $^1$H-NMR (CDCl$_3$)δ: 2.22–2.50 (2H, m), 4.26–4.40 (1H, m), 5.16 (1H, brs), 5.84 (1H, d, J=8.0 Hz), 7.16 (2H, d, J=8.0 Hz), 7.43 (1H, d, J=8.2 Hz), 7.57 (2H, d, J=8.0 Hz), 7.73 (1H, dd, J=8.2, 2.6 Hz), 8.41 (1H, d, J=2.6 Hz).

6) To a solution of (4RS,5SR)-5-(6-chloro-3-pyridyl)-4-((4-(trifluoromethyl)phenyl)methyl)-1,3-oxazolidin-2-one (500 mg, 1.40 mmol) in acetonitrile (5 ml) were added di-t-butyl-dicarbonate (367 mg, 1.68 mmol) and dimethylaminopyridine (17 mg, 0.14 mmol), and the mixture was stirred at room temperature for 2 hrs. The reaction solution was concentrated, diluted with water (20 ml) and extracted with ethyl acetate (20 ml×2). The extract was washed with saturated brine, dried over anhydrous magnesium sulfate and evaporated under reduced pressure. The residue was recrystallized from ethyl acetate-hexane to give 1,1-dimethylethyl(4RS,5SR)-5-(6-chloro-3-pyridyl)-2-oxo-4-((4-(trifluoromethyl)phenyl)methyl)-1,3-oxazolidin-3-carboxylate (1.19 g, 93%).

mp 170–174° C. IR ν max$^{KBr}$cm$^{-1}$: 1821, 1723, 1464, 1362. Anal. Calcd for C$_{21}$H$_{20}$N$_2$O$_4$ClF$_3$: C, 55.21; H, 4.41; N, 6.13. Found: C, 55.44; H, 4.28; N, 6.22. $^1$H-NMR (CDCl$_3$)δ: 1.49 (9H, s), 2.60 (1H, dd, J=14.2, 8.8 Hz), 3.01 (1H, dd, J=14.2, 5.2 Hz), 4.82–4.96 (1H, m), 5.70 (1H, d, J=7.0 Hz), 6.85 (2H, d, J=8.0 Hz), 7.18 (1H, d, J=8.4 Hz), 7.36–7.46 (3H, m), 8.27 (1H, d, J=2.2 Hz).

7) To a solution of 1,1-dimethylethyl(4RS,5SR)-5-(6-chloro-3-pyridyl)-2-oxo-4-((4-(trifluoromethyl)phenyl)methyl)-1,3-oxazolidine-3-carboxylate (600 mg, 1.31 mmol) in methanol (3.1 ml) was added 0.5N sodium hydroxide methanol solution (3.1 ml, 1.55 mmol) under ice-cooling, and the mixture was stirred at room temperature for 1 hr. To the reaction solution was added water (50 ml) and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give the title compound (321 mg, 57%).

mp 157–158° C. IR ν max$^{KBr}$cm$^{-1}$: 1682, 1618, 1588, 1522. $^1$H-NMR (CDCl$_3$)δ: 1.34 (9H, s), 2.70–2.90 (2H, m), 3.85 (1H, brs), 4.09 (1H, brs), 4.62 (1H, d, J=8.8 Hz), 4.96 (1H, s), 7.24 (2H, d, J=8.0 Hz), 7.35 (1H, d, J=8.0 Hz), 7.53 (2H, d, J=8.0 Hz), 7.73 (1H, dd, J=8.0, 2.6 Hz), 8.4 (1H, d, J=2.6 Hz).

Example 202

N-((1RS,2SR)-2-(6-chloro-3-pyridyl)-2-hydroxy-1-((4-(trifluoromethyl)phenyl)methyl)ethyl)-4-fluoro-1-naphthalenecarboxamide 1) To 1,1-dimethylethyl(1RS,2SR)-2-(6-chloro-3-pyridyl)-2-hydroxy-1-((4-(trifluoromethyl)phenyl)methyl)ethylcarbamate (880 mg, 2.04 mmol) was added trifluoroacetic acid (8 ml) at 0° C., and the mixture was stirred for 10 min. The reaction solution was concentrated, diluted with water (20 ml) and extracted with ethyl acetate (20 ml×2). The extract was washed with saturated brine, dried over anhydrous magnesium sulfate and evaporated under reduced pressure. The residue was recrystallized from ethyl acetate-diisopropyl ether to give (1RS,2SR)-2-amino-1-(6-chloro-3-pyridyl)-3-(4-(trifluoromethyl)phenyl)-1-propanol (602 mg, 89%).

mp 103–104° C. IR ν max$^{KBr}$cm$^{-1}$: 1588, 1568, 1460. Anal. Calcd for C$_{15}$H$_{14}$N$_2$OClF$_3$: C, 54.47; H, 4.27; N, 8.47. Found: C, 54.57; H, 4.19; N, 8.39. $^1$H-NMR (CDCl$_3$)δ: 2.42 (1H, dd, J=13.6, 10.4 Hz), 2.76 (1H, dd, J=13.6, 3.0 Hz), 3.30–3.44 (1H, m), 4.76 (1H, d, J=4.4 Hz), 7.24 (2H, d, J=8.4 Hz), 7.36 (1H, d, J=8.4 Hz), 7.55 (2H, d, J=8.4 Hz), 7.75 (1H, dd, J=8.4, 2.2 Hz).

2) To a solution of (1RS,2SR)-2-amino-1-(6-chloro-3-pyridyl)-3-(4-(trifluoromethyl)phenyl)-1-propanol (250 mg, 0.76 mmol) in acetonitrile (15 ml) were added 4-fluoronaphthalenecarboxylic acid (144 mg, 0.76 mmol), 1-ethyl-3-(3-dimethylaminopropyl)carbodiimide hydrochloride (218 mg, 1.14 mmol) and 1-hydroxy-1H-benzotriazole (116 mg, 0.76 mmol), and the mixture was stirred overnight at room temperature. The reaction solution was diluted with water (100 ml) and extracted with ethyl acetate (100 ml×2). The extract was washed successively with water and saturated brine, dried over anhydrous magnesium sulfate and evaporated under reduced pressure. The residue was recrystallized from ethyl acetate-hexane to give the title compound (324 mg, 85%).

mp 188–189° C. IR ν max$^{KBr}$cm$^{-1}$: 1642, 1626, 1601, 1534, 1462. Anal. Calcd for C$_{26}$H$_{19}$N$_2$O$_2$ClF$_4$.0.2H$_2$O: C, 61.66; H, 3.86; N, 5.53. Found: C, 61.56; H, 3.91; N, 5.37. $^1$H-NMR (CDCl$_3$)δ: 2.89 (1H, dd, J=14.6, 11.0 Hz), 3.08 (1H, dd, J=14.6, 4.4 Hz), 4.04 (1H, brs), 4.68–4.84 (1H, m), 5.13 (1H, d, J=3.6 Hz), 6.04 (1H, d, J=8.4 Hz), 6.92–7.20 (2H, m), 7.22–7.70 (8H, m), 7.82 (1H, dd, J=8.0, 2.6 Hz), 8.09 (1H, d, J=8.0 Hz), 8.44 (1H, d, J=2.6 Hz).

Example 203

N-((1RS,2SR)-2-(6-chloro-3-pyridyl)-2-hydroxy-1-((4-(trifluoromethyl)phenyl)methyl)ethyl)-3-phenylpropanamide To a solution of (1RS,2SR)-2-amino-1-(6-chloro-3-pyridyl)-3-(4-(trifluoromethyl)phenyl)-1-propanol (250 mg, 0.76 mmol) in ethyl acetate (10 ml) were added 3-phenylpropionyl chloride (168 ml, 1.13 mmol) and saturated aqueous sodium hydrogen carbonate (10 ml), and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (302 mg, 86%).

mp 149–150° C. IR ν max$^{KBr}$cm$^{-1}$: 1651, 1541, 1456. Anal. Calcd for $C_{24}H_{22}N_2O_2ClF_3$: C, 62.27; H, 4.79; N, 6.05. Found: C, 62.44; H, 4.96; N, 6.05. $^1$H-NMR (CDCl$_3$)δ: 2.30–2.50 (2H, m), 2.60–2.92 (4H, m), 3.90 (1H, s), 4.24–4.40 (1H, m), 4.80–4.90 (1H, m), 5.36 (1H, d, J=8.2 Hz), 7.00–7.40 (8H, m), 7.48 (2H, d, J=8.0 Hz), 7.56 (1H, dd, J=8.0, 2.6 Hz), 8.32 (1H, d, J=2.2 Hz).

Example 204

1,1-dimethylethyl(1RS,2RS)-2-(6-chloro-2-pyridyl)-2-hydroxy-1-((4-(trifluoromethyl)phenyl)methyl) ethylcarbamate 1) To a solution of 6-chloro-2-pyridinecarboxylic acid (10 g, 63.5 mmol) in tetrahydrofuran (150 ml) was added 1,1'-carbonylbis-1H-imidazole (11.3 g, 69.8 mmol), and the mixture was heated under reflux for 30 min. The reaction solution was cooled, and monoethyl malonate magnesium salt (10 g, 34.9 mmol) was added. The mixture was stirred at room temperature for 30 min. To the reaction solution was added water (200 ml) and the mixture was extracted with ethyl acetate (200 ml×2). The extract was washed with saturated brine, dried over anhydrous magnesium sulfate and evaporated under reduced pressure. The residue was purified by silica gel column chromatography (hexane:ethyl-acetate=4:1) to give ethyl 3-(6-chloro-2-pyridyl)-3-oxopropionate (7.96 g, 55%) as a brown oil. IR ν max$^{KBr}$cm$^{-1}$: 1738, 1713, 1651, 1645. Anal. Calcd for $C_{10}H_{10}NO_3Cl$: C, 52.76; H, 4.43; N, 6.15. Found: C, 52.63; H, 4.55; N, 6.02. $^1$H-NMR (CDCl$_3$)δ: 1.20–1.40 (3H, m), 4.15 (2H×2/3, s), 4.14–4.32 (2H, m), 6.35 (1H×1/3, s), 7.37 (1H×1/3, d, J=6.6 Hz), 7.53 (1H×2/3, d, J=7.0 Hz), 7.70–8.02 (2H, m), 12.31 (1H×1/3, s).

2) To a solution of ethyl 3-(6-chloro-2-pyridyl)-3-oxopropionate (7.6 g, 33.4 mmol) in 1,2-dimethoxyethane (50 ml) was added sodium hydride (60% in oil, 1.34 g, 33.4 mmol) under ice-cooling, and the mixture was stirred at room temperature for 2 hrs. To the reaction solution was dropwise added a solution of 4-trifluoromethylbenzyl bromide (7.98 g, 33.4 mmol) in 1,2-dimethoxyethane (50 ml), and the mixture was stirred overnight at room temperature. The reaction solution was poured into water (200 ml), saturated aqueous sodium hydrogen carbonate was added, and the mixture was extracted with ethyl acetate (200 ml×2). The extract was washed with water and saturated brine, dried over anhydrous magnesium sulfate and evaporated under reduced pressure. The residue was purified by silica gel column chromatography (toluene) to give ethyl 3-(6-chloro-2-pyridyl)-3-oxo-2-((4-(trifluoromethyl)phenyl) methyl)propionate (13.0 g, 100%) as a colorless oil.

IR ν max$^{KBr}$cm$^{-1}$: 1732, 1709, 1576, 1563. $^1$H-NMR (CDCl$_3$)δ: 1.14 (3H, t, J=7.0 Hz), 3.24–3.50 (2H, m), 4.02–4.20 (2H, m), 4.99 (1H, t, J=7.2 Hz), 7.42 (2H, d, J=8.0 Hz), 7.52 (2H, d, J=8.0 Hz), 7.81 (1H, t, J=8.0 Hz), 7.97 (1H, d, J=6.6 Hz).

3) To a solution of zinc chloride (9.0 g, 66.15 mmol) in diethyl ether (200 ml) was added sodium borohydride (5.0 g, 132 mmol), and the mixture was stirred at room temperature for 30 min. The insoluble material was filtered off to give a solution of zinc borohydride in diethyl ether. To a solution of ethyl 3-(6-chloro-2-pyridyl)-3-oxo-2-((4-(trifluoromethyl)phenyl)methyl)propionate (12.7 g, 33.1 mmol) in diethyl ether (100 ml) was dropwise added slowly at −20° C. the solution of zinc borohydride in diethyl ether prepared in advance. The reaction solution was stirred at −20° C. for 30 min., and 1N hydrochloric acid was added to quench the reaction. Water (200 ml) was added and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl 3-(6-chloro-2-pyridyl)-3-hydroxy-2-((4-(trifluoromethyl)phenyl)methyl)propionate (4.1 g, 32%, (2RS,3RS) form: (2RS,3SR)form=1:1, crude) as a colorless oil.

$^1$H-NMR (CDCl$_3$)δ: 0.95–1.10 (3H, m), 2.80–3.40 (3H, m), 3.82–4.08 (2H, m), 4.78 (1H×1/2, dd, J=9.6, 4.4 Hz), 5.08 (1H×1/2, t, J=5.0 Hz), 7.10–7.70 (7H, m).

4) To a solution of ethyl 3-(6-chloro-2-pyridyl)-3-hydroxy-2-((4-(trifluoromethyl)phenyl)methyl)propionate (4.1 g, 10.7 mmol) in methanol (20 ml) was added 2N aqueous sodium hydroxide solution (10.7 ml, 21.4 mmol), and the mixture was stirred overnight at room temperature. The reaction solution was acidified with 1N hydrochloric acid, saturated aqueous sodium hydrogen carbonate was added to adjust the pH to 8, and the mixture was extracted with ethyl acetate (200 ml×2). The extract was washed with water and saturated brine, dried over anhydrous magnesium sulfate and evaporated under reduced pressure. The residue was recrystallized from diisopropyl ether-hexane to give 3-(6-chloro-2-pyridyl)-3-hydroxy-2-((4-(trifluoromethyl) phenyl)methyl)propionic acid (3.3 g, 86%, (2RS,3RS) form: (2RS,3SR) form=1:1).

$^1$H-NMR (CDCl$_3$)δ: 2.20–2.60 (1H, m), 2.80–3.30 (2H, m), 4.73 (1H×1/2, d, J=7.4 Hz), 5.30 (1H×1/2, s), 6.64–7.40 (7H, m).

5) To a solution of 3-(6-chloro-2-pyridyl)-3-hydroxy-2-((4-(trifluoromethyl)phenyl)methyl)propionic acid (3.1 g, 8.6 mmol) in tetrahydrofuran (100 ml) were added diphenylphosphoryl azide (2.0 ml, 9.5 mmol) and triethylamine (1.8 ml, 12.9 mmol), and the mixture was heated under reflux for 1 hr. The reaction solution was allowed to cool, water (150 ml) was added, and the mixture was extracted with ethyl acetate (150 ml×2). The extract was washed successively with saturated aqueous sodium hydrogen carbonate and saturated brine, dried over anhydrous magnesium sulfate and evaporated under reduced pressure. The residue was recrystallized from diisopropyl ether-hexane to give 5-(6-chloro-2-pyridyl)-4-((4-(trifluoromethyl)phenyl) methyl)-1,3-oxazolidin-2-one (1.18 g, 38%, (4RS,5RS) form: (4RS,5SR) form=3:2).

$^1$H-NMR (CDCl$_3$)δ: 2.18 (1H×3/5, dd, J=13.4, 7.0 Hz), 2.62 (1H×3/5, dd, J=13.4, 3.8 Hz), 3.05 (1H×2/5, dd, J=13.4, 9.2 Hz), 3.36 (1H×2/5, dd, J=13.4, 4.4 Hz), 4.16–4.30 (1H×2/5, m), 4.40–4.56 (1H×3/5,m), 5.19 (1H×3/5, s), 5.29 (1H×2/5, d, J=5.0 Hz), 5.37 (1H×2/5, s), 5.83 (1H×3/5, d, J=8.0 Hz), 7.10–7.82 (7H, m).

6) To a solution of 5-(6-chloro-2-pyridyl)-4-((4-(trifluoromethyl)phenyl)methyl)-1,3-oxazolidin-2-one (1.08 g, 1.40 mmol, (4RS,5RS) form: (4RS,5SR) form=3:2) in acetonitrile (10 ml) were added di-t-butyl dicarbonate (793 mg, 3.63 mmol) and dimethylaminopyridine (37 mg, 0.30 mmol), and the mixture was stirred at room temperature for 30 min. The reaction solution was concentrated, diluted with water (20 ml), and extracted with ethyl acetate (20 ml×2). The extract was washed with saturated brine, dried over anhydrous magnesium sulfate and evaporated under reduced pressure. The residue was eluted with hexane:ethyl acetate= 4:1 by silica gel column chromatography and recrystallized from diisopropyl ether-hexane to give 1,1-dimethylethyl (4RS,5SR)-5-(6-chloro-2-pyridyl)-2-oxo-4-((4-(trifluoromethyl)phenyl)methyl)-1,3-oxazolidine-3-carboxylate (300 mg, 22%).

IR ν max$^{KBr}$cm$^{-1}$: 1817, 1726, 1566. mp 125–126° C. $^1$H-NMR (CDCl$_3$)δ: 1.55 (9H, s), 3.24 (1H, dd, J=13.6, 8.0 Hz), 3.44 (1H, dd, J=13.6, 4.4 Hz), 4.76–4.86 (1H, m), 5.13 (1H, d, J=2.6 Hz), 7.22–7.32 (2H, m), 7.40 (2H, d, J=8.0 Hz), 7.62 (2H, d, J=8.0 Hz), 7.66 (1H, t, j=7.8 Hz).

Further, the residue was eluted with hexane:ethyl acetate= 1:1, and recrystallized from ethyl acetate-hexane to give 1,1-dimethylethyl(4RS,5RS)-5-(6-chloro-2-pyridyl)-2-oxo-4-((4-(trifluoromethyl)phenyl)methyl)-1,3-oxazolidine-3-carboxylate (735 mg, 53%).

IR ν max$^{KBr}$cm$^{-1}$: 1823, 1726, 1566. mp 166–167° C. $^1$H-NMR (CDCl$_3$)δ: 1.44 (9H, s), 2.65 (1H, dd, J=14.0, 8.0 Hz), 2.89 (1H, dd, J=14.0, 5.4 Hz), 5.02–5.16 (1H, m), 5.66 (1H, d, J=6.6 Hz), 6.88 (2H, d, J=8.2 Hz), 7.26 (1H, d, J=8.2 Hz), 7.40 (2H, d, J=8.0 Hz), 7.50 (1H, d, J=7.6 Hz), 7.73 (1H, t, J=7.8 Hz).

7) To 1,1-dimethylethyl(4RS,5RS)-5-(6-chloro-2-pyridyl)-2-oxo-4-((4-(trifluoromethyl)phenyl)methyl)-1,3-oxazolidine-3-carboxylate (677 mg, 1.46 mmol) in methanol (3.5 ml) was added 0.5N sodium hydroxide methanol solution (3.5 ml, 1.75 mmol) under ice-cooling, and the mixture was stirred at room temperature for 1 hr. To the reaction solution was added water (50 ml), and the mixture was extracted with ethyl acetate (50 ml×2). The extract was washed with saturated brine, dried over anhydrous magnesium sulfate and evaporated under reduced pressure. The residue was purified by silica gel column chromatography (ethyl acetate) and recrystallized from diisopropyl ether-hexane to give the title compound (550 mg, 57%).

IR ν max$^{KBr}$cm$^{-1}$: 1682, 1530. mp 159–160° C. $^1$H-NMR (CDCl$_3$)δ: 1.36 (9H, s), 2.67 (1H, dd, J=15.0, 5.8 Hz), 2.87 (1H, dd, J=15.0, 8.4 Hz), 4.12–4.30 (1H, m), 4.60 (1H, d, J=5.6 Hz), 4.90–5.10 (2H, m), 7.19 (2H, d, J=7.8 Hz), 7.20–7.32 (2H, m), 7.45 (2H, d, J=7.8 Hz), 7.61 (1H, t, J=8.0 Hz).

Example 205

N-((1RS,2RS)-2-(6-chloro-2-pyridyl)-2-hydroxy-1-((4-(trifluoromethyl)phenyl)methyl)ethyl)-4-fluoro-1-naphthalenecarboxamide 1) To 1,1-dimethylethyl(1RS,2RS)-2-(6-chloro-2-pyridyl)-2-hydroxy-1-((4-(trifluoromethyl)phenyl)methyl) ethylcarbamate (500 mg, 1.16 mmol) was added trifluoroacetic acid (8 ml) at 0° C., and the mixture was stirred for 10 min. The reaction solution was concentrated, diluted with water (20 ml) and extracted with ethyl acetate (20 ml×2). The extract was washed with saturated brine, dried over anhydrous magnesium sulfate and evaporated under reduced pressure. The residue was recrystallized from diisopropyl ether-hexane to give (1RS,2RS)-2-amino-1-(6-chloro-2-pyridyl)-3-(4-(trifluoromethyl)phenyl)-1-propanol (302 mg, 79%).

IR ν max$^{KBr}$cm$^{-1}$: 1757, 1586, 1563. mp 89–90° C. $^1$H-NMR (CDCl$_3$)δ: 2.54 (1H, dd, J=13.6, 9.8 Hz), 2.77 (1H, d, J=13.0 Hz), 3.44–3.58 (1H, m), 4.74 (1H, d, J=4.4 Hz), 7.16–7.32 (3H, m), 7.57 (1H, d, J=7.4 Hz), 7.52 (2H, d, J=7.4 Hz), 7.62–7.74 (1H, m).

2) To a solution of (1RS,2RS)-2-amino-1-(6-chloro-2-pyridyl)-3-(4-(trifluoromethyl)phenyl)-1-propanol (250 mg, 0.76 mmol) in acetonitrile (15 ml) were added 4-fluoronaphthalenecarboxylic acid (144 mg, 0.76 mmol), 1-ethyl-3-(3-dimethylaminopropyl)carbodiimide hydrochloride (218 mg, 1.14 mmol) and 1-hydroxy-1H-benzotriazole (116 mg, 0.76 mmol), and the mixture was stirred overnight at room temperature. The reaction solution was diluted with water (100 ml) and extracted with ethyl acetate (100 ml×2). The extract was washed successively with water and saturated brine, dried over anhydrous magnesium sulfate and evaporated under reduced pressure. The residue was purified by silica gel column chromatography (hexane:ethyl acetate=4:1). Recrystallization from ethyl acetate-hexane gave the title compound (267 mg, 70%).

mp 225–226° C. IR ν max$^{KBr}$cm$^{-1}$: 1639, 1624. $^1$H-NMR (CDCl$_3$)δ: 2.83 (1H, dd, J=14.0, 5.2 Hz), 3.02 (1H, dd, J=14.0, 9.6 Hz), 4.74 (1H, d, J=5.6 Hz), 4.80–5.00 (1H, m), 5.10–5.20 (1H, m), 6.46 (1H, d, J=8.6 Hz), 7.00–7.12 (1H, m), 7.20–7.60 (9H, m), 7.64–7.76 (1H, m), 7.84 (1H, d, J=7.6 Hz), 8.11 (1H, d, J=8.0 Hz).

Example 206

1,1-dimethylethyl(1RS,2SR)-2-(6-chloro-2-pyridyl)-2-hydroxy-1-((4-(trifluoromethyl)phenyl)methyl) ethylcarbamate To a solution of 1,1-dimethylethyl(4RS,5SR)-5-(6-chloro-2-pyridyl)-2-oxo-4-((4-(trifluoromethyl)phenyl) methyl)-1,3-oxazolidine-3-carboxylate (237 mg, 0.52 mmol) in methanol (1.25 ml) was added 0.5N sodium hydroxide methanol solution (1.25 ml, 0.62 mmol) under ice-cooling, and the mixture was stirred at room temperature for 1 hr. To the reaction solution was added water (50 ml) and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give the title compound (150 mg, 67%).

IR ν max$^{KBr}$cm$^{-1}$: 1694, 1505. mp 134–135° C. $^1$H-NMR (CDCl$_3$)δ: 1.24 (9H, s), 3.13 (2H, d, J=7.8 Hz), 4.10–4.30 (1H, m), 4.62–4.90 (2H, m), 7.20–7.30 (2H, m), 7.30–7.52 (2H, m), 7.56–7.72 (3H, m).

Example 207

N-((1RS,2SR)-2-hydroxy-2-(3-phenoxyphenyl)-1-((4-(trifluoromethyl)phenyl)methyl)ethyl)-4-fluoro-1-naphthalenecarboxamide.

1) To a solution of 3-phenoxybenzoic acid (13.5 g, 63.0 mmol) in tetrahydrofuran (150 ml) was added 1,1'-carbonylbis-1H-imidazole (11.2 g, 69.3 mmol), and the mixture was stirred at room temperature for 30 min. To the reaction solution was added monoethyl malonate magnesium salt (10 g, 34.8 mmol) and the mixture was stirred at room temperature for 2 hrs. To the reaction solution were added ethyl acetate (50 ml) and water (50 ml), and conc. hydrochloric acid was added until the pH of the aqueous layer became acidic. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-oxo-3-(4-phenoxyphenyl) propionate (17.9 g, 100%) as a brown oil.

IR ν max$^{KBr}$cm$^{-1}$: 1744, 1694, 1582, 1489, 1439. Anal. Calcd for $C_{17}H_{16}O_4 \cdot 0.1H_2O$: C, 71.37; H, 5.70 Found: C, 71.11; H, 5.89. $^1$H-NMR (CDCl$_3$)δ: 1.20–1.40 (3H, m), 3.95 (2H×4/5, s), 4.12–4.30 (2H, m), 5.62 (1H×1/5, s), 7.02 (2H, d, J=7.4 Hz), 7.04–7.30 (2H, m), 7.30–7.60 (4H, m), 7.66 (1H, d, J=7.6 Hz).

2) To a solution of ethyl 3-oxo-3-(4-phenoxyphenyl) propionate (15 g, 52.8 mmol) in 1,2-dimethoxyethane (100 ml) was added sodium hydride (60% in oil, 2.11 g, 52.8 mmol) under ice-cooling, and the mixture was stirred at room temperature for 30 min. To the reaction solution was dropwise added a solution of 4-trifluoromethylbenzyl bromide (12.6 g, 52.8 mmol) in 1,2-dimethoxyethane (50 ml), and the mixture was stirred at room temperature for 4 hrs. The reaction solution was poured into water (200 ml) and extracted with ethyl acetate (200 ml×2). The extract was washed with water and saturated brine, dried over anhydrous magnesium sulfate and evaporated under reduced pressure. The residue was recrystallized from ethyl acetate-hexane to give ethyl 3-oxo-3-(4-phenoxyphenyl)-2-((4-(trifluoromethyl)phenyl)methyl)propionate (15.4 g, 66%).

mp 77–78° C. IR ν max$^{KBr}$cm$^{-1}$: 1738, 1694, 1582, 1489, 1437. Anal. Calcd for $C_{25}H_{21}F_3O_4$: C, 67.87; H, 4.78 Found: C, 67.92; H, 4.89. $^1$H-NMR (CDCl$_3$)δ: 1.10 (3H, t, J=7.4 Hz), 3.35 (1H, d, J=7.4 Hz), 4.09 (2H, q, J=7.4 Hz), 4.53 (1H, t, J=7.4 Hz), 6.94–7.04 (2H, m), 7.10–7.70 (11H, m).

3) To a solution of zinc chloride (7.39 g, 54.2 mmol) in diethyl ether (150 ml) was added sodium borohydride (4.11 g, 108.5 mmol), and the mixture was stirred at room temperature for 30 min. The insoluble material was filtered off, and a solution of ethyl 3-oxo-3-(4-phenoxyphenyl)-2-((4-(trifluoromethyl)phenyl)methyl)propionate (10 g, 25.9 mmol) in diethyl ether (50 ml) was added to the filtrate. The mixture was stirred at room temperature for 30 min. 1N Hydrochloric acid was added to the reaction solution under ice-cooling to quench the reaction. Water (200 ml) was added, and the mixture was extracted with ethyl acetate (300 ml×2). The extract was washed with water and saturated brine, dried over anhydrous magnesium sulfate and evaporated under reduced pressure. The residue was purified by silica gel column chromatography (ethyl acetate) to give ethyl(2RS,3RS)-3-hydroxy-3-(4-phenoxyphenyl)-2-((4-(trifluoromethyl)phenyl)methyl)propionate (12.0 g, 100%) as a colorless oil.

IR ν max$^{KBr}$cm$^{-1}$: 1728, 1713, 1584, 1487, 1447. Anal. Calcd for $C_{25}H_{23}F_3O_4$: C, 67.56; H, 5.22 Found: C, 67.46; H, 5.20 $^1$H-NMR (CDCl$_3$)δ: 0.94 (3H, t, J=7.2 Hz), 2.90–3.12 (4H, m), 3.90 (2H, q, J=7.2 Hz), 4.98–5.08 (1H, m), 6.90–7.40 (11H, m), 7.48 (2H, d, J=8.0 Hz).

4) To a solution of ethyl(2RS,3RS)-3-hydroxy-3-(4-phenoxyphenyl)-2-((4-(trifluoromethyl)phenyl)methyl) propionate (11.8 g, 26.6 mmol) in methanol (40 ml) was added 2N aqueous sodium hydroxide solution (26.6 ml, 53.2 mmol), and the mixture was stirred at room temperature for 4 hrs. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-hydroxy-3-(4-phenoxyphenyl)-2-((4-(trifluoromethyl)phenyl)methyl) propionic acid (9.0 g, 81%).

mp 128–129° C. IR ν max$^{KBr}$cm$^{-1}$: 1713, 1586, 1489, 1447. Anal. Calcd for $C_{23}H_{19}F_3O_4$: C, 66.34; H, 4.60 Found: C, 66.41; H, 4.58. $^1$H-NMR (CDCl$_3$)δ: 2.86–3.14 (3H, m), 5.10 (1H, s), 6.90–7.02 (3H, m), 7.02–7.22 (5H, m), 7.22–7.40 (3H, m), 7.47 (2H, d, J=8.0 Hz).

5) To a solution of (2RS,3RS)-3-hydroxy-3-(4-phenoxyphenyl)-2-((4-(trifluoromethyl)phenyl)methyl) propionic acid (7.0 g, 16.8 mmol) in tetrahydrofuran (180 ml) were added diphenylphosphoryl azide (4.0 ml, 18.5 mmol) and triethylamine (3.5 ml, 25.2 mmol), and the mixture was heated under reflux for 6 hrs. The reaction solution was allowed to cool and water (200 ml) was added. The mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate) and recrystallized from ethyl acetate-hexane to give (4RS, 5SR)-5-(4-phenoxyphenyl)-4-((4-(trifluoromethyl)phenyl)-methyl)-1,3-oxazolidin-2-one (6.40 g, 92%).

mp 110–111° C. IR ν max$^{KBr}$cm$^{-1}$: 1759, 1617, 1586, 1489. Anal. Calcd for $C_{23}H_{18}F_3NO_3$: C, 66.82; H, 4.39; N, 3.39. Found: C, 66.78; H, 4.25; N, 3.14. $^1$H-NMR (CDCl$_3$)δ: 2.30–2.50 (2H, m), 4.18–4.30 (1H, m), 5.22 (1H, s), 5.77 (1H, d, J=8.0 Hz), 6.96–7.04 (4H, m), 7.04–7.20 (4H, m), 7.30–7.44 (3H, m), 7.55 (2H, d, J=8.0 Hz).

6) To a solution of (4RS,5SR)-5-(4-phenoxyphenyl)-4-((4-(trifluoromethyl)phenyl)methyl)-1,3-oxazolidin-2-one (6.0 g, 14.5 mmol) in ethanol (100 ml) was added 8N aqueous sodium hydroxide solution (9.0 ml, 72 mmol), and the mixture was heated under reflux for 4 hrs. The reaction solution was concentrated, diluted with water (300 ml) and extracted with ethyl acetate (300 ml×2). The extract was washed with saturated brine, dried over anhydrous magnesium sulfate and evaporated under reduced pressure to give (1RS,2SR)-2-amino-1-(4-phenoxyphenyl)-3-(4-(trifluoromethyl)phenyl)-1-propanol (4.21 g, 75%) as a colorless oil. A portion thereof was recrystallized from ethanol-ether as hydrochloride, which was measured for elemental analysis values.

IR ν max$^{KBr}$cm$^{-1}$: 1584, 1489, 1443, 1418. Anal. Calcd for $C_{22}H_{21}ClF_3NO_2 \cdot 0.2H_2O$: C, 61.82; H, 5.04; N, 3.28. Found: C, 61.83; H, 5.26; N, 3.24. $^1$H-NMR (CDCl$_3$)δ: 2.44 (1H, dd, J=14.2, 10.2 Hz), 2.86 (1H, dd, J=14.0, 2.8 Hz), 3.20–3.36 (1H, m), 4.64 (1H, d, J=4.8 Hz), 6.90–7.20 (6H, m), 7.20–7.42 (5H, m), 7.53 (2H, d, J=8.0 Hz).

7) To a solution of (1RS,2SR)-2-amino-1-(4-phenoxyphenyl)-3-(4-(trifluoromethyl)phenyl)-1-propanol (400 mg, 1.03 mmol) in acetonitrile (30 ml) were added 4-fluoronaphthalenecarboxylic acid (196 mg, 1.03 mmol), 1-ethyl-3-(3-dimethylaminopropyl)-carbodiimide hydrochloride (247 mg, 1.55 mmol) and 1-hydroxy-1H-benzotriazole (158 mg, 1.03 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (446 mg, 77%).

mp 184–185° C. IR ν max$^{KBr}$cm$^{-1}$: 1642, 1537, 1489. Anal. Calcd for $C_{33}H_{25}F_4NO_3$: C, 70.83; H, 4.50; N, 2.50.

Found: C, 70.65; H, 4.56; N, 2.44. $^1$H-NMR (CDCl$_3$)δ: 2.88 (1H, dd, J=14.4, 10.6 Hz), 3.08 (1H, dd, J=14.4, 4.0 Hz), 4.76–4.94 (1H, m), 5.09 (1H, s), 6.04 (1H, d, J=8.8 Hz), 6.95–7.50 (14H, m), 7.50–7.60 (3H, m), 7.66 (1H, d, J=8.0 Hz), 8.10 (1H, d, J=8.4 Hz).

Example 208

N-((1RS,2SR)-2-hydroxy-2-(3-phenoxyphenyl)-1-((4-(trifluoromethyl)phenyl)methyl)ethyl)-3-phenylpropanamide To a solution of (1RS,2SR)-2-amino-1-(4-phenoxyphenyl)-3-(4-(trifluoromethyl)phenyl)-1-propanol (400 mg, 1.03 mmol) in ethyl acetate (20 ml) were added 3-phenylpropionyl chloride (230 ml, 1.55 mmol) and saturated aqueous sodium hydrogen carbonate (20 ml), and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (472 mg, 88%).

mp 134–135° C. IR ν max$^{KBr}$cm$^{-1}$: 1645, 1584, 1489, 1445. Anal. Calcd for C$_{31}$H$_{28}$F$_3$NO$_3$: C, 71.66; H, 5.43; N, 2.70. Found: C, 71.50; H, 5.47; N, 2.43. $^1$H-NMR (CDCl$_3$)δ: 2.37 (2H, t, J=7.6 Hz), 2.58–2.78 (2H, m), 2.85 (2H, t, J=7.6 Hz), 3.20 (1H, d, J=3.8 Hz), 4.30–4.48 (1H, m), 4.78–4.84 (1H, m), 5.37 (1H, d, J=8.4 Hz), 6.90–7.20 (10H, m), 7.20–7.40 (6H, m), 7.45 (2H, d, J=8.4 Hz).

Example 209

N-((1RS,2SR)-2-hydroxy-2-(4-phenoxyphenyl)-1-((4-(trifluoromethyl)phenyl)methyl)ethyl)-4-fluoro-1-naphthalenecarboxamide 1) To a solution of 4-phenoxybenzoic acid (10.4 g, 48.7 mmol) in tetrahydrofuran (150 ml) was added 1,1'-carbonylbis-1H-imidazole (8.68 g, 53.6 mmol), and the mixture was stirred at room temperature for 30 min. To the reaction solution was added monoethyl malonate magnesium salt (7.67 g, 26.8 mmol), and the mixture was stirred at room temperature for 2 hrs. Ethyl acetate (50 ml) and water (50 ml) were added to the reaction solution and conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate= 4:1) to give ethyl 3-oxo-3-(4-phenoxyphenyl)propionate (12.9 g, 93%) as a brown oil.

IR ν max$^{KBr}$cm$^{-1}$: 1738, 1682, 1586, 1505, 1489. Anal. Calcd for C$_{17}$H$_{16}$O$_4$: C, 71.82; H, 5.67 Found: C, 71.63; H, 5.56. $^1$H-NMR (CDCl$_3$)δ: 1.20–1.38 (3H, m), 3.95 (2H×5/6, s), 4.16–4.32 (2H, m), 5.60 (1H×1/6, s), 6.94–7.12 (4H, m), 7.12–7.28 (1H, m), 7.32–7.48 (2H, m), 7.72–7.80 (2H×1/6, m), 7.88–8.00 (2H×5/6, m).

2) To a solution of ethyl 3-oxo-3-(4-phenoxyphenyl) propionate (12 g, 42.2 mmol) in 1,2-dimethoxyethane (80 ml) was added sodium hydride (60% in oil, 1.69 g, 42.2 mmol) under ice-cooling, and the mixture was stirred at room temperature for 30 min. To the reaction solution was dropwise added a solution of 4-trifluoromethylbenzyl bromide (10.1 g, 42.2 mmol) in 1,2-dimethoxyethane (50 ml), and the reaction solution was stirred at room temperature for 4 hrs. The reaction solution was poured into water (200 ml), and extracted with ethyl acetate (200 ml×2). The extract was washed with water and saturated brine, dried over anhydrous magnesium sulfate and evaporated under reduced pressure. The residue was recrystallized from ethyl acetate-hexane to give ethyl 3-oxo-3-(4-phenoxyphenyl)-2-((4-(trifluoromethyl)phenyl)methyl)propionate (14.0 g, 75%).

mp 67–68° C. IR ν max$^{KBr}$cm$^{-1}$: 1738, 1682, 1586, 1505, 1489. Anal. Calcd for C$_{25}$H$_{21}$F$_3$O$_4$: C, 67.87; H, 4.78 Found: C, 67.88; H, 4.89. $^1$H-NMR (CDCl$_3$)δ: 1.13 (3H, t, J=7.2 Hz), 3.37 (2H, d, J=7.2 Hz ), 4.11 (2H, q, J=7.2 Hz), 4.57 (1H, t, J=7.2 Hz), 6.90–7.10 (4H, m), 7.12–7.26 (1H, m), 7.30–7.48 (4H, m), 7.51 (2H, d, J=8.2 Hz), 7.90–8.00 (2H, m).

3) To a solution of zinc chloride (7.39 g, 54.2 mmol) in diethyl ether (150 ml) was added sodium borohydride (4.11 g, 108.5 mmol) and the mixture was stirred at room temperature for 30 min. Insoluble material was filtered off and a solution of ethyl 3-oxo-3-(4-phenoxyphenyl)-2-((4-(trifluoromethyl)phenyl)methyl)propionate (12 g, 27.1 mmol) in diethyl ether (50 ml) was added to the filtrate. The mixture was stirred at room temperature for 30 min. 1N Hydrochloric acid was added to the reaction solution under ice-cooling to quench the reaction. Water (200 ml) was added and the mixture was extracted with ethyl acetate (300 ml×2). The extract was washed with water and saturated brine, dried over anhydrous magnesium sulfate and evaporated under reduced pressure. The residue was purified by silica gel column chromatography (ethyl acetate) to give ethyl(2RS,3RS)-3-hydroxy-3-(4-phenoxyphenyl)-2-((4-(trifluoromethyl)phenyl)methyl)propionate (11.9 g, 99%) as a colorless oil.

IR ν max$^{KBr}$cm$^{-1}$: 1728, 1618, 1590, 1507, 1489. Anal. Calcd for C$_{25}$H$_{23}$F$_3$O$_4$: C, 67.56; H, 5.22 Found: C, 67.40; H, 5.04. $^1$H-NMR (CDCl$_3$)δ: 0.94 (3H, t, J=7.2 Hz), 2.85 (1H, d, J=2.6 Hz), 2.90–3.12 (3H, m), 3.89 (2H, q, J=7.2 Hz), 4.98–5.06 (1H, m), 6.94–7.04 (4H, m), 7.04–7.18 (1H, m), 7.22 (2H, d, J=8.0 Hz), 7.30–7.42 (4H, m), 7.49 (2H, d, J=8.0 Hz).

4) To a solution of ethyl(2RS,3RS)-3-hydroxy-3-(4-phenoxyphenyl)-2-((4-(trifluoromethyl)phenyl)methyl) propionate (11.5 g, 25.9 mmol) in methanol (40 ml) was added 2N aqueous sodium hydroxide solution (25.9 ml, 51.8 mmol), and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from ethyl acetate-hexane to give (2RS,3RS)-3-hydroxy-3-(4-phenoxyphenyl)-2-((4-(trifluoromethyl)phenyl)methyl) propionic acid (9.65 g, 90%).

mp 140–141° C. IR ν max$^{KBr}$cm$^{-1}$: 1715, 1590, 1489. Anal. Calcd for C$_{23}$H$_{19}$F$_3$O$_4$: C, 66.34; H, 4.60 Found: C, 66.36; H, 4.49. $^1$H-NMR (CDCl$_3$)δ: 2.98–3.10 (3H, m), 5.08 (1H, s), 6.92–7.04 (4H, m), 7.04–7.30 (3H, m), 7.30–7.40 (4H, m), 7.48 (2H, d, J=8.2 Hz).

5) To a solution of (2RS,3RS)-3-hydroxy-3-(4-phenoxyphenyl)-2-((4-(trifluoromethyl)phenyl)methyl) propionic acid (7.0 g, 16.8 mmol) in tetrahydrofuran (180 ml) were added diphenylphosphoryl azide (4.0 ml,18.5 mmol) and triethylamine (3.5 ml, 25.2 mmol), and the mixture was heated under reflux for 6 hrs. The reaction solution was allowed to cool and water (200 ml) was added. The mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel-column chromatography (ethyl acetate) and recrystallized from ethyl acetate-hexane to give (4RS, 5SR)-5-(4-phenoxyphenyl)-4-((4-(trifluoromethyl)phenyl) methyl)-1,3-oxazolidin-2-one (6.40 g, 92%).

mp 162–163° C. IR ν max$^{KBr}$cm$^{-1}$: 1759, 1617, 1591, 1508, 1489. Anal. Calcd for $C_{23}H_{18}F_3NO_3$: C, 66.82; H, 4.39; N, 3.39. Found: C, 66.94; H, 4.17; N, 3.39. $^1$H-NMR (CDCl$_3$)δ: 2.30–2.50 (2H, m), 4.20–4.32 (1H, m), 5.11 (1H, brs), 5.80 (1H, d, J=7.8 Hz), 6.90–7.10 (4H, m), 7.10–7.22 (3H, m), 7.22–7.50 (4H, m), 7.56 (2H, d, J=8.0 Hz).

6) To a solution of (4RS,5SR)-5-(4-phenoxyphenyl)-4-((4-(trifluoromethyl)phenyl)methyl)-1,3-oxazolidin-2-one (6.0 g, 14.5 mmol) in ethanol (100 ml) was added 8N aqueous sodium hydroxide solution (9.0 ml, 72 mmol), and the mixture was heated under reflux for 4 hrs. The reaction solution was concentrated and diluted with water (300 ml). The mixture was extracted with ethyl acetate (300 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-phenoxyphenyl)-3-(4-(trifluoromethyl)phenyl)-1-propanol (5.03 g, 90%).

mp 114–115° C. IR ν max$^{KBr}$cm$^{-1}$: 1590, 1507, 1489. Anal. Calcd for $C_{22}H_{20}F_3NO_2$: C, 68.21; H, 5.20; N, 3.62. Found: C, 68.12; H, 5.27; N, 3.58. $^1$H-NMR (CDCl$_3$)δ: 2.46 (1H, dd, J=13.6, 10.2 Hz), 2.94 (1H, dd, J=13.6, 2.8 Hz), 3.24–3.38 (1H, m), 4.65. (1H, d, J=5.0 Hz), 6.98–7.18 (5H, m), 7.22–7.42 (6H, m), 7.55 (2H, d, J=8.0 Hz).

7) To a solution of (1RS,2SR)-2-amino-1-(4-phenoxyphenyl)-3-(4-(trifluoromethyl)phenyl)-1-propanol (400 mg, 1.03 mmol) in acetonitrile (30 ml) were added 4-fluoronaphthalenecarboxylic acid (196 mg, 1.03 mmol), 1-ethyl-3-(3-dimethylaminopropyl)carbodiimide hydrochloride (297 mg, 1.55 mmol) and 1-hydroxy-1H-benzotriazole (158 mg, 1.03 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (520 mg, 90%).

mp 205–210° C. IR ν max$^{KBr}$cm$^{-1}$: 1644, 1626, 1599, 1510. Anal. Calcd for $C_{33}H_{25}F_4NO_3$: C, 70.83; H, 4.50; N 2.50 Found: C, 70.59; H, 4.50; N, 2.57. $^1$H-NMR (CDCl$_3$)δ: 2.89 (1H, dd, J=14.2, 11.0 Hz), 3.06–3.24 (2H, m), 4.78–4.90 (1H, m), 5.09 (1H, d, J=4.0 Hz), 5.97 (1H, d, J=9.0 Hz), 6.96–7.20 (7H, m), 7.30–7.68 (11H, m), 8.08 (1H, d, J=8.0 Hz).

Example 210

N-((1RS,2SR)-2-hydroxy-2-(4-phenoxyphenyl)-1-((4-(trifluoromethyl)phenyl)methyl)ethyl)-6,7-dihydro-5H-benzo[a]cycloheptene-1-carboxamide To a solution of (1RS,2SR)-2-amino-1-(4-phenoxyphenyl)-3-(4-(trifluoromethyl)phenyl)-1-propanol (206 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl) carbodiimide hydrochloride (153 mg, 0.80 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (268 mg, 90%).

mp 191–192° C. IR ν max$^{KBr}$cm$^{-1}$: 1642, 1590, 1507, 1489, 1327. $^1$H-NMR (CDCl$_3$)δ: 1.90–2.06 (2H, m), 2.10–2.26 (2H, m), 2.60–2.70 (2H, m), 2.85 (1H, dd, J=14.4, 11.0 Hz), 3.07 (1H, dd, J=14.4, 3.4 Hz), 3.42 (1H, brs), 4.64–4.84 (1H, m), 5.03 (1H, d, J=4.0 Hz), 5.80 (1H, d, J=9.6 Hz), 5.80–5.96 (1H, m), 6.13 (1H, d, J=11.8 Hz), 6.90–7.20 (8H, m), 7.20–7.50 (6H, m), 7.54 (2H, d, J=8.2 Hz).

Example 211

N-((1RS,2SR)-2-hydroxy-2-(4-phenoxyphenyl)-1-((4-(trifluoromethyl)phenyl)methyl)ethyl)-3-phenylpropanamide To a solution of (1RS,2SR)-2-amino-1-(4-phenoxyphenyl)-3-(4-(trifluoromethyl)phenyl)-1-propanol (400 mg, 1.03 mmol) in ethyl acetate (20 ml) were added 3-phenylpropionyl chloride (230 ml, 1.55 mmol) and saturated aqueous sodium hydrogen carbonate (20 ml), and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give the title compound (416 mg, 78%).

mp 133–134° C. IR ν max$^{KBr}$cm$^{-1}$: 1645, 1590, 1507, 1489. Anal. Calcd for $C_{31}H_{28}F_3NO_3$: C, 71.66; H, 5.43; N, 2.70. Found: C, 71.84; H, 5.26; N, 2.69. $^1$H-NMR (CDCl$_3$)δ: 2.32–2.42 (2H, m), 2.60–2.90 (4H, m), 3.14–3.22 (1H, m), 4.32–4.50 (1H, m), 4.78–4.86 (1H, m), 5.36 (1H, d, J=8.4 Hz), 6.92–7.04 (4H, m), 7.06–7.40 (7H, m), 7.47 (2H, d, J=8.0 Hz).

Example 212

N-((1RS,2SR)-1-((4-fluorophenyl)methyl)-2-hydroxy-2-(4-(trifluoromethyl)phenyl)ethyl)-1-naphthalenecarboxamide 1) To a solution of 4-trifluoromethylacetophenone (57.8 g, 0.307 mol) and ethanol (1 ml) in ethyl carbonate (300 ml) was added sodium hydride (24.5 g, 60% in oil, 0.63 mol) by small portions. Because heat was generated gradually, the reaction solution was ice-cooled and thereafter stirred at room temperature for 2 hrs. 6N Hydrochloric acid was added thereto to stop the reaction. The mixture was diluted with water (300 ml) and extracted with ethyl acetate (200 ml×2). The extract was washed with water, dried over anhydrous magnesium sulfate and evaporated under reduced pressure. The residue was purified by silica gel column chromatography (hexane:ethyl acetate=50:1–5:1) to give ethyl 3-oxo-3-(4-trifluoromethylphenyl)propionate (71.2 g, 89%).

IR ν max$^{Neat}$cm$^{-1}$: 1744, 1696, 1431, 1325, 1202, 1132, 1069, 1017, 853. $^1$H-NMR (CDCl$_3$)δ: 1.28 (3H×0.62, t, J=7.8 Hz, keto), 1.37 (3H×0.38, t, J=7.8 Hz, enol), 4.04 (2H×0.62, s, keto), 4.25 (2H,×0.62, q, J=7.8 Hz, keto), 4.31 (2H×0.38, q, J=7.8 Hz, enol), 5.75 (1H×0.38, s, enol), 7.28 (1H×0.62, s, keto), 7.70 (2H×0.38, d, J=8.0 Hz, enol), 7.78

(2H×0.62, d, J=8.0 Hz, keto), 7.90 (2H×0.38, d, J=8.0 Hz), 8.08 (2H×0.62, d, J=8.0 Hz).

2) A mixture of ethyl 3-oxo-3-(4-trifluoromethylphenyl)propionate (38.2 g, 0.147 mol), 4-fluorobenzyl bromide (25 g, 0.13 mol), potassium carbonate (36.6 g, 0.26 mol) and acetonitrile (500 ml) was stirred at 60° C. for 3 hrs. The reaction solution was concentrated under reduced pressure, and water (500 ml) was added. The mixture was extracted with ethyl acetate (500, 200 ml). The extract was washed with water, dried over anhydrous magnesium sulfate and evaporated under reduced pressure. The residue was purified by silica gel column chromatography (hexane:ethyl acetate=50:1–10:1, hexane:toluene=1:1) and crystallized from cold hexane to give ethyl 2-((4-fluorophenyl)methyl)-3-oxo-3-(4-(trifluoromethyl)phenyl)propionate (29.5 g, 55%).

mp 52–53° C. IR ν max$^{KBr}$cm$^{-1}$: 1723, 1692, 1514, 1323, 1231, 1130, 1067, 853, 824. elemental analysis for $C_{19}H_{16}F_4O_3$ Calculated: C, 61.96; H, 4.38 Found: C, 61.97; H, 4.14. $^1$H-NMR (CDCl$_3$)δ: 1.12 (3H, t, J=7.1 Hz), 3.31 (2H, d, J=7.6 Hz), 4.10 (2H, q, J=7.1 Hz), 4.56 (1H, t, J=7.3 Hz), 6.88–8.03 (2H, m), 7.12–7.32 (2H, m), 7.71 (2H, t, J=8.0 Hz), 8.04 (2H, d, J=8.0 Hz)

3) To a solution of zinc chloride (21.54 g, 158 mmol) in ether (500 ml) was added sodium borohydride (11.96 g, 316 mmol), and the mixture was stirred at room temperature for 30 min. Precipitated sodium chloride was filtered off. To the filtrate was gradually added a solution of ethyl 2-((4-fluorophenyl)methyl)-3-oxo-3-(4-(trifluoromethyl)phenyl)propionate (28 g, 79 mmol) in ether (200 ml) under ice-cooling, and the mixture was stirred at room temperature for 30 min. The reaction solution was poured into 1N aqueous hydrochloric acid solution (500 ml), and extracted with ethyl acetate (500 ml×2). The extract was washed with saturated brine, dried over anhydrous magnesium sulfate and evaporated under reduced pressure. The residue was purified by silica gel column chromatography (hexane:ethyl acetate=4:1) to give ethyl(2RS,3RS)-2-((4-fluorophenyl)methyl)-3-hydroxy-3-(4-(trifluoromethyl)phenyl)propionate (28 g, 100%) as a colorless oil.

IR ν max$^{KBr}$cm$^{-1}$: 1713, 1510. Anal. Calcd for $C_{19}H_{18}F_4O_3$: C, 61.62; H, 4.90 Found: C, 61.51; H, 4.87. $^1$H-NMR (CDCl$_3$)δ: 0.95 (3H, t, J=7.4 Hz), 2.80–3.06 (3H, m), 3.15 (1H, d, J=2.6 Hz), 3.91 (2H, q, J=7.4 Hz), 5.11 (1H, brs), 6.84–7.06 (4H, m), 7.52 (2H, d, J=8.4 Hz), 7.63 (2H, d, J=8.4 Hz).

4) To a solution of ethyl(2RS,3RS)-2-((4-fluorophenyl)methyl)-3-hydroxy-3-(4-(trifluoromethyl)phenyl)propionate (27.5 g, 74.3 mmol) in methanol (300 ml) was added 1N aqueous sodium hydroxide solution (150 ml, 150 mmol), and the mixture was stirred overnight at room temperature. The reaction solution was poured into 1N aqueous hydrochloric acid solution (180 ml), and the mixture was extracted with ethyl acetate (300 ml×2). The extract was washed with saturated brine, dried over anhydrous magnesium sulfate and evaporated under reduced pressure. Recrystallization of the residue from ethyl acetate-hexane gave (2RS,3RS)-2-((4-fluorophenyl)methyl)-3-hydroxy-3-(4-(trifluoromethyl)phenyl)propionic acid (22.45 g, 88%).

mp 120–121° C. IR ν max$^{KBr}$cm$^{-1}$: 1713. Anal. Calcd for $C_{17}H_{14}F_4O_3$: C, 59.65; H, 4.12 Found: C, 59.56; H, 4.03. $^1$H-NMR (CDCl$_3$)δ: 2.90–3.10 (3H, m), 5.16 (1H, d, J=3.6 Hz), 6.82–7.12 (4H, m), 7.52 (2H, d, J=8.0 Hz), 7.63 (2H, d, J=8.0 Hz).

5) To a solution of (2RS,3RS)-2-((4-fluorophenyl)methyl)-3-hydroxy-3-(4-(trifluoromethyl)phenyl)propionic acid (21.0 g, 61.35 mmol) in tetrahydrofuran (500 ml) were added diphenylphosphoryl azide (14.5 ml, 67.5 mmol) and triethylamine (12.9 ml, 92 mmol), and the mixture was heated under reflux for 3 hrs. The reaction solution was diluted with water (500 ml), and the mixture was extracted with ethyl acetate (500 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave (4RS,5SR)-4-((4-fluorophenyl)methyl)-5-(4-(trifluoromethyl)phenyl)-1,3-oxazolidin-2-one (19.24 g, 92%).

mp 160–161° C. IR ν max$^{KBr}$cm$^{-1}$: 1738, 1508. Anal. Calcd for $C_{17}H_{13}F_4NO_2$: C, 60.18; H, 3.86 ; N, 4.13. Found: C, 60.01; H, 3.99; N, 4.06. $^1$H-NMR (CDCl$_3$)δ: 2.10–2.34 (2H, m), 4.20–4.34 (1H, m), 5.11 (1H, s), 5.86 (1H, d, J=7.8 Hz), 6.97 (4H, d, J=9.0 Hz), 7.51 (2H, d, J=8.2 Hz), 7.70 (2H, d, J=8.2 Hz).

6) To a solution of (4RS,5SR)-4-((4-fluorophenyl)methyl)-5-(4-(trifluoromethyl)phenyl)-1,3-oxazolidin-2-one (18 g, 53.1 mmol) in ethanol (300 ml) was added 8N aqueous sodium hydroxide solution (19.9 ml, 159 mmol), and the mixture was heated under reflux for 4 hrs. The reaction solution was concentrated, diluted with water (300 ml), and extracted with ethyl acetate (300 ml×2). The extract was washed with saturated brine, dried over anhydrous magnesium sulfate and evaporated under reduced pressure. Recrystallization of the residue from ethyl acetate-hexane gave (1RS,2SR)-2-amino-3-(4-fluorophenyl)-1-(4-(trifluoromethyl)phenyl)-1-propanol (14.1 g, 85%).

mp 130–131° C. IR ν max$^{KBr}$cm$^{-1}$: 1618, 1601, 1588. Anal. Calcd for $C_{16}H_{15}F_4NO$: C, 61.34; H, 4.83; N, 4.47. Found: C, 61.23; H, 4.72; N, 4.41. $^1$H-NMR (CDCl$_3$)δ: 2.32 (1H, dd, J=14.0, 10.6 Hz), 2.68 (1H, dd, J=14.0, 3.4 Hz), 3.20–3.36 (1H, m), 4.76 (1H, d, J=4.4 Hz), 6.90–7.16 (4H, m), 7.52 (2H, d, J=8.2 Hz), 7.65 (2H, d, J=8.2 Hz).

7) To a solution of (1RS,2SR)-2-amino-3-(4-fluorophenyl)-1-(4-(trifluoromethyl)phenyl)-1-propanol (450 mg, 1.44 mmol) in ethyl acetate (15 ml) were added 1-naphthoyl chloride (282 ml, 1.87 mmol) and saturated aqueous sodium hydrogen carbonate (15 ml), and the mixture was stirred at room temperature for 2 hrs. The reaction solution was diluted with water (100 ml) and extracted with ethyl acetate (100 ml×2). The extract was washed with saturated brine, dried over anhydrous magnesium sulfate and evaporated under reduced pressure. Recrystallization of the residue from ethyl acetate-hexane gave the title compound (614 mg, 91%).

mp 207–208° C. IR ν max$^{KBr}$cm$^{-1}$: 1640. Anal. Calcd for $C_{27}H_{21}F_4NO_2$: C, 69.37; H, 4.53; N, 3.00. Found: C, 69.21; H, 4.46; N, 2.87. $^1$H-NMR (CDCl$_3$)δ: 2.92 (1H, dd, J=14.2, 10.4 Hz), 3.13 (1H, dd, J=14.2, 4.0 Hz), 3.39 (1H, s), 4.72–4.90 (1H, m), 5.13 (1H, s), 5.98 (1H, d, J=8.4 Hz), 7.04–7.60 (12H, m), 7.70–7.92 (3H, m).

Example 213

4-fluoro-N-((1RS,2SR)-1-((4-fluorophenyl)methyl)-2-hydroxy-2-(4-(trifluoromethyl)phenyl)ethyl)-1-naphthalenecarboxamide To a solution of (1RS,2SR)-2-amino-3-(4-fluorophenyl)-1-(4-(trifluoromethyl)phenyl)-1-propanol (450 mg, 1.44 mmol) in acetonitrile (30 ml) were added 4-fluoronaphthalenecarboxylic acid (274 mg, 1.44 mmol), 1-ethyl-3-(3-dimethylaminopropyl)carbodiimide hydrochloride (358 mg, 1.87 mmol) and 1-hydroxy-1H-benzotriazole (220 mg, 1.44 mmol), and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave the title compound (430 mg, 62%).

mp 235–236° C. IR ν max$^{KBr}$cm$^{-1}$: 1651, 1605, 1510. Anal. Calcd for $C_{27}H_{20}F_5NO_2$: C, 66.80; H, 4.15; N, 2.89. Found: C, 66.59; H, 4.25; N, 2.90. $^1$H-NMR (CDCl$_3$)δ: 2.79 (1H, dd, J=14.2, 11.0 Hz), 2.98 (1H, dd, J=14.2, 4.4 Hz), 3.75 (1H, s), 4.70–4.88 (1H, m), 5.18–5.22 (1H, m), 5.91 (1H, d, J=8.4 Hz), 6.92–7.10 (3H, m), 7.12–7.22 (3H, m), 7.40–7.80 (7H, m), 8.10 (1H, d, J=8.4 Hz).

Example 214

N-((1RS,2SR)-1-((4-fluorophenyl)methyl)-2-hydroxy-2-(4-(trifluoromethyl)phenyl)ethyl) cyclohexanecarboxamide To a solution of (1RS,2SR)-2-amino-3-(4-fluorophenyl)-1-(4-(trifluoromethyl)phenyl)-1-propanol (450 mg, 1.44 mmol) in ethyl acetate (15 ml) were added cyclohexanecarbonyl chloride (288 ml, 2.15 mmol) and saturated aqueous sodium hydrogen carbonate (15 ml), and the mixture was stirred at room temperature for 3 hrs. The reaction solution was diluted with water (100 ml) and extracted with ethyl acetate (100 ml×2). The extract was washed with saturated brine, dried over anhydrous magnesium sulfate and evaporated under reduced pressure. Recrystallization of the residue from ethyl acetate-hexane gave the title compound (550 mg, 90%).

mp 220–221° C. IR ν max$^{KBr}$cm$^{-1}$: 1645, 1510, 1329. Anal. Calcd for $C_{23}H_{25}F_4NO_2$: C, 65.24; H, 5.95; N, 3.31. Found: C, 65.07; H, 5.85; N, 3.22. $^1$H-NMR (CDCl$_3$)δ: 1.04–1.40 (5H, m), 1.50–1.80 (5H, m), 1.82–2.10 (1H, m), 2.66 (1H, dd, J=14.4, 10.8 Hz), 2.83 (1H, dd, J=14.4, 4.6 Hz), 4.34–4.50 (2H, m), 5.04 (1H, brs), 5.36 (1H, d, J=7.4 Hz), 6.90–7.12 (4H, m), 7.52 (2H, d, J=8.0 Hz), 7.66 (2H, d, J=8.0 Hz).

Example 215

N-((1RS,2SR)-1-((4-fluorophenyl)methyl)-2-hydroxy-2-(4-(trifluoromethyl)phenyl)ethyl)-4-phenylbutyramide To a solution of (1RS,2SR)-2-amino-3-(4-fluorophenyl)-1-(4-(trifluoromethyl)phenyl)-1-propanol (450 mg, 1.44 mmol) in acetonitrile (30 ml) were added 4-phenyl-n-butyric acid (236 mg, 1.44 mmol), 1-ethyl-3-(3-dimethylaminopropyl)carbodiimide hydrochloride (358 mg, 1.87 mmol) and 1-hydroxy-1H-benzotriazole (220 mg, 1.44 mmol), and the mixture was stirred overnight at room temperature. The reaction solution was diluted with water (100 ml) and extracted with ethyl acetate (100 ml×2). The extract was washed with saturated brine, dried over anhydrous magnesium sulfate and evaporated under reduced pressure. The residue was purified by silica gel column chromatography (ethyl acetate). Recrystallization from ethyl acetate-hexane gave the title compound (450 mg, 68%).

mp 155–156° C. IR ν max$^{KBr}$cm$^{-1}$: 1645, 1537, 1510. Anal. Calcd for $C_{26}H_{25}F_4NO_2$: C, 67.96; H, 5.48; N, 3.05. Found: C, 67.98; H, 5.68; N, 3.06. $^1$H-NMR (CDCl$_3$)δ: 1.70–1.90 (2H, m), 2.00–2.20 (2H, m), 2.44–2.60 (2H, m), 2.62–2.84 (2H, m), 4.10 (1H, d, J=4.0 Hz), 4.32–4.48 (1H, m), 4.98–5.06 (1H, m), 5.40 (1H, d, J=7.6 Hz) 6.86–7.14 (6H, m), 7.16–7.34 (3H, m), 7.51 (2H, d, J=8.0 Hz), 7.63 (2H, d, J=8.0 Hz).

Example 216

N-[(1RS,2SR)-2-(4-chlorophenyl)-2-hydroxy-1-[3-(1,1,2,2-tetrafluoroethoxy)benzyl]ethyl]-6,7-dihydro-5H-benzo[a]cycloheptene-1-carboxamide 1) ethyl 3-(4-chlorophenyl)-3-oxo-2-[3-(1,1,2,2-tetrahydroethoxy)benzyl]propionate To 3-(1,1,2,2-tetrahydroethoxy)toluene (7.43 ml, 44 mmol) in carbon tetrachloride (30 ml) were added N-bromosuccinimide (7.83 g, 44 mmol) and 2,2'-azobisisobutyronitrile (0.2 g), and the mixture was heated under reflux for 30 min. After cooling the reaction solution, insoluble material was removed, and the mixture was washed with diethyl ether. The filtrate was evaporated under reduced pressure to give 3-(1,1,2,2-tetrahydroethoxy)-1-bromomethylbenzene. Ethyl 3-(4-chlorophenyl)-3-oxopropionate (9.07 g, 40 mmol) was dissolved in dimethoxyethane (100 ml). Sodium hydride (1.6 g, 60% in oil, 40 mmol) was added under ice-cooling, and the mixture was stirred for 1 hr. Thereto was dropwise added a solution of 3-(1,1,2,2-tetrahydroethoxy)-1-bromomethylbenzene in dimethoxyethane (20 ml) obtained above, and the mixture was stirred at room temperature for 15 hrs. Water (100 ml) was added to the reaction solution, and the mixture was extracted with ethyl acetate (100 ml×2). The extract was washed with water, dried over anhydrous magnesium sulfate and evaporated under reduced pressure. The residue was purified by silica gel chromatography (hexane:ethyl acetate= 20:1–4:1) and crystallized from hexane to give ethyl 3-(4-chlorophenyl)-3-oxo-2-[3-(1,1,2,2-tetrahydroethoxy) benzyl]propionate (7.85 g, 45%).

mp 60–61° C. IR ν max$^{KBr}$cm$^{-1}$: 1723, 1684, 1590, 1325, 1275, 1231, 1200, 1134, 1096. elemental analysis for $C_{20}H_{17}ClF_4O_4$ Calculated: C, 55.50;H, 3.96 Found: C, 55.55;H, 3.83 $^1$H-NMR (CDCl$_3$)δ: 1.12 (3H, t, J=7.2 Hz), 3.33 (2H, d, J=8.0 Hz), 4.10 (2H, q, J=7.2 Hz), 4.55 (1H, t, J=7.0 Hz), 5.89 (1H, tt, J=53.1 Hz, 2.2 Hz), 7.00–7.20 (3H, m), 7.20–7.35 (1H, m), 7.42 (2H, d, J=8.0 Hz), 7.89 (2H, d, J=8.0 Hz).

2) ethyl(2RS,3RS)-3-(4-chlorophenyl)-3-hydroxy-2-[3-(1,1,2,2-tetrahydroethoxy)benzyl]propionate To a suspension of anhydrous zinc chloride (4.09 g, 30 mmol) in diethyl ether (100 ml) was added sodium borohydride (2.53 g, 60 mmol) by small portions, and the mixture was stirred for 2. hrs. Insoluble material was filtered off, and the mixture was washed with diethyl ether. The filtrate was ice-cooled, and a solution of ethyl 3-(4-chlorophenyl)-3-oxo-2-[3-(1,1,2,2-tetrahydroethoxy) benzyl]propionate (6.5 g, 15 mmol) in diethyl ether (20 ml) was added thereto. After the mixture was stirred at room temperature for 1 hr., it was cooled with ice again, and the reaction was stopped by 1N hydrochloric acid. The obtained mixture was extracted with ethyl acetate (100 ml×2). After the mixture was washed with water, it was dried over anhydrous magnesium sulfate and evaporated under reduced pressure. The residue was purified by silica gel chromatography (hexane:ethyl acetate=10:1–3:1) to give ethyl(2RS, 3RS)-3-(4-chlorophenyl)-3-hydroxy-2-[3-(1,1,2,2-tetrahydroethoxy)benzyl]propionate (6.5 g, 99%) as a colorless oil.

IR ν max$^{Neat}$cm$^{-1}$: 1723, 1489, 1302, 1277, 1198, 1123, 1094. $^1$H-NMR (CDCl$_3$)δ: 0.94 (3H, t, J 7.2 Hz), 2.90–3.10

(3H, m), 3.90 (2H, d, J=7.2 Hz), 5.02 (1H, br), 5.88 (1H, tt, J=53.1 Hz, 2.3 Hz), 6.90–7.10 (3H, m), 7.22 (1H, d, J=7.6 Hz), 7.27 (1H, d, J=3.4 Hz).

3) (2RS,3RS)-3-(4-chlorophenyl)-3-hydroxy-2-[3-(1,1,2,2-tetrahydroethoxy)benzyl]propionic acid To a solution of ethyl(2RS,3RS)-3-(4-chlorophenyl)-3-hydroxy-2-[3-(1,1,2,2-tetrahydroethoxy)benzyl]propionate (6.45 g, 14.8 mmol) in methanol (30 ml) was added 2N aqueous sodium hydroxide solution (14.8 ml, 29.6 mmol), and the mixture was stirred at room temperature for 4 hrs. The reaction solution was acidified with 1N hydrochloric acid (100 ml), and the mixture was extracted with ethyl acetate (100 ml×2). After the extract was washed with water and dried over anhydrous magnesium sulfate, it was evaporated under reduced pressure. The residue was crystallized from hexane to give (2RS,3RS)-3-(4-chlorophenyl)-3-hydroxy-2-[3-(1,1,2,2-tetrahydroethoxy)benzyl]propionic acid (5.39 g, 89%).

mp 88–90° C. IR ν max$^{KBr}$cm$^{-1}$: 1694, 1489, 1277, 1206, 1127. elemental analysis for $C_{18}H_{15}ClF_4O_4$, Calculated: C, 53.15;H, 3.72, Found: C, 53.26;H, 3.87 $^1$H-NMR (CDCl$_3$)δ: 2.80–3.10 (3H, m), 5.07 (1H, d, J=3.6 Hz), 5.88 (1H, tt, J=53.1 Hz, 2.6 Hz), 6.90–7.15. (4H, m), 7.20–7.35 (4H, m).

4) (4RS,5SR)-5-(4-chlorophenyl)-4-[3-(1,1,2,2-tetrahydroethoxy)benzyl]-1,3-oxazolidin-2-one To a solution of (2RS,3RS)-3-(4-chlorophenyl)-3-hydroxy-2-[3-(1,1,2,2-tetrahydroethoxy)benzyl]propionic acid (5.39 g, 13.3 mmol) in tetrahydrofuran (100 ml) were added diphenylphosphoryl azide (3.70 ml, 17.2 mmol) and triethylamine (2.59 ml, 18.6 mmol). The mixture was stirred at room temperature for 1 hr. and heated under reflux for 3 hrs. The reaction solution was concentrated under reduced pressure. Water (100 ml) was added and the mixture was extracted with ethyl acetate (100 ml×2). The extract was washed with water, dried over anhydrous magnesium sulfate and evaporated under reduced pressure. The residue was purified by silica gel chromatography (hexane:ethyl acetate=2:1–1:1) and precipitated crystals were filtered by adding hexane to give (4RS,5SR)-5-(4-chlorophenyl)-4-[3-(1,1,2,2-tetrahydroethoxy)benzyl]-1,3-oxazolidin-2-one (4.65 g, 87%).

mp 134–135° C. IR ν max$^{KBr}$cm$^{-1}$: 3243, 1740, 1489, 1447, 1343, 1273, 1238, 1198, 1125, 1088. elemental analysis for $C_{18}H_{14}ClF_4NO_3$, Calculated: C, 53.55;H, 3.49;N, 3.47, Found: C, 53.56;H, 3.28;N, 3.48. $^1$H-NMR (CDCl$_3$)δ: 2.18–2.40 (2H, m), 4.20–4.35 (1H, m), 5.05 (1H, br s), 5.79 (1H, d, J=8.0 Hz), 5.90 (1H, tt, J=54.8 Hz, 2.6 Hz), 6.85–7.00 (2H, m), 7.05–7.20 (1H, m), 7.20–7.50 (5H, m).

5) (1RS,2SR)-2-amino-1-(4-chlorophenyl)-3-[3-(1,1,2,2-tetrahydroethoxy)phenyl]-1-propanol To a solution of (4RS,5SR)-5-(4-chlorophenyl)-4-[3-(1,1,2,2-tetrafluoroethoxy)benzyl]-1,3-oxazolidin-2-one (4.35 g, 10.8 mmol) in ethanol (20 ml) was added 8N aqueous sodium hydroxide solution (5.39 ml, 43.1 mmol), and the mixture was heated under reflux for 6 hrs. The reaction solution was concentrated under reduced pressure. Water (100 ml) was added, and the mixture was extracted with ethyl acetate (100 ml×2). The extract was washed with water, dried over anhydrous magnesium sulfate and evaporated under reduced pressure. The residue was crystallized from the mixture of hexane and diethyl ether to give (1RS,2SR)-2-amino-1-(4-chlorophenyl)-3-[3-(1,1,2,2-tetrahydroethoxy)phenyl]-1-propanol (3.61 g, 89%).

mp 96–97° C. IR ν max$^{KBr}$cm$^{-1}$: 1611, 1588, 1489, 1308, 1196, 1119. elemental analysis for $C_{17}H_{16}ClF_4NO_2$, Calculated: C, 54.05;H, 4.27;N, 3.71, Found: C, 54.08;H, 4.34;N, 3.75. $^1$H-NMR (CDCl$_3$)δ: 2.36 (1H, dd, J=13.6. Hz, 10.2 Hz), 2.77 (1H, dd, J=13.6 Hz, 3.2 Hz), 3.20–3.40 (1H, m), 4.66 (1H, d, J=4.6 Hz), 5.89 (1H, tt, J=53.0 Hz, 2.5 Hz), 6.99 (1H, s), 7.00–7.15 (2H, m), 7.20–7.40 (5H, m).

6) N-[(1RS,2SR)-2-(4-chlorophenyl)-2-hydroxy-1-[3-(1,1,2,2-tetrafluoroethoxy)benzyl]ethyl]-6,7-dihydro-5H-benzo[a]cycloheptene-1-carboxamide While stirring (1RS,2SR)-2-amino-1-(4-chlorophenyl)-3-[3-(1,1,2,2-tetrafluoroethoxy)phenyl]propan-1-ol (0.280 g, 0.741 mmol), 6,7-dihydro-5H-benzo[a]cycloheptene-1-carboxylic acid (0.14 g, 0.74 mmol) and 1-hydroxybenzotriazole hydrate (0.11 g, 0.74 mmol) in acetonitrile (10 ml), 1-ethyl-3-(3-dimethylaminopropyl) carbodiimide hydrochloride (0.14 g, 0.74 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance. white powder yield 0.373 g, 92% mp 182–183° C.; $^1$H-NMR (CDCl$_3$, 200 MHz) δ 1.93–2.06 (2H, m), 2.15–2.24 (2H, m), 2.67 (2H, t, J=6.1 Hz), 2.78 (1H, dd, J=10.9 Hz, 14.9 Hz), 2.98 (1H, dd, J=4.2 Hz, 14.6 Hz), 3.71 (1H, d, J=3.6 Hz), 4.60–4.73 (1H, m), 5.04 (1H, t, J=3.7 Hz), 5.74 (1H, d, J=8.4 Hz), 5.89 (1H, tt, J=2.7 Hz, 53.0 Hz), 5.93 (1H, td, J=5.6 Hz, 11.0 Hz), 6.21 (1H, d, J=11.6 Hz), 6.95–7.18 (6H, m), 7.31–7.43 (5H, m); IR (KBr) 3270, 2940, 1640, 1537, 1198, 1125 cm$^{-1}$; Anal. Calcd for $C_{29}H_{26}ClF_4NO_3$: C, 63.56; H, 4.78; N, 2.56. Found: C, 63.51; H, 4.69; N, 2.52.

Example 217

N-((1RS,2SR)-2-hydroxy-2-(4-(phenyloxy)phenyl)-1-((3-((1,1,2,2-tetrafluoroethyl)oxy)phenyl)methyl)ethyl)-6,7-dihydro-5H-benzo[a]cycloheptene-1-carboxamide 1) To a solution of 3-(1,1,2,2-tetrafluoroethoxy)toluene (7.8 g, 37.5 mmol) in carbon tetrachloride (80 ml) were added N-bromosuccinimide (7.33 g, 41.2 mmol) and 2,2'-azobis(isobutyronitrile) (300 mg, 1.87 mmol), and the mixture was heated under reflux for 6 hrs. After cooling, the reaction solution was filtered, and the filtrate was concentrated to prepare ethyl 3-(1,1,2,2-tetrafluoroethoxy)-α-bromotoluene. To a solution of ethyl 3-(4-phenoxyphenyl)-3-oxopropionate (10.7 g, 37.5 mmol) in 1,2-dimethoxyethane (120 ml) was added sodium hydride (60% in oil, 1.50 g, 37.5 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (10 ml), and the reaction solution was stirred at room temperature for 1 hr. The reaction solution was poured into water (100 ml), and the mixture was extracted with ethyl acetate (100 ml×2). The extract was washed with water and saturated brine, dried over anhydrous magnesium sulfate and evaporated under reduced pressure. The residue was purified by silica gel column chromatography (toluene) to give ethyl 3-oxo-3-(4-phenyloxyphenyl)-2-((3-((1,1,2,2-tetrafluoroethyl)oxy)phenyl)methyl)propionate (9.92 g, 54%) as a colorless oil.

$^1$H-NMR (CDCl$_3$)δ: 1.13 (3H, t, J=7.0 Hz), 3.33 (2H, d, J=6.8 Hz), 4.11 (2H, q, J=7.0 Hz), 4.56 (1H, t, J=7.6 Hz), 5.88 (1H, tt, J=53.0, 2.8 Hz), 6.90–7.48 (11H, m), 7.90–8.02 (2H, m).

IR ν max$^{KBr}$cm$^{-1}$: 1738, 1682, 1605, 1586, 1505, 1489, 1449, 1420. Anal. Calcd for $C_{26}H_{22}F_4O_5 \cdot 0.3H_2O$: C, 62.98; H, 4.59 Found: C, 62.84; H, 4.46.

2) To a solution of zinc chloride (5.34 g, 39.2 mmol) in diethyl ether (120 ml) was added sodium borohydride (2.97 g, 78.4 mmol), and the mixture was stirred at room temperature for 30 min. Insoluble material was filtered off, and a solution of ethyl 3-oxo-3-(4-phenyloxyphenyl)-2-((3-((1,1,2,2-tetrafluoroethyl)oxy)phenyl)methyl)propionate (9.61 g, 19.6 mmol) in diethyl ether (60 ml) was added to the filtrate. The mixture was stirred at room temperature for 30 min. 1N Hydrochloric acid was added to the reaction solution under ice-cooling to quench the reaction. Then, water (150 ml) was added and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-hydroxy-3-(4-(phenyloxy)phenyl)-2-((3-((1,1,2,2-tetrafluoroethyl)oxy)phenyl)methyl)propionate (6.50 g, 67%) as a colorless oil.

$^1$H-NMR (CDCl$_3$)δ: 0.94 (3H, t, J=7.0 Hz), 2.90–3.10 (4H, m), 3.89 (2H, q, J=7.0 Hz), 4.98–5.06 (1H, m), 5.89 (1H, tt, J=53.0, 2.8 Hz), 6.92–7.42 (13H, m). IR ν max$^{KBr}$cm$^{-1}$: 1725, 1611, 1590, 1507, 1489, 1449. Anal. Calcd for C$_{26}$H$_{24}$F$_4$O$_5$: C, 63.41; H, 4.91 Found: C, 63.32; H, 4.97.

3) To a solution of ethyl(2RS,3RS)-3-hydroxy-3-(4-(phenyloxy)phenyl)-2-((3-((1,1,2,2-tetrafluoroethyl)oxy)phenyl)methyl)propionate (6.14 g, 12.5 mmol) in methanol (30 ml) was added 2N aqueous sodium hydroxide solution (12.5 ml, 25.0 mmol), and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. Recrystallization of the residue from ethyl acetate-hexane gave (2RS,3RS)-3-hydroxy-3-(4-(phenyloxy)phenyl)-2-((3-((1,1,2,2-tetrafluoroethyl)oxy)phenyl)methyl)propionic acid (4.51 g, 89%).

$^1$H-NMR (CDCl$_3$)δ: 2.94–3.10 (3H, m), 5.07 (1H, d, J=4.2 Hz), 5.87 (1H, t, J=53.0, 3.0 Hz), 6.92–7.40 (13H, m). IR ν max$^{KBr}$cm$^{-1}$: 1711, 1613, 1590, 1508, 1489. mp 109–110° C. Anal. Calcd for C$_{24}$H$_{20}$F$_4$O$_5$: C, 62.07; H, 4.34 Found: C, 62.09; H, 4.42.

4) To a solution of (2RS,3RS)-3-hydroxy-3-(4-(phenyloxy)phenyl)-2-((3-((1,1,2,2-tetrafluoroethyl)oxy)phenyl)methyl)propionic acid (4.3 g, 10.6 mmol) in tetrahydrofuran (80 ml) were added diphenylphosphoryl azide (2.52 ml, 11.7 mmol) and triethylamine (2.23 ml, 16.0 mmol), and the mixture was heated under reflux for 2 hrs. The reaction solution was allowed to cool and water (200 ml) was added. The mixture was extracted with ethyl acetate (100 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=10:1–1:1). Recrystallization from ethyl acetate-hexane gave (4RS,5SR)-5-(4-(phenyloxy)phenyl)-4-((3-((1,1,2,2-tetrafluoroethyl)oxy)phenyl)methyl)-1,3-oxazolidin-2-one (3.92 g, 80%).

$^1$H-NMR (CDCl$_3$)δ: 2.24–2.44 (2H, m), 4.18–4.32 (1H, m), 5.08 (1H, brs), 5.79 (1H, d, J=8.0 Hz), 5.90 (1H, tt, J=53.0, 3.0 Hz), 6.86–7.20 (8H, m), 7.22–7.42 (5H, m). IR ν max$^{KBr}$cm$^{-1}$: 1759, 1612, 1590, 1508, 1489. mp 90–91° C. Anal. Calcd for C$_{24}$H$_{19}$F$_4$NO$_4$: C, 62.47; H, 4.15; N, 3.04. Found: C, 62.54; H, 4.05; N, 3.04.

5) To a solution of (4RS,5SR)-5-(4-(phenyloxy)phenyl)-4-((3-((1,1,2,2-tetrafluoroethyl)oxy)phenyl)methyl)-1,3-oxazolidin-2-one (3.7 g, 8.02 mmol) in ethanol (10 ml) was added 8N aqueous sodium hydroxide solution (5.0 ml, 40 mmol), and the mixture was heated under reflux for 4 hrs. The reaction solution was concentrated, diluted with water (100 ml) and extracted with ethyl acetate (100 ml×2). The extract was washed with saturated brine, dried over anhydrous magnesium sulfate and evaporated under reduced pressure. Recrystallization of the residue from ethyl acetate-hexane gave (1RS,2SR)-2-amino-1-(4-(phenyloxy)phenyl)-3-(3-((1,1,2,2-tetrafluoroethyl)oxy)phenyl)-1-propanol (3.05 g, 87%).

$^1$H-NMR (CDCl$_3$)δ: 1.20–2.00 (2H, br), 2.41 (1H, dd, J=13.8, 10.2 Hz), 2.88 (1H, dd, J=13.8, 3.2 Hz), 3.22–3.38 (1H, m), 4.65 (1H, d, J=5.2 Hz), 5.89 (1H, tt, J=53.0, 3.0 Hz), 6.98–7.18 (8H, m), 7.28–7.42 (5H, m). IR ν max$^{KBr}$cm$^{-1}$: 1611, 1590, 1507, 1489, 1449. mp 85–86° C. Anal. Calcd for C$_{23}$H$_{21}$F$_4$NO$_3$: C, 63.44; H, 4.86; N, 3.22. Found: C, 63.44; H, 4.76; N, 3.22.

6) To a solution of (1RS,2SR)-2-amino-1-(4-(phenyloxy)phenyl)-3-(3-((1,1,2,2-tetrafluoroethyl)oxy)phenyl)-1-propanol (300 mg, 0.69 mmol) in acetonitrile (16 ml) were added 6,7-dihydro-5H-benzo[a]cycloheptene-1-carboxylic acid (130 mg, 0.69 mmol), 1-ethyl-3-(3-dimethylaminopropyl)carbodiimide hydrochloride (198 mg, 1.03 mmol) and 1-hydroxy-1H-benzotriazole (106 mg, 0.69 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (285 mg, 68%).

$^1$H-NMR (CDCl$_3$)δ: 1.90–2.10 (2H, m), 2.12–2.28 (2H, m), 2.60–2.72 (2H, m), 2.8 (1H, dd, J=14.8, 10.4 Hz), 3.04 (1H, dd, J=14.8, 4.0 Hz), 3.53 (1H, s), 4.60–4.80 (1H, m), 5.02 (1H, s), 5.75 (1H, d, J=8.4 Hz), 5.89 (1H, tt, J=53.0, 2.8 Hz), 5.90–6.00 (1H, m), 6.23 (1H, d, J=11.8 Hz), 6.90–7.20 (12H, m), 7.22–7.48 (4H, m). IR ν max$^{KBr}$cm$^{-1}$: 1640, 1590, 1507, 1489, 1449. mp 95–96° C.

Example 218

N-((1RS,2SR)-2-(4-((4-chloro-3-ethylphenyl)oxy)phenyl)-2-hydroxy-1-((3-((1,1,2,2-tetrafluoroethyl)oxy)phenyl)methyl)ethyl)-6,7-dihydro-5H-benzo[a]cycloheptene-1-carboxamide 1) To a solution of 4-fluoroacetophenone (13.8 g, 100 mmol) in N,N-dimethylacetamide (100 ml) were added 4-chloro-3-ethylphenol (15.6 g, 100 mmol) and potassium carbonate (16.6 g, 120 mmol), and the mixture was heated under reflux for 10 hrs. The reaction solution was concentrated, diluted with water (300 ml) and extracted with ethyl acetate (300 ml×2). The extract was washed successively with water and saturated brine, dried over anhydrous magnesium sulfate and evaporated under reduced pressure. The residue was purified by silica gel column chromatography (hexane:ethyl acetate=10:1) to give 4-((4-chloro-3-ethylphenyl)oxy)acetophenone (24.2 g, 88%) as a colorless oil.

$^1$H-NMR (CDCl$_3$)δ: 1.22 (3H, t, J=7.4 Hz), 2.58 (3H, s), 2.74 (2H, q, J=7.4 Hz), 6.84 (1H, dd, J=8.8, 3.0 Hz), 6.94–7.04 (3H, m), 7.34 (1H, d, J=8.8 Hz), 7.90–8.00 (2H, m). IR ν max$^{KBr}$cm$^{-1}$: 1682, 1595, 1574, 1503, 1472. Anal. Calcd for $C_{16}H_{15}ClO_2$: C, 69.95; H, 5.50 Found: C, 69.93; H, 5.65

2) To a solution of 4-((4-chloro-3-ethylphenyl)oxy) acetophenone (24.2 g, 88.2 mmol) in diethyl carbonate (100 ml) were added ethanol (0.3 ml) and sodium hydride (60% in oil, 7.06 g, 176 mmol) under ice-cooling, and the mixture was stirred at room temperature for 2 hrs.

6N Hydrochloric acid was added to the reaction solution to quench the reaction. Water (300 ml) was added, and the mixture was extracted with ethyl acetate (300 ml×2). The extract was washed successively with water and saturated brine, dried over anhydrous magnesium sulfate and evaporated under reduced pressure. The residue was purified by silica gel column chromatography (hexane:ethyl acetate= 50:1–5:1) to give ethyl 3-(4-((4-chloro-3-ethylphenyl)oxy) phenyl)-3-oxopropionate (29.3 g, 96%) as a brown oil.

$^1$H-NMR (CDCl$_3$)δ: 1.08–1.20 (6H, m), 2.68–2.82 (2H, m), 3.95 (2H×7/8, s), 4.14–4.30 (2H, m), 5.60 (1H×1/8, s), 6.80–6.90 (1H, m), 6.92–7.04 (3H, m), 7.32 (1H×1/8, d, J=8.4 Hz), 7.35 (1H×7/8, d, J=8.4 Hz), 7.75 (2H×1/8, d, J=9.2 Hz), 7.93 (2H×7/8, d, J=9.2 Hz). IR ν max$^{KBr}$cm$^{-1}$: 1744, 1682, 1595, 1576, 1505, 1472, 1410. Anal. Calcd for $C_{19}H_{19}F_5ClO_4$: C, 65.80; H, 5.52 Found: C, 65.98; H, 5.53.

3) To a solution of 3-(1,1,2,2-tetrafluoroethoxy)toluene (6.0 g, 28.8 mmol) in carbon tetrachloride (60 ml) were added N-bromosuccinimide (5.65 g, 31.7 mmol) and 2,2'-azobis(isobutyronitrile) (237 mg, 1.44 mmol), and the mixture was heated under reflux for 6 hrs. After cooling, the reaction solution was filtered, and the filtrate was concentrated to give 3-(1,1,2,2-tetrafluoroethoxy)-α-bromotoluene. To a solution of ethyl 3-(4-((4-chloro-3-ethylphenyl)oxy) phenyl)-3-oxopropionate (10 g, 28.8 mmol) in 1,2-dimethoxyethane (100 ml) was added sodium hydride (60% in oil, 1.15 g, 28.8 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (10 ml), and the reaction solution was stirred at room temperature for 1 hr. The reaction solution was poured into water (100 ml), and the mixture was extracted with ethyl acetate (100 ml×2). The extract was washed with water and saturated brine, dried over anhydrous magnesium sulfate and evaporated under reduced pressure. The residue was purified by silica gel column chromatography (toluene) to give ethyl 3-(4-((4-chloro-3-ethylphenyl) oxy)phenyl)-3-oxo-2-((3-((1,1,2,2-tetrafluoroethyl)oxy) phenyl)methyl)propionate (9.26 g, 58%) as a colorless oil.

$^1$H-NMR (CDCl$_3$)δ: 1.13 (3H, t, J=7.0 Hz), 1.22 (3H, t, J=7.6 Hz), 2.74 (2H, q, J=7.6 Hz), 3.33 (2H, d, J=7.2 Hz), 4.11 (2H, q, J=7.0 Hz), 4.56 (1H, t, J=7.2 Hz), 5.88 (1H, tt, J=53.2, 2.8 Hz), 6.83 (1H, dd, J=8.6, 3.0 Hz), 6.90–7.38 (8H, m), 7.90–8.00 (2H, m). IR ν max$^{KBr}$cm$^{-1}$: 1738, 1682, 1595, 1576, 1505, 1472. Anal. Calcd for $C_{28}H_{25}ClF_4O_5$: C, 60.82; H, 4.56 Found: C, 60.79; H, 4.38.

4) To a solution of zinc chloride (4.44 g, 32.6 mmol) in diethyl ether (100 ml) was added sodium borohydride (2.46 g, 65.1. mmol), and the mixture was stirred at room temperature for 30 min. Insoluble material was filtered off, a solution of ethyl 3-(4-((4-chloro-3-ethylphenyl)oxy) phenyl)-3-oxo-2-((3-((1,1,2,2-tetrafluoroethyl)oxy)phenyl) methyl)propionate (9.0 g, 16.3 mmol) in diethyl ether (50 ml) was added to the filtrate, and the mixture was stirred at room temperature for 30 min. 1N Hydrochloric acid was added to the reaction solution under ice-cooling to quench the reaction. Then, water (150 ml) was added and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(4-((4-chloro-3-ethylphenyl)oxy) phenyl)-3-hydroxy-2-((3-((1,1,2,2-tetrafluoroethyl)oxy) phenyl)methyl)propionate (6.79 g, 75%) as a colorless oil.

$^1$H-NMR (CDCl$_3$)δ: 0.95 (3H, t, J=7.0 Hz), 1.21 (3H, t, J=7.6 Hz), 2.72 (2H, q, J=7.6 Hz), 2.90–3.10 (4H, m), 3.90 (2H, q, J=7.0 Hz), 4.93 (1H, brs), 5.89 (1H, tt, J=53.0, 3.0 Hz.), 6.76 (1H, dd, J=8.8, 3.0 Hz), 6.82–7.10 (6H, m), 7.20–7.42 (4H, m). IR ν max$^{KBr}$cm$^{-1}$: 1726, 1611, 1588, 1507, 1474. Anal. Calcd for $C_{28}H_{27}ClF_4O_5$: C, 60.60; H, 4.90 Found: C, 60.53; H, 4.90.

5) To a solution of ethyl(2RS,3RS)-3-(4-((4-chloro-3-ethylphenyl)oxy)phenyl)-3-hydroxy-2-((3-((1,1,2,2-tetrafluoroethyl)oxy)phenyl)methyl)propionate (6.6 g, 11.9 mmol) in methanol (30 ml) was added 2N aqueous sodium hydroxide solution (11.9 ml, 23.8 mmol), and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from hexane to give (2RS, 3RS)-3-(4-((4-chloro-3-ethylphenyl)oxy)phenyl)-3-hydroxy-2-((3-((1,1,2,2-tetrafluoroethyl)oxy)phenyl) methyl)propionic acid (5.28 g, 84%).

$^1$H-NMR (CDCl$_3$)δ: 1.21 (3H, t, J=7.6 Hz), 2.71 (2H, q, J=7.6 Hz), 2.92–3.10 (3H, m), 5.07 (1H, d, J=4.0 Hz), 5.87 (1H, tt, J=53.0, 3.0 Hz), 6.75 (1H, dd, J=8.4, 3.0 Hz), 6.88–7.10 (6H, m), 7.20–7.40 (4H, m). IR ν max$^{KBr}$cm$^{-1}$: 1713, 1611, 1599, 1507, 1472. mp 75–76° C. Anal. Calcd for $C_{26}H_{23}ClF_4O_5$: C, 59.27; H, 4.40 Found: C, 59.22; H, 4.43.

6) To a solution of (2RS,3RS)-3-(4-((4-chloro-3-ethylphenyl)oxy)phenyl)-3-hydroxy-2-((3-((1,1,2,2-tetrafluoroethyl)oxy)phenyl)methyl)propionic acid (5.18 g, 9.83 mmol) in tetrahydrofuran (75 ml) were added diphenylphosphoryl azide (2.33 ml, 10.8 mmol) and triethylamine (2.06 ml, 14.8 mmol), and the mixture was heated under reflux for 2 hrs. The reaction solution was allowed to cool and water (200 ml) was added. The mixture was extracted with ethyl acetate (100 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate). Recrystallization from ethyl acetate-hexane gave (4RS,5SR)-5-(4-((4-chloro-3-ethylphenyl)oxy)phenyl)-4-((3-((1,1,2,2-tetrafluoroethyl) oxy)phenyl)methyl)-1,3-oxazolidin-2-one (4.56 g, 89%).

$^1$H-NMR (CDCl$_3$)δ: 1.22 (3H, t, J=7.6 Hz), 2.20–2.44 (2H, m), 2.73 (2H, q, J=7.6 Hz), 4.18–4.32 (1H, m), 4.98 (1H, s), 5.80 (1H, d, J=7.8 Hz), 5.90 (1H, tt, J=53.0, 3.0 Hz), 6.80 (1H, dd, J=8.4, 3.0 Hz), 6.88–7.20 (5H, m), 7.22–7.44 (5H, m). IR ν max$^{KBr}$cm$^{-1}$: 1759, 1612, 1588, 1508, 1472. mp 100–101° C. Anal. Calcd for $C_{26}H_{22}ClF_4NO_4$: C, 59.61; H, 4.23; N, 2.67. Found: C, 59.67; H, 4.27; N, 2.76.

7) To a solution of (4RS,5SR)-5-(4-((4-chloro-3-ethylphenyl)oxy)phenyl)-4-((3-((1,1,2,2-tetrafluoroethyl) oxy)phenyl)methyl)-1,3-oxazolidin-2-one (4.3 g, 8.21 mmol) in ethanol (20 ml) was added 8N aqueous sodium hydroxide solution (5.13 ml, 41.1 mmol), and the mixture was heated under reflux for 4 hrs. The reaction solution was concentrated, diluted with water (100 ml), and extracted with ethyl acetate (100 ml×2). The extract was washed with saturated brine, dried over anhydrous magnesium sulfate and evaporated under reduced pressure to give (1RS,2SR)-2-amino-1-(4-((4-chloro-3-ethylphenyl)oxy)phenyl)-3-(3-((1,1,2,2-tetrafluoroethyl)oxy)phenyl)-1-propanol (3.64 g, 89%) as a colorless oil.

$^1$H-NMR (CDCl$_3$)δ: 1.21 (3H, t, J=7.6 Hz), 2.41 (1H, dd, J=13.6, 10.2 Hz), 2.72 (2H, q, J=7.6 Hz), 2.87 (1H, dd, J=13.6, 3.2 Hz), 4.65 (1H, d, J=5.2 Hz), 5.90 (1H, tt, J=53.0, 3.0 Hz), 6.78 (1H, dd, J=8.4, 3.0 Hz), 6.88–7.18 (6H, m), 7.28–7.40 (4H, m). IR ν max$^{KBr}$cm$^{-1}$: 1611, 1586, 1505, 1472, 1412. Anal. Calcd for C$_{25}$H$_{24}$ClF$_4$NO$_3$: C, 60.31; H, 4.86; N, 32.81 Found: C, 60.31; H, 5.18; N, 2.85.

8) To a solution of (1RS,2SR)-2-amino-1-(4-((4-chloro-3-ethylphenyl)oxy)phenyl)-3-(3-((1,1,2,2-tetrafluoroethyl)oxy)phenyl)-1-propanol (300 mg, 0.60 mmol) in acetonitrile (16 ml) were added 6,7-dihydro-5H-benzo[a]cycloheptene-1-carboxylic acid (114 mg, 0.60 mmol), 1-ethyl-3-(3-dimethylaminopropyl)carbodiimide hydrochloride (174 mg, 0.91 mmol) and 1-hydroxy-1H-benzotriazole (92 mg, 0.60 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (318 mg, 79%).

$^1$H-NMR (CDCl$_3$)δ: 1.20 (3H, t, J=7.2 Hz), 1.90–2.08 (2H, m), 2.10–2.26 (2H, m), 2.60–2.84 (5H, m), 3.02 (1H, dd, J=14.6, 4.0 Hz), 3.50–3.90 (1H, br), 4.60–4.78 (1H, m), 5.01 (1H, d, J=3.6 Hz), 5.60–6.22 (4H, m), 6.77 (1H, dd, J=8.8, 3.0 Hz), 6.84–7.20 (9H, m), 7.28 (2H, d, J=7.8 Hz), 7.41 (2H, d, J=8.8 Hz). IR ν max$^{KBr}$cm$^{-1}$: 1613, 1588, 1505, 1472, 1453. mp 116–117° C. Anal. Calcd for C$_{37}$H$_{34}$ClF$_4$NO$_4$: C, 66.51; H, 5.13; N, 2.10. Found: C, 66.22; H, 5.24; N, 2.25.

Example 219

1,1-dimethylethyl(1RS,2SR)-2-(2-fluoropyridin-4-yl)-2-hydroxy-1-((3-(1,1,2,2-tetrafluoroethoxy)phenyl)methyl)ethylcarbamate 1) To a solution of 2-amino-4-methylpyridine (100 g, 925 mmol) in 42% tetrafluoroboric acid (400 ml) was gradually added a solution of sodium nitrite (64 g, 927 mmol) in water (100 ml) while cooling with dry ice-acetone so that the inside temperature would not exceed 10° C. The reaction solution was stirred at 45° C. for 30 min., 8N aqueous sodium hydroxide solution (100 ml) was gradually added, and the mixture was extracted with diethyl ether (300 ml×2). The extract was concentrated under reduced pressure, and the residue was distilled away to give 2-fluoro-4-methylpyridine (48 g). A solution of potassium permanganate (100 g, 632 mmol) in water (1.2 L) was heated to 80° C. and 2-fluoro-4-methylpyridine (48 g) was added. The mixture was heated under reflux for 1 hr. Insoluble material was filtered off with celite from the reaction solution. The filtrate was concentrated to 200 ml, and 6N hydrochloric acid was added until the pH became about 3. The precipitated crystals were collected by filtration to give 2-fluoro-4-pyridinecarboxylic acid 2(19.8 g, 32%).

$^1$H-NMR (CDCl$_3$)δ: 7.50 (1H, s), 7.75 (1H, d, J=5.0 Hz), 8.40 (1H, d, J=5.0 Hz). IR ν max$^{KBr}$cm$^{-1}$: 3100, 1730, 1620. mp 258–260° C. Anal. Calcd for C$_6$H$_4$FNO$_2$: C, 51.07; H, 2.86; N, 9.93. Found: C, 50.77; H, 2.80; N, 10.04.

2) To a solution of 2-fluoro-4-pyridinecarboxylic acid (10 g, 70.9 mmol) in tetrahydrofuran (150 ml) was added 1,1'-carbonylbis-1H-imidazole (12.7 g, 78.0 mmol), and the mixture was heated under reflux for 30 min. The reaction solution was cooled and monoethyl malonate magnesium salt (11.2 g, 39.0 mmol) was added. The mixture was stirred at room temperature for 30 min. 1N Hydrochloric acid (200 ml) was added to the reaction solution, and the mixture was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) and recrystallized from hexane to give ethyl 3-(2-fluoro-4-pyridyl)-3-oxopropionate (7.32 g, 49%).

$^1$H-NMR (CDCl$_3$)δ: 1.20–1.40 (3H, m), 3.98 (2H×1/5, s), 4.18–4.40 (2H, m), 5.76 (1H×4/5, s), 7.26 (1H×4/5, s), 7.40 (1H×1/5, s), 7.50 (1H×4/5, d, J=7.4 Hz), 7.63 (1H×1/5, d, J=7.4 Hz), 8.32 (1H×4/5, d, J=7.0 Hz), 8.43-(1H×1/5, d, J=7.0 Hz), 12.44 (1H×4/5, s). IR ν max$^{KBr}$cm$^{-1}$: 1744, 1705, 1651, 1607, 1563. mp 66–67° C. Anal. Calcd for C$_{10}$H$_{10}$FNO$_3$: C, 56.87; H, 4.77; N, 6.63. Found: C, 56.92; H, 4.69; N, 6.82.

3) To a solution of 3-(1,1,2,2-tetrafluoroethoxy)toluene (3.80 g, 18.2 mmol) in carbon tetrachloride (50 ml) were added N-bromosuccinimide (3.54 g, 19.9 mmol) and 2,2'-azobis(isobutyronitrile) (136 mg, 0.83 mmol), and the mixture was heated under reflux for 4 hrs. After cooling, the reaction solution was filtered, and the filtrate was concentrated to give ethyl 3-(1,1,2,2-tetrafluoroethoxy)-α-bromotoluene. To a solution of ethyl 3-(2-fluoropyridin-4-yl)-3-oxopropionate (3.5 g, 16.6 mmol) in 1,2-dimethoxyethane (35 ml) was added sodium hydride (60% in oil, 0.66 g, 16.6 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (5 ml), and the mixture was stirred at room temperature for 1 hr. The reaction solution was poured into water (100 ml), and the mixture was extracted with ethyl acetate (100 ml×2). The extract was washed with water and saturated brine, dried over anhydrous magnesium sulfate and evaporated under reduced pressure. The residue was purified by silica gel column chromatography (toluene:hexane=1:1) to give ethyl 3-(2-fluoropyridin-4-yl)-3-oxo-2-((3-(1,1,2,2-tetrafluoroethoxy)phenyl)methyl)propionate (4.78 g, 69%) as a colorless oil.

$^1$H-NMR (CDCl$_3$)δ: 1.14 (3H, t, J=7.0 Hz), 3.35 (2H, d, J=7.4 Hz), 4.13 (2H, q, J=7.0 Hz), 4.44–4.56 (1H, m), 5.90 (1H, tt, J=53.0, 3.0 Hz), 7.00–7.38 (5H, m). IR ν max$^{KBr}$ cm$^{-1}$: 1740, 1703, 1607, 1588, 1566. Anal. Calcd for C$_{19}$H$_{16}$F$_5$NO$_4$: C, 54.68; H, 3.86; N, 3.36. Found: C, 54.44; H, 3.76; N, 3.55.

4) To a solution of zinc chloride (3.12 g, 22.9 mmol) in diethyl ether (100 ml) was added sodium borohydride (1.74 g, 45.8 mmol), and the mixture was stirred at room temperature for 30 min. Insoluble material was filtered off, and a solution of ethyl 3-(2-fluoropyridin-4-yl)-3-oxo-2-((3-(1,1,2,2-tetrafluoroethoxy)phenyl)methyl)propionate (4.78 g, 11.5 mmol) in diethyl ether (30 ml) was added to the filtrate. The mixture was stirred at room temperature for 30 min. 1N Hydrochloric acid was added to the reaction solution under ice-cooling to quench the reaction. Then, water (100 ml) was added and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) to give ethyl 3-(2-fluoropyridin-4-yl)-3-hydroxy-2-((3-(1,1,2,2-tetrafluoroethoxy)phenyl)methyl)propionate((2RS,3RS) form: (2RS,3SR) form=9:1, 4.05 g, 84%) as a colorless oil.

$^1$H-NMR (CDCl$_3$)δ: 0.92–1.06 (3H, m), 2.70–3.10 (3H, m), 3.54 (1H, dd, J=2.6 Hz), 3.90–4.04 (2H, m), 4.77 (1H×1/10, dd, J=8.8, 3.4 Hz), 5.13 (1H×9/10, s), 5.89 (1H, tt, J=53.0, 3.0 Hz), 6.90–7.30 (7H, m), 8.16–8.24 (1H, m). IR ν max$^{KBr}$cm$^{-1}$: 1728, 1615, 1588, 1572, 1487. Anal. Calcd for C$_{19}$H$_{18}$F$_5$NO$_4$: C, 54.42; H, 4.33; N, 3.34. Found: C, 54.37; H, 4.39; N, 3.35.

5) To a solution of ethyl(2RS,3RS)-3-(2-fluoropyridin-4-yl)-3-hydroxy-2-((3-(1,1,2,2-tetrafluoroethoxy)phenyl)methyl)propionate (3.8 g, 9.06 mmol, (2RS,3RS) form: (2RS,3SR) form=9:1) in methanol (20 ml) was added 2N aqueous sodium hydroxide solution (9.1 ml), 18.2 mmol), and the mixture was stirred at room temperature for 2 hrs. The reaction solution was acidified with 1N hydrochloric acid and extracted with ethyl acetate (200 ml×2). The extract was washed with water and saturated brine, dried over anhydrous magnesium sulfate and evaporated under reduced pressure. Recrystallization of the residue from ethyl acetate-hexane gave (2RS,3RS)-3-(2-fluoropyridin-4-yl)-3-hydroxy-2-((3-(1,1,2,2-tetrafluoroethoxy)phenyl)methyl) propionic acid (2.14 g, 60%).

$^1$H-NMR (CDCl$_3$)δ: 2.74–2.92, (1H, m), 2.98–3.16 (2H, m), 5.18 (1H, d, J=3.2 Hz), 5.88 (1H, tt, J=53.0, 3.0 Hz), 6.90–7.10 (4H, m), 7.16–7.30 (2H, m), 8.17 (1H, d, J=5.2 Hz). IR ν max$^{KBr}$cm$^{-1}$: 1717, 1615, 1588, 1570. mp 134–135° C. Anal. Calcd for C$_{17}$H$_{14}$F$_5$NO$_4$: C, 52.18; H, 3.61; N, 3.58. Found: C, 52.20; H, 3.51; N, 3.58.

6) To a solution of (2RS,3RS)-3-(2-fluoropyridin-4-yl)-3-hydroxy-2-((3-(1,1,2,2-tetrafluoroethoxy)phenyl)methyl) propionic acid (2.0 g, 5.11 mmol) in tetrahydrofuran (50 ml) were added diphenylphosphoryl azide (1.21 ml, 5.62 mmol) and triethylamine (1.07 ml, 7.67 mmol), and the mixture was heated under reflux for 2 hrs. The reaction solution was allowed to cool and water (200 ml) was added. The mixture was extracted with ethyl acetate (100 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=1:1). Recrystallization from ethyl acetate-hexane gave (4RS,5SR)-5-(2-fluoropyridin-4-yl)-4-((3-(1,1,2,2-tetrafluoroethoxy)phenyl)methyl)-1,3-oxazolidin-2-one (1.36 g, 69%).

$^1$H-NMR (CDCl$_3$)δ: 2.27 (1H, dd, J=14.0, 10.2 Hz), 2.41 (1H, dd, J=14.0, 4.4 Hz), 4.28–4.42 (1H, m), 5.49 (1H, s), 5.81 (1H, d, J=8.0 Hz), 5.91 (1H, tt, J=53.0, 2.6 Hz), 6.90–7.40 (6H, m), 8.30 (1H, d, J=5.2 Hz). IR ν max$^{KBr}$cm$^{-1}$: 1771, 1615, 1588, 1574, 1489. mp 118–119° C. Anal. Calcd for C$_{17}$H$_{13}$F$_5$N$_2$O$_3$: C, 52.59; H, 3.37; N, 7.21. Found: C, 52.70; H, 3.20; N, 7.20.

7) To a solution of (4RS,5SR)-5-(2-fluoropyridin-4-yl)-4-((3-(1,1,2,2-tetrafluoroethoxy)phenyl)methyl)-1,3-oxazolidin-2-one (1.25 g, 3.22 mmol) in acetonitrile (20 ml) were added di-t-butyl dicarbonate (0.84 g, 3.86 mmol) and dimethylaminopyridine (39 mg, 0.32 mmol), and the mixture was stirred at room temperature for 2 hrs. Water (50 ml) was added to the reaction solution and the mixture was extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give 1,1-dimethylethyl(4RS,5SR)-5-(2-fluoropyridin-4-yl)-2-oxo-4-((3-(1,1,2,2-tetrafluoroethoxy) phenyl)methyl)-1,3-oxazolidine-3-carboxylate (1.41 g, 89%).

$^1$H-NMR (CDCl$_3$)δ: 1.51 (9H, s), 2.60 (1H, dd, J=14.2, 8.8 Hz), 2.95 (1H, dd, J=14.2, 4.6 Hz), 4.82–4.98 (1H, m), 5.67 (1H, d, J=7.0 Hz), 5.90 (1H, tt, J=53.0, 3.0 Hz), 6.54 (1H, d, J=7.4 Hz), 6.73 (1H, s), 6.82 (1H, s), 6.94 (1H, d, J=5.0 Hz), 6.98–7.20 (2H, m), 8.09 (1H, d, J=5.2 Hz). IR ν max$^{KBr}$cm$^{-1}$: 1821, 1726, 1615, 1588, 1574, 1489, 1416. mp 113–114° C. Anal. Calcd for C$_{22}$H$_{21}$F$_5$N$_2$O$_5$: C, 54.10; H, 4.33; N, 5.74. Found: C, 54.10; H, 4.21; N, 5.72.

8) To a solution of 1,1-dimethylethyl(4RS,5SR)-5-(2-fluoropyridin-4-yl)-2-oxo-4-((3-(1,1,2,2-tetrafluoroethoxy) phenyl)methyl)-1,3-oxazolidine-3-carboxylate (1.30 g, 2.66 mmol) in methanol (7 ml) was added a solution (6.39 ml, 3.19 mmol) of 0.5N sodium hydroxide in methanol, and the mixture was stirred at room temperature for 10 min. To the reaction solution was added water (50 ml), and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give the title compound (1.08 g, 88%).

$^1$H-NMR (CDCl$_3$)δ: 1.37 (9H, s), 2.60–2.80 (2H, m), 3.82–4.10 (2H, m), 4.68 (1H, d, J=8.0 Hz), 5.01 (1H, s), 5.89 (1H, tt, J=53.0, 3.0 Hz), 6.92–7.12 (4H, m), 7.18–7.32 (2H, m), 8.20 (1H, d, J=5.0 Hz). IR ν max$^{KBr}$cm$^{-1}$: 1752, 1694, 1615, 1570, 1512, 1489, 1449, 1412. mp 143–144° C. Anal. Calcd for C$_{21}$H$_{23}$F$_5$N$_2$O$_4$: C, 54.55; H, 5.01; N, 6.06. Found: C, 54.32; H, 4.86; N, 6.07.

Example 220

N-((1RS,2SR)-2-(2-fluoropyridin-4-yl)-2-hydroxy-1-((3-(1,1,2,2-tetrafluoroethoxy)phenyl)methyl) ethyl)-6,7-dihydro-5H-benzo[a]cycloheptene-1-carboxamide 1) Trifluoroacetic acid (10 ml) was added to 1,1-dimethylethyl (1RS,2SR)-2-(2-fluoropyridin-4-yl)-2-hydroxy-1-((3-(1,1,2,2-tetrafluoroethoxy)phenyl)methyl) ethylcarbamate (0.8 g, 1.73 mmol), and the mixture was stirred at room temperature for 10 min. The reaction solution was concentrated under reduced pressure, 1N aqueous sodium hydroxide solution (10 ml) was added, and the mixture was extracted with ethyl acetate (20 ml×2). The extract was washed with saturated brine, dried over anhydrous magnesium sulfate and evaporated under reduced pressure. Recrystallization of the residue from ethyl acetate-hexane gave (1RS,2SR)-2-amino-1-(2-fluoropyridin-4-yl)-3-(3-(1,1,2,2-tetrafluoroethoxy)phenyl)-1-propanol (0.59 g, 93%).

$^1$H-NMR (CDCl$_3$)δ: 2.40 (1H, dd, J=13.6, 10.6 Hz), 2.63 (1H, dd, J=13.6, 3.2 Hz), 3.32–3.48 (1H, m), 4.79 (1H, d, J=4.0 Hz), 5.92 (1H, tt, J=53.0, 3.0 Hz), 6.92–7.40 (6H, m), 8.24 (1H, d, J=5.2 Hz). IR ν max$^{KBr}$cm$^{-1}$: 1613, 1588, 1568, 1487, 1449, 1410. mp 119–120° C. Anal. Calcd for C$_{16}$H$_{15}$F$_5$N$_2$O$_2$: C, 53.04; H, 4.17; N, 7.73. Found: C, 52.91; H, 4.08; N, 7.60.

2) To a solution of (1RS,2SR)-2-amino-1-(2-fluoropyridin-4-yl)-3-(3-(1,1,2,2-tetrafluoroethoxy) phenyl)-1-propanol (300 mg, 0.83 mmol) in acetonitrile (20 ml) were added 6,7-dihydro-5H-benzo[a]cycloheptene-1-carboxylic acid (156 mg, 0.83 mmol), 1-ethyl-3-(3- dimethylaminopropyl)carbodiimide hydrochloride (238 mg, 1.24 mmol) and 1-hydroxy-1H-benzotriazole (127 mg, 0.83 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (347 mg, 79%).

$^1$H-NMR (CDCl$_3$)δ: 1.90–2.08 (2H, m), 2.10–2.26 (2H, m), 2.60–2.72 (2H, m), 2.80–2.92 (2H, m), 4.40–4.70 (2H, m), 5.11 (1H, d, J=2.6 Hz), 5.89 (1H, tt, J=53.0, 3.0 Hz), 5.90–6.10 (2H, m), 6.24 (1H, d, J=11.6 Hz), 6.92–7.38 (9H, m), 8.08 (1H, d, J=5.2 Hz). IR ν max$^{KBr}$cm$^{-1}$: 1636, 1615, 1588, 1570, 1516, 1449, 1412. mp 159–160° C. Anal. Calcd for C$_{28}$H$_{25}$F$_5$N$_2$O$_3$.0.2H$_2$O: C, 62.73; H, 4.78; N, 5.23. Found: C, 62.64; H, 4.80; N, 5.37.

Example 221

1,1-dimethylethyl(1RS,2RS)-2-(6-fluoropyridin-2-yl)-2-hydroxy-1-((3-(1,1,2,2-tetrafluoroethoxy)phenyl)methyl)ethylcarbamate 1) To a solution of 2-amino-6-methylpyridine (75 g, 693 mmol) in 42% tetrafluoroboric acid (291 ml) was gradually added a solution of sodium nitrite (47.8 g, 693 mmol) in water (100 ml) while cooling with dry ice-acetone so that the inside temperature would not exceed 10° C. After the reaction solution was stirred at 45° C. for 30 min., 8N aqueous sodium hydroxide solution (100 ml) was gradually added, and the mixture was extracted with diethyl ether (300 ml×2). The extract was concentrated under reduced pressure, and the residue was distilled away to give 2-fluoro-6-methylpyridine (27.9 g). A solution of potassium permanganate (100 g, 632 mmol) in water (1.2 L) was heated to 80° C., and 2-fluoro-6-methylpyridine (27.9 g) was added. The mixture was heated under reflux for 4 hrs. Insoluble material was filtered off with celite from the reaction solution, and the filtrate was concentrated to 200 ml. Then, 6N hydrochloric acid was added until the pH became about 3. The precipitated crystals were collected by filtration to give 6-fluoro-2-pyridinecarboxylic acid (5.84 g, 14%).

$^1$H-NMR (CDCl$_3$)δ: 7.26 (1H, d, J=7.2 Hz), 7.36 (1H, s), 8.00–8.30 (1H, m). IR ν max$^{KBr}$cm$^{-1}$: 3100, 1730, 1620. mp 248–250° C. Anal. Calcd for C$_6$H$_4$FNO$_2$: C, 51.07; H, 2.86; N, 9.93. Found: C, 51.10; H, 2.81; N, 9.87.

2) To a solution of 6-fluoro-2-pyridinecarboxylic acid (15.0 g, 106.3 mmol) in tetrahydrofuran (200 ml) was added 1,1'-carbonylbis-1H-imidazole (19.0 g, 116.9 mmol), and the mixture was heated under reflux for 30 min. The reaction solution was cooled and monoethyl malonate magnesium salt (16.8 g, 58.5 mmol) was added. The mixture was stirred at room temperature for 30 min. 1N Hydrochloric acid (200 ml) was added to the reaction solution and the mixture was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(6-fluoro-2-pyridyl)-3-oxopropionate (20.16 g, 90%) as a brown oil.

$^1$H-NMR (CDCl$_3$)δ: 1.20–1.40 (3H, m), 4.13 (2H×2/3, s), 4.14–4.34 (2H, m), 6.30 (1H×1/3, s), 6.96–7.04 (1H×1/3, m), 7.12–7.24 (1H×2/3, m), 7.78–8.04 (2H, m), 12.32 (1H×1/3, s). IR ν max$^{KBr}$cm$^{-1}$: 1744, 1709, 1651, 1593, 1578, 1453. Anal. Calcd for C$_{10}$H$_{10}$FNO$_3$: C, 56.87; H, 4.77 Found: C, 56.74; H, 4.73

3) To a solution of 3-(1,1,2,2-tetrafluoroethoxy)toluene (7.51 g, 35.6 mmol) in carbon tetrachloride (100 ml) were added N-bromosuccinimide (7.60 g, 42.7 mmol) and 2,2'-azobis(isobutyronitrile) (290 mg, 1.78 mmol), and the mixture was heated under reflux for 4 hrs. After cooling, the reaction solution was filtered, the filtrate was concentrated to give 3-(1,1,2,2-tetrafluoroethoxy)-α-bromotoluene. To a solution of ethyl 3-(6-fluoropyridin-2-yl)-3-oxopropionate (7.51 g, 35.6 mmol) in 1,2-dimethoxyethane (70 ml) was added sodium hydride (60% in oil, 1.42 g, 35.6 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (10 ml), and the reaction solution was stirred at room temperature for 1 hr. The reaction solution was poured into water (100 ml), and the mixture was extracted with ethyl acetate (100 ml×2). The extract was washed with water and saturated brine, dried over anhydrous magnesium sulfate and evaporated under reduced pressure. The residue was purified by silica gel column chromatography (toluene:hexane=1:1) to give ethyl 3-(6-fluoropyridin-2-yl)-3-oxo-2-((3-(1,1,2,2-tetrafluoroethoxy)phenyl)methyl)propionate (7.74 g, 52%) as a colorless oil.

$^1$H-NMR (CDCl$_3$)δ: 1.13 (3H, t, J=9.0 Hz), 3.20–3.44 (2H, m), 4.11 (2H, q, J=9.0 Hz), 4.98 (1H, t, J=7.4 Hz), 5.89 (1H, tt, J=53.0, 3.0 Hz), 7.00–7.32 (5H, m), 7.90–8.04 (2H, m). IR ν max$^{KBr}$cm$^{-1}$: 1732, 1705, 1593, 1453. Anal. Calcd for C$_{19}$H$_{16}$F$_5$NO$_4$: C, 54.68; H, 3.86; N, 3.36. Found: C, 54.55; H, 3.92; N, 3.51.

4) To a solution of zinc chloride (4.19 g, 30.7 mmol) in diethyl ether (100 ml) was added sodium borohydride (2.33 g, 61.4 mmol), and the mixture was stirred at room temperature for 30 min. Insoluble material was filtered off, and a solution of ethyl 3-(6-fluoropyridin-2-yl)-3-oxo-2-((3-(1,1,2,2-tetrafluoroethoxy)phenyl)methyl)propionate (6.41 g, 15.4 mmol) in diethyl ether (50 ml) was added to the filtrate at −78° C. The mixture was stirred for 30 min. 1N Hydrochloric acid was added to the reaction solution to quench the reaction. Then, water (100 ml) was added and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) to give ethyl 3-(6-fluoropyridin-2-yl)-3-hydroxy-2-((3-(1,1,2,2-tetrafluoroethoxy)phenyl)methyl)propionate((2RS,3RS) form: (2RS,3SR) form=6:1, 5.70 g, 88%) as a colorless oil.

$^1$H-NMR (CDCl$_3$)δ: 0.96–1.00 (3H, m), 2.87 (1H, dd, J=5.0 Hz), 2.96–3.14 (1H, m), 3.20–3.40 (1H, m), 3.76 (1H, d, J=5.6 Hz), 3.90–4.04 (2H, m), 4.76 (1H×1/7, dd, J=9.6, 4.4 Hz), 5.00–5.08 (1H×6/7, m), 5.89 (1H, tt, J=53.0, 3.0 Hz), 6.83 (1H, dd, J=8.0, 2.6 Hz), 6.90–7.36 (5H, m), 7.70–7.86 (1H, m). IR ν max$^{KBr}$cm$^{-1}$: 1728, 1607, 1578, 1454. Anal. Calcd for C$_{19}$H$_{18}$F$_5$NO$_4$: C, 54.42; H, 4.33; N, 3.34. Found: C, 54.34; H, 4.37; N, 3.29.

5) To a solution of ethyl(2RS,3RS)-3-(6-fluoropyridin-2-yl)-3-hydroxy-2-((3-(1,1,2,2-tetrafluoroethoxy)phenyl)methyl)propionate (5.5 g, 13.1 mmol, (2RS,3RS) form: (2RS,3SR) form=6:1) in methanol (25 ml) was added 2N aqueous sodium hydroxide solution (13.1 ml, 26.2 mmol), and the mixture was stirred at room temperature for 2 hrs. The reaction solution was acidified with 1N hydrochloric acid and extracted with ethyl acetate (200 ml×2). The extract was washed with water and saturated brine, dried over anhydrous magnesium sulfate and evaporated under reduced pressure. Recrystallization of the residue from ethyl acetate-hexane gave (2RS,3RS)-3-(6-fluoropyridin-2-yl)-3-hydroxy-2-((3-(1,1,2,2-tetrafluoroethoxy)phenyl)methyl) propionic acid (3.82 g, 74%).

$^1$H-NMR (CDCl$_3$)δ: 2.85 (1H, dd, J=14.0, 5.2 Hz), 3.08 (1H, dd, J=14.0, 9.0 Hz), 3.26–3.38 (1H, m), 5.12 (1H, d, J=4.4 Hz), 5.88 (1H, tt, J=53.0, 3.0 Hz), 6.81 (1H, dd, J=8.2, 2.6 Hz), 6.90–7.04 (3H, m), 7.18 (1H, d, J=7.6 Hz), 7.27 (1H, dd, J=7.2, 2.2 Hz), 7.70–7.82 (1H, m). IR ν max$^{KBr}$ cm$^{-1}$: 1713, 1609, 1580, 1489, 1456. mp 103–104° C. Anal. Calcd for C$_{17}$H$_{14}$F$_5$NO$_4$: C, 52.18; H, 3.61; N, 3.58. Found: C, 52.16; H, 3.57; N, 3.57.

6) To a solution of (2RS,3RS)-3-(6-fluoropyridin-2-yl)-3-hydroxy-2-((3-(1,1,2,2-tetrafluoroethoxy)phenyl)methyl) propionic acid (3.6 g, 9.20 mmol) in tetrahydrofuran (90 ml) were added diphenylphosphoryl azide (2.18 ml, 10.1 mmol) and triethylamine (1.93 ml, 13.8 mmol), and the mixture was heated under reflux for 2 hrs. The reaction solution was allowed to cool and water (200 ml) was added. The mixture was extracted with ethyl acetate (100 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=1:1). Recrystallization from ethyl acetate-hexane gave (4RS,5RS)-5-(6-fluoropyridin-2-yl)-4-((3-(1,1,2,2-tetrafluoroethoxy)phenyl)methyl)-1,3-oxazolidin-2-one (2.34 g, 65%).

$^1$H-NMR (CDCl$_3$)δ: 2.14 (1H, dd, J=13.6, 9.0 Hz), 2.58 (1H, dd, J=13.6, 3.2 Hz), 4.36–4.50 (1H, m), 5.13 (1H, s), 5.78 (1H, d, J=8.0 Hz), 5.91 (1H, tt, J=53.0, 3.0 Hz), 6.90–7.20 (4H, m), 7.26–7.42 (1H, m), 7.52 (1H, d, J=5.2 Hz), 7.86–8.00 (1H, m). IR ν max$^{KBr}$cm$^{-1}$: 1767, 1607, 1584, 1489, 1458, 1447. mp 118–119° C. Anal. Calcd for C$_{17}$H$_{13}$F$_5$N$_2$O$_3$: C, 52.59; H, 3.37; N, 7.21. Found: C, 52.60; H, 3.31; N, 7.35.

7) To a solution of (4RS,5RS)-5-(6-fluoropyridin-2-yl)-4-((3-(1,1,2,2-tetrafluoroethoxy)phenyl)methyl)-1,3-oxazolidin-2-one (2.2 g, 5.67 mmol) in acetonitrile (20 ml) were added di-t-butyl dicarbonate (1.48 g, 6.80 mmol) and dimethylaminopyridine (70 mg, 0.57 mmol), and the mixture was stirred at room temperature for 2 hrs. To the reaction solution was added water (50 ml), and the mixture was extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give 1,1-dimethylethyl(4RS,5RS)-5-(6-fluoropyridin-2-yl)-2-oxo-4-((3-(1,1,2,2-tetrafluoroethoxy)phenyl)methyl)-1,3-oxazolidine-3-carboxylate (2.59 g, 94%).

$^1$H-NMR (CDCl$_3$)δ: 1.45 (9H, s), 2.65 (1H, dd, J=14.2, 7.4 Hz), 2.84 (1H, dd, J=14.2, 5.8 Hz), 4.97–5.08 (1H, m), 5.61 (1H, d, J=6.4 Hz), 5.88 (1H, tt, J=53.0, 3.0 Hz), 6.53 (1H, s), 6.75 (1H, d, J=7.6 Hz), 6.88 (1H, dd, J=8.0, 2.6 Hz), 7.02 (1H, d, J=9.6 Hz), 7.10–7.22 (1H, m), 7.43 (1H, dd, J=7.4, 2.6 Hz), 7.80–7.94 (1H, m). IR ν max$^{KBr}$cm$^{-1}$: 1823, 1728, 1607, 1584, 1460, 1447. mp 96–97° C. Anal. Calcd for C$_{22}$H$_{21}$F$_5$N$_2$O$_5$: C, 54.10; H, 4.33; N, 5.74. Found: C, 54.14; H, 4.25; N, 5.78.

8) To a solution of 1,1-dimethylethyl(4RS,5RS)-5-(6-fluoropyridin-2-yl)-2-oxo-4-((3-(1,1,2,2-tetrafluoroethoxy)phenyl)methyl)-1,3-oxazolidine-3-carboxylate (2.40 g, 4.91 mmol) in methanol (12 ml) was added a solution (11.8 ml, 5.90 mmol) of 0.5N sodium hydroxide in methanol, and the mixture was stirred at room temperature for 10 min. To the reaction solution was added water (50 ml) and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give the title compound (1.92 g, 84%).

$^1$H-NMR (CDCl$_3$)δ: 1.37 (9H, s), 2.65 (1H, dd, J=13.6, 5.0 Hz), 2.85 (1H, dd, J=13.6, 9.0 Hz), 4.08–4.30 (1H, m), 4.45 (1H, d, J=6.0 Hz), 4.88–5.02 (2H, m), 5.89 (1H, tt, J=53.0, 3.0 Hz), 6.85 (1H, dd, J=8.0, 2.2 Hz), 6.90–7.10 (3H, m), 7.10–7.32 (2H, m), 7.70–7.86 (1H, m). IR ν max$^{KBr}$ cm$^{-1}$: 1682, 1607, 1576, 1532, 1487, 1454. mp 140–141° C. Anal. Calcd for C$_{21}$H$_{23}$F$_5$N$_2$O$_4$: C, 54.55; H, 5.01; N, 6.06. Found: C, 54.27; H, 4.71; N, 6.12.

Example 222

N-((1RS,2RS)-2-(6-fluoropyridin-2-yl)-2-hydroxy-1-((3-(1,1,2,2-tetrafluoroethoxy)phenyl)methyl) ethyl)-6,7-dihydro-5H-benzo[a]cycloheptene-1-carboxamide 1) To a solution of 1,1-dimethylethyl(1RS,2RS)-2-(6-fluoropyridin-2-yl)-2-hydroxy-1-((3-(1,1,2,2-tetrafluoroethoxy)phenyl)methyl)ethylcarbamate (1.6 g, 3.46 mmol) was added trifluoroacetic acid (20 ml), and the mixture was stirred at room temperature for 10 min. The reaction solution was concentrated under reduced pressure, and 1N aqueous sodium hydroxide solution (10 ml) was added. The mixture was extracted with ethyl acetate (20 ml×2). The extract was washed with saturated brine, dried over anhydrous magnesium sulfate and evaporated under reduced pressure to give (1RS,2RS)-2-amino-1-(6-fluoropyridin-2-yl)-3-(3-(1,1,2,2-tetrafluoroethoxy) phenyl)-1-propanol (1.3 g, 100%).

$^1$H-NMR (CDCl$_3$)δ: 2.47 (1H, dd, J=13.8, 10.0 Hz), 2.73 (1H, dd, J=13.8, 3.4 Hz), 3.40–3.54 (1H, m), 4.70 (1H, d, J=4.4 Hz), 5.90 (1H, tt, J=53.0, 3.0 Hz), 6.86 (1H, dd, J=8.0, 2.6 Hz), 6.96–7.18 (3H, m), 7.20–7.40 (2H, m), 7.78–7.92 (1H, m). IR ν max$^{KBr}$cm$^{-1}$: 1755, 1607, 1578, 1489, 1454. Anal. Calcd for C$_{16}$H$_{15}$F$_5$N$_2$O$_2$: C, 53.04; H, 4.17; N, 7.73. Found: C, 53.19; H, 4.40; N, 7.51.

2) To a solution of (1RS,2RS)-2-amino-1-(6-fluoropyridin-2-yl)-3-(3-(1,1,2,2-tetrafluoroethoxy) phenyl)-1-propanol (300 mg, 0.83 mmol) in acetonitrile (20 ml) were added 6,7-dihydro-5H-benzo[a]cycloheptene-1-carboxylic acid (156 mg, 0.83 mmol), 1-ethyl-3-(3-dimethylaminopropyl)carbodiimide hydrochloride (238 mg, 1.24 mmol) and 1-hydroxy-1H-benzotriazole (127 mg, 0.83 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (293 mg, 66%).

$^1$H-NMR (CDCl$_3$)δ: 1.92–2.10 (2H, m), 2.12–2.26 (2H, m), 2.60–2.70 (2H, m), 2.81 (1H, dd, J=14.6, 5.2 Hz), 3.03 (1H, dd, J=14.6, 9.8 Hz), 4.66–4.82 (1H, m), 4.84 (1H, d,

J=5.8 Hz), 5.02–5.10 (1H, m), 5.89 (1H, tt, J=53.0, 3.0 Hz), 5.90–6.02 (1H, m), 6.18–6.32 (2H, m), 6.86 (1H, dd, J=8.0, 2.6 Hz), 7.00–7.30 (7H, m), 7.42 (1H, dd, J=7.4, 2.2 Hz), 7.76–7.90 (1H, m). IR ν max$^{KBr}$cm$^{-1}$: 1642, 1607, 1578, 1516, 1454. mp 151–152° C. Anal. Calcd for $C_{28}H_{25}F_5N_2O_3 \cdot 0.2H_2O$: C, 62.73; H, 4.78; N, 5.23. Found: C, 62.75; H, 4.75; N, 5.31.

Example 223

1,1-dimethylethyl(1RS,2SR)-2-(6-fluoropyridin-3-yl)-2-hydroxy-1-((3-(1,1,2,2-tetrafluoroethoxy)phenyl)methyl)ethylcarbamate 1) To a solution of 2-amino-5-methylpyridine (75 g, 693 mmol) in 42% tetrafluoroboric acid (291 ml) was added a solution of sodium nitrite (47.8 g, 693 mmol) in water (100 ml) while cooling with dry ice-acetone so that the inside temperature would not exceed 10° C. After the reaction solution was stirred at 45° C. for 30 min., 8N aqueous sodium hydroxide solution (100 ml) was gradually added, and the mixture was extracted with diethyl ether (300 ml×2). The extract was concentrated under reduced pressure and the residue was distilled away to give 2-fluoro-5-methylpyridine (30.4 g). A solution of potassium permanganate (100 g, 632 mmol) in water (1.2 L) was heated to 80° C. and 2-fluoro-5-methylpyridine (30.4 g, 274 mmol) was added. The mixture was heated under reflux for 4.5 hrs. Insoluble material was filtered off with celite from the reaction solution, and the filtrate was concentrated to 200 ml. Then, 6N hydrochloric acid was added until the pH became about 3. The precipitated crystals were collected by filtration to give 6-fluoro-3-pyridinecarboxylic acid (10.58 g, 11%).

mp 151–152° C. IR ν max$^{KBr}$cm$^{-1}$: 3100, 1730, 1620. Anal. Calcd for $C_6H_4FNO_2$: C, 51.07; H, 2.86; N, 9.93. Found: C, 50.78; H, 2.72; N, 9.87. $^1$H-NMR (CDCl$_3$)δ: 7.07 (1H, dd, J=8.8, 2.8 Hz), 8.40–8.52 (1H, m), 8.90–9.04 (1H, m).

2) To a solution of 6-fluoro-3-pyridinecarboxylic acid (9.5 g, 67.3 mmol) in tetrahydrofuran (150 ml) was added 1,1'-carbonylbis-1H-imidazole (12.0 g, 74.1 mmol), and the mixture was stirred at 80° C. for 10 min. The reaction solution was cooled to room temperature and monoethyl malonate magnesium salt (10.6 g, 37.0 mmol) was added. The mixture was stirred at room temperature for 2 hrs. To the reaction solution were added ethyl acetate (100 ml) and water (100 ml). Then, conc. hydrochloric acid was added until the aqueous layer showed acidic pH. The reaction solution was extracted with ethyl acetate (200 ml×2). The extract was washed with saturated brine, dried over anhydrous magnesium sulfate and evaporated under reduced pressure. The residue was purified by silica gel column chromatography (hexane:ethyl acetate=4:1) to give ethyl 3-(6-fluoropyridin-3-yl)-3-oxopropionate (9.74 g, 68%) as a brown oil.

IR ν max$^{KBr}$cm$^{-1}$: 1738, 1694, 1634, 1593, 1485. Anal. Calcd for $C_{10}H_{10}NO_3F$: C, 56.87; H, 4.77; N, 6.63. Found: C, 56.79; H, 4.78; N, 6.84. $^1$H-NMR (CDCl$_3$)δ: 1.27 (3H× 5/7, t, J=7.0 Hz), 1.35 (3H×2/7, t, J=7.4 Hz), 3.99 (2H×5/7, s), 4.16–4.36 (2H, m), 5.65 (1H×2/7, s), 6.96–7.10 (1H, m), 8.16 (1H×2/7, td, J=9.0, 3.8 Hz), 8.39 (1H×5/7, td, J=9.0, 3.8 Hz), 8.64 (1H×2/7, d, J=3.8 Hz), 8.81 (1H×5/7, d, J=3.8 Hz).

3) To a solution of 3-(1,1,2,2-tetrafluoroethoxy)toluene (15 g, 72.1 mmol) in chloroform (200 ml) were added N-bromosuccinimide (14.11 g, 79.3 mmol) and 2,2'-azobis(isobutyronitrile) (590 mg, 3.60 mmol) and the mixture was heated under reflux for 30 min. The reaction solution was cooled and water (100 ml) was added. The mixture was extracted with chloroform. The extract was washed successively with water (100 ml) and saturated brine (100 ml), dried over anhydrous magnesium sulfate and evaporated under reduced pressure. The residue was purified by silica gel column chromatography (hexane:ethyl acetate=10:1) to give 3-(1,1,2,2-tetrafluoroethoxy)-α-bromotoluene (19.4 g, purity 56%, 53%). This compound was used for the next reaction without further purification.

4) To a solution of ethyl 3-(6-fluoropyridin-3-yl)-3-oxopropionate (3.83 g, 18.1 mmol) in 1,2-dimethoxyethane (30 ml) was added sodium hydride (60% in oil, 725 mg, 18.1 mmol) under ice-cooling, and the mixture was stirred at room temperature for 30 min. To the reaction solution was dropwise added 3-(1,1,2,2-tetrafluoroethoxy)-α-bromotoluene (9.30 g, purity 56%, 18.1 mmol) in 1,2-dimethoxyethane (10 ml), and the mixture was stirred at room temperature for 2 hrs. The reaction solution was poured into water (100 ml), and the mixture was extracted with ethyl acetate (100 ml×2). The extract was washed with water and saturated brine, dried over anhydrous magnesium sulfate and evaporated under reduced pressure. The residue was purified by silica gel column chromatography (toluene-toluene:ethyl acetate=5:1) to give ethyl 3-(6-fluoropyridin-3-yl)-3-oxo-2-((3-(1,1,2,2-tetrafluoroethoxy)phenyl)methyl)propionate (6.67 g, 88%) as a colorless oil.

IR ν max$^{KBr}$cm$^{-1}$: 1738, 1694, 1590, 1487. Anal. Calcd for $C_{19}H_{16}F_5NO_4$: C, 54.68; H, 3.86; N, 3.36. Found: C, 54.56; H, 4.13; N, 3.51. $^1$H-NMR (CDCl$_3$)δ: 1.14 (3H, t, J=7.0 Hz), 3.36 (2H, d, J=7.4 Hz), 4.13 (2H, q, J=7.0 Hz), 4.54 (1H, d, J=7.4 Hz), 5.89 (1H, tt, J=53.0, 2.8 Hz), 6.98–7.20 (4H, m), 7.20–7.36 (1H, m), 8.35 (1H, td, J=8.4, 2.4 Hz), 8.82 (1H, d, J=2.4 Hz).

5) To a solution of zinc chloride (4.25 g, 31.2 mmol) in diethyl ether (100 ml) was added sodium borohydride (2.36 g, 62.3 mmol), and the mixture was stirred at room temperature for 30 min. Insoluble material was filtered off and a solution of ethyl 3-(6-fluoropyridin-3-yl)-3-oxo-2-((3-(1,1,2,2-tetrafluoroethoxy)phenyl)methyl)propionate (6.50 g, 15.6 mmol) in diethyl ether (50 ml) was added to the filtrate. The mixture was stirred at room temperature for 30 min. and 1N hydrochloric acid was added to the reaction solution under ice-cooling to quench the reaction. Then, water (100 ml) was added and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1–1:1) to give ethyl(2RS,3RS)-3-(6-fluoropyridin-3-yl)-3-hydroxy-2-1((3-(1,1,2,2-tetrafluoroethoxy)phenyl)methyl)propionate((1RS,2SR) form: (1RS,2RS) form=10:1,5.15 g, 79%) as a colorless oil.

IR ν max$^{KBr}$cm$^{-1}$: 1728, 1601, 1487. Anal. Calcd for $C_{19}H_{18}F_5NO_4 \cdot 0.1H_2O$: C, 54.19; H, 4.35; N, 3.33. Found: C, 54.10; H, 4.20; N, 3.39. $^1$H-NMR (CDCl$_3$)δ: 0.95 (3H× 10/11, t, J=7.0 Hz), 1.02 (3H×1/11, t, J=7.4 Hz), 2.80–3.16 (3H, m), 3.23 (1H, d, J=3.0 Hz), 3.84–4.00 (2H, m), 4.80–4.90 (1H×1/11, m), 5.09 (1H×10/11, s), 5.89 (1H, tt, J=53.0, 3.0 Hz), 6.90–7.12 (4H, m), 7.20–7.30 (1H, m), 7.86 (1H, td, J=8.2, 2.6 Hz), 8.16–8.24 (1H, m).

6) To a solution of ethyl(2RS,3RS)-3-(6-fluoropyridin-3-yl)-3-hydroxy-2-((3-(1,1,2,2-tetrafluoroethoxy)phenyl)methyl)propionate (5.0 g, 11.9 mmol, (2RS,3SR) form: (2RS,3RS) form=10:1) in methanol (20 ml) was added 2N aqueous sodium hydroxide solution (11.9 ml, 23.8 mmol), and the mixture was stirred overnight at room temperature.

The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was purified by silica gel column chromatography (ethyl acetate) to give (2RS,3RS)-3-(6-fluoropyridin-3-yl)-3-hydroxy-2-((3-(1,1,2,2-tetrafluoroethoxy)phenyl)methyl)propionic acid (3.75 g, (2RS,3SR) form: (2RS,3RS) form=10:1, 80%) as an amorphous compound.

IR ν max$^{KBr}$cm$^{-1}$: 1715, 1607, 1593, 1487. Anal. Calcd for $C_{17}H_{14}F_5NO_4$: C, 52.18; H, 3.61; N, 3.58. Found: C, 52.13; H, 3.43; N, 3.57. $^1$H-NMR (CDCl$_3$)δ: 2.80–3.12 (3H, m), 4.85 (1H×1/11, d, J=5.2 Hz), 5.10 (1H×10/11, s), 6.88–7.12 (4H, m), 7.22 (1H, t, J=7.6 Hz), 7.87 (1H, td, J=7.6, 2.2 Hz), 8.14 (1H, s).

7) To a solution of (2RS,3RS)-3-(6-fluoropyridin-3-yl)-3-hydroxy-2-((3-(1,1,2,2-tetrafluoroethoxy)phenyl)methyl) propionic acid (3.6 g, 9.20 mmol, (2RS,3SR) form: (2RS, 3RS) form=10:1) in tetrahydrofuran (90 ml) were added diphenylphosphoryl azide (2.18 ml, 10.1 mmol) and triethylamine (1.93 ml, 13.8 mmol), and the mixture was heated under reflux for 30 min. The reaction solution was allowed to cool and water (200 ml) was added. The mixture was extracted with ethyl acetate (100 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=1:1) to give (4RS,5SR)-5-(6-fluoropyridin-3-yl)-4-((3-(1,1,2,2-tetrafluoroethoxy)phenyl)methyl)-1,3-oxazolidin-2-one (3.31 g, (4RS,5SR) form: (4RS,5RS) form=10:1, 93%) as an amorphous compound.

IR ν max$^{KBr}$cm$^{-1}$: 1767, 1603, 1489. Anal. Calcd for $C_{17}H_{13}F_5N_2O_3$: C, 52.59; H, 3.37; N, 7.21. Found: C, 52.46; H, 3.55; N, 7.03. $^1$H-NMR (CDCl$_3$)δ: 2.34 (1H, d, J=4.0 Hz), 2.38 (1H, s), 4.04–4.20 (1H×1/11, m), 4.28–4.42 (1H× 10/11, m), 5.25 (1H×1/11, s), 5.29 (1H×10/11, s), 5.84 (1H, d, J=8.0 Hz), 5.91 (1H, tt, J=53.0, 3.0 Hz), 6.86–7.18 (4H, m), 7.22–7.40 (1H, m), 7.60–7.78 (1H×1/11, m), 7.85 (1H× 10/11, td, J=8.2, 2.6 Hz), 8.02 (1H×1/11, s), 8.22 (1H×10/11, s).

8) To a solution of (4RS,5SR)-5-(6-fluoropyridin-3-yl)-4-((3-(1,1,2,2-tetrafluoroethoxy)phenyl)methyl)-1,3-oxazolidin-2-one (3.10 g, 7.98 mmol) in acetonitrile (30 ml) were added di-t-butyl dicarbonate (2.09 g, 9.58 mmol) and dimethylaminopyridine (97 mg, 0.80 mmol), and the mixture was stirred at room temperature for 2 hrs. Water (50 ml) was added to the reaction solution, and the mixture was extracted with ethyl acetate (50 ml×2). The extract was washed with saturated brine, dried over anhydrous magnesium sulfate and evaporated under reduced pressure. The residue was purified by silica gel column chromatography (hexane:ethyl acetate=4:1) and recrystallized from ethyl acetate-hexane to give 1,1-dimethylethyl(4RS,5SR)-5-(6-fluoropyridin-3-yl)-2-oxo-4-((3-(1,1,2,2-tetrafluoroethoxy) phenyl)methyl)-1,3-oxazolidine-3-carboxylate (2.55 g, 65%).

mp 138–139° C. IR ν max$^{KBr}$cm$^{-1}$: 1821, 1725, 1603. Anal. Calcd for $C_{22}H_{21}F_5N_2O_5$: C, 54.10; H, 4.33; N, 5.74. Found: C, 54.14; H, 4.41; N, 5.77. $^1$H-NMR (CDCl$_3$)δ: 1.54 (9H, s), 2.06 (1H, dd, J=14.2, 9.6 Hz), 3.04 (1H, dd, J=14.2, 4.0 Hz), 4.82–4.96 (1H, m), 5.72 (1H, d, J=6.8 Hz), 5.89 (1H, tt, J=53.0, 3.0 Hz), 6.52–6.62 (2H, m), 6.81 (1H, dd, J=8.4, 2.8 Hz), 6.94–7.04 (1H, m), 7.04–7.20 (1H, m), 7.53 (1H, td, J=8.0, 2.6 Hz), 8.05 (1H, d, J=2.0 Hz).

9) To absolution of 1,1-dimethylethyl(4RS,5SR)-5-(6-fluoropyridin-3-yl)-2-oxo-4-((3-(1,1,2,2-tetrafluoroethoxy) phenyl)methyl)-1,3-oxazolidine-3-carboxylate (2.40 g, 4.91 mmol) in methanol (12 ml) was added a solution of 0.5N sodium hydroxide in methanol (11.8 ml, 5.90 mmol), and the mixture was stirred at room temperature for 10 min. To the reaction solution was added water (50 ml) and the mixture was extracted with ethyl acetate (50 ml×2). The extract was washed with saturated brine, dried over anhydrous magnesium sulfate and evaporated under reduced pressure. The residue was recrystallized from ethyl acetate-hexane to give the title compound (1.98 g, 87%).

mp 128–129° C. IR ν max$^{KBr}$cm$^{-1}$: 1694, 1601, 1487. Anal. Calcd for $C_{21}H_{23}F_5N_2O_4$: C, 54.55; H, 5.01; N, 6.06. Found: C, 54.49; H, 5.01; N, 6.23. $^1$H-NMR (CDCl$_3$)δ: 1.34 (9H, s), 2.62–2.90 (2H, m), 3.92 (1H, brs), 3.98–4.16 (1H, m), 4.62 (1H, d, J=7.4 Hz), 4.94 (1H, s), 5.90 (1H, tt, J=53.0, 3.0 Hz), 6.90–7.12 (4H, m), 7.22–7.32 (1H, m), 7.80–7.92 (1H, m), 8.21 (1H, s).

Example 224

N-((1RS,2SR)-2-(6-fluoropyridin-3-yl)-2-hydroxy-1-((3-(1,1,2,2-tetrafluoroethoxy)phenyl)methyl) ethyl)-4-fluoro-1-naphthalenecarboxamide 1) To a solution of 1,1-dimethylethyl(1RS,2SR)-2-(6-fluoropyridin-3-yl)-2-hydroxy-1-((3-(1,1,2,2-tetrafluoroethoxy)phenyl)methyl)ethylcarbamate (1.0 g, 2.16 mmol) was added trifluoroacetic acid (10 ml), and the mixture was stirred at room temperature for 10 min. The reaction solution was concentrated under reduced pressure and 1N aqueous sodium hydroxide solution (10 ml) was added. The mixture was extracted with ethyl acetate (20 ml×2). The extract was washed with saturated brine, dried over anhydrous magnesium sulfate and evaporated under reduced pressure. The residue was recrystallized from ethyl acetate-hexane to give (1RS,2SR)-2-amino-1-(6-fluoropyridin-3-yl)-3-(3-(1,1,2,2-tetrafluoroethoxy) phenyl)-1-propanol (750 mg, 96%).

mp 103–104° C. IR ν max$^{KBr}$cm$^{-1}$: 1597, 1485, 1449, 1399. Anal. Calcd for $C_{16}H_{15}F_5N_2O_2$: C, 53.04; H, 4.17; N, 7.73. Found: C, 52.97; H, 4.17; N, 7.84. $^1$H-NMR (CDCl$_3$)δ: 2.38 (1H, dd, J=13.4, 10.4 Hz), 2.74 (1H, dd, J=13.4, 3.0 Hz), 3.28–3.40 (1H, m), 4.76 (1H, d, J=4.4 Hz), 5.90 (1H, tt, J=53.0, 3.0 Hz), 6.90–7.12 (4H, m), 7.22–7.40 (1H, m),7.88 (1H, td, J=8.2, 2.6 Hz), 8.23 (1H, s).

2) To a solution of (1RS,2SR)-2-amino-1-(6-fluoropyridin-3-yl)-3-(3-(1,1,2,2-tetrafluoroethoxy) phenyl)-1-propanol (191 mg, 0.53 mmol) in acetonitrile (20 ml) were added 4-fluoronaphthalenecarboxylic acid (100 mg, 0.53 mmol), 1-ethyl-3-(3-dimethylaminopropyl) carbodiimide hydrochloride (151 mg, 0.79 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (130 mg, 48%).

mp 148–149° C. IR ν max$^{KBr}$cm$^{-1}$: 1640, 1626, 1601, 1514, 1485. Anal. Calcd for $C_{27}H_{20}F_6N_2O_3$: C, 60.68; H, 3.77; N, 5.24. Found: C, 60.87; H, 3.87; N, 5.11. $^1$H-NMR (CDCl$_3$)δ: 2.84 (1H, dd, J=14.2, 10.6 Hz), 3.09 (1H, dd, J=14.2, 4.0 Hz), 4.02 (1H, brs), 4.64–4.82 (1H, m), 5.15

(1H, d, J=4.0 Hz), 5.89 (1H, tt, J=53.0, 3.0 Hz), 5.97 (1H, d, J=8.4 Hz), 6.90–7.70 (9H, m), 7.78–7.90 (1H, m), 7.97 (1H, td, J=8.0, 2.2 Hz), 8.09 (1H, d, J=7.2 Hz), 8.26 (1H, s).

Example 225

N-((1RS,2SR)-2-(6-fluoropyridin-3-yl)-2-hydroxy-1-((3-(1,1,2,2-tetrafluoroethoxy)phenyl)methyl)ethyl)-6,7-dihydro-5H-benzo[a]cycloheptene-1-carboxamide To a solution of (1RS,2SR)-2-amino-1-(6-fluoropyridin-3-yl)-3-(3-(1,1,2,2-tetrafluoroethoxy)phenyl)-1-propanol (193 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl)carbodiimide hydrochloride (153 mg, 0.80 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (232 mg, 82%).

mp 140–142° C. IR ν max$^{KBr}$cm$^{-1}$: 1636, 1597, 1487. $^1$H-NMR (CDCl$_3$)δ: 1.90–2.10 (2H, m), 2.10–2.28 (2H, m), 2.58–2.72 (2H, m), 2.79 (1H, dd, J=14.4, 10.8 Hz), 3.03 (1H, dd, J=14.4, 4.0 Hz), 4.26 (1H, brs), 4.58–4.74 (1H, m), 5.07 (1H, d, J=3.6 Hz), 5.80 (1H, d, J=7.6 Hz), 5.89 (1H, tt, J=53.0, 3.0 Hz), 5.90–6.00 (1H, m), 6.10–6.24 (1H, m), 6.90–7.22 (7H, m), 7.22–7.40 (1H, m), 7.94 (1H, td, J=8.0, 2.2 Hz), 8.23 (1H, s).

Example 226

Optical Resolution of N-[(1RS,2SR)-2-(4-fluorophenyl)-2-hydroxy-1-[4-(trifluoromethyl)benzyl]ethyl]naphthalene-1-carboxamide The racemate was optically resolved by high performance liquid chromatography using an optically active column (CHIRALCELL OD, 50 mmID×500 mmL) (mobile layer: hexane/ethanol=9/1), and each optical isomer was obtained by recrystallization from ethanol.

(1R,2S) form mp 239–240° C.; [α]$_D^{20}$ +37.3° (c=0.507, MeOH); $^1$H-NMR (CDCl$_3$-CD$_3$OD, 200 MHz) δ 2.85 (1H, dd, J=10.8 Hz, 14.0 Hz), 3.08 (1H, dd, J=3.6 Hz, 13.8 Hz), 4.72–4.87 (1H, m), 5.02 (1H, d, J=4.6 Hz), 6.79 (1H, br d, J=8.8 Hz), 7.10 (2H, t, J=8.6 Hz), 7.21 (1H, d, J=7.0 Hz), 7.30–7.57 (10H, m), 7.77–7.88 (2H, m); IR (KBr) 3268, 1638, 1534, 1514, 1325, 1229, 1163, 1123, 1069, 831 cm$^{-1}$; Anal. Calcd for C$_{27}$H$_{21}$F$_4$NO$_2$: C, 69.37; H, 4.53; N, 3.00. Found: C, 69.30; H, 4.27; N, 2.76.

(1S,2R) form mp 238–239° C.; [α]$_D^{20}$ -37.9° (c=0.508, MeOH); $^1$H-NMR (CDCl$_3$-CD$_3$OD, 200 MHz) δ 2.85 (1H, dd, J=11.4 Hz, 14.2 Hz), 3.09 (1H, dd, J=3.9 Hz, 13.7 Hz), 4.72–4.86 (1H, m), 5.01 (1H, d, J=4.8 Hz), 6.90 (1H, br d, J=9.6 Hz), 7.11 (2H, t, J=8.8 Hz), 7.20 (1H, dd, J=1.2 Hz, 7.0 Hz), 7.29–7.57 (10H, m), 7.79–7.88 (2H, m); IR (KBr) 3279, 1638, 1534, 1514, 1325, 1229, 1163, 1123, 1069, 833 cm$^{-1}$; Anal. Calcd for C$_{27}$H$_{21}$F$_4$NO$_2$: C, 69.37; H, 4.53; N, 3.00. Found: C, 69.28; H, 4.50; N, 2.98.

Example 227

Optical Resolution of 4-fluoro-N-[(1RS,2SR)-2-(4-fluorophenyl)-2-hydroxy-1-[4-(trifluoromethyl)benzyl]ethyl]naphthalene-1-carboxamide The racemate was optically resolved by high performance liquid chromatography using an optically active column (CHIRALCELL OD, 50 mmID×500 mmL) (mobile layer:hexane/ethanol=95/5), and each optical isomer was obtained by recrystallization from ethanol-diisopropyl ether.

(1R,2S) form mp 251–252° C.; [α]$_D^{20}$ +33.4° (c=0.499, MeOH); $^1$H-NMR (CDCl$_3$-DMSO-d$_6$, 200 MHz) δ 2.92 (1H, dd, J=11.0 Hz, 13.8 Hz), 3.19 (1H, dd, J=3.3 Hz, 14.3 Hz), 4.62–4.76 (1H, m), 4.89 (1H, t, J=5.2 Hz), 5.49 (1H, d, J=4.4 Hz), 7.01–7.18 (4H, m), 7.32–7.42 (4H, m), 7.48–7.60 (5H, m), 7.91 (1H, d, J=9.6 Hz), 8.03 (1H, d, J=8.6 Hz); IR (KBr) 3275, 1642, 1626, 1539, 1514, 1327, 1229, 1167, 1125, 1069, 835 cm$^{-1}$; Anal. Calcd for C$_{27}$H$_{20}$F$_5$NO$_2$: C, 66.80; H, 4.15; N, 2.89. Found: C, 66.55; H, 4.16; N, 2.76.

(1S,2R) form mp 252–253° C.; [α]$_D^{20}$ -33.9° (c=0.504, MeOH); $^1$H-NMR (CDCl$_3$-DMSO-d$_6$, 200 MHz) δ 2.93 (1H, dd, J=11.0 Hz, 14.0 Hz), 3.15 (1H, dd, J=3.2 Hz, 14.0 Hz), 4.66–4.79 (1H, m), 4.93 (1H, t, J=4.8 Hz), 5.42 (1H, d, J=3.6 Hz), 7.01–7.21 (4H, m), 7.34–7.60 (9H, m), 7.78 (1H, d, J=9.6 Hz), 8.04 (1H, d, J=8.2 Hz); IR (KBr) 3275, 1642, 1626, 1539, 1514, 1327, 1227, 1167, 1125, 1069, 835 cm$^{-1}$; Anal. Calcd for C$_{27}$H$_{20}$F$_5$NO$_2$: C, 66.80; H, 4.15; N, 2.89. Found: C, 66.69; H, 4.09; N, 2.82.

Example 228

Optical Resolution of 4-fluoro-N-[(1RS,2SR)-2-(4-fluorophenyl)-2-hydroxy-1-[3-(1,1,2,2-tetrafluoroethoxy)benzyl]ethyl]naphthalene-1-carboxamide The racemate was optically resolved by high performance liquid chromatography using an optically active column (CHIRALCELL OD, 50 mmID×500 mmL) (mobile layer: hexane/ethanol=95/5), and each optical isomer was obtained by recrystallization from ethyl acetate-diisopropyl ether-hexane.

(1R,2S) form mp 213–214° C.; [α]$_D^{20}$ +20.6° (c=0.506, MeOH); $^1$H-NMR (CDCl$_3$-DMSO-d$_6$, 200 MHz) δ 2.82–3.03 (2H, m), 4.70–4.84 (2H, m), 5.07 (1H, t, J=3.3 Hz), 5.90 (1H, tt, J=2.8 Hz, 53.0 Hz), 6.92 (1H, d, J=9.4 Hz), 6.98–7.33 (8H, m), 7.42–7.57 (4H, m), 7.79 (1H, d, J=8.4 Hz), 8.07 (1H, d, J=7.4 Hz); IR (KBr) 3270, 1642, 1624, 1601, 1537, 1512, 1235, 1198, 1127, 835, 760 cm$^{-1}$; Anal. Calcd for C$_{28}$H$_{21}$F$_6$NO$_3$: C, 63.04; H, 3.97; N, 2.63. Found: C, 62.87; H, 3.84; N, 2.64.

(1S,2R) form mp 213–214° C.; [α]$_D^{20}$ -20.6° (c=0.520, MeOH); $^1$H-NMR (CDCl$_3$-DMSO-d$_6$, 200 MHz) δ 2.82–3.03 (2H, m), 4.70–4.85 (2H, m), 5.07 (1H, t, J=3.7 Hz), 5.90 (1H, tt, J=2.9 Hz, 53.0 Hz), 6.92 (1H, d, J=8.8 Hz), 6.98–7.33 (8H, m), 7.40–7.58 (4H, m), 7.80 (1H, d, J=8.0 Hz), 8.07 (1H, d, J=7.8 Hz); IR (KBr) 3272, 1642, 1624, 1601, 1537, 1512, 1235, 1198, 1127, 835, 760 cm$^{-1}$; Anal. Calcd for C$_{28}$H$_{21}$F$_6$NO$_3$: C, 63.04; H, 3.97; N, 2.63. Found: C, 62.97; H, 3.87; N, 2.57.

Example 229

Optical Resolution of N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide The racemate was optically resolved by high performance liquid chromatography using an optically active column (CHIRALCELL OD, 50 mmID×500 mmL) (mobile layer: hexane/ethanol=95/5), and each optical isomer was obtained by recrystallization from ethyl acetate-diisopropyl ether-hexane.

(1R,2S) form mp 199–200° C.; [α]$_D^{20}$ +20.3° (c=0.536, MeOH); $^1$H-NMR (CDCl$_3$, 200 MHz) δ 1.93–2.06 (2H, m), 2.15–2.24 (2H, m), 2.67 (2H, t, J=5.7 Hz), 2.79 (1H, dd, J=10.8 Hz, 14.4 Hz), 3.00 (1H, dd, J=3.7 Hz, 14.5 Hz), 3.59 (1H, d, J=3.6 Hz), 4.60–4.74 (1H, m), 5.04 (1H, t, J=3.7 Hz), 5.72 (1H, d, J=8.8 Hz), 5.89 (1H, tt, J=2.8 Hz, 53.0 Hz), 5.91 (1H, td, J=5.3 Hz, 11.6 Hz), 6.21 (1H, d, J=11.6 Hz), 6.95–7.17 (8H, m), 7.31 (1H, t, J=8.0 Hz), 7.44 (2H, dd, J=5.3 Hz, 8.7 Hz); IR (KBr) 3264, 1640, 1512, 1227, 1198, 1128 cm$^{-1}$; Anal. Calcd for $C_{29}H_{26}F_5NO_3$: C, 65.53; H, 4.93; N, 2.64. Found: C, 65.52; H, 4.85; N, 2.63.

(1S,2R) form mp 200–201° C.; $[\alpha]_D^{20}$ –20.8° (c=0.544, MeOH); $^1$H-NMR (CDCl$_3$, 200 MHz) δ 1.93–2.06 (2H, m), 2.15–2.24 (2H, m), 2.67 (2H, t, J=5.8 Hz), 2.79 (1H, dd, J=10.6 Hz, 14.6 Hz), 3.00 (1H, dd, J=4.3 Hz, 14.7 Hz), 3.59 (1H, d, J=3.8 Hz), 4.60–4.74 (1H, m), 5.04 (1H, t, J=3.7 Hz), 5.72 (1H, d, J=8.8 Hz), 5.89 (1H, tt, J=3.0 Hz, 53.1 Hz), 5.91 (1H, td, J=5.3 Hz, 12.0 Hz), 6.21 (1H, d, J=12.0 Hz), 6.95–7.17 (8H, m), 7.31 (1H, t, J=7.6 Hz), 7.44 (2H, dd, J=5.4 Hz, 8.6 Hz); IR (KBr) 3264, 1637, 1512, 1227, 1198, 1130 cm$^{-1}$; Anal. Calcd for $C_{29}H_{26}F_5NO_3$: C, 65.53; H, 4.93; N, 2.64. Found: C, 65.56; H, 4.87; N, 2.64.

Example 230

N-((1RS,2SR)-2-(4-fluorophenyl)-2-hydroxy-1-((5-methyl-3-(1,1,2,2-tetrafluoroethoxy)phenyl)methyl) ethyl)-4-fluoro-1-naphthalenecarboxamide 1) To a solution of 3,5-dimethyl1-(1,1,2,2-tetrafluoropropyloxy)benzene (8.22 g, 32.8 mmol) in carbon tetrachloride (100 ml) were added N-bromosuccinimide (6.42 g, 36.1 mmol) and 2,2'-azobis(isobutyronitrile) (270 mg, 1.64 mmol), and the mixture was heated under reflux overnight. Insoluble material was filtered off with celite, and the filtrate was concentrated to give a bromo form. To a solution of ethyl 3-(4-fluorophenyl)-3-oxopropionate (6.20 g, 29.5 mmol) in 1,2-dimethoxyethane (60 ml) was added sodium hydride (60% in oil, 1.18 g, 29.5 mmol) under ice-cooling, and the mixture was stirred at room temperature for 30 min. To the reaction solution was dropwise added a solution of the bromo form synthesized earlier in 1,2-dimethoxyethane (20 ml), and the mixture was stirred at room temperature for 1 hr. The reaction solution was poured into water (200 ml), and the mixture was extracted with ethyl acetate (200 ml×2). The extract was washed with water and saturated brine, dried over anhydrous magnesium sulfate and evaporated under reduced pressure. The residue was purified by silica gel column chromatography (toluene:hexane=1:1-ethyl acetate). Recrystallization from ethyl acetate-hexane gave ethyl 3-(4-fluorophenyl)-2-((3-methyl-5-(1,1,2,2-tetrafluoroethoxy)phenyl)methyl)-3-oxopropionate (6.68 g, 53%).

mp 56–57° C. IR ν max$^{KBr}$cm$^{-1}$: 1738, 1688, 1599, 1508. Anal. Calcd for $C_{21}H_{19}F_5O_4$: C, 58.12; H, 4.50 Found: C, 57.94; H, 4.27. $^1$H-NMR (CDCl$_3$)δ: 1.13 (3H, t, J=7.0 Hz), 2.30 (3H, s), 3.28 (2H, d, J=7.4 Hz), 4.12 (2H, q, J=7.0 Hz), 4.54 (1H, t, J=7.4 Hz), 5.87 (1H, tt, J=53.0, 3.0 Hz), 6.87 (2H, s), 6.94 (1H, s), 7.12 (2H, t, J=8.4 Hz), 7.92–8.06 (2H, m).

2) To a solution of zinc chloride (4.12 g, 30.2 mmol) in diethyl ether (100 ml) was added sodium borohydride (2.29 g, 60.4 mmol), and the mixture was stirred at room temperature for 30 min. Insoluble material was filtered off, and a solution of ethyl 3-(4-fluorophenyl)-2-((5-methyl-3-(1,1,2,2-tetrafluoroethoxy)phenyl)methyl)-3-oxopropionate (6.50 g, 15.1 mmol) in diethyl ether (50 ml) was added to the filtrate. The mixture was stirred at room temperature for 30 min. and 1N hydrochloric acid was added to the reaction solution under ice-cooling to quench the reaction. Then, water (200 ml) was added and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl(2RS,3RS)-3-(4-fluorophenyl)-3-hydroxy-2-((5-methyl-3-(1,1,2 2-tetrafluoroethoxy)phenyl)methyl)propionate (6.56 g, 100%) as a colorless oil.

IR ν max$^{KBr}$cm$^{-1}$: 1715, 1605, 1512. Anal. Calcd for $C_{21}H_{21}F_5O_4 \cdot 0.3H_2O$: C, 57.62; H, 4.97 Found: C, 57.54; H, 4.85. $^1$H-NMR (CDCl$_3$)δ: 0.94 (3H, t, J=7.0 Hz), 2.29 (3H, s), 2.92–3.02 (4H, m), 3.89 (2H, q, J=7.0 Hz), 5.00 (1H, s), 5.86 (1H, tt, J=53.0, 3.0 Hz), 6.72–6.86 (3H, m), 7.00–7.10 (2H, m), 7.30–7.42 (2H, m).

3) To a solution of ethyl(2RS,3RS)-3-(4-fluorophenyl)-3-hydroxy-2-((5-methyl-3-(1,1,2,2-trifluoroethoxy)phenyl) methyl)propionate (6.30 g, 14.6 mmol) in methanol (50 ml) was added 2N aqueous sodium hydroxide solution (14.6 ml, 29.2 mmol), and the mixture was stirred overnight at room temperature. The reaction solution was acidified with 1N hydrochloric acid, and the mixture was extracted with ethyl acetate (100 ml×2). The extract was washed with water and saturated brine, dried over anhydrous magnesium sulfate and evaporated under reduced pressure. The residue was recrystallized from diethyl ether-hexane to give (2RS,3RS)-3-(4-fluorophenyl)-3-hydroxy-2-((5-methyl-3-(1,1,2,2-trifluoroethoxy)phenyl)methyl)propionic acid (6.0 g, 100%).

mp 82–83° C. IR ν max$^{KBr}$cm$^{-1}$: 1713, 1607, 1512. Anal. Calcd for $C_{19}H_{17}F_5O_4$: C, 56.19; H, 4.26 Found: C, 56.05; H, 4.13. $^1$H-NMR (CDCl$_3$)δ: 2.27 (3H, s), 2.80–3.08 (3H, m), 5.06 (1H, d, J=4.0 Hz), 5.86 (1H, tt, J=53.0, 2.8 Hz), 6.76 (2H, d, J=6.6 Hz), 6.84 (1H, s), 6.98–7.12 (2H, m), 7.30–7.42 (2H, m).

4) To a solution of (2RS,3RS)-3-(4-fluorophenyl)-3-hydroxy-2-((5-methyl-3-(1,1,2,2-tetrafluoroethoxy)phenyl) methyl)propionic acid (5.8 g, 14.3 mmol) in tetrahydrofuran (100 ml) were added diphenylphosphoryl azide (3.4 ml, 15.8 mmol) and triethylamine (3.0 ml, 21.5 mmol), and the mixture was heated under reflux for 30 min. The reaction solution was allowed to cool and water (200 ml) was added. The mixture was extracted with ethyl acetate (200 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (hexane:ethyl acetate=1:1) and recrystallized from ethyl acetate-hexane to give (4RS,5SR)-5-(4-fluorophenyl)-4-((5-methyl-3-(1,1,2, 2-tetrafluoroethoxy)phenyl)methyl)-1,3-oxazolidin-2-one (4.1 g, 71%).

mp 107–108° C. IR ν max$^{KBr}$cm$^{-1}$: 1761, 1611, 1597, 1514. Anal. Calcd for $C_{19}H_{16}F_5NO_3$: C, 56.86; H, 4.02; N, 3.49. Found: C, 56.64; H, 4.01; N, 3.58. $^1$H-NMR (CDCl$_3$)δ: 1.16–2.40 (2H, m), 2.32 (3H, s), 4.18–4.32 (1H, m), 5.12 (1H, brs), 5.79 (1H, d, J=7.8 Hz), 5.89 (1H, tt, J=53.0, 3.0 Hz), 6.70 (2H, d, J=8.0 Hz), 6.91. (1H, s), 7.04–7.20 (2H, m), 7.30–7.42 (2H, m).

5) To a solution of (4RS,5SR)-5-(4-fluorophenyl)-4-((5-methyl-3-(1,1,2,2-tetrafluoroethoxy)phenyl)methyl)-1,3-oxazolidin-2-one (3.0 g, 7.48 mmol) in ethanol (30 ml) was added 8N aqueous sodium hydroxide solution (4.7 ml, 37.4 mmol), and the mixture was heated under reflux for 3 hrs. The reaction solution was concentrated, diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give (1RS,2SR)-2-amino-1-(4-fluorophenyl)-3-(5-methyl-3-(1,1,2,2-tetrafluoroethoxy)phenyl)-1-propanol (2.34 g, 83%).

mp 96–98° C. IR ν max$^{KBr}$cm$^{-1}$: 1617, 1595, 1508, 1458. Anal. Calcd for $C_{18}H_{18}F_5NO_2$: C, 57.60; H, 4.83; N, 3.73. Found: C, 57.59; H, 4.79; N, 3.73. $^1$H-NMR (CDCl$_3$)δ: 2.20–2.50 (1H, m), 2.32 (3H, s), 2.76 (1H, dd, J=13.4, 3.2 Hz), 3.20–3.32 (1H, m), 4.65 (1H, d, J=4.8 Hz), 5.88 (1H, tt, J=53.0, 3.0 Hz), 6.80 (1H, s), 6.82–6.90 (2H, m), 7.00–7.12 (2H, m), 7.30–7.42 (2H, m).

6) To a solution of (1RS,2SR)-2-amino-1-(4-fluorophenyl)-3-(5-methyl-3-(1,1,2,2-tetrafluoroethoxy)phenyl)-1-propanol (197 mg, 0.53 mmol) in acetonitrile (20 ml) were added 4-fluoronaphthalenecarboxylic acid (100 mg, 0.53 mmol), 1-ethyl-3-(3-dimethylaminopropyl)carbodiimide hydrochloride (151 mg, 0.79 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (234 mg, 81%).

mp 189–190° C. IR ν max$^{KBr}$cm$^{-1}$: 1642, 1626, 1601, 1512. Anal. Calcd for $C_{29}H_{23}F_6NO_3$·0.1H$_2$O: C, 63.41; H, 4.25; N, 2.55. Found: C, 63.22; H, 4.24; N, 2.77. $^1$H-NMR (CDCl$_3$)δ: 2.29 (3H, s), 2.77 (1H, dd, J=14.0, 11.0 Hz), 3.00 (1H, dd, J=14.0, 4.0 Hz), 4.62–4.82 (1H, m), 5.07 (1H, d, J=3.6 Hz), 5.87 (1H, tt, J=53.0, 3.0 Hz), 5.95 (1H, d, J=8.8 Hz), 6.80–7.20 (7H, m), 7.38–7.60 (4H, m), 7.80 (1H, d, J=8.0 Hz), 8.08 (1H, d, J=7.6 Hz).

Example 231

N-((1RS,2SR)-2-(4-fluorophenyl)-2-hydroxy-1-((5-methyl-3-(1,1,2,2-tetrafluoroethoxy)phenyl)methyl)ethyl)-6,7-dihydro-5H-benzo[a]cycloheptene-1-carboxamide To a solution of (1RS,2SR)-2-amino-1-(2-fluorophenyl)-3-(5-methyl-3-(1,1,2,2-tetrafluoroethoxy)phenyl)-1-propanol (200 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl)carbodiimide hydrochloride (153 mg, 0.80 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (228 mg, 78%).

mp 175–176° C. IR ν max$^{KBr}$cm$^{-1}$: 1636, 1510, 1449. $^1$H-NMR (CDCl$_3$)δ: 1.90–2.10 (2H, m), 2.10–2.28 (2H, m), 2.31 (3H, s), 2.60–2.82 (3H, m), 3.87 (1H, brs), 4.56–4.72 (1H, m), 5.01 (1H, d, J=3.8 Hz), 5.76 (1H, d, J=8.4 Hz), 5.87 (1H, tt, J=53.0, 3.0 Hz), 5.90–6.00 (1H, m), 6.22 (1H, d, J=11.6 Hz), 6.82 (1H, s), 6.84–7.20 (7H, m), 7.36–7.50 (2H, m).

Example 232

N-((1RS,2SR)-2-(4-fluorophenyl)-2-hydroxy-1-((4-chloro-3-(1,1,2,2-tetrafluoroethoxy)phenyl)methyl)ethyl)-4-fluoro-1-naphthalenecarboxamide 1) To a solution of 4-chloro-3-(1,1,2,2-tetrafluoropropyloxy)toluene (7.63 g, 28.3 mmol, 90% purity) in carbon tetrachloride (100 ml) were added N-bromosuccinimide (5.54 g, 31.1 mmol) and 2,2'-azobis(isobutyronitrile) (255 mg, 1.56 mmol), and the mixture was heated under reflux overnight. Insoluble material was filtered off with celite, and the filtrate was concentrated to give a bromo form. To a solution of ethyl 3-(4-fluorophenyl)-3-oxopropionate (5.35 g, 25.5 mmol) in 1,2-dimethoxyethane (50 ml) was added sodium hydride (60% in oil, 1.02 g, 25.5 mmol) under ice-cooling, and the mixture was stirred at room temperature for 30 min. To the reaction solution was dropwise added a solution of the bromo form synthesized earlier in 1,2-dimethoxyethane (20 ml), and the mixture was stirred at room temperature for 1 hr. The reaction solution was poured into water (200 ml), and extracted with ethyl acetate (200 ml×2). The extract was washed with water and saturated brine, dried over anhydrous magnesium sulfate and evaporated under reduced pressure. The residue was purified by silica gel column chromatography (toluene:hexane=1:1-ethyl acetate). Recrystallization from ethyl acetate-hexane gave ethyl 2-((4-chloro-3-(1,1,2,2-tetrafluoroethoxy)phenyl)methyl)-3-(4-fluorophenyl)-3-oxopropionate (6.71 g, 56%).

mp 73–74° C. IR ν max$^{KBr}$cm$^{-1}$: 1738, 1688, 1599. Anal. Calcd for $C_{20}H_{16}ClF_5O_4$: C, 53.29; H, 3.58 Found: C, 53.38; H, 3.35. $^1$H-NMR (CDCl$_3$)δ: 1.13 (3H, t, J=7.0 Hz), 3.32 (2H, d, J=7.2 Hz), 4.11 (2H, q, J=7.0 Hz), 4.54 (1H, t, J=7.2 Hz), 5.97 (1H, tt, J=53.2, 3.0 Hz), 7.06–7.40 (5H, m), 7.92–8.08 (2H, m).

2) To a solution of zinc chloride (4.0 g, 29.3 mmol) in diethyl ether (100 ml) was added sodium borohydride (2.22 g, 58.6 mmol), and the mixture was stirred at room temperature for 30 min. Insoluble material was filtered off, and a solution of ethyl 2-((4-chloro-3-(1,1,2,2-tetrafluoroethoxy)phenyl)methyl)-3-(4-fluorophenyl)-3-oxopropionate (6.60 g, 14.6 mmol) in diethyl ether (50 ml) was added to the filtrate. The mixture was stirred at room temperature for 30 min. and 1N hydrochloric acid was added to the reaction solution under ice-cooling to quench the reaction. Then, water (200 ml) was added and the mixture was extracted with ethyl acetate (300 ml×2). The extract was washed with water and saturated brine, dried over anhydrous magnesium sulfate and evaporated under reduced pressure. The residue was purified by silica gel column chromatography (hexane:ethyl acetate=4:1) to give ethyl(2RS,3RS)-2-((4-chloro-3-(1,1,2,2-tetrafluoroethoxy)phenyl)methyl)-3-(4-fluorophenyl)-3-hydroxypropionate (5.85 g, 88%) as a colorless oil.

IR ν max$^{KBr}$cm$^{-1}$: 1717, 1605, 1510, 1487. Anal. Calcd for $C_{20}H_{18}ClF_5O_4$: C, 53.05; H, 4.01 Found: C, 53.17; H, 4.13. $^1$H-NMR (CDCl$_3$)δ: 0.95 (3H, t, J=7.0 Hz), 2.84–3.04 (4H, m), 3.89 (2H, q, J=7.0 Hz), 4.98–5.06 (1H, m), 5.96 (1H, tt, J=53.0, 3.4 Hz), 6.92–7.10 (4H, m), 7.30–7.44 (3H, m).

3) To a solution of ethyl(2RS,3RS)-2-((4-chloro-3-(1,1,2,2-trifluoroethoxy)phenyl)methyl)-3-(4-fluorophenyl)-3-hydroxypropionate (5.60 g, 12.37 mmol) in methanol (50 ml) was added 2N aqueous sodium hydroxide solution (12.3 ml, 24.6 mmol), and the mixture was stirred overnight at room temperature. After the reaction solution was acidified with 1N hydrochloric acid, the mixture was extracted with ethyl acetate (100 ml×2). The extract was washed with water and saturated brine, dried over anhydrous magnesium sulfate and evaporated under reduced pressure. The residue was recrystallized from diethyl ether-hexane to give (2RS,3RS)-2-((4-chloro-3-(1,1,2,2-trifluoroethoxy)phenyl)methyl)-3-(4-fluorophenyl)-3-hydroxypropionic acid (4.12 g, 78%).

mp 121–122° C. IR ν max$^{KBr}$cm$^{-1}$: 1713, 1607, 1512, 1489. Anal. Calcd for $C_{18}H_{14}ClF_5O_4$: C, 50.90; H, 3.32 Found: C, 50.92; H, 3.07. $^1$H-NMR (CDCl$_3$)δ: 2.90–3.06 (3H, m), 5.07 (1H, s), 5.96 (1H, tt, J=53.0, 3.2 Hz), 6.94 (1H, dd, J=8.2, 2.0 Hz), 7.00–7.12 (3H, m), 7.24–7.40 (3H, m).

4) To a solution of (2RS,3RS)-2-((4-chloro-3-(1,1,2,2-tetrafluoroethoxy)phenyl)methyl)-3-(4-fluorophenyl)-3-hydroxypropionic acid (2.0 g, 4.71 mmol) in tetrahydrofuran (40 ml) were added diphenylphosphoryl azide (1.12 ml, 5.18 mmol) and triethylamine (0.99 ml, 7.07 mmol), and the mixture was heated under reflux for 3 hrs. The reaction solution was allowed to cool and water (200 ml) was added. The mixture was extracted with ethyl acetate (200 ml×2). The extract was washed successively with 1N hydrochloric acid, saturated aqueous sodium hydrogen carbonate solution and saturated brine, dried over anhydrous magnesium sulfate and evaporated under reduced pressure. The residue was purified by silica gel column chromatography (hexane:ethyl acetate=1:1) to give (4RS,5SR)-4-((4-chloro-3-(1,1,2,2-tetrafluoroethoxy)phenyl)methyl)-5-(4-fluorophenyl)-1,3-oxazolidin-2-one (1.72 g, 87%) as a colorless oil. IR ν max$^{KBr}$cm$^{-1}$: 1759, 1514, 1489. Anal. Calcd for $C_{18}H_{13}ClF_5NO_3$: C, 51.26; H, 3.11; N, 3.32. Found: C, 51.16; H, 3.13; N, 3.24. $^1$H-NMR (CDCl$_3$)δ: 2.30 (2H, d, J=6.8 Hz), 4.25 (1H, q, J=6.8 Hz), 5.30 (1H, brs), 5.80 (1H, d, J=8.0 Hz), 5.98 (1H, tt, J=53.0, 3.0 Hz), 6.89 (1H, dd, J=8.0, 2.0 Hz), 6.99 (1H, s), 7.06–7.20 (2H, m), 7.30–7.42 (3H, m).

5) To a solution of (4RS,5SR)-4-((4-chloro-3-(1,1,2,2-tetrafluoroethoxy)phenyl)methyl)-5-(4-fluorophenyl)-1,3-oxazolidin-2-one (1.42 g, 3.37 mmol) in ethanol (20 ml) was added 8N aqueous sodium hydroxide solution (2.1 ml, 16.9 mmol), and the mixture was heated under reflux for 3 hrs. The reaction solution was concentrated, diluted with water (100 ml) and extracted with ethyl acetate (100 ml×2). The extract was washed with saturated brine, dried over anhydrous magnesium sulfate and evaporated under reduced pressure. The residue was recrystallized from ethyl acetate-hexane to give (1RS,2SR)-2-amino-3-(4-chloro-3-(1,1,2,2-tetrafluoroethoxy)phenyl)-1-(4-fluorophenyl)-1-propanol (1.17 g, 88%).

mp 109–110° C. IR ν max$^{KBr}$cm$^{-1}$: 1605, 1508, 1489. Anal. Calcd for $C_{17}H_{15}ClF_5NO_2$: C, 51.59; H, 3.82; N, 3.54. Found: C, 51.62; H, 3.78; N, 3.55. $^1$H-NMR (CDCl$_3$)δ: 2.39 (1H, dd, J=14.0, 10.0 Hz), 2.81 (1H, dd, J=14.0, 3.4 Hz), 3.18–3.32 (1H, m), 4.63 (1H, d, J=5.2 Hz), 5.98 (1H, tt, J=53.0, 3.0 Hz), 7.00–7.20 (4H, m), 7.30–7.44 (3H, m).

6) To a solution of (1RS,2SR)-2-amino-3-(4-chloro-3-(1,1,2,2-tetrafluoroethoxy)phenyl)-1-(4-fluorophenyl)-1-propanol (208 mg, 0.53 mmol) in acetonitrile (20 ml) were added 4-fluoronaphthalenecarboxylic acid (100 mg, 0.53 mmol), 1-ethyl-3-(3-dimethylaminopropyl)carbodiimide hydrochloride (151 mg, 0.79 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (273 mg, 91%).

mp 206–207° C. IR ν max$^{KBr}$cm$^{-1}$: 1642, 1626, 1601, 1512. $^1$H-NMR (CDCl$_3$)δ: 2.84 (1H, dd, J=14.2, 10.6 Hz), 3.02 (1H, dd, J=14.2, 4.2 Hz), 4.68–4.84 (1H, m), 5.07 (1H, d, J=4.0 Hz), 5.95 (1H, tt, J=53.0, 3.0 Hz), 5.99 (1H, d, J=9.0 Hz), 6.92–7.30 (6H, m), 7.30–7.60 (5H, m), 7.73 (1H, d, J=8.2 Hz), 8.08 (1H, d, J=8.2 Hz)

Example 233

N-((1RS,2SR)-1-((4-chloro-3-(1,1,2,2-tetrafluoroethoxy)phenyl)methyl)ethyl)-2-(4-fluorophenyl)-2-hydroxy-6,7-dihydro-5H-benzo[a]cycloheptene-1-carboxamide To a solution of (1RS,2SR)-2-amino-3-(4-chloro-3-(1,1,2,2-tetrafluoroethoxy)phenyl)-1-(2-fluorophenyl)-1-propanol (210 mg, 0.53 mmol) in acetonitrile (20 ml) were added 6,7-dihydro-5H-benzo[a]cycloheptene-1-carboxylic acid (100 mg, 0.53 mmol), 1-ethyl-3-(3-dimethylaminopropyl)carbodiimide hydrochloride (153 mg, 0.80 mmol) and 1-hydroxy-1H-benzotriazole (81 mg, 0.53 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (213 mg, 71%).

mp 174–175° C. IR ν max$^{KBr}$cm$^{-1}$: 1640, 1508, 1489. $^1$H-NMR (CDCl$_3$)δ: 1.90–2.10 (2H, m), 2.12–2.26 (2H, m), 2.60–2.72 (2H, m), 2.78 (1H, dd, J=14.6, 10.4 Hz), 2.96 (1H, dd, J=14.6, 4.4 Hz), 3.40 (1H, brs), 4.58–4.72 (1H, m), 5.01 (1H, d, J=4.0 Hz), 5.80 (1H, d, J=8.8 Hz), 5.82–5.98 (1H, m), 5.95 (1H, tt, J=53.0, 3.0 Hz), 6.16 (1H, d, J=11.6 Hz), 6.92–7.20 (7H, m), 7.32–7.50 (3H, m).

Example 234

N-((1RS,2SR)-2-(4-fluorophenyl)-2-hydroxy-1-((4-methyl-3-((1,1,2,2-tetrafluoroethyl)oxy)phenyl)methyl)ethyl)-6,7-dihydro-5H-benzo[a]cycloheptene-1-carboxamide 1) To a solution of lithium aluminum hydride (1.02 g, 26.8 mmol) in tetrahydrofuran (100 ml) was added a solution of ethyl 4-methyl-3-((1,1,2,2-tetrafluoroethyl)oxy)benzoate (5.0 g, 17.8 mmol) in tetrahydrofuran (20 ml) under ice-cooling. After the reaction solution was stirred at room temperature for 30 min., 1N aqueous sodium hydroxide solution (20 ml) was added, and the mixture was filtered with celite. The filtrate was concentrated and water was added. The mixture was extracted with ethyl acetate (50 ml×2). The extract was washed with saturated brine, dried over anhydrous magnesium sulfate and evaporated under reduced pressure to give (4-methyl-3-((1,1,2,2-tetrafluoroethyl)oxy)phenyl)methanol (4.45 g, 100%) as a colorless oil.

$^1$H-NMR (CDCl$_3$)δ: 2.27 (3H, s), 4.67 (2H, s), 5.94 (1H, tt, J=53.0, 2.6,Hz), 7.14–7.28 (3H, m). IR ν max$^{KBr}$cm$^{-1}$: 1584, 1508, 1456, 1418. Anal. Calcd for $C_{10}H_{10}F_4O_2$: C, 50.43; H, 4.23 Found: C, 50.44; H, 4.18.

2) To a solution of (4-methyl-3-((1,1,2,2-tetrafluoroethyl)oxy)phenyl)methanol (4.26 g, 17.9 mmol) in ethyl acetate (60 ml) were added methanesulfonyl chloride (2.25 g, 19.7 mmol) and triethylamine (3.0 ml, 21.5 mmol) at 0° C., and the mixture was stirred for 30 min. Insoluble material was filtered off, and the filtrate was concentrated to give a mesyl form. To a solution of ethyl 3-(4-fluorophenyl)-3-oxopropionate (3.76 g, 17.9 mmol) in 1,2-dimethoxyethane (40 ml) was added sodium hydride (60% in oil, 0.72 g, 17.9 mmol) under ice-cooling, and the mixture was stirred at room temperature for 30 min. To the reaction solution was dropwise added a solution of the mesyl form synthesized earlier in 1,2-dimethoxyethane (20 ml), and the mixture was stirred overnight at room temperature. The reaction solution was poured into water (200 ml), and extracted with ethyl acetate (200 ml×2). The extract was washed with water and saturated brine, dried over anhydrous magnesium sulfate and evaporated under reduced pressure. The residue was purified by silica gel column chromatography (toluene) and recrystallized from hexane to give ethyl 3-(4-fluorophenyl)-2-((4-methyl-3-((1,1,2,2-tetrafluoroethyl)oxy)phenyl)methyl)-3-oxopropionate (4.91 g, 64%).

$^1$H-NMR (CDCl$_3$)δ: 1.13 (3H, t, J=7.0 Hz), 2.21 (3H, s), 3.30 (2H, d, J=7.4 Hz), 4.10 (2H, q, J=7.0 Hz), 4.54 (1H, t, J=7.4 Hz), 5.92 (1H, tt, J=53.0, 2.8 Hz), 7.00–7.20 (5H, m), 7.94–8.04 (2H, m). IR ν max$^{KBr}$cm$^{-1}$: 1736, 1688, 1599, 1508, 1447, 1412. mp 52–53° C. Anal. Calcd for C$_{21}$H$_{19}$F$_5$O$_4$: C, 58.61; H, 4.45 Found: C, 58.61; H, 4.55.

3) To a solution of zinc chloride (3.04 g, 22.3 mmol) in diethyl ether (70 ml) was added sodium borohydride (1.69 g, 44.6 mmol), and the mixture was stirred at room temperature for 30 min. Insoluble material was filtered off and a solution of ethyl 3-(4-fluorophenyl)-2-((4-methyl-3-((1,1,2,2-tetrafluoroethyl)oxy)phenyl)methyl)-3-oxopropionate (4.8 g, 11.2 mmol) in diethyl ether (50 ml) was added to the filtrate. The mixture was stirred at room temperature for 30 min. and 1N hydrochloric acid was added to the reaction solution under ice-cooling to quench the reaction. Then, water (100 ml) was added and the mixture was extracted with ethyl acetate (200 ml×2). The extract was washed with water and saturated brine, dried over anhydrous magnesium sulfate and evaporated under reduced pressure. The residue was purified by silica gel column chromatography (hexane:ethyl acetate=4:1) to give ethyl (2RS,3RS)-3-(4-fluorophenyl)-3-hydroxy-2-((4-methyl-3-((1,1,2,2-tetrafluoroethyl)oxy)phenyl)methyl)propionate (4.69 g, 97%) as a colorless oil.

$^1$H-NMR (CDCl$_3$)δ: 0.94 (3H, t, J=7.4 Hz), 2.21 (3H, s), 2.80–3.10 (3H, m), 3.89 (2H, q, J=7.4 Hz), 4.96–5.02 (1H, m), 5.92 (1H, tt, J=52.2, 2.6 Hz), 6.86–7.12 (5H, m), 7.30–7.42 (2H, m). IR ν max$^{KBr}$cm$^{-1}$: 1717, 1605, 1580, 1510, 1447. Anal. Calcd for C$_{21}$H$_{21}$F$_5$O$_4$: C, 58.33; H, 4.90 Found: C, 58.29; H, 4.88.

4) To a solution of ethyl(2RS,3RS)-3-(4-fluorophenyl)-3-hydroxy-2-((4-methyl-3-((1,1,2,2-tetrafluoroethyl)oxy)phenyl)methyl)propionate (4.5 g, 10.4 mmol) in methanol (20 ml) was added 2N aqueous sodium hydroxide solution (10.4 ml, 20.8 mmol), and the mixture was stirred overnight at room temperature. The reaction solution was acidified with 1N hydrochloric acid and extracted with ethyl acetate (200 ml×2). The extract was washed with water and saturated brine, dried over anhydrous magnesium sulfate and evaporated under reduced pressure. The residue was recrystallized from diethyl ether-hexane to give (2RS,3RS)-3-(4-fluorophenyl)-3-hydroxy-2-((4-methyl-3-((1,1,2,2-tetrafluoroethyl)oxy)phenyl)methyl)propionic acid (3.56 g, 85%).

$^1$H-NMR (CDCl$_3$)δ: 2.21 (3H, s), 2.80–3.02 (3H, m), 5.04 (1H, d, J=3.8 Hz), 5.90 (1H, tt, J=53.0, 2.6 Hz), 6.84–7.12 (5H, m), 7.30–7.40 (2H, m), IR ν max$^{KBr}$cm$^{-1}$: 1713, 1607, 1510, 1449, 1422. mp 102–103° C. Anal. Calcd for C$_{19}$H$_{17}$F$_5$O$_4$: C, 56.44; H, 4.24 Found: C, 56.56; H, 4.20.

5) To a solution of (2RS,3RS)-3-(4-fluorophenyl)-3-hydroxy-2-((4-methyl-3-((1,1,2,2-tetrafluoroethyl)oxy)phenyl)methyl)propionic acid (3.3 g, 8.16 mmol) in tetrahydrofuran (60 ml) were added diphenylphosphoryl azide (1.93 ml, 8.98 mmol) and triethylamine (1.71 ml, 12.2 mmol), and the mixture was heated under reflux for 2 hrs. The reaction solution was allowed to cool and water (200 ml) was added. The mixture was extracted with ethyl acetate (100 ml×2). The extract was washed successively with 1N hydrochloric acid, saturated aqueous sodium hydrogen carbonate and saturated brine, dried over anhydrous magnesium sulfate and evaporated under reduced pressure. The residue was purified by silica gel column chromatography (ethyl acetate). Recrystallization from ethyl acetate-hexane gave (4RS,5SR)-5-(4-fluorophenyl)-4-((4-methyl-3-((1,1,2,2-tetrafluoroethyl)oxy)phenyl)methyl)-1,3-oxazolidin-2-one (2.97 g, 91%).

$^1$H-NMR (CDCl$_3$)δ: 2.23 (3H, s), 2.12–2.30 (2H, m), 4.18–4.30 (1H, m), 5.21 (1H, s), 5.78 (1H, d, J=8.0 Hz), 5.93 (1H, tt, J=53.0, 2.6 Hz), 6.80–6.90 (2H, m), 7.04–7.20 (3H, m), 7.30–7.42 (2H, m). IR ν max$^{KBr}$cm$^{-1}$: 1759, 1609, 1580, 1514, 1422. mp 112–113° C. Anal. Calcd for C$_{19}$H$_{16}$F$_5$NO$_3$: C, 56.86; H, 4.02; N, 3.49. Found: C, 56.87; H, 3.91; N, 3.59.

6) To a solution of (4RS,5SR)-5-(4-fluorophenyl)-4-((4-methyl-3-((1,1,2,2-tetrafluoroethyl)oxy)phenyl)methyl)-1,3-oxazolidin-2-one (2.7 g, 6.73 mmol) in ethanol (10 ml) was added 8N aqueous sodium hydroxide solution (4.2 ml, 33.6 mmol), and the mixture was heated under reflux for 4 hrs. The reaction solution was concentrated, diluted with water (100 ml), and the mixture was extracted with ethyl acetate (100 ml×2). The extract was washed with saturated brine, dried over anhydrous magnesium sulfate and evaporated under reduced pressure. The residue-was recrystallized from ethyl acetate-hexane to give (1RS,2SR)-2-amino-1-(4-fluorophenyl)-3-(4-methyl-3-((1,1,2,2-tetrafluoroethyl)oxy)phenyl)-1-propanol (2.25 g, 89%).

$^1$H-NMR (CDCl$_3$)δ: 2.24 (3H, s), 2.33 (1H, dd, J=14.0, 10.6 Hz), 2.77 (1H, dd, J=14.0, 3.2 Hz), 3.20–3.32 (1H, m), 4.65 (1H, d, J=4.8 Hz), 5.93 (1H, tt, J=53.0, 3.0 Hz), 6.92–7.18 (5H, m), 7.30–7.42 (2H, m). IR ν max$^{KBr}$cm$^{-1}$: 1605, 1582, 1508. mp 112–113° C. Anal. Calcd for C$_{18}$H$_{18}$F$_5$NO$_2$: C, 57.60; H, 4.83; N, 3.73. Found: C, 57.59; H, 4.75; N, 3.73.

7) To a solution of (1RS,2SR)-2-amino-1-(4-fluorophenyl)-3-(4-methyl-3-((1,1,2,2-tetrafluoroethyl)oxy)phenyl)-1-propanol (300 mg, 0.80 mmol) in acetonitrile (20 ml) were added 6,7-dihydro-5H-benzo[a]cycloheptene-1-carboxylic acid (150 mg, 0.80 mmol), 1-ethyl-3-(3-dimethylaminopropyl)carbodiimide hydrochloride (230 mg, 1.20 mmol) and 1-hydroxy-1H-benzotriazole (123 mg, 0.80 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried over anhydrous magnesium sulfate and evaporated under reduced pressure. Recrystallization of the residue from ethyl acetate-hexane gave the title compound (363 mg, 83%).

1H-NMR (CDCl$_3$)δ: 1.90–2.08 (2H, m), 2.12–2.30 (2H, m), 2.24 (3H, s), 2.60–2.80 (3H, m), 2.95 (1H, dd, J=15.0, 4.0 Hz), 4.60–4.76 (1H, m), 5.00 (1H, d, J=3.6 Hz), 5.60–6.24 (4H, m), 6.94–7.20 (8H, m), 7.38–7.48 (2H, m). IR ν max$^{KBr}$cm$^{-1}$: 1640, 1607, 1508, 1447, 1424. mp 168–169° C. Anal. Calcd for $C_{30}H_{28}F_5NO_3 \cdot 0.1H_2O$: C, 65.83; H, 5.19; N, 2.56. Found: C, 65.60; H, 4.89; N, 2.82.

Example 235

N-((1RS,2SR)-2-(3-fluorophenyl)-2-hydroxy-1-[3-(1,1,2,2-tetrafluoroethoxy)benzyl]ethyl)-6,7-dihydro-5H-benzo[a][7]annulene-1-carboxamide 1) ethyl 3-(3-fluorophenyl)-3-oxo-2-[3-(1,1,2,2-tetrafluoroethoxy)benzyl]propanoate To a solution of 3-(1,1,2,2-tetrafluoroethoxy)toluene (8.91 g, 42.8 mmol) in ethyl acetate (100 ml) were added N-bromosuccinimide (8.35 g, 46.9 mmol) and 2,2'-azobis(isobutyronitrile) (335 mg, 2.04 mmol), and the mixture was heated under reflux for 5 hrs. The reaction solution was concentrated and the crystals were filtered with hexane. The filtrate was concentrated to prepare 3-(1,1,2,2-tetrafluoroethoxy)-a-bromotoluene. To a solution of ethyl 3-(3-fluorophenyl)-3-oxopropanoate (8.57 g, 40.8 mmol) in 1,2-dimethoxyethane (80 ml) was added sodium hydride (60% in oil, 1.63 g, 40.8 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (10 ml), and the mixture was stirred overnight at room temperature. The reaction solution was poured into water (100 ml), and the mixture was extracted with ethyl acetate (100 ml×2). The extract was washed with water and saturated brine, dried (anhydrous magnesium sulfate), and evaporated under reduced pressure. The residue was purified by silica gel column chromatography (hexane:ethyl acetate=10:1–6:1) and recrystallized from ethyl acetate-hexane to give the objective substance (8.86 g, 52%).

$^1$H-NMR (CDCl$_3$)δ: 1.12 (3H, t, J=7.2 Hz), 3.33 (2H, d, J=7.5 Hz), 4.02–4.18 (2H, m), 4.54 (1H, t, J=7.2 Hz), 5.89 (1H, tt, J=53.1, 2.7 Hz), 7.02–7.10 (2H, m), 7.14 (1H, d, J=7.8 Hz), 7.26–7.32 (2H, m), 7.38–7.48 (1H, m), 7.60–7.68 (1H, m), 7.72 (1H, d, J=7.8 Hz). IR ν max$^{KBr}$cm$^{-1}$: 1738, 1694, 1613, 1590, 1487, 1445. mp 52–53° C. Anal. Calcd for $C_{20}H_{17}O_4F_5$: C, 57.70; H, 4.12 Found: C, 57.72; H, 4.13.

2) ethyl(2RS,3RS)-3-(3-fluorophenyl)-3-hydroxy-2-[3-(1,1,2,2-tetrafluoroethoxy)benzyl]propanoate To a solution of zinc chloride (5.60 g, 41.1 mmol) in diethyl ether (140 ml) was added sodium borohydride (3.11 g, 82.2 mmol), and the mixture was stirred at room temperature for 30 min. Insoluble material was filtered off. To the filtrate was added a solution of ethyl 3-(3-fluorophenyl)-3-oxo-2-[3-(1,1,2,2-tetrafluoroethoxy)benzyl]propanoate (8.56 g, 20.6 mmol) in diethyl ether (50 ml) at 0° C., and the mixture was stirred for 30 min. 1N Hydrochloric acid was added to the reaction solution to stop the reaction. Then, water (100 ml) was added and the mixture was extracted with ethyl acetate (200 ml×2). The extract was washed with water and saturated brine, dried (anhydrous magnesium sulfate), and evaporated under reduced pressure. The residue was purified by silica gel column chromatography (hexane:ethyl acetate=4:1) to give the objective substance (7.04 g, 82%) as a colorless oil.

$^1$H-NMR (CDCl$_3$)δ: 0.95 (3H, t, J=7.0 Hz), 2.86–3.06 (3H, m), 3.10 (1H, d, J=3.0 Hz), 3.92 (2H, q, J=7.0 Hz), 5.06 (1H, s), 5.88 (1H, tt, J=53.0, 3.0 Hz), 6.90–7.08. (4H, m), 7.10–7.40 (4H, m).

IR ν max$^{KBr}$cm$^{-1}$: 1724, 1715, 1614, 1591, 1489, 1451. Anal. Calcd for $C_{20}H_{19}O_4F_5$: C, 57.42; H, 4.58 Found: C, 57.36; H, 4.55.

3) (2RS,3RS)-3-(3-fluorophenyl)-3-hydroxy-2-[3-(1,1,2,2-tetrafluoroethoxy)benzyl]propanoic acid To a solution of ethyl(2RS,3RS)-3-(3-fluorophenyl)-3-hydroxy-2-[3-(1,1,2,2-tetrafluoroethoxy)benzyl]propanoate (6.92 g, 16.5 mmol) in methanol (50 ml) was added 2N aqueous sodium hydroxide solution (16.5 ml, 33.0 mmol), and the mixture was stirred at room temperature for 2 hrs. The reaction solution was acidified with 1N hydrochloric acid and extracted with ethyl acetate (200 ml×2). The extract was washed with water and saturated brine, dried (anhydrous magnesium sulfate) and evaporated under reduced pressure. Recrystallization of the residue from ethyl acetate-hexane gave the objective substance (4.28 g, 66%).

$^1$H-NMR (CDCl$_3$)δ: 2.80–3.16 (3H, m), 5.14 (1H, d, J=3.6 Hz), 5.90 (1H, tt, J=53.0, 3.0 Hz), 6.90–7.40 (8H, m). IR ν max$^{KBr}$cm$^{-1}$: 1713, 1615, 1591, 1489, 1451. mp 116–117° C. Anal. Calcd for $C_{18}H_{15}O_4F_5$: C, 55.39; H, 3.87 Found: C, 55.42; H, 3.86.

4) (4RS,5SR)-5-(3-fluorophenyl)-4-[3-(1,1,2,2-tetrafluoroethoxy)benzyl]-1,3-oxazolidin-2-one To a solution of (2RS,3RS)-3-(3-fluorophenyl)-3-hydroxy-2-[3-(1,1,2,2-tetrafluoroethoxy)benzyl]propanoic acid (4.15 g, 10.6 mmol) in tetrahydrofuran (80 ml) were added diphenylphosphoryl azide (2.52 ml, 11.7 mmol) and triethylamine (2.23 ml, 16.0 mmol), and the mixture was heated under reflux for 3 hrs. The reaction solution was allowed to cool and water (200 ml) was added. The mixture was extracted with ethyl acetate (100 ml×2). The extract was washed successively with 1N hydrochloric acid, aqueous sodium hydrogen carbonate and saturated brine, dried (anhydrous magnesium sulfate) and evaporated under reduced pressure. Recrystallization of the residue from ethyl acetate-hexane gave the objective substance (3.46 g, 84%).

$^1$H-NMR (CDCl$_3$)δ: 2.20–2.40 (2H, m), 4.20–4.30 (1H, m), 5.17 (1H, s), 5.80 (1H, d, J=7.8 Hz), 5.90 (1H, tt, J=53.1, 2.7 Hz), 6.89 (1H, s), 6.96 (1H, d, J=8.1 Hz), 7.04–7.20 (4H, m), 7.24–7.36 (1H, m), 7.36–7.46 (1H, m). IR ν max$^{KBr}$cm$^{-1}$: 1767, 1615, 1593, 1489, 1453. mp 110–111° C. Anal. Calcd for $C_{18}H_{14}NO_3F_5$: C, 55.82; H, 3.64; N, 3.62. Found: C, 55.81; H, 3.62; N, 3.58.

5) (1RS,2SR)-2-amino-1-(3-fluorophenyl)-3-[3-(1,1,2,2-tetrafluoroethoxy)phenyl]propan-1-ol To a solution of (4RS,5SR)-5-(3-fluorophenyl)-4-[3-(1,1,2,2-tetrafluoroethoxy)benzyl]-1,3-oxazolidin-2-one (3.30 g, 8.52 mmol) in ethanol (12 ml) was added 8N aqueous sodium hydroxide solution (5.3 ml, 42 mmol), and the mixture was heated under reflux for 5 hrs. The reaction solutions was concentrated, diluted with water (100 ml), and extracted with ethyl acetate (100 ml×2). The extract was washed with saturated brine, dried (anhydrous magnesium sulfate) and evaporated under reduced pressure. The residue was recrystallized from diisopropyl ether-hexane to give the objective substance (2.60 g, 84%).

$^1$H-NMR (CDCl$_3$)δ: 1.85 (2H, brs), 2.38 (1H, dd, J=13.8, 10.6 Hz), 2.77 (1H, dd, J=13.8, 3.4 Hz), 3.24–3.36 (1H, m), 4.69 (1H, d, J=4.8 Hz), 5.89 (1H, tt, J=53.0, 3.0 Hz), 6.94–7.22 (5H, m), 7.22–7.40 (3H, m). IR ν max$^{KBr}$cm$^{-1}$: 1613, 1590, 1487, 1449, 1304, 1279. mp 51–52° C. Anal. Calcd for $C_{17}H_{16}NO_2F_5$: C, 56.51; H, 4.46; N, 3.88. Found: C, 56.42; H, 4.39; N, 3.72.

6) N-{(1RS,2SR)-2-(3-fluorophenyl)-2-hydroxy-1-[3-(1,1,2,2-tetrafluoroethoxy)benzyl]ethyl}-6,7-dihydro-5H-benzo[a][7]annulene-1-carboxamide To a solution of (1RS,2SR)-2-amino-1-(3-fluorophenyl)-3-[3-(1,1,2,2-tetrafluoroethoxy)phenyl]propan-1-ol (448 mg, 1.24 mmol) in acetonitrile (20 ml) were added 6,7-dihydro-5H-benzo[a]cycloheptene-1-carboxylic acid (234 mg, 1.24 mmol), 1-ethyl-3-(3-dimethylaminopropyl) carbodiimide hydrochloride (357 mg, 1.86 mmol) and 1-hydroxybenzotriazole hydrate (190 mg, 1.24 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried (anhydrous magnesium sulfate) and evaporated under reduced pressure. Recrystallization of the residue from ethyl acetate-hexane gave the objective substance (444 mg, 67%).

$^1$H-NMR (CDCl$_3$)δ: 1.94–2.06 (2H, m), 2.16–2.24 (2H, m), 2.62–2.68 (2H, m), 2.79 (1H, dd, J=14.7, 10.8 Hz), 2.96 (1H, dd, J=14.7, 4.2 Hz), 4.60–4.74 (1H, m), 5.07 (1H, d, J=3.3 Hz), 5.81 (1H, d, J=8.1 Hz), 5.88 (1H, tt,=53.1, 3.0 Hz), 5.90–6.00 (1H, m), 6.23 (1H, d, J=11.7 Hz), 6.94–7.40 (11H, m). IR ν max$^{KBr}$cm$^{-1}$: 1634, 1615, 1590, 1514, 1489, 1451. mp 150–155° C. Anal. Calcd for C$_{29}$H$_{26}$NO$_3$F$_5$: C, 65.53; H, 4.93; N, 2.64. Found: C, 65.25; H, 4.95; N, 2.66.

Example 236

N-{(1RS,2SR)-2-[4-(benzyloxy)phenyl]-2-hydroxy-1-[3-(1,1,2,2-tetrafluoroethoxy)benzyl]ethyl}-6,7-dihydro-5H-benzo[a][7]annulene-1-carboxamide 1) 4-benzyloxyacetophenone To a solution of 4-hydroxyacetophenone (25 g, 184 mmol) in acetone (500 ml) were added potassium carbonate (50.7 g, 367 mmol) and benzyl bromide (32 g, 187 mmol), and the mixture was stirred overnight at room temperature. The reaction solution was concentrated, diluted with water (500 ml) and extracted with ethyl acetate (500 ml×2). The extract was washed successively with water and saturated brine, dried (anhydrous magnesium sulfate) and evaporated under reduced pressure. Recrystallization of the residue from ethyl acetate-hexane gave the objective substance (36.8 g, 89%).

$^1$H-NMR (CDCl$_3$)δ: 2.56 (3H, s), 5.13 (2H, s), 7.01 (2H, d, J=9.0 Hz), 7.30–7.44 (5H, m), 7.94 (2H, d, J=9.0 Hz). IR ν max$^{KBr}$cm$^{-1}$: 1674, 1601, 1576, 1508, 1454, 1420. mp 87–88° C. Anal. Calcd for C$_{15}$H$_{14}$O$_2$ C, 79.62; H, 6.24 Found: C, 79.68; H, 6.23.

2) ethyl 3-[4-(benzyloxy)phenyl]-3-oxopropanoate

To a solution of 4-benzyloxyacetophenone (36 g, 159 mmol) in diethyl carbonate (200 ml) was added ethanol (0.6 ml) and sodium hydride (60% in oil, 12.7 g, 318 mmol) was added under ice-cooling. The mixture was stirred at room temperature for 2 hrs. To the reaction solution was added 6N hydrochloric acid to stop the reaction, and water (500 ml) was added. Then, the mixture was extracted with ethyl acetate (500 ml×2). The extract was washed successively with water and saturated brine, dried (anhydrous magnesium sulfate) and evaporated under reduced pressure. The residue was purified by silica gel column chromatography (ethyl acetate) and recrystallized from ethyl acetate-hexane to give the objective substance (49.3 g, 100%).

$^1$H-NMR (CDCl$_3$)δ: 1.26 (3H, t, J=7.2 Hz), 3.94 (2H, s), 4.21 (2H, q, J=7.2 Hz), 5.14 (2H, s), 6.98–7.06 (2H, m), 7.30–7.48 (5H, m), 7.88–7.96 (2H, m). IR ν max$^{KBr}$cm$^{-1}$: 1740, 1678, 1601, 1576, 1510. mp 53–54° C. Anal. Calcd for C$_{18}$H$_{18}$O$_4$ C, 72.47; H, 6.08 Found: C, 72.56; H, 6.10.

3) ethyl 3-[4-(benzyloxy)phenyl]-3-oxo-2-[3-(1,1,2,2-tetrafluoroethoxy)benzyl]propanoate To a solution of 3-(1,1,2,2-tetrafluoroethoxy)toluene (27.8 g, 133 mmol) in ethyl acetate (250 ml) were added N-bromosuccinimide (26.1 g, 147 mmol) and 2,2'-azobis (isobutyronitrile) (440 mg, 2.67 mmol), and the mixture was heated under reflux for 5 hrs. After concentration of the reaction solution, crystals were filtered with hexane and the filtrate was concentrated to give 3-(1,1,2,2-tetrafluoroethoxy)-α-bromotoluene. To a solution of ethyl 3-[4-(benzyloxy)phenyl]-3-oxopropanoate (37.8 g, 127 mmol) in 1,2-dimethoxyethane (250 ml) was added sodium hydride (60% in oil, 5.07 g, 127 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (50 ml), and the mixture was stirred overnight at room temperature. The reaction solution was poured into water (500 ml), and the mixture was extracted with ethyl acetate (500 ml×2). The extract was washed with water and saturated brine, dried (anhydrous magnesium sulfate) and evaporated under reduced pressure. The residue was purified by silica gel column chromatography (hexane:ethyl acetate=4:1–1:1) and recrystallized from ethyl acetate-hexane to give the objective substance (43.4 g, 68%).

$^1$H-NMR (CDCl$_3$)δ: 1.12 (3H, t, J=7.0 Hz), 3.20–3.42 (2H, m), 4.09 (2H, q, J=7.0 Hz), 4.56 (1H, t, J=7.4 Hz), 5.12 (2H, s), 5.88 (1H, tt, J=53.0, 3.0 Hz), 6.92–7.50 (11H, m), 7.88–8.00 (2H, m). IR ν max$^{KBr}$cm$^{-1}$: 1732, 1680, 1601, 1576, 1510, 1454, 1422. mp 71–72° C. Anal. Calcd for C$_{27}$H$_{24}$O$_5$F$_4$ C, 64.28; H, 4.80 Found: C, 64.47; H, 4.78.

4) ethyl(2RS,3RS)-3-[4-(benzyloxy)phenyl]-3-hydroxy-2-[3-(1,1,2,2-tetrafluoroethoxy) benzyl]propanoate To a solution of zinc chloride (18.9 g, 139 mmol) in diethyl ether (500 ml) was added sodium borohydride (10.5 g, 278 mmol), and the mixture was stirred at room temperature for 30 min. Insoluble material was filtered off. To the filtrate was added a solution of ethyl 3-[4-(benzyloxy) phenyl]-3-oxo-2-[3-(1,1,2,2-tetrafluoroethoxy)benzyl] propanoate (35.0 g, 69.4 mmol) in diethyl ether (200 ml) at 0° C., and the mixture was stirred for 30 min. 1N Hydrochloric acid was added to the reaction solution to stop the reaction. Then, water (500 ml) was added and the mixture was extracted with ethyl acetate (500 ml×2). The extract was washed with water and saturated brine, dried (anhydrous magnesium sulfate) and evaporated under reduced pressure. The residue was purified by silica gel column chromatography (hexane:ethyl acetate=4:1) and recrystallized from ethyl acetate-hexane to give the objective substance (30.3 g, 86%).

$^1$H-NMR (CDCl$_3$)δ: 0.91 (3H, t, J=7.0 Hz), 2.77 (1H, d, J=2.8 Hz), 2.90–3.08 (3H, m), 3.87 (2H, q, J=7.0 Hz), 4.92–5.00 (1H, m), 5.06 (2H, s), 5.88 (1H, tt, J=53.0, 3.0 Hz), 6.92–7.08 (5H, m), 7.20–7.50 (8H, m). IR ν max$^{KBr}$cm$^{-1}$: 1725, 1611, 1586, 1512, 1487, 1454. mp 67–68° C. Anal. Calcd for C$_{27}$H$_{26}$O$_5$F$_4$ C, 64.03; H, 5.17 Found: C, 64.02; H, 5.15.

5) (2RS,3RS)-3-[4-(benzyloxy)phenyl]-3-hydroxy-2-[3-(1,1,2,2-tetrafluoroethoxy)benzyl]propanoic acid To a solution of ethyl(2RS,3RS)-3-[4-(benzyloxy) phenyl]-3-hydroxy-2-[3-(1,1,2,2-tetrafluoroethoxy)benzyl] propanoate (25.0 g, 49.4 mmol) in methanol (200 ml) was added 2N aqueous sodium hydroxide solution (49.0 ml, 98.0 mmol), and the mixture was stirred overnight at room temperature. The reaction solution was acidified with 1N hydrochloric acid and extracted with ethyl acetate (500 ml×2). The extract was washed with water and saturated brine, dried (anhydrous magnesium sulfate) and evaporated under reduced pressure. The residue was purified by silica gel column chromatography (ethyl acetate). Recrystallization from ethyl acetate-hexane gave the objective substance (21 g, 89%).

$^1$H-NMR (CDCl$_3$)δ: 2.90–3.08 (3H, m), 5.02 (1H, d, J=3.9 Hz), 5.05 (2H, s), 5.86 (1H, tt, J=53.1, 3.0 Hz), 6.90–7.48 (13H, m). IR ν max$^{KBr}$cm$^{-1}$: 1709, 1611, 1586, 1512, 1489, 1454. mp 76–77° C. Anal. Calcd for $C_{25}H_{22}O_5F_4$ C, 62.76; H, 4.63 Found: C, 62.98; H, 4.57.

6) (4RS,5SR)-5-[4-(benzyloxy)phenyl]-4-[3-(1,1,2,2-tetrafluoroethoxy)benzyl]-1,3-oxazolidin 2-one To a solution of (2RS,3RS)-3-[4-(benzyloxy)phenyl]-3-hydroxy-2-[3-(1,1,2,2-tetrafluoroethoxy)benzyl]propanoic acid (21.0 g, 43.9 mmol) in tetrahydrofuran (300 ml) were added diphenylphosphoryl azide (10.4 ml, 48.3 mmol) and triethylamine (9.2 ml, 65.9 mmol), ant the mixture was heated under reflux for 2 hrs. The reaction solution was allowed to cool and water (400 ml) was added. The mixture was extracted with ethyl acetate (200 ml×2). The extract was washed successively with 1N hydrochloric acid, aqueous sodium hydrogen carbonate and saturated brine, dried (anhydrous magnesium sulfate) and evaporated under reduced pressure. The residue was purified by silica gel column chromatography (hexane:ethyl acetate=1:1). Recrystallization from ethyl acetate-hexane gave the objective substance (16.4 g, 79%).

$^1$H-NMR (CDCl$_3$)δ: 2.22–2.40 (2H, m), 4.16–4.30 (1H, m), 5.08 (2H, s), 5.25 (1H, s), 5.75 (1H, d, J=8.0 Hz), 5.89 (1H, tt, J=53.0, 3.0 Hz), 6.80–7.50 (13H, m). IR ν max$^{KBr}$cm$^{-1}$: 1759, 1613, 1588, 1514, 1489, 1454. mp 115–116° C. Anal. Calcd for $C_{25}H_{21}NO_4F_4$: C, 63.16; H, 4.45; N, 2.95. Found: C, 62.89; H, 4.48; N, 2.75.

7) (1RS,2SR)-2-amino-1-[4-(benzyloxy)phenyl]-3-[3-(1,1,2,2-tetrafluoroethoxy)phenyl]propan-1-ol To a solution of (4RS,5SR)-5-[4-(benzyloxy)phenyl]-4-[3-(1,1,2,2-tetrafluoroethoxy)benzyl]-1,3-oxazolidin-2-one (2.50 g, 5.26 mmol) in ethanol (30 ml) was added 8N aqueous sodium hydroxide solution (2 ml, 16 mmol), and the mixture was heated under reflux for 5 hrs. The reaction solution was concentrated and diluted with water (100 ml). The mixture was extracted with ethyl acetate (100 ml×2). The extract was washed with saturated brine, dried (anhydrous magnesium sulfate) and evaporated under reduced pressure to give the objective substance (2.4 g, 100%)

$^1$H-NMR (CDCl$_3$)δ: 1.69 (2H, brs), 2.40 (1H, dd, J=13.8, 10.2 Hz), 2.90 (1H, dd, J=13.8, 3.0 Hz), 3.22–3.30 (1H, m), 4.59 (1H, d, J=5.4 Hz), 5.08 (2H, s), 5.89 (1H, tt, J=53.1, 3.0 Hz), 6.96–7.10 (5H, m), 7.26–7.50 (8H, m). IR ν max$^{KBr}$cm$^{-1}$: 1611, 1586, 1510, 1487, 1454. Anal. Calcd for $C_{24}H_{23}NO_3F_4$: C, 64.14; H, 5.16; N, 3.12. Found: C, 63.87; H, 5.20; N, 2.96.

8) N-{(1RS,2SR)-2-[4-(benzyloxy)phenyl]-2-hydroxy-1-[3-(1,1,2,2-tetrafluoroethoxy)benzyl]ethyl}-6,7-dihydro-5H-benzo[a][7]annulene-1-carboxamide To a solution of (1RS,2SR)-2-amino-1-[4-(benzyloxy) phenyl]-3-[3-(1,1,2,2-tetrafluoroethoxy)-phenyl]propan-1-ol (617 mg, 1.37 mmol) in acetonitrile (20 ml) were added 6,7-dihydro-5H-benzo[a]cycloheptene-1-carboxylic acid (258 mg, 1.37 mmol), 1-ethyl-3-(3-dimethylaminopropyl)-carbodiimide hydrochloride (394 mg, 2.06 mmol) and 1-hydroxybenzotriazole hydrate (210 mg, 1.37 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried (anhydrous magnesium sulfate) and evaporated under reduced pressure. Recrystallization of the residue from ethyl acetate-hexane gave the objective substance (474 mg, 56%).

$^1$H-NMR (CDCl$_3$)δ: 1.94–2.04 (2H, m), 2.12–2.24 (2H, m), 2.62–2.70 (2H, m), 2.78 (1H, dd, J=14.7, 10.5 Hz), 3.02 (1H, dd, J=14.7, 4.2 Hz), 3.40 (1H, brs), 4.64–4.76 (1H, m), 4.97 (1H, d, J=3.9 Hz), 5.07 (2H, s), 5.72 (1H, d, J=9.9 Hz), 5.70–6.08 (2H, m), 6.19 (1H, d, J=11.7 Hz), 6.92–7.18 (8H, m), 7.26–7.48 (8H, m). IR ν max$^{KBr}$cm$^{-1}$: 1644, 1613, 1586, 1510, 1454. mp 115–116° C. Anal. Calcd for $C_{36}H_{33}NO_4F_4$.0.1H$_2$O: C, 69.58; H, 5.38; N, 2.25. Found: C, 69.45; H, 5.40; N, 2.27.

Example 237

N-{(1RS,2SR)-2-(3-chlorophenyl)-2-hydroxy-1-[3-(1,1,2,2-tetrafluoroethoxy)benzyl]ethyl}-6,7-dihydro-5H-benzo[a][7]annulene-1-carboxamide 1) ethyl 3-(3-chlorophenyl)-3-oxopropanoate To a solution of 3-chloroacetophenone (23.9 g, 154 mmol) in diethyl carbonate (150 ml) was added ethanol (0.3 ml), and sodium hydride (60% in oil, 12.4 g, 309 mmol) was added under ice-cooling. The mixture was stirred at room temperature for 2 hrs. To the reaction solution was added 6N hydrochloric acid to stop the reaction, and water (500 ml) was added. Then, the mixture was extracted with ethyl acetate (500 ml×2). The extract was washed successively with water and saturated brine, dried (anhydrous magnesium sulfate) and evaporated under reduced pressure. The residue was purified by silica gel column chromatography (hexane:ethyl acetate=50:1–5:1) to give the objective substance (24.8 g, 71%).

$^1$H-NMR (CDCl$_3$)δ: 1.20–1.40 (3H, m), 3.97 (2H×3/4, s), 4.16–4.32 (2H, m), 5.65 (1H×1/4, s), 7.30–7.50 (1H, m), 7.54–7.68 (1H, m), 7.76–7.84 (1H, m), 7.90–7.96 (1H, m). IR ν max$^{KBr}$cm$^{-1}$: 1740, 1694, 1651, 1628, 1568, 1474. Anal. Calcd for $C_{11}H_{11}O_3Cl$: C, 58.29; H, 4.89 Found: C, 58.54; H, 4.84.

2) ethyl 3-(3-chlorophenyl)-3-oxo-2-[3-(1,1,2,2-tetrafluoroethoxy)benzyl]propanoate To a solution of 3-(1,1,2,2-tetrafluoroethoxy)toluene (10.2 g, 49.0 mmol) in ethyl acetate (80 ml) were added N-bromosuccinimide (9.6 g, 53.9 mmol) and 2,2'-azobis (isobutyronitrile) (161 mg, 0.98 mmol), and the mixture was heated under reflux for 5 hrs. The reaction solution was concentrated and crystals were filtered with hexane. The filtrate was concentrated to give 3-(1,1,2,2-tetrafluoroethoxy)-α-bromotoluene. To a solution of ethyl 3-(3-chlorophenyl)-3-oxopropanoate (10.0 g, 44.1 mmol) in 1,2-dimethoxyethane (100 ml) was added sodium hydride (60% in oil, 1.76 g, 44.1 mmol) under ice-cooling, and the mixture was stirred at room temperature for 30 min. To the reaction solution was dropwise added a solution of 3-(1,1,2,2-tetrafluoroethoxy)-α-bromotoluene prepared earlier in 1,2-dimethoxyethane (50 ml), and the mixture was stirred overnight at room temperature. The reaction solution was poured into water (300 ml), and the mixture was extracted with ethyl acetate (300 ml×2). The extract was washed with water and saturated brine, dried (anhydrous magnesium sulfate) and evaporated under reduced pressure. The residue was purified by silica gel column chromatography (hexane:ethyl acetate=4:1–1:1) to give the objective substance (7.5 g, 39%).

$^1$H-NMR (CDCl$_3$)δ: 1.13 (3H, t, J=7.2 Hz), 3.33 (2H, d, J=7.4 Hz), 4.02–4.20 (2H, m), 4.54 (1H, t, J=7.2 Hz), 5.89 (1H, tt, J=53.0, 3.0 Hz), 7.00–7.20 (2H, m), 7.20–7.46 (2H, m), 7.50–7.60 (1H, m), 7.78–7.84 (1H, m), 7.90–7.98 (1H, m). IR ν max$^{KBr}$cm$^{-1}$: 1738, 1694, 1613, 1588, 1572.

3) ethyl (2RS,3RS)-3-(3-chlorophenyl)-3-hydroxy-2-[3-(1,1,2,2-tetrafluoroethoxy)benzyl]propanoate To a solution of zinc chloride (4.66 g, 34.2 mmol) in diethyl ether (100 ml) was added sodium borohydride (2.59 g, 68.4 mmol), and the mixture was stirred at room temperature for 30 min. Insoluble material was filtered off, and a solution of ethyl 3-(3-chlorophenyl)-3-oxo-2-[3-(1,1,2,2-tetrafluoroethoxy)benzyl]propanoate (7.40 g, 17.1 mmol) in diethyl ether (30 ml) was added to the filtrate at 0° C. The mixture was stirred for 30 min. and 1N hydrochloric acid was added to the reaction solution to stop the reaction. Then, water (100 ml) was added and the mixture was extracted with ethyl acetate (100 ml×2). The extract was washed with water and saturated brine, dried (anhydrous magnesium sulfate) and evaporated under reduced pressure. The residue was purified by silica gel column chromatography (hexane:ethyl acetate=4:1) to give the objective substance (6.6 g, 89%).

$^1$H-NMR (CDCl$_3$)δ: 0.95 (3H, t, J=7.2 Hz), 2.90–3.08 (3H, m), 3.10–3.16 (1H, m), 3.91 (2H, q, J=7.2 Hz), 5.02 (1H, s), 5.88 (1H, tt, J=53.1, 3.0 Hz), 6.92–7.08 (3H, m), 7.20–7.32 (4H, m), 7.42 (1H, s). IR ν max$^{KBr}$cm$^{-1}$: 1725, 1613, 1588, 1487, 1449. Anal. Calcd for C$_{20}$H$_{19}$O$_4$ClF$_4$: C, 55.25; H, 4.40 Found: C, 58.33; H, 4.43.

4) (2RS,3RS)-3-(3-chlorophenyl)-3-hydroxy-2-[3-(1,1,2,2-tetrafluoroethoxy)benzyl]propanoic acid To a solution of ethyl (2RS,3RS)-3-(3-chlorophenyl)-3-hydroxy-2-[3-(1,1,2,2-tetrafluoroethoxy)benzyl]propanoate (6.08 g, 14.0 mmol) in methanol (30 ml) was added 2N aqueous sodium hydroxide solution (14 ml, 28 mmol), and the mixture was stirred at room temperature for 2 hrs. The reaction solution was acidified with 1N hydrochloric acid and extracted with ethyl acetate (200 ml×2). The extract was washed with water and saturated brine, dried (anhydrous magnesium sulfate) and evaporated under reduced pressure. Recrystallization of the residue from ethyl acetate-hexane gave the objective substance (4.6 g, 81%).

$^1$H-NMR (CDCl$_3$)δ: 2.80–3.12 (3H, m), 5.11 (1H, d, J=3.6 Hz), 5.88 (1H, tt, J=53.2, 3.0 Hz), 6.90–7.10 (3H, m), 7.18–7.32 (4H, m), 7.42 (1H, s). IR ν max$^{KBr}$cm$^{-1}$: 1713, 1613, 1588, 1489, 1451. mp 94–95° C. Anal. Calcd for C$_{18}$H$_{15}$O$_4$F$_4$: C, 53.15; H, 3.72 Found: C, 53.03; H, 3.69.

5) (4RS,5SR)-5-(3-chlorophenyl)-4-[3-(1,1,2,2-tetrafluoroethoxy)benzyl]-1,3-oxazolidin-2-one To a solution of (2RS,3RS)-3-(3-chlorophenyl)-3-hydroxy-2-[3-(1,1,2,2-tetrafluoroethoxy)benzyl]propanoic acid (4.50 g, 11.1 mmol) in tetrahydrofuran (90 ml) were added diphenylphosphoryl azide (2.62 ml, 12.2 mmol.) and triethylamine (2.32 ml, 16.6 mmol), and the mixture was heated under reflux for 4 hrs. The reaction solution was allowed to cool and water (200 ml) was added. The mixture was extracted with ethyl acetate (100 ml×2). The extract was washed successively with 1N hydrochloric acid, aqueous sodium hydrogen carbonate solution and saturated brine, dried (anhydrous magnesium sulfate) and evaporated under reduced pressure. The residue was purified by silica gel column chromatography (ethyl acetate) and neutral alumina column chromatography (ethyl acetate). Recrystallization from ethyl acetate-hexane gave the objective substance (4.70 g, 100%).

$^1$H-NMR (CDCl$_3$)δ: 2.20–2.42 (2H, m), 4.20–4.34 (1H, m), 5.06 (1H, s), 5.78 (1H, d, J=8.0 Hz), 5.90 (1H, tt, J=53.0, 2.6 Hz), 6.89 (1H, s), 6.96 (1H, d, J=7.6 Hz), 7.06–7.18 (1H, m), 7.20–7.44 (5H, m). IR ν max$^{KBr}$cm$^{-1}$: 1767, 1613, 1588, 1489, 1435. mp 102–103° C. Anal. Calcd for C$_{18}$H$_{14}$NO$_3$ClF$_4$: C, 53.55; H, 3.49; N, 3.47. Found: C, 53.57; H, 3.55; N, 3.38.

6) (1RS,2SR)-2-amino-1-(3-chlorophenyl)-3-[3-(1,1,2,2-tetrafluoroethoxy)phenyl]propan-1-ol To a solution of (4RS,5SR)-5-(3-chlorophenyl)-4-[3-(1,1,2,2-tetrafluoroethoxy)benzyl]-1,3-oxazolidin-2-one (3.70 g, 9.16 mmol) in ethanol (30 ml) was added 8N aqueous sodium hydroxide solution (5.7 ml, 46 mmol), and the mixture was heated under reflux for 3 hrs. The reaction solution was concentrated and diluted with water (100 ml). The mixture was extracted with ethyl acetate (100 ml×2). The extract was washed with saturated brine, dried (anhydrous magnesium sulfate) and evaporated under reduced pressure to give the objective substance (3.0 g, 87%).

$^1$H-NMR (CDCl$_3$)δ: 2.38 (1H, dd, J=14.0, 10.2 Hz), 2.77 (1H, dd, J=14.0, 3.0 Hz), 3.24–3.36 (1H, m), 4.67 (1H, d, J=4.8 Hz), 5.90 (1H, tt, J=53.0, 3.0 Hz), 6.94–7.18 (3H, m), 7.22–7.43 (5H, m). IR ν max$^{KBr}$cm$^{-1}$: 1613, 1586,.1487, 1449, 1431.

7) N-{(1RS,2SR)-2-(3-chlorophenyl)-2-hydroxy-1-[3-(1,1,2,2-tetrafluoroethoxy)benzyl]ethyl}-6,7-dihydro-5H-benzo[a][7]annulene-1-carboxamide To a solution of (1RS,2SR)-2-amino-1-(3-chlorophenyl)-3-[3-(1,1,2,2-tetrafluoroethoxy)phenyl]propan-1-ol (448 mg, 1.24 mmol) in acetonitrile (20 ml) were added 6,7-dihydro-5H-benzo[a]cycloheptene-1-carboxylic acid (234 mg, 1.24 mmol), 1-ethyl-3-(3-dimethylaminopropyl)carbodiimide hydrochloride (357 mg, 1.86 mmol) and 1-hydroxybenzotriazole hydrate (190 mg, 1.24 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried (anhydrous magnesium sulfate) and evaporated under reduced pressure. Recrystallization of the residue from ethyl acetate-hexane gave the objective substance (444 mg, 67%).

$^1$H-NMR (CDCl$_3$)δ: 1.92–2.04 (2H, m), 2.10–2.24 (2H, m), 2.60–2.70 (2H, m), 2.73–2.82 (1H, m), 2.90–3.00 (1H, m), 3.87 (1H, d, J=3.6 Hz), 4.60–4.70 (1H, m), 5.00–5.06 (1H, m), 5.70–6.08 (2H, m), 5.80 (1H, d, J=8.4 Hz), 6.22 (1H, d, J=11.7 Hz), 6.92–7.18 (6H, m), 7.22–7.36 (4H, m), 7.47 (1H, s). IR ν max$^{KBr}$cm$^{-1}$: 1634, 1588, 1514, 1451, 1302. mp 160–161° C. Anal. Calcd. for C$_{29}$H$_{26}$NO$_3$ClF$_4$: C, 63.56; H, 4.78; N, 2.56. Found: C, 63.40; H, 4.65; N, 2.42.

Example 238 tert-butyl (1RS,2SR)-2-(4-fluorophenyl)-2-hydroxy-1-{[6-(1,1,2,2-tetrafluoroethoxy)pyridin-2-yl]methyl}ethylcarbamate 1) [6-(1,1,2,2-tetrafluoroethoxy)pyridin-2-yl]methanol To a solution of ethyl 6-(1,1,2,2-tetrafluoroethoxy)-pyridine-2-carboxylate (5.65 g, 21.2 mmol) in tetrahydrofuran (60 ml) was added Red-Al (registered trademark, 6.11 g, 21.2 mmol). The reaction solution was stirred at room temperature for 30 min. and acetone (2 ml) was added. Water (100 ml) was added to the reaction solution and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl-acetate=4:1) to give the objective substance (4.2 g, 88%).

$^1$H-NMR (CDCl$_3$)δ: 3.02 (1H, brs), 4.74 (2H, s), 6.17 (1H, tt, J=53.0, 3.8 Hz), 6.96 (H, d, J=8.2 Hz), 7.23 (1H, d, J=8.2 Hz), 7.79 (1H, t, J=7.8 Hz). IR ν max$^{KBr}$cm$^{-1}$: 1607, 1580, 1443, 1352.

2) ethyl 3-(4-fluorophenyl)-3-oxo-2-{[6-(1,1,2,2-tetrafluoroethoxy)pyridin-2-yl]methyl}propanoate To a solution of [6-(1,1,2,2-tetrafluoroethoxy)pyridin-2-yl]methanol (4.14 g, 18.39 mmol) in ethyl acetate (50 ml) were added methanesulfonyl chloride (2.32 g, 20.23 mmol) and triethylamine (3.08 ml, 22.07 mmol), and the mixture was stirred at room temperature for 2 hrs. Insoluble material was filtered off, and the filtrate was evaporated under reduced pressure to give a mesyl form. To a solution of ethyl 3-(4-fluorophenyl)-3-oxopropanoate (3.87 g, 18.4 mmol) in 1,2-dimethoxyethane (40 ml) was added sodium hydride (740 mg, 60% in oil, 18.4 mmol), and the mixture was stirred at room temperature for 2 hrs. To the reaction solution was dropwise added a solution of the mesyl form prepared earlier in 1,2-dimethoxyethane (10 ml), and the mixture was stirred overnight at room temperature. The reaction solution was acidified with 1N hydrochloric acid and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1) to give the objective substance (1.46 g, 19%).

$^1$H-NMR (CDCl$_3$)δ: 1.15 (3H, t, J=7.0 Hz), 3.47 (2H, d, J=7.4 Hz), 4.13 (2H, q, J=7.0 Hz), 5.08 (1H, t, J=7.2 Hz), 6.12 (1H, tt, J=53.0, 3.6 Hz), 6.83 (1H, d, J=8.0 Hz), 7.06–7.22 (3H, m), 7.60–7.72 (1H, m), 8.02–8.18 (2H, m). IR ν max$^{KBr}$cm$^{-1}$: 1738, 1688, 1601, 1578, 1508, 1456, 1441.

3) ethyl (2RS,3RS)-3-(4-fluorophenyl)-3-hydroxy-2-{[6-(1,1,2,2-tetrafluoroethoxy)pyridin-2-yl]methyl}propanoate To a solution of zinc chloride (915 mg, 6.71 mmol) in diethyl ether (20 ml) was added sodium borohydride (508 mg, 13.4 mmol), and the mixture was-stirred at room temperature for 30 min. Insoluble material was filtered off, and a solution of ethyl 3-(4-fluorophenyl)-3-oxo-2-{[6-(1,1,2,2-tetrafluoroethoxy)pyridin-2-yl]methyl}propanoate (1.40 g, 3.35 mmol) in diethyl ether (10 ml) was added to the filtrate at 0° C. The mixture was stirred for 30 min. and 1N hydrochloric acid was added to the reaction solution to stop the reaction. Then, water (50 ml) was added and the mixture was extracted with ethyl-acetate (50 ml×2). The extract was washed with water and saturated brine, dried (anhydrous magnesium sulfate) and evaporated under reduced pressure. The residue was purified by silica gel column chromatography (hexane:ethyl acetate=4:1–1:1) to give the objective substance (1.28 g, 91%).

$^1$H-NMR (CDCl$_3$)δ: 1.03 (3H, t, J=7.2 Hz), 2.92–3.10 (1H, m), 3.18–3.30 (2H, m), 3.43 (1H, d, J=3.3 Hz), 3.92–4.06 (2H, m), 5.04–5.10 (1H, m), 6.26 (1H, tt, J=53.1, 3.9 Hz), 6.84 (1H, d, J=8.4 Hz), 6.96–7.06 (3H, m), 7.32–7.40 (2H, m), 7.64 (1H, t, J=8.1 Hz). IR ν max$^{KBr}$cm$^{-1}$: 1728, 1605, 1576, 1512, 1456, 1443. Anal. Calcd for C$_{19}$H$_{18}$NO$_4$F$_5$: C, 54.42; H, 4.33; N, 3.34. Found: C, 54.55; H, 4.16; N, 3.22.

4) (2RS,3RS)-3-(4-fluorophenyl)-3-hydroxy-2-{[6-(1,1,2,2-tetrafluoroethoxy)pyridin-2-yl]methyl}propanoic acid To a solution of ethyl (2RS,3RS)-3-(4-fluorophenyl)-3-hydroxy-2-{[6-(1,1,2,2-tetrafluoroethoxy)pyridin-2-yl]methyl}propanoate (1.28 g, 3.05 mmol) in methanol (6 ml) was added 2N aqueous sodium hydroxide solution (3.05 ml, 6.1 mmol), and the mixture was stirred overnight at room temperature. The reaction solution was acidified with 1N hydrochloric acid, saturated aqueous sodium hydrogen carbonate was added and the mixture was extracted with ethyl acetate (50 ml×2). The extract was washed with water and saturated brine, dried (anhydrous magnesium sulfate) and evaporated under reduced pressure to give the objective substance (1.20 g, 100%).

$^1$H-NMR (CDCl$_3$)δ: 2.82–3.10 (1H, m), 3.18–3.32 (2H, m), 5.24 (1H, d, J=3.9 Hz), 6.14 (1H, tt, J=53.4, 3.6 Hz), 6.84–7.08 (4H, m), 7.28–7.40 (2H, m), 7.62–7.70 (1H, m). IR ν max$^{KBr}$cm$^{-1}$: 1713, 1605, 1578, 1512, 1456, 1443.

5) (4RS,5SR)-5-(4-fluorophenyl)-4-{[6-(1,1,2,2-tetrafluoroethoxy)pyridin-2-yl]methyl}-1,3-oxazolidin-2-one To a solution of (2RS,3RS)-3-(4-fluorophenyl)-3-hydroxy-2-{[6-(1,1,2,2-tetrafluoroethoxy)pyridin-2-yl]methyl}propanoic acid (1.20 g, 3.07 mmol) in tetrahydrofuran (20 ml) were added diphenylphosphoryl azide (730 μl, 3.37 mmol) and triethylamine (706 μl, 5.06 mmol), and the mixture was heated under reflux for 4 hrs. The reaction solution was allowed to cool and water (100 ml) was added. The mixture was extracted with ethyl acetate (50 ml×2). The extract was washed successively with saturated aqueous sodium hydrogen carbonate, water and saturated brine, dried (anhydrous magnesium sulfate) and evaporated under reduced pressure. The residue was purified by silica gel column chromatography (hexane:ethyl acetate=3:1–1:1) to give the objective substance (808 mg, 68%).

$^1$H-NMR (CDCl$_3$)δ: 2.39 (1H, dd, J=15.8, 4.0 Hz), 2.58 (1H, dd, J=15.8, 10.2 Hz), 4.52–4.66 (1H, m), 5.81 (1H, d, J=8.0 Hz), 6.03 (1H, tt, J=53.2, 3.0 Hz), 6.80 (1H, d, J=7.2 Hz), 6.88 (1H, d, J=8.2 Hz), 7.00–7.16 (2H, m), 7.24–7.40 (2H, m), 7.63 (1H, t, J=8.0 Hz) IR ν max$^{KBr}$cm$^{-1}$: 1761, 1607, 1576, 1514, 1456, 1441.

6) tert-butyl (4RS,5SR)-5-(4-fluorophenyl)-2-oxo-4-{[6-(1,1,2,2-tetrafluoroethoxy)pyridin-2-yl]methyl}-1,3-oxazolidine-3-carboxylate To a solution of (4RS,5SR)-5-(4-fluorophenyl)-4-{[6-(1,1,2,2-tetrafluoroethoxy)pyridin-2-yl]methyl}-1,3-oxazolidin-2-one (808 mg, 2.08 mmol) in acetonitrile (20 ml) were added di-tert-butyl bicarbonate (545 mg, 2.50 mmol) and 4-N,N-dimethylaminopyridine (25.6 mg, 0.21 mmol), and the mixture was stirred at room temperature for 6 hrs. To the reaction solution was added water (50 ml), and the mixture was extracted with ethyl acetate (50 ml×2). The extract was washed with saturated brine, dried (anhydrous magnesium sulfate) and evaporated under reduced pressure. The residue was purified by silica gel column chromatography (hexane:ethyl acetate=10:1) to give the objective substance (850 g, 84%).

$^1$H-NMR (CDCl$_3$)δ: 1.53 (9H, s), 2.70 (1H, dd, J=14.8, 10.0 Hz), 3.12 (1H, dd, J=14.8, 3.4 Hz), 5.30–5.42 (1H, m), 5.70 (1H, d, J=7.4 Hz), 6.20 (1H, d, J=7.2 Hz), 6.22 (1H, tdd, J=53.4, 4.4, 3.0 Hz), 6.68–6.88 (3H, m), 6.98–7.10 (2H, m), 7.30–7.40 (1H, m). IR ν max$^{KBr}$cm$^{-1}$: 1821, 1725, 1607, 1578, 1514, 1456, 1443, 1370. Anal. Calcd for C$_{22}$H$_{21}$F$_5$N$_2$O$_5$: C, 54.10; H, 4.33; N, 5.74. Found: C, 54.06; H, 4.23; N, 5.52.

7) tert-butyl (1RS,2SR)-2-(4-fluorophenyl)-2-hydroxy-1-{[6-(1,1,2,2-tetrafluoroethoxy)pyridin-2-yl]methyl}ethylcarbamate To a solution of tert-butyl (4RS,5SR)-5-(4-fluorophenyl)-2-oxo-4-{[6-(1,1,2,2-tetrafluoroethoxy)pyridin-2-yl]methyl}-1,3-oxazolidine-3-carboxylate (840 mg, 1.72 mmol) in methanol (4 ml) was added a solution (4.12 ml, 2.06 mmol) of 0.5N sodium hydroxide in methanol, and the mixture was stirred at room temperature for 15 min. To the reaction solution was added water (50 ml), and the mixture was extracted with ethyl acetate (50 ml×2). The extract was washed with saturated brine, dried (anhydrous magnesium sulfate) and evaporated under reduced pressure. The residue was purified by silica gel column chromatography (hexane:ethyl acetate=1:1) and recrystallized from ethyl acetate-hexane to give the objective substance (390 mg, 49%).

$^1$H-NMR (CDCl$_3$)δ: 1.37 (9H, s), 2.90–3.02 (2H, m), 3.85 (1H, brs), 4.16–4.30 (1H, m), 4.89 (1H, brs), 5.26 (1H, d, J=7.2 Hz), 6.19 (1H, tt, J=53.0, 3.6 Hz), 6.91 (1H, d, J=8.0

Hz), 7.00–7.14 (3H, m), 7.34–7.44 (2H, m), 7.71 (1H, t, J=8.0 Hz) IR ν max$^{KBr}$cm$^{-1}$: 1694, 1605, 1578, 1510, 1456, 1441. mp 109–110° C. Anal. Calcd for $C_{21}H_{23}F_5N_2O_4$·0.1H$_2$O: C, 54.34; H, 5.03; N, 6.03 Found: C, 54.12; H, 4.93; N, 5.87.

Example 239

N-((1RS,2SR)-2-(4-fluorophenyl)-2-hydroxy-1-{[6-(1,1,2,2-tetrafluoroethoxy)pyridin-2-yl]methyl}ethyl)-6,7-dihydro-5H-benzo[a][7]annulene-1-carboxamide Trifluoroacetic acid (3 ml) was added to tert-butyl (1RS,2SR)-2-(4-fluorophenyl)-2-hydroxy-1-{[6-(1,1,2,2-tetrafluoroethoxy)pyridin-2-yl]methyl}ethylcarbamate (300 mg, 0.65 mmol) at 0° C., and the mixture was stirred at 0° C. for 10 min. To the reaction solution was added saturated aqueous sodium hydrogen carbonate and the mixture was extracted with ethyl acetate (20 ml×2). The extract was washed with saturated brine, dried (anhydrous magnesium sulfate) and evaporated under reduced pressure. To a solution of the residue in acetonitrile (25 ml) were added 6,7-dihydro-5H-benzo[a]cycloheptene-1-carboxylic acid (122 mg, 0.65 mmol), 1-ethyl-3-(3-dimethylaminopropyl)carbodiimide hydrochloride (187 mg, 0.97 mmol) and 1-hydroxybenzotriazole hydrate (99 mg, 0.65 mmol), and the mixture was stirred overnight at room temperature. The reaction solution was diluted with water (100 ml) and extracted with ethyl acetate (100 ml×2). The extract was washed successively with saturated aqueous sodium hydrogen carbonate and saturated brine, dried (anhydrous magnesium sulfate) and evaporated under reduced pressure. The residue was purified by silica gel column chromatography (hexane:ethyl acetate=2:1–1:1). Recrystallization from ethyl acetate-hexane gave the objective substance (196 mg, 57%).

$^1$H-NMR (CDCl$_3$)δ: 1.92–2.06 (2H, m), 2.14–2.24 (2H, m), 2.62–2.70 (2H, m), 3.06 (1H, dd, J=15.0, 6.9 Hz), 3.16 (1H, dd, J=15.0, 5.1 Hz), 4.34 (1H, d, J=5.1 Hz), 4.70–4.82 (1H, m), 5.00 (1H, t, J=4.8 Hz), 5.88–6.26 (3H, m), 6.44 (1H, d, J=7.8 Hz), 6.93 (1H, d, J=7.8 Hz), 7.00–7.12 (4H, m), 7.12–7.20 (2H, m), 7.40–7.50 (2H, m), 7.72 (1H, t, J=7.5 Hz). IR ν max$^{KBr}$cm$^{-1}$: 1645, 1605, 1576, 1508, 1456, 1441. mp 134–135° C. Anal. Calcd for $C_{28}H_{25}N_2O_3F_5$·0.1H$_2$O: C, 62.94; H., 4.75; N, 5.24. Found: C, 62.84; H, 4.77; N, 5.16.

Example 240

N-{(1RS,2SR)-2-[3-(benzyloxy)phenyl]-2-hydroxy-1-[3-(1,1,2,2-tetrafluoroethoxy)benzyl]ethyl}-6,7-dihydro-5H-benzo[a][7]annulene-1-carboxamide 1) 3-benzyloxyacetophenone To a solution of 3-hydroxyacetophenone (101 g, 744 mmol) in acetone (1 L) were added potassium carbonate (154 g, 1.12 mol) and benzyl bromide (130 g, 759 mmol), and the mixture was stirred overnight at room temperature. The reaction solution was concentrated, diluted with water (500 ml) and extracted with ethyl acetate (500 ml×2). The extract was washed successively with water and saturated brine, dried (anhydrous magnesium sulfate) and evaporated under reduced pressure. The residue was purified by silica gel column chromatography (hexane:ethyl acetate=10:1–4:1) to give the objective substance (128 g, 76%).

$^1$H-NMR (CDCl$_3$)δ: 2.58 (3H, s), 5.11 (2H, s), 7;14–7.20 (1H, m), 7.30–7.48 (6H, m), 7.54–7.60 (2H, m). IR ν max$^{KBr}$cm$^{-1}$: 1684, 1593, 1582, 1497, 1483, 1439. Anal. Calcd for $C_{15}H_{14}O_2$: C, 79.62; H, 6.24 Found: C, 79.44; H, 6.22.

2) ethyl 3-[3-(benzyloxy)phenyl]-3-oxopropanoate

To a solution of 3-benzyloxyacetophenone (90 g, 400 mmol) in diethyl carbonate (500 ml) was added ethanol (1.5 ml) and sodium hydride (60% in oil, 31.8 g, 800 mmol) was added under ice-cooling. The mixture was stirred at room temperature for 4 hrs. To the reaction solution was added 6N hydrochloric acid to stop the reaction, and water (500 ml) was added. The mixture was extracted with ethyl acetate (500 ml×2). The extract was washed successively with water and saturated brine, dried (anhydrous magnesium sulfate) and evaporated under reduced pressure. The residue was purified by silica gel column chromatography (hexane:ethyl acetate=50:1–10:1) to give the objective substance (107 g, 90%).

$^1$H-NMR (CDCl$_3$)δ: 1.20–1.38 (3H, m), 3.96 (2H×6/7, s), 4.18–4.32 (2H, m), 5.09 (2H×1/7, s), 5.11 (2H×6/7, s), 5.65 (1H×1/7, s), 7.02–7.60 (9H, m). IR ν max$^{KBr}$cm$^{-1}$: 1740, 1688, 1582, 1485, 1441. Anal. Calcd for $C_{15}H_{14}O_2$: C, 72.47; H, 6.08 Found: C, 72.77; H, 6.01.

3) ethyl 3-[3-(benzyloxy)phenyl]-3-oxo-2-[3-(1,1,2,2-tetrafluoroethoxy)benzyl]propanoate To a solution of [3-(1,1,2,2-tetrafluoroethoxy)-phenyl]methanol (7.91 g, 35.3 mmol) in ethyl acetate (100 ml) were added methanesulfonyl chloride (3.00 ml, 38.8 mmol) and triethylamine (5.91 ml, 42.4 mmol), and the mixture was stirred at room temperature for 2 hrs. Insoluble material was filtered off, and the filtrate was evaporated under reduced pressure to give a mesyl form. To a solution of ethyl 3-[3-(benzyloxy)phenyl]-3-oxopropanoate (10 g, 33.5 mmol) in 1,2-dimethoxyethane (80 ml) was added sodium hydride (1.34 g, 60% in oil, 33.5 mmol), and the mixture was stirred at room temperature for 3 hrs. To the reaction solution was dropwise added a solution of the mesyl form prepared earlier in 1,2-dimethoxyethane (10 ml), and the mixture was stirred overnight at room temperature. The reaction solution was acidified with 1N hydrochloric acid and extracted-with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=4:1–1:1) to give the objective substance (19.0 g).

$^1$H-NMR (CDCl$_3$)δ: 1.12 (3H, t, J=7.0 Hz), 3.32 (2H, d, J=7.4 Hz), 4.09 (2H, q, J=7.0 Hz), 4.56 (1H, t, J=7.4 Hz), 5.09 (2H, s), 5.88 (1H, tt, J=53.2, 3.0 Hz), 7.00–7.60 (13H, m).

4) ethyl (2RS,3RS)-3-[3-(benzyloxy)phenyl]-3-hydroxy-2-[3-(1,1,2,2-tetrafluoroethoxy)benzyl]propanoate To a solution of zinc chloride (9.14 g, 67.0 mmol) in diethyl ether (100 ml) was added sodium borohydride (5.07 g, 134 mmol), and the mixture was stirred at room temperature for 30 min. Insoluble material was filtered off, and to the filtrate was added a solution of ethyl 3-[3-(benzyloxy)phenyl]-3-oxo-2-[3-(1,1,2,2-tetrafluoroethoxy)-benzyl]propanoate (19.0 g, 33.5 mmol) in diethyl ether (200 ml) at 0° C. The mixture was stirred for 30 min. and 1N hydrochloric acid was added to stop the reaction. Then, water (500 ml) was added and the mixture was extracted with ethyl acetate (500 ml×2). The extract was washed with water and saturated brine, dried (anhydrous magnesium sulfate) and evaporated under reduced pressure. The residue was purified by silica gel column chromatography (hexane:ethyl acetate=1:1-ethyl acetate) to give the objective substance (10.7 g, crude).

5) (2RS,3RS)-3-[3-(benzyloxy)phenyl]-3-hydroxy-2-[3-(1,1,2,2-tetrafluoroethoxy)benzyl]propanoic acid To a solution of ethyl (2RS,3RS)-3-[3-(benzyloxy)phenyl]-3-hydroxy-2-[3-(1,1,2,2-tetrafluoroethoxy)benzyl]

propanoate (10.7 g, 21.2 mmol, crude) in methanol (50 ml) was added. 2N aqueous sodium hydroxide solution (21 ml, 42 mmol), and the mixture was stirred overnight at room temperature. The reaction solution was acidified with 1N hydrochloric acid and extracted with ethyl acetate (50 ml×2). The extract was washed with water and saturated brine, dried (anhydrous magnesium sulfate) and evaporated under reduced pressure. The obtained crude crystals were washed with hexane to give the objective substance (7.90 g, 49% in 3 steps).

$^1$H-NMR (CDCl$_3$)δ: 2.80–3.08 (3H, m), 5.06 (2H, 5), 5.00–5.10 (1H, m), 5.86 (1H, tt, J=53.2, 2.8 Hz), 6.86–7.10 (6H, m), 7.10–7.50 (7H, m). IR ν max$^{KBr}$cm$^{-1}$: 1713, 1588, 1489, 1451. mp 103–104° C. Anal. Calcd for C$_{25}$H$_{22}$O$_5$F$_4$: C, 62.76; H, 4.63 Found: C, 63.01; H, 4.58.

6) (4RS,5SR)-5-[3-(benzyloxy)phenyl]-4-[3-(1,1,2,2-tetrafluoroethoxy)benzyl]-1,3-oxazolidin-2-one To a solution of (2RS,3RS)-3-[3-(benzyloxy)phenyl]-3-hydroxy-2-[3-(1,1,2,2-tetrafluoroethoxy)benzyl]propanoic acid (7.8 g, 16.3 mmol) in tetrahydrofuran (100 ml) were added diphenylphosphoryl azide (3.86 ml, 17.9 mmol) and triethylamine (3.42 ml, 24.5 mmol), and the mixture was heated under reflux for 4 hrs. The reaction solution was allowed to cool and water (100 ml) was added. The mixture was extracted with ethyl acetate (100 ml×2). The extract was washed successively with 1N hydrochloric acid, aqueous sodium hydrogen carbonate solution and saturated brine, dried (anhydrous magnesium sulfate) and evaporated under reduced pressure. Recrystallization of the residue from ethyl acetate-hexane gave the objective substance (6.72 g, 87%).

$^1$H-NMR (CDCl$_3$)δ: 2.10–2.38 (2H, m), 4.10–4.28 (1H, m), 5.05 (1H, brs), 5.10 (2H, s), 5.77 (1H, d, J=7.6 Hz), 5.90 (1H, tt, J=53.2, 2.8 Hz), 6.80–7.38 (6H, m), 7.20–7.50 (7H, m). IR ν max$^{KBr}$cm$^{-1}$: 1759, 1613, 1588, 1489, 1451. mp 97–99° C. Anal. Calcd for C$_{25}$H$_{21}$NO$_4$F$_4$: C, 63.16; H, 4.45; N, 2.95. Found: C, 62.91; H, 4.30; N, 2.85.

7) (1RS,2SR)-2-amino-1-(3-(benzyloxy)phenyl)-3-(3-((1,1,2,2-tetrafluoroethyl)oxy)phenyl)-1-propanol To a solution of (4RS,5SR)-5-[3-(benzyloxy)phenyl]-4-[3-(1,1,2,2-tetrafluoroethoxy)benzyl]-1,3-oxazolidin-2-one (6.5 g, 13.7 mmol) in ethanol (70 ml) was added 8N aqueous sodium hydroxide solution (5.13 ml, 41 mmol), and the mixture was heated under reflux for 4 hrs. The reaction solution was concentrated, diluted with water (100 ml) and extracted with ethyl acetate (100 ml×2). The extract was washed with saturated brine, dried (anhydrous magnesium sulfate) and evaporated under reduced pressure to give the objective substance (6.26 g, 100%).

$^1$H-NMR (CDCl$_3$)δ: 2.36 (1H, dd, J=14.0, 10.4 Hz), 2.82 (1H, dd, J=14.0, 3.0 Hz), 3.20–3.32 (1H, m), 4.63 (1H, d, J=4.8 Hz), 5.10 (2H, s), 5.89 (1H, tt, J=53.0, 3.0 Hz), 6.90–7.12 (6H, m), 7.24–7.48 (7H, m). IR ν max$^{KBr}$cm$^{-1}$: 1740, 1609, 1586, 1487, 1449. Anal. Calcd for C$_{24}$H$_{23}$NO$_3$F$_4$: C, 64.14; H, 5.16; N, 3.12. Found: C, 63.87; H, 5.26; N, 2.93.

8) N-{(1RS,2SR)-2-[3-(benzyloxy)phenyl]-2-hydroxy-1-[3-(1,1,2,2-tetrafluoroethoxy)benzyl]ethyl}-6,7-dihydro-5H-benzo[a][7]annulene-1-carboxamide To a solution of (1RS,2SR)-2-amino-1-(3-(benzyloxy)phenyl)-3-(3-((1,1,2,2-tetrafluoroethyl)oxy)-phenyl)-1-propanol (405 mg, 0.90 mmol) in acetonitrile (30 ml) were added 6,7-dihydro-5H-benzo[a]cycloheptene-1-carboxylic acid (170 mg, 0.90 mmol), 1-ethyl-3-(3-dimethylaminopropyl)carbodiimide hydrochloride (259 mg, 1.35 mmol) and 1-hydroxybenzotriazole hydrate (138 mg, 0.90 mmol), and the mixture was stirred overnight at room temperature. The reaction solution was diluted with water (100 ml) and extracted with ethyl acetate (100 ml×2). The extract was washed successively with 1N hydrochloric acid, 1N aqueous sodium hydroxide solution and saturated brine, dried (anhydrous magnesium sulfate) and evaporated under reduced pressure. The residue was purified by silica gel column chromatography (hexane:ethyl acetate=2:1–1:1). Recrystallization from ethyl acetate-hexane gave the objective substance (407 mg, 73%).

$^1$H-NMR (CDCl$_3$)δ: 1.92–2.02 (2H, m), 2.12–2.20 (2H, m), 2.60–2.70 (2H, m), 2.74 (1H, dd, J=14.4, 10.5 Hz), 2.96 (1H, dd, J=14.4, 3.9 Hz), 3.49 (1H, d, J=3.6 Hz), 4.64–4.76 (1H, m), 5.00–5.10 (3H, m), 5.76 (1H, d, J=8.7 Hz), 5.68–6.08 (2H, m), 6.23 (1H, d, J=11.7 Hz), 6.90–7.18 (9H, m), 7.24–7.44 (7H, m). IR ν max$^{KBr}$cm$^{-1}$: 1640, 1611, 1588, 1510, 1489, 1449. mp 128–129° C. Anal. Calcd for C$_{36}$H$_{33}$NO$_4$F$_4$: C, 69.78; H, 5.37; N, 2.26. Found: C, 69.62; H, 5.34; N, 2.03.

Example 241

N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide 1) 4-{(1RS,2SR)-2-amino-1-hydroxy-3-[3-(1,1,2,2-tetrafluoroethoxy)phenyl]propyl}phenol To a solution of (1RS,2SR)-2-amino-1-[4-(benzyloxy)phenyl]-3-[3-(1,1,2,2-tetrafluoroethoxy)phenyl]-propan-1-ol (2.60 g, 5.79 mmol) in ethanol (20 ml) was added 10% palladium/carbon (containing water by 50%, 260 mg), and the mixture was stirred overnight under a hydrogen stream. The catalyst was removed from the reaction solution using celite, and the filtrate was concentrated. The residue was purified neutral alumina column chromatography (ethanol) to give the objective substance (0.80 g, 39%) as an amorphous compound.

$^1$H-NMR (CDCl$_3$)δ: 2.45 (1H, dd, J=13.6, 10.0 Hz), 2.97. (1H, dd, J=13.6, 2.6 Hz), 3.16–3.28 (1H, m), 4.55 (1H, d, J=5.4 Hz), 5.89 (1H, tt, J=53.2, 3.0 Hz), 6.75 (2H, d, J=8.0 Hz), 7.00–7.34 (6H, m). IR ν max$^{KBr}$cm$^{-1}$: 1613, 1588, 1514, 1489, 1449. Anal. Calcd for C$_{17}$H$_{17}$NO$_3$F$_4$.0.5H$_2$O: C, 55.44; H, 4.92; N, 3.80. Found: C, 55.41; H, 4.83; N, 3.61.

2) N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide To a solution of 4-{(1RS,2SR)-2-amino-1-hydroxy-3-[3-(1,1,2,2-tetrafluoroethoxy)phenyl]propyl}phenol (125 mg, 0.35 mmol) in acetonitrile (30 ml) were added 6,7-dihydro-5H-benzo[a]cycloheptene-1-carboxylic acid (66 mg, 0.35 mmol), 1-ethyl-3-(3-dimethylaminopropyl)carbodiimide hydrochloride (100 mg, 0.52 mmol) and 1-hydroxybenzotriazole hydrate (53 mg, 0.35 mmol), and the mixture was stirred overnight at room temperature. The reaction solution was diluted with water (100 ml) and extracted with ethyl acetate (100 ml×2). The extract was washed successively with 1N hydrochloric acid, saturated aqueous sodium hydrogen carbonate and saturated brine, dried (anhydrous magnesium sulfate) and evaporated under reduced pressure. The residue was purified by silica gel column chromatography (hexane:ethyl acetate=1:1) and recrystallized from chloroform-hexane to give the objective substance (162 mg, 88%).

$^1$H-NMR (CDCl$_3$)δ: 1.90–2.08 (2H, m), 2.10–2.22 (2H, m), 2.58–2.70 (2H, m), 2.80 (1H, dd, J=14.4, 10.0 Hz), 3.06 (1H, dd, J=14.4, 4.0 Hz), 3.24 (1H, brs), 4.64–4.82 (1H, m), 4.88 (1H, brs), 5.73 (1H, d, J=8.8 Hz), 5.60–6.20 (3H, m), 6.82 (2H, d, J=8.4 Hz), 6.86–7.18 (5H, m), 7.22–7.40 (3H, m). IR ν max$^{KBr}$cm$^{-1}$: 1732, 1615, 1588, 1516, 1451. mp

271

167–168° C. Anal. Calcd for $C_{29}H_{27}NO_4F_4 \cdot 0.2H_2O$: C, 65.34; H, 5.18; N, 2.63. Found: C, 65.11; H, 4.99; N, 2.42.

Example 242

N-{(1RS,2SR)-2-hydroxy-2-(4-methoxyphenyl)-1-[3-(1,1,2,2-tetrafluoroethoxy)benzyl]ethyl}-6,7-dihydro-5H-benzo[a][7]annulene-1-carboxamide To a solution of N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and methyl iodide (2 ml), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate= 2:1). Recrystallization from ethyl acetate-hexane gave the objective substance (80 mg, 19%).

$^1$H-NMR (CDCl$_3$)δ: 1.90–2.06 (2H, m), 2.08–2.24 (2H, m), 2.58–2.72 (2H, m), 2.78 (1H, dd, J=14.2, 10.2 Hz), 3.02 (1H, dd, J=14.2, 4.0 Hz), 3.38 (1H, brs), 3.82 (3H, s), 4.60–4.78 (1H, m), 4.94–5.00 (1H, m), 5.73 (1H, d, J=8.4 Hz), 5.60–6.24 (3H, m), 6.84–7.20 (8H, m), 7.20–7.46 (3H, m). IR ν max$^{KBr}$cm$^{-1}$: 1645, 1613, 1512, 1449. mp 151–152° C. Anal. Calcd for $C_{30}H_{29}NO_4F_4 \cdot 0.1H_2O$: C, 66.07; H, 5.39; N, 2.57. Found: C, 65.92; H, 5.23; N, 2.51.

Example 243

N-{(1RS,2SR)-2-hydroxy-2-(4-isopropoxyphenyl)-1-[3-(1,1,2,2-tetrafluoroethoxy)benzyl]ethyl}-6,7-dihydro-5H-benzo[a][7]annulene-1-carboxamide To a solution of N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and 2-iodopropane (226 μl, 2.27 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1). Recrystallization from ethyl acetate-hexane gave the objective substance (287 mg, 66%).

$^1$H-NMR (CDCl$_3$)δ: 1.33 (3H, s), 1.36 (3H, s), 1.90–2.08 (2H, m), 2.10–2.26 (2H, m), 2.78 (1H, dd, J=14.6, 10.2 Hz), 3.03 (1H, dd, J=14.2, 4.0 Hz), 3.33 (1H, d, J=3.4 Hz), 4.48–4.62 (1H, m), 4.62–4.80 (1H, m), 4.92–5.00 (1H, m), 5.72 (1H, d, J=8.4 Hz), 5.60–6.24 (3H, m), 6.84–7.20 (8H, m), 7.20–7.40 (3H, m); IR ν max$^{KBr}$cm$^{-1}$: 1641, 1613, 1588, 1508, 1451. mp 134–135° C. Anal. Calcd for $C_{32}H_{33}NO_4F_4 \cdot 0.2H_2O$: C, 66.82; H, 5.85; N, 2.44. Found: C, 66.72; H, 5.85; N, 2.52.

Example 244

N-{(1RS,2SR)-2-(4-butoxyphenyl)-2-hydroxy-1-[3-(1,1,2,2-tetrafluoroethoxy)benzyl]ethyl}-6,7-dihydro-5H-benzo[a][7]annulene-1-carboxamide To a solution of N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and 1-iodobutane (417 mg, 2.27 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. Recrystallization of the residue from ethyl acetate-hexane gave the objective substance (298 mg, 67%).

$^1$H-NMR (CDCl$_3$)δ: 0.98 (3H, t, J=7.4 Hz), 1.40–1.60 (2H, m), 1.68–1.88 (2H, m), 1.90–2.10 (2H, m), 2.12–2.28 (2H, m), 2.60–2.72 (2H, m), 2.77 (1H, dd, J=14.6, 10.6 Hz), 3.02 (1H, dd, J=14.6, 4.0 Hz), 3.36 (1H, d, J=3.6 Hz), 3.96 (2H, t, J=6.4 Hz), 4.62–4.78 (1H, m), 4.96 (1H, t, J=4.0 Hz), 5.72 (1H, d, J=8.6 Hz), 5.60–6.22 (3H, m), 6.86–7.20 (7H, m), 7.22–7.40 (4H, m). IR ν max$^{KBr}$cm$^{-1}$: 1644, 1613, 1586, 1512, 1449. mp 126–127° C. Anal. Calcd for $C_{33}H_{35}NO_4F_4$: C, 67.68; H, 6.02; N, 2.39. Found: C, 67.64; H, 6.04; N, 2.23.

Example 245

N-{(1RS,2SR)-2-{4-[(4-fluorobenzyl)oxy]phenyl}-2-hydroxy-1-[3-(1,1,2,2-tetrafluoroethoxy)benzyl]ethyl}-6,7-dihydro-5H-benzo[a][7]annulene-1-carboxamide To a solution of N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and 4-fluorobenzyl bromide (428 mg, 2.27 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. Recrystallization of the residue from ethyl acetate-hexane gave the objective substance (381 mg, 79%).

$^1$H-NMR (CDCl$_3$)δ: 1.90–2.08 (2H, m), 2.10–2.26 (2H, m), 2.60–2.76 (2H, m), 2.77 (1H, dd, J=14.6, 10.2 Hz), 3.02 (1H, dd, J=14.6, 4.0 Hz), 3.43 (1H, d, J=3.4 Hz), 4.80–4.98 (1H, m), 4.97 (1H, t, J=4.0 Hz), 5.02 (2H, s), 5.74 (1H, d, J=8.4 Hz), 5.60–6.24 (3H, m), 6.90–7.20 (10H, m), 7.24–7.48 (8H, m). IR ν max$^{KBr}$cm$^{-1}$: 1644, 1611, 1586, 1512, 1449. mp 144–145° C. Anal. Calcd for $C_{36}H_{32}NO_4F_5$: C, 67.81; H, 5.06; N, 2.20. Found: C, 67.69; H, 4.95; N, 1.98.

Example 246

N-{(1RS,2SR)-2-[4-(cyclohexylmethoxy)phenyl]-2-hydroxy-1-[3-(1,1,2,2-tetrafluoroethoxy)benzyl]ethyl}-6,7-dihydro-5H-benzo[a][7]annulene-1-carboxamide To a solution of N-{(1RS,2SR)-2-hydroxy-2-(4-hydroxyphenyl)-1-[3-(1,1,2,2-tetrafluoroethoxy)benzyl]ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and (bromomethyl)cyclohexane (401 mg, 2.27 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=1:1). Recrystallization from ethyl acetate-hexane gave the objective substance (129 mg, 27%).

$^1$H-NMR (CDCl$_3$)δ: 0.90–1.45 (6H, m), 1.66–2.10 (7H, m), 2.12–2.28 (2H, m), 2.60–2.72 (2H, m), 2.79 (1H, dd, J=14.8, 10.6 Hz), 3.03 (1H, dd, J=14.8, 4.0 Hz), 3.38 (1H, d, J=3.4 Hz), 3.77 (2H, d, J=5.8 Hz), 4.64–4.80 (1H, m), 4.90–5.02 (1H, m), 5.74 (1H, d, J=8.8 Hz), 5.62–6.24 (3H, m), 6.88–7.20 (7H, m), 7.20–7.42 (4H, m). IR ν max$^{KBr}$ cm$^{-1}$: 1644, 1613, 1586, 1512, 1451. mp 141–142° C. Anal. Calcd for C$_{36}$H$_{39}$NO$_4$F$_4$: C, 69.11; H, 6.28; N, 2.24. Found: C, 69.05; H, 6.47; N, 2.14.

Example 247

N-{(1RS,2SR)-2-hydroxy-2-[4-(3-phenoxypropoxy) phenyl]-1-[3-(1,1,2,2-tetrafluoroethoxy)benzyl] ethyl}-6,7-dihydro-5H-benzo[a][7]annulene-1-carboxamide To a solution of N-{(1RS,2SR)-2-hydroxy-2-(4-hydroxyphenyl)-1-[3-(1,1,2,2-tetrafluoroethoxy)benzyl] ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and 3-phenoxy-1-bromopropane (487 mg, 2.27 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1). Recrystallization from ethyl acetate-hexane gave the objective substance (245 mg, 50%).

$^1$H-NMR (CDCl$_3$)δ: 1.92–2.02 (2H, m), 2.12–2.22 (2H, m), 2.22–2.32 (2H, m), 2.62–2.70 (2H, m), 2.76 (1H, dd, J=14.4, 10.2 Hz), 3.00 (1H, dd, J=14.4, 3.9 Hz), 3.39 (1H, d, J=3.6 Hz), 4.14–4.22 (4H, m), 4.64–4.76 (1H, m), 4.96–5.00 (1H, m), 5.68–6.10 (3H, m), 6.19 (1H, d, J=11.7 Hz), 6.88–7.00 (6H, m), 7.00–7.16 (5H, m), 7.24–7.40 (5H, m). IR ν max$^{KBr}$cm$^{-1}$: 1644, 1613, 1601, 1588, 1512, 1499. mp 142–143° C. Anal. Calcd for C$_{38}$H$_{37}$NO$_5$F$_4$: C, 68.77; H, 5.62; N, 2.11. Found: C, 68.67;, H, 5.38; N, 1.92.

Example 248 methyl 4-[(4-{(1RS,2SR)-2-[(6,7-dihydro-5H-benzo [a][7]annulen-1-ylcarbonyl)amino]-1-hydroxy-3-[3-(1,1,2,2-tetrafluoroethoxy)phenyl]propyl}phenoxy) methyl]benzoate To a solution of N-{(1RS,2SR)-2-hydroxy-2-(4-hydroxyphenyl)-1-[3-(1,1,2,2-tetrafluoroethoxy)benzyl] ethyl}-6,7-dihydro-5H-benzo[a][7]annulene-1-carboxamide (600 mg, 1.13 mmol) in N,N-dimethylformamide (20 ml) were added potassium carbonate (470 mg, 3.40 mmol) and methyl 4-(bromomethyl)-benzoate (780 mg, 3.40 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (361 mg, 47%).

$^1$H-NMR (CDCl$_3$)δ: 1.90–2.08 (2H, m), 2.10–2.24 (2H, m), 2.60–2.70 (2H, m), 2.78 (1H, dd, J=14.2, 10.4 Hz), 3.02 (1H, dd, J=14.2, 4.0 Hz), 3.39 (1H, s), 3.92 (3H, s), 4.60–4.80 (1H, m), 4.98 (1H, s), 5.13 (2H, s), 5.72 (1H, d, J=8.8 Hz), 5.60–6.24 (3H, m), 6.90–7.18 (8H, m), 7.20–7.36 (1H, m), 7.38 (2H, d, J=8.4 Hz), 7.51 (2H, d, J=8.0. Hz), 8.06 (2H, d, J=8.0 Hz). IR ν max$^{KBr}$cm$^{-1}$: 1719, 1640, 1613, 1586, 1510, 1437. mp 169–170° C. Anal. Calcd for C$_{38}$H$_{35}$F$_4$NO$_6$: C, 67.35; H, 5.21; N, 2.07. Found: C, 67.19; H, 4.94; N, 1.83.

Example 249

(4-{(1RS,2SR)-2-[(6,7-dihydro-5H-benzo[a][7] annulen-1-ylcarbonyl)amino]-1-hydroxy-3-[3-(1,1,2, 2-tetrafluoroethoxy)phenyl]propyl}phenoxy)ethyl acetate To a solution of N-{(1RS,2SR)-2-hydroxy-2-(4-hydroxyphenyl)-1-[3-(1,1,2,2-tetrafluoroethoxy)benzyl] ethyl}-6,7-dihydro-5H-benzo[a][7]annulene-1-carboxamide (600 mg, 1.13 mmol) in N,N-dimethylformamide (20 ml) were added potassium carbonate (470 mg, 3.40 mmol) and ethyl bromoacetate (570 mg, 3.40 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1). Recrystallization from ethyl acetate-hexane gave the objective substance (167 mg, 24%).

$^1$H-NMR (CDCl$_3$)δ: 1.30 (3H, t, J=7.2 Hz), 1.90–2.08 (2H, m), 2.12–2.24 (2H, m), 2.58–2.70 (2H, m), 2.77 (1H, dd, J=14.1, 10.8 Hz), 3.00 (1H, dd, J=14.1, 3.9 Hz), 3.48 (1H, d, J=3.6 Hz), 4.28 (2H, q, J=7.2 Hz), 4.63 (2H, s), 4.60–4.76 (1H, m), 4.96–5.06 (1H, m), 5.70–6.10 (3H, m), 6.21 (1H, d, J=11.7 Hz), 6.88–7.20 (8H, m), 7.26–7.38 (1H, m), 7.38 (2H, d, J=8.7 Hz). IR ν max$^{KBr}$cm$^{-1}$: 1755, 1645, 1613, 1588, 1512, 1449. mp 125–126° C. Anal. Calcd for C$_{33}$H$_{33}$F$_4$NO$_6$: C, 64.38; H, 5.40; N, 2.28. Found: C, 64.15; H, 5.36; N, 2.02.

Example 250

4-[(4-{(1RS,2SR)-2-[(6,7-dihydro-5H-benzo[a][7] annulen-1-ylcarbonyl)amino]-1-hydroxy-3-[3-(1,1,2, 2-tetrafluoroethoxy)phenyl]propyl}phenoxy)methyl] benzoic acid To a solution of methyl 4-[(4-{(1RS,2SR)-2-[(6,7-dihydro-5H-benzo[a][7]annulen-1-ylcarbonyl)amino]-1-hydroxy-3-[3-(1,1,2,2-tetrafluoroethoxy)phenyl] propyl}phenoxy)methyl]-benzoate (260 mg, 0.384 mmol) in methanol (10 ml) was added 2N aqueous sodium hydroxide solution (0.38 ml, 0.76 mmol), and the mixture was stirred at 60° C. overnight. The reaction solution was acidified with 1N hydrochloric acid and extracted with ethyl acetate (100 ml×2). The extract was washed with water and saturated brine, dried (anhydrous magnesium sulfate) and evaporated under reduced pressure. Recrystallization of the residue from ethyl acetate-hexane gave the objective substance (209 mg, 82%).

$^1$H-NMR (CDCl$_3$)δ: 1.90–2.06 (2H, m), 2.10–2.26 (2H, m), 2.60–2.80 (2H, m), 2.77 (1H, dd, J 14.6, 10.6 Hz), 3.03

(1H, dd, J=14.6, 4.4 Hz), 4.62–4.80 (1H, m), 4.99 (1H, d, J=3.6 Hz), 5.15 (2H, s), 5.75 (1H, d, J=8.8 Hz), 5.58–6.24 (3H, m), 6.90–7.20 (8H, m), 7.20–7.40 (1H, m), 7.39 (2H, d, J=8.4 Hz) 7.54 (2H, d, J=8.4 Hz), 8.12 (2H, d, J=8.2 Hz). IR ν max$^{KBr}$cm$^{-1}$: 1696, 1640, 1613, 1586, 1510, 1489, 1449. mp 190–191° C. Anal. Calcd for $C_{37}H_{33}F_4NO_6$: C, 66.96; H, 5.01; N, 2.11. Found: C, 66.86; H, 4.88; N, 2.01.

Example 251

(4-{(1RS,2SR)-2-[(6,7-dihydro-5H-benzo[a][7] annulen-1-ylcarbonyl)amino]-1-hydroxy-3-[3-(1,1,2, 2-tetrafluoroethoxy)phenyl]propyl}phenoxy)acetic acid To a solution of ethyl (4-{(1RS,2SR)-2-[(6,7-dihydro-5H-benzo[a][7]annulen-1-ylcarbonyl)amino]-1-hydroxy-3-[3-(1,1,2,2-tetrafluoroethoxy)phenyl]propyl}phenoxy)acetate (100 mg, 0.163 mmol) in methanol (20 ml) was added 2N aqueous sodium hydroxide solution (0.16 ml, 0.32 mmol), and the mixture was stirred overnight at room temperature. The reaction solution was acidified with 1N hydrochloric acid and extracted with ethyl acetate (100 ml×2). The extract was washed with water and saturated brine, dried (anhydrous magnesium sulfate) and evaporated under reduced pressure. The residue was purified by silica gel column chromatography (hexane:ethyl acetate=4:1-ethyl acetate-methanol=10:1). Recrystallization from ethyl acetate-hexane gave the objective substance (87 mg, 91%).

$^1$H-NMR (CDCl$_3$)δ: 1.86–2.04 (2H, m), 2.10–2.24 (2H, m), 2.58–2.70 (2H, m), 2.75 (1H, dd, J=14.6, 10.6 Hz), 2.98 (1H, dd, J=14.6, 3.6 Hz), 4.50–4.96 (5H, m), 4.96 (1H, d, J=3.8 Hz), 5.58–6.20 (4H, m), 6.82–7.20 (8H, m), 7.20–7.40 (3H, m). IR ν max$^{KBr}$cm$^{-1}$: 1744, 1640, 1613, 1588, 1512. mp 119–120° C. Anal. Calcd for $C_{31}H_{29}NO_6F_4·0.2H_2O$: C, 62.99; H, 5.01; N, 2.37. Found: C, 62.82; H, 5.13; N, 2.32.

Example 252

N-{(1RS,2SR)-2-hydroxy-2-(3-hydroxyphenyl)-1-[3-(1,1,2,2-tetrafluoroethoxy)benzyl]ethyl}-6,7-dihydro-5H-benzo[a][7]annulene-1-carboxamide 1) 3-{(1RS,2SR)-2-amino-1-hydroxy-3-[3-(1,1,2,2-tetrafluoroethoxy)phenyl]propyl}phenol To a solution of (1RS,2SR)-2-amino-1-[3-(benzyloxy)phenyl]-3-[3-(1,1,2,2-tetrafluoroethoxy)phenyl]propan-1-ol (5.50 g, 12.23 mmol) in ethanol (100 ml) was added 10% palladium/carbon (containing water by 50%, 500 mg), and the mixture was stirred under a hydrogen stream overnight. The catalyst was removed from the reaction solution using celite, and the filtrate was concentrated to give the objective substance (4.04 g, 92%, crude). To obtain data, a portion was purified by alumina column chromatography (ethanol) and recrystallized from diisopropyl, ether-hexane.

$^1$H-NMR (CDCl$_3$)δ: 2.47 (1H, t, J=12.6 Hz), 2.99 (1H, d, J=13.5 Hz), 3.22 (2H, s), 3.33 (2H, brs), 4.56 (1H, d, J=3.4 Hz), 5.88 (1H, t, J=53.1 Hz), 6.70–7.40 (8H, m). IR ν max$^{KBr}$cm$^{-1}$: 1586, 1487, 1456. mp 130–131° C. Anal. Calcd for $C_{17}H_{17}F_4NO_3$: C, 56.83; H, 4.77; N, 3.90. Found: C, 56.73; H, 4.59; N, 3.79.

2) N-{(1RS,2SR)-2-hydroxy-2-(3-hydroxyphenyl)-1-[3-(1,1,2,2-tetrafluoroethoxy)benzyl]ethyl}-6,7-dihydro-5H-benzo[a][7]annulene-1-carboxamide To a solution of 3-{(1RS,2SR)-2-amino-1-hydroxy-3-[3-(1,1,2,2-tetrafluoroethoxy)phenyl]propyl}phenol (2.89 g, 8.04 mmol) in acetonitrile (50 ml) were added 6,7-dihydro-5H-benzo[a]cycloheptene-1-carboxylic acid (1.51 g, 8.04 mmol), 1-ethyl-3-(3-dimethylaminopropyl)carbodiimide hydrochloride (2.31 g, 12.06 mmol) and 1-hydroxybenzotriazole hydrate (1.23 g, 8.04 mmol), and the mixture was stirred overnight at room temperature. The reaction solution was diluted with water (200 ml) and extracted with ethyl acetate (200 ml×2). The extract was washed successively with 1N hydrochloric acid, saturated aqueous sodium hydrogen carbonate and saturated brine, dried (anhydrous magnesium sulfate) and evaporated under reduced pressure. The residue was purified by silica gel column chromatography (hexane:ethyl acetate=2:1–1:1) to give the objective substance (2.75 g, 65%) as an amorphous compound.

$^1$H-NMR (CDCl$_3$)δ: 1.88–2.00 (2H, m), 2.08–2.18 (2H, m), 2.54–2.64 (2H, m), 2.74 (1H, dd, J=14.4, 10.5 Hz), 2.98 (1H, dd, J=14.4, 7.5 Hz), 4.07 (1H, brs), 4.64–4.78 (1H, m), 4.86–4.92 (1H, m), 5.66–6.04 (4H, m), 6.72–6.80 (1H, m), 6.84–7.28 (9H, m), 7.58 (1H, brs). IR ν max$^{KBr}$cm$^{-1}$: 1636, 1588, 1520, 1489, 1453. Anal. Calcd for $C_{29}H_{27}NO_4F_4·0.2H_2O$: C, 65.34; H, 5.18; N, 2.63. Found: C, 65.27; H, 5.34; N, 2.45.

Example 253

N-{(1RS,2SR)-2-hydroxy-2-(3-methoxyphenyl)-1-[3-(1,1,2,2-tetrafluoroethoxy)benzyl]ethyl}-6,7-dihydro-5H-benzo[a][7]annulene-1-carboxamide To a solution of N-{(1RS,2SR)-2-hydroxy-2-(3-hydroxyphenyl)-1-[3-(1,1,2,2-tetrafluoroethoxy)benzyl]ethyl}-6,7-dihydro-5H-benzo[a][7]annulene-1-carboxamide (400 mg, 0.755 mmol) in N,N-dimethylformamide (15 ml) were added potassium carbonate (313 mg, 2.27 mmol) and methyl iodide (2 ml), and the mixture was stirred overnight at room temperature. The reaction solution was diluted with water (100 ml) and extracted with ethyl acetate (100 ml×2). The extract was is washed successively with water and saturated brine, dried (anhydrous magnesium sulfate) and evaporated under reduced pressure. The residue was purified by silica gel column chromatography (hexane:ethyl acetate= 2:1). Recrystallization from ethyl acetate-hexane gave the objective substance (115 mg, 28%).

$^1$H-NMR (CDCl$_3$)δ: 1.90–2.06 (2H, m), 2.12–2.26 (2H, m), 2.60–2.70 (2H, m), 2.79 (1H, dd, J=14.2, 10.6 Hz), 3.00 (1H, dd, J=14.2, 4.0 Hz), 3.47 (1H, d, J=3.6 Hz), 3.81 (3H, s), 4.64–4.80 (1H, m), 5.00–5.06 (1H, m), 5.79 (1H, d, J=8.4 Hz), 5.60–6.26 (3H, m), 6.80–6.90 (1H, m), 6.90–7.20 (7H, m), 7.20–7.38 (3H, m). IR ν max$^{KBr}$cm$^{-1}$: 1640, 1611, 1588, 1514, 1489, 1453, 1439. mp 155–156° C. Anal. Calcd for $C_{30}H_{29}F_4NO_4$: C, 66.29; He 5.38; N, 2.58. Found: C, 66.06; H, 5.08; N, 2.36.

Example 254 tert-butyl (1RS,2RS)-2-hydroxy-2-(5-phenoxypyridin-2-yl)-1-[3-(1,1,2,2-tetrafluoroethoxy)benzyl]ethylcarbamate 1) 2-methyl-5-phenoxypyridine To a solution of 6-methylpyridin-3-ol (25.2 g, 231 mmol) in N,N-dimethylformamide (100 ml) was added potassium tert-butoxide (25.9 g, 231 mmol), and the mixture was stirred at room temperature for 1 hr. The reaction solution was evaporated under reduced pressure and diluted with N,N-dimethylformamide (100 ml). A copper powder (3.7 g, 58 mmol) and bromobenzene (36.3 g, 231 mmol) were added, and the mixture was stirred at 120° C. overnight. Methanol was added to the reaction solution and insoluble material was filtered off using celite. The filtrate was diluted with water (500 ml) and the mixture was extracted with ethyl acetate (500 ml×2). The extract was washed successively with water and saturated brine, dried (anhydrous magnesium sulfate) and evaporated under reduced pressure. The residue was purified by silica gel column chromatography (hexane:ethyl acetate=4:1) to give the objective substance (31 g, 72%).

$^1$H-NMR (CDCl$_3$)δ: 2.55 (3H, s), 6.94–7.04 (2H, m), 7.06–7.40 (5H, m), 8.30 (1H, d, J=2.4 Hz). IR ν max$^{KBr}$ cm$^{-1}$: 1603, 1590, 1574, 1483, 1385. Anal. Calcd for C$_{12}$H$_{11}$NO: C, 77.81; H, 5.99; N, 7.56. Found: C, 77.51; H, 5.99; N, 7.41.

2) 5-phenoxypyridine-2-carboxylic acid

To a solution of 2-methyl-5-phenoxypyridine (30 g, 162 mmol) in pyridine (90 ml) was added selenium dioxide (18.0 g, 162 mmol), and the mixture was stirred at 110° C. overnight. The reaction solution was filtered with celite and the filtrate was concentrated. The residue was diluted with chloroform (300 ml), washed successively with 0.2N aqueous hydrochloric acid solution, water and saturated brine, dried (anhydrous magnesium sulfate), and evaporated under reduced pressure. The residue was recrystallized from ethanol to give the objective substance (10.1 g, 29%).

$^1$H-NMR (CDCl$_3$)δ: 7.04–7.18 (2H, m), 7.20–7.54 (4H, m), 8.18 (1H, d, J=8.4 Hz), 8.43 (1H, d, J=2.6 Hz), 9.59 (1H, brs). IR ν max$^{KBr}$cm$^{-1}$: 1705, 1574, 1489. mp 149–150° C. Anal. Calcd for C$_{12}$H$_9$NO$_3$: C, 66.97; H, 4.22; N, 6.51. Found: C, 66.99; H, 4.04; N, 6.42.

3) benzyl 3-oxo-3-(5-phenoxypyridin-2-yl)propanoate

To a solution of 5-phenoxypyridine-2-carboxylic acid (10 g, 46.5 mmol) in tetrahydrofuran (150 ml) was added N,N'-carbonyldiimidazole (8.29. g, 51.1 mmol), and the mixture was heated under reflux for 1 hr. After cooling the reaction solution to room temperature, monobenzyl malonate magnesium salt (10.5 g, 25.6 mmol) was added, and the mixture was heated under reflux for 2 hrs. The reaction solution was concentrated, and the residue was purified by silica gel column chromatography (hexane:ethyl acetate=2:1) to give the objective substance (11.2 g, 76%).

$^1$H-NMR (CDCl$_3$)δ: 4.19 (2H, s), 5.18 (2H, s), 7.00–7.50 (11H, m), 8.04 (1H, d, J=8.8 Hz), 8.28 (1H, d, J=3.0 Hz). IR ν max$^{KBr}$cm$^{-1}$: 1740, 1699, 1640, 1570, 1489, 1472.

4) benzyl 3-oxo-3-(5-phenoxypyridin-2-yl)-2-[3-(1,1,2,2-tetrafluoroethoxy)benzyl]propanoate To a solution of [3-(1,1,2,2-tetrafluoroethoxy)phenyl]-methanol (8.29 g, 37.0 mmol) in ethyl acetate (100 ml) were added methanesulfonyl chloride (3.15 ml, 40.68 mmol) and triethylamine (6.19 ml, 44.4 mmol), and the mixture was stirred at room temperature for 2 hrs. Insoluble material was filtered off, and the filtrate was evaporated under reduced pressure to give a mesyl form. To a solution of benzyl 3-oxo-3-(5-phenoxypyridin-2-yl)propanoate (11.2 g, 35.1 mmol) in 1,2-dimethoxyethane (80 ml) was added sodium hydride (1.41 g, 60% in oil, 35.1 mmol), and the mixture was stirred at room temperature for 1 hr. To the reaction solution was dropwise added a solution of the mesyl form prepared earlier in 1,2-dimethoxyethane (10 ml), and the mixture was stirred at 70° C. overnight. The reaction solution was acidified with 1N hydrochloric acid, neutralized with saturated aqueous sodium hydrogen carbonate and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=4:1) to give the objective substance (9.32 g, 48%, crude). The present compound was used for next reaction as a crude compound.

5) benzyl 3-hydroxy-3-(5-phenoxypyridin-2-yl)-2-[3-(1,1,2,2-tetrafluoroethoxy)benzyl]propanoate To a solution of zinc chloride (4.57 g, 33.6 mmol) in diethyl ether (100 ml) was added sodium borohydride (2.54 g, 67.1 mmol), and the mixture was stirred at room temperature for 30 min. Insoluble material was filtered off, and to the filtrate was added a solution of benzyl 3-oxo-3-(5-phenoxypyridin-2-yl)-2-[3-(1,1,2,2-tetrafluoroethoxy)-benzyl]propanoate (9.32 g, 16.8 mmol, crude) in diethyl ether (100 ml) at 0° C. The mixture was stirred for 30 min. and 1N hydrochloric acid was added to stop the reaction. After neutralization with saturated aqueous sodium hydrogen carbonate, water (200 ml) was further added and the mixture was extracted with ethyl acetate (500 ml×2). The extract was washed with water and saturated brine, dried (anhydrous magnesium sulfate) and evaporated under reduced pressure. The residue was purified by silica gel column chromatography (hexane:ethyl acetate=2:1–1:1) to give the objective substance (5.07 g, 54%, crude). The present compound was used for the next reaction as a crude compound.

6) 3-hydroxy-3-(5-phenoxypyridin-2-yl)-2-[3-(1,1,2,2-tetrafluoroethoxy)benzyl]propanoic acid To a solution of benzyl 3-hydroxy-3-(5-phenoxypyridin-2-yl)-2-[3-(1,1,2,2-tetrafluoroethoxy)benzyl]propanoic acid (5.07 g, 9.09 mmol, crude) in ethanol (500 ml) was added 10% palladium/carbon (containing water by 50%) (500 mg), and the mixture was stirred overnight under a 1 atm hydrogen stream. The reaction solution was filtered with celite, and the filtrate was concentrated to give the objective substance (4.22 g, 100%, crude). The present compound was used for the next reaction as a crude compound.

7) 5-(5-phenoxypyridin-2-yl)-4-[3-(1,1,2,2-tetrafluoroethoxy)benzyl]-1,3-oxazolidin-2-one To a solution of 3-hydroxy-3-(5-phenoxypyridin-2-yl)-2-[3-(1,1,2,2-tetrafluoroethoxy)benzyl]propanoic acid (4.22 g, 9.07 mmol, crude) in tetrahydrofuran (200 ml) were added diphenylphosphoryl azide (2.15 ml, 9.97 mmol) and triethylamine (1.90 mmol, 13.6 mmol), and the mixture was heated under reflux for 3 hrs. The reaction solution was allowed to cool and water (100 ml) was added. The mixture was extracted with ethyl acetate (100 ml×2). The extract was washed successively with 1N hydrochloric acid, aqueous sodium hydrogen carbonate solution and saturated brine, dried (anhydrous magnesium sulfate) and evaporated under reduced pressure. The residue was purified by silica gel column chromatography (hexane:ethyl acetate=2:1–1:1) to give the objective substance in a (4RS,5RS) form (1.06 g, highly polar component, 25%) and a (4RS,5SR) form (1.94 g, less polar component, 46%, recrystallized from hexane-ethyl acetate). (4RS,5RS) form: $^1$H-NMR (CDCl$_3$)δ: 2.04–2.22 (1H, m), 2.53 (1H, dd, J=14.0, 3.4 Hz), 4.38–4.50 (1H, m), 5.12 (1H, s), 5.87 (1H, d, J=8.4 Hz), 5.90 (1H, tt, J=53.2, 3.0 Hz), 6.90–7.48 (10H, m), 7.54 (1H, d, J=8.4 Hz), 8.39 (1H, d, J=2.6 Hz). IR ν max$^{KBr}$cm$^{-1}$: 1761, 1588, 1574, 1487. (4RS,5SR) form: $^1$H-NMR (CDCl$_3$)δ: 2.98 (1H, dd, J=13.6, 9.2 Hz), 3.28 (1H, dd, J=13.6, 4.4 Hz), 4.20–4.34 (1H, m), 5.12 (1H, brs), 5.32 (1H, d, J=5.4 Hz), 5.91 (1H, tt, J=53.2, 3.0 Hz), 7.00–7.48 (11H, m), 8.38 (1H, d, J=2.4 Hz). IR ν max$^{KBr}$cm$^{-1}$1761, 1588, 1576, 1489. mp 87–88° C. Anal. Calcd for C$_{23}$H$_{18}$F$_4$N$_2$O$_4$: C, 59.74; H, 3.92; N, 6.06. Found: C, 59.70; H, 3.81; N, 6.03.

8) tert-butyl (4RS,5RS)-2-oxo-5-(5-phenoxypyridin-2-yl)-4-[3-(1,1,2,2-tetrafluoroethoxy)benzyl]-1,3-oxazolidine-3-carboxylate To a solution of (4RS,5RS)-5-(5-phenoxypyridin-2-yl)-4-[3-(1,1,2,2-tetrafluoroethoxy)benzyl]-1,3-oxazolidin-2-one (1.01 g, 2.18 mmol) in acetonitrile (15 ml) were added di-tert-butyl dicarbonate (571 mg, 2.62 mmol) and 4-N,N-dimethylpyridine (26.9 mg, 0.22 mmol), and the mixture was stirred at room temperature for 1 hr. To the reaction solution was added water (50 ml) and the mixture was extracted with ethyl acetate (50 ml×2). The extract was washed successively with water and saturated brine, dried (anhydrous magnesium sulfate) and evaporated under reduced pressure. The residue was purified by silica gel column chromatography (hexane:ethyl acetate=10:1–1:1). Recrystallization from ethyl acetate-hexane gave the objective substance (1.07 g, 87%).

$^1$H-NMR (CDCl$_3$)δ: 1.44 (9H, s), 2.66 (1H, dd, J=14.2, 7.4 Hz), 2.83 (1H, dd, J=14.2, 5.8 Hz), 5.02 (1H, q, J=7.0 Hz), 5.70 (1H, d, J=7.0 Hz), 5.88 (1H, tt, J=53.0, 3.0 Hz), 6.60 (1H, s), 6.76 (1H, d, J=7.6 Hz), 6.98–7.10 (3H, m), 7.10–7.32 (3H, m), 7.34–7.50 (3H, m), 8.18 (1H, d, J=3.0 Hz). IR ν max$^{KBr}$cm$^{-1}$: 1825, 1725, 1588, 1574, 1489. mp 113–114° C. Anal. Calcd for C$_{28}$H$_{26}$N$_2$O$_6$F$_4$: C, 59.79; H, 4.66; N, 4.98. Found: C, 59.75; H, 4.58; N, 4.90.

9) tert-butyl (1RS,2RS)-2-hydroxy-2-(5-phenoxypyridin-2-yl)-1-[3-(1,1,2,2-tetrafluoroethoxy)benzyl]ethylcarbamate To a solution of tert-butyl (4RS,5RS)-2-oxo-5-(5-phenoxypyridin-2-yl)-4-[3-(1,1,2,2-tetrafluoroethoxy)benzyl]-1,3-oxazolidine-3-carboxylate (1.00 g, 1.78 mmol) in methanol (12 ml) was added a solution (4.3 ml, 2.13 mmol) of 0.5N sodium hydroxide in methanol, and the mixture was stirred at room temperature for 1 hr. To the reaction solution was added water (50 ml), and the mixture was extracted with ethyl acetate (50 ml×2). The extract was washed with saturated brine, dried (anhydrous magnesium sulfate) and evaporated under reduced pressure. The residue was recrystallized from ethyl acetate-hexane to give the objective substance (0.81 g, 85%).

$^1$H-NMR (CDCl$_3$)δ: 1.37 (9H, s), 2.58 (1H, dd, J=14.6, 5.4 Hz), 2.78 (1H, dd, J=14.6, 8.8 Hz), 4.10–4.30 (1H, m), 4.76 (1H, d, J=5.6 Hz), 4.84–4.96 (1H, m), 5.13 (1H, d, J=9.0 Hz), 5.89 (1H, tt, J=53.0, 3.0 Hz), 6.90–7.10 (5H, m), 7.12–7.30 (4H, m), 7.30–7.48 (2H, m), 8.32 (1H, s). IR ν max$^{KBr}$cm$^{-1}$: 1694, 1588, 1483. mp 129–130° C. Anal. Calcd for C$_{27}$H$_{28}$F$_4$N$_2$O$_5$: C, 60.44; H, 5.26; N, 5.22. Found: C, 60.21; H, 5.23; N, 5.22.

Example 255

N-{(1RS,2RS)-2-hydroxy-2-(5-phenoxypyridin-2-yl)-1-[3-(1,1,2,2-tetrafluoroethoxy)benzyl]ethyl}-6,7-dihydro-5H-benzo[a][7]annulene-1-carboxamide Trifluoroacetic acid (5 ml) was added to tert-butyl (1RS,2RS)-2-hydroxy-2-(5-phenoxypyridin-2-yl)-1-[3-(1,1,2,2-tetrafluoroethoxy)benzyl]ethylcarbamate (300 mg, 0.56 mmol), and the mixture was stirred at 0° C. for 10 min. The reaction solution was neutralized with saturated aqueous sodium hydrogen carbonate, and extracted with ethyl acetate (20 ml×2). The extract was washed with saturated brine, dried (anhydrous magnesium sulfate) and evaporated under reduced pressure. To the residue in acetonitrile (20 ml) were added 6,7-dihydro-5H-benzo[a]cycloheptene-1-carboxylic acid (105 mg, 0.56 mmol), 1-ethyl-3-(3-dimethylaminopropyl)carbodiimide hydrochloride (161 mg, 0.84 mmol) and 1-hydroxybenzotriazole hydrate (86 mg, 0.56 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1). Recrystallization from ethyl acetate-hexane gave the objective substance (140 mg, 41%).

$^1$H-NMR (CDCl$_3$)δ: 1.92–2.12 (2H, m), 2.18–2.30 (2H, m), 2.64–2.80 (3H, m), 2.94 (1H, dd, J=14.8, 9.6 Hz), 4.78–4.92 (1H, m), 4.96 (1H, d, J=5.4 Hz), 5.02–5.10 (1H, m), 5.91 (1H, tt, J=53.0, 3.0 Hz), 5.94–6.04 (1H, m), 6.30–6.44 (2H, m), 7.00–7.50 (14H, m), 8.34 (1H, d, J=2.6 Hz). IR ν max$^{KBr}$cm$^{-1}$: 1638, 1588, 1572, 1483. mp 147–148° C. Anal. Calcd for C$_{34}$H$_{30}$F$_4$N$_2$O$_4$: C, 67.32; H, 4.98; N, 4.62. Found: C, 67.16; H, 4.79; N, 4.52.

Example 256

4-fluoro-N-{(1RS,2RS)-2-hydroxy-2-(5-phenoxypyridin-2-yl)-1-[3-(1,1,2,2-tetrafluoroethoxy)benzyl]ethyl}-1-naphthamide To tert-butyl (1RS,2RS)-2-hydroxy-2-(5-phenoxypyridin-2-yl)-1-[3-(1,1,2,2-tetrafluoroethoxy)benzyl]ethylcarbamate (300 mg, 0.56 mmol) was added trifluoroacetic acid (5 ml), and the mixture was stirred at 0° C. for 10 min. The reaction solution was neutralized with saturated aqueous sodium hydrogen carbonate and extracted with ethyl acetate (20 ml×2). The extract was washed with saturated brine, dried (anhydrous magnesium sulfate) and evaporated under reduced pressure. To a solution of the residue in acetonitrile (20 ml) were added 4-fluoronaphthalenecarboxylic acid (106 mg, 0.56 mmol), 1-ethyl-3-(3-dimethylaminopropyl)carbodiimide hydrochloride (161 mg, 0.84 mmol) and 1-hydroxybenzotriazole hydrate (86 mg, 0.56 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1). Recrystallization from ethyl acetate-hexane gave the objective substance (133 mg, 39%).

$^1$H-NMR (CDCl$_3$)δ: 2.72 (1H, dd, J=14.4, 4.5 Hz), 2.92 (1H, dd, J=14.7, 9.6 Hz), 4.88–5.00 (2H, m), 5.10–5.16 (1H, m), 5.88 (1H, tt, J=53.1, 3.0 Hz), 6.55 (1H, d, J=9.0 Hz), 7.00–7.60 (15H, m), 7.98 (1H, d, J=8.1 Hz), 8.10 (1H, d, J=8.1 Hz), 8.34 (1H, d, J=2.7 Hz). IR ν max$^{KBr}$cm$^{-1}$: 1642, 1626, 1601, 1586, 1535, 1485. mp 146–147° C. Anal. Calcd for C$_{33}$H$_{25}$F$_5$N$_2$O$_4$: C, 65.13; H, 4.14; N, 4.60. Found: C, 64.99; H, 4.11; N, 4.53.

Example 257 tert-butyl (1RS,2SR)-2-hydroxy-2-[4-(pyridin-2-yloxy)phenyl]-1-[3-(1,1,2,2-tetrafluoroethoxy)benzyl]ethylcarbamate 1) benzyl 4-(pyridin-2-yloxy)benzoate To a solution of benzyl 4-hydroxybenzoate (25.3 g, 111 mmol) in N,N-dimethylformamide (60 ml) was added potassium tert-butoxide (12.4 g, 111 mmol), and the mixture was stirred at room temperature for 1 hr. The reaction solution was evaporated under reduced pressure and 2-bromopyridine (24.5 g, 155 mmol), a copper powder (1.76 g, 27.7 mmol) and N,N-imethylformamide (80 ml) were added. The mixture was stirred at 120° C. for 8 hrs. The reaction solution was filtered with celite, and the filtrate was evaporated under reduced pressure. To the residue was added water (500 ml), and the mixture was extracted with ethyl acetate (500 ml). The extract was washed successively with water and saturated brine, dried (anhydrous magnesium sulfate) and evaporated under reduced pressure. The residue was purified by silica gel column chromatography (hexane:ethyl acetate=10:1). Recrystallization from ethyl acetate-hexane gave the objective substance (25.5 g, 73%).

$^1$H-NMR (CDCl$_3$)δ: 5.36 (2H, s), 6.97 (1H, d, J=8.4 Hz), 7.00–7.10 (1H, m), 7.16–7.22 (2H, m), 7.30–7.48 (5H, m), 7.68–7.78 (1H, m), 8.08–8.16 (2H, m), 8.18–8.24 (1H, m). IR ν max$^{KBr}$cm$^{-1}$: 1717, 1589, 1574, 1505, 1466, 1429. mp 68–69° C. Anal. Calcd for C$_{19}$H$_{15}$NO$_3$: C, 74.74; H, 4.95; N, 4.59. Found: C, 74.90; H, 5.14; N, 4.67.

2) 4-(pyridin-2-yloxy)benzoic acid

To a solution of benzyl 4-(pyridin-2-yloxy)benzoate (24.8 g, 81.5 mmol) in ethanol (300 ml) was added 10% palladium/carbon (containing water by 50%) (2.0 g), and the mixture was stirred overnight under a hydrogen stream at 80° C. The reaction solution was filtered with celite and the filtrate was concentrated. The residue was recrystallized from ethanol to give the objective substance (14.1 g, 80%).

$^1$H-NMR (CDCl$_3$)δ: 7.04–7.20 (2H, m), 7.20–7.52 (4H, m), 8.18 (1H, d, J=8.4 Hz), 8.43 (1H, d, J=2.6 Hz), 9.59 (1H, brs). IR ν max$^{KBr}$cm$^{-1}$: 1682, 1599, 1588, 1570, 1508. mp 175–176° C. Anal. Calcd for C$_{12}$H$_9$NO$_3$: C, 66.97; H, 4.22; N, 6.51. Found: C, 66.78; H, 3.94; N, 6.37.

3) benzyl 3-oxo-3-[4-(pyridin-2-yloxy)phenyl]propanoate

To 4-(pyridin-2-yloxy)benzoic acid (20 g, 92.9 mmol) in tetrahydrofuran (300 ml) was added N,N'-carbonyldiimidazole (16.6 g, 102 mmol), and the mixture was heated under reflux for 1 hr. After cooling the reaction solution to room temperature, monobenzyl malonate magnesium salt (21 g, 51.2 mmol) was added, and the mixture was heated under reflux for 2 hrs. The reaction solution was concentrated and the residue was purified by silica gel column chromatography (hexane:ethyl acetate=2:1) to give the objective substance (20.6 g, 64%).

$^1$H-NMR (CDCl$_3$)δ: 4.03 (2H, s), 5.17 (2H, s), 6.90–7.50 (7H, m), 7.70–7.88 (2H, m), 7.90–8.02 (2H, m), 8.10–8.24 (2H, m). IR ν max$^{KBr}$cm$^{-1}$: 1740, 1684, 1590, 1572, 1505, 1466, 1429. Anal. Calcd for C$_{21}$H$_{17}$NO$_4$: C, 72.61; H, 4.93; N, 4.03. Found: C, 72.48; H, 4.88; N, 4.06.

4) benzyl 3-oxo-3-[4-(pyridin-2-yloxy)phenyl]-2-[3-(1,1,2,2-tetrafluoroethoxy)benzyl]propanoate To a solution of [3-(1,1,2,2-tetrafluoroethoxy)phenyl] methanol (6.79 g, 30.3 mmol) in ethyl acetate (100 ml) were added methanesulfonyl chloride (2.58 ml, 33.3 mmol) and triethylamine (5.07 ml, 36.4 mmol), and the mixture was stirred at room temperature for 2 hrs. Insoluble material was filtered off, and the filtrate was evaporated under reduced pressure to give a mesyl form. To a solution of benzyl 3-oxo-3-[4-(pyridin-2-yloxy)phenyl]propanoate (10 g, 28.8 mmol) in 1,2-dimethoxyethane (80 ml) was added sodium hydride (1.15 g, 60% in oil, 28.8 mmol), and the mixture was stirred at room temperature for 1 hr. To the reaction solution was dropwise added a solution of the mesyl form prepared earlier in 1,2-dimethoxyethane (10 ml), and the reaction solution was stirred at 60° C. overnight. The reaction solution was acidified with 1N hydrochloric acid, neutralized with saturated aqueous sodium hydrogen carbonate and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=4:1) to give the objective substance (13.0 g, 74%).

$^1$H-NMR (CDCl$_3$)δ: 3.35 (2H, d, J=7.5 Hz), 4.63 (1H, t, J=7.5 Hz), 5.08 (2H, s), 5.88 (1H, tt, J=53.1, 3.0 Hz), 6.98–7.20 (13H, m), 7.72–7.80 (1H, m), 7.96–8.02 (2H, m), 8.20–8.26 (1H, m). IR ν max$^{KBr}$cm$^{-1}$: 1738, 1684, 1590, 1580.

5) benzyl (2RS,3RS)-3-hydroxy-3-[4-(pyridin-2-yloxy)phenyl]-2-[3-(1,1,2,2-tetrafluoroethoxy)benzyl]propanoate To a solution of zinc chloride (3.19 g, 23.4 mmol) in diethyl ether (100 ml) was added sodium borohydride (1.77 g, 67.1 mmol), and the mixture was stirred at room temperature for 30 min. Insoluble material was filtered off, and to the filtrate was added a solution of benzyl 3-oxo-3-[4-(pyridin-2-yloxy)phenyl]-2-[3-(1,1,2,2-tetrafluoroethoxy)benzyl]propanoate (6.5 g, 11.7 mmol) in diethyl ether (50 ml) at 0° C. The mixture was stirred for 30 min. and 1N hydrochloric acid was added to stop the reaction. After neutralization with saturated aqueous sodium hydrogen carbonate, water (200 ml) was added and the mixture was extracted with ethyl acetate (200 ml×2). The extract was washed with water and saturated brine, dried (anhydrous magnesium sulfate) and evaporated under reduced pressure. The residue was purified by silica gel column chromatography (hexane:ethyl acetate=2:1–1:1) to give the objective substance (4.78 g, 73%).

$^1$H-NMR (CDCl$_3$)δ: 2.83 (1H, d, J=3.0 Hz), 2.96–3.20 (3H, m), 4.84 (2H, s), 4.98–5.04 (1H, m), 5.88 (1H, tt, J=53.2, 3.0 Hz), 6.88–7.30 (13H, m), 7.30–7.44 (2H, m), 7.62–7.76 (1H, m), 8.16–8.22 (1H, m), IR ν max$^{KBr}$cm$^{-1}$: 1728, 1593, 1507, 1468, 1429.

6) (2RS,3RS)-3-hydroxy-3-[4-(pyridin-2-yloxy)phenyl]-2-[3-(1,1,2,2-tetrafluoroethoxy)benzyl]propanoic acid To a solution of benzyl (2RS,3RS)-3-hydroxy-3-[4-(pyridin-2-yloxy)phenyl]-2-[3-(1,1,2,2-tetrafluoroethoxy)benzyl]propanoate (4.99 g, 8.95 mmol) in ethanol (500 ml) was added 10% palladium/carbon (containing water by 50%, 500 mg), and the mixture was stirred under a 1 atm hydrogen stream for 2 hrs. The reaction solution was filtered with celite and the filtrate was concentrated to give the objective substance (4.50 g, 100%, crude). The present compound was used for the next reaction as a crude compound.

$^1$H-NMR (CDCl$_3$)δ: 2.90–3.10 (3H, m), 3.83 (1H, brs), 5.01 (1H, d, J=3.0 Hz), 5.87 (1H, tt, J=53.0, 3.0 Hz), 6.86–7.16 (7H, m), 7.18–7.30 (1H, m), 7.40 (2H, d, J=8.4 Hz), 7.64–7.76 (1H, m), 8.14 (1H, d, J=3.8 Hz). IR ν max$^{KBr}$cm$^{-1}$: 1717, 1597, 1508, 1470, 1431.

7) (4RS,5SR)-5-[4-(pyridin-2-yloxy)phenyl]-4-[3-(1,1,2,2-tetrafluoroethoxy)benzyl]-1,3-oxazolidin-2-one To a solution of (2RS,3RS)-3-hydroxy-3-[4-(pyridin-2-yloxy)phenyl]-2-[3-(1,1,2,2-tetrafluoroethoxy)benzyl]propanoic acid (4.49 g, 9.65 mmol, crude) in tetrahydrofuran (60 ml) were added diphenylphosphoryl azide (2.29 ml, 10.6 mmol) and triethylamine (2.02 mmol, 14.5 mmol), and the mixture was heated under reflux for 2 hrs. The reaction solution was allowed to cool and water (100 ml) was added. The mixture was extracted with ethyl acetate (100 ml×2). The extract was washed successively with aqueous sodium hydrogen carbonate solution and saturated brine, dried (anhydrous magnesium sulfate) and evaporated under reduced pressure. The residue was purified by silica gel column chromatography (hexane:ethyl acetate=2:1–1:1). Recrystallization from ethyl acetate-hexane gave the objective substance (3.56 g, 80%).

$^1$H-NMR (CDCl$_3$)δ: 2.28–2.44 (2H, m), 4.20–4.30 (1H, m), 5.20–5.30 (1H, m), 5.81 (1H, d, J=7.5 Hz), 5.90 (1H, tt, J=53.1, 2.7 Hz), 6.84–7.00 (3H, m), 7.00–7.38 (5H, m), 7.39 (2H, d, J=8.4 Hz), 7.68–7.78 (1H, m), 8.16–8.24 (1H, m). IR ν max$^{KBr}$cm$^{-1}$: 1753, 1589, 1508, 1489, 1468, 1431. mp 99–100° C. Anal. Calcd for C23H18N$_2$O$_4$F$_4$: C, 59.74; H, 3.92; N, 6.06. Found: C, 59.60; H, 3.85; N, 6.11.

8) tert-butyl (4RS,5SR)-2-oxo-5-[4-(pyridin-2-yloxy)phenyl]-4-[3-(1,1,2,2-tetrafluoroethoxy)benzyl]-1,3-oxazolidine-3-carboxylate To a solution of (4RS,5SR)-5-[4-(pyridin-2-yloxy)phenyl]-4-[3-(1,1,2,2-tetrafluoroethoxy)benzyl]-1,3-oxazolidin-2-one (3.3 g, 7.14 mmol) in acetonitrile (50 ml) were added di-tert-butyl dicarbonate (1.87 g, 8.56 mmol) and 4-N,N-dimethylpyridine (87 mg, 0.71 mmol), and the mixture was stirred at room temperature for 15 min. To the reaction solution was added water (100 ml), and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (3.46 g, 86%).

$^1$H-NMR (CDCl$_3$)δ: 1.50 (9H, s), 2.67 (1H, dd, J=14.2, 8.4 Hz), 2.89 (1H, dd, J=14.2, 4.8 Hz), 4.72–4.84 (1H, m), 5.71 (1H, d, J=7.0 Hz), 5.89 (1H, tt, J=53.1, 3.0 Hz), 6.59 (1H, d, J=7.6 Hz), 6.66 (1H, s), 6.88–7.28 (8H, m), 7.64–7.78 (1H, m), 8.16–8.22 (1H, m). IR ν max$^{KBr}$cm$^{-1}$: 1817, 1719, 1595, 1510, 1468. mp 123–124° C. Anal. Calcd for C$_{28}$H$_{26}$N$_2$O$_6$F$_4$: C, 59.79; H, 4.66; N, 4.98. Found: C, 59.83; H, 4.68; N, 4.96.

9) tert-butyl (1RS,2SR)-2-hydroxy-2-[4-(pyridin-2-yloxy)phenyl]-1-[3-(1,1,2,2-tetrafluoroethoxy)benzyl]ethylcarbamate To a solution of tert-butyl (4RS,5SR)-2-oxo-5-[4-(pyridin-2-yloxy)phenyl]-4-[3-(1,1,2,2-tetrafluoroethoxy)benzyl]-1,3-oxazolidine-3-carboxylate (3.00 g, 5.33 mmol) in methanol (20 ml) was added a solution (12.8 ml, 6.4 mmol) of 0.5N sodium hydroxide in methanol, and the mixture was stirred at room temperature for 1 hr. To the reaction solution was added water (100 ml), and the mixture was extracted with ethyl acetate (100 ml×2). The extract was washed with saturated brine, dried (anhydrous magnesium sulfate) and evaporated under reduced pressure. The residue was recrystallized from ethyl acetate-hexane to give the objective substance (2.67 g, 93%).

$^1$H-NMR (CDCl$_3$)δ: 1.35 (9H, m), 2.64–2.80 (1H, m), 2.85 (1H, dd, J=15.0, 4.2 Hz), 3.23 (1H, s), 4.12 (1H, s), 4.64 (1H, d, J=8.4 Hz), 4.93 (1H, s), 5.89 (1H, tt, J=53.1, 3.0 Hz), 6.92 (1H, d, J=8.4 Hz), 6.96–7.10 (4H, m), 7.10–7.20 (2H, m), 7.20–7.36 (1H, m), 7.38–7.46 (2H, m), 7.66–7.72 (1H, m), 8.18–8.24 (1H, m). IR ν max$^{KBr}$cm$^{-1}$: 1696, 1590, 1574, 1507, 1468, 1431. mp 130–131° C. Anal. Calcd for C$_{27}$H$_{28}$F$_4$N$_2$O$_5$: C, 60.44; H, 5.26; N, 5.22. Found: C, 60.36; H, 5.06; N, 5.23.

Example 258

N-{(1RS,2SR)-2-hydroxy-2-[4-(pyridin-2-yloxy)phenyl]-1-[3-(1,1,2,2-tetrafluoroethoxy)benzyl]ethyl}-6,7-dihydro-5H-benzo[a][7]annulene-1-carboxamide To a solution of tert-butyl (1RS,2SR)-2-hydroxy-2-[4-(pyridin-2-yloxy)phenyl]-1-[3-(1,1,2,2-tetrafluoroethoxy)benzyl]ethylcarbamate (500 mg, 0.93 mmol) was added trifluoroacetic acid (10 ml), and the mixture was stirred at 0° C. for 10 min. The reaction solution was neutralized with saturated aqueous sodium hydrogen carbonate, and extracted with ethyl acetate, (30 ml×2). The extract was washed with saturated brine, dried (anhydrous magnesium sulfate) and evaporated under reduced pressure. To a solution of the residue in acetonitrile (20 ml) were added 6,7-dihydro-5H-benzo[a]cycloheptene-1-carboxylic acid (175 mg, 0.93 mmol), 1-ethyl-3-(3-dimethylaminopropyl)carbodiimide hydrochloride (268 mg, 1.40 mmol) and 1-hydroxybenzotriazole hydrate (143 mg, 0.93 mmol), and the mixture was stirred overnight at room temperature. The reaction solution was diluted with water (150 ml), and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (181 mg, 32%).

$^1$H-NMR (CDCl$_3$)δ: 1.90–2.08 (2H, m), 2.10–2.24 (2H, m), 2.60–2.70 (2H, m), 2.82 (1H, dd, J=14.6, 10.6 Hz), 3.04 (1H, dd, J=14.6, 4.0 Hz), 3.71 (1H, d, J=3.4 Hz), 4.62–4.80 (1H, m), 5.00–5.08 (1H, m), 5.60–6.20 (2H, m), 6.23 (1H, d, J=11.6 Hz), 6.84–7.20 (10H, m), 7.20–7.38 (1H, m), 7.48 (2H, d, J=8.4 Hz), 7.64–7.76 (1H, m), 8.16–8.24 (1H, m). IR ν max$^{KBr}$cm$^{-1}$: 1644, 1590, 1507, 1468, 1429. mp 160–161° C. Anal. Calcd for C$_{34}$H$_{30}$F$_4$N$_2$O$_4$: C, 67.32; H, 4.98; N, 4.62. Found: C, 67.09; H, 4.96; N, 4.56.

Example 259

4-fluoro-N-{(1RS,2SR)-2-hydroxy-2-[4-(pyridin-2-yloxy)phenyl]-1-[3-(1,1,2,2-tetrafluoroethoxy)benzyl]ethyl}-1-naphthamide To a solution of tert-butyl (1RS,2SR)-2-hydroxy-2-[4-(pyridin-2-yloxy)phenyl]-1-[3-(1,1,2,2-tetrafluoroethoxy)benzyl]ethylcarbamate (500 mg, 0.93 mmol) as added trifluoroacetic acid (10 ml), and the mixture was stirred at 0° C. for 10 min. The reaction solution was neutralized with saturated aqueous-sodium hydrogen carbonate, and extracted with ethyl acetate (30 ml×2). The extract was washed with saturated brine, dried (anhydrous magnesium sulfate) and evaporated under reduced pressure. To a solution of the residue in acetonitrile (20 ml) were added, 4-fluoronaphthalenecarboxylic acid (177 mg, 0.93 mmol), 1-ethyl-3-(3-dimethylaminopropyl)carbodiimide hydrochloride (268 mg, 1.40 mmol) and 1-hydroxybenzotriazole hydrate (143 mg, 0.93 mmol), and the mixture was stirred overnight at room temperature. The reaction solution was diluted with water (150 ml), and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (312 mg, 55%).

$^1$H-NMR (CDCl$_3$)δ: 2.88 (1H, dd, J=14.4, 10.8 Hz), 3.11 (1H, dd, J=14.4, 4.2 Hz), 3.59 (1H, s), 4.76–4.90 (1H, m), 5.08 (1H, s), 5.88 (1H, tt, J=53.1, 2.7 Hz), 6.05 (1H, d, J=7.8 Hz), 6.90–7.10 (3H, m), 7.10–7.22 (6H, m), 7.22–7.38 (1H, m), 7.40–7.60 (4H, m), 7.64–7.74 (1H, m), 7.84 (1H, d, J=8.4 Hz), 8.07 (1H, d, J=8.1 Hz), 8.14–8.20 (1H, m). IR ν max$^{KBr}$cm$^{-1}$: 1715, 1644, 1597, 1508, 1468, 1431. mp 176–177° C. Anal. Calcd for C$_{33}$H$_{25}$N$_2$O$_4$F$_5$·1.0H$_2$O: C, 63.26; H, 4.34; N, 4.47. Found: C, 63.41; H, 4.07; N, 4.57.

Example 260 tert-butyl (1RS,2SR)-2-hydroxy-2-[4-(pyridin-3-yloxy)phenyl]-1-[3-(1,1,2,2-tetrafluoroethoxy)benzyl]ethylcarbamate 1) benzyl 4-(pyridin-3-yloxy)benzoate To a solution of benzyl 4-hydroxybenzoate (25.0 g, 110 mmol) in N,N-dimethylformamide (60 ml) was added potassium tert-butoxide (12.3 g, 110 mmol), and the mixture was stirred at room temperature for 1 hr. The reaction solution was evaporated under reduced pressure, and 3-bromopyridine (25.0 g, 110 mmol), a copper powder (1.76 g, 27.2 mmol) and N,N-dimethylformamide (80 ml) were added. The mixture was stirred at 120° C. for 8 hrs. The reaction solution was filtered with celite and the filtrate was evaporated under reduced pressure. To the residue was added water (500 ml) and the mixture was extracted with ethyl acetate (500 ml). The extract was washed successively with water and saturated brine, dried (anhydrous magnesium sulfate) and evaporated under reduced pressure. The residue was purified by silica gel column chromatography (hexane:ethyl acetate=10:1–2:1) to give the objective substance (18.0 g, 54%, crude).

$^1$H-NMR (CDCl$_3$)δ: 5.36 (2H, s), 6.96–7.08 (2H, m), 7.26–7.50 (7H, m), 8.04–8.12 (2H, m), 8.46 (2H, brs). IR ν max$^{KBr}$cm$^{-1}$: 1717, 1605, 1574, 1505, 1474, 1424.

2) 4-(pyridin-3-yloxy)benzoic acid

To a solution of benzyl 4-(pyridin-3-yloxy)benzoate (18.0 g, 5.90 mmol) in ethanol (300 ml) was added 10% palladium/carbon (containing water by 50%, 2.0 g), and the mixture was stirred under a hydrogen stream at 80° C. overnight. The reaction solution was filtered with celite and the filtrate was concentrated. The residue was recrystallized from ethanol-hexane to give the objective substance (11.2 g, 88%).

$^1$H-NMR (DMSO-d$_6$)δ: 7.10 (2H, d, J=8.8 Hz), 7.42–7.66 (2H, m), 7.98 (2H, d, J=8.8 Hz), 8.47 (2H, s) IR ν max$^{KBr}$cm$^{-1}$: 1690, 1597, 1574. mp 204–205° C. Anal. Calcd for C$_{12}$H$_9$NO$_3$: C, 66.97; H, 4.22; N, 6.51. Found: C, 66.88; H, 4.15; N, 6.42.

3) benzyl 3-oxo-3-[4-(pyridin-3-yloxy)phenyl]propanoate

To a solution of 4-(pyridin-3-yloxy)benzoic acid (11.2 g, 52.0 mmol) in tetrahydrofuran (160 ml) was added N,N'-carbonyldiimidazole (9.28 g, 57.3 mmol), and the mixture was heated under reflux for 3 hrs. After cooling the reaction solution to room temperature, monobenzyl malonate magnesium salt (11.7 g, 28.6 mmol) was added, and the mixture was heated under reflux for 2 hrs. The reaction solution was concentrated and the residue was purified by silica gel column chromatography (hexane:ethyl acetate=1:1) to give the objective substance (14.1 g, 78%).

$^1$H-NMR (CDCl$_3$)δ: 4.02 (2H, s), 5.20 (2H, s), 6.94–7.08 (2H, m), 7.30–7.48 (6H, m), 7.90–7.96 (2H, m), 8.40–8.52 (3H, m). IR ν max$^{KBr}$cm$^{-1}$: 1740, 1682, 1601, 1574, 1505, 1473, 1424.

4) benzyl 3-oxo-3-[4-(pyridin-3-yloxy)phenyl]-2-[3-(1,1,2,2-tetrafluoroethoxy)benzyl]propanoate To a solution of [3-(1,1,2,2-tetrafluoroethoxy)phenyl] methanol (4.97 g, 22.2 mmol) in ethyl acetate (100 ml) were added methanesulfonyl chloride (1.87 ml, 24.2 mmol) and triethylamine (3.65 ml, 26.2 mmol), and the mixture was stirred at room temperature for 2 hrs. Insoluble material was filtered off, and the filtrate was evaporated under reduced pressure to give a mesyl form. To a solution of benzyl 3-oxo-3-[4-(pyridin-3-yloxy)phenyl]propanoate (7 g, 20.2 mmol) in 1,2-dimethoxyethane (80 ml) was added sodium hydride (806 mg, 60% in oil, 20.2 mmol), and the mixture was stirred at room temperature for 1 hr. To the reaction solution was dropwise added a solution of the mesyl form prepared earlier in 1,2-dimethoxyethane (10 ml), and the reaction solution was stirred at 60° C. overnight. The reaction solution was acidified with 1N hydrochloric acid, neutralized with saturated aqueous sodium hydrogen carbonate and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=2:1) to give the objective substance (6.0 g, 54%, crude).

$^1$H-NMR (CDCl$_3$)δ: 3.35 (2H, d, J=7.6 Hz), 4.60 (1H, t, J=7.6 Hz), 5.08 (2H, s), 5.88 (1H, tt, J=53.0, 3.0 Hz), 6.90–7.40 (13H, m), 7.86–7.98 (2H, m), 8.40–8.52 (2H, m). IR ν max$^{KBr}$cm$^{-1}$: 1740, 1684, 1601, 1574, 1505, 1473, 1424.

5) benzyl (2RS,3RS)-3-hydroxy-3-[4-(pyridin-3-yloxy) phenyl]-2-[3-(1,1,2,2-tetrafluoroethoxy)benzyl]propanoate To a solution of zinc chloride (2.95 g, 21.6 mmol) in diethyl ether (100 ml) was added sodium borohydride (1.64 g, 43.3 mmol), and the mixture was stirred at room temperature for 30 min. Insoluble material was filtered off, and a solution of benzyl 3-oxo-3-[4-(pyridin-3-yloxy)phenyl]-2-[3-(1,1,2,2-tetrafluoroethoxy)benzyl]propanoate (6.0 g, 10.8 mmol, crude) in diethyl ether (50 ml) was added to the filtrate at 0° C. The mixture was stirred for 30 min. and 1N hydrochloric acid was added to stop the reaction. After neutralization with saturated aqueous sodium hydrogen carbonate, water (200 ml) was further added and the mixture was extracted with ethyl acetate (200 ml×2). The extract-was washed with water and saturated brine, dried (anhydrous magnesium sulfate) and evaporated under reduced pressure. The residue was purified by silica gel column chromatography (hexane:ethyl acetate=2:1) and recrystallized from ethyl acetate-hexane to give the objective substance (3.13 g, 73%).

$^1$H-NMR (CDCl$_3$)δ: 2.92–3.14 (4H, m), 4.86 (2H, d, J=3.3 Hz), 5.03 (1H, s), 5.88 (1H, tt, J=53.1, 3.0 Hz), 6.90–7.08 (7H, m), 7.18–7.32 (6H, m), 7.36 (2H, d, J=8.4 Hz), 8.34–8.40 (2H, m). IR ν max$^{KBr}$cm$^{-1}$: 1730, 1611, 1576, 1507, 1478, 1451, 1426. mp 120–122° C. Anal. Calcd for C$_{30}$H$_{25}$NO$_5$F$_4$: C, 64.86; H, 4.54; N, 2.52. Found: C, 64.91; H, 4.75; N, 2.56.

6) (2RS,3RS)-3-hydroxy-3-[4-(pyridin-3-yloxy)phenyl]-2-[3-(1,1,2,2-tetrafluoroethoxy)benzyl]propanoic acid To a solution of benzyl (2RS,3RS)-3-hydroxy-3-[4-(pyridin-3-yloxy)phenyl]-2-[3-(1,1,2,2-tetrafluoroethoxy) benzyl]propanoate (3.00 g, 5.38 mmol) in ethanol (200 ml) was added 10% palladium/carbon (containing water by 50%, 300 mg), and the mixture was stirred under a 1 atm hydrogen stream for 1 hr. The reaction solution was filtered with celite and the filtrate was concentrated to give the objective substance (2.8 g, 100%, crude). The present compound was used for, the next reaction as a crude compound.

$^1$H-NMR (CDCl$_3$)δ: 2.92–3.10 (3H, m), 5.05 (1H, m), 5.88 (1H, tt, J=53.0, 3.0 Hz), 6.96–7.16 (5H, m), 7.20–7.48 (5H, m), 8.20–8.32 (2H, m). IR ν max$^{KBr}$cm$^{-1}$: 1711, 1611, 1578, 1507, 1480, 1427.

7) (4RS,5SR)-5-[4-(pyridin-3-yloxy)phenyl]-4-[3-(1,1,2,2-tetrafluoroethoxy)benzyl]-1,3-oxazolidin-2-one To a solution of (2RS,3RS)-3-hydroxy-3-[4-(pyridin-3-yloxy)phenyl]-2-[3-(1,1,2,2-tetrafluoroethoxy)benzyl] propanoic acid (2.83 g, 6.08 mmol, crude) in tetrahydrofuran (100 ml) were added diphenylphosphoryl azide (1.44 ml, 6.69 mmol) and triethylamine (1.27 mmol, 9.12 mmol), and the mixture was heated under reflux for 1 hr. The reaction solution was allowed to cool and water (100 ml) was added. The mixture was extracted with ethyl acetate (100 ml×2). The extract was washed successively with aqueous sodium hydrogen carbonate solution, saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (3.56 g, 73%).

¹H-NMR (CDCl₃)δ: 2.24–2.42 (2H, m), 4.22–4.32 (1H, m), 5.12–5.22 (1H, m), 5.80 (1H, d, J=7.8 Hz), 5.90 (1H, tt, J 53.1, 2.7 Hz), 6.89 (1H, s), 6.96 (1H, d, J=7.8 Hz), 7.00–7.18 (3H, m), 7.26–7.40 (5H, m), 8.18–8.24 (2H, m), IR ν max$^{KBr}$cm⁻¹: 1759, 1613, 1576, 1508, 1478, 1424. mp 123–124° C. Anal. Calcd for C₂₃H₁₈N₂O₄F₄: C, 59.74; H, 3.92; N, 6.06. Found: C, 59.60; H, 3.85; N, 6.11.

8) tert-butyl (4RS,5SR)-2-oxo-5-[4-(pyridin-3-yloxy) phenyl]-4-[3-(1,1,2,2-tetrafluoroethoxy)benzyl]-1,3-oxazolidine-3-carboxylate To a solution of (4RS,5SR)-5-[4-(pyridin-3-yloxy) phenyl]-4-[3-(1,1,2,2-tetrafluoroethoxy)benzyl]-1,3-oxazolidin-2-one (1.80 g, 3.89 mmol) in acetonitrile (40 ml) were added di-tert-butyl dicarbonate (1.02 g, 4.67 mmol) and 4-N,N-dimethylpyridine (47 mg, 0.39 mmol), and the mixture was stirred at room temperature for 1 hr. To the reaction solution was added water (100 ml), and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (1.87 g, 85%).

¹H-NMR (CDCl₃)δ: 1.51 (9H, s), 2.65 (1H, dd, J=14.2, 8.8 Hz), 2.93 (1H, dd, J=14.2, 4.4 Hz), 4.76–4.88 (1H, m), 5.69 (1H, d, J=7.0 Hz), 5.91 (1H, tt, J=53.0, 3.0 Hz), 6.58 (1H, s), 6.66 (1H, d, J=7.6 Hz), 6.84–7.04 (3H, m), 7.08–7.20 (3H, m), 7.26–7.36 (2H, m), 8.36–8.44 (2H, m). IR ν max$^{KBr}$cm⁻¹: 1819, 1721, 1613, 1578, 1508, 1476, 1424. mp 146–147° C. Anal. Calcd for C₂₈H₂₆N₂O₆F₄: C, 59.79; H, 4.66; N, 4.98. Found: C, 59.83; H, 4.65; N, 4.84.

9) tert-butyl (1RS,2SR)-2-hydroxy-2-[4-(pyridin-3-yloxy)phenyl]-1-[3-(1,1,2,2-tetrafluoroethoxy)benzyl]ethylcarbamate To a solution of tert-butyl (4RS,5SR)-2-oxo-5-[4-(pyridin-3-yloxy)phenyl]-4-[3-(1,1,2,2-tetrafluoroethoxy)benzyl]-1,3-oxazolidine-3-carboxylate (1.70 g, 3.02 mmol) in methanol (10 ml) was added a solution (7.26 ml, 3.63 mmol) of 0.5N sodium hydroxide in methanol, and the mixture was stirred at room temperature for 1 hr. To the reaction solution was added water (100 ml), and the mixture was extracted with ethyl acetate (100 ml×2). The extract was washed with saturated brine, dried (anhydrous magnesium sulfate) and evaporated under reduced pressure. The residue was recrystallized from ethyl acetate-hexane to give the objective substance (1.39 g, 86%).

¹H-NMR (CDCl₃)δ: 1.35 (9H, s), 2.60–2.84 (2H, m), 3.45 (1H, s), 4.02–4.16 (1H, m), 4.63 (1H, d, J=8.4 Hz), 4.93 (1H, s), 5.90 (1H, tt, J=52.8, 3.0 Hz), 6.96–7.10 (5H, m), 7.24–7.34 (3H, m), 7.41 (2H, d, J=8.4 Hz), 8.34–8.44 (2H, m). IR ν max$^{KBr}$cm⁻¹: 1698, 1576, 1505, 1478. mp 123–124° C. Anal. Calcd for C₂₇H₂₈F₄N₂O₅: C, 60.44; H, 5.26; N, 5.22. Found: C, 60.24; H, 5.45; N, 5.15.

Example 261

N-{(1RS,2SR)-2-hydroxy-2-[4-(pyridin-3-yloxy) phenyl]-1-[3-(1,1,2,2-tetrafluoroethoxy)benzyl] ethyl}-6,7-dihydro-5H-benzo[a][7]annulene-1-carboxamide Trifluoroacetic acid (10 ml) was added to tert-butyl (1RS, 2SR)-2-hydroxy-2-[4-(pyridin-3-yloxy)phenyl]-1-[3-(1,1,2, 2-tetrafluoroethoxy)benzyl]ethylcarbamate (500 mg, 0.93 mmol), and the mixture was stirred at 0° C. for 10 min. The reaction solution was neutralized with saturated aqueous sodium hydrogen carbonate, and extracted with ethyl acetate (30 ml×2). The extract was washed with saturated brine, dried (anhydrous magnesium sulfate) and evaporated under reduced pressure. To a solution of the residue in acetonitrile (20 ml) were added 6,7-dihydro-5H-benzo[a]cycloheptene-1-carboxylic acid (175 mg, 0.93 mmol), 1-ethyl-3-(3-dimethylaminopropyl)carbodiimide hydrochloride (268 mg, 1.40 mmol) and 1-hydroxybenzotriazole hydrate (143 mg, 0.93 mmol), and the mixture was stirred overnight at room temperature. The reaction solution was diluted with water (150 ml), and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=1:1-ethyl acetate). Recrystallization from ethyl acetate-hexane gave the objective substance (317 mg, 56%).

¹H-NMR (CDCl₃)δ: 1.90–2.08 (2H, m), 2.10–2.28 (2H, m), 2.60–2.70 (2H, m), 2.81 (1H, dd, J=14.8, 10.2 Hz), 3.02 (1H, dd, J=14.8, 4.0 Hz), 3.97 (1H, s), 4.60–4.80 (1H, m), 5.00–5.08 (1H, m), 5.60–6.18 (2H, m), 6.21 (1H, d, J=11.8 Hz), 6.90–7.20 (8H, m), 7.20–7.40 (3H, m), 7.40–7.52 (2H, m), 8.35 (2H, s). IR ν max$^{KBr}$cm⁻¹: 1642, 1613, 1576, 1505, 1478, 1426. mp 133–134° C. Anal. Calcd for C₃₄H₃₀F₄N₂O₄: C, 67.12; H, 5.00; N, 4.60. Found: C, 66.98; H, 4.85; N, 4.61.

Example 262

4-fluoro-N-{(1RS,2SR)-2-hydroxy-2-[4-(pyridin-3-yloxy)phenyl]-1-[3-(1,1,2,2-tetrafluoroethoxy) benzyl]ethyl}-1-naphthamide To tert-butyl (1RS,2SR)-2-hydroxy-2-[4-(pyridin-3-yloxy)phenyl]-1-[3-(1,1,2,2-tetrafluoroethoxy)benzyl] ethylcarbamate (500 mg, 0.93 mmol) was added trifluoroacetic acid (10 ml), and the mixture was stirred at 0° C. for 10 min. The reaction solution was neutralized with saturated aqueous sodium hydrogen carbonate, and extracted with ethyl acetate (30 ml×2). The extract was washed with saturated brine, dried (anhydrous magnesium sulfate) and evaporated under reduced pressure. To a solution of the residue in acetonitrile (20 ml) were added 4-fluoronaphthalenecarboxylic acid (177 mg, 0.93 mmol), 1-ethyl-3-(3-dimethylaminopropyl)carbodiimide hydrochloride (268 mg, 1.40 mmol) and 1-hydroxybenzotriazole hydrate (143 mg, 0.93 mmol), and the mixture was stirred overnight at room temperature. The reaction solution was diluted with water (150 ml), and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (347 mg, 61%).

¹H-NMR (CDCl₃)δ: 2.89 (1H, dd, J=14.6, 10.6 Hz), 3.12 (1H, dd, J=14.6, 4.0 Hz), 3.59 (1H, s), 4.70–4.90 (1H, m), 5.14 (1H, s), 5.91 (1H, tt, J=53.0, 3.0 Hz), 6.00 (1H, d, J=8.4 Hz), 6.90–7.65 (14H, m), 7.88 (1H, d, J=8.0 Hz), 8.11 (1H, d, J=8.0 Hz), 8.41 (2H, brs). IR ν max$^{KBr}$cm⁻¹: 1642, 1626, 1582, 1505, 1480, 1426. mp 183–184° C. Anal. Calcd for C₃₃H₂₅F₅N₂O₄: C, 65.13; H, 4.14; N, 4.60. Found: C, 65.03; H, 4.01; N, 4.35.

Example 263

4-fluoro-N-{(1RS,2SR)-2-(3-fluorophenyl)-2-hydroxy-1-[3-(1,1,2,2-tetrafluoroethoxy)benzyl] ethyl}-1-naphthamide To a solution of (1RS,2SR)-2-amino-1-(3-fluorophenyl)-3-[3-(1,1,2,2-tetrafluoroethoxy)phenyl]propan-1-ol (300 mg, 0.83 mol) in acetonitrile (20 ml) were added 4-fluoronaphthalenecarboxylic acid (156 mg, 0.83 mmol), 1-ethyl-3-(3-dimethylaminopropyl)carbodiimide hydrochloride (239 mg, 1.25 mmol) and 1-hydroxybenzotriazole hydrate (127 mg, 0.83 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (283 mg, 64%).

$^1$H-NMR (CDCl$_3$)δ: 2.85 (1H, dd, J=14.6, 10.6 Hz), 3.03 (1H, dd, J=14.6, 4.4 Hz), 3.60 (1H, d, J=3.8 Hz), 4.68–4.86 (1H, m), 5.10–5.20 (1H, m), 5.88 (1H, tt, J=53.0, 3.0 Hz), 5.99 (1H, d, J=8.4 Hz), 6.92–7.60 (12H, m), 7.84 (1H, d, J=8.0 Hz), 8.08 (1H, d, J=7.8 Hz). IR ν max$^{KBr}$cm$^{-1}$: 1642, 1626, 1601, 1590, 1539. mp 175–176° C. Anal. Calcd for C$_{28}$H$_{21}$F$_6$NO$_3$.0.1H$_2$O: C, 62.83; H, 3.99; N, 2.62. Found: C, 62.62; H, 3.79; N, 2.52.

Example 264

4-fluoro-N-{(1RS,2SR)-2-(3-chlorophenyl)-2-hydroxy-1-[3-(1,1,2,2-tetrafluoroethoxy)benzyl]ethyl}-1-naphthamide To a solution of (1RS,2SR)-2-amino-1-(3-chlorophenyl)-3-[3-(1,1,2,2-tetrafluoroethoxy)phenyl]propan-1-ol (300 mg, 0.79 mmol) in acetonitrile (20 ml) were added 4-fluoronaphthalenecarboxylic acid (151 mg, 0.79 mmol), 1-ethyl-3-(3-dimethylaminopropyl)carbodiimide hydrochloride (228 mg, 1.19 mmol) and 1-hydroxybenzotriazole hydrate (122 mg, 0.79 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1-ethyl acetate). Recrystallization from ethyl acetate-hexane gave the objective substance (163 mg, 37%).

$^1$H-NMR (CDCl$_3$)δ: 2.84 (1H, dd, J=14.4, 10.8 Hz), 3.01 (1H, dd, J=14.4, 4.2 Hz), 3.73 (1H, d, J=3.9 Hz), 4.68–4.80 (1H, m), 5.06–5.12 (1H, m), 5.88 (1H, tt, J=52.8, 3.0 Hz), 6.02 (1H, d, J=8.7 Hz), 6.92–7.00 (1H, m), 7.06 (1H, s) 7.08–7.18 (3H, m), 7.24–7.40 (4H, m), 7.40–7.58 (3H, m), 7.80 (1H, d, J=8.4 Hz), 8.07 (1H, d, J=8.1 Hz). IR ν max$^{KBr}$cm$^{-1}$: 1642, 1626, 1601, 1537. mp 177–178° C. Anal. Calcd for C$_{28}$H$_{21}$ClF$_5$NO$_3$: C, 61.15; H, 3.85; N, 2.55. Found: C, 61.09; H, 3.70; N, 2.49.

Example 265

4-fluoro-N-{(1RS,2SR)-2-(2-fluoropyridin-4-yl)-2-hydroxy-1-[3-(1,1,2,2-tetrafluoroethoxy)benzyl]ethyl}-1-naphthamide To a solution of (1RS,2SR)-2-amino-1-(2-fluoropyridin-4-yl)-3-[3-(1,1,2,2-tetrafluoroethoxy)phenyl]propan-1-ol (194 mg, 0.54 mmol) in acetonitrile (20 ml) were added 4-fluoronaphthalenecarboxylic acid (101 mg, 0.54 mmol), 1-ethyl-3-(3-dimethylaminopropyl)carbodiimide hydrochloride (154 mg, 0.80 mmol) and 1-hydroxybenzotriazole hydrate (82 mg, 0.54 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1-ethyl acetate). Recrystallization from ethyl acetate-hexane gave the objective substance (189 mg, 66%).

$^1$H-NMR (CDCl$_3$)δ: 2.80–3.02 (2H, m), 4.39 (1H, s), 4.62–4.80 (1H, m), 5.18 (1H, s), 5.60–6.20 (1H, m), 6.27 (1H, d, J=7.4 Hz), 6.90–7.20 (6H, m), 7.20–7.40 (2H, m), 7.42–7.62 (2H, m), 7.88 (1H, d, J=8.0 Hz), 8.02–8.20 (2H, d, J=6.2 Hz). IR ν max$^{KBr}$cm$^{-1}$: 1642, 1615, 1601, 1585. mp 170–171° C. Anal. Calcd for C$_{27}$H$_{20}$F$_6$N$_2$O$_3$.0.2H$_2$O: C, 60.27; H, 3.82; N, 5.21. Found: C, 60.04; H, 3.63; N, 5.20.

Example 266

4-fluoro-N-{(1RS,2RS)-2-(6-fluoropyridin-2-yl)-2-hydroxy-1-[3-(1,1,2,2-tetrafluoroethoxy)benzyl]ethyl}-1-naphthamide To a solution of (1RS,2RS)-2-amino-1-(6-fluoropyridin-2-yl)-3-[3-(1,1,2,2-tetrafluoroethoxy)phenyl]propan-1-ol hydrochloride (300 mg, 0.75 mmol) in acetonitrile (20 ml) were added 4-fluoronaphthalenecarboxylic acid (141 mg, 0.75 mmol), 1-ethyl-3-(3-dimethylaminopropyl) carbodiimide hydrochloride (216 mg, 1.13 mmol), 1-hydroxybenzotriazole hydrate (115 mg, 0.75 mmol) and triethylamine (1.03 ml, 0.75 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1-ethyl acetate). Recrystallization from ethyl acetate-hexane gave the objective substance (306 mg, 76%).

$^1$H-NMR (CDCl$_3$)δ: 2.82 (1H, dd, J=14.4, 5.0 Hz), 3.02 (1H, dd, J=14.4, 9.8 Hz), 4.67 (1H, d, J=5.4 Hz), 4.80–4.96 (1H, m), 5.10–5.20 (1H, m), 5.88 (1H, tt, J=53.0, 3.0 Hz), 6.42 (1H, d, J=8.8 Hz), 6.89 (1H, dd, J=8.2, 2.6 Hz), 7.00–7.20 (4H, m), 7.20–7.40 (2H, m), 7.40–7.62 (3H, m), 7.78–7.94 (1H, m), 7.97 (1H, d, J=8.4 Hz), 8.10 (1H, d, J=7.2 Hz). IR ν max$^{KBr}$cm$^{-1}$: 1642, 1626, 1603, 1578, 1535, 1454. mp 185–186° C. Anal. Calcd for C$_{27}$H$_{20}$F$_6$N$_2$O$_3$: C, 60.68; H, 3.77; N, 5.24. Found: C, 60.40; H, 3.61; N, 5.14.

Example 267

4-fluoro-N-{(1RS,2SR)-2-hydroxy-2-(4-phenoxyphenyl)-1-[3-(1,1,2,2-tetrafluoroethoxy)benzyl]ethyl}-1-naphthamide To a solution of (1RS,2SR)-2-amino-1-(4-phenoxyphenyl)-3-[3-(1,1,2,2-tetrafluoroethoxy)phenyl]propan-1-ol (300 mg, 0.69 mmol) in acetonitrile (20 ml) were added 4-fluoronaphthalenecarboxylic acid (131 mg, 0.69 mmol), 1-ethyl-3-(3-dimethylaminopropyl) carbodiimide hydrochloride (198 mg, 1.03 mmol) and 1-hydroxybenzotriazole hydrate (105 mg, 0.69 mmol), and the mixture was stirred overnight at room temperature. The reaction solution was diluted-with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1-ethyl acetate). Recrystallization from ethyl-acetate-hexane gave the objective substance (286 mg, 68%).

$^1$H-NMR (CDCl$_3$)δ: 2.85 (1H, dd, J=14.4, 10.8 Hz), 3.10 (1H, dd, J=14.4, 4.2 Hz), 3.41 (1H, d, J=3.0 Hz), 4.72–4.86 (1H, m), 5.04–5.10 (1H, m), 5.88 (1H, tt, J=52.8, 3.0 Hz), 5.95 (1H, d, J=8.7 Hz), 6.94–7.04 (5H, m), 7.06–7.20 (5H, m), 7.28–7.40 (3H, m), 7.40–7.60 (4H, m), 7.81 (1H, d, J=8.4 Hz), 8.08 (1H, d, J=8.1 Hz). IR ν max$^{KBr}$cm$^{-1}$: 1644, 1626, 1599, 1590, 1537, 1508, 1489. mp 155–156° C. Anal. Calcd for C$_{34}$H$_{26}$F$_5$NO$_4$: C, 67.21; H, 4.31; N, 2.31. Found: C, 67.02; H, 4.27; N, 2.21.

Example 268 ethyl N-((1RS,2SR)-2-(4-fluorophenyl)-2-hydroxy-1-{3-[(trifluoromethyl)thio]benzyl}ethyl)-6,7-dihydro-5H-benzo[a][7]annulene-1-carboxamide 1) ethyl 3-(4-fluorophenyl)-3-oxo-2-{3-[(trifluoromethyl)thio]benzyl}propanoate To a solution of 3-[(trifluoromethyl)thio]benzyl alcohol (4.82 g, 23.1 mmol) in ethyl acetate (60 ml) were added methanesulfonyl chloride (2.92 g, 25.5 mmol) and triethylamine (3.87 ml, 27.8 mmol), and the mixture was stirred at room temperature for 2 hrs. Insoluble material was filtered off, and the filtrate was evaporated under reduced pressure to give a mesyl form. To a solution of ethyl 3-(4-fluorophenyl)-3-oxopropanoate (4.87 g, 23.2 mmol) in 1,2-dimethoxyethane (50 ml) was added sodium hydride (0.93 g, 60% in oil, 23.2 mmol), and the mixture was stirred at room temperature for 1 hr. To the reaction solution was dropwise added a solution of the mesyl form prepared earlier in 1,2-dimethoxyethane (10 ml), and the reaction solution was stirred overnight at room temperature. The reaction solution was acidified with 1N hydrochloric acid, neutralized with saturated aqueous sodium hydrogen carbonate and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=4:1) and recrystallized from ethyl acetate-hexane to give the objective substance (5.67 g, 61%).

$^1$H-NMR (CDCl$_3$)δ: 1.12 (3H, t, J=7.2 Hz), 3.26–7.42 (2H, m), 4.11 (2H, q, J=7.2 Hz), 4.56 (1H, t, J=7.5 Hz), 7.06–7.16 (2H, m), 7.26–7.38 (2H, m), 7.44–7.54 (2H, m), 7.94–8.02 (2H, m). IR ν max$^{KBr}$cm$^{-1}$: 1738, 1688, 1599, 1508. mp 72–73° C. Anal. Calcd for C$_{19}$H$_{16}$F$_3$O$_3$S: C,. 57.00; H, 4.03 Found: C, 56.99; H, 4.06.

2) ethyl(2RS,3RS)-3-(4-fluorophenyl)-3-hydroxy-2-{3-[(trifluoromethyl)thio]benzyl}propanoate To a solution of zinc chloride (3.74 g, 27.4 mmol) in diethyl ether (100 ml) was added sodium borohydride (2.08 g, 54.8 mmol), and the mixture was stirred at room temperature for 30 min. Insoluble material was filtered off, and to the filtrate was added a solution of ethyl 3-(4-fluorophenyl)-3-oxo-2-{3-[(trifluoromethyl)thio]benzyl}propanoate (5.5 g, 13.7 mmol) in diethyl ether (50 ml) at 0° C. The mixture was stirred for 30 min. and 1N hydrochloric acid was added to the reaction solution to stop the reaction. After neutralization with saturated aqueous sodium hydrogen carbonate, water (200 ml) was further added, and the mixture was extracted with ethyl acetate (200 ml×2). The extract was washed with water and saturated brine, dried (anhydrous magnesium sulfate) and evaporated under reduced pressure. The residue was purified by silica gel column chromatography (hexane:ethyl acetate=4:1) to give the objective substance (5.40 g, 98%).

$^1$H-NMR (CDCl$_3$)δ: 0.91 (3H, t, J=7.2 Hz), 2.88–3.10 (4H, m), 3.87 (2H, q, J=7.2 Hz), 5.02 (1H, d, J=4.8 Hz), 6.98–7.12 (2H, m), 7.18–7.52 (6H, m). IR ν max$^{KBr}$cm$^{-1}$: 1725, 1605, 1510.

3) (2RS,3RS)-3-(4-fluorophenyl)-3-hydroxy-2-{3-[(trifluoromethyl)thio]benzyl}propanoic acid To a solution of ethyl (2RS,3RS)-3-(4-fluorophenyl)-3-hydroxy-2-{3-[(trifluoromethyl)thio]benzyl}propanoate (5.30 g, 13.17 mmol) in methanol (150 ml) was added 2N aqueous sodium hydroxide solution (13.2 ml, 26.4 mmol), and the mixture was stirred overnight at room temperature. After the reaction solution was concentrated, 1N hydrochloric acid was added. The mixture was acidified and extracted with ethyl acetate (200 ml×2). The extract was washed with water and saturated brine, dried (anhydrous magnesium sulfate) and evaporated under reduced pressure. The residue was recrystallized from ethyl acetate-hexane to give the objective substance (3.98 g, 81%).

$^1$H-NMR (CDCl$_3$)δ: 2.90–3.10 (3H, m), 5.07 (1H, s), 6.98–7.10 (2H, m), 7.12–7.42 (5H, m), 7.47 (1H, d, J=7.4 Hz). IR ν max$^{KBr}$cm$^{-1}$: 1712, 1607. mp 121–122° C. Anal. Calcd for C$_{17}$H$_{14}$O$_3$SF$_4$: C, 54.54; H, 3.77 Found: C, 54.58; H, 3.80.

5) (4RS,5SR)-5-(4-fluorophenyl)-4-{3-[(trifluoromethyl)thio]benzyl}-1,3-oxazolidin-2-one To a solution of (2RS,3RS)-3-(4-fluorophenyl)-3-hydroxy-2-{3-[(trifluoromethyl)thio]benzyl}propanoic acid (3.9 g, 10.42 mmol) in tetrahydrofuran (150 ml) were added diphenylphosphoryl azide (2.47 ml, 11.5 mmol) and triethylamine (2.18 ml, 15.6 mmol), and the mixture was heated under reflux for 1 hr. The reaction solution was allowed to cool and the mixture was evaporated under reduced pressure. The residue was purified by silica gel column chromatography (hexane:ethyl acetate=2:1-ethyl acetate). Recrystallization from ethyl acetate-hexane gave the objective substance (3.45 g, 89%).

$^1$H-NMR (CDCl$_3$)δ: 2.31 (1H, d, J=3.0 Hz), 2.35 (1H, s), 4.20–4.34 (1H, m), 5.13 (1H, brs), 5.79 (1H, d, J=7.8 Hz), 7.04–7.20 (3H, m), 7.20–7.44 (4H, m), 7.54 (1H, d, J=7.6 Hz). IR ν max$^{KBr}$cm$^{-1}$: 1755, 1609, 1595, 1514. mp 132–133° C. Anal. Calcd for C$_{17}$H$_{13}$NO$_2$SF$_4$: C, 54.98; H, 3.53; N, 3.77. Found: C, 55.28; H, 3.47; N, 3.98.

6) (1RS,2SR)-2-amino-1-(4-fluorophenyl)-3-{3-[(trifluoromethyl)thio]phenyl}propan-1-ol To a solution of (4RS,5SR)-5-(4-fluorophenyl)-4-{3-[(trifluoromethyl)thio]benzyl}-1,3-oxazolidin-2-one (1.30 g, 3.50 mmol) in ethanol (3 ml) was added 8N aqueous sodium hydroxide solution (1.31 ml, 10.5 mmol), and the mixture was stirred at 80° C. for 4 hrs. To the reaction solution was added water (20 ml), and the mixture was extracted with ethyl acetate (50 ml×2). The extract was washed with water and saturated brine, dried (anhydrous magnesium sulfate) and evaporated under reduced pressure to give the objective substance (0.8 g, 77%).

$^1$H-NMR (CDCl$_3$)δ: 1.80–2.30 (2H, m), 2.42 (1H, dd, J=13.6, 10.2 Hz), 2.83 (1H, dd, J=14.0, 2.6 Hz), 3.20–3.40 (1H, m), 4.69 (1H, d, J=4.8 Hz), 7.00–7.20 (2H, m), 7.20–7.56 (6H, m). IR ν max$^{KBr}$cm$^{-1}$: 1752, 1605, 1508, 1476.

7) N-((1RS,2SR)-2-(4-fluorophenyl)-2-hydroxy-1-{3-[(trifluoromethyl)thio]benzyl}ethyl)-6,7-dihydro-5H-benzo[a][7]annulene-1-carboxamide To a solution of (1RS,2SR)-2-amino-1-(4-fluorophenyl)-3-{3-[(trifluoromethyl)thio]phenyl}propan-1-ol (450 mg, 1.51 mmol) in acetonitrile (20 ml) were added 6,7-dihydro-5H-benzo[a]cycloheptene-1-carboxylic acid (284 mg, 1.51 mmol), 1-ethyl-3-(3-dimethylaminopropyl)carbodiimide hydrochloride (435 mg, 2.27 mmol) and 1-hydroxybenzotriazole hydrate (231 mg, 1.51 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1-ethyl acetate). Recrystallization from ethyl acetate-hexane gave the objective substance (396 mg, 51%).

$^1$H-NMR (CDCl$_3$)δ: 1.90–2.08 (2H, m), 2.12–2.24 (2H, m), 2.60–2.72 (2H, m), 2.81 (1H, dd, J=14.7, 10.5 Hz), 3.00 (1H, dd, J=14.7, 4.2 Hz), 3.52 (1H, d, J=3.6 Hz), 4.62–4.74 (1H, m), 5.00–5.08 (1H, m), 5.77 (1H, d, J=8.7 Hz), 5.88–5.96 (1H, m), 6.19 (1H, d, J=12.0 Hz), 6.90–7.00 (1H, m), 7.00–7.20 (4H, m), 7.30–7.60 (6H, m). IR ν max$^{KBr}$ cm$^{-1}$: 1638, 1512. mp 163–164° C. Anal. Calcd for C$_{28}$H$_{25}$F$_4$NO$_2$ S: C, 65.23; H, 4.89; N, 2.72; S, 6.22 Found: C, 65.02; H, 5.02; N, 2.79; S, 6.22.

Example 269

4-fluoro-N-((1RS,2SR)-2-(4-fluorophenyl)-2-hydroxy-1-{3-[(trifluoromethyl)thio]benzyl}ethyl)-1-naphthamide To a solution of (1RS,2SR)-2-amino-1-(4-fluorophenyl)-3-{3-[(trifluoromethyl)thio]phenyl}propan-1-ol (450 mg, 1.51 mmol) in acetonitrile (20 ml) were added 4-fluoronaphthalenecarboxylic acid (287 mg, 1.51 mmol), 1-ethyl-3-(3-dimethylaminopropyl)carbodiimide hydrochloride (435 mg, 2.27 mmol) and 1-hydroxybenzotriazole hydrate (231 mg, 1.51 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=2:1-ethyl acetate). Recrystallization from ethyl acetate-hexane gave the objective substance (447 mg, 57%).

$^1$H-NMR (CDCl$_3$)δ: 2.85 (1H, dd, J=15.2, 10.8 Hz), 3.04 (1H, dd, J=15.0, 3.9 Hz), 3.43 (1H, d, J=3.6 Hz), 4.70–4.82 (1H, m), 5.04–5.10 (1H, m), 5.98 (1H, d, J=9.3 Hz), 6.92–7.02 (1H, m), 7.02–7.12 (3H, m), 7.30–7.58 (8H, m), 7.77 (1H, d, J=8.7 Hz), 8.08 (1H, d, J=8.4 Hz). IR ν max$^{KBr}$cm$^{-1}$: 1642, 1626, 1601, 1537, 1512. mp 192–193° C. Anal. Calcd for C$_{27}$H$_{20}$F$_5$NO$_2$ S: C, 62.66; H, 3.90; N, 2.71; S, 6.20 Found: C, 62.56; H, 3.86; N, 2.66; S, 6.34.

Example 270

N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-6,7-dihydro-5H-benzo[a][7]annulene-1-carboxamide 1) 2,2,3,3-tetrafluoro-2,3-dihydro-1,4-benzodioxine-6-carboxylic acid To a solution of 2,2,3,3-tetrafluoro-2,3-dihydro-1,4-benzodioxine-6-carbonitrile (5.0 g, 21.44 mmol) in acetic acid (20 ml) was added conc. hydrochloric acid (20 ml), and the mixture was heated under reflux overnight. The reaction solution was concentrated, and the precipitated crystals were filtered and washed with water to give the objective substance (4.76 g, 88%).

$^1$H-NMR (CDCl$_3$)δ: 7.26 (1H, d, J=8.7 Hz), 7.90–8.00 (2H, m), 11.00–11.80 (1H, br). IR ν max$^{KBr}$cm$^{-1}$: 1726, 1701, 1624, 1597, 1508. mp 103–104° C. Anal. Calcd for C$_9$H$_4$O$_4$F$_4$: C, 42.88; H, 1.60 Found: C, 43.13; H 11.60.

2) (2,2,3,3-tetrafluoro-2,3-dihydro-1,4-benzodioxin-6-yl)methanol

To a solution of lithium aluminum hydride (1.40 g, 36.89 mmol) in tetrahydrofuran (30 ml) was gradually added 2,2,3,3-tetrafluoro-2,3-dihydro-1,4-benzodioxine-6-carboxylic acid (4.65 g, 18.44 mmol) at 0° C. After the reaction solution was stirred at 0° C. for 10 min., 1N aqueous sodium hydroxide solution was added. Insoluble material was filtered off with celite and the filtrate was concentrated. The residue was purified by silica gel column chromatography (hexane:ethyl acetate=4:1) to give the objective substance (3.54 g, 81%).

$^1$H-NMR (CDCl$_3$)δ: 1.87 (1H, t, J=6.0 Hz), 4.69 (2H, d, J=6.0 Hz), 7.08–7.20 (3H, m). IR ν max$^{KBr}$cm$^{-1}$: 1611, 1510, 1441.

3) ethyl 3-(4-fluorophenyl)-3-oxo-2-[(2,2,3,3-tetrafluoro-2,3-dihydro-1,4-benzodioxin-6-yl)methyl]propanoate To a solution of (2,2,3,3-tetrafluoro-2,3-dihydro-1,4-benzodioxin-6-yl)methanol (3.48 g, 14.6 mmol) in ethyl acetate (100 ml) were added methanesulfonyl chloride (1.25 ml, 16.1 mmol) and triethylamine (3.05 ml, 21.9 mmol), and the mixture was stirred at room temperature for 2 hrs. Insoluble material was filtered off, and the filtrate was evaporated under reduced pressure to give a mesyl form. To a solution of ethyl 3-(4-fluorophenyl)-3-oxopropanoate (3.07 g, 14.6 mmol) in 1,2-dimethoxyethane (20 ml) was added sodium hydride (0.58 g, 60% in oil, 14.6 mmol), and the mixture was stirred at room temperature for 1 hr. To the reaction solution was dropwise added a solution of the mesyl form prepared earlier in 1,2-dimethoxyethane (10 ml), and the mixture was stirred overnight at room temperature. The reaction solution was acidified with 1N hydrochloric acid, neutralized with saturated aqueous sodium hydrogen carbonate and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=4:1) and recrystallized from ethyl acetate-hexane to give the objective substance (4.49 g, 71%).

$^1$H-NMR (CDCl$_3$)δ: 1.12 (3H, t, J=7.2 Hz), 3.30 (2H, d, J=7.5 Hz), 4.11 (2H, q, J=7.2 Hz), 4.51 (1H, t, J=7.5 Hz), 7.03 (3H, s), 7.08–7.20 (2H, m), 7.96–8.04 (2H, m). IR ν max$^{KBr}$cm$^{-1}$: 1736, 1688, 1599, 1508. mp 83–84° C. Anal. Calcd for C$_{20}$H$_{15}$O$_5$F$_5$: C, 55.82; H, 3.51 Found: C, 55.87; H, 3.42.

4) ethyl (2RS,3RS)-3-(4-fluorophenyl)-3-hydroxy-2-[(2,2,3,3-tetrafluoro-2,3-dihydro-1,4-benzodioxin-6-yl)methyl]propanoate To a solution of zinc chloride (2.79 g, 20.5 mmol) in diethyl ether (100 ml) was added sodium borohydride (1.55 g, 40.9 mmol), and the mixture was stirred at room temperature for 30 min. Insoluble material was filtered off, and to the filtrate was added a solution of ethyl 3-(4-fluorophenyl)-3-oxo-2-[(2,2,3,3-tetrafluoro-2,3-dihydro-1,4-benzodioxin-6-yl)methyl]propanoate (4.4 g, 10.2 mmol) in diethyl ether (50 ml) at 0° C. The mixture was stirred for 30 min. and 1N hydrochloric acid was added to stop the reaction. After neutralization with saturated aqueous hydrogen carbonate solution, water (200 ml) was further added and the mixture was extracted with ethyl acetate (200 ml×2). The extract was washed with water and saturated brine, dried (anhydrous magnesium sulfate) and evaporated under reduced pressure to give the objective substance (4.40 g, 100%).

$^1$H-NMR (CDCl$_3$)δ: 0.95 (3H, t, J=7.2 Hz), 2.84–3.02 (4H, m), 3.80–4.00 (2H, m), 4.96–5.04 (1H, m), 6.84–6.90 (2H, m), 6.96–7.10 (3H, m), 7.30–7.40 (2H, m). IR ν max$^{KBr}$cm$^{-1}$: 1725, 1607, 1510. Anal. Calcd for C$_{20}$H$_{17}$O$_5$F$_5$: C, 55.56; H, 3.96 Found: C, 55.33; H, 3.97.

5) (2RS,3RS)-3-(4-fluorophenyl)-3-hydroxy-2-[(2,2,3,3-tetrafluoro-2,3-dihydro-1,4-benzodioxin-6-yl)methyl]propanoic acid To a solution of ethyl (2RS,3RS)-3-(4-fluorophenyl)-3-hydroxy-2-[(2,2,3,3-tetrafluoro-2,3-dihydro-1,4-benzodioxin-6-yl)methyl]propanoate (4.20 g, 9.71 mmol) in methanol (20 ml) was added 2N aqueous sodium hydroxide solution (9.7 ml, 19.4 mmol), and the mixture was stirred overnight at room temperature. The reaction solution was concentrated, acidified with 1N hydrochloric acid and extracted with ethyl acetate (200 ml×2). The extract was washed with water and saturated brine, dried (anhydrous magnesium sulfate) and evaporated under reduced pressure. The residue was recrystallized from ethyl acetate-hexane to give the objective substance (3.50 g, 89%)

$^1$H-NMR (CDCl$_3$)δ: 2.84–3.10 (3H, m), 5.08 (1H, s), 6.80–6.92 (2H, m), 6.92–7.12 (3H, m), 7.26–7.42 (2H, m). IR ν max$^{KBr}$cm$^{-1}$: 1752, 1676. mp 90–91° C. Anal. Calcd for C$_{18}$H$_{13}$O$_5$F$_5$: C, 53.48; H, 3.24 Found: C, 53.48; H, 3.18.

6) (4RS,5SR)-5-(4-fluorophenyl)-4-[(2,2,3,3-tetrafluoro-2,3-dihydro-1,4-benzodioxin-6-yl)methyl]-1,3-oxazolidin-2-one To a solution of (2RS,3RS)-3-(4-fluorophenyl)-3-hydroxy-2-[(2,2,3,3-tetrafluoro-2,3-dihydro-1,4-benzodioxin-6-yl)methyl]propanoic acid (3.3 g, 8.16 mmol) in tetrahydrofuran (120 ml) were added diphenylphosphoryl azide (1.94 ml, 8.98. mmol) and triethylamine (1.71 ml, 12.2 mmol), and the mixture was heated under reflux for 1 hr. The reaction solution was allowed to cool and the mixture was evaporated under reduced pressure. The residue was purified by silica gel column chromatography (ethyl acetate). Recrystallization from ethyl acetate-hexane gave the objective substance (2.74 g, 84%).

$^1$H-NMR (CDCl$_3$)δ: 2.20–2.40 (2H, m), 4.18–4.30 (1H, m), 5.28 (1H, brs), 5.79 (1H, d, J=8.2 Hz), 6.77 (1H, s), 6.81 (1H, d, J=8.8 Hz), 7.00–7.20 (3H, m), 7.20–7.40 (2H, m). IR ν max$^{KBr}$cm$^{-1}$: 1751, 1736, 1611, 1513. mp 191–192° C. Anal. Calcd for C$_{18}$H$_{12}$F$_5$NO$_4$: C, 53.88; H, 3.01; N, 3.49. Found: C, 54.06; H, 3.22; N, 3.60.

7) (1RS,2SR)-2-amino-1-(4-fluorophenyl)-3-(2,2,3,3-tetrafluoro-2,3-dihydro-1,4-benzodioxin-6-yl)propan-1-ol To a solution of (4RS,5SR)-5-(4-fluorophenyl)-4-[(2,2,3,3-tetrafluoro-2,3-dihydro-1,4-benzodioxin-6-yl)methyl]-1,3-oxazolidin-2-one (1.50 g, 3.74 mmol) in ethanol (10 ml) was added 8N aqueous sodium hydroxide solution (1.40 ml, 11.2 mmol), and the mixture was stirred at 80° C. overnight.

To the reaction solution was added water (20 ml) and the mixture was extracted with ethyl acetate (50 ml×2). The extract was washed with water and saturated brine, dried (anhydrous magnesium sulfate) and evaporated under reduced pressure. The residue was recrystallized from ethyl acetate-hexane to give the objective substance (0.81 g, 58%).

$^1$H-NMR (CDCl$_3$)δ: 1.00–1.60 (2H, br), 2.36 (1H, dd, J=14.0, 10.2 Hz), 2.80 (1H, dd, J=14.0, 2.8 Hz), 3.18–3.30 (1H, m), 4.62 (1H, d, J=5.2 Hz), 6.90–7.00 (2H, m), 7.00–7.14 (3H, m), 7.30–7.42 (2H, m). IR ν max$^{KBr}$cm$^{-1}$: 1605, 1508, 1279, 1219. mp 87–88° C. Anal. Calcd for C$_{17}$H$_{14}$F$_5$NO$_3$: C, 54.41; H, 3.76; N, 3.73. Found: C, 54.40; H, 3.66; N, 3.66.

8) N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-6,7-dihydro-5H-benzo[a][7]annulene-1-carboxamide To a solution of (1RS,2SR)-2-amino-1-(4-fluorophenyl)-3-(2,2,3,3-tetrafluoro-2,3-dihydro-1,4-benzodioxin-6-yl)propan-1-ol (250 mg, 0.67 mmol) in acetonitrile (20 ml) were added 6,7-dihydro-5H-benzo[a]cycloheptene-1-carboxylic acid (125 mg, 0.67 mmol), 1-ethyl-3-(3-dimethylaminopropyl)carbodiimide hydrochloride (191 mg, 1.00 mmol) and 1-hydroxybenzotriazole hydrate (102 mg, 0.67 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (ethyl acetate). Recrystallization from ethyl acetate-hexane gave the objective substance (257 mg, 69%).

$^1$H-NMR (CDCl$_3$)δ: 1.90–2.10 (2H, m), 2.12–2.26 (2H, m), 2.60–2.74 (2H, m), 2.79 (1H, dd, J=14.6, 10.2 Hz), 2.95 (1H, dd, J=14.6, 4.4 Hz), 3.35 (1H, d, J=3.8 Hz), 4.50–4.70 (1H, m), 4.98–5.08 (1H, m), 5.78 (1H, d, J=8.8 Hz), 5.84–6.00 (1H, m), 6.19 (1H, d, J=11.6 Hz), 6.90–7.20 (8H, m), 7.38–7.50 (2H, m). IR ν max$^{KBr}$cm$^{-1}$: 1636, 1607, 1510. mp 184–185° C. Anal. Calcd for C$_{29}$H$_{24}$NO$_4$F$_5$: C, 63.85; H, 4.43; N, 2.57. Found: C, 63.79; H, 4.70; N, 2.64.

Example 271

4-fluoro-N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-1-naphthamide To a solution of (1RS,2SR)-2-amino-1-(4-fluorophenyl)-3-(2,2,3,3-tetrafluoro-2,3-dihydro-1,4-benzodioxin-6-yl)propan-1-ol (250 mg, 0.67 mmol) in acetonitrile (20 ml) were added 4-fluoronaphthalenecarboxylic acid (127 mg, 0.67 mmol), 1-ethyl-3-(3-dimethylaminopropyl)carbodiimide hydrochloride (191 mg, 1.00 mmol) and 1-hydroxybenzotriazole-hydrate (102 mg, 0.67 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (ethyl acetate). Recrystallization from ethyl acetate-hexane gave the objective substance (290 mg, 80%).

$^1$H-NMR (CDCl$_3$)δ: 2.84 (1H, dd, J=14.6, 10.6 Hz), 3.02 (1H, dd, J=14.6, 4.0 Hz), 3.27 (1H, s), 4.64–4.82 (1H, m), 5.09 (1H, s), 6.04 (1H, d, J=9.0 Hz), 6.90–7.22 (7H, m), 7.36–7.66 (4H, m), 7.77 (1H, d, J=8.0 Hz), 8.01 (1H, d, J=8.2 Hz). IR ν max$^{KBr}$cm$^{-1}$: 1642, 1626, 1603, 1534, 1512. mp 193–194° C. Anal. Calcd for C$_{28}$H$_{19}$NO$_4$F$_6$: C, 61.43; H, 3.50; N, 2.56. Found: C, 61.32; H, 3.57; N, 2.58.

Example 272

N-[(1RS,2SR)-1-(4-tert-butylbenzyl)-2-(3-chlorophenyl)-2-hydroxyethyl]-6,7-dihydro-5H-benzo[a][7]annulene-1-carboxamide 1) ethyl 2-(4-tert-butylbenzyl)-3-(3-chlorophenyl)-3-oxopropanoate To a solution of (4-tert-butylphenyl)methanol (14.1 g, 86.0 mmol) in ethyl acetate (200 ml) were added methanesulfonyl chloride (7.47 ml, 94.6 mmol) and triethylamine (18.0 ml, 129 mmol), and the mixture was stirred at room temperature for 2 hrs. Insoluble material was filtered off, and the filtrate was evaporated under reduced pressure to give a mesyl form. To a solution of ethyl 3-(3-chlorophenyl)-3-oxopropanoate (19.5 g, 86.0 mmol) in 1,2-dimethoxyethane (100 ml) was added sodium hydride (3.44 g, 60% in oil, 86.0 mmol), and the mixture was stirred at room temperature for 1 hr. To the reaction solution was dropwise added a solution of the mesyl form prepared earlier in 1,2-dimethoxyethane (10 ml), and the reaction solution was stirred overnight at room temperature. The reaction solution was acidified with 1N hydrochloric acid and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate= 4:1) to give the objective substance (31.1 g, 97%).

$^1$H-NMR (CDCl$_3$)δ: 1.13 (3H, t, J=7.0 Hz), 1.28 (9H, s), 3.29 (2H, d, J=7.4 Hz), 4.11 (2H, q, J=7.0 Hz), 4.54 (1H, t, J=7.4 Hz), 7.08–7.18 (2H, m), 7.22–7.44 (3H, m), 7.48–7.56 (1H, m), 7.81 (1H, dt, J=7.6, 1.6 Hz), 7.89 (1H, t, J=1.8 Hz). IR ν max$^{KBr}$cm$^{-1}$: 1738, 1694, 1570. Anal. Calcd for C$_{22}$H$_{25}$ClO$_3$ 0.1H$_2$O: C, 70.53; H, 6.77 Found: C, 70.38; H, 7.02.

2) ethyl (2RS,3RS)-2-(4-tert-butylbenzyl)-3-(3-chlorophenyl)-3-hydroxypropanoate To a solution of zinc chloride (22.3 g, 163.6 mmol) in diethyl ether (500 ml) was added sodium borohydride (12.4 g, 327.2 mmol), and the mixture was stirred at room temperature for 30 min. Insoluble material was filtered off, and to the filtrate was added a solution of ethyl 2-(4-tert-butylbenzyl)-3-(3-chlorophenyl)-3-oxopropanoate (30.5 g, 81.8 mmol) in diethyl ether. (200 ml) at 0° C. The mixture was stirred for 30 min. and 1N hydrochloric acid was added to stop the reaction. Water (200 ml) was further added, and the mixture was extracted with ethyl acetate (200 ml×2). The extract was washed with water and saturated brine; dried (anhydrous magnesium sulfate) and evaporated under reduced pressure to give the objective substance (26.8 g, 87%).

$^1$H-NMR (CDCl$_3$)δ: 0.92 (3H, t, J=7.0 Hz), 1.27 (9H, s), 2.80–3.00 (3H, m), 3.14 (1H, d, J=3.0 Hz), 3.80–4.00 (2H, m), 4.96–5.04 (1H, m), 7.01 (2H, d, J=8.4 Hz), 7.18–7.30 (5H, m), 7.41 (1H, s). IR ν max$^{KBr}$cm$^{-1}$: 1728, 1713, 1597, 1574. Anal. Calcd for C$_{22}$H$_{27}$ClO$_3$ 0.5H$_2$O: C, 68.83; H, 7.34 Found: C, 68.71; H, 7.32.

3) (2RS,3RS)-2-(4-tert-butylbenzyl)-3-(3-chlorophenyl)-3-hydroxypropanoic acid

To a solution of ethyl (2RS,3RS)-2-(4-tert-butylbenzyl)-3-(3-chlorophenyl)-3-hydroxypropanoate (26.5 g, 70.7 mmol) in ethanol (200 ml) was added 2N aqueous sodium hydroxide solution (70 ml, 140 mmol), and the mixture was stirred overnight at room temperature. The reaction solution was concentrated, acidified with 1N hydrochloric acid and extracted with ethyl acetate (500 ml×2). The extract was washed with water and saturated brine, dried (anhydrous magnesium sulfate) and evaporated under reduced pressure. The residue was recrystallized from ethyl acetate-hexane to give the objective substance (15.0 g, 59%).

$^1$H-NMR (CDCl$_3$)δ: 1.28 (9H, s), 2.80–3.10 (3H, m), 5.08 (1H, d, J=4.0 Hz), 7.00 (2H, d, J=8.4 Hz), 7.20–7.30 (5H, m), 7.41 (1H, s). IR ν max$^{KBr}$cm$^{-1}$: 1713, 1599, 1576. mp 117–118° C. Anal. Calcd for C$_{20}$H$_{23}$ClO$_3$: C, 69.26; H, 6.68 Found: C, 69.18; H, 6.68.

4) (4RS,5SR)-4-(4-tert-butylbenzyl)-5-(3-chlorophenyl)-1,3-oxazolidin-2-one

To a solution of (2RS,3RS)-2-(4-tert-butylbenzyl)-3-(3-chlorophenyl)-3-hydroxypropanoic acid (14.5 g, 40.6 mmol) in tetrahydrofuran (400 ml) were added diphenylphosphoryl azide (9.63 ml, 44.7 mmol) and triethylamine (8.50 ml, 60.9 mmol), and the mixture was heated under reflux for 1 hr. The reaction solution was cooled and evaporated under reduced pressure. To the residue was added water (500 ml), and mixture was extracted with ethyl acetate-tetrahydrofuran. The extract was washed with water and saturated brine, dried (anhydrous magnesium sulfate) and evaporated under reduced pressure. The residue was washed with ethyl acetate to give the objective substance (9.6 g, 69%).

$^1$H-NMR (CDCl$_3$)δ: 1.29 (9H, s), 2.04–2.36 (2H, m), 4.16–4.30 (1H, m) 5.03 (1H, brs), 5.76 (1H, d, J=7.6 Hz), 6.96 (2H, d, J=8.4 Hz), 7.24–7.40 (6H, m). IR ν max$^{KBr}$cm$^{-1}$: 1734. mp 215–216° C. Anal. Calcd for C$_{20}$H$_{22}$Cl.NO$_2$: C, 69.86; H, 6.45; N, 4.07. Found: C, 69.65; H, 6.46; N, 4.10.

5) (1RS,2SR)-2-amino-3-(4-tert-butylphenyl)-1-(3-chlorophenyl)propan-1-ol

To a solution of (4RS,5SR)-4-(4-tert-butylbenzyl)-5-(3-chlorophenyl)-1,3-oxazolidin-2-one (9.50 g, 27.6 mmol) in ethanol (70 ml) was added 8N aqueous sodium hydroxide solution (17.3 ml, 138 mmol), and the mixture was stirred at 80° C. overnight. To the reaction solution was added water (20 ml) and the mixture was extracted with ethyl acetate (50 ml×2). The extract was washed with water and saturated brine, dried (anhydrous magnesium sulfate) and evaporated under reduced pressure to give the objective substance (8.82 g, 100%).

$^1$H-NMR (CDCl$_3$)δ: 1.30 (9H, s), 2.31 (1H, dd, J=14.0, 10.6 Hz), 2.73 (1H, dd, J=14.0, 3.4 Hz), 3.22–3.34 (1H, m), 4.67 (1H, d, J=4.8 Hz), 7.05 (2H, d, J=8.0 Hz), 7.24–7.36 (5H, m), 7.42 (1H, s). IR ν max$^{KBr}$cm$^{-1}$: 1597, 1574, 1512, 1474.

6) N-[(1RS,2SR)-1-(4-tert-butylbenzyl)-2-(3-chlorophenyl)-2-hydroxyethyl]-6,7-dihydro-5H-benzo[a][7]annulene-1-carboxamide To a solution of (1RS,2SR)-2-amino-3-(4-tert-butylphenyl)-1-(3-chlorophenyl)propan-1-ol (355 mg, 1.17 mmol) in acetonitrile (20 ml) were added 6,7-dihydro-5H-benzo[a]cycloheptene-1-carboxylic acid (220 mg, 1.17 mmol), 1-ethyl-3-(3-dimethylaminopropyl)carbodiimide hydrochloride (336 mg, 1.76 mmol) and 1-hydroxybenzotriazole hydrate (179 mg, 1.17 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (348 mg, 64%).

$^1$H-NMR (CDCl$_3$)δ: 1.30 (9H, s), 1.90–2.08 (2H, m), 2.10–2.24 (2H, m), 2.60–2.78 (3H, m), 2.96 (1H, dd, J=14.4, 4.8 Hz), 4.35 (1H, d, J=4.4 Hz), 4.60–4.76 (1H, m), 4.98–5.06 (1H, m), 5.67 (1H, d, J=7.8 Hz), 5.88–6.02 (1H, m), 6.28 (1H, d, J=11.8 Hz), 6.88 (1H, dd, J=7.4, 1.4 Hz), 6.98–7.18 (4H, m), 7.20–7.38 (8H, m), 7.47 (1H, s). IR ν max$^{KBr}$cm$^{-1}$: 1633, 1514. mp 142–143° C. Anal. Calcd for C$_{31}$H$_{34}$Cl NO$_2$: C, 76.29; H, 7.02; N, 2.87. Found: C, 76.19; H, 7.15; N, 2.83.

Example 273

N-[(1RS,2SR)-1-(4-tert-butylbenzyl)-2-(3-chlorophenyl)-2-hydroxyethyl]-4-fluoro-1-naphthamide To a solution of (1RS,2SR)-2-amino-3-(4-tert-butylphenyl)-1-(3-chlorophenyl)propan-1-ol (355 mg, 1.17 mmol) in acetonitrile (20 ml) were added 4-fluoronaphthalenecarboxylic acid (223 mg, 1.17 mmol), 1-ethyl-3-(3-dimethylaminopropyl)carbodiimide hydrochloride (336 mg, 1.76 mmol) and 1-hydroxybenzotriazole hydrate (179 mg, 1.17 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (333 mg, 61%).

$^1$H-NMR (CDCl$_3$)δ: 2.74 (1H, dd, J=14.4, 11.0 Hz), 3.02 (1H, dd, J=14.4, 4.4 Hz), 4.15 (1H, d, J=4.4 Hz), 4.70–4.86 (1H, m), 5.04–5.12 (1H, m), 5.85 (1H, d, J=8.0 Hz), 6.90–7.20 (4H, m), 7.24–7.60 (8H, m), 7.89 (1H, d, J=7.6 Hz), 8.07 (1H, d, J=8.0 Hz) IR ν max$^{KBr}$cm$^{-1}$: 1640, 1624, 1599, 1580, 1514. mp 144–145° C. Anal. Calcd for C$_{30}$H$_{29}$Cl FNO$_2$.0.1H$_2$O: C, 73.27; H, 5.98; N, 2.85. Found: C, 73.05; H, 5.74; N, 3.09.

Example 274

N-[(1RS,2SR)-1-(4-tert-butylbenzyl)-2-(3-chlorophenyl)-2-hydroxyethyl]-5-chloro-1-naphthamide To a solution of (1RS,2SR)-2-amino-3-(4-tert-butylphenyl)-1-(3-chlorophenyl)propan-1-ol (1.0 g, 3.15 mmol) in acetonitrile (40 ml) were added 5-chloronaphthalenecarboxylic acid (651 mg, 3.15 mmol), 1-ethyl-3-(3-dimethylaminopropyl)carbodiimide hydrochloride (725 mg, 3.78 mmol) and 1-hydroxybenzotriazole hydrate (482 mg, 3.15 mmol), and the mixture was stirred overnight at room temperature. The reaction solution was diluted with water (200 ml), and the mixture was extracted with ethyl acetate (200 ml×2). The extract was washed successively with water and saturated brine, dried (anhydrous magnesium sulfate) and evaporated under reduced pressure. The residue was purified by silica gel column chromatography (hexane:ethyl acetate=4:1–1:1). Recrystallization from ethyl acetate-hexane gave the objective substance (1.04 g, 66%).

$^1$H-NMR (CDCl$_3$)δ: 1.31 (9H, s), 2.74 (1H, dd, J=14.2, 11.0 Hz) 3.01 (1H, dd, J=14.2, 4.4 Hz), 3.98 (1H, d, J=4.4 Hz), 4.70–4.88 (1H, m), 5.02–5.10 (1H, m), 5.90 (1H, d, J=8.0 Hz), 7.13 (2H, d, J=8.4 Hz), 7.22–7.60 (10H, m), 7.73 (1H, d, J=8.8 Hz), 8.31 (1H, d, J=8.4 Hz). IR ν max$^{KBr}$cm$^{-1}$: 1636, 1572, 1518. mp 112–113° C. Anal. Calcd for C$_{30}$H$_{29}$Cl$_2$NO$_2$: C, 71.15; H, 5.77; N, 2.77. Found: C, 71.10; H, 5.83; N, 2.56.

Example 275

N-[(1RS,2SR)-1-(4-tert-butylbenzyl)-2-(3-chlorophenyl)-2-hydroxyethyl]-5-fluoro-1-naphthamide To a solution of (1RS,2SR)-2-amino-3-(4-tert-butylphenyl)-1-(3-chlorophenyl)propan-1-ol (300 mg, 0.94 mmol) in acetonitrile (20 ml) were added 5-fluoronaphthalenecarboxylic acid (180 mg, 0.94 mmol), 1-ethyl-3-(3-dimethylaminopropyl)carbodiimide hydrochloride (217 mg, 1.13 mmol) and 1-hydroxybenzotriazole hydrate (145 mg, 0.94 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1). Recrystallization from ethyl acetate-hexane gave the objective substance (0.24 g, 53%).

$^1$H-NMR (CDCl$_3$)δ: 1.31 (9H, s), 2.74 (1H, dd, J=14.2, 10.6 Hz), 3.01 (1H, dd, J=14.2, 4.4 Hz), 4.02 (1H, s), 4.70–4.88 (1H, m), 5.07 (1H, t, J=4.0 Hz), 5.89 (1H, d, J=7.0 Hz), 7.04–7.20 (4H, m), 7.22–7.44 (7H, m), 7.50 (1H, s), 7.60 (1H, d, J=8.4 Hz), 8.12 (1H, d, J=8.4 Hz). IR ν max$^{KBr}$cm$^{-1}$: 1636, 1595, 1584, 1520, 1507. mp 102–103° C. Anal. Calcd for C$_{30}$H$_{29}$ClFNO$_2$: C, 72.47; H, 6.04; N, 2.82. Found: C, 72.47; H, 6.23; N, 2.60.

Example 276

N-[(1RS,2SR)-1-(4-tert-butoxybenzyl)-2-(3-chlorophenyl)-2hydroxyethyl]-6,7-dihydro-5H-benzo[a][7]annulene-1-carboxamide 1) ethyl 2-(4-tert-butoxybenzyl)-3-(3-chlorophenyl)-3-oxopropanoate To a solution of (4-tert-butoxyphenyl)methanol (5.0 g, 27.7 mmol) in ethyl acetate (70 ml) were added methanesulfonyl chloride (2.36 ml, 30.5 mmol) and triethylamine (5.8 ml, 41.6 mmol), and the mixture was stirred at room temperature for 2 hrs. Insoluble material was filtered off, and the filtrate was evaporated under reduced pressure to give a mesyl form. To a solution of ethyl 3-(3-chlorophenyl)-3-oxopropanoate (6.29 g, 27.7 mmol) in 1,2-dimethoxyethane (50 ml) was added sodium hydride (1.11 g, 60% in oil, 27.7 mmol), and the mixture was stirred at room temperature for 1 hr. To the reaction solution was dropwise added a solution of the mesyl form prepared earlier in 1,2-dimethoxyethane (10 ml), and the reaction, solution was stirred at room temperature overnight. The reaction solution was acidified with 1N hydrochloric acid and extracted with ethyl acetate (300 ml×2). The extract was washed successively with water and saturated brine, dried (anhydrous magnesium sulfate) and evaporated under reduced pressure. The residue was purified by silica gel column chromatography (hexane:ethyl acetate=4:1) to give the objective substance (8.26 g, 77%, crude).

2) ethyl (2RS,3RS)-2-(4-tert-butoxybenzyl)-3-(3-chlorophenyl)-3-hydroxypropanoate To a solution of zinc chloride (5.79 g, 42.5 mmol) in diethyl ether (150 ml) was added sodium borohydride (3.22 g, 85.0 mmol), and the mixture was stirred at room temperature for 30 min. Insoluble material was filtered off, and to the filtrate was added a solution of ethyl 2-(4-tert-butoxybenzyl)-3-(3-chlorophenyl)-3-oxopropanoate (8.26 g, 21.2 mmol) in diethyl ether (100 ml) at 0° C. The mixture was stirred for 30 min. and 1N hydrochloric acid was added to stop the reaction. Water (200 ml) was further added and the mixture was extracted with ethyl acetate (200 ml×2). The extract was washed with water and saturated brine, dried (anhydrous magnesium sulfate) and evaporated under reduced pressure. The residue was purified by silica gel column chromatography (hexane:ethyl acetate=10:1-2:1) to give the objective substance (7.12 g, 86%).

$^1$H-NMR (CDCl$_3$)δ: 0.94 (3H, t, J=7.0 Hz), 1.30 (9H, s), 2.80–3.00 (3H, m), 3.12–3.22 (1H, m), 3.89 (2H, q, J=7.0 Hz), 5.01 (1H, s), 6.80–6.88 (2H, m), 6.92–7.00 (2H, m), 7.20–7.30 (3H, m), 7.42 (1H, s). IR ν max$^{KBr}$cm$^{-1}$: 1726, 1609, 1597, 1574, 1507.

3) (2RS,3RS)-2-(4-tert-butoxybenzyl)-3-(3-chlorophenyl)-3-hydroxypropanoic acid

To a solution of ethyl (2RS,3RS)-2-(4-tert-butoxybenzyl)-3-(3-chlorophenyl)-3-hydroxypropanoate (7.12 g, 18.2 mmol) in methanol (60 ml) was added 2N aqueous sodium hydroxide solution (18.2 ml, 36.4 mmol), and the mixture was stirred overnight at room temperature. The reaction solution was concentrated and acidified with 1N hydrochloric acid. The mixture was extracted with ethyl acetate (200 ml×2). The extract was washed with water and saturated brine, dried (anhydrous magnesium sulfate) and evaporated under reduced pressure. The residue was recrystallized from ethyl acetate-hexane to give the objective substance (4.70 g, 82%).

$^1$H-NMR (CDCl$_3$)δ: 1.29 (9H, t), 2.80–3.02 (3H, m), 5.06 (1H, d, J=4.4 Hz), 6.80–6.90 (2H, m), 6.90–7.02 (2H, m), 7.20–7.30 (3H, m), 7.42 (1H, s). IR ν max$^{KBr}$cm$^{-1}$: 1713, 1705. mp 81–82° C.

4) (4RS,5SR)-4-(4-tert-butoxybenzyl)-5-(3-chlorophenyl)-1,3-oxazolidin-2-one

To a solution of (2RS,3RS)-2-(4-tert-butoxylbenzyl)-3-(3-chlorophenyl)-3-hydroxypropanoic acid (4.50 g, 14.3 mmol) in tetrahydrofuran (150 ml) were added diphenylphosphoryl azide (3.39 ml, 15.7 mmol) and triethylamine (3.00 ml, 21.4 mmol), and the mixture was heated under reflux for 1 hr. The reaction solution was allowed to cool and the mixture was evaporated under reduced pressure. To the residue was added water (200 ml), and the mixture was extracted with ethyl acetate. The extract was washed with water and saturated brine, dried (anhydrous magnesium sulfate) and evaporated under reduced pressure. The residue was recrystallized from hexane-ethyl acetate to give the objective substance (4.01 g, 80%).

$^1$H-NMR (CDCl$_3$)δ: 1.32 (9H, s), 2.18 (1H, dd, J=13.8, 11.1 Hz), 2.28 (1H, dd, J=13.8, 3.9 Hz), 4.18–4.28 (1H, m), 4.95 (1H, s), 5.76 (1H, d, J=7.8 Hz), 6.90–6.98 (2H, m), 7.24–7.30 (2H, m), 7.30–7.40 (4H, m). IR ν max$^{KBr}$cm$^{-1}$: 1734, 1507, 1476, 1435, 1391, 1364. mp 165–166° C. Anal. Calcd for C$_{20}$H$_{22}$NO$_3$Cl: C, 66.75; H, 6.16; N, 3.89. Found: C, 66.65; H, 6.26; N, 3.69.

5) (1RS,2SR)-2-amino-3-(4-tert-butoxyphenyl)-1-(3-chlorophenyl)propan-1-ol

To a solution of (4RS,5SR)-4-(4-tert-butoxybenzyl)-5-(3-chlorophenyl)-1,3-oxazolidin-2-one (3.80 g, 10.6 mmol) in ethanol (20 ml) was added 8N aqueous sodium hydroxide solution (3.96 ml, 31.7 mmol), and the mixture was stirred at 80° C. for 6 hrs. To the reaction solution was added water (20 ml) and the mixture was extracted with ethyl acetate (50 ml×2). The extract was washed with water and saturated brine, dried (anhydrous magnesium sulfate) and evaporated under reduced pressure. The residue was recrystallized from hexane-ethyl acetate to give the objective substance (2.67 g, 76%).

$^1$H-NMR (CDCl$_3$)δ: 1.32 (9H, s), 2.30 (1H, dd, J=13.8, 10.4 Hz), 2.70 (1H, dd, J=13.8, 3.4 Hz), 3.22–3.34 (1H, m), 4.67 (1H, d, J=4.8 Hz), 6.86–6.96 (2H, m), 6.96–7.06 (2H, m), 7.20–7.34 (3H, m), 7.42 (1H, s). IR ν max$^{KBr}$cm$^{-1}$: 1574, 1507, 1476, 1366. mp 93–94° C. Anal. Calcd for C$_{19}$H$_{24}$NO$_2$Cl: C, 68.35; H, 7.25; N, 4.20. Found: C, 68.21; H, 7.28; N, 4.18.

6) N-[(1RS,2SR)-1-(4-tert-butoxybenzyl)-2-(3-chlorophenyl)-2-hydroxyethyl]-6,7-dihydro-5H-benzo[a][7]annulene-1-carboxamide To a solution of (1RS,2SR)-2-amino-3-(4-tert-butoxyphenyl)-1-(3-chlorophenyl)propan-1-ol (300 mg, 0.90 mmol) in acetonitrile (20 ml) were added 6,7-dihydro-5H-benzo[a]cycloheptene-1-carboxylic acid (169 mg, 0.90 mmol), 1-ethyl-3-(3-dimethylaminopropyl)carbodiimide hydrochloride (258 mg, 1.35 mmol) and 1-hydroxybenzotriazole hydrate (138 mg, 0.90 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (351 mg, 77%).

$^1$H-NMR (CDCl$_3$)δ: 1.32 (9H, s), 1.90–2.08 (2H, m), 2.12–2.24 (2H, m), 2.60–2.76 (3H, m), 2.94 (1H, dd, J=14.6, 4.4 Hz), 4.32 (1H, d, J=4.0 Hz), 4.58–4.72 (1H, m), 5.00–5.08 (1H, m), 5.73 (1H, d, J=7.6 Hz), 5.92–6.08 (1H, m), 6.33 (1H, d, J=12.0 Hz), 6.88–7.20 (7H, m), 7.24–7.36 (3H, m), 7.47 (1H, s). IR ν max$^{KBr}$cm$^{-1}$: 1640, 1507. mp 180–181° C. Anal. Calcd for C$_{31}$H$_{34}$NO$_3$Cl: C, 73.87; H, 6.80; N, 2.78. Found: C, 73.62; H, 6.81; N, 2.85.

Example 277

N-[(1RS,2SR)-1-(4-tert-butoxybenzyl)-2-(3-chlorophenyl)-2-hydroxyethyl]-4-fluoro-1-naphthamide To a solution of (1RS,2SR)-2-amino-3-(4-tert-butoxyphenyl)-1-(3-chlorophenyl)propan-1-ol (300 mg, 0.90 mmol) in acetonitrile (20 ml) were added 4-fluoronaphthalenecarboxylic acid (171 mg, 0.90 mmol), 1-ethyl-3-(3-dimethylaminopropyl)carbodiimide hydrochloride (258 mg, 1.35 mmol) and 1-hydroxybenzotriazole hydrate (138 mg, 0.90 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (278 mg, 61%).

$^1$H-NMR (CDCl$_3$)δ: 1.32 (9H, s), 2.73 (1H, dd, J=14.6, 11.0 Hz), 3.01 (1H, dd, J=14.6, 4.4 Hz), 4.13 (1H, d, J=4.0 Hz), 4.66–4.82 (1H, m), 5.10 (1H, s), 5.87 (1H, d, J=8.6 Hz), 6.90–7.02 (3H, m), 7.04–7.16 (3H, m), 7.26–7.38 (3H, m), 7.44–7.60 (3H, m), 7.95 (1H, d, J=7.6 Hz), 8.02–8.10 (1H, m). IR ν max$^{KBr}$cm$^{-1}$: 1640, 1626, 1599, 1582, 1507. mp 161–162° C. Anal. Calcd for C$_{30}$H$_{29}$NO$_3$ClF: C, 71.21; H, 5.78; N, 2.77. Found: C 71.10; H, 5.94; N, 2.53.

Example 278

N-[(1RS,2SR)-1-(4-tert-butoxybenzyl)-2-(3-chlorophenyl)-2-hydroxyethyl]-5-chloro-1-naphthamide To a solution of (1RS,2SR)-2-amino-3-(4-tert-butoxyphenyl)-1-(3-chlorophenyl)propan-1-ol (300 mg, 0.90 mmol) in acetonitrile (20 ml) were added 5-chloronaphthalenecarboxylic acid (186 mg, 0.90 mmol), 1-ethyl-3-(3-dimethylaminopropyl)carbodiimide hydrochloride (258 mg, 1.35 mmol) and 1-hydroxybenzotriazole hydrate (138 mg, 0.90 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (136 mg, 29%).

$^1$H-NMR (CDCl$_3$)δ: 1.32 (9H, s), 2.72 (1H, dd, J=14.4, 11.0 Hz), 3.00 (1H, dd, J=14.4, 4.0 Hz), 3.96 (1H, d, J=3.6

Hz), 4.70–4.84 (1H, m), 5.09 (1H, s), 5.90 (1H, d, J=8.2 Hz), 6.93 (2H, d, J=8.4 Hz), 7.10 (2H, d, J=8.4 Hz), 7.14–7.62 (8H, m), 7.78 (1H, d, J=8.4 Hz), 8.32 (1H, d, J=8.4 Hz). IR ν max$^{KBr}$cm$^{-1}$: 1638, 1572, 1507. mp 132–133° C. Anal. Calcd for $C_{30}H_{29}NO_3Cl_2$: C, 68.97; H, 5.59; N, 2.68. Found: C, 68.68; H, 5.69; N, 2.53.

Example 279 tert-butyl (1RS,2SR)-2-(4-fluorophenyl)-2-hydroxy-1-{3-[(trifluoromethyl)sulfonyl]benzyl}ethylcarbamate 1) tert-butyl (4RS,5SR)-5-(4-fluorophenyl)-2-oxo-4-{3-[(trifluoromethyl)thio]benzyl}-1,3-oxazolidine-3-carboxylate To a solution of (4RS,5RS)-5-(4-fluorophenyl)-4-{3-[(trifluoromethyl)thio]benzyl}-1,3-oxazolidin-2-one (2.06 g, 5.55 mmol) in acetonitrile (20 ml) were added di-tert-butyl dicarbonate (1.45 g, 6.66 mmol) and 4-N,N-dimethylpyridine (68 mg, 0.56 mmol), and the mixture was stirred at room temperature for 1 hr. To the reaction solution was added water (100 ml) and the mixture was extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=10:1–1:1). Recrystallization from ethyl acetate-hexane gave the objective substance (2.17 g, 83%).

$^1$H-NMR (CDCl$_3$)δ: 1.54 (9H, s), 2.62 (1H, dd, J=14.4, 9.0 Hz), 2.96 (1H, dd, J=14.4, 4.0 Hz), 4.76–4.88 (1H, m), 5.67 (1H, d, J=6.8 Hz), 6.73 (1H, d, J=7.8 Hz), 6.82–7.00 (3H, m), 7.04–7.20 (3H, m), 7.39 (1H, d, J=7.8 Hz). IR ν max$^{KBr}$cm$^{-1}$: 1823, 1725, 1611, 1597, 1514. mp 112–113° C. Anal. Calcd for $C_{22}H_{21}NO_4SF_4$: C, 56.05; H, 4.49; N, 2.97. Found: C, 56.08; H, 4.56; N, 2.98.

2) tert-butyl (4RS,5SR)-5-(4-fluorophenyl)-2-oxo-4-{3-[(trifluoromethyl)sulfonyl]benzyl}-1,3-oxazolidine-3-carboxylate To a solution of tert-butyl (4RS,5SR)-5-(4-fluorophenyl)-2-oxo-4-{3-[(trifluoromethyl)thio]benzyl}-1,3-oxazolidine-3-carboxylate (1.0 g, 2.12 mmol) in acetonitrile (100 ml) was added an aqueous solution (50 ml) of sodium periodate (1.36 g, 6.36 mmol). After the reaction solution was stirred for 10 min., ruthenium chloride (41 mg, 0.21 mmol) was added, and the mixture was stirred overnight. After the reaction solution was concentrated, water (100 ml) was added and the mixture was extracted with ethyl acetate (200 ml×2). The extract was washed with water and saturated brine, dried (anhydrous magnesium sulfate) and evaporated under reduced pressure. Recrystallization of the residue from ethyl acetate-hexane gave the objective substance (0.93 g, 87%).

$^1$H-NMR (CDCl$_3$)δ: 1.54 (9H, s), 2.76 (1H, dd, J=14.6, 9.2 Hz), 3.03 (1H, dd, J=14.6, 4.0 Hz), 4.78–4.92 (1H, m), 5.70 (1H, d, J=6.8 Hz), 6.90–7.20 (5H, m), 7.30–7.44 (2H, m), 7.79 (1H, d, J=8.2 Hz). IR ν max$^{KBr}$cm$^{-1}$: 1817, 1725, 1611, 1514. mp 158–159° C. Anal. Calcd for $C_{22}H_{21}NO_6SF_4$: C, 52.48; H, 4.20; N, 2.78; F, 15.09; S, 6.37 Found: C, 52.51; H, 4.00; N, 2.55; F, 15.06; S, 6.40.

3) tert-butyl (1RS,2SR)-2-(4-fluorophenyl)-2-hydroxy-1-{3-[(trifluoromethyl)sulfonyl]benzyl}ethylcarbamate To a solution of tert-butyl (4RS,5SR)-5-(4-fluorophenyl)-2-oxo-4-{3-[(trifluoromethyl)sulfonyl]benzyl}-1,3-oxazolidine-3-carboxylate (0.90 g, 1.79 mmol) in methanol (10 ml) was added a solution of 0.5N sodium hydroxide in methanol (10.8 ml, 5.40 mmol), and the mixture was stirred at room temperature for 30 min. To the reaction solution was added water (50 ml), and the mixture was extracted with ethyl acetate (100 ml×2). The extract was washed with saturated brine, dried (anhydrous magnesium sulfate) and evaporated under reduced pressure. The residue was recrystallized from ethyl acetate-hexane to give the objective substance (0.72 g, 84%).

$^1$H-NMR (CDCl$_3$)δ: 1.31 (9H, s), 2.74–3.00 (3H, m), 3.96–4.16 (1H, m), 4.69 (1H, d, J=8.4 Hz), 4.95 (1H, s), 7.02–7.14 (2H, m), 7.32–7.44 (2H, m), 7.50–7.64 (2H, m), 7.77 (1H, s), 7.87 (1H, d, J=6.6 Hz). IR ν max$^{KBr}$cm$^{-1}$: 1694, 1510, 1368. mp 152–153° C. Anal. Calcd for $C_{21}H_{23}NO_5SF_4$: C, 52.83; H, 4.86; N, 2.93. Found: C, 52.67; H, 4.74; N, 2.97.

Example 280

N-((1RS,2SR)-2-(4-fluorophenyl)-2-hydroxy-1-{3-[(trifluoromethyl)sulfonyl]benzyl}ethyl)-6,7-dihydro-5H-benzo[a][7]annulene-1-carboxamide 1) (1RS,2SR)-2-amino-1-(4-fluorophenyl)-3-{3-[(trifluoromethyl)sulfonyl]phenyl}propan-1-ol To a solution of tert-butyl (1RS,2SR)-2-(4-fluorophenyl)-2-hydroxy-1-{3-[(trifluoromethyl)sulfonyl]benzyl}-ethylcarbamate (620 mg, 1.30 mmol) was added trifluoroacetic acid (5 ml), and mixture was stirred at 0° C. for 10 min. After the reaction solution was concentrated, saturated aqueous sodium hydrogen carbonate was added and the mixture was extracted with ethyl acetate (30 ml×2). The extract was washed with saturated brine, dried (anhydrous magnesium sulfate) and evaporated under reduced pressure to give the objective substance (0.52 g, 100%).

$^1$H-NMR (CDCl$_3$)δ: 2.55 (1H, dd, J=13.8, 9.9 Hz), 2.98 (1H, dd, J=13.8, 3.0 Hz), 3.22–3.36 (1H, m), 4.63 (1H, d, J=5.1 Hz), 7.02–7.12 (2H, m), 7.30–7.42 (2H, m), 7.52–7.70 (2H, m), 7.85 (1H, s), 7.90 (1H, d, J=8.4 Hz). IR ν max$^{KBr}$cm$^{-1}$: 1603, 1508, 1431, 1366.

2) N-((1RS,2SR)-2-(4-fluorophenyl)-2-hydroxy-1-{3-[(trifluoromethyl)sulfonyl]benzyl}ethyl)-6,7-dihydro-5H-benzo[a][7]annulene-1-carboxamide To a solution of (1RS,2SR)-2-amino-1-(4-fluorophenyl)-3-{3-[(trifluoromethyl)sulfonyl]phenyl}propan-1-ol (260 mg, 0.69 mmol) in acetonitrile (20 ml) were added 6,7-dihydro-5H-benzo[a]cycloheptene-1-carboxylic acid (130 mg, 0.69 mmol), 1-ethyl-3-(3-dimethylaminopropyl) carbodiimide hydrochloride (198 mg, 1.03 mmol) and 1-hydroxybenzotriazdle hydrate (105 mg, 0.69 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (252 mg, 67%).

$^1$H-NMR (CDCl$_3$)δ: 1.90–2.06 (2H, m), 2.12–2.26 (2H, m), 2.60–2.70 (2H, m), 2.90–3.20 (3H, m), 4.60–4.80 (1H, m), 5.04 (1H, s), 5.82–5.98 (2H, m), 6.13 (1H, d, J=11.8 Hz), 6.95 (1H, dd, J=7.4, 1.8 Hz), 7.00–7.20 (4H, m), 7.40–7.50 (2H, m), 7.52–7.64 (1H, m), 7.70 (1H, d, J=7.6 Hz), 7.81 (1H, s), 7.89 (1H, d, J=7.8 Hz). IR ν max$^{KBr}$cm$^{-1}$: 1638, 1508, 1449, 1366. mp 156–157° C. Anal. Calcd for $C_{28}H_{25}NO_4SF_4$: C, 61.42; H, 4.60; N, 2.56. Found: C, 61.25; H, 4.57; N, 2.57.

Example 281

4-fluoro-N-((1RS,2SR)-2-(4-fluorophenyl)-2-hydroxy-1-{3-[(trifluoromethyl)sulfonyl]benzyl}ethyl)-1-naphthamide To a solution of (1RS,2SR)-2-amino-1-(4-fluorophenyl)-3-{3-[(trifluoromethyl)sulfonyl]phenyl}propan-1-ol (260 mg, 0.69 mmol) in acetonitrile (20 ml) were added 4-fluoronaphthalenecarboxylic acid (131 mg, 0.69 mmol), 1-ethyl-3-(3-dimethylaminopropyl)carbodiimide hydrochloride (198 mg, 1.03 mmol) and 1-hydroxybenzotriazole hydrate (105 mg, 0.69 mmol), and the mixture was stirred overnight at room temperature. The reaction solution was diluted with water (100 ml) and extracted with ethyl acetate (100 ml×2). The extract was washed successively with water and saturated brine, dried (anhydrous magnesium sulfate) and evaporated under reduced pressure. The residue was purified by silica gel column chromatography (hexane:ethyl acetate=4:1–2:1). Recrystallization from ethyl acetate-hexane gave the objective substance (218 mg, 58%).

$^1$H-NMR (CDCl$_3$)δ: 2.84–3.20 (3H, m), 4.70–4.86 (1H, m), 5.09 (1H, s), 6.10 (1H, d, J=9.0 Hz), 6.96–7.24 (4H, m), 7.40–7.62 (5H, m), 7.64–7.80 (2H, m), 7.84–7.94 (2H, m), 8.08 (1H, d, J=7.6 Hz). IR ν max$^{KBr}$cm$^{-1}$: 1642, 1626, 1601, 1514, 1369. mp 157–158° C. Anal. Calcd for C$_{27}$H$_{20}$NO$_4$SF$_5$: C, 59.01; H, 3.67; N, 2.55. Found: C, 58.88; H, 3.64; N, 2.53.

Example 282

N-[(1RS,2SR)-2-(4-fluorophenyl)-2-hydroxy-1-(3-isopropoxybenzyl)ethyl]-6,7-dihydro-5H-benzo[a]cycloheptene-1-carboxamide 1) ethyl 3-isopropyloxybenzoate To a solution of ethyl 3-hydroxybenzoate (15.2 g, 0.10 mol) in N,N-dimethylformamide (100 ml) were added isopropyl bromide (12.1 ml, 0.13 mol) and sodium iodide (19.5 g, 0.13 mol), and the mixture was stirred at 70° C. for 15 hrs. To the reaction solution was added water (500 ml), and the mixture was extracted with ethyl acetate (500,200 ml). The extract was washed with water, dried over anhydrous magnesium sulfate and evaporated under reduced pressure. The residue was purified by silica gel chromatography (hexane:ethyl acetate=10:1) to give the objective substance (12.4 g, 64%) as an oil.

$^1$H-NMR (CDCl$_3$)δ: 1.35(6H, d, J=6.2 Hz), 3.90(3H, s), 4.55–4.65(1H, m), 7.07(1H, dd, J=8.2, 1.8 Hz), 7.33(1H, t, J=8.2 Hz), 7.50–7.70(2H, m).

2) 3-isopropyloxybenzyl alcohol

To a solution of ethyl 3-isopropyloxybenzoate (12.0. g, 61.8 mmol) in tetrahydrofuran (100 ml) was added lithium aluminum hydride (3.52 g, 92.7 mmol) by small portions under ice-cooling. The mixture was stirred at room temperature for 1 hr. and water (10 ml) was added under ice-cooling to allow decomposition. Insoluble material was filtered off and the solvent was evaporated under reduced pressure. The residue was purified by silica gel chromatography (hexane:ethyl acetate=3:1) to give the objective substance (10.0 g, 97%) as an oil.

$^1$H-NMR (CDCl$_3$) δ: 1.34(6H, d, J=6.4 Hz), 4.50–4.65 (1H, m), 4.66(1H, d, J=6.2 Hz), 6.78–6.90(1H, m), 6.90–7.00(2H, m), 7.26(1H, t, J=8.2 Hz).

3) ethyl 3-(4-fluorophenyl)-3-oxo-2-[3-(isopropyloxy)benzyl]propanoate

To a solution of 3-isopropyloxybenzyl alcohol (7.31 g, 44 mmol) in ethyl acetate (50 ml) were added under ice-cooling methanesulfonyl chloride (3.56 ml, 46 mmol) and triethylamine (6.69 ml, 48 mmol), and the mixture was stirred at room temperature for 2.5 hrs. Insoluble material was filtered off, and the solvent was evaporated under reduced pressure to give mesylate.

To a solution of ethyl 3-(4-fluorophenyl)-3-oxopropanoate (8.41 g, 40 mmol) in dimethoxyethane (50 ml) was added sodium hydride (1.60 g, 60% in oil, 40 mmol) under ice-cooling, and the mixture was stirred for 1 hr. To the solution was dropwise added a solution of the mesylate obtained above in dimethoxyethane (20 ml), and the mixture was stirred at room temperature for 10 hrs. To the reaction solution was added water (200 ml), and the mixture was extracted with ethyl acetate (200 ml). The extract was washed with water, dried over anhydrous magnesium sulfate and evaporated under reduced pressure. The residue was purified by silica gel chromatography (hexane:ethyl acetate= 10:1–5:1) to give the objective substance (12.5 g, 87%).

IR ν max$^{Neat}$cm$^{-1}$: 1736, 1688, 1599, 1508, 1258, 1233, 1157. $^1$H-NMR (CDCl$_3$) δ: 1.13(3H, t, J=7.2 Hz), 1.30(6H, d, J=6.2 Hz), 3.28(2H, d, J=7.4 Hz), 4.15(2H, q, J=7.2 Hz), 4.57(1H, d, J=7.8 Hz), 4.40–4.60(1H, m), 6.60–6.80(3H, m), 7.00–7.25(3H, m), 7.90–8.10(2H, m).

4) ethyl (2RS,3RS)-3-(4-fluorophenyl)-3-hydroxy-2-[3-(isopropyloxy)benzyl]propanoate To a suspension of anhydrous zinc chloride (9.12 g, 67.0 mmol) in diethyl ether (100 ml) was added sodium borohydride (5.07 g, 134 mmol) by small portions, and the mixture was stirred for 2 hrs. Insoluble material was filtered off, and washed with diethyl ether. The filtrate was ice-cooled, and to the filtrate was added a solution of ethyl 3-(4-fluorophenyl)-3-oxo-2-[3-(isopropyloxy)benzyl] propanoate (12.0 g, 33.5 mmol) in diethyl ether (20 ml). The mixture was stirred at room temperature for 2 hrs. and ice-cooled again. 1N Hydrochloric acid was added to stop the reaction. The mixture was washed with water, dried over anhydrous magnesium sulfate and evaporated under reduced pressure. The residue was purified by silica gel chromatography(hexane:ethyl acetate=10:1) to give the objective substance (10 g, 83%) as a colorless oil IR ν max$^{Neat}$cm$^{-1}$: 1728, 1603, 1510, 1260, 1157. $^1$H-NMR (CDCl$_3$) δ: 0.94(3H, t, J=7.2 Hz), 1.30(6H, d, J=6.2 Hz), 2.80–3.00(4H, m), 3.89(2H, d, J=7.2 Hz), 4.40–4.60(1H, m), 5.01(1H, s), 6.58–6.75(3H, m), 6.98–7.20(3H, m), 7.30–7.45(2H, m).

5) (2RS,3RS)-3-(4-fluorophenyl)-3-hydroxy-2-[3-(isopropyloxy)benzyl]propanoic acid To a solution-of ethyl (2RS,3RS)-3-(4-fluorophenyl)-3-hydroxy-2-[3-(isopropyloxy)benzyl]propanoate (9.8 g, 27.2 mmol) in methanol (50 ml) was added 2N aqueous sodium hydroxide solution (27.2 ml, 54.4 mmol), and the mixture was stirred at room temperature for 3 hrs. The reaction solution was acidified with 6N hydrochloric acid (100 ml). The mixture was extracted with ethyl acetate (200, 100 ml). The extract was washed with water, dried over anhydrous magnesium sulfate, and evaporated under reduced pressure. The residue was crystallized from hexane to give the objective substance (7.44 g, 82%).

mp 101–102° C. IR ν max$^{KBr}$cm$^{-1}$: 1694, 1514, 1451, 1292, 1260, 1229, 1152, 1119. Anal. Calcd for C$_{19}$H$_{21}$FO$_4$ (MW332.37) Calcd: C, 68.66; H, 6.37 Found: C, 68.52; H, 6.37 $^1$H-NMR (CDCl$_3$) δ: 1.29(6H, d, J=6.2 Hz), 2.80–3.15 (3H, m), 4.40–4.60(1H, m), 5.00–5.10(1H, m), 6.55–6.80 (3H, m), 6.95–7.20(3H, m), 7.30–7.45(2H, m).

6) (4RS,5SR)-5-(4-fluorophenyl)-4-[3-(isopropyloxy) benzyl]-1,3-oxazolidin-2-one To a solution of (2RS,3RS)-3-(4-fluorophenyl)-3-hydroxy-2-[3-(isopropyloxy)benzyl]propanoic acid (7.14 g, 21.5 mmol) in tetrahydrofuran (100 ml) were added diphenylphosphoryl azide (6.0 ml, 27.9 mmol) and triethylamine (4.19 ml, 30.1 mmol), and the mixture was stirred at room temperature for 1 hr. The mixture was heated under reflux for 5 hrs. and concentrated under reduced pressure. The saturated aqueous sodium hydrogen carbonate (100 ml) was added and the mixture was extracted with ethyl acetate (200 ml). The extract was washed with water, dried over anhydrous magnesium sulfate and evaporated under reduced pressure. The residue was purified by silica gel chromatography (hexane:ethyl acetate=4:1–2:1) to give the-objective substance (14.7 g, 91%).

mp 114–115° C. IR ν max$^{KBr}$cm$^{-1}$: 1738, 1582, 1514, 1385, 1248, 1227, 1157. Anal. Calcd for $C_{19}H_{20}FNO_3$ (MW329.36) Calcd: C, 69.29; H, 6.12; N, 4.25. Found: C, 69.27; H, 6.16; N, 4.26. $^1$H-NMR (CDCl$_3$) δ: 1.32(6H, d, J=6.0 Hz), 2.05–2.35(2H, m), 4.15–4.60(1H, m), 4.96(1H, brs), 5.78(1H, d, J=7.6 Hz), 6.50–6.65(2H, m), 6.70–6.80 (1H, m), 7.00–7.25(3H, m), 7.30–7.45(2H, m).

7) (1RS,2SR)-2-amino-1-(4-fluorophenyl)-3-[3-(isopropyloxy)phenyl]-1-propanol

To a solution of (4RS,5SR)-5-(4-fluorophenyl)-4-[3-(isopropyloxy)benzyl]-1,3-oxazolidin-2-one (5.85 g, 17.8 mmol) in ethanol (30 ml) was added 8N aqueous sodium hydroxide solution (8.9 ml, 71.0 mmol), and the mixture was heated under reflux for 5 hrs. The reaction solution-was concentrated under reduced pressure. To the solution was added water (100 ml) and the mixture was extracted with ethyl acetate (100 ml×2). The extract was washed with water, dried over anhydrous magnesium sulfate and evaporated under reduced pressure. The residue was crystallized from hexane-diethyl ether to give the objective substance (5.0 g, 93%).

mp 98–99° C. IR ν max$^{KBr}$cm$^{-1}$: 3364, 1605, 1582, 1508, 1252, 1211, 1154, 1044. Anal. Calcd for $C_{18}H_{22}FNO_2$ (MW303.37) Calcd: C, 71.26; H, 7.31; N, 4.62. Found: C, 71.30; H, 7.46; N, 4.55. $^1$H-NMR (CDCl$_3$) δ: 1.32(6H, d, J=6.0 Hz), 2.28(1H, dd, J=13.6, 10.2 Hz), 2.73(1H, dd, J=13.6, 3.0 Hz), 3.20–3.40(1H, m), 4.45–4.60(1H, m), 4.67 (1H, d, J=4.8 Hz), 6.60–6.80(3H, m), 7.00–7.45(5H, m).

8) N-[(1RS,2SR)-2-(4-fluorophenyl)-2-hydroxy-1-(3-isopropoxybenzyl)ethyl]-6,7-dihydro-5H-benzo[a]cycloheptene-1-carboxamide To a solution of (1RS,2SR)-2-amino-1-(4-fluorophenyl)-3-[3-(isopropyloxy)phenyl]-1-propanol (0.46 g, 1.5 mmol) and 6,7-dihydro-5H-benzo[a]cycloheptene-1-carboxylic acid (0.34 g, 1.8 mmol) in acetonitrile (20 ml) were added 1-ethyl-3-(3-dimethylaminopropyl)carbodiimide hydrochloride (0.36 g, 2.1 mmol) and 1-hydroxybenzotriazole hydrate (0.32 g, 2.1 mmol), and the mixture was stirred at room temperature for 5 hrs. To the reaction solution was added water (100 ml), and the mixture was extracted with-ethyl acetate (100 ml×2). The extract was washed with water, dried over anhydrous magnesium sulfate and evaporated under reduced pressure. The residue was purified by silica gel chromatography (hexane:ethyl acetate=4:1) to give the objective substance (0.55 g, 77%) as crystals.

mp 161–162° C. IR ν max$^{KBr}$cm$^{-1}$: 3274, 1638, 1510, 1258, 1225, 833. Anal. Calcd for $C_{30}H_{32}FNO_3$ (MW473.58) Calcd: C, 76.08; H; 6.81; N, 2.96. Found: C, 76.10; H, 6.73; N, 2.89. $^1$H-NMR (CDCl$_3$) δ: 1.30(6H, d, J=6.0 Hz), 1.90–2.10(2H, m), 2.10–2.30(2H, m), 2.60–2.80(2H, m), 2.96(1H, dd, J=14.0, 4.4 Hz), 4.10(1H, d, J=4.4 Hz), 4.40–4.60(1H, m), 4.60–4.80(1H, m), 5.00–5.10(1H, m), 5.66(1H, d, J=7.8 Hz), 5.90–6.00(1H, m), 6.40(1H, d, J=11.8 Hz), 6.65–6.85(3H, m), 6.95–7.25(7H, m), 7.35–7.50(2H, m).

Example 283

4-fluoro-N-[(1RS,2SR)-2-(4-fluorophenyl)-2-hydroxy-1-(3-isopropoxybenzyl)ethyl]-1-naphthamide To a solution of (1RS,2SR)-2-amino-1-(4-fluorophenyl)-3-[3-(isopropyloxy)phenyl]-1-propanol (0.46 g, 1.5 mmol) and 4-fluoronaphthalene-1-carboxylic acid (0.34 g, 1.8 mmol) in acetonitrile (20 ml) were added 1-ethyl-3-(3-dimethylaminopropyl)carbodiimide hydrochloride (0.36 g, 2.1 mmol) and 1-hydroxybenzotriazole hydrate (0.32 g, 2.1 mmol), and the mixture was stirred at room temperature for 5 hrs. To the reaction solution was added water (100 ml), and the mixture was extracted with ethyl acetate (100 ml×2). The extract was washed with water, dried over anhydrous magnesium sulfate and evaporated under reduced pressure. The residue was purified by silica gel chromatography (chloroform:ethyl acetate=10:1) to give the objective substance (0.65 g, 91%) as crystals.

mp 190–191° C. IR ν max$^{KBr}$cm$^{-1}$: 3281, 1640, 1624, 1539, 1514, 1256, 1229. Anal. Calcd for $C_{29}H_{27}F_2NO_3$ (MW475.53) Calcd: C, 73.25; H, 5.72; N, 2.95. Found: C, 72.87; H, 5.57; N, 2.84. $^1$H-NMR (CDCl$_3$-DMSO-d$_6$ (1 drop)) δ: 1.26(6H, d, J=6.0 Hz), 2.70–3.00(2H, m), 4.40–4.60(1H, m), 4.65–4.85(1H, m), 4.95–5.10(2H, m), 6.70–6.85(3H, m), 6.85–7.60(10H, m), 7.74(1H, d, J=6.8 Hz), 8.06(1H, d, J=7.6 Hz).

Example 284

4-fluoro-N-[(1RS,2SR)-1-(3-tert-butyloxybenzyl) ethyl]-2-(4-fluorophenyl)-2-hydroxy-1-naphthamide 1) ethyl 3-tert-butyloxybenzoate To a solution of ethyl 3-hydroxybenzoate (20 g, 0.13 mol) in dichloromethane (200 ml) were added isobutene (about 30 g) and conc. sulfuric acid (0.5 ml), and the mixture was left for 2 days. The reaction solution was washed with saturated aqueous sodium hydrogen carbonate solution, dried over anhydrous magnesium sulfate and evaporated under reduced pressure. The residue was purified by silica gel chromatography (hexane:ethyl acetate=10:1) to give the objective substance (17.3 g, 63%) as an oil.

$^1$H-NMR (CDCl$_3$) δ: 1.37(9H, s, Bu$^t$), 3.91(3H, s), 7.15–7.25(1H, m), 7.33(1H, t, J=7.9 Hz), 7.65–7.70(1H, m), 7.76(1H, d, J=7.9 Hz).

2) 3-tert-butyloxybenzyl alcohol

To a solution of ethyl 3-tert-butyloxybenzoate (16.7 g, 80 mmol) in tetrahydrofuran (100 ml) was added lithium aluminum hydride (4.55 g, 120 mmol) by small portions under ice-cooling. The mixture was stirred at room temperature for 1 hr. and water (10 ml) was added under ice-cooling to allow decomposition. Insoluble material was filtered off and the solvent was evaporated under reduced pressure. The residue was purified by silica gel chromatography (hexane:ethyl acetate=3:1–2:1) to give the objective substance (12.8 g, 88%) as an oil.

$^1$H-NMR (CDCl$_3$) δ: 1.35(9H, s, Bu$^t$), 4.66(2H, d, H=6.0 Hz), 6.93(1H, m), 7.00(1H, brs), 7.07(1H, d, J=7.4 Hz), 7.25(1H, t, J=7.4 Hz).

3) ethyl 3-(4-fluorophenyl)-2-[3-(tert-butyloxy)benzyl]-3-oxopropanoate

To a solution of 3-tert-butyloxybenzyl alcohol (10.8 g, 60 mmol) in ethyl acetate (100 ml) were added methanesulfonyl chloride (4.88 ml, 63 mmol) and triethylamine (9.2 ml, 66 mmol) under ice-cooling, and the mixture was stirred at room temperature for 1 hr. Insoluble material was filtered off, and the solvent was evaporated under reduced pressure to give mesylate.

To a solution of ethyl 3-(4-fluorophenyl)-3-oxopropanoate (12.6 g., 60 mmol) in dimethoxyethane (100 ml) was added sodium hydride (2.4 g, 60% in oil, 60 mmol) under ice-cooling, and the mixture was stirred for 10 min. To the solution was dropwise added a solution of mesylate obtained above in dimethoxyethane (20 ml), and the mixture was stirred at room temperature for 4 hrs. To the reaction solution was added water (200 ml), and the mixture was extracted with ethyl acetate (200 ml×2). The extract was washed with water, dried over anhydrous magnesium-sulfate and evaporated under reduced pressure. The residue was purified by silica gel chromatography (hexane:ethyl acetate=10:1) to give the objective substance (20.1 g, 90%).

IR ν max$^{Neat}$cm$^{-1}$: 1740, 1686, 1599, 1508, 1485, 1366, 1233, 1152. $^1$H-NMR (CDCl$_3$) δ: 1.13(3H, t, J=7.0 Hz), 1.28(9H, s, Bu$^t$), 3.29(2H, d, J=7.4 Hz), 4.10 (2H, q, J=7.0 Hz), 4.56(1H, t, J=7.4 Hz), 6.67–6.90(2H, m), 6.95(1H, d, J=7.6 Hz), 7.05–7.20(3H, m), 7.90–8.05(2H, m).

4) ethyl (2RS,3RS)-2-[3-(tert-butyloxy)benzyl]-3-(4-fluorophenyl)-3-hydroxypropanoate To a suspension of anhydrous zinc chloride (8.17 g, 60 mmol) in diethyl ether (100 ml) was added sodium borohydride (4.54 g, 120 mmol) by small portions, and the mixture was stirred for 2 hrs. Insoluble material was filtered off and washed with diethyl ether. The filtrate was ice-cooled, and a solution of ethyl 3-(4-fluorophenyl)-2-[3-(tert-butyloxy)benzyl]-3-oxopropanoate (10.8 g, 30 mmol) in diethyl ether (20 ml) was added. The mixture was stirred at room temperature for 1 hr., ice-cooled again and water was added to stop the reaction. The mixture was washed with 5% aqueous potassium hydrogen sulfate solution and water, dried over anhydrous magnesium sulfate and evaporated under reduced pressure. The residue was purified by silica gel chromatography (hexane:ethyl acetate=10:1) to give the objective substance (8.9 g, 79%) as a colorless oil. IR ν max$^{Neat}$cm$^{-1}$: 1728, 1605, 1510, 1260, 1225, 1179, 1154. $^1$H-NMR (CDCl$_3$) δ: 0.93(3H, t, J=7.2 Hz), 1.31(9H, s, Bu$^t$), 2.90–3.05(3H, m), 3.87(2H, d, J=7.2 Hz), 4.95–5.10(1H, m), 6.70–6.80(1H, m), 6.80(1H, d, J=7.8 Hz), 7.00–7.20(3H, m), 7.30–7.45(2H, m).

5) (4RS,5SR)-4-[3-(tert-butyloxy)benzyl]-5-(4-fluorophenyl)-1,3-oxazolidin-2-one To a solution of ethyl (2RS,3RS)-2-[3-(tert-butyloxy)benzyl]-3-(4-fluorophenyl)-3-hydroxypropanoate (8.8 g, 23.5 mmol) in methanol (100 ml) was added 2N aqueous sodium hydroxide solution (23.5 ml, 47 mmol), and the mixture was stirred at room temperature for 3 hrs. The reaction solution was acidified with 5% aqueous potassium hydrogen sulfate solution (100 ml). The mixture was extracted with ethyl acetate (200 ml). The extract was washed with water, dried over anhydrous magnesium sulfate, and evaporated under reduced pressure. The residue was crystallized from hexane to give (2RS,3RS)-2-[3-(tert-butyloxy)benzyl]-3-(4-fluorophenyl)-3-hydroxypropanoic acid.

To a solution of the compound obtained above in tetrahydrofuran (150 ml) were added diphenylphosphoryl azide (6.57 ml, 30.6 mmol) and triethylamine (4.59 ml, 32.9 mmol), and the mixture was stirred at room temperature for 1 hr. Then, the mixture was heated under reflux for 2 hrs., and concentrated under reduced pressure. Water (200 ml) was added, and the mixture was extracted with ethyl acetate (200 ml). The extract was washed with water, dried over anhydrous magnesium sulfate and evaporated under reduced pressure. The residue was purified by silica gel: chromatography (hexane:ethyl acetate=3:1-2:1) to give the objective substance (6.92 g, 86%). mp 131–132° C.

IR ν max$^{KBr}$cm$^{-1}$: 1742, 1603, 1514, 1364, 1240, 1223, 1148. Anal. Calcd for C$_{20}$H$_{22}$FNO$_3$ (MW343.40) Calcd: C, 69.95; H, 6.46; N, 4.08. Found: C, 69.96; H, 6.38; N, 4.11. $^1$H-NMR (CDCl$_3$) δ: 1.33(9H, s, Bu$^t$), 2.10–2.40(2H, m), 4.15–4.30(1H, m), 4.91(1H, brs), 5.79(1H; d, J=7.8 Hz), 6.60–6.80(2H, m), 6.80–6.95(1H, m), 7.05–7.25(3H, m), 7.30–7.50 (2H, m).

6) (1RS,2SR)-2-amino-3-[3-(tert-butyloxy)phenyl]-1-(4-fluorophenyl)-1-propanol

To a solution of (4RS,5SR)-4-[3-(tert-butyloxy)benzyl]-5-(4-fluorophenyl)-1,3-oxazolidin-2-one (6.6 g, 19.2 mmol) in ethanol (30 ml) was added 8N aqueous sodium hydroxide solution (9.6 ml, 76.9 mmol), and the mixture was heated under reflux for 4 hrs. The reaction solution was concentrated under reduced pressure. Water (150 ml) was added, and the mixture was extracted with ethyl acetate (200 ml). The extract was washed with water, dried over anhydrous magnesium sulfate and evaporated under reduced pressure. The residue was crystallized from hexane-diethyl ether to give the objective substance (5.86 g, 96%).

mp 132–133° C. IR ν max$^{KBr}$cm$^{-1}$: 3362, 3295, 1601, 1582, 1507, 1485, 1363, 1208, 1152, 1036. Anal. Calcd for C$_{19}$H$_{24}$FNO$_2$ (MW317.40) Calcd: C, 71.90; H, 7.62; N, 4.41. Found: C, 71.69; H, 7.65; N, 4.35. $^1$H-NMR (CDCl$_3$) δ: 1.33(9H, s, Bu$^t$), 2.29(1H, dd, J=14.0, 10.2 Hz), 2.74(1H, dd, J=14.0, 3.0 Hz), 3.20–3.35(1H, m), 4.66(1H, d, J=5.2 Hz), 6.75–6.90(3H, m), 7.70–7.25 (3H, m), 7.30–7.45(2H, m).

7) 4-fluoro-N-[(1RS,2SR)-1-(3-tert-butyloxybenzyl)ethyl]-2-(4-fluorophenyl)-2-hydroxy-1-naphthamide To a solution of (1RS,2SR)-2-amino-3-[3-(tert-butyloxy)phenyl]-1-(4-fluorophenyl)-1-propanol (1.59 g, 5.0 mmol) and 4-fluoronaphthalene-1-carboxylic acid (1.14 g, 6.0 mmol) in acetonitrile (30 ml) were added 1-ethyl-3-(3-dimethylaminopropyl)carbodiimide hydrochloride (1.20 g, 7.0 mmol) and 1-hydroxybenzotriazole hydrate (1.07 g, 7.0 mmol), and the mixture was stirred at room temperature for 5 hrs. To the reaction solution was added water (100 ml), and the mixture was extracted with ethyl acetate (150 ml). The extract was washed with water, dried over anhydrous magnesium sulfate and evaporated under reduced pressure. The residue was purified by silica gel chromatography (chloroform:ethyl acetate=10:1) to give the objective substance (2.27 g, 93%) as crystals.

mp 180–181° C. IR ν max$^{KBr}$cm$^{-1}$: 3420, 3312, 1644, 1539, 1508, 1223, 1150. Anal. Calcd for C$_{30}$H$_{29}$F$_2$NO$_3$ (MW489.55) Calcd: C, 73.60; H, 5.97; N, 2.86. Found: C, 73.61; H, 6.00; N, 2.76. $^1$H-NMR (CDCl$_3$) δ: 1.28(9H, s, Bu$^t$), 2.73(1H, dd, J=14.1, 10.6 Hz), 3.03(1H, dd, J=14.4, 4.4 Hz), 3.90(1H, d, J=3.6 Hz), 4.70–4.90(1H, m), 5.00–5.15 (1H, m), 5.85(1H, brd, J=4.4 Hz), 6.80–7.30(8H, m), 7.4–7.60(4H, m), 7.83(1H, d, J=8.0 Hz), 8.08(1H, d, J=7.2 Hz).

Example 285

N-[(1RS,2SR)-1-(3-tert-butyloxybenzyl)ethyl]-2-(4-fluorophenyl)-2-hydroxy-6,7-dihydro-5H-benzo[a]cycloheptene-1-carboxamide To a solution of (1RS,2SR)-2-amino-3-[3-(tert-butyloxy)phenyl]-1-(4-fluorophenyl)-1-propanol (0.48 g, 1.5 mmol) and 6,7-dihydro-5H-benzo[a]cycloheptene-1-carboxylic acid (0.34 g, 1.8 mmol) in acetonitrile (20 ml) were added 1-ethyl-3-(3-dimethylaminopropyl)carbodiimide hydrochloride (0.36 g, 2.1 mmol) and 1-hydroxybenzotriazole hydrate (0.32 g, 2.1 mmol) and the mixture was stirred at room temperature for 5 hrs. To the reaction solution was added water (100 ml) and the mixture was extracted with ethyl acetate (150 ml). The extract was washed with water, dried over anhydrous magnesium sulfate and evaporated under reduced pressure. The residue was purified by silica gel chromatography (hexane:ethyl acetate=4:1–3:1) to give the objective substance (0.63 g,. 86%) as crystals.

mp 149–150° C. IR ν max$^{KBr}$cm$^{-1}$: 3303, 1638, 1537, 1512, 1443, 1256, 1225, 1150, 1032. Anal. Calcd for $C_{31}H_{34}FNO_3$ (MW487.61) Calcd: C, 76.36; H, 7.03; N, 2.87. Found: C, 76.29; H, 7.20; N, 2.80. $^1$H-NMR (CDCl$_3$) δ: 1.30(9H, s, Bu$^t$), 1.90–2.10(2H, m), 2.10–2.30(2H, m), 2.60–2.80 (2H, m), 2.96(1H, dd, J=7.3, 4.4 Hz), 4.06(1H, d, J=4.0 Hz), 4.60–4.80(1H, m), 5.01(1H, t, J=3.7 Hz), 5.65 (1H, brd, J=8.0 Hz), 5.90–6.05(1H, m), 6.25(1H, d, J=11.4 Hz), 6.78–7.30 (9H, m), 7.30–7.50(2H, m).

Example 286

4-fluoro-N-[(1RS,2SR)-2-(4-fluorophenyl)-2-hydroxy-1-(3-hydroxybenzyl)ethyl]-1-naphthamide To a solution of 4-fluoro-N-[(1RS,2SR)-1-(3-tert-butyloxybenzyl)ethyl]-2-(4-fluorophenyl)-2-hydroxy-1-naphthamide (0.30 g, 0.61 mmol) in tetrahydrofuran (10 ml) was added trifluoroacetic acid (5 ml), and the mixture was stirred at 50° C. for 2 hrs. The solvent was evaporated under reduced pressure, and the residue was purified by silica gel chromatography (chloroform:ethyl acetate=5:1) to give the objective substance (0.18 g, 68%) as crystals.

mp 179–180° C. IR ν max$^{KBr}$cm$^{-1}$: 1644, 1601, 1537, 1512, 1262, 1231, 1157, 1053. Anal. Calcd for $C_{26}H_{21}F_2NO_3$ (MW433.45) Calcd: C, 72.05; H, 4.88; N, 3.23. Found: C, 71.61; H, 5.14; N, 3.07. $^1$H-NMR (CDCl$_3$) δ: 2.50–2.75(2H, m), 3.10–3.30(1H, m), 4.30–4.55(1H, m), 4.55–4.65 (1H, m), 5.73(1H, d, J=4.4 Hz), 6.60–6.75(3H, m), 7.00–7.70(9H, m), 7.99(1H, d, J=7.6 Hz), 8.25–8.40(1H, m), 9.21(1H, s).

Example 287 benzyl N-[(1RS,2SR)-2-(4-fluorophenyl)-2-hydroxy-1-[3-(1,1,2,2-tetrafluoroethoxy)benzyl]ethyl]carbamate While stirring (1RS,2SR)-2-amino-1-(4-fluorophenyl)-3-[3-(1,1,2,2-tetrafluoroethoxy)phenyl]propan-1-ol (0.278 g, 0.769 mmol) and sodium hydrogen carbonate (0.13 g, 1.54 mmol) in tetrahydrofuran (10 ml), benzyl chlorocarbonate (0.12 ml, 0.85 mmol) was-added at room temperature and the mixture was stirred as it was for 3 hrs. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white crystal yield 0.344 g, 90% mp 136–137° C.; $^1$H-NMR (CDCl$_3$, 200 MHz) δ 2.64–2.91 (3H, m), 4.09–4.20 (1H, m), 4.82 (1H, br d, J=9.2 Hz), 4.85–5.04 (3H, m), 5.88 (1H, tt, J=2.9 Hz, 53.1 Hz), 6.96–7.09 (5H, m), 7.21–7.39 (8H, m); IR (KBr) 3326, 1692, 1545, 1198, 1115 cm$^{-1}$; Anal. Calcd for $C_{25}H_{22}F_5NO_4$: C, 60.61; H, 4.48; N, 2.83. Found: C, 60.81; H, 4.53; N, 2.99.

Example 288

N-[(1RS,2SR)-2-(4-fluorophenyl)-2-hydroxy-1-[3-(1,1,2,2-tetrafluoroethoxy)benzyl]ethyl]-6,6-dimethyl-6,7-dihydro-5H-benzo[a]cycloheptene-1-carboxamide 1) ethyl (E)-4,4-dimethyl-5-phenyl-2-pentenoate A suspension (17.8 g, 445 mmol) of 60% sodium hydride in liquid paraffin was suspended in toluene (300 ml), and a solution of ethyl diethylphosphonoacetate (99.8 g, 445 mmol) in toluene (50 ml) was added at room temperature. The mixture was stirred for 30 min. A solution of 2,2-dimethyl-3-phenylpropanal (see Tetrahedron Lett., 1273–1275 (1973)) (60.16 g, 370.8 mmol) in toluene (50 ml) was dropwise added, and the mixture was stirred at room temperature for 2 hrs. The reaction solution was poured into water, and the mixture was extracted twice with diethyl ether. The recovered organic layer was dried over anhydrous magnesium sulfate and the solvent was evaporated under reduced pressure. The obtained crude product was purified by silica gel column chromatography (hexane/ethyl acetate= 20/1–9/1) to give the objective substance.

colorless liquid yield 55.97 g, 65% $^1$H-NMR (CDCl$_3$, 200 MHz) δ 1.06 (6H, s), 1.29 (3H, t, J=7.2 Hz), 2.66 (2H, s), 4.19 (2H, q, J=7.1 Hz), 5.63 (1H, d, J=16.2 Hz), 7.03 (1H, d, J=16.2 Hz), 7.06–7.10 (2H, m), 7.20–7.38 (3H, m); IR (neat) 2963, 1717, 1310, 1167, 1038, 702 cm$^{-1}$ 2) ethyl 4,4-dimethyl-5-phenylpentanoate A solution of ethyl (E)-4,4-dimethyl-5-phenyl-2-pentenoate (55.97 g, 240.9 mmol) in ethanol (150 ml) was hydrogenated using 10% palladium/carbon (containing water by 50%) (5 g) as a catalyst at room temperature overnight under normal pressure. The recovered catalyst of the reaction solution was filtered off and the catalyst was washed with ethanol. The recovered solvent of the filtrate was evaporated under reduced pressure. The obtained crude product was purified by silica gel column chromatography (hexane/ethyl acetate=15/1–9/1) to give the objective substance.

colorless liquid yield 45.47 g, 81% $^1$H-NMR (CDCl$_3$, 200 MHz) δ 0.86 (6H, s), 1.26 (3H, t, J =7.2 Hz), 1.56–1.64 (2H, m), 2.30–2.38 (2H, m), 2.51 (2H, s), 4.13 (2H, q, J=7.1 Hz), 7.10–7.15 (2H, m), 7.20–7.32 (3H, m); IR (neat) 2961, 1736, 1171, 704 cm$^{-1}$ 3) 4,4-dimethyl-5-phenylpentanoic acid A mixture of ethyl 4,4-dimethyl-5-phenylpentanoate (45.47 g, 194.0 mmol) and sodium hydroxide (15.5 g, 388 mmol), water (200 ml), methanol (200 ml) and tetrahydrofuran (100 ml) was stirred overnight at room temperature. The reaction solution was concentrated under reduced pressure and diluted with water. After washing with diethyl ether, the mixture was acidified with conc. hydrochloric acid and extracted twice with ethyl acetate. The recovered organic layer was dried over anhydrous sodium sulfate and the solvent was evaporated under reduced pressure. The obtained crude product was purified by silica gel column chromatography (ethyl acetate) to give the objective substance.

colorless liquid yield 38.35 g, 96% $^1$H-NMR (CDCl$_3$, 200 MHz) δ 0.88 (6H, s), 1.57–1.65 (2H, m), 2.35–2.43 (2H, m), 2.52 (2H, s), 7.10–7.15 (2H, m), 7.21–7.32 (3H, m); IR (neat) 3100–2850, 1715, 1452, 1416, 1302, 702 cm$^{-1}$ 4) 8,8-dimethyl-6,7,8,9-tetrahydro-5H-benzo[a]cyclohepten-5-one To a solution of 4,4-dimethyl-5-phenylpentanoic acid (38.30 g, 185.7 mmol) and N,N-dimethylformamide (0.1 ml) in tetrahydrofuran (150 ml) was dropwise added oxalyl chloride (24.3 ml, 279 mmol) at room temperature, and the mixture was stirred as it was at room temperature for 0.5 hr. The solvent of the reaction mixture was evaporated under reduced pressure to give acid chloride as a yellow liquid. While stirring a suspension of aluminum chloride (49.5 g, 371 mmol) in methylene chloride (250 ml), absolution of the acid-chloride obtained above in methylene chloride (800 ml) was dropwise added over 2 days. While ice-cooling the reaction solution, water was added to terminate the reaction. The methylene chloride layer was separated and the aqueous layer was extracted with diethyl ether. The recovered organic layer was dried over anhydrous magnesium sulfate and the solvent was evaporated under reduced pressure. The obtained residue was purified by silica gel column chromatography (hexane/ethyl acetate=15/1–6/1) to give the objective substance.

yellow liquid yield 29.55 g, 85% $^1$H-NMR (CDCl$_3$, 200 MHz) δ 1.02 (6H, s), 1.45–1.51 (2H, m), 2.62 (2H, s), 2.63–2.69 (2H, m), 7.12 (1H, dd, J=1.0 Hz, 7.2 Hz), 7.31 (1H, dt, J=1.5 Hz, 7.5 Hz), 7.43 (1H, dt, J=1.6 Hz, 7.5 Hz), 7.72 (1H, dd, J=1.4 Hz, 7.4 Hz); IR (neat) 2953, 2928, 1682, 1601, 1468, 1289, 770 cm$^{-1}$ 5) 8,8-dimethyl-6,7,8,9-tetrahydro-5H-benzo[a]cyclohepten-5-ol To a solution of 8,8-dimethyl-6,7,8,9-tetrahydro-5H-benzo[a]cyclohepten-5-one (29.20 g, 155.1 mmol) in methanol (150 ml) was added sodium borohydride (5.87 g, 155 mmol) by small portions under ice-cooling, and the mixture was stirred at room temperature for 1 hr. The reaction solution was diluted with water and extracted twice with ethyl acetate. The recovered organic layer was-dried over anhydrous sodium sulfate, and the solvent was evaporated under reduced pressure. The obtained residue was purified by silica gel column chromatography (hexane/ethyl acetate= 9/1–6/1) to give the objective substance.

yellow liquid yield 28.96 g, 98% $^1$H-NMR (CDCl$_3$, 200 MHz) δ 0.72 (3H, s), 0.94 (3H, s), 1.54–1.97 (4H, m), 1.78 (1H, d, J=4.0 Hz), 2.67 (2H, br s), 4.85–4.93 (1H, m), 7.02 (1H, dd, J=1.6 Hz, 7.2 Hz), 7.11–7.23 (2H, m), 7.42 (1H, d, J=7.0 Hz); IR (neat) 3353, 2951, 2928, 1456, 1044, 756 cm$^{-1}$ 6) 4-(hydroxymethyl)-8,8-dimethyl-6,7,8,9-tetrahydro-5H-benzo[a]cyclohepten-5-ol To a solution of 8,8-dimethyl-6,7,8,9-tetrahydro-5H-benzo[a]cyclohepten-5-ol (28.72 g, 150.9 mmol) and N,N,N',N'-tetramethylethylenediamine (50.1 ml, 332 mmol) in hexane (200 ml) was added a solution (208 ml, 332 mmol) of 1.6 M n-butyllithium in hexane under ice-cooling and the mixture was stirred at 35° C. overnight. After cooling the reaction mixture at −78° C., crushed dry ice (50 g) was added, and the mixture was warmed to room temperature under stirring. The reaction solution was diluted with water acidified with conc. hydrochloric acid and washed three times with ethyl acetate. The recovered organic layer was dried over anhydrous magnesium sulfate and the solvent was evaporated under reduced pressure. The obtained crude product was passed through silica gel column chromatography (hexane/ethyl acetate=6/1) to give a crude product (31.00 g) of 7,7-dimethyl-7,8,9,9a-tetrahydrocyclohepta[cd][2]benzofuran-2(6H)-one as a yellow wet solid.

To a suspension of lithium aluminum hydride (5.73 g, 151 mmol) in tetrahydrofuran (200 ml) was dropwise added a solution of the solid obtained above in tetrahydrofuran (100 ml) under ice-cooling, and the mixture was stirred at room temperature for 1 hr. After ice-cooling the reaction solution, water (6 ml), 15% aqueous sodium hydroxide solution (6 ml) and water (15 ml) were successively added dropwise to decompose excess lithium aluminum hydride. The mixture was stirred as it was at room temperature for 2 hrs. The resulting precipitate was removed by filtration, and the precipitate was washed with ethyl acetate. The solvent of the recovered filtrate was evaporated under reduced pressure. The obtained crude product was purified by silica gel column chromatography (hexane/ethyl acetate=6/1–1/2). Crystallization from hexane gave the objective substance.

white crystal yield 19.15 g, 58% mp 107–108° C.; $^1$H-NMR (CDCl$_3$, 200 MHz) δ 0.76. (3H, s), 0.99 (3H, s), 1.16–1.28 (1H, m), 1.68–1.82 (1H, m), 1.91–2.03 (2H, m), 2.30 (1H, d, J=13.6 Hz), 2.63 (1H, br t, J=5.3 Hz), 2.93 (1H, br s), 3.22 (1H, d, J=13.8 Hz), 4.58 (1H, dd, J=5.3 Hz, 11.9 Hz), 4.85 (1H, dd, J=5.7 Hz, 11.9 Hz), 5.24–5.32 (1H, m), 7.00–7.06 (1H, m), 7.08–7.17 (2H, m); IR (KBr) 3312, 2951, 1402, 1016, 997, 762 cm$^{-1}$; Anal. Calcd for C$_{14}$H$_{20}$O$_2$: C, 76.33; H, 9.15. Found: C, 76.37; H, 9.28.

7) 4-[[[tert-butyl(dimethyl)silyl]oxy]methyl]-8,8-dimethyl-6,7,8,9-tetrahydro-5H-benzo[a]cyclohepten-5-ol To a solution of 4-(hydroxymethyl)-8,8-dimethyl-6,7,8,9-tetrahydro-5H-benzo[a]cyclohepten-5-ol (18.87 g, 85.65 mmol), 4-N,N-dimethylaminopyridine (0.5 g) and triethylamine (14.3 ml, 103 mmol) in tetrahydrofuran (100 ml) was added tert-butyldimethylchlorosilane (14.2 g, 94.2 mmol) at room temperature, and the mixture was stirred as it was overnight. The reaction solution was poured into water, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=15/1–9/1) to give the objective substance.

colorless liquid yield 28.90 g, 100% $^1$H-NMR (CDCl$_3$, 200 MHz) δ 0.08 (3H, s), 0.11 (3H, s), 0.76 (3H, s), 0.90 (9H, s), 0.99 (3H, s), 1.16–1.30 (1H, m), 1.67–1.80 (1H, m), 1.88–2.05 (2H, m), 2.30 (1H, d, J=13.6 Hz), 3.02 (1H, br s), 3.23 (1H, d, J=14.0 Hz), 4.64 (1H, d, J=11.8 Hz), 4.94 (1H, d, J=12.0 Hz), 5.23–5.31 (1H, m), 6.98–7.04 (1H, m), 7.06–7.15 (2H, m); IR (neat) 3391, 2951, 2928, 2857, 1470, 1254, 1076, 837, 775 cm$^{-1}$ 8) tert-butyl (6,6-dimethyl-6,7-dihydro-5H-benzo[a]cyclohepten-1-ylmethoxy)dimethylsilane To a solution of 4-[[[tert-butyl(dimethyl)silyl]oxy]methyl]-8,8-dimethyl-6,7,8,9-tetrahydro-5H-benzo[a]cyclohepten-5-ol (28.90 g, 86.38 mmol), triethylamine (24.1 ml, 173 mmol) and 4-N,N-dimethylaminopyridine (1.06 g, 8.64 mmol) in acetonitrile (100 ml) was dropwise added a solution of methanesulfonyl chloride (14.8 g, 130 mmol) in acetonitrile (10 ml) under ice-cooling. Lithium chloride (5.49 g, 130 mmol) was added thereto, and the mixture was stirred at room temperature for 6 hrs. The reaction solution was poured into water and extracted twice with ethyl acetate. The recovered organic layer was dried over anhydrous magnesium sulfate, and the solvent was evaporated under reduced pressure. The obtained residue was dissolved in N,N-dimethylformamide (100 ml), and 1,8-diazabicyclo[5.4.0]-7-undecene (25.8 ml, 173 mmol) was added. The mixture was stirred at 80° C. overnight. The reaction solution was-poured into water and extracted twice with ethyl acetate. The recovered organic layer was dried over anhydrous magnesium sulfate, and the solvent was evaporated under reduced pressure. The obtained crude product was purified by silica gel column chromatography (hexane/ethyl acetate=15/1) to give the objective substance.

pale-yellow liquid yield 10.25 g, 38% $^1$H-NMR (CDCl$_3$, 200 MHz) δ 0.09 (6H, s), 0.94 (9H, s), 1.01 (6H, s), 1.65 (2H, d, J=7.0 Hz), 2.32 (2H, s), 4.71 (2H, s), 6.25 (1H, td, J=7.0 Hz, 10.7 Hz), 6.64 (1H, d, J=10.8 Hz), 7.07 (1H, d, J=8.8 Hz), 7.17 (1H, t, J=7.5 Hz), 7.37 (1H, d, J=8.0 Hz); IR (neat) 2953, 2928, 1464, 1256, 1111, 1074, 837, 775 cm$^{-1}$ 9) 6,6-dimethyl-6,7-dihydro-5H-benzo[a]cyclohepten-1-ylmethanol To a solution of tert-butyl (6,6-dimethyl-6,7-dihydro-5H-benzo[a]cyclohepten-1-ylmethoxy)dimethylsilane (7.306 g, 23.08 mmol) in tetrahydrofuran (30 ml) was added a solution of 1.0 M tetrabutylammonium fluoride in tetrahydrofuran (27.7 ml, 27.7 mmol) at room temperature, and the mixture was stirred at room temperature for 15 min. The reaction solution was poured into water, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 4.484 g, 96% $^1$H-NMR (CDCl$_3$, 200 MHz) δ 1.02 (6H, s), 1.59 (1H, t, J=5.9 Hz), 1.67 (2H, d, J=7.4 Hz), 2.35 (2H, s), 4.70 (2H, d, J=6.2 Hz), 6.32 (1H, td, J=7.0 Hz, 10.6 Hz), 6.79 (1H, d, J=10.6 Hz), 7.11–7.31 (3H, m); IR (neat) 3318, 2951, 1454, 774 cm$^{-1}$ 10) 6,6-dimethyl-6,7-dihydro-5H-benzo[a]cycloheptene-1-carboxylic acid To a solution of 6,6-dimethyl-6,7-dihydro-5H-benzo[a]cyclohepten-1-ylmethanol (4.429 g, 21.90 mmol) in acetone (100 ml) was dropwise added slowly a solution of chromic anhydride (5.47 g, 53.7 mmol) and conc. sulfuric acid (4 ml) in water (15 ml) under ice-cooling. After completion of the dropwise addition, the mixture was stirred at room temperature for 1.5 hrs. The reaction solution was ice-cooled again and isopropanol (20 ml) was added. The mixture was stirred as it was for 0.5 hr. and acetone of the reaction solution was evaporated under reduced pressure. The residue was diluted with ethyl acetate, washed three times with water and dried over anhydrous magnesium sulfate. The solvent was evaporated under reduced pressure and the obtained residue was crystallized from ethyl acetate-hexane to give the objective substance.

yellow crystal yield 3.087 g, 65% mp 132–134° C.; $^1$H-NMR (CDCl$_3$, 200 MHz) δ 1.03 (6H, s), 1.66 (2H, d, J=7.4 Hz), 2.37 (2H, s), 6.33 (1H, td, J=7.3 Hz, 10.6 Hz), 7.23 (1H, d, J=10.6 Hz), 7.26 (1H, t, J=7.5 Hz), 7.39 (1H, dd, J=1.3 Hz, 7.5 Hz), 8.00 (1H, dd, J=1.5 Hz, 7.6 Hz); IR (KBr) 3050–2550, 1682, 1464, 1451, 1308, 1279, 775 cm$^{-1}$; Anal. Calcd for C$_{14}$H$_{16}$O$_2$: C, 77.75; H, 7.46. Found: C, 77.97; H, 7.57.

11) N-[(1RS,2SR)-2-(4-fluorophenyl)-2-hydroxy-1-[3-(1,1,2,2-tetrafluoroethoxy)benzyl]ethyl]-6,6-dimethyl-6,7-dihydro-5H-benzo[a]cycloheptene-1-carboxamide While stirring (1RS,2SR)-2-amino-1-(4-fluorophenyl)-3-[3-(1,1,2,2-tetrafluoroethoxy)phenyl]propan-1-ol (0.367 g, 1.016 mmol), 6,6-dimethyl-6,7-dihydro-5H-benzo[a]cycloheptene-1-carboxylic acid (0.22 g, 1.02 mmol) and 1-hydroxybenzotriazole hydrate (0.16 g, 1.02 mmol) in acetonitrile. (10 ml), 1-ethyl-3-(3-dimethylaminopropyl)carbodiimide hydrochloride (0.19 g, 1.02 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white powder yield 0.443 g, 78% mp 115–116° C.; $^1$H-NMR (CDCl$_3$, 300 MHz) δ 0.99 (6H, s), 1.64 (2H, d, J=7.2 Hz), 2.29 (2H, s), 2.79 (1H, dd, J=10.4 Hz, 14.6 Hz), 2.98 (1H, dd, J=4.1 Hz, 14.6 Hz), 3.78 (1H, d, J=4.2 Hz), 4.59–4.68 (1H, m), 5.04 (1H, t, J=3.8 Hz), 5.76 (1H, d, J=8.4 Hz), 5.89 (1H, tt, J=2.8 Hz, 53.0 Hz), 6.13 (1H, td, J=7.1 Hz, 10.6 Hz), 6.34 (1H, d, J=10.5 Hz), 7.01–7.14 (7H, m), 7.17–7.22 (1H, m), 7.30 (1H, t, J=7.8 Hz), 7.42 (2H, dd, J=5.3 Hz, 8.6 Hz); IR (KBr) 3287, 1638, 1512, 1227, 1200, 1125 cm$^{-1}$; Anal. Calcd for C$_{31}$H$_{30}$F$_5$NO$_3$: C, 66.54; H, 5.40; N, 2.50. Found: C, 66.47; H, 5.46; N, 2.49.

Example 289

N-[(1RS,2RS)-2-(5-chloro-2-thienyl)-2-hydroxy-1-[3-(1,1,2,2-tetrafluoroethoxy)benzyl]ethyl]-6,7-dihydro-5H-benzo[a]cycloheptene-1-carboxamide 1) ethyl 3-(5-chloro-2-thienyl)-3-oxo-2-[3-(1,1,2,2-tetrafluoroethoxy)benzyl]propionate A solution of 3-(1,1,2,2-tetrafluoroethoxy)toluene (12.5 g, 60.0 mmol), N-bromosuccinimide (10.7 g, 60.0 mmol) and 2,2'-azobis(isobutyronitrile) (30 mg) in carbon tetrachloride (30 ml) was heated under reflux for 0.5 hr. After cooling the reaction solution to room temperature, white precipitate was removed by filtration, and the precipitate was washed with diethyl ether. The solvent of the recovered filtrate was evaporated under reduced pressure to give a crude product of 3-(1,1,2,2-tetrafluoroethoxy)benzyl bromide as a pale-yellow liquid.

To a solution of ethyl 3-(5-chloro-2-thienyl)-3-oxopropionate (11.63 g, 49.98 mmol) in 1,2-dimethoxyethane (50 ml) was added a suspension (2.00 g, 50.0 mmol) of 60% sodium hydride in liquid paraffin under ice-cooling, and the mixture was stirred as it was for 0.5 hr. A solution of 3-(1,1,2,2-tetrafluoroethoxy)benzyl bromide obtained above in 1,2-dimethoxyethane (10 ml) was added at room temperature, and the mixture was stirred at room temperature for 8 hrs. The reaction solution was poured into water and extracted twice with ethyl acetate. The recovered organic layer was dried over anhydrous magnesium sulfate and the solvent was evaporated under reduced pressure. The obtained residue was purified by silica gel column chromatography (hexane/ethyl acetate=15/1–9/1). Crystallization from hexane gave the objective substance.

white crystal yield 12.58 g, 57% mp 49–51° C.; $^1$H-NMR (CDCl$_3$, 200 MHz) δ 1.16 (3H, t, J=7.2 Hz), 3.27 (1H, dd, J=7.5 Hz, 14.1 Hz), 3.36 (1H, dd, J=7.5 Hz, 14.1 Hz), 4.13 (2H, q, J=7.1 Hz), 4.34 (1H, t, J=7.5 Hz), 5.89 (1H, tt, J=2.9 Hz, 53.1 Hz), 6.93 (1H, d, J=4.2 Hz), 7.04–7.14 (3H, m), 7.23–7.32 (1H, m), 7.53 (1H, d, J=4.0 Hz); IR (KBr) 1725, 1661, 1434, 1215, 1148, 1132 cm$^{-1}$; Anal. Calcd for C$_{18}$H$_{15}$ClF$_4$O$_4$S: C, 49.27; H, 3.45. Found: C, 49.24; H, 3.20.

2) ethyl (2RS,3RS)-3-(5-chloro-2-thienyl)-3-hydroxy-2-[3-(1,1,2,2-tetrafluoroethoxy)benzyl]propionate While stirring zinc chloride (7.76 g, 57.0 mmol) in diethyl ether (150 ml), sodium borohydride (4.31 g, 114 mmol) was added at room temperature, and the mixture was stirred at it was for 2 hrs. The insoluble material of the mixture was removed by filtration and washed with diethyl ether to give a solution of zinc borohydride in diethyl ether. To the obtained solution was added ethyl 3-(5-chloro-2-thienyl)-3-oxo-2-[3-(1,1,2,2-tetrafluoroethoxy)benzyl]propionate (12.50 g, 28.48 mmol) under ice-cooling, and the mixture was stirred at room temperature for 2 hrs. To the reaction solution was added dilute hydrochloric acid by small portions to decompose excess zinc borohydride. The mixture was extracted twice with ethyl acetate. The recovered organic layer was dried over anhydrous magnesium sulfate, and the solvent was evaporated under reduced pressure. The obtained crude product was purified by silica gel column chromatography (hexane/ethyl acetate=6/1–1/1) to give the objective substance.

colorless liquid yield 12.70 g, 100% $^1$H-NMR (CDCl$_3$, 200 MHz) δ 1.00 (3H, t, J=7.2 Hz), 2.95–3.09 (3H, m), 3.14 (1H, d, J=3.6 Hz), 3.96 (2H, q, J=7.2 Hz), 5.14 (1H, t, J=3.9 Hz), 5.90 (1H, tt, J=2.9 Hz, 53.1 Hz), 6.75 (1H, d, J=4.0 Hz), 6.79 (1H, d, J=4.0 Hz), 7.00 (1H, s), 7.06 (2H, d, J=7.8 Hz), 7.28 (1H, t, J=7.9 Hz); IR (neat) 3463, 1725, 1451, 1302, 1277, 1198, 1125, 801 cm$^{-1}$ 3) (2RS,3RS)-3-(5-chloro-2-thienyl)-3-hydroxy-2-[3-(1,1,2, 2-tetrafluoroethoxy)benzyl]propionic acid A mixture of ethyl (2RS,3RS)-3-(5-chloro-2-thienyl)-3-hydroxy-2-[3-(1,1,2,2-tetrafluoroethoxy)benzyl]propionate (14.27 g, 32.37 mmol), sodium hydroxide (2.39 g, 64.7 mmol), methanol (50 ml) and tetrahydrofuran (50 ml) was stirred at room temperature for 6 hrs. The reaction solution was concentrated, diluted with water, acidified with dilute hydrochloric acid, and extracted twice with ethyl acetate. The recovered organic layer was dried over anhydrous sodium sulfate, and the solvent was evaporated under reduced pressure. The residue was crystallized from diethyl ether-hexane to give the objective substance.

white crystal yield 9.181 g, 69% mp 105–106° C.; $^1$H-NMR (CDCl$_3$, 300 MHz) δ 3.03–3.11 (3H, m), 5.15–5.17 (1H, m), 5.89 (1H, tt, J=2.9 Hz, 53.1 Hz), 6.76 (1H, d, J=3.9 Hz), 6.79 (1H, d, J=3.6 Hz), 7.01 (1H, s), 7.06 (2H, d, J=8.7 Hz), 7.27 (1H, t, J=7.8 Hz); IR (KBr) 3358, 3100–2550, 1692, 1453, 1287, 1204, 1117, 801 cm$^{-1}$; Anal. Calcd for C$_{16}$H$_{13}$ClF$_4$O$_4$S: C, 46.56; H, 3.17. Found: C, 46.59; H, 3.20.

4) (4RS,5RS)-5-(5-chloro-2-thienyl)-4-[3-(1,1,2,2-tetrafluoroethoxy)benzyl]-1,3-oxazolidin-2-one To a solution of (2RS,3RS)-3-(5-chloro-2-thienyl)-3-hydroxy-2-[3-(1,1,2,2 tetrafluoroethoxy)benzyl]propionic acid (8.996 g, 21.79 mmol) in tetrahydrofuran (80 ml) were added triethylamine (3.65 ml, 26.2 mmol) and diphenylphosphoryl azide (6.60 g, 24.0 mmol), and the mixture was heated under reflux overnight. The solvent of the reaction solution was evaporated under reduced pressure and the obtained crude product was purified by silica gel column chromatography (hexane/ethyl acetate=3/1–1/1) to give the objective substance.

brown liquid yield 8.480 g, 95% $^1$H-NMR (CDCl$_3$, 200 MHz) δ 2.55 (1H, dd, J=9.8 Hz, 14.0 Hz), 2.66 (1H, dd, J=4.6 Hz, 13.4 Hz), 4.20–4.31 (1H, m), 5.19 (1H, br s), 5.86 (1H, d, J=7.6 Hz), 5.91 (1H, tt, J=2.8 Hz, 53.0 Hz), 6.87 (2H, s), 6.94 (1H, s), 7.01 (1H, d, J=7.6 Hz), 7.13 (1H, dd, J=1.2 Hz, 8.2 Hz), 7.34 (1H, t, J=7.9 Hz); IR (neat) 3274, 1761, 1451, 1196, 1119, 1001 cm$^{-1}$ 5) (1RS,2RS)-2-amino-1-(5-chloro-2-thienyl)-3-[3-(1,1,2,2-tetrafluoroethoxy)phenyl]propan-1-ol (4RS,5RS)-5-(5-Chloro-2-thienyl)-4-[3-(1,1,2,2-tetrafluoroethoxy)benzyl]-1,3-oxazolidin-2-one (8.480 g, 20.69 mmol) and sodium hydroxide (3.31 g, 82.8 mmol) were heated in ethanol (40 ml)-water (3 ml) under reflux for 4 hrs. The reaction solution was diluted with brine, and extracted twice with ethyl acetate. The recovered organic layer was dried over anhydrous sodium sulfate, and the solvent was evaporated under reduced pressure. The residue was purified by silica gel (APS type) column chromatography (hexane/ethyl acetate=3/1-ethyl acetate) to give the objective substance.

yellow liquid yield 7.648 g, 96% $^1$H-NMR (CDCl$_3$, 200 MHz) δ 2.45 (1H, dd, J=9.8 Hz, 13.8 Hz), 2.86 (1H, dd, J=4.1 Hz, 13.5 Hz), 3.27–3.36 (1H, m), 4.76 (1H, d, J=4.8 Hz), 5.91 (1H, tt, J=2.7 Hz, 53.1 Hz), 6.78 (1H, d, J=3.6 Hz), 6.83 (1H, d, J=3.6 Hz), 7.06 (2H, d, J=7.4 Hz), 7.12 (1H, d, J=1.6 Hz), 7.32 (1H, t, J=7.8 Hz); IR (neat) 3360–2860, 1586, 1487, 1451, 1302, 1279, 1196, 1121, 801 cm$^{-1}$ 6) N-[(1RS,2RS)-2-(5-chloro-2-thienyl)-2-hydroxy-1-[3-(1,1,2,2-tetrafluoroethoxy)benzyl]ethyl]-6,7-dihydro-5H-benzo[a]cycloheptene-1-carboxamide While stirring (1RS,2RS)-2-amino-1-(5-chloro-2-thienyl)-3-[3-(1,1,2,2-tetrafluoroethoxy)phenyl]propan-1-ol (0.582 g, 1.516 mmol), 6,7-dihydro-5H-benzo[a] cycloheptene-1-carboxylic acid (0.29 g, 1.52 mmol) and 1-hydroxybenzotriazole hydrate (0.23 g, 1.52 mmol) in acetonitrile (10 ml), 1-ethyl-3-(3-dimethylaminopropyl) carbodiimide hydrochloride (0.29 g, 1.52 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white powder yield 0.623 g, 74% mp 177–178° C.; $^1$H-NMR (CDCl$_3$, 200 MHz) δ 1.95–2.07 (2H, m), 2.16–2.25 (2H, m), 2.68 (2H, t, J=5.9 Hz), 2.80 (1H, dd, J=10.4 Hz, 14.6 Hz), 3.06 (1H, dd, J=4.8 Hz, 14.2 Hz), 4.40 (1H, d, J=4.2 Hz), 4.62–4.76 (1H, m), 5.15 (1H, t, J=3.6 Hz), 5.81 (1H, d, J=7.6 Hz), 5.90 (1H, tt, J=2.9 Hz, 53.1 Hz), 5.96 (1H, td, J=5.3 Hz, 11.6 Hz), 6.27 (1H, d, J=11.8 Hz), 6.83 (2H, s), 7.02–7.21 (6H, m), 7.35 (1H, t, J=7.7 Hz); IR (KBr) 3264, 1640, 1537, 1451, 1202, 1117 cm$^{-1}$; Anal. Calcd for C$_{27}$H$_{24}$ClF$_4$NO$_3$S: C, 58.54; H, 4.37; N, 2.53. Found: C, 58.29; H, 4.36; N, 2.47.

Example 290

N-[(1RS,2SR)-2-(4-bromophenyl)-2-hydroxy-1-[3-(1,1,2,2-tetrafluoroethoxy)benzyl]ethyl]-6,7-dihydro-5H-benzo[a]cycloheptene-1-carboxamide 1) ethyl 3-(4-bromophenyl)-3-oxopropanoate To a mixture of 4-bromoacetophenone (80 g, 0.40 mol), ethanol (1 ml) and diethyl carbonate (350 ml) was added sodium hydride (32 g, 60% in oil) by small portions under ice-cooling and the mixture was stirred at room temperature for 4 hrs. The reaction solution was cooled to 0° C. and 6N hydrochloric acid (200 ml) was added. The mixture was extracted with ethyl acetate (200, 100 ml). The extract was washed with water, dried over anhydrous magnesium sulfate and evaporated under reduced pressure. The residue was purified by silica gel chromatography (hexane:ethyl acetate= 10:1–5:1) to give the objective substance (108.9 g, quantitative) as an oil.

IR ν max$^{Neat}$cm$^{-1}$: 1742, 1688, 1586, 1424, 1323, 1264, 1200, 1073, 1009. $^1$H-NMR (CDCl$_3$) δ: 1.26(3H×3/4, t, J=7.2 Hz), 1.31(3H×1/4, t, J=7.2 Hz), 3.96(2H×3/4, s), 4.21(2H×3/4, q, J=7.2 Hz), 4.27(2H×1/4, q, J=7.2 Hz), 5.65(1H×1/4, s), 7.50–7.70(2H×5/4, m) 7.75–7.90(2H×3/4, m).

2) ethyl 3-(4-bromophenyl)-3-oxo-2-[3-(1,1,2,2-tetrafluoroethoxy)benzyl]propanoate To a solution of 3-(1,1,2,2-tetrafluoroethoxy)toluene (25 g, 0.12 mol) in ethyl acetate (400 ml) were added N-bromosuccinimide (21.4, 0.12 mol) and 2,2'-azobisisobutyronitrile (0.2 g) and the mixture was heated under reflux for 2.5 hrs. The reaction solution was concentrated under reduced pressure, and diethyl ether and hexane were added. Insoluble material was removed, and washed with diethyl ether. The filtrate was evaporated under reduced pressure to give 3-(1,1,2,2-tetrafluoroethoxy)-1-bromomethylbenzene. To a solution of ethyl 3-(4-bromophenyl)-3-oxopropanoate (27.1 g, 100 mmol) in dimethoxyethane (150 ml) was added sodium hydride (4.0 g, 60% in oil, 0.1 mol) under ice-cooling and the mixture was stirred for 1 hr. A solution of 3-(1,1,2,2-tetrafluoroethoxy)-1-bromomethylbenzene obtained above in dimethoxyethane (20 ml) was dropwise added and the mixture was stirred at room temperature for 15 hrs. To the reaction solution was added water (300 ml) and the mixture was extracted with ethyl acetate (200 ml×2). The extract was washed with water, dried over anhydrous magnesium sulfate and evaporated under reduced pressure. The residue was purified by silica gel chromatography (hexane:toluene=1:2–1:5). Crystallization from hexane gave the objective substance (21.1 g, 44%).

mp 48–49° C. IR ν max$^{KBr}$cm$^{-1}$: 1721, 1684, 1588, 1277, 1198, 1134, 845. Anal. Calcd for $C_{20}H_{17}BrF_4O_4$ (MW477.24) Calcd: C, 50.33; H, 3.96 Found: C, 55.55; H, 3.83 $^1$H-NMR (CDCl$_3$) δ: 1.12 (3H, t, J=7.2 Hz), 3.33 (2H, d, J=8.0 Hz), 4.10 (2H, q, J=7.2 Hz), 4.55 (1H, t, J=7.0 Hz), 5.89 (1H, tt, J=53.1, 2.2 Hz), 7.00–7.20 (3H, m), 7.20–7.35 (1H, m), 7.42 (2H, d, J=8.0 Hz), 7.89 (2H, d, J=8.0 Hz).

3) ethyl (2RS,3RS)-3-(4-bromophenyl)-3-hydroxy-2-[3-(1,1,2,2-tetrafluoroethoxy)benzyl]propanoate To a suspension of anhydride zinc chloride (11.4 g, 83.8 mmol) in diethyl ether (200 ml) was added sodium borohydride (6.34 g, 168 mmol) by small portions, and the mixture was stirred for 2 hrs. The insoluble material was removed by filtration and washed with diethyl ether. The filtrate was ice-cooled, and a solution of ethyl 3-(4-bromophenyl)-3-oxo-2-[3-(1,1,2,2-tetrafluoroethoxy)benzyl]propanoate (20 g, 41.9 mmol) in diethyl ether (50 ml) was added. The mixture was stirred at room temperature for 2 hrs. After cooling again, 2N hydrochloric acid was added to terminate the reaction. The obtained mixture was extracted with ethyl acetate (200, 100 ml), washed with water, dried over anhydrous magnesium sulfate and evaporated under reduced pressure. The residue was purified by silica gel chromatography (hexane:ethyl acetate=5:1–2:1) to give the objective substance (20 g, quantitative) as a colorless oil.

IR ν max$^{Neat}$cm$^{31\ 1}$: 1715, 1590, 1487, 1302, 1279, 1198, 1123, 1011. $^1$H-NMR (CDCl$_3$) δ: 0.95 (3H, t, J=7.2 Hz), 2.90–3.15 (4H, m), 3.90 (2H, d, J=7.2 Hz), 5.02 (1H, br), 5.89 (1H, tt, J=53.1, 2.8 Hz), 6.90–7.15 (3H, m), 7.20–7.40 (3H, m), 7.40–7.60 (2H, m).

4) (2RS,3RS)-3-(4-bromophenyl)-3-hydroxy-2-[3-(1,1,2,2-tetrafluoroethoxy)benzyl]propanoic acid To a solution of ethyl (2RS,3RS)-3-(4-bromophenyl)-3-hydroxy-2-[3-(1,1,2,2-tetrafluoroethoxy)benzyl]propanoate (19.5 g, 40.7 mmol) in methanol (100 ml) was added 2N aqueous sodium hydroxide solution (40.7 ml, 81.4 mmol) and the mixture was stirred at room temperature for 2.5 hrs. 6N Hydrochloric acid (50 ml) was added to acidify the solution and the mixture was extracted with ethyl acetate (100 ml×2). The extract was washed with water, dried over anhydrous magnesium sulfate and evaporated under reduced pressure. The residue was crystallized from hexane to give the objective substance (16.7 g, 91%).

mp 85–86° C. IR ν max$^{KBr}$cm$^{-1}$:1696, 1487, 1279, 1206, 1127. Anal. Calcd for $C_{18}H_{15}BrF_4O_4$ (MW451.21) Calcd: C, 47.91; H, 3.35 Found: C, 47.97; H, 3.33 $^1$H-NMR (CDCl$_3$) δ: 2.85–3.15 (3H, m), 5.06 (1H, d, J=3.8 Hz), 5.88 (1H, tt, J=53.1, 2.8 Hz), 6.90–7.15 (3H, m), 7.20–7.40 (2H, m), 7.49 (2H, d, J=8.4 Hz).

5) (4RS,5SR)-5-(4-bromophenyl)-4-[3-(1,1,2,2-tetrafluoroethoxy)benzyl]-1,3-oxazolidin-2-one To a solution of (2RS,3RS)-3-(4-bromophenyl)-3-hydroxy-2-[3-(1,1,2,2-tetrafluoroethoxy)benzyl]propanoic acid (16.2 g, 35.9 mmol) in tetrahydrofuran (150 ml) was added diphenylphosphoryl azide (10.0 ml, 46.7 mmol) and triethylamine (7.0 ml, 50.3 mmol) was added. The mixture was stirred at room temperature for 1 hr and heated under reflux for 2 hrs. The reaction solution was concentrated under reduced pressure, and water (100 ml) was added. The mixture was extracted with ethyl acetate (100 ml×2). The extract was washed with 1N hydrochloric acid and saturated aqueous sodium hydrogen carbonate solution, dried over anhydrous magnesium sulfate and evaporated under reduced pressure. The residue was purified by silica gel chromatography (hexane:ethyl acetate=3:1–1:1). Hexane was added to the precipitated crystals and the mixture was filtered to give the objective substance (14.7 g, 91%).

mp 136–137° C. IR ν max$^{KBr}$cm$^{-1}$: 1738, 1489, 1200, 1125, 848. Anal. Calcd for $C_{18}H_{14}BrF_4NO_3$ (MW448.21) Calcd: C, 48.24; H, 3.15; N, 3.13. Found: C, 48.30; H, 2.87; N, 3.14. $^1$H-NMR (CDCl$_3$) δ: 2.15–2.40 (2H, m), 4.20–4.35 (1H, m), 5.03 (1H, brs), 5.77 (1H, d, J=8.0 Hz), 5.90 (1H, tt, J=53.2, 2.7 Hz), 6.87 (1H, s), 6.94 (1H, d, J=7.6 Hz), 7.05–7.15 (1H, m), 7.20–7.40 (3H, m), 7.55–7.65 (2H, m).

6) (1RS,2SR)-2-amino-1-(4-bromophenyl)-3-[3-(1,1,2,2-tetrafluoroethoxy)phenyl]-1-propanol To a solution of (4RS,5SR)-5-(4-bromophenyl)-4-[3-(1,1,2,2-tetrafluoroethoxy)benzyl]-1,3-oxazolidin-2-one (14.0 g, 31.2 mmol) in ethanol (50 ml) was added 8N aqueous sodium hydroxide solution (15.6 ml, 125 mmol) and the mixture was heated under reflux for 2 hrs. The reaction solution was concentrated under reduced pressure, and water (200 ml) was added. The mixture was extracted with ethyl acetate (200 ml×2). The extract was washed with water, dried over anhydrous magnesium sulfate and evaporated under reduced pressure. The residue was crystallized from hexane-diethyl ether to give the objective substance (12.8 g, 97%).

mp 84–86° C. IR ν max$^{KBr}$cm$^{-1}$: 3362, 1611, 1588, 1485, 1308, 1196, 1119, 1034, 1007. Anal. Calcd for $C_{17}H_{16}BrF_4NO_2$ (MW422.21) Calcd: C, 48.36; H, 3.82; N, 3.32. Found: C, 48.59; H, 3.57; N, 3.37. $^1$H-NMR (CDCl$_3$) δ: 2.36(1H, dd, J=13.4, 10.6 Hz), 2.76(1H, dd, J=13.4, 3.4 Hz), 3.20–3.40(1H, m), 4.65(1H, d, J=4.8 Hz), 5.91(1H, tt, J=53.1, 2.8 Hz), 6.99(1H, s), 7.06(2H, t, J=6.6 Hz), 7.20–7.40(3H, m), 7.51(2H, d, J=8.6 Hz).

7) N-[(1RS,2SR)-2-(4-bromophenyl)-2-hydroxy-1-[3-(1,1,2,2-tetrafluoroethoxy)benzyl]ethyl]-6,7-dihydro-5H-benzo[a]cycloheptene-1-carboxamide While stirring (1RS,2SR)-2-amino-1-(4-bromophenyl)-3-[3-(1,1,2,2-tetrafluoroethoxy)phenyl]-1-propanol (5.647 g, 13.37 mmol), 6,7-dihydro-5H-benzo[a]cycloheptene-1-carboxylic acid (2.52 g, 13.4 mmol) and 1-hydroxybenzotriazole hydrate (2.05 g, 13.4 mmol) in acetonitrile (40 ml), 1-ethyl-3-(3-dimethylaminopropyl)carbodiimide hydrochloride (2.56 g, 13.4 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white powder yield 7.306 g, 92% mp 184–185° C.; $^1$H-NMR (CDCl$_3$, 300 MHz) δ 1.95–2.04 (2H, m), 2.16–2.23 (2H, m), 2.66 (2H, t, J=5.9 Hz), 2.77 (1H, dd, J=10.7 Hz, 14.6 Hz), 2.97 (1H, dd, J=4.1 Hz, 14.6 Hz), 3.76 (1H, d, J=3.9 Hz), 4.61–4.70 (1H, m), 5.02 (1H, t, J=3.9 Hz), 5.75 (1H, d, J=8.4 Hz), 5.89 (1H, tt, J=2.8 Hz, 53.1 Hz), 5.92 (1H, td, J=5.9 Hz, 11.4 Hz), 6.20 (1H, d, J=11.7 Hz), 6.96 (1H, dd, J=1.5 Hz, 7.8 Hz), 7.01 (1H, s), 7.03–7.17 (4H, m), 7.30 (1H, t, J=7.8 Hz), 7.34 (2H, d, J=8.1 Hz), 7.51 (2H, d, J=8.4 Hz); IR (KBr) 3260, 1640, 1532, 1487, 1198, 1125 cm$^{-1}$; Anal. Calcd for $C_{29}H_{26}BrF_4NO_3$: C, 58.80; H, 4.42; N, 2.36. Found: C, 58.75; H, 4.43; N, 2.35.

Example 291

N-[(1RS,2SR)-2-(1,1'-biphenyl-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo

[a]cycloheptene-1-carboxamide (0.511 g, 0.863 mmol), phenylboronic acid (0.16 g, 1.29 mmol), tetrakis(triphenylphosphine)palladium(0) (0.10 g, 0.086 mmol) and sodium carbonate (0.18 g, 1.73 mmol) were stirred in toluene (8 ml)-water (8 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether gave the objective substance.

white powder yield 0.269 g, 53% mp 122–123° C.; $^1$H-NMR (CDCl$_3$, 200 MHz) δ 1.96–2.05 (2H, m), 2.14–2.24 (2H, m), 2.66 (2H, t, J=5.8 Hz), 2.83 (1H, dd, J=10.8 Hz, 14.6 Hz), 3.06 (1H, dd, J=4.5 Hz, 14.7 Hz), 3.60 (1H, d, J=3.6 Hz), 4.72–4.82 (1H, m), 5.11 (1H, t, J=3.7 Hz), 5.80 (1H, d, J=8.0 Hz), 5.88 (1H, tt, J=3.0 Hz, 53.1 Hz), 5.91 (1H, td, J=5.4 Hz, 11.6 Hz), 6.23 (1H, d, J=11.6 Hz), 6.97–7.17 (6H, m), 7.31–7.64 (10H, m); IR (KBr) 3250, 1634, 1530, 1487, 1285, 1194, 1115, 770, 700 cm$^{-1}$; Anal. Calcd for C$_{35}$H$_{31}$F$_4$NO$_3$.0.1H$_2$O.0.5i-Pr$_2$O: C, 71.04; H, 5.99; N, 2.18. Found: C, 70.75; H, 5.99; N, 2.23.

Example 292

N-[(1RS,2SR)-2-hydroxy-1-[3-(1,1,2,2-tetrafluoroethoxy)benzyl]-2-[4-(3-thienyl)phenyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.519 g, 0.876 mmol), thiophene-3-boronic acid (0.17 g, 1.31 mmol), tetrakis(triphenylphosphine)palladium(0) (0.10 g, 0.088 mmol) and sodium carbonate (0.19 g, 1.75 mmol) were stirred in toluene (8 ml)-water (8 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from ethyl acetate-diisopropyl ether-hexane gave the objective substance.

pale-brown powder yield 0.334 g, 64% mp 178–179° C.; $^1$H-NMR (CDCl$_3$, 200 MHz) δ 1.92–2.04 (2H, m), 2.14–2.23 (2H, m), 2.66 (2H, t, J=5.9 Hz), 2.81 (1H, dd, J=10.5 Hz, 14.7 Hz), 3.03 (1H, dd, J=4.6 Hz, 14.4 Hz), 3.63 (1H, d, J=3.6 Hz), 4.67–4.81 (1H, m), 5.07 (1H, t, J=3.7 Hz), 5.80 (1H, d, J=8.4 Hz), 5.88 (1H, tt, J=2.9 Hz, 53.1 Hz), 5.90 (1H, td, J=5.0 Hz, 12.2 Hz), 6.22 (1H, d, J=11.8 Hz), 6.95–7.17 (6H, m), 7.26–7.50 (6H, m), 7.62 (2H, d, J=8.2 Hz); IR (KBr) 3283, 2936, 1640, 1532, 1200, 1123, 783 cm$^{-1}$; Anal. Calcd for C$_{33}$H$_{29}$F$_4$NO$_3$S: C, 66.54; H, 4.91; N, 2.35. Found: C, 66.37; H, 4.86; N, 2.28.

Example 293

N-[(1RS,2SR)-2-(2'-chloro[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.529 g, 0.893 mmol), 2-chlorophenylboronic acid (0.42 g, 2.68 mmol), tetrakis(triphenylphosphine)palladium(0) (0.20 g, 0.18 mmol) and sodium carbonate (0.38 g, 3.58 mmol) were stirred in toluene (8 ml)-water (8 ml) at 90° C. for 2 days. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

white powder yield 0.203 g, 36% mp 172–173° C.; $^1$H-NMR (CDCl$_3$, 300 MHz) δ 1.95–2.04 (2H, m), 2.16–2.22 (2H, m), 2.66 (2H, t, J=5.9 Hz), 2.86, (1H, dd, J=10.8 Hz, 14.4 Hz), 3.07 (1H, dd, J=4.5 Hz, 14.7. Hz), 3.62 (1H, d, J=3.9 Hz), 4.72–4.81 (1H, m), 5.11 (1H, t, J=3.9 Hz), 5.83 (1H, d, J=8.4 Hz), 5.89 (1H, tt, J=2.9 Hz, 53.0 Hz), 5.93 (1H, td, J=5.7 Hz, 11.6 Hz), 6.25 (1H, d, J=11.7 Hz), 6.96–7.16 (6H, m), 7.26–7.36 (4H, m), 7.46–7.54 (5H, m); IR (KBr) 3753, 3233, 3061, 1640, 1306, 1198, 1123, 1030, 762 cm$^{-1}$; Anal. Calcd for C$_{35}$H$_{30}$ClF$_4$NO$_3$: C, 67.36; H, 4.85; N, 2.24. Found: C, 66.99; H, 5.05; N, 2.08.

Example 294

N-[(1RS,2SR)-2-(4'-chloro[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.500 g, 0.844 mmol), 4-chlorophenylboronic acid (0.26 g, 1.69 mmol), tetrakis(triphenylphosphine)palladium(0) (0.20 g, 0.17 mmol) and sodium carbonate (0.27 g, 2.53 mmol) were stirred in toluene (10 ml)-water (10 ml) at 90° C. for 2 days. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

pale-brown crystal yield 0.136 g, 26% mp 167–168° C.; $^1$H-NMR (CDCl$_3$, 300 MHz) δ 1.95–2.03 (2H, m), 2.15–2.22 (2H, m), 2.66 (2H, t, J=5.9 Hz), 2.83 (1H, dd, J=10.7 Hz, 14.6 Hz), 3.04 (1H, dd, J=4.1 Hz, 14.9 Hz), 3.63 (1H, d, J=3.6 Hz), 4.71–4.79 (1H, m), 5.11 (1H, t, J=3.8 Hz), 5.80 (1H, d, J=8.4 Hz), 5.88 (1H, tt, J=2.9 Hz, 53.1 Hz), 5.90 (1H, td, J=5.7 Hz, 11.4 Hz), 6.23 (1H, d, J=12.0 Hz), 6.96–7.16 (6H, m), 7.30 (1H, t, J=8.0 Hz), 7.41 (2H, d, J=8.7 Hz), 7.50–7.59 (6H, m); IR (KBr) 3289, 2932, 1638, 1530, 1487, 1204, 1123, 1096, 818 cm$^{-1}$; Anal. Calcd for C$_{35}$H$_{30}$ClF$_4$NO$_3$: C, 67.36; H, 4.85; N, 2.24. Found: C, 67.37; H, 4.87; N, 2.15.

Example 295

N-[(1RS,2SR)-2-(3'-chloro[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.500 g, 0.844 mmol), 3-chlorophenylboronic acid (0.26 g, 1.69 mmol), tetrakis(triphenylphosphine)palladium(0) (0.20 g, 0.17 mmol) and sodium carbonate (0.27 g, 2.53 mmol) were stirred in toluene (10 ml)-water (10 ml) at 90° C. for 2 days. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisbpropyl ether-hexane gave the objective substance.

pale-brown crystal yield 0.165 g, 31% mp 131–132° C.; $^1$H-NMR (CDCl$_3$, 300 MHz) δ 1.95–2.03 (2H, m), 2.16–2.22 (2H, m), 2.67 (2H, t, J=5.9 Hz), 2.83 (1H, dd, J=10.5 Hz, 14.4 Hz), 3.03 (1H, dd, J=4.2 Hz, 14.7 Hz), 3.66 (1H, d, J=3.9 Hz), 4.70–4.79 (1H, m), 5.11 (1H, t, J=3.8 Hz), 5.80, (1H, d, J=8.1 Hz), 5.88 (1H, tt, J=2.9 Hz, 53.0 Hz), 5.91. (1H, td, J=5.7 Hz, 11.4 Hz), 6.23 (1H, d, J=11.7 Hz), 6.98–7.17 (6H, m), 7.28–7.43 (3H, m), 7.46–7.60 (6H, m); IR (KBr) 3270, 2938, 1640, 1514, 1200, 1125, 783 cm$^{-1}$; Anal. Calcd for C$_{35}$H$_{30}$ClF$_4$NO$_3$: C, 67.36; H, 4.85; N, 2.24. Found: C, 67.42; H, 4.80; N, 2.10.

Example 296

N-[(1RS,2SR)-2-hydroxy-2-(2'-methoxy[1,1'-biphenyl]-4-yl)-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.530 g, 0.895 mmol), 2-methoxyphenylboronic acid (0.20 g, 1.34 mmol), tetrakis(triphenylphosphine)palladium(0) (0.10 g, 0.089 mmol) and sodium carbonate (0.19 g, 1.79 mmol) were stirred in toluene (8 ml)-water (8 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from ethyl acetate-diisopropyl ether-hexane gave the objective substance.

white powder yield 0.307 g, 55% mp 148–150° C.; $^1$H-NMR (CDCl$_3$, 300 MHz) δ 1.95–2.05 (2H, m), 2.16–2.22 (2H, m), 2.66 (2H, t, J=5.7 Hz), 2.85 (1H, dd, J=10.7 Hz, 14.9 Hz), 3.08 (1H, dd, J=4.2 Hz, 14.7 Hz), 3.48 (1H, d, J=3.9 Hz), 3.82 (3H, s), 4.74–4.82 (1H, m), 5.09 (1H, t, J=3.6 Hz), 5.79 (1H, d, J=8.7 Hz), 5.89 (1H, tt, J=2.9 Hz, 53.1 Hz), 5.91 (1H, td, J=5.5 Hz, 11.2 Hz), 6.24 (1H, d, J=11.7 Hz), 6.97–7.18 (8H, m), 7.28–7.36 (3H, m), 7.49 (2H, d, J=8.1 Hz), 7.57 (2H, d, J=8.1 Hz); IR (KBr) 3264, 2938, 1638, 1528, 1487, 1275, 1190, 1117, 762 cm$^{-1}$; Anal. Calcd for C$_{36}$H$_{33}$F$_4$NO$_4$.0.2H$_2$O: C, 69.38; H, 5.40; N, 2.25. Found: C, 69.11; H, 5.33; N, 2.05.

Example 297

N-[(1RS,2SR)-2-hydroxy-2-(4'-methoxy[1,1'-biphenyl]-4-yl)-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.500 g, 0.844 mmol), 4-methoxyphenylboronic acid (0.26 g, 1.69 mmol), tetrakis(triphenylphosphine)palladium(0) (0.20 g, 0.17 mmol) and sodium carbonate (0.27 g, 2.53 mmol) were stirred in toluene (10 ml)-water (10 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

white crystal yield 0.310 g, 59% mp 162–163° C.; $^1$H-NMR (CDCl$_3$, 300 MHz) δ 1.94–2.03 (2H, m), 2.15–2.22 (2H, m), 2.66 (2H, t, J=5.9 Hz), 2.83 (1H, dd, J=10.7 Hz, 14.6 Hz), 3.05 (1H, dd, J=4.2 Hz, 14.7 Hz), 3.54 (1H, d, J=3.6 Hz), 3.86 (3H, s), 4.73–4.81 (1H, m), 5.09 (1H, t, J=3.9 Hz), 5.78 (1H, d, J=8.7 Hz), 5.88 (1H, tt, J=2.9 Hz, 53.1 Hz), 5.90 (1H, td, J=5.7 Hz, 11.4 Hz), 6.23 (1H, d, J=11.7 Hz), 6.96–7.16 (8H, m), 7.30 (1H, t, J=8.0 Hz), 7.49–7.59 (6H, m); IR (KBr) 3299, 2930, 1638, 1530, 1503, 1277, 1229, 1198, 1125, 820 cm$^{-1}$; Anal. Calcd for C$_{36}$H$_{33}$F$_4$NO$_4$: C, 69.78; H, 5.37; N, 2.26. Found: C, 69.69; H, 5.17; N, 2.10.

Example 298

N-[(1RS,2SR)-2-hydroxy-2-(3'-methoxy[1,1'-biphenyl]-4-yl)-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.500 g, 0.844 mmol), 3-methoxyphenylboronic acid (0.26 g, 1.69 mmol), tetrakis(triphenylphosphine)palladium(0) (0.20 g, 0.17 mmol) and sodium carbonate (0.27 g, 2.53 mmol) were stirred in toluene (10 ml)-water (10 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

white crystal yield 0.241 g, 46% mp 79–81° C.; $^1$H-NMR (CDCl$_3$, 300 MHz) δ 1.95–2.03 (2H, m), 2.16–2.22 (2H, m), 2.66 (2H, t, J=5.7 Hz), 2.83 (1H, dd, J=10.5 Hz, 14.7 Hz), 3.05 (1H, dd, J=4.1 Hz, 14.6 Hz), 3.60 (1H, d, J=3.9 Hz), 3.87 (3H, s), 4.73–4.80 (1H, m), 5.10 (1H, t, J=3.8 Hz), 5.79 (1H, d, J=8.4 Hz), 5.88 (1H, tt, J=2.9 Hz, 53.0 Hz), 5.91 (1H, td, J=5.7 Hz, 11.4 Hz), 6.23 (1H, d, J=11.7 Hz), 6.91 (1H, dd, J=2.1 Hz, 7.8 Hz), 6.99 (1H, dd, J=1.5 Hz, 7.5 Hz), 7.03–7.20 (7H, m), 7.30 (1H, t, J=7.8 Hz), 7.37 (1H, t, J=8.0 Hz), 7.52 (2H, d, J=8.1 Hz), 7.61 (2H, d, J=8.1 Hz); IR (KBr) 3268, 2932, 1638, 1518, 1483, 1298, 1277, 1194, 1121, 779 cm$^{-1}$; Anal. Calcd for C$_{36}$H$_{33}$F$_4$NO$_4$: C, 69.78; H, 5.37; N, 2.26. Found: C, 69.76; H, 5.70; N, 2.07.

Example 299

N-[(1RS,2SR)-2-(4'-formyl[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.822 g, 1.388 mmol), 4-formylphenylboronic acid (0.31 g, 2.08 mmol), tetrakis(triphenylphosphine)palladium(0) (0.16 g, 0.14 mmol) and sodium carbonate (0.29 g, 2.78 mmol) were stirred in toluene (10 ml)-water (10 ml) at 90° C. for 1 day. The reaction solution was poured into water, and extracted twice with ethyl acetate. The recovered organic layer was dried over anhydrous sodium. sulfate and the solvent was evaporated under reduced pressure. The residue was purified by silica gel column chromatography (hexane/ethyl acetate=3/1–1/1). Crystallization from diisopropyl ether-hexane gave the objective substance.

white powder yield 0.214 g, 25% mp 174–176° C.; $^1$H-NMR (CDCl$_3$, 300 MHz) δ 1.97–2.04 (2H, m), 2.16–2.22. (2H, m), 2.67 (2H, t, J=5.9 Hz), 2.85 (1H, dd, J=10.5 Hz, 14.7 Hz), 3.04 (1H, dd, J=3.8 Hz, 14.3 Hz), 3.69 (1H, d, J=3.9 Hz), 4.72–4.80 (1H, m), 5.14 (1H, t, J=3.5 Hz), 5.81 (1H, d, J=8.4 Hz), 5.88 (1H, tt, J=2.6 Hz, 53.0 Hz), 5.91 (1H, td, J=5.6 Hz, 11.4 Hz), 6.24 (1H, d, J=11.7 Hz), 6.98–7.17 (6H, m), 7.31 (1H, t, J=7.8 Hz), 7.58 (2H, d, J=8.1 Hz), 7.67 (2H, d, J=8.4 Hz), 7.77 (2H, d, J=8.1 Hz), 7.97 (2H, d, J=8.1 Hz), 10.06 (1H, s); IR (KBr) 3324, 2940, 1701, 1626, 1605, 1532, 1308, 1275, 1200, 1119, 806, 774 cm$^{-1}$; Anal. Calcd for C$_{36}$H$_{31}$F$_4$NO$_4$: C, 70.01; H, 5.06; N, 2.27. Found: C, 69.89; H, 5.19; N, 2.01.

Example 300

N-[(1RS,2SR)-2-(3'-formyl[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethbxy)benzyl]ethyl]-6,7-dihydro-5H-benzo[a]cycloheptene-1-carboxamide (0.812 g, 1.371 mmol), 3-formylphenylboronic acid (0.41 g, 2.74 mmol), tetrakis(triphenylphosphine)palladium(0) (0.32 g, 0.27 mmol) and sodium carbonate. (0.44 g, 4.11 mmol) were stirred in toluene. (10 ml)-water (10 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

pale-brown powder yield 0.285 g, 34% mp 103–105° C.; $^1$H-NMR (CDCl$_3$, 300 MHz) δ 1.95–2.04 (2H, m), 2.16–2.22 (2H, m), 2.67 (2H, t, J=5.9. Hz), 2.84 (1H, dd, J=10.8 Hz, 14.7 Hz), 3.05 (1H, dd, J=4.2 Hz, 14.4 Hz), 3.67 (1H, d, J=3.9 Hz), 4.71–4.80 (1H, m), 5.14 (1H, t, J=3.9 Hz), 5.81 (1H, d, J=8.4 Hz), 5.89 (1H, tt, J=2.8 Hz, 53.0 Hz), 5.91 (1H, td, J=5.4 Hz, 12.9 Hz), 6.25 (1H, d, J=12.0 Hz), 6.98–7.17 (6H, m), 7.31 (1H, t, J=8.0 Hz), 7.57–7.67 (5H, m), 7.88 (2H, dd, J=2.1 Hz, 7.2 Hz), 8.12 (1H, s), 10.10 (1H, s); IR (KBr) 3264, 2938, 1701, 1640, 1518, 1449, 1304, 1279, 1198, 1123, 793 cm$^{-1}$; Anal. Calcd for C$_{36}$H$_{31}$F$_4$NO$_4$: C, 70.01; H, 5.06; N, 2.27. Found: C, 70.08; H, 5.19; N, 2.16.

Example 301

N-[(1RS,2SR)-2-(2'-formyl[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide N-[(1RS,2SR)-2-(4-Bromophenyl)-2-hydroxy-1-[3-(1,1,2,2-tetrafluoroethoxy)benzyl]ethyl]-6,7-dihydro-5H-benzo[a]cycloheptene-1-carboxamide (0.812 g, 1.371 mmol), 2-formylphenylboronic acid (0.41 g, 2.74 mmol), tetrakis(triphenylphosphine)palladium(0) (0.32 g, 0.27 mmol) and sodium carbonate (0.44 g, 4.11 mmol) were stirred in toluene (10 ml)-water (10 ml) at 90° C. for 1 day. The reaction solution was poured into water, and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

pale-brown crystal yield 0.423 g, 50% mp 195–196° C.; $^1$H-NMR (CDCl$_3$, 300 MHz) δ 1.96–2.04 (2H, m), 2.16–2.22 (2H, m), 2.67 (2H, t, J=5.9 Hz), 2.86 (1H, dd, J=10.5 Hz, 14.7 Hz), 3.06 (1H, dd, J=4.4 Hz, 14.6 Hz), 3.77 (1H, d, J=3.9 Hz), 4.72–4.81 (1H, m), 5.16 (1H, t, J=3.6 Hz), 5.85 (1H, d, J=8.4 Hz), 5.90 (1H, tt, J=2.7 Hz, 53.0 Hz), 5.93 (1H, td, J=5.7 Hz, 11.4 Hz), 6.26 (1H, d, J=11.7 Hz), 6.98–7.18 (6H, m), 7.32 (1H, t, J=7.8 Hz), 7.40–7.68 (7H, m), 8.04 (1H, d, J=8.1 Hz), 9.99 (1H, s); IR (KBr) 3227, 2930, 1688, 1636, 1304, 1198, 1123, 770 cm$^{-1}$; Anal. Calcd for C$_{36}$H$_{31}$F$_4$NO$_4$: C, 70.01; H, 5.06; N, 2.27. Found: C, 70.00; H, 5.13; N, 2.20.

Example 302

N-[(1RS,2SR)-2-[2'-(hydroxymethyl)[1,1'-biphenyl]-4-yl]-2-hydroxy-1-[3-(1,1,2,2-tetrafluoroethoxy)benzyl]ethyl]-6,7-dihydro-5H-benzo[a]cycloheptene-1-carboxamide To a solution of N-[(1RS,2SR)-2-(2'-formyl[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide (168 mg, 0.272 mmol) in methanol (3 ml) was added sodium borohydride (10 mg, 0.27 mmol) at room temperature and the mixture was stirred as it was for 0.5 hr. To the reaction solution was added aqueous ammonium chloride solution, and the mixture was stirred as it was for 1 hr. The recovered precipitate was washed with water and diisopropyl ether-hexane to give the objective substance.

white powder yield 137 mg, 81% mp 152–154° C.; $^1$H-NMR (CDCl$_3$, 300 MHz) δ 1.60 (1H, t, J=5.7 Hz), 1.95–2.04 (2H, m), 2.16–2.22 (2H, m), 2.64–2.69 (2H, m), 2.86 (1H, dd, J=10.7 Hz, 14.9 Hz), 3.08 (1H, dd, J=4.1 Hz, 14.6 Hz), 3.62 (1H, d, J=3.0 Hz), 4.62 (2H, d, J=5.4 Hz), 4.72–4.80 (1H, m), 5.11 (1H, t, J=3.8 Hz), 5.82 (1H, d, J=8.7 Hz), 5.90 (1H, tt, J=2.7 Hz, 53.0 Hz), 5.93 (1H, td, J=5.8 Hz, 11.6 Hz), 6.25 (1H, d, J=11.7 Hz), 6.98 (1H, dd, J=1.5 Hz, 7.5 Hz), 7.04–7.17 (5H, m), 7.27–7.43 (6H, m), 7.51–7.58 (3H, m); IR (KBr) 3289, 1638, 1526, 1200, 1125, 1036, 762 cm$^{-1}$; Anal. Calcd for C$_{36}$H$_{33}$F$_4$NO$_4$: C, 69.78; H, 5.37; N, 2.26. Found: C, 69.47; H, 5.39; N, 2.16.

Example 303

N-[(1RS,2SR)-2-[3'-(hydroxymethyl)[1,1'-biphenyl]-4-yl]-2-hydroxy-1-[3-(1,1,2,2-tetrafluoroethoxy)benzyl]ethyl]-6,7-dihydro-5H-benzo[a]cycloheptene-1-carboxamide To a solution of N-[(1RS,2SR)-2-(3'-formyl[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide (123 mg, 0.199 mmol) in methanol (3 ml) was added sodium borohydride (8 mg, 0.20 mmol) at room temperature and the mixture was stirred as it was for 0.5 hr. To the reaction solution was added aqueous ammonium chloride solution, and the mixture was stirred as it was for 1 hr. The recovered precipitate was washed with water and diisopropyl ether-hexane to give the objective substance.

white powder yield 101 mg, 82% mp 178–179° C.; $^1$H-NMR (CDCl$_3$, 300 MHz) δ 1.74 (1H, t, J=5.3 Hz), 1.95–2.03 (2H, m), 2.16–2.22 (2H, m), 2.66 (2H, t, J=5.9 Hz), 2.83 (1H, dd, J=10.4 Hz, 14.6 Hz), 3.05 (1H, dd, J=4.2 Hz, 14.4 Hz), 3.60 (1H, d, J=3.9 Hz), 4.72–4.80 (1H, m), 4.78 (2H, d, J=4.2 Hz), 5.11 (1H, t, J=3.6 Hz), 5.79 (1H, d, J=8.4 Hz), 5.88 (1H, tt, J=3.2 Hz, 53.0 Hz), 5.91 (1H, td, J=5.9 Hz, 11.7 Hz), 6.24 (1H, d, J=12.0 Hz), 6.98–7.16 (6H, m), 7.26–7.64 (9H, m); IR (KBr) 3268, 1638, 1532, 1198, 1127, 787 cm$^{-1}$; Anal. Calcd for C$_{36}$H$_{33}$F$_4$NO$_4$: C, 69.78; H, 5.37; N, 2.26. Found: C, 69.47; H, 5.22; N, 2.15.

Example 304

N-[(1RS,2SR)-2-[4'-(hydroxymethyl)[1,1'-biphenyl]-4-yl]-2-hydroxy-1-[3-(1,1,2,2-tetrafluoroethoxy)benzyl]ethyl]-6,7-dihydro-5H-benzo[a]cycloheptene-1-carboxamide To a solution of N-[(1RS,2SR)-2-(4'-formyl[1,1'-biphenyl]-4-yl)-2-hydroxy-1-[3-(1,1,2,2-tetrafluoroethoxy)benzyl]ethyl]-6,7-dihydro-5H-benzo[a]cycloheptene-1-carboxamide (107 mg, 0.173 mmol) in methanol (3 ml) was added sodium borohydride (7 mg, 0.17 mmol) at room temperature and the mixture was stirred as it was for 0.5 hr. To the reaction solution was added aqueous ammonium chloride solution, and the mixture was stirred as it was for 1 hr. The recovered precipitate was washed with water and diisopropyl ether-hexane to give the objective substance.

white powder yield 85 mg, 80% mp 189–191° C.; $^1$H-NMR (CDCl$_3$-DMSO-d$_6$, 300 MHz) δ 1.95–2.01 (2H, m), 2.14–2.24 (2H, m), 2.67 (2H, t, J=5.6 Hz), 2.89 (1H, dd, J=11.0 Hz, 14.3 Hz), 2.98 (1H, dd, J=4.1 Hz, 14.6 Hz), 3.69 (1H, br s), 4.72 (2H, d, J=5.1 Hz), 4.72–4.81 (1H, m), 4.87 (1H, d, J=2.7 Hz), 5.06 (1H, t, J=3.5 Hz), 5.87 (1H, td, J=5.7 Hz, 11.6 Hz), 5.92 (1H, tt, J=2.9 Hz, 53.1 Hz), 6.20 (1H, d, J=12.3 Hz), 6.69 (1H, d, J=8.7 Hz), 6.96 (1H, d, J=7.5 Hz), 7.02–7.16 (5H, m), 7.27 (1H, t, J=7.8 Hz), 7.46 (2H, d, J=7.8 Hz), 7.56–7.63 (6H, m); IR (KBr) 3268, 1636, 1520, 1206, 1119 cm$^{-1}$; Anal. Calcd for C$_{36}$H$_{33}$F$_4$NO$_4$: C, 69.78; H, 5.37; N, 2.26. Found: C, 69.53; H, 5.24; N, 2.14.

Example 305

N-[(1RS,2SR)-2-(4-fluorophenyl)-2-hydroxy-1-[3-(1,1,2,2-tetrafluoroethoxy)benzyl]ethyl]-5,5-dimethyl-6,7-dihydro-5H-benzo[a]cycloheptene-1-carboxamide 1) 3-methyl-3-phenylbutanoic acid While stirring powdery magnesium (9.56 g, 393 mmol) and iodine (one crumb) in tetrahydrofuran (10 ml), a solution of 1-chloro-2-methyl-2-phenylpropane (26.53 g, 157.3 mmol) and 1,2-dibromoethane (29.6 g, 157 mmol) in tetrahydrofuran (100 ml) was dropwise added at a rate permitting the reaction solution to gently reflux. After completion of the dropwise addition, the mixture was stirred at 60° C. for 4 hrs. The reaction solution was cooled to −78° C., and pulverized dry ice (50 g) was carefully added. After completion of the dropwise addition, the reaction solution was gradually warmed to room temperature with stirring. The reaction solution was diluted with water, acidified with conc. hydrochloric acid, and extracted twice with ethyl acetate. The solvent of the recovered organic layer was evaporated under reduced pressure. The obtained residue was mixed with sodium hydroxide (6 g) and water (200 ml). The obtained aqueous solution was washed with diethyl ether-hexane, acidified with conc. hydrochloric acid, and extracted twice with ethyl acetate. The recovered organic layer was dried over anhydrous magnesium sulfate and the solvent was evaporated under reduced pressure to give the objective substance.

yellow liquid yield 20.83 g, 74% $^1$H-NMR (CDCl$_3$, 200 MHz) δ 1.47 (6H, s), 2.65 (2H, s), 7.17–7.40 (5H, m), 10.48 (1H, br s); IR (neat) 2967, 1699, 1634, 1260, 1167, 772, 700 cm$^{-1}$ 2) 3-methyl-3-phenyl-1-butanol To a suspension of lithium aluminum hydride (8.62 g, 228 mmol) in tetrahydrofuran (200 ml) was added dropwise a solution of 3-methyl-3-phenylbutanoic acid (20.26 g, 113.7 mmol) in tetrahydrofuran (100 ml) under ice-cooling, and the mixture was stirred overnight at room temperature. After ice-cooling the reaction solution, water (8 ml), 15% aqueous sodium hydroxide solution (8 ml) and water (20 ml) were successively added dropwise to decompose excess lithium aluminum hydride. The mixture was stirred as it was at room temperature for 2 hrs. The resulting precipitate was removed by filtration, and the precipitate was washed with ethyl acetate. The solvent of the recovered filtrate was evaporated under reduced pressure. The obtained residue was purified by silica gel column chromatography (hexane/ethyl acetate=1/1) to give the objective substance.

colorless liquid yield 18.09 g, 97% $^1$H-NMR (CDCl$_3$, 200 MHz) δ 1.00 (1H, t, J=5.3 Hz), 1.35 (6H, s), 1.95 (2H, t, J=7.4 Hz), 3.44–3.54 (2H, m), 7.14–7.40 (5H, m); IR (neat) 3333, 2965, 1497, 1445, 1057, 1022, 764, 700 cm$^{-1}$ 3) 5,5-dimethyl-5-phenyl-2-pentanoic acid To a solution of 3-methyl-3-phenyl-1-butanol (18.09 g, 110.1 mmol) and triethylamine (23.0 ml, 165 mmol) in ethyl acetate (150 ml) was dropwise added a solution of methanesulfonyl chloride (15.1 g, 132 mmol) in ethyl acetate (30 ml) under ice-cooling, and the mixture was stirred as it was for 15 min. The resulting precipitate (triethylamine hydrochloride) was removed by filtration, and the precipitate was washed with ethyl acetate. The recovered ethyl acetate solution was concentrated under reduced pressure to give a crude product of mesylate as a yellow liquid.

To a solution of diethyl malonate (22.8 g, 132 mmol) in tetrahydrofuran (100 ml) was gradually added a suspension (5.29 g, 132 mmol) of 60% sodium hydride in paraffin under ice-cooling, and the mixture was stirred as it was for 0.5 hr. A solution of the liquid obtained above in tetrahydrofuran (50 ml) was dropwise added thereto at room temperature, and the mixture was stirred at 60° C. overnight. Water was added to the reaction solution, and the mixture was stirred and extracted twice with ethyl acetate. The recovered organic layer was dried over anhydrous magnesium sulfate and the solvent was evaporated under reduced pressure. The obtained residue was purified by silica gel column chromatography (hexane/ethyl acetate=15/1–6/1) to give diethyl (3-methyl-3-phenylbutyl)malonate (31.8 g) as a colorless liquid.

The obtained liquid and conc. hydrochloric acid (50 ml) in acetic. acid (100 ml) were stirred at 100° C. overnight. The reaction solution was evaporated under reduced pressure and the obtained residue was stirred at 175° C. for 4 hrs. to give the objective substance.

yellow liquid yield 18.86 g, 83% $^1$H-NMR (CDCl$_3$, 200 MHz) 1.21–1.47 (2H, m), 1.31 (6H, s), 1.63–1.69 (2H, m), 2.25 (2H, t, J=7.3 Hz), 7.14–7.23 (1H, m), 7.29–7.35 (4H, m); IR (neat) 2963, 1709, 1279, 766, 700 cm$^{-1}$ 4) 9,9-dimethyl-6,7,8,9-tetrahydro-5H-benzo[a]cyclohepten-5-one To a solution of 5,5-dimethyl-5-phenyl-2-pentanoic acid (18.86 g, 91.43 mmol) and N,N-dimethylformamide (2 drops) in tetrahydrofuran (100 ml) was dropwise added oxalyl chloride (12.0 ml, 137 mmol) at room temperature and the mixture was stirred as it was for 0.5 hr. The solvent of the reaction mixture was evaporated under reduced pressure to give acid chloride as a yellow liquid.

While stirring a suspension of aluminum chloride (24.4 g, 183 mmol) in methylene chloride (100 ml), a solution of acid chloride obtained above in methylene chloride (400 ml) was dropwise added for 2 days. While ice-cooling the reaction solution, water was added to terminate the reaction. The methylene chloride layer of the mixture was separated, and the aqueous layer was extracted with diethyl ether. The recovered organic layer was dried over anhydrous magnesium sulfate and the solvent was-evaporated under reduced pressure. The obtained residue was purified by silica gel column chromatography (hexane/ethyl acetate=15/1–6/1) to give the objective substance.

yellow liquid yield 5.780 g, 34% $^1$H-NMR (CDCl$_3$, 200 MHz) δ 1.36 (6H, s), 1.83–2.02 (4H, m), 2.75 (2H, t, J=6.8 Hz), 7.21–7.29 (1H, m), 7.36–7.43 (3H, m); IR (neat) 2965, 1684, 1597, 1456, 1250, 764 cm$^{-1}$ 5) 9,9-dimethyl-6,7,8,9-tetrahydro-5H-benzo[a]cyclohepten-5-ol To a solution of 9,9-dimethyl-6,7,8,9-tetrahydro-5H-benzo[a]cyclohepten-5-one (5.780 g, 30.70 mmol) in methanol (40 ml) was added sodium borohydride (1.16 g, 30.7 mmol) by small portions under ice-cooling, and the mixture was stirred overnight at room temperature. The reaction solution was concentrated under reduced pressure, diluted with water, and extracted twice with ethyl acetate. The recovered organic layer was dried over anhydrous magnesium sulfate and the solvent was evaporated under reduced pressure. The obtained residue was purified by silica gel column chromatography (hexane/ethyl acetate=9/1–6/1) to give the objective substance.

yellow liquid yield 5.245 g, 90% $^1$H-NMR (CDCl$_3$, 300 MHz) δ 1.33 (3H, s), 1.45 (3H, s), 1.61–1.94 (5H, m), 1.76 (1H, d, J=4.5 Hz), 2.01–2.10 (1H, m), 5.15–5.20 (1H, m), 7.19–7.25 (2H, m), 7.39–7.44 (1H, m), 7.58–7.62 (1H, m); IR (neat) 3335, 2926, 1476, 1443, 1362, 1030, 760 cm$^{-1}$ 6) 4-bromo-9,9-dimethyl-6,7,8,9-tetrahydro-5H-benzo[a]cyclohepten-5-ol To a solution of 9,9-dimethyl-6,7,8,9-tetrahydro-5H-benzo[a]cyclohepten-5-ol (5.128 g, 26.95 mmol) and N,N,N',N'-tetramethylethylenediamine (6.89 g, 59.3 mmol) in hexane (100 ml) was dropwise added a solution (37.1 ml, 59.3 mmol) of 1.6 M n-butyllithium in hexane under ice-cooling, and the mixture was stirred at 35° C. overnight. After the reaction mixture was cooled to −78° C., 1,2-dibromotetrafluoroethane (14.0 g, 53.9 mmol) was added. The mixture was warmed to room temperature with stirring, and stirred at room temperature for 2 hrs. The reaction solution was poured into water, and extracted twice with ethyl acetate. The recovered organic layer was dried over anhydrous magnesium sulfate, and the solvent was evaporated under reduced pressure. The obtained crude product was purified by silica gel column chromatography (hexane/ethyl acetate=15/1) to give the objective substance.

yellow solid yield 4.614 g, 64% Recrystallization from hexane gave white crystals. mp 91–92° C.; $^1$H-NMR (CDCl$_3$, 300 MHz) δ 1.38 (3H, s), 1.40 (3H, s), 1.54–1.62 (1H, m), 1.71–1.88 (2H, m), 2.05–2.36 (3H, m), 2.22 (1H, d, J=4.8 Hz), 5.56–5.59 (1H, m), 7.05 (1H, t, J=8.0 Hz), 7.42–7.45 (2H, m); IR (KBr) 3354, 2955, 1447, 945, 918, 775, 747 cm$^{-1}$; Anal. Calcd for C$_{13}$H$_{17}$BrO: C, 58.01; H, 6.37. Found: C, 58.34; H, 6.51.

7) 1-bromo-5,5-dimethyl-6,7-dihydro-5H-benzo[a]cycloheptene

A solution of 4-bromo-9,9-dimethyl-6,7,8,9-tetrahydro-5H-benzo[a]cyclohepten-5-ol (4.402 g, 16.35 mmol) and p-toluenesulfonic acid monohydrate (0.31 g, 1.64 mmol) in toluene (80 ml) was heated under reflux in a reaction vessel equipped with a Dean-Stark trap under dehydrating conditions for 0.5 hr. After the reaction solution was cooled to room temperature, the solvent was evaporated under reduced pressure. The obtained crude product was purified by silica gel column chromatography (hexane) to give the objective substance.

colorless liquid yield 3.887 g, 95% $^1$H-NMR (CDCl$_3$, 200 MHz) δ 1.34 (6H, s), 1.83 (2H, t, J=6.8 Hz), 2.42–2.52 (2H, m), 6.05 (1H, td, J=4.4 Hz, 12.5 Hz), 6.91 (1H, td, J=1.9 Hz), 6.98 (1H, t, J=8.0 Hz), 7.33 (1H, d, J=7.8 Hz), 7.49 (1H, dd, J=1.3 Hz, 7.9 Hz); IR (neat) 2965, 2919, 1454, 1420, 1404, 885, 766 cm$^{-1}$ 8) 5,5-dimethyl-6,7-dihydro-5H-benzo[a]cycloheptene-1-carboxylic acid To a solution of 1-bromo-5,5-dimethyl-6,7-dihydro-5H-benzo[a]cycloheptene (3.879 g, 15.44 mmol) in diethyl ether (30 ml) was dropwise added a solution (11.6 ml, 18.5 mmol) of 1.6 M n-butyllithium in hexane at −78° C., and the mixture was stirred at room temperature for 4 hrs. After the reaction mixture was cooled to −78° C., pulverized dry ice (5 g) was added, and the mixture was warmed to room temperature with stirring. The reaction solution was diluted with water and washed with diethyl ether. The mixture was acidified with 1N hydrochloric acid, and extracted twice with ethyl acetate. The recovered organic layer was dried over anhydrous magnesium sulfate and the solvent was evaporated under reduced pressure. The obtained crude crystals were washed with hexane to give the objective substance.

white crystal yield 1.540 g, 46% mp 165–166° C.; $^1$H-NMR (CDCl$_3$, 200 MHz) δ 1.37 (6H, s), 1.89 (2H, t, J=6.6 Hz), 2.44–2.54 (2H, m), 6.08 (1H, td, J=4.4 Hz, 12.4 Hz), 6.92 (1H, td, J=2.0 Hz, 12.3 Hz), 7.22 (1H, t, J=7.9 Hz), 7.57 (1H, dd, J=1.2 Hz, 8.0 Hz), 7.66 (1H, dd, J=1.4 Hz, 7.6 Hz); IR (KBr) 3050–2650, 1688, 1426, 1306, 1279, 775, 764 cm$^{-1}$; Anal. Calcd for C$_{14}$H$_{16}$O$_2$: C, 77.75; H, 7.46. Found: C, 77.99; H, 7.34.

9) N-[(1RS,2SR)-2-(4-fluorophenyl)-2-hydroxy-1-[3-(1,1,2,2-tetrafluoroethoxy)benzyl]ethyl]-5,5-dimethyl-6,7-dihydro-5H-benzo[a]cycloheptene-1-carboxamide While stirring (1RS,2SR)-2-amino-1-(4-fluorophenyl)-3-[3-(1,1,2,2-tettafluoroethoxy)phenyl]propan-1-ol (0.379 g, 1.049 mmol), 5,5-dimethyl-6,7-dihydro-5H-benzo[a]cycloheptene-1-carboxylic acid (0.23 g, 1.05 mmol) and 1-hydroxybenzotriazole hydrate (0.16 g, 1.05 mmol) in acetonitrile (10 ml), 1-ethyl-3-(3-dimethylaminopropyl)carbodiimide hydrochloride (0.20 g, 1.05 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 0.545 g, 93% mp 101–104° C.; $^1$H-NMR (CDCl$_3$, 200 MHz) δ 1.28 (6H, s), 1.76 (2H, t, J=6.6 Hz), 2.36–2.45 (2H, m), 2.74 (1H, dd, J=10.6 Hz, 14.2 Hz), 3.00 (1H, dd, J=3.8 Hz, 14.4 Hz), 3.45 (1H, br s), 4.65–4.79 (1H, m), 5.01 (1H, d, J=3.6 Hz), 5.69 (1H, d, J=9.4 Hz), 5.74 (1H, td, J=4.2 Hz, 12.3 Hz), 5.89 (1H, tt, J=2.9 Hz, 53.3 Hz), 6.12 (1H, d, J=13.2 Hz), 6.77 (1H, d, J=6.6 Hz), 7.02–7.15 (6H, m), 7.26–7.40 (2H, m), 7.45 (2H, dd, J=5.3 Hz, 8.7 Hz); IR (KBr) 3357, 2965, 1638, 1505, 1227, 1198, 1130 cm$^{-1}$; Anal. Calcd for $C_{31}H_{30}F_5NO_3$: C, 66.54; H, 5.40; N, 2.50. Found: C, 66.30; H, 5.50; N, 2.60.

Example 306

N-[(1RS,2SR)-2-hydroxy-2-[4-(methylsulfonyl)phenyl]-1-[3-(1,1,2,2-tetrafluoroethoxy)benzyl]ethyl]-6,7-dihydro-5H-benzo[a]cycloheptene-1-carboxamide 1) ethyl 3-[4-(methylsulfonyl)phenyl]-3-oxopropanoate To a mixed solution of 4-(methylsulfonyl)acetophenone (10 g, 42.2 mmol), ethanol (0.2 ml) and diethyl carbonate (50 ml) was added sodium hydride (3.37 g, 60% in oil, 84.4 mmol) by small portions at room and the mixture was stirred temperature for 2 hrs. and at 60° C. for 1 hr. The reaction solution was cooled, 1N hydrochloric acid (30 ml) was added and the mixture was extracted with ethyl acetate (100 ml). The extract was washed with water, dried over anhydrous magnesium sulfate and evaporated under reduced pressure. The residue was purified by silica gel chromatography (hexane:ethyl acetate=3:1) to give the objective substance (3.76 g, 33%) as crystals.

mp 50–52° C. IR ν max$^{KBr}$cm$^-$:1738, 1622, 1427, 1304, 1250, 1198, 1148, 1090. Anal. Calcd for $C_{12}H_{14}O_5S$ (MW270.30) Calcd: C, 53.32; H, 5.22 Found: C, 53.46; H, 5.25. $^1$H-NMR (CDCl$_3$) δ: 1.27 (3H×1/2, t, J=7.1 Hz), 1.36 (3H×1/2, t, J=7.1 Hz), 3.08 (3H×1/2, s), 3.10 (3H×1/2, s), 4.04 (2H×1/2, q, J=7.1 Hz), 4.23 (2H×1/2, q, J=7.1 Hz), 5.76 (1H×1/2, s), 7.95–8.20 (4H, m).

2) ethyl 3-[4-(methylsulfonyl)phenyl]-3-oxo-2-[3-(1,1,2,2-tetrafluoroethoxy)benzyl]propanoate To a solution of 3-(1,1,2,2-tetrafluoroethoxy)toluene (2.84 ml, 16.8 mmol) in ethyl acetate (30 ml) were added N-bromosuccinimide (3.0 g, 16.8 mmol) and 2,2'-azobisisobutyronitrile (0.1 g) and the mixture was heated under reflux for 2 hrs. The reaction solution was concentrated under reduced pressure and diethyl ether and hexane were added. Insoluble material was removed and washed with diethyl ether. The filtrate was evaporated under reduced pressure to give 3-(1,1,2,2-tetrafluoroethoxy)-1-bromomethylbenzene. To a solution of ethyl 3-[4-(methylsulfonyl)phenyl]-3-oxopropanoate (3.5 g, 13.0 mmol) in 1,2-dimethoxyethane (30 ml) was added sodium hydride (0.52 g, 60% in oil, 13.0 mmol) under ice-cooling and the mixture was stirred for 10 min. A solution of 3-(1,1,2,2-tetrafluoroethoxy)-1-bromomethylbenzene obtained above in 1,2-dimethoxyethane (5 ml) was dropwise added, and the mixture was stirred at room temperature for 4 hrs. To the reaction solution was added water (100 ml) and the mixture was extracted with ethyl acetate (100 ml). The extract was washed with water, dried over anhydrous magnesium sulfate and evaporated under reduced pressure. The residue was purified by silica gel chromatography (hexane:ethyl acetate=3:1–2:1) to give the objective substance (3.03 g, 49%) as an oil.

IR ν max$^{Neat}$cm$^{-1}$:1738, 1694, 1319, 1302, 1196, 1154, 1121. $^1$H-NMR (CDCl$_3$) δ: 1.13 (3H, t, J=7.1 Hz), 3.07(3H, s), 3.37(2H, d, J=7.6 Hz), 4.11(2H, q, J=7.1 Hz), 4.60(1H, t, J=7.6 Hz), 5.89(1H, tt, J=53.2, 3.0 Hz), 7.00–7.35 (4H, m), 7.95–8.20(4H, m).

3) ethyl (2RS,3RS)-3-[4-(methylsulfonyl)phenyl]-3-hydroxy-2-[3-(1,1,2,2-tetrafluoroethoxy)benzyl]propanoate To a suspension of zinc chloride anhydride (1.72 g, 12.6 mmol) in diethyl ether (20 ml) was added sodium borohydride (0.95 g, 25.2 mmol) by small portions, and the mixture was stirred for 1 hr. Insoluble material was removed by filtration, and washed with diethyl ether. The filtrate was ice-cooled, and a solution of ethyl 3-[4-(methylsulfonyl)phenyl]-3-oxo-2-[3-(1,1,2,2-tetrafluoroethoxy)benzyl]propanoate (3.0 g, 6.30 mmol) in diethyl ether (10 ml) was added. The mixture was stirred at room temperature for 1 hr. After ice-cooling again, 1N hydrochloric acid was added to terminate the reaction. The obtained mixture was extracted with ethyl acetate (100 ml), washed with water, dried over anhydrous magnesium sulfate and evaporated under reduced pressure. The residue was purified by silica gel chromatography (hexane:ethyl acetate=2:1–1:1) to give the objective substance (2.60 g, 86%) as a colorless oil.

IR ν max$^{Neat}$cm$^{-1}$:1726, 1306, 1198, 1152, 1090, 774. $^1$H-NMR (CDCl$_3$) δ: 0.97(3H, t, J=7.1 Hz), 2.80–3.10(3H, m), 3.06(3H, s), 3.35(1H, d, J=2.6 Hz), 3.95(2H, d, J=7.1 Hz), 5.15–5.25(1H, m), 5.89 (1H, tt, J=53.1, 3.0 Hz), 6.85–7.10(3H, m), 7.21(1H, d, J=7.6 Hz), 7.61(2H, d, J=8.6 Hz), 7.94(2H, d, J=8.6 Hz).

4) (2RS,3RS)-3-[4-(methylsulfonyl)phenyl]-3-hydroxy-2-[3-(1,1,2,2-tetrafluoroethoxy)benzyl]propanoic acid To a solution of ethyl (2RS,3RS)-3-[4-(methylsulfonyl)phenyl]-3-hydroxy-2-[3-(1,1,2,2-tetrafluoroethoxy)benzyl]propanoate (2.55 g, 5.33 mmol) in ethanol (20 ml) was added 1N aqueous sodium hydroxide solution (10.7 ml, 10.7 mmol) and the mixture was stirred at room temperature for 1 hr. 1N Hydrochloric acid (30 ml) was added to acidify the reaction solution and the mixture was extracted with ethyl acetate (100 ml). The extract was washed with water, dried over anhydrous magnesium sulfate and evaporated under reduced pressure to give the objective substance (2.30 g, 96%) as an oil.

IR ν max$^{Neat}$cm$^{-1}$:1715, 1302, 1198, 1148, 1121, 1090, 961. $^1$H-NMR (CDCl$_3$) δ: 2.80–3.05(2H, m), 3.05 (3H, s), 3.08(1H, d, J=4.0 Hz), 5.22 (1H, d, J=4.0 Hz), 5.89(1H, tt, J=53.0, 2.8 Hz), 6.90–7.10(3H, m), 7.22(1H, d, J=8.0 Hz), 7.60(2H, d, J=8.2 Hz), 7.90(2H, d, J=8.2 Hz).

5) (4RS,5SR)-5-[4-(methylsulfonyl)phenyl]-4-[3-(1,1,2,2-tetrafluoroethoxy)benzyl]-1,3-oxazolidin-2-one To a solution of (2RS,3RS)-3-[4-(methylsulfonyl)phenyl]-3-hydroxy-2-[3-(1,1,2,2-tetrafluoroethoxy)benzyl]propanoic acid (2.20 g, 4.88 mmol) in tetrahydrofuran (20 ml) were added diphenylphosphoryl azide (1.37 ml, 6.35 mmol) and triethylamine (0.95 ml, 6.84 mmol) and the mixture was stirred at room temperature for 1 hr. After heating under reflux for 1 hr, water (100 ml) was added and the mixture was extracted, with ethyl acetate (100 ml×2). The extract was washed with saturated aqueous sodium hydrogen carbonate solution, dried over anhydrous magnesium sulfate and evaporated under reduced pressure. The residue was purified by silica gel chromatography (hexane:ethyl acetate=1:1–1:3). Hexane was added to the precipitated crystals and the mixture was filtered to give the objective substance (2.07 g, 95%).

mp 123–125° C. IR ν max$^{KBr}$cm$^-$:1740, 1588, 1314, 1152, 1115, 959. Anal. Calcd for $C_{19}H_{17}F_4NO_5S$ (MW447.40) Calcd: C, 51.01; H, 3.83; N, 3.13. Found: C, 50.87; H, 3.68; N, 2.98. $^1$H-NMR (CDCl$_3$) δ: 2.20–2.40(2H, m), 3.10(3H, s), 4.25–4.45(1H, m), 5.10(1H, s), 5.89(1H, d, J=7.8 Hz), 5.90(1H, tt, J=53.2, 3.0 Hz), 6.80–7.00(2H, m), 7.10–7.20(1H, m), 7.34(1H, d, J=8.0 Hz), 7.60(2H, d, J=8.0 Hz).

6) (1RS,2SR)-2-amino-1-[4-(methylsulfonyl)phenyl]-3-[3-(1,1,2,2-tetrafluoroethoxy)phenyl]-1-propanol To a solution of (4RS,5SR)-5-[4-(methylsulfonyl)phenyl]-4-[3-(1,1,2,2-tetrafluoroethoxy)benzyl]-1,3- oxazolidin-2-one (1.80 g, 4.02 mmol) in ethanol (20 ml) was added 8N aqueous sodium hydroxide solution (1.51 ml, 12.07 mmol) and the mixture was heated under reflux for 3 hrs. To the reaction solution was added water (100 ml) and the mixture was extracted with ethyl acetate (200 ml×2). The extract was washed with water, dried over anhydrous magnesium sulfate and evaporated under reduced pressure. The residue was crystallized from hexane-diethyl ether to give the objective substance (1.49 g, 86%).

mp 93–95° C. IR ν max$^{KBr}$cm$^{-1}$:1586, 1298, 1200, 1148, 1117, 766. Anal. Calcd for $C_{18}H_{19}F_4NO_4S.1/2H_2O$ (MW430.42) Calcd: C, 50.22; H, 4.68; N, 3.25. Found: C, 50.11; H, 4.43; N, 3.10. $^1$H-NMR (CDCl$_3$) δ: 2.37(1H, dd, J=13.6, 10.2 Hz), 2.66(1H, dd, J=13.6, 2.8 Hz), 3.08(3H, s), 3.30–3.50(1H, m), 4.81(1H, d, J=4.4 Hz), 5.90(1H, tt, J=53.1, 2.5 Hz), 6.9–7.20(3H, m), 7.30–7.40(1H, m), 7.62 (2H, d, J=8.2 Hz), 7.96(2H, d, J=8.2 Hz).

7) N-[(1RS,2SR)-2-hydroxy-2-[4-(methylsulfonyl)phenyl]-1-[3-(1,1,2,2-tetrafluoroethoxy)benzyl]ethyl]-6,7-dihydro-5H-benzo[a]cycloheptene-1-carboxamide While stirring (1RS,2SR)-2-amino-1-[4-(methylsulfonyl) phenyl]-3-[3-(1,1,2,2-tetrafluoroethoxy)phenyl]-1-propanol (0.301 g, 0.714 mmol), 6,7-dihydro-5H-benzo[a] cycloheptene-1-carboxylic acid (0.13 g, 0.71 mmol) and 1-hydroxybenzotriazole hydrate (0.11 g, 0.71 mmol) in acetonitrile (10 ml), 1-ethyl-3-(3-dimethylaminopropyl) carbodiimide hydrochloride (0.14 g, 0.71 mmol) was added and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the residue was purified by silica gel column chromatography (hexane/ethyl acetate=3/1-ethyl acetate). Crystallization from ethyl acetate-diisopropyl ether-hexane gave the objective substance.

white powder yield 0.293 g, 69% mp 154–157° C.; $^1$H-NMR (CDCl$_3$, 200 MHz) δ 1.93–2.06 (2H, m), 2.15–2.24 (2H, m), 2.67 (2H, t, J=5.6 Hz), 2.80 (1H, dd, J=11.8 Hz, 14.6 Hz), 2.95 (1H, dd, J=4.6 Hz, 14.4 Hz), 3.06 (3H, s), 4.22 (1H, d, J=4.2 Hz), 4.62–4.75 (1H, m), 5.19 (1H, t, J=3.5 Hz), 5.86 (1H, d, J=8.2 Hz), 5.89 (1H, tt, J=3.0 Hz, 53.1 Hz), 5.95 (1H, td, J=5.5 Hz, 11.8 Hz), 6.25 (1H, d, J=12.0 Hz), 6.97–7.35 (7H, m), 7.67 (2H, d, J=8.4 Hz), 7.93 (2H, d, J=8.0 Hz); IR (KBr) 3486, 3330, 2932, 1645, 1532, 1302, 1271, 1200, 1146, 1123, 768 cm$^{-1}$; Anal. Calcd for CHFNOS. 0.5H$_2$O: C, 59.99; H, 5.03; N, 2.33. Found: C, 60.02; H, 4.88; N, 2.48.

Example 307

1-(2-ethylbutyl)-N-[(1RS,2SR)-2-(4-fluorophenyl)-2-hydroxy-1-[3-(1,1,2,2-tetrafluoroethoxy)benzyl] ethyl]cyclohexanecarboxamide.

While stirring (1RS,2SR)-2-amino-1-(4-fluorophenyl)-3-[3-(1,1,2,2-tetrafluoroethoxy)phenyl]propan-1-ol (0.335 g, 0.927 mmol), 1-(2-ethylbutyl)cyclohexanecarboxylic acid (0.22 g, 1.02 mmol), 4-N,N-dimethylaminopyridine (0.11 g, 0.93 mmol) and 1-hydroxybenzotriazole hydrate (0.14 g, 0.93 mmol) in acetonitrile (10 ml), 1-ethyl-3-(3-dimethylaminopropyl)carbodiimide hydrochloride (0.18 g, 0.93 mmol) was added, and the mixture was stirred at 80° C. for 1 day. The reaction solution was diluted with ethyl acetate, washed with aqueous sodium hydrogen carbonate solution and dried over anhydrous magnesium sulfate. The solvent was evaporated under reduced pressure and the residue was purified by silica gel column chromatography (hexane/ethyl acetate=3/1–2/1) to give the objective substance.

colorless liquid yield 0.416 g, 81% $^1$H-NMR (CDCl$_3$, 300 MHz) δ 0.69–0.75 (6H, m), 0.96–1.47 (15H, m), 1.64–1.76 (2H, m), 2.67 (1H, dd, J=11.0 Hz, 14.6 Hz), 4.1 Hz, 14.6 Hz), 4.03 (1H, d, J=4.2 Hz), 4.42–4.50 (1H, m), 4.98 (1H, t, J=3.0 Hz), 5.60 (1H, d, J=7.2 Hz), 5.88 (1H, tt, J=2.9 Hz, 53.1 Hz), 6.97 (1H, s), 7.04–7.11 (4H, m), 7.28 (1H, t, J=8.0 Hz), 7.40 (2H, dd, J=5.3 Hz, 8.6 Hz); IR (neat) 3378, 2932, 2861, 1636, 1609, 1508, 1449, 1304, 1279, 1223, 1196, 1123 cm$^{-1}$

Example 308 methyl 4-[(1RS,2SR)-2-[(tert-butoxycarbonyl) amino]-1-hydroxy-3-[3-(1,1,2,2-tetrafluoroethoxy) phenyl]propyl]benzoate 1) benzyl 3-[4-(methoxycarbonyl)phenyl]-3-oxopropionate To a solution of 4-(methoxycarbonyl)benzoic acid (50.95 g, 282.8 mmol) in tetrahydrofuran (400 ml) was added 1,1'-carbonyldiimidazole (50.4 g, 311 mmol) at room temperature and the mixture was stirred as it was for 2 hrs. Dimethyl sulfoxide (200 ml), monobenzyl malonate monopotassium salt (78.8 g, 339 mmol) and sodium magnesium (16.2 g, 170 mmol) were added at room temperature, and the mixture was stirred overnight at room temperature. The reaction solution was diluted with ethyl acetate and water and acidified with conc. hydrochloric acid. The ethyl acetate layer was separated and the aqueous layer was extracted with ethyl acetate. The recovered organic layer was dried over anhydrous sodium sulfate and the solvent was evaporated under reduced pressure. The obtained crude product was purified by silica gel column chromatography (hexane/ethyl acetate=3/1–2/1) to give the objective substance.

pale-yellow solid yield 31.19 g, 35%

Recrystallization from ethyl acetate-diethyl ether-hexane gave pale-yellow crystals.

mp 74–75° C.; $^1$H-NMR (CDCl$_3$, 200 MHz) δ 3.94 (1.2H, s), 3.96 (1.8H, s), 4.07 (1.2 Hz, s), 5.20 (1.2H, s), 5.27 (0.8H, s), 5.80 (0.4H, s), 7.22–7.43 (5H, m), 7.84 (0.8H, d, J=8.8 Hz), 7.97 (1.2H, d, J=8.4 Hz), 8.08 (0.8H, d, J=8.0 Hz), 8.12 (1.2H, d, J=8.8 Hz); IR (KBr) 1721, 1281, 1211, 1204, 1109, 818, 731 cm$^{-1}$; Anal. Calcd for $C_{18}H_{16}O_5$: C, 69.22; H, 5.16. Found: C, 69.40; H, 5.24.

2) benzyl 3-[4-(methoxycarbonyl)phenyl]-3-oxo-2-[3-(1,1,2,2-tetrafluoroethoxy)benzyl]propionate 3-(1,1,2,2-Tetrafluoroethoxy)toluene (48.4 g, 233 mmol), N-bromosuccinimide (41.4 g, 233 mmol) and 2,2'-azobis (isobutyronitrile) (0.1 g) were heated under reflux in carbon tetrachloride (100 ml) for 0.5 hr. After cooling the reaction solution to room temperature, the white precipitate was removed by filtration, and the precipitate was washed with diethyl ether. The solvent of the recovered filtrate was evaporated under reduced pressure to give a crude product of 3-(1,1,2,2-tetrafluoroethoxy)benzyl bromide as a pale-yellow liquid.

To a solution of benzyl 3-[4-(methoxycarbonyl)phenyl]-3-oxopropionate (66.08 g, 211.6 mmol) in 1,2-dimethoxyethane (200 ml) was added a suspension (8.89 g, 222 mmol) of 60% sodium hydride in liquid paraffin under ice-cooling, and the mixture was stirred as it was for 0.5 hr. A solution of 3-(1,1,2,2-tetrafluoroethoxy)benzyl bromide obtained above in 1,2-dimethoxyethane (50 ml) was added at room temperature and the mixture was stirred overnight at room temperature. The reaction solution was poured into water, and extracted twice with ethyl acetate. The recovered organic layer was dried over anhydrous magnesium sulfate and the solvent was evaporated under reduced pressure. The obtained residue was purified by silica gel column chromatography (hexane/ethyl acetate=3/1–2/1) to give the objective substance.

pale-yellow liquid yield 98.99 g, 90% $^1$H-NMR (CDCl$_3$, 300 MHz) δ 3.36 (2H, d, J=7.2 Hz), 3.95 (3H, s), 4.63 (1H, t, J=7.4 Hz), 5.03 (1H, d, J=16.8 Hz), 5.08 (1H, d, J=15.9 Hz), 5.88 (1H, tt, J=2.7 Hz, 53.1 Hz), 7.01–7.49 (9H, m), 7.93 (2H, d, J=8.4 Hz), 8.05 (2H, d, J=8.1 Hz); IR (neat) 1728, 1694, 1281, 1196, 1119 cm$^{-1}$ 3) benzyl (2RS,3RS)-3-hydroxy-3-[4-(methoxycarbonyl) phenyl]-2-[3-(1,1,2,2-tetrafluoroethoxy)benzyl]propionate While stirring zinc chloride (52.0 g, 382 mmol) in diethyl ether (250 ml), sodium borohydride (28.9 g, 764 mmol) was added at room temperature and the mixture was stirred as it was for 2 hrs. Insoluble material in the mixture was removed by filtration and washed with diethyl ether to give a solution of zinc borohydride in diethyl ether. A solution of benzyl 3-[4-(methoxycarbonyl)phenyl]-3-oxo-2-[3-(1,1,2,2-tetrafluoroethoxy)benzyl]propionate (98.98 g, 190.9 mmol) in diethyl ether (100 ml) was added dropwise to the obtained solution under ice-cooling, and the mixture was stirred as it was for 1 hr. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ ethyl acetate=6/1–2/1) to give the objective substance.

colorless liquid yield 69.90 g yield 70% $^1$H-NMR (CDCl$_3$, 300 MHz) δ 2.93–3.10 (4H, m), 3.92 (3H, s), 4.83 (1H, d, J=12.3 Hz), 4.89 (1H, d, J=12.3 Hz), 5.11 (1H, t, J=3.6 Hz), 5.87 (1H, tt, J=2.9 Hz, 53.2 Hz), 6.91–7.03 (5H, m), 7.16–7.38 (4H, m), 7.44 (2H, d, J=8.4 Hz), 7.99 (2H, d, J=8.4 Hz); IR (neat) 3480, 1723, 1281, 1196, 1119 cm$^{-1}$ 4) (4RS,5SR)-5-[4-(methoxycarbonyl)phenyl]-4-[3-(1,1,2,2-tetrafluoroethoxy)benzyl]-1,3-oxazolidin-2-one A solution of benzyl (2RS,3RS)-3-hydroxy-3-[4-(methoxycarbonyl)phenyl]-2-[3-(1,1,2,2-tetrafluoroethoxy) benzyl]propionate (69.90 g, 134.3 mmol) in ethanol (200 ml) was hydrogenated overnight using 10% palladium/ carbon (containing water by 50%). (5 g) as a catalyst under normal pressure. The catalyst was removed by filtration, washed with ethanol, and the solvent of the recovered filtrate was evaporated under reduced pressure to give crude (2RS, 3RS)-3-hydroxy-3-[4-(methoxycarbonyl)phenyl]-2-[3-(1,1, 2,2-tetrafluoroethoxy)benzyl]propionic acid as a colorless foam.

The foam obtained above was dissolved in tetrahydrofuran (150 ml), and triethylamine (22.5 ml, 161 mmol) and diphenylphosphoryl azide (40.7 g, 148 mmol) were added. The mixture was stirred at 70° C. overnight. The solvent of the reaction solution was evaporated under reduced pressure and the obtained residue was purified by silica gel column chromatography (hexane/ethyl acetate=3/1-ethyl acetate). Crystallization from N,N-dimethylformamide-diisopropyl ether gave the objective substance.

white powder yield 40.33 g, 70% mp 155–158° C.; $^1$H-NMR (CDCl$_3$, 200 MHz) δ 2.17–2.34 (2H, m), 3.95 (3H, s), 4.25–4.36 (1H, m), 5.07 (1H, br s), 5.87 (1H, d, J=7.8 Hz), 5.89 (1H, tt, J=2.8 Hz, 53.0 Hz), 6.85 (1H, s), 6.94 (1H, d, J=7.8 Hz), 7.10 (1H, d, J=8.4 Hz), 7.30 (1H, t, J=8.0 Hz), 7.46 (2H, d, J=8.0 Hz), 8.11 (2H, d, J=8.4 Hz); IR (KBr) 3250, 1736, 1279, 1206, 1113 cm$^{-1}$; Anal. Calcd for C$_{20}$H$_{17}$F$_4$NO$_5$.0.5DMF: C, 55.67; H, 4.45; N, 4.53. Found: C, 55.60; H, 4.18; N, 4.83.

5) tert-butyl (4RS,5SR)-5-[4-(methoxycarbonyl)phenyl]-2-oxo-4-[3-(1,1,2,2-tetrafluoroethoxy)benzyl]-1,3-oxazolidine-3-carboxylate A solution of (4RS,5SR)-5-[4-(methoxycarbonyl) phenyl]-4-[3-(1,1,2,2-tetrafluoroethoxy)benzyl]-1,3-oxazolidin-2-one (20.04 g, 46.89 mmol), di-tert-butyl dicarbonate (12.3 g, 56.3 mmol) and 4-N,N-dimethylaminopyridine (0.57 g, 4.69 mmol) in acetonitrile (150 ml) was stirred overnight at room. temperature. The solvent of the reaction solution was evaporated under reduced pressure. The obtained residue was purified by silica gel column chromatography (hexane/ethyl acetate=3/1–2/1). Crystallization from ethyl acetate-diisopropyl ether-hexane gave the objective substance.

white crystal yield 21.14 g, 86% mp 140–141° C.; $^1$H-NMR (CDCl$_3$, 300 MHz) δ 1.52 (9H, s), 2.59 (1H, dd, J=8.9 Hz, 14.3 Hz), 2.91 (1H, dd, J=4.2 Hz, 14.1 Hz), 3.93 (3H, s), 4.81–4.88 (1H, m), 5.73 (1H, d, J=6.9 Hz), 5.85 (1H, tt, J=2.9 Hz, 53.1 Hz), 6.35 (1H, s), 6.62 (1H, d, J=7.5 Hz), 6.95 (1H, d, J=8.7 Hz), 7.06 (1H, t, J=8.0 Hz), 7.24 (2H, d, J=8.1 Hz), 7.93 (2H, d, J=8.7 Hz); IR (KBr) 17.86, 1717, 1360, 1331, 1281, 1200, 1113, 1071 cm$^{-1}$; Anal. Calcd for C$_{25}$H$_{25}$F$_4$NO$_7$: C, 56.93; H, 4.78; N, 2.66. Found: C, 57.05; H, 4.76; N, 2.71.

6) methyl 4-[(1RS,2SR)-2-[(tert-butoxycarbonyl)amino]-1-hydroxy-3-[3-(1,1,2,2-tetrafluoroethoxy)phenyl]propyl] benzoate To a solution of tert-butyl (4RS,5SR)-5-[4-(methoxycarbonyl)phenyl]-2-oxo-4-[3-(1,1,2,2-tetrafluoroethoxy)benzyl]-1,3-oxazolidine-3-carboxylate (20.82 g, 39.47 mmol) in methanol (50 ml)-tetrahydrofuran (100 ml) was added a solution of sodium hydroxide (1.66 g, 41.4 mmol) in methanol (20 ml) under ice-cooling and the mixture was stirred at room temperature for 10 min. The reaction solution was diluted with ethyl acetate, washed with water, dried over anhydrous magnesium sulfate and passed through silica gel. The solvent was evaporated under reduced pressure. The obtained residue was crystallized from ethyl acetate-hexane to give the objective substance.

white crystal yield 16.05 g, 81% mp 148–150° C.; $^1$H-NMR (CDCl$_3$, 300 MHz) δ 1.36 (9H, s), 2.73 (2H, d, J=6.0 Hz), 3.45 (1H, br s), 3.93 (3H, s), 4.05–4.11 (1H, m), 4.61 (1H, br d, J=8.4 Hz), 5.03 (1H, br s), 5.89 (1H, tt, J=2.9 Hz, 53.1 Hz), 6.94 (1H, s), 7.00 (1H, d, J=7.5 Hz), 7.05 (1H, dd, J=1.4 Hz, 8.3 Hz), 7.26 (1H, t, J=8.0 Hz), 7.49 (2H, d, J=8.1 Hz), 8.05 (2H, d, J=8.4 Hz); IR (KBr) 3330, 3206, 1721, 1678, 1551, 1300, 1283, 1202, 1175, 1113, 1098 cm$^{-1}$; Anal. Calcd for C$_{24}$H$_{27}$F$_4$NO$_6$: C, 57.48; H, 5.43; N, 2.79. Found: C, 57.43; H, 5.71; N, 2.62.

Example 309 methyl 4-[(1RS,2SR)-2-[(6,7-dihydro-5H-benzo[a] cyclohepten-1-ylcarbonyl)amino]-1-hydroxy-3-[3-(1,1,2,2-tetrafluoroethoxy)phenyl]propyl]benzoate 1) methyl 4-[(1RS,2SR)-2-amino-1-hydroxy-3-[3-(1,1,2,2-tetrafluoroethoxy)phenyl]propyl]benzoate A solution of methyl 4-[(1RS,2SR)-2-[(tert-butoxycarbonyl)amino]-1-hydroxy-3-[3-(1,1,2,2-tetrafluoroethoxy)phenyl]propyl]benzoate (15.72 g, 31.35 mmol) and conc. hydrochloric acid (10 ml) in methanol (150 ml) was stirred at 60° C. for 1 hr. The reaction solution was concentrated under reduced pressure, diluted with water, alkalified with potassium carbonate, and extracted twice with ethyl acetate. The recovered organic layer was dried over anhydrous sodium sulfate and the solvent was evaporated under reduced pressure. The residue was crystallized from diisopropyl ether-hexane to give the objective substance.

white crystal yield 12.27 g, 98% mp 100–101° C.; $^1$H-NMR (CDCl$_3$, 300 MHz) δ 2.37 (1H, dd, J=10.5 Hz, 13.8 Hz), 2.72 (1H, dd, J=3.2 Hz, 13.7 Hz), 3.34 (1H, ddd, J=3.4 Hz, 4.3 Hz, 10.4 Hz), 3.93 (3H, s), 4.77 (1H, d, J=4.5

Hz), 5.89 (1H, tt, J=2.8 Hz, 53.3 Hz), 6.97 (1H, s), 7.02–7.09 (2H, m), 7.29 (1H, t, J=7.8 Hz), 7.48 (2H, d, J=8.1 Hz), 8.06 (2H, d, J=8.4 Hz); IR (KBr) 3.150–2850, 1725, 1281, 1198, 1111 cm$^{-1}$; Anal. Calcd for $C_{19}H_{19}F_4NO_4$: C, 56.86; H, 4.77; N, 3.49. Found: C, 56.68; H, 4.92; N, 3.26.

2) methyl 4-[(1RS,2SR)-2-[(6,7-dihydro-5H-benzo[a]cyclohepten-1-ylcarbonyl)amino]-1-hydroxy-3-[3-(1,1,2,2-tetrafluoroethoxy)phenyl]propyl]benzoate While stirring methyl 4-[(1RS,2SR)-2-amino-1-hydroxy-3-[3-(1,1,2,2-tetrafluoroethoxy)phenyl]propyl]benzoate (10.80 g, 26.91 mmol), 6,7-dihydro-5H-benzo[a]cycloheptene-1-carboxylic acid (5.06 g, 26.9 mmol) and 1-hydroxybenzotriazole hydrate (4.12 g, 26.9 mmol) in acetonitrile (10 ml), 1-ethyl-3-(3-dimethylaminopropyl)carbodiimide hydrochloride (5.16 g, 26.9 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether to give the objective substance.

white crystal yield 13.24 g, 86% mp 137–138° C.; $^1$H-NMR (CDCl$_3$, 300 MHz) δ 1.98–2.04 (2H, m), 2.16–2.22 (2H, m), 2.66 (2H, t, J=5.9 Hz), 2.80 (1H, dd, J=10.8 Hz, 14.4 Hz), 2.95 (1H, dd, J=4.4 Hz, 14.6 Hz), 3.86 (1H, d, J=4.2 Hz), 3.93 (3H, s), 4.66–4.72 (1H, m), 5.15 (1H, t, J=3.8 Hz), 5.79 (1H, d, J=8.4 Hz), 5.88 (1H, tt, J=2.9 Hz, 53.1 Hz), 5.92 (1H, td, J=5.7 Hz, 11.4 Hz), 6.23 (1H, d, J=11.4 Hz), 6.97–7.11 (5H, m), 7.16 (1H, dd, J=1.1 Hz, 7.4 Hz), 7.29 (1H, t, J=8.0 Hz), 7.55 (2H, d, J=8.4 Hz), 8.06 (2H, d, J=8.1 Hz); IR (Kr) 3256, 2934, 1719, 1636, 1528, 1439, 1285, 1194, 1115, 775 cm$^{-1}$; Anal. Calcd for $C_{31}H_{29}F_4NO_5$: C, 65.14; H, 5.11; N, 2.45. Found: C, 64.98; H, 5.39; N, 2.35.

Example 310

4-[(1RS,2SR)-2-[(6,7-dihydro-5H-benzo[a]cyclohepten-1-ylcarbonyl)amino]-1-hydroxy-3-[3-(1,1,2,2-tetrafluoroethoxy)phenyl]propyl]benzoic acid To a solution of methyl 4-[(1RS,2SR)-2-[(6,7-dihydro-5H-benzo[a]cyclohepten-1-ylcarbonyl)amino]-1-hydroxy-3-[3-(1,1,2,2-tetrafluoroethoxy)phenyl]propyl]benzoate (12.93 g, 22.62 mmol) in methanol (40 ml)-tetrahydrofuran (50 ml) was added 1N aqueous sodium hydroxide solution (67.9 ml, 67.9 mmol) and the mixture was stirred overnight at room temperature. The reaction solution was concentrated, diluted with water, acidified with dilute hydrochloric acid, and extracted twice with ethyl acetate. The recovered organic layer was dried over anhydrous sodium sulfate and the solvent was evaporated under reduced pressure. The obtained solid was washed with ethyl acetate-diisopropyl ether to give the objective substance.

white powder yield 10.52 g, 83% mp 210–211° C.; $^1$H-NMR (CDCl$_3$-DMSO-d$_6$, 300 MHz) δ 1.92–2.00 (2H, m), 2.18–2.26 (2H, m), 2.65–2.69 (2H, m), 2.82–2.93 (2H, m), 4.64–4.74 (1H, m), 5.03 (1H, d, J=3.6 Hz), 5.31 (1H, br s), 5.85 (1H, td, J=5.3 Hz, 11.8 Hz), 5.98 (1H, tt, J=3.0 Hz, 53.1 Hz), 6.14 (1H, d, J=11.7 Hz), 6.89 (1H, dd, J=1.5 Hz, 7.8 Hz), 7.01–7.13 (5H, m), 7.26 (1H, t, J=8.1 Hz), 7.61 (2H, d, J=8.4 Hz), 8.05 (2H, d, J=8.1 Hz); IR (KBr) 3268, 3020–2860, 1686, 1640, 1279, 1202, 1123 cm$^{-1}$; Anal. Calcd for $C_{30}H_{27}F_4NO_5$: C, 64.63; H, 4.88; N, 2.51. Found: C, 64.50; H, 4.80; N, 2.39.

Example 311

N-[(1RS,2SR)-2-[4-(aminocarbonyl)phenyl]-2-hydroxy-1-[3-(1,1,2,2-tetrafluoroethoxy)benzyl]ethyl]-6,7-dihydro-5H-benzo[a]cycloheptene-1-carboxamide While stirring 4-[(1RS,2SR)-2-[(6,7-dihydro-5H-benzo[a]cyclohepten-1-ylcarbonyl)amino]-1-hydroxy-3-[3-(1,1,2,2-tetrafluoroethoxy)phenyl]propyl]benzoic acid (0.284 g, 0.509 mmol) and 1-hydroxybenzotriazole hydrate (86 mg, 0.56 mmol) in acetonitrile (10 ml)-N,N-dimethylformamide (2 ml), 1-ethyl-3-(3-dimethylaminopropyl)carbodiimide hydrochloride (0.11 g, 0.56 mmol) was added and the mixture was stirred at room temperature for 0.5 hr. Thereto were added ammonium chloride (54 mg, 1.02 mmol) and triethylamine (0.21 ml, 1.53 mmol) and the mixture was stirred at room temperature for 1 hr. To the reaction solution was added aqueous sodium hydrogen carbonate solution, and the mixture was stirred at room temperature for 0.5 hr. The recovered precipitate was washed with water and diisopropyl ether-hexane to give the objective substance.

white powder yield 0.227 g, 80% mp 197–199° C.; $^1$H-NMR (CDCl$_3$-DMSO-d$_6$, 300 MHz) δ 1.91–1.99 (2H, m), 2.20–2.25 (2H, m), 2.67 (2H, t, J=5.6 Hz), 2.81–2.95 (2H, m), 4.64–4.73 (1H, m), 5.01 (1H, d, J=4.2 Hz), 5.35 (1H, br s), 5.84 (1H, td, J=5.1 Hz, 11.7 Hz), 6.00 (1H, tt, J=2.9 Hz, 53.0 Hz), 6.11 (1H, d, J=12.0 Hz), 6.29 (1H, br s), 6.87 (1H, dd, J=1.5 Hz, 7.5 Hz), 7.00–7.14 (5H, m), 7.22–7.29 (2H, m), 7.61 (2H, d, J=8.1 Hz), 7.91 (2H, d, J=8.4 Hz); IR (KBr) 3310, 1636, 1615, 1524, 1206, 1121, 777 cm$^{-1}$; Anal. Calcd for $C_{30}H_{28}F_4N_2O_4 \cdot 0.5H_2O$: C, 63.71; H, 5.17; N, 4.95. Found: C, 63.68; H, 5.30; N, 4.88.

Example 312

N-[(1RS,2SR)-2-[4-[(dimethylamino)carbonyl]phenyl]-2-hydroxy-1-[3-(1,1,2,2-tetrafluoroethoxy)benzyl]ethyl]-6,7-dihydro-5H-benzo[a]cycloheptene-1-carboxamide Using dimethylamine hydrochloride as amine and in the same manner as in Example 311, the objective substance (0.244 g, 82%) was obtained as a white powder.

mp 165–166° C.; $^1$H-NMR (CDCl$_3$, 300 MHz) δ 1.96–2.05 (2H, m), 2.16–2.22 (2H, m), 2.66 (2H, t, J=5.9 Hz), 2.75 (1H, dd, J=10.8 Hz, 14.7 Hz), 2.93 (1H, dd, J=3.9 Hz, 15.6 Hz), 2.97 (3H, s), 3.11 (3H, s), 4.41 (1H, d, J=4.2 Hz), 4.67–4.74 (1H, m), 5.03 (1H, t, J=3.8 Hz), 5.86 (1H, d, J=8.4 Hz), 5.89 (1H, tt, J=2.7 Hz, 53.1 Hz), 5.94 (1H, td, J=5.6 Hz, 11.3 Hz), 6.26 (1H, d, J=12.0 Hz), 6.99–7.17 (6H, m), 7.29 (1H, t, J=8.1 Hz), 7.38 (2H, d, J=8.1 Hz), 7.45 (2H, d, J=8.1 Hz); IR (KBr) 3326, 2942, 1638, 1620, 1518, 1194, 1115 cm$^{-1}$; Anal. Calcd for $C_{32}H_{32}F_4N_2O_4$: C, 65.74; H, 5.52; N, 4.79. Found: C, 65.58; H, 5.63; N, 4.81.

Example 313

N-[(1RS,2SR)-2-hydroxy-2-[4-(piperidinocarbonyl)phenyl]-1-[3-(1,1,2,2-tetrafluoroethoxy)benzyl]ethyl]-6,7-dihydro-5H-benzo[a]cycloheptene-1-carboxamide Using piperidine as amine and in the same manner as in Example 311, the objective substance (0.275 g, 86%) was obtained as white crystals.

mp 176–177° C.; $^1$H-NMR (CDCl$_3$, 300 MHz) δ 1.51 (2H, br s), 1.68 (4H, br s), 1.96–2.04 (2H, m), 2.16–2.22 (2H, m), 2.66 (2H, t, J=5.9 Hz), 2.75 (1H, dd, J=10.7 Hz, 14.6 Hz), 2.95 (1H, dd, J=3.9 Hz, 14.7 Hz), 3.32 (2H, br s), 3.70 (2H, br s), 4.36 (1H, d, J=3.6 Hz), 4.67–4.75 (1H, m), 5.03 (1H, t, J=3.8 Hz), 5.82 (1H, d, J=8.1 Hz), 5.89 (1H, tt, J=2.9 Hz, 53.2 Hz), 5.94 (1H, td, J=5.7 Hz, 11.3 Hz), 6.25 (1H, d, J=11.7 Hz), 6.99–7.17 (6H, m), 7.29 (1H, t, J=7.8 Hz), 7.36 (2H, d, J=8.1 Hz), 7.45 (2H, d, J=8.1 Hz); IR (KBr) 3430, 3328, 2940, 2863, 1640, 1516, 1437, 1277, 1209, 1123, 768 cm$^{-1}$; Anal. Calcd for $C_{35}H_{36}F_4N_2O_4$: C, 67.30; H, 5.81; N, 4.48. Found: C, 67.20; H, 5.78; N, 4.47.

Example 314

N-[(1RS,2SR)-2-[4-(anilinocarbonyl)phenyl]-2-hydroxy-1-[3-(1,1,2,2-tetrafluoroethoxy)benzyl]ethyl]-6,7-dihydro-5H-benzo[a]cycloheptene-1-carboxamide Using aniline as amine and in the same manner as in Example 311, the objective substance (0.275 g, 85%) was obtained as a white powder.

mp 205–206° C.; $^1$H-NMR (CDCl$_3$-DMSO-d$_6$, 300 MHz) δ 1.94–2.00 (2H, m), 2.19–2.25 (2H, m), 2.67 (2H, t, J=5.4 Hz), 2.88 (2H, d, J=7.5 Hz), 4.68–4.76 (1H, m), 5.06 (1H, t, J=3.5 Hz), 5.25 (1H, d, J=3.6 Hz), 5.88 (1H, td, J=5.6 Hz, 11.4 Hz), 5.95 (1H, tt, J=2.9 Hz, 53.0 Hz), 6.17 (1H, d, J=11.4 Hz), 6.92 (1H, dd, J=1.1 Hz, 7.4 Hz), 7.01–7.13 (7H, m), 7.27 (1H, t, J=8.3 Hz), 7.35 (2H, t, J=7.8 Hz), 7.64 (2H, d, J=8.4 Hz), 7.76 (2H, d, J=7.8 Hz), 7.99 (2H, d, J=8.4 Hz), 9.31 (1H, s); IR (KBr) 3297, 2938, 1647, 1532, 1507, 1443, 1323, 1200, 1121, 752, 694 cm$^{-1}$; Anal. Calcd for C$_{36}$H$_{32}$F$_4$N$_2$O$_4$: C, 68.35; H, 5.10; N, 4.43. Found: C, 68.10; H, 5.07; N, 4.42.

Example 315

N-[(1RS,2SR)-2-hydroxy-2-[4-[(isopropylamino)carbonyl]phenyl]-1-[3-(1,1,2,2-tetrafluoroethoxy)benzyl]ethyl]-6,7-dihydro-5H-benzo[a]cycloheptene-1-carboxamide Using isopropylamine as amine and in the same manner as in Example 311, the objective substance (0.258 g, 84%) was obtained as a white powder.

mp 215–217° C.; $^1$H-NMR (CDCl$_3$-DMSO-d$_6$, 300 MHz) δ 1.27 (6H, d, J=6.6 Hz), 1.93–2.02 (2H, m), 2.19–2.25 (2H, m), 2.67 (2H, t, J=5.1 Hz), 2.85 (2H, d, J=7.5 Hz), 4.25–4.32 (1H, m), 4.67–4.75 (1H, m), 5.06 (2H, s), 5.88 (1H, td, J=5.7 Hz, 11.4 Hz), 5.92 (1H, tt, J=3.0 Hz, 53.0 Hz), 6.18 (1H, d, J=12.0 Hz), 6.46 (1H, d, J=7.8 Hz), 6.80 (1H, d, J=9.0 Hz), 6.94 (1H, dd, J=1.2 Hz, 7.5 Hz), 7.01–7.14 (5H, m), 7.26 (1H, t, J=7.8 Hz), 7.58 (2H, d, J=8.4 Hz), 7.80 (2H, d, J=8.4 Hz); IR (KBr) 3295, 2971, 2930, 1638, 1537, 1213, 1123 cm$^{-1}$; Anal. Calcd for C$_{33}$H$_{34}$F$_4$N$_2$O$_4$: C, 66.21; H, 5.72; N, 4.68. Found: C, 66.00; H, 5.50; N, 4.65.

Example 316

N-[(1RS,2SR)-2-[4-[(benzylamino)carbonyl]phenyl]-2-hydroxy-1-[3-(1,1,2,2-tetrafluoroethoxy)benzyl]ethyl]-6,7-dihydro-5H-benzo[a]cycloheptene-1-carboxamide Using benzylamine as amine and in the same manner as in Example 311, the objective substance (0.297 g, 90%) was obtained as a white powder.

mp 216–217° C.; $^1$H-NMR (CDCl$_3$-DMSO-d$_6$, 300 MHz) δ 1.91–1.99 (2H, m), 2.19–2.24 (2H, m), 2.67 (2H, t, J=5.9 Hz), 2.86–2.89 (2H, m), 4.62 (2H, d, J=6.0 Hz), 4.65–4.71 (1H, m), 5.01 (1H, t, J=3.8 Hz), 5.30 (1H, d, J=3.3 Hz), 5.84 (1H, td, J=5.5 Hz, 11.3 Hz), 5.99 (1H, tt, J=2.8 Hz, 52.9 Hz), 6.11 (1H, d, J=12.0 Hz), 6.88 (1H, dd, J=1.2 Hz, 7.5 Hz), 7.00–7.05 (3H, m), 7.11 (2H, d, J=9.9 Hz), 7.17–7.39 (7H, m), 7.60 (2H, d, J=8.1 Hz), 7.93 (2H, d, J=8.1 Hz), 8.05 (1H, t, J=5.6 Hz); IR (KBr) 3297, 2932, 1638, 1615, 1537, 1200, 1130, 698 cm$^{-1}$; Anal. Calcd for C$_{37}$H$_{34}$F$_4$N$_2$O$_4$: C, 68.72; H, 5.30; N, 4.33. Found: C, 68.59; H, 5.06; N, 4.22.

Example 317

N-[(1RS,2SR)-2-[4-[(butylamino)carbonyl]phenyl]-2-hydroxy-1-[3-(1,1,2,2-tetrafluoroethoxy)benzyl]ethyl]-6,7-dihydro-5H-benzo[a]cycloheptene-1-carboxamide Using butylamine as amine and in the same manner as in Example 311, the objective substance (0.284 g, 91%) was obtained as a white powder.

mp 207–208° C.; $^1$H-NMR (CDCl$_3$-DMSO-d$_6$, 300 MHz) δ 0.96 (3H, t, J=7.4 Hz), 1.35–1.48 (2H, m), 1.56–1.66 (2H, m), 1.94–2.01 (2H, m), 2.20–2.26 (2H, m), 2.68 (2H, t, J=6.0 Hz), 2.87 (2H, d, J=8.4 Hz), 3.42 (2H, q, J=6.7 Hz), 4.64–4.72 (1H, m), 5.03 (1H, t, J=3.8 Hz), 5.23 (1H, d, J=3.6 Hz), 5.86 (1H, td, J=5.2 Hz, 12.1 Hz), 5.97 (1H, tt, J=2.9 Hz, 53.0 Hz), 6.14 (1H, d, J=11.7 Hz), 6.90 (1H, dd, J=1.2 Hz, 7.5 Hz), 7.01–7.17 (7H, m), 7.26 (1H, t, J=8.3 Hz), 7.59 (2H, d, J=7.8 Hz), 7.84 (2H, d, J=8.4 Hz); IR (KBr) 3308, 2934, 1640, 1612, 1537, 1201, 1128, 696. cm$^{-1}$; Anal. Calcd for C$_{34}$H$_{36}$F$_4$N$_2$O$_4$: C, 66.66; H, 5.92; N, 4.57. Found: C, 66.44; H, 5.8.8; N, 4.40.

Example 318

N-[(1RS,2SR)-2-(4-fluorophenyl)-2-hydroxy-1-[3-(1,1,2,2-tetrafluoroethoxy)benzyl]ethyl]-4-methyl-6,7-dihydro-5H-benzo[a]cycloheptene-1-carboxamide 1) ethyl (E)-5-(2-methylphenyl)-3-oxo-4-pentenoate To a solution of 2-methylcinnamic acid (50.71 g, 312.7 mmol) in tetrahydrofuran (500 ml) was added 1,1'-carbonyldiimidazole (55.8 g, 344 mmol) at room temperature, and the mixture was stirred as it was for 1 hr. To the mixture were added monoethyl malonate monopotassium salt (58.5 g, 344 mmol) and magnesium chloride (16.4 g, 172 mmol) at room temperature, and the mixture was stirred at 60° C. overnight. The reaction solution was diluted with ethyl acetate and water and acidified with conc. hydrochloric acid. The ethyl acetate layer was separated, and the aqueous layer was extracted with ethyl acetate. The recovered organic layer was dried over anhydrous sodium sulfate and the solvent was evaporated under reduced pressure. The obtained crude product was purified by silica gel column chromatography (hexane/ethyl acetate=9/1–6/1) to give the objective substance.

yellow liquid yield 37.24 g, 51% $^1$H-NMR (CDCl$_3$, 200 MHz) δ 1.29 (1.2H, t, J=7.1 Hz), 1.32 (1.8H, t, J=7.1 Hz), 2.43 (1.8H, s), 2.45 (1.2H, s), 3.70 (0.8H, s), 4.23 (0.8H, q, J=7.2 Hz), 4.24 (1.2H, q, J=7.1 Hz), 5.17 (0.6H, s), 6.36 (0.6H, dd, J=1.4 Hz, 15.8 Hz), 6.74 (0.4H, d, J=15.8 Hz), 7.15–7.35 (3H, m), 7.52–7.61 (1H, m), 7.70 (0.6H, d, J=15.8 Hz), 7.93 (0.4H, d, J=16.2 Hz); IR (neat) 2980, 1740, 1636, 1595, 1420, 1236, 1148, 1038, 754 cm$^{-1}$ 2) ethyl 5-(2-methylphenyl)pentanoate To a solution of ethyl (E)-5-(2-methylphenyl)-3-oxo-4-pentenoate (37.24 g, 160.3 mmol) in ethanol (100 ml) was added sodium borohydride (3.03 g, 80.2 mmol) by small portions under ice-cooling, and the mixture was stirred as it was for 10 min. The reaction solution was diluted with water, and extracted twice with ethyl acetate. The recovered organic layer was dried over anhydrous sodium sulfate and the solvent was evaporated under reduced pressure to give a crude product of ethyl (E)-3-hydroxy-5-(2-methylphenyl)penta-4-enoate as a yellow liquid.

To a solution of the liquid obtained above and triethylamine (33.5 ml, 240 mmol) in ethyl acetate (180 ml) was dropwise added methanesulfonyl chloride (22.0 g, 192 mmol) under ice-cooling, and the mixture was stirred as it was for 15 min. The resulting precipitate (triethylamine hydrochloride) was removed by filtration, and washed with ethyl acetate. The recovered ethyl acetate solution was concentrated under reduced pressure. The obtained residue was dissolved in tetrahydrofuran (200 ml) and 1,8-diazabicyclo[5.4.0]-7-undecene (28.8 ml, 192 mmol) was added. The mixture was stirred at room temperature for 0.5 hr. The reaction solution was poured into water, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=15/1–9/1) to give ethyl 5-(2-methylphenyl)penta-2,4-dienoate (a mixture of (2E,4E) form and (2Z,4E) form) as a yellow liquid.

A solution of the liquid obtained above in ethanol (40 ml) was hydrogenated at normal temperature and under normal pressure using 10% palladium/carbon. (containing water by 50%) (1.5 g) as a catalyst until the starting material disappeared. The catalyst was removed by filtration and the solvent was evaporated under reduced pressure. The obtained crude product was purified by silica gel column chromatography (hexane/ethyl acetate=15/1–6/1) to give the objective substance.

colorless liquid yield 13.92 g, 39% $^1$H-NMR (CDCl$_3$, 200 MHz) δ 1.25. (3H, t, J=7.2 Hz), 1.52–1.80 (4H, m), 2.30 (3H, s), 2.34 (2H, t, J=7.0 Hz), 2.61 (2H, t, J=7.6 Hz), 4.12 (2H, q, J=7.2 Hz), 7.12 (4H, s); IR (neat) 2938, 1736, 1181, 745 cm$^{-1}$ 3) 5-(2-methylphenyl)pentanoic acid A mixture of ethyl 5-(2-methylphenyl)pentanoate (13.92 g, 63.18 mmol), sodium hydroxide (5.05 g, 126 mmol), water (30 ml), methanol (50 ml) and tetrahydrofuran (50 ml) was stirred overnight at room temperature. The reaction solution was concentrated, diluted with water, and washed with diethyl ether. The obtained aqueous solution was acidified with conc. hydrochloric acid, and extracted twice with ethyl acetate. The recovered organic layer was dried over anhydrous sodium sulfate and the solvent was evaporated under reduced pressure to give the objective substance.

white crystal yield 12.04 g, 99% mp 57–58° C.; $^1$H-NMR (CDCl$_3$, 200 MHz) δ 1.54–1.82 (4H, m), 2.30 (3H, s), 2.40 (2H, t, J=7.1 Hz), 2.62 (2H, t, J=7.6 Hz), 7.12 (4H, s); IR (KBr) 3070–2520, 1698, 1462, 1437, 1406, 1329, 1289, 1260, 1208, 941, 739 cm$^{-1}$ 4) 1-methyl-6,7,8,9-tetrahydro-5H-benzo[a]cyclohepten-5-one To a solution of 5-(2-methylphenyl)pentanoic acid (11.92 g, 62.00 mmol) and N,N-dimethylformamide (2 drops) in tetrahydrofuran (50 ml) was dropwise added oxalyl chloride (8.11 ml, 93.0 mmol) at room temperature, and the mixture was stirred as it was for 0.5 hr. The solvent of the reaction mixture was evaporated under reduced pressure to give acid chloride as a yellow liquid.

While stirring a suspension of aluminum chloride (16.5 g, 124 mmol) in methylene chloride (100 ml), a solution of acid chloride obtained above in methylene chloride (250 ml) was dropwise added over 1 day. While ice-cooling the reaction solution, water was added to terminate the reaction. The methylene chloride layer of the mixture was separated, and the aqueous layer was extracted with diethyl ether. The recovered organic layer was dried over anhydrous magnesium sulfate and the solvent was evaporated under reduced pressure. The obtained residue was purified by silica gel column chromatography (hexane/ethyl acetate=9/1) to give the objective substance.

pale-yellow solid yield 10.14 g, 94%

Recrystallization from hexane gave white crystals.

mp 65–66° C.; $^1$H-NMR (CDCl$_3$, 200 MHz) δ 1.69–1.91 (4H, m), 2.37 (3H, s), 2.67 (2H, t, J=5.9 Hz), 2.88 (2H, t, J=6.2 Hz), 7.17 (1H, t, J=7.5 Hz), 7.30 (1H, d, J=6.6 Hz), 7.44 (1H, d, J=7.4 Hz); IR (KBr) 2940, 1671, 1586, 1460, 1271, 793 cm$^{-1}$; Anal. Calcd for C$_{12}$H$_{14}$O: C, 82.72; H, 8.10. Found: C, 82.68; H, 8.15.

5) 1-methyl-6,7,8,9-tetrahydro-5H-benzo[a]cyclohepten-5-ol

To a solution of 1-methyl-6,7,8,9-tetrahydro-5H-benzo[a]cyclohepten-5-one (9.797 g, 56.23 mmol) in methanol (40 ml) was added sodium borohydride (2.13 g, 56.2 mmol) by small portions under ice-cooling and the mixture was stirred at room temperature for 1 hr. The reaction solution was diluted with water, and extracted twice with ethyl acetate. The recovered organic layer was dried over anhydrous magnesium sulfate and the solvent was evaporated under-reduced pressure. The obtained residue was purified by silica gel column chromatography (hexane/ethyl acetate=6/1). Crystallization from ethyl acetate-hexane gave the objective substance.

white crystal yield 8.345 g, 84% mp 109–110° C.; $^1$H-NMR (CDCl$_3$, 300 MHz) δ 1.30–1.42 (1H, m), 1.66–1.86 (4H, m), 1.91–2.05 (2H, m), 2.32 (3H, s), 2.57 (1H, dd, J=11.1 Hz, 12.9 Hz), 3.08 (1H, ddd, J=1.6 Hz, 7.9 Hz, 14.5 Hz), 5.01 (1H, dd, J=3.6 Hz, 9.0 Hz), 7.06 (1H, dd, J=1.7 Hz, 7.7 Hz), 7.11 (1H, t, J=7.4 Hz), 7.32 (1H, d, J=6.9 Hz); IR (KBr) 3293, 3189, 2928, 1466, 1439, 1096, 1049, 781, 747 cm$^{-1}$; Anal. Calcd for C$_{12}$H$_{16}$O: C, 81.77; H, 9.15. Found: C, 81.73; H, 8.93.

6) 4-bromo-1-methyl-6,7,8,9-tetrahydro-5H-benzo[a]cyclohepten-5-ol

To a solution of 1-methyl-6,7,8,9-tetrahydro-5H-benzo[a]cyclohepten-5-ol (8.193 g, 46.48 mmol) and N,N,N',N'-tetramethylethylenediamine (11.9 g, 102 mmol) in hexane (100 ml) was added a solution of 1.6 M n-butyllithium in hexane (63.9 ml, 102 mmol) under ice-cooling, and the mixture was stirred at 35° C. as it was overnight. After the reaction mixture was cooled to −78° C., 1,2-dibromotetrafluoroethane (24.2 g, 93.0 mmol) was added, and the mixture was warmed to room temperature with stirring. The mixture was stirred at room temperature for 2 hrs. The reaction solution was poured into water, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=15/1) to give the objective substance.

yellow solid yield 6.439 g, 54%

Recrystallization from hexane gave white crystals.

mp 74–75° C.; $^1$H-NMR (CDCl$_3$, 200 MHz) δ 1.25–1.44 (1H, m), 1.57–2.23 (6H, m), 2.26 (3H, s), 2.88 (1H, ddd, J=1.7 Hz, 6.8 Hz, 14.3 Hz), 3.26 (1H, dt, J=1.8 Hz, 13.0 Hz), 5.65–5.71 (1H, m), 6.90 (1H, d, J=8.2 Hz), 7.26 (1H, d, J=8.0 Hz); IR (KBr) 3326, 2930, 1456, 1090, 1049, 995, 930, 856, 806 cm$^{-1}$; Anal. Calcd for C$_{12}$H$_{15}$BrO: C, 56.49; H, 5.93. Found: C, 56.48; H, 5.83.

7) 1-bromo-4-methyl-6,7-dihydro-5H-benzo[a]cycloheptene

A solution of 4-bromo-1-methyl-6,7,8,9-tetrahydro-5H-benzo[a]cyclohepten-5-ol (6.213 g, 24.35 mmol) and p-toluenesulfonic acid monohydrate (0.46 g, 2.44 mmol) in toluene (100 ml) was heated under reflux in a reaction vessel equipped with a Dean-Stark trap under dehydrating conditions for 0.5 hr. After the reaction solution was cooled to room temperature, the solvent was evaporated under reduced pressure. The obtained crude product was purified by silica gel column chromatography (hexane) to give the objective substance.

colorless liquid yield 2.485 g, 43% $^1$H-NMR (CDCl$_3$, 300 MHz) δ 1.99–2.13 (4H, m), 2.31 (3H, s), 2.6.4 (2H, t, J=6.3 Hz), 6.22 (1H, td, J=6.2 Hz, 11.2 Hz), 6.71 (1H, d, J=11.1 Hz), 6.90 (1H, d, J=8.1 Hz), 7.31 (1H, d, J=8.1 Hz); IR (neat) 2930, 1451, 1127, 802, 779 cm$^{-1}$ 8) 4-methyl-6,7-dihydro-5H-benzo[a]cycloheptene-1-carboxylic acid To a solution of 1-bromo-4-methyl-6,7-dihydro-5H-benzo[a]cycloheptene (2.485 g, 10.48 mmol) in diethyl ether (30 ml) was dropwise added a solution of 1.6 M n-butyllithium in hexane (9.82 ml, 15.7 mmol) at −78° C., and the mixture was stirred at room temperature for 4 hrs. After the reaction mixture was cooled to −78° C., pulverized dry ice (5 g) was added, and the mixture was warmed to room temperature with stirring. The reaction solution was diluted with water and washed with diethyl ether. The obtained aqueous solution was acidified with 1N hydrochloric acid, and extracted twice with ethyl acetate. The recovered organic layer was dried over anhydrous magnesium sulfate and the solvent was evaporated under reduced pressure. The obtained crude crystals were washed with hexane to give the objective substance.

white crystal yield 1.080 g, 51%. mp 152–153° C.; $^1$H-NMR (CDCl$_3$, 200 MHz) δ 1.91–2.18 (4H, m), 2.43 (3H, s), 2.66 (2H, t, J=6.6 Hz), 6.26 (1H, td, J=6.6 Hz, 11.0 Hz), 7.13 (1H, d, J=7.8 Hz), 7.21 (1H, d, J=11.0 Hz), 7.85 (1H, d, J=8.2 Hz); IR (KBr) 3044–2510, 1686, 1300, 1271, 1258 cm$^{-1}$; Anal. Calcd for C$_{13}$H$_{14}$O$_2$: C, 77.20; H, 6.98. Found: C, 76.98; H, 7.03.

9) N-[(1RS,2SR)-2-(4-fluorophenyl)-2-hydroxy-1-[3-(1,1,2,2-tetrafluoroethoxy)benzyl]ethyl]-4-methyl-6,7-dihydro-5H-benzo[a]cycloheptene-1-carboxamide While stirring (1RS,2SR)-2-amino-1-(4-fluorophenyl)-3-[3-(1,1,2,2-tetrafluoroethoxy)phenyl]propan-1-ol (0.366 g, 1.013 mmol), 4-methyl-6,7-dihydro-5H-benzo[a]cycloheptene-1-carboxylic acid (0.20 g, 1.01 mmol) and 1-hydroxybenzotriazole hydrate (0.16 g, 1.01 mmol) in acetonitrile (10 ml), 1-ethyl-3-(3-dimethylaminopropyl)carbodiimide hydrochloride (0.19 g, 1.01 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white crystal yield 0.461 g yield 83% mp 177–178° C.; $^1$H-NMR (CDCl$_3$, 300 MHz) δ 1.95–2.07 (4H, m), 2.33 (3H, s), 2.59 (2H, t, J=5.7 Hz), 2.78 (1H, dd, J=10.7 Hz, 14.6 Hz), 2.98 (1H, dd, J=4.2 Hz, 14.4 Hz), 3.90 (1H; d, J=3.9 Hz), 4.58–4.67 (1H, m), 5.03 (1H, t, J=3.6 Hz), 5.74 (1H, d, J=7.5 Hz), 5.89 (1H, tt, J=2.8 Hz, 53.0 Hz), 6.02 (1H, td, J=6.2 Hz, 11.3 Hz), 6.29 (1H, d, J=11.1 Hz), 6.96–7.11 (7H, m), 7.29 (1H, t, J=7.8 Hz), 7.42 (2H, dd, J=5.4 Hz, 8.7 Hz); IR (KBr) 3279, 1638, 1512, 1200, 1127 cm$^{-1}$; Anal. Calcd for C$_{30}$H$_{28}$F$_5$NO$_3$: C, 66.05; H, 5.17; N, 2.57. Found: C, 66.03; H, 5.21; N, 2.52.

Example 319 tert-butyl N-[(1RS,2SR)-2-(4-fluorophenyl)-2-hydroxy-1-[[3-(1,1,2,2-tetrafluoroethoxy)isooxazol-5-yl]methyl]ethyl]carbamate 1) ethyl 3-(4-fluorophenyl)-3-oxo-2-[[3-(1,1,2,2-tetrafluoroethoxy)isoxazol-5-yl]methyl]propionate To a solution of methyl 3-(1,1,2,2-tetrafluoroethoxy)-5-isoxazole carboxylate (1.975 g, 8.124 mmol) in methanol (30 ml) was added sodium borohydride (0.40 g, 10.6 mmol) by small portions under ice-cooling, and the mixture was stirred overnight at room temperature. To the reaction solution was added dilute hydrochloric acid, the mixture was stirred at room temperature for 1 hr and washed three times with ethyl acetate. The recovered organic layer was dried over anhydrous magnesium sulfate, and passed through silica gel. The solvent was evaporated under reduced pressure to give a crude product of [3-(1,1,2,2-tetrafluoroethoxy)isoxazol-5-yl]methanol as a yellow liquid (1.72 g).

To a solution of the liquid obtained above and triethylamine (1.70 ml, 12.2 mmol) in ethyl acetate (40 ml) was dropwise added methanesulfonyl chloride (0.75 ml, 9.75 mmol) under ice-cooling, and the mixture was stirred as it was for 10 min. The resulting precipitate was removed by filtration, and the precipitate was washed with ethyl acetate. The solvent of the recovered filtrate was evaporated under reduced pressure to give a crude product of methanesulfonic acid ester as a yellow liquid.

To a solution of ethyl (4-fluorobenzoyl)acetate (1.88 g, 8.94 mmol) in 1,2-dimethoxyethane (30 ml) was added a suspension (0.36 g, 8.94 mmol) of 60% sodium hydride in liquid paraffin under ice-cooling, and the mixture was stirred as it was for 0.5 hr. A solution of methanesulfonic acid ester obtained above in 1,2-dimethoxyethane (10 ml) was added at room temperature, and the mixture was stirred at 70° C. for 4 hrs. The reaction solution was poured into water, and extracted twice with ethyl acetate. The recovered organic layer was dried over anhydrous magnesium sulfate and the solvent was evaporated under reduced pressure. The obtained residue was purified by silica gel column chromatography (hexane/ethyl acetate=9/1–6/1) to give the objective substance.

pale-yellow liquid yield 2.418 g, 73% $^1$H-NMR (CDCl$_3$, 200 MHz) δ 1.16 (3H, t, J=7.2 Hz), 3.46 (2H, d, J=7.4 Hz), 4.16 (2H, q, J=7.1 Hz), 4.77 (1H, t, J=7.4 Hz), 6.00 (1H, tt, J=3.3 Hz, 52.7 Hz), 6.07 (1H, s), 7.18 (2H, t, J=8.7 Hz), 8.06 (2H, dd, J=5.3 Hz, 8.9 Hz); IR (neat) 1738, 1690, 1601, 1447, 1283, 1233, 1182, 1159 cm$^{-1}$ 2) ethyl (2RS,3SR)-3-(4-fluorophenyl)-3-hydroxy-2-[[3-(1,1,2,2-tetrafluoroethoxy)isoxazol-5-yl]methyl]propionate While stirring zinc chloride (6.35 g, 46.6 mmol) in diethyl ether (100 ml), sodium borohydride (3.53 g, 93.2 mmol) was added at room temperature, and the mixture was stirred as it was for 2 hrs. The insoluble material of the mixture was removed by filtration and washed with diethyl ether to give a solution of zinc borohydride in diethyl ether. A solution of ethyl 3-(4-fluorophenyl)-3-oxo-2-[[3-(1,1,2,2-tetrafluoroethoxy)isoxazol-5-yl]methyl]propionate (2.372 g, 5.824 mmol) in diethyl ether (30 ml) was added to the obtained solution under ice-cooling, and the mixture was heated under reflux for 4 hrs. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 1.402 g, 59% $^1$H-NMR (CDCl$_3$, 300 MHz) δ 1.11 (3H, t, J=7.1 Hz), 2.72 (1H, d, J=3.0 Hz), 2.98–3.26 (3H, m), 4.02–4.11 (2H, m), 5.11 (1H, dd, J=3.3 Hz, 5.1 Hz), 5.93 (1H, s), 6.00 (1H, tt, J=3.3 Hz, 52.7 Hz), 7.06 (2H, t, J=8.7 Hz), 7.36 (2H, dd, J=5.3 Hz, 8.6 Hz); IR (neat) 3465, 1728, 1609, 1512, 1449, 1225, 1184, 1146 cm$^{-1}$ 3) (4RS,5SR)-5-(4-fluorophenyl)-4-[[3-(1,1,2,2-tetrafluoroethoxy)isoxazol-5-yl]methyl]-1,3-oxazolidin-2-one To a solution of ethyl (2RS,3SR)-3-(4-fluorophenyl)-3-hydroxy-2-[[3-(1,1,2,2-tetrafluoroethoxy)isoxazol-5-yl]methyl]propionate (1.402 g, 3.425 mmol) in methanol (30 ml) was added 1N aqueous sodium hydroxide solution (6.85 ml, 6.85 mmol), and the mixture was stirred at room temperature for 2 hrs. The reaction solution was concentrated and diluted with water. The reaction solution was acidified with 1N hydrochloric acid, and extracted twice with ethyl acetate. The recovered organic layer was dried over anhydrous sodium sulfate and the solvent was evaporated under reduced pressure to give a crude product of (2RS,3SR)-3-(4-fluorophenyl)-3-hydroxy-2-[[3-(1,1,2,2-tetrafluoroethoxy)isoxazol-5-yl]methyl]propionic acid as a colorless liquid.

To a solution of the liquid obtained above in tetrahydrofuran (30 ml) were added triethylamine (0.57 ml, 4.11 mmol) and diphenylphosphoryl azide (1.04 g, 3.77 mmol), and the mixture was stirred at 70° C. overnight. The solvent of the reaction solution was evaporated under reduced pressure, and the obtained crude product was purified by silica gel column chromatography (hexane/ethyl acetate=3/1–1/1). Crystallization from diethyl ether-hexane gave the objective substance.

white crystal yield 0.921 g, 71% mp 124–125° C.; $^1$H-NMR (CDCl$_3$, 300 MHz) δ 2.48 (1H, dd, J=5.3 Hz, 15.5 Hz), 2.59 (1H, dd, J=8.4 Hz, 15.6 Hz), 4.45–4.53 (1H, m), 5.52 (1H, br s), 5.83 (1H, s), 6.00 (1H, tt, J=3.2 Hz, 52.7 Hz), 7.12 (2H, t, J=8.6 Hz), 7.32 (2H, dd, J=5.3 Hz, 8.3 Hz); IR (KBr) 3156, 1755, 1447, 1235, 1209, 1150, 1119 cm$^{-1}$; Anal. Calcd for C$_{15}$H$_{11}$F$_5$N$_2$O$_4$: C, 47.63; H, 2.93; N, 7.41. Found: C, 47.60; H, 2.98; N, 7.21.

4) tert-butyl (4RS,5SR)-5-(4-fluorophenyl)-2-oxo-4-[[3-(1,1,2,2-tetrafluoroethoxy)isoxazol-5-yl]methyl]-1,3-oxazolidine-3-carboxylate A solution of (4RS,5SR)-5-(4-fluorophenyl)-4-[[3-(1,1,2,2-tetrafluoroethoxy)isoxazol-5-yl]methyl]-1,3-oxazolidin-2-one (0.866 g, 2.289 mmol), di-tert-butyl dicarbonate (0.60 g, 2.75 mmol) and 4-N,N-dimethylaminopyridine (28 mg, 0.23 mmol) in acetonitrile (10 ml) was stirred overnight at room temperature. The solvent of the reaction solution was evaporated under reduced pressure, and the obtained crude product was purified by silica gel column chromatography (ethyl acetate). Crystallization from ethyl acetate-diisopropyl ether-hexane gave the objective substance.

white crystal yield 0.785 g, 72% mp 177–178° C.; $^1$H-NMR (CDCl$_3$, 300 MHz) δ 1.55 (9H, s), 2.81 (1H, dd, J=9.3 Hz, 15.6 Hz), 3.01 (1H, ddd, J=1.0 Hz, 4.6 Hz, 15.4 Hz), 4.96–5.03 (1H, m), 5.36 (1H, s), 5.72 (1H, d, J=7.2 Hz), 5.97 (1H, tt, J=3.3 Hz, 52.8 Hz), 7.04 (2H, t, J=8.6 Hz), 7.23 (2H, dd, J=5.3 Hz, 8.6 Hz); IR.(KBr) 1802, 1372, 1298, 1163 cm$^{-1}$; Anal. Calcd for C$_{20}$H$_{19}$F$_5$N$_2$O$_6$: C, 50.22; H, 4.00; N, 5.86. Found: C, 50.16; H, 3.79; N, 5.88.

5) tert-butyl N-[(1RS,2SR)-2-(4-fluorophenyl)-2-hydroxy-1-[[3-(1,1,2,2-tetrafluoroethoxy)isoxazol-5-yl]methyl]ethyl]carbamate To a solution of tert-butyl (4RS,5SR)-5-(4-fluorophenyl)-2-oxo-4-[[3-(1,1,2,2-tetrafluoroethoxy)isoxazol-5-yl]methyl]-1,3-oxazolidine-3-carboxylate (0.735 g, 1.536 mmol) in tetrahydrofuran (10 ml) was added a solution of sodium hydroxide (61 mg; 1.54 mmol) in methanol (2 ml) under ice-cooling, and the mixture was stirred at room temperature for 10 min. The reaction solution was diluted with-ethyl acetate, washed with water, dried over anhydrous magnesium sulfate and passed through silica gel. The solvent was evaporated under reduced pressure and the obtained residue was crystallized from diisopropyl ether-hexane to give the objective substance.

white crystal yield 0.626 g 90% mp 114–115° C.; $^1$H-NMR (CDCl$_3$, 300 MHz) δ 1.39 (9H, s), 2.69 (1H, br d, J=2.7 Hz), 2.86 (1H, dd, J=4.2 Hz, 15.3 Hz), 3.01 (1H, dd, J=10.7 Hz, 15.5 Hz), 4.09–4.18 (1H, m), 4.89 (1H, br d, J=7.5 Hz), 4.94 (1H, br s), 6.00 (1H, tt, J=3.4 Hz, 52.7 Hz), 6.03 (1H, s), 7.08 (2H, t, J=8.7 Hz), 7.38 (2H, dd, J=5.1 Hz, 8.4 Hz); IR (KBr) 3360, 1680, 1530, 1449, 1190, 1125 cm$^{-1}$; Anal. Calcd for C$_{19}$H$_{21}$F$_5$N$_2$O$_5$: C, 50.45; H, 4.68; N, 6.19. Found: C, 50.32; H, 4.58; N, 6.25.

Example 320

N-[(1RS,2SR)-2-(4-fluorophenyl)-2-hydroxy-1-[[3-(1,1,2,2-tetrafluoroethoxy)isoxazol-5-yl]methyl]ethyl]-6,7-dihydro-5H-benzo[a]cycloheptene-1-carboxamide A solution of tert-butyl N-[(1RS,2SR)-2-(4-fluorophenyl)-2-hydroxy-1-[[3-(1,1,2,2-tetrafluoroethoxy)isoxazol-5-yl]methyl]ethyl]carbamate (0.291 g, 0.643 mmol) and conc. hydrochloric acid. (0.2 ml) in methanol (5 ml) was stirred at 60° C. for 0.5 hr. The reaction solution was diluted with water, alkalified with potassium carbonate, and extracted twice with ethyl acetate. The recovered organic layer was dried over anhydrous sodium sulfate and the solvent was evaporated under reduced pressure to give a crude product of (1RS,2SR)-2-amino-1-(4-fluorophenyl)-3-[3-(1,1,2,2-tetrafluoroethoxy)isoxazol-5-yl]propan-1-ol as a white solid (0.227 g).

While stirring the solid obtained above, 6,7-dihydro-5H-benzo[a]cycloheptene-1-carboxylic acid (0.13 g, 0.71 mmol) and 1-hydroxybenzotriazole hydrate (0.10 g, 0.71 mmol) in acetonitrile (10 ml), 1-ethyl-3-(3-dimethylaminopropyl)carbodiimide hydrochloride (0.14 g, 0.71 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=3/1–1/1). Crystallization from diisopropyl ether-hexane gave the objective substance.

white powder yield 0.251 g, 75% mp 127–128° C.; $^1$H-NMR (CDCl$_3$, 300 MHz) δ 1.98–2.06 (2H, m), 2.20–2.26 (2H, m), 2.67–2.71 (2H, m), 3.01 (1H, dd, J=4.2 Hz, 15.9 Hz), 3.12 (1H, d, J=3.9 Hz), 3.16 (1H, dd, J=10.2 Hz, 16.2 Hz), 4.61–4.70 (1H, m), 5.02 (1H, t, J=3.9 Hz), 6.00 (1H, tt, J=3.3 Hz, 52.5 Hz), 6.03 (1H, td, J=5.6 Hz, 11.7 Hz), 6.11 (1H, s), 6.15 (1H, d, J=8.7 Hz), 6.33 (1H, d, J=11.7 Hz), 7.05–7.14 (4H, m), 7.16–7.22 (1H, m), 7.42 (2H, dd, J=5.3 Hz, 8.9 Hz); IR (KBr) 3289, 1640, 1514, 1449, 1188, 1146 cm$^{-1}$; Anal. Calcd for C$_{26}$H$_{23}$F$_5$N$_2$O$_4$: C, 59.77; H, 4.44; N, 5.36. Found: C, 59.82; H, 4.48; N, 5.34.

Example 321

N-[(1RS,2SR)-2-[4-[(tert-butoxycarbonyl)amino]phenyl]-2-hydroxy-1-[3-(1,1,2,2-tetrafluoroethoxy)benzyl]ethyl]-6,7-dihydro-5H-benzo[a]cycloheptene-1-carboxamide To a solution of 4-[(1RS,2SR)-2-[(6,7-dihydro-5H-benzo[a]cyclohepten-1-ylcarbonyl)amino]-1-hydroxy-3-[3-(1,1,2,2-tetrafluoroethoxy)phenyl]propyl]benzoic acid (3.283 g, 5.888 mmol) in tert-butyl alcohol (60 ml) were added triethylamine (1.23 ml, 8.83 mmol) and diphenylphosphoryl azide (1.78 g, 6.48 mmol), and the mixture was stirred at 80° C. for 2 days. The solvent was evaporated under reduced pressure, and the obtained crude product was purified by silica gel column chromatography (hexane-hexane/ethyl acetate=1/1). Crystallization from diisopropyl ether-hexane gave the objective substance.

white powder yield 2.714 g, 73% mp 153–156° C.; $^1$H-NMR (CDCl$_3$, 300 MHz) δ 1.52 (9H, s), 1.95–2.03 (2H, m), 2.16–2.23 (2H, m), 2.66 (2H, t, J=5.7 Hz), 2.75 (1H, dd, J=10.5 Hz, 14.4 Hz), 2.99 (1H, dd, J=3.6 Hz, 14.4 Hz), 3.57 (1H, d, J=3.6 Hz), 4.65–4.75 (1H, m), 5.00 (1H, t, J=3.6 Hz), 5.74 (1H, d, J=8.4 Hz), 5.89 (1H, tt, J=2.9 Hz, 53.0 Hz), 5.91 (1H, td, J=5.6 Hz, 11.4 Hz), 6.22 (1H, d, J=12.0 Hz), 6.52 (1H, s), 6.95–7.16 (6H, m), 7.30 (1H, t, J=7.8 Hz), 7.38 (4H, s); IR (KBr) 3314, 1694, 1676, 1636, 1532, 1314, 1211, 1161, 1115 cm$^{-1}$; Anal. Calcd for $C_{34}H_{36}F_4N_2O_5$, DMF: C, 63.33; H, 6.18; N, 5.99. Found: C, 63.30; H, 6.07; N, 5.84.

Example 322

N-[(1RS,2SR)-2-(4-aminophenyl)-2-hydroxy-1-[3-(1,1,2,2-tetrafluoroethoxy)benzyl]ethyl]-6,7-dihydro-5H-benzo[a]cycloheptene-1-carboxamide A solution of N-[(1RS,2SR)-2-[4-[(tert-butoxycarbonyl)amino]phenyl]-2-hydroxy-1-[3-(1,1,2,2-tetrafluoroethoxy)benzyl]ethyl]-6,7-dihydro-5H-benzo[a]cycloheptene-1-carboxamide (1.547 g, 2.461 mmol) and conc. hydrochloric acid (0.5 ml) in methanol (10 ml) was stirred at 60° C. for 2 hrs. The reaction solution was diluted with water, alkalified with potassium carbonate, and extracted twice with ethyl acetate. The recovered organic layer was dried over anhydrous sodium sulfate. The solvent was evaporated under reduced pressure and the obtained residue was purified by silica gel column chromatography (hexane/ethyl acetate=1/1–1/3). Crystallization from diisopropyl ether-hexane gave the objective substance.

pale-brown powder yield 0.150 g, 12%. mp 153–155° C.; $^1$H-NMR (CDCl$_3$, 300 MHz) δ 1.94–2.03 (2H, m), 2.15–2.23 (2H, m), 2.66 (2H, t, J=5.9 Hz), 2.77 (1H, dd, J=10.2 Hz, 14.7 Hz), 3.03 (1H, dd, J=4.2 Hz, 14.4 Hz), 3.19 (1H, d, J=3.9 Hz), 3.70 (2H, br s), 4.65–4.74 (1H, m), 4.90 (1H, t, J=3.8 Hz), 5.71 (1H, d, J=8.4 Hz), 5.89 (1H, tt, J=2.9 Hz, 53.1 Hz), 5.91 (1H, td, J=5.3 Hz, 11.7 Hz), 6.20 (1H, d, J=11.7 Hz), 6.69 (2H, d, J=8.1 Hz), 6.97 (1H, dd, J=1.4 Hz, 7.7 Hz), 7.03–7.15 (5H, m), 7.21–7.32 (3H, m); IR (KBr) 3270, 1642, 1518, 1275, 1198, 1125 cm$^{-1}$; Anal. Calcd for $C_{29}H_{28}F_4N_2O_3$: C, 65.90; H, 5.34; N, 5.30. Found: C, 65.68; H, 5.15; N, 5.02.

Example 323

N-[(1RS,2SR)-2-(4-fluorophenyl)-2-hydroxy-1-(3-isopropylbenzyl)ethyl]-6,7-dihydro-5H-benzo[a]cycloheptene-1-carboxamide 1) 3-isopropylbenzyl alcohol While stirring of powdery magnesium (3.33 g, 137 mmol) and iodine (one crumb) in tetrahydrofuran (10 ml), a solution of 3-isopropylbromobenzene (10.91 g, 54.80 mmol) and 1,2-dibromoethane (10.3 g, 54.8 mmol) in tetrahydrofuran (100 ml) was dropwise added slowly. After completion of the dropwise addition, the mixture was stirred at 70° C. for 1 hr. The reaction solution was cooled to −78° C., and pulverized dry ice (10 g) was carefully added. The reaction solution was gradually warmed to room temperature with stirring. The reaction solution was diluted with water, acidified with conc. hydrochloric acid, and extracted twice with ethyl acetate. The solvent of the recovered organic layer was evaporated under reduced pressure to give a crude product of 3-isopropylbenzoic acid as a yellow liquid.

To a suspension of lithium aluminum hydride (3.12 g, 82.2 mmol) in tetrahydrofuran (100 ml) was dropwise added a solution of the liquid obtained above in tetrahydrofuran (50 ml) under ice-cooling, and the mixture was stirred at room temperature for 1 hr. After ice-cooling the reaction solution, water (3 ml), 15% aqueous sodium hydroxide solution (3 ml) and water (7.5 ml) were successively added dropwise to decompose excess lithium aluminum hydride. The mixture was stirred as it was at room temperature for 1 hr. The resulting precipitate was removed by filtration and washed with ethyl acetate. The solvent of the recovered filtrate was evaporated under reduced pressure and the obtained residue was purified by silica gel column chromatography (hexane/ethyl acetate=6/1–3/1) to give the objective substance.

yellow liquid yield 5.610 g, 68% $^1$H-NMR (CDCl$_3$, 200 MHz) δ 1.26 (6H, d, J=7.0 Hz), 1.64 (1H, t, J=5.9 Hz), 2.85–2.99 (1H, m), 4.68 (2H, d, J=5.6 Hz), 7.15–7.34 (4H, m); IR (neat) 3320, 2961, 1464, 1017, 791, 704 cm$^{-1}$ 2) ethyl 3-(4-fluorophenyl)-2-(3-isopropylbenzyl)-3-oxopropionate To a solution of 3-isopropylbenzyl alcohol (2.595 g, 17.27 mmol) and triethylamine (3.61 ml, 25.9 mmol) in ethyl acetate (30 ml) was dropwise added a solution of methanesulfonyl chloride (2.37 g, 20.7 mmol) in ethyl acetate (10 ml) under ice-cooling, and the mixture was stirred as it was for 10 min. The resulting precipitate was removed by filtration and washed with ethyl acetate. The solvent of the recovered filtrate was evaporated under reduced pressure to give a crude product of methanesulfonic acid ester as a yellow liquid.

To a solution of ethyl (4-fluorobenzoyl)acetate (3.63 g, 17.3 mmol) in 1,2-dimethoxyethane (30 ml) was added a suspension (0.69 g, 17.3 mmol) of 60% sodium hydride in liquid paraffin under ice-cooling, and the mixture was stirred as it was for 0.5 hr. A solution of methanesulfonic acid ester obtained above in 1,2-dimethoxyethane (10 ml) was added at room temperature, and the mixture was stirred at 60° C. overnight. The reaction solution was poured into water, and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=9/1–6/1) to give the objective substance.

pale-yellow liquid yield 5.108 g, 86% $^1$H-NMR (CDCl$_3$, 200 MHz) δ 1.13 (3H, t, J=7.2 Hz), 1.18 (6H, d, J=7.0 Hz), 2.76–2.90 (1H, m), 3.30 (1H, d, J=7.4 Hz), 3.31 (1H, d, J=7.4 Hz), 4.11 (2H, q, J=7.1 Hz), 4.57 (1H, t, J=7.3 Hz), 7.00–7.22 (6H, m), 7.96 (2H, dd, J=5.4 Hz, 9.0 Hz); IR (neat) 2961, 1738, 1688, 1599, 1507, 1271, 1233, 1159 cm$^{-1}$ 3) ethyl (2RS,3RS)-3-(4-fluorophenyl)-3-hydroxy-2-(3-isopropylbenzyl)propionate While stirring zinc chloride (3.99 g, 29.3 mmol) in diethyl ether (30 ml), sodium borohydride (2.22 g, 58.6 mmol) was added at room temperature, and the mixture was stirred as it was for 2 hrs. The insoluble material in the mixture was removed by filtration and washed with diethyl ether to give a solution of zinc borohydride in diethyl ether. To the obtained solution was added a solution of ethyl 3-(4-fluorophenyl)-2-(3-isopropylbenzyl)-3-oxopropionate (5.016 g, 14.65 mmol) in diethyl ether (30 ml) under ice-cooling, and the mixture was stirred at 0° C. for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=6/1–3/1) to give the objective substance.

colorless liquid yield 4.166 g, 83% $^1$H-NMR (CDCl$_3$, 300 MHz) δ 0.91 (3H, t, J=7.2 Hz), 1.20 (6H, d, J=7.2 Hz), 2.78–2.87 (1H, m), 2.91–3.00 (4H, m), 3.87 (2H, q, J=7.2 Hz), 5.01 (1H, t, J=3.3 Hz), 6.89–6.93 (2H, m), 7.02–7.08

(3H, m), 7.16 (1H, t, J=7.5 Hz), 7.38 (2H, dd, J=5.7 Hz, 8.7 Hz); IR (neat) 3466, 2961, 1726, 1713, 1605, 1510, 1375, 1225, 1179, 1157, 1032, 837 cm$^{-1}$ 4) (2RS,3RS)-3-(4-fluorophenyl)-3-hydroxy-2-(3-isopropylbenzyl)propionic acid A mixture of ethyl (2RS,3RS)-3-(4-fluorophenyl)-3-hydroxy-2-(3-isopropylbenzyl)propionate (4.166 g, 12.10 mmol), sodium hydroxide (0.97 g, 24.2 mmol), methanol (30 ml), water (30 ml) and tetrahydrofuran (30 ml) was stirred at 60° C. for 6 hrs. The reaction solution was concentrated, diluted with water, acidified with 1N hydrochloric acid, and extracted twice with ethyl acetate. The recovered organic layer was dried over anhydrous sodium sulfate and the solvent was evaporated under reduced pressure. The residue was crystallized from diisopropyl ether-hexane to give the objective substance.

white crystal yield 3.208 g, 84% mp 102–104° C.; $^1$H-NMR (CDCl$_3$, 300 MHz) δ 1.19 (6H, d, J=6.9 Hz), 2.77–2.86 (1H, m), 2.89–3.07 (3H, m), 5.04 (1H, d, J=4.8 Hz), 6.88–6.91 (2H, m), 7.01–7.07 (3H, m), 7.15 (1H, t, J=7.5 Hz), 7.36 (2H, dd, J=5.6 Hz, 8.6 Hz); IR (KBr) 3341, 3100–2550, 1694, 1514, 1229, 1020, 837, 785, 702 cm$^{-1}$; Anal. Calcd for C$_{19}$H$_{21}$FO$_3$: C, 72.13; H, 6.69. Found: C, 72.02; H, 6.64.

5) (4RS,5SR)-5-(4-fluorophenyl)-4-(3-isopropylbenzyl)-1,3-oxazolidin-2-one

To a solution of (2RS,3RS)-3-(4-fluorophenyl)-3-hydroxy-2-(3-isopropylbenzyl)propionic acid (2.982 g, 9.426 mmol) in tetrahydrofuran (50 ml) were added triethylamine (1.58 ml, 11.3 mmol) and diphenylphosphoryl azide (2.85 g, 10.4 mmol), and the mixture was stirred at 65° C. overnight. The solvent of the reaction solution was evaporated under reduced pressure, and the obtained crude product was purified by silica gel column chromatography (hexane/ethyl acetate=3/1–1/1). Crystallization from diisopropyl ether-hexane gave the objective substance.

white crystal yield 2.680 g, 91% mp 153–154° C.; $^1$H-NMR (CDCl$_3$, 300 MHz) δ 1.21 (6H, d, J=6.9 Hz), 2.19 (1H, dd, J=10.8 Hz, 13.8 Hz), 2.28 (1H, dd, J=4.1 Hz, 13.7 Hz), 2.77–2.91 (1H, m), 4.24 (1H, ddd, J=3.7 Hz, 8.2 Hz, 11.2 Hz), 4.94 (1H, br s), 5.79 (1H, d, J=8.1 Hz), 6.84–6.87 (2H, m), 7.09–7.24 (4H, m), 7.38 (2H, dd, J=5.3 Hz, 8.6 Hz); IR (KBr) 3306, 2969, 1759, 1723, 1701, 1510, 1424, 1225, 1078, 1007 cm$^{-1}$; Anal. Calcd for C$_{19}$H$_{20}$FNO$_2$: C, 72.82; H, 6.43; N, 4.47. Found: C, 72.81; H, 6.60; N, 4.41.

6) (1RS,2SR)-2-amino-1-(4-fluorophenyl)-3-(3-isopropylphenyl)propan-1-ol (4RS,5SR)-5-(4-fluorophenyl)-4-(3-isopropylbenzyl)-1,3-oxazolidin-2-one (2.453 g, 7.828 mmol) and sodium hydroxide (1.25 g, 31.3 mmol) were heated under reflux in ethanol (25 ml)-water (1.5 ml) for 3 hrs. The reaction solution was diluted with water, and extracted twice with ethyl acetate. The recovered organic layer was dried over anhydrous sodium sulfate, passed through APS-silica gel, and the solvent was evaporated under reduced pressure. The residue was crystallized from diisopropyl ether-hexane to give the objective substance.

white crystal yield 1.999 g, 89% mp 88–90° C.; $^1$H-NMR (CDCl$_3$, 300 MHz) δ 1.23 (6H, d, J=6.6 Hz), 2.30 (1H, dd, J=10.4 Hz, 13.4 Hz), 2.77 (1H, dd, J=3.3 Hz, 13.5 Hz), 2.82–2.91 (1H, m), 3.29 (1H, ddd, J=3.3 Hz, 5.0 Hz, 10.4 Hz), 4.67 (1H, d, J=5.1 Hz), 6.94–6.98 (2H, m), 7.05–7.11 (3H, m), 7.22 (1H, t, J=7.4 Hz), 7.38 (2H, dd, J=5.6 Hz, 8.6 Hz); IR (KBr) 3150–2780, 1508, 1215, 1046, 980, 818, 710 cm$^{-1}$; Anal. Calcd for C$_{18}$H$_{22}$FNO: C, 75.23; H, 7.72; N, 4.87. Found: C, 75.33; H, 7.82; N, 4.78.

7) N-[(1RS,2SR)-2-(4-fluorophenyl)-2-hydroxy-1-(3-isopropylbenzyl)ethyl]-6,7-dihydro-5H-benzo[a]cycloheptene-1-carboxamide While stirring (1RS,2SR)-2-amino-1-(4-fluorophenyl)-3-(3-isopropylphenyl)propan-1-ol (0.250 g, 0.870 mmol), 6,7-dihydro-5H-benzo[a]cycloheptene-1-carboxylic acid (0.16 g, 0.87 mmol) and 1-hydroxybenzotriazole hydrate (0.13 g, 0.87 mmol) in acetonitrile (10 ml), 1-ethyl-3-(3-dimethylaminopropyl)carbodiimide hydrochloride (0.17 g, 0.87 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 0.330 g, 83% mp 165–167° C.; $^1$H-NMR (CDCl$_3$, 300 MHz) δ 1.20 (6H, d, J=6.9 Hz), 1.94–2.03 (2H, m), 2.14–2.22 (2H, m), 2.66 (2H, t, J=5.9 Hz), 2.68 (1H, dd, J=11.1 Hz, 14.1 Hz), 2.80–2.89 (1H, m), 2.99 (1H, dd, J=4.5 Hz, 14.1 Hz), 4.18 (1H, d, J=3.9 Hz), 4.64–4.73 (1H, m), 5.02 (1H, t, J=3.6 Hz), 5.65 (1H, d, J=7.5 Hz), 5.91 (1H, td, J=5.6 Hz, 11.2 Hz), 6.24 (1H, d, J=11.7 Hz), 6.89 (1H, dd, J=0.9 Hz, 7.2 Hz), 6.98–7.15 (7H, m), 7.22 (1H, t, J=8.0 Hz), 7.43 (2H, dd, J=5.4 Hz, 8.7 Hz); IR (KBr) 3281, 2961, 2942, 1640, 1510, 1225, 833, 704 cm$^{-1}$; Anal. Calcd for C$_{30}$H$_{32}$FNO$_2$: C, 78.75; H, 7.05; N, 3.06. Found: C, 78.66; H, 7.15; N, 2.98.

Example 324

4-fluoro-N-[(1RS,2SR)-2-(4-fluorophenyl)-2-hydroxy-1-(3-isopropylbenzyl)ethyl]naphthalene-1-carboxamide While stirring (1RS,2SR)-2-amino-1-(4-fluorophenyl)-3-(3-isopropylphenyl)propan-1-ol (0.250 g, 0.870 mmol), 4-fluoro-1-naphthoic acid (0.17 g, 0.87 mmol) and 1-hydroxybenzotriazole hydrate (0.13 g, 0.87 mmol) in acetonitrile (10 ml), 1-ethyl-3-(3-dimethylaminopropyl)carbodiimide hydrochloride (0.17 g, 0.87 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white crystal yield 0.355 g, 89% mp 159–160° C.; $^1$H-NMR (CDCl$_3$, 300 MHz) δ 1.18 (3H, d, J=7.2 Hz), 1.19 (3H, d, J=7.2 Hz), 2.73 (1H, dd, J=11.1 Hz, 14.4 Hz), 2.80–2.89 (1H, m), 3.06 (1H, dd, J=4.2 Hz, 14.4 Hz), 4.02 (1H, d, J=4.2 Hz), 4.74–4.83 (1H, m), 5.08 (1H, t, J=3.9 Hz), 5.81 (1H, d, J=7.8 Hz), 6.96 (1H, dd, J=8.1 Hz, 9.9 Hz), 7.01–7.15 (6H, m), 7.25 (1H, t, J=7.5 Hz), 7.42–7.47 (3H, m), 7.54 (1H, t, J=8.1 Hz), 7.80 (1H, d, J=8.4 Hz), 8.07 (1H, d, J=8.4 Hz); IR (KBr) 3272, 2965, 1640, 1626, 1601, 1539, 1512, 1329, 1264, 1229, 1051, 833, 760 cm$^{-1}$; Anal. Calcd for C$_{29}$H$_{27}$F$_2$NO$_2$.0.1H$_2$O: C, 75.50; H, 5.94; N, 3.04. Found: C, 75.24; H, 5.94; N, 3.44.

Example 325 tert-butyl N-[(1RS,2SR)-2-(4-formylphenyl)-2-hydroxy-1-[3-(1,1,2,2-tetrafluoroethoxy)benzyl]ethyl]carbamate 1) (4RS,5SR)-5-[4-(hydroxymethyl)phenyl]-4-[3-(1,1,2,2-tetrafluoroethoxy)benzyl]-1,3-oxazolidin-2-one A solution of (4RS,5SR)-5-[4-(methoxycarbonyl)phenyl]-4-[3-(1,1,2,2-tetrafluoroethoxy)benzyl]-1,3-oxazolidin-2-one (1.518 g, 3.552 mmol) and sodium borohydride (1.34 g, 35.5 mmol) in methanol (3 ml)-tetrahydrofuran (50 ml) was heated under reflux for 6 hrs. After cooling the reaction solution to room temperature, dilute hydrochloric acid was added by small portions at room temperature and the mixture was stirred for 0.5 hr, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=1/1–1/2). Crystallization from diisopropyl ether-hexane gave the objective substance.

white crystal yield 0.899 g, 63% mp 124–125° C.; $^1$H-NMR (CDCl$_3$, 300 MHz) δ 1.75 (1H, t, J=5.9 Hz), 2.26 (1H, dd, J=10.2 Hz, 13.8 Hz), 2.33 (1H, dd, J=4.5 Hz, 13.8 Hz), 4.22–4.29 (1H, m), 4.75 (2H, d, J=6.0 Hz), 4.94 (1H, br s), 5.83 (1H, d, J=8.1 Hz), 5.90 (1H, tt, J=2.8 Hz, 53.0 Hz), 6.85 (1H, s), 6.96 (1H, d, J=7.8 Hz), 7.10 (1H, dd, J=1.1 Hz, 8.3 Hz), 7.31 (1H, t, J=8.0 Hz), 7.37 (2H, d, J=8.1 Hz), 7.45 (2H, d, J=8.4 Hz); IR (KBr) 3243, 1746, 1208, 1123 cm$^{-1}$; Anal. Calcd for C$_{19}$H$_{17}$F$_4$NO$_4$: C, 57.15; H, 4.29; N, 3.51. Found: C, 56.95; H, 4.05; N, 3.40.

2) 4-[(4RS,5SR)-2-oxo-4-[3-(1,1,2,2-tetrafluoroethoxy)benzyl]-1,3-oxazolidin-5-yl]benzaldehyde To a solution of oxalyl chloride (5.58 g, 44.0 mmol) in tetrahydrofuran (100 ml) was dropwise added a solution of dimethyl sulfoxide (6.24 ml, 88.0 mmol) in tetrahydrofuran (30 ml) was dropwise added at −78° C. and the mixture was stirred for 5 min. A solution of (4RS,5SR)-5-[4-(hydroxymethyl)phenyl]-4-[3-(1,1,2,2-tetrafluoroethoxy)benzyl]-1,3-oxazolidin-2-one (11.71 g, 29.32 mmol) in tetrahydrofuran (50 ml)-dichloromethane (70 ml)-dimethyl sulfoxide (30 ml) was added at −78° C., and the mixture was stirred for 15 min. Triethylamine (24.5 ml, 176 mmol) was added thereto, and the mixture was warmed to room temperature. The reaction mixture was poured into water, and extracted twice with ethyl acetate. The recovered organic layer was dried over anhydrous magnesium sulfate and passed through silica gel. The solvent was evaporated under reduced pressure and the obtained crude product was crystallized from diisopropyl ether-hexane to give the objective substance.

pale-yellow crystal yield 11.39 g, 98% mp 132–133° C.; $^1$H-NMR (CDCl$_3$, 300 MHz) δ 2.26 (1H, dd, J=9.9 Hz, 13.5 Hz), 2.33 (1H, dd, J=4.8 Hz, 13.8 Hz), 4.30–4.37 (1H, m), 5.10 (1H, br s), 5.89 (1H, d, J=8.1 Hz), 5.89 (1H, tt, J=2.8 Hz, 53.1 Hz), 6.85 (1H, s), 6.94 (1H, d, J=7.8 Hz), 7.11 (1H, dd, J=1.2 Hz, 8.1 Hz), 7.30 (1H, t, J=8.0 Hz), 7.57 (2H, d, J=7.8 Hz), 7.96 (2H, d, J=8.4 Hz), 10.06 (1H, s); IR (KBr) 3243, 3144, 1742, 1703, 1238, 1198, 1144, 1121, 1090 cm$^{-1}$; Anal. Calcd for C$_{19}$H$_{15}$F$_4$NO$_4$: C, 57.44; H, 3.81; N, 3.53. Found: C, 57.28; H, 3.87; N, 3.39.

3) tert-butyl (4RS,5SR)-5-(4-formylphenyl)-2-oxo-4-[3-(1,1,2,2-tetrafluoroethoxy)benzyl]-1,3-oxazolidine-3-carboxylate A solution of 4-[(4RS,5SR)-2-oxo-4-[3-(1,1,2,2-tetrafluoroethoxy)benzyl]-1,3-oxazolidine-5-yl]benzaldehyde (11.29 g, 28.41 mmol), di-tert-butyl dicarbonate (7.44 g, 34.1 mmol) and 4-N,N-dimethylaminopyridine (0.35 g, 2.84 mmol) in acetonitrile (50 ml) was stirred overnight at room temperature. The solvent of the reaction solution was evaporated under reduced pressure, and the obtained residue was purified by silica gel column chromatography (hexane/ethyl acetate=3/1–2/1). Crystallization from ethyl acetate-diisopropyl ether-hexane gave the objective substance.

white crystal yield 12.38 g, 88% mp 143–144° C.; $^1$H-NMR (CDCl$_3$, 300 MHz) δ 1.53 (9H, s), 2.59 (1H, dd, J=8.9 Hz, 14.6 Hz), 2.94 (1H, dd, J=4.4 Hz, 14.3 Hz), 4.85–4.91 (1H, m), 5.75 (1H, d, J=6.9 Hz), 5.84 (1H, tt, J=2.9 Hz, 53.1 Hz), 6.37 (1H, s), 6.60 (1H, d, J=7.8 Hz), 6.94 (1H, dd, J=1.4 Hz, 8.0 Hz), 7.05 (1H, t, J=8.0 Hz)., 7.34 (2H, d, J=8.1 Hz), 7.77 (2H, d, J=8.7 Hz), 9.99 (1H, s); IR (KBr) 1804, 1690, 1364, 1348, 1304, 1196, 1155, 1121, 1092, 1061 cm$^{-1}$; Anal. Calcd for C$_{24}$H$_{23}$F$_4$NO$_6$: C, 57.95; H, 4.66; N, 2.82. Found: C, 57.88; H, 4.49; N, 2.71.

4) tert-butyl N-[(1RS,2SR)-2-(4-formylphenyl)-2-hydroxy-1-[3-(1,1,2,2-tetrafluoroethoxy)benzyl]ethyl]carbamate To a solution of tert-butyl (4RS,5SR)-5-(4-formylphenyl)-2-oxo-4-[3-(1,1,2,2-tetrafluoroethoxy)benzyl]-1,3-oxazolidine-3-carboxylate (12.20 g, 24.53 mmol) in methanol (20 ml)-tetrahydrofuran (50 ml) was added a solution of sodium hydroxide (1.03 g, 25.8 mmol) in methanol (15 ml) under ice-cooling, and the mixture was stirred at room temperature for 1 hr. The reaction solution was diluted with ethyl acetate, washed with water, dried over anhydrous magnesium sulfate and passed-through silica gel. The solvent was evaporated under reduced pressure and the obtained residue was crystallized from ethyl acetate-diisopropyl ether-hexane to give the objective substance.

white crystal yield 8.681 g, 75% mp 140–142° C.; $^1$H-NMR (CDCl$_3$, 300 MHz) δ 1.36 (9H, s), 2.75 (2H, d, J=7.5 Hz), 3.54 (1H, br s), 4.04–4.13 (1H, m), 4.63 (1H, br d, J=8.1 Hz), 5.06 (1H, br s), 5.89 (1H, tt, J=2.9 Hz, 53.0 Hz), 6.94 (1H, s), 7.00 (1H, d, J=7.8 Hz), 7.06 (1H, dd, J=1.4 Hz, 8.3 Hz), 7.26 (1H, t, J=8.0 Hz), 7.59 (2H, d, J=8.4 Hz), 7.90 (2H, d, J=8.1 Hz), 10.03 (1H, s); IR (KBr) 3358, 1684, 1530, 1277, 1211, 1169, 1125 cm$^{-1}$; Anal. Calcd for C$_{23}$H$_{25}$F$_4$NO$_5$.0.5H$_2$O: C, 57.50; H, 5.45; N, 2.92. Found: C, 57.33; H, 5.27; N, 2.89.

Example 326

N-[(1RS,2SR)-2-(4-formylphenyl)-2-hydroxy-1-[3-(1,1,2,2-tetrafluoroethoxy)benzyl]ethyl]-6,7-dihydro-5H-benzo[a]cycloheptene-1-carboxamide A solution of tert-butyl N-[(1RS,2SR)-2-(4-formylphenyl)-2-hydroxy-1-[3-(1,1,2,2-tetrafluoroethoxy)benzyl]ethyl]carbamate (8.465 g, 17.96 mmol) and trifluoroacetic acid (20 ml) in tetrahydrofuran (20 ml) was stirred at 50° C. for 0.5 hr. The reaction solution was evaporated under reduced pressure, diluted with water, alkalified with potassium carbonate, and extracted twice with ethyl acetate. The recovered organic layer was dried over anhydrous sodium sulfate and the solvent was evaporated under reduced pressure to give a brown liquid.

While stirring the liquid obtained above, 6,7-dihydro-5H-benzo[a]cycloheptene-1-carboxylic acid (3.38 g, 18.0 mmol) and 1-hydroxybenzotriazole hydrate (2.75 g, 18.0 mmol) in acetonitrile, 1-ethyl-3-(3-dimethylaminopropyl)carbodiimide hydrochloride (3.44 g, 18.0 mmol) was added, and the mixture was stirred at room temperature for 3 days. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=2/1–3/2). Crystallization from ethyl acetate-diisopropyl ether-hexane gave the objective substance.

white crystal yield 4.388 g, 45% mp 164–166° C.; $^1$H-NMR (CDCl$_3$, 300 MHz) δ 1.96–2.04 (2H, m), 2.15–2.22 (2H, m), 2.66 (2H, t, J=6.0 Hz), 2.82 (1H, dd, J=10.8 Hz, 14.4 Hz), 2.96 (1H, dd, J=4.4 Hz, 14.6 Hz), 3.96 (1H, d, J=3.9 Hz), 4.65–4.74 (1H, m), 5.18 (1H, t, J=3.8 Hz), 5.82 (1H, d, J=7.8 Hz), 5.88 (1H, tt, J=2.7 Hz, 53.0 Hz), 5.93 (1H, td, J=5.7 Hz, 11.4 Hz), 6.23 (1H, d, J=11.7 Hz), 6.97–7.11 (5H, m), 7.17 (1H, d, J=7.2 Hz), 7.30 (1H, t, J=8.1 Hz), 7.66 (2H, d, J=8.4 Hz), 7.91 (2H, d, J=8.1 Hz), 10.03 (1H, s); IR (KBr) 3503, 3252, 1694, 1636, 1537, 1285, 1190, 1107, 775 cm$^{-1}$; Anal. Calcd for C$_{30}$H$_{27}$F$_4$NO$_4$: C, 66.54; H, 5.03; N, 2.59. Found: C, 66.20; H, 5.00; N, 2.32.

Example 327

A solution of N-[(1RS,2SR)-2-(4-formylphenyl)-2-hydroxy-1-[3-(1,1,2,2-tetrafluoroethoxy)benzyl]ethyl]-6,7-dihydro-5H-benzo[a]cycloheptene-1-carboxamide (0.300 g, 0.554 mmol), piperidine (0.11 ml, 1.1 mmol) and acetic acid (0.06 ml, 1.1 mmol) in methanol (10 ml) was stirred at room temperature for 1 hr. The sodium cyanoborohydride (70 mg, 1.1 mmol) was added at room temperature, and the mixture was stirred overnight at room temperature. The reaction mixture was poured into aqueous sodium hydrogen carbonate solution and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=3:2-chloroform/methanol=20/1). Precipitation from hexane gave three kinds of products.

N-[(1RS,2SR)-2-hydroxy-2-[4-(piperidinomethyl)phenyl]-1-[3-(1,1,2,2-tetrafluoroethoxy)benzyl]ethyl]-6,7-dihydro-5H-benzo[a]cycloheptene-1-carboxamide white powder yield 0.127 g, 38% mp 104–106° C.; $^1$H-NMR (CDCl$_3$, 300 MHz) δ 1.40–1.46 (2H, m), 1.53–1.60 (4H, m), 1.94–2.02 (2H, m), 2.15–2.22 (2H, m), 2.37 (4H, br s), 2.65 (2H, t, J=5.6 Hz), 2.79 (1H, dd, J=10.7 Hz, 14.9 Hz), 3.00 (1H, dd, J=4.5 Hz, 14.7 Hz), 3.46 (2H, s), 3.67 (1H, br s), 4.68–4.75 (1H, m), 5.01 (1H, d, J=3.6 Hz), 5.81. (1H, d, J=8.4 Hz), 5.88 (1H, tt, J=2.7 Hz, 53.1 Hz), 5.90 (1H, td, J=5.1 Hz, 12.3 Hz), 6.19 (1H, d, J=12.0 Hz), 6.95 (1H, dd, J=1.2 Hz, 7.8 Hz), 7.01–7.15 (5H, m), 7.26–7.33 (3H, m), 7.39 (2H, d, J=8.1 Hz); IR (KBr) 3258, 2932, 1632, 1535, 1285, 1198, 1113 cm$^{-1}$; Anal. Calcd for C$_{35}$H$_{38}$F$_4$N$_2$O$_3$. 1.0H$_2$O: C, 66.86; H, 6.41; N, 4.46. Found: C, 66.55; H, 6.35; N, 4.54.

N-[(1RS,2SR)-2-[4-[cyano(piperidino)methyl]phenyl]-2-hydroxy-1-[3-(1,1,2,2-tetrafluoroethoxy)benzyl]ethyl]-6,7-dihydro-5H-benzo[a]cycloheptene-1-carboxamide white powder yield 35 mg) mp 152–154° C.; $^1$H-NMR (CDCl$_3$, 300 MHz) δ 1.43–1.67 (6H, m), 1.96–2.04 (2H, m), 2.16–2.22 (2H, m), 2.51 (4H, br s), 2.66 (2H, t, J=5.9 Hz), 2.74–2.84 (1H, m), 2.94–3.02 (1H, m), 3.78 (0.5H, d, J=3.9 Hz), 3.81 (0.5H, d, J=4.2 Hz), 4.67–4.74 (1H, m), 4.81 (1H, s), 5.06–5.93 (1H, m), 5.79–5.84 (1H, m), 5.88–5.96 (1H, m), 5.89 (1H, tt, J=2.9 Hz, 53.0 Hz), 6.17–6.24 (1H, m), 6.94–7.17 (6H, m), 7.29 (1H, t, J=7.8 Hz), 7.48 (2H, d, J=8.7 Hz), 7.55 (2H, d, J=8.4 Hz); IR (KBr) 3353, 2940, 1638, 1522, 1202, 1121 cm$^{-1}$; Anal. Calcd for C$_{36}$H$_{37}$F$_4$N$_3$O$_3$: C, 68.02; H, 5.87; N, 6.61. Found: C, 67.81; H, 6.02; N, 6.54.

N-[(1RS,2SR)-2-hydroxy-2-[4-(hydroxymethyl)phenyl]-1-[3-(1,1,2,2-tetrafluoroethoxy)benzyl]ethyl]-6,7-dihydro-5H-benzo[a]cycloheptene-1-carboxamide white powder yield 41 g) mp 151–152° C.; $^1$H-NMR (CDCl$_3$, 300 MHz) δ 1.75 (1H, t, J=5.7 Hz), 1.96–2.04 (2H, m), 2.16–2.22 (2H, m), 2.66 (2H, t, J=5.9 Hz), 2.78 (1H, dd, J=10.8 Hz, 14.7 Hz), 2.99 (1H, dd, J=4.1 Hz, 14.6 Hz), 3.61 (1H, d, J=4.2 Hz), 4.68–4.75 (1H, m), 4.71 (2H, d, J=6.0 Hz), 5.06 (1H, t, J=3.6 Hz), 5.77 (1H, d, J=8.1 Hz), 5.89 (1H, tt, J=2.9 Hz, 53.0 Hz), 5.91 (1H, td, J=5.4 Hz, 11.7 Hz), 6.22 (1H, d, J=11.4 Hz), 6.96–7.16 (6H, m), 7.29 (1H, t, J=8.0 Hz), 7.38 (2H, d, J=8.1 Hz), 7.46 (2H, d, J=7.8 Hz); IR (KBr) 3270, 2932, 1638, 1522, 1202, 1123 cm$^{-1}$; Anal. Calcd for C$_{30}$H$_{29}$F$_4$NO$_4$.0.1H$_2$O: C, 66.07; H, 5.40; N, 2.57. Found: C, 65.88; H, 5.29; N, 2.47.

Example 328 tert-butyl N-[(1RS,2SR)-2-(6-chloropyridin-3-yl)-2-hydroxy-1-[3-(1,1,2,2-tetrafluoroethoxy)benzyl]ethyl]carbamate 1) ethyl 3-(6-chloropyridin-3-yl)-3-oxo-2-[3-(1,1,2,2-tetrafluoroethoxy)benzyl]propionate To a solution of 3-(1,1,2,2-tetrafluoroethoxy)benzyl alcohol (10.5 g, 46.8 mmol) and triethylamine (7.83 ml, 56.2 mmol) in ethyl acetate (80 ml) was dropwise added a solution of methanesulfonyl chloride (5.90 g, 51.5 mmol) in ethyl acetate (20 ml) under ice-cooling, and the mixture was stirred as it was for 10 min. The resulting precipitate was removed by filtration, and the precipitate was washed with diethyl ether. The solvent of the recovered filtrate was evaporated under reduced pressure to give a crude product of methanesulfonic acid ester as a yellow liquid.

To a solution of ethyl 3-(6-chloropyridin-3-yl)-3-oxopropionate (10.66 g, 46.83 mmol) in 1,2-dimethoxyethane (100 ml) was added a suspension (1.87 g, 46.8 mmol) of 60% sodium hydride in liquid paraffin under ice-cooling, and the mixture was stirred as it was for 0.5 hr. A solution of methanesulfonic acid ester obtained above in 1,2-dimethoxyethane (10 ml) was added thereto at room temperature, and the mixture was stirred at 60° C. overnight. The reaction solution was poured into water, and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=9/1–6/1) to give the objective substance.

pale-yellow liquid yield 17.22 g, 85% $^1$H-NMR (CDCl$_3$, 300 MHz) δ 1.14 (3H, t, J=7.2 Hz), 3.36 (2H, d, J=7.2 Hz), 4.12 (2H, q, J=7.1 Hz), 4.52 (1H, t, J=7.4 Hz), 5.89 (1H, t, J=2.8 Hz, 53.2 Hz), 7.05–7.07 (2H, m), 7.13 (1H, d, J=7.8 Hz), 7.29 (1H, t, J=8.3 Hz), 7.42 (1H, dd, J=0.8 Hz, 8.3 Hz), 8.16 (1H, dd, J=2.6 Hz, 8.3 Hz), 8.92 (1H, dd, J=0.8 Hz, 2.7 Hz); IR (neat) 1738, 1694, 1582, 1364, 1302, 1277, 1196, 1113 cm$^{-1}$ 2) ethyl (2RS,3RS)-3-(6-chloropyridin-3-yl)-3-hydroxy-2-[3-(1,1,2,2-tetrafluoroethoxy)benzyl]propionate While stirring zinc chloride (10.8 g, 79.0 mmol) in diethyl ether (50 ml), sodium borohydride (5.98 g, 158 mmol) was added at room temperature, and the mixture was stirred as it was for 2 hrs. The insoluble material in the mixture was removed by filtration and washed with diethyl ether to give a solution of zinc borohydride in diethyl ether. To the obtained solution was added a solution of ethyl 3-(6-chloropyridin-3-yl)-3-oxo-2-[3-(1,1,2,2-tetrafluoroethoxy)benzyl]propionate (17.14 g, 39.51 mmol) in diethyl ether (50 ml) under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=3/1–2/1) to give the objective substance.

pale-yellow liquid yield 13.52 g, 79% $^1$H-NMR (CDCl$_3$, 300 MHz) δ 0.97 (3H, t, J=7.1 Hz), 2.90–3.07 (3H, m), 3.28 (1H, d, J=3.0 Hz), 3.93 (2H, q, J=7.2 Hz), 5.10 (1H, t, J=3.3 Hz), 5.89 (1H, tt, J=2.8 Hz, 53.2 Hz), 6.95 (1H, s), 6.98–7.07 (2H, m), 7.27 (1H, t, J=7.8 Hz), 7.33 (1H, d, J=8.4 Hz), 7.73 (1H, ddd, J=0.5 Hz, 2.5 Hz, 8.3 Hz), 8.39 (1H, dd, J=0.9 Hz, 2.1 Hz); IR (neat) 3353, 1728, 1588, 1460, 1375, 1302, 1279, 1198, 1119, 1026 cm$^{-1}$ 3) (2RS,3RS)-3-(6-chloropyridin-3-yl)-3-hydroxy-2-[3-(1,1,2,2-tetrafluoroethoxy)benzyl]propionic acid A mixture of ethyl (2RS,3RS)-3-(6-chloropyridin-3-yl)-3-hydroxy-2-[3-(1,1,2,2-tetrafluoroethoxy)benzyl]propionate (13.52 g, 31.02 mmol), sodium hydroxide (2.48 g, 62.0 mmol), methanol (50 ml), tetrahydrofuran (20 ml) and water (50 ml) was stirred at room temperature for 2 hrs. The reaction solution was concentrated, diluted with water, acidified with hydrochloric acid, and extracted twice with ethyl acetate. The recovered organic layer was dried over anhydrous sodium sulfate and the solvent was evaporated under reduced pressure. The residue was crystallized from diisopropyl ether-hexane to give the objective substance.

pale-yellow crystal yield 11.32 g, 90% mp 88–91° C.; $^1$H-NMR (CDCl$_3$, 300 MHz) δ 2.92–3.11 (3H, m), 5.10 (1H, d, J=4.5 Hz), 5.88 (1H, tt, J=2.9 Hz, 53.1 Hz), 6.99–7.10 (3H, m), 7.23 (1H, t, J=7.8 Hz), 7.31 (1H, d, J=8.1 Hz), 7.77 (1H, dd, J=2.4 Hz, 8.4 Hz), 8.34 (1H, d, J=2.4 Hz); IR (KBr) 3364, 2900–2400, 1686, 1590, 1462, 1316, 1279, 1227, 1202, 1113, 1082 cm$^{-1}$; Anal. Calcd for C$_{17}$H$_{14}$ClF$_4$NO$_4$: C, 50.08; H, 3.46; N, 3.44. Found: C, 50.01; H, 3.53; N, 3.42.

4) (4RS,5SR)-5-(6-chloropyridin-3-yl)-4-[3-(1,1,2,2-tetrafluoroethoxy)benzyl]-1,3-oxazolidin-2-one To a solution of (2RS,3RS)-3-(6-chloropyridin-3-yl)-3-hydroxy-2-[3-(1,1,2,2-tetrafluoroethoxy)benzyl]propionic acid (10.94 g, 26.83 mmol) in tetrahydrofuran (80 ml) were added triethylamine (4.49 ml, 32.2 mmol) and diphenylphosphoryl azide (8.12 g, 29.5 mmol), and the mixture was stirred at 65° C. overnight. The solvent of the reaction solution was evaporated under reduced pressure and the obtained crude product was purified by silica gel column chromatography (hexane/ethyl acetate=3/1–1/1). Crystallization from diisopropyl ether-hexane gave the objective substance.

white crystal yield 8.107 g, 75% mp 131–132° C.; $^1$H-NMR (CDCl$_3$, 300 MHz) δ 2.31 (1H, dd, J=10.5 Hz, 13.8 Hz), 2.38 (1H, dd, J=5.1 Hz, 13.8 Hz), 4.30–4.38 (1H, m), 5.23 (1H, s), 5.83 (1H, d, J=7.8 Hz), 5.91 (1H, tt, J=2.9 Hz, 53.0 Hz), 6.89 (1H, s), 6.93 (1H, d, J=7.8 Hz), 7.13 (1H, d, J=8.1 Hz), 7.32 (1H, t, J=7.8 Hz), 7.42 (1H, d, J=8.4 Hz), 7.71 (1H, dd, J=2.4 Hz, 8.4 Hz), 8.39 (1H, d, J=2.4 Hz); IR (KBr) 3252, 1740, 1208, 1134, 1105, 758 cm$^{-1}$; Anal. Calcd for C$_{17}$H$_{13}$ClF$_4$N$_2$O$_3$: C, 50.45; H, 3.24; N, 6.92. Found: C, 50.41; H, 3.04; N, 6.95.

5) tert-butyl (4RS,5SR)-5-(6-chloropyridin-3-yl)-2-oxo-4-[3-(1,1,2,2-tetrafluoroethoxy)benzyl]-1,3-oxazolidine-3-carboxylate A solution of (4RS,5SR)-5-(6-chloropyridin-3-yl)-4-[3-(1,1,2,2-tetrafluoroethoxy)benzyl]-1,3-oxazolidin-2-one (7.889 g, 19.49 mmol), di-tert-butyl dicarbonate (5.10 g, 23.4 mmol) and 4-N,N-dimethylaminopyridine (0.24 g, 1.95 mmol) in acetonitrile (80 ml) was stirred overnight at room temperature. The solvent of the reaction solution was evaporated under reduced pressure and the obtained residue was purified by silica gel column chromatography (hexane/ethyl acetate=3/1–1/1). Crystallization from diisopropyl ether-hexane gave the objective substance.

white crystal yield 9.444 g, 96% mp 130–131° C.; $^1$H-NMR (CDCl$_3$, 200 MHz) δ 1.54 (9H, s), 2.58 (1H, dd, J=9.7 Hz, 14.5 Hz), 3.03 (1H, dd, J=4.2 Hz, 14.2 Hz), 4.83–4.93 (1H, m), 5.70 (1H, d, J=7.0 Hz), 5.90 (1H, tt, J=2.6 Hz, 53.0 Hz), 6.52–6.57 (2H, m), 7.01 (1H, br d, J=8.2 Hz), 7.11 (1H, d, J=7.2 Hz), 7.19 (1H, d, J=8.4 Hz), 7.39 (1H, dd, J=2.6 Hz, 8.4 Hz), 8.19 (1H, d, J=1.8 Hz); IR (KBr) 2988, 1796, 1730, 1366, 1343, 1319, 1204, 1154, 1115, 1074, 1024, 845, 760 cm$^{-1}$; Anal. Calcd for C$_{22}$H$_{21}$ClF$_4$N$_2$O$_5$: C, 52.34; H, 4.19; N, 5.55. Found: C, 52.27; H, 4.03; N, 5.35.

6) tert-butyl N-[(1RS,2SR)-2-(6-chloropyridin-3-yl)-2-hydroxy-1-[3-(1,1,2,2-tetrafluoroethoxy)benzyl]ethyl]carbamate To a solution of tert-butyl (4RS,5SR)-5-(6-chloropyridin-3-yl)-2-oxo-4-[3-(1,1,2,2-tetrafluoroethoxy)benzyl]-1,3-oxazolidin-3-carboxylate (9.144 g, 18.11 mmol) in methanol (10 ml)-tetrahydrofuran (50 ml) was added a solution of sodium hydroxide (0.76 g, 19.0 mmol) in methanol (10 ml) under ice-cooling, and the mixture was stirred at room temperature for 10 min. The reaction solution was diluted with ethyl acetate, washed with water, dried over anhydrous magnesium sulfate and passed through silica gel. The solvent was evaporated under reduced pressure. The obtained residue was crystallized from ethyl acetate-diisopropyl ether-hexane to give the objective substance.

white crystal yield 8.441 g, 97% mp 119–121° C.; $^1$H-NMR (CDCl$_3$, 300 MHz) δ 1.36 (9H, s), 2.70–2.85 (2H, m), 3.86 (1H, br s), 4.00–4.09 (1H, m), 4.55 (1H, d, J=8.1 Hz), 4.95 (1H, s), 5.90 (1H, tt, J=2.8 Hz, 53.1 Hz), 6.98 (1H, s), 7.03 (1H, d, J=7.8 Hz), 7.08 (1H, d, J=7.8 Hz), 7.26–7.36 (2H, m), 7.73 (1H, dd, J=2.3 Hz, 8.0 Hz), 8.39 (1H, d, J=1.8 Hz); IR (KBr) 3378, 3175, 2982, 1682, 1524, 1460, 1196, 1125, 1105 cm$^{-1}$; Anal. Calcd for C$_{21}$H$_{23}$ClF$_4$N$_2$O$_4$: C, 52.67; H, 4.84; N, 5.85. Found: C, 52.95; H, 4.88; N, 5.83.

Example 329

N-[(1RS,2SR)-2-(6-chloropyridin-3-yl)-2-hydroxy-1-[3-(1,1,2,2-tetrafluoroethoxy)benzyl]ethyl]-6,7-dihydro-5H-benzo[a]cycloheptene-1-carboxamide 1) (1RS,2SR)-2-amino-1-(6-chloropyridin-3-yl)-3-[3-(1,1,2,2-tetrafluoroethoxy)phenyl]propan-1-ol A mixture of tert-butyl N-[(1RS,2SR)-2-(6-chloropyridin-3-yl)-2-hydroxy-1-[3-(1,1,2,2-tetrafluoroethoxy)benzyl]ethyl]carbamate (8.196 g, 17.12 mmol) and trifluoroacetic acid (20 ml) was stirred at room temperature for 1 hr. The reaction solution was evaporated under reduced pressure, diluted with water, alkalified with potassium carbonate, and extracted twice with ethyl acetate. The recovered organic layer was dried over anhydrous sodium sulfate and passed through APS-silica gel. The solvent was evaporated under reduced pressure and the obtained residue was crystallized from diisopropyl ether-hexane to give the objective substance.

white crystal yield 6.118 g, 94% mp 97–98° C.; $^1$H-NMR (CDCl$_3$, 300 MHz) δ 2.37 (1H, dd, J=10.4 Hz, 13.7 Hz), 2.70 (1H, dd, J=3.2 Hz, 14.0 Hz), 3.34 (1H, ddd, J=3.5 Hz, 4.2 Hz, 10.1 Hz), 3.58 (1H, br s), 4.75 (1H, d, J=4.2 Hz), 5.90 (1H, tt, J=2.9 Hz, 53.1 Hz), 6.98 (1H, s), 7.04 (1H, d, J=7.5 Hz), 7.09 (1H, d, J=8.1 Hz), 7.31 (1H, t, J=7.8 Hz), 7.36 (1H, d, J=8.1 Hz), 7.75 (1H, dd, J=2.6 Hz, 8.3 Hz), 8.40 (1H, d, J=2.4 Hz); IR (KBr) 3358, 3065–2755, 1588, 1568, 1454, 1279, 1202, 1119, 1100, 1047 cm$^{-1}$; Anal. Calcd for C$_{16}$H$_{15}$ClF$_4$N$_2$O$_2$: C, 50.74; H, 3.99; N, 7.40. Found: C, 50.60; H, 3.72; N, 7.13.

2) N-[(1RS,2SR)-2-(6-chloropyridin-3-yl)-2-hydroxy-1-[3-(1,1,2,2-tetrafluoroethoxy)benzyl]ethyl]-6,7-dihydro-5H-benzo[a]cycloheptene-1-carboxamide While stirring (1RS,2SR)-2-amino-1-(6-chloropyridin-3-yl)-3-[3-(1,1,2,2-tetrafluoroethoxy)phenyl]propan-1-ol (1.000 g, 2.640 mmol), 6,7-dihydro-5H-benzo[a]cycloheptene-1-carboxylic acid (0.50 g, 2.64 mmol) and 1-hydroxybenzotriazole hydrate (0.40 g, 2.64 mmol) in acetonitrile (20 ml), 1-ethyl-3-(3-dimethylaminopropyl) carbodiimide hydrochloride (0.51 g, 2.64 mmol). was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white crystal yield 1.311 g, 91% mp 170–172° C.; $^1$H-NMR (CDCl$_3$, 300 MHz) δ 1.96–2.05 (2H, m), 2.14–2.22 (2H, m), 2.66 (2H, t, J=6.0 Hz), 2.79 (1H, dd, J=11.0 Hz, 14.3 Hz), 3.01 (1H, dd, J=4.2 Hz, 14.4 Hz), 4.29 (1H, d, J=3.9 Hz), 4.61–4.69 (1H, m), 5.08 (1H, t, J=3.9 Hz), 5.76 (1H, d, J=7.8 Hz), 5.90 (1H, tt, J=2.8. Hz, 53.0 Hz), 5.94 (1H, td, J=5.8 Hz, 11.7 Hz), 6.19 (1H, d, J=11.4 Hz), 6.96 (1H, dd, J=1.5 Hz, 7.8 Hz), 7.03–7.18 (5H, m), 7.33 (1H, t, J=8.0 Hz), 7.35 (1H, d, J=8.1 Hz), 7.81 (1H, dd, J=2.4 Hz, 8.4 Hz), 8.42 (1H, d, J=2.7 Hz); IR (KBr) 3247, 1634, 1530, 1462, 1277, 1198, 1121 cm$^{-1}$; Anal. Calcd for C$_{28}$H$_{25}$ClF$_4$N$_2$O$_3$: C, 61.26; H, 4.59; N, 5.10. Found: C, 61.32; H, 4.75; N, 5.07.

Example 330

N-[(1RS,2SR)-2-hydroxy-2-(6-phenylpyridin-3-yl)-1-[3-(1,1,2,2-tetrafluoroethoxy)benzyl]ethyl]-6,7-dihydro-5H-benzo[a]cycloheptene-1-carboxamide N-[(1RS,2SR)-2-(6-Chloropyridin-3-yl)-2-hydroxy-1-[3-(1,1,2,2-tetrafluoroethoxy)benzyl]ethyl]-6,7-dihydro-5H-benzo[a]cycloheptene-1-carboxamide (0.523 g, 0.953 mmol), phenylboronic acid (0.35 g, 2.86 mmol), tetrakis (triphenylphosphine)palladium(0) (0.22 g, 0.19 mmol) and sodium carbonate (0.40 g, 3.81 mmol) were stirred in toluene (10 ml)-water (10 ml) at 110° C. for 3 days. The reaction solution was poured into water and extracted twice with ethyl acetate. The recovered organic layer was dried over anhydrous sodium sulfate and the solvent was evaporated under reduced pressure. The residue was purified by silica gel column chromatography (hexane/ethyl acetate=3/1–1/1). Crystallization from diisopropyl ether-hexane gave the objective substance.

pale-brown powder yield 0.344 g, 61% mp 174–175° C.; $^1$H-NMR (CDCl$_3$, 300 MHz) δ 1.95–2.03 (2H, m), 2.14–2.20 (2H, m), 2.66 (2H, t, J=5.9 Hz), 2.82 (1H, dd, J=10.7 Hz, 14.0 Hz), 3.07 (1H, dd, J=4.1 Hz, 14.9 Hz), 4.25 (1H, d, J=3.9 Hz), 4.70–4.79 (1H, m), 5.12 (1H, t, J=3.3 Hz), 5.79 (1H, d, J=8.4 Hz), 5.89 (1H, tt, J=2.7 Hz, 53.0 Hz), 5.91 (1H, td, J=5.5 Hz, 11.4 Hz), 6.21 (1H, d, J=11.7 Hz), 6.98 (1H, dd, J=1.0 Hz, 7.5 Hz), 7.03–7.17 (5H, m), 7.32 (1H, t, J=8.0 Hz), 7.40–7.52 (3H, m), 7.75 (1H, d, J=8.1 Hz), 7.90 (1H, dd, J=2.3 Hz, 8.3 Hz), 7.99 (2H, dd, J=2.1 Hz, 8.7 Hz), 8.70 (1H, d, J=2.1 Hz); IR (KBr) 3270, 2932, 1640, 1518, 1478, 1277, 1200, 1123, 743, 694 cm$^{-1}$; Anal. Calcd for C$_{34}$H$_{30}$F$_4$N$_2$O$_3$: C, 69.14; H, 5.12; N, 4.74. Found: C, 69.04; H, 5.04; N, 4.71.

Example 331

N-[(1RS,2SR)-2-(6-chloropyridin-3-yl)-2-hydroxy-1-[3-(1,1,2,2-tetrafluoroethoxy)benzyl]ethyl]-4-fluoronaphthalene-1-carboxamide While stirring (1RS,2SR)-2-amino-1-(6-chloropyridin-3-yl)-3-[3-(1,1,2,2-tetrafluoroethoxy)phenyl]propan-1-ol (1.000 g, 2.640 mmol), 4-fluoro-1-naphthoic acid (0.50 g, 2.64 mmol) and 1-hydroxybenzotriazole hydrate (0.40 g, 2.64 mmol) in acetonitrile (20 ml), 1-ethyl-3-(3-dimethylaminopropyl)carbodiimide hydrochloride (0.51 g, 2.64 mmol) was added and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance.

white crystal yield 1.338 g, 92% mp 185–187° C.; $^1$H-NMR (CDCl$_3$-DMSO-d$_6$, 300 MHz). δ 2.91 (1H, dd, J=10.8 Hz, 14.1 Hz), 3.17 (1H, dd, J=3.8 Hz, 14.0 Hz), 4.68–4.78 (1H, m), 4.95 (1H, t, J=5.0 Hz), 5.61 (1H, d, J=4.2 Hz), 6.00 (1H, tt, J=2.9 Hz, 53.0 Hz), 7.03 (1H, dd, J=7.7 Hz, 10.1 Hz), 7.08–7.23 (4H, m), 7.29–7.38 (2H, m), 7.42–7.56 (3H, m), 7.85 (1H, d, J=9.3 Hz), 7.93 (1H, dd, J=2.4 Hz, 8.1 Hz), 8.05 (1H, d, J=8.1 Hz), 8.49 (1H, d, J=2.1 Hz); IR (KBr) 3291, 1638, 1624, 1539, 1456, 1196, 1125, 837, 766 cm$^{-1}$; Anal. Calcd for C$_{27}$H$_{20}$ClF$_5$N$_2$O$_3$: C, 58.87; H, 3.66; N, 5.08. Found: C, 58.84; H, 3.59; N, 5.13.

Example 332

4-fluoro-N-[(1RS,2SR)-2-hydroxy-2-(6-phenylpyridin-3-yl)-1-[3-(1,1,2,2-tetrafluoroethoxy)benzyl]ethyl]naphthalene-1-carboxamide N-[(1RS,2SR)-2-(6-Chloropyridin-3-yl)-2-hydroxy-1-[3-(1,1,2,2-tetrafluoroethoxy)benzyl]ethyl]-4-fluoronaphthalene-1-carboxamide (0.516 g, 0.937 mmol), phenylboronic acid (0.34 g, 2.81 mmol), tetrakis (triphenylphosphine)palladium(0) (0.22 g, 0.19 mmol) and sodium carbonate (0.40 g, 3.74 mmol) were stirred in toluene (10 ml)-water (10 ml) at 110° C. for 3 days. The reaction solution was poured into water and extracted twice with ethyl acetate. The recovered organic layer was dried over anhydrous sodium sulfate and the solvent was evaporated. under reduced pressure. The residue was purified by silica gel column chromatography (hexane/ethyl acetate=3/1-ethyl acetate). Crystallization from diisopropyl ether-hexane gave the objective substance.

brown amorphous powder yield 0.154 g, 28% $^1$H-NMR (CDCl$_3$-DMSO-d$_6$, 300 MHz) δ 2.95 (1H, dd, J=10.8 Hz, 14.4 Hz), 3.10 (1H, dd, J=3.6 Hz, 14.1 Hz), 4.82–4.90 (1H, m), 5.12 (1H, t, J=3.9 Hz), 5.32 (1H, d, J=3.9 Hz), 5.92 (1H, tt, J=2.8 Hz, 53.1 Hz), 7.02 (1H, dd, J=7.8 Hz, 10.2 Hz), 7.09 (1H, d, J=7.8 Hz), 7.15 (1H, s), 7.19–7.53 (9H, m), 7.73 (1H, d, J=9.0 Hz), 7.78 (1H, d, J=8.4 Hz), 7.97–8.07 (4H, m), 8.82 (1H, d, J=2.4 Hz); IR (KBr) 3289, 1644, 1601, 1532, 1476, 1264, 1236, 1202, 1123, 758 cm$^{-1}$; Anal. Calcd for $C_{33}H_{25}F_5N_2O_3$: C, 66.89; H, 4.25; N, 4.73. Found: C. 66.57; H, 4.13; N, 4.82.

Example 333

5-chloro-N-[(1RS,2SR)-2-(4-fluorophenyl)-2-hydroxy-1-[3-(1,1,2,2-tetrafluoroethoxy)benzyl]ethyl]naphthalene-1-carboxamide While stirring (1RS,2SR)-2-amino-1-(4-fluorophenyl)-3-[3-(1,1,2,2-tetrafluoroethoxy)phenyl]propan-1-ol (0.200 g, 0.554 mmol), 5-chloro-1-naphthoate (0.11 g, 0.55 mmol) and 1-hydroxybenzotriazole hydrate (85 mg, 0.55 mmol) in acetonitrile (10 ml), 1-ethyl-3-(3-dimethylaminopropyl) carbodiimide hydrochloride (0.11 g, 0.55 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white powder yield 0.258 g, 85% mp 174–175° C.; $^1$H-NMR (CDCl$_3$-DMSO-d$_6$, 300 MHz) δ 2.87 (1H, dd, J=10.7 Hz, 14.9 Hz), 2.98 (1H, dd, J=4.7 Hz, 14.0 Hz), 4.64 (1H, d, J=3.3 Hz), 4.75–4.84 (1H, m), 5.06 (1H, t, J=4.1 Hz), 5.90 (1H, tt, J=2.9 Hz, 53.3 Hz), 6.93 (1H, d, J=9.3 Hz), 7.04–7.16 (5H, m), 7.26–7.32 (3H, m), 7.45–7.62 (5H, m), 8.31 (1H, d, J=8.4 Hz); IR (KBr) 3270, 1634, 1537, 1512, 1227, 1192, 1119, 785 cm$^{-1}$; Anal. Calcd for $C_{28}H_{21}ClF_5NO_3$: C, 61.16; H, 3.85; N, 2.55. Found: C, 61.23; H, 3.86; N, 2.39.

Example 334

5-fluoro-N-[(1RS,2SR)-2-(4-fluorophenyl)-2-hydroxy-1-[3-(1,1,2,2-tetrafluoroethoxy)benzyl]ethyl]naphthalene-1-carboxamide While stirring (1RS,2SR)-2-amino-1-(4-fluorophenyl)-3-[3-(1,1,2,2-tetrafluoroethoxy)phenyl]propan-1-ol (0.200 g, 0.554 mmol), 5-fluoro-1-naphthoate (0.11 g, 0.55 mmol) and 1-hydroxybenzotriazole hydrate (85 mg, 0.55 mmol) in acetonitrile (10 ml), 1-ethyl-3-(3-dimethylaminopropyl) carbodiimide hydrochloride (0.11 g, 0.55 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 0.240 g, 81% mp 178–180° C.; $^1$H-NMR (CDCl$_3$-DMSO-d$_6$, 300 MHz) δ 2.89 (1H, dd, J=10.7 Hz, 14.6 Hz), 2.98 (1H, dd, J=4.5 Hz, 14.7 Hz), 4.73 (1H, d, J=3.6 Hz), 4.75–4.84 (1H, m), 5.07 (1H, t, J=3.8 Hz), 5.90 (1H, tt, J=2.9 Hz, 53.1 Hz), 6.98 (1H, d, J=9.0 Hz), 7.05–7.17 (6H, m), 7.26–7.35 (3H, m), 7.41–7.55 (4H, m), 8.12 (1H, d, J=8.4 Hz); IR (KBr) 3275, 1640, 1541, 1512, 1250, 1229, 1198, 1128, 785 cm$^{-1}$; Anal. Calcd for $C_{28}H_{21}F_6NO_3$: C, 63.04; H, 3.97; N, 2.63. Found: C, 63.09; H, 4.24; N, 2.56.

Example 335

N-[(1RS,2SR)-2-(4-fluorophenyl)-2-hydroxy-1-[3-(2,3,3-trifluoro-1-propenyl)benzyl]ethyl]-6,7-dihydro-5H-benzo[a]cycloheptane-1-carboxamide 1) 2,2,3,3-tetrafluoro-1-(3-methylphenyl)propane-1-one While stirring a solution of magnesium (14.1 g, 579 mmol) and iodine (one crumb) in diethyl ether (100 ml), 3-methylbromobenzene (90.0 g, 526 mmol) in diethyl ether (200 ml) was dropwise added at room temperature. After completion of the dropwise addition, the mixture was stirred overnight at room temperature. The reaction solution was cooled to −78° C. and a solution of 2,2,3,3-tetrafluoropropionic acid (25.61 g, 175.4 mmol) in diethyl ether (100 ml) was dropwise added, and the mixture was heated under reflux for 4 hrs. To the reaction solution was dropwise added 1N hydrochloric acid under ice-cooling. The diethyl ether layer was separated, and the aqueous layer was extracted with diethyl ether. The recovered diethyl ether solution was dried over anhydrous magnesium sulfate. The solvent was evaporated under reduced pressure and the obtained residue was purified by silica gel column chromatography (hexane-hexane/ethyl acetate=15/1) to give the objective substance.

pale-yellow liquid yield 27.97 g, 72% $^1$H-NMR (CDCl$_3$, 300 MHz) δ 2.45 (3H, s), 6.29 (1H, tt, J=5.5 Hz, 53.6 Hz), 7.42 (1H, dt, J=1.2 Hz, 7.4 Hz), 7.51 (1H, dd, J=0.6 Hz, 7.8 Hz), 7.89–7.92 (2H, m); IR (neat) 1698, 1240, 1142, 1115, 1092, 789, 770, 743 cm$^{-1}$ 2) 2,2,3,3-tetrafluoro-1-(3-methylphenyl)propan-1-ol To a solution of 2,2,3,3-tetrafluoro-1-(3-methylphenyl) propane-1-one (9.11 g, 41.4 mmol) in methanol (50 ml) was added sodium borohydride (0.76 g, 20 mmol) by small portions under ice-cooling and the mixture was stirred at room temperature for 1 hr. The reaction solution was diluted with water, and extracted twice with ethyl acetate. The recovered organic layer was dried over anhydrous sodium sulfate and the solvent was evaporated under reduced pressure. The residue was purified by silica gel column chromatography (hexane/ethyl acetate=9/1–3/1) to give the objective substance.

colorless liquid yield 6.131 g, 67% $^1$H-NMR (CDCl$_3$, 200 MHz) δ 2.3.5 (1H, d, J=4.8 Hz), 2.39 (3H, s), 4.95–5.10 (1H, m), 5.97 (1H, ddt, J=3.3 Hz, 8.1 Hz, 53.2 Hz), 7.21–7.36 (4H, m); IR (neat) 3426, 1240, 1161, 1107, 1059, 762, 743 cm$^{-1}$ 3) O-phenyl O-[2,2,3,3-tetrafluoro-1-(3-methylphenyl) propyl]carbonate To a solution of 2,2,3,3-tetrafluoro-1-(3-methylphenyl) propan-1-ol (3.814 g, 17.17 mmol) and phenylchlorothionoformate (3.26 g, 18.9 mmol) in acetonitrile (40 ml) was added 4-N,N-dimethylaminopyridine (4.62 g, 37.8 mmol) under ice-cooling, and the mixture was stirred overnight at room temperature. The resulting precipitate was removed by filtration and washed with acetonitrile. The solvent of the recovered filtrate was evaporated under reduced pressure and the obtained crude product was purified by silica gel column chromatography (hexane/ethyl acetate=9/1–6/1) to give the objective substance.

colorless liquid yield 6.189 g, 100% $^1$H-NMR (CDCl$_3$, 300 MHz) δ 2.41 (3H, s), 5.89 (1H, tt, J=5.0 Hz, 53.0 Hz), 6.56 (1H, dd, J=10.7 Hz, 14.0 Hz), 7.08 (2H, d, J=7.5 Hz), 7.21–7.49 (7H, m); IR (neat) 1591, 1489, 1279, 1211, 1127, 1107, 1065, 774, 689 cm$^{-1}$ 4) 1-methyl-3-(2,2,3,3-tetrafluoropropyl)benzene A solution of O-phenyl O-[2,2,3,3-tetrafluoro-1-(3-(methylphenyl)propy]thiocarbonate (6.189 g, 17.27 mmol), tributyltin hydride (7.49 g, 25.7 mmol) and 2,2'-azobis (isobutyronitrile) (0.56 g, 3.43 mmol) in benzene (50 ml) was stirred at 80° C. for 6 hrs. After cooling the reaction solution to room temperature, the solvent was evaporated under recduced pressure and the obtained residue was purified by silica gel column chromatography (hexane) to give the objective substance.

colorless liquid yield 1.412 g, 40% $^1$H-NMR (CDCl$_3$, 300 MHz) δ 2.36 (3H, s), 3.24 (2H, t, J=17.7 Hz), 5.69 (1H, tt, J=3.5 Hz, 53.7 Hz), 7.08–7.15 (3H, m), 7.23 (1H, d, J=7.8 Hz); IR (neat) 1165, 1101, 1057 cm$^{-1}$ 5) ethyl 3-(4-fluorophenyl)-2-[3-(2,2,3,3-tetrafluoropropyl) benzyl]-3-oxopropionate A solution of 1-methyl-3-(2,2,3,3-tetrafluoropropyl) benzene (1.363 g, 6.611 mmol), N-bromosuccinimide (1.18 g, 6.61 mmol) and 2,2'-azobis(isobutyronitrile) (30 mg) in carbon tetrachloride (20 ml) was heated under reflux for 1.5 hrs. After cooling the reaction solution to room temperature, the white precipitate was collected by filtration and the precipitate was washed with hexane. The solvent of the recovered filtrate was evaporated under reduced pressure to give a crude product of 3-(2,2,3,3-tetrafluoropropyl)benzyl bromide as a colorless liquid.

To a solution of ethyl (4-fluorobenzoyl)acetate (1.39 g, 6.61 mmol) in 1,2-dimethoxyethane (30 ml) was added a suspension (0.26 g, 6.61 mmol) of 60% sodium hydride in liquid paraffin under ice-cooling, and the mixture was stirred as it was for 0.5 hr. A solution of 3-(2,2,3,3-tetrafluoropropyl)benzyl bromide obtained above in 1,2-dimethoxyethane (10 ml) was added thereto at room temperature, and the mixture was stirred overnight at room temperature. The reaction solution was poured into water, and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=15/1–9/1) to give the objective substance.

yellow liquid yield 1.849 g, 68% $^1$H-NMR (CDCl$_3$, 300 MHz) δ 1.12 (3H, t, J=7.1 Hz), 3.22 (2H, t, J=18.0 Hz), 3.32 (1H, d, J=7.5 Hz), 3.33 (1H, d, J=7.2 Hz), 4.10 (2H, dq, J=1.7 Hz, 7.2 Hz), 4.56 (1H, t, J=7.7 Hz), 5.63 (1H, tt, J=3.3 Hz, 53.6 Hz), 7.08–7.24 (6H, m), 7.97 (2H, dd, 5.6 Hz, 8.9 Hz); IR (neat) 1738, 1688, 1599, 1508, 1233, 1159, 1101, 849 cm$^{-1}$ 6) ethyl (2RS,3RS)-3-(4-fluorophenyl)-3-hydroxy-2-[3-(2,2,3,3-tetrafluoropropyl)benzyl]propionate While stirring zinc chloride (1.22 g, 8.92 mmol) in diethyl ether (30 ml), sodium borohydride (0.68 g, 17.8 mmol) was added at room temperature, and the mixture was stirred as it was for 2 hrs. Insoluble material in the mixture was removed by filtration and washed with diethyl ether to give a solution of zinc borohydride in diethyl ether. A solution of ethyl 3-(4-fluorophenyl)-2-[3-(2,2,3,3-tetrafluoropropyl)benzyl]-3-oxopropionate (1.849 g, 4.462 mmol) in diethyl ether (20 ml) was added to the obtained solution under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=3/1) to give the objective substance.

colorless liquid yield 1.378 g, 74% $^1$H-NMR (CDCl$_3$, 300 MHz) δ 0.91 (3H, t, J=7.1 Hz), 2.92 (1H, d, J=2.7 Hz), 2.98 (2H, s), 3.20 (2H, t, J=17.9 Hz), 3.87 (2H, dq, J=2.0 Hz, 7.2 Hz), 5.01 (1H, t, J=3.6 Hz), 5.66 (1H, tt, J=3.3 Hz, 53.7 Hz), 7.01–7.11 (5H, m), 7.22 (1H, t, J=7.5 Hz), 7.37 (2H, dd, J=5.3 Hz, 8.6 Hz); IR (neat) 3445, 1715, 1607, 1512, 1375, 1346, 1223, 1159, 1100, 1057, 839 cm$^{-1}$ 7) (4RS,5SR)-5-(4-fluorophenyl)-4-[3-(2,2,3,3-tetrafluoropropyl)benzyl]-1,3-oxazolidin-2-one A mixture of ethyl (2RS,3RS)-3-(4-fluorophenyl)-3-hydroxy-2-[3-(2,2,3,3-tetrafluoropropyl)benzyl]propionate (1.378 g, 3.309 mmol), sodium hydroxide (0.26 g, 6.62 mmol), methanol (10 ml), water (5 ml) and tetrahydrofuran (10 ml) was stirred overnight at room, temperature. The reaction solution was concentrated and diluted with water, acidified with 1N hydrochloric acid and extracted twice with ethyl acetate. The recovered organic layer was dried over anhydrous sodium sulfate, and the solvent was evaporated under reduced pressure to give a crude product of (2RS,3RS)-3-(4-fluorophenyl)-3-hydroxy-2-[3-(2,2,3,3-tetrafluoropropyl)benzyl]propionic acid as a liquid.

To a solution of the liquid obtained above in tetrahydrofuran (30 ml) were added triethylamine (0.55 ml, 3.97 mmol) and diphenylphosphoryl azide (1.00 g, 3.64 mmol), and the mixture was stirred at 65° C. overnight. The solvent of the reaction solution was evaporated under reduced pressure and the obtained crude product was purified by silica gel column chromatography (hexane/ethyl acetate=3/1–1/1). Crystallization from diisopropyl ether-hexane gave the objective substance.

white crystal yield 1.022 g, 80% mp 91–93° C.; $^1$H-NMR (CDCl$_3$, 300 MHz) δ 2.24 (1H, dd, J=10.1 Hz, 14.0 Hz), 2.31 (1H, dd, J=4.8 Hz, 13.5 Hz), 3.22 (2H, t, J=17.9 Hz), 4.21–4.28 (1H, m), 5.15 (1H, s), 5.72 (1H, tt, J=3.0 Hz, 53.9 Hz), 5.79 (1H, d, J=7.8 Hz), 6.95 (1H, s), 6.99 (1H, d, J=7.8 Hz), 7.10–7.18 (3H, m), 7.28 (1H, t, J=7.7 Hz), 7.36 (2H, dd, J=5.1 Hz, 8.4 Hz); IR (KBr) 3241, 1757, 1740, 1512, 1343, 1223, 1167, 1094, 1051, 835, 712 cm$^{-1}$; Anal. Calcd for C$_{19}$H$_{16}$F$_5$NO$_2$: C, 59.22; H, 4.19; N, 3.63. Found: C, 59.20; H, 4.22; N, 3.66.

8) (1RS,2SR)-2-amino-1-(4-fluorophenyl)-3-[3-(2,3,3-trifluoro-1-propenyl)phenyl]propan-1-ol (4RS,5SR)-5-(4-fluorophenyl)-4-[3-(2,2,3,3-tetrafluoropropyl)benzyl]-1,3-oxazolidin-2-one (0.880 g, 2.284 mmol) and sodium hydroxide (0.37 g, 9.14 mmol) were heated under reflux in ethanol (10 ml)-water (0.5 ml) for 3 hrs. The reaction solution was diluted with water and extracted twice with ethyl acetate. The recovered organic layer was dried over anhydrous sodium sulfate and passed through APS-silica gel. The solvent was evaporated under reduced pressure and the residue was crystallized from ethyl acetate-diethyl ether-hexane to give the objective substance.

white crystal yield 0.462 g, 60% mp 98–99° C.; $^1$H-NMR (CDCl$_3$, 300 MHz) δ 2.36 (1H, dd, J=10.2 Hz, 13.5 Hz), 2.81 (1H, dd, J=3.3 Hz, 13.8 Hz), 3.26–3.32 (1H, m), 4.67 (1H, d, J=4.8 Hz), 6.07 (1H, d, J=37.2 Hz), 6.15 (1H, dt, J=7.2 Hz, 53.8 Hz), 7.05–7.14 (3H, m), 7.28–7.43 (5H, m); IR (KBr) 3100-2750, 1508, 1406, 1362, 1223, 1103, 1042 cm$^{-1}$; Anal. Calcd for C$_{18}$H$_{17}$F$_4$NO: C, 63.71; H, 5.05; N, 4.13. Found: C, 63.49; H, 5.07; N, 4.12.

9) N-[(1RS,2SR)-2-(4-fluorophenyl)-2-hydroxy-1-[3-(2,3,3-trifluoro-1-propenyl)benzyl]ethyl]-6,7-dihydro-5H-benzo[a]cycloheptene-1-carboxamide While stirring (1RS,2SR)-2-amino-1-(4-fluorophenyl)-3-[3-(2,3,3-trifluoro-1-propenyl)phenyl]propan-1-ol (0.100 g, 0.295 mmol), 6,7-dihydro-5H-benzo[a]cyclohepten-1-carboxylic acid (55 mg, 0.29 mmol) and 1-hydroxybenzotriazole hydrate (45 mg, 0.29 mmol) in acetonitrile (10 ml), 1-ethyl-3-(3-dimethylaminopropyl) carbodiimide hydrochloride (56 mg, 0.29 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white powder yield 0.122 g, 81% mp 165–167° C.; $^1$H-NMR (CDCl$_3$, 300 MHz) δ 1.95–2.03 (2H, m), 2.16–2.22 (2H, m), 2.66 (2H, t, J=6.2 Hz), 2.76 (1H, dd, J=10.8 Hz, 14.7 Hz), 3.00 (1H, dd, J=4.4 Hz, 14.6 Hz), 3.69 (1H, d, J=4.2 Hz), 4.64–4.73 (1H, m), 5.04 (1H, t, J=3.9 Hz), 5.72 (1H, d, J=8.1 Hz), 5.89 (1H, td, J=5.6 Hz, 11.3 Hz), 6.06 (1H, d, J=37.2 Hz), 6.14 (1H, dt, J=7.2 Hz, 53.7 Hz), 6.17 (1H, d, J=11.7 Hz), 6.97 (1H, dd, J=1.5 Hz, 7.8 Hz), 7.03–7.19 (5H, m), 7.29–7.34 (2H, m), 7.41–7.48 (3H, m); IR (KBr) 3272, 2938, 1638, 1512, 1345, 1227, 1182, 1101, 1038, 772 cm$^{-1}$; Anal. Calcd for C$_{30}$H$_{27}$F$_4$NO$_2$: C, 70.72; H, 5.34; N, 2.75. Found: C, 70.43; H, 5.26; N, 2.71.

Example 336

4-fluoro-N-[(1RS,2SR)-2-(4-fluorophenyl)-2-hydroxy-1-[3-(2,3,3-trifluoro-1-propenyl)benzyl]ethyl]naphthalene-1-carboxamide While stirring (1RS,2SR)-2-amino-1-(4-fluorophenyl)-3-[3-(2,3,3-trifluoro-1-propenyl)phenyl]propan-1-ol (0.100 g, 0.295 mmol), 4-fluoro-1-naphthoic acid (56 mg, 0.29 mmol) and 1-hydroxybenzotriazole hydrate (45 mg, 0.29 mmol) in acetonitrile (10 ml), 1-ethyl-3-(3-dimethylaminopropyl)carbodiimide hydrochloride (56 mg, 0.29 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from diisopropyl ether-hexane to give the objective substance.

white powder yield 0.122 g, 81% mp 184–185° C.; $^1$H-NMR (CDCl$_3$, 300 MHz) δ 2.81 (1H, dd, J=10.7 Hz, 14.3 Hz), 3.06 (1H, dd, J=4.1 Hz, 14.6 Hz), 3.49 (1H, d, J=3.3 Hz), 4.73–4.82 (1H, m), 5.10 (1H, t, J=3.8 Hz), 5.89 (1H, d, J=8.1 Hz), 6.05 (1H, d, J=37.2 Hz), 6.12 (1H, dt, J=7.2 Hz, 53.7 Hz), 7.01 (1H, dd, J=7.7 Hz, 10.1 Hz), 7.09 (2H, t, J=8.6 Hz), 7.16–7.57 (9H, m), 7.75 (1H, d, J=8.7 Hz), 8.08 (1H, d, J=8.4 Hz); IR (KBr) 3275, 1642, 1512, 1229, 1051, 837, 760 cm$^{-1}$; Anal. Calcd for C$_{29}$H$_{22}$F$_5$NO$_2$: C, 68.10; H, 4.34; N, 2.74. Found: C, 67.77; H, 4.19; N, 2.74.

Example 337 tert-butyl N-[(1RS,2SR)-2-(4-fluorophenyl)-2-hydroxy-1-[3-(2,2,3,3-tetrafluoropropyl)benzyl]ethyl]carbamate 1) tert-butyl (4RS,5SR)-5-(4-fluorophenyl)-2-oxo-4-[3-(2,2,3,3-tetrafluoropropyl)benzyl]-1,3-oxazolidine-3-carboxylate A solution of (4RS,5SR)-5-(4-fluorophenyl)-4-[3-(2,2,3,3-tetrafluoropropyl)benzyl]-1,3-oxazolidin-2-one (2.368 g, 6.145 mmol), di-tert-butyl dicarbonate (1.61 g, 7.37 mmol) and 4-N,N-dimethylaminopyridine (75 mg, 0.61 mmol) in acetonitrile (30 ml) was stirred overnight at room temperature. The solvent of the reaction solution was evaporated under reduced pressure and the obtained residue was purified by silica gel column chromatography (hexane/ethyl acetate=3/1–1/1) to give the objective substance.

pale-yellow liquid yield 3.014 g, 100% $^1$H-NMR (CDCl$_3$, 200 MHz) δ 1.51 (9H, s), 2.57 (1H, dd, J=9.0 Hz, 14.0 Hz), 2.90 (1H, dd, J=4.4 Hz, 14.4 Hz), 3.11 (2H, br t, J=18.3 Hz), 4.77–4.87 (1H, m), 5.67 (1H, d, J=8.0 Hz), 5.69 (1H, tt, J=3.2 Hz, 53.8 Hz), 6.60–6.64 (2H, m), 6.93 (2H, t, J=8.6 Hz), 7.03–7.16 (4H, m); IR (neat) 2982, 1817, 1723, 1514, 1360, 1302, 1227, 1155, 1101, 1067 cm$^{-1}$ 2) tert-butyl N-[(1RS,2SR)-2-(4-fluorophenyl)-2-hydroxy-1-[3-(2,2,3,3-tetrafluoropropyl)benzyl]ethyl]carbamate To a solution of tert-butyl (4RS,5SR)-5-(4-fluorophenyl)-2-oxo-4-[3-(2,2,3,3-tetrafluoropropyl)benzyl]-1,3-oxazolidine-3-carboxylate (3.014 g, 6.209 mmol) in tetrahydrofuran (30 ml) was added a solution of sodium hydroxide (0.26 g, 6.52 mmol) in methanol (10 ml) under ice-cooling, and the mixture was stirred at 0° C. for 0.5 hr. The reaction solution was diluted with ethyl acetate, washed with water, dried over anhydrous magnesium sulfate and passed through silica gel. The solvent was evaporated under reduced pressure. The obtained residue was crystallized from ethyl acetate-diisopropyl ether-hexane to give the objective substance.

white crystal yield 2.367 g, 83% mp 168–169° C.; $^1$H-NMR (CDCl$_3$-DMSO-d$_6$, 300 MHz) δ 1.30 (9H, s), 2.64–2.78 (2H, m), 3.21 (2H, t, J=17.7 Hz), 4.05 (1H, br s), 4.54 (1H, s), 4.87 (1H, br s), 5.08 (1H, br d, J=8.4 Hz), 5.70 (1H, tt, J=3.9 Hz, 53.4 Hz), 7.01–7.10 (5H, m), 7.21 (1H, t, J=7.7 Hz), 7.41 (2H, dd, J=5.6 Hz, 8.6 Hz); IR (KBr) 3349, 1680, 1535, 1227, 1173, 1113, 1007, 837 cm$^{-1}$; Anal. Calcd for C$_{23}$H$_{26}$F$_5$NO$_3$: C, 60.13; H, 5.70; N, 3.05. Found: C, 60.04; H, 5.73; N, 2.91.

Example 338

N-[(1RS,2SR)-2-(4-fluorophenyl)-2-hydroxy-1-[3-(2,2,3,3-tetrafluoropropyl)benzyl]ethyl]-6,7-dihydro-5H-benzo[a]cycloheptene-1-carboxamide 1) (1RS,2SR)-2-amino-1-(4-fluorophenyl)-3-[3-(2,2,3,3-tetrafluoropropyl)phenyl]propan-1-ol A mixture of tert-butyl N-[(1RS,2SR)-2-(4-fluorophenyl)-2-hydroxy-1-[3-(2,2,3,3-tetrafluoropropyl)benzyl]ethyl]carbamate (2.188 g, 4.762 mmol) and trifluoroacetic acid (10 ml) were stirred at room temperature for 1 hr. The reaction solution was evaporated under reduced pressure, diluted with water, alkalified with potassium carbonate, and extracted twice with ethyl acetate. The recovered organic layer was dried over anhydrous sodium sulfate and passed through APS-silica gel. The solvent was evaporated under reduced pressure to give the objective substance.

yellow liquid yield 1.720 g, 100% $^1$H-NMR (CDCl$_3$, 300 MHz) δ 2.35 (1H, dd, J=10.4 Hz, 13.7 Hz) 2.80 (1H, dd, J=3.3 Hz, 13.5 Hz), 3.24 (2H, t, J=18.6 Hz), 3.25–3.29 (1H, m), 4.66 (1H, d, J=4.8 Hz), 5.70 (1H, tt, J=3.2 Hz, 53.8 Hz), 7.04–7.16 (5H, m), 7.28 (1H, t, J=7.7 Hz), 7.37 (2H, dd, J=5.4 Hz, 8.7 Hz); IR (neat) 3365-2860, 1605, 1508, 1223, 1157, 1101, 1057, 837 cm$^{-1}$ 2) N-[(1RS,2SR)-2-(4-fluorophenyl)-2-hydroxy-1-[3-(2,2,3,3-tetrafluoropropyl)benzyl]ethyl]-6,7-dihydro-5H-benzo[a]cycloheptene-1-carboxamide While stirring (1RS,2SR)-2-amino-1-(4-fluorophenyl)-3-[3-(2,2,3,3-tetrafluoropropyl)phenyl]propan-1-ol (0.300 g, 0.835 mmol), 6,7-dihydro-5H-benzo[a]cycloheptene-1-carboxylic acid (0.16 g, 0.83 mmol) and 1-hydroxybenzotriazole hydrate (0.13 g, 0.83 mmol) in acetonitrile (10 ml), 1-ethyl-3-(3-dimethylaminopropyl)carbodiimide hydrochloride (0.16 g, 0.83 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 0.325 g, 74% mp 165–166° C.; $^1$H-NMR (CDCl$_3$, 300 MHz) δ 1.95–2.04 (2H, m), 2.16–2.22 (2H, m), 2.64–2.68 (2H, m), 2.74 (1H, dd, J=10.5 Hz, 14.4 Hz), 2.99 (1H, dd; J=4.1 Hz, 14.6 Hz), 3.22 (2H, t, J=18.0 Hz), 3.75 (1H, d, J=3.9 Hz), 4.65–4.74 (1H, m), 5.02 (1H, t, J=3.9 Hz), 5.68 (1H, tt, J=3.4 Hz, 53.7 Hz), 5.70 (1H, d, J=9.0 Hz), 5.91 (1H, td, J=5.5 Hz, 11.7 Hz), 6.21 (1H, d, J=11.7 Hz), 6.91 (1H, d, J=7.8 Hz), 7.02–7.10 (4H, m), 7.14–7.17 (3H, m), 7.7.28 (1H, t, J=7.2 Hz), 7.43 (2H, dd, J=5.3 Hz, 8.6 Hz); IR (KBr) 3281, 1638, 1514, 1229, 1105, 835 cm$^{-1}$; Anal. Calcd for C$_{30}$H$_{28}$F$_5$NO$_2$: C, 68.04; H, 5.33; N, 2.65. Found: C, 67.89; H, 5.34; N, 2.47.

Example 339

4-fluoro-N-[(1RS,2SR)-2-(4-fluorophenyl)-2-hydroxy-1-[3-(2,2,3,3-tetrafluoropropyl)benzyl]ethyl]naphthalene-1-carboxamide While stirring (1RS,2SR)-2-amino-1-(4-fluorophenyl)-3-[3-(2,2,3,3-tetrafluoropropyl)phenyl]propan-1-ol (0.300 g, 0.835 mmol), 4-fluoro-1-naphthoic acid (0.16 g, 0.83 mmol) and 1-hydroxybenzotriazole hydrate (0.13 g, 0.83 mmol) in acetonitrile (10 ml), 1-ethyl-3-(3-dimethylaminopropyl) carbodiimide hydrochloride (0.16 g, 0.83 mol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from ethyl acetate-diisopropyl ether-hexane to give the objective substance.

white powder yield 0.349 g, 79% mp 172–173° C.; $^1$H-NMR (CDCl$_3$-DMSO-d$_6$, 300 MHz) δ 2.86 (1H, dd, J=10.7 Hz, 14.3 Hz), 2.97 (1H, dd, J=4.2 Hz, 14.1 Hz), 3.20 (2H, t, J=17.9 Hz), 4.73–4.82 (1H, m), 4.92 (1H, d, J=3.6 Hz), 5.06 (1H, t, J=3.5 Hz), 5.69 (1H, tt, J=3.5 Hz, 53.5 Hz), 6.90 (1H, d, J=9.0 Hz), 7.01 (1H, dd, J=7.7 Hz, 10.1 Hz), 7.08 (2H, t, J=8.4 Hz), 7.14–7.29 (5H, m), 7.43 (1H, t, J=7.5 Hz), 7.50–7.55 (3H, m), 7.73 (1H, d, J=8.4 Hz), 8.06 (1H, d, J=8.1 Hz); IR (KBr) 3274, 1644, 1539, 1514, 1236, 1103, 1055, 837, 760 cm$^{-1}$; Anal. Calcd for C$_{29}$H$_{23}$F$_6$NO$_2$: C, 65.54; H, 4.36; N, 2.64. Found: C, 65.53; H, 4.39; N, 2.34.

Example 340

5-chloro-N-[(1RS,2SR)-2-(4-fluorophenyl)-2-hydroxy-1-[3-(2,2,3,3-tetrafluoropropyl)benzyl]ethyl]naphthalene-1-carboxamide While stirring (1RS,2SR)-2-amino-1-(4-fluorophenyl)-3-[3-(2,2,3,3-tetrafluoropropyl)phenyl]propan-1-ol (0.300 g, 0.835 mmol), 5-chloro-1-naphthoic acid (0.16 g, 0.83 mmol) and 1-hydroxybenzotriazole hydrate (0.13 g, 0.83 mmol) in acetonitrile (10 ml), 1-ethyl-3-(3-dimethylaminopropyl) carbodiimide hydrochloride (0.16 g, 0.83 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=3/1–1/1). Crystallization from ethyl acetate-diisopropyl ether-hexane gave the objective substance.

white crystal yield 0.285 g, 62% mp 174–175° C.; $^1$H-NMR (CDCl$_3$-DMSO-d$_6$, 300 MHz) δ 2.85 (1H, dd, J=11.0 Hz, 14.3 Hz), 2.98 (1H, dd, J=3.6 Hz, 14.7 Hz), 3.21 (2H, t, J=18.0 Hz), 4.75–4.85 (1H, m), 4.90 (1H, d, J=3.6 Hz), 5.05 (1H, t, J=3.5 Hz), 5.69 (1H, tt, J=3.6 Hz, 53.7 Hz), 7.00 (1H, d, J=9.0 Hz), 7.05–7.29 (8H, m), 7.45–7.56 (5H, m), 8.30 (1H, d, J=8.4 Hz); IR (KBr) 3275, 1638, 1539, 1514, 1233, 1100, 837, 785, 708 cm$^{-1}$; Anal. Calcd for C$_{29}$H$_{23}$ClF$_5$NO$_2$: C, 63.57; H, 4.23; N, 2.56. Found: C, 63.59; H, 4.14; N, 2.68.

Example 341 tert-butyl N-[(1RS,2SR)-1-[3-(1,2-difluoro-2-methylpropyl)benzyl]-2-(4-fluorophenyl)-2-hydroxyethyl]carbamate 1) ethyl 2-methyl-2-(3-methylphenyl)propionate To a solution of ethyl 3-tolylacetate (30.92 g, 173.5 mmol) in N,N-dimethylformamide (150 ml) was added a suspension (15.3 g, 382 mmol) of 60% sodium hydride in liquid paraffin under ice-cooling, and the mixture was stirred at room temperature for 0.5 hr. Methyl iodide (32.2 ml, 520 mmol) was added thereto at 0° C., and the mixture was stirred overnight at room temperature. The reaction solution was poured into water and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=50/1–15/1) to give the objective substance.

colorless liquid yield 30.22 g, 84% $^1$H-NMR (CDCl$_3$, 200 MHz) δ 1.19 (3H, t, J=7.1 Hz), 1.56 (6H, s), 2.35 (3H, s), 4.12 (2H, q, J=7.2 Hz), 7.03–7.22 (4H, m); IR (neat) 2976, 1730, 1252, 1146, 702 cm$^{-1}$ 2) 2-methyl-2-(3-methylphenyl)propan-1-ol To a suspension of lithium aluminum hydride (3.52 g, 92.9 mmol) in tetrahydrofuran (150 ml) was dropwise added a solution of ethyl 2-methyl-2-(3-methylphenyl)propionate (19.16 g, 92.88 mmol) in tetrahydrofuran (100 ml) under ice-cooling, and the mixture was stirred at room temperature for 1 hr. After ice-cooling the reaction solution, water (3.5 ml), 15% aqueous sodium hydroxide solution (3.5 ml) and water (9 ml) were successively added dropwise to decompose excess lithium aluminum hydride. The mixture was stirred as it was at room temperature for 2 hrs. The resulting precipitate was removed by filtration, and the precipitate was washed with ethyl acetate. The solvent of the recovered filtrate was evaporated under reduced pressure and the obtained residue was purified by silica gel column chromatography (hexane/ethyl acetate=6/1) to give the objective substance.

colorless liquid yield 12.99 g, 85% $^1$H-NMR (CDCl$_3$, 300 MHz) δ 1.22 (1H, t, J=6.6 Hz), 1.33 (6H, s), 2.36 (3H, s), 3.61 (2H, d, J=6.9 Hz), 7.04 (1H, d, J=7.2 Hz), 7.17–7.27 (3H, m); IR (neat) 3370, 2963, 1042, 783, 704 cm$^{-1}$ 3) 2-methyl-2-(3-methylphenyl)propanal To a solution of oxalyl chloride (15.1 g, 119 mmol) in tetrahydrofuran (150 ml) was dropwise added a solution of dimethyl-sulfoxide (16.8 ml, 237 mmol) in tetrahydrofuran (50 ml) at −78° C., and the mixture was stirred for 5 min. A solution of 2-methyl-2-(3-methylphenyl)propan-1-ol (12.99 g, 79.09 mmol) in tetrahydrofuran (80 ml) was added at −78° C., and the mixture was stirred for 15 min. Triethylamine (66.1 ml, 475 mmol) was added thereto, and the mixture was warmed to room temperature. The reaction mixture was poured into water and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=15/1) to give the objective substance.

pale-yellow liquid yield 11.72 g, 91% $^1$H-NMR (CDCl$_3$, 300 MHz) δ 1.45 (6H, s), 2.36 (3H, s), 7.07–7.7.12 (3H, m), 7.27 (1H, t, J=8.0 Hz), 9.49 (1H, s); IR (neat) 2975, 1728, 785, 704 cm$^{-1}$ 4) 1-(1,2-difluoro-2-methylpropyl)-3-methylbenzene To a solution of (diethylamino)sulfur trifluoride (7.31 g, 45.4 mmol) in methylene chloride (20 ml) at −78° C. was added a solution of 2-methyl-2-(3-methylphenyl)propanal (7.360 g, 45.37 mmol) in methylene chloride (10 ml) at room temperature, and the mixture was stirred at room temperature for 0.5 hr. To the reaction solution was added water, and the mixture was stirred. The methylene chloride layer was separated and the aqueous layer was extracted with diethyl ether. The recovered organic layer was dried over anhydrous magnesium sulfate. The solvent was evaporated under reduced pressure and the obtained residue was purified by silica gel column chromatography (hexane-hexane/ethyl acetate=30/1) to give the objective substance.

colorless liquid yield 2.747 g, 33% $^1$H-NMR (CDCl$_3$, 300 MHz) δ 1.33 (3H, dd, J=1.5 Hz, 16.2 Hz), 1.40 (3H, dd, J=2.0 Hz, 16.4 Hz), 2.37 (3H, s), 5.29 (1H, dd, J=13.8 Hz, 45.3 Hz), 7.14–7.18 (3H, m), 7.27 (1H, t, J=7.8 Hz); IR (neat) 2988, 1387, 1157, 1036, 775, 702 cm$^{-1}$ 5) ethyl 2-[3-(1,2-difluoro-2-methylpropyl)benzyl]-3-(4-fluorophenyl)-3-oxopropionate A solution of 1-(1,2-difluoro-2-methylpropyl)-3-methylbenzene (2.747 g, 14.91 mmol), N-bromosuccinimide (2.65 g, 14.9 mmol) and 2,2'-azobis(isobutyronitrile) (0.1 g) in carbon tetrachloride (30 ml) was heated under reflux for 1.5 hrs. After cooling the reaction solution to room temperature, white precipitate was collected by filtration and washed with hexane. The solvent of the recovered filtrate was evaporated under reduced pressure to give a crude product of 3-(1,2-difluoro-2-methylpropyl)benzyl bromide as a yellow liquid.

To a solution of ethyl (4-fluorobenzoyl)acetate (3.13 g, 14.9 mmol) in 1,2-dimethoxyethane (40 ml) was added a suspension (0.60 g, 14.9 mmol) of 60% sodium hydride in liquid paraffin under ice-cooling, and the mixture was stirred as it was for 0.5 hr. A solution of the liquid obtained above in 1,2-dimethoxyethane (10 ml) was added thereto at room temperature, and the mixture was stirred overnight at room temperature. The reaction solution was poured into water, and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=15/1–9/1) to give the objective substance.

yellow liquid yield 3.484 g, 60% $^1$H-NMR (CDCl$_3$, 300 MHz) δ 1.12 (3H, t, J=7.1 Hz), 1.23–1.39 (6H, m), 3.34 (1H, d, J=7.5 Hz), 3.35 (1H, d, J=7.2 Hz), 4.10 (2H, q, J=7.1 Hz), 4.55 (0.5H, t, J=7.7 Hz), 4.58 (0.5H, t, J=7.5 Hz), 5.25 (0.5H, dd, J=14.1 Hz, 45.0 Hz), 5.26 (0.5H, dd, J=13.4 Hz, 45.2 Hz), 7.10 (2H, t, J=8.4 Hz), 7.16–7.24 (4H, m), 7.97 (2H, dd, J=5.4 Hz, 9.0 Hz); IR (neat) 2986, 1736, 1686, 1599, 1508, 1269, 1236, 1159, 1032, 849 cm$^{-1}$ 6) ethyl (2RS,3RS)-2-[3-(1,2-difluoro-2-methylpropyl)benzyl]-3-(4-fluorophenyl)-3-hydroxypropionate While stirring zinc chloride (2.37 g, 17.4 mmol) in diethyl ether (50 ml), sodium borohydride (1.32 g, 34.8 mmol) was added at room temperature, and the mixture was stirred as it was for 2 hrs. The insoluble material in the mixture was removed by filtration and washed with diethyl ether to give a solution of zinc borohydride in diethyl ether. A solution of ethyl 2-[3-(1,2-difluoro-2-methylpropyl)benzyl]-3-(4-fluorophenyl)-3-oxopropionate(3.412 g, 8.695 mmol) in diethyl ether (20 ml) was added to the obtained solution under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=3/1) to give the objective substance.

colorless liquid yield 2.919 g, 85% $^1$H-NMR (CDCl$_3$, 200 MHz) δ 0.92 (3H, t, J=7.1 Hz), 1.25–1.42 (6H, m), 2.89–2.93 (1H, m), 2.96–3.05 (3H, m), 3.86 (2H, q, J=7.1 Hz), 5.00 (1H, t, J=3.7 Hz), 5.24 (1H, dd, J=14.2 Hz, 45.2 Hz), 7.00–7.29 (6H, m), 7.37 (2H, dd, J=5.2 Hz, 8.8 Hz); IR (neat) 3445, 2986, 1728, 1605, 1510, 1375, 1225, 1159, 1032, 839 cm$^{-1}$ 7) (4RS,5SR)-4-[3-(1,2-difluoro-2-methylpropyl)benzyl]-5-(4-fluorophenyl)-1,3-oxazolidin-2-one A mixture of ethyl (2RS,3RS)-2-[3-(1,2-difluoro-2-methylpropyl)benzyl]-3-(4-fluorophenyl)-3-hydroxypropionate (2.849 g, 7.223 mmol), sodium hydroxide (0.58 g, 14.4 mmol), methanol (10 ml), water (10 ml) and tetrahydrofuran (10 ml) was stirred overnight at room temperature. The reaction solution was concentrated, diluted with water, acidified with hydrochloric acid, and extracted twice with ethyl acetate. The recovered organic layer was dried over anhydrous sodium sulfate, and the solvent was evaporated under reduced pressure to give a crude product of (2RS,3RS)-2-[3-(1,2-difluoro-2-ethylpropyl)benzyl]-3-(4-fluorophenyl)-3-hydroxypropionic acid as a liquid.

To a solution of the liquid obtained above in tetrahydrofuran (40 ml) were added triethylamine (1.21 ml, 8.67 mmol) and diphenylphosphoryl azide (2.19 g, 7.95 mmol), and the mixture was stirred at 65° C. overnight. The solvent of the reaction solution was evaporated under reduced pressure and the obtained crude product was purified by silica gel column chromatography (hexane/ethyl acetate=3/1–1/1) to give the objective substance.

white solid yield 2.245 g, 86% mp 130–131° C.; $^1$H-NMR (CDCl$_3$, 300 MHz) δ 1.28–1.41 (6H, m), 2.20–2.36 (2H, m), 4.21–4.30 (1H, m), 4.97 (1H, s), 5.24 (0.5H, dd, J=13.7 Hz, 44.9 Hz), 5.25 (0.5H, dd, J=14.0 Hz, 45.2 Hz), 5.80 (1H, d, J=8.1 Hz), 7.01–7.39 (8H, m); IR (KBr) 3250, 1742, 1514, 1236, 1223, 1022, 849 cm$^{-1}$; Anal. Calcd for C$_{20}$H$_{20}$F$_3$NO$_2$.0.1H$_2$O: C, 65.78; H, 5.58; N, 3.84. Found: C, 65.64; H, 5.50; N, 3.96.

8) tert-butyl (4RS,5SR)-4-[3-(1,2-difluoro-2-methylpropyl)benzyl]-5-(4-fluorophenyl)-2-oxo-1,3-oxazolidine-3-carboxylate A solution of (4RS,5SR)-4-[3-(1,2-difluoro-2-methylpropyl)benzyl]-5-(4-fluorophenyl)-1,3-oxazolidin-2-one (2.124 g, 5.845 mmol), di-tert-butyl dicarbonate (1.53 g, 7.01 mmol) and 4-N,N-dimethylaminopyridine (71 mg, 0.58 mmol) in acetonitrile (40 ml) was stirred overnight at room temperature. The solvent of the reaction solution was evaporated under reduced pressure and the obtained residue was purified by silica gel column chromatography (hexane/ethyl acetate=3/1–2/1) to give the objective substance.

pale-yellow liquid yield 2.633 g, 97% $^1$H-NMR (CDCl$_3$, 300 MHz) δ 1.24–1.38 (6H, m), 1.49 (4.5H, s), 1.53 (4.5H, s), 2.55–2.64 (1H, m), 2.85–2.96 (1H, m), 4.79–4.86 (1H, m), 5.10 (0.5H, dd, J=13.2 Hz, 45.0 Hz), 5.17 (0.5H, dd, J=14.6 Hz, 45.2 Hz), 5.66 (0.5H, d, J=7.2 Hz), 5.67 (0.5H, d, J=6.6 Hz), 6.59–6.65 (1H, m), 6.67 (0.5H, s), 6.82 (0.5H, s), 6.91–6.98 (2H, m), 7.04–7.17 (4H, m); IR (neat) 2984, 1817, 1723, 1514, 1358, 1308, 1229, 1155, 1069 cm$^{-1}$ 9) tert-butyl N-[(1RS,2SR)-1-[3-(1,2-difluoro-2-methylpropyl)benzyl]-2-(4-fluorophenyl)-2-hydroxyethyl]carbamate To a solution of tert-butyl (4RS,5SR)-4-[3-(1,2-difluoro-2-methylpropyl)benzyl]-5-(4-fluorophenyl)-2-oxo-1,3-oxazolidine-3-carboxylate (2.584 g, 5.575 mmol) in tetrahydrofuran (20 ml) was added a solution of sodium hydroxide (0.22 g, 5.57 mmol) in methanol (5 ml) under ice-cooling, and the mixture was stirred at room temperature for 1 hr. The reaction solution was diluted with ethyl acetate, washed with water, dried over anhydrous magnesium sulfate and passed through silica gel. The solvent was evaporated under reduced pressure to give the objective substance.

white solid yield 2.300 g, 94% mp 148–149° C.; $^1$H-NMR (CDCl$_3$, 300 MHz) δ 1.28–1.41 (6H, m), 1.34 (9H, s), 2.65 (1H, dd, J=10.1 Hz, 14.3 Hz), 2.80 (1H, dd, J=4.7 Hz, 14.3 Hz), 3.38 (1H, br s), 4.09 (1H, br s), 4.50 (1H, br d, J=6.9 Hz), 4.90 (1H, br s), 5.27 (1H, dd, J=13.7 Hz, 45.2 Hz), 7.07 (2H, t, J=8.7 Hz), 7.11–7.13 (2H, m), 7.18–7.31 (2H, m), 7.37 (2H, dd, J=5.6 Hz, 8.6 Hz); IR (KBr) 3366, 2988, 1682, 1532, 1514, 1225, 1171, 1007 cm$^{-1}$; Anal. Calcd for $C_{24}H_{30}F_3NO_3$: C, 65.89; H, 6.91; N, 3.20. Found: C, 65.62; H, 6.88; N, 3.22.

Example 342

N-[(1RS,2SR)-1-[3-(1,2-difluoro-2-methylpropyl)benzyl]-2-(4-fluorophenyl)-2-hydroxyethyl]-6,7-dihydro-5H-benzo[a]cycloheptene-1-carboxamide 1) (1RS,2SR)-2-amino-3-[3-(1,2-difluoro-2-methylpropyl)phenyl]-1-(4-fluorophenyl)propan-1-ol A mixture of tert-butyl N-[(1RS,2SR)-1-[3-(1,2-difluoro-2-methylpropyl)benzyl]-2-(4-fluorophenyl)-2-hydroxyethyl]carbamate (2.139 g, 4.889 mmol) and trifluoroacetic acid (10 ml) was stirred at room temperature for 1 hr. The reaction solution was evaporated under reduced pressure, diluted with water, alkalified with potassium carbonate, and extracted twice with ethyl acetate. The recovered organic layer was dried over anhydrous sodium sulfate and passed through APS-silica gel. The solvent was evaporated under reduced pressure to give the objective substance.

pale-yellow liquid yield 1.650 g, 100% $^1$H-NMR (CDCl$_3$, 300 MHz) δ 1.31 (3H, d, J=15.3 Hz), 1.38 (3H, d, J=14.7 Hz), 2.36 (1H, dd, J=10.2 Hz, 13.5 Hz), 2.81 (1H, dd, J=3.2 Hz, 13.4 Hz), 3.25–3.32 (1H, m), 4.66 (1H, d, J=4.8 Hz), 5.28 (1H, dd, J=13.8 Hz, 45.3 Hz), 7.08 (2H, t, J=8.7 Hz), 7.11–7.33 (4H, m), 7.37 (2H, dd, J=5.6 Hz, 8.6 Hz); IR (neat) 3360-2860, 1605, 1508, 1387, 1373, 1223, 1157, 1034, 839 cm$^{-1}$ 2) N-[(1RS,2SR)-1-[3-(1,2-difluoro-2-methylpropyl)benzyl]-2-(4-fluorophenyl)-2-hydroxyethyl]-6,7-dihydro-5H-benzo[a]cycloheptene-1-carboxamide While stirring (1RS,2SR)-2-amino-3-[3-(1,2-difluoro-2-methylpropyl)phenyl]-1-(4-fluorophenyl)propan-1-ol (0.200 g, 0.593 mmol), 6,7-dihydro-5H-benzo[a]cycloheptene-1-carboxylic acid (0.11 g, 0.59 mmol) and 1-hydroxybenzotriazole hydrate (91 mg, 0.59 mmol) in acetonitrile (10 ml), 1-ethyl-3-(3-dimethylaminopropyl)carbodiimide hydrochloride (0.11 g, 0.59 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=3/1–1/1). Crystallization from diisopropyl ether-hexane gave the objective substance.

white powder yield 0.184 g, 61% mp 102–104° C.; $^1$H-NMR (CDCl$_3$, 300 MHz) δ 1.25–1.39 (6H, m), 1.95–2.03 (2H, m), 2.16–2.22 (2H, m), 2.66 (2H, t, J=5.7 Hz), 2.69–2.82 (1H, m), 2.98–3.03 (1H, m), 3.79 (0.5H, d, J=3.9 Hz), 3.82 (0.5H, d, J=3.9 Hz), 4.65–4.74 (1H, m), 5.02 (1H, t, J=3.6 Hz), 5.24 (0.5H, dd, J=14.0 Hz, 45.2 Hz), 5.27 (0.5H, dd, J=13.5 Hz, 45.0 Hz), 5.70 (1H, d, J=8.7 Hz), 5.88–5.96 (1H, m), 6.20 (1H, d, J=12.3 Hz), 6.91–6.95 (1H, m), 7.02–7.34 (8H, m), 7.43 (2H, dd, J=5.3 Hz, 8.6 Hz); IR (KBr) 3295, 2938, 1638, 1510, 1225, 1034, 772 cm$^{-1}$; Anal. Calcd for $C_{31}H_{32}F_3NO_2 \cdot 0.1H_2O$: C, 73.09; H, 6.37; N, 2.75. Found: C, 72.87; H, 6.31; N, 2.62.

Example 343

4-fluoro-N-[(1RS,2SR)-1-[3-(1,2-difluoro-2-methylpropyl)benzyl]-2-(4-fluorophenyl)-2-hydroxyethyl]naphthalene-1-carboxamide While stirring (1RS,2SR)-2-amino-3-[3-(1,2-difluoro-2-methylpropyl)phenyl]-1-(4-fluorophenyl)propan-1-ol (0.200 g, 0.593 mmol), 4-fluoro-1-naphthoic acid (0.11 g, 0.59 mmol) and 1-hydroxybenzotriazole hydrate (91 mg, 0.59 mmol) in acetonitrile (10 ml), 1-ethyl-3-(3-dimethylaminopropyl)carbodiimide hydrochloride (0.11 g, 0.59 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=3/1–1/1). Crystallization from diisopropyl ether-hexane gave the objective substance.

white powder yield 0.218 g, 72% mp 163–165° C.; $^1$H-NMR (CDCl$_3$, 300 MHz) δ 1.24–1.38 (6H, m), 2.74–2.87 (1H, m), 3.07 (1H, dd, J=4.1 Hz, 14.3 Hz), 3.62–3.64 (1H, m), 4.74–4.83 (1H, m), 5.07 (0.5H, t, J=4.1 Hz), 5.08 (0.5H, t, J=3.9 Hz), 5.22 (0.5H, dd, J=14.9 Hz, 45.2 Hz), 5.27 (0.5H, dd, J=13.4 Hz, 44.9 Hz), 5.86 (0.5H, d, J=8.1 Hz), 5.88 (0.5H, d, J=8.1 Hz), 6.96–7.37 (8H, m), 7.43–7.57 (4H, m), 7.77–7.84 (1H, m), 8.08 (1H, d, J=8.1 Hz); IR (KBr) 3291, 1642, 1626, 1512, 1231, 837, 768 cm$^{-1}$; Anal. Calcd for $3C_{30}H_{27}F_4NO_2 \cdot 0.2H_2O$: C, 70.22; H, 5.38; N, 2.73. Found: C, 69.96; H, 5.24; N, 2.70.

Example 344

N-[(1RS,2SR)-2-(3-chlorophenyl)-2-hydroxy-1-(4-neopentylbenzyl)ethyl]-6,7-dihydro-5H-benzo[a]cycloheptene-1-carboxamide 1) 4-neopentylbenzoic acid While stirring a suspension of aluminum chloride (4.43 g, 33.2 mmol) in methylene chloride (20 ml), a solution of trichloroacetyl chloride (6.04 g, 33.2 mmol) in methylene chloride (10 ml) was added dropwise at −78° C. The reaction solution was stirred for 15 min warmed to −50° C., and a solution of neopentylbenzene (4.922 g, 33.20 mmol) in methylene chloride (10 ml) was added. The mixture was stirred overnight at room temperature. The reaction solution was poured into ice water and the methylene chloride layer of the mixture was separated. The aqueous layer was extracted with diethyl ether. The recovered organic layer was dried over anhydrous magnesium sulfate and the solvent was evaporated under reduced pressure and the obtained residue was dissolved in tetrahydrofuran (30 ml), a solution of potassium hydroxide (3.73 g, 66.4 mmol) in water (40 ml) was added, and the mixture was stirred at room temperature for 10 min. The reaction solution was diluted with diethyl ether and water and the aqueous layer was separated. The obtained aqueous solution was acidified with conc. hydrochloric acid, and extracted twice with ethyl acetate. The recovered organic layer was dried over anhydrous magnesium sulfate, and the solvent was evaporated under reduced pressure to give the objective substance.

brown crystal yield 5.343 g, 84%

Recrystallization from diisopropyl ether-hexane gave white crystals.

mp 193–194° C.; $^1$H-NMR (CDCl$_3$, 300 MHz) δ 0.92 (9H, s), 2.58 (2H, s), 2.24 (2H, d, J=8.1 Hz), 8.02 (2H, d, J=8.4 Hz), 8.02 (1H, br s); IR (KBr) 3100-2550, 1682, 1426, 1319, 1296, 951, 731 cm$^{-1}$; Anal. Calcd for C$_{12}$H$_{16}$O$_2$: C, 74.97; H, 8.39. Found: C, 74.85; H, 8.47.

2) 4-neopentylbenzyl alcohol

To a suspension of lithium aluminum hydride (1.13 g, 29.9 mmol) in tetrahydrofuran (50 ml) was added dropwise a solution of 4-neopentylbenzoic acid (3.830 g, 19.92 mmol) in tetrahydrofuran (30 ml) under ice-cooling, and the mixture was stirred overnight at room temperature. After ice-cooling the reaction solution, water (1 ml), a 15% aqueous sodium hydroxide solution (1 ml) and water (2.5 ml) were successively added dropwise to decompose excess lithium aluminum hydride. The mixture was stirred as it was at room temperature for 2 hrs. The resulting precipitate was removed by filtration, and the precipitate was washed with ethyl acetate. The solvent of the recovered filtrate was evaporated under reduced pressure and the obtained residue was purified by silica gel column chromatography (hexane/ethyl acetate=6/1–3/1) to give the objective substance.

yellow liquid yield 2.446 g, 69% $^1$H-NMR (CDCl$_3$, 300 MHz) δ 0.90 (9H, s), 1.62 (1H, t, J=5.9 Hz), 2.49 (2H, s), 4.67 (2H, d, J=5.7 Hz), 7.12 (2H, d, J=8.1 Hz), 7.27 (2H, d, J=7.8 Hz); IR (neat) 3330, 2951, 1364, 1017 cm$^{-1}$ 3) ethyl 3-(3-chlorophenyl)-2-(4-neopentylbenzyl)-3-oxopropionate To a solution of 4-neopentylbenzyl alcohol (2.446 g, 13.72 mmol) and triethylamine (2.87 ml, 20.6 mmol) in ethyl acetate (50 ml) was added dropwise a solution of methanesulfonyl chloride (1.89 g, 16.5 mmol) in ethyl acetate (10 ml) under ice-cooling, and the mixture was stirred as it was for 10 min. The resulting precipitate was removed by filtration, and the precipitate was washed with diethyl ether. The solvent of the recovered filtrate was evaporated under reduced pressure to give a crude product of methanesulfonic acid ester as a yellow liquid.

To a solution of ethyl (3-chlorobenzoyl)acetate (3.11 g, 13.7 mmol) in 1,2-dimethoxyethane (20 ml) was added a suspension (0.55 g, 13.7 mmol) of 60% sodium hydride in liquid paraffin under ice-cooling, and the mixture was stirred as it was for 0.5 hr. A solution of methanesulfonic acid ester obtained above in 1,2-dimethoxyethane (20 ml) was added thereto at room temperature, and the mixture was stirred at room temperature for 3 days. The reaction solution was poured into water, and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=15/1) to give the objective substance.

pale-yellow liquid yield 4.648 g, 88% $^1$H-NMR (CDCl$_3$, 300 MHz) δ 0.85 (9H, s), 1.13 (3H, t, J=7.1 Hz), 2.42 (2H, s), 3.28–3.31 (2H, m), 4.07–4.15 (2H, m), 4.55 (1H, t, J=7.4 Hz), 7.00 (2H, d, J=7.8 Hz), 7.09 (2H, d, J=8.1 Hz), 7.36 (1H, t, J=7.7 Hz), 7.51 (1H, ddd, J=1.1 Hz, 1.9 Hz, 8.0 Hz), 7.78 (1H, ddd, J=1.1 Hz, 1.7 Hz, 7.7 Hz), 7.89 (1H, t, J=1.8 Hz); IR (neat) 2953, 1738, 1694, 1229 cm$^{-1}$ 4) ethyl (2RS,3RS)-3-(3-chlorophenyl)-3-hydroxy-2-(4-neopentylbenzyl)propionate While stirring zinc chloride (3.22 g, 23.6 mmol) in diethyl ether (30 ml), sodium borohydride (1.78 g, 47.2 mmol) was added at room temperature, and the mixture was stirred as it was for 2 hrs. Insoluble material in the mixture was removed by filtration and washed with diethyl ether to give a solution of zinc borohydride in diethyl ether. To the obtained solution was added a solution of ethyl 3-(3-chlorophenyl)-2-(4-neopentylbenzyl)-3-oxopropionate (4.564 g, 11.80 mmol) in diethyl ether (30 ml) under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=15/1–6/1) to give the objective substance.

colorless liquid yield 3.828 g, 83% $^1$H-NMR (CDCl$_3$, 200 MHz) δ 0.86 (9H, s), 0.95 (3H, t, J=7.2 Hz), 2.42 (2H, s), 2.84–3.00 (3H, m), 3.13 (1H, d, J=2.6 Hz), 3.91 (2H, q, J=7.1 Hz), 5.03 (1H, t, J=3.1 Hz), 6.98 (4H, s), 7.26 (3H, s), 7.42 (1H, s); IR (neat) 3468, 2951, 1726, 1709, 1476, 1375, 1364, 1236, 1184, 1032 cm$^{-1}$ 5) (4RS,5SR)-5-(3-chlorophenyl)-4-(4-neopentylbenzyl)-1,3-oxazolidin-2-one A mixture of ethyl (2RS,3RS)-3-(3-chlorophenyl)-3-hydroxy-2-(4-neopentylbenzyl)propionate (3.756 g, 9.657 mmol), sodium hydroxide (0.77 g, 19.3 mmol), methanol (20 ml), water (10 ml) and tetrahydrofuran (20 ml) was stirred overnight at room temperature. The reaction solution was concentrated, diluted with water, acidified with hydrochloric acid, and extracted twice with ethyl acetate. The recovered organic layer was dried over anhydrous sodium sulfate and the solvent was evaporated under reduced pressure to give a crude product of (2RS,3RS)-3-(3-chlorophenyl)-3-hydroxy-2-(4-neopentylbenzyl)propionic acid as a white solid.

To a solution of the solid obtained above in tetrahydrofuran (30 ml) were added triethylamine (1.62 ml, 11.6 mmol) and diphenylphosphoryl azide (2.92,g, 10.6 mmol) and the mixture was stirred at 65° C. overnight. The solvent of the reaction solution was evaporated under reduced pressure and the obtained crude product was purified by silica gel column chromatography (hexane/ethyl acetate=3/1–1/1). Crystallization from ethyl acetate-diisopropyl ether-hexane gave the objective substance.

white crystal yield 2.517 g, 73% mp 197–198° C.; $^1$H-NMR (CDCl$_3$, 200 MHz) δ 0.87 (9H, s), 2.18 (1H, dd, J=11.0 Hz, 13.6 Hz), 2.30 (1H, dd, J=4.0 Hz, 13.8 Hz), 2.44 (2H, s), 4.18–4.30 (1H, m), 4.99 (1H, br s), 5.76 (1H, d, J=8.2 Hz), 6.92 (2H, d, J=8.0 Hz), 7.04 (2H, d, J=8.0 Hz), 7.24–7.38 (4H, m); IR (KBr) 3268, 2959, 1740, 1240, 1017, 791 cm$^{-1}$; Anal. Calcd for C$_{21}$H$_{24}$ClNO$_2$: C, 70.48; H, 6.76; N, 3.91. Found: C, 70.56; H, 7.00; N, 3.62.

6) (1RS,2SR)-2-amino-1-(3-chlorophenyl)-3-(4-neopentylphenyl)propan-1-ol (4RS,5SR)-5-(3-Chlorophenyl)-4-(4-neopentylbenzyl)-1,3-oxazolidin-2-one (2.335 g, 6.525 mmol) and sodium hydroxide (1.04 g, 26.1 mmol) was heated under reflux in ethanol (30 ml)-water (1 ml) for 5 hrs. The reaction solution was diluted with water, and the mixture was stirred as it was for 0.5 hr. The resulting precipitate was collected and washed with water and diisopropyl ether-hexane to give the objective substance.

white powder yield 1.814 g, 84% mp 118–120° C.; $^1$H-NMR (CDCl$_3$, 300 MHz) δ 0.88 (9H, s), 2.31 (1H, dd, J=10.5 Hz, 13.8 Hz), 2.45 (2H, s), 2.72 (1H, dd, J=3.3 Hz, 13.8 Hz), 3.29 (1H, ddd, J=3.3 Hz, 4.8 Hz, 10.5 Hz), 4.67 (1H, d, J=4.5 Hz), 7.00–7.06 (5H, m), 7.24–7.32 (2H, m), 7.42 (1H, s); IR (KBr) 3130-2770, 2953, 1576, 1476, 1420, 1364, 1192, 1040, 949, 855, 779, 729 cm$^{-1}$; Anal. Calcd for C$_{20}$H$_{26}$ClNO: C, 72.38; H, 7.90; N, 4.22. Found: C, 72.24; H, 7.97; N, 4.02.

7) N-[(1RS,2SR)-2-(3-chlorophenyl)-2-hydroxy-1-(4-neopentylbenzyl)ethyl]-6,7-dihydro-5H-benzo[a]cycloheptene-1-carboxamide While stirring (1RS,2SR)-2-amino-1-(3-chlorophenyl)-3-(4-neopentylphenyl)propan-1-ol (0.300 g, 0.904 mmol), 6,7-dihydro-5H-benzo[a]cycloheptene-1-carboxylic acid (0.17 g, 0.90 mmol) and 1-hydroxybenzotriazole hydrate (0.14 g, 0.90 mmol) in acetonitrile (10 ml)-N,N-dimethylformamide (2 ml), 1-ethyl-3-(3-dimethylaminopropyl)carbodiimide hydrochloride (0.17 g, 0.90 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 0.377 g, 83% mp 147–149° C.; $^1$H-NMR (CDCl$_3$, 300 MHz) δ 0.88 (9H, s), 1.95–2.04 (2H, m), 2.17–2.23 (2H, m), 2.46 (2H, s), 2.62–2.71 (3H, m), 2.97 (1H, dd, J=4.2 Hz, 14.4 Hz), 4.38 (1H, d, J=4.2 Hz), 4.63–4.72 (1H, m), 5.04 (1H, t, J=3.8 Hz), 5.69 (1H, d, J=7.5 Hz), 5.99 (1H, td, J=5.4 Hz, 12.0 Hz), 6.33 (1H, d, J=11.7 Hz), 6.88 (1H, dd, J=1.2 Hz, 7.5 Hz), 7.01 (1H, t, J=7.5 Hz), 7.05 (4H, s), 7.14 (1H, d, J=6.3 Hz), 7.27–7.35 (3H, m), 7.48 (1H, s); IR (KBr) 3376, 3331, 2959, 1626, 1528, 779, 766 cm$^{-1}$; Anal. Calcd for C$_{32}$H$_{36}$ClNO$_2$: C, 76.55; H, 7.23; N, 2.79. Found: C, 76.38; H, 7.19; N, 2.52.

Example 345

4-fluoro-N-[(1RS,2SR)-2-(3-chlorophenyl)-2-hydroxy-1-(4-neopentylbenzyl)ethyl]naphthalene-1-carboxamide While stirring (1RS,2SR)-2-amino-1-7(3-chlorophenyl)-3-(4-neopentylphenyl)propan-1-ol (0.300 g, 0.904 mmol), 4-fluoro-1-naphthoic acid (0.17 g, 0.90 mmol) and 1-hydroxybenzotriazole hydrate (0.14 g, 0.90 mmol) in acetonitrile (10 ml)-N,N-dimethylformamide (2 ml), 1-ethyl-3-(3-dimethylaminopropyl)carbodiimide hydrochloride (0.17 g, 0.90 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 0.300 g, 66% mp 150–151° C.; $^1$H-NMR (CDCl$_3$, 300 MHz) δ 0.89 (9H, s), 2.48 (2H, s), 2.73 (1H, dd, J=11.3 Hz, 14.6 Hz), 3.04 (1H, dd, J=4.2 Hz, 14.4 Hz), 4.19 (1H, d, J=4.5 Hz), 4.72–4.81 (1H, m), 5.11 (1H, t, J=3.9 Hz), 5.86 (1H, d, J=8.1 Hz), 6.94 (1H, dd, J=8.1 Hz, 9.9 Hz), 7.04–7.12 (5H, m), 7.27–7.40 (3H, m), 7.46–7.58 (3H, m), 7.94 (1H, d, J=8.1 Hz), 8.08 (1H, d, J=7.5 Hz); IR (KBr) 3275, 2955, 1642, 1626, 1541, 1426, 1264, 1236, 1051, 760 cm$^{-1}$; Anal. Calcd for C$_{31}$H$_{31}$ClFNO$_2$: C, 73.87; H, 6.20; N, 2.78. Found: C, 73.69; H, 6.02; N, 2.59.

Example 346

5-chloro-N-[(1RS,2SR)-2-(3-chlorophenyl)-2-hydroxy-1-(4-neopentylbenzyl)ethyl]naphthalene-1-carboxamide While stirring (1RS,2SR)-2-amino-1-(3-chlorophenyl)-3-(4-neopentylphenyl)propan-1-ol (0.300 g, 0.904 mmol), 5-chloro-1-naphthoic acid (0.19 g, 0.90 mmol) and 1-hydroxybenzotriazole hydrate (0.14 g, 0.90 mmol) in acetonitrile (10 ml)-N,N-dimethylformamide (2 ml), 1-ethyl-3-(3-dimethylaminopropyl)carbodiimide hydrochloride (0.17 g, 0.90 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white crystal yield 0.367 g, 78% mp 168–169° C.; $^1$H-NMR (CDCl$_3$-DMSO-d$_6$, 200 MHz) δ 0.88 (9H, s), 2.46 (2H, s), 2.81 (1H, dd, J=10.6 Hz, 14.6 Hz), 2.94 (1H, dd, J=4.6 Hz, 14.4 Hz), 4.72–4.86 (1H, m), 5.04–5.11 (2H, m), 6.97–7.14 (5H, m), 7.23–7.37 (4H, m), 7.42–7.58 (4H, m), 7.67 (1H, d, J=8.4 Hz), 8.29 (1H, d, J=8.6 Hz); IR (KBr) 3272, 2957, 1636, 1537, 785 cm$^{-1}$; Anal. Calcd for C$_{31}$H$_{31}$Cl$_2$NO$_2$: C, 71.54; H, 6.00; N, 2.69. Found: C, 71.63; H, 6.09; N, 2.58.

Example 347 tert-butyl N-[(1RS,2SR)-2-(4-fluorophenyl)-2-hydroxyethyl-1-[3-(2,2,3,3-tetrafluoropropionyl)benzyl]]carbamate 1) ethyl 3-(4-fluorophenyl)-2-[3-(2,2,3,3-tetrafluoropropionyl)benzyl]-3-oxopropionate A solution of 2,2,3,3-tetrafluoro-1-(3-methylphenyl)propan-1-one (7.484 g, 33.99 mmol), N-bromosuccinimide (6.05 g, 34.0 mmol) and 2,2'-azobis(isobutyronitrile) (0.2 g) in carbon tetrachloride (40 ml) was heated under reflux for 1.5 hrs. After cooling the reaction solution to room temperature, the white precipitate was removed by filtration, and washed with hexane. The solvent of the recovered filtrate was evaporated under reduced pressure to give a pale-yellow liquid.

To a solution of ethyl (4-fluorobenzoyl)acetate (7.15 g, 34.0 mmol) in 1,2-dimethoxyethane (50 ml) was added a suspension (1.36 g, 34.0 mmol) of 60% sodium hydride in liquid paraffin under ice-cooling, and the mixture was stirred as it was for 0.5 hr. A solution of the liquid obtained above in 1,2-dimethoxyethane (30 ml) was added thereto at room temperature, and the mixture was stirred overnight at room temperature. The reaction solution was poured into water, and extracted twice with ethyl acetate. The recovered organic layer was dried over anhydrous magnesium sulfate. The solvent was evaporated under reduced pressure and the obtained residue was purified by silica gel column chromatography (hexane/ethyl acetate=15/1–9/1) to give the objective substance.

yellow, liquid yield 6.608 g, 45% $^1$H-NMR (CDCl$_3$, 300 MHz) δ 1.12 (3H, t, J=7.2 Hz), 3.41 (2H, d, J=7.5 Hz), 3.40–4.15 (2H, m), 4.59 (1H, t, J=7.4 Hz), 6.28 (1H, tt, J=5.6 Hz, 52.5 Hz), 7.13 (2H, t, J=8.7 Hz), 7.44 (1H, t, J=8.0 Hz), 7.59 (1H, d, J=7.5 Hz), 7.93–7.96 (2H, m), 8.01 (2H, dd, J=5.6 Hz, 8.9 Hz); IR (neat) 1736, 1686, 1599, 1508, 1302, 1273, 1238, 1159, 1115, 849 cm$^{-1}$ 2) ethyl (2RS,3RS)-3-(4-fluorophenyl)-3-hydroxy-2-[3-(2,2,3,3-tetrafluoro-1-hydroxypropyl)benzyl]propionate While stirring zinc chloride (4.16 g, 30.5 mmol) in diethyl ether (50 ml), sodium borohydride (2.31 g, 61.1 mmol) was added at room temperature, and the mixture was stirred as it was for 2 hrs. Insoluble material in the mixture was removed by filtration and washed with diethyl ether to give a solution of zinc borohydride in diethyl ether. To the obtained solution was added a solution of ethyl 3-(4-fluorophenyl)-2-[3-(2,2,3,3-tetrafluoropropionyl)benzyl]-3-oxopropionate (6.540 g, 15.27 mmol) in diethyl ether (30 ml) under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=3/1–1/1) to give the objective substance.

pale-yellow liquid yield 5.958 g, 90% $^1$H-NMR (CDCl$_3$, 300 MHz) δ0.90 (3H, t, J=7.1 Hz), 2.78 (1H, s), 2.93–3.03 (4H, m), 3.78–3.89 (2H, m), 4.93–5.03 (2H, m), 5.96 (1H, ddt, J=2.4 Hz, 8.5 Hz, 53.2 Hz), 7.03 (2H, t, J=8.7 Hz), 7.11–7.15 (1H, m), 7.19 (1H, d, J=7.2 Hz), 7.24–7.28 (2H, m), 7.34 (2H, dd, J=5.4 Hz, 9.0 Hz); IR (neat) 3418, 1715, 1607, 1512, 1377, 1229, 1186, 1159, 1100, 1057, 839 cm$^{-1}$ 3) (4RS,5SR)-5-(4-fluorophenyl)-4-[3-(2,2,3,3-tetrafluoro-1-hydroxypropyl)benzyl]-1,3-oxazolidin-2-one A mixture of ethyl (2RS,3RS)-3-(4-fluorophenyl)-3-hydroxy-2-[3-(2,2,3,3-tetrafluoro-1-hydroxypropyl)benzyl] propionate (5.878 g, 13.59 mmol), sodium hydroxide (1.09 g, 27.2 mmol), methanol (20 ml), water (30 ml) and tetrahydrofuran (20 ml) was stirred overnight at room temperature. The reaction solution was concentrated, diluted with water, acidified with hydrochloric acid, and extracted twice with ethyl acetate. The recovered organic layer was dried over anhydrous sodium sulfate and the solvent was evaporated under reduced pressure to give a crude product of (2RS,3RS)-3-(4-fluorophenyl)-3-hydroxy-2-[3-(2,2,3,3-tetrafluoro-1-hydroxypropyl)benzyl]propionic acid as a liquid.

To a solution of the liquid obtained above in tetrahydrofuran (50 ml) were added triethylamine (2.27 ml, 16.3 mmol) and diphenylphosphoryl azide (4.12 g, 15.0 mmol) were added, and the mixture was stirred at 65° C. overnight. The solvent of the reaction solution was evaporated under reduced pressure and the obtained crude product was purified by silica gel column chromatography (hexane/ethyl acetate=3/1–1/2) to give the objective substance.

pale-yellow liquid yield 5.001 g, 92% $^1$H-NMR (CDCl$_3$, 300 MHz) δ 2.14–2.38 (2H, m), 4.17–4.25 (1H, m), 4.34–4.42 (0.5H, m), 4.87–4.89 (0.5H, m), 4.96 (0.5H, br s), 5.02 (0.5H, br s), 5.73 (0.5H, d, J=8.7 Hz), 5.78 (0.5H, d, J=8.7 Hz), 6.08 (1H, dt, J=9.7 Hz, 53.4 Hz), 6.85 (0.5H, s), 6.99–7.36 (7.5H, m); IR (neat) 3304, 1744, 1514, 1236, 1101, 1067, 735 cm$^{-1}$ 4) (4RS,5SR)-5-(4-fluorophenyl)-4-[3-(2,2,3,3-tetrafluoropropionyl)benzyl]-1,3-oxazolidin-2-one While stirring (4RS,5SR)-5-(4-fluorophenyl)-4-[3-(2,2,3,3-tetrafluoro-1-hydroxypropyl)benzyl]-1,3-oxazolidin-2-one (5.779 g, 14.40 mmol) and triethylamine (16.1 ml, 115 mmol) in dimethyl sulfoxide (20 ml), a solution of sulfur trioxide pyridine complex (9.17 g, 57.6 mmol) in dimethyl sulfoxide (30 ml) was added at room temperature, and the mixture was stirred as it was overnight. The reaction mixture was poured into water, acidified with conc. hydrochloric acid, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=2/1–1/1) to give the objective substance.

yellow solid yield 3.772 g, 66%

Recrystallization from diisopropyl ether gave a white powder.

mp 149–150° C.; $^1$H-NMR (CDCl$_3$, 300 MHz) δ 2.41 (2H, d, J=7.5 Hz), 4.31 (1H, q, J=7.4 Hz), 5.69 (1H, s), 5.79 (1H, d, J=8.1 Hz), 6.27 (1H, tt, J=5.4 Hz, 52.6 Hz), 7.11 (2H, t, J=8.6 Hz), 7.31–7.36 (3H, m), 7.46 (1H, t, J=7.7 Hz), 7.68 (1H, s), 7.96 (1H, d, J=8.1 Hz); IR (KBr) 3250, 1740, 1690, 1516, 1240, 1115, 1096 cm$^{-1}$; Anal. Calcd for C$_{19}$H$_{14}$F$_5$NO$_3$: C, 57.15; H, 3.53; N, 3.51. Found: C, 57.12; H, 3.57; N, 3.41.

5) tert-butyl (4RS,5SR)-5-(4-fluorophenyl)-2-oxo-4-[3-(2,2,3,3-tetrafluoropropionyl)benzyl]-1,3-oxazolidine-3-carboxylate A solution of (4RS,5SR)-5-(4-fluorophenyl)-4-[3-(2,2,3-3-tetrafluoropropionyl)benzyl]-1,3-oxazolidin-2-one (2.199 g, 5.507 mmol), di-tert-butyl dicarbonate (1.44 g, 6.61 mmol) and 4-N,N-dimethylaminopyridine (67 mg, 0.55 mmol) in acetonitrile (30 ml) was stirred overnight at room temperature. The solvent of the reaction solution was evaporated under reduced pressure and the obtained residue was purified by silica gel column chromatography (hexane/ethyl acetate=3/1). Crystallization from diisopropyl ether-hexane gave the objective substance.

white crystal yield 2.178 g, 79% mp 116–118° C.; $^1$H-NMR (CDCl$_3$, 300 MHz) δ 1.52 (9H, s), 2.69 (1H, dd, J=9.0 Hz, 14.4 Hz), 2.99 (1H, dd, J=4.1 Hz, 14.3 Hz), 4.83 (1H, ddd, J=4.4 Hz, 7.1 Hz, 9.2 Hz), 5.68 (1H, d, J=7.2 Hz), 6.27 (1H, tt, J=5.6 Hz, 52.5 Hz), 6.94 (2H, t, J=8.7 Hz), 7.04 (1H, d, J=7.8 Hz), 7.13 (2H, dd, J=5.1 Hz, 8.4 Hz), 7.28 (1H, t, J=8.0 Hz), 7.33 (1H, s), 7.84 (1H, d, J=8.1 Hz); IR (KBr) 1806, 1701, 1516, 1372, 1159, 1113, 1076 cm$^{-1}$; Anal. Calcd for C$_{24}$H$_{22}$F$_5$NO$_5$: C, 57.72; H, 4.44; N, 2.80. Found: C, 57.66; H, 4.41; N, 2.66.

6) tert-butyl N-[(1RS,2SR)-2-(4-fluorophenyl)-2-hydroxyethyl-1-[3-(2,2,3,3-tetrafluoropropionyl)benzyl]]carbamate To a solution of tert-butyl, (4RS,5SR)-5-(4-fluorophenyl)-2-oxo-4-[3-(2,2,3,3-tetrafluoropropionyl)benzyl]-1,3-oxazolidine-3-carboxylate (2.030 g, 4.065 mmol) in tetrahydrofuran (20 ml) was added a solution of sodium hydroxide (0.16 g, 4.06 mmol) in methanol (10 ml) under ice-cooling, and the mixture was stirred at room temperature for 1 hr. The reaction solution was diluted with ethyl acetate, washed with water, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 1.692 g, 88% mp 157–158° C.; $^1$H-NMR (CDCl$_3$, 300 MHz) δ 1.31 (9H, s), 2.76 (1H, dd, J=9.9 Hz, 14.4 Hz), 2.86 (1H, dd, J=4.2 Hz, 14.1 Hz), 3.07 (1H, s), 4.04–4.13 (1H, m), 4.65 (1H, br d, J=9.3 Hz), 4.94 (1H, s), 6.29 (1H, tt, J=5.6 Hz, 52.5 Hz), 7.08 (2H, t, J=8.7 Hz), 7.34–7.48 (4H, m), 7.81 (1H, s), 7.93 (1H, d, J=6.9 Hz); IR (KBr) 3353, 1682, 1534, 1514, 1242, 1225, 1171, 1113, 1005 cm$^{-1}$; Anal. Calcd for C$_{23}$H$_{24}$F$_5$NO$_4$: C, 58.35; H, 5.11; N, 2.96. Found: C, 58.12; H, 4.94; N, 2.79.

Example 348

4-fluoro-N-[(1RS,2SR)-2-(4-fluorophenyl)-2-hydroxy-1-[3-(2,2,3,3-tetrafluoropropionyl)benzyl]ethyl]naphthalene-1-carboxamide A solution of tert-butyl N-[(1RS,2SR)-2-(4-fluorophenyl)-2-hydroxyethyl-1-[3-(2,2,3,3- tetrafluoropropionyl)benzyl]]carbamate (0.423 g, 0.893 mmol) in trifluoroacetic acid (5 ml) was stirred at room temperature for 15 min. The reaction solution was evaporated under reduced pressure, diluted with water, alkalified with potassium carbonate, and extracted twice with ethyl acetate. The recovered organic layer was dried over anhydrous sodium sulfate and the solvent was evaporated under reduced pressure to give a pale-yellow liquid.

While stirring the liquid obtained above, 4-fluoro-1-naphthoic acid (0.17 g, 0.89 mmol) and 1-hydroxybenzotriazole hydrate (0.14 g, 0.89 mmol) in acetonitrile (15 ml), 1-ethyl-3-(3-dimethylaminopropyl)carbodiimide hydrochloride (0.17 g, 0.89 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=2/1–1/1). Crystallization from diisopropyl ether-hexane gave the objective substance.

white crystal yield 0.364 g, 75% mp 160–162° C.; $^1$H-NMR (CDCl$_3$-DMSO-d$_6$, 300 MHz) δ 2.94 (1H, dd, J=10.5 Hz, 14.4 Hz), 3.01 (1H, dd, J=5.1 Hz, 14.1 Hz), 4.66 (1H, d, J=3.6 Hz), 4.74–4.83 (1H, m), 5.07 (1H, t, J=3.6 Hz), 6.26 (1H, tt, J=5.6 Hz, 52.5 Hz), 6.97–7.11 (4H, m), 7.24 (1H, dd, J=5.3 Hz, 8.0 Hz), 7.38–7.61 (6H, m), 7.68 (1H, d, J=8.7 Hz), 7.90 (1H, s), 7.96 (1H, d, J=8.1 Hz), 8.06 (1H, d, J=8.1 Hz); IR (KBr) 3277, 1703, 1644, 1626, 1601, 1512, 1231, 1113, 835, 762 cm$^{-1}$; Anal. Calcd for C$_{29}$H$_{21}$F$_6$NO$_3$: C, 63.86; H, 3.88; N, 2.57. Found: C, 63.49; H, 3.49; N, 2.45.

Example 349

4-fluoro-N-[(1RS,2SR)-2-(4-fluorophenyl)-2-hydroxy-1-[3-[1-(1,1,2,2-tetrafluoroethyl)vinyl]benzyl]ethyl]naphthalene-1-carboxamide To a solution of methyltriphenylphosphonium bromide (0.36 g, 1.00 mmol) in tetrahydrofuran (15 ml) was added tert-potassium tert-butoxide (0.11 g, 1.00 mmol) at room temperature, and the mixture was stirred for 0.5 hr. A solution of 4-fluoro-N-[(1RS,2SR)-2-(4-fluorophenyl)-2-hydroxy-1-[3-(2,2,3,3-tetrafluoropropionyl)benzyl]ethyl]naphthalene-1-carboxamide (0.181 g, 0.332 mmol) in tetrahydrofuran (10 ml) was added thereto, and the mixture was stirred at room temperature for 3 days. The reaction solution was poured into water, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=2/1–1/1). Crystallization from diisopropyl ether-hexane gave the objective substance.

white solid yield 0.146 g, 81% mp 162–163° C.; $^1$H-NMR (CDCl$_3$-DMSO-d$_6$, 200 MHz) δ 2.86 (1H, dd, J=10.6 Hz, 14.2 Hz), 2.99 (1H, dd, J=6.6 Hz, 14.2 Hz), 4.73–4.86 (1H, m), 5.01–5.06 (2H, m), 5.63 (1H, s), 5.75 (1H, tt, J=4.6 Hz, 53.2 Hz), 5.87 (1H, t, J=1.7 Hz), 6.96–7.27 (9H, m), 7.37–7.57 (4H, m), 7.67 (1H, d, J=8.6 Hz), 8.06 (1H, d, J=8.4 Hz); IR (KBr) 3262, 1642, 1626, 1601, 1537, 1510, 1264, 1229, 1111, 1053, 833, 758 cm$^{-1}$; Anal. Calcd for C$_{30}$H$_{23}$F$_6$NO$_2$.0.3H$_2$O: C, 65.64; H, 4.33; N, 2.55. Found: C, 65.53; H, 4.04; N, 2.37.

Example 350

5-chloro-N-[(1RS,2SR)-2-(4-fluorophenyl)-2-hydroxy-1-[3-(2,2,3,3-tetrafluoropropionyl)benzyl]ethyl]naphthalene-1-carboxamide A solution of tert-butyl N-[(1RS,2SR)-2-(4-fluorophenyl)-2-hydroxyethyl-1-[3-(2,2,3,3-tetrafluoropropionyl)benzyl]]carbamate (0.462 g, 0.976 mmol) in trifluoroacetic acid (5 ml) was stirred at room temperature for 15 min. The reaction solution was evaporated under reduced pressure, diluted with water, alkalified with potassium carbonate, and extracted twice with ethyl acetate. The recovered organic layer was dried over anhydrous sodium sulfate and the solvent was evaporated under reduced pressure to give a pale-yellow liquid.

While stirring the liquid obtained above, 5-chloro-1-naphthoate (0.20 g, 0.98 mmol) and 1-hydroxybenzotriazole hydrate (0.15 g, 0.98 mmol) in acetonitrile (15 ml), 1-ethyl-3-(3-dimethylaminopropyl)carbodiimide hydrochloride (0.19 g, 0.98 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=2/1–1/1). Crystallization from diisopropyl ether-hexane gave the objective substance.

white crystal yield 0.429 g, 78% mp 154–155° C.; $^1$H-NMR (CDCl$_3$-DMSO-d$_6$, 300 MHz) δ 2.94 (1H, dd, J=10.7 Hz, 14.0 Hz), 3.04 (1H, dd, J=4.1 Hz, 14.0 Hz), 4.75–4.85 (1H, m), 4.87 (1H, d, J=3.6 Hz), 5.05 (1H, t, J=3.9 Hz), 6.28 (1H, tt, J=5.5 Hz, 52.4 Hz), 7.09 (2H, t, J=8.6 Hz), 7.23 (1H, t, J=8.0 Hz), 7.33 (1H, t, J=9.0 Hz), 7.44–7.56 (6H, m), 7.61 (1H, d, J=7.5 Hz), 7.91 (1H, s), 7.98 (1H, t, J=8.4 Hz), 8.30 (1H, d, J=8.1 Hz); IR (KBr) 3279, 1703, 1640, 1537, 1512, 1231, 1113, 787 cm$^{-1}$; Anal. Calcd for C$_{29}$H$_{21}$ClF$_5$NO$_3$.0.5H$_2$O: C, 61.01; H, 3.88; N, 2.45. Found: C, 61.21; H, 3.96; N, 2.82.

Example 351

5-chloro-N-[(1RS,2SR)-2-(4-fluorophenyl)-2-hydroxy-1-[3-[1-(1,1,2,2-tetrafluoroethyl)vinyl]benzyl]ethyl]naphthalene-1-carboxamide To a solution of methyltriphenylphosphonium bromide (0.39 g, 1.10 mmol) in tetrahydrofuran (15 ml) was added potassium tert-butoxide (0.12 g, 1.10 mmol) at room temperature, and the mixture was stirred for 0.5 hr. A solution of 5-chloro-N-[(1RS,2SR)-2-(4-fluorophenyl)-2-hydroxy-1-[3-(2,2,3,3-tetrafluoropropionyl)benzyl]ethyl]naphthalene-1-carboxamide (0.206 g, 0.367 mmol) in tetrahydrofuran (10 ml) was added, and the mixture was stirred at room temperature for 3 days. The reaction solution was poured into water, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate= 2/1–1/1). Crystallization from diisopropyl ether-hexane gave the objective substance.

white powder yield 0.100 g; 49% mp 162–163° C.; $^1$H-NMR (CDCl$_3$, 300 MHz) δ 2.81 (1H, dd, J=10.7 Hz, 14.3 Hz), 3.08 (1H, dd, J=4.2 Hz, 14.1 Hz), 3.28 (1H, d, J=3.6 Hz), 4.79–4.89 (1H, m), 5.08 (1H, t, J=3.8 Hz), 5.63 (1H, s), 5.72 (1H, tt, J=4.0 Hz, 53.4 Hz), 5.89 (1H, s), 7.10 (2H, t, J=8.7 Hz), 7.18–7.32 (7H, m), 7.43–7.50 (3H, m), 7.57 (1H, d, J=8.4 Hz), 7.59 (1H, d, J=8.4 Hz), 8.33 (1H, d, J=8.4 Hz); IR (KBr) 3621, 3248, 1638, 1541, 1508, 1223, 1101, 789 cm$^{-1}$

Example 352 tert-butyl N-[(1RS,2SR)-2-(3-chlorophenyl)-1-[4-(2,2-difluoro-3-methylbutyl)benzyl]-2-hydroxyethyl]carbamate

1) 3-methyl-1-(4-methylphenyl)butan-2-one

While stirring magnesium (22.5 g, 925 mmol) and iodine (1 crumb) in diethyl ether (400 ml), a solution of 4-methylbenzyl chloride (65.0 g, 463 mmol) in diethyl ether (500 ml) was dropwise added slowly at room temperature. After completion of the dropwise addition, the mixture was stirred at room temperature for 0.5 hr. To the reaction solution was added dropwise a solution of isobutyronitrile (21.31 g, 308.3 mmol) in diethyl ether (100 ml) under ice-cooling, and the mixture was stirred overnight at room temperature. To the reaction solution was added dropwise 1N hydrochloric acid under ice-cooling, and the mixture was stirred at room temperature for 1 hr. The diethyl ether layer was separated from the mixture, and the aqueous layer was extracted with diethyl ether. The recovered organic layer was dried over anhydrous magnesium sulfate. The solvent was evaporated under reduced pressure and the obtained residue was purified by silica gel column chromatography (hexane/ethyl acetate=15/1–9/1) to give the objective substance.

pale-yellow liquid yield 52.64 g, 97% $^1$H-NMR (CDCl$_3$, 300 MHz) δ 1.09 (6H, d, J=6.9 Hz), 2.33 (3H, s), 2.67–2.77 (1H, m), 3.70 (2H, s), 7.08 (2H, d, J=8.1 Hz), 7.13 (2H, d, J=7.8 Hz); IR (neat) 2971, 1713, 1514, 1464, 1042, 781 cm$^{-1}$ 2) 4-(2,2-difluoro-3-methylbutyl)toluene A mixture of 3-methyl-1-(4-methylphenyl)butan-2-one (25.00 g, 141.8 mmol) and (diethylamino)sulfur trifluoride (25.1 g, 156 mmol) was stirred overnight at room temperature. The reaction solution was poured into ice water, and the mixture was stirred and extracted twice with diethyl ether. The recovered organic layer was dried over anhydrous magnesium sulfate. The solvent was evaporated under reduced pressure and the obtained residue was purified by silica gel column chromatography (hexane-hexane/ethyl acetate=20/1) to give the objective substance.

colorless liquid yield 8.562 g, 31% $^1$H-NMR (CDCl$_3$, 300 MHz) δ1.04 (6H, d, J=6.9 Hz), 1.91–2.05 (1H, m), 2.33 (3H, s), 3.09 (2H, t, J=17.0 Hz), 7.12 (2H, d, J=8.1 Hz), 7.17 (2H, d, J=8.4 Hz); IR (neat) 2975, 1514, 999 cm$^{-1}$ 3) tert-butyl (4RS,5SR)-5-(3-chlorophenyl)-4-[4-(2,2-difluoro-3-methylbutyl)benzyl]-2-oxo-1,3-oxazolidine-3-carboxylate solution of 4-(2,2-difluoro-3-methylbutyl)toluene (4.06 g), N-bromosuccinimide (3.64 g, 20.5 mmol) and 2,2'-azobis(isobutyronitrile) (30 mg) in carbon tetrachloride (30 ml) was heated under reflux for 1.5 hrs. After cooling the reaction solution to room temperature, the white precipitate was removed by filtration and washed with hexane. The solvent of the recovered filtrate was evaporated under reduced pressure to give a yellow liquid.

To a solution of ethyl (3-chlorobenzoyl)acetate (4.64 g, 20.5 mmol) in 1,2-dimethoxyethane (40 ml) was added a suspension (0.82 g, 20.5 mmol) of 60% sodium hydride in liquid paraffin under ice-cooling, and the mixture was stirred as it was for 0.5 hr. A solution of the liquid obtained above in 1,2-dimethoxyethane (20 ml) was added thereto at room temperature, and the mixture was stirred overnight at room temperature. The reaction solution was poured into water, and extracted twice with ethyl acetate. The recovered organic layer was dried over anhydrous magnesium sulfate and the solvent was evaporated under reduced pressure. The obtained residue was passed through silica gel column chromatography (hexane/ethyl acetate=15/1–9/1) to give a crude product of ethyl 3-(3-chlorophenyl)-2-[4-(2,2-difluoro-3-methylbutyl)benzyl]-3-oxopropionate as a yellow liquid.

While stirring zinc chloride (2.49 g, 18.3 mmol) in diethyl ether (30 ml), sodium borohydride (1.38 g, 36.6 mmol) was added at room temperature, and the mixture was stirred as it was for 2 hrs. The insoluble material in the mixture was removed by filtration and washed with diethyl ether to give a solution of zinc borohydride in diethyl ether. To the obtained solution was added a solution of the liquid obtained above in diethyl ether (20 ml) under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained residue was passed through silica gel column chromatography (hexane/ethyl acetate=9/1–6/1) to give a crude product of ethyl (2RS,3RS)-3-(3-chlorophenyl)-2-[4-(2,2-difluoro-3-methylbutyl)benzyl]-3-hydroxypropionate as a yellow liquid.

A mixture of the liquid obtained above, 1N aqueous sodium hydroxide solution (9.26 ml, 9.26 mmol), methanol (20 ml) and tetrahydrofuran (20 ml) was stirred overnight at room temperature. The reaction solution was concentrated, diluted with water, acidified with hydrochloric acid, and extracted twice with ethyl acetate. The recovered organic layer was dried over anhydrous sodium sulfate, and the solvent was evaporated under reduced pressure to give a crude product of (2RS,3RS)-3-(3-chlorophenyl)-2-[4-(2,2-difluoro-3-methylbutyl)benzyl]-3-hydroxypropionic acid as a yellow solid.

To a solution of the solid obtained above in tetrahydrofuran (40 ml) were added triethylamine (0.77 ml, 5.56 mmol) and diphenylphosphoryl azide (1.40 g, 5.09 mmol), and the mixture was stirred at 65° C. overnight. The solvent of the reaction solution was evaporated under reduced pressure and the obtained residue was passed through silica gel column chromatography (hexane/ethyl acetate=3/1–1/1) to give a crude product of (4RS,5SR)-5-(3-chlorophenyl)-4-[4-(2,2-difluoro-3-methylbutyl)benzyl]-1,3-oxazolidin-2-one as a white solid.

A solution of the solid obtained above, di-tert-butyl dicarbonate (0.69 g, 3.18 mmol) and 4-N,N-dimethylaminopyridine (32 mg, 0.27 mmol) in acetonitrile (30 ml) was stirred overnight at room temperature. The solvent of the reaction solution was evaporated under reduced pressure and the obtained residue was purified by silica gel column chromatography (hexane/ethyl acetate=9/1–6/1) to give the objective substance.

pale-yellow liquid yield 0.684 g, 7% $^1$H-NMR (CDCl$_3$, 300 MHz) δ 1.03 (6H, d, J=6.9 Hz), 1.49 (9H, s), 1.88–2.02 (1H, m), 2.57 (1H, dd, J=8.7 Hz, 14.1 Hz), 2.86 (1H, dd, J=4.7 Hz, 14.3 Hz), 3.02 (2H, t, J=17.3 Hz), 4.82 (1H, ddd, J=4.9 Hz, 7.1 Hz, 8.5 Hz), 5.64 (1H, d, J=7.2 Hz), 6.63 (2H, d, J=7.8 Hz), 6.99–7.05 (3H, m), 7.15–7.20 (2H, m), 7.27 (1H, d, J=8.1 Hz); IR (neat) 2980, 1809, 1728, 1360, 1312, 1155, 1071, 733 cm$^{-1}$ 4) tert-butyl N-[(1RS,2SR)-2-(3-chlorophenyl)-1-[4-(2,2-difluoro-3-methylbutyl)benzyl]-2-hydroxyethyl]carbamate To a solution of tert-butyl (4RS,5SR)-5-(3-chlorophenyl)-4-[4-(2,2-difluoro-3-methylbutyl)benzyl]-2-oxo-1,3-oxazolidine-3-carboxylate (0.684 g, 1.385 mmol) in tetrahydrofuran (20 ml) was added a solution of sodium hydroxide (58 mg, 1.45 mmol) in methanol (2 ml) under ice-cooling, and the mixture was stirred as it was for 0.5 hr. The reaction solution was diluted with ethyl acetate, washed with water, dried over anhydrous magnesium sulfate and passed through silica gel. The solvent was evaporated under reduced pressure and the obtained residue was crystallized from ethyl acetate-diisopropyl ether-hexane to give the objective substance.

white powder yield 0.524 g, 81% mp 139–141° C.; $^1$H-NMR (CDCl$_3$, 200 MHz) δ 1.03 (6H, d, J=6.8 Hz), 1.37 (9H, s), 1.85–2.06 (1H, m), 2.64 (1H, dd, J=10.2 Hz, 14.6 Hz), 2.75 (1H, dd, J=5.4 Hz, 14.6 Hz), 3.09 (2H, t, J=17.0 Hz), 3.63 (1H, br s), 4.12 (1H, br s), 4.53 (1H, br d, J=6.2 Hz), 4.91 (1H, br s), 7.07 (2H, d, J=8.0 Hz), 7.19 (2H, d, J=8.0 Hz), 7.28 (3H, s), 7.41 (1H, s); IR (KBr) 3358, 2984, 1682, 1530, 1167, 1009 cm$^{-1}$; Anal. Calcd for C$_{25}$H$_{32}$ClF$_2$NO$_3$: C, 64.16; H, 6.89; N, 2.99. Found: C, 64.21; H, 6.90; N, 3.01.

Example 353

N-[(1RS,2SR)-2-(3-chlorophenyl)-1-[4-(2,2-difluoro-3-methylbutyl)benzyl]-2-hydroxyethyl]-4-fluoronaphthalene-1-carboxamide A solution of tert-butyl N-[(1RS,2SR)-2-(3-chlorophenyl)-1-[4-(2,2-difluoro-3-methylbutyl)benzyl]-2-hydroxyethyl]carbamate (0.200 g, 0.427 mmol) in trifluoroacetic acid (2 ml) was stirred at room temperature for 15 min. The reaction solution was evaporated under reduced pressure, diluted with water, alkalified with potassium carbonate, and extracted twice with ethyl acetate. The recovered organic layer was dried over anhydrous sodium sulfate and the solvent was evaporated under reduced pressure to give as a white solid.

While stirring a solution of the solid obtained above, 4-fluoro-1-naphthoate (81 mg, 0.43 mmol) and 1-hydroxybenzotriazole hydrate (65 mg, 0.43 mmol) in acetonitrile (10 ml), 1-ethyl-3-(3-dimethylaminopropyl)carbodiimide hydrochloride (82 mg, 0.43 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=2/1–1/1). Crystallization from diisopropyl ether-hexane gave the objective substance.

white crystal yield 0.153 g, 66% mp 181–182° C.; $^1$H-NMR (CDCl$_3$-DMSO-d$_6$, 200 MHz) δ 1.02 (3H, d, J=7.0 Hz), 1.02 (3H, d, J=6.8 Hz), 1.86–2.06 (1H, m), 2.80–2.97 (2H, m), 3.09 (2H, t, J=17.2 Hz), 4.68–4.82 (1H, m), 5.07 (1H, t, J=4.0 Hz), 5.19 (1H, d, J=3.6 Hz), 6.98–7.37 (9H, m), 7.40–7.58 (4H, m), 7.82 (1H, d, J=8.2 Hz), 8.06 (1H, d, J=8.4 Hz); IR (KBr) 3297, 1640, 1534, 1264, 1057, 774, 760 cm$^{-1}$; Anal. Calcd for C$_{31}$H$_{29}$ClF$_3$NO$_2$: C, 68.95; H, 5.41; N, 2.59. Found: C, 68.88; H, 5.33; N, 2.55.

Example 354

5-chloro-N-[(1RS,2SR)-2-(3-chlorophenyl)-1-[4-(2,2-difluoro-3-methylbutyl)benzyl]-2-hydroxyethyl]naphthalene-1-carboxamide A solution of tert-butyl N-[(1RS,2SR)-2-(3-chlorophenyl)-1-[4-(2,2-difluoro-3-methylbutyl)benzyl]-2-hydroxyethyl]carbamate (0.200 g, 0.427 mmol) in trifluoroacetic acid (2 ml) was stirred at room temperature for 15 min. The reaction solution was evaporated under reduced pressure, diluted with water, alkalified with potassium carbonate, and extracted twice with ethyl acetate. The recovered organic layer was dried over anhydrous sodium sulfate and the solvent was evaporated under reduced pressure to give a white solid.

While stirring the solid obtained above, 5-chloro-1-naphthoate (88 mg, 0.43 mmol) and 1-hydroxybenzotriazole hydrate (65 mg, 0.43 mmol) in acetonitrile (10 ml), 1-ethyl-3-(3-dimethylaminopropyl)carbodiimide hydrochloride (82 mg, 0.43 mmol) was added, and the mixture was stirred overnight at room temperature. The reaction solution was diluted with ethyl acetate, washed with aqueous sodium hydrogen carbonate solution and dried over anhydrous magnesium sulfate. The solvent was evaporated under reduced pressure and the obtained residue was purified by silica gel column chromatography (hexane/ethyl acetate=2/1–1/1). Crystallization from diisopropyl ether-hexane gave the objective substance.

white crystal yield 0.178 g, 75% mp 170–171° C.; $^1$H-NMR (CDCl$_3$-DMSO-d$_6$, 300 MHz) δ 1.02 (3H, d, J=6.9 Hz), 1.03 (3H, d, J=6.9 Hz), 1.89–2.03 (1H, m), 2.86 (1H, dd, J=10.8 Hz, 14.1 Hz), 2.95 (1H, dd, J=4.5 Hz, 14.4 Hz), 3.10 (2H, t, J=17.4 Hz), 4.73–4.82 (1H, m), 5.05 (1H, t, J=3.8 Hz), 5.19 (1H, d, J=3.9 Hz), 7.16–7.38 (8H, m), 7.44–7.58 (5H, m), 7.64 (1H, d, J=8.7 Hz), 8.29 (1H, d, J=8.7 Hz); IR (KBr) 3272, 1638, 1535, 1202, 785 cm$^{-1}$; Anal. Calcd for C$_{31}$H$_{29}$Cl$_2$F$_2$NO$_2$: C, 66.91; H, 5.25; N, 2.52. Found: C, 67.01; H, 5.27; N, 2.41.

Example 355

4-fluoro-N-[(1RS,2SR)-2-(3-chlorophenyl)-2-hydroxy-1-[4-(tert-pentyl)benzyl]ethyl]naphthalene-1-carboxamide 1) 4-(tert-pentyl)benzyl alcohol A solution of tert-pentylbenzene (10.04 g, 67.72 mmol) and hexamethylenetetramine (9.49 g, 67.7 mmol) in trifluoroacetic acid (100 ml) was stirred at 90° C. overnight. The reaction solution was evaporated under reduced pressure, diluted with water, alkalified with potassium carbonate, and extracted twice with ethyl acetate. The recovered organic layer was dried over anhydrous sodium sulfate, and the solvent was evaporated under reduced pressure to give a crude product of 4-(tert-pentyl)benzaldehyde as a dark brown liquid.

To a solution of the liquid obtained above in methanol (100 ml) was added sodium borohydride (1.28 g, 33.9 mmol) by small portions under ice-cooling and the mixture was stirred overnight at room temperature. The reaction solution was concentrated, diluted with water, and extracted twice with diethyl ether. The recovered organic layer was dried over anhydrous sodium sulfate and the solvent was evaporated under reduced pressure. The residue was purified by silica gel column chromatography (hexane/ethyl acetate=9/1–6/1) to give the objective substance.

yellow liquid yield 10.83 g, 74% $^1$H-NMR (CDCl$_3$, 300 MHz) δ 0.68 (3H, t, J=7.4 Hz), 1.28 (6H, s), 1.65 (2H, q, J=7.4 Hz), 4.66 (2H, d, J=5.7 Hz), 7.30 (2H, d, J=8.4 Hz), 7.33 (2H, d, J=8.7 Hz); IR (neat) 3281, 2965, 1462, 1015 cm$^{-1}$ 2) ethyl 3-(3-chlorophenyl)-3-oxo-2-[4-(tert-pentyl)benzyl]propionate To a solution of 4-(tert-pentyl)benzyl alcohol (4.075 g, 22.86 mmol) and triethylamine (4.78 ml, 34.3 mmol) in ethyl acetate (50 ml) was added dropwise a solution of methanesulfonyl chloride (3.14 g, 27.4 mmol) in ethyl acetate (10 ml) under ice-cooling, and the mixture was stirred as it as for 10 min. The resulting precipitate was removed by filtration and washed with diethyl ether. The solvent of the recovered filtrate was evaporated under reduced pressure to give a crude product of methanesulfonic acid ester as a yellow liquid.

To a solution of ethyl (3-chlorobenzoyl)acetate (5.18 g, 22.9 mmol) in 1,2-dimethoxyethane (40 ml) was added a suspension (0.91 g, 22.9 mmol) of 60% sodium hydride in liquid paraffin under ice-cooling, and the mixture was stirred as it was for 0.5 hr. A solution of methanesulfonic acid ester obtained above in 1,2-dimethoxyethane (20 ml) was added thereto at room temperature, and the mixture was stirred at 50° C. overnight. The reaction solution was poured into water, and extracted-twice with ethyl acetate. The recovered organic layer was dried over anhydrous magnesium sulfate. The solvent was evaporated under reduced pressure and the obtained residue was purified by silica gel column chromatography (hexane/ethyl acetate=15/1) to give the objective substance.

yellow liquid yield 6.969 g, 79% $^1$H-NMR (CDCl$_3$, 300 MHz) δ 0.62 (3H, t, J=7.4 Hz), 1.12 (3H, t, J=7.2 Hz), 1.23 (6H, s), 1.59 (2H, q, J=7.4 Hz), 3.26 (1H, dd, J=7.5 Hz, 14.1 Hz), 3.32 (1H, dd, J=7.2 Hz, 14.4 Hz), 4.10 (1H, q, J=7.0 Hz), 4.11 (1H, q, J=7.2 Hz), 4.54 (1H, t, J=7.4 Hz), 7.13 (2H, d, J=8.4 Hz), 7.21 (2H, d, J=8.4 Hz), 7.36 (1H, t, J=8.0 Hz), 7.51 (1H, dd, J=1.2 Hz, 7.8 Hz), 7.78 (1H, dd, J=1.5 Hz, 7.8 Hz), 7.89 (1H, t, J=1.8 Hz); IR (neat) 2965, 1736, 1692, 1229 cm$^{-1}$ 3) ethyl (2RS,3RS)-3-(3-chlorophenyl)-3-hydroxy-2-[4-(tert-pentyl)benzyl]propionate While stirring zinc chloride (4.91 g, 36.0 mmol) in diethyl ether (50 ml), sodium borohydride (2.73 g, 72.0 mmol) was added at room temperature, and the mixture was stirred as it was for 2 hrs. Insoluble material in the mixture was removed by filtration and washed with diethyl ether to give a solution of zinc borohydride in diethyl ether. To the obtained solution was added a solution of ethyl 3-(3-chlorophenyl)-3-oxo-2-[4-(tert-pentyl)benzyl]propionate (6.969 g, 18.01 mmol) in diethyl ether (30 ml) under ice-cooling, and the mixture was stirred as it was for 20 min. To the reaction solution was added dilute hydrochloric acid by small portions to decompose excess zinc borohydride, and the mixture was extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=15/1–6/1) to give the objective substance.

yellow liquid yield 6.751 g, 96%
$^1$H-NMR (CDCl$_3$, 200 MHz) δ 0.63 (3H, t, J=7.4 Hz), 0.923 (3H, t, J=7.1 Hz), 1.23 (6H, s), 1.59 (2H, q, J=7.4 Hz), 2.84–2.99 (3H, m), 3.13 (1H, d, J=3.0 Hz), 3.90 (1H, q, J=7.2 Hz), 3.91 (1H, q, J=7.4 Hz), 5.02 (1H, t, J=3.1 Hz), 7.00 (2H, d, J=8.0 Hz), 7.18 (2H, d, J=8.0 Hz), 7.26 (3H, s), 7.42 (1H, s); IR (neat) 3480, 2965, 1728, 1715, 1375, 1192, 1159, 1032, 789 cm$^{-1}$ 4) (4RS,5SR)-5-(3-chlorophenyl)-4-[4-(tert-pentyl)benzyl]-1,3-oxazolidin-2-one A mixture of ethyl (2RS,3RS)-3-(3-chlorophenyl)-3-hydroxy-2-[4-(tert-pentyl)benzyl]propionate (6.650 g, 17.10 mmol), sodium hydroxide (1.37 g, 34.2 mmol), methanol (20 ml), water (20 ml) and tetrahydrofuran (20 ml) was stirred overnight at room temperature. The reaction solution was concentrated, diluted with water, acidified with hydrochloric acid, and extracted twice with ethyl acetate. The recovered organic layer was dried over anhydrous sodium sulfate and the solvent was evaporated under reduced pressure to give a crude product of (2RS,3RS)-3-(3-chlorophenyl)-3-hydroxy-2-[4-(tert-pentyl)benzyl]propionic acid as a white solid.

To a solution of the solid obtained above in tetrahydrofuran (70 ml) were added triethylamine (2.86 ml, 20.5 mmol) and diphenylphosphoryl azide (5.18 g, 18.8 mmol), and the mixture was stirred at 65° C. overnight. The solvent of the reaction solution was evaporated under reduced pressure, and diluted with ethyl acetate. The obtained aqueous ethyl acetate solution was washed with water, passed through silica gel, and the solvent was evaporated under reduced pressure. The obtained crystals were washed with diisopropyl ether to give the objective substance.

white crystal yield 4.312 g, 71% mp 223–224° C.; $^1$H-NMR (CDCl$_3$-DMSO-d$_6$, 300 MHz) δ 0.65 (3H, t, J=7.4 Hz), 1.24 (6H, s), 1.60 (2H, q, J=7.4 Hz), 2.30 (1H, dd, J=6.3 Hz, 14.1 Hz), 2.37 (1H, dd, J=9.0 Hz, 14.4 Hz), 4.33–4.41 (1H, m), 5.70 (1H, d, J=7.8 Hz), 6.84–6.87 (3H, m), 7.15–7.23 (3H, m), 7.27–7.33 (3H, m); IR (KBr) 3247, 2965, 1738, 1240, 1019 cm$^{-1}$; Anal. Calcd for C$_{21}$H$_{24}$ClNO$_2$: C, 70.48; H, 6.76; N, 3.91. Found: C, 70.35; H, 6.59; N, 3.77.

5) (1RS,2SR)-2-amino-1-(3-chlorophenyl)-3-[4-(tert-pentyl)phenyl]propan-1-ol (4RS,5SR)-5-(3-chlorophenyl)-4-[4-(tert-pentyl)benzyl]-1,3-oxazolidin-2-one (4.046 g, 11.31 mmol) and sodium hydroxide (1.81 g, 45.2 mmol) were heated under reflux in ethanol (40 ml)-water (2 ml) for 5 hrs. The reaction solution was diluted with water, and the mixture was stirred as it was for 0.5 hr. The recovered precipitate was washed with water and diisopropyl ether-hexane to give the objective substance.

white crystal yield 2.833 g, 76% mp 86–87° C.; $^1$H-NMR (CDCl$_3$, 200 MHz) δ 0.66 (3H, t, J=7.3 Hz), 1.26 (6H, s), 1.61 (2H, a, J=7.4 Hz), 2.30 (1H, dd, J=10.2 Hz, 14.0 Hz), 2.72 (1H, dd, J=3.2 Hz, 13.6 Hz), 3.30 (1H, ddd, J=3.5 Hz, 4.7 Hz, 10.4 Hz), 4.67 (1H, d, J=4.8 Hz), 7.05 (2H, d, J=8.4 Hz), 7.22–7.30 (5H, m), 7.42 (1H, s); IR (KBr) 3400-2700, 1576, 1474, 1460, 1420, 1044, 781 cm$^{-1}$; Anal. Calcd for C$_{20}$H$_{26}$ClNO.0.1H$_2$O: C, 71.99; H, 7.91; N, 4.20. Found: C, 71.96; H, 7.85; N, 4.14.

6) 4-fluoro-N-[(1RS,2SR)-2-(3-chlorophenyl)-2-hydroxy-1-[4-(tert-pentyl)benzyl]ethyl]naphthalene-1-carboxamide While stirring (1RS,2SR)-2-amino-1-(3-chlorophenyl)-3-[4-(tert-pentyl)phenyl]propan-1-ol (0.300 g, 0.904 mmol), 4-fluoro-1-naphthoic acid (0.17 g, 0.90 mmol) and 1-hydroxybenzotriazole hydrate (0.14 g, 0.90 mmol) in acetonitrile (10 ml)-N,N-dimethylformamide (2 ml), 1-ethyl-3-(3-dimethylaminopropyl)carbodiimide hydrochloride (0.17 g, 0.90 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white amorphous powder yield 0.381 g, 84% $^1$H-NMR (CDCl$_3$-DMSO-d$_6$, 300 MHz) δ 0.64 (3H, t, J=7.5 Hz), 1.25 (6H, s), 1.61 (2H, q, J=7.5 Hz), 2.84 (1H, dd, J=10.5 Hz, 14.4 Hz), 2.93 (1H, dd, J=4.2 Hz, 14.4 Hz), 4.72–4.81 (1H, m), 5.05 (1H, t, J=3.6 Hz), 5.28 (1H, d, J=3.6 Hz), 7.00 (1H, dd, J=8.1 Hz, 10.2 Hz), 7.12–7.35 (8H, m), 7.41–7.58 (4H, m), 7.82 (1H, d, J=8.1 Hz), 8.05 (1H, d, J=8.1 Hz); IR (KBr) 3414, 3250, 2965, 1638, 1628, 1599, 1514, 1262, 1233, 766 cm$^{-1}$; Anal. Calcd for C$_{31}$H$_{31}$ClFNO$_2$: C, 73.87; H, 6.20; N, 2.78. Found: C, 73.53; H, 6.13; N, 2.84.

Example 356

5-chloro-N-[(1RS,2SR)-2-(3-chlorophenyl)-2-hydroxy-1-[4-(tert-pentyl)benzyl]ethyl]naphthalene-1-carboxamide While stirring (1RS,2SR)-2-amino-1-(3-chlorophenyl)-3-[4-(tert-pentyl)phenyl]propan-1-ol (0.300 g, 0.904 mmol), 5-chloro-1-naphthoic acid (0.19 g, 0.90 mmol) and 1-hydroxybenzotriazole hydrate (0.14 g, 0.90 mmol) in acetonitrile (10 ml)-N,N-dimethylformamide (2 ml), 1-ethyl-3-(3-dimethylaminopropyl)carbodiimide hydrochloride (0.17 g, 0.90 mmol) was added, and the mixture was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure and the obtained residue was crystallized from ethyl acetate-diisopropyl ether-hexane to give the objective substance.

white amorphous powder yield 0.363 g, 77% $^1$H-NMR (CDCl$_3$-DMSO-d$_6$, 300 MHz) δ 0.64 (3H, t, J=7.4 Hz), 1.26 (6H, s), 1.62 (2H, q, J=7.4 Hz), 2.83 (1H, dd, J=11.0 Hz, 14.6 Hz), 2.95 (1H, dd, J=4.2 Hz, 14.7 Hz), 4.73–4.82 (1H, m), 5.03 (1H, t, J=3.9 Hz), 5.26 (1H, d, J=3.9 Hz), 7.16 (2H, d, J=8.4 Hz), 7.22–7.36 (7H, m), 7.42–7.49 (2H, m), 7.55 (1H, d, J=7.5 Hz), 7.58 (1H, s), 7.65 (1H, d, J=8.4 Hz), 8.28 (1H, d, J=8.7 Hz); IR (KBr) 3262, 2963, 1636, 1516, 785 cm$^{-1}$; Anal. Calcd for C$_{31}$H$_{31}$Cl$_2$NO$_2$: C, 71.54; H, 6.00; N, 2.69. Found: C, 71.24; H, 6.11; N, 2.42.

Example 357

N-[(1RS,2SR)-1-(4-tert-butylbenzyl)-2-(4-fluorophenyl)-2-hydroxyethyl]-4-fluoro-1-naphthamide 1) ethyl 2-[4-(tert-butyl)benzyl]-3-(4-fluorophenyl)-3-oxopropionate To a solution of p-tert-butylbenzyl alcohol (5 ml, 28.2 mmol) in ethyl acetate (60 ml) was added triethylamine (5.9 ml, 42.3 mmol) and methanesulfonyl chloride (2.4 ml, 31.0 mmol) was added under ice-cooling. The mixture was stirred as it was for 1 hr. The precipitated crystals were filtered, and concentrated to give mesylate, which was used as it was in the next reaction.

A solution of ethyl 3-(4-fluorophenyl)-3-oxopropionate (5.68 g, 27 mmol) in dimethoxyethane (50 ml) was ice-cooled and sodium hydride (60%, 1.13 g, 28 mmol) was added. The mixture was stirred under ice-cooling for 30 min. A solution of the mesylate in dimethoxyethane (30 ml) was added thereto, and the mixture was stirred at room temperature for 1 hr. After completion of the reaction, 1N hydrochloric acid was added to quench the reaction. The mixture was extracted with ethyl acetate, dried over anhydrous magnesium sulfate, filtered and concentrated under reduced pressure. The residue was purified by silica gel column chromatography (hexane:ethyl acetate=10:1, 8:1) to give ethyl 2-[4-(tert-butyl)benzyl]-3-(4-fluorophenyl)-3-oxopropionate (8.97 g, 93%) as a colorless transparent oil.

IR ν max$^{KBr}$ (cm$^{-1}$): 1736, 1685, 1599, 1508, 1267, 1234, 1159 $^1$H-NMR (CDCl$_3$)δ (ppm) 1.11 (3H, t, J=4.8 Hz), 1.27 (9H, s) 3.28 (1H, dd, J=2.0, 4.8 Hz), 4.10 (2H, q, J=4.8 Hz), 4.56 (1H, t, J=4.8 Hz), 7.07–7.15 (4H, m), 7.27 (2H, d, J=5.4 Hz), 7.95–8.00 (2H, m).

2) ethyl (2RS,3RS)-2-[4-(tert-butyl)benzyl]-3-(4-fluorophenyl)-3-hydroxypropionate To a suspension (80 ml) of zinc chloride (6.59 g, 48.3 mol) in ether was added sodium borohydride (3.66 g, 96.6 mol) at room temperature and the mixture was stirred as it was for 2 hrs. A solution of ethyl 2-[4-(tert-butyl)benzyl]-3-(4-fluorophenyl)-3-oxopropionate (8.61 g, 24.15 mmol) in ether (40 ml) was added, and the mixture was stirred at room temperature for 15 min. The reaction was stopped with 1N hydrochloric acid, and the reaction solution was diluted with ethyl acetate, washed with water, dried over anhydrous magnesium sulfate, filtered and concentrated under reduced pressure. The residue was purified by silica gel column chromatography (hexane:ethyl acetate=8:1, 5:1) to give ethyl (2RS,3RS)-2-[4-(tert-butyl)benzyl]-3-(4-fluorophenyl)-3-hydroxypropionate (8.00 g, 92%) as a colorless transparent oil.

IR ν max$^{KBr}$ (cm$^{-1}$): 3452, 1726, 1604, 1510, 1464, 1394, 1373, 1224, 1157, 1030 $^1$H-NMR (CDCl$_3$) δ (ppm) 0.89 (3H, t, J=7.4 Hz), 1.27 (9H, s) 2.95 (2H, s) 3.04 (1H, d, J=3.0 Hz), 3.87–3.95 (2H, m), 4.99 (1H, s) 6.97–7.07 (4H, m), 7.21–7.28 (2H, m), 7.32–7.39 (2H, m).

3) (2RS,3RS)-2-[4-(tert-butyl)benzyl]-3-(4-fluorophenyl)-3-hydroxypropionic acid To a solution of ethyl 2-[4-(tert-butyl)benzyl]-3-(4-fluorophenyl)-3-oxopropionate (7.43 g, 20.7 mmol) in tetrahydrofuran-methanol (20 ml-20 ml) was added sodium hydroxide at room temperature, and the mixture was stirred overnight at room temperature. After completion of the reaction, the organic solvent was evaporated under reduced pressure, and the residue was acidified with 1N hydrochloric acid and extracted with ethyl acetate. The organic layer was dried over anhydrous magnesium sulfate, filtered and concentrated under reduced pressure. Recrystallization from hexane-ethyl acetate gave (2RS,3RS)-2-[4-(tert-butyl)benzyl]-3-(4-fluorophenyl)-3-hydroxypropionic acid (5.51 g, 81%) as colorless crystals.

mp 102–104° C. IR ν max$^{KBr}$ (cm$^{-1}$): 2500-3300, 1709, 1606, 1510, 1226, 1159, 839 $^1$H-NMR (CDCl$_3$) δ (ppm) 1.27 (9H, s) 2.85–3.02 (3H, m), 5.04 (1H, d, J=4.4 Hz), 6.98–7.06 (4H, m), 7.22–7.27 (2H, m), 7.31–7.38 (2H, m).

4) (4RS,5SR)-4-[4-(tert-butyl)benzyl]-5-(4-fluorophenyl)-1,3-oxazolidin-2-one

To a solution of (2RS,3RS)-2-[4-(tert-butyl)benzyl]-3-(4-fluorophenyl)-3-hydroxypropionic acid (5.07 g, 15.3 mmol) in tetrahydrofuran (150 ml) were added triethylamine (3.2 ml, 22.95 mmol) and diphenylphosphoryl azide (3.63 ml, 16.8 mmol) at room temperature, and the mixture was heated under reflux for 5 hrs. The solvent was evaporated, passed through silica gel column, and purified by recrystallization (hexane-ethyl acetate) to give (4RS,5SR)-4-[4-(tert-butyl)benzyl]-5-(4-fluorophenyl)-1,3-oxazolidin-2-one (3.98 g, 79%) as colorless crystals.

mp 218–219° C. IR ν max$^{KBr}$ (cm$^{-1}$): 3284, 1736, 1610, 1514, 1363, 1230 $^1$H-NMR (CDCl$_3$) δ (ppm) 1.28 (9H, s) 2.10–2.86 (2H, m), 4.15–4.26 (1H, m), 4.95 (1H, s) 5.78 (1H, d, J=7.6 Hz), 6.95 (2H, d, J=8.4 Hz), 7.08–7.18 (2H, m), 7.26–7.40 (4H, m).

5) (1RS,2RS)-2-amino-3-[4-(tert-butyl)benzyl]-1-(4-fluorophenyl)propan-1-ol

To a solution of (4RS,5SR)-4-[4-(tert-butyl)benzyl]-5-(4-fluorophenyl)-1,3-oxazolidin-2-one (3.80 g, 11.6 mmol) in ethanol was added 8N aqueous sodium hydroxide solution (7.3 ml, 58.4 mmol), and the mixture was heated under reflux for 5 hrs. After completion of the reaction, the reaction solution was diluted with water, and extracted with ethyl acetate. The organic layers were combined, washed with saturated brine, dried over anhydrous magnesium sulfate, filtered and concentrated under reduced pressure. The residue was purified by recrystallization (hexane-ethyl acetate) to give (1RS,2RS)-2-amino-3-[4-(tert-butyl)benzyl]-1-(4-fluorophenyl)propan-1-ol (2.57 g, 74%) as colorless crystals.

mp 139–140° C. IR ν max$^{KBr}$ (cm$^{-1}$): 2500-3300, 1603, 1508, 1363, 1224, 1155, 1043 $^1$H-NMR (CDCl$_3$) δ (ppm) 1.29 (9H, s) 2.06 (2H, br) 2.30 (1H, dd, J=10.4, 13.6 Hz), 2.72 (1H, dd, J=3.4, 14.0 Hz), 3.26 (1H, ddd, J=3.8, 4.8, 10.6 Hz), 4.69 (1H, d, J=4.8 Hz), 7.01–7.10 (4H, m), 7.25–7.40 (4H, m).

6) N-[(1RS,2SR)-1-(4-tert-butylbenzyl)-2-(4-fluorophenyl)-2-hydroxyethyl]-4-fluoro-1-naphthamide To a solution of (1RS,2RS)-2-amino-3-[4-(tert-butyl)benzyl]-1-(4-fluorophenyl)propan-1-ol (0.30 g, 0.998 mmol) in acetonitrile (10 ml) were added 4-fluoronaphthalene-1-carboxylic acid (0.20 g, 1.05 mmol) and 1-hydroxybenzotriazole monohydrate (0.16 g, 1.05 mmol), and 1-ethyl-3-(3-dimethylaminopropyl) carbodiimide hydrochloride (0.20 g, 1.05 mmol) was finally added. The mixture was stirred at room temperature for 12 hrs. The mixture was diluted with ethyl acetate, washed with saturated aqueous sodium hydrogen carbonate, water and saturated brine, dried over anhydrous magnesium sulfate, filtered and concentrated under reduced pressure. The residue was purified by silica gel column chromatography (hexane:ethyl acetate=5:1, 3:1).

Recrystallization (hexane-ethyl acetate) gave N-[(1RS,2SR)-1-(4-tert-butylbenzyl)-2-(4-fluorophenyl)-2-hydroxyethyl]-4-fluoro-1-naphthamide (0.30 g, 64%) as colorless crystals.

mp 149–150° C. elemental analysis C$_{30}$H$_{29}$NO$_2$F$_2$ Calculated: C, 76.09; H, 6.17; N, 2.96. Found: C, 76.07; H, 6.09; N, 2.92. IR ν max$^{KBr}$(cm$^{-1}$): 3263, 1639, 1601, 1510, 1263, 1226, 1051, 835 $^1$H-NMR (CDCl$_3$) δ (ppm) 1.31 (9H, s) 2.72 (1H, dd, J=10.6, 14.4 Hz) 3.03 (1H, dd, J=4.4, 14.2 Hz), 4.70–4.84 (1H, m), 5.04–5.08 (1H, m), 5.83 (1H, d, J=8.0 Hz), 6.90–7.15 (6H, m), 7.31–7.57 (6H, m), 7.85 (1H, d, J=8.0 Hz), 8.97 (1H, d, J=7.6 Hz).

Example 358

N-[(1RS,2SR)-1-(4-tert-butylbenzyl)-2-(4-fluorophenyl)-2-hydroxyethyl]-6,7-dihydro-5H-benzo[a]cycloheptene-1-carboxamide To a solution of (1RS,2RS)-2-amino-3-[4-(tert-butyl)benzyl]-1-(4-fluorophenyl)propan-1-ol (0.41 g, 1.36 mmol) in acetonitrile (10 ml) were added 6,7-dihydro-5H-benzo[a]cycloheptene-1-carboxylic acid (0.20 g, 1.05 mmol) and 1-hydroxybenzotriazole monohydrate (0.16 g, 1.05 mmol), and 1-ethyl-3-(3-dimethylaminopropyl)carbodiimide hydrochloride (0.20 g, 1.05 mmol) was finally added. The mixture was stirred at room temperature for 3 days. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=5:1, 2:1). Recrystallization (hexane-ethyl acetate) gave N-[(1RS,2SR)-1-(4-tert-butylbenzyl)-2-(4-fluorophenyl)-2-hydroxyethyl]-6,7-dihydro-5H-benzo[a]cycloheptene-1-carboxamide (0.43 g, 67%) as colorless crystals.

mp 140–142° C. elemental analysis C$_{31}$H$_{34}$NO$_2$.0.25H$_2$O Calculated: C, 78.20; H, 7.30; N, 2.94. Found: C; 78.16; H, 7.20; N, 2.86. IR ν max$^{KBr}$ (cm$^{-1}$): 1637, 1508, 1363, 1222, 1155 $^{-1}$H-NMR (CDCl$_3$)δ (ppm) 1.29 (9H, s) 1.96–2.04 (2H, m), 2.13–2.23 (2H, m), 2.62–2.73 (3H, m), 2.96 (1H, dd, J=4.4, 14.6 Hz), 4.17 (1H, d, J=3.2 Hz), 4.99–5.01 (1H, m), 5.63 (1H, d, J=7.6 Hz) 5.90 (1H, dt, J=5.6, 11.4 Hz), 6.24 (1H, d, J=11.8 Hz), 6.87 (1H, d, J=1.0 Hz), 7.01–7.16 (5H, m), 7.25–7.33 (3H, m), 7.38–7.45 (2H, m).

Example 359

N-[(1RS,2SR)-1-[3-(1,1-difluoroethyl)benzyl]-2-(4-fluorophenyl)-2-hydroxyethyl]-4-fluoro-1-naphthamide 1) 3-(1,1-difluoroethyl)benzonitrile.

To a round-bottomed flask containing 3-acetylbenzophenone (5.81 g, 40.0 mmol) was dropwise added bis(2-methoxyethyl)aminosulfur trifluoride (12.5 ml, 67.8 mmol) and ethanol (0.46 ml, 8.14 mmol) was dropwise added slowly. The mixture was stirred at 80 to 85° C. overnight. The reaction mixture was poured into saturated aqueous sodium hydrogen carbonate solution, and the mixture was extracted with ether. After drying over anhydrous magnesium sulfate, the residue was filtered and concentrated under reduced pressure. The residue was purified by silica gel column chromatography (hexane:ether=10:1, 8:1, 5:1) to give 3-(1,1-difluoroethyl)benzonitrile (5.16 g, 77%) as a colorless transparent oil.

IR ν max$^{KBr}$ (cm$^{-1}$): 2223, 1485, 1429, 1386, 1304, 1186 $^1$H-NMR (CDCl$_3$) δ (ppm) 1.93 (3H, t, J=18.3 Hz), 7.55–7.60 (1H, m) 7.72–7.80 (3H, m).

2) 3-(1,1-difluoroethyl)benzoic acid

To a suspension (100 ml) of 3-(1,1-difluoroethyl)benzonitrile (5.10 g, 30.5 mmol) in water was added sodium hydroxide (3.05 g, 76.25 mmol), and the mixture was stirred at 100° C. for 5 hrs. After completion of the reaction, the reaction solution was acidified with 6N hydrochloric acid and extracted with ethyl acetate. The organic layer was washed with saturated brine, dried over anhydrous magnesium sulfate, filtered and concentrated under reduced pressure to give 3-(1,1-difluoroethyl)benzoic acid (5.10 g, 90%) as colorless crystals.

mp 96–97° C. IR ν max$^{KBr}$ (cm$^{-1}$): 2500-3300, 1689, 1616, 1423, 1385, 1323, 1278, 1263, 1176 1H-NMR (CDCl$_3$) δ (ppm): 1.97 (3H, t, J=18.4 Hz), 7.52–7.65 (1H, m) 7.76–7.79 (1H, m), 8.17–8.34 (2H, m).

3) 3-(1,1-difluoroethyl)benzyl alcohol

To a suspension (100 ml) of lithium aluminum hydride (2.24 g, 54.4 mmol) in ether was added dropwise a solution of 3-(1,1-difluoroethyl)benzonitrile (5.48 g, 29.4 mmol) in ether (50 ml) under ice-cooling, and the mixture was stirred at room temperature for 4 hrs. After completion of the reaction, water (2.24 ml), 15% aqueous sodium hydroxide solution (2.24 ml) and water (6.72 ml) were successively added dropwise under ice-cooling. The obtained solid was filtered with celite and washed with ethyl acetate. The filtrate was concentrated, and the residue was purified by silica gel column chromatography (hexane:ethyl acetate=3:1, 1:1) to give 3-(1,1-difluoroethyl)benzyl alcohol (3.82 g, 75%) to give a colorless transparent oil.

IR ν max$^{KBr}$ (cm$^{-1}$): 3292, 1439, 1389, 1305, 1180, 1143 $^1$H-NMR (CDCl$_3$) δ (ppm) 1.91 (3H, t, J=17.8 Hz), 2.08 (1H, s) 4.71 (2H, s) 7.41–7.44 (3H, m), 7.50 (1H, s).

4) ethyl 2-[3-(1,1-difluoroethyl)benzyl]-3-(4-fluorophenyl)-3-oxopropionate

To a solution of 3-(1,1-difluoroethyl)benzyl alcohol (3.71 ml, 21.5 mmol) in ethyl acetate (50 ml) was added triethylamine (4.5 ml, 32.25 mmol). To the mixture was added dropwise methanesulfonyl chloride (1.83 ml, 23.6 mmol) under ice-cooling, and the mixture was stirred as it was for 45 min. The precipitated crystals were filtered, and the filtrate was concentrated to give mesylate, which was directly used in the next reaction.

A solution of ethyl 3-(4-fluorophenyl)-3-oxopropionate (4.52 g, 21.5 mmol) in dimethoxyethane (50 ml) was ice-cooled, and sodium hydride (60%, 0.86 g, 21.5 mmol) was added thereto and the mixture was stirred for 30 min under ice-cooling. A solution of the mesylate in dimethoxyethane (50 ml) was added thereto, and the mixture was stirred overnight at room temperature. After completion of the reaction, the reaction was quenched with 1N hydrochloric acid, and the mixture was diluted with ethyl acetate, washed with water and saturated brine, dried over anhydrous magnesium sulfate and filtered. The filtrate was concentrated under reduced pressure, and the residue was purified by silica gel column chromatography (hexane:ethyl acetate= 8:1, 5:1) to give ethyl 2-[3-(1,1-difluoroethyl)benzyl]-3-(4-fluorophenyl)-3-oxopropionate (7.31 g, 93%) as a colorless transparent oil.

IR ν max$^{KBr}$ (cm$^{-1}$): 1736, 1685, 1508, 1446, 1385, 1304, 1234, 1159 $^1$H-NMR (CDCl$_3$) δ (ppm) 1.12 (3H, t, J=7.2 Hz), 1.86 (3H, t, J=18.3 Hz), 3.35 (2H, dd, J=2.7, 7.2 Hz), 4.10 (2H, q, J=7.2 Hz) 4.57 (1H, t, J=7.5 Hz), 7.08–7.15 (2H, m), 7.26–7.35 (4H, m) 7.96–8.01 (2H, m).

5) ethyl (2RS,3RS)-2-[3-(1,1-difluoroethyl)benzyl]-3-(4-fluorophenyl)-3-hydroxypropionate To a suspension (40 ml) of zinc chloride (5.35 g, 39.2 mmol) in ether was added sodium borohydride (2.97 g, 78.4 mmol) at room temperature, and the mixture was stirred as it was for 2 hrs. Insoluble material was filtered off. To the filtrate was added a solution of ethyl 2-[3-(1,1-difluoroethyl)benzyl]-3-(4-fluorophenyl)-3-oxopropionate (7.16 g, 19.6 mmol) in ether (40 ml), and the mixture was stirred at room temperature for 1.5 hrs. The reaction was quenched with 1N hydrochloric acid, and the mixture was diluted with ethyl acetate and washed with water and saturated brine. The mixture was dried over anhydrous magnesium sulfate, filtered and concentrated under reduced pressure. The residue was purified by silica gel column chromatography (hexane:ethyl acetate=8:1, 4:1) to give ethyl (2RS,3RS)-2-[3-(1,1-difluoroethyl)benzyl]-3-(4-fluorophenyl)-3-hydroxypropionate (6.24 g, 87%) as a colorless transparent oil.

IR ν max$^{KBr}$ (cm$^{-1}$): 1728, 1604, 1510, 1446, 1385, 1304 $^1$H-NMR (CDCl$_3$) δ (ppm) 0.91 (3H, t, J=7.4 Hz), 1.87 (3H, t, J=17.6 Hz), 2.90–3.05 (4H, m), 3.87 (1H, q, J=7.8 Hz), 4.99–5.02 (1H, m), 6.98–7.40 (8H, m).

6) (2RS,3RS)-2-[3-(1,1-difluoroethyl)benzyl]-3-(4-fluorophenyl)-3-hydroxypropionic acid To a solution of ethyl (2RS,3RS)-2-[3-(1,1-difluoroethyl)benzyl]-3-(4-fluorophenyl)-3-hydroxypropionate (5.97 g, 17.6 mmol) in tetrahydrofuran-ethanol (30 ml)–(20 ml) was added 2N sodium hydroxide (18 ml, 36 mmol) at room temperature, and the mixture was stirred overnight at room temperature. After completion of the reaction, the organic solvent was evaporated under reduced pressure, and the aqueous layer was acidified with 1N hydrochloric acid. The mixture was extracted with ethyl acetate. The organic layer was dried over anhydrous magnesium sulfate, filtered and concentrated under reduced pressure. The filtrate was recrystallized from hexane-ethyl acetate to give (2RS,3RS)-2-[3-(1,1-difluoroethyl)benzyl]-3-(4-fluorophenyl)-3-hydroxypropionic acid(4.48 g, 82%) as colorless crystals.

mp 132–133° C. IR ν max$^{KBr}$ (cm$^{-1}$): 2800-3300, 1709, 1606, 1512, 1385, 1304, 1226, 1178 $^1$H-NMR (CDCl$_3$) δ (ppm) 1.85 (3H, t, J=18.2 Hz), 3.01 (3H, m), 5.06 (1H, s) 6.99–7.39 (8H, m).

7) (4RS,5SR)-4-[3-(1,1-difluoroethyl)benzyl]-5-(4-fluorophenyl)-1,3-oxazolidin-2-one To a solution of (2RS,3RS)-2-[3-(1,1-difluoroethyl)benzyl]-3-(4-fluorophenyl)-3-hydroxypropionic acid (4.22 g, 13.6 mmol) in tetrahydrofuran (130 ml) were added triethylamine (2.85 ml, 20.4 mmol) and diphenylphosphoryl azide (3.23 ml, 14.96 mmol), and the mixture was heated under reflux for 5 hrs. The solvent was evaporated, and the residue was diluted with ethyl acetate, washed with water, saturated aqueous sodium hydrogen carbonate and saturated brine. The organic layer was dried over anhydrous magnesium sulfate, filtered and concentrated under reduced pressure. The residue was recrystallized from hexane-ethyl acetate to give [4RS,5SR]-4-(3-[1,1-difluoroethyl)benzyl]-5-(4-fluorophenyl)-1,3-oxazolidin-2-one (3.99 g, 95%) as colorless crystals.

mp 143–144° C. IR ν max$^{KBr}$ (cm$^{-1}$): 3231, 1763, 1608, 1512, 1386, 1300, 1230 $^1$H-NMR (CDCl$_3$) δ (ppm) 1.88 (3H, t, J=18.4 Hz), 2.29–2.38 (2H, m) 4.22–4.33 (1H, m), 5.17 (1H, s) 5.79 (1H, d, J=8.0 Hz) 7.06–7.18 (4H, m), 7.29–7.39 (4H, m).

8) (1RS,2SR)-2-amino-3-[3-(1,1-difluoroethyl)phenyl]-1-(4-fluorophenyl)-1-propanol To a solution of (4RS,5SR)-4-[3-(1,1-difluoroethyl)benzyl]-5-(4-fluorophenyl)-1,3-oxazolidin-2-one (3.83 g, 12.5 mmol) in ethanol (100 ml) was added 8N aqueous sodium hydroxide solution (7.8 ml, 39.0 mmol), and the mixture was heated under reflux for 5 hrs. After completion of the reaction, the mixture was diluted with water, and extracted with ethyl acetate. The organic layers were combined, washed with saturated brine, dried over anhydrous magnesium sulfate, filtered and concentrated under reduced pressure. The residue was recrystallized from (hexane-ethyl acetate) to give (1RS,2SR)-2-amino-3-[3-(1,1-difluoroethyl)phenyl]-1-(4-fluorophenyl)-1-propanol (3.08 g, 88%) as colorless crystals.

mp 101–102° C. IR ν max$^{KBr}$ (cm$^{-1}$): 3363, 1604, 1508, 1448, 1385, 1302, 1224, 1176 $^1$H-NMR (CDCl$_3$) δ (ppm) 1.89 (3H, t, J=18.4 Hz), 2.39 (1H, dd, J=10.4, 13.6 Hz), 2.82 (1H, dd, J=3.0, 13.6 Hz), 3.25–3.34 (1H, m), 4.69 (1H, d, J=5.0 Hz), 7.03–7.11 (2H, m), 7.11–7.21 (1H, m), 7.26–7.41 (5H, m).

9) N-[(1RS,2SR)-1-[3-(1,1-difluoroethyl)benzyl]-2-(4-fluorophenyl)-2-hydroxyethyl]-4-fluoro-1-naphthamide To a solution of (1RS,2SR)-2-amino-3-[3-(1,1-difluoroethyl)phenyl]-1-(4-fluorophenyl)-1-propanol (0.40 g, 1.42 mmol) in acetonitrile (10 ml) were added 4-fluoronaphthalene-1-carboxylic acid (0.283 g, 1.49 mmol) and 1-hydroxybenzotriazole monohydrate (0.22 g, 1.49 mmol), and 1-ethyl-3-(3-dimethylaminopropyl) carbodiimide hydrochloride (0.27 g, 1.49 mmol) was finally added. The mixture was stirred at room temperature overnight. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=5:1, 2:1) and recrystallization (hexane-ethyl acetate) to give N-[(1RS,2SR)-1-[3-(1,1-difluoroethyl)benzyl]-2-(4-fluorophenyl)-2-hydroxyethyl]-4-fluoro-1-naphthamide (0.52 g, 81%) as colorless crystals.

mp 182–183° C. Elemental analysis for $C_{28}H_{23}NO_2F_4$ Calcd: C, 69.85; H, 4.81; N, 2.91. Found: C, 69.86; H, 4.75; N, 2.74. IR ν max$^{KBr}$ (cm$^{-1}$): 3277, 1641, 1626, 1601, 1512, 1425, 1307, 1230 $^1$H-NMR (CDCl$_3$) δ (ppm) 1.84 (3H, t, J=18.0 Hz), 2.84 (1H, dd, J=10.2, 14.1 Hz), 3.07 (1H, dd, J=4.2, 14.7 Hz), 3.55 (1H, s) 4.72–4.81 (1H, m), 5.08 (1H, s) 5.92 (1H, d, J=8.7 Hz) 6.98 (1H, dd, J=8.1, 9.9 Hz), 7.05–7.15 (3H, m), 7.27–7.48 (7H, m) 7.50–7.55 (1H, m), 7.75 (1H, d, J=8.7 Hz), 8.07 (1H, d, J=8.7 Hz).

Example 360

N-[(1RS,2SR)-1-[3-(1,1-difluoroethyl)benzyl]-2-(4-fluorophenyl)-2-hydroxyethyl]-6,7-dihydro-5H-benzo[a]cycloheptene-1-carboxamide To a solution of (1RS,2SR)-2-amino-3-[3-(1,1-difluoroethyl)phenyl]-1-(4-fluorophenyl)-1-propanol (0.40 g, 1.42 mmol) in acetonitrile (10 ml) were added 6,7-dihydro-5H-benzo[a]cycloheptene-1-carboxylic acid (0.28 g, 1.49 mmol) and 1-hydroxybenzotriazole monohydrate (0.22 g, 1.49 mmol), and 1-ethyl-3-(3-dimethylaminopropyl)carbodiimide hydrochloride (0.27 g, 1.49 mmol) was finally added. The mixture was stirred overnight at room temperature. The mixture was diluted with ethyl acetate, washed with saturated aqueous sodium hydrogen carbonate, water and saturated brine, dried over anhydrous magnesium sulfate, filtered and concentrated under reduced pressure. The residue was purified by silica gel column chromatography (hexane:ethyl acetate=5:1, 2:1) and recrystallization (hexane-ethyl acetate) to give N-[(1RS, 2SR)-1-[3-(1,1-difluoroethyl)benzyl]-2-(4-fluorophenyl)-2-hydroxyethyl]-6,7-dihydro-5H-benzo[a]cycloheptene-1-carboxamide (0.50 g, 78%) as colorless crystals.

mp 170–171° C. IR ν max$^{KBr}$ (cm$^{-1}$): 1639, 1510, 1448, 1385, 1305, 1222, 1174, 1086 Elemental analysis for C$_{29}$H$_{28}$NO$_2$F$_3$ Calcd: C, 72.64; H, 5.89; N, 2.92. Found: C, 72.61; H, 5.91; N, 2.65. $^1$H-NMR (CDCl$_3$) δ (ppm) 1.87 (3H, t, J=18.3 Hz), 1.96–2.04 (2H, m) 2.15–2.21 (2H, m), 2.63–2.67 (2H, m), 2.78 (1H, dd, J=10.8, 14.4 Hz), 3.01 (1H, dd, J=4.5, 14.7 Hz), 3.70 (1H, d, J=3.3 Hz) 4.65–4.72 (1H, m), 5.03 (1H, t, J=3.9 Hz), 5.72 (1H, d, J=7.8 Hz), 5.90 (1H, dt, J=5.1, 12.0 Hz), 6.16 (1H, d, J=11.7 Hz), 6.93 (1H, dd, J=1.2, 7.5 Hz), 7.04–7.15 (4H, m), 7.25–7.31 (2H, m), 7.34–7.38 (2H, m), 7.41–7.46 (2H, m).

Example 361 tert-butyl (1RS,2RS)-2-hydroxy-2-(2-phenyl-1,3-thiazol-4-yl)-1-[3-(1,1,2,2-tetrafluoroethoxy)benzyl]ethylcarbamate 1) ethyl 3-oxo-3-(2-phenyl-1,3-thiazol-4-yl)propionate To a solution of 2-phenyl-1,3-thiazole-4-carboxylic acid (1 g, 4.87 mmol) in tetrahydrofuran (10 ml) was added N,N'-carbonyldiimidazole (0.87 g, 5.37 mmol), and the mixture was stirred at room temperature for 3 hrs to give an imidazolide solution. A round-bottomed flask prepared separately, was charged with a solution of ethyl hydrogen malonate (0.78 g, 5.84 mmol) in tetrahydrofuran (10 ml), and magnesium ethoxide (0.34 g, 2.92 mmol) was added. The mixture was stirred at room temperature for 1 hr, and the solvent was concentrated under reduced pressure to give a pale-yellow amorphous powder. The imidazolide solution prepared as above was added dropwise, and the mixture was stirred overnight at room temperature. The mixture was diluted with ethyl acetate, washed with 1M potassium hydrogen sulfate, saturated aqueous sodium hydrogen carbonate, water and saturated brine, dried over anhydrous magnesium sulfate, filtered and concentrated under reduced pressure. The residue was purified by silica gel column chromatography (hexane:ethyl acetate=4:1) to give ethyl 3-oxo-3-(2-phenyl-1,3-thiazol-4-yl)propionate (1.29 g, 96%) as colorless crystals.

mp 66–68° C. IR ν max$^{KBr}$ (cm$^{-1}$): 3117, 1739, 1693, 1628, 1483, 1304, 1219, 1153, 1028 $^1$H-NMR (CDCl$_3$) δ (ppm) 1.24, 1.34 (3H, each t, J=7.0, 7.2 Hz respectively) 4.15 (1.2H, s) 4.21, 4.28 (2H, each q, J=6.8, 7.2 Hz respectively) 6.21 (0.4H, s) 7.41–7.49 (3H, m), 7.83 (0.4H, s) 7.93–7.99 (2H, m), 8.19 (0.6H, s) 12.16 (0.4H, s)

2) ethyl 3-oxo-3-(2-phenyl-1,3-thiazol-4-yl)-2-[3-(1,1,2,2-tetrafluoroethoxy)benzyl]propionate To a solution of 3-(1,1,2,2-tetrafluoroethoxy)benzyl alcohol (5.53 ml, 24.7 mmol) in ethyl acetate (50 ml) was added triethylamine (5.2 ml, 37.05 mmol). Methanesulfonyl chloride (2.1 ml, 27.17 mmol) was added dropwise under ice-cooling, and the mixture was stirred as it was for 30 min. The precipitated crystals were filtered off, and the filtrate was concentrated to give mesylate, which was directly used in the next reaction.

A solution of ethyl 3-oxo-3-(2-phenyl-1,3-thiazol-4-yl)propionate (6.80 g, 24.7 mmol) in dimethoxyethane (50 ml) was ice-cooled. Sodium hydride (60%, 0.99 g, 24.7 mmol) was added, and the mixture was stirred under ice-cooling for 30 min. A solution of the mesylate in dimethoxyethane (50 ml) was added thereto, and the mixture was stirred overnight at room temperature. After completion of the reaction, the reaction was quenched with 1N hydrochloric acid, and the mixture was diluted with ethyl acetate, washed with water and saturated brine, dried over anhydrous magnesium sulfate, filtered and concentrated under reduced pressure. The residue was purified by silica gel column chromatography (hexane:ethyl acetate=10:1, 5:1) to give ethyl 3-oxo-3-(2-phenyl-1,3-thiazol-4-yl)-2-[3-(1,1,2,2-tetrafluoroethoxy)benzyl]propionate (8.65 g, 73%) as a pale-yellow oil.

IR ν max$^{KBr}$ (cm$^{-1}$): 1736, 1691, 1612, 1587, 1487, 1467, 1444, 1197, 1122 $^1$H-NMR (CDCl$_3$) δ (ppm) 1.12 (3H, t, J=7.2 Hz), 3.37 (2H, m), 4.12 (2H, q, J=7.0 Hz), 4.84 (1H, dd, J=7.0, 7.8 Hz), 5.87 (1H, dt, J=2.8, 53.0 Hz), 7.02–7.06 (1H, m), 7.18–7.32 (3H, m), 7.44–7.51 (3H, m), 7.94–7.98 (2H, m), 8.19 (1H, s).

3) ethyl 3-hydroxy-3-(2-phenyl-1,3-thiazol-4-yl)-2-[3-(1,1,2,2-tetrafluoroethoxy)benzyl]propionate To a suspension (50 ml) of zinc chloride (3.41 g, 25 mmol) in ether was added sodium borohydride (1.89 g, 50 mmol) at room temperature, and the mixture was stirred as it was for 2 hrs. Insoluble material was filtered off. To the filtrate was added a solution of ethyl 3-oxo-3-(2-phenyl-1,3-thiazol-4-yl)-2-[3-(1,1,2,2-tetrafluoroethoxy)benzyl]propionate (6.01 g, 12.5 mmol) in ether (40 ml) under ice-cooling, and the mixture was stirred as it was for 1 hr. The reaction was quenched with 1N hydrochloric acid. The mixture was diluted with ethyl acetate, washed with water and saturated brine, dried over anhydrous magnesium sulfate, filtered and concentrated under reduced pressure. The residue was purified by silica gel column chromatography (hexane:ethyl acetate=6:1, 4:1) to give ethyl 3-hydroxy-3-(2-phenyl-1,3-thiazol-4-yl)-2-[3-(1,1,2,2-tetrafluoroethoxy)benzyl]propionate (4.61 g, 76%) as a colorless transparent oil.

IR ν max$^{KBr}$ (cm$^{-1}$): 1726, 1612, 1587, 1460, 1302, 1277, 1197, 1120 $^1$H-NMR (CDCl$_3$) δ (ppm) 0.96–107 (3H, m), 2.93–3.15 (2H, m), 3.36–3.49 (1H, m), 3.54 (0.74H, d, J=5.2 Hz), 3.69 (0.26H, d, J=9.4 Hz), 3.99, 4.01 (2H, each q, J=6.8, 7.0 Hz), 4.94 (0.26H, dd, J=5.6, 9.6 Hz), 5.18–5.23 (0.74H, m), 5.85, 5.89 (1H, each dt, J=3.0, 53.0 Hz), 6.99–7.32 (5H, m), 7.39–7.47 (3H, m), 7.89–7.95 (2H, m). (The syn:anti-ratio was determined to be 2.8:1 according to the integral ratio of the peaks at 4.94 ppm and 5.18–5.23 ppm.)

4) 3-hydroxy-3-(2-phenyl-1,3-thiazol-4-yl)-2-[3-(1,1,2,2-tetrafluoroethoxy)benzyl]propionic acid To a solution of ethyl 3-hydroxy-3-(2-phenyl-1,3-thiazol-4-yl)-2-[3-(1,1,2,2-tetrafluoroethoxy)benzyl]propionate (6.28 g, 13.0 mmol) in tetrahydrofuran-ethanol (20 ml—20 ml) was added 2N sodium hydroxide (17 ml, 34 mmol) at room temperature, and the mixture was stirred overnight at room temperature. After completion of the reaction, the organic solvent was evaporated under reduced pressure and diluted with water. The aqueous layer was washed with ether and acidified with 1N hydrochloric acid, and the mixture was extracted with ethyl acetate. The organic layer was dried over anhydrous magnesium sulfate, filtered, and concentrated under reduced pressure to give 3-hydroxy-3-(2-phenyl-1,3-thiazol-4-yl)-2-[3-(1,1,2,2-tetrafluoroethoxy)benzyl]propionic acid (5.51 g, 93%) as a pale-yellow oil.

IR ν max$^{KBr}$ (cm$^{-1}$): 250-3300, 1707, 1612, 1587, 1458, 1278, 1197, 1120 $^1$H-NMR (CDCl$_3$) δ (ppm) 2.85–3.14 (2H, m), 3.39–3.52 (1H, m), 4.93 (0.33H, d, J=5.8 Hz), 5.24 (0.66H, d, J=4.4 Hz), 5.81, 5.85 (1H, dt, J=3.0, 53.0 Hz, J=3.0, 56.0 Hz respectively) 6.98–7.31 (5H, m), 7.39–7.45 (3H, m), 7.82–7.89 (2H, m).
(The syn:anti-ratio was determined to be 2:1 according to the integral ratio of the peaks at 4.93 ppm and 5.24 ppm.)

5) 5-(2-phenyl-1,3-thiazol-4-yl)-4-[3-(1,1,2,2-tetrafluoroethoxy)benzyl]-1,3-oxazolidin-2-one To a solution of 3-hydroxy-3-(2-phenyl-1,3-thiazol-4-yl)-2-[3-(1,1,2,2-tetrafluoroethoxy)benzyl]propionic acid (5.23 g, 11.48 mmol) in tetrahydrofuran (120 ml) were added triethylamine (2.40 ml, 17.22 mmol) and diphenylphosphoryl azide (2.73 ml, 12.63 mmol), and the mixture was heated under reflux for 5 hrs. The solvent was evaporated, and the residue was diluted with ethyl acetate and washed with water, saturated aqueous sodium hydrogen carbonate and saturated brine. The organic layer was dried over anhydrous magnesium sulfate, filtered and concentrated under reduced pressure. The residue was purified by silica gel column chromatography (hexane:ethyl acetate=3:1, 1:1) to give 5-(2-phenyl-1,3-thiazol-4-yl)-4-[3-(1,1,2,2-tetrafluoroethoxy)benzyl]-1,3-oxazolidin-2-one (4.57 g, 88%) as a pale-yellow oil.

IR ν max$^{KBr}$ (cm$^{-1}$): 3260, 1761, 1612, 1587, 1462, 1302, 1277, 1197, 1120 $^1$H-NMR (CDCl$_3$) δ (ppm) 2.33 (0.66H, dd, J=11.0, 13.8 Hz), 2.71 (0.66H, dd, J=4.0, 14.0 Hz), 3.01 (0.33H, dd, J=8.8, 13.8 Hz) 3.26 (0.33H, dd, J=5.0, 13.4 Hz), 4.27–4.51 (1H, m), 5.20 (0.66H, m), 5.42 (0.33H, d, J=5.5 Hz), 5.30–5.50 (0.33H, br) 5.61–5.65 (0.25H, m), 5.87–5.91 (0.5H, m), 6.00 (0.66H, d, J=8.2 Hz), 6.13–6.16 (0.25H, m), 6.95–7.19 (3H, m), 7.19–7.47 (5H, m) 7.90–7.95 (2H, m).

6) tert-butyl (4RS,5RS)-2-oxo-5-(2-phenyl-1,3-thiazol-4-yl)-4-[3-(1,1,2,2-tetrafluoroethoxy)benzyl]-1,3-oxazolidine-3-carboxylate To a solution of 5-(2-phenyl-1,3-thiazol-4-yl)-4-[3-(1,1,2,2-tetrafluoroethoxy)benzyl]-1,3-oxazolidin-2-one (4.43 g, 9.79 mmol) in acetonitrile (50 ml) were successively added di-tert-butyl-dicarbonate (2.58 g, 11.8 mmol) and 4-(dimethylamino)pyridine (0.12 g, 0.98 mmol), and the mixture was stirred overnight at room temperature. The solvent was evaporated under reduced pressure, and the residue was purified by flash column chromatography (hexane:ethyl acetate:toluene=4:1:1) to give tert-butyl (4RS,5RS)-2-oxo-5-(2-phenyl-1,3-thiazol-4-yl)-4-[3-(1,1,2,2-tetrafluoroethoxy)benzyl]-1,3-oxazolidine-3-carboxylate (3.40 g, 63%) to give a pale-yellow oil.

Syn (4RS,5RS) form (more polar) IR ν max$^{KBr}$ (cm$^{-1}$): 1824, 1724, 1612, 1587, 1489, 1464, 1356, 1116 $^1$H-NMR (CDCl$_3$) δ (ppm): 1.49 (9H, s) 2.78 (1H, dd, J=8.2, 14.0 Hz), 2.94 (1H, dd, J=4.6, 13.8 Hz), 4.98–5.08 (1H, m), 5.79–5.83 (1H, m), 5.82 (1H, dt, J=3.0, 53.0 Hz), 6.69 (2H, d, J=7.4 Hz), 6.81 (1H, d, J=8.0 Hz), 6.99–7.07 (1H, m), 7.15–7.29 (1H, m), 7.34–7.43 (3H, m), 7.68–7.73 (2H, m). anti (4RS, 5SR) form (less polar) IR ν max$^{KBr}$ (cm$^{-1}$): 1871, 1724, 1612, 1587, 1489, 1464, 1356, 1116 $^1$H-NMR (CDCl$_3$) δ (ppm): 1.59 (9H, s) 3.06 (1H, dd, J=8.8, 13.6 Hz), 3.44 (1H, dd, J=4.2, 14.0 Hz), 4.73–4.81 (1H, m), 5.28 (1H, dd, J=1.2, 3.0 Hz), 5.90 (1H, dt, J=2.8, 53.0 Hz) 7.18–7.25 (4H, m), 7.34–7.45 (4H, m), 7.82–7.87 (2H, m).

7) tert-butyl (1RS,2RS)-2-hydroxy-2-(2-phenyl-1,3-thiazol-4-yl)-1-[3-(1,1,2,2-tetrafluoroethoxy)benzyl]ethylcarbamate To a solution of tert-butyl (4RS,5RS)-2-oxo-5-(2-phenyl-1,3-thiazol-4-yl)-4-[3-(1,1,2,2-tetrafluoroethoxy)benzyl]-1,3-oxazolidine-3-carboxylate (3.17 g, 5.74 mmol) in methanol (60 ml) was added 1N sodium hydroxide (6.9 ml, 6.9 mmol), and the mixture was stirred overnight at room temperature. The mixture was diluted with water and extracted with ethyl acetate. The organic layer was washed with saturated brine, dried over anhydrous magnesium sulfate, filtered and concentrated under reduced pressure. The residue was purified by recrystallization (hexane-ethyl acetate) to give tert-butyl (1RS,2RS)-2-hydroxy-2-(2-phenyl-1,3-thiazol-4-yl)-1-[3-(1,1,2,2-tetrafluoroethoxy)benzyl]ethylcarbamate (1.72 g, 57%) as colorless crystals.

mp 127–128° C. IR ν max$^{KBr}$ (cm$^{-1}$): 3341, 1691, 1612, 1587, 1508, 1558, 1367, 1278, 1195, 1167, 1122 $^1$H-NMR (CD$_3$OD) δ (ppm): 1.39 (9H, s) 2.80 (1H, dd, J=6.0, 14.1 Hz), 2.92 (1H, dd, J=8.7, 14.1 Hz), 3.96 (1H, d, J=6.0 Hz) 4.29–4.34 (1H, m), 4.97 (1H, s) 5.22 (1H, d, J=5.8 Hz) 5.88 (1H, dt, J=2.7, 53.7 Hz), 7.07 (2H, s) 7.12 (1H, d, J=7.2 Hz), 7.24–7.30 (2H, m), 7.44–7.46 (3H, m), 7.95–7.98 (2H, m).

Example 362

4-fluoro-N-{(1RS,2RS)-2-hydroxy-2-(2-phenyl-1,3-thiazol-4-yl)-1-[3-(1,1,2,2-tetrafluoroethoxy)benzyl]ethyl}-1-naphthamide 1) (1RS,2RS)-2-amino-1-(2-phenyl-1,3-thiazol-4-yl)-3-[3-(1,1,2,2-tetrafluoroethoxy)phenyl]-1-propanol To a solution of tert-butyl (1RS,2RS)-2-hydroxy-2-(2-phenyl-1,3-thiazol-4-yl)-1-[3-(1,1,2,2-tetrafluoroethoxy)benzyl]ethylcarbamate (1.67 g, 3.17 mmol) in chloroform (20 ml) was added trifluoroacetic acid (20 ml), and the mixture was stirred at room temperature for 1 hr. The mixture was concentrated under reduced pressure. To the residue was added water, and the mixture was basified with saturated aqueous sodium hydrogen carbonate. The aqueous layer was extracted with ethyl acetate, dried over anhydrous magnesium sulfate, filtered and concentrated under reduced pressure. The residue was purified by recrystallization (hexane-ethyl acetate) to give (1RS,2RS)-2-amino-1-(2-phenyl-1,3-thiazol-4-yl)-3-[3-(1,1,2,2-tetrafluoroethoxy)phenyl]-1-propanol (1.17 g, 87%) as colorless crystals.

mp 128–130° C. IR ν max$^{KBr}$ (cm$^{-1}$): 3300, 1676, 1462, 1199, 1126 $^1$H-NMR (CDCl$_3$) δ (ppm): 2.76 (1H, dd, J=7.8, 14.1 Hz), 3.00 (1H, dd, J=6.3, 14.1 Hz), 3.77–3.83 (1H, m), 4.93 (1H, dd, J=0.9, 4.2 Hz), 6.27 (1H, dt, J=3.0, 52.5 Hz), 7.07 (1H, d, J=8.1 Hz), 7.16–7.20 (2H, m), 7.33 (1H, t, J=7.8 Hz), 7.46–7.49 (4H, m), 7.93–7.97 (2H, m).

2) 4-fluoro-N-{(1RS,2RS) 2-hydroxy-2-(2-phenyl-1,3-thiazol-4-yl)-1-[3-(1,1,2,2-tetrafluoroethoxy)benzyl]ethyl}-1-naphthamide To a solution of (1RS,2RS)-2-amino-1-(2-phenyl-1,3-thiazol-4-yl)-3-[3-(1,1,2,2-tetrafluoroethoxy)phenyl]-1-propanol (311 mg, 0.73 mmol) in N,N-dimethylformamide (10 ml) were added 4-fluoronaphthalene-1-carboxylic acid (133 mg, 0.70 mmol) and 1-hydroxybenzotriazole monohydrate (112 mg, 0.73 mmol), and 1-ethyl-3-(3-dimethylaminopropyl)carbodiimide hydrochloride (140 mg, 0.73 mmol) was finally added. The mixture was stirred at room temperature for 3 days. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=5:1, 1:2)

and recrystallization (hexane-ethyl acetate) to give 4-fluoro-N-{(1RS,2RS)-2-hydroxy-2-(2-phenyl-1,3-thiazol-4-yl)-1-[3-(1,1,2,2-tetrafluoroethoxy)benzyl]ethyl}-1-naphthamide (217 mg, 52%) as colorless crystals.

mp 148–150° C. IR ν max$^{KBr}$ (cm$^{-1}$): 3258, 1641, 1514, 1462, 1197, 1124 Elemental analysis for $C_{31}H_{23}N_2O_3SF_5$ Calcd: C, 62.20; H, 3.87; N, 4.68. Found: C, 62.06; H, 3.78; N, 4.63. $^1$H-NMR (CDCl$_3$) δ (ppm) 2.95 (1H, dd, J=6.0, 13.6 Hz), 3.13 (1H, dd, J=5.6, 14.0 Hz), 3.95 (1H, d, J=6.0 Hz), 4.89–5.02 (1H, m) 5.08–512 (1H, m), 5.87 (1H, dt, J=2.8, 53.0 Hz), 6.99–7.08 (4H, m), 7.21–7.59 (8H, m), 7.81–7.86 (2H, m), 8.09–8.15 (2H, m).

Example 363

N-{(1RS,2RS)-2-hydroxy-2-(2-phenyl-1,3,-thiazol-4-yl)-1-[3-(1,1,2,2-tetrafluoroethoxy)benzyl]ethyl}-6,7-dihydro-5H-benzo[a]cycloheptene-1-carboxamide To a solution of (1RS,2RS)-2-amino-1-(2-phenyl-1,3-thiazol-4-yl)-3-[3-(1,1,2,2-tetrafluoroethoxy)phenyl]-1-propanol (310 mg, 0.73 mmol) in acetonitrile (10 ml) were added 6,7-dihydro-5H-benzo[a]cycloheptene-1-carboxylic acid (132 mg, 0.70 mmol) and 1-hydroxybenzotriazole monohydrate (112 mg, 0.73 mmol), and 1-ethyl-3-(3-dimethylaminopropyl)carbodiimide hydrochloride (140 mg, 0.73 mmol) was finally added. The mixture was stirred at room temperature for 3 days. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=5:1, 2:1) and recrystallization (hexane-ethyl acetate) to give N-{(1RS,2RS)-2-hydroxy-2-(2-phenyl-1,3-thiazol-4-yl)-1-[3-(1,1,2,2-tetrafluoroethoxy)benzyl]ethyl}-6,7-dihydro-5H-benzo[a]cycloheptene-1-carboxamide (247 mg, 59%) as colorless crystals.

mp 137–138° C. Elemental analysis for $C_{32}H_{28}N_2O_3SF_4$ Calcd: C, 64.42; H, 4.73; N, 4.70. Found: C, 64.34; H, 4.64; N, 4.55. IR ν max$^{KBr}$ (cm$^{-1}$): 3265, 1641, 1512, 1304, 1195, 1122 $^1$H-NMR (CDCl$_3$) δ (ppm) 1.96–2.05 (2H, m), 2.12–2.22 (2H, m), 2.64–2.70 (2H, m), 3.00 (1H, dd, J=6.2, 14.2 Hz), 3.14 (1H, dd, J=8.6, 13.8 Hz), 4.34 (1H, d, J=5.8 Hz), 4.75–4.89 (1H, m), 5.08 (1H, dd, J=2.6, 5.4 Hz), 5.88 (1H, dt, J=3.0, 53.0 Hz) 5.94 (1H, dt, J=5.6, 11.6 Hz), 6.36 (1H, d, J=11.8 Hz), 6.50 (1H, d, J=8.0 Hz), 7.04–7.34 (8H, m), 7.42–7.47 (3H, m), 7.89–7.93 (2H, m).

Example 364

N-[(1RS,2SR)-1-(4-tert-butylbenzyl)-2-(4-fluorophenyl)-2-hydroxyethyl]-5-fluoro-1-naphthamide To a solution of (1RS,2RS)-2-amino-3-[4-(tert-butyl)benzyl]-1-(4-fluorophenyl)propan-1-ol (0.22 g, 0.70 mmol) in N,N-dimethylformamide (10 ml) were added 5-fluoronaphthalene-1-carboxylic acid (122 mg, 0.64 mmol) and 1-hydroxybenzotriazole monohydrate (108 mg, 0.70 mmol), and 1-ethyl-3-(3-dimethylaminopropyl)carbodiimide hydrochloride (134 mg, 0.70 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=2:1) and recrystallization (hexane-ethyl acetate) to give N-[(1RS,2SR)-1-(4-tert-butylbenzyl)-2-(4-fluorophenyl)-2-hydroxyethyl]-5-fluoro-1-naphthamide (153 mg, 50%) as colorless crystals.

mp 148–149° C. Elemental analysis for $C_{30}H_{29}NO_2F_2$ Calcd: C, 76.09; H, 6.17; N, 2.96. Found: C, 76.02; H, 6.16; N, 2.78. IR ν max$^{KBr}$ (cm$^{-1}$): 3267, 1637, 1508, 1412, 1244, 1224 $^1$H-NMR (CDCl$_3$) δ (ppm) 1.31 (9H, s) 2.73 (1H, dd, J=10.8, 14.4 Hz), 3.03 (1H, dd, J=4.5, 14.4 Hz), 3.82 (1H, d, J=2.6 Hz) 4.77–4.84 (1H, m), 5.06–5.08 (1H, m), 5.84 (1H, d, J=5.6 Hz) 7.04–7.17 (6H, m), 7.26–7.57 (6H, m), 7.59 (1H, d, J=5.6 Hz) 8.14 (1H, d, J=5.4 Hz).

Example 365

N-[(1RS,2SR)-1-(4-tert-butylbenzyl)-2-(4-fluorophenyl)-2-hydroxyethyl]-5-chloro-1-naphthamide To a solution of (1RS,2RS)-2-amino-3-[4-(tert-butyl)benzyl]-1-(4-fluorophenyl)propan-1-ol (0.34 g, 1.1 mmol) in N,N-dimethylformamide (10 ml) were added 5-chloronaphthalene-1-carboxylic acid (208 mg, 1.0 mmol) and 1-hydroxybenzotriazole monohydrate (170 mg, 1.1 mmol), and 1-ethyl-3-(3-dimethylaminopropyl)carbodiimide hydrochloride (210 mg, 1.1 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=2:1) and recrystallization (hexane-ethyl acetate) to give N-[(1RS,2SR)-1-(4-tert-butylbenzyl)-2-(4-fluorophenyl)-2-hydroxyethyl]-5-chloro-1-naphthamide (265 mg, 57%) as colorless crystals.

Elemental analysis for $C_{30}H_{29}NO_2ClF$ Calcd: C, 73.53; H, 5.97; N, 2.86. Found: C, 73.68; H, 5.93; N, 2.75. IR ν max$^{KBr}$ (cm$^{-1}$): 3261, 1637, 1508, 1222, 1157 $^1$H-NMR (CDCl$_3$) δ (ppm) 1.31 (9H, s) 2.72 (1H, dd, J=10.6, 14.2 Hz), 3.03 (1H, dd, J=4.4, 14.4 Hz), 3.73 (1H, d, J=3.6 Hz) 4.72–4.86 (1H, m), 5.03–5.07 (1H, m), 5.83 (1H, d, J=8.4 Hz) 7.01–7.13 (5H, m), 7.15–7.47 (6H, m), 7.56 (1H, dd, J=1.0, 7.6 Hz), 7.70 (1H, d, J=8.8 Hz), 8.31 (1H, d, J=8.4 Hz).

Example 366

N-[(1RS,2SR)-1-[3-(neopentyloxy)benzyl]-2-(3-chlorophenyl)-2-hydroxyethyl]-4-fluoro-1-naphthamide 1) methyl 3-(neopentyloxy)benzoate To a solution of methyl 3-hydroxybenzoate (7.68 g, 50.5 mmol) in N,N-dimethylformamide (100 ml) were added potassium carbonate (13.96 g, 101 mmol) and neopentyl iodide (10 g, 50.5 mmol), and the mixture was stirred at 100° C. overnight. The mixture was diluted with ethyl acetate, water and saturated brine, dried over anhydrous magnesium sulfate, filtered and concentrated under reduced pressure. The residue was purified by silica gel column chromatography (hexane:ethyl acetate=20:1, 10:1) to give methyl 3-(neopentyloxy)benzoate (4.69 g, 42%) as a colorless transparent oil.

IR ν max$^{KBr}$ (cm$^{-1}$): 1724, 1601, 1587, 1489, 1477, 1444, 1400, 1365, 1292, 1278, 1224 $^1$H-NMR (CDCl$_3$) δ (ppm) 1.04 (9H, s) 3.63 (2H, s) 3.91 (3H, s) 7.10 (1H, ddd, J=0.8, 2.6, 8.2 Hz), 7.32 (1H, t, J=7.8 Hz) 7.54–7.56 (1H, m), 7.60 (1H, dt, J=1.4, 7.8 Hz).

2) 3-(neopentyloxy)benzyl lcohol

To a solution of methyl 3-(neopentyloxy)benzoate (4.51 g, 20.3 mmol) in tetrahydrofuran (100 ml) was added lithium aluminum hydride (1.93 g, 50.75 mmol) by small portions under ice-cooling, and the mixture was stirred at room temperature for 2 hrs. To the mixture were successively added slowly water (2 ml), 15% aqueous sodium hydroxide solution (2 ml) and water (6 ml) under ice-cooling. The obtained solid was filtered with celite, washed thoroughly with ethyl acetate and concentrated under reduced pressure. The residue was purified by silica gel column chromatography (hexane:ethyl acetate=5:1) to give 3-(neopentyloxy)benzyl alcohol (3.81 g, 97%) as a colorless transparent oil.

IR ν max$^{KBr}$ (cm$^{-1}$): 3231, 1601, 1585, 1489, 1477, 1448, 1400, 1363, 1259, 1155 $^1$H-NMR (CDCl$_3$) δ (ppm) 1.03 (9H, s) 1.81 (1H, br) 3.59 (2H, s) 4.65 (2H, s) 6.80–6.93 (3H, m), 7.25 (1H, t, J=7.6 Hz).

3) 6-ethyl 2-[3-(neopentyloxy)benzyl]-3-(3-chlorophenyl)-3-oxopropionate

To a solution of 3-(neopentyloxy)benzyl alcohol (3.76 g, 19.4 mmol) in ethyl acetate (40 ml) was added triethylamine (4.06 ml, 29.1 mmol). Methanesulfonyl chloride (1.65 ml, 21.34 mmol) was added dropwise under ice-cooling, and the mixture was stirred as it was for 45 min. The precipitated crystals were filtered off, and the filtrate was concentrated to give mesylate, which was directly used in the next reaction.

A solution of ethyl 3-(3-chlorophenyl)-3-oxopropionate (4.40 g, 19.4 mmol) in dimethoxyethane (40 ml) was ice-cooled, and sodium hydride (60%, 0.78 g, 19.4 mmol) was added, and the mixture was stirred under ice-cooling for 30 min. A solution of the mesylate in dimethoxyethane (30 ml) was added thereto, and the mixture was stirred overnight at room temperature. After completion of the reaction, the reaction was quenched with 1N hydrochloric acid. The mixture was diluted with ethyl acetate, washed with water and saturated brine, dried over anhydrous magnesium sulfate, filtered and concentrated under reduced pressure. The residue was purified by silica gel column chromatography (hexane:ethyl acetate=15:1, 7:1) to give ethyl 2-[3-(neopentyloxy)benzyl]-3-(3-chlorophenyl)-3-oxopropionate (7.11 g, 91%) as a pale-yellow oil.

IR ν max$^{KBr}$ (cm$^{-1}$): 1736, 1691, 1585, 1475, 1448, 1365, 1255, 1226, 1159 $^1$H-NMR (CDCl$_3$) δ (ppm) 1.01 (9H, s) 1.14 (3H, t, J=7.2 Hz) 3.28 (2H, d, J=7.4 Hz), 3.52 (2H, s) 4.12 (2H, q, J=6.8 Hz) 4.55 (1H, t, J=7.4 Hz), 6.69–6.78 (3H, m), 7.11–7.18 (1H, m), 7.33–7.41 (1H, m), 7.49–7.55 (1H, m), 7.82 (1H, dt, J=1.0, 7.6 Hz) 7.90–7.92 (1H, m).

4) ethyl (2RS,3RS)-2-[3-(neopentyloxy)benzyl]-3-(3-chlorophenyl)-3-hydroxypropionate To a suspension (60 ml) of zinc chloride (4.75 g, 34.8 mmol) in ether was added sodium borohydride (2.64 g, 69.6 mmol) at room temperature, and the mixture was stirred as it was for 2 hrs. Insoluble material was filtered off. To the filtrate was added a solution of ethyl 2-[3-(neopentyloxy)benzyl]-3-(3-chlorophenyl)-3-oxopropionate (2.64 g, 69.6 mmol) in ether (40 ml), and the mixture was stirred at room temperature for 1 hr. The reaction was quenched with 1N hydrochloric acid. The mixture was diluted with ethyl acetate, washed with water and saturated brine, dried over anhydrous magnesium sulfate, filtered and concentrated under reduced pressure. The residue was purified by silica gel column chromatography (hexane:ethyl acetate=8:1, 3:1) to give ethyl (2RS,3RS)-2-[3-(neopentyloxy)benzyl]-3-(3-chlorophenyl)-3-hydroxypropionate (5.82 g, 81%) as a colorless transparent oil.

IR ν max$^{KBr}$ (cm$^{-1}$): 3472, 1726, 1599, 1583, 1477, 1448, 1400, 1257, 1159 $^1$H-NMR (CDCl$_3$) δ (ppm) 0.98 (3H, t, J=7.4 Hz), 1.01 (9H, s) 2.84–2.99 (3H, m), 3.10 (1H, d, J=2.4 Hz), 3.93 (2H, q, J=7.4 Hz), 5.01 (1H, t, J=3.0 Hz), 6.61–6.72 (3H, m), 7.08–7.15 (1H, m), 7.25–7.28 (3H, m), 7.41 (1H, s).

5) (4RS,5SR)-4-[3-(neopentyloxy)benzyl]-5-(3-chlorophenyl)-1,3-oxazolidin-2-one

To a solution of ethyl (2RS,3RS)-2-[3-(neopentyloxy)benzyl]-3-(3-chlorophenyl)-3-hydroxypropionate (5.71 g, 14.1 mmol) in tetrahydrofuran-ethanol (15 ml—15 ml) was added 2N sodium hydroxide (15 ml, 30 mmol) at room temperature, and the mixture was stirred overnight at room temperature. After completion of the reaction, the organic solvent was evaporated under reduced pressure, and the aqueous layer was acidified with 1N hydrochloric acid and extracted with ethyl acetate. The organic layer was dried over anhydrous magnesium sulfate and filtered, and the filtrate was concentrated under reduced pressure to give a colorless transparent oil.

To a solution of the oil obtained above in tetrahydrofuran (150 ml) were added triethylamine (2.95 ml, 21.15 mmol) and diphenylphosphoryl azide (3.35 ml, 15.51 mmol), and the mixture was heated under reflux for 4 hrs. The solvent was evaporated. The mixture was diluted with ethyl acetate, and washed with water, saturated aqueous sodium hydrogen carbonate and saturated brine. The organic layer was dried over anhydrous magnesium sulfate, filtered and concentrated under reduced pressure. Recrystallization from hexane-ethyl acetate gave (4RS,5SR)-4-[3-(neopentyloxy)benzyl]-5-(3-chlorophenyl)-1,3-oxazolidin-2-one (4.15 g, 79%) as colorless crystals.

mp 141–142° C. IR ν max$^{KBr}$ (cm$^{-1}$): 3248, 1763, 1601, 1583, 1477, 1400, 1363 $^1$H-NMR (CDCl$_3$) δ (ppm) 1.02 (9H, s) 2.15 (1H, dd, J=10.8, 13.2 Hz), 2.29 (1H, dd; J=4.2, 14.1 Hz), 3.54 (2H, s) 4.21–4.28 (1H, m), 4.99 (1H, s) 5.76 (1H, d, J=7.8 Hz), 6.57–6.62 (2H, m), 6.76 (1H, dd, J=2.1, 7.8 Hz), 7.16–7.21 (1H, m), 7.26–7.28 (1H, m), 7.34–7.39 (3H, m).

6) (1RS,2SR)-2-amino-3-[3-(neopentyloxy)phenyl]-1-(3-chlorophenyl)-1-propanol

To a solution of (4RS,5SR)-4-[3-(neopentyloxy)benzyl]-5-(3-chlorophenyl)-1,3-oxazolidin-2-one (4.0 g, 10.7 mmol) in ethanol (80 ml) was added 8N aqueous sodium hydroxide solution (6.7 ml, 53.5 mmol), and the mixture was heated under reflux for 5 hrs. After completion of the reaction, the mixture was diluted with water and extracted with ethyl acetate. The organic layers were combined, washed with saturated brine, dried over anhydrous magnesium sulfate, filtered and concentrated under reduced pressure. The residue was purified by recrystallization (hexane-ethyl acetate) to give (1RS,2SR)-2-amino-3-[3-(neopentyloxy)phenyl]-1-(3-chlorophenyl)-1-propanol (2.95 g, 79%) as colorless crystals.

mp 115–116° C. IR ν max$^{KBr}$ (cm$^{-1}$): 3300, 1599, 1583, 1477, 1448, 1400, 1363, 1255, 1159, 1053 $^1$H-NMR (CDCl$_3$) δ (ppm) 1.02 (9H, s) 2.29 (1H, dd, J=10.4, 13.6 Hz), 2.72 (1H, dd, J=3.0, 13.6 Hz), 3.30 (1H, dt, J=3.8, 14.4 Hz), 3.55 (2H, s) 4.66 (1H, d, J=4.8 Hz), 6.67–6.77 (3H, m) 7.14–7.30 (4H, m), 7.41 (1H, s).

7) N-[(1RS,2SR)-1-[3-(neopentyloxy)benzyl]-2-(3-chlorophenyl)-2-hydroxyethyl]-4-fluoro-1-naphthamide To a solution of (1RS,2SR)-2-amino-3-[3-(neopentyloxy)phenyl]-1-(3-chlorophenyl)-1-propanol (0.30 g, 0.86 mmol) in N,N-dimethylformamide (5 ml) were added 4-fluoronaphthalene-1-carboxylic acid (0.17 g, 0.90 mmol) and 1-hydroxybenzotriazole monohydrate (0.138 g, 0.90 mmol), and 1-ethyl-3-(3-dimethylaminopropyl)carbodiimide hydrochloride (0.173 g, 0.90 mmol) was finally added. The mixture was stirred at room temperature overnight. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by recrystallization (hexane-ethyl acetate) to give N-[(1RS,2SR)-1-[3-(neopentyloxy)benzyl]-2-(3-chlorophenyl)-2-hydroxyethyl]-4-fluoro-1-naphthamide (0.354 g, 79%) as colorless crystals.

mp 165–166° C. IR ν max$^{KBr}$ (cm$^{-1}$): 3263, 1639, 1599, 1583, 1518, 1477, 1448, 1400, 1259 $^1$H-NMR (CDCl$_3$) δ (ppm) 0.99 (9H, s) 2.73 (1H, dd, J=11.0, 14.4 Hz) 3.01 (1H, dd, J=4.0, 14.4 Hz), 3.52 (2H, dd, J=8.6, 11.4 Hz), 4.17 (1H, br) 4.70–4.81 (1H, m), 5.09 (1H, s) 5.87 (1H, d, J=7.2 Hz), 6.74–6.83 (3H, m), 7.00 (1H, dd, J=7.6, 9.8 Hz) 7.18–7.36 (5H, m), 7.41–7.57 (3H, m), 7.80 (1H, d, J=7.6 Hz) 8.07 (1H, d, J=7.6 Hz).

Example 367

N-[(1RS,2SR)-1-[3-(neopentyloxy)benzyl]-2-(3-chlorophenyl)-2-hydroxyethyl]-5-chloro-1-naphthamide To a solution of (1RS,2SR)-2-amino-3-[3-(neopentyloxy)phenyl]-1-(3-chlorophenyl)-1-propanol (0.30 g, 0.86 mmol) in N,N-dimethylformamide (5 ml) were added 5-chloronaphthalene-1-carboxylic acid (0.186 g, 0.90 mmol) and 1-hydroxybenzotriazole monohydrate (0.138 g, 0.90 mmol), and 1-ethyl-3-(3-dimethylaminopropyl)carbodiimide hydrochloride (0.173 g, 0.90 mmol) was finally added. The mixture was stirred at room temperature overnight. The mixture was diluted with ethyl acetate, washed with saturated aqueous sodium hydrogen carbonate solution, water and saturated brine, dried over anhydrous magnesium sulfate, filtered, and concentrated under reduced pressure. The residue was purified by recrystallization (hexane-ethyl acetate) to give N-[(1RS,2SR)-1-[3-(neopentyloxy)benzyl]-2-(3-chlorophenyl)-2-hydroxyethyl]-5-chloro-1-naphthamide (0.350 g, 76%) as colorless crystals.

mp 142–143° C. IR ν max$^{KBr}$ (cm$^{-1}$): 3252, 1637, 1518, 1477, 1448, 1398, 1363, 1255, 1159, 1059, 1022 $^1$H-NMR (CDCl$_3$) δ (ppm) 0.99 (9H, s) 2.71 (1H, dd, J=11.0, 14.4 Hz), 2.98 (1H, dd, J=4.2, 14.4 Hz), 3.51 (2H, dd, J=8.8, 11.6 Hz), 4.05 (1H, br) 4.70–4.79 (1H, m), 5.04 (1H, d, J=3.4 Hz) 5.97 (1H, d, J=7.6 Hz), 6.72–6.81 (3H, m), 7.16–7.62 (10H, m) 8.28 (1H, d, J=8.4 Hz).

Example 368

N-[(1RS,2SR)-1-[3-(neopentyloxy)benzyl]-2-(3-chlorophenyl)-2-hydroxyethyl]-6,7-dihydro-5H-benzo[a]cycloheptene-1-carboxamide To a solution of (1RS,2SR)-2-amino-3-[3-(neopentyloxy)phenyl]-1-(3-chlorophenyl)-1-propanol (0.40 g, 0.86 mmol) in N,N-dimethylformamide (5 ml) were added 6,7-dihydro-5H-benzo[a]cycloheptene-1-carboxylic acid (0.17 g, 0.90 mmol) and 1-hydroxybenzotriazole monohydrate (0.138 g, 0.90 mmol), and 1-ethyl-3-(3-dimethylaminopropyl)carbodiimide hydrochloride (0.173 g, 0.90 mmol) was finally added. The mixture was stirred at room temperature overnight. The mixture was diluted with ethyl acetate, washed with saturated aqueous sodium hydrogen carbonate solution, water and saturated brine, dried over anhydrous magnesium sulfate, filtered, and concentrated under reduced pressure. The residue was purified by silica gel column chromatography (hexane:ethyl acetate=1:1, 0:1), and recrystallization (hexane-ethyl acetate) to give N-[(1RS,2SR)-1-[3-(neopentyloxy)benzyl]-2-(3-chlorophenyl)-2-hydroxyethyl]-6,7-dihydro-5H-benzo[a]cycloheptene-1-carboxamide (0.174 g, 39%) as colorless crystals.

mp 128–129° C. IR ν max$^{KBr}$ (cm$^{-1}$): 3265, 1633, 1599, 1585, 1514, 1477, 1450, 1363, 1255, 1159 $^1$H-NMR (CDCl$_3$) δ (ppm) 1.01 (9H, s) 1.99–2.01 (1H, m), 2.14–2.20 (1H, m), 2.63–2.73 (3H, m), 2.94 (1H, dd, J=3.8, 13.6 Hz), 3.54 (2H, s) 4.33 (1H, d, J=4.4 Hz), 4.65 (1H, m), 5.03 (1H, br) 5.71 (1H, d, J=6.6 Hz), 5.90–6.01 (1H, m), 6.26 (1H, d, J=11.6 Hz), 6.71–6.78 (3H, m), 7.02–7.30 (7H, m).

Example 369

N-[(1RS,2SR)-1-[3-(tert-butyl)benzyl]-2-(3-chlorophenyl)-2-hydroxyethyl]-4-fluoro-1-naphthamide 1) 3-tert-butylphenyl trifluoromethanesulfonate To a solution of 3-tert-butylphenol (15 g, 100 mmol) in dichloromethane (300 ml) were added N-ethyldiisopropylamine (17.5 ml, 100 mmol) and N-phenyltrifluoromethanesulfonimide (44.7 g, 125 mmol), and the mixture was stirred overnight at room temperature. Dichloromethane was evaporated under reduced pressure. The mixture was diluted with ethyl acetate, washed with water and saturated brine, dried over anhydrous magnesium sulfate, filtered, and concentrated under reduced pressure. The residue was purified by silica gel column chromatography (hexane:ethyl acetate=30:1) to give 3-tert-butylphenyl trifluoromethanesulfonate (7.17 g, 25%) as a colorless transparent oil.

IR ν max$^{KBr}$ (cm$^{-1}$): 1612, 1577, 1489, 1423, 1246, 1215, 1145, 925 $^1$H-NMR (CDCl$_3$) δ (ppm) 1.33 (9H, s) 7.06–7.10 (1H, m), 7.24–7.25 (1H, m), 7.33–7.42 (2H, m).

2) 3-tert-butylbenzylbenzonitrile

To a solution of 3-tert-butylphenyl trifluoromethanesulfonate (6.17 g, 21.9 mmol) in acetonitrile (80 ml) were added sodium cyanide (2.15 g, 43.8 mmol) and copper iodide (0.42 g, 2.19 mmol). To the mixture was added tetrakis(triphenylphosphine)palladium (1.27 g, 1.10 mmol) under nitrogen stream and the mixture was heated under reflux for 5 hrs. The mixture was diluted with ethyl acetate, and insoluble material was filtered off with celite. The filtrate was washed with water and saturated brine, dried over anhydrous magnesium sulfate, filtered, and concentrated under reduced pressure. The residue was purified by silica gel column chromatography (hexane:ether=1:0, 20:1) to give 3-tert-butylbenzylbenzonitrile (4.13 g) as a colorless transparent oil. The compound included impurities, but was directly used in the next reaction.

IR ν max$^{KBr}$ (cm$^{-1}$): 2229, 1599, 1579, 1485, 1417, 1365, 1273, 1113 $^1$H-NMR (CDCl$_3$) δ (ppm) 1.32 (9H, s) 7.33–7.35 (2H, m), 7.39–7.50 (1H, m), 7.60–7.66 (1H, m).

3) 3-tert-butylbenzoic acid

To a suspension of 3-tert-butylbenzylbenzonitrile (4.13 g, 21.9 mmol) in water (80 ml) was added sodium hydroxide (2.19 g, 54.8 mmol) and the mixture was heated under reflux overnight. After completion of the reaction, the mixture was diluted with water, and the aqueous layer was washed with ether. The aqueous layer was then acidified with 6N hydrochloric acid, and extracted with ethyl acetate. The combined organic layer was washed with saturated brine, dried over anhydrous magnesium sulfate, filtered, and concentrated under reduced pressure to give 3-tert-butylbenzoic acid (3.23 g, 83% in 2 steps) as colorless crystals.

mp 96–97° C. IR ν max$^{KBr}$ (cm$^{-1}$): 2500–3300, 1693, 1604, 1585, 1440, 1412, 1286, 1259 $^1$H-NMR (CDCl$_3$) δ (ppm): 1.36 (9H, s) 7.41 (1H, t, J=7.5 Hz) 7.65 (1H, ddd, J=1.5, 2.1, 7.8 Hz), 7.94 (1H, dt, J=1.5, 7.8 Hz), 8.16 (1H, t, J=1.8 Hz).

4) 3-tert-butylbenzyl Alcohol

To a suspension (40 ml) of lithium aluminum hydride (1.38 g, 36.2 mmol) in ether was added dropwise a solution of 3-tert-butylbenzoic acid (3.13 g, 17.6 mmol) in ether (40 ml) under ice-cooling, and the mixture was stirred at room temperature for 2 hrs. After completion of the reaction, water (1.38 ml), 15% aqueous sodium hydroxide solution (1.38 ml) and water (4.2 ml) were successively added dropwise slowly under ice-cooling. The obtained solid was filtered with celite, and washed with ethyl acetate. The filtrate was concentrated, and the residue was purified by silica gel column chromatography (hexane:ethyl acetate= 8:1, 4:1) to give 3-tert-butylbenzyl alcohol (2.59 g, 90%) as a colorless transparent oil.

IR ν max$^{KBr}$ (cm$^{-1}$): 3277, 1606, 1489, 1363, 1275, 1203, 1016 $^1$H-NMR (CDCl$_3$) δ (ppm) 1.32 (9H, s) 1.85 (1H, s) 4.66 (2H, s) 7.14–7.19 (1H, m), 7.29–7.38 (3H, m).

5) ethyl 2-[3-(tert-butyl)benzyl]-3-(3-chlorophenyl)-3-oxopropionate

To a solution of 3-tert-butylbenzyl alcohol (2.50 g, 15.2 mmol) in ethyl acetate (30 ml) was added triethylamine (3.18 ml, 22.8 mmol). Methanesulfonyl chloride (1.29 ml, 16.72 mmol) was added dropwise under ice-cooling, and the mixture was stirred as it was for 1 hr. The precipitated crystals were filtered off, and the filtrate was concentrated to give mesylate, which was directly used in the next reaction.

A solution of ethyl 3-(3-chlorophenyl)-3-oxopropionate (3.45 g, 15.2 mmol) in dimethoxyethane (30 ml) was ice-cooled, and sodium hydride (60%, 0.61 g, 15.2 mmol) was added. The mixture was stirred for 30 min under ice-cooling. A solution of the mesylate in dimethoxyethane (25 ml) was added, and the mixture was stirred overnight at room temperature. After completion of the reaction, the reaction was quenched with 1N hydrochloric acid. The mixture was diluted with ethyl acetate, washed with water and saturated brine, dried over anhydrous magnesium sulfate, filtered, and concentrated under reduced pressure. The residue was purified by silica gel column chromatography (hexane-ethyl acetate=10:1, 8:1) to give ethyl 2-[3-(tert-butyl)benzyl]-3-(3-chlorophenyl)-3-oxopropionate (5.01 g, 88%) as a pale-yellow oil.

IR ν max$^{KBr}$ (cm$^{-1}$): 1739, 1691, 1572, 1475, 1423, 1365, 1228 $^{-1}$H-NMR (CDCl$_3$) δ (ppm) 1.13 (3H, t, J=7.0 Hz), 1.25 (9H, s) 3.32 (2H, dd, J=2.2, 7.8 Hz), 4.12 (2H, dq, J=1.8, 7.4 Hz) 4.55 (1H, t, J=7.4 Hz), 6.98–7.03 (1H, m), 7.18–7.21 (3H, m), 7.29–7.39 (1H, m), 7.48–7.53 (1H, m), 7.77 (1H, dt, J=1.6, 7.8 Hz) 7.85–7.87 (1H, m).

6) ethyl (2RS,3RS)-2-[3-(tert-butyl)benzyl]-3-(3-chlorophenyl)-3-hydroxypropionate To a suspension (50 ml) of zinc chloride (3.60 g, 26.4 mmol) in ether was added sodium borohydride (2.0 g, 52.8 mmol) at room temperature, and the mixture was stirred as it was for 2 hrs. Insoluble material was filtered off. To the filtrate was added a solution of ethyl 2-[3-(tert-butyl) benzyl]-3-(3-chlorophenyl)-3-oxopropionate (4.91 g, 13.2 mmol) in ether (40 ml), and the mixture was stirred at room temperature for 1 hr. The reaction was quenched with 1N hydrochloric acid. The mixture was diluted with ethyl acetate, washed with water and saturated brine, dried over anhydrous magnesium sulfate, filtered, and concentrated under reduced pressure. The residue was purified by silica gel column chromatography (hexane:ethyl acetate=10:1, 3:1) to give ethyl (2RS,3RS)-2-[3-(tert-butyl)benzyl]-3-(3-chlorophenyl)-3-hydroxypropionate (4.16 g, 82%) as a colorless transparent oil.

IR ν max$^{KBr}$ (cm$^{-1}$): 3456, 1728, 1599, 1477, 1373, 1346, 1180, 1032 $^1$H-NMR (CDCl$_3$) δ (ppm) 0.92 (3H, t, J=7.0 Hz), 1.27 (9H, s) 2.88–3.02 (3H, m), 3.14 (1H, d, J=3.0 Hz), 3.88 (2H, q, J=7.4 Hz), 4.99–5.01 (1H, m), 6.86–6.91 (1H, m), 7.07 (1H, s) 7.15–7.18 (2H, m), 7.25–7.27 (3H, m), 7.41 (1H, s).

7) (4RS,5SR)-4-[3-(tert-butyl)benzyl]-5-(3-chlorophenyl)-1,3-oxazolidin-2-one

To a solution of ethyl (2RS,3RS)-2-[3-(tert-butyl)benzyl]-3-(3-chlorophenyl)-3-hydroxypropionate (4.05 g, 10.8 mmol) in tetrahydrofuran-ethanol (10 ml-10 ml) was added 2N sodium hydroxide (11 ml, 22 mmol) at room temperature, and the mixture was stirred overnight at room temperature. After completion of the reaction, the organic solvent was evaporated under reduced pressure, and the aqueous layer was acidified with 1N hydrochloric acid and extracted with ethyl acetate. The organic layer was dried over anhydrous magnesium sulfate, filtered, and concentrated under reduced pressure to give a colorless transparent oil.

To a solution of the oil obtained above in tetrahydrofuran (100 ml) were added triethylamine (2.26 ml, 16.2 mmol) and diphenylphosphoryl azide (2.56 ml, 11.88 mmol), and the mixture was heated under reflux for 4 hrs. The solvent was evaporated, and the residue was diluted with ethyl acetate, washed with water, saturated aqueous sodium hydrogen carbonate and saturated brine. The organic layer was dried over anhydrous magnesium sulfate, filtered, and concentrated under reduced pressure and recrystallized from hexane-ethyl acetate to give (4RS,5SR)-4-[3-(tert-butyl) benzyl]-5-(3-chlorophenyl)-1,3-oxazolidin-2-one (2.47 g, 60%) as colorless crystals.

mp 136–137° C. IR ν max$^{KBr}$ (cm$^{-1}$): 3263, 1763, 1601, 1477, 1433, 1363, 1234 $^1$H-NMR (CDCl$_3$) δ (ppm) 1.28 (9H, s) 2.20 (1H, dd, J=11.1, 13.8 Hz), 2.32 (1H, dd, J=3.9, 13.8 Hz), 4.23–4.30 (1H, m), 4.99 (1H, s) 5.77 (1H, d, J=8.1 Hz), 6.85 (1H, d, J=7.2 Hz) 7.01 (1H, s) 7.19–7.31 (3H, m), 7.34–7.40 (3H, m).

8) (1RS,2SR)-2-amino-3-[3-(tert-butyl)phenyl]-1-(3-chlorophenyl)-1-propanol

To a solution of (4RS,5SR)-4-[3-(tert-butyl)benzyl]-5-(3-chlorophenyl)-1,3-oxazolidin-2-one (2.36 g, 6.86 mmol) in ethanol (60 ml) was added 8N aqueous sodium hydroxide (4.3 ml, 34.3 mmol), and the mixture was heated under reflux for 5 hrs. After the completion of the reaction, ethanol was evaporated under reduced pressure. The residue was diluted with water and extracted with ethyl acetate. The organic layers were combined, washed with saturated brine, dried over anhydrous magnesium sulfate, filtered, and concentrated under reduced pressure. The residue was purified by recrystallization (hexane-ethyl acetate) to give (1RS, 2SR)-2-amino-3-[3-(tert-butyl)phenyl]-1-(3-chlorophenyl)-1-propanol (1.21 g, 55%) as colorless crystals.

mp 102–103° C. IR ν max$^{KBr}$ (cm$^{-1}$): 3063, 1597, 1576, 1476, 1429, 1363, 1199 $^1$H-NMR (CDCl$_3$) δ (ppm) 1.30 (9H, s) 2.32 (1H, dd, J=10.4, 13.6 Hz), 2.75 (1H, dd, J=3.2, 13.8 Hz), 3.31 (1H, dt, J=4.0, 9.6 Hz), 4.68 (1H, d, J=4.8 Hz), 6.94–6.96 (1H, m), 7.13 (1H, s) 7.21–7.31 (5H, m), 7.42 (1H, s)

9) N-[(1RS,2SR)-1-[3-(tert-butyl)benzyl]-2-(3-chlorophenyl)-2-hydroxyethyl]-4-fluoro-1-naphthamide To a solution of (1RS,2SR)-2-amino-3-[3-(tert-butyl) phenyl]-1-(3-chlorophenyl)-1-propanol (0.30 g, 0.944 mmol) in N,N-dimethylformamide (5 ml) were added 4-fluoronaphthalene-1-carboxylic acid (0.189 g, 0.99 mmol) and 1-hydroxybenzotriazole monohydrate (0.152 g, 0.99 mmol), and 1-ethyl-3-(3-dimethylaminopropyl)carbodiimide hydrochloride (0.190 g, 0.99 mmol) was finally added. The mixture was stirred at room temperature overnight. The mixture was diluted with ethyl acetate, washed with saturated aqueous sodium hydrogen carbonate solution, water and saturated brine, dried over anhydrous magnesium sulfate, filtered and concentrated under reduced pressure. The residue was purified by silica gel column chromatography (hexane:ethyl acetate=1:1, 0:1) and recrystallization (hexane-ethyl acetate) to give N-[(1RS,2SR)-1-[3-(tert-butyl)benzyl]-2-(3-chlorophenyl)-2-hydroxyethyl]-4-fluoro-1-naphthamide (0.245 g, 53%) as colorless crystals.

mp 76–78° C. IR ν max$^{KBr}$ (cm$^{-1}$): 3312, 1639, 1599, 1516, 1425, 1261, 1236, 1201, 1051 $^1$H-NMR (CDCl$_3$) δ (ppm) 0.99 (9H, s) 2.73 (1H, dd, J=11.0, 14.4 Hz), 3.01 (1H, dd, J=4.0, 14.4 Hz), 3.52 (2H, dd, J=8.6, 11.4 Hz), 4.17 (1H, br) 4.70–4.81 (1H, m), 5.09 (1H, s) 5.87 (1H, d, J=7.2 Hz), 6.74–6.83 (3H, m), 7.00 (1H, dd, J=7.6, 9.8 Hz) 7.18–7.36 (5H, m), 7.41–7.57 (3H, m), 7.80 (1H, d, J=7.6 Hz) 8.07 (1H, d, J=7.6 Hz).

Example 370

N-[(1RS,2SR)-1-[3-(tert-butyl)benzyl]-2-(3-chlorophenyl)-2-hydroxyethyl]-6,7-dihydro-5H-benzo[a]cycloheptene-1-carboxamide To a solution of (1RS,2SR)-2-amino-3-[3(tert-butyl)phenyly]-(3-chlorophenyl)-1-propanol (0.30 g, 0.944 mmol) in N,N-dimethylformamide (5 ml) were added 6,7-dihydro-5H-benzo[a]cycloheptene-1-carboxylic acid (0.187 g, 0.99 mmol) and 1-hydroxybenzotriazole monohydrate (0.152 g, 0.99 mmol), and 1-ethyl-3-(3-dimethyla1ninopropyl)carbodiimide hydrochloride (0.190 g, 0.99 mmol) was finally added. The mixture was stirred at room temperature overnight, The mixture was diluted with ethyl acetate, washed with saturated aqueous sodium hydrogen carbonate solution, water and saturated brine, dried over anhydrous magnesium sulfate, filtered, and concentrated under reduced pressure. The residue was purified by silica gel column chromatography (hexane:ethyl acetate=1:1, 0:1) and recrystallization (hexane-ethyl acetate) to give N-[(1RS,2SR)-1-[3-(tert-butyl)benzyl]-2(3-chlorophenyl)2-hydroxyethyl]-6,7-dihydro-5H-benzo[a]cycloheptene-1-carboxamide (0.230 g, 50%) as colorless crystals.

mp 104–105° C. IR ν max$^{KBr}$ (cm$^{-1}$): 3300, 1635, 1514, 1425, 1363, 1298, 1273, 1197, 1103, 1076 $^1$H-NMR (CDCl$_3$) δ (ppm) 1.27 (9H, s) 1.95–2.01 (2H, m), 2.14–2.20 (2H, m), 2.63–2.75 (3H, m), 297 (1H, dd, J=4.0, 14.2 Hz), 4.36 (1H, s) 4.67–4.69 (1H, m), 5.02 (1H, s) 5.69 (1H, d, J=7.4 Hz) 5.87–5.98 (1H, m), 6.26 (1H, d, J=12.0 Hz), 6.86–7.30 (10H, m) 7.47 (1H, s).

Example 371

N-[(1RS,2SR)-1-[3-(tert-butyl)benzyl]-2-(3-chlorophenyl)-2-hydroxyethyl]-5-chloro-1-naphthamide To a solution of (1RS,2SR)-2-amino-3-[3-(tert-butyl)phenyl]-1-(3-chlorophenyl)-1-propanol (0.313 g, 0.985 mmol) in N,N-dimethylformamide (5 ml) were added 5-chloronaphthalene-1-carboxylic acid (0.214 g, 1.04 mmol) and 1-hydroxybenzotriazole monohydrate (0.160 g, 1.04 mmol), and 1-ethyl-3-(3-dimethylaminopropyl)carbodiimide hydrochloride (0.20 g, 1.04 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, filtered, and concentrated under reduced pressure. The residue was purified by recrystallization (hexane-ethyl acetate) to give N-[(1RS,2SR)-1-[3-(tert-butyl)benzyl]-2-(3-chlorophenyl)-2-hydroxyethyl]-5-chloro-1-naphthamide (0.307 g, 62%) as colorless crystals.

mp 91–93° C. IR ν max$^{KBr}$ (cm$^{-1}$): 3267, 1631, 1572, 1518, 1203, 1037 $^1$H-NMR (CDCl$_3$) δ (ppm) 1.25 (9H, s) 2.74 (1H, dd, J=11.0, 14.4 Hz), 3.05 (1H, dd, J=4.0, 14.2 Hz), 4.02 (1H, d, J=4.4 Hz) 4.77–4.86 (1H, m), 5.05–5.09 (1H, m), 5.87 (1H, d, J=7.8 Hz) 7.01 (1H, d, J=7.4 Hz), 7.12–7.66 (12H, m), 8.29 (1H, d, J=8.8 Hz).

Example 372 tert-butyl (1RS,2SR)-2-(3-chlorophenyl)-2-hydroxy-1-[4-(2,2,3,3,3-pentafluoropropyl)benzyl]ethylcarbamate 1) 2,2,3,3,3-pentafluoro-1-(4-methylphenyl)propan-1-ol In a three neck flask purged with nitrogen were charged magnesium (12.2 g, 502 mmol) and ether (100 ml). A solution of 4-bromotoluene (56.1 ml, 456 mmol) in ether (200 ml) was added dropwise, and the mixture was heated under reflux for 1.5 hrs. The reaction vessel was cooled in a dry ice-acetone bath. A solution of pentafluoropropionic acid (25 g, 152 mmol) in ether (100 ml) was added dropwise, and the temperature was slowly raised to room temperature. The mixture was heated under reflux for 3 hrs, and stirred overnight at room temperature. The reaction mixture was ice-cooled, and quenched with 3N hydrochloric acid. The mixture was diluted with ethyl acetate, and the organic layer was separated and washed with saturated aqueous sodium hydrogen carbonate and saturated brine, dried over anhydrous magnesium sulfate, filtered and concentrated under reduced pressure. The residue was purified by silica gel column chromatography (hexane:ethyl acetate=1:0, 30:1) to give a colorless transparent oil. This was dissolved in methanol, and sodium borohydride was added under ice-cooling. The temperature was raised to, room temperature, and the mixture was stirred for 1 hr. After completion of the reaction, the reaction was quenched with 6N hydrochloric acid, and the mixture was extracted with ethyl acetate. The organic layer was washed with saturated brine, dried over anhydrous magnesium sulfate, filtered, and concentrated under reduced pressure. The residue was purified by silica gel column chromatography (hexane:ethyl acetate=10:1, 5:1) to give 2,2,3,3,3-pentafluoro-1-(4-methylphenyl)propan-1-ol (20.28 g, 56%) as a colorless transparent oil.

IR ν max$^{KBr}$ (cm$^{-1}$): 3400, 1616, 1518, 1363, 1331, 1213, 1184, 1132 $^1$H-NMR (CDCl$_3$) δ (ppm) 2.37 (3H, s) 2.50 (1H, d, J=4.8 Hz) 4.98–5.13 (1H, m), 7.21 (2H, d, J=8.4 Hz), 7.33 (2H, d, J=8.0 Hz).

2) O-phenyl O-[2,2,3,3,3-pentafluoro-1-(4-methylphenyl)propyl]thiocarbonate

To a solution of 2,2,3,3,3-pentafluoro-1-(4-methylphenyl)propan-1-ol (15.93 g, 66.3 mmol) in ethyl acetate (200 ml) was added triethylamine (13.9 ml, 99.45 mmol), and chlorophenyl thionoformate (10.1 ml, 72.8 mmol) was added under ice-cooling, and the mixture was stirred under ice-cooling for 2 hrs. The precipitated solid was filtered off, and the filtrated was washed with ethyl acetate and concentrated under reduced pressure. The residue was purified by silica gel column chromatography (hexane:ethyl acetate=30:1) to give O-phenyl O-[2,2,3,3,3-pentafluoro-1-(4-methylphenyl)propyl]thiocarbonate (22.82 g, 91%) as a colorless transparent oil.

IR ν max$^{KBr}$ (cm$^{-1}$): 1616, 1591, 1518, 1491, 1290, 1192, 1143 $^1$H-NMR (CDCl$_3$) δ (ppm) 2.39 (3H, s) 6.67 (1H, dd, J=7.5, 16.5 Hz) 7.05 (2H, d, J=8.1 Hz), 7.24–7.31 (3H, m), 7.37–7.42 (4H, m).

3) 4-(2,2,3,3,3-pentafluoropropyl)toluene

To a solution of O-phenyl O-[2,2,3,3,3-pentafluoro-1-(4-methylphenyl)propyl]thiocarbonate (16.55 g, 44.0 mmol) in benzene (100 ml) were added 2,2'-azobisisobutyronitrile (1.45 g, 8.8 minol) and tri-n-butyltin hydride (17.8 ml, 66.0 mmol), and the mixture was stirred at 80° C. for 5 hrs. After completion of the reaction, benzene was evaporated under reduced pressure, and the residue was purified by silica gel column chromatography (hexane) to give 4-(2,2,3,3,3-pentafluoropropyl)toluene (11.13 g) as a colorless transparent oil. This contained some impurities, which were assumed to be tin compounds, but was directly used in the next reaction.

IR ν max$^{KBr}$ (cm$^{-1}$): 1518, 1464, 1377, 1315, 1203, 1118, 1080, 1030 $^1$H-NMR (CDCl$_3$) δ (ppm) 2.34 (3H, s) 3.26 (2H, t, J=18.8 Hz) 7.16 (4H, s).

4) 1-(bromomethyl)-4-(2,2,3,3,3-pentafluoropropyl) benzene

To a solution of 4-(2,2,3,3,3-pentafluoropropyl)toluene (9.97 g, 39.4 mmol) in carbon tetrachloride (300 ml) were added 2,2'-azobisisobutyronitrile (0.33 g, 197 mmol) and N-bromosuccinimide (8.50 g, 47.3 mmol) and the mixture was heated under reflux overnight. After cooling to room temperature, insoluble material was filtered off, and the filtrated was concentrated under reduced pressure. The residue was purified by silica gel column chromatography (hexane:ethyl acetate=1:0, 50:1, 20:1) to give 1-(bromomethyl)-4-(2,2,3,3,3-pentafluoropropyl)benzene (3.66 g, 31% (yield by two steps)) as colorless crystals.

mp 62–63° C. IR ν max$^{KBr}$ (cm$^{-1}$): 1518, 1437, 1323, 1190, 1101, 1070, 1045 $^1$H-NMR (CDCl$_3$) δ (ppm) 3.31 (2H, t, J=17.8 Hz), 7.27 (2H, d, J=8.0 Hz), 7.40 (2H, d, J=8.4 Hz).

5) ethyl 3-(3-chlorophenyl)-3-oxo-2-[4-(2,2,3,3,3-pentafluoropropyl)benzyl]propionate A solution of ethyl 3-(3-chlorophenyl)-3-oxopropionate (2.74 g, 12.08 mmol) in dimethoxyethane (30 ml) was ice-cooled, and sodium hydride (60%, 0.49 g, 12.08 mmol) was added, and the mixture was stirred under ice-cooling for 30 min. A solution of 1-(bromomethyl)-4-(2,2,3,3,3-pentafluoropropyl)benzene (3.66 g, 12.08 mmol) in dimethoxyethane (15 ml) was added, and the mixture was stirred overnight at room temperature. After completion of the reaction, the reaction was quenched with 0.5N hydrochloric acid. The mixture was diluted with ethyl acetate, washed with water and saturated brine, dried over anhydrous magnesium sulfate, filtered, and concentrated under reduced pressure. The residue was purified by silica gel column chromatography (hexane:ethyl acetate=15:1, 10:1) to give ethyl 3-(3-chlorophenyl)-3-oxo-2-[4-(2,2,3,3,3-pentafluoropropyl)benzyl]propionate (4.64 g, 86%) as colorless crystals.

mp 81–82° C. IR ν max$^{KBr}$ (cm$^{-1}$): 1738, 1693, 1572, 1425, 1317, 1195, 1028 $^1$H-NMR (CDCl$_3$) δ (ppm) 1.11 (3H, t, J=7.2 Hz), 3.25 (2H, t, J=18.3 Hz), 3.32 (2H, d, J=7.2 Hz), 4.05–4.14 (2H, m), 4.54 (1H, t, J=7.5 Hz), 7.16–7.23 (4H, m), 7.37 (1H, t, J=8.1 Hz) 7.51–7.54 (1H, m), 7.77–7.81 (1H, m), 7.90–7.92 (1H, m).

6) ethyl (2RS,3RS)-3-(3-chlorophenyl)-3-hydroxy-2-[4-(2,2,3,3,3-pentafluoropropyl)benzyl]propionate To a suspension (30 ml) of zinc chloride (2.70 g, 19.84 mmol) in ether was added sodium borohydride (1.50 g, 39.68 mmol) at room temperature and the mixture was stirred as it was for 2 hrs. Insoluble material was filtered off. To the filtrate was added a solution of ethyl 3-(3-chlorophenyl)-3-oxo-2-[4-(2,2,3,3,3-pentafluoropropyl) benzyl]propionate (4.45 g, 9.92 mmol) in ether (20 ml), and the mixture was stirred at room temperature for 1 hr. The reaction was quenched with 1N hydrochloric acid. The mixture was diluted with ethyl acetate, washed with water and saturated brine, dried over anhydrous magnesium sulfate, filtered, and concentrated under reduced pressure. The residue was purified by silica gel column chromatography (hexane:ethyl acetate=10:1, 5:1) to give ethyl (2RS, 3RS)-3-(3-chlorophenyl)-3-hydroxy-2-[4-(2,2,3,3,3-pentafluoropropyl)benzyl]propionate (3.95 g, 89%) as a colorless transparent oil.

IR ν max$^{KBr}$ (cm$^{-1}$): 3450, 1709, 1576, 1518, 1435, 1315, 1195, 1113, 1030 $^1$H-NMR (CDCl$_3$) δ (ppm) 0.91 (3H, t, J=7.0 Hz), 2.87–3.02 (3H, m) 3.18 (1H, d, J=2.6 Hz), 3.25 (2H, t, J=18.2 Hz), 3.88 (2H, q, J=6.8 Hz), 5.02 (1H, d, J=1.8 Hz), 7.04–7.17 (4H, m), 7.26–7.28 (3H, m), 7.41–7.42 (1H, m).

7) (2RS,3RS)-3-(3-chlorophenyl)-3-hydroxy-2-[4-(2,2,3,3,3-pentafluoropropyl)benzyl]propionic acid To a solution of ethyl (2RS,3RS)-3-(3-chlorophenyl)-3-hydroxy-2-[4-(2,2,3,3,3-pentafluoropropyl)benzyl] propionate (3.84 g, 8.52 mmol) in tetrahydrofuran-ethanol (20 ml—20 ml) was added 1N sodium hydroxide (17 ml, 17 mmol) at room temperature, and the mixture was stirred overnight at room temperature. After completion of the reaction, the organic solvent was evaporated under reduced pressure, and the aqueous layer was acidified with 1N hydrochloric acid and extracted with ethyl acetate. The organic layer was dried over anhydrous magnesium sulfate, filtered, and concentrated under reduced pressure. The residue was recrystallized from hexane-ethyl acetate to give (2RS,3RS)-3-(3-chlorophenyl)-3-hydroxy-2-[4-(2,2,3,3,3-pentafluoropropyl)benzyl]propionic acid (2.85 g, 79%) as colorless crystals.

mp 150–151° C. IR ν max$^{KBr}$ (cm$^{-1}$): 2500-3300, 1693, 1433, 1315, 1238, 1194, 1103, 1078, 1030 $^1$H-NMR (CDCl$_3$) δ (ppm) 2.87–3.05 (3H, m), 3.24 (2H, t, J=18.4 Hz) 5.09 (1H, d, J=4.0 Hz), 7.05 (2H, d, J=8.0 Hz), 7.14 (2H, d, J=8.4 Hz), 7.24–7.29 (3H, m), 7.41 (1H, s).

8) (4RS,5SR)-5-(3-chlorophenyl)-4-[4-(2,2,3,3,3-pentafluoropropyl)benzyl]-1,3-oxazolidin-2-one To a solution of (2RS,3RS)-3-(3-chlorophenyl)-3-hydroxy-2-[4-(2,2,3,3,3-pentafluoropropyl)benzyl] propionic acid (2.75 g, 6.50 mmol) in tetrahydrofuran (70 ml) were added triethylamine (1.36 ml, 9.75 mmol) and diphenylphosphoryl azide (1.54 ml, 7.15 mmol), and the mixture was heated under reflux for 4 hrs. The solvent was evaporated and the residue was diluted with ethyl acetate, washed with water, saturated. aqueous sodium hydrogen carbonate and saturated brine. The organic layer was dried over anhydrous magnesium sulfate, filtered, and concentrated under reduced pressure. The residue as recrystallized from hexane-ethyl acetate to give (4RS,5SR)-5-(3-chlorophenyl)-4-[4-(2,2,3,3,3-pentafluoropropyl)benzyl]-1, 3-oxazolidin-2-one (2.54 g, 93%) as colorless crystals.

mp 137–138° C. IR ν max$^{KBr}$ (cm$^{-1}$): 3234, 1761, 1435, 1317, 1194, 1030, 912 $^1$H-NMR (CDCl$_3$) δ (ppm) 2.17–2.36 (2H, m), 3.28 (2H, t, J=18.6 Hz) 4.19–4.30 (1H, m), 4.95 (1H, s) 5.77 (1H, d, J=8.2 Hz) 7.03 (2H, d, J=7.6 Hz), 7.27–7.38 (3H, m).

9) tert-butyl (4RS,5SR)-5-(3-chlorophenyl)-2-oxo-4-[4-(2, 2,3,3,3-pentafluoropropyl)benzyl]-1,3-oxazolidine-3-carboxylate To a solution of (4RS,5SR)-5-(3-chlorophenyl)-4-[4-(2,2, 3,3,3-pentafluoropropyl)benzyl]-1,3-oxazolidin-2-one (2.43 g, 5.79 mmol) in acetonitrile (40 ml) were successively added di-tert-butyl dicarbonate (1.52 g, 6.95 mmol) and 4-(dimethylamino)pyridine (71 mg, 0.579 mmol), and the mixture was stirred overnight at room temperature. The solvent was evaporated under reduced pressure, and the residue was recrystallized from hexane-ethyl acetate to give tert-butyl (4RS,5SR)-5-(3-chlorophenyl)-2-oxo-4-[4-(2,2,3,3,3-pentafluoropropyl)benzyl]-1,3-oxazolidine-3-carboxylate (2.77 g, 92%) as colorless crystals.

mp 136–138° C. IR ν max$^{KBr}$ (cm$^{-1}$): 1813, 1724, 1358, 1315, 1251, 1195, 157, 1076, 1028 $^1$H-NMR (CDCl$_3$) δ (ppm): 1.49 (9H, s) 2.58 (1H, dd, J=8.8, 14.4 Hz) 2.88 (1H, dd, J=4.6, 14.4 Hz), 3.21 (2H, t, J=18.4H) 4.77–4.87 (1H, m), 5.64 (1H, d, J=7.0 Hz), 6.67 (2H, d, J=8.0 Hz), 6.99–7.03 (3H, m), 7.12–7.19 (2H, m), 7.24–7.30 (1H, m).

10) tert-butyl (1RS,2SR)-2-(3-chlorophenyl)-2-hydroxy-1-[4-(2,2,3,3,3-pentafluoropropyl)benzyl]ethylcarbamate To a solution of tert-butyl (4RS,5SR)-5-(3-chlorophenyl)-2-oxo-4-[4-(2,2,3,3,3-pentafluoropropyl)benzyl]-1,3-oxazolidine-3-carboxylate (2.66 g, 5.12 mmol) in methanol-tetrahydrofuran (20 ml-20 ml) was added 1N sodium hydroxide (6.2 ml, 6.2 mmol), and the mixture was stirred overnight at room temperature. The mixture was diluted with water and extracted with ethyl acetate. The organic layer was washed with saturated brine, dried over anhydrous magnesium sulfate, filtered, and concentrated under reduced pressure. The residue was purified by recrystallization (hexane-ethyl acetate) to give tert-butyl (1RS,2SR)-2-(3-chlorophenyl)-2-hydroxy-1-[4-(2,2,3,3,3-pentafluoropropyl)benzyl]ethylcarbamate (2.11 g, 83%) as colorless crystals.

mp 156–157° C. IR ν max$^{KBr}$ (cm$^{-1}$): 3348, 1682, 1531, 1444, 1311, 1244, 1178, 1032 $^1$H-NMR (CDCl$_3$) δ (ppm): 1.34 (9H, s) 2.59–2.79 (2H, m), 3.26 (2H, t, J=18.4 Hz), 3.49 (1H, br) 4.09 (1H, br) 4.55 (1H, d, J=7.6 Hz), 4.91 (1H, br) 7.08–7.20 (4H, m), 7.26–7.29 (3H, m), 7.1 (1H, s).

Example 373

N-[(1RS,2SR)-1-[4-(2,2,3,3,3-pentafluoropropyl)benzyl]-2-(3-chlorophenyl)-2-hydroxyethyl]-4-fluoro-1-naphthamide 1) (1RS,2SR)-2-amino-1-(3-chlorophenyl)-3-[4-(2,2,3,3,3-pentafluoropropyl)phenyl]-1-propanol To a solution of tert-butyl (1RS,2SR)-2-(3-chlorophenyl)-2-hydroxy-1-[4-(2,2,3,3,3-pentafluoropropyl)benzyl]ethylcarbamate (2.00 g, 4.05 mmol) in chloroform (20 ml) was added trifluoroacetic acid (20 ml), and the mixture was stirred at room temperature for 1 hr. The mixture was concentrated under reduced pressure. To the residue was added water, and the mixture was basified with saturated aqueous sodium hydrogen carbonate. The aqueous layer was extracted with ethyl acetate, dried over anhydrous magnesium sulfate, filtered and concentrated under the reduced pressure. The residue was recrystallized from (hexane-ethyl acetate) to give (1RS,2SR)-2-amino-1-(3-chlorophenyl)-3-[4-(2,2,3,3,3-pentafluoropropyl)phenyl]-1-propanol (1.08 g, 68%) as colorless crystals.

mp 109–110° C. IR ν max$^{KBr}$ (cm$^{-1}$) 3000-3300, 1576, 1518, 1433, 1317, 1078, 1028 $^1$H-NMR (CDCl$_3$) δ (ppm): 1.60 (2H, br) 2.35 (1H, dd, J=10.2, 13.4 Hz), 2.75 (1H, dd, J=3.0, 13.6 Hz), 3.18–3.36 (3H, m), 4.66 (1H, d, J=4.8 Hz), 7.10–7.35 (7H, m), 7.41 (1H, s).

2) N-[(1RS,2SR)-1-[4-(2,2,3,3,3-pentafluoropropyl)benzyl]-2-(3-chlorophenyl)-2-hydroxyethyl]-4-fluoro-1-naphthamide To a solution of 4-fluoronaphthalene-1-carboxylic acid (153 mg, 0.801 mmol) in N,N-dimethylformamide (5 ml) were added 1-ethyl-3-(3-dimethylaminopropyl)carbodiimide hydrochloride (154 g, 0.801 mmol) and 1-hydroxybenzotriazole monohydrate (123 mg, 0.801 mmol), and (1RS,2SR)-2-amino-1-(3-chlorophenyl)-3-[4-(2,2,3,3,3-pentafluoropropyl)phenyl]-1-propanol (0.30 g, 0.763 mmol) was finally added. The mixture was stirred at room temperature overnight. The mixture was diluted with ethyl acetate, washed with saturated aqueous sodium hydrogen carbonate solution, water and saturated brine, and dried over anhydrous magnesium sulfate. The mixture was filtered using a glass filter filled with silica gel, and the filtrate was washed with ethyl acetate and concentrated under reduced pressure. The residue was purified by recrystallization (hexane-ethyl acetate) to give N-[(1RS,2SR)-1-[4-(2,2,3,3,3-pentafluoropropyl)benzyl]-2-(3-chlorophenyl)-2-hydroxyethyl]-4-fluoro-1-naphthamide (0.284 g, 66%) as colorless crystals.

mp 191–192° C. Elemental analysis for $C_{29}H_{22}NO_2ClF_6$ Calcd: C, 61.55; H, 3.92; N, 2.47. Found: C, 61.27; H, 3.75; N, 2.45. IR ν max$^{KBr}$ (cm$^{-1}$): 3265, 1641, 1626, 1516, 1425, 1236, 1178, 1032 $^1$H-NMR (CDCl$_3$) δ (ppm) 2.80 (1H, dd, J=10.8, 14.1 Hz), 3.02 (1H, dd, J=4.2, 14.4 Hz), 3.29 (2H, t, J=18.0 Hz), 3.91 (1H, s) 4.70–4.77 (1H, m), 5.10 (1H, d, J=2.2 Hz), 5.95 (1H, d, J=8.1 Hz), 6.90–6.96 (1H, m), 7.03 (1H, dd, J=5.4, 7.8 Hz), 7.17–7.36 (7H, m), 7.43–7.56 (3H, m), 7.88 (1H, d, J=8.4 Hz), 8.07 (1H, d, J=8.4 Hz).

Example 374

N-[(1RS,2SR)-1-[4-(2,2,3,3,3-pentafluoropropyl)benzyl]-2-(3-chlorophenyl)-2-hydroxyethyl]-6,7-dihydro-5H-benzo[a]cycloheptene-1-carboxamide To a solution of 6,7-dihydro-5H-benzo[a]cycloheptene-1-carboxylic acid (151 mg, 0.801 mmol) in N,N-dimethylformamide (5 ml) were added 1-ethyl-3-(3-dimethylaminopropyl)carbodiimide hydrochloride (154 g, 0.801 mmol) and 1-hydroxybenzotriazole monohydrate (123 mg, 0.801 mmol), and (1RS,2SR)-2-amino-1-(3-chlorophenyl)-3-[4-(2,2,3,3,3-pentafluoropropyl)phenyl]-1-propanol (0.30 g, 0.763 mmol) was finally added. The mixture was stirred at room temperature, overnight. The mixture was diluted with ethyl acetate, saturated aqueous sodium hydrogen carbonate solution, water and saturated brine, and dried over anhydrous magnesium sulfate. The mixture was filtered using a glass filter filled with silica gel, and the filtrate was washed with ethyl acetate and concentrated under reduced pressure. The residue was purified by recrystallization (hexane-ethyl acetate) to give N-[(1RS,2SR)-1-[4-(2,2,3,3,3-pentafluoropropyl)benzyl]-2-(3-chlorophenyl)-2-hydroxyethyl]-6,7-dihydro-5H-benzo[a]cycloheptene-1-carboxamide (0.284 g, 66%) as colorless crystals.

mp 176–177° C. Elemental analysis for $C_{30}H_{27}NO_2ClF_5$ Calcd: C, 63.89; H, 4.83; N, 2.48. Found: C, 63.70; H, 4.85; N, 2.22. IR ν max$^{KBr}$ (cm$^{-1}$): 3281, 1635, 1518, 1433, 1315, 1197, 1030 $^1$H-NMR (CDCl$_3$) δ (ppm) 1.95–2.04 (2H, m)2.16–2.28 (2H, m), 2.64–2.68 (2H, m), 2.75 (1H, dd, J=11.1, 14.7 Hz), 2.97 (1H, dd, J=4.5, 14.7 Hz), 3.28 (2H, t, J=18.3 Hz), 4.01 (1H, br) 4.62–4.71 (1H, m), 5.05 (1H, d, J=2.7 Hz), 5.74 (1H, d, J=7.8 Hz) 5.95 (1H, dt, J=5.7, 11.4 Hz), 6.29 (1H, d, J=11.7 Hz), 6.88 (1H, dd, J=1.2, 7.2 Hz), 7.03 (1H, t, J=7.8 Hz), 7.0–7.36 (8H, m), 7.48 (1H, s).

Example 375

5-chloro-N-{(1RS,2SR)-2-(3-chlorophenyl)-2-hydroxy-1-[4-(2,2,3,3,3-pentafluoropropyl)benzyl]ethyl}-1-naphthamide To a solution of 5-chloronaphthalene-1-carboxylic acid (176 mg, 0.849 mmol) in N,N-dimethylformamide (5 ml)

were added 1-ethyl-3-(3-dimethylaminopropyl)carbodiimide hydrochloride (163 mg, 0.849 mmol) and 1-hydroxybenzotriazole monohydrate (130 mg, 0.849 mmol), and (1RS,2SR)-2-amino-1-(3-chlorophenyl)-3-[4-(2,2,3,3,3-pentafluoropropyl)phenyl]-1-propanol (318 mg, 0.809 mmol) was finally added. The mixture was stirred at room temperature overnight. The mixture was diluted with ethyl acetate, washed with saturated aqueous sodium hydrogen carbonate solution, water and saturated brine, and dried over anhydrous magnesium sulfate. The mixturewas filtered using a glass filter filled with silica gel, and the filtrate was washed with ethyl actate and concentrated under reduced pressure. The residue was purified by recrystallization (hexane-ethyl acetate) to give 5-chloro-N-{(1RS,2SR)-2-(3-chlorophenyl)-2-hydroxy-1-[4-(2,2,3,3,3-pentafluoropropyl)benzyl]ethyl}-1-naphthamide (330 mg, 70%) as colorless crystals.

mp 216–217° C. Elemental analysis for $C_{29}H_{22}NO_2Cl_2F_5$ Calcd: C, 59.81; H, 3.81; N, 2.41. Found: C, 59.75; H, 3.81; N, 2.41. IR ν $max^{KBr}$ ($cm^{-1}$): 3260, 1637, 1539, 1319, 1180, 1118, 1030 $^1$H-NMR ($CDCl_3$) δ (ppm) 2.80 (1H, dd, J=11.0, 14.4 Hz), 3.02 (1H, dd, J=4.0, 14.6 Hz), 3.30 (2H, t, J=18.2 Hz), 3.74 (1H, br) 4.72–4.84 (1H, m), 5.09 (1H, s) 5.96 (1H, d, J=8.6 Hz), 7.11–7.58 (12H, m), 7.74 (1H, d, J=8.8 Hz), 8.31 (1H, d, J=8.4 Hz).

Example 376

N-{(1RS,2SR)-2-(3-chlorophenyl)-1-[(3,3-dimethyl-2,3-dihydro-1-benzofuran-5-yl)methyl]-2-hydroxyethyl}-4-fluoro-1-naphthamide 1) 2-bromo-4-methyl-1-[(2-methyl-2-propenyl)oxy]benzene To a solution of 2-bromo-p-cresol (10 ml, 82.7 mmol) in N,N-dimethylformamide (200 ml) were added potassium carbonate (17.2 g, 124 mmol) and methallyl chloride (9.8 ml, 99.2 mmol), and the mixture was stirred at 100° C. overnight. The mixture was diluted with ethyl acetate, and washed with water and saturated brine. The mixture was dried over anhydrous magnesium sulfate, filtered, and concentrated. The residue was purified by silica gel column chromatography (hexane:ethyl acetate=5:1) to give 2-bromo-4-methyl-1-[(2-methyl-2-propenyl)oxy]benzene (19.67 g, 99%) as a colorless transparent oil.

IR ν $max^{KBr}$ ($cm^{-1}$): 1658, 1604, 1494, 1452, 1377, 1286, 1251, 1230, 1207, 1153 $^1$H-NMR ($CDCl_3$) δ (ppm) 1.84 (3H, s) 2.25 (3H, s) 4.45 (2H, s) 4.98–5.00 (1H, m), 5.13–5.14 (1H, m), 6.56 (1H, d, J=8.4 Hz) 6.99–7.03 (1H, m), 7.35–7.36 (1H, m).

2) 3,3,5-trimethyl-2,3-dihydro-1-benzofuran

To a solution of 2-bromo-4-methyl-1-[(2-methyl-2-propenyl)oxy]benzene (5.0 g, 20.7 mmol) in toluene (100 ml) were added 2,2'-azobisisobutyronitrile (1.45 g, 8.8 mmol) and tri-n-butyltin hydride (8.34 ml, 31 mmol), and the mixture was heated under reflux overnight. After completion of the reaction, the solvent was evaporated under reduced pressure, and the residue was purified by silica gel column chromatography (hexane:ethyl acetate=1:0, 50:1) to give 3,3,5-trimethyl-2,3-dihydro-1-benzofuran (3.70 g, 100%) as a colorless transparent oil.

IR ν $max^{KBr}$ ($cm^{-1}$): 1612, 1489, 1464, 1192, 991 $^1$H-NMR ($CDCl_3$) δ (ppm) 1.32 (6H, s) 2.29 (3H, s) 4.20 (2H, s) 6.67 (1H, d, J=8.4 Hz), 6.90–6.92 (2H, m).

3) ethyl 3-(3-chlorophenyl)-2-[(3,3-dimethyl-2,3-dihydro-1-benzofuran-5-yl)methyl]-3-oxopropionate To a solution of 3,3,5-trimethyl-2,3-dihydro-1-benzofuran (9.42 g, 58 mmol) in carbon tetrachloride (300 ml) were added 2,2'-azobisisobutyronitrile (0.48 g, 2.9 mmol) and N-bromosuccinimide (10.84 g, 60.9 mmol), and the mixture was heated under reflux overnight. After cooling to room temperature, insoluble material was filtered off, and the filtrate was concentrated under reduced pressure to give a bromine form.

A solution of ethyl 3-(3-chlorophenyl)-3-oxopropionate (13.15 g, 58 mmol) in dimethoxyethane (100 ml) was ice-cooled and sodium hydride (60%, 2.32 g, 58 mmol) was added. The mixture was stirred for 30 min. under ice-cooling. To the mixture was added a solution of the bromine form (58 mmol) in dimethoxyethane (150 ml), and the mixture was stirred at room temperature overnight. After completion of the reaction, the reaction was quenched with 0.5N hydrochloric acid. The reaction mixture was diluted with ethyl acetate, and washed with water and saturated brine. The mixture was dried over anhydrous magnesium sulfate, filtered, and concentrated under reduced pressure. The residue was purified by silica gel column chromatography (hexane:ethyl acetate=20:1, 15:1) to give ethyl 3-(3-chlorophenyl)-2-[(3,3-dimethyl-2,3-dihydro-1-benzofuran-5-yl)methyl]-3-oxopropionate (14.04 g, 63%) as a pale-yellow oil.

IR ν $max^{KBr}$ ($cm^{-1}$): 1738, 1693, 1612, 1572, 1487, 1469, 1423, 1365, 1228, 1192 $^1$H-NMR ($CDCl_3$) δ (ppm) 1.14 (3H, t, J=7.0 Hz), 1.24 (3H, s) 1.28 (3H, s) 3.27 (2H, dd, J=1.8, 7.6 Hz), 4.06–4.17 (4H, q, J=7.2 Hz), 6.65 (1H, d, J=8.0 Hz), 6.89–6.90 (1H, m), 6.95 (1H, dd, J=1.8, 8.0 Hz), 7.36 (1H, t, J=8.0 Hz), 7.51 (1H, ddd, J=1.2, 2.2, 8.0 Hz), 7.77 (1H, dt, J=1.0, 7.6 Hz) 7.85–7.86 (1H, m).

4) ethyl (2RS,3RS)-3-(3-chlorophenyl)-2-[(3,3-dimethyl-2,3-dihydro-1-benzofuran-5-yl)methyl]-3-hydroxypropionate To a suspension (140 ml) of zinc chloride (9.90 g, 72.6 mmol) in ether was added sodium borohydride (5.50 g, 145.2 mmol) at room temperature, and the mixture was stirred as it was for 2 hrs. Insoluble material was filtered off, and to the filtrate was added a solution of ethyl 3-(3-chlorophenyl)-2-[(3,3-dimethyl-2,3-dihydro-1-benzofuran-5-yl)methyl]-3-oxopropionate (14.04 g, 36.3 mmol) in ether (50 ml), and the mixture was stirred at room temperature for 1.5 hrs. The reaction was quenched with 3N hydrochloric acid, and the reaction mixture was diluted with ethyl acetate and washed with water and saturated brine. The mixture was dried over anhydrous magnesium sulfate, filtered, and concentrated under reduced pressure. The residue was purified by silica gel column chromatography (hexane:ethyl acetate= 10:1, 5:1) to give ethyl (2RS,3RS)-3-(3-chlorophenyl)-2-[(3,3-dimethyl-2,3-dihydro-1-benzofuran-5-yl)methyl]-3-hydroxypropionate (12.07 g, 86%) as a pale-yellow oil.

IR ν $max^{KBr}$ ($cm^{-1}$): 3460, 1726, 1487, 1467, 1373, 1190, 1032, 987 $^1$H-NMR ($CDCl_3$) δ (ppm) 0.95 (3H, t, J=7.0 Hz), 1.27 (3H, s) 1.29 (3H, s) 2.89–2.97 (3H, m), 3.18 (1H, d, J=2.4 Hz), 3.90 (2H, q, J=7.0 Hz), 4.18 (2H, s) 4.98–4.99 (1H, m), 6.03 (1H, d, J=8.2 Hz), 6.78–6.84 (2H, m), 7.24–7.28 (3H, m), 7.40–7.42 (1H, m).

5) (4RS,5SR)-5-(3-chlorophenyl)-4-[(3,3-dimethyl-2,3-dihydro-1-benzofuran-5-yl)methyl]-1,3-oxazolidin-2-one To a solution of ethyl (2RS,3RS)-3-(3-chlorophenyl)-2-[(3,3-dimethyl-2,3-dihydro-1-benzofuran-5-yl)methyl]-3-hydroxypropionate (11.44 g, 29.4 mmol) in tetrahydrofuran-ethanol (60 ml-60 ml) was added 1N sodium hydroxide (60 ml, 60 mmol) at room temperature, and the mixture was stirred overnight at room temperature. After completion of the reaction, the organic solvent was evaporated under reduced pressure. The aqueous layer was acidified with 1N hydrochloric acid, and the mixture was extracted with ethyl acetate. The organic layer was dried over anhydrous magnesium sulfate and filtered, and concentrated under reduced pressure to give a colorless transparent oil. To a solution of the oil in tetrahydrofuran (300 ml) were added triethylamine (6.2 ml, 44.1 mmol) and diphenylphosphoryl azide (7.6 ml, 35.3 mmol), and the mixture was heated under reflux for 4 hrs. The solvent was evaporated, and the residue was diluted with ethyl acetate and washed with water, saturated aqueous sodium hydrogen carbonate and saturated brine. The organic layer was dried over anhydrous magnesium sulfate, filtered, and concentrated under reduced pressure. The residue was recrystallized from hexane-ethyl acetate to give (4RS,5SR)-5-(3-chlorophenyl)-4-[(3,3-dimethyl-2,3-dihydro-1-benzofuran-5-yl)methyl]-1,3-oxazolidin-2-one (8.11 g, 77%) as colorless crystals.

mp 183–184° C. IR ν $max^{KBr}$ ($cm^{-1}$): 3271, 1759, 1489, 1236, 1194 $^1$H-NMR ($CDCl_3$) δ (ppm) 1.29, 1.30 (each s, 6H) 2.15 (1H, dd, J=11.4, 13.8 Hz), 2.27 (1H, dd, J=3.9, 13.8 Hz), 4.18–4.25 (3H, m) 4.98 (1H, s) 5.75 (1H, d, J=7.8 Hz), 6.68 (1H, d, J=8.1 Hz) 6.74–6.79 (2H, m), 7.25–7.28 (1H, m), 7.34–7.39 (3H, m).

6) (1RS,2SR)-2-amino-1-(3-chlorophenyl)-3-(3,3-dimethyl-2,3-dihydro-1-benzofuran-5-yl)-1-propanol To a solution of (4RS,5SR)-5-(3-chlorophenyl)-4-[(3,3-dimethyl-2,3-dihydro-1-benzofuran-5-yl)methyl]-1,3-oxazolidin-2-one (5.33 g, 14.9 mmol) in ethanol (100 ml) was added 8N aqueous sodium hydroxide solution (9.3 ml, 74.5 mmol), and the mixture was heated under reflux for 5 hrs. After completion of the reaction, ethanol was evaporated under reduced pressure. The residue was diluted with water, and the mixture was extracted with ethyl acetate. The organic layers were combined, washed with saturated brine, dried over anhydrous magnesium sulfate and filtered. The filtrate was concentrated under reduced pressure, and the residue was purified by recrystallization (hexane-ethyl acetate) to give (1RS,2SR)-2-amino-1-(3-chlorophenyl)-3-(3,3-dimethyl-2,3-dihydro-1-benzofuran-5-yl)-1-propanol (3.68 g, 74%) as colorless crystals.

mp 83–86° C. IR ν $max^{KBr}$ ($cm^{-1}$): 3000-3300, 1597, 1574, 1487, 1469, 1192, 1076, 987 $^1$H-NMR ($CDCl_3$) δ (ppm) 1.30 (3H, s) 1.31 (3H, s) 2.28 (1H, dd, J=7.5, 13.8 Hz), 2.70 (1H, dd, J=3.3, 13.8 Hz), 3.21–3.27 (1H, m) 4.20 (2H, s) 4.66 (1H, d, J=5.1 Hz), 6.69 (1H, d, J=7.8 Hz) 6.84–6.88 (2H, m), 7.24–7.33 (3H, m), 7.41 (1H, s).

7) N-{(1RS,2SR)-2-(3-chlorophenyl)-1-[(3,3-dimethyl-2,3-dihydro-1-benzofuran-5-yl)methyl]-2-hydroxyethyl}-4-fluoro-1-naphthamide To a solution of 4-fluoronaphthalene-1-carboxylic acid (242 mg, 1.27 mmol) in N,N-dimethylformamide (10 ml) were added 1-ethyl-3-(3-dimethylaminopropyl)carbodiimide hydrochloride (243 mg, 1.27 mmol) and 1-hydroxybenzotriazole monohydrate (195 mg, 1.27 mmol), and (1RS,2SR)-2-amino-1-(3-chlorophenyl)-3-(3,3-dimethyl-2,3-dihydro-1-benzofuran-5-yl)-1-propanol (0.40 g, 1.21 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, and filtered using a glass filter filled with silica gel. The filtrate was washed with ethyl acetate and concentrated under reduced pressure. The residue was purified by recrystallization (hexane-ethyl acetate) to give N-{(1RS,2SR)-2-(3-chlorophenyl)-1-[(3,3-dimethyl-2,3-dihydro-1-benzofuran-5-yl)methyl]-2-hydroxyethyl}-4-fluoro-1-naphthamide (383 mg, 68%) as colorless crystals.

Elemental analysis for $C_{30}H_{27}NO_3ClF \cdot H_2O$ Calcd: C, 71.63; H, 5.81; N, 2.78. Found: C, 71.28; H, 5.54; N, 2.79.

IR ν $max^{KBr}$ ($cm^{-1}$): 3281, 1641, 1626, 1518, 1487, 1464, 1425, 1261, 1236, 1194 $^1$H-NMR ($CDCl_3$) δ (ppm) 1.22 (3H, s) 1.27 (3H, s) 2.71 (1H, dd, J=11.1, 14.7 Hz), 3.00 (1H, dd, J=4.2, 14.4 Hz), 4.12 (1H, d, J=4.2 Hz), 4.21 (2H, d, J=0.9 Hz), 4.69–4.78 (1H, m), 5.08–5.10 (1H, m), 5.83 (1H, d, J=7.5 Hz), 6.72 (1H, d, J=8.4 Hz) 6.91–7.02 (3H, m), 7.16 (1H, dd, J=5.4, 7.8 Hz), 7.27–7.38 (3H, m) 7.45–7.57 (3H, m), 7.80 (1H, d, J=8.1 Hz), 8.07 (1H, d, J=7.8 Hz).

Example 377

N-{(1RS,2SR)-2-(3-chlorophenyl)-1-[(3,3-dimethyl-2,3-dihydro-1-benzofuran-5-yl)methyl]-2-hydroxyethyl}-6,7-dihydro-5H-benzo[a]cycloheptene-1-carboxamide To a solution of 6,7-dihydro-5H-benzo[a]cycloheptene-1-carboxylic acid (239 mg, 1.27 mmol) in N,N-dimethylformamide (5 ml) were added 1-ethyl-3-(3-dimethylaminopropyl)carbodiimide hydrochloride (243 mg, 1.27 mmol) and 1-hydroxybenzotriazole monohydrate (195 mg, 1.27 mmol), and (1RS,2SR)-2-amino-1-(3-chlorophenyl)-3-(3,3-dimethyl-2,3-dihydro-1-benzofuran-5-yl)-1-propanol (0.40 g, 1.21 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, and filtered using a glass filter filled with silica gel. The filtrate was washed with ethyl acetate and concentrated under reduced pressure. The residue was purified by recrystallization (hexane-ethyl acetate) to give N-{(1RS,2SR)-2-(3-chlorophenyl)-1-[(3,3-dimethyl-2,3-dihydro-1-benzofuran-5-yl)methyl]-2-hydroxyethyl}-6,7-dihydro-5H-benzo[a]cycloheptene-1-carboxamide (326 mg, 54%) as colorless crystals.

mp 149–150° C. Elemental analysis for $C_{31}H_{32}NO_3Cl \cdot 0.5H_2O$ Calcd: C, 72.86; H, 6.51; N, 2.74. Found: C, 73.04; H, 6.26; N, 3.04. IR ν $max^{KBr}$ ($cm^{-1}$): 3304, 1635, 1514, 1487, 1192, 1076, 987, 910 $^1$H-NMR ($CDCl_3$) δ (ppm) 1.28 (6H, s) 1.98–2.01 (2H, m), 2.16–2.21 (2H, m), 2.58–2.69 (3H, m), 2.87–2.95 (1H, m), 4.20 (2H, s) 4.62 (1H, br) 5.00 (1H, s) 5.71 (1H, d, J=7.4 Hz), 5.89–6.00 (1H, m) 6.26 (1H, d, J=11.8 Hz) 6.68 (1H, d, J=8.8 Hz), 6.88–7.16 (5H, m), 7.26–7.30 (3H, m), 7.46 (1H, s)

Example 378

5-chloro-N-{(1RS,2SR)-2-(3-chlorophenyl)-1-[(3,3-dimethyl-2,3-dihydro-1-benzofuran-5-yl)methyl]-2-hydroxyethyl}-1-naphthamide To a solution of 5-chloronaphthalene-1-carboxylic acid (260 mg, 1.26 mmol) in N,N-dimethylformamide (5 ml) were added 1-ethyl-3-(3-dimethylaminopropyl)carbodiimide hydrochloride (242 mg, 1.26 mmol) and 1-hydroxybenzotriazole monohydrate (193 mg, 1.26 mmol), and (1RS,2SR)-2-amino-1-(3-chlorophenyl)-3-(3,3-dimethyl-2,3-dihydro-1-benzofuran-5-yl)-1-propanol (0.40 g, 1.20 mmol) was finally added. The mixture was stirred overnight at room temperature. The mixture was diluted with ethyl acetate, washed with saturated aqueous sodium hydrogen carbonate, water and saturated brine, dried over anhydrous magnesium sulfate, and filtered using a glass filter filled with silica gel. The filtrate was washed with ethyl acetate and concentrated under reduced pressure. The residue was purified by recrystallization (hexane-ethyl acetate)

to give 5-chloro-N-{(1RS,2SR)-2-(3-chlorophenyl)-1-[(3,3-dimethyl-2,3-dihydro-1-benzofuran-5-yl)methyl]-2-hydroxyethyl}-1-naphthamide (473 mg, 76%) as colorless crystals.

mp 191–192° C. Elemental analysis for $C_{30}H_{27}NO_3Cl_2$ Calcd: C, 69.23; H, 5.23; N, 2.69. Found: C, 69.02; H, 5.04; N, 2.71. IR ν max$^{KBr}$ (cm$^{-1}$): 3271, 1639, 1572, 1520, 1487, 1194, 908 $^1$H-NMR (CDCl$_3$)δ (ppm) 1.23 (3H, s) 1.26 (3H, s) 2.70 (1H, dd, J=11.0, 14.6 Hz), 2.99 (1H, dd, J=4.4, 14.8 Hz), 4.21 (2H, s) 4.71–4.78 (1H, m), 5.07 (1H, d, J=3.2 Hz), 5.86 (1H, d, J=8.2 Hz), 6.71 (1H, d, J=8.8 Hz), 6.90–6.93 (2H, m), 7.22–7.64 (9H, m), 8.31 (1H, d, J=8.4 Hz).

Example 379

N-{(1RS,2SR)-2-(3-chlorophenyl)-1-[4-(1,1-difluoro-2,2-dimethylpropyl)benzyl]-2-hydroxyethyl}-4-fluoro-1-naphthamide 1) 2,2-dimethyl-1-(4-methylphenyl)-1-propanone To a suspension (200 ml) of magnesium (7.14 g, 294 mmol) in ether in a three necked flask was added dropwise a solution of p-bromotoluene (34 ml, 276 mmol) in ether (100 ml), and the mixture was heated under reflux for 1.5 hrs. Thereafter, to the mixture was added a solution of trimethylacetonitrile (25 ml, 226 mmol) in ether (100 ml), and the mixture was stirred for 2 hrs. The mixture was then ice-cooled. To the mixture was added dropwise 6N hydrochloric acid, and the mixture was stirred at room temperature for 30 min. The mixture was diluted with ether, and washed with water and saturated brine. The mixture was dried over anhydrous magnesium sulfate, filtered and concentrated under reduced pressure. The residue was purified by silica gel column chromatography (hexane:ethyl acetate=1:0, 10:1) to give 2,2-dimethyl-1-(4-methylphenyl)-1-propanone (10.94 g, 27%) as a colorless transparent oil.

IR ν max$^{KBr}$ (cm$^{-1}$): 1672, 1608, 1477, 1396, 1365, 1278, 960 $^1$H-NMR (CDCl$_3$) δ (ppm)1.35 (9H, s) 2.38 (3H, s) 7.20 (2H, d, J=8.1 Hz), 7.66 (2H, d, J=8.4 Hz).

2) 1-(1,1-difluoro-2,2-dimethylpropyl)-4-methylbenzene

To a flask containing 2,2-dimethyl-1-(4-methylphenyl)-1-propanone (4.69 g, 26.6 mmol) was added dropwise bis(2-methoxyethyl)aminosulfur trifluoride (10 g; 45.2 mmol), and the mixture was stirred at 80 to 85° C. overnight. The reaction mixture was poured into saturated aqueous sodium hydrogen carbonate, and the mixture was extracted with ethyl acetate. The mixture was dried over anhydrous magnesium sulfate, filtered, and concentrated under reduced pressure. The residue was purified by silica gel column chromatography (hexane) to give 1-(1,1-difluoro-2,2-dimethylpropyl)-4-methylbenzene (5.16 g, 77%) as a colorless transparent oil.

IR ν max$^{KBr}$ (cm$^{-1}$): 1618, 1518, 1485, 1464, 1308, 1286, 1259, 1209, 1093, 1072, 976 $^1$H-NMR (CDCl$_3$) δ (ppm) 1.02 (9H, s) 2.37 (3H, s) 7.15–7.19 (2H, m) 7.31 (2H, d, J=8.4 Hz).

3) ethyl 3-(3-chlorophenyl)-2-[4-(1,1-difluoro-2,2-dimethylpropyl)benzyl]-3-oxopropionate To a solution of 1-(1,1-difluoro-2,2-dimethylpropyl)-4-ethylbenzene (4.52 g, 22.8 mmol) in carbon tetrachloride (150 ml) were added 2,2'-azobisisobutyronitrile (188 mg, 1.14 mmol) and N-bromosuccinimide (4.06 g, 22.8 mmol), and the mixture was heated under reflux overnight. After cooling to room temperature, insoluble material was filtered off, and the residue was concentrated under reduced pressure to give a bromine form, which was directly used in the next reaction.

A solution of ethyl 3-(3-chlorophenyl)-3-oxopropionate (5.17 g, 22.8 mmol) in dimethoxyethane (60 ml) was ice-cooled. To the solution was added sodium hydride (60%, 0.92 g, 22.8 mmol) under ice-cooling, and the mixture was stirred for 15 min. To the mixture was added a solution of the bromine form (22.8 mmol) in dimethoxyethane (40 ml), and the mixture was stirred overnight at room temperature. After completion of the reaction, the reaction was quenched with 1N hydrochloric acid, and the mixture was diluted with ethyl acetate and washed with water and saturated brine. The mixture was dried over anhydrous magnesium sulfate, filtered, and concentrated under reduced pressure. The residue was purified by silica gel column chromatography (hexane:ethyl acetate=20:1, 15:1) to give ethyl 3-(3-chlorophenyl)-2-[4-(1,1-difluoro-2,2-dimethylpropyl)benzyl]-3-oxopropionate (7.44 g, 77%) as a pale-yellow oil.

IR ν max$^{KBr}$ (cm$^{-1}$): 1736, 1691, 1570, 1483, 1425, 1367, 1259, 1093, 1072 $^1$H-NMR (CDCl$_3$) δ (ppm) 0.99 (9H, s) 1.12 (3H, t, J=6.9 Hz) 3.34 (2H, d, J=7.5 Hz), 3.96–4.15 (2H, m), 4.56 (1H, t, J=7.2 Hz), 7.21–7.45 (5H, m), 7.50–7.55 (1H, m), 7.78–7.90 (1H, m), 7.90–7.92 (1H, m).

4) ethyl (2RS,3RS)-3-(3-chlorophenyl)-3-hydroxy-2-[4-(1,1-difluoro-2,2-dimethylpropyl)benzyl]propionate To a suspension (70 ml) of zinc chloride (4.94 g, 36.2 mmol) in ether was added sodium borohydride (2.74 g, 72.4 mmol) at room temperature, and the mixture was stirred as it was for 2 hrs. Insoluble material was filtered off. To the filtrate was added a solution of ethyl 3-(3-chlorophenyl)-2-[4-(1,1-difluoro-2,2-dimethylpropyl)benzyl]-3-oxopropionate (7.59 g, 18.1 mmol) in ether (50 ml), and the mixture was stirred at room temperature for 1 hr. The reaction was quenched with 1N hydrochloric acid, and the mixture was diluted with ethyl acetate, washed with water and saturated brine. The mixture was dried over anhydrous magnesium sulfate, filtered and concentrated. The residue was purified by silica gel column chromatography (hexane:ethyl acetate=15:1, 10:1, 5:1) to give ethyl (2RS,3RS)-3-(3-chlorophenyl)-3-hydroxy-2-[4-(1,1-difluoro-2,2-dimethylpropyl)benzyl]propionate (6.12 g, 80%) as a pale-yellow oil.

IR ν max$^{KBr}$ (cm$^{-1}$): 3454, 1712, 1616, 1597, 1576, 1483, 1398, 1371, 1398, 1286, 1259, 1190 $^1$H-NMR (CDCl$_3$) δ (ppm) 0.94 (3H, t, J=7.2 Hz), 1.00 (9H, s) 2.90–3.04 (2H, m), 3.11 (1H, d, J=1.8 Hz), 3.90 (2H, q, J=7.0 Hz), 5.03 (1H, d, J=2.2 Hz), 7.09 (2H, d, J=8.0 Hz) 7.25–7.29 (5H, m), 7.42 (1H, s).

5) (2RS,3RS)-3-(3-chlorophenyl)-3-hydroxy-2-[4-(1,1-difluoro-2,2-dimethylpropyl)benzyl]propionic acid To a solution of ethyl (2RS,3RS)-3-(3-chlorophenyl)-3-hydroxy-2-[4-(1,1-difluoro-2,2-dimethylpropyl)benzyl]propionate (5.88 g, 13.8 mmol) in tetrahydrofuran-ethanol (30 ml—30 ml) was added 1N sodium hydroxide (28 ml, 28 mmol) at room temperature, and the mixture was stirred overnight at room temperature. After completion of the reaction, the organic solvent was evaporated under reduced pressure. The aqueous layer was acidified with 1N hydrochloric acid, and the mixture was extracted with ethyl acetate. The organic layer was dried over anhydrous magnesium sulfate. The mixture was filtered, and the filtrate was concentrated under reduced pressure. The residue was recrystallized from hexane-ethyl acetate to give (2RS,3RS)-3-(3-chlorophenyl)-3-hydroxy-2-[4-(1,1-difluoro-2,2-dimethylpropyl)benzyl]propionic acid (4.24 g, 77%) as colorless crystals.

mp 141–142° C. IR ν max$^{KBr}$ (cm$^{-1}$) 2500-3300, 1709, 1599, 1574, 1483, 1413, 1398, 1369, 1286, 1259 $^1$H-NMR (CDCl$_3$) δ (ppm) 0.99 (9H, s) 2.90–3.05 (3H, m), 5.10 (1H, d, J=3.6 Hz), 7.07 (2H, d, J=8.1 Hz), 7.25–7.28 (5H, m), 7.42 (1H, s).

6) (4RS,5SR)-5-(3-chlorophenyl)-4-[4-(1,1-difluoro-2,2-dimethylpropyl)benzyl]-1,3-oxazolidin-2-one To a solution of (2RS,3RS)-3-(3-chlorophenyl)-3-hydroxy-2-[4-(1,1-difluoro-2,2-dimethylpropyl)benzyl] propionic acid (4.09 g, 10.3 mmol) in tetrahydrofuran (100 ml) were added triethylamine (2.16 ml, 15.45 mmol) and diphenylphosphoryl azide (2.67 ml, 12.36 mmol), and the mixture was heated under reflux for 4 hrs. The solvent was evaporated, and the residue was diluted with ethyl acetate, and washed with 1N hydrochloric acid, saturated aqueous sodium hydrogen carbonate and saturated brine. The organic layer was dried over anhydrous magnesium sulfate, filtered, and concentrated under reduced pressure. The residue was recrystallized from hexane-ethyl acetate to give (4RS,5SR)-5-(3-chlorophenyl)-4-[4-(1,1-difluoro-2,2-dimethylpropyl) benzyl]-1,3-oxazolidin-2-one (3.97 g, 98%) as colorless crystals.

mp 188–190° C. IR ν max$^{KBr}$ (cm$^{-1}$): 3246, 1739, 1437, 1369, 1286, 1238, 1078 $^1$H-NMR (CDCl$_3$) δ (ppm) 1.01 (9H, s) 2.27 (1H, dd, J=10.8, 13.1 Hz), 2.36 (1H, dd, J=4.2, 12.8 Hz), 4.23–4.31 (1H, m), 5.09 (1H, s) 5.77 (1H, d, J=8.1 Hz), 7.05 (2H, d, J=8.1 Hz) 7.24–7.29 (1H, m), 7.32–7.38 (5H, m).

7) (1RS,2SR)-2-amino-1-(3-chlorophenyl)-3-[4-(1,1-difluoro-2,2-dimethylpropyl)phenyl]-1-propanol To a solution of (4RS,5SR)-5-(3-chlorophenyl)-4-[4-(1, 1-difluoro-2,2-dimethylpropyl)benzyl]-1,3-oxazolidin-2-one (3.82 g, 9.70 mmol) in ethanol (100 ml) was added 8N aqueous sodium hydroxide solution (6.1 ml, 48.5 mmol), and the mixture was heated under reflux for 4 hrs. After completion of the reaction, ethanol was evaporated under reduced pressure. The residue was diluted with water, and the mixture was extracted with ethyl acetate. The organic layers were combined, washed with saturated brine, dried over anhydrous magnesium sulfate, filtered, and concentrated under reduced pressure. The residue was purified by recrystallization (hexane-ethyl acetate) to give (1RS,2SR)-2-amino-1-(3-chlorophenyl)-3-[4-(1,1-difluoro-2,2-dimethylpropyl)phenyl]-1-propanol (2.56 g, 72%) to give colorless crystals.

mp 105–107° C. IR ν max$^{KBr}$ (cm$^{-1}$): 3352, 1597, 1483, 1286, 1259, 1093, 1068, 1037, 1008, 978 $^1$H-NMR (CDCl$_3$) δ (ppm) 1.02 (9H, s) 2.38 (1H, dd, J=10.6, 13.6 Hz), 2.80 (1H, dd, J=2.8, 13.2 Hz), 3.27–3.36 (1H, m), 4.68 (1H, d, J=4.8 Hz), 7.15 (2H, d, J=8.2 Hz), 7.26–7.35 (5H, m), 7.42 (1H, s).

8) N-{(1RS,2SR)-2-(3-chlorophenyl)-1-[4-(1,1-difluoro-2, 2-dimethylpropyl)benzyl]-2-hydroxyethyl}-4-fluoro-1-naphthamide To a solution of 4-fluoronaphthalene-1-carboxylic acid (216 mg, 1.15 mmol) in N,N-dimethylformamide (5 ml) were added 1-ethyl-3-(3-dimethylaminopropyl) carbodiimide hydrochloride (220 mg, 1.15 mmol) and 1-hydroxybenzotriazole monohydrate (176 mg, 1.15 mmol), and (1RS,2SR)-2-amino-1-(3-chlorophenyl)-3-[4-(1,1-difluoro-2,2-dimethylpropyl)phenyl]-1-propanol (0.40 g, 1.09 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, and filtered using a glass filter filled with silica gel. The filtrate was washed with ethyl acetate and concentrated under reduced pressure. The residue was purified by recrystallization (hexane-ethyl acetate) to give N-{(1RS,2SR)-2-(3-chlorophenyl)-1-[4-(1, 1-difluoro-2,2-dimethylpropyl)benzyl]-2-hydroxyethyl}-4-fluoro-1-naphthamide (289 mg, 49%) as colorless crystals.

mp 104–106° C. IR ν max$^{KBr}$ (cm$^{-1}$): 3244, 1639, 1626, 1599, 1516, 1425, 1286, 1261, 1091, 1072, 1008, 978 $^1$H-NMR (CDCl$_3$) δ (ppm) 1.01 (9H, s) 2.82 (1H, dd, J=11.0, 14.4 Hz), 3.03 (1H, dd, 4.4, 14.4 Hz), 3.85 (1H, s) 4.72–4.81 (1H, m), 5.10 (1H, d, J=3.4 Hz), 5.98 (1H, d, J=8.4 Hz), 6.93 (1H, dd, J=7.6, 9.8 Hz), 7.10 (1H, dd, J=5.0, 7.6 Hz), 7.19–7.56 (10H, m), 7.75 (1H, d, J=7.6 Hz), 8.06 (1H, d, J=8.0 Hz).

Example 380

N-{(1RS,2SR)-2-(3-chlorophenyl)-1-[4-(1,1-difluoro-2,2-dimethylpropyl)benzyl]-2-hydroxyethyl}-6,7-dihydro-5H-benzo[a]cycloheptene-1-carboxamide To a solution of 6,7-dihydro-5H-benzo[a]cycloheptene-1-carboxylic acid (216 mg, 1.15 mmol) in N,N-dimethylformamide (5 ml) were added 1-ethyl-3-(3-dimethylaminopropyl)carbodiimide hydrochloride (220 mg, 1.15 mmol) and 1-hydroxybenzotriazole monohydrate (176 mg, 1.15 mmol), and (1RS,2SR)-2-amino-1-(3-chlorophenyl)-3-[4-(1,1-difluoro-2,2-dimethylpropyl) phenyl]-1-propanol (0.40 g, 1.09 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, and filtered using a glass filter filled with silica gel. The filtrate was washed with ethyl acetate, and concentrated under reduced pressure. The residue was purified by recrystallization (hexane-ethyl acetate) to give N-{(1RS,2SR)-2-(3-chlorophenyl)-1-[4-(1,1-difluoro-2,2-dimethylpropyl) benzyl]-2-hydroxyethyl}-6,7-dihydro-5H-benzo[a] cycloheptene-1-carboxamide (316 mg, 54%) as colorless crystals.

mp 119–120° C. IR ν max$^{KBr}$ (cm$^{-1}$): 3265, 1635, 1516, 1485, 1286, 1259 $^1$H-NMR (CDCl$_3$) δ (ppm) 1.28 (6H, s) 1.98–2.01 (2H, m), 2.16–2.21 (2H, m), 2.58–2.69 (3H, m), 2.87–2.95 (1H, m), 4.20 (2H, s) 4.62 (1H, br) 5.00 (1H, s) 5.71 (1H, d, J=7.4 Hz), 5.89–6.00 (1H, m) 6.26 (1H, d, J=11.8 Hz), 6.68 (1H, d, J=8.8 Hz), 6.88–7.16 (5H, m), 7.26–7.30 (3H, m), 7.46 (1H, s)

Example 381

5-chloro-N-{(1RS,2SR)-2-(3-chlorophenyl)-1-[4-(1, 1-difluoro-2,2-dimethylpropyl)benzyl]-2-hydroxyethyl}-1-naphthamide To a solution of 5-chloronaphthalene-1-carboxylic acid (238 mg, 1.15 mmol) in N,N-dimethylformamide (5 ml) were added 1-ethyl-3-(3-dimethylaminopropyl) carbodiimide hydrochloride (220 mg, 1.15 mmol) and 1-hydroxybenzotriazole monohydrate (176 mg, 1.15 mmol), and (1RS,2SR)-2-amino-1-(3-chlorophenyl)-3-[4-(1,1-difluoro-2,2-dimethylpropyl)phenyl]-1-propanol (0.40 g, 1.09 mmol) was finally added. The mixture was stirred overnight at room temperature. The mixture was diluted with ethyl acetate, washed with saturated aqueous sodium hydrogen carbonate solution, water and saturated brine, dried over anhydrous magnesium sulfate, and filtered using a glass filter filled with silica gel. The filtrate was washed with ethyl acetate and concentrated under reduced pressure. The residue was purified by recrystallization (hexane-ethyl acetate) to give 5-chloro-N-{(1RS,2SR)-2-(3-chlorophenyl)-1-[4-(1,1-difluoro-2,2-dimethylpropyl) benzyl]-2-hydroxyethyl}-1-naphthamide (252 mg, 42%) as colorless crystals.

mp 99–101° C. IR ν max$^{KBr}$ (cm$^{-1}$): 3260, 1635, 1521, 1286, 1093, 1072, 1037, 1008, 978, 908 $^1$H-NMR (CDCl$_3$) δ (ppm) 1.01 (9H, s) 2.79 (1H, dd, J=11.1, 14.4 Hz), 3.02 (1H, dd, J=3.6, 14.1 Hz), 4.74–4.82 (1H, m), 5.07 (1H, d, J=3.6 Hz), 6.02 (1H, d, J=8.7 Hz), 7.15–7.41 (10H, m), 7.53–7.57 (3H, m), 8.28 (1H, d, J=8.7 Hz).

Example 382

(1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl acetate A mixture of N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide (0.359 g, 0.675 mmol), acetic anhydride (2 ml) and pyridine (5 ml) was stirred at 100° C. overnight. The solvent of the reaction solution was evaporated under reduced pressure and the obtained residue was purified by silica gel column chromatography (ethyl acetate). Crystallization from diisopropyl ether-hexane gave the objective substance.

white crystals yield 0.347 g, 90% mp 176–177° C.; $^1$H-NMR (CDCl$_3$, 200 MHz) δ 1.91–2.05 (2H, m), 2.15 (3H, s), 2.13–2.32 (2H, m), 2.63–2.66 (2H, m), 2.71 (1H, dd, J=10.2 Hz, 15.2 Hz), 3.07 (1H, dd, J=4.3 Hz, 14.7 Hz), 4.89–5.03 (1H, m), 5.51 (1H, d, J=9.6 Hz), 5.89 (1H, tt, J=2.9 Hz, 53.0 Hz), 5.81–6.06 (3H, m), 6.82 (1H, dd, J=2.0 Hz, 7.2 Hz), 6.97–7.15 (7H, m), 7.32 (1H, t, J=7.9 Hz), 7.41 (2H, dd, J=5.4 Hz, 8.6 Hz); IR (KBr) 3241, 1746, 1642, 1512, 1275, 1236, 1113, 772 cm$^{-1}$; Anal. Calcd for C$_{31}$H$_{28}$F$_5$NO$_4$: C, 64.92; H, 4.92; N, 2.44. Found: C, 64.87; H, 4.84; N, 2.30.

Example 383

(1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl methyl succinate A solution of N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide (0.301 g, 0.566 mmol), monomethyl succinate monochloride (0.10 ml, 0.85 mmol) and 4-N,N-dimethylaminopyridine (0.14 g, 1.13 mmol) in acetonitrile (15 ml) was stirred at 80° C. for 2 hrs. The solvent of the reaction solution was evaporated under reduced pressure, and the obtained residue was purified by silica gel column chromatography (hexane/ethyl acetate=3/1–2/1) to give the objective substance.

white solid yield 0.365 g, 100%

Recrystallization from ethyl acetate-hexane gave white crystals.

mp 170–171° C.; $^1$H-NMR (CDCl$_3$, 300 MHz) δ 1.92–2.00 (2H, m), 2.18–2.24 (2H, m), 2.61–2.81 (7H, m), 3.02 (1H, dd, J=4.2 Hz, 14.4 Hz), 3.50 (3H, s), 4.87–4.97 (1H, m), 5.85 (1H, td, J=5.2 Hz, 11.9 Hz), 5.89 (1H, tt, J=2.8 Hz, 53.0 Hz), 5.90 (1H, d, J=9.9 Hz), 6.03 (1H, d, J=12.0 Hz), 6.16 (1H, d, J=4.8 Hz), 6.86 (1H, dd, J=1.5 Hz, 7.5 Hz), 6.99–7.13, (7H, m), 7.30 (1H, t, J=8.0 Hz), 7.43 (2H, dd, J=5.3 Hz, 8.6 Hz); IR (KBr) 3239, 1742, 164.0, 1512, 1223, 1165, 1128 cm$^{-1}$; Anal. Calcd for C$_{34}$H$_{32}$F$_5$NO$_6$: C, 63.25; H, 5.00; N, 2.17. Found: C, 63.21; H, 5.03; N, 2.13.

Example 384

(1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl hydrogen succinate To a solution of N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide (0.566 g, 1.065 mmol) and succinic chloride (0.41 g, 2.66 mmol) in acetonitrile (30 ml) was added 4-N,N-dimethylaminopyridine (0.26 g, 2.13 mmol), and the mixture was stirred at 70° C. for 3 hrs. After cooling the reaction solution to room temperature, water (30 ml) was added, and the mixture was stirred as it was for 0.5 hr. The reaction solution was acidified with diluted hydrochloric acid, and extracted twice with ethyl acetate. The recovered organic layer was dried over anhydrous magnesium sulfate, and the solvent was evaporated under reduced pressure. The obtained crude product was purified by silica gel column chromatography (hexane/ethyl acetate=1/1-ethyl acetate). Crystallization from diisopropyl ether-hexane gave the objective substance.

pale-brown powder yield 0.466 g, 69% mp 154–155° C.; $^1$H-NMR (CDCl$_3$, 300 MHz) δ 1.92–2.01 (2H, m), 2.17–2.23 (2H, m), 2.58–2.77 (7H, m), 3.04 (1H, dd, J=3.8 Hz, 14.3 Hz), 4.89–4.99 (1H, m), 5.71 (1H, d, J=9.3 Hz), 5.85 (1H, td, J=5.1 Hz, 11.7 Hz), 5.89 (1H, tt, J=2.9 Hz, 53.1 Hz), 6.00 (1H, d, J=11.7 Hz), 6.06, (1H, d, J=5.4 Hz), 6.84 (1H, dd, J=1.4 Hz, 7.7 Hz), 6.98–7.13 (7H, m), 7.30 (1H, t, J=7.8 Hz), 7.41 (2H, dd, J=5.3 Hz, 8.6 Hz); IR (KBr) 3243, 3067, 2940, 1734, 1640, 1512, 1211, 1155, 1123 cm$^{-1}$; Anal. Calcd for C$_{33}$H$_{30}$F$_5$NO$_6$.0.5H$_2$O: C, 61.87; H, 4.88; N, 2.19. Found: C, 61.78; H, 4.77; N, 2.15.

Example 385 sodium (1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl succinate To a solution of (1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl hydrogen succinate (165 mg, 0.261 mmol) in tetrahydrofuran (2 ml) was added 1N aqueous sodium hydroxide solution (0.26 ml, 0.26 mmol), and the mixture was stirred at room temperature for 5 min. The solvent of the reaction solution was evaporated under reduced pressure, and the obtained residue was crystallized from ethanol-hexane to give the objective substance.

pale-brown powder yield 130 mg, 76% mp 165–170° C.; $^1$H-NMR (CDCl$_3$, 300 MHz) δ 1.92–2.00 (2H, m), 2.17–2.23 (2H, m), 2.60–2.75 (7H, m), 3.03 (1H, dd, J=3.9 Hz, 14.1 Hz), 4.90–5.00 (1H, m), 5.66 (1H, d, J=9.6 Hz), 5.85 (1H, td, J=5.3 Hz, 10.5 Hz), 5.89 (1H, tt, J=2.9 Hz, 53.0 Hz), 6.01 (1H, d, J=12.0 Hz), 6.04 (1H, d, J=5.1 Hz), 6.83 (1H, dd, J=1.5 Hz, 7.5 Hz), 6.99–7.13 (7H, m), 7.29 (1H, t, J=7.8 Hz), 7.40 (2H, dd, J=5.3 Hz, 8.9 Hz); IR (KBr) 3400-2900, 1730, 1640, 1534, 1514, 1200, 1159, 1128 cm$^{-1}$; Anal. Calcd for C$_{33}$H$_{29}$F$_5$NO$_6$Na.2.0H$_2$O: C, 57.48; H, 4.82; N, 2.03. Found: C, 57.49; H, 4.46; N, 1.88.

Example 386

N-(tert-butoxycarbonyl)glycine (1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl ester A solution of N-[(1RS,2SR)-2-(4-fluorophenyl)-2-hydroxy-1-[3-(1,1,2,2-tetrafluoroethoxy)benzyl]ethyl]-6,7-dihydro-5H-benzo[a]cycloheptene-1-carboxamide (0.304 g, 0.572 mmol), BOC-glycine (0.12 g, 0.69 mmol), 4-N,N-dimethylaminopyridine (0.14 g, 1.14 mmol) and 1-ethyl-3-(3-dimethylaminopropyl)carbodiimide hydrochloride (0.16 g, 0.86 mmol) in acetonitrile (10 ml) was stirred overnight at room temperature. The reaction solution was diluted with ethyl acetate, washed with aqueous sodium hydrogen carbonate solution, and dried over anhydrous magnesium sulfate. After passing through silica gel, the solvent was evaporated under reduced pressure to give the objective substance.

white solid yield 0.411 g, 100%

Crystallization from diisopropyl ether-hexane gave white powder.

mp 151–152° C.; $^1$H-NMR (CDCl$_3$, 300 MHz) δ 1.41 (9H, s), 1.93–2.01 (2H, m), 2.18–2.24 (2H, m), 2.66 (2H, t, J=5.9 Hz), 2.70 (1H, dd, J=10.5 Hz, 14.4 Hz), 3.04 (1H, dd, J=4.1 Hz, 14.3 Hz), 3.91–4.06 (2H, m), 4.91–5.00 (1H, m), 5.07 (1H, br t, J=4.5 Hz), 5.68 (1H, d, J=9.9 Hz), 5.86 (1H, td, J=5.4 Hz, 12.0 Hz), 5.89 (1H, tt, J=2.9 Hz, 53.1 Hz), 6.02 (1H, d, J=11.7 Hz), 6.11 (1H, d, J=5.4 Hz), 6.87 (1H, d, J=7.2 Hz), 7.01–7.13 (7H, m), 7.31 (1H, t, J=8.0 Hz), 7.41 (2H, dd, J=5.4 Hz, 8.7 Hz); IR (KBr) 3370, 3310, 2936, 1750, 1684, 1638, 1512, 1225, 1196, 1157, 1125 cm$^{-1}$; Anal. Calcd for C$_{36}$H$_{37}$F$_5$N$_2$O$_6$: C, 62.79; H, 5.42; N, 4.07. Found: C, 62.60; H, 5.49; N, 4.00.

Example 387 glycine (1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl ester hydrochloride A mixture of N-(tert-butoxycarbonyl)glycine (1RS,2SR)-2-[(6,7-dihydro-5H-benzo[a]cyclohepten-1-ylcarbonyl)amino]-1-(4-fluorophenyl)-3-[3-(1,1,2,2-tetrafluoroethoxy)phenyl]propyl ester (0.351 g, 0.510 mmol), conc. hydrochloric acid (0.3 ml) and methanol (8 ml) was stirred at 50° C. for 1 hr. The solvent of the reaction solution was evaporated under reduced pressure, and the obtained residue was crystallized from diethyl ether to give the objective substance.

white powder yield 0.270 g yield 85% mp 174–177° C. (dec.); $^1$H-NMR (CD$_3$OD, 300 MHz) δ 1.88–1.96 (2H, m), 2.19–2.24 (2H, m), 2.63–2.72 (3H, m), 3.24 (1H, dd, J=3.3 Hz, 14.1 Hz), 3.90 (1H, d, J=17.1 Hz), 3.99 (1H, d, J=17.1 Hz), 4.86–4.98 (1H, m), 5.69–5.79 (2H, m), 6.04 (1H, d, J=6.9 Hz), 6.24 (1H, tt, J=2.9 Hz, 52.6 Hz), 6.59 (1H, dd, J=1.2 Hz, 7.5 Hz), 7.00 (1H, t, J=7.4 Hz), 7.10–7.17 (5H, m), 7.23 (1H, d, J=7.8 Hz), 7.38 (1H, t, J=7.8 Hz), 7.55 (2H, dd, J=5.3 Hz, 8.9 Hz); IR (KBr) 3283, 3100–2800, 1744, 1640, 1514, 1271, 1233, 1200, 1125 cm$^{-1}$; Anal. Calcd for C$_{31}$H$_{30}$ClF$_5$N$_2$O$_4$.0.5H$_2$O: C, 58.72; H, 4.93; N, 4.42. Found: C, 58.46; H, 4.84; N, 4.51.

Example 388

(1RS,2SR)-2-[(4-fluoro-1-naphthoyl)amino]-1-(4-fluorophenyl)-3-[3-(1,1,2,2-tetrafluoroethoxy)phenyl]propyl hydrogen succinate To a solution of 4-fluoro-N-[(1RS,2SR)-2-(4-fluorophenyl)-2-hydroxy-1-[3-(1,1,2,2-tetrafluoroethoxy)benzyl]ethyl]naphthalene-1-carboxamide (0.664 g, 1.245 mmol) and succinic chloride (0.48 g, 3.11 mmol) in acetonitrile (30 ml) was added 4-N,N-dimethylaminopyridine (0.30 g, 2.49 mmol), and the mixture was stirred at 70° C. for 3 hrs. After cooling the reaction solution to room temperature, water (30 ml) was added, and the mixture was stirred as it was for 0.5 hr. The reaction solution was acidified with dilute hydrochloric acid, and extracted twice with ethyl acetate. The recovered organic layer was dried over anhydrous magnesium sulfate, and the solvent was evaporated under reduced pressure. The obtained crude product was purified by silica gel column chromatography (hexane/ethyl acetate=1/1-ethyl acetate). Crystallization from diisopropyl ether-hexane gave the objective substance.

pale-brown powder yield 0.438 g, 56% mp 181–182° C.; $^1$H-NMR (CDCl$_3$-DMSO-d$_6$, 300 MHz) δ 2.70–2.76 (4H, m), 2.84 (1H, dd, J=11.7 Hz, 14.4 Hz), 3.07 (1H, dd, J=3.9 Hz, 14.4 Hz), 4.93–5.02 (1H, m), 5.94 (1H, tt, J=2.9 Hz, 53.0 Hz), 6.27 (1H, d, J=5.4 Hz), 7.01–7.32 (8H, m), 7.40–7.53 (5H, m), 8.03 (1H, d, J=9.0 Hz); IR (KBr) 3308, 3100–2800, 1740, 1723, 1640, 1624, 1530, 1516, 1235, 1179, 1119 cm$^{-1}$; Anal. Calcd for C$_{32}$H$_{25}$F$_6$NO$_6$: C, 60.67; H, 3.98; N, 2.21. Found: C, 60.37; H, 3.76; N, 2.05.

Example 389 sodium (1RS,2SR)-2-[(4-fluoro-1-naphthoyl)amino]-1-(4-fluorophenyl)-3-[3-(1,1,2,2-tetrafluoroethoxy)phenyl]propyl succinate To a solution of (1RS,2SR)-2-[(4-fluoro-1-naphthoyl)amino]-1-(4-fluorophenyl)-3-[3-(1,1,2,2-tetrafluoroethoxy)phenyl]propyl hydrogen succinate (242 mg, 0.382 mmol) in tetrahydrofuran (2 ml) was added 1N aqueous sodium hydroxide solution (0.38 ml, 0.38 mmol), and the mixture was stirred at room temperature for 5 min. The solvent of the reaction solution was evaporated under reduced pressure, and the obtained residue was crystallized from ethanol-hexane to give the objective substance.

pale-brown powder yield 165 mg, 66% mp 192–198° C.; $^1$H-NMR (DMSO-d$_6$, 300 MHz) δ 2.42–2.64 (4H, m), 2.81 (1H, dd, J=11.7 Hz, 13.2 Hz), 3.08 (1H, dd, J=2.1 Hz, 13.5 Hz), 4.68–4.79 (1H, m), 5.93 (1H, d, J=6.9 Hz), 6.73 (1H, tt, J=2.9 Hz, 51.8 Hz), 7.08–7.42 (10H, m), 7.50 (2H, dd, J=5.7 Hz, 8.4 Hz), 7.58 (1H, t, J=7.4 Hz), 8.01 (1H, d, J=8.7 Hz), 8.73 (1H, d, J=9.3 Hz); IR (KBr) 3304, 1738, 1842, 1574, 1530, 1514, 1119 cm$^{-1}$; Anal. Calcd for C$_{32}$H$_{24}$F$_6$NO$_6$Na.1.0H$_2$O: C, 57.06; H, 3.89; N, 2.08. Found: C, 56.79; H, 3.86; N, 1.90.

Example 390

N-(tert-butoxycarbonyl)glycine (1RS,2SR)-2-[(4-fluoro-1-naphthoyl)amino]-1-(4-fluorophenyl)-3-[3-(1,1,2,2-tetrafluoroethoxy)phenyl]propyl ester A solution of 4-fluoro-N-[(1RS,2SR)-2-(4-fluorophenyl)-2-hydroxy-1-[3-(1,1,2,2-tetrafluoroethoxy)benzyl]ethyl]naphthalene-1-carboxamide (0.486 g, 0.911 mmol), BOC-glycine (0.19 g, 1.09 mmol), 4-N,N-dimethylaminopyridine (0.22 g, 1.82 mmol) and 1-ethyl-3-(3-dimethylaminopropyl)carbodiimide hydrochloride (0.26 g, 1.37 mmol) in acetonitrile (20 ml) was stirred overnight at room temperature. The reaction solution was diluted with ethyl acetate, washed with aqueous sodium hydrogen carbonate solution, dried over anhydrous magnesium sulfate and passed through silica gel. The solvent was evaporated under reduced pressure. The obtained residue was crystallized from diisopropyl ether-hexane to give the objective substance white powder yield 0.582 g, 93% mp 126–127° C.; $^1$H-NMR (CDCl$_3$, 300 MHz) δ 1.33 (9H, s), 2.81 (1H, dd, J=11.0 Hz, 14.6 Hz), 3.10 (1H, dd, J=3.9 Hz, 14.4 Hz), 3.93 (1H, dd, J=6.0 Hz, 17.4 Hz), 4.04 (1H, dd, J=5.9 Hz, 1.9 Hz), 4.98–5.09 (2H, m), 5.88 (1H, tt, J=2.8 Hz, 53.2 Hz), 6.08 (1H, d, J=9.9 Hz), 6.26 (1H, d, J=3.9 Hz), 7.00 (1H, dd, J=7.8 Hz, 9.9 Hz), 7.08–7.19 (6H, m), 7.32 (1H, t, J=8.0 Hz), 7.40–7.54 (4H, m), 7.62 (1H, d, J=7.8 Hz), 8.06 (1H, d, J=7.8 Hz); IR (KBr) 3360, 3297, 2982, 1746, 1682, 1642, 1530, 1514, 1227, 2300, 1161, 1125 cm⁻; Anal. Calcd for $C_{35}H_{32}F_6N_2O_6$: C, 60.87; H, 4.67; N, 4.06. Found: C, 60.73; H, 4.65; N, 4.05.

Example 391 glycine (1RS,2SR)-2-[(4-fluoro-1-naphthoyl) amino]-1-(4-fluorophenyl)-3-[3-(1,1,2,2-tetrafluoroethoxy)phenyl]propyl ester hydrochloride A mixture of N-(tert-butoxycarbonyl)glycine (1RS,2SR)-2-[(4-fluoro-1-naphthoyl)amino]-1-(4-fluorophenyl)-3-[3-(1,1,2,2-tetrafluoroethoxy)phenyl]propyl ester (0.404 g, 0.585 mmol), conc. hydrochloric acid (0.4 ml) and methanol (6 ml) was stirred at 50° C. for 1 hr. The solvent of the reaction solution was evaporated under reduced pressure, and the obtained residue was crystallized from diethyl ether to give the objective substance.

white powder yield 0.331 g, 90% mp 209–212° C. (dec.); $^1$H-NMR (CD$_3$OD, 300 MHz) δ 2.78 (1H, dd, J=11.9 Hz, 14.3 Hz), 3.33 (1H, dd, J=3.9 Hz, 14.3 Hz), 3.95 (1H, d, J=17.4 Hz), 4.04 (1H, d, J=17.4 Hz), 4.98–5.06 (1H, m), 6.08 (1H, d, J=7.5 Hz), 6.249 (1H, tt, J=2.9 Hz, 52.7 Hz), 7.00 (1H, dd, J=5.4 Hz, 8.1 Hz), 7.07 (1H, dd, J=7.7 Hz, 10.1 Hz), 7.14–7.28 (6H, m), 7.36–7.41 (2H, m), 7.51–7.61 (3H, m), 8.03 (1H, d, J=8.4 Hz); IR (KBr) 3301, 3100–2800, 1740, 1644, 1514, 1275, 1235, 1206, 1121 cm⁻¹; Anal. Calcd for $C_{30}H_{25}ClF_6N_2O_4 \cdot 0.5H_2O$: C, 5.6.66; H, 4.12; N, 4.40. Found: C, 56.81; H, 4.35; N, 4.62.

Example 392

(1RS,2SR)-3-(4-tert-butylphenyl)-2-[(5-chloro-1-naphthoyl)amino]-1-3-chloro phenyl)propyl hydrogen succinate To a solution of N-[(1RS,2SR)-1-(4-tert-butylbenzyl)-2-(3-chlorophenyl)-2-hydroxyethyl]-5-chloro-1-naphthamide (0.499 g, 0.985 mmol) and succinic chloride (0.38 g, 2.46 mmol) in acetonitrile (30 ml) was added 4-N,N-dimethylaminopyridine (0.24 g, 1.97 mmol), and the mixture was stirred at 70° C. for 3 hrs. After cooling the reaction solution to room temperature, water (30 ml) was added, and the mixture was stirred as it was for 0.5 hr. The reaction solution was acidified with dilute hydrochloric acid, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=2/1–1/1). Crystallization from diisopropyl ether-hexane gave the objective substance.

white crystal yield 0.325 g, 54% mp 161–162° C.; $^1$H-NMR (CDCl$_3$, 300 MHz) δ 1.31 (9H, s), 2.63–2.84 (5H, m), 3.02 (1H, dd, J=4.1 Hz, 14.0 Hz), 4.98–5.06 (1H, m), 5.97 (1H, d, J=9.3 Hz), 6.21 (1H, d, J=4.8 Hz), 7.11 (2H, d, J=8.4 Hz), 7.18–7.54 (11H, m), 8.28 (1H, d, J=8.7 Hz); IR (KBr) 3300–3020, 2961, 1734, 1644, 1532, 1213, 1165, 783 cm⁻¹; Anal. Calcd for $C_{34}H_{33}Cl_2NO_5 \cdot 0.5H_2O$: C, 66.34; H, 5.57; N, 2.28. Found: C, 66.28; H, 5.34; N, 2.28.

Example 393 sodium (1RS,2SR)-3-(4-tert-butylphenyl)-2-[(5-chloro-1-naphthoyl)amino]-1-(3-chloro phenyl) propyl succinate To a solution of (1RS,2SR)-3-(4-tert-butylphenyl)-2-[(5-chloro-1-naphthoyl)amino]-1-(3-chloro phenyl)propyl hydrogen sucemate (217 mg, 0.358 mmol) in tetrahydrofuran (3 ml) was added 1N aqueous sodium hydroxide solution (0.36 ml, 0.36 mmol), and the mixture was stirred at room temperature for 5 mm. The solvent of the reaction solution was evaporated under reduced pressure, and the obtained residue was crystallized from methanol-diethyl ether-hexane to give the objective substance.

white powder yield 200 mg, 89% mp 174–178° C.; $^1$H-NMR (CDCl$_3$-CD$_3$OD, 300 MHz) δ 1.30 (9H, s), 2.53–2.58 (2H, m), 2.65–2.83 (3H, m), 3.00 (1H, dd, J=2.7 Hz, 14.4 Hz), 4.89–4.98 (1H, m), 6.17 (1H, d, J=4.8 Hz), 7.12 (2H, d, J=8.4 Hz), 7.20–7.54 (11H, m), 8.28 (1H, d, J=8.4 Hz); IR (KBr) 3245, 2965, 1730, 1640, 1574, 1418, 1157, 785 cm⁻¹; Anal. Calcd for $C_{34}H_{32}Cl_2NO_5Na \cdot 1.0H_2O$: C, 63.16; H, 5.30; N, 2.17. Found: C, 62.93; H, 5.57; N, 2.04.

Example 394

(1RS,2SR)-2-[(5-chloro-1-naphthoyl)amino]-1-(4-fluorophenyl)-3-[4-(trifluoromethyl)phenyl]propyl hydrogen succinate To a solution of 5-chloro-N-[(1RS,2SR)-2-(4-fluorophenyl)-2-hydroxy-1-[4-(trifluoromethyl)benzyl] ethyl]naphthalene-1-carboxamide (0.549 g, 1.094 mmol) and succinic chloride (0.42 g, 2.73 mmol) in acetonitrile (30 ml) was added 4-N,N-dimethylaminopyridine (0.27 g, 2.19 mmol), and the mixture was stirred at 70° C. for 3 hrs. After cooling the reaction solution to room temperature, water (30 ml) was added, and the mixture was stirred as it was for 0.5 hr. The reaction solution was acidified with dilute hydrochloric acid, and extracted twice with ethyl acetate. The recovered organic layer was dried over anhydrous magnesium sulfate, and the solvent was evaporated under reduced pressure. The obtained crude product was purified by silica gel column chromatography (hexane/ethyl acetate=2/1–1/1). Crystallization from diisopropyl ether-hexane gave the objective substance.

white crystal yield 0.408 g, 62% mp 228–229° C.; $^1$H-NMR (CDCl$_3$-DMSO-d$_6$, 300 MHz) δ 2.65–2.79 (4H, m), 2.87 (1H, dd, J=11.7 Hz, 13.5 Hz), 3.13 (1H, dd, J=3.3 Hz, 14.1 Hz), 4.94–5.04 (1H, m), 6.21 (1H, d, J=6.0 Hz), 7.08–7.23 (5H, m), 7.38 (2H, d, J=7.8 Hz), 7.47–7.54 (6H, m), 7.75 (1H, d, J=9.6 Hz), 8.25 (1H, d, J=8.4 Hz); IR (KBr) 3300–2640, 1730, 1636, 1528, 1510, 1323, 1221, 1177, 1155, 1109 cm⁻¹; Anal. Calcd for $C_{31}H_{24}ClF_4NO_5 \cdot 0.3H_2O$: C, 61.30; H, 4.08; N, 2.31. Found: C, 61.21; H, 3.72; N, 2.36.

Example 395 sodium (1RS,2SR)-2-[(5-chloro-1-naphthoyl) amino]-1-(4-fluorophenyl)-3-[4-(trifluoromethyl) phenyl]propyl succinate To a solution of (1RS,2SR)-2-[(5-chloro-1-naphthoyl) amino]-1-(4-fluorophenyl)-3-[4-(trifluoromethyl)phenyl] propyl hydrogen succinate (214 mg) in tetrahydrofuran (3 ml) was added 1N-aqueous sodium hydroxide solution (0.36 ml, 0.36 mmol), and the mixture was stirred at room temperature for 5 min. The solvent of the reaction solution was evaporated under reduced pressure, and the obtained residue was crystallized from methanol-diethyl ether-hexane to give the objective substance.

pale-yellow amorphous powder yield 132 mg) $^1$H-NMR (CDCl$_3$-DMSO-d$_6$-CD$_3$OD, 300 MHz) δ 2.54–2.79 (4H, m), 2.91 (1H, dd, J=11.7 Hz, 14.1 Hz), 3.08 (1H, dd, J=2.6

Hz, 14.0 Hz), 4.86–4.93 (1H, m), 6.18 (1H, d, J=5.7 Hz), 7.04–7.22 (4H, m), 7.26 (1H, d, J=6.6 Hz), 7.39 (2H, d, J=8.4 Hz), 7.47–7.55 (6H, m), 8.26 (1H, d, J=8.1 Hz); IR (KBr) 3650–2940, 1730, 1640, 1574, 1539, 1512, 1327, 1159, 1123 cm$^{-1}$; Anal. Calcd for $C_{31}H_{23}ClF_4NO_5Na \cdot 1.1H_2O$: C, 57.84; H, 3.95; N, 2.18. Found: C, 57.68; H, 3.97; N, 2.13.

Example 396

(1RS,2SR)-1-(4-fluorophenyl)-2-[(4-fluoro-1-naphthoyl)amino]-3-(2,2,3,3-tetrafluoro-2,3-dihydro-1,4-benzodioxin-6-yl)propyl hydrogen succinate To a solution of 4-fluoro-N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-1-naphthamide (0.278 g, 0.508 mmol) and succinic chloride (0.20 g, 1.27 mmol) in acetonitrile (30 ml) was added 4-N,N-dimethylaminopyridine (0.12 g, 1.02 mmol), and the mixture was stirred at 70° C. for 3 hrs. After cooling the reaction solution to room temperature, water (30 ml) was added, and the mixture was stirred as it was for 0.5 hr. The reaction solution was acidified with dilute hydrochloric acid, and extracted twice with ethyl acetate. The recovered organic layer was dried over anhydrous magnesium sulfate and the solvent was evaporated under reduced pressure. The obtained crude product was purified by silica gel column chromatography (hexane/ethyl acetate=2/1–1/1). Crystallization from diisopropyl ether-hexane gave the objective substance.

white crystal yield 0.184 g, 56% mp 196–197° C.; $^1$H-NMR (CDCl$_3$-DMSO-d$_6$, 300 MHz) δ 2.71–2.75 (4H, m), 2.78 (1H, dd, J=11.4 Hz, 14.4 Hz), 2.98 (1H, dd, J=3.6 Hz, 14.7 Hz), 4.89–4.98 (1H, m), 6.33 (1H, d, J=4.5 Hz), 7.01–7.16 (6H, m), 7.27 (1H, dd, J=5.4 Hz, 8.1 Hz), 7.38–7.54 (6H, m), 8.05 (1H, d, J=7.8 Hz); IR (KBr) 3285–2620, 1728, 1512, 1279, 1223, 1159, 1084 cm$^{-1}$; Anal. Calcd for $C_{32}H_{23}F_6NO_7 \cdot 0.5H_2O$: C, 58.54; H, 3.68; N, 2.13. Found: C, 58.76; H, 3.85; N, 2.31.

Example 397 sodium (1RS,2SR)-1-(4-fluorophenyl)-2-[(5-fluoro-1-naphthoyl)amino]-3-(2,2,3,3-tetrafluoro-2,3-dihydro-1,4-benzodioxin-6-yl)propyl succinate To a solution of (1RS,2SR)-1-(4-fluorophenyl)-2-[(4-fluoro-1-naphthoyl)amino]-3-(2,2,3,3-tetrafluoro-2,3-dihydro-1,4-benzodioxin-6-yl)propyl hydrogen succinate (145 mg) in tetrahydrofuran (3 ml) was added 1N aqueous sodium hydroxide solution (0.22 ml, 0.22 mmol), and the mixture was stirred at room temperature for 5 min. The solvent of the reaction solution was evaporated under reduced pressure, and the obtained residue was crystallized from methanol-diethyl ether-hexane to give the objective substance.

white powder yield 79 mg) $^1$H-NMR (CDCl$_3$-DMSO-d$_6$-CD$_3$OD, 300 MHz) δ 2.54–2.76 (4H, m), 2.85 (1H, dd, J=11.6 Hz, 14.3 Hz), 2.98 (1H, dd, J=3.5 Hz, 14.3 Hz), 4.80–4.86 (1H, m), 6.21 (1H, d, J=4.8 Hz), 7.03–7.14 (6H, m), 7.25 (1H, dd, J=5.4 Hz, 7.8 Hz), 7.40 (1H, dd, J=6.5 Hz, 8.6 Hz), 7.50–7.53 (4H, m), 8.04 (1H, d, J=8.7 Hz); IR (KBr) 3630–2930, 1728, 1642, 1601, 1574, 1512, 1279, 1227, 1157, 1084 cm$^{-1}$; Anal. Calcd for $C_{32}H_{22}F_6NO_7Na \cdot 1.5H_2O$: C, 55.18; H, 3.62; N, 2.01. Found: C, 55.41; H, 3.67; N, 2.00.

INDUSTRIAL APPLICABILITY

Since Compound (I) and Compound (I') of the present invention have superior cholesteryl ester transfer protein inhibitory action and the like, pharmaceutical agents containing these compounds can be used safely and advantageously as, for example, lipid-lowering agents and the like.

This application is based on a patent application No. 19280/2001 filed in Japan, the contents of which are hereby incorporated by reference.

What is claimed is:

1. A compound represented by the formula

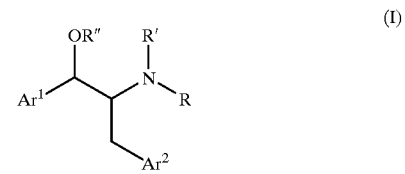

wherein
Ar$^1$ is an aromatic ring group optionally having substituents,
Ar$^2$ is an aromatic ring group having substituents,
OR" is an optionally protected hydroxyl group,
R is an acyl group, and
R' is a hydrogen atom or a hydrocarbon group optionally having substituents, or a salt thereof;
except tert-butyl benzyl-[2(S)-hydroxy-2-thiazol-2-yl-1 (S)-(4-trifluoromethyl-benzyl)-ethyl]-carbamate.

2. The compound of claim 1, wherein Ar$^1$ is a 5- or 6-membered aromatic ring group optionally having substituents.

3. The compound of claim 1, wherein Ar$^1$ is a phenyl group optionally having substituents.

4. The compound of claim 1, wherein Ar$^2$ is a 5- or 6-membered aromatic ring group having substituents.

5. The compound of claim 1, wherein Ar$^2$ is a phenyl group having substituents.

6. The compound of claim 1, wherein R is a group represented by the formula R$^{1N}$CO— (R$^{1N}$ is a hydrocarbon group optionally having substituents or a heterocyclic group optionally having substituents).

7. The compound of claim 6, wherein R$^{1N}$ is a cyclic hydrocarbon group optionally having substituents or a heterocyclic group optionally having substituents.

8. The compound of claim 1, wherein R" is a hydrogen atom or an acyl group.

9. The compound of claim 1, wherein R" is a group represented by the formula R$^{10}$CO— (R$^{10}$ is a hydrocarbon group optionally having substituents or a heterocyclic group optionally having substituents).

10. The compound of claim 8, wherein R$^{10}$ is an alkyl group optionally having substituents.

11. The compound of claim 1, wherein R" is a hydrogen atom.

12. The compound of claim 1, wherein R' is a hydrogen atom.

13. The compound of claim 1, wherein R is a group represented by the formula R$^{1N}$CO— (R$^{1N}$ is a cyclic hydrocarbon group optionally having substituents or a heterocyclic group optionally having substituents), R" is a hydrogen atom and R' is a hydrogen atom.

14. The compound of claim 1, wherein Ar$^1$ is a 5- or 6-membered aromatic ring group optionally having substituents selected from halogen atom, optionally halogenated lower alkyl group, optionally halogenated lower alkoxy group and aryloxy group optionally having substituents, Ar$^2$ is a 5- or 6-membered aromatic ring group having substituents selected from halogen atom, optionally halogenated lower alkyl group and optionally halogenated lower alkoxy group, R is a $C_{1-6}$alkoxy-carbonyl, a $C_{1-6}$alkyl-carbonyl, a $C_{6-10}$aryl-carbonyl, dihydronaphthalenecarbonyl, tetrahydronaphthalenecarbonyl, benzocycloheptenecarbonyl or benzocyclooctenecarbonyl, each of which may have substituent(s) selected from halogen atom, optionally halogenated $C_{1-6}$alkoxy and optionally halogenated $C_{1-6}$alkyl, R" is a hydrogen atom, and R' is a hydrogen atom.

15. The compound of claim 14, wherein the 5- or 6-membered aromatic ring group is a phenyl group, a pyridyl group, a thienyl group, a furyl group or a thiazolyl group.

16. The compound of claim 14, wherein the 5- or 6-membered aromatic ring group is a phenyl group, a pyridyl group or a thienyl group, and R is naphthalenecarbonyl, dihydronaphthalenecarbonyl, tetrahydronaphthalenecarbonyl, benzocycloheptenecarbonyl or benzocyclooctenecarbonyl, each of which may have substituent(s) selected from halogen atom, optionally halogenated $C_{1-6}$alkoxy and optionally halogenated $C_{1-6}$alkyl.

17. The compound of claim 1, which is
N[(1RS2SR)-2-(4-fluorophenyl)-2-hydroxy-1-[4-fluoromethyl)benzyl]ethyl]-6,7-dihydro-5H-benzo[a]cycloheptene-1-carboxamide,
4-fluoro-N-((1R,2S)-2-(4-fluorophenyl)-2-hydroxy-1-((4-(trifluoromethyl)phenyl)methyl)ethyl)-1-naphthalenecarboxamide,
N-[(1R,2S)-2-(4-fluorophenyl)-2-hydroxy-1-[3-1,1,2,2-tetrafluoroethoxy)benzyl]ethyl]-6,7-dihydro-5H-benzo[a]cycloheptene-1-carboxamide,
N-[(1RS,2SR)-2-(4-fluorophenyl)-2-hydroxy-1-[3-(1,1,2,2-tetrafluoroethoxy)benzyl]ethyl]-5,6-dihydronaphthalene-1-carboxamide,
N-[(1RS,2SR)-2-(4-fluorophenyl)-2-hydroxy-1-[3-(1,1,2,2-tetrafluoroethoxy)benzyl]ethyl]-6,7,8,9-tetrahydro-5H-benzo[a]cycloheptene-1-carboxamide,
4-fluoro-N-[(1R,2S)-2-(4-fluorophenyl)-2-hydroxy-1-[3-(1,1,2,2-tetrafluoroethoxy)benzyl]ethyl]naphthalene-1-carboxamide,
N-[(1RS,2SR)-2-(4-fluorophenyl)-2-hydroxy-1-[3-(1,1,2,2-tetrafluoroethoxy)benzyl]ethyl]-5,6,7,8-tetrahydrobenzo[a]cyclooctene-1-carboxamide,
N-[(1RS2SR)2-(4-fluorophenyl)-2-hydroxy-1-(4-isopropylbenzyl)ethyl]-6,7-dihydro-5H-benzo[a]cycloheptene-1-carboxamide,
N-((1RS,2SR)-2-(3-fluorophenyl)-2-hydroxy-1-((4-(trifluoromethyl)phenyl)methyl)ethyl)-6,7-dihydro-5H-benzo[a]cycloheptene-1-carboxamide,
N-((1RS,2SR)-2-hydroxy-2-(4-phenoxyphenyl)-1-((4 (trifluoromethyl)phenyl)methyl)ethyl)-6,7-dihydro-5H-benzo[a]cycloheptene-1-carboxamide,
N-((1RS,2SR)-2-(4-chlorophenyl)-2-hydroxy-1-[3-(1,1,2,2-tetrafluoroethoxy)benzyl]ethyl-6,7-dihydro-5H-benzo[a]cycloheptene-1-carboxamide,
N-((1RS,2SR)-2-hydroxy-2-(4-(phenyloxy)phenyl)-1-((3-((1,1,2,2-tetrafluoroethoxy)phenyl)methyl)ethyl)-6,7-dihydro-5H-benzo[a]cycloheptene-1-carboxamide,
N-((1RS,2SR)-2-(4-((4-chloro-3-ethylphenyl)oxy)phenyl)-2-hydroxy-1-((3-((1,1,2,2-tetrafluoroethyl)oxy)phenyl)methyl)ethyl)-6,7-dihydro-5H-benzo[a]cycloheptene-1-carboxamide,
N-((1RS,2SR)-2-(2-fluoropyridin-4-yl)-2-hydroxy-1-((3-(1,1,2,2-tetrafluoroetoxy)phenyl)mehyl)ethyl)-6,7-dihydro-5H-benzo[a]cycloheptene 1-carboxamide,
N-((1RS,2RS)-2-(6-fluoropyridin2-yl)-2-hydroxy-1-((3-(1,1,2,2-tetrafluoroethoxy)phenyl)methyl)ethyl)-6,7-dihydro-5H-benzo[a]cycloheptene-1-carboxamide,
N-[(1RS,2SR)-1-(4-tert-butylbenzyl)-2-(3-chorophenyl)-2-hydroxyethyl]-5- chlorol-1-naphthamide,
4-fluoro-N-{(1RS,2SR)-2-(4-fluorophenyl)-2-hydroxy-1-[(2,2,3,3-tetrafluoro-2,3-dihydro-1,4-benzodioxin-6-yl)methyl]ethyl}-1-naphthamide or a salt thereof.

18. A prodrug of a compound represented by the formula

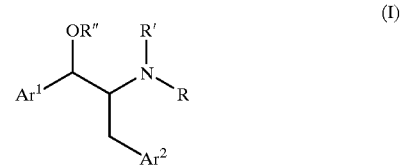

(I)

wherein
Ar$^1$ is an aromatic ring group optionally having substituents
Ar$^2$ is an aromatic ring group having substituents,
OR" is an optionally protected hydroxyl group,
R is an acyl group, and R' is a hydrogen atom or a hydrocarbon group optionally having substituents, or a salt thereof,
except tert-butyl benzyl-[2(S)-hydroxy-2-thiazol-2-yl-1 (S)-(4-trifluoromethyl-benzyl)-ethyl]-carbamate.

19. A pharmaceutical composition comprising a compound represented by the formula

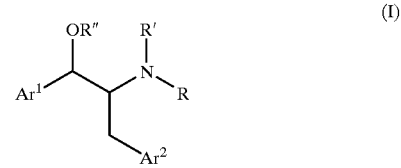

(I)

wherein
Ar$^1$ is an aromatic ring group optionally having substituents,
Ar$^2$ is an aromatic ring group having substituents,
OR" is an optionally protected hydroxyl group,
R is an acyl group, and
R' is a hydrogen atom or a hydrocarbon group optionally having substituents,
or a salt thereof of a prodrug thereof.

20. The composition of claim 19, which is a cholesteryl ester transfer protein inhibitor.

21. The composition of claim 19, which is a high density lipoprotein-cholesterol elevating agent.

22. The composition of claim 19, which is a low density lipoprotein-cholesterol lowering agent.

23. The composition of claim 19, which is an very low density lipoprotein-cholesterol lowering agent.

24. The composition of claim 19, which is a triglyceride lowering agent.

25. The composition of claim 19, which is a prophylactic or therapeutic agent of acute coronart syndrome.

26. The composition of claim 19, which is a prophylactic or therapeutic agent of acute cardiac infarction.

27. The composition of claim 19, which is a prophylactic or therapeutic agent of unstable angina pectoris.

28. The composition of claim 19, which is a prophylactic or therapeutic agent of PTCA or arterial restenosis after stent placement.

29. The composition of claim 19, which is a prophylactic or therapeutic agent of peripheral arterial occlusion.

30. The composition of claim 19, which is a prophylactic or therapeutic agent of hyperlipidemia.

31. The composition of claim 19, which is a prophylactic or therapeutic agent of cerebral infarction.

32. The composition of claim 19, which is a prophylactic or therapeutic agent of stroke.

33. The composition of claim 19, which is a suppressor of progression of focal arteriosclerosis.

34. A cholesteryl ester transfer protein inhibitor comprising a compound represented by the formula

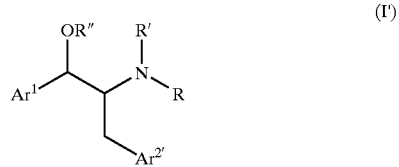
(I')

wherein
$Ar^1$ is an aromatic ring group optionally having substituents,
$Ar^2$ is an aromatic ring group optionally having substituents,
OR" is an optionally protected hydroxyl group,
R is an acyl group, and
R' is a hydrogen atom or a hydrocarbon group optionally having substituents,
or a salt thereof or a prodrug thereof.

35. The agent of claim 34, which is a prophylactic or therapeutic agent of hyperlipidemia.

36. The agent of claim 34, which is a prophylactic or therapeutic agent of acute coronary syndrome.

37. The agent of claim 34, which is a prophylactic or therapeutic agent of acute cardiac infarction.

38. The agent of claim 34, which is a prophylactic or therapeutic agent of unstable angina pectoris.

39. The agent of claim 34, which is a prophylactic or therapeutic agent of PTCA or arterial restenosis after stent placement.

40. The agent of claim 34, which is a prophylactic or therapeutic agent of peripheral arterial occlusion.

41. The agent of claim 34, which is a prophylactic or therapeutic agent of cerebral infarction.

42. The agent of claim 34, which is a prophylactic or therapeutic agent of stroke.

43. The agent of claim 34, which is a suppressor of progression of focal arteriosclerosis.

44. A method of inhibiting cholesteryl ester transfer protein in a mammal, which comprises administering an effective amount of a compound of claim 1 or a salt thereof to the mammal.

45. A method for the prophylaxis or treatment of hyperlipidemia in a mammal, which comprises administering an effective amount of a compound of claim 1 or a salt thereof to the mammal.

46. A method for the prophylaxis or treatment of acute coronary syndrome in a mammal, which comprises administering an effective amount of a compound of claim 1 or a salt thereof to the mammal.

47. A method for the prophylaxis or treatment of acute cardiac infarction in a mammal, which comprises administering an effective amount of a compound of claim 1 or a salt thereof to the mammal.

48. A method for the prophylaxis or treatment of unstable angina pectoris in a mammal, which comprises administering an effective amount of a compound of claim 1 or a salt thereof to the mammal.

49. A method for the prophylaxis or treatment of PTCA or coronary resteiiosis after stent placement in a mammal, which comprises administering an effective amount of a compound of claim 1 or a salt thereof to the mammal.

50. A method for the prophylaxis or treatment of peripheral arterial occlusion in a mammal, which comprises administering an effective amount of a compound of claim 1 or a salt thereof to the mammal.

51. A method for the prophylaxis or treatment of cerebral infarction in a mammal, which comprises administering an effective amount of a compound of claim 1 or a salt thereof to the mammal.

52. A method for the prophylaxis or treatment of stroke in a mammal, which comprises admimistering an effective amount of a compound of claim 1 or a salt thereof to the mammal.

53. A method of suppressing progression of focal arteriosclerosis in a mammal, which comprises administering an effective amount of a compound of claim 1 or a salt thereof to the mammal.

54. A method of inhibiting cholesteryl ester transfer protein in a mammal, which comprises administering an effective amount of a compound represented by the formula (I') of claim 34 or a salt thereof or a prodrug thereof to the mammal.

55. A production method of claim 1 or a salt thereof, which comprises subjecting a compound represented by the formula

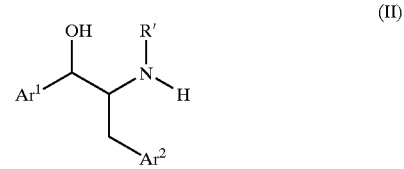
(II)

wherein each symbol is as defined in claim 1, or a salt thereof to an acylation reaction to give a compound represented by the formula

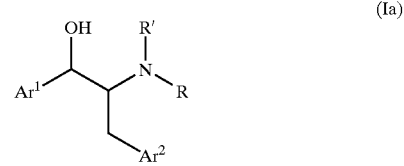
(Ia)

wherein each symbol is as defined in claim 1, or a salt thereof, and, where desired, subjecting the compound to a hydroxyl group-protecting reaction.

* * * * *